United States Patent
Morgans, Jr. et al.

(10) Patent No.: US 11,814,367 B2
(45) Date of Patent: Nov. 14, 2023

(54) INHIBITORS OF GLYCOGEN SYNTHASE 1 (GYS1) AND METHODS OF USE THEREOF

(71) Applicant: Maze Therapeutics, Inc., South San Francisco, CA (US)

(72) Inventors: David John Morgans, Jr., Los Altos, CA (US); Kevin Mellem, Redwood City, CA (US); Hannah L. Powers, San Diego, CA (US); Patrick Sang Tae Lee, Walnut Creek, CA (US); Walter Won, San Diego, CA (US); Christopher Joseph Sinz, Walnut Creek, CA (US)

(73) Assignee: MAZE THERAPEUTICS, INC., South San Francisco, CA (US)

( * ) Notice: Subject to any disclaimer, the term of this patent is extended or adjusted under 35 U.S.C. 154(b) by 0 days.

(21) Appl. No.: 17/694,311

(22) Filed: Mar. 14, 2022

(65) Prior Publication Data

US 2023/0104740 A1 Apr. 6, 2023

Related U.S. Application Data

(60) Provisional application No. 63/266,572, filed on Jan. 9, 2022, provisional application No. 63/161,347, filed on Mar. 15, 2021.

(51) Int. Cl.
C07D 403/12 (2006.01)
C07D 207/16 (2006.01)
(Continued)

(52) U.S. Cl.
CPC ......... *C07D 403/12* (2013.01); *C07D 207/16* (2013.01); *C07D 401/06* (2013.01);
(Continued)

(58) Field of Classification Search
CPC .. C07D 207/16; C07D 401/12; C07D 403/12; C07D 413/12; C07D 401/06;
(Continued)

(56) References Cited

U.S. PATENT DOCUMENTS 3,752,800 A 8/1973 Wissmann et al.
5,444,049 A 8/1995 De et al.
(Continued)

FOREIGN PATENT DOCUMENTS

CA 2116181 A1 8/1994
CN 102050867 A 5/2011
(Continued)

OTHER PUBLICATIONS

Bajusz, S. et al. (1972). "Amide Protection In Classical Peptide Synthesis," Chem. Biol. Pept. Process. Am. Pept. Symp 3rd pp. 325-329.
(Continued)

*Primary Examiner* — Kortney L. Klinkel
*Assistant Examiner* — Padmaja S Rao
(74) *Attorney, Agent, or Firm* — MORRISON & FOERSTER LLP

(57) ABSTRACT

Provided herein are compounds of formula (I'):

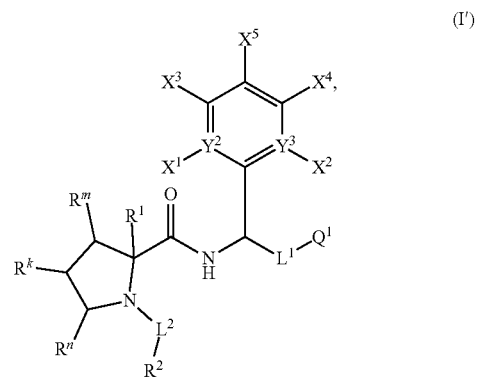

(I')

or a stereoisomer or tautomer thereof, or a pharmaceutically acceptable salt of any of the foregoing, wherein $Y^2$, $Y^3$, $L^1$, $L^2$, $X^1$, $X^2$, $X^3$, $X^4$, $X^5$, $Q^1$, $R^1$, $R^2$, $R^k$, $R^m$, and $R^n$ are as defined elsewhere herein. Also provided herein are methods of preparing compounds of formula (I'). Also provided herein are methods of inhibiting GYS1 and methods of
(Continued)

treating a GYS1-mediated disease, disorder, or condition in an individual in need thereof.

41 Claims, 5 Drawing Sheets

(51) Int. Cl.

| | |
|---|---|
| C07D 401/06 | (2006.01) |
| C07D 401/12 | (2006.01) |
| C07D 401/14 | (2006.01) |
| C07D 403/06 | (2006.01) |
| C07D 405/06 | (2006.01) |
| C07D 413/06 | (2006.01) |
| C07D 413/14 | (2006.01) |
| C07D 417/06 | (2006.01) |
| C07D 471/04 | (2006.01) |
| C07D 487/04 | (2006.01) |
| C07D 487/10 | (2006.01) |
| C07D 491/048 | (2006.01) |
| C07D 491/08 | (2006.01) |
| C07D 498/10 | (2006.01) |

(52) U.S. Cl.
CPC ......... *C07D 401/12* (2013.01); *C07D 401/14* (2013.01); *C07D 403/06* (2013.01); *C07D 405/06* (2013.01); *C07D 413/06* (2013.01); *C07D 413/14* (2013.01); *C07D 417/06* (2013.01); *C07D 471/04* (2013.01); *C07D 487/04* (2013.01); *C07D 487/10* (2013.01); *C07D 491/048* (2013.01); *C07D 491/08* (2013.01); *C07D 498/10* (2013.01)

(58) Field of Classification Search
CPC .. C07D 403/06; C07D 405/06; C07D 413/06; C07D 417/06; C07D 401/14; C07D 403/14; C07D 413/14; C07D 471/04; C07D 487/04; C07D 487/10; C07D 498/10; C07D 491/048; C07D 491/08; C07D 491/107; C07D 209/52

See application file for complete search history.

(56) References Cited

U.S. PATENT DOCUMENTS

| | | | |
|---|---|---|---|
| 5,658,885 | A | 8/1997 | Lee et al. |
| 7,524,870 | B2 | 4/2009 | Gillespie et al. |
| 7,579,320 | B2 | 8/2009 | Boudreault |
| 7,645,741 | B2 | 1/2010 | Boudreault et al. |
| 7,790,770 | B2 | 9/2010 | Salvati et al. |
| 7,888,376 | B2 | 2/2011 | Salvati et al. |
| 8,076,330 | B2 | 12/2011 | Kroth et al. |
| 8,551,955 | B2 | 10/2013 | Sun et al. |
| 8,987,198 | B2 | 3/2015 | Burow et al. |
| 10,730,870 | B2 | 8/2020 | Crew et al. |
| 2002/0177725 | A1 | 11/2002 | Priestley |
| 2010/0093645 | A1 | 4/2010 | Wang et al. |
| 2011/0136792 | A1 | 6/2011 | Bolin et al. |
| 2011/0177060 | A1 | 7/2011 | Jaquith |
| 2012/0082640 | A1 | 4/2012 | Hanson et al. |
| 2019/0077793 | A1 | 3/2019 | Ashcraft et al. |
| 2020/0038378 | A1 | 2/2020 | Crew et al. |
| 2020/0055825 | A1 | 2/2020 | Crew et al. |

FOREIGN PATENT DOCUMENTS

| | | |
|---|---|---|
| CN | 104558102 A | 4/2015 |
| CN | 105854851 A | 8/2016 |
| CN | 107056786 A | 8/2017 |
| CN | 109020977 A | 12/2018 |
| CS | 208543 B1 | 9/1981 |
| CS | 247585 B1 | 1/1987 |
| DE | 2033600 A1 | 1/1972 |
| EP | 0498680 A1 | 8/1992 |
| EP | 0805147 A1 | 11/1997 |
| EP | 1541148 A1 | 6/2005 |
| WO | 200102424 A2 | 1/2001 |
| WO | 200102424 A3 | 1/2001 |
| WO | 2004007428 A1 | 1/2004 |
| WO | 2004028339 A2 | 4/2004 |
| WO | 2004058264 A1 | 7/2004 |
| WO | 2004028339 A3 | 8/2004 |
| WO | 2005056013 A1 | 6/2005 |
| WO | 2005069888 A2 | 8/2005 |
| WO | 2005069888 A3 | 8/2005 |
| WO | 2005080390 A1 | 9/2005 |
| WO | 2006017295 A2 | 2/2006 |
| WO | 2006017295 A3 | 2/2006 |
| WO | 2006127550 A1 | 11/2006 |
| WO | 2007062308 A2 | 5/2007 |
| WO | 2007062308 A3 | 5/2007 |
| WO | 2007062314 A2 | 5/2007 |
| WO | 2007062314 A3 | 5/2007 |
| WO | 2007104162 A1 | 9/2007 |
| WO | 2008128121 A1 | 10/2008 |
| WO | 2009136290 A1 | 11/2009 |
| WO | 2011057477 A1 | 5/2011 |
| WO | 2011059763 A2 | 5/2011 |
| WO | 2011059763 A3 | 5/2011 |
| WO | 2011087857 A2 | 7/2011 |
| WO | 2011087857 A3 | 10/2011 |
| WO | 2016027195 A1 | 2/2016 |
| WO | 2017044592 A1 | 3/2017 |
| WO | 2017219017 A1 | 12/2017 |
| WO | 2019023553 A1 | 1/2019 |
| WO | 2019198833 A1 | 10/2019 |
| WO | 2019198834 A1 | 10/2019 |
| WO | 2020041301 A1 | 2/2020 |
| WO | 2020185982 A1 | 9/2020 |
| WO | 2020185983 A1 | 9/2020 |
| WO | 2020223403 A1 | 11/2020 |
| WO | 2021071821 A1 | 4/2021 |
| WO | 2021236475 A1 | 11/2021 |
| WO | 2022198196 A1 | 9/2022 |

OTHER PUBLICATIONS

Bajusz, S. et al. (1973). "An Improved Method For The Synthesis of The Thyrotropin Releasing Hormone (TRH)," Acta Chimica Academiae Scientiarum Hungaricae 75(4):419-422. English Translation.

Bajusz, S. et al. (1973). "Side Chain Protection In The Synthesis of Peptide Amides," Pept. Proc. Eur. Pept. Symp. 12th pp. 93-96.

Bhanot, H, et al. (Jul. 2015). "Pathological Glycogenesis Through Glycogen Synthase I and Suppression of Excessive AMP Kinase Activity in Myeloid Leukemia Cells," Leukemia 29(7):1555-1563, 22 pages.

Byrne, B.J. et al. (2011, e-pub. Feb. 11, 2011). "Pompe Disease: Design, Methodology, and Early Findings From the Pompe Registry," Mol. Genet. Metab. 103:1-11.

Chen, S.-L. et al. (Jul. 14, 2020). "GYS1 Induces Glycogen Accumulation and Promotes Tumor Progression via The NF-κB Pathway In Clear Cell Renal Carcinoma," Theranostics 10(20):9186-9199.

Chown, E.E. et al. (2020). "GYS1 or PPP1R3C Deficiency Rescues Murine Adult Polyglucosan Body Disease," Annals of Clinical and Translational Neurology 7(11):2186-2198.

Claussnitzer, M. et al. (Jan. 9, 2020, e-pub. Jan. 8, 2020). "Review: A Brief History of Human Disease Genetics," Nature 557:179-189.

Clayton, N.P. et al. (2014, e-pub. Oct. 28, 2014). "Antisense Oligonucleotide-Mediated Suppression of Muscle Glycogen Synthase 1 Synthesis as an Approach For Substrate Reduction Therapy of Pompe Disease," Molecular Therapy—Nucleic Acids 3:e206, 11 pages.

Cuypers, B. et al. (Mar./Apr. 12, 2016). "Apolipoprotein L1 Variant Associated With Increased Susceptibility To Trypanosome Infection," MBio 7(2):e02198-15, 8 pages.

(56) References Cited

OTHER PUBLICATIONS

Douillard-Guilloux, G. et al. (2008, e-pub. Sep. 9, 2008). "Modulation of Glycogen Synthesis by RNA Interference: Towards a New Therapeutic Approach for Glycogenosis Type II", Human Molecular Genetics 17(24):3876-3886.
Douillard-Guilloux, G. et al. (Dec. 3, 2009). "Restoration of Muscle Functionality by Genetic Suppression of Glycogen Synthesis in a Murine Model of Pompe Disease," Human Molecular Genetics 19(4):684-696. Supplementary figure 1, (Feb. 10, 2010), Retrieved from the Internet: URL:http://hmg.oxfordjournals.org/content/suppl/2009/12/05/ddp535.DC1/ddp535supp.pdf.
Falantes, J.F. et al. (Apr. 2015, e-pub. Oct. 23, 2014). "Overexpression of GYS1, MIF, and MYC is Associated With Adverse Outcome and poor Response To Azacitidine In Myelodysplastic Syndromes and Acute Myeloid eukemia," Clinical Lymphoma, Myeloma & Leukemia 15(4):236-244.
Giatromanolaki, A. et al. (May-Jun. 2017, e-pub. Jun. 23, 2017). "Expression of Enzymes Related To Glucose Metabolism In Non-Small Cell Lung Cancer and Prognosis," Experimental Lung Research 43(4-5):167-174.
Heinicke, K. et al. (Oct. 8, 2014). "Reproducibility and Absolute Quantification of Muscle Glycogen in Patients With Glycogen Storage Disease By 13C NMR Spectroscopy at 7 Tesla," PLOS One 9(10):e108706, 6 pages.
Hirt, J. et al. (1979). "A Convenient Synthesis of Human Calcitonin Mainly via The Repetitive Excess Mixed Anhydride Method," Recueil des Travaux Chimiques des Pays-Bas 98(4):143-154.
International Search Report and Written Opinion, dated May 10, 2022 for PCT/US2022/071139, filed Mar. 14, 2022, 2 pages.
Invitation To Pay Additional Fees, dated May 10, 2022, for PCT/US2022/071139, filed Mar. 14, 2022, 2 pages.
Kasafirek, E. et al. (1977). "Use of the Ammonium Salt of Pyroglutamic Acid For The Synthesis of TRF," Collection of Czechoslovak Chemical Communications 42(6):1903-1906.
Kasafirek, E. et al. (1980). "Synthesis of Analogs of the Thyrotropin Releasing Factor Containing 2-oxomidazolidine-1-carboxylic acid," Collection of Czechoslovak Chemical Communications 45(2):452-456.
Kerdphon, S. et al. (May 30, 2019). "Diastereo- and Enantioselective Synthesis of Structurally Diverse Succinate, Butyrolactone, and Trifluoromethyl Derivatives by Iridium-Catalyzed Hydrogenation of Tetrasubstituted Olefins," ACS Catalysis 9(7):6169-6176.
Kishnani, P. et al. (Jul. 2010). "Glycogen Storage Disease Type III Diagnosis and Management Guidelines," Genetics in Medicine 12(7):446-463.
Koenig, W. et al. (1972). "Pyroglutamylpeptides," Chemische Berichte 105(9):2872-2882. English Abstract.
Kruszyński, M. et al. (1976). "Use of O-[N-acylaminoacyl]-α-isonitroso Ketones In Peptide Synthesis," Roczniki Chemii 50(6):1099-1115. With English Translation.
Li, X. et al. (2022, e-pub. Jan. 10, 2022). "Environmental Modulation of Chiral Prolinamide Catalysts For Stereodivergent Conjugate Addition," Journal of Catalysis 406:126-133.
Li, X. et al. (Aug. 1, 2019). "Chiral Gating for Size- and Shape-Selective Asymmetric Catalysis," Journal of American Chemical Society 141(35):13749-13752.
López-Soldado, I. et al. (2017, e-pub. Mar. 15, 2017). "Effects of Hepatic Glycogen on Food Intake and Glucose Homeostasis Are Mediated By the Vagus Nerve In Mice," Diabetologia 60:1076-1083.
Matheau-Raven, D. et al. (Oct. 11, 2021). "A Three-Component Ugi-Type Reaction of N-Carbamoyl Imines Enables a Broad Scope Primary α-Amino 1,3,4-Oxadiazole Synthesis," Organic Letters 23(21):8209-8213.
Mbatchou, J. et al. (Jul. 2021). "Computationally Efficient Whole-Genome Regression For Quantitative and Binary Trait," Nat. Genet. 53:1097-1103.
Meena, N.K. et al. (Sep. 18, 2020). "Pompe Disease: New Developments in an Old Lysosomal Storage Disorder," Biomolecules 10:1339, 19 pages.
Oost, T.K. et al. (2004). "Discovery of Potent Antagonists of the Antiapoptotic Protein XIAP for the Treatment of Cancer," Journal of Medicinal Chemistry 47(18):4417-4426.
Pedersen, B. et al. (Aug. 2013). "Inhibiting Glycogen Synthesis Prevents Lafora Disease in a Mouse Model," Annals of Neurology 74(2):297-300, 9 pages.
Platt, F.M. et al. (2007). "Chapter 19—Substrate Reduction Therapy," in Gaucher Disease pp. 355-376.
Raben N. et al. (Feb. 15, 2012). "Autophagy and Mitochondria In Pompe Disease: Nothing Is So New as What Has Long Been Forgotten," American Journal Medical Genetics C. Semin. Med Genet. 160(1):13-21, 16 pages.
Riberio, L.F.P. et al. (May 2012, e-pub. Apr. 3, 2012). "Effects of Swimming Training on Tissue Glycogen Content in Experimental Thyrotoxic Rats," Canadian Journal of Physiology and Pharmacology 90(5):587-593.
Savage, D.B. et al. (Jan. 29, 2008). "A Prevalent Variant in PPP1R3A Impairs Glycogen Synthesis and Reduces Muscle Glycogen Content in Humans and Mice," PLOS Medicine 5(1):e27, 10 pages.
Schaub, C. et al. (2020). "Cation Channel Conductance and PH Gating of the Innate Immunity Factor APOL1 Are Governed by Pore-Lining Residues Within the C-Terminal Domain," J. Biol. Chem. 295(38):13138-13149.
Schoser, B. et al. (2017). "The Humanistic Burden of Pompe disease: Are There Still Unmet Needs? A Systematic Review," BMC Neurology 17:202, 17 pages.
Schoser, B. et al. (2019, e-pub. May 2, 2019). "A Systematic Review of the Health Economics of Pompe Disease," PharmacoEconomics—Open 3:479-493.
Shemesh E. et al. (2015). "Enzyme Replacement and Substrate Reduction Therapy For Gaucher Disease (Review)," Cochrane Database of Systematic Reviews 3(CD010324):1-47.
Tang, B. (Mar. 5, 2020). "Discovery and Development of Small-Molecule Inhibitors of Glycogen Synthase," Journal of Medicinal Chemistry, 14 pages.
Van Der Ploeg, A.T. et al. (Oct. 11, 2008). "Lysosmal Storage Disease 2: Pompe's Disease," Lancet 372:1342-1353.
Van Goethem, S. et al. (Jun. 29, 2011). "Structure-Activity Relationship Studies on Isoindoline Inhibitors of Dipeptidyl Peptidases 8 and 9 (DPP8, DPP9): is DPP8-Selectivity an Attainable Goal?," Journal of Medicinal Chemistry 54(16):5737-5746.
Varea, O. et al. (2020, e-pub. Nov. 7, 2020). "Suppression of Glycogen Synthesis as a Treatment For Lafora Disease: Establishing The Window of Opportunity," Neurobiology of Disease 147:105173, 13 pages.
Yi, H. et al. (2012). "Characterization of a Canine Model of Glycogen Storage Disease Type IIIa," Disease Models & Mechanisms 5:804-811.
Yu, C. et al. (May 2012). "A Chiral Amino-Naphthalene-Derived Prolinamide Catalyst for the Enantioselective Michael Addition of Ketones To Nitroolefins," Journal of Chemical Research 36(5):278-282.
Zakhariev, S. et al. (1988). "New Methods For Synthesis of thyroliberin (L-pyroglutamyl-L-histidyl-L-prolinamide)," Doklady Bolgarskoi Akademil Nauk 41(9):69-72. English Abstract.
International Search Report and Written Opinion, dated Jul. 8, 2022 for PCT/US2022/071139, filed Mar. 14, 2022, 16 pages.
Yamada, T. et al. (2003). "Synthesis and Separation of Diastereomers of Tripeptides Containing α,α-di(2-pyridyl) glycine," Peptide Science 40:131-132.
Qian, Y. et al. (2013, e-pub. Mar. 12, 2013). "N-Substituted Sultam Carboxylic Acids as Novel Glycogen Synthase Activators," Med. Chem. Commun. 4:833-838.

INHIBITORS OF GLYCOGEN SYNTHASE 1 (GYS1) AND METHODS OF USE THEREOF

CROSS REFERENCE TO RELATED APPLICATIONS

This application claims priority to U.S. Provisional Application No. 63/161,347 filed on Mar. 15, 2021, and U.S. Provisional Application No. 63/266,572, filed Jan. 9, 2022, the contents of which are incorporated herein by reference in their entireties.

BACKGROUND OF THE INVENTION

Pathological accumulation of glycogen is a hallmark of several devastating and chronic human diseases. For some of these disorders, the cellular etiology driving this aberrant accumulation has clear genetic underpinnings and for others the mechanistic driving force is more complex. Nonetheless, the consequence of elevated levels of glycogen is altered cellular homeostasis and impaired tissue function over time. The rate limiting enzyme in the glycogen synthesis pathway is the protein Glycogen Synthase (GYS). In humans there are two isoforms GYS1 & GYS2. The former is ubiquitously expressed but highly abundant in muscle cells, while the latter is expressed exclusively in liver. Glycogen synthesis ultimately begins with transport of glucose into cells via the GLUT transporter family of proteins. Conversion of glucose into glycogen follows along a well characterized biochemical conversion pathway to the step where GYS covalently links glucose molecules into long branches via $\alpha 1,4$-glycosidic linkages. The final spherical structure of glycogen results from the action of Glycogen Branching Enzyme (GBE) which introduces $\alpha 1,6$-linkage branch points along the strands. The result of this biochemical chain of events is the generation of an energy dense and highly soluble molecule that can be stored in the cytosol of cells for rapid catabolism into glucose energy when needed. An imbalance in the equilibrium of either glycogen synthesis or glycogenolysis can result in aberrant accumulation of cellular stores of glycogen. It has long been hypothesized that substrate reduction therapy targeted to inhibit glycogen synthase could be an effective treatment for diseases of glycogen storage. Indeed, substrate reduction therapy drugs have been very successful in modulating patient disease course in other storage disorders including Gaucher and Fabry diseases (Platt F M, Butters T D. Substrate Reduction Therapy. Lysosomal Storage Disorders, Springer US chapter 11, pgs 153-168, 2007; Shemesh E, et al. Enzyme replacement and substrate reduction therapy for Gaucher disease. Cochrane Database of Systematic Reviews, Issue 3, 2015). It is the aim of this invention to inhibit glycogen synthase enzyme activity resulting in reduction of tissue glycogen stores with therapeutic benefit to patients suffering the consequences of aberrant cellular glycogen accumulation.

Pompe Disease is a rare genetic disorder caused by the pathological buildup of cellular glycogen due to loss of function (LOF) mutations in the lysosomal enzyme $\alpha$-glucosidase (GAA). GAA catabolizes lysosomal glycogen and in its absence, glycogen builds up in lysosomes. This triggers a disease cascade beginning with lysosome and autophagosome dysfunction, leading ultimately to cell death and muscle atrophy over time (Raben N, et al. Autophagy and mitochondria in Pompe Disease: nothing is so new as what has long been forgotten. American Journal of Medical Genetics, vol. 160, 2012. van der Ploeg A T and Reuser A J J, Pompe's Disease. Lancet vol. 372, 2008). In humans, the clinical manifestation of the disease results in a spectrum of severity and occurs at a prevalence of one in 40,000 live births (Meena N K, Raben N. Pompe disease: new developments in an old lysosomal storage disorder. Biomolecules, vol. 10, 2020). Infantile onset patients are born with cellular pathology and rapidly develop severe impairments including myopathy, heart defects, organomegaly, and hypotonia which collectively left untreated will take the child's life within a year. The later onset children may develop heart enlargement but are characterized consistently by the progressive loss of motor function, degeneration of skeletal muscle, and ultimate failure of the respiratory system leading to early death. Late onset adult Pompe patients exhibit normal heart function but develop progressive muscle weakness and respiratory decline then failure. The current standard of care for Pompe patients is enzyme replacement therapy (ERT) with recombinant human GAA. ERT treatment has been successful in slowing the rate of disease progression but in the majority of patients there remains incredible unmet need (Schoser B, et al. The humanistic burden of Pompe disease: are there still unmet needs? A systematic review. BMC Neurology, vol. 17, 2017). For over a decade, substrate reduction therapy targeting GYS1 has been hypothesized to be beneficial for the treatment of Pompe disease. In fact, three separate preclinical modalities have demonstrated that GYS1 genetic LOF in Pompe model mice effectively reduces tissue glycogen and improves mouse disease outcomes (Douillard-Guilloux G, et al. Modulation of glycogen synthesis by RNA interference: towards a new therapeutic approach for glycogenosis type II. Human Molecular Genetics, vol. 17, no. 24, 2008; Douillard-Guilloux G, et al. Restoration of muscle functionality by genetic suppression of glycogen synthesis in a murine model of Pompe disease. Human Molecular Genetics, vol. 19, no. 4, 2010; Clayton N P, et al. Antisense oligonucleotide-mediated suppression of muscle glycogen synthase 1 synthesis as an approach for substrate reduction therapy of Pompe Disease. Molecular Therapy—Nucleic Acids, vol. 3, 2014). A small molecule GYS1 inhibitor could be used to address the current unmet needs for Pompe patients either as a single therapy or in combination with standard of care ERT.

Pompe disease is only one of more than a dozen diseases caused by an inborn error of metabolism that result in aberrant build-up of glycogen in various tissues of the body. For some glycogen storage diseases (GSDs), specific dietary regimes effectively manage the disease but for others there are no clinically approved therapeutic interventions to modify disease course. Therefore, inhibition of glycogen synthesis and the concomitant reduction in tissue glycogen levels may be a viable treatment option for these patients. Cori disease, GSD III, is caused by mutations in the glycogen debranching enzyme (GDE) which results in pathological glycogen accumulation in the heart, skeletal muscle, and liver (Kishnani P, et al. Glycogen storage disease type III diagnosis and management guidelines. Genetics in Medicine, vol. 12, no. 7, 2010). While dietary management can be effective in ameliorating aspects of the disease there is currently no treatment to prevent the progressive myopathy in GSD III. Adult polyglucosan body disease (APBD) is an adult-onset disorder caused by loss of activity in the glycogen branching enzyme (GBE1). Deficiency in GBE results in accumulation of long strands of unbranched glycogen which precipitate in the cytosol generating polyglucosan bodies, and ultimately triggering neurological deficits in both the central and peripheral nervous systems. Genetic deletion of GYS1 in the APBD mouse model rescued deleterious accumulation of glycogen, improved life span, and neuromuscular function (Chown E E, et al. GYS1 or PPP1R3C deficiency rescues murine adult polyglucosan body disease. Annals of Clinical and Translational Neurology, vol. 7, no. 11, 2020). Lafora Disease (LD) is a very debilitating juvenile onset epilepsy disorder also characterized by accumulation of polyglucason bodies. Genetic cross of LD mouse models with GYS1 knock out (KO) mice resulted in rescue of disease phenotypes (Pedersen B, et al.

Inhibiting glycogen synthesis prevents Lafora disease in a mouse model. Annals of Neurology, vol. 74, no. 2, 2013; Varea O, et al. Suppression of glycogen synthesis as a treatment for Lafora disease: establishing the window of opportunity. Neurobiology of Disease, 2020).

The reliance on high levels of glycogen by clear cell cancers has recently emerged as a novel therapeutic target. Ewing sarcoma (ES), clear cell renal cell carcinoma (ccRCC), glycogen rich clear cell carcinoma breast cancer (GRCC), acute myeloid leukemia (AML), and nonsmall-cell lung carcinoma (NSCLC) are all examples of cancers histopathologically defined by PAS+ abnormally high levels of cellular glycogen. Elevated transcriptional levels of GYS1 have been significantly correlated with poor disease outcomes in NSCLC (Giatromanolaki A, et al. Expression of enzymes related to glucose metabolism in non-small cell lung cancer and prognosis. Experimental Lung Research, vol. 43, no. 4-5, 2017) and AML (Falantes J F, et al. Overexpression of GYS1, MIF, and MYC is associated with adverse outcome and poor response to azacitidine in myelodysplastic syndromes and acute myeloid leukemia. Clinical Lymphoma, Myeloma & Leukemia, vol. 15, no. 4, 2015). Lentiviral knockdown of GYS1 in cultured myeloid leukemia cells potently inhibited in vitro cancer cell growth and in vivo tumorigenesis (Bhanot H, et al. Pathological glycogenesis through glycogen synthase I and suppression of excessive AMP kinase activity in myeloid leukemia cells. Leukemia, vol. 29, no. 7, 2015). Genetic knock-down of GYS1 in ccRCC cell models both suppresses tumor growth in vivo and increases the synthetic lethality of sunitinub (Chen S, et al. GYS1 induces glycogen accumulation and promotes tumor progression via the NF-kB pathway in clear cell renal carcinoma. Theranostics, vol. 10, no. 20, 2020).

Reduction of GYS1 enzyme activity and reduced cellular stores of glycogen in preclinical models of Pompe disease, APBD, LD, AML, ccRCC, and NSCLC all provide compelling evidence of the potential therapeutic benefit of inhibiting glycogen synthesis. It is the aim of this invention to inhibit glycogen synthase enzyme activity resulting in reduction of tissue glycogen stores with therapeutic benefit to patients suffering the consequences of accumulated cellular glycogen.

BRIEF SUMMARY OF THE INVENTION

In one aspect, provided herein is a compound of formula (I'):

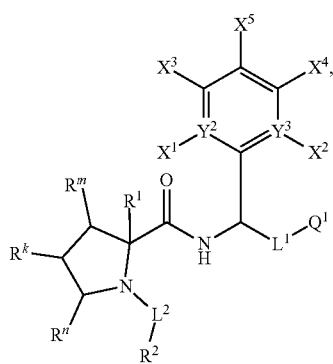

(I')

or a stereoisomer or tautomer thereof, or a pharmaceutically acceptable salt of any of the foregoing, wherein:

$Y^2$ and $Y^3$ are each C, or
one of $Y^2$ and $Y^3$ is N and the other of $Y^2$ and $Y^3$ is C;
$X^1$ and $X^2$ are each independently H, $C_{1-6}$alkyl, or $C_{1-6}$alkoxy;
$X^3$ and $X^4$ are each independently H, halo, $C_{1-6}$alkyl, $C_{1-6}$alkoxy, or 5-20 membered heteroaryl, wherein the $C_{1-6}$alkyl of $X^3$ and $X^4$ is optionally substituted with one of more halo;
$X^5$ is H, $C_{1-6}$alkyl, $C_{1-6}$alkoxy, or $C_{3-10}$cycloalkyl;
either
(1) $L^1$ is absent; and
$Q^1$ is selected from (i) to (iv):
(i) phenyl, wherein the phenyl of $Q^1$ is substituted with one or more halo, $C_{1-6}$alkyl, $C_{2-6}$alkenyl, —$NH_2$, —NH—C(O)—($C_{1-6}$alkyl), —NH—C(O)-(3-15 membered heterocyclyl), $C_{3-10}$cycloalkyl, or 5-20 membered heteroaryl, wherein
the $C_{1-6}$alkyl is optionally substituted with one or more halo, —NH—C(O)—NH($C_{1-6}$alkyl), —NH—C(O)—$C_{1-6}$alkyl, or —NH—C(O)—$C_{1-6}$alkoxy,
the $C_{3-10}$cycloalkyl is optionally substituted with one or more halo or $C_{1-6}$alkyl, and
the 5-20 membered heteroaryl is optionally substituted with one or more $C_{1-6}$alkyl,
(ii) 3-15 membered heterocyclyl, wherein the 3-15 membered heterocyclyl of $Q^1$ is optionally substituted with one or more oxo, or $C_{1-6}$alkyl,
(iii) 5-20 membered heteroaryl, wherein the 5-20 membered heteroaryl of $Q^1$ is optionally substituted with one or more halo, $C_{1-6}$alkyl, $C_{2-6}$alkenyl, $C_{1-6}$alkoxy, —$NH_2$, or $C_{3-10}$cycloalkyl, wherein,
the $C_{1-6}$alkyl is optionally substituted with one or more halo, and
the $C_{3-10}$cycloalkyl is optionally substituted with one or more halo or $C_{1-6}$alkyl, and
(iv) $C_{3-10}$cycloalkyl;
or
(2) $L^1$ is —$CH_2$—; and
$Q^1$ is $C_{3-10}$cycloalkyl;
$L^2$ is —C(O)— or —S(O)$_2$—
$R^1$ is H or $C_{1-6}$alkyl;
$R^k$ is H, halo, —OH, —$NH_2$, or —NH—C(O)$C_{1-6}$alkyl;
$R^m$ is H, —OH, or $C_{1-6}$alkyl;
$R^n$ is H, $C_{1-6}$alkyl, or $C_{3-10}$cycloalkyl or $R^n$ taken together with the carbon atom to which it is attached forms $C_{3-5}$ cycloalkyl;
or $R^k$ is taken together with either $R^m$ or $R^n$, and the atoms to which they are attached, to form cyclopropyl; and
$R^2$ is selected from (i) to (vii):
(i) $C_{1-6}$alkyl, wherein the $C_{1-6}$alkyl of $R^2$ is optionally substituted with one or more $R^a$, wherein $R^a$ is:
(a) —OH,
(b) cyano,
(c) $C_{2-6}$alkynyl,
(d) $C_{6-20}$aryl, wherein the $C_{6-20}$aryl of $R^a$ is optionally substituted with one or more halo, cyano, $C_{1-6}$alkoxy, or —NH—C(O)—$C_{1-6}$alkyl,
(e) 3-15 membered heterocyclyl, wherein the 3-15 membered heterocyclyl of $R^a$ is optionally substituted with one or more $R^c$, wherein
$R^c$ is halo, oxo, $C_{1-6}$alkyl, $C_{1-6}$alkoxy, —C(O)—$C_{1-6}$alkyl, or —C(O)—$C_{1-6}$alkoxy, wherein
the $C_{1-6}$alkyl of $R^c$ is optionally substituted with one or more halo or $C_{2-6}$alkynyl, and
the —C(O)—$C_{1-6}$alkoxy of $R^c$ is optionally substituted with one or more halo, (f) —N(R$^c$)(R$^d$), wherein R$^c$ and R$^d$ of N(R$^c$)(R$^d$) are, independently of each other, H, C$_{1-6}$alkyl, —C(O)—C$_{1-6}$alkyl, —C(O)—C$_{1-6}$alkoxy, —C(O)—NH$_2$, —C(O)—NH(C$_{1-6}$alkyl), —C(O)—N(C$_{1-6}$alkyl)$_2$, —C(O)-(3-15 membered heterocyclyl), —CH$_2$—C(O)—NH$_2$, 3-15 membered heterocyclyl, or 5-20 membered heteroaryl, wherein
the C$_{1-6}$alkyl of R$^c$ or R$^d$ is optionally substituted with one or more —C(O)—NH$_2$,
the —C(O)—C$_{1-6}$alkyl of R$^c$ or R$^d$ is optionally substituted with one or more halo,
the 3-15 membered heterocyclyl and the 5-20 membered heteroaryl of R$^c$ or R$^d$ are independently optionally substituted with one or more C$_{1-6}$alkyl,
the —C(O)-(3-15 membered heterocyclyl) of R$^c$ or R$^d$ is optionally substituted with one or more halo, —C(O)—C$_{1-6}$alkoxy, or C$_{1-6}$alkyl, wherein the C$_{1-6}$alkyl is optionally substituted with one or more halo, C$_{1-6}$alkoxy, or C$_{3-10}$cycloalkyl, and
the C$_{1-6}$alkyl of the —C(O)—N(C$_{1-6}$alkyl)$_2$ of R$^c$ or R$^d$ are, independently of each other, optionally substituted with one or more halo or C$_{6-20}$aryl,
(g) —O—R$^e$, wherein R$^e$ is C$_{1-6}$alkyl, C$_{6-20}$aryl, —C(O)-(3-15 membered heterocyclyl), —C(O)—N—(C$_{1-6}$alkyl)$_2$, or 5-20 membered heteroaryl, wherein
the C$_{1-6}$alkyl of R$^e$ is optionally substituted with one or more C$_{1-6}$alkoxy, wherein the C$_{1-6}$alkoxy is optionally substituted with one or more C$_{2-6}$alkynyl,
the C$_{6-20}$aryl of R$^e$ is optionally substituted with one or more C$_{1-6}$alkyl, and
the —C(O)-(3-15 membered heterocyclyl) of R$^e$ is optionally substituted with one or more C$_{1-6}$alkyl, C$_{1-6}$alkoxy, or —C(O)—C$_{1-6}$alkoxy, wherein the C$_{1-6}$alkyl is optionally substituted with one or more halo, C$_{1-6}$alkoxy, or C$_{3-10}$cycloalkyl,
(h) —C(O)—R$^e$, wherein R$^e$ of —C(O)—R$^e$ is —NH$_2$, —OH, or 3-15 membered heterocyclyl, or
(i) —S(O)$_2$—R$^f$, wherein R$^f$ is C$_{1-6}$alkyl or 3-15 membered heterocyclyl,
provided that, when R$^2$ is unsubstituted methyl, then either
(1) Q$^1$ is 5-20 membered heteroaryl, wherein the 5-20 membered heteroaryl of Q$^1$ is optionally substituted with one or more halo, C$_{1-6}$alkyl, C$_{2-6}$alkenyl, C$_{1-6}$alkoxy, —NH$_2$, C$_{3-10}$cycloalkyl, or —OH, and wherein Q$^1$ is not unsubstituted pyridyl, or
(2) Q$^1$ is phenyl, wherein the phenyl of Q$^1$ is substituted with
(i) at least one C$_{3-6}$alkyl, wherein the at least one C$_{3-6}$alkyl is optionally substituted with one or more halo, or
(ii) at least one C$_{3-10}$cycloalkyl, wherein the at least one C$_{3-10}$cycloalkyl is optionally substituted with one or more halo or C$_{1-6}$alkyl, or
(iii) at least one 5-20 membered heteroaryl, wherein the at least one 5-20 membered heteroaryl is optionally substituted with one or more C$_{1-6}$alkyl,
(ii) C$_{3-10}$cycloalkyl, wherein the C$_{3-10}$cycloalkyl of R$^2$ is optionally substituted with one or more R$^q$, wherein R$^q$ is 5-20 membered heteroaryl or C$_{6-20}$aryl, wherein the C$_{6-20}$aryl of R$^q$ is optionally substituted with one or more C$_{1-6}$alkoxy,
(iii) 3-15 membered heterocyclyl, wherein the 3-15 membered heterocyclyl of R$^2$ is optionally substituted with one or more halo, oxo, C$_{1-6}$alkyl, —C(O)—C$_{1-6}$alkyl, or 5-20 membered heteroaryl, (iv) 5-20 membered heteroaryl or —(C$_{1-4}$alkyl)(5-20 membered heteroaryl), wherein the C$_{1-4}$ alkyl is optionally substituted with one or more or more —OH, halo, —NH$_2$, —NH(C$_{1-6}$alkyl), —N(C$_{1-6}$alkyl)$_2$, and wherein the 5-20 membered heteroaryl is optionally substituted with one or more R$^s$, wherein
R$^s$ is halo, C$_{1-6}$alkyl, C$_{1-6}$alkoxy, —NH$_2$, —NH(C$_{1-6}$alkyl), —N(C$_{1-6}$alkyl)$_2$, —NH—C(O)—C$_{1-6}$alkyl, C$_{6-20}$aryl, C$_{3-10}$cycloalkyl, 3-15 membered heterocyclyl, 5-20 membered heteroaryl, or —C(O)—C$_{1-6}$alkoxy, wherein
the C$_{1-6}$alkyl of R$^s$ is optionally substituted with one or more halo, C$_{1-6}$alkoxy, —NH$_2$, —NH(C$_{1-6}$alkyl), —N(C$_{1-6}$alkyl)$_2$, —NH—C(O)C$_{1-6}$alkyl, or —NH—C(O)—C$_{1-6}$alkoxy, and
the 3-15-membered heterocyclyl of R$^s$ is optionally substituted with one or more halo or —C(O)—C$_{1-6}$alkoxy,
(v) —N(R$^g$)(R$^h$), wherein R$^g$ and R$^h$ are independently H or C$_{1-6}$alkyl,
(vi) —C(O)—R$^j$, wherein R$^j$ is C$_{3-10}$cycloalkyl, —NH(C$_{1-6}$alkyl), —N(C$_{1-6}$alkyl)$_2$, or —NH (5-20 membered heteroaryl), and
(vii) C$_{6-20}$aryl, wherein the C$_{6-20}$aryl of R$^2$ is optionally substituted with one or more 5-20 membered heteroaryl or —O—R$^p$, wherein R$^p$ is 3-15 membered heterocyclyl, wherein the 3-15 membered heterocyclyl of R$^p$ is optionally substituted with one or more —C(O)—C$_{1-6}$alkyl.

In one aspect, provided herein is a compound of formula (I):

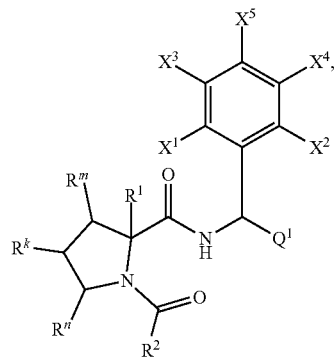

or a stereoisomer or tautomer thereof, or a pharmaceutically acceptable salt of any of the foregoing, wherein:
X$^1$ and X$^2$ are each independently H, C$_{1-6}$alkyl, or C$_{1-6}$alkoxy;
X$^3$ and X$^4$ are each independently H, halo, C$_{1-6}$alkyl, C$_{1-6}$alkoxy, or 5-20 membered heteroaryl;
X$^5$ is H, C$_{1-6}$alkyl, C$_{1-6}$alkoxy, or C$_{3-10}$cycloalkyl; Q$^1$ is selected from (i) to (iii):
(i) phenyl, wherein the phenyl of Q$^1$ is substituted with one or more halo, C$_{1-6}$alkyl, C$_{2-6}$alkenyl, —NH$_2$, —NH—C(O)—(C$_{1-6}$alkyl), —NH—C(O)-(3-15 membered heterocyclyl), or C$_{3-10}$cycloalkyl, wherein
the C$_{1-6}$alkyl is optionally substituted with one or more halo, and
the C$_{3-10}$cycloalkyl is optionally substituted with one or more halo or C$_{1-6}$alkyl,
(ii) 3-15 membered heterocyclyl, wherein the 3-15 membered heterocyclyl of Q$^1$ is optionally substituted with one or more oxo, and (iii) 5-20 membered heteroaryl, wherein the 5-20 membered heteroaryl of $Q^1$ is optionally substituted with one or more halo, $C_{1-6}$alkyl, $C_{2-6}$alkenyl, $C_{1-6}$alkoxy, —$NH_2$, or $C_{3-10}$cycloalkyl, wherein
the $C_{3-10}$cycloalkyl is optionally substituted with one or more halo or $C_{1-6}$alkyl;

$R^1$ is H or $C_{1-6}$alkyl;

$R^k$ is H, halo, —OH, —$NH_2$, or —NH—$C(O)C_{1-6}$alkyl;

$R^m$ is H, —OH, or $C_{1-6}$alkyl;

$R^n$ is H, $C_{1-6}$alkyl, or $C_{3-10}$cycloalkyl;

or $R^k$ is taken together with either $R^m$ or $R^n$, and the atoms to which they are attached, to form cyclopropyl; and $R^2$ is selected from (i) to (vii):

(i) $C_{1-6}$alkyl, wherein the $C_{1-6}$alkyl of $R^2$ is optionally substituted with one or more $R^a$, wherein $R^a$ is:
  (a) —OH,
  (b) cyano,
  (c) $C_{2-6}$alkynyl,
  (d) $C_{6-20}$aryl, wherein the $C_{6-20}$aryl of $R^a$ is optionally substituted with one or more halo, cyano, $C_{1-6}$alkoxy, or —NH—C(O)—$C_{1-6}$alkyl,
  (e) 5-20 membered heteroaryl, wherein the 5-20 membered heteroaryl of $R^a$ is optionally substituted with one or more $R^b$, wherein
    $R^b$ is halo, $C_{1-6}$alkyl, $C_{1-6}$alkoxy, —$NH_2$, —NH($C_{1-6}$alkyl), —N($C_{1-6}$alkyl)$_2$, $C_{3-10}$cycloalkyl, 3-15 membered heterocyclyl, or —C(O)—$C_{1-6}$alkoxy, wherein
      the $C_{1-6}$alkyl of $R^b$ is optionally substituted with one or more halo, —$NH_2$, —NH($C_{1-6}$alkyl), —N($C_{1-6}$alkyl)$_2$, —NH—$C(O)C_{1-6}$alkyl, or —NH—C(O)—$C_{1-6}$alkoxy, and
      the 3-15-membered heterocyclyl of $R^b$ is optionally substituted with one or more halo or —C(O)—$C_{1-6}$alkoxy,
  (f) 3-15 membered heterocyclyl, wherein the 3-15 membered heterocyclyl of $R^a$ is optionally substituted with one or more $R^c$, wherein
    $R^c$ is halo, oxo, $C_{1-6}$alkyl, $C_{1-6}$alkoxy, —C(O)—$C_{1-6}$alkyl, or —C(O)—$C_{1-6}$alkoxy, wherein
      the $C_{1-6}$alkyl of $R^c$ is optionally substituted with one or more halo or $C_{2-6}$alkynyl, and
      the —C(O)—$C_{1-6}$alkoxy of $R^c$ is optionally substituted with one or more halo,
  (g) —N($R^c$)($R^d$), wherein $R^c$ and $R^d$ are, independently of each other, H, $C_{1-6}$alkyl, —C(O)—$C_{1-6}$alkyl, —C(O)—$C_{1-6}$alkoxy, —C(O)—$NH_2$, —C(O)—NH($C_{1-6}$alkyl), —C(O)—N($C_{1-6}$alkyl)$_2$, —C(O)-(3-15 membered heterocyclyl), —$CH_2$—C(O)—$NH_2$, 3-15 membered heterocyclyl, or 5-20 membered heteroaryl, wherein
      the —C(O)—$C_{1-6}$alkyl of $R^c$ or $R^d$ is optionally substituted with one or more halo,
      the 3-15 membered heterocyclyl and the 5-20 membered heteroaryl of $R^c$ or $R^d$ are independently optionally substituted with one or more $C_{1-6}$alkyl, and
      the —C(O)-(3-15 membered heterocyclyl) of $R^c$ or $R^d$ is optionally substituted with one or more halo, —C(O)—$C_{1-6}$alkoxy, or $C_{1-6}$alkyl, wherein the $C_{1-6}$alkyl is optionally substituted with one or more halo, $C_{1-6}$alkoxy, or $C_{3-10}$cycloalkyl,
  (h) —O—$R^e$, wherein $R^e$ is $C_{1-6}$alkyl, $C_{6-20}$aryl, —C(O)-(3-15 membered heterocyclyl), —C(O)—N—($C_{1-6}$alkyl)$_2$, or 5-20 membered heteroaryl, wherein
    the $C_{1-6}$alkyl of $R^e$ is optionally substituted with one or more $C_{1-6}$alkoxy, wherein the $C_{1-6}$alkoxy is optionally substituted with one or more $C_{2-6}$alkynyl,
    the $C_{6-20}$aryl of $R^e$ is optionally substituted with one or more $C_{1-6}$alkyl, and
    the —C(O)-(3-15 membered heterocyclyl) of $R^e$ is optionally substituted with one or more $C_{1-6}$alkyl, $C_{1-6}$alkoxy, or —C(O)—$C_{1-6}$alkoxy, wherein the $C_{1-6}$alkyl is optionally substituted with one or more halo, $C_{1-6}$alkoxy, or $C_{3-10}$cycloalkyl,
  (i) —C(O)—$R^e$, wherein $R^e$ is —$NH_2$, —OH, or 3-15 membered heterocyclyl, or
  (j) —S(O)$_2$—$R^f$, wherein $R^f$ is $C_{1-6}$alkyl or 3-15 membered heterocyclyl, provided that, when $R^2$ is unsubstituted methyl, then either (1) $Q^1$ is 5-20 membered heteroaryl, wherein the 5-20 membered heteroaryl of $Q^1$ is substituted with one or more halo, $C_{1-6}$alkyl, $C_{2-6}$alkenyl, $C_{1-6}$alkoxy, —$NH_2$, $C_{3-10}$cycloalkyl, or —OH, or (2) $Q^1$ is phenyl, wherein the phenyl of $Q^1$ is substituted with at least one $C_{3-6}$alkyl or at least one $C_{3-10}$cycloalkyl, wherein the at least one $C_{3-6}$alkyl is optionally substituted with one or more halo, and the at least one $C_{3-10}$cycloalkyl is optionally substituted with one or more halo or $C_{1-6}$alkyl, (ii) $C_{3-10}$cycloalkyl, wherein the $C_{3-10}$cycloalkyl of $R^2$ is optionally substituted with one or more $R^q$, wherein $R^q$ is 5-20 membered heteroaryl or $C_{6-20}$aryl, wherein the $C_{6-20}$aryl of $R^q$ is optionally substituted with one or more $C_{1-6}$alkoxy, (iii) 3-15 membered heterocyclyl, wherein the 3-15 membered heterocyclyl of $R^2$ is optionally substituted with one or more halo, oxo, $C_{1-6}$alkyl, —C(O)—$C_{1-6}$alkyl, or 5-20 membered heteroaryl, (iv) 5-20 membered heteroaryl, wherein the 5-20 membered heteroaryl of $R^2$ is optionally substituted with one or more $R^s$, wherein $R^s$ is $C_{1-6}$alkyl, $C_{1-6}$alkoxy, —NH—C(O)—$C_{1-6}$alkyl, $C_{6-20}$aryl, or 5-20 membered heteroaryl, wherein the $C_{1-6}$alkyl of $R^s$ is optionally substituted with one or more $C_{1-6}$alkoxy, (v) —N($R^g$)($R^h$), wherein $R^g$ and $R^h$ are independently H or $C_{1-6}$alkyl, (vi) —C(O)—$R^j$, wherein $R^j$ is $C_{3-10}$cycloalkyl, —NH($C_{1-6}$alkyl), —N($C_{1-6}$alkyl)$_2$, or —NH (5-20 membered heteroaryl), and (vii) $C_{6-20}$aryl, wherein the $C_{6-20}$aryl of $R^2$ is optionally substituted with one or more 5-20 membered heteroaryl or —O—$R^p$, wherein $R^p$ is 3-15 membered heterocyclyl, wherein the 3-15 membered heterocyclyl of $R^p$ is optionally substituted with one or more —C(O)—$C_{1-6}$alkyl.

In one aspect, provided herein is a compound of formula (I-A):

(I-A)

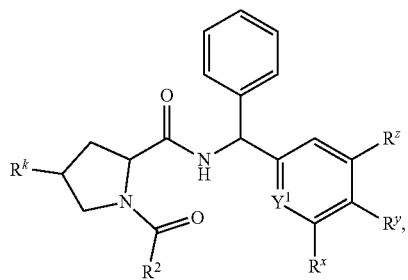

or a stereoisomer or tautomer thereof, or a pharmaceutically acceptable salt of any of the foregoing, wherein $Y^1$, $R^2$, $R^k$, $R^x$, $R^y$, and $R^z$ are as defined elsewhere herein. In another variation, $Y^1$, $R^2$, $R^k$, $R^x$, $R^y$, and $R^z$ of formula (I-A) are as defined for a compound of formula (I'), or formula (I) elsewhere herein, or a stereoisomer or tautomer thereof, or a pharmaceutically acceptable salt of any of the foregoing, or any variation or embodiment thereof.

In one aspect, provided herein is a compound of formula (I-B):

(I-B)

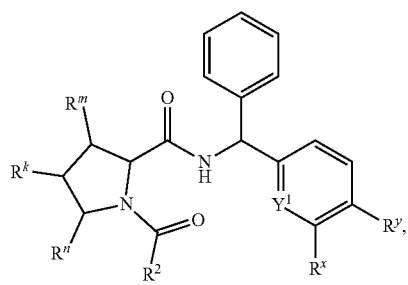

or a stereoisomer or tautomer thereof, or a pharmaceutically acceptable salt of any of the foregoing, wherein $Y^1$, $R^2$, $R^k$, $R^m$, $R^n$, $R^x$, and $R^y$ are as defined elsewhere herein. In another variation, $Y^1$, $R^2$, $R^k$, $R^m$, $R^n$, $R^x$, and $R^y$ of formula (I-B) are as defined for a compound of formula (I'), or formula (I) elsewhere herein, or a stereoisomer or tautomer thereof, or a pharmaceutically acceptable salt of any of the foregoing, or any variation or embodiment thereof.

In one aspect, provided herein is a compound of formula (I-C):

(I-C)

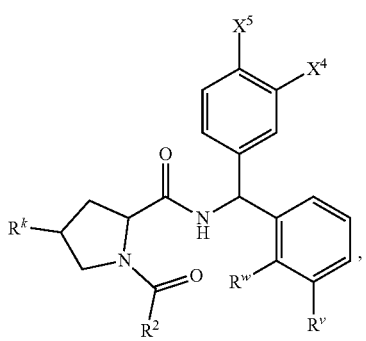

or a stereoisomer or tautomer thereof, or a pharmaceutically acceptable salt of any of the foregoing, wherein $X^4$, $X^5$, $R^2$, $R^k$, $R^v$, and $R^w$ are as defined elsewhere herein. In another variation, $X^4$, $X^5$, $R^2$, $R^k$, $R^v$, and $R^w$ of formula (I-C) are as defined for a compound of formula (I'), or formula (I) elsewhere herein, or a stereoisomer or tautomer thereof, or a pharmaceutically acceptable salt of any of the foregoing, or any variation or embodiment thereof.

In one aspect, provided herein is a compound of formula (I-D):

(I-D)

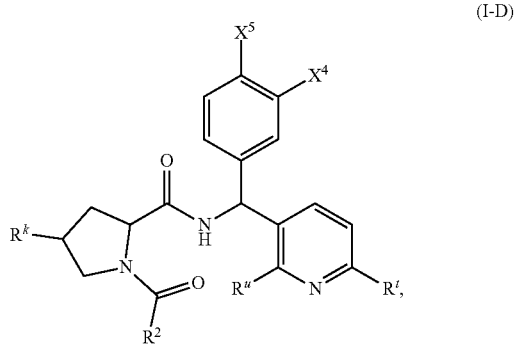

or a stereoisomer or tautomer thereof, or a pharmaceutically acceptable salt of any of the foregoing, wherein $X^4$, $X^5$, $R^2$, $R^k$, $R^u$, and $R^t$ are as defined elsewhere herein. In another variation, $X^4$, $X^5$, $R^2$, $R^k$, $R^u$, and $R^t$ of formula (I-D) are as defined for a compound of formula (I'), or formula (I) elsewhere herein, or a stereoisomer or tautomer thereof, or a pharmaceutically acceptable salt of any of the foregoing, or any variation or embodiment thereof.

In one aspect, provided is a compound of formula (I'), wherein the compound is a compound of formula (I-D1):

(I-D1)

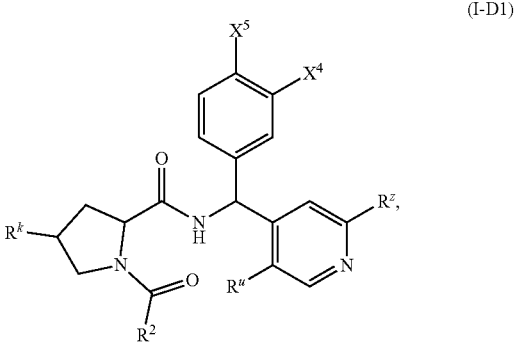

wherein $X^4$, $X^5$, $R^2$, $R^k$, $R^u$, and $R^z$ of formula (I-D1) are as defined for a compound of formula (I') elsewhere herein, or a stereoisomer or tautomer thereof, or a pharmaceutically acceptable salt of any of the foregoing, or any variation or embodiment thereof.

In one aspect, provided is a compound of formula (I'), wherein the compound is a compound of formula (I-D1):

(I-D2)

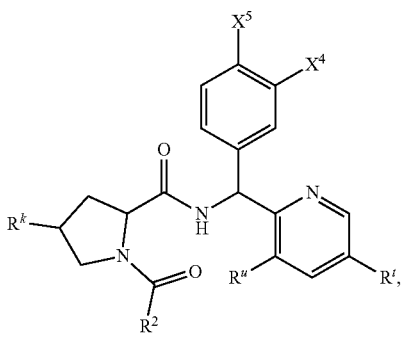

wherein $X^4$, $X^5$, $R^2$, $R^k$, $R^t$, and $R^u$ of formula (I-D2) are as defined for a compound of formula (I') elsewhere herein, or a stereoisomer or tautomer thereof, or a pharmaceutically acceptable salt of any of the foregoing, or any variation or embodiment thereof.

In one aspect, provided herein is a compound of formula (I-E):

(I-E)

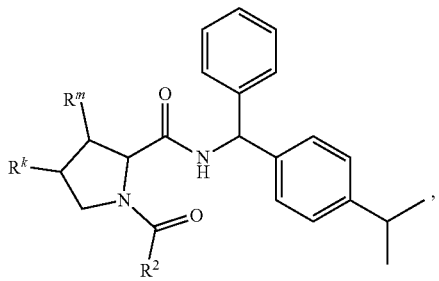

or a stereoisomer or tautomer thereof, or a pharmaceutically acceptable salt of any of the foregoing, wherein $R^2$, $R^k$, and $R^m$ are as defined elsewhere herein. In another variation, $R^2$, $R^k$, and $R^m$ of formula (I-E) are as defined for a compound of formula (I'), or formula (I) elsewhere herein, or a stereoisomer or tautomer thereof, or a pharmaceutically acceptable salt of any of the foregoing, or any variation or embodiment thereof.

In one aspect, provided herein is a compound of formula (I-F):

(I-F)

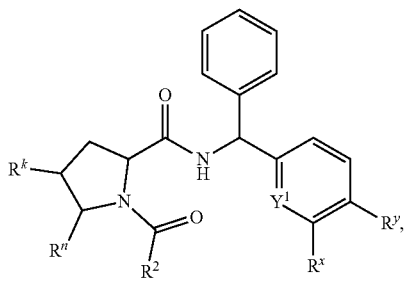

or a stereoisomer or tautomer thereof, or a pharmaceutically acceptable salt of any of the foregoing, wherein $Y^1$, $R^2$, $R^k$, $R^n$, $R^x$, and $R^y$ are as defined elsewhere herein. In another variation, $R^2$, $R^k$, and $R^m$ of formula (I-F) are as defined for a compound of formula (I'), or formula (I) elsewhere herein, or a stereoisomer or tautomer thereof, or a pharmaceutically acceptable salt of any of the foregoing, or any variation or embodiment thereof.

In one aspect, provided herein is a compound of formula (I') wherein the compound is of the formula (I-G):

(I-G)

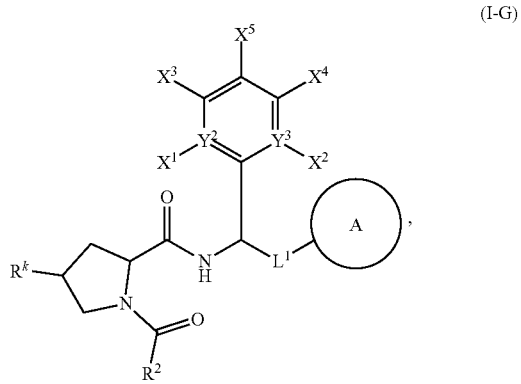

or a stereoisomer or tautomer thereof, or a pharmaceutically acceptable salt of any of the foregoing, wherein ring A, $L^1$, $Y^2$, $Y^3$, $R^2$, $R^k$, $X^1$, $X^2$, $X^3$, $X^4$, and $X^5$ are as defined elsewhere herein.

In one aspect, provided herein is a compound of formula (I') wherein the compound is of the formula (I-H):

(I-H)

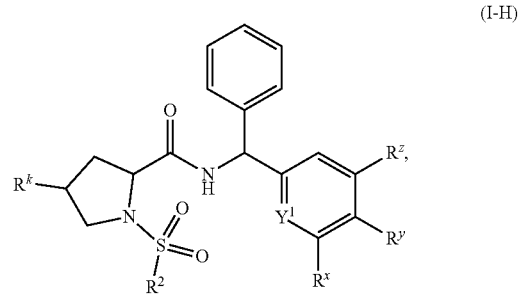

or a stereoisomer or tautomer thereof, or a pharmaceutically acceptable salt of any of the foregoing, wherein $Y^1$, $R^2$, $R^k$, $R^n$, $R^x$, and $R^y$ are as defined elsewhere herein.

In one aspect, provided herein is a pharmaceutical composition, comprising (i) a compound of formula (I), or any variation or embodiment thereof, or a stereoisomer or tautomer thereof, or a pharmaceutically acceptable salt of any of the foregoing, and (ii) one or more pharmaceutically acceptable excipients. In another variation, provided herein is a pharmaceutical composition, comprising (i) a compound of formula (I'), or any variation or embodiment thereof, or a stereoisomer or tautomer thereof, or a pharmaceutically acceptable salt of any of the foregoing, and (ii) one or more pharmaceutically acceptable excipients.

In one aspect, provided herein is a method of modulating GYS1 in a cell, comprising exposing the cell to (i) a composition comprising an effective amount of a compound of formula (I), or any variation or embodiment thereof, or a stereoisomer or tautomer thereof, or a pharmaceutically acceptable salt of any of the foregoing, or (ii) a pharmaceutical composition, comprising a compound of formula (I), or any variation or embodiment thereof, or a stereoisomer or tautomer thereof, or a pharmaceutically acceptable salt of any of the foregoing, and one or more pharmaceutically acceptable excipients. In another variation, provided herein is a method of modulating GYS1 in a cell, comprising exposing the cell to (i) a composition comprising an effective amount of a compound of formula (I'), or any variation or embodiment thereof, or a stereoisomer or tautomer thereof, or a pharmaceutically acceptable salt of any of the foregoing, or (ii) a pharmaceutical composition, comprising a compound of formula (I'), or any variation or embodiment thereof, or a stereoisomer or tautomer thereof, or a pharmaceutically acceptable salt of any of the foregoing, and one or more pharmaceutically acceptable excipients.

In one aspect, provided herein is a method of inhibiting GYS1 in a cell, comprising exposing the cell to (i) a composition comprising an effective amount of a compound of formula (I), or any variation or embodiment thereof, or a stereoisomer or tautomer thereof, or a pharmaceutically acceptable salt of any of the foregoing, or (ii) a pharmaceutical composition, comprising a compound of formula (I), or any variation or embodiment thereof, or a stereoisomer or tautomer thereof, or a pharmaceutically acceptable salt of any of the foregoing, and one or more pharmaceutically acceptable excipients. In another variation, provided herein is a method of inhibiting GYS1 in a cell, comprising exposing the cell to (i) a composition comprising an effective amount of a compound of formula (I'), or any variation or embodiment thereof, or a stereoisomer or tautomer thereof, or a pharmaceutically acceptable salt of any of the foregoing, or (ii) a pharmaceutical composition, comprising a compound of formula (I'), or any variation or embodiment thereof, or a stereoisomer or tautomer thereof, or a pharmaceutically acceptable salt of any of the foregoing, and one or more pharmaceutically acceptable excipients.

In one aspect, provided herein is a method of reducing tissue glycogen stores in an individual in need thereof, comprising administering to the individual an effective amount of (i) a GYS1 inhibitor, or (ii) a pharmaceutical composition comprising a GYS1 inhibitor and one or more pharmaceutically acceptable excipients. In some embodiments, the GYS1 inhibitor is selective for GYS1 over GYS2. In some embodiments, the GYS1 inhibitor is greater than 500 or 1,000 or 1,500 or 1,700-fold selective for GYS1 over GYS2. In some embodiments, the GYS1 inhibitor is a small molecule.

In one aspect, provided herein is a method of reducing tissue glycogen stores in an individual in need thereof, comprising administering to the individual an effective amount of (i) a composition comprising an effective amount of a compound of formula (I), or any variation or embodiment thereof, or a stereoisomer or tautomer thereof, or a pharmaceutically acceptable salt of any of the foregoing, or (ii) a pharmaceutical composition, comprising a compound of formula (I), or any variation or embodiment thereof, or a stereoisomer or tautomer thereof, or a pharmaceutically acceptable salt of any of the foregoing, and one or more pharmaceutically acceptable excipients. In another variation, provided herein is a method of reducing tissue glycogen stores in an individual in need thereof, comprising administering to the individual an effective amount of (i) a composition comprising an effective amount of a compound of formula (I'), or any variation or embodiment thereof, or a stereoisomer or tautomer thereof, or a pharmaceutically acceptable salt of any of the foregoing, or (ii) a pharmaceutical composition, comprising a compound of formula (I'), or any variation or embodiment thereof, or a stereoisomer or tautomer thereof, or a pharmaceutically acceptable salt of any of the foregoing, and one or more pharmaceutically acceptable excipients.

In one aspect, provided herein is a method of modulating GYS1 in a cell of an an individual in need thereof, comprising administering to the individual an effective amount of (i) a composition comprising an effective amount of a compound of formula (I), or formula (I') or any variation or embodiment thereof, or a stereoisomer or tautomer thereof, or a pharmaceutically acceptable salt of any of the foregoing, or (ii) a pharmaceutical composition, comprising a compound of formula (I), or any variation or embodiment thereof, or a stereoisomer or tautomer thereof, or a pharmaceutically acceptable salt of any of the foregoing, and one or more pharmaceutically acceptable excipients.

In one aspect, provided herein is a method of treating a GYS1-mediated disease, disorder, or condition in an individual in need thereof, comprising subjecting the individual to glycogen substrate reduction therapy. In some embodiments, the glycogen substrate reduction therapy comprises administration of a GYS1 inhibitor. In some embodiments, the GYS1 inhibitor is a small molecule. In some embodiments, the GYS1 inhibitor is selective for GYS1 over GYS2. In some embodiments, the GYS1 inhibitor is greater than 500 or 1,000 or 1,500 or 1,700-fold selective for GYS1 over GYS2.

In one aspect, provided herein is a method of treating a GYS1-mediated disease, disorder, or condition in an individual in need thereof, comprising administering to the individual an effective amount of (i) a composition comprising an effective amount of a compound of formula (I), or any variation or embodiment thereof, or a stereoisomer or tautomer thereof, or a pharmaceutically acceptable salt of any of the foregoing, or (ii) a pharmaceutical composition, comprising a compound of formula (I), or any variation or embodiment thereof, or a stereoisomer or tautomer thereof, or a pharmaceutically acceptable salt of any of the foregoing, and one or more pharmaceutically acceptable excipients. In another variation, provided herein is a method of treating a GYS1-mediated disease, disorder, or condition in an individual in need thereof, comprising administering to the individual an effective amount of (i) a composition comprising an effective amount of a compound of formula (I'), or any variation or embodiment thereof, or a stereoisomer or tautomer thereof, or a pharmaceutically acceptable salt of any of the foregoing, or (ii) a pharmaceutical composition, comprising a compound of formula (I'), or any variation or embodiment thereof, or a stereoisomer or tautomer thereof, or a pharmaceutically acceptable salt of any of the foregoing, and one or more pharmaceutically acceptable excipients.

In one aspect, provided herein is a method of treating a glycogen storage disease, disorder, or condition in an individual in need thereof, comprising subjecting the individual to glycogen substrate reduction therapy. In some embodiments, the glycogen substrate reduction therapy comprises administration of a GYS1 inhibitor. In some embodiments, the GYS1 inhibitor is a small molecule. In some embodiments, the GYS1 inhibitor is selective for GYS1 over GYS2. In some embodiments, the GYS1 inhibitor is greater than 500 or 1,000 or 1,500 or 1,700-fold selective for GYS1 over GYS2.

In one aspect, provided herein is a kit, comprising (i) a composition comprising an effective amount of a compound of formula (I), or any variation or embodiment thereof, or a stereoisomer or tautomer thereof, or a pharmaceutically acceptable salt of any of the foregoing, or a pharmaceutical composition, comprising a compound of formula (I), or any variation or embodiment thereof, or a stereoisomer or tautomer thereof, or a pharmaceutically acceptable salt of any of the foregoing, and one or more pharmaceutically acceptable excipients, and (ii) instructions for use in treating an GYS1-mediated disease, disorder, or condition in an individual in need thereof. In another variation, provided herein is a kit, comprising (i) a composition comprising an effective amount of a compound of formula (I'), or any variation or embodiment thereof, or a stereoisomer or tautomer thereof, or a pharmaceutically acceptable salt of any of the foregoing, or a pharmaceutical composition, comprising a compound of formula (I'), or any variation or embodiment thereof, or a stereoisomer or tautomer thereof, or a pharmaceutically acceptable salt of any of the foregoing, and one or more pharmaceutically acceptable excipients, and (ii) instructions for use in treating an GYS1-mediated disease, disorder, or condition in an individual in need thereof.

In some aspect, provided herein are methods of preparing a compound of formula (I) or (I'), or any embodiment or variation thereof, such as a compound of formula (I), (I-A), (I-A1), (I-A2), (I-A3), (I-A4), (I-B), (I-B1), (I-B32), (I-C), (I-D), (I-D1), (I-D32), (I-E), (I-F), (I-G), or (I-H) or a stereoisomer or tautomer thereof, or a pharmaceutically acceptable salt of any of the foregoing.

DETAILED DESCRIPTION OF THE INVENTION

Figure 1:
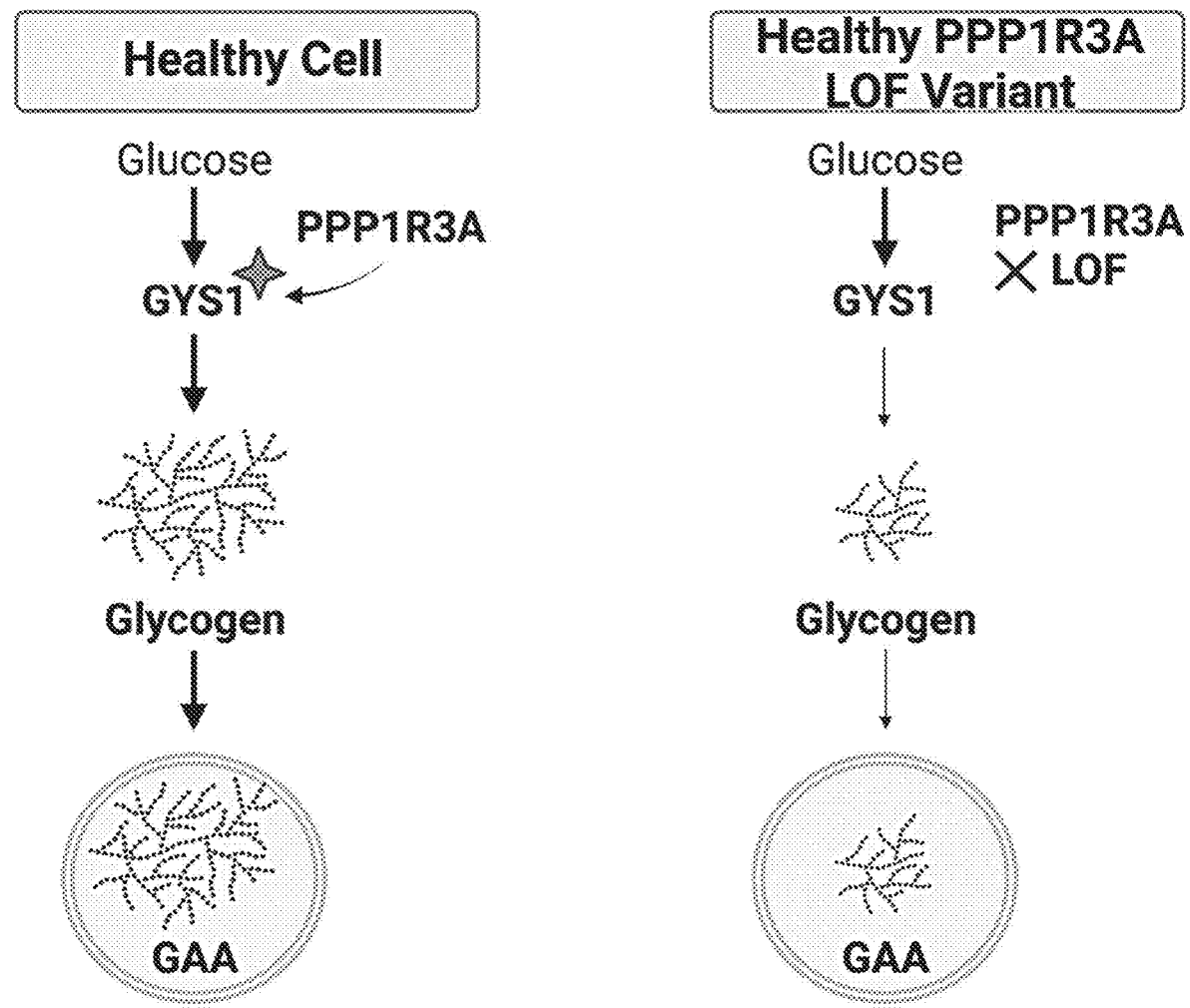
FIG. 1 depicts the pathway in which PPP1R3A Loss of Function (LoF) leads to reduction in muscle glycogen.
Figure 2A:
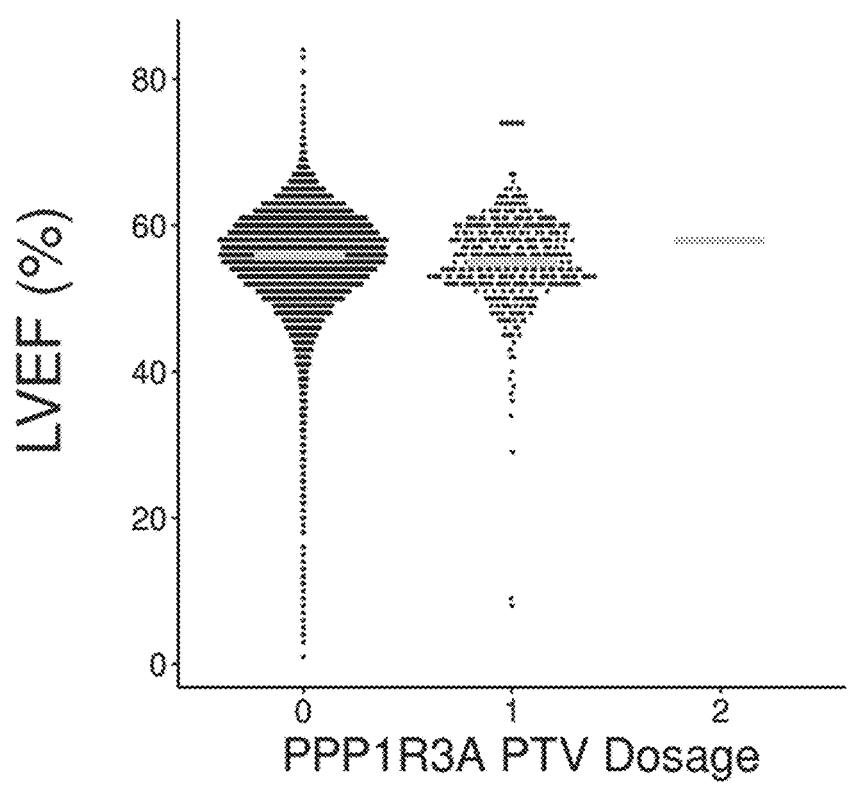
FIGS. 2A and 2B depict the association between PPP1R3A protein truncating variant (PTV) and left ventricular ejection (LVEF) (%) and left ventricle wall thickness (mm) in UK Biobank.
Figure 2B:
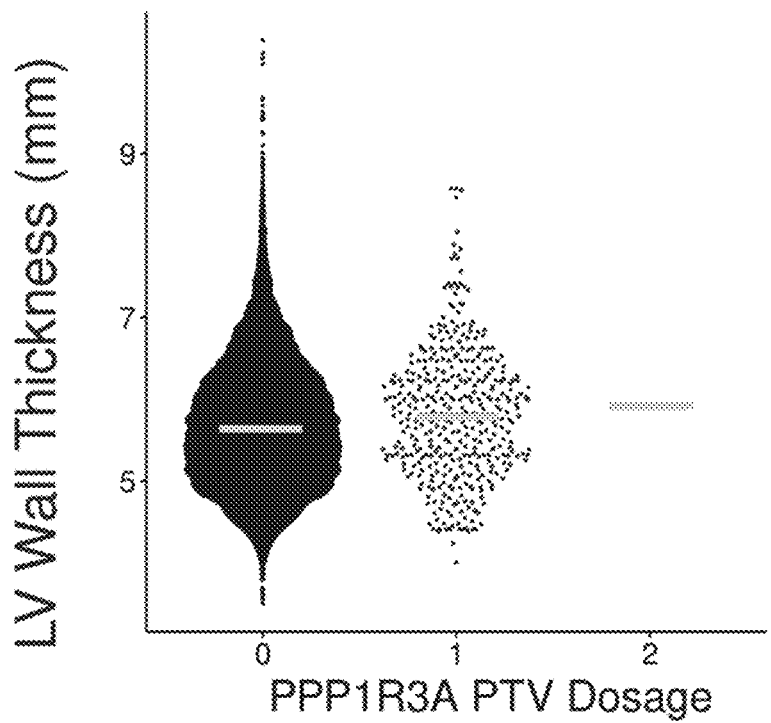
Figure 2C:
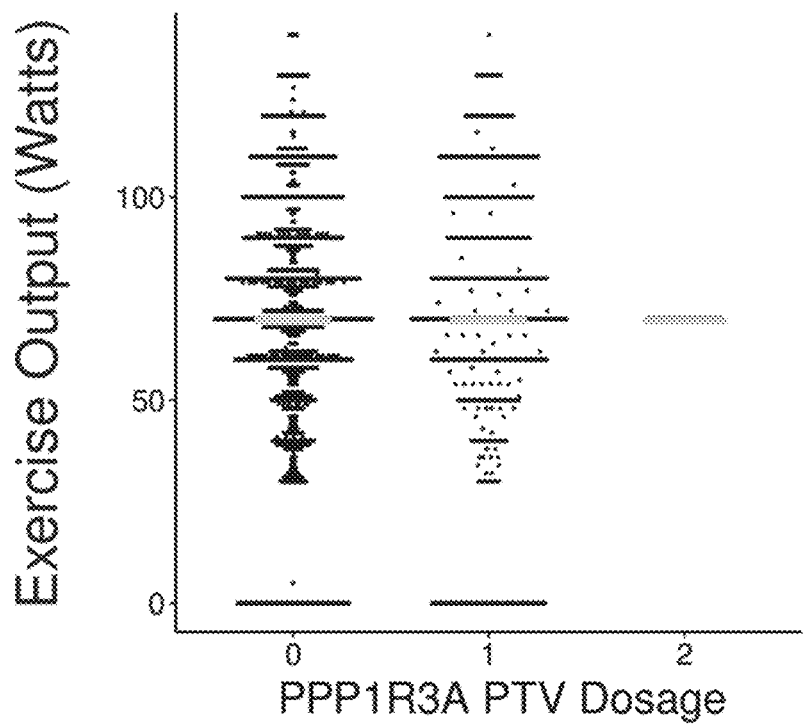
FIGS. 2C and 2D depict the association between PPP1R3A protein truncating variant (PTV) and exercise output (watts) and max heart rate (HR) exercise (bpm) in UK Biobank.
Figure 2D:
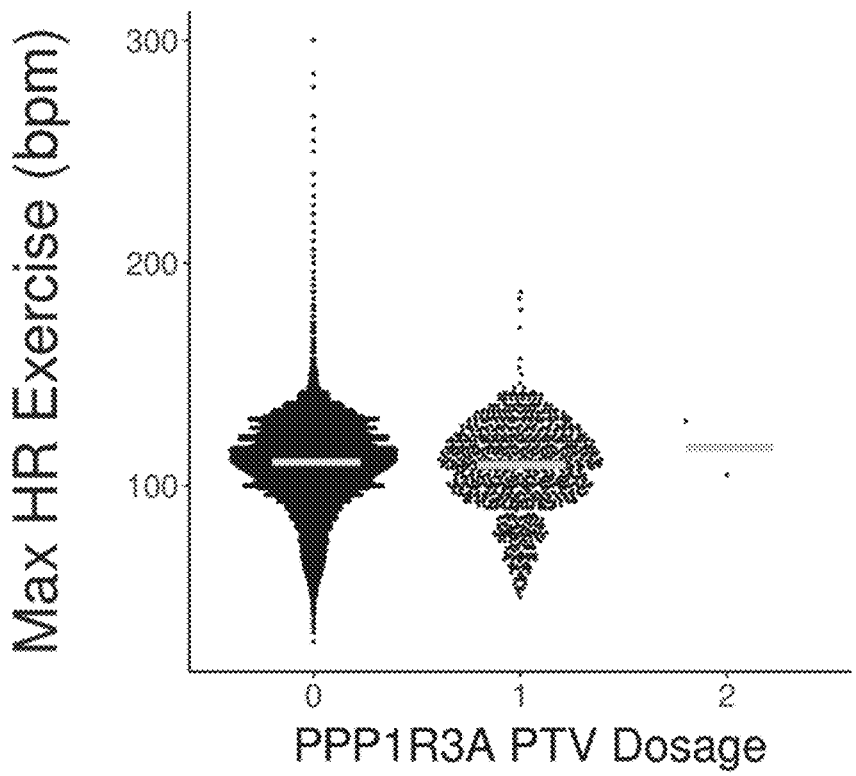
Figure 2E:
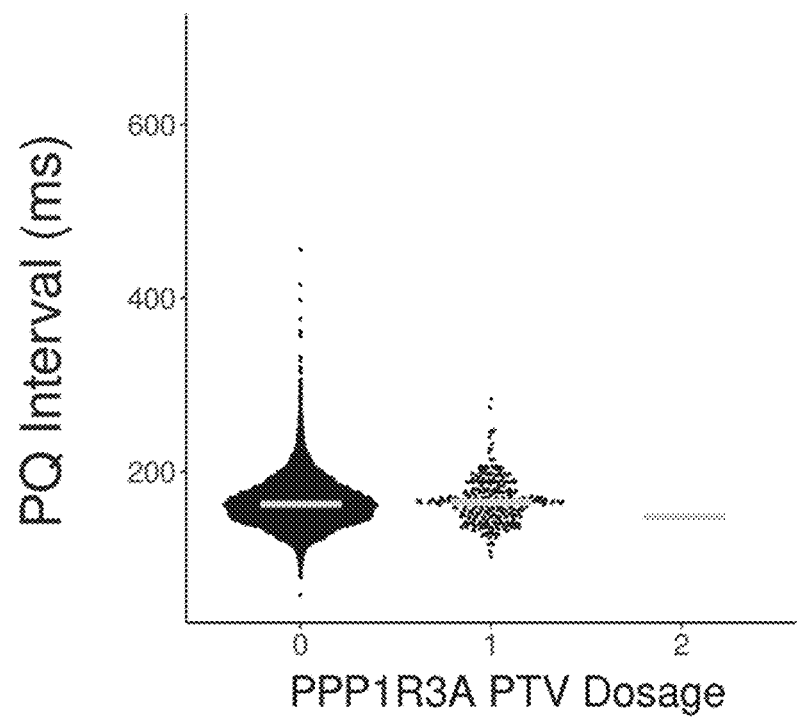
FIGS. 2E and 2F depict the association between PPP1R3A protein truncating variant (PTV) and PQ interval (ms) and QRS duration (ms) in UK Biobank.
Figure 2F:
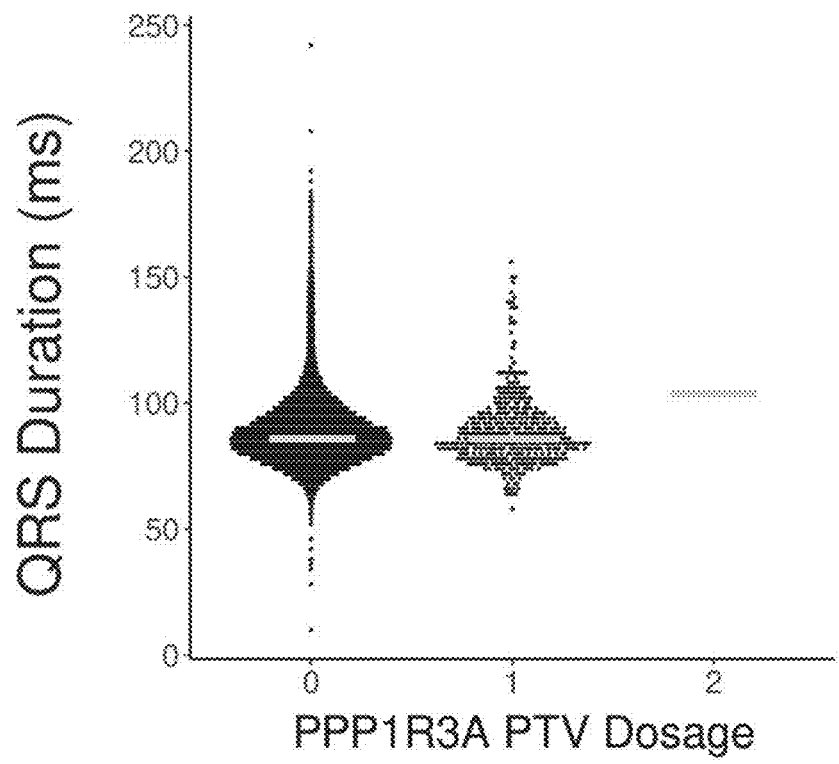
Figure 2G:
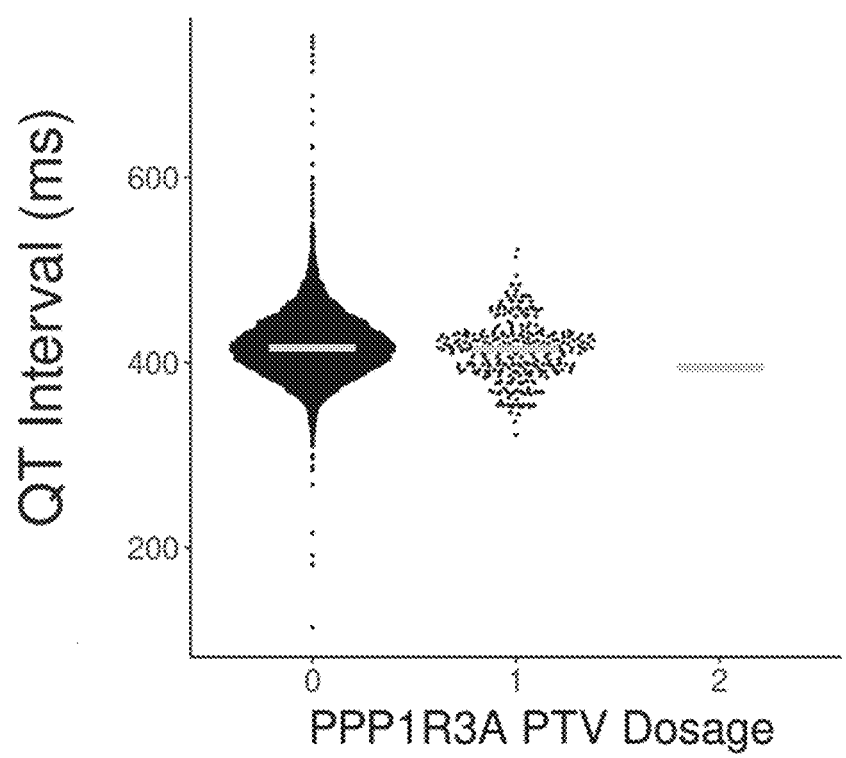
FIGS. 2G and 2H depict the association between PPP1R3A protein truncating variant (PTV) and QT interval (ms) and serum glucose (mmol/L) in UK Biobank.
Figure 2H:
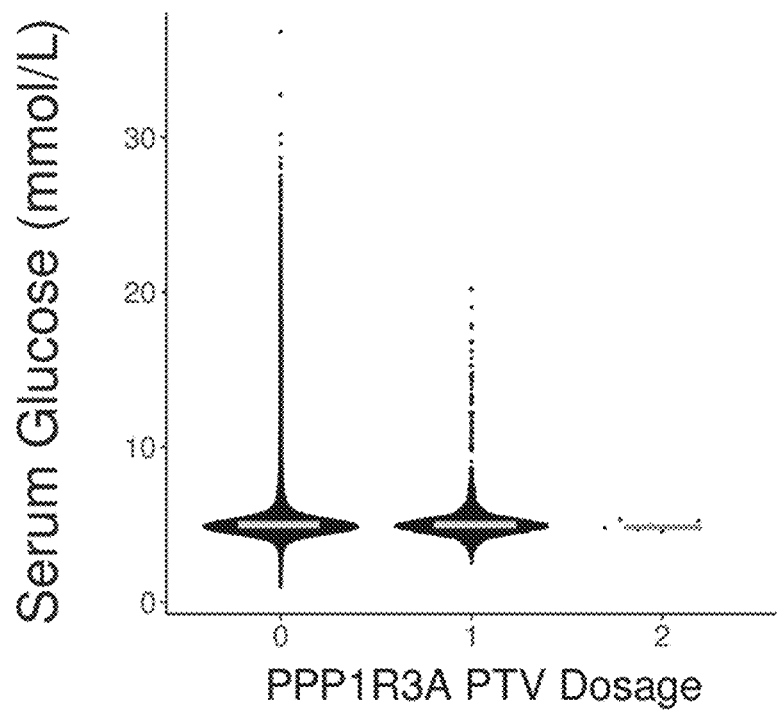

"Individual" refers to mammals and includes humans and non-human mammals. Examples of individuals include, but are not limited to, mice, rats, hamsters, guinea pigs, pigs, rabbits, cats, dogs, goats, sheep, cows, and humans. In some embodiments, individual refers to a human.

As used herein, "about" a parameter or value includes and describes that parameter or value per se. For example, "about X" includes and describes X per se.

As used herein, an "at risk" individual is an individual who is at risk of developing a disease or condition. An individual "at risk" may or may not have a detectable disease or condition, and may or may not have displayed detectable disease prior to the treatment methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s).

"Treatment" or "treating" is an approach for obtaining beneficial or desired results including clinical results. Beneficial or desired results may include one or more of the following: decreasing one or more symptom resulting from the disease or condition; diminishing the extent of the disease or condition; slowing or arresting the development of one or more symptom associated with the disease or condition (e.g., stabilizing the disease or condition, preventing or delaying the worsening or progression of the disease or condition); and relieving the disease, such as by causing the regression of clinical symptoms (e.g., ameliorating the disease state, enhancing the effect of another medication, delaying the progression of the disease, increasing the quality of life, and/or prolonging survival).

As used herein, "delaying" development of a disease or condition means to defer, hinder, slow, retard, stabilize and/or postpone development of the disease or condition. This delay can be of varying lengths of time, depending on the history of the disease and/or individual being treated. As is evident to one skilled in the art, a sufficient or significant delay can, in effect, encompass prevention, in that the individual does not develop the disease or condition.

As used herein, the term "therapeutically effective amount" or "effective amount" intends such amount of a compound of the disclosure or a pharmaceutically salt thereof sufficient to effect treatment when administered to an individual. As is understood in the art, an effective amount may be in one or more doses, e.g., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved.

As used herein, "unit dosage form" refers to physically discrete units, suitable as unit dosages, each unit containing a predetermined quantity of active ingredient, or compound, which may be in a pharmaceutically acceptable carrier.

As used herein, by "pharmaceutically acceptable" is meant a material that is not biologically or otherwise undesirable, e.g., the material may be incorporated into a pharmaceutical composition administered to an individual without causing significant undesirable biological effects.

The term "alkyl", as used herein, refers to an unbranched or branched saturated univalent hydrocarbon chain. As used herein, alkyl has 1-20 carbons (i.e., $C_{1-20}$alkyl), 1-16 carbons (i.e., $C_{1-16}$alkyl), 1-12 carbons (i.e., $C_{1-12}$alkyl), 1-10 carbons (i.e., $C_{1-10}$alkyl), 1-8 carbons (i.e., $C_{1-8}$alkyl), 1-6 carbons (i.e., $C_{1-6}$alkyl), 1-4 carbons (i.e., $C_{1-4}$alkyl), or 1-3 carbons (i.e., $C_{1-3}$alkyl). Examples of alkyl groups include, but are not limited to, methyl, ethyl, propyl, iso-propyl, n-butyl, sec-butyl, iso-butyl, tert-butyl, pentyl, 2-pentyl, iso-pentyl, neo-pentyl, hexyl, 2-hexyl, 3-hexyl, and 3-methylpentyl. When an alkyl residue having a specific number of carbons is named by chemical name or molecular formula, all positional isomers having that number of carbon atoms may be encompassed—for example, "butyl" includes n-butyl, sec-butyl, iso-butyl, and tert-butyl; and "propyl" includes n-propyl and iso-propyl. Certain commonly used alternative names may be used and will be understood by those of ordinary skill in the art. For instance, a divalent group, such as a divalent "alkyl" group, may be referred to as an "alkylene".

The term "alkenyl", as used herein, refers to a branched or unbranched univalent hydrocarbon chain comprising at least one carbon-carbon double bond. As used herein, alkenyl has 2-20 carbons (i.e., $C_{2-20}$alkenyl), 2-16 carbons (i.e., $C_{2-16}$alkenyl), 2-12 carbons (i.e., $C_{2-12}$alkenyl), 2-10 carbons (i.e., $C_{2-10}$alkenyl), 2-8 carbons (i.e., $C_{2-8}$alkenyl), 2-6 carbons (i.e., $C_{2-6}$alkenyl), 2-4 carbons (i.e., $C_{2-4}$alkenyl), or 2-3 carbons (i.e., $C_{2-3}$alkenyl). Examples of alkenyl include, but are not limited to, ethenyl, prop-1-enyl, prop-2-enyl 1,2-butadienyl, and 1,3-butadienyl. When an alkenyl residue having a specific number of carbons is named by chemical name or molecular formula, all positional isomers having that number of carbon atoms may be encompassed—for example, "propenyl" includes prop-1-enyl and prop-2-enyl. Certain commonly used alternative names may be used and will be understood by those of ordinary skill in the art. For instance, a divalent group, such as a divalent "alkenyl" group, may be referred to as an "alkenylene".

The term "alkynyl", as used herein, refers to a branched or unbranched univalent hydrocarbon chain comprising at least one carbon-carbon triple bond. As used herein, alkynyl has 2-20 carbons (i.e., $C_{2-20}$alkynyl), 2-16 carbons (i.e., $C_{2-16}$alkynyl), 2-12 carbons (i.e., $C_{2-12}$alkynyl), 2-10 carbons (i.e., $C_{2-10}$alkynyl), 2-8 carbons (i.e., $C_{2-8}$alkynyl), 2-6 carbons (i.e., $C_{2-6}$alkynyl), 2-4 carbons (i.e., $C_{2-4}$alkynyl), or 2-3 carbons (i.e., $C_{2-3}$alkynyl). Examples of alkynyl include, but are not limited to, ethynyl, prop-1-ynyl, prop-2-ynyl, but-1-ynyl, but-2-ynyl, and but-3-ynyl. When an alkynyl residue having a specific number of carbons is named by chemical name or molecular formula, all positional isomers having that number of carbon atoms may be encompassed—for example, "propynyl" includes prop-1-ynyl and prop-2-ynyl. Certain commonly used alternative names may be used and will be understood by those of ordinary skill in the art. For instance, a divalent group, such as a divalent "alkynyl" group, may be referred to as an "alkynylene".

The term "alkoxy", as used herein, refers to an —O-alkyl moiety. Examples of alkoxy groups include, but are not limited to, methoxy, ethoxy, n-propoxy, iso-propoxy, n-butoxy, tert-butoxy, sec-butoxy, n-pentoxy, n-hexoxy, and 1,2-dimethylbutoxy.

The term "aryl", as used herein, refers to a fully unsaturated carbocyclic ring moiety. The term "aryl" encompasses monocyclic and polycyclic fused-ring moieties. As used herein, aryl encompasses ring moieties comprising, for example, 6 to 20 annular carbon atoms (i.e., $C_{6-20}$aryl), 6 to 16 annular carbon atoms (i.e., $C_{6-16}$aryl), 6 to 12 annular carbon atoms (i.e., $C_{6-12}$aryl), or 6 to 10 annular carbon atoms (i.e., $C_{6-10}$aryl). Examples of aryl moieties include, but are not limited to, phenyl, naphthyl, fluorenyl, and anthryl.

The term "cycloalkyl", as used herein, refers to a saturated or partially unsaturated carbocyclic ring moiety. The term "cycloalkyl" encompasses monocyclic and polycyclic ring moieties, wherein the polycyclic moieties may be fused, branched, or spiro. Cycloalkyl includes cycloalkenyl groups, wherein the ring moiety comprises at least one annular double bond. Cycloalkyl includes any polycyclic carbocyclic ring moiety comprising at least one non-aromatic ring, regardless of the point of attachment to the remainder of the molecule. As used herein, cycloalkyl includes rings comprising, for example, 3 to 20 annular carbon atoms (i.e., a $C_{3-20}$cycloalkyl), 3 to 16 annular carbon atoms (i.e., a $C_{3-16}$cycloalkyl), 3 to 12 annular carbon atoms (i.e., a $C_{3-12}$cycloalkyl), 3 to 10 annular carbon atoms (i.e., a $C_{3-10}$cycloalkyl), 3 to 8 annular carbon atoms (i.e., a $C_{3-8}$cycloalkyl), 3 to 6 annular carbon atoms (i.e., a $C_{3-6}$cycloalkyl), or 3 to 5 annular carbon atoms (i.e., a $C_{3-5}$cycloalkyl). Monocyclic cycloalkyl ring moieties include, for example, cyclopropyl, cyclobutyl, cyclopentyl, cyclohexyl, cycloheptyl, and cyclooctyl. Polycyclic groups include, for example, bicyclo[2.2.1]heptanyl, bicyclo[2.2.2]octanyl, adamantyl, norbonyl, decalinyl, 7,7-dimethyl-bicyclo [2.2.1]heptanyl, and the like. Still further, cycloalkyl also includes spiro cycloalkyl ring moieties, for example, spiro[2.5]octanyl, spiro[4.5]decanyl, or spiro [5.5]undecanyl.

The term "halo", as used herein, refers to atoms occupying groups VIIA of The Periodic Table and includes fluorine (fluoro), chlorine (chloro), bromine (bromo), and iodine (iodo).

The term "heteroaryl", as used herein, refers to an aromatic (fully unsaturated) ring moiety that comprises one or more annular heteroatoms independently selected from the group consisting of nitrogen, oxygen, and sulfur. The term "heteroaryl" includes both monocyclic and polycyclic fused-ring moieties. As used herein, a heteroaryl comprises, for example, 5 to 20 annular atoms (i.e., a 5-20 membered heteroaryl), 5 to 16 annular atoms (i.e., a 5-16 membered heteroaryl), 5 to 12 annular atoms (i.e., a 5-12 membered heteroaryl), 5 to 10 annular atoms (i.e., a 5-10 membered heteroaryl), 5 to 8 annular atoms (i.e., a 5-8 membered heteroaryl), or 5 to 6 annular atoms (i.e., a 5-6 membered heteroaryl). Any monocyclic or polycyclic aromatic ring moiety comprising one or more annular heteroatoms is considered a heteroaryl, regardless of the point of attachment to the remainder of the molecule (i.e., the heteroaryl moiety may be attached to the remainder of the molecule through any annular carbon or any annular heteroatom of the heteroaryl moiety). Examples of heteroaryl groups include, but are not limited to, acridinyl, benzimidazolyl, benzothiazolyl, benzindolyl, benzofuranyl, benzothiazolyl, benzothiadiazolyl, benzonaphthofuranyl, benzoxazolyl, benzothienyl (benzothiophenyl), benzotriazolyl, benzo[4,6]imidazo[1,2-a]pyridyl, carbazolyl, cinnolinyl, dibenzofuranyl, dibenzothiophenyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, and triazinyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl, and imidazo[1,5-a]pyridinyl, wherein the heteroaryl can be bound via either ring of the fused system.

The term "heterocyclyl", as used herein, refers to a saturated or partially unsaturated cyclic moiety that encompasses one or more annular heteroatoms independently selected from the group consisting of nitrogen, oxygen, and sulfur. The term "heterocyclyl" includes both monocyclic and polycyclic ring moieties, wherein the polycyclic ring moieties may be fused, bridged, or spiro. Any non-aromatic monocyclic or polycyclic ring moiety comprising at least one annular heteroatom is considered a heterocyclyl, regardless of the point of attachment to the remainder of the molecule (i.e., the heterocyclyl moiety may be attached to the remainder of the molecule through any annular carbon or any annular heteroatom of the heterocyclyl moiety). Further, the term heterocyclyl is intended to encompass any polycyclic ring moiety comprising at least one annular heteroatom wherein the polycyclic ring moiety comprises at least one non-aromatic ring, regardless of the point of attachment to the remainder of the molecule. As used herein, a heterocyclyl comprises, for example, 3 to 20 annular atoms (i.e., a 3-20 membered heterocyclyl), 3 to 16 annular atoms (i.e., a 3-16 membered heterocyclyl), 3 to 12 annular atoms (i.e., a 3-12 membered heterocyclyl), 3 to 10 annular atoms (i.e., a 3-10 membered heterocyclyl), 3 to 8 annular atoms (i.e., a 3-8 membered heterocyclyl), 3 to 6 annular atoms (i.e., a 3-6 membered heterocyclyl), 3 to 5 annular atoms (i.e., a 3-5 membered heterocyclyl), 5 to 8 annular atoms (i.e., a 5-8 membered heterocyclyl), or 5 to 6 annular atoms (i.e., a 5-6 membered heterocyclyl). Examples of heterocyclyl groups include, e.g., azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiophenyl (i.e., thienyl), thiomorpholinyl, thiamorpholinyl, 1-oxo-thiomorpholinyl, and 1,1-dioxothiomorpholinyl. Examples of spiro heterocyclyl rings include, but are not limited to, bicyclic and tricyclic ring systems, such as oxabicyclo[2.2.2]octanyl, 2-oxa-7-azaspiro[3.5]nonanyl, 2-oxa-6-azaspiro[3.4]octanyl, and 6-oxa-1-azaspiro[3.3]heptanyl. Examples of fused heterocyclyl rings include, but are not limited to, 1,2,3,4-tetrahydroisoquinolinyl, 4,5,6,7-tetrahydrothieno[2,3-c]pyridinyl, indolinyl, and isoindolinyl, where the heterocyclyl can be bound via either ring of the fused system.

The term "oxo", as used herein, refers to a =O moiety.

The terms "optional" and "optionally", as used herein, mean that the subsequently described event or circumstance may or may not occur and that the description includes instances where the event or circumstance occurs and instances where it does not. Accordingly, the term "optionally substituted" infers that any one or more (e.g., 1, 2, 1 to 5, 1 to 3, 1 to 2, etc.) hydrogen atoms on the designated atom or moiety or group may be replaced or not replaced by an atom or moiety or group other than hydrogen. By way of illustration and not limitation, the phrase "methyl optionally substituted with one or more chloro" encompasses —CH₃, —CH₂Cl, —CHCl₂, and —CCl₃ moieties.

It is understood that aspects and embodiments described herein as "comprising" include "consisting of" and "consisting essentially of" embodiments.

The term "pharmaceutically acceptable salt", as used herein, of a given compound refers to salts that retain the biological effectiveness and properties of the given compound and which are not biologically or otherwise undesirable. "Pharmaceutically acceptable salts" include, for example, salts with inorganic acids, and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. See, e.g., *Handbook of Pharmaceutical Salts Properties, Selection, and Use*, International Union of Pure and Applied Chemistry, John Wiley & Sons (2008), which is incorporated herein by reference. Those skilled in the art will recognize various synthetic methodologies that may be used to prepare nontoxic pharmaceutically acceptable addition salts. Pharmaceutically acceptable acid addition salts may be prepared from inorganic or organic acids. Salts derived from inorganic acids include, e.g., hydrochloric acid, hydrobromic acid, sulfuric acid, nitric acid, phosphoric acid, and the like. Salts derived from organic acids include, e.g., acetic acid, propionic acid, gluconic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, trifluoroacetic acid, and the like. Likewise, pharmaceutically acceptable base addition salts can be prepared from inorganic or organic bases. Salts derived from inorganic bases include, by way of example only, sodium, potassium, lithium, aluminum, ammonium, calcium, and magnesium salts. Salts derived from organic bases include, but are not limited to, salts of primary, secondary, and tertiary amines. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

Isotopically labeled forms of the compounds depicted herein may be prepared. Isotopically labeled compounds have structures depicted herein, except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$ $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. In some embodiments, a compound of formula (A) is provided wherein one or more hydrogen is replaced by deuterium or tritium.

Some of the compounds provided herein may exist as tautomers. Tautomers are in equilibrium with one another. By way of illustration, amide containing compounds may exist in equilibrium with imidic acid tautomers. Regardless of which tautomer is shown and regardless of the nature of the equilibrium among tautomers, the compounds of this disclosure are understood by one of ordinary skill in the art to comprise both amide and imidic acid tautomers. Thus, for example, amide-containing compounds are understood to include their imidic acid tautomers. Likewise, imidic-acid containing compounds are understood to include their amide tautomers.

Also provided herein are prodrugs of the compounds depicted herein, or a pharmaceutically acceptable salt thereof. Prodrugs are compounds that may be administered to an individual and release, in vivo, a compound depicted herein as the parent drug compound. It is understood that prodrugs may be prepared by modifying a functional group on a parent drug compound in such a way that the modification is cleaved in vitro or in vivo to release the parent drug compound. See, e.g., Rautio, J., Kumpulainen, H., Heimbach, T. et al. Prodrugs: design and clinical applications. *Nat Rev Drug Discov* 7, 255-270 (2008), which is incorporated herein by reference.

The compounds of the present disclosure, or their pharmaceutically acceptable salts, may include an asymmetric center and may thus give rise to enantiomers, diastereomers, and other stereoisomeric forms that may be defined, in terms of absolute stereochemistry, as (R)- or (S)-(or as (D)- or (L)- for amino acids). The present disclosure is meant to include all such possible isomers, as well as their racemic and optically pure forms and mixtures thereof in any ratio. Optically active (+) and (−), (R)- and (S)-, or (D)- and (L)-isomers may be prepared using chiral synthons or chiral reagents, or may be resolved using conventional techniques, for example, chromatography and/or fractional crystallization. Conventional techniques for the preparation/isolation of individual enantiomers include chiral synthesis from a suitable optically pure precursor or the resolution of the racemate (or the racemate of a salt or derivative) using, for example, chiral high pressure liquid chromatography (HPLC), and chiral supercritical fluid chromatography (SFC). When the compounds described herein contain olefinic double bonds or other centers of geometric asymmetry, unless specified otherwise, it is intended that the present disclosure includes both E and Z geometric isomers. Likewise, cis- and trans- are used in their conventional sense to describe relative spatial relationships.

A "stereoisomer" refers to a compound made up of the same atoms bonded by the same bonds, but having different three-dimensional structures, which are not interchangeable. The present disclosure contemplates various stereoisomers, or mixtures thereof, and includes "enantiomers," which refers to two stereoisomers whose structures are non-superimposable mirror images of one another. "Diastereomers" are stereoisomers that have at least two asymmetric atoms, but which are not mirror images of each other.

Where enantiomeric and/or diastereomeric forms exist of a given structure, flat bonds indicate that all stereoisomeric forms of the depicted structure may be present, e.g.,

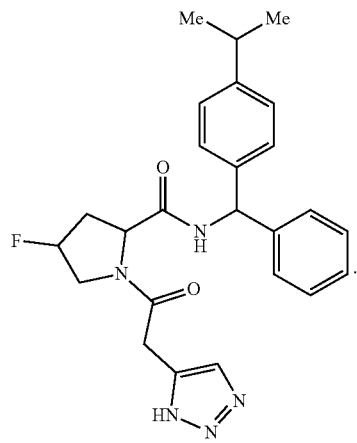 [SMILES: CC(C)c1ccc(C(NC(=O)C2CC(F)CN2C(=O)Cc2cnn[nH]2)c2ccccc2)cc1]

Where enantiomeric and/or diastereomeric forms exist of a given structure, flat bonds and the presence of a "*" symbol indicate that the composition is made up of at least 90%, by weight, of a single isomer with unknown stereochemistry, e.g.,

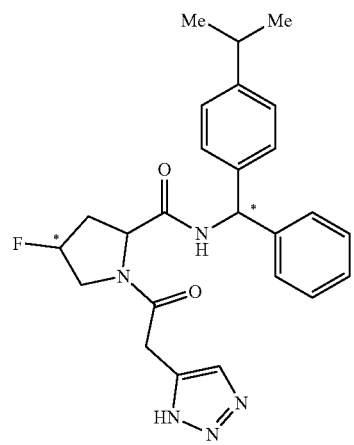 [SMILES: CC(C)c1ccc(C(NC(=O)C2CC(F)CN2C(=O)Cc2cnn[nH]2)c2ccccc2)cc1]

Where enantiomeric and/or diastereomeric forms exist of a given structure, wedged or hashed bonds indicate the composition is made up of at least 90%, by weight, of a single enantiomer or diastereomer with known stereochemistry, e.g.,

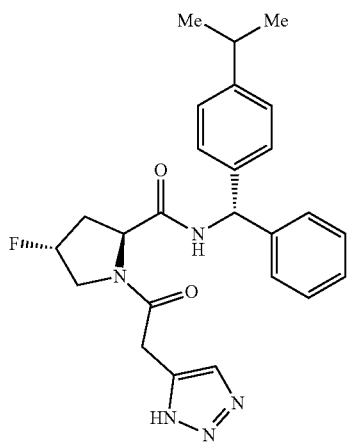 [SMILES: CC(C)c1ccc([C@@H](NC(=O)[C@@H]2C[C@@H](F)CN2C(=O)Cc2cnn[nH]2)c2ccccc2)cc1]

Where relevant, combinations of the above notation may be used. Exemplified species may contain stereogenic centers with known stereochemistry and stereogenic centers with unknown stereochemistry, stereochemistry, e.g.,

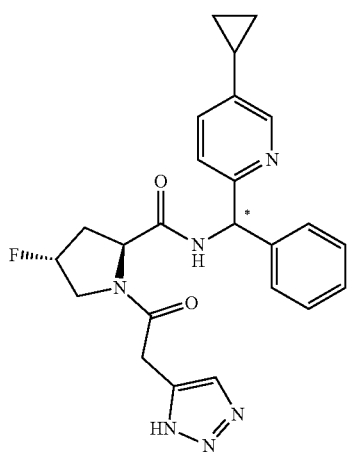 [SMILES: O=C(NC(c1ccccc1)c1ccc(C2CC2)cn1)[C@@H]1C[C@@H](F)CN1C(=O)Cc1cnn[nH]1]

Where relevant, combinations of the above notation may be used. Exemplified species may contain stereogenic centers with known stereochemistry and stereogenic centers bearing a mixture of isomers, e.g.,

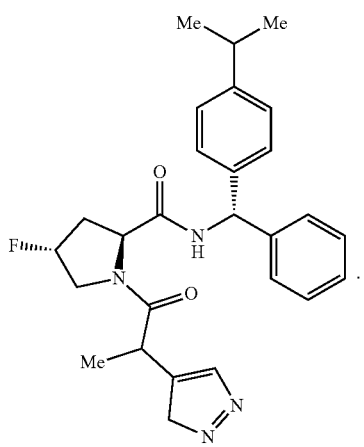 [SMILES: CC(C(=O)N1C[C@H](F)C[C@H]1C(=O)N[C@@H](c1ccccc1)c1ccc(C(C)C)cc1)C1=CN=NC1]

Compounds

In one aspect, provided herein is a compound of formula (I'):

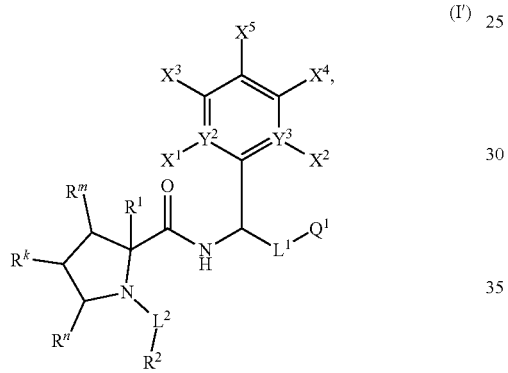

or a stereoisomer or tautomer thereof, or a pharmaceutically acceptable salt of any of the foregoing, wherein:
$Y^2$ and $Y^3$ are each C, or
one of $Y^2$ and $Y^3$ is N and the other of $Y^2$ and $Y^3$ is C;
$X^1$ and $X^2$ are each independently H, $C_{1-6}$alkyl, or $C_{1-6}$alkoxy;
$X^3$ and $X^4$ are each independently H, halo, $C_{1-6}$alkyl, $C_{1-6}$alkoxy, or 5-20 membered heteroaryl, wherein the $C_{1-6}$alkyl of $X^3$ and $X^4$ is optionally substituted with one of more halo;
$X^5$ is H, $C_{1-6}$alkyl, $C_{1-6}$alkoxy, or $C_{3-10}$cycloalkyl; either
(1) $L^1$ is absent; and
$Q^1$ is selected from (i) to (iv):
(i) phenyl, wherein the phenyl of $Q^1$ is substituted with one or more halo, $C_{1-6}$alkyl, $C_{2-6}$alkenyl, —$NH_2$, —NH—C(O)—($C_{1-6}$alkyl), —NH—C(O)-(3-15 membered heterocyclyl), $C_{3-10}$cycloalkyl, or 5-20 membered heteroaryl, wherein
  the $C_{1-6}$alkyl is optionally substituted with one or more halo, —NH—C(O)—NH($C_{1-6}$alkyl), —NH—C(O)—$C_{1-6}$alkyl, or —NH—C(O)—$C_{1-6}$alkoxy,
  the $C_{3-10}$cycloalkyl is optionally substituted with one or more halo or $C_{1-6}$alkyl, and
  the 5-20 membered heteroaryl is optionally substituted with one or more $C_{1-6}$alkyl,
(ii) 3-15 membered heterocyclyl, wherein the 3-15 membered heterocyclyl of $Q^1$ is optionally substituted with one or more oxo, or $C_{1-6}$alkyl, (iii) 5-20 membered heteroaryl, wherein the 5-20 membered heteroaryl of $Q^1$ is optionally substituted with one or more halo, $C_{1-6}$alkyl, $C_{2-6}$alkenyl, $C_{1-6}$alkoxy, —$NH_2$, or $C_{3-10}$cycloalkyl, wherein,
  the $C_{1-6}$alkyl is optionally substituted with one or more halo, and
  the $C_{3-10}$cycloalkyl is optionally substituted with one or more halo or $C_{1-6}$alkyl, and
(iv) $C_{3-10}$cycloalkyl;
or
(2) $L^1$ is —$CH_2$—; and
$Q^1$ is $C_{3-10}$cycloalkyl;
$L^2$ is —C(O)— or —S(O)$_2$—
$R^1$ is H or $C_{1-6}$alkyl;
$R^k$ is H, halo, —OH, —$NH_2$, or —NH—C(O)$C_{1-6}$alkyl;
$R^m$ is H, —OH, or $C_{1-6}$alkyl;
$R^n$ is H, $C_{1-6}$alkyl, or $C_{3-10}$cycloalkyl or $R^n$ taken together with the carbon atom to which it is attached forms $C_{3-5}$ cycloalkyl;
or $R^k$ is taken together with either $R^m$ or $R^n$, and the atoms to which they are attached, to form cyclopropyl; and
$R^2$ is selected from (i) to (vii):
(i) $C_{1-6}$alkyl, wherein the $C_{1-6}$alkyl of $R^2$ is optionally substituted with one or more $R^a$, wherein $R^a$ is:
  (a) —OH,
  (b) cyano,
  (c) $C_{2-6}$alkynyl,
  (d) $C_{6-20}$aryl, wherein the $C_{6-20}$aryl of $R^a$ is optionally substituted with one or more halo, cyano, $C_{1-6}$alkoxy, or —NH—C(O)—$C_{1-6}$alkyl,
  (e) 3-15 membered heterocyclyl, wherein the 3-15 membered heterocyclyl of $R^a$ is optionally substituted with one or more $R^c$, wherein
    $R^c$ is halo, oxo, $C_{1-6}$alkyl, $C_{1-6}$alkoxy, —C(O)—$C_{1-6}$alkyl, or —C(O)—$C_{1-6}$alkoxy, wherein
      the $C_{1-6}$alkyl of $R^c$ is optionally substituted with one or more halo or $C_{2-6}$alkynyl, and
      the —C(O)—$C_{1-6}$alkoxy of $R^c$ is optionally substituted with one or more halo,
  (f) —N($R^c$)($R^d$), wherein $R^c$ and $R^d$ of N($R^c$)($R^d$) are, independently of each other, H, $C_{1-6}$alkyl, —C(O)—$C_{1-6}$alkyl, —C(O)—$C_{1-6}$alkoxy, —C(O)—$NH_2$, —C(O)—NH($C_{1-6}$alkyl), —C(O)—N($C_{1-6}$alkyl)$_2$, —C(O)-(3-15 membered heterocyclyl), —$CH_2$—C(O)—$NH_2$, 3-15 membered heterocyclyl, or 5-20 membered heteroaryl, wherein
    the $C_{1-6}$alkyl of $R^c$ or $R^d$ is optionally substituted with one or more —C(O)—$NH_2$,
    the —C(O)—$C_{1-6}$alkyl of $R^c$ or $R^d$ is optionally substituted with one or more halo,
    the 3-15 membered heterocyclyl and the 5-20 membered heteroaryl of $R^c$ or $R^d$ are independently optionally substituted with one or more $C_{1-6}$alkyl,
    the —C(O)-(3-15 membered heterocyclyl) of $R^c$ or $R^d$ is optionally substituted with one or more halo, —C(O)—$C_{1-6}$alkoxy, or $C_{1-6}$alkyl, wherein the $C_{1-6}$alkyl is optionally substituted with one or more halo, $C_{1-6}$alkoxy, or $C_{3-10}$cycloalkyl, and
    the $C_{1-6}$alkyl of the —C(O)—N($C_{1-6}$alkyl)$_2$ of $R^c$ or $R^d$ are, independently of each other, optionally substituted with one or more halo or $C_{6-20}$aryl,
  (g) —O—$R^e$, wherein $R^e$ is $C_{1-6}$alkyl, $C_{6-20}$aryl, —C(O)-(3-15 membered heterocyclyl), —C(O)—N—($C_{1-6}$alkyl)$_2$, or 5-20 membered heteroaryl, wherein the $C_{1-6}$alkyl of $R^e$ is optionally substituted with one or more $C_{1-6}$alkoxy, wherein the $C_{1-6}$alkoxy is optionally substituted with one or more $C_{2-6}$alkynyl, the $C_{6-20}$aryl of $R^e$ is optionally substituted with one or more $C_{1-6}$alkyl, and the —C(O)-(3-15 membered heterocyclyl) of $R^e$ is optionally substituted with one or more $C_{1-6}$alkyl, $C_{1-6}$alkoxy, or —C(O)—$C_{1-6}$alkoxy, wherein the $C_{1-6}$alkyl is optionally substituted with one or more halo, $C_{1-6}$alkoxy, or $C_{3-10}$cycloalkyl, (h) —C(O)—$R^e$, wherein $R^e$ of —C(O)—$R^e$ is —NH$_2$, —OH, or 3-15 membered heterocyclyl, or (i) —S(O)$_2$—$R^f$, wherein $R^f$ is $C_{1-6}$alkyl or 3-15 membered heterocyclyl, provided that, when $R^2$ is unsubstituted methyl, then either (1) $Q^1$ is 5-20 membered heteroaryl, wherein the 5-20 membered heteroaryl of $Q^1$ is optionally substituted with one or more halo, $C_{1-6}$alkyl, $C_{2-6}$alkenyl, $C_{1-6}$alkoxy, —NH$_2$, $C_{3-10}$cycloalkyl, or —OH, and wherein $Q^1$ is not unsubstituted pyridyl, or (2) $Q^1$ is phenyl, wherein the phenyl of $Q^1$ is substituted with (i) at least one $C_{3-6}$alkyl, wherein the at least one $C_{3-6}$alkyl is optionally substituted with one or more halo, or (ii) at least one $C_{3-10}$cycloalkyl, wherein the at least one $C_{3-10}$cycloalkyl is optionally substituted with one or more halo or $C_{1-6}$alkyl, or (iii) at least one 5-20 membered heteroaryl, wherein the at least one 5-20 membered heteroaryl is optionally substituted with one or more $C_{1-6}$alkyl, (ii) $C_{3-10}$cycloalkyl, wherein the $C_{3-10}$cycloalkyl of $R^2$ is optionally substituted with one or more $R^q$, wherein $R^q$ is 5-20 membered heteroaryl or $C_{6-20}$aryl, wherein the $C_{6-20}$aryl of $R^q$ is optionally substituted with one or more $C_{1-6}$alkoxy, (iii) 3-15 membered heterocyclyl, wherein the 3-15 membered heterocyclyl of $R^2$ is optionally substituted with one or more halo, oxo, $C_{1-6}$alkyl, —C(O)—$C_{1-6}$alkyl, or 5-20 membered heteroaryl, (iv) 5-20 membered heteroaryl or —($C_{1-4}$alkyl)(5-20 membered heteroaryl), wherein the $C_{1-4}$ alkyl is optionally substituted with one or more —OH, halo, —NH$_2$, —NH($C_{1-6}$alkyl), —N($C_{1-6}$alkyl)$_2$, and wherein the 5-20 membered heteroaryl is optionally substituted with one or more $R^s$, wherein $R^s$ is halo, $C_{1-6}$alkyl, $C_{1-6}$alkoxy, —NH$_2$, —NH($C_{1-6}$alkyl), —N($C_{1-6}$alkyl)$_2$, —NH—C(O)—$C_{1-6}$alkyl, $C_{6-20}$aryl, $C_{3-10}$cycloalkyl, 3-15 membered heterocyclyl, 5-20 membered heteroaryl, or —C(O)—$C_{1-6}$alkoxy, wherein the $C_{1-6}$alkyl of $R^s$ is optionally substituted with one or more halo, $C_{1-6}$alkoxy, —NH$_2$, —NH($C_{1-6}$alkyl), —N($C_{1-6}$alkyl)$_2$, —NH—C(O)$C_{1-6}$alkyl, or —NH—C(O)—$C_{1-6}$alkoxy, and the 3-15-membered heterocyclyl of $R^s$ is optionally substituted with one or more halo or —C(O)—$C_{1-6}$alkoxy, (v) —N($R^g$)($R^h$), wherein $R^g$ and $R^h$ are independently H or $C_{1-6}$alkyl, (vi) —C(O)—$R^j$, wherein $R^j$ is $C_{3-10}$cycloalkyl, —NH($C_{1-6}$alkyl), —N($C_{1-6}$alkyl)$_2$, or —NH (5-20 membered heteroaryl), and (vii) $C_{6-20}$aryl, wherein the $C_{6-20}$aryl of $R^2$ is optionally substituted with one or more 5-20 membered heteroaryl or —O—$R^p$, wherein $R^p$ is 3-15 membered heterocyclyl, wherein the 3-15 membered heterocyclyl of $R^p$ is optionally substituted with one or more —C(O)—$C_{1-6}$alkyl.

In one aspect, provided is a compound of formula (I):

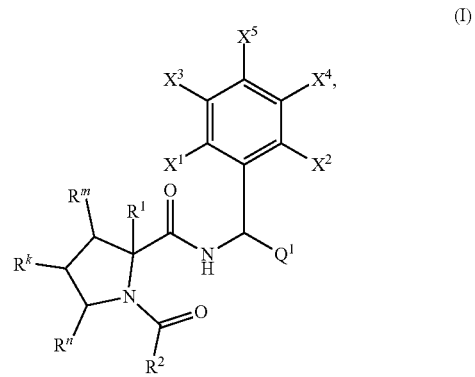

or a stereoisomer or tautomer thereof, or a pharmaceutically acceptable salt of any of the foregoing, wherein:

$X^1$ and $X^2$ are each independently H, $C_{1-6}$alkyl, or $C_{1-6}$alkoxy;

$X^3$ and $X^4$ are each independently H, halo, $C_{1-6}$alkyl, $C_{1-6}$alkoxy, or 5-20 membered heteroaryl;

$X^5$ is H, $C_{1-6}$alkyl, $C_{1-6}$alkoxy, or $C_{3-10}$cycloalkyl;

$Q^1$ is selected from (i) to (iii):

(i) phenyl, wherein the phenyl of $Q^1$ is substituted with one or more halo, $C_{1-6}$alkyl, $C_{2-6}$alkenyl, —NH$_2$, —NH—C(O)—($C_{1-6}$alkyl), —NH—C(O)-(3-15 membered heterocyclyl), or $C_{3-10}$cycloalkyl, wherein the $C_{1-6}$alkyl is optionally substituted with one or more halo, and the $C_{3-10}$cycloalkyl is optionally substituted with one or more halo or $C_{1-6}$alkyl, (ii) 3-15 membered heterocyclyl, wherein the 3-15 membered heterocyclyl of $Q^1$ is optionally substituted with one or more oxo, and (iii) 5-20 membered heteroaryl, wherein the 5-20 membered heteroaryl of $Q^1$ is optionally substituted with one or more halo, $C_{1-6}$alkyl, $C_{2-6}$alkenyl, $C_{1-6}$alkoxy, —NH$_2$, or $C_{3-10}$cycloalkyl, wherein the $C_{3-10}$cycloalkyl is optionally substituted with one or more halo or $C_{1-6}$alkyl;

$R^1$ is H or $C_{1-6}$alkyl;

$R^k$ is H, halo, —OH, —NH$_2$, or —NH—C(O)$C_{1-6}$alkyl;

$R^m$ is H, —OH, or $C_{1-6}$alkyl;

$R^n$ is H, $C_{1-6}$alkyl, or $C_{3-10}$cycloalkyl;

or $R^k$ is taken together with either $R^m$ or $R^n$, and the atoms to which they are attached, to form cyclopropyl; and $R^2$ is selected from (i) to (vii):

(i) $C_{1-6}$alkyl, wherein the $C_{1-6}$alkyl of $R^2$ is optionally substituted with one or more $R^a$, wherein $R^a$ is:

(a) —OH, (b) cyano, (c) $C_{2-6}$alkynyl, (d) $C_{6-20}$aryl, wherein the $C_{6-20}$aryl of $R^a$ is optionally substituted with one or more halo, cyano, $C_{1-6}$alkoxy, or —NH—C(O)—$C_{1-6}$alkyl, (e) 5-20 membered heteroaryl, wherein the 5-20 membered heteroaryl of $R^a$ is optionally substituted with one or more $R^b$, wherein $R^b$ is halo, $C_{1-6}$alkyl, $C_{1-6}$alkoxy, —NH$_2$, —NH($C_{1-6}$alkyl), —N($C_{1-6}$alkyl)$_2$, $C_{3-10}$cycloalkyl, 3-15 membered heterocyclyl, or —C(O)—$C_{1-6}$alkoxy, wherein the $C_{1-6}$alkyl of $R^b$ is optionally substituted with one or more halo, —NH$_2$, —NH(C$_{1-6}$alkyl), —N(C$_{1-6}$alkyl)$_2$, —NH—C(O)C$_{1-6}$alkyl, or —NH—C(O)—C$_{1-6}$alkoxy, and the 3-15-membered heterocyclyl of $R^b$ is optionally substituted with one or more halo or —C(O)—C$_{1-6}$alkoxy, (f) 3-15 membered heterocyclyl, wherein the 3-15 membered heterocyclyl of $R^a$ is optionally substituted with one or more $R^c$, wherein $R^c$ is halo, oxo, C$_{1-6}$alkyl, C$_{1-6}$alkoxy, —C(O)—C$_{1-6}$alkyl, or —C(O)—C$_{1-6}$alkoxy, wherein the C$_{1-6}$alkyl of $R^c$ is optionally substituted with one or more halo or C$_{2-6}$alkynyl, and the —C(O)—C$_{1-6}$alkoxy of $R^c$ is optionally substituted with one or more halo, (g) —N($R^c$)($R^d$), wherein $R^c$ and $R^d$ are, independently of each other, H, C$_{1-6}$alkyl, —C(O)—C$_{1-6}$alkyl, —C(O)—C$_{1-6}$alkoxy, —C(O)—NH$_2$, —C(O)—NH(C$_{1-6}$alkyl), —C(O)—N(C$_{1-6}$alkyl)$_2$, —C(O)-(3-15 membered heterocyclyl), —CH$_2$—C(O)—NH$_2$, 3-15 membered heterocyclyl, or 5-20 membered heteroaryl, wherein the —C(O)—C$_{1-6}$alkyl of $R^c$ or $R^d$ is optionally substituted with one or more halo, the 3-15 membered heterocyclyl and the 5-20 membered heteroaryl of $R^c$ or $R^d$ are independently optionally substituted with one or more C$_{1-6}$alkyl, and the —C(O)-(3-15 membered heterocyclyl) of $R^c$ or $R^d$ is optionally substituted with one or more halo, —C(O)—C$_{1-6}$alkoxy, or C$_{1-6}$alkyl, wherein the C$_{1-6}$alkyl is optionally substituted with one or more halo, C$_{1-6}$alkoxy, or C$_{3-10}$cycloalkyl, (h) —O—$R^e$, wherein $R^e$ is C$_{1-6}$alkyl, C$_{6-20}$aryl, —C(O)-(3-15 membered heterocyclyl), —C(O)—N—(C$_{1-6}$alkyl)$_2$, or 5-20 membered heteroaryl, wherein the C$_{1-6}$alkyl of $R^e$ is optionally substituted with one or more C$_{1-6}$alkoxy, wherein the C$_{1-6}$alkoxy is optionally substituted with one or more C$_{2-6}$alkynyl, the C$_{6-20}$aryl of $R^e$ is optionally substituted with one or more C$_{1-6}$alkoxy, and the —C(O)-(3-15 membered heterocyclyl) of $R^e$ is optionally substituted with one or more C$_{1-6}$alkyl, C$_{1-6}$alkoxy, or —C(O)—C$_{1-6}$alkoxy, wherein the C$_{1-6}$alkyl is optionally substituted with one or more halo, C$_{1-6}$alkoxy, or C$_{3-10}$cycloalkyl, (i) —C(O)—$R^e$, wherein $R^e$ is —NH$_2$, —OH, or 3-15 membered heterocyclyl, or (j) —S(O)$_2$—$R^f$, wherein $R^f$ is C$_{1-6}$alkyl or 3-15 membered heterocyclyl, provided that, when $R^2$ is unsubstituted methyl, then either (1) $Q^1$ is 5-20 membered heteroaryl, wherein the 5-20 membered heteroaryl of $Q^1$ is substituted with one or more halo, C$_{1-6}$alkyl, C$_{2-6}$alkenyl, C$_{1-6}$alkoxy, —NH$_2$, C$_{3-10}$cycloalkyl, or —OH, or (2) $Q^1$ is phenyl, wherein the phenyl of $Q^1$ is substituted with at least one C$_{3-6}$alkyl or at least one C$_{3-10}$cycloalkyl, wherein the at least one C$_{3-6}$alkyl is optionally substituted with one or more halo, and the at least one C$_{3-10}$cycloalkyl is optionally substituted with one or more halo or C$_{1-6}$alkyl, (ii) C$_{3-10}$cycloalkyl, wherein the C$_{3-10}$cycloalkyl of $R^2$ is optionally substituted with one or more $R^q$, wherein $R^q$ is 5-20 membered heteroaryl or C$_{6-20}$aryl, wherein the C$_{6-20}$aryl of $R^q$ is optionally substituted with one or more C$_{1-6}$alkoxy, (iii) 3-15 membered heterocyclyl, wherein the 3-15 membered heterocyclyl of $R^2$ is optionally substituted with one or more halo, oxo, C$_{1-6}$alkyl, —C(O)—C$_{1-6}$alkyl, or 5-20 membered heteroaryl, (iv) 5-20 membered heteroaryl, wherein the 5-20 membered heteroaryl of $R^2$ is optionally substituted with one or more $R^s$, wherein $R^s$ is C$_{1-6}$alkyl, C$_{1-6}$alkoxy, —NH—C(O)—C$_{1-6}$alkyl, C$_{6-20}$aryl, or 5-20 membered heteroaryl, wherein the C$_{1-6}$alkyl of $R^s$ is optionally substituted with one or more C$_{1-6}$alkoxy, (v) —N($R^g$)($R^h$), wherein $R^g$ and $R^h$ are independently H or C$_{1-6}$alkyl, (vi) —C(O)—$R^j$, wherein $R^j$ is C$_{3-10}$cycloalkyl, —NH(C$_{1-6}$alkyl), —N(C$_{1-6}$alkyl)$_2$, or —NH (5-20 membered heteroaryl), and (vii) C$_{6-20}$aryl, wherein the C$_{6-20}$aryl of $R^2$ is optionally substituted with one or more 5-20 membered heteroaryl or —O—$R^p$, wherein $R^p$ is 3-15 membered heterocyclyl, wherein the 3-15 membered heterocyclyl of $R^p$ is optionally substituted with one or more —C(O)—C$_{1-6}$alkyl.

Any embodiments provided herein of a compound of formula (I), or a stereoisomer or tautomer thereof, or a pharmaceutically acceptable salt of any of the foregoing, or any variation or embodiment thereof, are also, where applicable, embodiments of a compound of formula (I'), or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing, $L^2$ is —C(O) or —S(O)$_2$—. In some embodiments, $L^2$ is —C(O)—. In some embodiments, $L^2$ is —S(O)$_2$—.

In some embodiments of a compound of formula (I), or a stereoisomer or tautomer thereof, or a pharmaceutically acceptable salt of any of the foregoing, $Q^1$ is 5-20 membered heteroaryl, wherein the 5-20 membered heteroaryl of $Q^1$ is optionally substituted with one or more halo, C$_{1-6}$alkyl, C$_{2-6}$alkenyl, C$_{1-6}$alkoxy, —NH$_2$, or C$_{3-10}$cycloalkyl, wherein the C$_{3-10}$cycloalkyl is optionally substituted with one or more C$_{1-6}$alkyl or halo. In some embodiments, $Q^1$ is 5-6 membered heteroaryl, wherein the 5-6 membered heteroaryl of $Q^1$ is optionally substituted with one or more halo, C$_{1-6}$alkyl, C$_{2-6}$alkenyl, C$_{1-6}$alkoxy, —NH$_2$, or C$_{3-10}$cycloalkyl, wherein the C$_{3-10}$cycloalkyl is optionally substituted with one or more C$_{1-6}$alkyl or halo. In some embodiments, $Q^1$ is pyridinyl, wherein the pyridinyl of $Q^1$ is optionally substituted with one or more halo, C$_{1-6}$alkyl, C$_{2-6}$alkenyl, C$_{1-6}$alkoxy, —NH$_2$, or C$_{3-10}$cycloalkyl, wherein the C$_{3-10}$cycloalkyl is optionally substituted with one or more C$_{1-6}$alkyl or halo. In some embodiments, $Q^1$ is 2-pyridinyl or 3-pyridinyl, wherein the 2-pyridinyl or 3-pyridinyl of $Q^1$ is optionally substituted with one or more halo, C$_{1-6}$alkyl, C$_{2-6}$alkenyl, C$_{1-6}$alkoxy, —NH$_2$, or C$_{3-10}$cycloalkyl, wherein the C$_{3-10}$cycloalkyl is optionally substituted with one or more C$_{1-6}$alkyl or halo. In some embodiments, $Q^1$ is 2-pyridinyl, wherein the 2-pyridinyl of $Q^1$ is optionally substituted with one or more halo, C$_{1-6}$alkyl, C$_{1-6}$alkoxy, —NH$_2$, or C$_{3-10}$cycloalkyl, wherein the C$_{3-10}$cycloalkyl is optionally substituted with one or more C$_{1-6}$alkyl or halo. In some embodiments $Q^1$ is 2-pyridinyl, wherein the 2-pyridinyl of $Q^1$ is optionally substituted with one or more halo, C$_{1-6}$alkyl, or C$_{3-10}$cycloalkyl, wherein the C$_{3-10}$cycloalkyl is optionally substituted with one or more $C_{1-6}$alkyl or halo. In some embodiments, $Q^1$ is 2-pyridinyl, wherein the 2-pyridinyl of $Q^1$ is optionally substituted with one or more fluoro, chloro, methyl, iso-propyl, tert-butyl, cyclopropyl, or cyclobutyl, wherein the cyclopropyl and cyclobutyl are independently optionally substituted with one or more methyl or fluoro.

In some embodiments of a compound of formula (I'), or a stereoisomer or tautomer thereof, or a pharmaceutically acceptable salt of any of the foregoing, $Q^1$ is 5-20 membered heteroaryl, wherein the 5-20 membered heteroaryl of $Q^1$ is optionally substituted with one or more halo, $C_{1-6}$alkyl, $C_{2-6}$alkenyl, $C_{1-6}$alkoxy, —$NH_2$, or $C_{3-10}$cycloalkyl, wherein the $C_{1-6}$alkyl is optionally substituted with one or more halo, and the $C_{3-10}$cycloalkyl is optionally substituted with one or more $C_{1-6}$alkyl or halo. In some embodiments, $Q^1$ is 5-6 membered heteroaryl, wherein the 5-6 membered heteroaryl of $Q^1$ is optionally substituted with one or more halo, $C_{1-6}$alkyl, $C_{2-6}$alkenyl, $C_{1-6}$alkoxy, —$NH_2$, or $C_{3-10}$cycloalkyl, wherein the $C_{1-6}$alkyl is optionally substituted with one or more halo, and the $C_{3-10}$cycloalkyl is optionally substituted with one or more $C_{1-6}$alkyl or halo. In some embodiments, $Q^1$ is pyridinyl, wherein the pyridinyl of $Q^1$ is optionally substituted with one or more halo, $C_{1-6}$alkyl, $C_{2-6}$alkenyl, $C_{1-6}$alkoxy, —$NH_2$, or $C_{3-10}$cycloalkyl, wherein the $C_{1-6}$alkyl is optionally substituted with one or more halo, and the $C_{3-10}$cycloalkyl is optionally substituted with one or more $C_{1-6}$alkyl or halo. In some embodiments, $Q^1$ is 2-pyridinyl or 3-pyridinyl, wherein the 2-pyridinyl or 3-pyridinyl of $Q^1$ is optionally substituted with one or more halo, $C_{1-6}$alkyl, $C_{2-6}$alkenyl, $C_{1-6}$alkoxy, —$NH_2$, or $C_{3-10}$cycloalkyl, wherein the $C_{1-6}$alkyl is optionally substituted with one or more halo, and the $C_{3-10}$cycloalkyl is optionally substituted with one or more $C_{1-6}$alkyl or halo. In some embodiments, $Q^1$ is 2-pyridinyl, wherein the 2-pyridinyl of $Q^1$ is optionally substituted with one or more halo, $C_{1-6}$alkyl, $C_{1-6}$alkoxy, —$NH_2$, or $C_{3-10}$cycloalkyl, wherein the $C_{1-6}$alkyl is optionally substituted with one or more halo, and the $C_{3-10}$cycloalkyl is optionally substituted with one or more $C_{1-6}$alkyl or halo. In some embodiments $Q^1$ is 2-pyridinyl, wherein the 2-pyridinyl of $Q^1$ is optionally substituted with one or more halo, $C_{1-6}$alkyl, $C_{1-6}$alkoxy, or $C_{3-10}$cycloalkyl, wherein the $C_{1-6}$alkyl is optionally substituted with one or more halo, and the $C_{3-10}$cycloalkyl is optionally substituted with one or more $C_{1-6}$alkyl or halo. In some embodiments, $Q^1$ is 2-pyridinyl, wherein the 2-pyridinyl of $Q^1$ is optionally substituted with one or more fluoro, chloro, methyl, iso-propyl, tert-butyl, cyclopropyl, cyclobutyl, or methoxy, wherein the methyl is optionally substituted with one or more fluoro and the cyclopropyl and cyclobutyl are independently optionally substituted with one or more methyl or fluoro.

In some embodiments of a compound of formula (I), or a stereoisomer or tautomer thereof, or a pharmaceutically acceptable salt of any of the foregoing, $Q^1$ is selected from the group consisting of

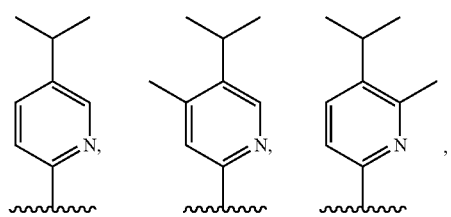

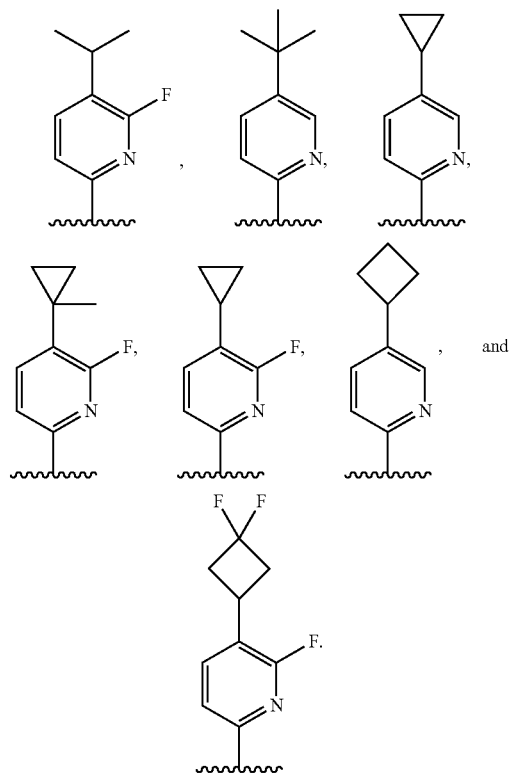

In some embodiments of a compound of formula (I'), or a stereoisomer or tautomer thereof, or a pharmaceutically acceptable salt of any of the foregoing, $Q^1$ is selected from the group consisting of

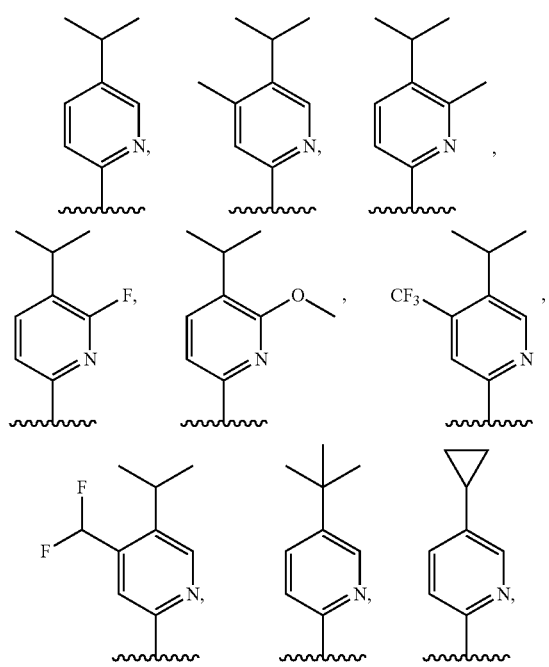

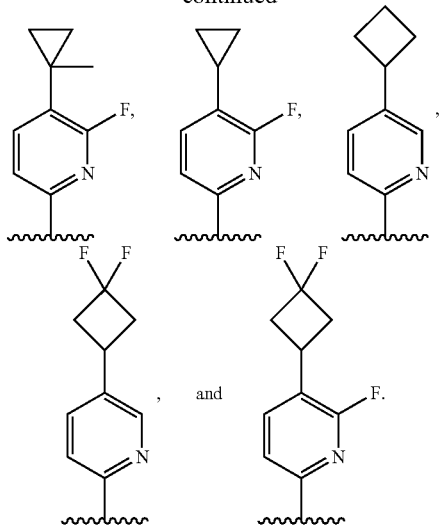

In some embodiments of a compound of formula (I), or a stereoisomer or tautomer thereof, or a pharmaceutically acceptable salt of any of the foregoing, $Q^1$ is selected from the group consisting of

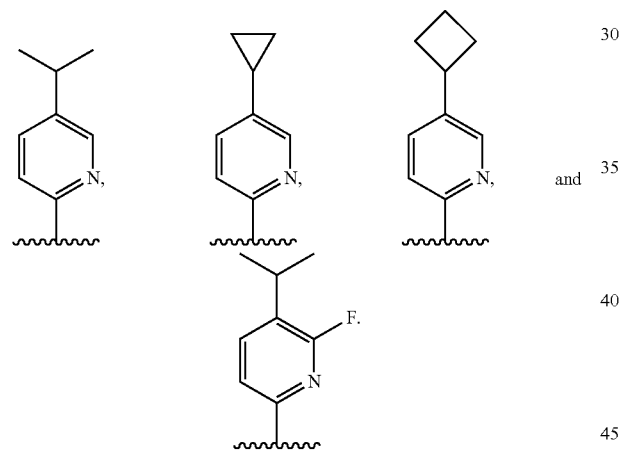

In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $Q^1$ is phenyl, wherein the phenyl of $Q^1$ is substituted with one or more halo, $C_{1-6}$alkyl, $C_{2-6}$ alkenyl, —NH$_2$, —NH—C(O)—($C_{1-6}$alkyl), —NH—C(O)-(3-15 membered heterocyclyl), or $C_{3-10}$cycloalkyl, wherein the $C_{1-6}$alkyl is optionally substituted with one or more halo, and the $C_{3-10}$cycloalkyl is optionally substituted with one or more halo or $C_{1-6}$alkyl. In some embodiments, $Q^1$ is phenyl, wherein the phenyl of $Q^1$ is substituted with one or more halo, $C_{1-6}$alkyl, $C_{2-6}$ alkenyl, or $C_{3-10}$cycloalkyl, wherein the $C_{1-6}$alkyl is optionally substituted with one or more halo, and the $C_{3-10}$cycloalkyl is optionally substituted with one or more halo or $C_{1-6}$alkyl. In some embodiments, $Q^1$ is phenyl, wherein the phenyl of $Q^1$ is substituted with one or more fluoro, chloro, methyl, iso-propyl, sec-butyl, tert-butyl, prop-1-en-2-yl, cyclopropyl, or cyclobutyl, wherein the methyl, iso-propyl, sec-butyl, and tert-butyl are independently optionally substituted with one or more halo, and the cyclopropyl and cyclobutyl are independently optionally substituted with one or more fluoro or methyl. In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing, $Q^1$ is phenyl, wherein the phenyl of $Q^1$ is substituted with one or more halo, $C_{1-6}$alkyl, $C_{2-6}$alkenyl, —NH$_2$, —NH—C(O)—($C_{1-6}$alkyl), —NH—C(O)-(3-15 membered heterocyclyl), $C_{3-10}$cycloalkyl, or 5-20 membered heteroaryl, wherein the $C_{1-6}$alkyl is optionally substituted with one or more halo, —NH—C(O)—NH($C_{1-6}$alkyl), —NH—C(O)—$C_{1-6}$alkyl, or —NH—C(O)—$C_{1-6}$alkoxy, the $C_{3-10}$cycloalkyl is optionally substituted with one or more halo or $C_{1-6}$alkyl, and the 5-20 membered heteroaryl is optionally substituted with one or more $C_{1-6}$alkyl.

In some embodiments of a compound of formula (I), or a stereoisomer or tautomer thereof, or a pharmaceutically acceptable salt of any of the foregoing, Q is selected from the group consisting of

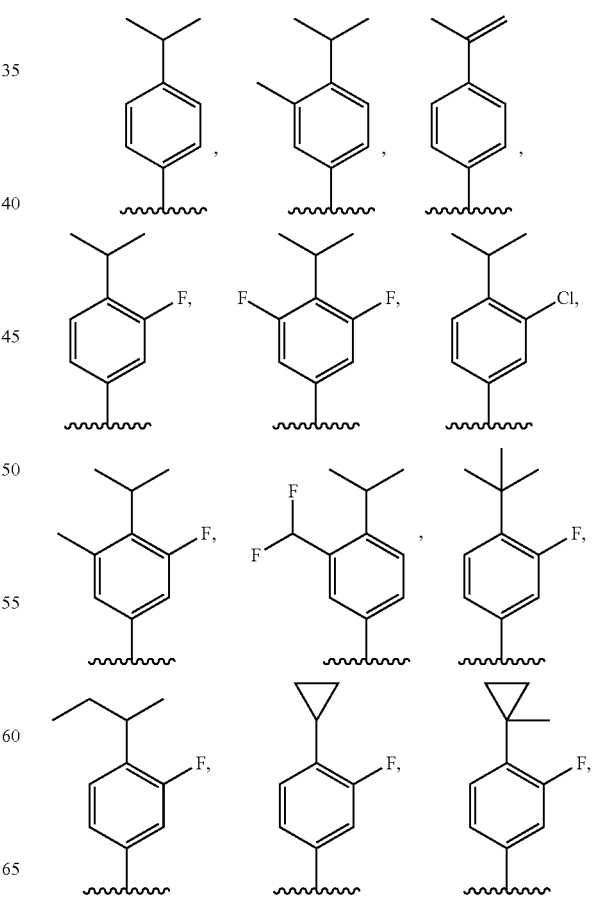

33
-continued
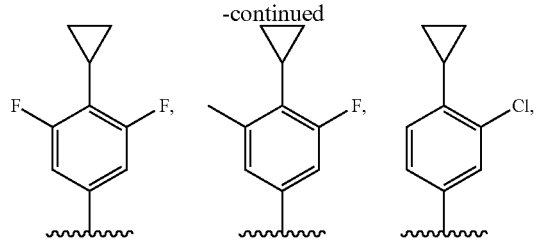
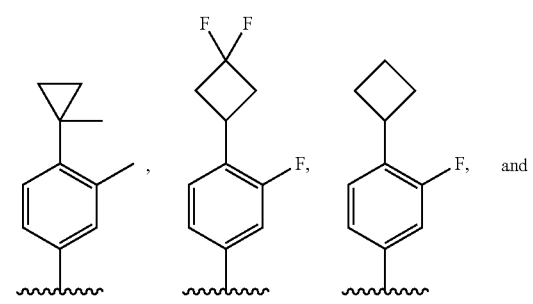
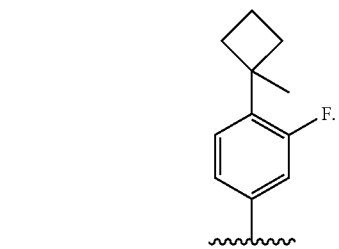
34
-continued
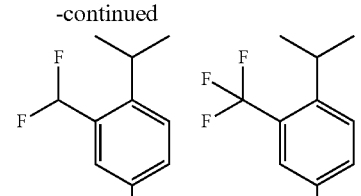
In some embodiments of a compound of formula (I), or a stereoisomer or tautomer thereof, or a pharmaceutically acceptable salt of any of the foregoing, $Q^1$ is selected from the group consisting of
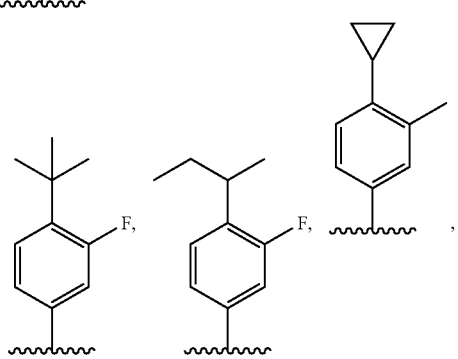
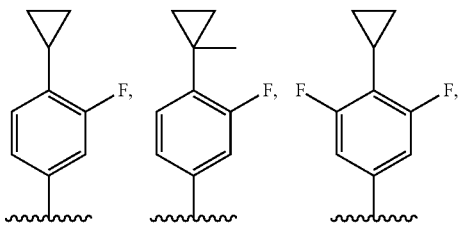
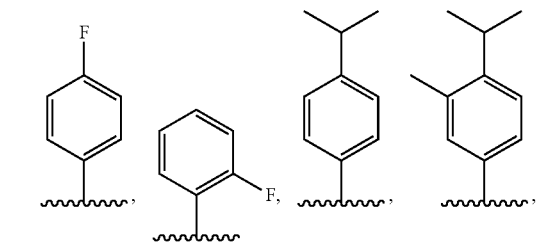
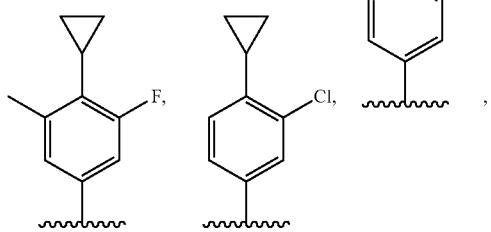
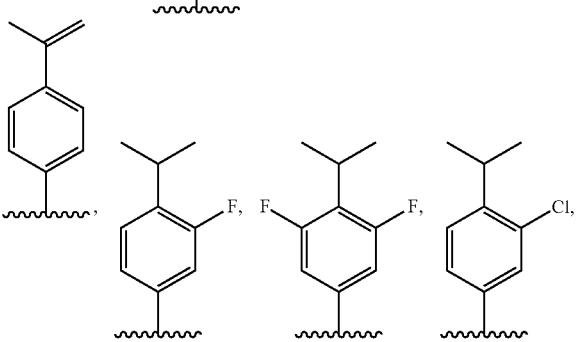
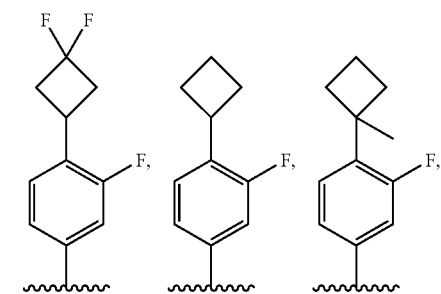

-continued

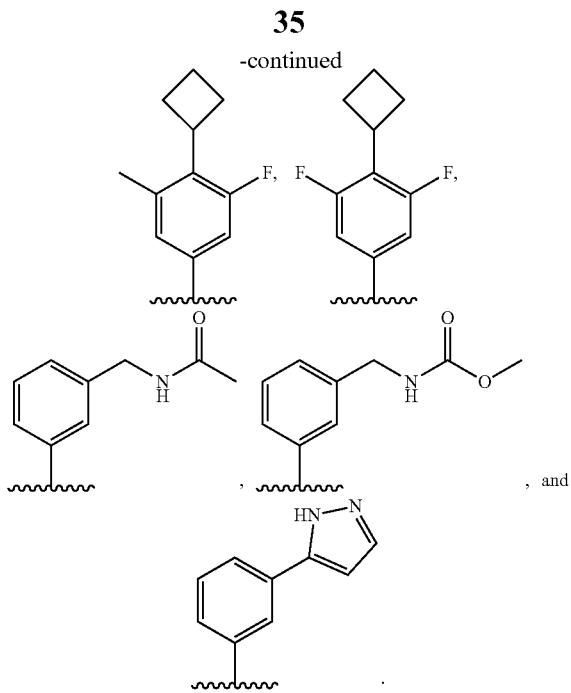

In some embodiments of a compound of formula (I), or a stereoisomer or tautomer thereof, or a pharmaceutically acceptable salt of any of the foregoing, $Q^1$ is selected from the group consisting of

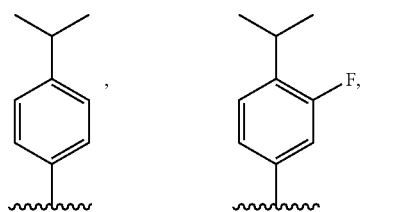

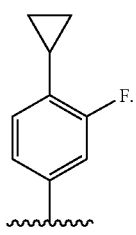

In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $Q^1$ is 3-15 membered heterocyclyl, wherein the 3-15 membered heterocyclyl of $Q^1$ is optionally substituted with one or more oxo. In some embodiments, $Q^1$ is

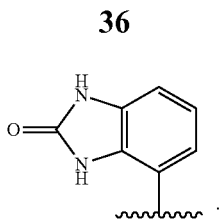

In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing, $Q^1$ is (i) 3-15 membered heterocyclyl, wherein the 3-15 membered heterocyclyl of $Q^1$ is optionally substituted with one or more oxo, or $C_{1-6}$alkyl, (ii) 5-20 membered heteroaryl, wherein the 5-20 membered heteroaryl of $Q^1$ is optionally substituted with one or more halo, $C_{1-6}$alkyl, $C_{2-6}$alkenyl, $C_{1-6}$alkoxy, —$NH_2$, or $C_{3-10}$cycloalkyl, wherein, the $C_{1-6}$alkyl is optionally substituted with one or more halo, and the $C_{3-10}$cycloalkyl is optionally substituted with one or more halo or $C_{1-6}$alkyl, or (iii) $C_{3-10}$cycloalkyl.

In some embodiments of a compound of formula (I'), or a stereoisomer or tautomer thereof, or a pharmaceutically acceptable salt of any of the foregoing, $Q^1$ is 3-15 membered heterocyclyl, wherein the 3-15 membered heterocyclyl of $Q^1$ is optionally substituted with one or more oxo, or $C_{1-6}$alkyl. In some embodiments $Q^1$ is selected from the group consisting of

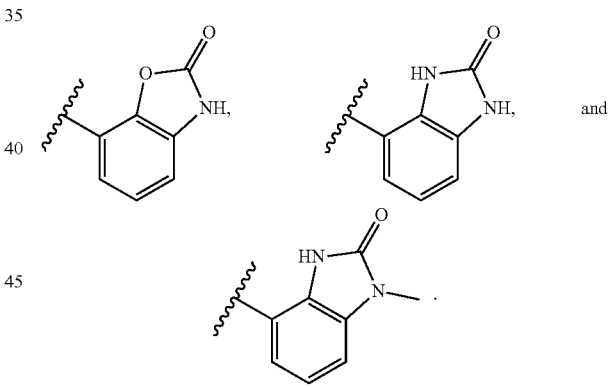

In some embodiments of a compound of formula (I'), or a stereoisomer or tautomer thereof, or a pharmaceutically acceptable salt of any of the foregoing, $Q^1$ is 5-20 membered heteroaryl, wherein the 5-20 membered heteroaryl of $Q^1$ is optionally substituted with one or more halo, $C_{1-6}$alkyl, $C_{2-6}$alkenyl, $C_{1-6}$alkoxy, —$NH_2$, or $C_{3-10}$cycloalkyl, wherein, the $C_{1-6}$alkyl is optionally substituted with one or more halo, and the $C_{3-10}$cycloalkyl is optionally substituted with one or more halo or $C_{1-6}$alkyl. In some embodiments $Q^1$ is 5-20 membered heteroaryl, wherein the 5-20 membered heteroaryl of $Q^1$ is optionally substituted with one or more $C_{1-6}$alkyl. In some embodiments, is 5-20 membered heteroaryl, wherein the 5-20 membered heteroaryl of $Q^1$ comprises one or more annular N. In some embodiments, is 5-20 membered heteroaryl, wherein the 5-20 membered heteroaryl of $Q^1$ comprises two annular N. In some embodiments, is 5-20 membered heteroaryl, wherein the 5-20 membered heteroaryl of $Q^1$ is monocyclic of bicyclic. In some embodiments, is 5-20 membered heteroaryl, wherein the 5-20 membered heteroaryl of $Q^1$ is monocyclic. In some embodiments, is 5-20 membered heteroaryl, wherein the 5-20 membered heteroaryl of Q is bicyclic. In some embodiments $Q^1$ is selected from the group consisting of

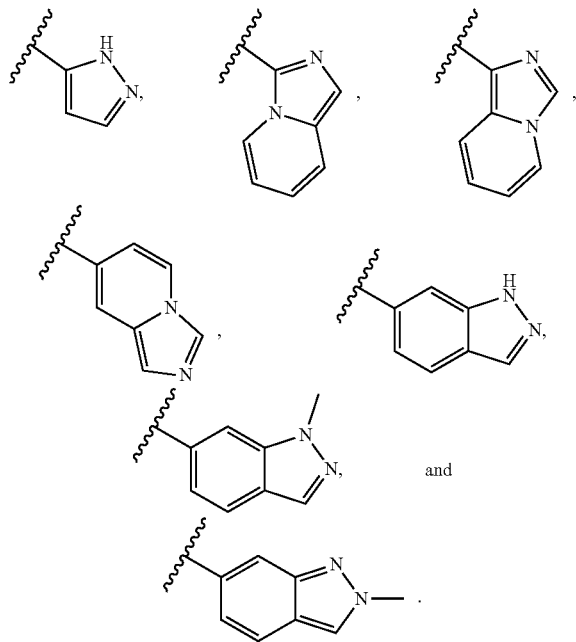

In some embodiments of a compound of formula (I'), (I-G), or a stereoisomer or tautomer thereof, or a pharmaceutically acceptable salt of any of the foregoing, $Q^1$ is $C_{3-10}$cycloalkyl. In some embodiments, $Q^1$ is $C_{3-6}$cycloalkyl. In some embodiments $Q^1$ is cyclopropyl.

In some embodiments of a compound of formula (I'), (I-G), or a stereoisomer or tautomer thereof, or a pharmaceutically acceptable salt of any of the foregoing, $L^1$ is absent or is —$CH_2$—. In some embodiments, $L^1$ is absent. In some embodiments, $L^1$ is —$CH_2$—. In some embodiments, $L^1$ is absent and $Q^1$ is $C_{3-10}$cycloalkyl. In some embodiments, $L^1$ is absent and $Q^1$ is $C_{3-6}$cycloalkyl. In some embodiments $L^1$ is absent and $Q^1$ is cyclopropyl. In some embodiments, $L^1$ is —$CH_2$— and $Q^1$ is $C_{3-10}$cycloalkyl. In some embodiments, $L^1$ is —$CH_2$— and $Q^1$ is $C_{3-6}$cycloalkyl. In some embodiments $L^1$ is —$CH_2$— and $Q^1$ is cyclopropyl.

In some embodiments of a compound of formula (I), or a stereoisomer or tautomer thereof, or a pharmaceutically acceptable salt of any of the foregoing, $X^1$, $X^2$, $X^3$, $X^4$, and $X^5$ are each H. In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing, $R^1$ is H or $C_{1-6}$alkyl. In some embodiments $R^1$ is H. In some embodiments, $R^1$ is $C_{1-3}$alkyl. In some embodiments, $R^1$ is methyl.

In some embodiments of a compound of formula (I'), or a stereoisomer or tautomer thereof, or a pharmaceutically acceptable salt of any of the foregoing, $R^k$ is H, halo, —OH, —$NH_2$, or —NH—C(O)$C_{1-6}$alkyl. In some embodiments, $R^k$ is H. In some embodiments, $R^k$ is halo. In some embodiments, $R^k$ is F.

In some embodiments of a compound of formula (I'), or a stereoisomer or tautomer thereof, or a pharmaceutically acceptable salt of any of the foregoing, $R^m$ is H, —OH, or $C_{1-6}$alkyl. In some embodiments $R^m$ is H.

In some embodiments of a compound of formula (I), or a stereoisomer or tautomer thereof, or a pharmaceutically acceptable salt of any of the foregoing, $R^n$ is H, $C_{1-6}$alkyl, or $C_{3-10}$cycloalkyl. In some embodiments $R^n$ is H.

In some embodiments of a compound of formula (I), or a stereoisomer or tautomer thereof, or a pharmaceutically acceptable salt of any of the foregoing, $R^m$ is H, $R^n$ is H, and $R^k$ is H, halo, —OH, —$NH_2$, or —NH—C(O)$C_{1-6}$alkyl. In some embodiments, $R^m$ is H, $R^n$ is H, and $R^k$ is halo, —OH, or —$NH_2$. In some embodiments, $R^m$ is H, $R^n$ is H, and $R^k$ is halo. In some embodiments, $R^m$ is H, $R^n$ is H, and $R^k$ is fluoro. In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $R^k$ is taken together with either $R^m$ or $R^n$, and the atoms to which they are attached, to form cyclopropyl. In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $R^n$ taken together with the carbon atom to which it is attached forms $C_{3-5}$ cycloalkyl. In some embodiments, $R^n$ taken together with the carbon atom to which it is attached forms cyclopropyl.

In some embodiments of a compound of formula (I), or a stereoisomer or tautomer thereof, or a pharmaceutically acceptable salt of any of the foregoing, $R^1$ is H. In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $R^2$ is $C_{1-6}$alkyl, wherein the $C_{1-6}$alkyl of $R^2$ is optionally substituted with one or more $R^a$. In some embodiments, $R^2$ is $C_{1-6}$alkyl, wherein the $C_{1-6}$alkyl of $R^2$ is substituted with one or more $R^a$, wherein $R^a$ is —OH or 5-20 membered heteroaryl, wherein the 5-20 membered heteroaryl of $R^a$ is optionally substituted with one or more $R^b$. In some embodiments, $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more $R^b$. In some embodiments, $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more $C_{1-6}$alkyl, wherein the $C_{1-6}$alkyl is optionally substituted with one or more halo, —$NH_2$, —NH($C_{1-6}$alkyl), —N($C_{1-6}$alkyl)$_2$, —NH—C(O)$C_{1-6}$alkyl, or —NH—C(O)—$C_{1-6}$alkoxy. In some embodiments, $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more methyl, wherein the methyl is optionally substituted with one or more fluoro.

In some embodiments of a compound of formula (I'), or a stereoisomer or tautomer thereof, or a pharmaceutically acceptable salt of any of the foregoing, $R^2$ is 5-20 membered heteroaryl or —($C_{1-4}$alkyl)(5-20 membered heteroaryl), wherein the $C_{1-4}$ alkyl is optionally substituted with one or more or more —OH, halo, —$NH_2$, —$NH(C_{1-6}alkyl)$, —$N(C_{1-6}alkyl)_2$, and wherein the 5-20 membered heteroaryl is optionally substituted with one or more $R^s$. In some embodiments, $R^2$ is 5-20 membered heteroaryl, wherein the $C_{1-4}$ alkyl is optionally substituted with one or more —OH, halo, —$NH_2$, —$NH(C_{1-6}alkyl)$, —$N(C_{1-6}alkyl)_2$, and wherein the 5-20 membered heteroaryl is optionally substituted with one or more $R^s$. In some embodiments, $R^2$ is (methyl)(5-20 membered heteroaryl), wherein the methyl is optionally substituted with one or more or more —OH, halo, —$NH_2$, —$NH(C_{1-6}alkyl)$, —$N(C_{1-6}alkyl)_2$, and wherein the 5-20 membered heteroaryl is optionally substituted with one or more $R^s$. In some embodiments, $R^s$ is halo, $C_{1-6}$alkyl, $C_{1-6}$alkoxy, —$NH_2$, —$NH(C_{1-6}alkyl)$, —$N(C_{1-6}alkyl)_2$, —NH—C(O)—$C_{1-6}$alkyl, $C_{6-20}$aryl, $C_{3-10}$cycloalkyl, 3-15 membered heterocyclyl, 5-20 membered heteroaryl, or —C(O)—$C_{1-6}$alkoxy. In some embodiments, the $C_{1-6}$alkyl of $R^s$ is optionally substituted with one or more halo, $C_{1-6}$alkoxy, —$NH_2$, —$NH(C_{1-6}alkyl)$, —$N(C_{1-6}alkyl)_2$, —NH—C(O)$C_{1-6}$alkyl, or —NH—C(O)—$C_{1-6}$alkoxy, and the 3-15-membered heterocyclyl of $R^s$ is optionally substituted with one or more halo or —C(O)—$C_{1-6}$alkoxy.

In some embodiments of a compound of formula (I), or a stereoisomer or tautomer thereof, or a pharmaceutically acceptable salt of any of the foregoing, $R^2$ is selected from the group consisting of

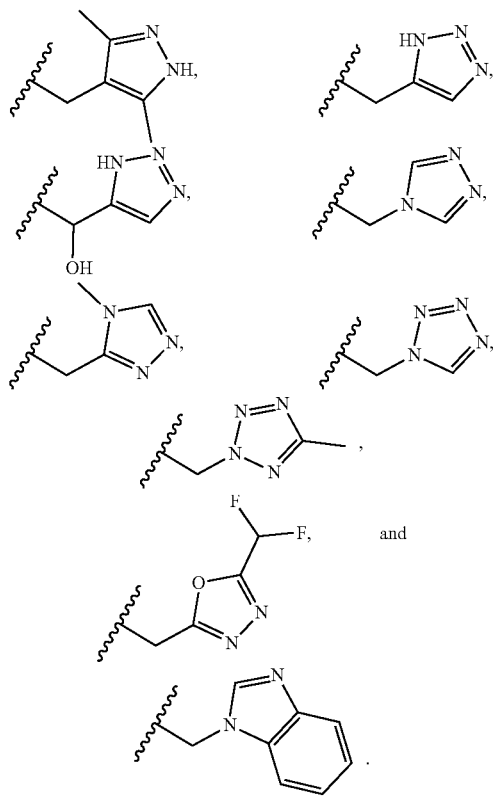

In some embodiments of a compound of formula (I), or a stereoisomer or tautomer thereof, or a pharmaceutically acceptable salt of any of the foregoing, $R^2$ is

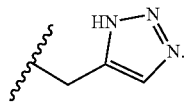

In some embodiments of a compound of formula (I'), (I-C), (I-D), (I-E), or (I-F), or a stereoisomer or tautomer thereof, or a pharmaceutically acceptable salt of any of the foregoing, $R^2$ is selected from the group consisting of

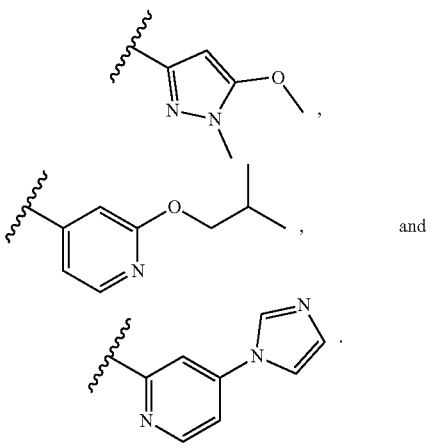

and

In some embodiments of a compound of formula (I'), or a stereoisomer or tautomer thereof, or a pharmaceutically acceptable salt of any of the foregoing, $R^2$ is selected from the group consisting of

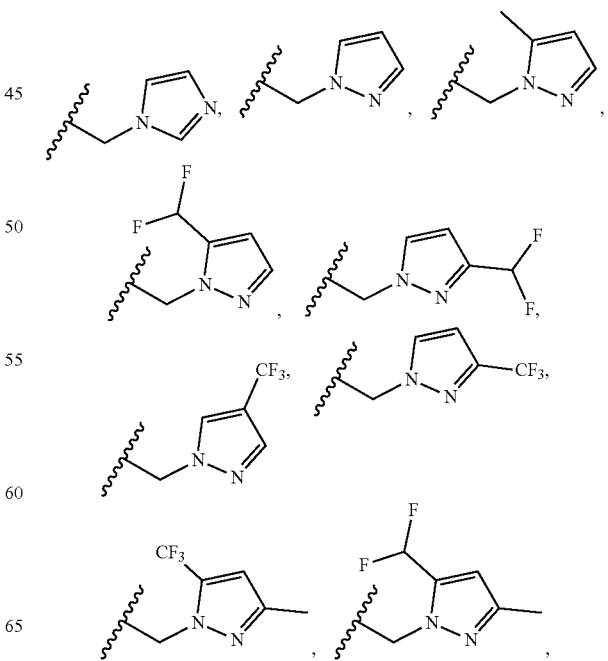

-continued
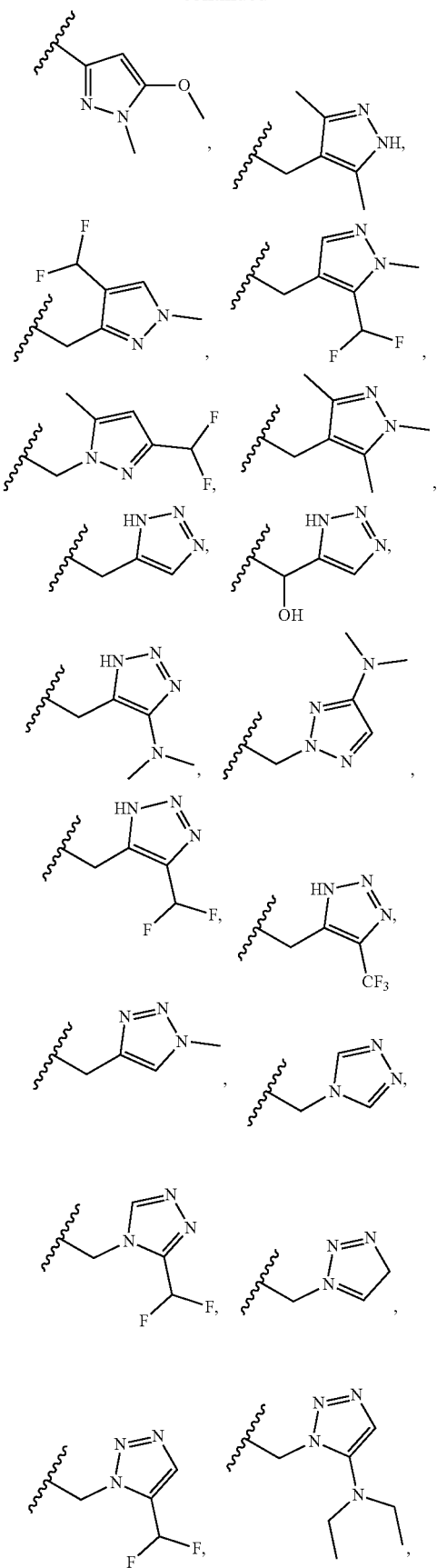
-continued
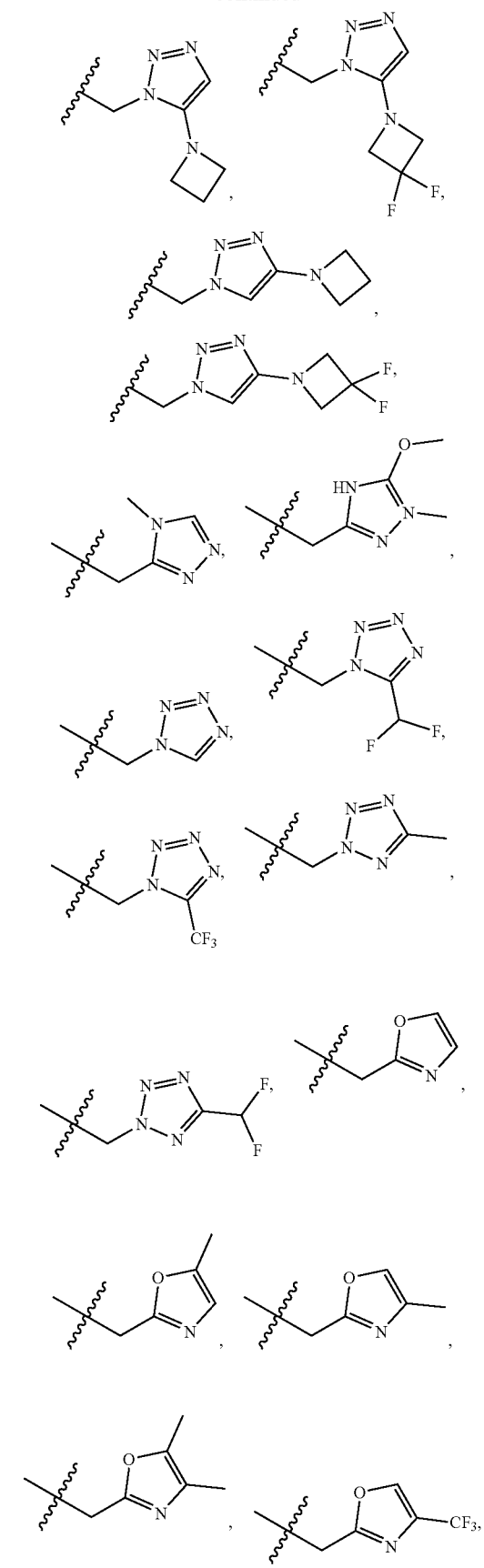

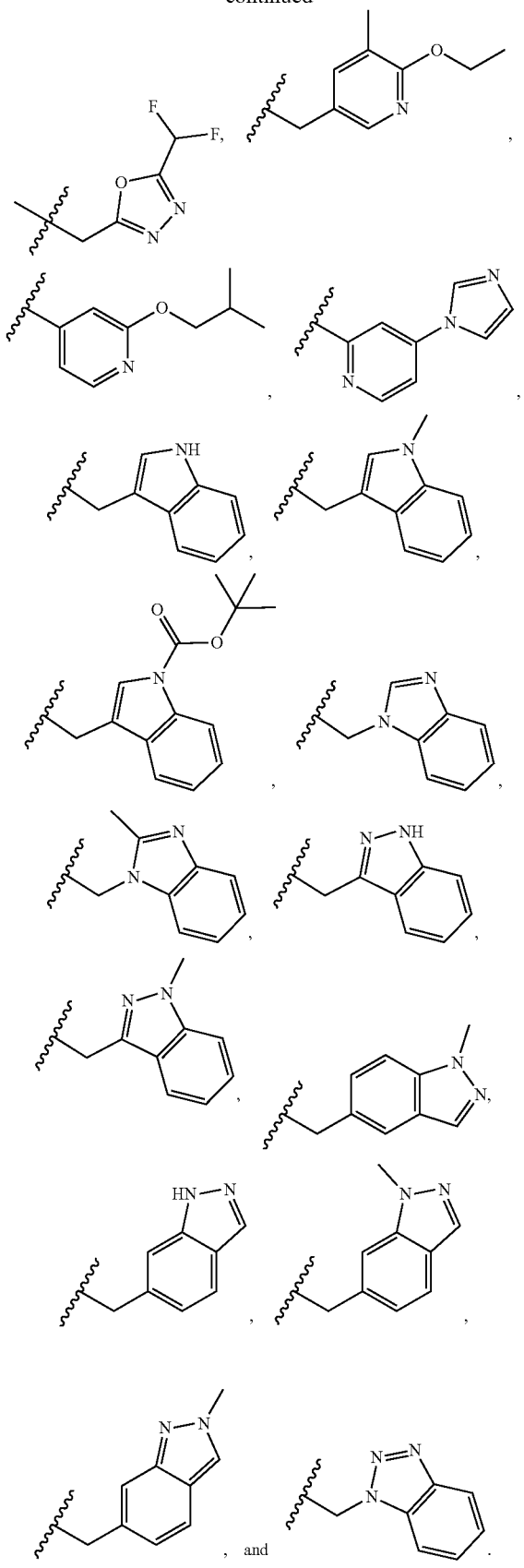
, and

In some embodiments, $R^2$ is

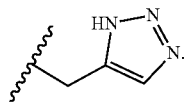

In some embodiments of a compound of formula (I), or a stereoisomer or tautomer thereof, or a pharmaceutically acceptable salt of any of the foregoing, $R^2$ is $C_{1-6}$alkyl, wherein the $C_{1-6}$alkyl of $R^2$ is substituted with one or more $R^a$, wherein $R^a$ is 3-15 membered heterocyclyl, wherein the 3-15 membered heterocyclyl of $R^a$ is optionally substituted with one or more $R^c$.

In some embodiments of a compound of formula (I), or a stereoisomer or tautomer thereof, or a pharmaceutically acceptable salt of any of the foregoing, $R^2$ is methyl, wherein the methyl of $R^2$ is substituted with one or more $R^a$, wherein $R^a$ is 3-15 membered heterocyclyl, wherein the 3-15 membered heterocyclyl of $R^a$ is optionally substituted with one or more $R^c$. In some embodiments, $R^2$ is methyl, wherein the methyl of $R^2$ is substituted with one or more $R^a$, wherein $R^a$ is 3-8 membered heterocyclyl, wherein the 3-8 membered heterocyclyl of $R^a$ is optionally substituted with one or more $R^c$. In some embodiments, $R^2$ is methyl, wherein the methyl of $R^2$ is substituted with one or more $R^a$, wherein $R^a$ is 3-8 membered heterocyclyl, wherein the 3-8 membered heterocyclyl of $R^a$ is optionally substituted with one or more oxo or $C_{1-6}$alkyl. In some embodiments, $R^2$ is

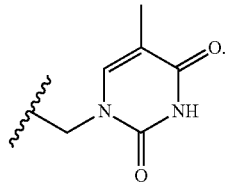 [SMILES: *Cn1cc(C)c(=O)[nH]c1=O]

In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing, In some embodiments, $R^2$ is methyl, wherein the methyl of $R^2$ is substituted with one or more $R^a$, wherein $R^a$ is 3-8 membered heterocyclyl, wherein the 3-8 membered heterocyclyl of $R^a$ is optionally substituted with one or more $R^c$, wherein $R^c$ is oxo, $C_{1-6}$alkyl, or —C(O)—$C_{1-6}$alkoxy, wherein the $C_{1-6}$alkyl of $R^c$ is optionally substituted with one or more halo, and the —C(O)—$C_{1-6}$alkoxy of $R^c$ is optionally substituted with one or more halo. In some embodiments, $R^2$ is selected from the group consisting of

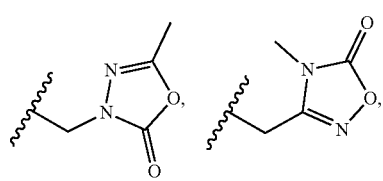

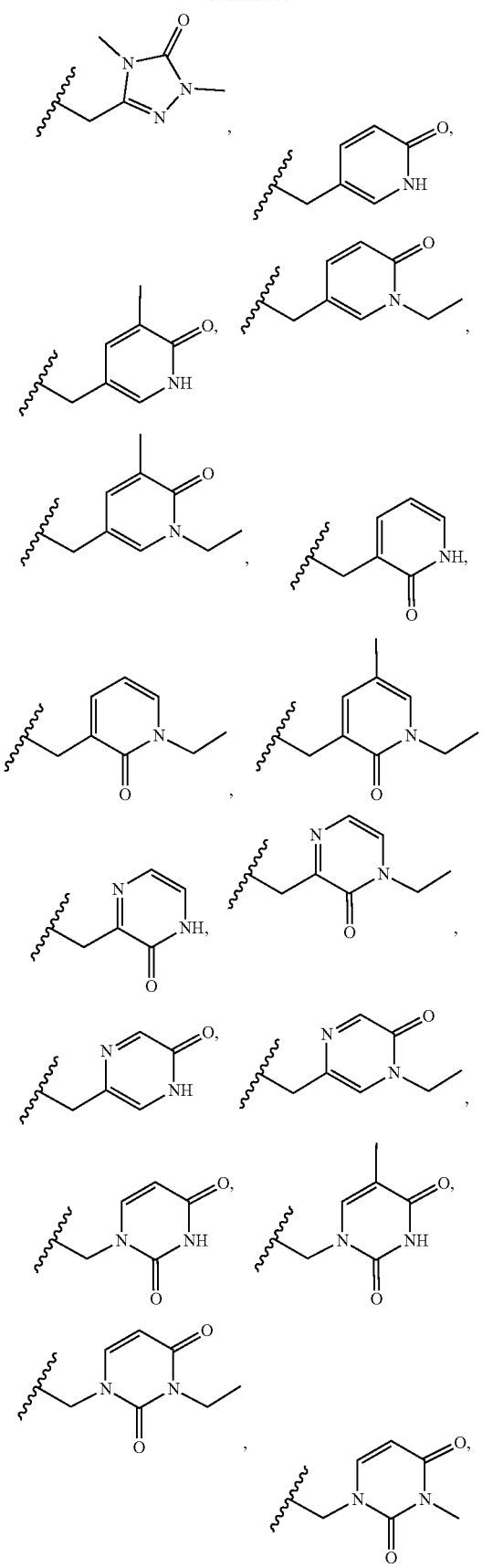
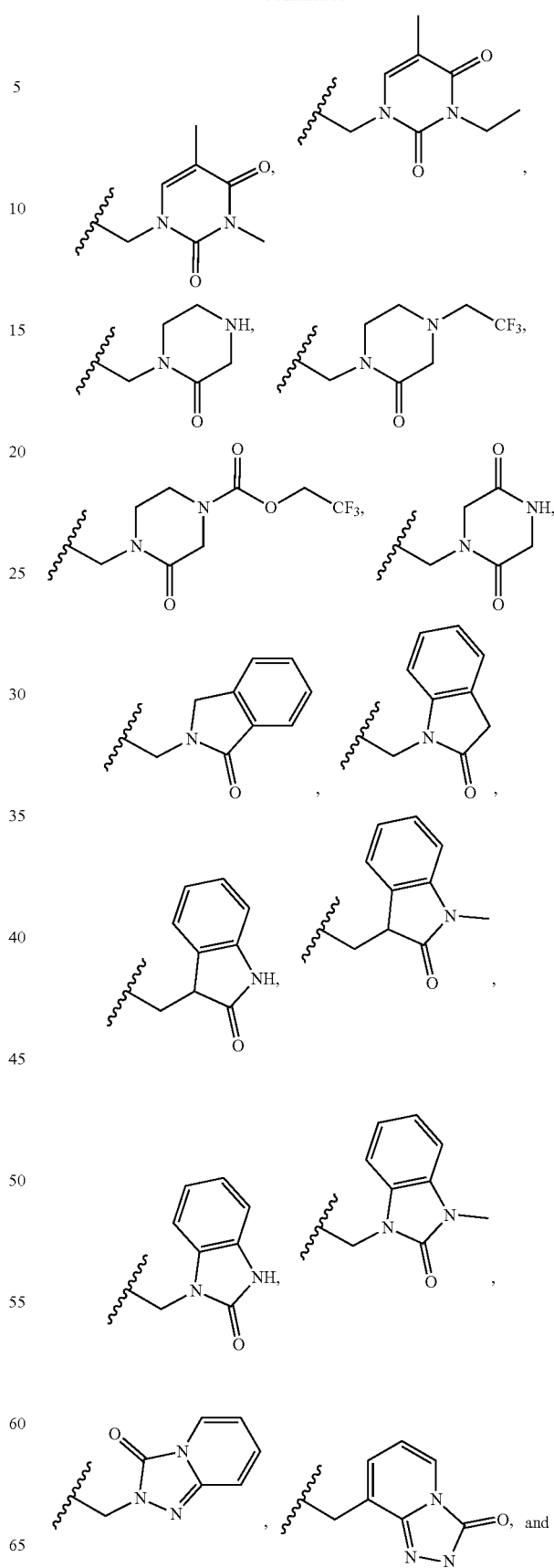

-continued

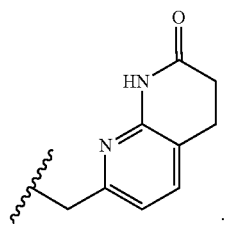

In some embodiments of a compound of formula (I), or a stereoisomer or tautomer thereof, or a pharmaceutically acceptable salt of any of the foregoing, $R^2$ is $C_{1-6}$alkyl, wherein the $C_{1-6}$alkyl of $R^2$ is substituted with one or more $R^a$, wherein $R^a$ is —O—$R^e$. In some embodiments, $R^2$ is methyl, wherein the methyl of $R^2$ is substituted with one or more $R^a$, wherein $R^a$ is —O—$R^e$, wherein $R^e$ is —C(O)-(3-15 membered heterocyclyl). In some embodiments, $R^2$ is

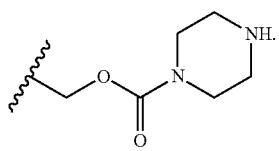 [SMILES: *COC(=O)N1CCNCC1]

In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I'), (I-A), or a stereoisomer or tautomer thereof, or a pharmaceutically acceptable salt of any of the foregoing, $R^2$ is methyl, wherein the methyl of $R^2$ is substituted with one or more $R^a$, wherein $R^a$ is —O—$R^e$, wherein $R^e$ is —C(O)-(3-15 membered heterocyclyl) wherein the —C(O)-(3-15 membered heterocyclyl) of $R^e$ is optionally substituted with one or more $C_{1-6}$alkyl, wherein the $C_{1-6}$alkyl is optionally substituted with one or more halo, $C_{1-6}$alkoxy, or $C_{3-10}$cycloalkyl. In some embodiments, $R^2$ is selected from the group consisting of

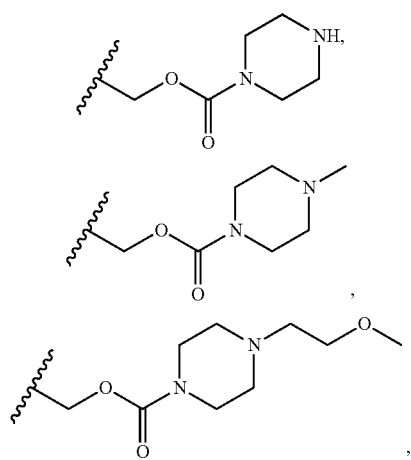

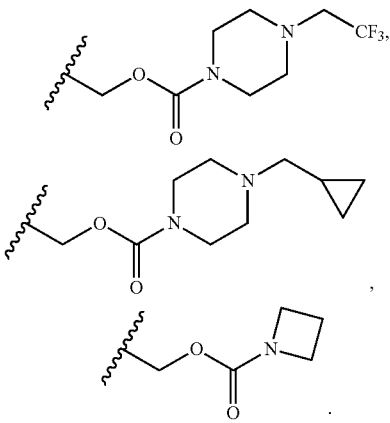

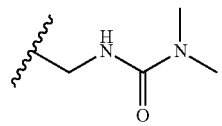

, and

In some embodiments of a compound of formula (I), or a stereoisomer or tautomer thereof, or a pharmaceutically acceptable salt of any of the foregoing, $R^2$ is $C_{1-6}$alkyl, wherein the $C_{1-6}$alkyl of $R^2$ is substituted with one or more $R^a$, wherein $R^a$ is —N($R^c$)($R^d$). In some embodiments, $R^2$ is methyl, wherein the methyl of $R^2$ is substituted with one or more $R^a$, wherein $R^a$ is —N($R^c$)($R^d$). In some embodiments, $R^2$ is methyl, wherein the methyl of $R^2$ is substituted with one or more $R^a$, wherein $R^a$ is —N($R^c$)($R^d$), wherein one of $R^c$ and $R^d$ is H, and the other of $R^c$ and $R^d$ is —C(O)—N($C_{1-6}$alkyl)$_2$. In some embodiments, $R^2$ is

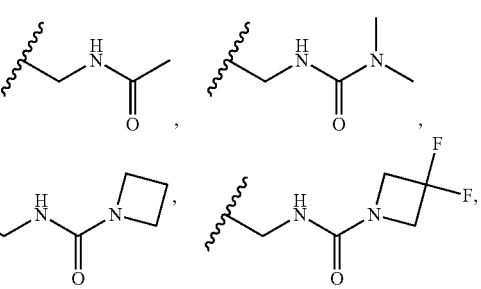

In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing, $R^2$ is methyl, wherein the methyl of $R^2$ is substituted with one or more $R^a$, wherein $R^a$ is —N($R^c$)($R^d$), wherein one of $R^c$ and $R^d$ is H, and the other of $R^c$ and $R^d$, —C(O)—$C_{1-6}$alkyl, —C(O)—N($C_{1-6}$alkyl)$_2$, or —C(O)-(3-15 membered heterocyclyl). In some embodiments, $R^2$ is selected from the group consisting of

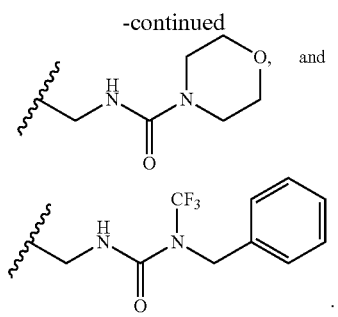

In some embodiments of a compound of formula (I'), (I-A1), or a stereoisomer or tautomer thereof, or a pharmaceutically acceptable salt of any of the foregoing, $R^2$ is ethyl, wherein the ethyl of $R^2$ is substituted with one or more $R^a$, wherein $R^a$ is —N($R^c$)($R^d$), wherein one of $R^c$ and $R^d$ is H, and the other of $R^c$ and $R^d$ is —C(O)—$C_{1-6}$alkyl. In some embodiments, $R^2$ is

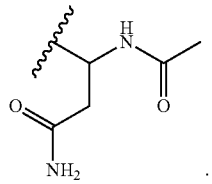 [SMILES: *C(CC(N)=O)NC(C)=O]

In some embodiments of a compound of formula (I'), (I-A1), or a stereoisomer or tautomer thereof, or a pharmaceutically acceptable salt of any of the foregoing, $X^1$ and $X^2$ are each independently H, $C_{1-6}$alkyl, or $C_{1-6}$alkoxy. In some embodiments, $X^1$ and $X^2$ are each H.

In some embodiments of a compound of formula (I'), (I-A1), or a stereoisomer or tautomer thereof, or a pharmaceutically acceptable salt of any of the foregoing, $X^3$ and $X^4$ are each independently H, halo, $C_{1-6}$alkyl, $C_{1-6}$alkoxy, or 5-20 membered heteroaryl, wherein the $C_{1-6}$alkyl of $X^3$ and $X^4$ is optionally substituted with one of more halo.

In some embodiments of a compound of formula (I'), (I-A1), or a stereoisomer or tautomer thereof, or a pharmaceutically acceptable salt of any of the foregoing, $X^5$ is H, $C_{1-6}$alkyl, $C_{1-6}$alkoxy, or $C_{3-10}$cycloalkyl. In some embodiments, $X^5$ is H, $C_{1-4}$alkyl, $C_{1-3}$alkoxy, or $C_{3-6}$cycloalkyl. In some embodiments, $X^5$ is H. In some embodiments, $X^5$ is isopropyl, n-butyl, iso-butyl or t-butyl.

In some embodiments of a compound of formula (I), $X^1$—$X^5$ are each H, and $Q^1$ is a 5-20 membered heteroaryl optionally substituted with one or more halo, $C_{1-6}$alkyl, —NH$_2$, or $C_{3-10}$cycloalkyl, wherein the $C_{3-10}$cycloalkyl is optionally substituted with one or more halo or $C_{1-6}$alkyl. In some embodiments, $X^1$—$X^5$ are each H, and $Q^1$ is a 5-6 membered heteroaryl optionally substituted with one or more halo, $C_{1-6}$alkyl, —NH$_2$, or $C_{3-10}$cycloalkyl, wherein the $C_{3-10}$cycloalkyl is optionally substituted with one or more halo or $C_{1-6}$alkyl. In some embodiments, $X^1$—$X^5$ are each H, and $Q^1$ is a pyridinyl optionally substituted with one or more halo, $C_{1-6}$alkyl, —NH$_2$, or $C_{3-10}$cycloalkyl, wherein the $C_{3-10}$cycloalkyl is optionally substituted with one or more halo or $C_{1-6}$alkyl. In some embodiments, $X^1$—$X^5$ are each H, and $Q^1$ is a pyridinyl optionally substituted with one or more halo, $C_{1-4}$alkyl, —NH$_2$, or $C_{3-4}$cycloalkyl, wherein the $C_{3-4}$cycloalkyl is optionally substituted with one or more halo or $C_{1-6}$alkyl. In some embodiments of the foregoing, $R^m$ is H and $R^n$ is H. In some embodiments of the foregoing, $R^1$ is H. In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I), $X^1$—$X^5$ are each H, and $Q^1$ is phenyl substituted with one or more halo, $C_{1-6}$alkyl, $C_{2-6}$ alkenyl, —NH$_2$, —NH—C(O)—($C_{1-6}$alkyl), —NH—C(O)-(3-15 membered heterocyclyl), or $C_{3-10}$cycloalkyl, wherein the $C_{1-6}$alkyl is optionally substituted with one or more halo, and the $C_{3-10}$cycloalkyl is optionally substituted with one or more halo or $C_{1-6}$alkyl. In some embodiments, $X^1$—$X^5$ are each H, and $Q^1$ is phenyl substituted with one or more halo, $C_{1-6}$alkyl, $C_{2-6}$ alkenyl, —NH$_2$, —NH—C(O)—($C_{1-6}$alkyl), —NH—C(O)-(3-10 membered heterocyclyl), or $C_{3-10}$cycloalkyl, wherein the $C_{1-6}$alkyl is optionally substituted with one or more halo, and the $C_{3-10}$cycloalkyl is optionally substituted with one or more halo or $C_{1-6}$alkyl. In some embodiments, $X^1$—$X^5$ are each H, and $Q^1$ is phenyl substituted with one or more halo, $C_{1-4}$alkyl, $C_{2-4}$ alkenyl, —NH$_2$, —NH—C(O)—($C_{1-4}$alkyl), —NH—C(O)-(3-10 membered heterocyclyl), or $C_{3-4}$cycloalkyl, wherein the $C_{1-4}$alkyl is optionally substituted with one or more halo, and the $C_{3-4}$cycloalkyl is optionally substituted with one or more halo or $C_{1-6}$alkyl. In some variations, the embodiments provided herein also apply to a compound of formula (I') or a stereoisomer or tautomer thereof, or a pharmaceutically acceptable salt of any of the foregoing, or any variation or embodiment thereof.

In some embodiments of the foregoing, $R^1$ is H. In some embodiments of the foregoing, $R^m$ is H and $R^n$ is H. In some embodiments of the foregoing, $R^k$ is taken together with either $R^m$ or $R^n$, and the atoms to which they are attached, to form cyclopropyl. In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I') or (I), or any embodiment or variation thereof, such as a compound of formula (I-A), (I-A1), (I-A2), (I-A3), (I-A4), (I-B), (I-B1), (I-B2), (I-C), (I-D), (I-D1), (I-D2), (I-E), (I-F), (I-G), or (I-H), or a stereoisomer or tautomer thereof, or a pharmaceutically acceptable salt of any of the foregoing, the moiety represented by

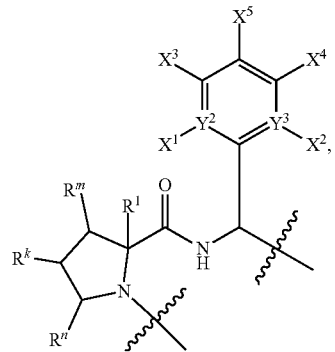

with carbon atoms bearing moieties

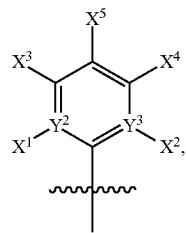

$R^k$, $R^m$, $R^n$, and $R^1$, has a stereochemical configuration of the formula

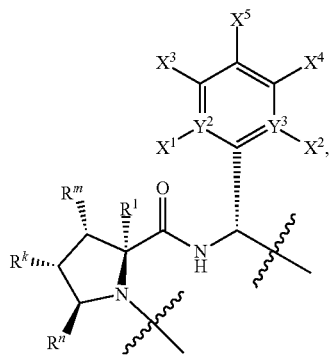

wherein $X^1$, $X^2$, $X^3$, $X^4$, $X^5$, $Y^2$, $Y^3$, $R^1$, $R^k$, $R^m$ and $R^n$ are as defined elsewhere herein.

In some embodiments of a compound of formula (I') or (I), or any embodiment or variation thereof, such as a compound of formula (I-A), (I-A1), (I-A2), (I-A3), (I-A4), (I-B), (I-B1), (I-B2), (I-C), (I-D), (I-D1), (I-D2), (I-E), (I-F), (I-G), or (I-H), or a stereoisomer or tautomer thereof, or a pharmaceutically acceptable salt of any of the foregoing, the moiety represented by

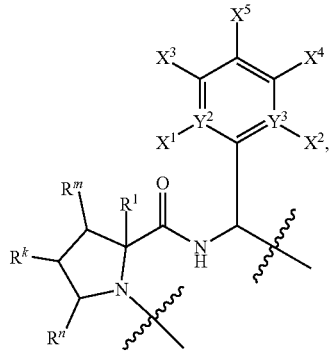

with carbon atoms bearing moieties

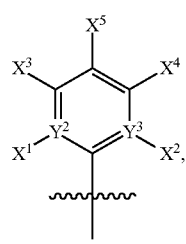

$R^k$, $R^m$, $R^n$, and $R^1$, has a stereochemical configuration of the formula

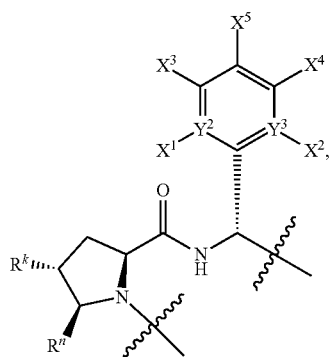

wherein $R^1$ and $R^m$ are both H, and $X^1$, $X^2$, $X^3$, $X^4$, $X^5$, $Y^2$, $Y^3$, $R^k$, and $R^n$ are as defined elsewhere herein.

In some embodiments of a compound of formula (I') or (I), or any embodiment or variation thereof, such as a compound of formula (I-A), (I-A1), (I-A2), (I-A3), (I-A4), (I-B), (I-B1), (I-B2), (I-C), (I-D), (I-D1), (I-D2), (I-E), (I-F), (I-G), or (I-H), or a stereoisomer or tautomer thereof, or a pharmaceutically acceptable salt of any of the foregoing, the moiety represented by

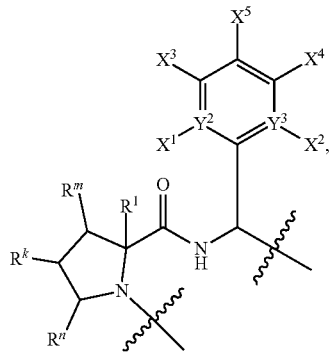

with carbon atoms bearing moieties

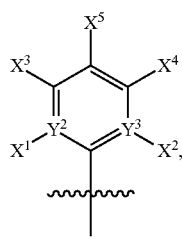

$R^k$, $R^m$, $R^n$, and $R^1$, has a stereochemical configuration of the formula

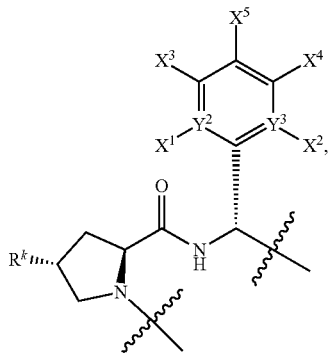

wherein $R^1$, $R^m$, and $R^n$ are each H, and $X^1$, $X^2$, $X^3$, $X^4$, $X^5$, $Y^2$, $Y^3$, and $R^k$ are as defined elsewhere herein.

In some embodiments of a compound of formula (I') or (I), or any embodiment or variation thereof, such as a compound of formula (I-A), (I-A1), (I-A2), (I-A3), (I-A4), (I-B), (I-B1), (I-B2), (I-C), (I-D), (I-D1), (I-D2), (I-E), (I-F), (I-G), or (I-H), or a stereoisomer or tautomer thereof, or a pharmaceutically acceptable salt of any of the foregoing, the moiety represented by

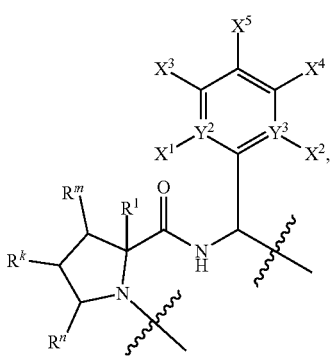

with carbon atoms bearing moieties

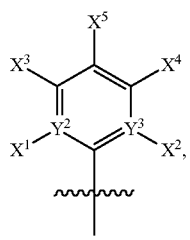

$R^k$, $R^m$, $R^n$, and $R^1$, has a stereochemical configuration of the formula

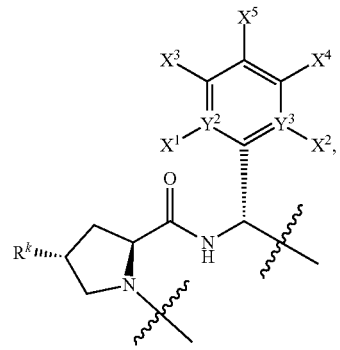

wherein $R^1$, $R^m$, and $R^n$ are each H, $R^k$ is halo or H, and $X^1$, $X^2$, $X^3$, $X^4$, $X^5$, $Y^2$, and $Y^3$ are as defined elsewhere herein. In some embodiments, the moiety $R^k$ is fluoro.

In some embodiments of a compound of formula (I') or (I), or any embodiment or variation thereof, such as a compound of formula (I-A), (I-A1), (I-A2), (I-A3), (I-A4), (I-B), (I-B1), (I-B2), (I-C), (I-D), (I-D1), (I-D2), (I-E), (I-F), (I-G), or (I-H), or a stereoisomer or tautomer thereof, or a pharmaceutically acceptable salt of any of the foregoing, the moiety represented by

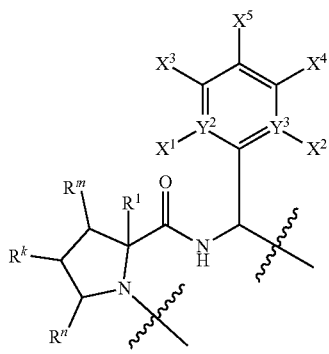

with carbon atoms bearing moieties

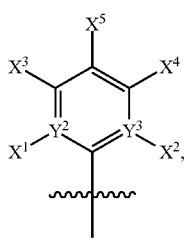

$R^k$, $R^m$, $R^n$, and $R^1$, has a stereochemical configuration of the formula

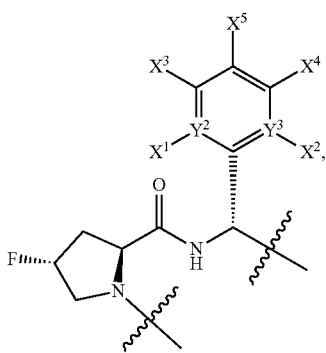

wherein $R^1$, $R^m$, and $R^n$ are each H, $R^k$ is fluoro, and $X^1$, $X^2$, $X^3$, $X^4$, $X^5$, $Y^2$, and $Y^3$ are as defined elsewhere herein. In some embodiments $Y^2$ and $Y^3$ are each C. In some embodiments one $Y^2$ and $Y^3$ is C and the other of $Y^2$ and $Y^3$ is N.

In some embodiments, provided herein is a compound of formula (I), or a stereoisomer or tautomer thereof, or a pharmaceutically acceptable salt thereof, wherein the compound is a compound of formula (I-A):

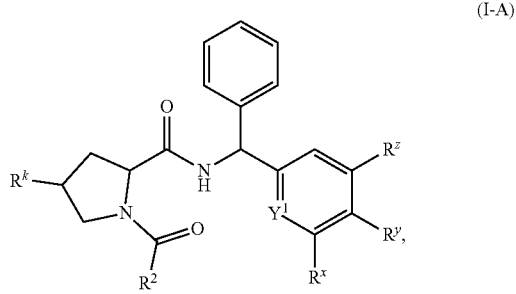

(I-A)

or a stereoisomer or tautomer thereof, or a pharmaceutically acceptable salt of any of the foregoing, wherein $Y^1$ is CH or N; $R^x$ and $R^z$ are independently H, halo, $C_{1-6}$alkyl, or —$NH_2$, wherein, when $Y^1$ is CH, the $C_{1-6}$alkyl of $R^x$ or $R^z$ may be optionally substituted with one or more halo; and $R^y$ is (i) $C_{1-6}$alkyl, (ii), $C_{2-6}$alkenyl, or (iii) $C_{3-10}$cycloalkyl, wherein the $C_{3-10}$cycloalkyl is optionally substituted with one or more halo or $C_{1-6}$alkyl. In some variations, $R^2$, $R^k$, $R^x$, $R^y$, and $R^z$ of formula (I-A1) are as defined for a compound of formula (I'), or a stereoisomer or tautomer thereof, or a pharmaceutically acceptable salt of any of the foregoing, or any variation or embodiment thereof, wherein $Y^1$ is $CR^x$ or N; wherein, when the ring bearing $R^x$, $R^y$ and $R^z$ is phenyl, $R^x$, $R^y$ and $R^z$ is H, halo, $C_{1-6}$alkyl, $C_{2-6}$alkenyl, —$NH_2$, —NH—C(O)—($C_{1-6}$alkyl), —NH—C(O)-(3-15 membered heterocyclyl), $C_{3-10}$cycloalkyl, or 5-20 membered heteroaryl, wherein the $C_{1-6}$alkyl is optionally substituted with one or more halo, —NH—C(O)—NH($C_{1-6}$alkyl), —NH—C(O)—$C_{1-6}$alkyl, or —NH—C(O)—$C_{1-6}$alkoxy, the $C_{3-10}$cycloalkyl is optionally substituted with one or more halo or $C_{1-6}$alkyl, and the 5-20 membered heteroaryl is optionally substituted with one or more $C_{1-6}$alkyl; and wherein when the ring bearing $R^x$, $R^y$ and $R^z$ is pyridyl, $R^x$, $R^y$ and $R^z$ are each independently H, halo, $C_{1-6}$alkyl, $C_{2-6}$alkenyl, $C_{1-6}$alkoxy, —$NH_2$, or $C_{3-10}$cycloalkyl, wherein, the $C_{1-6}$alkyl is optionally substituted with one or more halo, and the $C_{3-10}$cycloalkyl is optionally substituted with one or more halo or $C_{1-6}$alkyl.

In some embodiments of a compound of formula (I-A), or a stereoisomer or tautomer thereof, or a pharmaceutically acceptable salt of any of the foregoing, $R^x$ and $R^z$ are independently H, fluoro, chloro, or methyl; and $R^y$ is (i) isopropyl, (ii) isopropenyl, or (iii) $C_{3-4}$cycloalkyl, wherein the $C_{3-4}$cycloalkyl is optionally substituted with one or more fluoro or methyl. In some embodiments, $R^x$ and $R^z$ are independently H, fluoro, chloro, or methyl; and $R^y$ is (i) isopropyl or (ii) $C_{3-4}$cycloalkyl, wherein the $C_{3-4}$cycloalkyl is optionally substituted with one or more fluoro or methyl. In some embodiments, $R^x$ is H, fluoro, chloro, or methyl; $R^z$ is H; and $R^y$ is (i) isopropyl, or (ii) $C_{3-4}$cycloalkyl, wherein the $C_{3-4}$cycloalkyl is optionally substituted with one or more fluoro or methyl. In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I'), (I-A), or a stereoisomer or tautomer thereof, or a pharmaceutically acceptable salt of any of the foregoing, $R^x$ is fluoro or methyl optionally substituted with one or more fluoro; $R^y$ is (i) isopropyl (ii) isopropenyl or (iii) $C_{3-4}$cycloalkyl optionally substituted with one or more halo or $C_{1-6}$alkyl or (iv) butyl; and $R^z$ is fluoro or methyl; provided that at least one of $R^x$ and $R^z$ is halo, $CF_2$ or $CF_3$.

In some embodiments of a compound of formula (I-A), or a stereoisomer or tautomer thereof, or a pharmaceutically acceptable salt of any of the foregoing, $R^k$ is H or halo. In some embodiments of a compound of formula (I-A), or a stereoisomer or tautomer thereof, or a pharmaceutically acceptable salt of any of the foregoing, $R^k$ is H or fluoro. In some embodiments of a compound of formula (I-A), or a stereoisomer or tautomer thereof, or a pharmaceutically acceptable salt of any of the foregoing, $R^k$ is fluoro. In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I-A), or a stereoisomer or tautomer thereof, or a pharmaceutically acceptable salt of any of the foregoing, $R^2$ is $C_{1-6}$alkyl, wherein the $C_{1-6}$alkyl of $R^2$ is optionally substituted with one or more $R^a$. In some embodiments, $R^2$ is $C_{1-6}$alkyl, wherein the $C_{1-6}$alkyl of $R^2$ is substituted with one or more $R^a$, wherein $R^a$ is —OH or 5-20 membered heteroaryl, wherein the 5-20 membered heteroaryl of $R^a$ is optionally substituted with one or more $R^b$. In some embodiments, $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more $R^b$. In some embodiments, $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more $C_{1-6}$alkyl, wherein the $C_{1-6}$alkyl is optionally substituted with one or more halo, —$NH_2$, —NH($C_{1-6}$alkyl), —N($C_{1-6}$alkyl)$_2$, —NH—C(O) $C_{1-6}$alkyl, or —NH—C(O)—$C_{1-6}$alkoxy. In some embodiments, $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more methyl, wherein the methyl is optionally substituted with one or more fluoro.

In some embodiments of a compound of formula (I'), (I-A), or a stereoisomer or tautomer thereof, or a pharmaceutically acceptable salt of any of the foregoing, $R^2$ is 5-20 membered heteroaryl or —(C$_{1-4}$alkyl)(5-20 membered heteroaryl), wherein the C$_{1-4}$ alkyl is optionally substituted with one or more or more —OH, halo, —NH$_2$, —NH(C$_{1-6}$alkyl), —N(C$_{1-6}$alkyl)$_2$, and wherein the 5-20 membered heteroaryl is optionally substituted with one or more R$^s$. In some embodiments, R$^s$ is halo, C$_{1-6}$alkyl, C$_{1-6}$alkoxy, —NH$_2$, —NH(C$_{1-6}$alkyl), —N(C$_{1-6}$alkyl)$_2$, —NH—C(O)—C$_{1-6}$alkyl, C$_{6-20}$aryl, C$_{3-10}$cycloalkyl, 3-15 membered heterocyclyl, 5-20 membered heteroaryl, or —C(O)—C$_{1-6}$alkoxy. In some embodiments, the C$_{1-6}$alkyl of R$^s$ is optionally substituted with one or more halo, C$_{1-6}$alkoxy, —NH$_2$, —NH(C$_{1-6}$alkyl), —N(C$_{1-6}$alkyl)$_2$, —NH—C(O)C$_{1-6}$alkyl, or —NH—C(O)—C$_{1-6}$alkoxy, and the 3-15-membered heterocyclyl of R$^s$ is optionally substituted with one or more halo or —C(O)—C$_{1-6}$alkoxy.

In some embodiments of a compound of formula (I-A), or a stereoisomer or tautomer thereof, or a pharmaceutically acceptable salt of any of the foregoing, R$^2$ is selected from the group consisting of

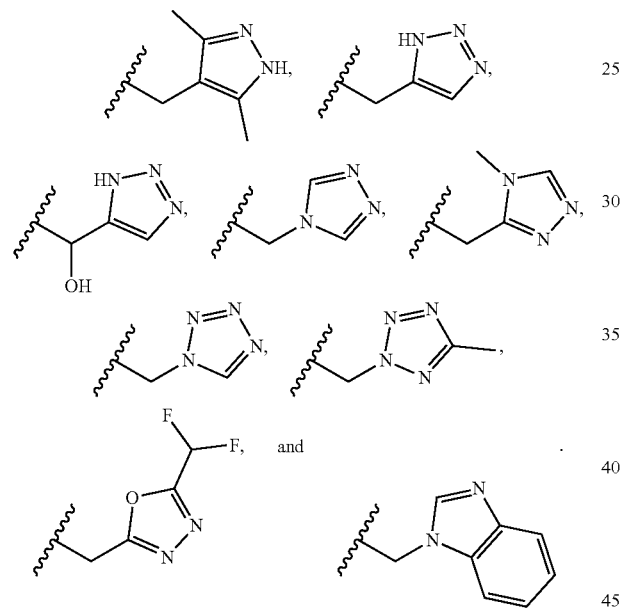

In some embodiments, R$^2$ is

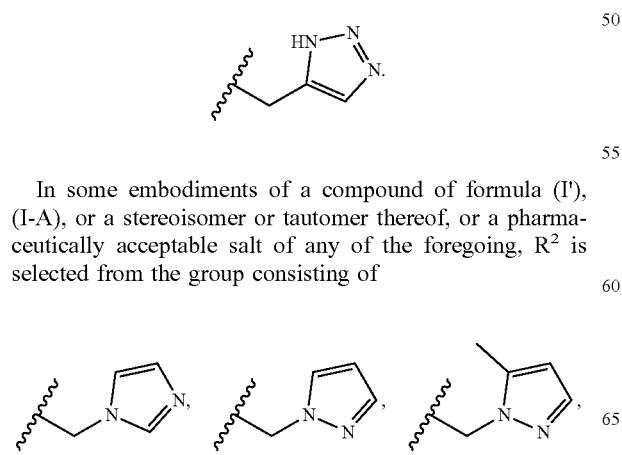

In some embodiments of a compound of formula (I'), (I-A), or a stereoisomer or tautomer thereof, or a pharmaceutically acceptable salt of any of the foregoing, R$^2$ is selected from the group consisting of

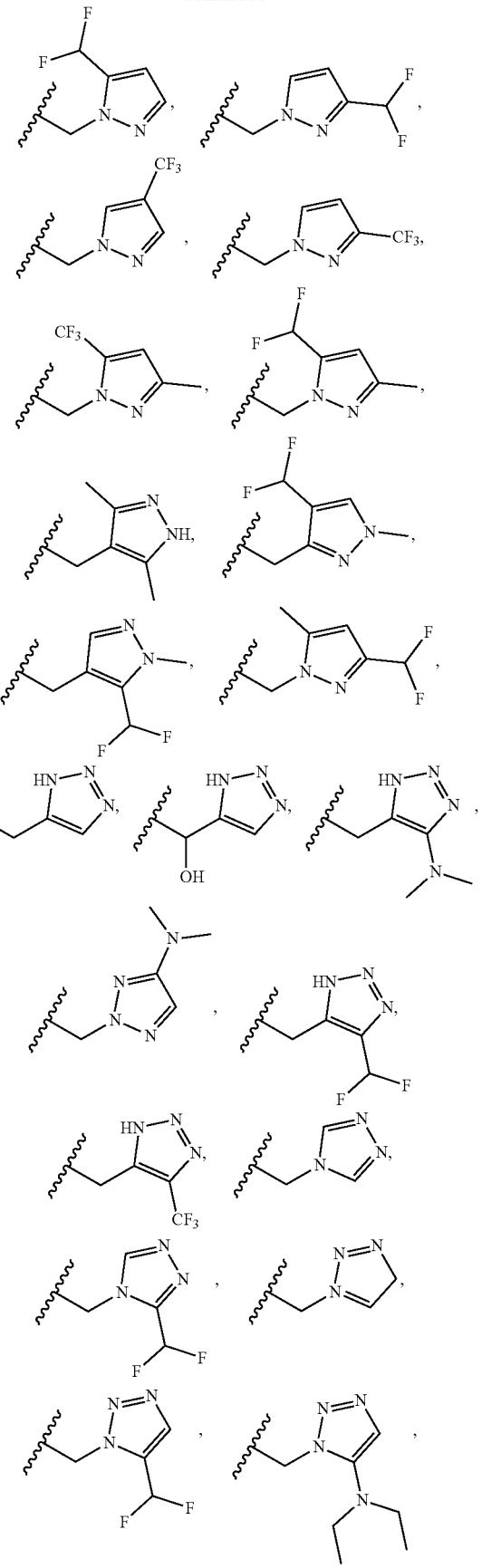

-continued

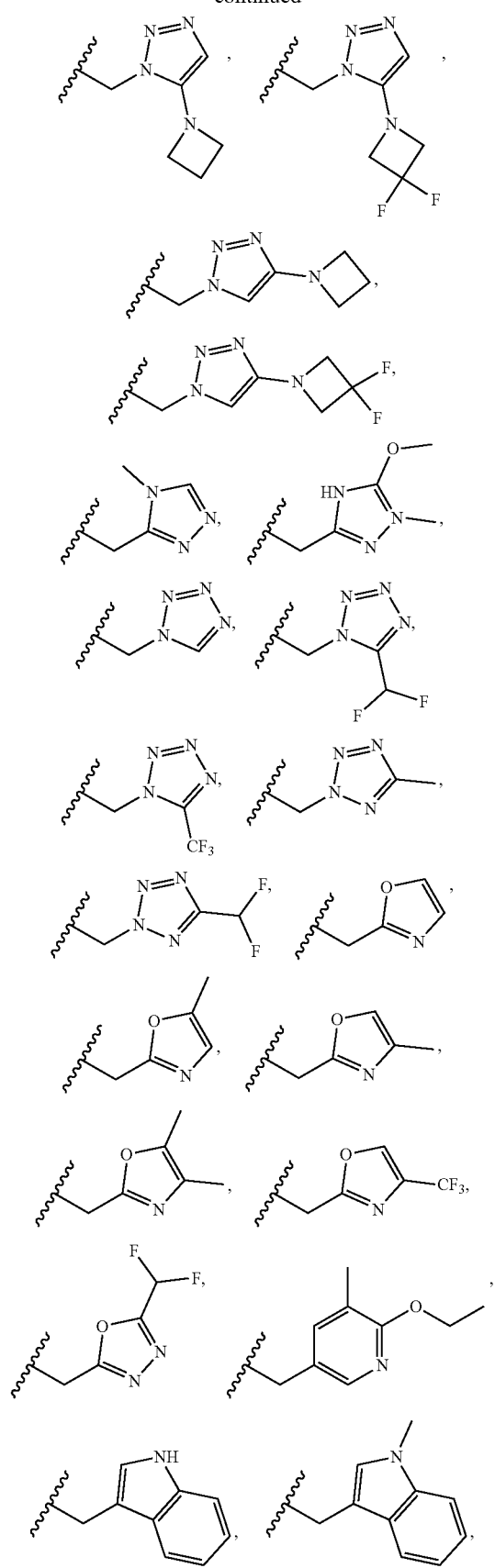

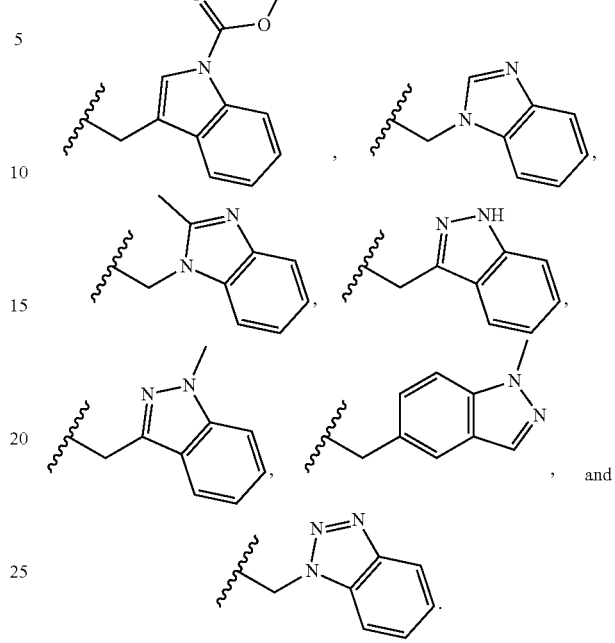

In some embodiments, R² is

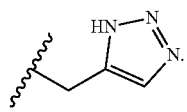

In some embodiments of a compound of formula (I-A), or a stereoisomer or tautomer thereof, or a pharmaceutically acceptable salt of any of the foregoing, R² is $C_{1-6}$alkyl, wherein the $C_{1-6}$alkyl of R² is substituted with one or more $R^a$, wherein $R^a$ is 3-15 membered heterocyclyl, wherein the 3-15 membered heterocyclyl of $R^a$ is optionally substituted with one or more $R^c$. In some embodiments, R² is methyl, wherein the methyl of R² is substituted with one or more $R^a$, wherein $R^a$ is 3-15 membered heterocyclyl, wherein the 3-15 membered heterocyclyl of $R^a$ is optionally substituted with one or more $R^c$. In some embodiments, R² is methyl, wherein the methyl of R² is substituted with one or more $R^a$, wherein $R^a$ is 3-8 membered heterocyclyl, wherein the 3-8 membered heterocyclyl of $R^a$ is optionally substituted with one or more $R^c$. In some embodiments, R² is methyl, wherein the methyl of R² is substituted with one or more $R^a$, wherein $R^a$ is 3-8 membered heterocyclyl, wherein the 3-8 membered heterocyclyl of $R^a$ is optionally substituted with one or more oxo or $C_{1-6}$alkyl. In some embodiments, R² is

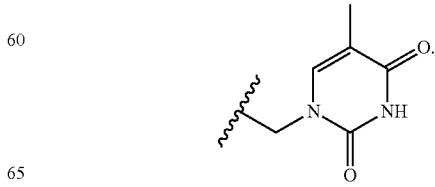

In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I'), (I-A), or a stereoisomer or tautomer thereof, or a pharmaceutically acceptable salt of any of the foregoing, In some embodiments, $R^2$ is methyl, wherein the methyl of $R^2$ is substituted with one or more $R^a$, wherein $R^a$ is 3-8 membered heterocyclyl, wherein the 3-8 membered heterocyclyl of $R^a$ is optionally substituted with one or more $R^c$, wherein $R^c$ is oxo, $C_{1-6}$alkyl, or —C(O)—$C_{1-6}$alkoxy, wherein the $C_{1-6}$alkyl of $R^c$ is optionally substituted with one or more halo, and the —C(O)—$C_{1-6}$alkoxy of $R^c$ is optionally substituted with one or more halo. In some embodiments, $R^2$ is selected from the group consisting of

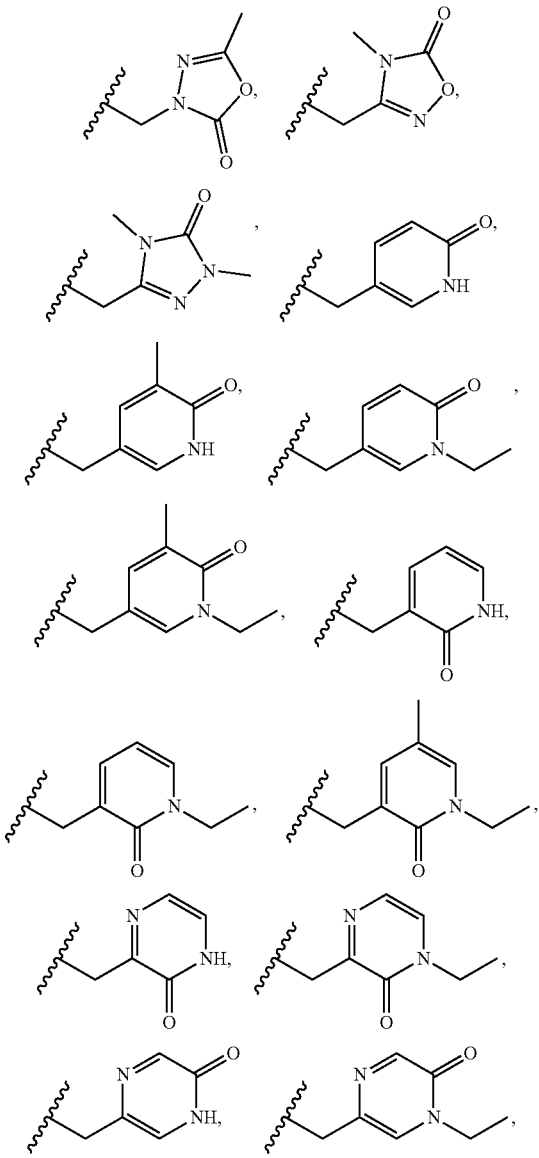

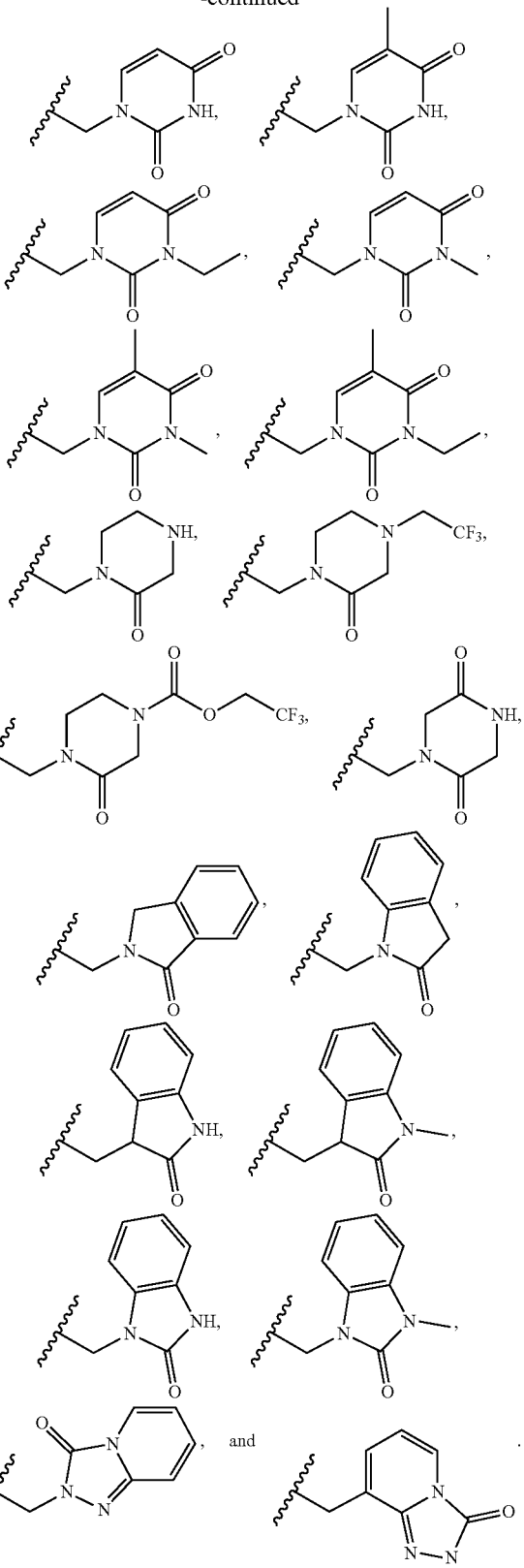

In some embodiments of a compound of formula (I-A), or a stereoisomer or tautomer thereof, or a pharmaceutically acceptable salt of any of the foregoing, $R^2$ is $C_{1-6}$alkyl, wherein the $C_{1-6}$alkyl of $R^2$ is substituted with one or more $R^a$, wherein $R^a$ is —O—$R^e$. In some embodiments, $R^2$ is methyl, wherein the methyl of $R^2$ is substituted with one or more $R^a$, wherein $R^a$ is —O—$R^e$. In some embodiments, $R^2$ is methyl, wherein the methyl of $R^2$ is substituted with one or more $R^a$, wherein $R^a$ is —O—$R^e$, wherein $R^e$ is —C(O)-(3-15 membered heterocyclyl). In some embodiments, $R^2$ is

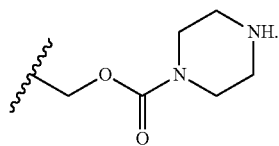 [SMILES: *COC(=O)N1CCNCC1]

In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I'), (I-A), or a stereoisomer or tautomer thereof, or a pharmaceutically acceptable salt of any of the foregoing, $R^2$ is methyl, wherein the methyl of $R^2$ is substituted with one or more $R^a$, wherein $R^a$ is —O—$R^e$, wherein $R^e$ is —C(O)-(3-15 membered heterocyclyl) wherein the —C(O)-(3-15 membered heterocyclyl) of $R^e$ is optionally substituted with one or more $C_{1-6}$alkyl, wherein the $C_{1-6}$alkyl is optionally substituted with one or more halo, $C_{1-6}$alkoxy, or $C_{3-10}$cycloalkyl. In some embodiments, $R^2$ is selected from the group consisting of

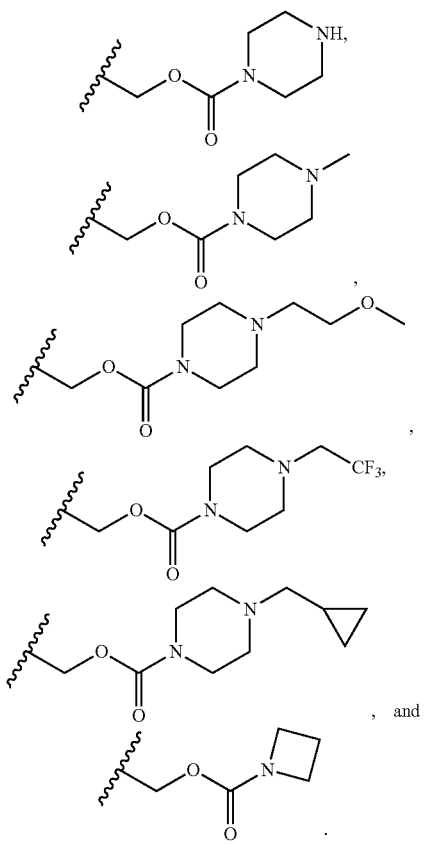

In some embodiments of a compound of formula (I-A), or a stereoisomer or tautomer thereof, or a pharmaceutically acceptable salt of any of the foregoing, $R^2$ is $C_{1-6}$alkyl, wherein the $C_{1-6}$alkyl of $R^2$ is substituted with one or more $R^a$, wherein $R^a$ is —N($R^c$)($R^d$). In some embodiments, $R^2$ is methyl, wherein the methyl of $R^2$ is substituted with one or more $R^a$, wherein $R^a$ is —N($R^c$)($R^d$). In some embodiments, $R^2$ is methyl, wherein the methyl of $R^2$ is substituted with one or more $R^a$, wherein $R^a$ is —N($R^c$)($R^d$), wherein one of $R^c$ and $R^d$ is H, and the other of $R^c$ and $R^d$ is —C(O)—N($C_{1-6}$alkyl)$_2$. In some embodiments, $R^2$ is

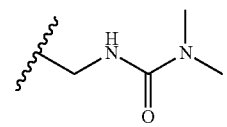

In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I'), (I-A1), or a stereoisomer or tautomer thereof, or a pharmaceutically acceptable salt of any of the foregoing, $R^2$ is methyl, wherein the methyl of $R^2$ is substituted with one or more $R^a$, wherein $R^a$ is —N($R^c$)($R^d$), wherein one of $R^c$ and $R^d$ is H, and the other of $R^c$ and $R^d$, —C(O)—$C_{1-6}$alkyl, —C(O)—N($C_{1-6}$alkyl)$_2$, or —C(O)-(3-15 membered heterocyclyl). In some embodiments, $R^2$ is selected from the group consisting of

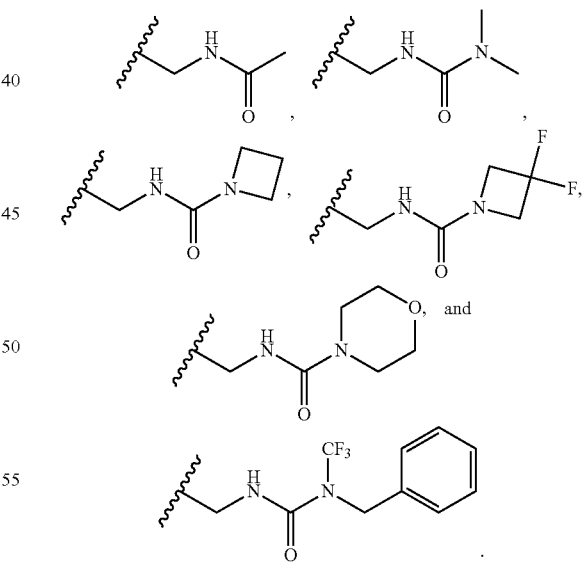

In some embodiments of a compound of formula (I'), (I-A1), or a stereoisomer or tautomer thereof, or a pharmaceutically acceptable salt of any of the foregoing, $R^2$ is ethyl, wherein the ethyl of $R^2$ is substituted with one or more $R^a$, wherein $R^a$ is —N($R^c$)($R^d$), wherein one of $R^c$ and $R^d$ is H, and the other of $R^c$ and $R^d$, is —C(O)—$C_{1-6}$alkyl. In some embodiments, $R^2$ is

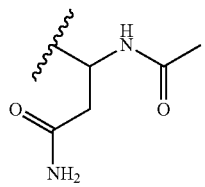

In some embodiments of a compound of formula (I-A), or a stereoisomer or tautomer thereof, or a pharmaceutically acceptable salt of any of the foregoing, $Y^1$ is CH or N; $R^x$ and $R^z$ are independently H or halo; $R^y$ is $C_{1-6}$alkyl or $C_{3-10}$cycloalkyl; $R^k$ is H or halo; and $R^2$ is selected from (i) to (iii):

(i) $C_{1-6}$alkyl, wherein the $C_{1-6}$alkyl of $R^2$ is substituted with one or more $R^a$, wherein $R^a$ is
  (a) —OH,
  (b) $C_{6-20}$aryl, wherein the $C_{6-20}$aryl of $R^a$ is optionally substituted with one or more halo, cyano, $C_{1-6}$alkoxy, or —NH—C(O)—$C_{1-6}$alkyl,
  (c) 3-15 membered heterocyclyl, wherein the 3-15 membered heterocyclyl of $R^a$ is optionally substituted with one or more $R^c$, wherein
    $R^c$ is halo, oxo, $C_{1-6}$alkyl, $C_{1-6}$alkoxy, —C(O)—$C_{1-6}$alkyl, or —C(O)—$C_{1-6}$alkoxy, wherein
    the $C_{1-6}$alkyl of $R^c$ is optionally substituted with one or more halo or $C_{2-6}$alkynyl, and
    the —C(O)—$C_{1-6}$alkoxy of $R^c$ is optionally substituted with one or more halo,
  (d) —N($R^c$)($R^d$), wherein $R^c$ and $R^d$ of N($R^c$)($R^d$) are, independently of each other, H, $C_{1-6}$alkyl, —C(O)—$C_{1-6}$alkyl, —C(O)—$C_{1-6}$alkoxy, —C(O)—$NH_2$, —C(O)—NH($C_{1-6}$alkyl), —C(O)—N($C_{1-6}$alkyl)$_2$, —C(O)-(3-15 membered heterocyclyl), —$CH_2$—C(O)—$NH_2$, 3-15 membered heterocyclyl, or 5-20 membered heteroaryl, wherein
    the $C_{1-6}$alkyl of $R^c$ or $R^d$ is optionally substituted with one or more —C(O)—$NH_2$,
    the —C(O)—$C_{1-6}$alkyl of $R^c$ or $R^d$ is optionally substituted with one or more halo,
    the 3-15 membered heterocyclyl and the 5-20 membered heteroaryl of $R^c$ or $R^d$ are independently optionally substituted with one or more $C_{1-6}$alkyl,
    the —C(O)-(3-15 membered heterocyclyl) of $R^c$ or $R^d$ is optionally substituted with one or more halo, —C(O)—$C_{1-6}$alkoxy, or $C_{1-6}$alkyl, wherein the $C_{1-6}$alkyl is optionally substituted with one or more halo, $C_{1-6}$alkoxy, or $C_{3-10}$cycloalkyl, and
    the $C_{1-6}$alkyl of the —C(O)—N($C_{1-6}$alkyl)$_2$ of $R^c$ or $R^d$ are, independently of each other, optionally substituted with one or more halo or $C_{6-20}$aryl,
  (e) —O—$R^e$, wherein $R^e$ is $C_{1-6}$alkyl, $C_{6-20}$aryl, —C(O)-(3-15 membered heterocyclyl), —C(O)—N—($C_{1-6}$alkyl)$_2$, or 5-20 membered heteroaryl, wherein
    the $C_{1-6}$alkyl of $R^e$ is optionally substituted with one or more $C_{1-6}$alkoxy, wherein the $C_{1-6}$alkoxy is optionally substituted with one or more $C_{2-6}$alkynyl,
    the $C_{6-20}$aryl of $R^e$ is optionally substituted with one or more $C_{1-6}$alkyl, and
    the —C(O)-(3-15 membered heterocyclyl) of $R^e$ is optionally substituted with one or more $C_{1-6}$alkyl, $C_{1-6}$alkoxy, or —C(O)—$C_{1-6}$alkoxy, wherein the $C_{1-6}$alkyl is optionally substituted with one or more halo, $C_{1-6}$alkoxy, or $C_{3-10}$cycloalkyl, or
  (f) —C(O)—$R^e$, wherein $R^e$ of —C(O)—$R^e$ is —$NH_2$, —OH, or 3-15 membered heterocyclyl, (ii) 3-15 membered heterocyclyl, wherein the 3-15 membered heterocyclyl of $R^2$ is optionally substituted with one or more halo, oxo, $C_{1-6}$alkyl, —C(O)—$C_{1-6}$alkyl, or 5-20 membered heteroaryl, (iii) 5-20 membered heteroaryl or —($C_{1-4}$alkyl)(5-20 membered heteroaryl), wherein the $C_{1-4}$ alkyl is optionally substituted with one or more or more —OH, halo, —$NH_2$, —NH($C_{1-6}$alkyl), —N($C_{1-6}$alkyl)$_2$, and wherein the 5-20 membered heteroaryl is optionally substituted with one or more $R^s$, wherein
  $R^s$ is halo, $C_{1-6}$alkyl, $C_{1-6}$alkoxy, —$NH_2$, —NH($C_{1-6}$alkyl), —N($C_{1-6}$alkyl)$_2$, —NH—C(O)—$C_{1-6}$alkyl, $C_{6-20}$aryl, $C_{3-10}$cycloalkyl, 3-15 membered heterocyclyl, 5-20 membered heteroaryl, or —C(O)—$C_{1-6}$alkoxy, wherein
    the $C_{1-6}$alkyl of $R^s$ is optionally substituted with one or more halo, $C_{1-6}$alkoxy, —$NH_2$, —NH($C_{1-6}$alkyl), —N($C_{1-6}$alkyl)$_2$, —NH—C(O)$C_{1-6}$alkyl, or —NH—C(O)—$C_{1-6}$alkoxy, and
    the 3-15-membered heterocyclyl of $R^s$ is optionally substituted with one or more halo or —C(O)—$C_{1-6}$alkoxy.

In some embodiments of formula (I-A), $Y^1$ is CH or N; $R^x$ and $R^z$ are independently H or halo; $R^y$ is $C_{1-6}$alkyl or $C_{3-10}$cycloalkyl; $R^k$ is H or halo; $R^2$ is $C_{1-6}$alkyl, wherein the $C_{1-6}$alkyl of $R^2$ is substituted with one or more $R^a$; $R^a$ is
(a) —OH,
(b) $C_{6-10}$aryl optionally substituted with one or more halo, cyano, $C_{1-3}$alkoxy, or —NH—C(O)—$C_{1-3}$alkyl, or
(c) 3-15 membered heterocyclyl optionally substituted with one or more halo, oxo, $C_{1-6}$alkyl, $C_{1-6}$alkoxy, —C(O)—$C_{1-6}$alkyl, or —C(O)—$C_{1-6}$alkoxy.

In some embodiments of formula (I-A), $Y^1$ is CH or N; $R^x$ and $R^z$ are independently H or halo; $R^y$ is $C_{1-3}$alkyl or $C_{3-5}$cycloalkyl; $R^k$ is halo; $R^2$ is $C_{1-4}$alkyl substituted with one or more $R^a$; $R^a$ is
(a) —OH,
(b) $C_{6-10}$aryl optionally substituted with one or more halo, cyano, $C_{1-3}$alkoxy, or —NH—C(O)—$C_{1-3}$alkyl, or
(c) $C_{3-8}$heteroaryl optionally substituted with one or more halo, oxo, $C_{1-6}$alkyl, $C_{1-6}$alkoxy, —C(O)—$C_{1-6}$alkyl, or —C(O)—$C_{1-6}$alkoxy.

In some embodiments, provided herein is a compound of formula (I) or formula (I-A), or a stereoisomer or tautomer thereof, or a pharmaceutically acceptable salt thereof, wherein the compound is of formula (I-A1):

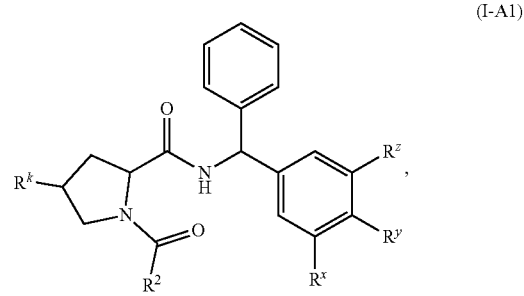

(I-A1)

or a stereoisomer or tautomer thereof, or a pharmaceutically acceptable salt of any of the foregoing, wherein $R^x$ and $R^z$ are independently H, halo, $C_{1-6}$alkyl, or —$NH_2$, wherein the $C_{1-6}$alkyl is optionally substituted with one or more halo. In some embodiments, $R^x$ is H, halo, or $C_{1-6}$alkyl; $R^y$ is (i) $C_{1-6}$alkyl, (ii) $C_{2-6}$alkenyl, or (ii) $C_{3-10}$cycloalkyl; and $R^z$ is H, halo or $C_{1-6}$alkyl. In some embodiments, $R^z$ is H. In some embodiments, at least one of $R^x$ and $R^z$ is halo. In some variations, $R^2$, $R^k$, $R^x$, $R^y$, and $R^z$ of formula (I-A1) are as defined for a compound of formula (I'), or a stereoisomer or tautomer thereof, or a pharmaceutically acceptable salt of any of the foregoing, or any variation or embodiment thereof, wherein $R^x$, $R^y$ and $R^z$ are independently H, halo, $C_{1-6}$alkyl, $C_{2-6}$alkenyl, —$NH_2$, —NH—C(O)—($C_{1-6}$alkyl), —NH—C(O)-(3-15 membered heterocyclyl), $C_{3-10}$cycloalkyl, or 5-20 membered heteroaryl, wherein the $C_{1-6}$alkyl is optionally substituted with one or more halo, —NH—C(O)—NH($C_{1-6}$alkyl), —NH—C(O)—$C_{1-6}$alkyl, or —NH—C(O)—$C_{1-6}$alkoxy, the $C_{3-10}$cycloalkyl is optionally substituted with one or more halo or $C_{1-6}$alkyl, and the 5-20 membered heteroaryl is optionally substituted with one or more $C_{1-6}$alkyl. In some embodiments, $R^x$ is H, halo, or $C_{1-6}$alkyl optionally substituted with one or more halo; $R^y$ is (i) $C_{1-6}$alkyl, (ii) $C_{2-6}$alkenyl, (iii) $C_{3-10}$cycloalkyl optionally substituted with one or more halo or $C_{1-6}$alkyl or (iv) butyl; and $R^z$ is H, halo or $C_{1-6}$alkyl. In some embodiments, $R^z$ is H. In some embodiments, at least one of $R^x$ and $R^z$ is halo or $C_{1-6}$alkyl optionally substituted with one or more halo.

In some embodiments of a compound of formula (I-A1), or a stereoisomer or tautomer thereof, or a pharmaceutically acceptable salt of any of the foregoing, $R^x$ is fluoro or methyl; $R^y$ is (i) isopropyl or (ii) $C_{3-4}$cycloalkyl; and $R^z$ is fluoro or methyl; provided that at least one of $R^x$ and $R^z$ is halo. In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I'), (I-A1), or a stereoisomer or tautomer thereof, or a pharmaceutically acceptable salt of any of the foregoing, $R^x$ is fluoro or methyl optionally substituted with one or more fluoro; $R^y$ is (i) isopropyl (ii) $C_{3-4}$cycloalkyl optionally substituted with one or more halo or $C_{1-6}$alkyl or (iii) butyl; and $R^z$ is fluoro or methyl; provided that at least one of $R^x$ and $R^z$ is halo, $CF_2$ or $CF_3$.

In some embodiments of a compound of formula (I-A1), or a stereoisomer or tautomer thereof, or a pharmaceutically acceptable salt of any of the foregoing, $R^k$ is H or halo. In some embodiments of a compound of formula (I-A1), or a stereoisomer or tautomer thereof, or a pharmaceutically acceptable salt of any of the foregoing, $R^k$ is H or fluoro. In some embodiments of a compound of formula (I-A1), or a stereoisomer or tautomer thereof, or a pharmaceutically acceptable salt of any of the foregoing, $R^k$ is fluoro. In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I-A1), or a stereoisomer or tautomer thereof, or a pharmaceutically acceptable salt of any of the foregoing, $R^2$ is $C_{1-6}$alkyl, wherein the $C_{1-6}$alkyl of $R^2$ is optionally substituted with one or more $R^a$. In some embodiments, $R^2$ is $C_{1-6}$alkyl, wherein the $C_{1-6}$alkyl of $R^2$ is substituted with one or more $R^a$, wherein $R^a$ is —OH or 5-20 membered heteroaryl, wherein the 5-20 membered heteroaryl of $R^a$ is optionally substituted with one or more $R^b$. In some embodiments, $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more $R^b$. In some embodiments, $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more $C_{1-6}$alkyl, wherein the $C_{1-6}$alkyl is optionally substituted with one or more halo, —$NH_2$, —NH($C_{1-6}$alkyl), —N($C_{1-6}$alkyl)$_2$, —NH—C(O) $C_{1-6}$alkyl, or —NH—C(O)—$C_{1-6}$alkoxy. In some embodiments, $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more methyl, wherein the methyl is optionally substituted with one or more fluoro.

In some embodiments of a compound of formula (I'), (I-A1), or a stereoisomer or tautomer thereof, or a pharmaceutically acceptable salt of any of the foregoing, $R^2$ is 5-20 membered heteroaryl or —($C_{1-4}$alkyl)(5-20 membered heteroaryl), wherein the $C_{1-4}$ alkyl is optionally substituted with one or more or more —OH, halo, —$NH_2$, —NH($C_{1-6}$alkyl), —N($C_{1-6}$alkyl)$_2$, and wherein the 5-20 membered heteroaryl is optionally substituted with one or more $R^s$. In some embodiments, $R^s$ is halo, $C_{1-6}$alkyl, $C_{1-6}$alkoxy, —$NH_2$, —NH($C_{1-6}$alkyl), —N($C_{1-6}$alkyl)$_2$, —NH—C(O)—$C_{1-6}$alkyl, $C_{6-20}$aryl, $C_{3-10}$cycloalkyl, 3-15 membered heterocyclyl, 5-20 membered heteroaryl, or —C(O)—$C_{1-6}$alkoxy. In some embodiments, the $C_{1-6}$alkyl of $R^s$ is optionally substituted with one or more halo, $C_{1-6}$alkoxy, —$NH_2$, —NH($C_{1-6}$alkyl), —N($C_{1-6}$alkyl)$_2$, —NH—C(O)$C_{1-6}$alkyl, or —NH—C(O)—$C_{1-6}$alkoxy, and the 3-15-membered heterocyclyl of $R^s$ is optionally substituted with one or more halo or —C(O)—$C_{1-6}$alkoxy.

In some embodiments of a compound of formula (I-A1), or a stereoisomer or tautomer thereof, or a pharmaceutically acceptable salt of any of the foregoing, $R^2$ is selected from the group consisting of

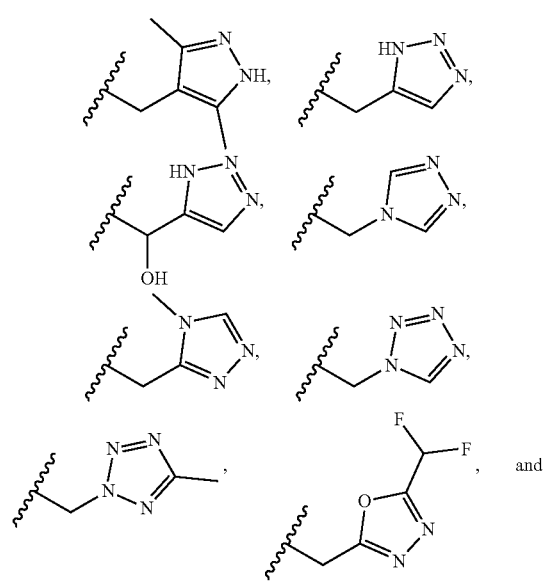

-continued

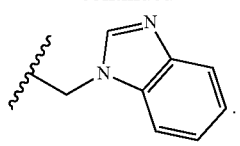

In some embodiments, R² is

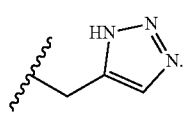 [SMILES: *Cc1cnn[nH]1]

In some embodiments of a compound of formula (I'), (I-A1), or a stereoisomer or tautomer thereof, or a pharmaceutically acceptable salt of any of the foregoing, R² is selected from the group consisting of

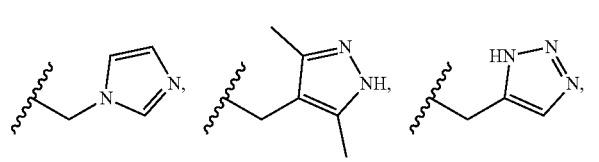

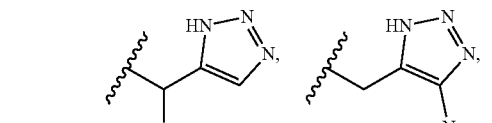

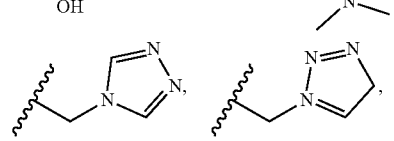

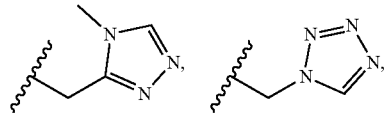

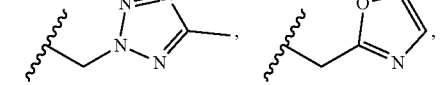

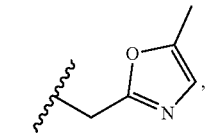

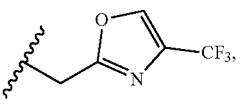

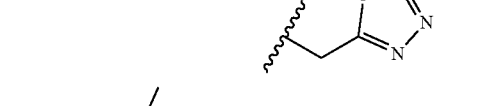

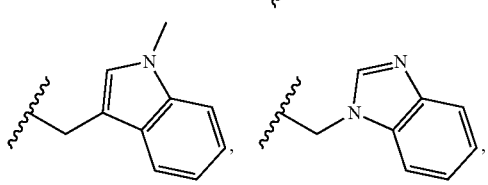

-continued

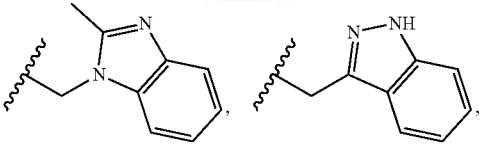

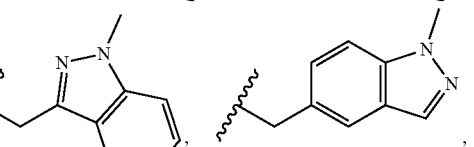

, and

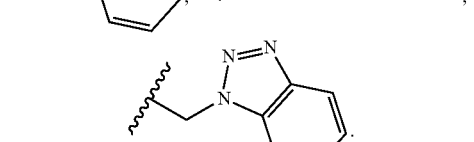

In some embodiments, R² is

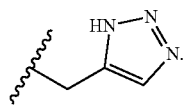

In some embodiments of a compound of formula (I-A1), or a stereoisomer or tautomer thereof, or a pharmaceutically acceptable salt of any of the foregoing, R² is $C_{1-6}$alkyl, wherein the $C_{1-6}$alkyl of R² is substituted with one or more $R^a$, wherein $R^a$ is 3-15 membered heterocyclyl, wherein the 3-15 membered heterocyclyl of $R^a$ is optionally substituted with one or more $R^c$. In some embodiments, R² is methyl, wherein the methyl of R² is substituted with one or more $R^a$, wherein $R^a$ is 3-15 membered heterocyclyl, wherein the 3-15 membered heterocyclyl of $R^a$ is optionally substituted with one or more $R^c$. In some embodiments, R² is methyl, wherein the methyl of R² is substituted with one or more $R^a$, wherein $R^a$ is 3-8 membered heterocyclyl, wherein the 3-8 membered heterocyclyl of $R^a$ is optionally substituted with one or more $R^c$. In some embodiments, R² is methyl, wherein the methyl of R² is substituted with one or more $R^a$, wherein $R^a$ is 3-8 membered heterocyclyl, wherein the 3-8 membered heterocyclyl of $R^a$ is optionally substituted with one or more oxo or $C_{1-6}$alkyl. In some embodiments, R² is

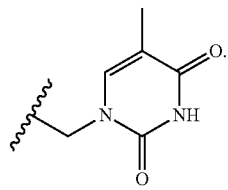 [SMILES: *Cn1cc(C)c(=O)[nH]c1=O]

In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I'), (I-A1), or a stereoisomer or tautomer thereof, or a pharmaceutically acceptable salt of any of the foregoing, In some embodiments, R² is methyl, wherein the methyl of R² is substituted with one or more R$^a$, wherein R$^a$ is 3-8 membered heterocyclyl, wherein the 3-8 membered heterocyclyl of R$^a$ is optionally substituted with one or more R$^c$, wherein R$^c$ is oxo, C$_{1-6}$alkyl, or —C(O)—C$_{1-6}$alkoxy, wherein the C$_{1-6}$alkyl of R$^c$ is optionally substituted with one or more halo, and the —C(O)—C$_{1-6}$alkoxy of R$^c$ is optionally substituted with one or more halo. In some embodiments, R$^2$ is

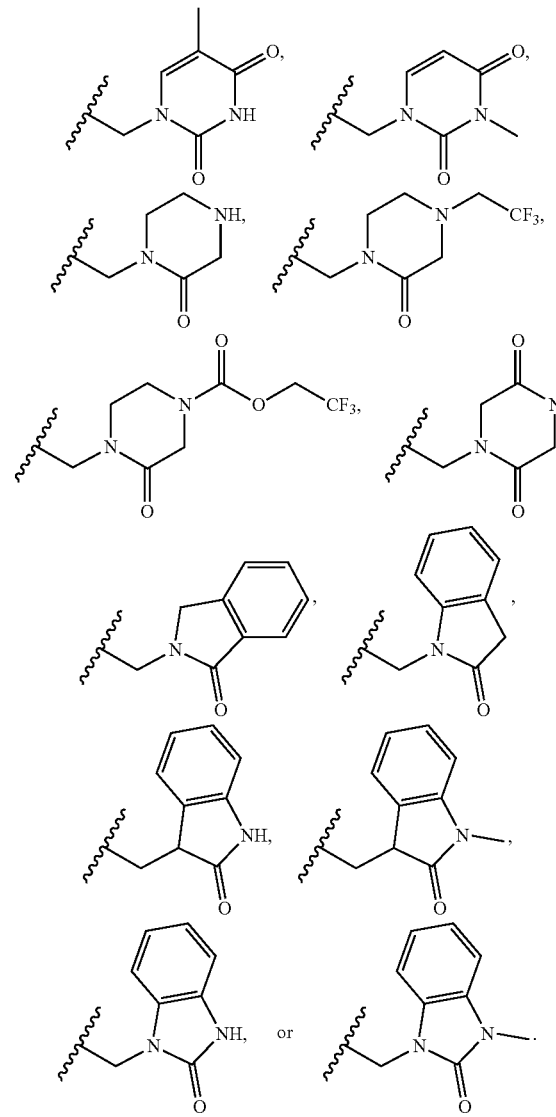

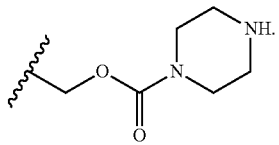 [SMILES: *COC(=O)N1CCNCC1]

In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I'), (I-A1), or a stereoisomer or tautomer thereof, or a pharmaceutically acceptable salt of any of the foregoing, R$^2$ is methyl, wherein the methyl of R$^2$ is substituted with one or more R$^a$, wherein R$^a$ is —O—R$^e$, wherein R$^e$ is —C(O)-(3-15 membered heterocyclyl) wherein the —C(O)-(3-15 membered heterocyclyl) of R$^e$ is optionally substituted with one or more C$_{1-6}$alkyl, wherein the C$_{1-6}$alkyl is optionally substituted with one or more halo, C$_{1-6}$alkoxy, or C$_{3-10}$cycloalkyl. In some embodiments, R$^2$ is

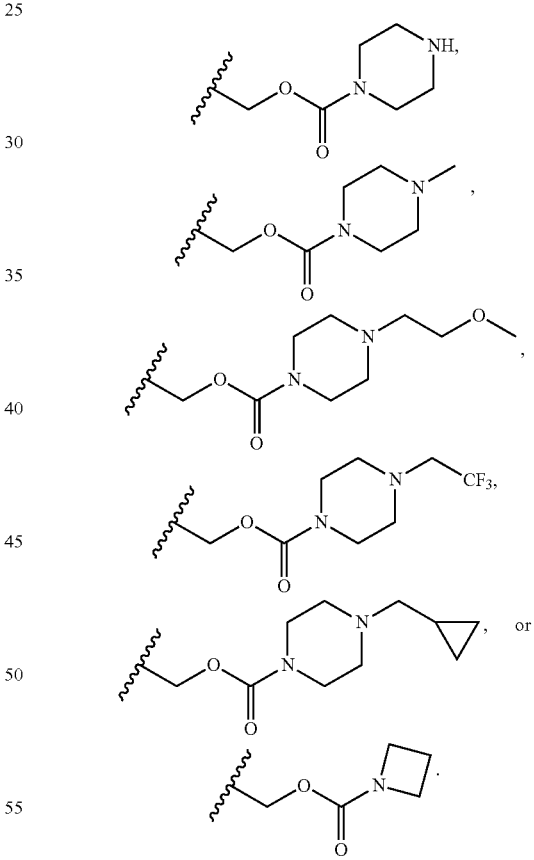

In some embodiments of a compound of formula (I-A1), or a stereoisomer or tautomer thereof, or a pharmaceutically acceptable salt of any of the foregoing, R$^2$ is C$_{1-6}$alkyl, wherein the C$_{1-6}$alkyl of R$^2$ is substituted with one or more R$^a$, wherein R$^a$ is —O—R$^e$. In some embodiments, R$^2$ is methyl, wherein the methyl of R$^2$ is substituted with one or more R$^a$, wherein R$^a$ is —O—R$^e$. In some embodiments, R$^2$ is methyl, wherein the methyl of R$^2$ is substituted with one or more R$^a$, wherein R$^a$ is —O—R$^e$, wherein R$^e$ is —C(O)-(3-15 membered heterocyclyl). In some embodiments, R$^2$ is In some embodiments of a compound of formula (I-A1), or a stereoisomer or tautomer thereof, or a pharmaceutically acceptable salt of any of the foregoing, R$^2$ is C$_{1-6}$alkyl, wherein the C$_{1-6}$alkyl of R$^2$ is substituted with one or more R$^a$, wherein R$^a$ is —N(R$^c$)(R$^d$). In some embodiments, R$^2$ is methyl, wherein the methyl of R$^2$ is substituted with one or more R$^a$, wherein R$^a$ is —N(R$^c$)(R$^d$). In some embodiments, R$^2$ is methyl, wherein the methyl of R$^2$ is substituted with one or more R$^a$, wherein R$^a$ is —N(R$^c$)(R$^d$), wherein one of $R^c$ and $R^d$ is H, and the other of $R^c$ and $R^d$ is —C(O)—N(C$_{1-6}$alkyl)$_2$. In some embodiments, $R^2$ is

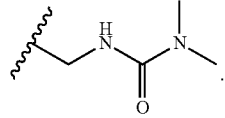 [SMILES: *CNC(=O)N(C)C]

In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I') (I-A1), or a stereoisomer or tautomer thereof, or a pharmaceutically acceptable salt of any of the foregoing, $R^2$ is methyl, wherein the methyl of $R^2$ is substituted with one or more $R^a$, wherein $R^a$ is —N($R^c$)($R^d$), wherein one of $R^c$ and $R^d$ is H, and the other of $R^c$ and $R^d$, —C(O)—C$_{1-6}$alkyl, —C(O)—N(C$_{1-6}$alkyl)$_2$, or —C(O)-(3-15 membered heterocyclyl). In some embodiments, $R^2$ is

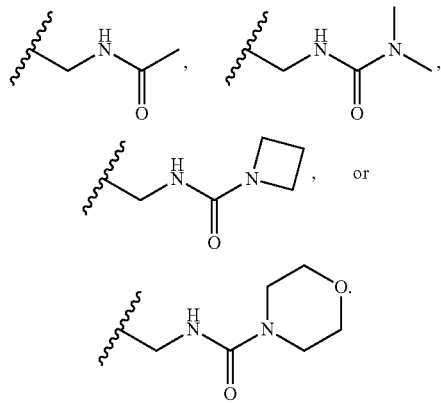

In some embodiments of a compound of formula (I') (I-A1), or a stereoisomer or tautomer thereof, or a pharmaceutically acceptable salt of any of the foregoing, $R^2$ is ethyl, wherein the ethyl of $R^2$ is substituted with one or more $R^a$, wherein $R^a$ is —N($R^c$)($R^d$), wherein one of $R^c$ and $R^d$ is H, and the other of $R^c$ and $R^d$, is —C(O)—C$_{1-6}$alkyl. In some embodiments, $R^2$ is

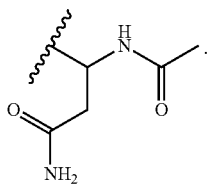 [SMILES: *C(CC(N)=O)NC(C)=O]

In some embodiments, provided is a compound of formula (I) or formula (I-A), or a stereoisomer or tautomer thereof, or a pharmaceutically acceptable salt of any of the foregoing, wherein the compound is a compound of formula (I-A2):

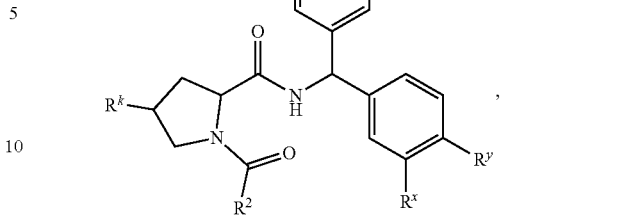

(I-A2)

or a stereoisomer or tautomer thereof, or a pharmaceutically acceptable salt of any of the foregoing, wherein $R^x$ is H, halo, C$_{1-6}$alkyl, or —NH$_2$, wherein the C$_{1-6}$alkyl is optionally substituted with one or more halo; and $R^y$ is (i) C$_{1-6}$alkyl, (ii), C$_{2-6}$alkenyl, or (iii) C$_{3-10}$cycloalkyl, wherein the C$_{3-10}$cycloalkyl is optionally substituted with one or more halo or C$_{1-6}$alkyl. In some embodiments, $R^x$ is H, halo, or C$_{1-6}$alkyl, wherein the C$_{1-6}$alkyl is optionally substituted with one or more halo; and $R^y$ is (i), C$_{1-6}$alkyl, (ii) C$_{2-6}$alkenyl, or (iii) C$_{3-10}$cycloalkyl, wherein the C$_{3-10}$cycloalkyl is optionally substituted with one or more halo or C$_{1-6}$alkyl. In some embodiments, $R^x$ is H, halo, or C$_{1-6}$alkyl; and $R^y$ is (i) C$_{1-6}$alkyl, (ii) C$_{2-6}$alkenyl, or (iii) C$_{3-10}$cycloalkyl, wherein the C$_{3-10}$cycloalkyl is optionally substituted with one or more halo or C$_{1-6}$alkyl. In some variations, $R^2$, $R^k$, $R^x$, and $R^y$ of formula (I-A2) are as defined for a compound of formula (I'), or a stereoisomer or tautomer thereof, or a pharmaceutically acceptable salt of any of the foregoing, or any variation or embodiment thereof, wherein $R^x$ and $R^y$ are each independently H, halo, C$_{1-6}$alkyl, C$_{2-6}$alkenyl, —NH$_2$, —NH—C(O)—(C$_{1-6}$alkyl), —NH—C(O)-(3-15 membered heterocyclyl), C$_{3-10}$cycloalkyl, or 5-20 membered heteroaryl, wherein the C$_{1-6}$alkyl is optionally substituted with one or more halo, —NH—C(O)—NH(C$_{1-6}$alkyl), —NH—C(O)—C$_{1-6}$alkyl, or —NH—C(O)—C$_{1-6}$alkoxy, the C$_{3-10}$cycloalkyl is optionally substituted with one or more halo or C$_{1-6}$alkyl, and the 5-20 membered heteroaryl is optionally substituted with one or more C$_{1-6}$alkyl. In some embodiments, $R^x$ is H, halo, or C$_{1-6}$alkyl optionally substituted with one or more halo; and $R^y$ is (i) C$_{1-6}$alkyl, (ii) C$_{3-10}$cycloalkyl optionally substituted with one or more halo or C$_{1-6}$alkyl or (iii) butyl.

In some embodiments of a compound of formula (I-A2), or a stereoisomer or tautomer thereof, or a pharmaceutically acceptable salt of any of the foregoing, $R^x$ is H, fluoro, chloro, or methyl, wherein the methyl is optionally substituted with one or more fluoro; and $R^y$ is (i) isopropyl, (ii) isopropenyl, (iii) sec-butyl, (iv) tert-butyl, or (v) C$_{3-4}$cycloalkyl, wherein the C$_{3-4}$cycloalkyl is optionally substituted with one or more fluoro or methyl. In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I'), (I-A2), or a stereoisomer or tautomer thereof, or a pharmaceutically acceptable salt of any of the foregoing, $R^x$ is fluoro or methyl optionally substituted with one or more fluoro; and $R^y$ is (i) isopropyl (ii) C$_{3-4}$cycloalkyl optionally substituted with one or more halo or C$_{1-6}$alkyl or (iii) butyl.

In some embodiments of a compound of formula (I-A2), or a stereoisomer or tautomer thereof, or a pharmaceutically acceptable salt of any of the foregoing, $R^k$ is H or halo. In some embodiments of a compound of formula (I-A2), or a stereoisomer or tautomer thereof, or a pharmaceutically acceptable salt of any of the foregoing, $R^k$ is H or fluoro. In some embodiments of a compound of formula (I-A2), or a stereoisomer or tautomer thereof, or a pharmaceutically acceptable salt of any of the foregoing, $R^k$ is fluoro. In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I-A2), or a stereoisomer or tautomer thereof, or a pharmaceutically acceptable salt of any of the foregoing, $R^2$ is $C_{1-6}$alkyl, wherein the $C_{1-6}$alkyl of $R^2$ is optionally substituted with one or more $R^a$. In some embodiments, $R^2$ is $C_{1-6}$alkyl, wherein the $C_{1-6}$alkyl of $R^2$ is substituted with one or more $R^a$, wherein $R^a$ is —OH or 5-20 membered heteroaryl, wherein the 5-20 membered heteroaryl of $R^a$ is optionally substituted with one or more $R^b$. In some embodiments, $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more $R^b$. In some embodiments, $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more $C_{1-6}$alkyl, wherein the $C_{1-6}$alkyl is optionally substituted with one or more halo, —$NH_2$, —$NH(C_{1-6}$alkyl$)$, —$N(C_{1-6}$alkyl$)_2$, —NH—C(O)$C_{1-6}$alkyl, or —NH—C(O)—$C_{1-6}$alkoxy. In some embodiments, $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more methyl, wherein the methyl is optionally substituted with one or more fluoro.

In some embodiments of a compound of formula (I'), (I-A2), or a stereoisomer or tautomer thereof, or a pharmaceutically acceptable salt of any of the foregoing, $R^2$ is —($C_{1-4}$alkyl)(5-20 membered heteroaryl), wherein the $C_{1-4}$ alkyl is optionally substituted with one or more or more —OH, and wherein the 5-20 membered heteroaryl is optionally substituted with one or more $R^s$. In some embodiments, $R^s$ is halo, $C_{1-6}$alkyl, $C_{1-6}$alkoxy, —$NH_2$, —$NH(C_{1-6}$alkyl$)$, —$N(C_{1-6}$alkyl$)_2$, —NH—C(O)—$C_{1-6}$alkyl, $C_{6-20}$aryl, $C_{3-10}$cycloalkyl, 3-15 membered heterocyclyl, 5-20 membered heteroaryl, or —C(O)—$C_{1-6}$alkoxy. In some embodiments, the $C_{1-6}$alkyl of $R^s$ is optionally substituted with one or more halo, $C_{1-6}$alkoxy, —$NH_2$, —$NH(C_{1-6}$alkyl$)$, —$N(C_{1-6}$alkyl$)_2$, —NH—C(O)$C_{1-6}$alkyl, or —NH—C(O)—$C_{1-6}$alkoxy, and the 3-15-membered heterocyclyl of $R^s$ is optionally substituted with one or more halo or —C(O)—$C_{1-6}$alkoxy.

In some embodiments of a compound of formula (I-A2), or a stereoisomer or tautomer thereof, or a pharmaceutically acceptable salt of any of the foregoing, $R^2$ is selected from the group consisting of

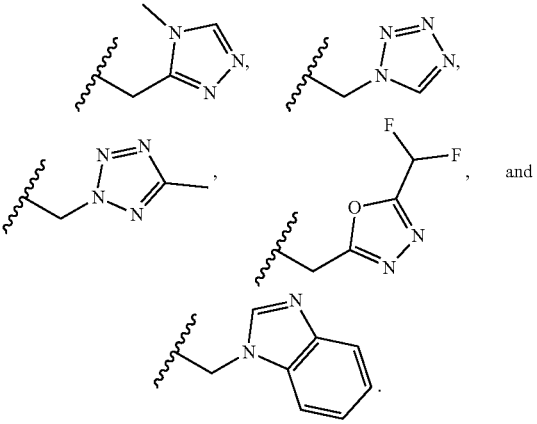

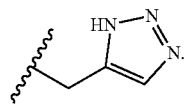

In some embodiments, $R^2$ is

In some embodiments of a compound of formula (I'), (I-A2), or a stereoisomer or tautomer thereof, or a pharmaceutically acceptable salt of any of the foregoing, $R^2$ is selected from the group consisting of

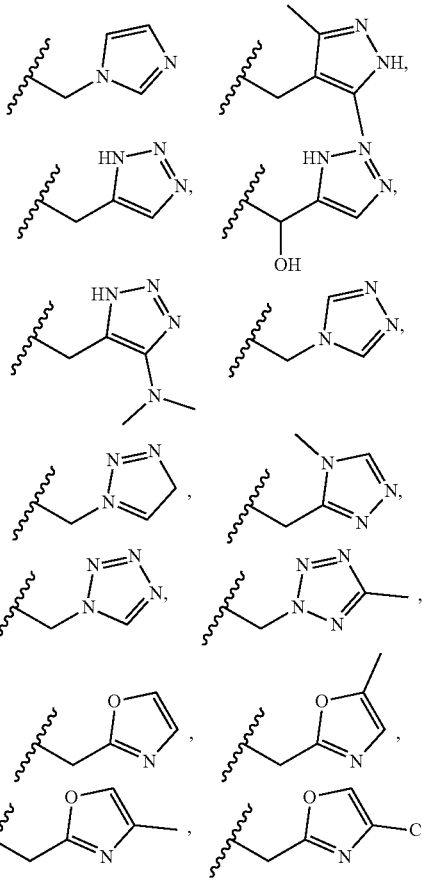

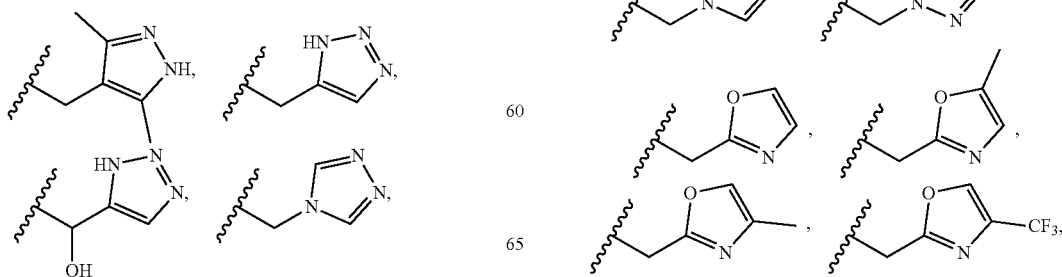

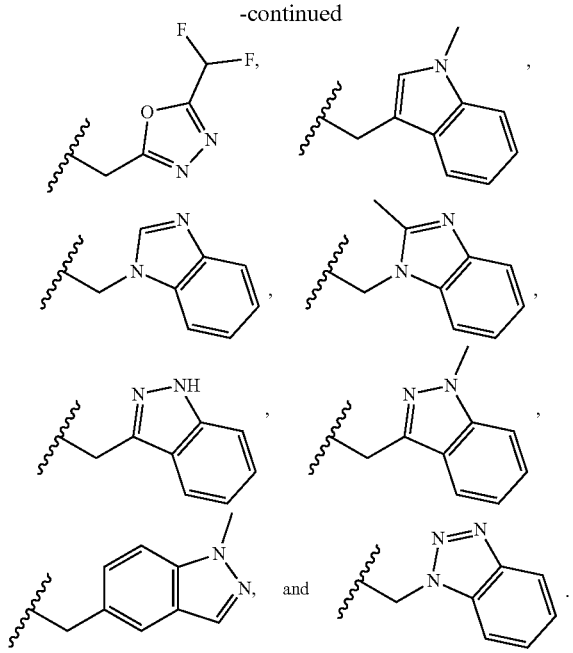

In some embodiments, R² is

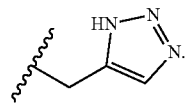 [SMILES: *Cc1cnn[nH]1]

In some embodiments of a compound of formula (I-A2), or a stereoisomer or tautomer thereof, or a pharmaceutically acceptable salt of any of the foregoing, R² is $C_{1-6}$alkyl, wherein the $C_{1-6}$alkyl of R² is substituted with one or more R$^a$, wherein R$^a$ is 3-15 membered heterocyclyl, wherein the 3-15 membered heterocyclyl of R$^a$ is optionally substituted with one or more R$^c$. In some embodiments, R² is methyl, wherein the methyl of R² is substituted with one or more R$^a$, wherein R$^a$ is 3-15 membered heterocyclyl, wherein the 3-15 membered heterocyclyl of R$^a$ is optionally substituted with one or more R$^c$. In some embodiments, R² is methyl, wherein the methyl of R² is substituted with one or more R$^a$, wherein R$^a$ is 3-8 membered heterocyclyl, wherein the 3-8 membered heterocyclyl of R$^a$ is optionally substituted with one or more R$^c$. In some embodiments, R² is methyl, wherein the methyl of R² is substituted with one or more R$^a$, wherein R$^a$ is 3-8 membered heterocyclyl, wherein the 3-8 membered heterocyclyl of R$^a$ is optionally substituted with one or more oxo or $C_{1-6}$alkyl. In some embodiments, R² is

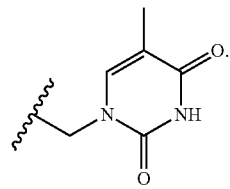 [SMILES: *Cn1cc(C)c(=O)[nH]c1=O]

In some variations, the embodiments provided herein also apply to a compound of formula (I) or a stereoisomer or tautomer thereof, or a pharmaceutically acceptable salt of any of the foregoing, or any variation or embodiment thereof.

In some embodiments of a compound of formula (I'), (I-A2), or a stereoisomer or tautomer thereof, or a pharmaceutically acceptable salt of any of the foregoing, R² is methyl, wherein the methyl of R² is substituted with one or more R$^a$, wherein R$^a$ is 3-8 membered heterocyclyl, wherein the 3-8 membered heterocyclyl of R$^a$ is optionally substituted with one or more R$^c$, wherein R$^c$ is oxo, $C_{1-6}$alkyl, or —C(O)—$C_{1-6}$alkoxy, wherein the $C_{1-6}$alkyl of R$^c$ is optionally substituted with one or more halo, and the —C(O)—$C_{1-6}$alkoxy of R$^c$ is optionally substituted with one or more halo. In some embodiments, R² is selected from the group consisting of

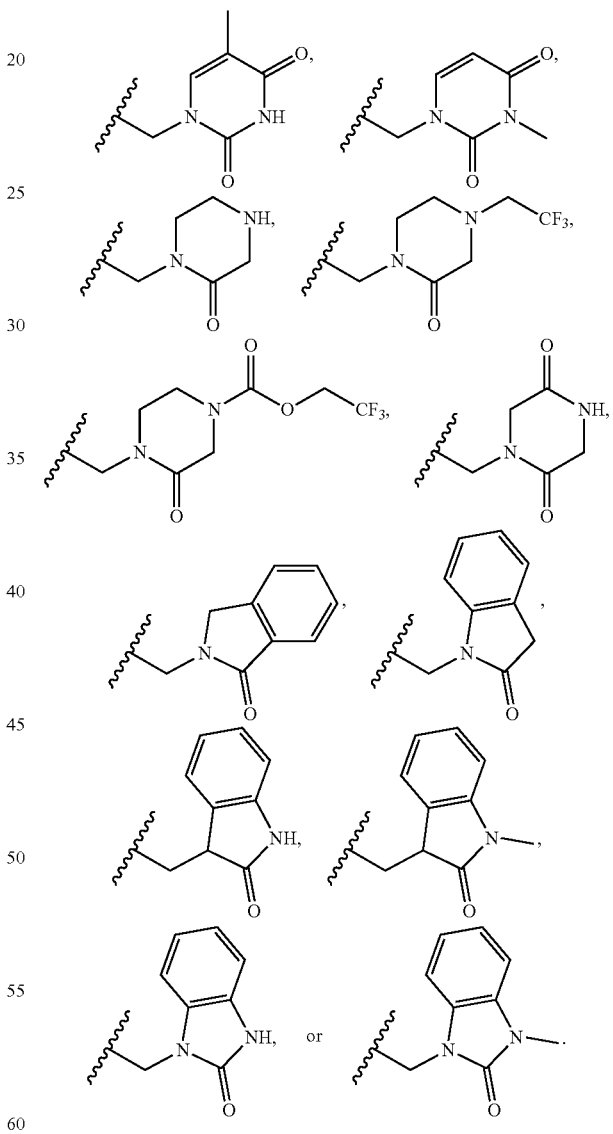

In some embodiments of a compound of formula (I-A2), or a stereoisomer or tautomer thereof, or a pharmaceutically acceptable salt of any of the foregoing, R² is $C_{1-6}$alkyl, wherein the $C_{1-6}$alkyl of R² is substituted with one or more R$^a$, wherein R$^a$ is —O—R$^e$. In some embodiments, R² is methyl, wherein the methyl of R² is substituted with one or more $R^a$, wherein $R^a$ is —O—$R^e$. In some embodiments, $R^2$ is methyl, wherein the methyl of $R^2$ is substituted with one or more $R^a$, wherein $R^a$ is —O—$R^e$ wherein $R^e$ is —C(O)-(3-15 membered heterocyclyl). In some embodiments, $R^2$ is

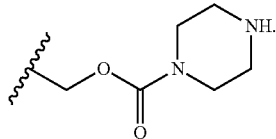 [SMILES: *COC(=O)N1CCNCC1]

In some embodiments of a compound of formula (I), (I-A2), or a stereoisomer or tautomer thereof, or a pharmaceutically acceptable salt of any of the foregoing, $R^2$ is methyl, wherein the methyl of $R^2$ is substituted with one or more $R^a$, wherein $R^a$ is —O—$R^e$, wherein $R^e$ is —C(O)-(3-15 membered heterocyclyl) wherein the —C(O)-(3-15 membered heterocyclyl) of $R^e$ is optionally substituted with one or more $C_{1-6}$alkyl, wherein the $C_{1-6}$alkyl is optionally substituted with one or more halo, $C_{1-6}$alkoxy, or $C_{3-10}$cycloalkyl. In some embodiments, $R^2$ is selected from the group consisting of

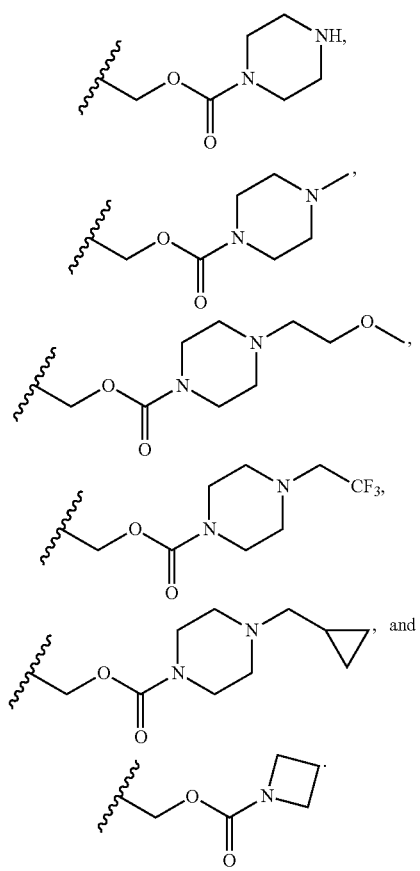

In some embodiments of a compound of formula (I-A2), or a stereoisomer or tautomer thereof, or a pharmaceutically acceptable salt of any of the foregoing, $R^2$ is $C_{1-6}$alkyl, wherein the $C_{1-6}$alkyl of $R^2$ is substituted with one or more $R^a$, wherein $R^a$ is —N($R^c$)($R^d$). In some embodiments, $R^2$ is methyl, wherein the methyl of $R^2$ is substituted with one or more $R^a$, wherein $R^a$ is —N($R^c$)($R^d$). In some embodiments, $R^2$ is methyl, wherein the methyl of $R^2$ is substituted with one or more $R^a$, wherein $R^a$ is —N($R^c$)($R^d$), wherein one of $R^c$ and $R^d$ is H, and the other of $R^c$ and $R^d$ is —C(O)—N($C_{1-6}$alkyl)$_2$. In some embodiments, $R^2$ is

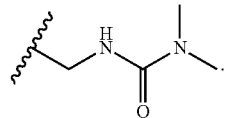

In some variations, the embodiments provided herein also apply to a compound of formula (I') or a stereoisomer or tautomer thereof, or a pharmaceutically acceptable salt of any of the foregoing, or any variation or embodiment thereof. In some embodiments of a compound of formula (I), (I-A2), or a stereoisomer or tautomer thereof, or a pharmaceutically acceptable salt of any of the foregoing, $R^2$ is methyl, wherein the methyl of $R^2$ is substituted with one or more $R^a$, wherein $R^a$ is —N($R^c$)($R^d$), wherein one of $R^c$ and $R^d$ is H, and the other of $R^c$ and $R^d$, —C(O)—$C_{1-6}$alkyl, —C(O)—N($C_{1-6}$alkyl)$_2$, or —C(O)-(3-15 membered heterocyclyl). In some embodiments, $R^2$ is selected from the group consisting of

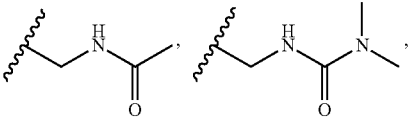

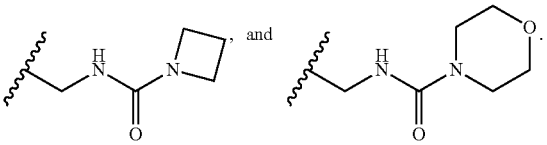

In some embodiments of a compound of formula (I') (I-A2), or a stereoisomer or tautomer thereof, or a pharmaceutically acceptable salt of any of the foregoing, $R^2$ is ethyl, wherein the ethyl of $R^2$ is substituted with one or more $R^a$, wherein $R^a$ is —N($R^c$)($R^d$), wherein one of $R^c$ and $R^d$ is H, and the other of $R^c$ and $R^d$, is —C(O)—$C_{1-6}$alkyl. In some embodiments, $R^2$ is

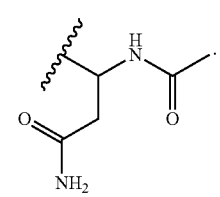 [SMILES: *C(CC(N)=O)NC(C)=O]

In some embodiments, provided herein is a compound of formula (I) or formula (I-A), or a stereoisomer or tautomer thereof, or a pharmaceutically acceptable salt of any of the foregoing, wherein the compound is a compound of formula (I-A3):

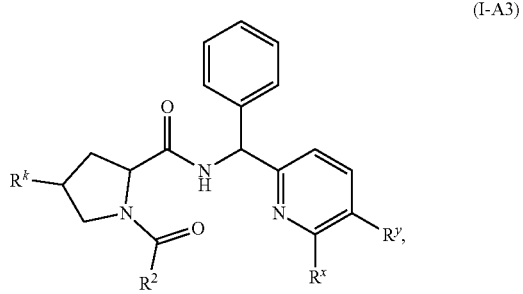

(I-A3)

or a stereoisomer or tautomer thereof, or a pharmaceutically acceptable salt of any of the foregoing, wherein $R^x$ is H, halo, $C_{1-6}$alkyl, or —$NH_2$, wherein the $C_{1-6}$alkyl is optionally substituted with one or more halo; and $R^y$ is (i) $C_{1-6}$alkyl, (ii) $C_{2-6}$alkenyl, or (iii) $C_{3-10}$cycloalkyl, wherein the $C_{3-10}$cycloalkyl is optionally substituted with one or more halo or $C_{1-6}$alkyl. In some embodiments, $R^x$ is H, halo, $C_{1-6}$alkyl, or —$NH_2$; and $R^y$ is (i) $C_{1-6}$alkyl or (ii) $C_{3-10}$cycloalkyl, wherein the $C_{3-10}$cycloalkyl is optionally substituted with one or more halo or $C_{1-6}$alkyl. In some variations, $R^2$, $R^k$, $R^x$, and $R^y$ of formula (I-A3) are as defined for a compound of formula (I'), or a stereoisomer or tautomer thereof, or a pharmaceutically acceptable salt of any of the foregoing, or any variation or embodiment thereof, wherein $R^x$ and $R^y$ are each independently H, halo, $C_{1-6}$alkyl, $C_{2-6}$alkenyl, $C_{1-6}$alkoxy, —$NH_2$, or $C_{3-10}$cycloalkyl, wherein, the $C_{1-6}$alkyl is optionally substituted with one or more halo, and the $C_{3-10}$cycloalkyl is optionally substituted with one or more halo or $C_{1-6}$alkyl. In some embodiments, $R^x$ is H, halo, $C_{1-6}$alkyl, or —$NH_2$; and $R^y$ is (i) $C_{1-6}$alkyl or (ii) $C_{3-10}$cycloalkyl, wherein the $C_{3-10}$cycloalkyl is optionally substituted with one or more halo or $C_{1-6}$alkyl.

In some embodiments of a compound of formula (I-A3), or a stereoisomer or tautomer thereof, or a pharmaceutically acceptable salt of any of the foregoing, $R^x$ is H, fluoro, or methyl; and $R^y$ is (i) H, (ii) isopropyl, (iii) tert-butyl, or (iv) $C_{3-4}$cycloalkyl, wherein the $C_{3-4}$cycloalkyl is optionally substituted with one or more fluoro or methyl. In some embodiments, $R^x$ is H, fluoro, or methyl; and $R^y$ is (i) isopropyl or (ii) $C_{3-4}$cycloalkyl, wherein the $C_{3-4}$cycloalkyl is optionally substituted with one or more fluoro or methyl. In some variations, the embodiments provided herein also apply to a compound of formula (I') or a stereoisomer or tautomer thereof, or a pharmaceutically acceptable salt of any of the foregoing, or any variation or embodiment thereof. In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I-A3), or a stereoisomer or tautomer thereof, or a pharmaceutically acceptable salt of any of the foregoing, $R^k$ is H or halo. In some embodiments of a compound of formula (I-A3), or a stereoisomer or tautomer thereof, or a pharmaceutically acceptable salt of any of the foregoing, $R^k$ is H or fluoro. In some embodiments of a compound of formula (I-A3), or a stereoisomer or tautomer thereof, or a pharmaceutically acceptable salt of any of the foregoing, $R^k$ is fluoro. In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I-A3), or a stereoisomer or tautomer thereof, or a pharmaceutically acceptable salt of any of the foregoing, $R^2$ is $C_{1-6}$alkyl, wherein the $C_{1-6}$alkyl of $R^2$ is optionally substituted with one or more $R^a$. In some embodiments, $R^2$ is $C_{1-6}$alkyl, wherein the $C_{1-6}$alkyl of $R^2$ is substituted with one or more $R^a$, wherein $R^a$ is —OH or 5-20 membered heteroaryl, wherein the 5-20 membered heteroaryl of $R^a$ is optionally substituted with one or more $R^b$. In some embodiments, $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more $R^b$. In some embodiments, $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more $C_{1-6}$alkyl, wherein the $C_{1-6}$alkyl is optionally substituted with one or more halo, —$NH_2$, —$NH(C_{1-6}$alkyl), —$N(C_{1-6}$alkyl$)_2$, —NH—C(O)$C_{1-6}$alkyl, or —NH—C(O)—$C_{1-6}$alkoxy. In some embodiments, $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more methyl, wherein the methyl is optionally substituted with one or more fluoro. In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I'), (I-A3), or a stereoisomer or tautomer thereof, or a pharmaceutically acceptable salt of any of the foregoing, $R^2$ is —($C_{1-4}$alkyl)(5-20 membered heteroaryl), wherein the 5-20 membered heteroaryl is optionally substituted with one or more $R^s$. In some embodiments, $R^s$ is halo, $C_{1-6}$alkyl, $C_{1-6}$alkoxy, —$NH_2$, —$NH(C_{1-6}$alkyl), —$N(C_{1-6}$alkyl$)_2$, —NH—C(O)—$C_{1-6}$alkyl, $C_{6-20}$aryl, $C_{3-10}$cycloalkyl, 3-15 membered heterocyclyl, 5-20 membered heteroaryl, or —C(O)—$C_{1-6}$alkoxy. In some embodiments, the $C_{1-6}$alkyl of $R^s$ is optionally substituted with one or more halo, $C_{1-6}$alkoxy, —$NH_2$, —$NH(C_{1-6}$alkyl), —$N(C_{1-6}$alkyl$)_2$, —NH—C(O)$C_{1-6}$alkyl, or —NH—C(O)—$C_{1-6}$alkoxy, and the 3-15-membered heterocyclyl of $R^s$ is optionally substituted with one or more halo or —C(O)—$C_{1-6}$alkoxy.

In some embodiments of a compound of formula (I-A3), or a stereoisomer or tautomer thereof, or a pharmaceutically acceptable salt of any of the foregoing, $R^2$ is selected from the group consisting of

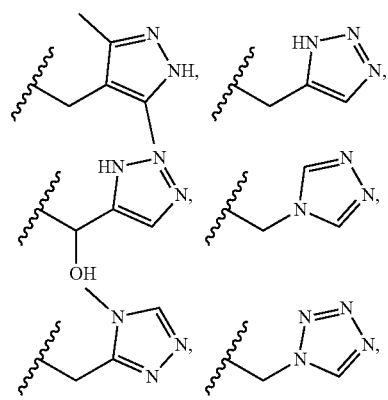

-continued

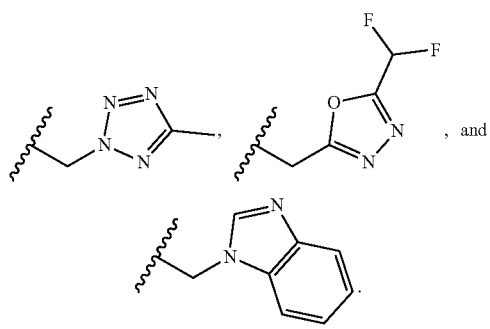

In some embodiments, $R^2$ is

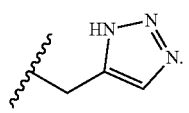 [SMILES: *Cc1cnn[nH]1]

In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I'), (I-A3), or a stereoisomer or tautomer thereof, or a pharmaceutically acceptable salt of any of the foregoing, $R^2$ is selected from the group consisting of

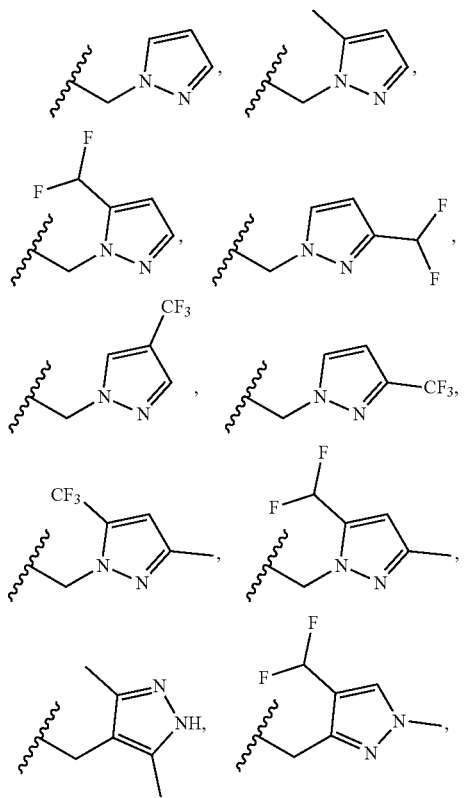
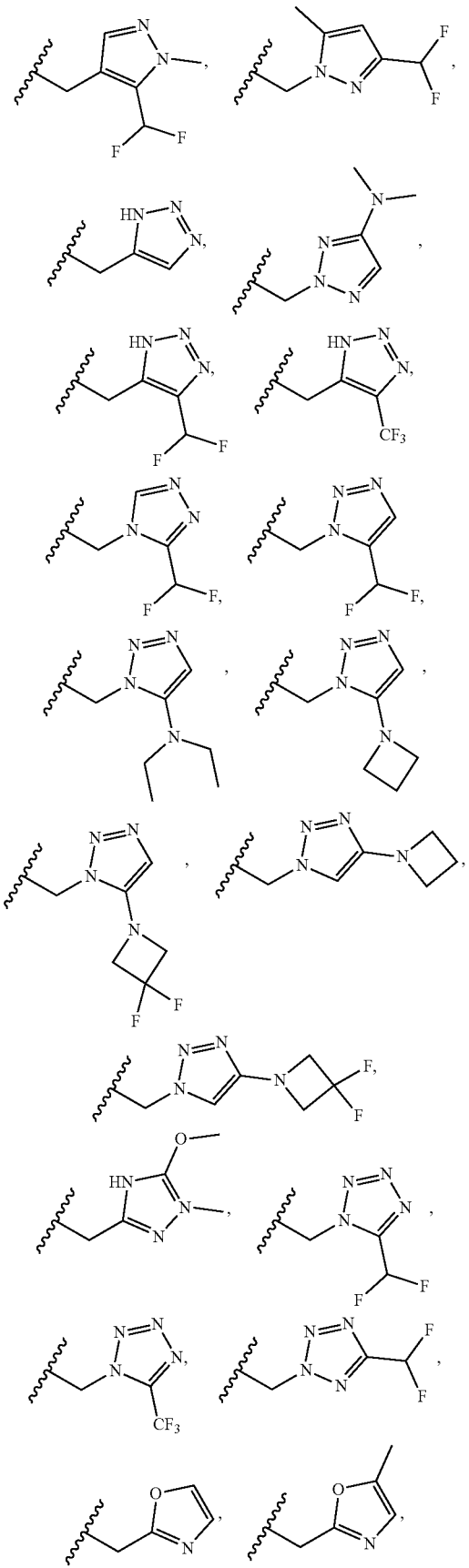

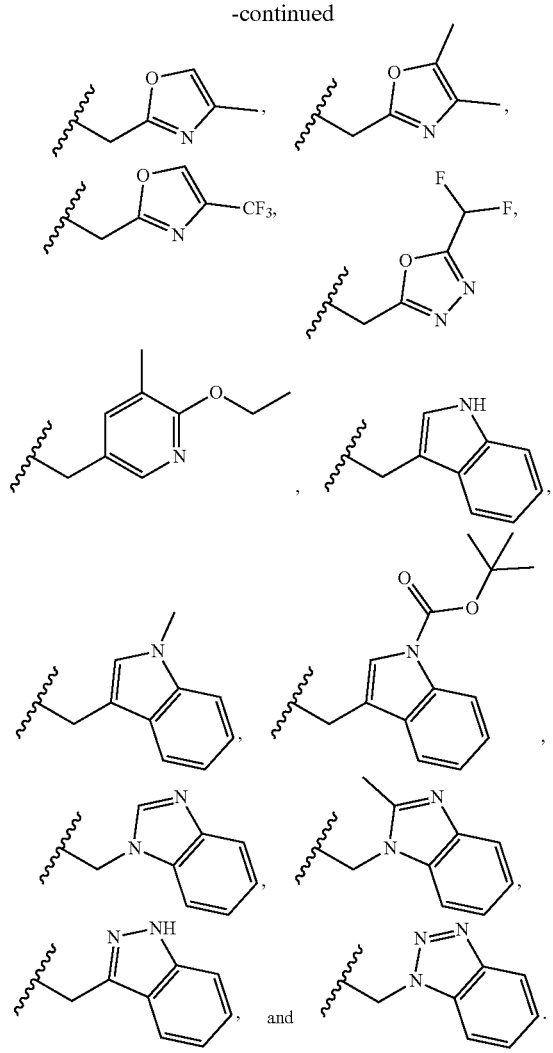

In some embodiments, R² is

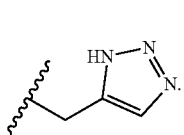 [SMILES: *Cc1cnn[nH]1]

In some embodiments, R² is

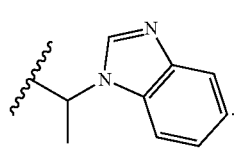 [SMILES: *C(C)n1cnc2ccccc21]

In some embodiments of a compound of formula (I-A3), or a stereoisomer or tautomer thereof, or a pharmaceutically acceptable salt of any of the foregoing, R² is C₁₋₆alkyl, wherein the C₁₋₆alkyl of R² is substituted with one or more Rᵃ, wherein Rᵃ is 3-15 membered heterocyclyl, wherein the 3-15 membered heterocyclyl of Rᵃ is optionally substituted with one or more Rᶜ. In some embodiments, R² is methyl, wherein the methyl of R² is substituted with one or more Rᵃ, wherein Rᵃ is 3-15 membered heterocyclyl, wherein the 3-15 membered heterocyclyl of Rᵃ is optionally substituted with one or more Rᶜ. In some embodiments, R² is methyl, wherein the methyl of R² is substituted with one or more Rᵃ, wherein Rᵃ is 3-8 membered heterocyclyl, wherein the 3-8 membered heterocyclyl of Rᵃ is optionally substituted with one or more Rᶜ. In some embodiments, R² is methyl, wherein the methyl of R² is substituted with one or more Rᵃ, wherein Rᵃ is 3-8 membered heterocyclyl, wherein the 3-8 membered heterocyclyl of Rᵃ is optionally substituted with one or more oxo or C₁₋₆alkyl. In some embodiments, R² is

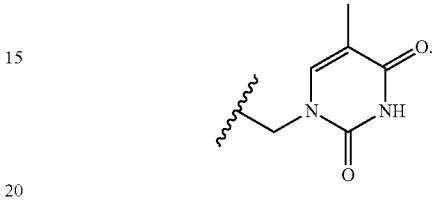

In some variations, the embodiments provided herein also apply to a compound of formula (I') or a stereoisomer or tautomer thereof, or a pharmaceutically acceptable salt of any of the foregoing, or any variation or embodiment thereof. In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I'), (I-A3), or a stereoisomer or tautomer thereof, or a pharmaceutically acceptable salt of any of the foregoing, In some embodiments, R² is methyl, wherein the methyl of R² is substituted with one or more Rᵃ, wherein Rᵃ is 3-8 membered heterocyclyl, wherein the 3-8 membered heterocyclyl of Rᵃ is optionally substituted with one or more Rᶜ, wherein Rᶜ is oxo, C₁₋₆alkyl, or —C(O)—C₁₋₆alkoxy, wherein the C₁₋₆alkyl of Rᶜ is optionally substituted with one or more halo, and the —C(O)—C₁₋₆alkoxy of Rᶜ is optionally substituted with one or more halo. In some embodiments, R² is

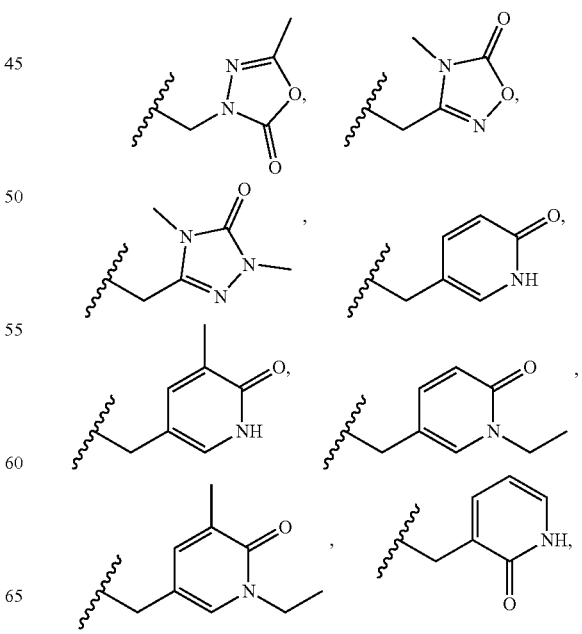

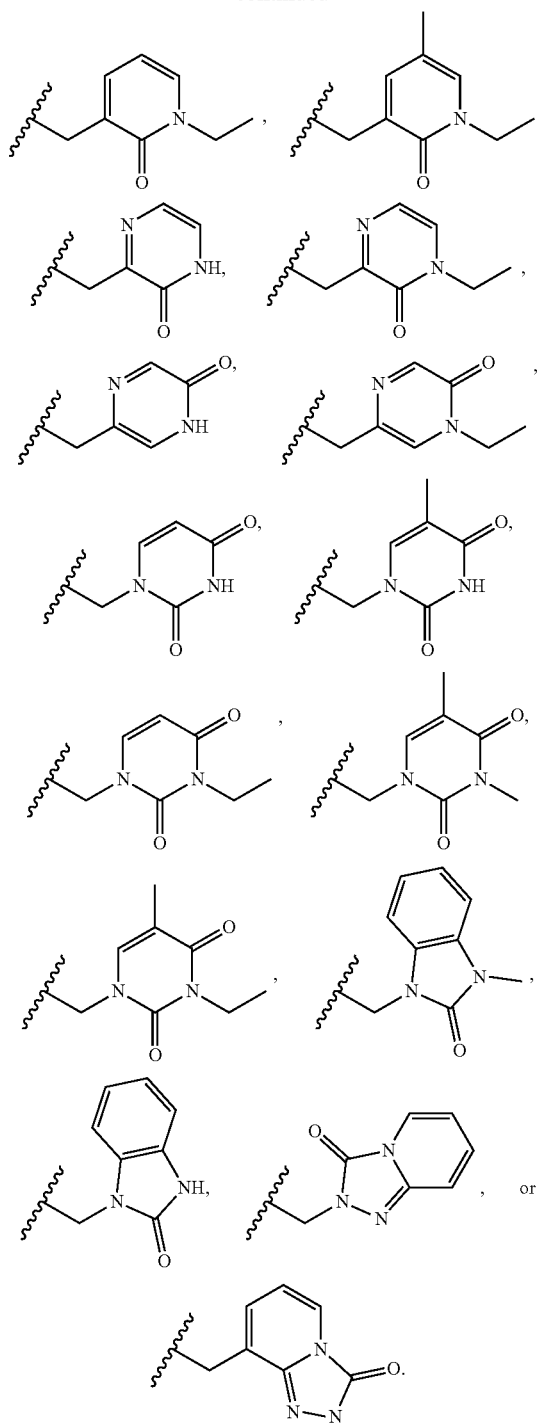

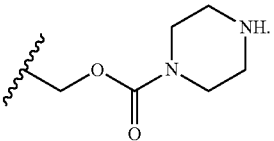

In some variations, the embodiments provided herein also apply to a compound of formula (I') or a stereoisomer or tautomer thereof, or a pharmaceutically acceptable salt of any of the foregoing, or any variation or embodiment thereof. In some embodiments of a compound of formula (I-A3), or a stereoisomer or tautomer thereof, or a pharmaceutically acceptable salt of any of the foregoing, $R^2$ is $C_{1-6}$alkyl, wherein the $C_{1-6}$alkyl of $R^2$ is substituted with one or more $R^a$, wherein $R^a$ is —N($R^c$)($R^d$). In some embodiments, $R^2$ is methyl, wherein the methyl of $R^2$ is substituted with one or more $R^a$, wherein $R^a$ is —N($R^c$)($R^d$). In some embodiments, $R^2$ is methyl, wherein the methyl of $R^2$ is substituted with one or more $R^a$, wherein $R^a$ is —N($R^c$)($R^d$), wherein one of $R^c$ and $R^d$ is H, and the other of $R^c$ and $R^d$ is —C(O)—N($C_{1-6}$alkyl)$_2$. In some embodiments, $R^2$ is In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I'), (I-A3), or a stereoisomer or tautomer thereof, or a pharmaceutically acceptable salt of any of the foregoing, $R^2$ is methyl, wherein the methyl of $R^2$ is substituted with one or more $R^a$, wherein $R^a$ is —N($R^c$)($R^d$), wherein one of $R^c$ and $R^d$ is H, and the other of $R^c$ and $R^d$, —C(O)—$C_{1-6}$alkyl, —C(O)—N($C_{1-6}$alkyl)$_2$, or —C(O)-(3-15 membered heterocyclyl), wherein the —C(O)-(3-15 membered heterocyclyl) of $R^c$ or $R^d$ is optionally substituted with one or more halo, —C(O)—$C_{1-6}$alkoxy, or $C_{1-6}$alkyl, and the $C_{1-6}$alkyl of the —C(O)—N($C_{1-6}$alkyl)$_2$ of $R^c$ or $R^d$ are, independently of each other, optionally substituted with one or more halo or $C_{6-20}$aryl. In some embodiments, $R^2$ is

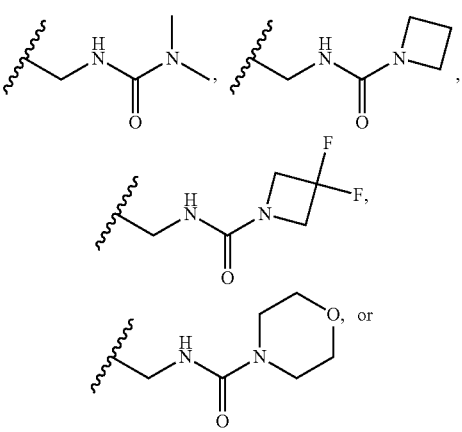

In some embodiments of a compound of formula (I-A3), or a stereoisomer or tautomer thereof, or a pharmaceutically acceptable salt of any of the foregoing, $R^2$ is $C_{1-6}$alkyl, wherein the $C_{1-6}$alkyl of $R^2$ is substituted with one or more $R^a$, wherein $R^a$ is —O—$R^e$. In some embodiments, $R^2$ is methyl, wherein the methyl of $R^2$ is substituted with one or more $R^a$, wherein $R^a$ is —O—$R^e$. In some embodiments, $R^2$ is methyl, wherein the methyl of $R^2$ is substituted with one or more $R^a$, wherein $R^a$ is —O—$R^e$, wherein $R^e$ is —C(O)-(3-15 membered heterocyclyl). In some embodiments, $R^2$ is

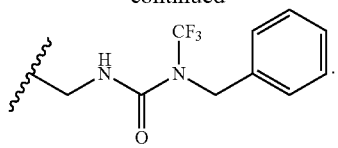

In some embodiments of a compound of formula (I'), (I-A3), or a stereoisomer or tautomer thereof, or a pharmaceutically acceptable salt of any of the foregoing, $R^2$ is methyl, wherein the methyl of $R^2$ is substituted with one or more $R^a$, wherein $R^a$ is —N($R^c$)($R^d$), wherein one of $R^c$ and $R^d$ is H, and the other of $R^c$ and $R^d$ is 5-20 membered heteroaryl, wherein the 5-20 membered heteroaryl of $R^c$ or $R^d$ are independently optionally substituted with one or more $C_{1-6}$alkyl. In some embodiments, $R^2$ is

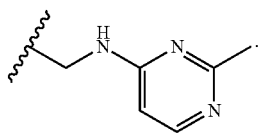 [SMILES: *CNc1ccnc(C)n1]

In some embodiments, provided herein is a compound of formula (I) or formula (I-A), or a stereoisomer or tautomer thereof, or a pharmaceutically acceptable salt of any of the foregoing, wherein the compound is a compound of formula (I-A4):

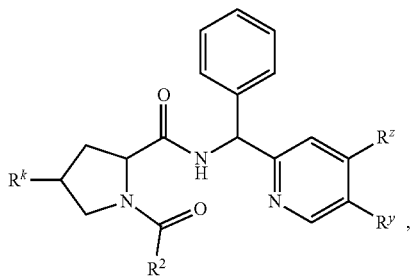

(I-A4)

or a stereoisomer or tautomer thereof, or a pharmaceutically acceptable salt of any of the foregoing, wherein $R^z$ is H, halo, $C_{1-6}$alkyl, or —NH$_2$ and $R^y$ is (i) $C_{1-6}$alkyl, (ii), $C_{2-6}$alkenyl, or (iii) $C_{3-10}$cycloalkyl, wherein the $C_{3-10}$cycloalkyl is optionally substituted with one or more halo or $C_{1-6}$alkyl. In some embodiments, $R^z$ is H, halo, or $C_{1-6}$alkyl; and $R^y$ is (i) $C_{1-6}$alkyl, (ii), $C_{2-6}$alkenyl, or (iii) $C_{3-10}$cycloalkyl, wherein the $C_{3-10}$cycloalkyl is optionally substituted with one or more halo or $C_{1-6}$alkyl. In some embodiments, $R^z$ is H or $C_{1-6}$alkyl; and $R^y$ is (i) $C_{1-6}$alkyl or (ii) $C_{3-10}$cycloalkyl, wherein the $C_{3-10}$cycloalkyl is optionally substituted with one or more halo or $C_{1-6}$alkyl. In some embodiments of a compound of formula (I-A4), or a stereoisomer or tautomer thereof, or a pharmaceutically acceptable salt of any of the foregoing, $R^z$ is H or methyl; and $R^y$ is (i) isopropyl, or (ii) $C_{3-4}$cycloalkyl. In some variations, $R^2$, $R^k$, $R^y$, and $R^z$ of formula (I-A4) are as defined for a compound of formula (I'), or a stereoisomer or tautomer thereof, or a pharmaceutically acceptable salt of any of the foregoing, or any variation or embodiment thereof, wherein $R^y$ and $R^z$ are each independently H, halo, $C_{1-6}$alkyl, $C_{2-6}$alkenyl, $C_{1-6}$alkoxy, —NH$_2$, or $C_{3-10}$cycloalkyl, wherein, the $C_{1-6}$alkyl is optionally substituted with one or more halo, and the $C_{3-10}$cycloalkyl is optionally substituted with one or more halo or $C_{1-6}$alkyl. In some embodiments, $R^z$ is H, halo, or $C_{1-6}$alkyl, wherein the $C_{1-6}$alkyl of $R^z$ is optionally substituted with one or more halo; and $R^y$ is (i) $C_{1-6}$alkyl, (ii), or (ii) $C_{3-10}$cycloalkyl, wherein the $C_{3-10}$cycloalkyl is optionally substituted with one or more halo or $C_{1-6}$alkyl. In some embodiments of a compound of formula (I-A4), or a stereoisomer or tautomer thereof, or a pharmaceutically acceptable salt of any of the foregoing, $R^z$ is H or methyl, wherein the methyl of $R^z$ is optionally substituted with one or more halo; and $R^y$ is (i) isopropyl, or (ii) $C_{3-4}$cycloalkyl.

In some embodiments of a compound of formula (I-A4), or a stereoisomer or tautomer thereof, or a pharmaceutically acceptable salt of any of the foregoing, $R^k$ is H or halo. In some embodiments of a compound of formula (I-A4), or a stereoisomer or tautomer thereof, or a pharmaceutically acceptable salt of any of the foregoing, $R^k$ is H or fluoro. In some embodiments of a compound of formula (I-A4), or a stereoisomer or tautomer thereof, or a pharmaceutically acceptable salt of any of the foregoing, $R^k$ is fluoro. In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I-A4), or a stereoisomer or tautomer thereof, or a pharmaceutically acceptable salt of any of the foregoing, $R^2$ is $C_{1-6}$alkyl, wherein the $C_{1-6}$alkyl of $R^2$ is optionally substituted with one or more $R^a$. In some embodiments, $R^2$ is $C_{1-6}$alkyl, wherein the $C_{1-6}$alkyl of $R^2$ is substituted with one or more $R^a$, wherein $R^a$ is —OH or 5-20 membered heteroaryl, wherein the 5-20 membered heteroaryl of $R^a$ is optionally substituted with one or more $R^b$. In some embodiments, $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more $R^b$. In some embodiments, $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more $C_{1-6}$alkyl, wherein the $C_{1-6}$alkyl is optionally substituted with one or more halo, —NH$_2$, —NH($C_{1-6}$alkyl), —N($C_{1-6}$alkyl)$_2$, —NH—C(O)$C_{1-6}$alkyl, or —NH—C(O)—$C_{1-6}$alkoxy. In some embodiments, $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more methyl, wherein the methyl is optionally substituted with one or more fluoro.

In some embodiments of a compound of formula (I-A4), or a stereoisomer or tautomer thereof, or a pharmaceutically acceptable salt of any of the foregoing, $R^2$ is selected from the group consisting of

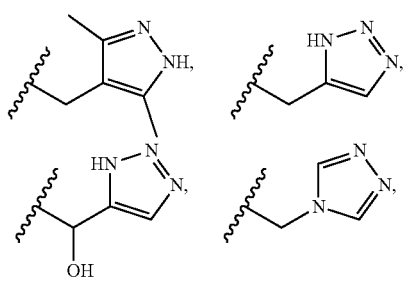

-continued

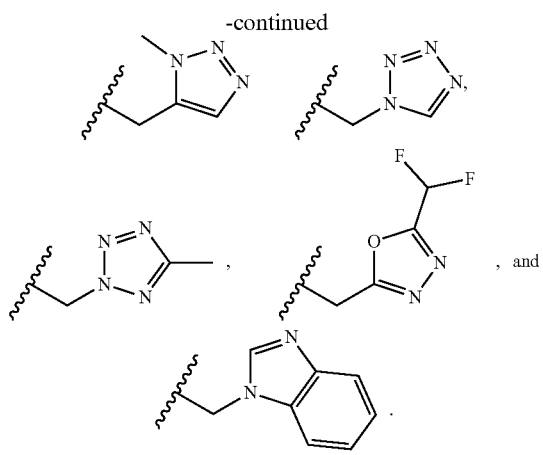

In some embodiments, $R^2$ is

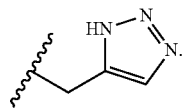

In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I-A4), or a stereoisomer or tautomer thereof, or a pharmaceutically acceptable salt of any of the foregoing, $R^2$ is $C_{1-6}$alkyl, wherein the $C_{1-6}$alkyl of $R^2$ is substituted with one or more $R^a$, wherein $R^a$ is 3-15 membered heterocyclyl, wherein the 3-15 membered heterocyclyl of $R^a$ is optionally substituted with one or more $R^c$. In some embodiments, $R^2$ is methyl, wherein the methyl of $R^2$ is substituted with one or more $R^a$, wherein $R^a$ is 3-15 membered heterocyclyl, wherein the 3-15 membered heterocyclyl of $R^a$ is optionally substituted with one or more $R^c$. In some embodiments, $R^2$ is methyl, wherein the methyl of $R^2$ is substituted with one or more $R^a$, wherein $R^a$ is 3-8 membered heterocyclyl, wherein the 3-8 membered heterocyclyl of $R^a$ is optionally substituted with one or more $R^c$. In some embodiments, $R^2$ is methyl, wherein the methyl of $R^2$ is substituted with one or more $R^a$, wherein $R^a$ is 3-8 membered heterocyclyl, wherein the 3-8 membered heterocyclyl of $R^a$ is optionally substituted with one or more oxo or $C_{1-6}$alkyl. In some embodiments, $R^2$ is

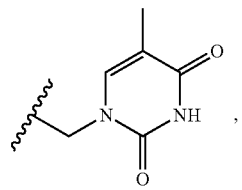 [SMILES: *Cn1cc(C)c(=O)[nH]c1=O]

In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I-A4), or a stereoisomer or tautomer thereof, or a pharmaceutically acceptable salt of any of the foregoing, $R^2$ is $C_{1-6}$alkyl, wherein the $C_{1-6}$alkyl of $R^2$ is substituted with one or more $R^a$, wherein $R^a$ is —O—$R^e$. In some embodiments, $R^2$ is methyl, wherein the methyl of $R^2$ is substituted with one or more $R^a$, wherein $R^a$ is —O—$R^e$. In some embodiments, $R^2$ is methyl, wherein the methyl of $R^2$ is substituted with one or more $R^a$, wherein $R^a$ is —O—$R^e$, wherein $R^e$ is —C(O)-(3-15 membered heterocyclyl). In some embodiments, $R^2$ is

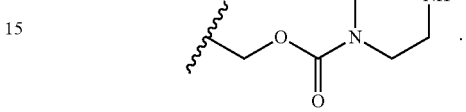

In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I-A4), or a stereoisomer or tautomer thereof, or a pharmaceutically acceptable salt of any of the foregoing, $R^2$ is $C_{1-6}$alkyl, wherein the $C_{1-6}$alkyl of $R^2$ is substituted with one or more $R^a$, wherein $R^a$ is —N($R^c$)($R^d$). In some embodiments, $R^2$ is methyl, wherein the methyl of $R^2$ is substituted with one or more $R^a$, wherein $R^a$ is —N($R^c$)($R^d$). In some embodiments, $R^2$ is methyl, wherein the methyl of $R^2$ is substituted with one or more $R^a$, wherein $R^a$ is —N($R^c$)($R^d$), wherein one of $R^c$ and $R^d$ is H, and the other of $R^c$ and $R^d$ is —C(O)—N($C_{1-6}$alkyl)$_2$. In some embodiments, $R^2$ is

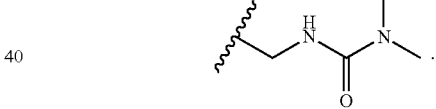

In some variations, the embodiments provided herein also apply to a compound of formula (I) or a stereoisomer or tautomer thereof, or a pharmaceutically acceptable salt of any of the foregoing, or any variation or embodiment thereof.

In some embodiments, provided herein is a compound of formula (I), or a stereoisomer or tautomer thereof, or a pharmaceutically acceptable salt of any of the foregoing, wherein the compound is a compound of formula (I-B):

(I-B)

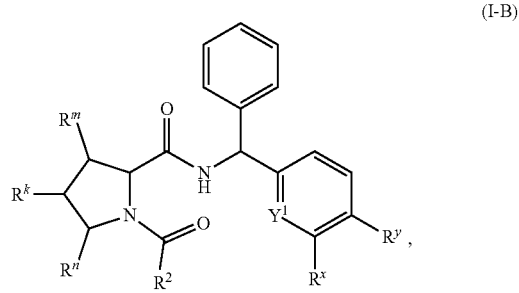

or a stereoisomer or tautomer thereof, or a pharmaceutically acceptable salt of any of the foregoing, wherein $Y^1$ is CH or N; $R^x$ is H, halo, $C_{1-6}$alkyl, or —NH$_2$, wherein, when $Y^1$ is CH, the $C_{1-6}$alkyl of Rx may be optionally substituted with one or more halo; $R^y$ is (i) $C_{1-6}$alkyl, (ii) $C_{2-6}$alkenyl, or (iii) $C_{3-10}$cycloalkyl, wherein the $C_{3-10}$cycloalkyl is optionally substituted with one or more halo or $C_{1-6}$alkyl; and Rk is taken together with either Rm or Rn, and the atoms to which they are attached, to form cyclopropyl. In some variations, $Y^1$, $R^2$, $R^k$, $R^m$, $R^n$, $R^x$, $R^y$, and $R^z$ of formula (I-B) are as defined for a compound of formula (I'), or a stereoisomer or tautomer thereof, or a pharmaceutically acceptable salt of any of the foregoing, or any variation or embodiment thereof, wherein Y1 is $CR^x$ or N; wherein, when the ring bearing $R^x$, and $R^y$ is phenyl, $R^x$, and $R^y$ are each independently H, halo, $C_{1-6}$alkyl, $C_{2-6}$alkenyl, —NH$_2$, —NH—C(O)—($C_{1-6}$alkyl), —NH—C(O)-(3-15 membered heterocyclyl), $C_{3-10}$cycloalkyl, or 5-20 membered heteroaryl, wherein the $C_{1-6}$alkyl is optionally substituted with one or more halo, —NH—C(O)—NH($C_{1-6}$alkyl), —NH—C(O)—$C_{1-6}$alkyl, or —NH—C(O)—$C_{1-6}$alkoxy, and the $C_{3-10}$cycloalkyl is optionally substituted with one or more halo or $C_{1-6}$alkyl, and the 5-20 membered heteroaryl is optionally substituted with one or more $C_{1-6}$alkyl; and wherein when the ring bearing $R^x$, and $R^y$ is pyridyl, $R^x$, and $R^y$ are each independently H, halo, $C_{1-6}$alkyl, $C_{2-6}$alkenyl, $C_{1-6}$alkoxy, —NH$_2$, or $C_{3-10}$cycloalkyl, wherein, the $C_{1-6}$alkyl is optionally substituted with one or more halo, and the $C_{3-10}$cycloalkyl is optionally substituted with one or more halo or $C_{1-6}$alkyl.

In some embodiments of a compound of formula (I-B), or a stereoisomer or tautomer thereof, or a pharmaceutically acceptable salt of any of the foregoing, $Y^1$ is CH or N; $R^x$ is H, halo, $C_{1-6}$alkyl, or NH$_2$, wherein, when $Y^1$ is CH, the $C_{1-6}$alkyl of $R^x$ may be optionally substituted with one or more halo; and $R^y$ is (i) $C_{1-6}$alkyl, (ii) $C_{2-6}$alkenyl, or (iii) $C_{3-10}$cycloalkyl, wherein the $C_{3-10}$cycloalkyl is optionally substituted with one or more halo or $C_{1-6}$alkyl. In some embodiments, $Y^1$ is CH or N; $R^x$ is H or halo; $R^y$ is $C_{1-6}$alkyl or $C_{3-10}$cycloalkyl; and $R^k$ is taken together with either $R^m$ or $R^n$, and the atoms to which they are attached, to form cyclopropyl. In some embodiments, $Y^1$ is CH or N; $R^x$ is H or fluoro; $R^y$ is (i) isopropyl or (ii) $C_{3-4}$cycloalkyl; and $R^k$ is taken together with either $R^m$ or $R^n$, and the atoms to which they are attached, to form cyclopropyl. In some embodiments, $Y^1$ is CH or N; $R^x$ is H or fluoro; $R^y$ is (i) isopropyl or (ii) $C_{3-4}$cycloalkyl; and $R^k$ is taken together with $R^m$ and the atoms to which they are attached to form cyclopropyl. In some embodiments, $Y^1$ is CH or N; $R^x$ is H or fluoro; $R^y$ is (i) isopropyl or (ii) $C_{3-4}$cycloalkyl; and $R^k$ is taken together with $R^n$ and the atoms to which they are attached to form cyclopropyl. In some embodiments, $Y^1$ is CH; $R^x$ is H or fluoro; $R^y$ is (i) isopropyl or (ii) $C_{3-4}$cycloalkyl; and $R^k$ is taken together with $R^m$ or $R^n$ and the atoms to which they are attached to form cyclopropyl. In some embodiments, $Y^1$ is N; $R^x$ is H or fluoro; $R^y$ is (i) isopropyl or (ii) $C_{3-4}$cycloalkyl; and $R^k$ is taken together with $R^m$ or $R^n$ and the atoms to which they are attached to form cyclopropyl. In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I-B), or a stereoisomer or tautomer thereof, or a pharmaceutically acceptable salt of any of the foregoing, $R^2$ is $C_{1-6}$alkyl, wherein the $C_{1-6}$alkyl of $R^2$ is optionally substituted with one or more $R^a$. In some embodiments, $R^2$ is $C_{1-6}$alkyl, wherein the $C_{1-6}$alkyl of $R^2$ is substituted with one or more $R^a$, wherein $R^a$ is —OH or 5-20 membered heteroaryl, wherein the 5-20 membered heteroaryl of $R^a$ is optionally substituted with one or more $R^b$. In some embodiments, $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more $R^b$. In some embodiments, $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more $C_{1-6}$alkyl, wherein the $C_{1-6}$alkyl is optionally substituted with one or more halo, —NH$_2$, —NH($C_{1-6}$alkyl), —N($C_{1-6}$alkyl)$_2$, —NH—C(O) $C_{1-6}$alkyl, or —NH—C(O)—$C_{1-6}$alkoxy. In some embodiments, $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more methyl, wherein the methyl is optionally substituted with one or more fluoro. In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I-B), or a stereoisomer or tautomer thereof, or a pharmaceutically acceptable salt of any of the foregoing, $R^2$ is selected from the group consisting of

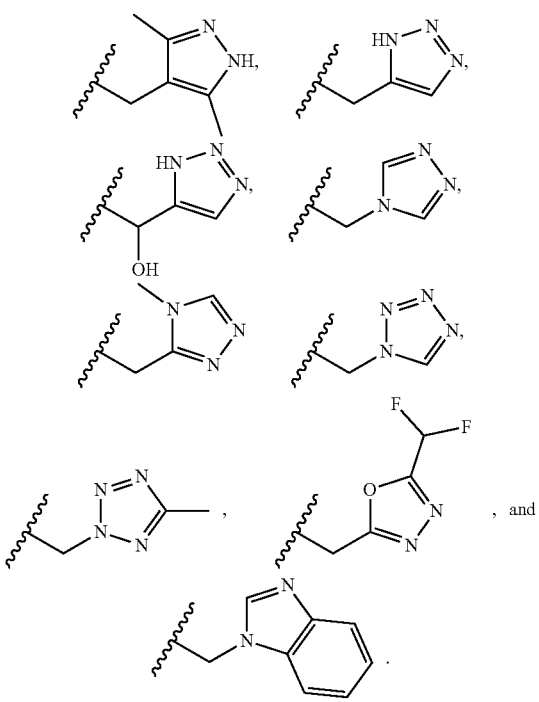

In some embodiments, $R^2$ is

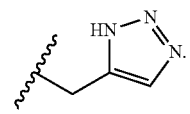

In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I-B), or a stereoisomer or tautomer thereof, or a pharmaceutically acceptable salt of any of the foregoing, $R^2$ is $C_{1-6}$alkyl, wherein the $C_{1-6}$alkyl of $R^2$ is substituted with one or more $R^a$, wherein $R^a$ is 3-15 membered heterocyclyl, wherein the 3-15 membered heterocyclyl of $R^a$ is optionally substituted with one or more $R^c$. In some embodiments, $R^2$ is methyl, wherein the methyl of $R^2$ is substituted with one or more $R^a$, wherein $R^a$ is 3-15 membered heterocyclyl, wherein the 3-15 membered heterocyclyl of $R^a$ is optionally substituted with one or more $R^c$. In some embodiments, $R^2$ is methyl, wherein the methyl of $R^2$ is substituted with one or more $R^a$, wherein $R^a$ is 3-8 membered heterocyclyl, wherein the 3-8 membered heterocyclyl of $R^a$ is optionally substituted with one or more $R^c$. In some embodiments, $R^2$ is methyl, wherein the methyl of $R^2$ is substituted with one or more $R^a$, wherein $R^a$ is 3-8 membered heterocyclyl, wherein the 3-8 membered heterocyclyl of $R^a$ is optionally substituted with one or more oxo or $C_{1-6}$alkyl. In some embodiments, $R^2$ is

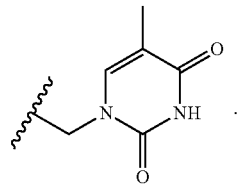 [SMILES: *Cn1cc(C)c(=O)[nH]c1=O]

In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I-B), or a stereoisomer or tautomer thereof, or a pharmaceutically acceptable salt of any of the foregoing, $R^2$ is $C_{1-6}$alkyl, wherein the $C_{1-6}$alkyl of $R^2$ is substituted with one or more $R^a$, wherein $R^a$ is —O—$R^e$. In some embodiments, $R^2$ is methyl, wherein the methyl of $R^2$ is substituted with one or more $R^a$, wherein $R^a$ is —O—$R^e$. In some embodiments, $R^2$ is methyl, wherein the methyl of $R^2$ is substituted with one or more $R^a$, wherein $R^a$ is —O—$R^e$, wherein $R^e$ is —C(O)-(3-15 membered heterocyclyl). In some embodiments, $R^2$ is

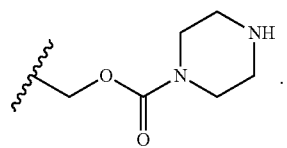 [SMILES: *COC(=O)N1CCNCC1]

In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I-B), or a stereoisomer or tautomer thereof, or a pharmaceutically acceptable salt of any of the foregoing, $R^2$ is $C_{1-6}$alkyl, wherein the $C_{1-6}$alkyl of $R^2$ is substituted with one or more $R^a$, wherein $R^a$ is —N($R^c$)($R^d$). In some embodiments, $R^2$ is methyl, wherein the methyl of $R^2$ is substituted with one or more $R^a$, wherein $R^a$ is —N($R^c$)($R^d$). In some embodiments, $R^2$ is methyl, wherein the methyl of $R^2$ is substituted with one or more $R^a$, wherein $R^a$ is —N($R^c$)($R^d$), wherein one of $R^c$ and $R^d$ is H, and the other of $R^c$ and $R^d$ is —C(O)—N($C_{1-6}$alkyl)$_2$. In some embodiments, $R^2$ is

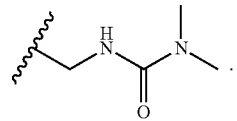 [SMILES: *CNC(=O)N(C)C]

In some variations, the embodiments provided herein also apply to a compound of formula (I') or a stereoisomer or tautomer thereof, or a pharmaceutically acceptable salt of any of the foregoing, or any variation or embodiment thereof.

In some embodiments, provided here is a compound of formula (I) or formula (I-B), or a stereoisomer or tautomer thereof, or a pharmaceutically acceptable salt of any of the foregoing, wherein the compound is a compound of formula (I-B1):

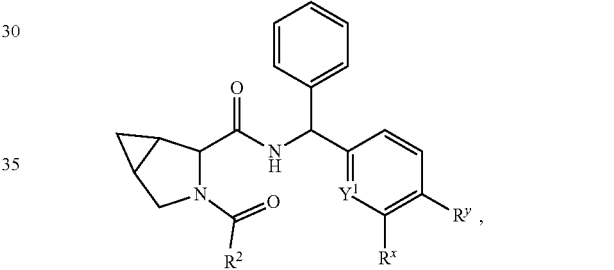

(I-B1)

or a stereoisomer or tautomer thereof, or a pharmaceutically acceptable salt of any of the foregoing, wherein $Y^1$ is CH or N; $R^x$ is H or halo; and $R^y$ is $C_{1-6}$alkyl or $C_{3-10}$cycloalkyl. In some embodiments, $Y^1$ is CH or N; $R^x$ is H or fluoro; and $R^y$ is (i) isopropyl or (ii) $C_{3-4}$cycloalkyl. In some embodiments, $Y^1$ is CH; $R^x$ is H or fluoro; and $R^y$ is (i) isopropyl or (ii) $C_{3-4}$cycloalkyl. In some embodiments, $Y^1$ is N; $R^x$ is H or fluoro; and $R^y$ is (i) isopropyl or (ii) $C_{3-4}$cycloalkyl. In some variations, $Y^1$, $R^2$, $R^x$, and $R^y$ of formula (I-B1) are as defined for a compound of formula (I'), or a stereoisomer or tautomer thereof, or a pharmaceutically acceptable salt of any of the foregoing, or any variation or embodiment thereof, wherein $Y^1$ is $CR^x$ or N; wherein, when the ring bearing $R^x$, and $R^y$ is phenyl, $R^x$, and $R^y$ are each independently H, halo, $C_{1-6}$alkyl, $C_{2-6}$alkenyl, —NH$_2$, —NH—C(O)—($C_{1-6}$alkyl), —NH—C(O)-(3-15 membered heterocyclyl), $C_{3-10}$cycloalkyl, or 5-20 membered heteroaryl, wherein the $C_{1-6}$alkyl is optionally substituted with one or more halo, —NH—C(O)—NH($C_{1-6}$alkyl), —NH—C(O)—$C_{1-6}$alkyl, or —NH—C(O)—$C_{1-6}$alkoxy, the $C_{3-10}$cycloalkyl is optionally substituted with one or more halo or $C_{1-6}$alkyl, and the 5-20 membered heteroaryl is optionally substituted with one or more $C_{1-6}$alkyl; and wherein when the ring bearing $R^x$, and $R^y$ is pyridyl, $R^x$, and $R^y$ are each independently H, halo, $C_{1-6}$alkyl, $C_{2-6}$alkenyl, $C_{1-6}$alkoxy, —NH$_2$, or $C_{3-10}$cycloalkyl, wherein, the $C_{1-6}$alkyl is optionally substituted with one or more halo, and the $C_{3-10}$cycloalkyl is optionally substituted with one or more halo or $C_{1-6}$alkyl. In some embodiments, $Y^1$ is CH or N; $R^x$ is H or fluoro; and $R^y$ is (i) isopropyl or (ii) $C_{3-4}$cycloalkyl. In some embodiments, $Y^1$ is CH; $R^x$ is H or fluoro; and $R^y$ is (i) isopropyl or (ii) $C_{3-4}$cycloalkyl. In some embodiments, $Y^1$ is N; $R^x$ is H or fluoro; and $R^y$ is (i) isopropyl or (ii) $C_{3-4}$cycloalkyl.

In some embodiments of a compound of formula (I-B1), or a stereoisomer or tautomer thereof, or a pharmaceutically acceptable salt of any of the foregoing, $R^2$ is $C_{1-6}$alkyl, wherein the $C_{1-6}$alkyl of $R^2$ is optionally substituted with one or more $R^a$. In some embodiments, $R^2$ is $C_{1-6}$alkyl, wherein the $C_{1-6}$alkyl of $R^2$ is substituted with one or more $R^a$, wherein $R^a$ is —OH or 5-20 membered heteroaryl, wherein the 5-20 membered heteroaryl of $R^a$ is optionally substituted with one or more $R^b$. In some embodiments, $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more $R^b$. In some embodiments, $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more $C_{1-6}$alkyl, wherein the $C_{1-6}$alkyl is optionally substituted with one or more halo, —NH$_2$, —NH($C_{1-6}$alkyl), —N($C_{1-6}$alkyl)$_2$, —NH—C(O)$C_{1-6}$alkyl, or —NH—C(O)—$C_{1-6}$alkoxy. In some embodiments, $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more methyl, wherein the methyl is optionally substituted with one or more fluoro. In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I-B1), or a stereoisomer or tautomer thereof, or a pharmaceutically acceptable salt of any of the foregoing, $R^2$ is selected from the group consisting of

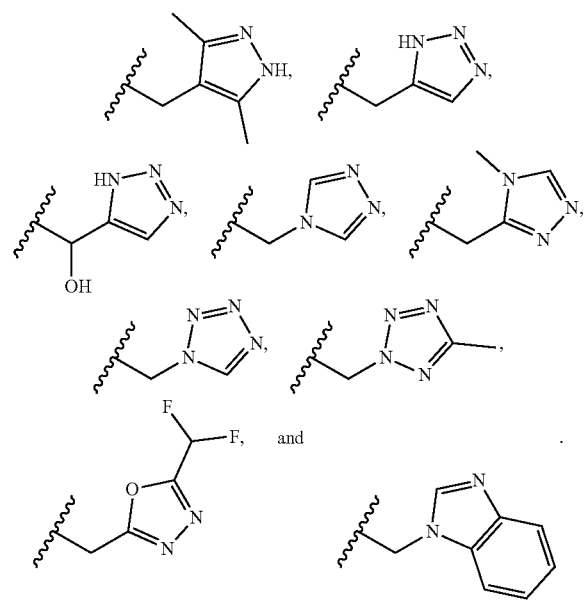

In some embodiments, $R^2$ is

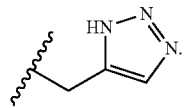 [SMILES: *Cc1cnn[nH]1]

In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I-B1), or a stereoisomer or tautomer thereof, or a pharmaceutically acceptable salt of any of the foregoing, $R^2$ is $C_{1-6}$alkyl, wherein the $C_{1-6}$alkyl of $R^2$ is substituted with one or more $R^a$, wherein $R^a$ is 3-15 membered heterocyclyl, wherein the 3-15 membered heterocyclyl of $R^a$ is optionally substituted with one or more $R^c$. In some embodiments, $R^2$ is methyl, wherein the methyl of $R^2$ is substituted with one or more $R^a$, wherein $R^a$ is 3-15 membered heterocyclyl, wherein the 3-15 membered heterocyclyl of $R^a$ is optionally substituted with one or more $R^c$. In some embodiments, $R^2$ is methyl, wherein the methyl of $R^2$ is substituted with one or more $R^a$, wherein $R^a$ is 3-8 membered heterocyclyl, wherein the 3-8 membered heterocyclyl of $R^a$ is optionally substituted with one or more $R^c$. In some embodiments, $R^2$ is methyl, wherein the methyl of $R^2$ is substituted with one or more $R^a$, wherein $R^a$ is 3-8 membered heterocyclyl, wherein the 3-8 membered heterocyclyl of $R^a$ is optionally substituted with one or more oxo or $C_{1-6}$alkyl. In some embodiments, $R^2$ is

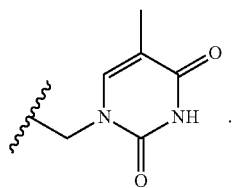 [SMILES: *Cn1cc(C)c(=O)[nH]c1=O]

In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I-B1), or a stereoisomer or tautomer thereof, or a pharmaceutically acceptable salt of any of the foregoing, $R^2$ is $C_{1-6}$alkyl, wherein the $C_{1-6}$alkyl of $R^2$ is substituted with one or more $R^a$, wherein $R^a$ is —O—$R^e$. In some embodiments, $R^2$ is methyl, wherein the methyl of $R^2$ is substituted with one or more $R^a$, wherein $R^a$ is —O—$R^e$. In some embodiments, $R^2$ is methyl, wherein the methyl of $R^2$ is substituted with one or more $R^a$, wherein $R^a$ is —O—$R^e$, wherein $R^e$ is —C(O)-(3-15 membered heterocyclyl). In some embodiments, $R^2$ is

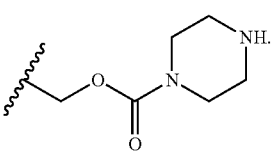 [SMILES: *COC(=O)N1CCNCC1]

In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I-B1), or a stereoisomer or tautomer thereof, or a pharmaceutically acceptable salt of any of the foregoing, $R^2$ is $C_{1-6}$alkyl, wherein the $C_{1-6}$alkyl of $R^2$ is substituted with one or more $R^a$, wherein $R^a$ is —N($R^c$)($R^d$). In some embodiments, $R^2$ is methyl, wherein the methyl of $R^2$ is substituted with one or more $R^a$, wherein $R^a$ is —N($R^c$)($R^d$). In some embodiments, $R^2$ is methyl, wherein the methyl of $R^2$ is substituted with one or more $R^a$, wherein $R^a$ is —N($R^c$)($R^d$), wherein one of $R^c$ and $R^d$ is H, and the other of $R^c$ and $R^d$ is —C(O)—N($C_{1-6}$alkyl)$_2$. In some embodiments, $R^2$ is

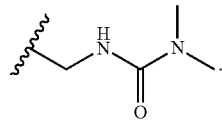 [SMILES: *CNC(=O)N(C)C]

In some variations, the embodiments provided herein also apply to a compound of formula (I') or a stereoisomer or tautomer thereof, or a pharmaceutically acceptable salt of any of the foregoing, or any variation or embodiment thereof.

In some embodiments, provided herein is a compound of formula (I) or formula (I-B), or a stereoisomer or tautomer thereof, or a pharmaceutically acceptable salt of any of the foregoing, wherein the compound is a compound of formula (I-B2):

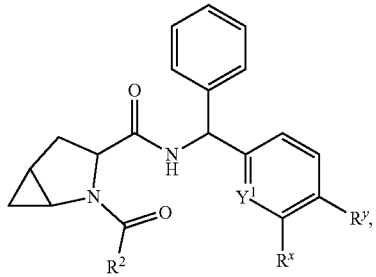

(I-B2)

or a stereoisomer or tautomer thereof, or a pharmaceutically acceptable salt of any of the foregoing, wherein $Y^1$ is CH or N; $R^x$ is H or halo; and $R^y$ is $C_{1-6}$alkyl or $C_{3-10}$cycloalkyl. In some embodiments, $Y^1$ is CH or N; $R^x$ is H or fluoro; and $R^y$ is (i) isopropyl or (ii) $C_{3-4}$cycloalkyl. In some embodiments, $Y^1$ is CH; $R^x$ is H or fluoro; and $R^y$ is (i) isopropyl or (ii) $C_{3-4}$cycloalkyl. In some embodiments, $Y^1$ is N; $R^x$ is H or fluoro; and $R^y$ is (i) isopropyl or (ii) $C_{3-4}$cycloalkyl. In some variations, $Y^1$, $R^2$, $R^x$, and $R^y$ of formula (I-B2) are as defined for a compound of formula (I'), or a stereoisomer or tautomer thereof, or a pharmaceutically acceptable salt of any of the foregoing, or any variation or embodiment thereof, wherein $Y^1$ is is $CR^x$ or N; wherein, when the ring bearing $R^x$, and $R^y$ is phenyl, $R^x$, and $R^y$ are each independently H, halo, $C_{1-6}$alkyl, $C_{2-6}$alkenyl, —NH$_2$, —NH—C(O)—($C_{1-6}$alkyl), —NH—C(O)-(3-15 membered heterocyclyl), $C_{3-10}$cycloalkyl, or 5-20 membered heteroaryl, wherein the $C_{1-6}$alkyl is optionally substituted with one or more halo, —NH—C(O)—NH($C_{1-6}$alkyl), —NH—C(O)—$C_{1-6}$alkyl, or —NH—C(O)—$C_{1-6}$alkoxy, the $C_{3-10}$cycloalkyl is optionally substituted with one or more halo or $C_{1-6}$alkyl, and the 5-20 membered heteroaryl is optionally substituted with one or more $C_{1-6}$alkyl; and wherein when the ring bearing $R^x$, and $R^y$ is pyridyl, $R^x$, and $R^y$ are each independently H, halo, $C_{1-6}$alkyl, $C_{2-6}$alkenyl, $C_{1-6}$alkoxy, —NH$_2$, or $C_{3-10}$cycloalkyl, wherein, the $C_{1-6}$alkyl is optionally substituted with one or more halo, and the $C_{3-10}$cycloalkyl is optionally substituted with one or more halo or $C_{1-6}$alkyl. In some embodiments, $Y^1$ is CH or N; $R^x$ is H or fluoro; and $R^y$ is (i) isopropyl or (ii) $C_{3-4}$cycloalkyl. In some embodiments, $Y^1$ is CH; $R^x$ is H or fluoro; and $R^y$ is (i) isopropyl or (ii) $C_{3-4}$cycloalkyl. In some embodiments, $Y^1$ is N; $R^x$ is H or fluoro; and $R^y$ is (i) isopropyl or (ii) $C_{3-4}$cycloalkyl.

In some embodiments of a compound of formula (I-B2), or a stereoisomer or tautomer thereof, or a pharmaceutically acceptable salt of any of the foregoing, $R^2$ is $C_{1-6}$alkyl, wherein the $C_{1-6}$alkyl of $R^2$ is optionally substituted with one or more $R^a$. In some embodiments, $R^2$ is $C_{1-6}$alkyl, wherein the $C_{1-6}$alkyl of $R^2$ is substituted with one or more $R^a$, wherein $R^a$ is —OH or 5-20 membered heteroaryl, wherein the 5-20 membered heteroaryl of $R^a$ is optionally substituted with one or more $R^b$. In some embodiments, $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more $R^b$. In some embodiments, $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more $C_{1-6}$alkyl, wherein the $C_{1-6}$alkyl is optionally substituted with one or more halo, —NH$_2$, —NH($C_{1-6}$alkyl), —N($C_{1-6}$alkyl)$_2$, —NH—C(O)$C_{1-6}$alkyl, or —NH—C(O)—$C_{1-6}$alkoxy. In some embodiments, $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more methyl, wherein the methyl is optionally substituted with one or more fluoro. In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I-B2), or a stereoisomer or tautomer thereof, or a pharmaceutically acceptable salt of any of the foregoing, $R^2$ is selected from the group consisting of

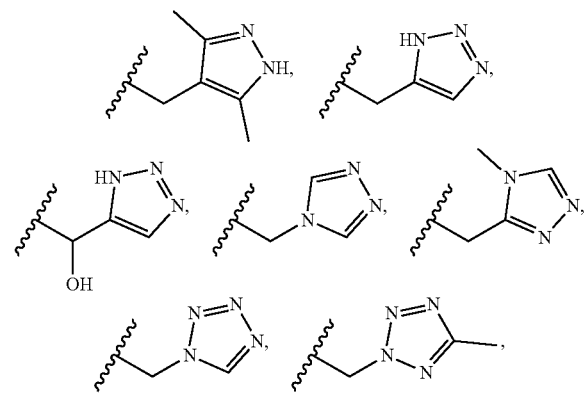

-continued

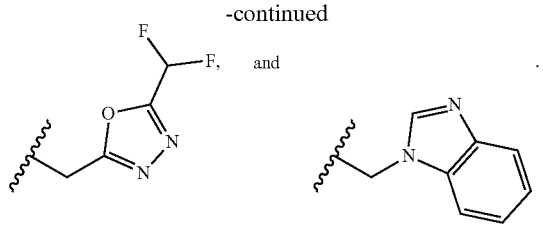

In some embodiments, R² is

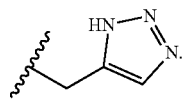

In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I-B2), or a stereoisomer or tautomer thereof, or a pharmaceutically acceptable salt of any of the foregoing, R² is $C_{1-6}$alkyl, wherein the $C_{1-6}$alkyl of R² is substituted with one or more $R^a$, wherein $R^a$ is 3-15 membered heterocyclyl, wherein the 3-15 membered heterocyclyl of $R^a$ is optionally substituted with one or more $R^c$. In some embodiments, R² is methyl, wherein the methyl of R² is substituted with one or more $R^a$, wherein $R^a$ is 3-15 membered heterocyclyl, wherein the 3-15 membered heterocyclyl of $R^a$ is optionally substituted with one or more $R^c$. In some embodiments, R² is methyl, wherein the methyl of R² is substituted with one or more $R^a$, wherein $R^a$ is 3-8 membered heterocyclyl, wherein the 3-8 membered heterocyclyl of $R^a$ is optionally substituted with one or more $R^c$. In some embodiments, R² is methyl, wherein the methyl of R² is substituted with one or more $R^a$, wherein $R^a$ is 3-8 membered heterocyclyl, wherein the 3-8 membered heterocyclyl of $R^a$ is optionally substituted with one or more oxo or $C_{1-6}$alkyl. In some embodiments, R² is

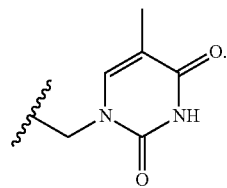 [SMILES: *Cn1cc(C)c(=O)[nH]c1=O]

In some variations, the embodiments provided herein also apply to a compound of formula (I) or a stereoisomer or tautomer thereof, or a pharmaceutically acceptable salt of any of the foregoing, or any variation or embodiment thereof.

In some embodiments of a compound of formula (I-B2), or a stereoisomer or tautomer thereof, or a pharmaceutically acceptable salt of any of the foregoing, R² is $C_{1-6}$alkyl, wherein the $C_{1-6}$alkyl of R² is substituted with one or more $R^a$, wherein $R^a$ is —O—$R^e$. In some embodiments, R² is methyl, wherein the methyl of R² is substituted with one or more $R^a$, wherein $R^a$ is —O—$R^e$. In some embodiments, R² is methyl, wherein the methyl of R² is substituted with one or more $R^a$, wherein $R^a$ is —O—$R^e$, wherein $R^e$ is —C(O)-(3-15 membered heterocyclyl). In some embodiments, R² is

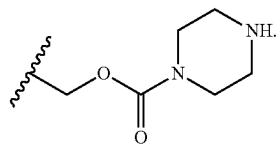 [SMILES: *COC(=O)N1CCNCC1]

In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I-B2), or a stereoisomer or tautomer thereof, or a pharmaceutically acceptable salt of any of the foregoing, R² is $C_{1-6}$alkyl, wherein the $C_{1-6}$alkyl of R² is substituted with one or more $R^a$, wherein $R^a$ is —N($R^c$)($R^d$). In some embodiments, R² is methyl, wherein the methyl of R² is substituted with one or more $R^a$, wherein $R^a$ is —N($R^c$)($R^d$). In some embodiments, R² is methyl, wherein the methyl of R² is substituted with one or more $R^a$, wherein $R^a$ is —N($R^c$)($R^d$), wherein one of $R^c$ and $R^d$ is H, and the other of $R^c$ and $R^d$ is —C(O)—N($C_{1-6}$alkyl)₂. In some embodiments, R² is

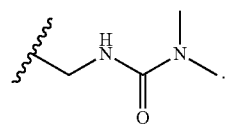 [SMILES: *CNC(=O)N(C)C]

In some variations, the embodiments provided herein also apply to a compound of formula (I') or a stereoisomer or tautomer thereof, or a pharmaceutically acceptable salt of any of the foregoing, or any variation or embodiment thereof.

In some embodiments, provided herein is a compound of formula (I), or a stereoisomer or tautomer thereof, or a pharmaceutically acceptable salt of any of the foregoing, wherein the compound is a compound of formula (I-C):

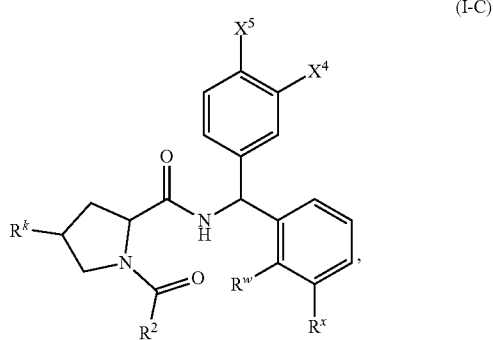

(I-C)

wherein $X^5$ is H, $C_{1-6}$alkyl, $C_{1-6}$alkoxy, or $C_{3-10}$cycloalkyl; $X^4$ is H, halo, $C_{1-6}$alkyl, $C_{1-6}$alkoxy, or 5-20 membered heteroaryl; $R^v$ is —NH₂, —NH—C(O)—($C_{1-6}$alkyl), or —NH—C(O)-(3-15 membered heterocyclyl); and $R^w$ is H, —NH₂, —NH—C(O)—($C_{1-6}$alkyl), or —NH—C(O)-(3-15 membered heterocyclyl). In some embodiments, $X^5$ is H or $C_{1-6}$alkyl; $X^4$ is H; $R^v$ is —$NH_2$, —NH—C(O)—($C_{1-6}$alkyl), or —NH—C(O)-(3-15 membered heterocyclyl); and $R^w$ is H, —$NH_2$, —NH—C(O)—($C_{1-6}$alkyl), or —NH—C(O)-(3-15 membered heterocyclyl). In some embodiments, $R^w$ is H and $R^v$ is —NH—C(O)$C_{1-6}$alkyl. In some embodiments, $R^w$ is H and $R^v$ is —NH—C(O)$CH_3$. In some variations, $R^2$, $R^k$, $R^w$, $R^v$, $X^4$ and $X^5$ of formula (I-C) are as defined for a compound of formula (I'), or a stereoisomer or tautomer thereof, or a pharmaceutically acceptable salt of any of the foregoing, or any variation or embodiment thereof, wherein $X^5$ is H, $C_{1-6}$alkyl, $C_{1-6}$alkoxy, or $C_{3-10}$cycloalkyl; $X^4$ is H, halo, $C_{1-6}$alkyl, $C_{1-6}$alkoxy, or 5-20 membered heteroaryl; $R^v$ is —$NH_2$, —NH—C(O)—($C_{1-6}$alkyl), or —NH—C(O)-(3-15 membered heterocyclyl); and $R^w$ is H, —$NH_2$, —NH—C(O)—($C_{1-6}$alkyl), or —NH—C(O)-(3-15 membered heterocyclyl). In some embodiments, $X^5$ is H or $C_{1-6}$alkyl; $X^4$ is H; $R^v$ is —$NH_2$, —NH—C(O)—($C_{1-6}$alkyl), or —NH—C(O)-(3-15 membered heterocyclyl); and $R^w$ is H, —$NH_2$, —NH—C(O)—($C_{1-6}$alkyl), or —NH—C(O)-(3-15 membered heterocyclyl). In some embodiments, $R^w$ is H and $R^v$ is —NH—C(O)$C_{1-6}$alkyl. In some embodiments, $R^w$ is H and $R^v$ is —NH—C(O)$CH_3$.

In some embodiments, provided is a compound of formula (I), or a stereoisomer or tautomer thereof, or a pharmaceutically acceptable salt of any of the foregoing, wherein the compound is a compound of formula (I-D):

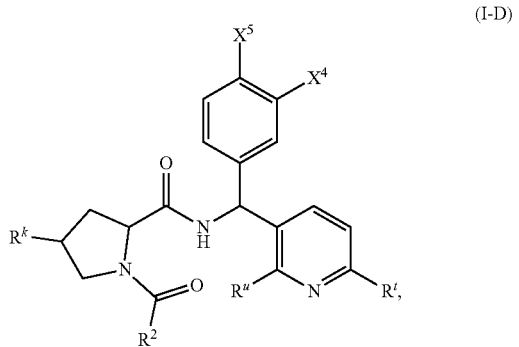

(I-D)

wherein $X^5$ is H, $C_{1-6}$alkyl, $C_{1-6}$alkoxy, or $C_{3-10}$cycloalkyl; $X^4$ is H, halo, $C_{1-6}$alkyl, $C_{1-6}$alkoxy, or 5-20 membered heteroaryl; and $R^t$ and $R^u$ are independently H, $C_{1-6}$alkoxy, or —$NH_2$. In some embodiments, $X^5$ is $C_{1-6}$alkyl; $X^4$ is H, halo, or $C_{1-6}$alkyl; and $R^t$ and $R^u$ are independently H or —$NH_2$. In some embodiments, at least one of $R^t$ and $R^u$ is —$NH_2$. In some embodiments, $R^t$ is H and $R^u$ is —$NH_2$. In some embodiments, $R^t$ is —$NH_2$ and $R^u$ is H. In some variations, $R^2$, $R^k$, $R^t$, $R^u$, $X^4$ and $X^5$ of formula (I-D) are as defined for a compound of formula (I'), or a stereoisomer or tautomer thereof, or a pharmaceutically acceptable salt of any of the foregoing, or any variation or embodiment thereof, wherein $X^5$ is H, $C_{1-6}$alkyl, $C_{1-6}$alkoxy, or $C_{3-10}$cycloalkyl; $X^4$ is H, halo, $C_{1-6}$alkyl, $C_{1-6}$alkoxy, or 5-20 membered heteroaryl; and $R^t$ and $R^u$ are independently H, $C_{1-6}$alkoxy, or —$NH_2$. In some embodiments, $X^5$ is $C_{1-6}$alkyl; $X^4$ is H, halo, or $C_{1-6}$alkyl; and $R^t$ and $R^u$ are independently H or —$NH_2$. In some embodiments, at least one of $R^t$ and $R^u$ is —$NH_2$. In some embodiments, $R^t$ is H and $R^u$ is —$NH_2$. In some embodiments, $R^t$ is —$NH_2$ and $R^u$ is H.

In some embodiments of a compound of formula (I-C) or (I-D), or a stereoisomer or tautomer thereof, or a pharmaceutically acceptable salt of any of the foregoing, $R^k$ is H or halo. In some embodiments of a compound of formula (I-C) or (I-D), or a stereoisomer or tautomer thereof, or a pharmaceutically acceptable salt of any of the foregoing, $R^k$ is H or fluoro. In some embodiments of a compound of formula (I-C) or (I-D), or a stereoisomer or tautomer thereof, or a pharmaceutically acceptable salt of any of the foregoing, $R^k$ is fluoro. In some variations, the embodiments provided herein also apply to a compound of formula (I') or a stereoisomer or tautomer thereof, or a pharmaceutically acceptable salt of any of the foregoing, or any variation or embodiment thereof.

In some embodiments, provided is a compound of formula (I'), or a stereoisomer or tautomer thereof, or a pharmaceutically acceptable salt of any of the foregoing, wherein the compound is a compound of formula (I-D1):

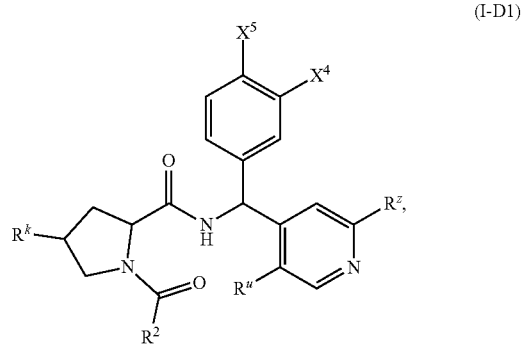

(I-D1)

wherein $X^5$ is H, $C_{1-6}$alkyl, $C_{1-6}$alkoxy, or $C_{3-10}$cycloalkyl; $X^4$ is H, halo, $C_{1-6}$alkyl, $C_{1-6}$alkoxy, or 5-20 membered heteroaryl; and $R^u$ and $R^z$ are independently H, $C_{1-6}$alkoxy, or —$NH_2$. In some embodiments, $X^5$ is $C_{1-6}$alkyl; $X^4$ is H, halo, or $C_{1-6}$alkyl; and $R^u$ and $R^z$ are independently H, halo or —$NH_2$. In some embodiments, at least one of $R^u$ and $R^z$ is —$NH_2$. In some embodiments, $R^u$ is H and $R^z$ is —$NH_2$. In some embodiments, $R^u$ is —$NH_2$ and $R^z$ is H. In some embodiments, at least one of $R^u$ and $R^z$ is halo. In some embodiments, $R^u$ is H and $R^z$ is fluoro. In some embodiments, $R^u$ is fluoro and $R^z$ is H.

In some embodiments, provided is a compound of formula (I'), or a stereoisomer or tautomer thereof, or a pharmaceutically acceptable salt of any of the foregoing, wherein the compound is a compound of formula (I-D2):

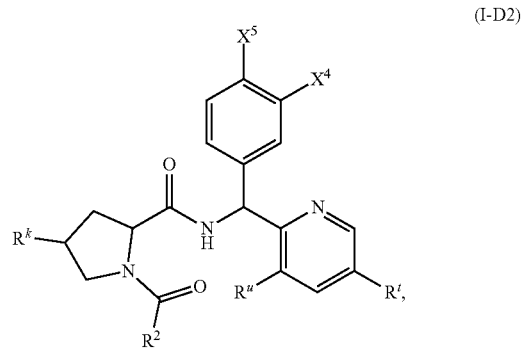

(I-D2)

wherein $X^5$ is H, $C_{1-6}$alkyl, $C_{1-6}$alkoxy, or $C_{3-10}$cycloalkyl; $X^4$ is H, halo, $C_{1-6}$alkyl, $C_{1-6}$alkoxy, or 5-20 membered heteroaryl, wherein the $C_{1-6}$alkyl of $X^4$ is optionally substituted with one of more halo; and $R^t$ and $R^u$ are independently H, C$_{1-6}$alkoxy, or —NH$_2$. In some embodiments, X$^5$ is C$_{1-6}$alkyl; X$^4$ is H, halo, or C$_{1-6}$alkyl; and R$^u$ and R$^z$ are independently H, halo or —NH$_2$. In some embodiments, at least one of R$^u$ and R$^z$ is —NH$_2$. In some embodiments, R$^u$ is H and R$^z$ is —NH$_2$. In some embodiments, R$^u$ is —NH$_2$ and R$^z$ is H. In some embodiments, at least one of R$^u$ and R$^z$ is halo. In some embodiments, R$^u$ is H and R$^z$ is fluoro. In some embodiments, R$^u$ is fluoro and R$^z$ is H.

In some embodiments, provided is a compound of formula (I), or a stereoisomer or tautomer thereof, or a pharmaceutically acceptable salt of any of the foregoing, wherein the compound is a compound of formula (I-E):

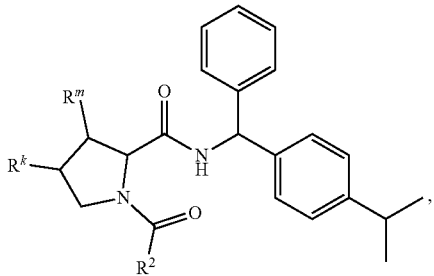

(I-E)

wherein R$^k$ and R$^m$ are independently H, OH, —NH$_2$, or —NH—C(O)C$_{1-6}$alkyl. In some embodiments, R$^k$ is H and R$^m$ is H, OH, —NH$_2$, or —NH—C(O)C$_{1-6}$alkyl. In some embodiments, R$^k$ is H and R$^m$ is OH. In some embodiments, R$^k$ is H, OH, —NH$_2$, or —NH—C(O)C$_{1-6}$alkyl, and R$^m$ is H. In some embodiments, R$^k$ is OH, —NH$_2$, or —NH—C(O)C$_{1-6}$alkyl, and R$^m$ is H. In some embodiments, R$^k$ is OH, —NH$_2$, or —NH—C(O)CH$_3$, and R$^m$ is H. In some variations, R$^2$, R$^k$, and R$^m$ of formula (I-E) are as defined for a compound of formula (I'), or a stereoisomer or tautomer thereof, or a pharmaceutically acceptable salt of any of the foregoing, or any variation or embodiment thereof, wherein R$^k$ and R$^m$ are independently H, OH, —NH$_2$, or —NH—C(O)C$_{1-6}$alkyl. In some embodiments, R$^k$ is H and R$^m$ is H, OH, —NH$_2$, or —NH—C(O)C$_{1-6}$alkyl. In some embodiments, R$^k$ is H and R$^m$ is OH. In some embodiments, R$^k$ is H, OH, —NH$_2$, or —NH—C(O)C$_{1-6}$alkyl, and R$^m$ is H. In some embodiments, R$^k$ is OH, —NH$_2$, or —NH—C(O)C$_{1-6}$alkyl, and R$^m$ is H. In some embodiments, R$^k$ is OH, —NH$_2$, or —NH—C(O)CH$_3$, and R$^m$ is H.

In some embodiments, provided is a compound of formula (I), or a stereoisomer or tautomer thereof, or a pharmaceutically acceptable salt of any of the foregoing, wherein the compound is a compound of formula (I-F):

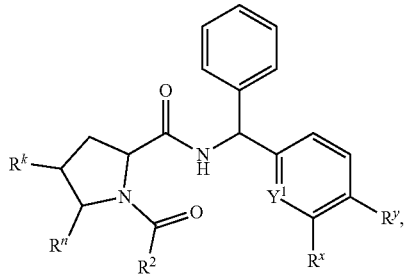

(I-F)

wherein Y$^1$ is CH or N; R$^x$ is H, halo, C$_{1-6}$alkyl, or —NH$_2$, wherein, when Y$^1$ is CH, the C$_{1-6}$alkyl of R$^x$ may be optionally substituted with one or more halo; R$^y$ is (i) C$_{1-6}$alkyl, (ii), C$_{2-6}$alkenyl, or (iii) C$_{3-10}$cycloalkyl, wherein the C$_{3-10}$cycloalkyl is optionally substituted with one or more halo or C$_{1-6}$alkyl; R$^k$ is H, halo, —OH, —NH$_2$, or —NH—C(O)C$_{1-6}$alkyl; and R$^n$ is H, C$_{1-6}$alkyl, or C$_{3-10}$cycloalkyl. In some embodiments, Y$^1$ is CH or N; R$^x$ is H, halo, or C$_{1-6}$alkyl; R$^y$ is (i) C$_{1-6}$alkyl, (ii), C$_{2-6}$alkenyl, or (iii) C$_{3-10}$cycloalkyl, wherein the C$_{3-10}$cycloalkyl is optionally substituted with one or more halo or C$_{1-6}$alkyl; R$^k$ is H, halo, —OH, —NH$_2$, or —NH—C(O)C$_{1-6}$alkyl; and R$^n$ is H, C$_{1-6}$alkyl, or C$_{3-10}$cycloalkyl. In some variations, R$^2$, R$^k$, R$^x$, R$^y$, and R$^z$ of formula (I-F) are as defined for a compound of formula (I'), or a stereoisomer or tautomer thereof, or a pharmaceutically acceptable salt of any of the foregoing, or any variation or embodiment thereof, wherein Y$^1$ is CH or N; R$^x$ is H, halo, C$_{1-6}$alkyl, or —NH$_2$, wherein, when Y$^1$ is CH, the C$_{1-6}$alkyl of R$^x$ may be optionally substituted with one or more halo; R$^y$ is (i) C$_{1-6}$alkyl, (ii), C$_{2-6}$alkenyl or (iii) C$_{3-10}$cycloalkyl, wherein the C$_{3-10}$cycloalkyl is optionally substituted with one or more halo or C$_{1-6}$alkyl; R$^k$ is H, halo, —OH, —NH$_2$, or —NH—C(O)C$_{1-6}$alkyl; and R$^n$ is H, C$_{1-6}$alkyl, or C$_{3-10}$cycloalkyl. In some embodiments, Y$^1$ is CH or N; R$^x$ is H, halo, or C$_{1-6}$alkyl; R$^y$ is (i) C$_{1-6}$alkyl, or (ii) C$_{3-10}$cycloalkyl, wherein the C$_{3-10}$cycloalkyl is optionally substituted with one or more halo or C$_{1-6}$alkyl; R$^k$ is H, halo, —OH, —NH$_2$, or —NH—C(O)C$_{1-6}$alkyl; and R$^n$ is H, C$_{1-6}$alkyl, or C$_{3-10}$cycloalkyl.

In some embodiments of a compound of formula (I-F), Y$^1$ is CH or N; R$^x$ is H, halo, or C$_{1-6}$alkyl; R$^y$ is (i) C$_{1-6}$alkyl, (ii), C$_{2-6}$alkenyl, or (iii) C$_{3-10}$cycloalkyl, wherein the C$_{3-10}$ cycloalkyl is optionally substituted with one or more halo or C$_{1-6}$alkyl; R$^k$ is H or halo; and R$^n$ is H, C$_{1-6}$alkyl, or C$_{3-6}$cycloalkyl. In some embodiments, Y$^1$ is N or CH, R$^x$ is H or halo, R$^y$ is C$_{1-6}$alkyl or C$_{3-6}$cycloalkyl, R$^k$ is H or halo, and R$^n$ is C$_{1-6}$alkyl or C$_{3-6}$cycloalkyl. In some embodiments, Y$^1$ is N or CH, R$^x$ is H or fluoro, R$^y$ is C$_{1-6}$alkyl or C$_{3-6}$cycloalkyl, R$^k$ is H or fluoro, and R$^n$ is C$_{1-6}$alkyl or C$_{3-6}$cycloalkyl. In some embodiments, Y$^1$ is N or CH, R$^x$ is H or fluoro, R$^y$ is C$_{1-6}$alkyl or C$_{3-6}$cycloalkyl, R$^k$ is H or fluoro, and R$^n$ is C$_{1-6}$alkyl or C$_{3-6}$cycloalkyl. In some embodiments, Y$^1$ is N or CH, R$^x$ is H or fluoro, R$^y$ is C$_{1-6}$alkyl or C$_{3-6}$cycloalkyl, R$^k$ is H, and R$^n$ is C$_{1-6}$alkyl or C$_{3-6}$cycloalkyl. In some embodiments, Y$^1$ is N or CH, R$^x$ is H or fluoro, R$^y$ is C$_{1-3}$alkyl or C$_{3-6}$cycloalkyl, R$^k$ is H, and R$^n$ is C$_{1-3}$lkyl or C$_{3-6}$cycloalkyl. In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I-C), (I-D), (I-E), or (I-F), or a stereoisomer or tautomer thereof, or a pharmaceutically acceptable salt of any of the foregoing, R$^2$ is C$_{1-6}$alkyl, wherein the C$_{1-6}$alkyl of R$^2$ is optionally substituted with one or more R$^a$. In some embodiments, R$^2$ is C$_{1-6}$alkyl, wherein the C$_{1-6}$alkyl of R$^2$ is substituted with one or more R$^a$, wherein R$^a$ is —OH or 5-20 membered heteroaryl, wherein the 5-20 membered heteroaryl of R$^a$ is optionally substituted with one or more R$^b$. In some embodiments, R$^2$ is methyl, wherein the methyl of R$^2$ is substituted with one or more R$^a$, wherein R$^a$ is —OH or 5-10 membered heteroaryl, wherein the 5-10 membered heteroaryl of R$^a$ is optionally substituted with one or more R$^b$. In some embodiments, R$^2$ is methyl, wherein the methyl of R$^2$ is substituted with one or more R$^a$, wherein R$^a$ is —OH or 5-10 membered heteroaryl, wherein the 5-10 membered heteroaryl of R$^a$ is optionally substituted with one or more C$_{1-6}$alkyl, wherein the C$_{1-6}$alkyl is optionally substituted with one or more halo, —NH$_2$, —NH(C$_{1-6}$alkyl), —N(C$_{1-6}$alkyl)$_2$, —NH—C(O)C$_{1-6}$alkyl, or —NH—C(O)—C$_{1-6}$alkoxy. In some embodiments, R$^2$ is methyl, wherein the methyl of R$^2$ is substituted with one or more R$^a$, wherein R$^a$ is —OH or 5-10 membered heteroaryl, wherein the 5-10 membered heteroaryl of R$^a$ is optionally substituted with one or more methyl, wherein the methyl is optionally substituted with one or more fluoro. In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I-C), (I-D), (I-E), or (I-F), or a stereoisomer or tautomer thereof, or a pharmaceutically acceptable salt of any of the foregoing, R$^2$ is selected from the group consisting of

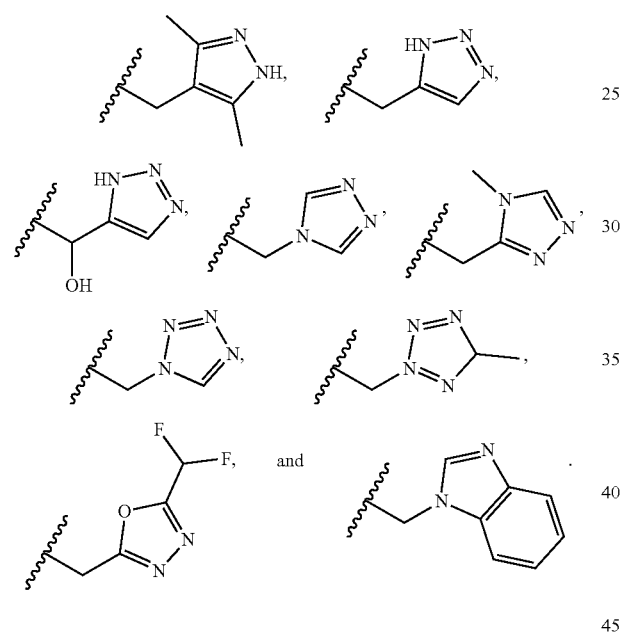

In some embodiments, R$^2$ is

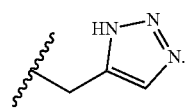 [SMILES: *Cc1cnn[nH]1]

In some embodiments of a compound of formula (I'), (I-C), (I-D), (I-E), or (I-F), or a stereoisomer or tautomer thereof, or a pharmaceutically acceptable salt of any of the foregoing, R$^2$ is selected from the group consisting of

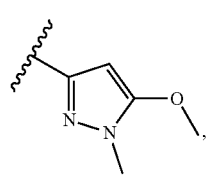

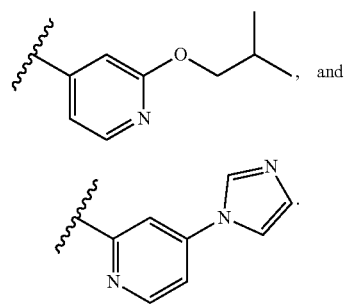

In some embodiments of a compound of formula (I'), (I-C), (I-D), (I-E), or (I-F), or a stereoisomer or tautomer thereof, or a pharmaceutically acceptable salt of any of the foregoing, R$^2$ is selected from the group consisting of

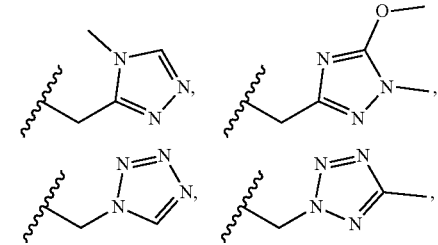

-continued

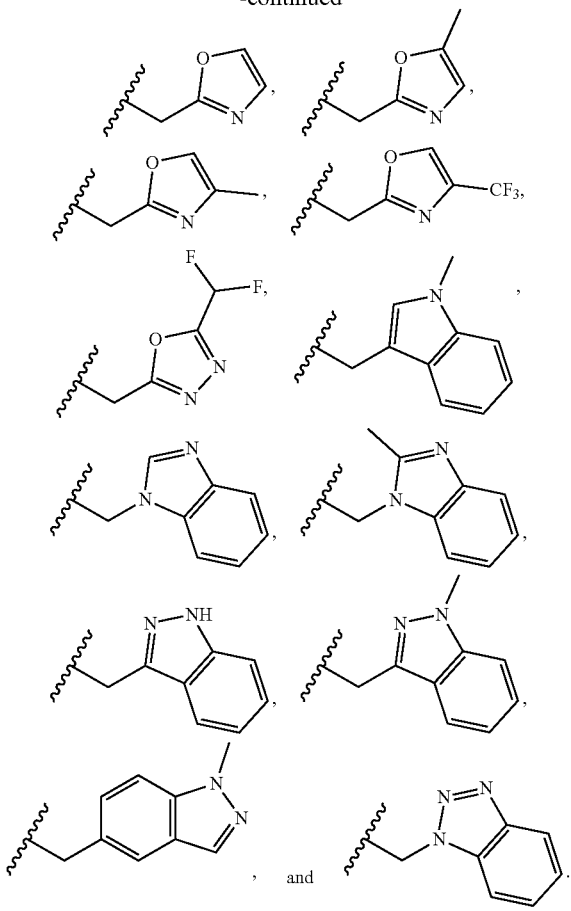

In some embodiments, $R^2$ is

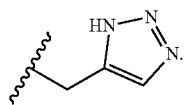 [SMILES: *Cc1cnn[nH]1]

In some embodiments of a compound of formula (I), (I-C), (I-D), (I-E), or (I-F), or a stereoisomer or tautomer thereof, or a pharmaceutically acceptable salt of any of the foregoing, $R^2$ is

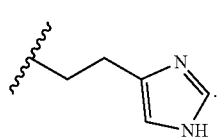 [SMILES: *CCc1c[nH]cn1]

In some embodiments of a compound of formula (I-C), (I-D), (I-E), or (I-F), or a stereoisomer or tautomer thereof, or a pharmaceutically acceptable salt of any of the foregoing, $R^2$ is $C_{1-6}$alkyl, wherein the $C_{1-6}$alkyl of $R^2$ is substituted with one or more $R^a$, wherein $R^a$ is 3-15 membered heterocyclyl, wherein the 3-15 membered heterocyclyl of $R^a$ is optionally substituted with one or more $R^c$. In some embodiments, $R^2$ is methyl, wherein the methyl of $R^2$ is substituted with one or more $R^a$, wherein $R^a$ is 3-15 membered heterocyclyl, wherein the 3-15 membered heterocyclyl of $R^a$ is optionally substituted with one or more $R^c$. In some embodiments, $R^2$ is methyl, wherein the methyl of $R^2$ is substituted with one or more $R^a$, wherein $R^a$ is 3-8 membered heterocyclyl, wherein the 3-8 membered heterocyclyl of $R^a$ is optionally substituted with one or more $R^c$. In some embodiments, $R^2$ is methyl, wherein the methyl of $R^2$ is substituted with one or more $R^a$, wherein $R^a$ is 3-8 membered heterocyclyl, wherein the 3-8 membered heterocyclyl of $R^a$ is optionally substituted with one or more oxo or $C_{1-6}$alkyl. In some embodiments, $R^2$ is

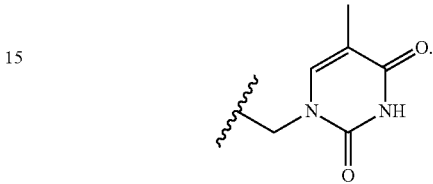

In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I') (I-C), (I-D), (I-E), or (I-F), or a stereoisomer or tautomer thereof, or a pharmaceutically acceptable salt of any of the foregoing, $R^2$ is methyl, wherein the methyl of $R^2$ is substituted with one or more $R^a$, wherein $R^a$ is 3-8 membered heterocyclyl, wherein the 3-8 membered heterocyclyl of $R^a$ is optionally substituted with one or more $R^c$, wherein $R^c$ is oxo, $C_{1-6}$alkyl, or —C(O)—$C_{1-6}$alkoxy, wherein the $C_{1-6}$alkyl of $R^c$ is optionally substituted with one or more halo, and the —C(O)—$C_{1-6}$alkoxy of $R^c$ is optionally substituted with one or more halo. In some embodiments, $R^2$ is selected from the group consisting of

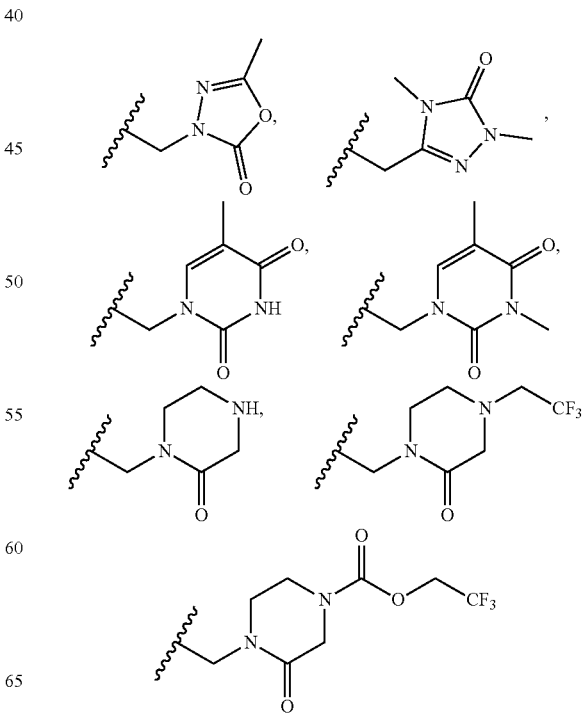

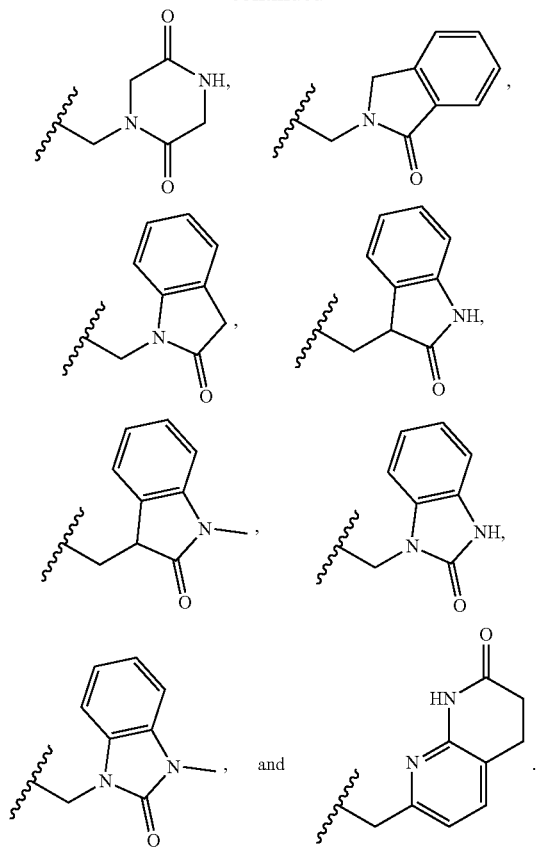

In some embodiments of a compound of formula (I-C), (I-D), (I-E), or (I-F), or a stereoisomer or tautomer thereof, or a pharmaceutically acceptable salt of any of the foregoing, $R^2$ is $C_{1-6}$alkyl, wherein the $C_{1-6}$alkyl of $R^2$ is substituted with one or more $R^a$, wherein $R^a$ is —O—$R^e$. In some embodiments, $R^2$ is methyl, wherein the methyl of $R^2$ is substituted with one or more $R^a$, wherein $R^a$ is —O—$R^e$. In some embodiments, $R^2$ is methyl, wherein the methyl of $R^2$ is substituted with one or more $R^a$, wherein $R^a$ is —O—$R^e$, wherein $R^e$ is —C(O)-(3-15 membered heterocyclyl). In some embodiments, $R^2$ is

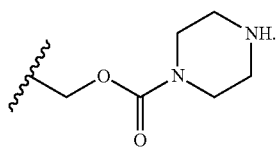 [SMILES: *COC(=O)N1CCNCC1]

In some embodiments of a compound of formula (I'), (I-C), (I-D), (I-E), or (I-F), or a stereoisomer or tautomer thereof, or a pharmaceutically acceptable salt of any of the foregoing, $R^2$ is methyl, wherein the methyl of $R^2$ is substituted with one or more $R^a$, wherein $R^a$ is —O—$R^e$, wherein $R^e$ is —C(O)-(3-15 membered heterocyclyl) wherein the —C(O)-(3-15 membered heterocyclyl) of $R^e$ is optionally substituted with one or more $C_{1-6}$alkyl, wherein the $C_{1-6}$alkyl is optionally substituted with one or more halo, $C_{1-6}$alkoxy, or $C_{3-10}$cycloalkyl. In some embodiments, $R^2$ is selected from the group consisting of In some embodiments of a compound of formula (I-C), (I-D), (I-E), or (I-F), or a stereoisomer or tautomer thereof, or a pharmaceutically acceptable salt of any of the foregoing, $R^2$ is $C_{1-6}$alkyl, wherein the $C_{1-6}$alkyl of $R^2$ is substituted with one or more $R^a$, wherein $R^a$ is —N($R^c$)($R^d$). In some embodiments, $R^2$ is methyl, wherein the methyl of $R^2$ is substituted with one or more $R^a$, wherein $R^a$ is —N($R^c$)($R^d$). In some embodiments, $R^2$ is methyl, wherein the methyl of $R^2$ is substituted with one or more $R^a$, wherein $R^a$ is —N($R^c$)($R^d$), wherein one of $R^c$ and $R^d$ is H, and the other of $R^c$ and $R^d$ is —C(O)—N($C_{1-6}$alkyl)$_2$. In some embodiments, $R^2$ is

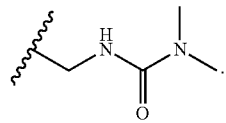 [SMILES: *CNC(=O)N(C)C]

In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I'), (I-C), (I-D), (I-E), or (I-F), or a stereoisomer or tautomer thereof, or a pharmaceutically acceptable salt of any of the foregoing, $R^2$ is methyl, wherein the methyl of $R^2$ is substituted with one or more $R^a$, wherein $R^a$ is —N($R^c$)($R^d$), wherein one of $R^c$ and $R^d$ is H, and the other of $R^c$ and $R^d$, —C(O)—$C_{1-6}$alkyl, —C(O)—N($C_{1-6}$alkyl)$_2$, or —C(O)-(3-15 membered heterocyclyl). In some embodiments, $R^2$ is

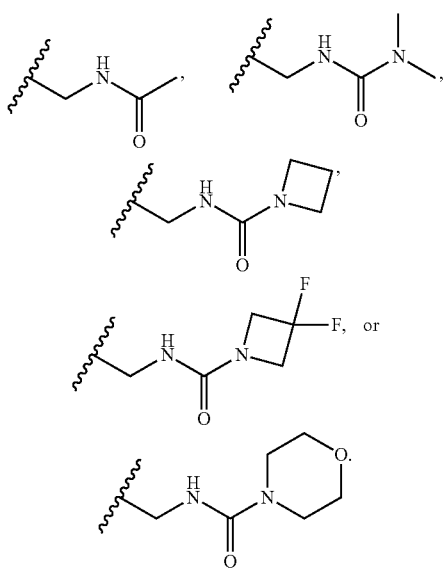

In some embodiments, provided herein is a compound of formula (I'), or a stereoisomer or tautomer thereof, or a pharmaceutically acceptable salt thereof, wherein the compound is a compound of formula (I-G):

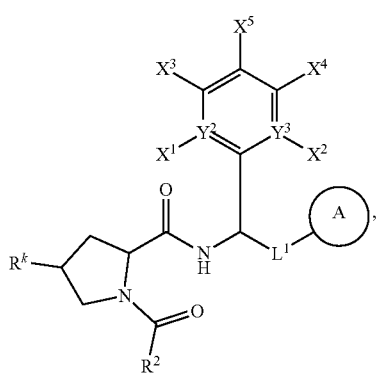

(I-G)

or a stereoisomer or tautomer thereof, or a pharmaceutically acceptable salt of any of the foregoing, wherein ring A is (i) 3-15 membered heterocyclyl, wherein the 3-15 membered heterocyclyl of ring A is optionally substituted with one or more oxo, (ii) 5-20 membered heteroaryl, wherein the 5-20 membered heteroaryl of ring A is optionally substituted with one or more halo, $C_{1-6}$alkyl, $C_2$-6alkenyl, $C_{1-6}$alkoxy, —$NH_2$, or $C_{3-10}$cycloalkyl, wherein, the $C_{1-6}$alkyl is optionally substituted with one or more halo, and the $C_{3-10}$cycloalkyl is optionally substituted with one or more halo or $C_{1-6}$alkyl, or (iii) $C_{3-10}$cycloalkyl.

In some embodiments of a compound of formula (I'), (I-G), or a stereoisomer or tautomer thereof, or a pharmaceutically acceptable salt of any of the foregoing, $X^3$ is H, fluoro or methyl optionally substituted with one or more fluoro; $X^4$ is (i) isopropyl (ii) $C_{3-4}$cycloalkyl optionally substituted with one or more halo or $C_{1-6}$alkyl or (iii) butyl; and $R^z$ is fluoro or methyl; provided that at least one of $X^3$ and $X^4$ is halo, $CF_2$ or $CF_3$.

In some embodiments of a compound of formula (I'), (I-G), or a stereoisomer or tautomer thereof, or a pharmaceutically acceptable salt of any of the foregoing, $R^k$ is H or halo. In some embodiments of a compound of formula (I-G), or a stereoisomer or tautomer thereof, or a pharmaceutically acceptable salt of any of the foregoing, $R^k$ is H or fluoro. In some embodiments of a compound of formula (I-G), or a stereoisomer or tautomer thereof, or a pharmaceutically acceptable salt of any of the foregoing, $R^k$ is fluoro.

In some embodiments of a compound of formula (I'), (I-G), or a stereoisomer or tautomer thereof, or a pharmaceutically acceptable salt of any of the foregoing, $R^2$ is 5-20 membered heteroaryl or —($C_{1-4}$alkyl)(5-20 membered heteroaryl), wherein the $C_{1-4}$ alkyl is optionally substituted with one or more or more —OH, halo, —$NH_2$, —NH($C_{1-6}$alkyl), —N($C_{1-6}$alkyl)$_2$, and wherein the 5-20 membered heteroaryl is optionally substituted with one or more $R^s$. In some embodiments, $R^s$ is halo, $C_{1-6}$alkyl, $C_{1-6}$alkoxy, —$NH_2$, —NH($C_{1-6}$alkyl), —N($C_{1-6}$alkyl)$_2$, —NH—C(O)—$C_{1-6}$alkyl, $C_{6-20}$aryl, $C_{3-10}$cycloalkyl, 3-15 membered heterocyclyl, 5-20 membered heteroaryl, or —C(O)—$C_{1-6}$alkoxy. In some embodiments, the $C_{1-6}$alkyl of $R^s$ is optionally substituted with one or more halo, $C_{1-6}$alkoxy, —$NH_2$, —NH($C_{1-6}$alkyl), —N($C_{1-6}$alkyl)$_2$, —NH—C(O)$C_{1-6}$alkyl, or —NH—C(O)—$C_{1-6}$alkoxy, and the 3-15-membered heterocyclyl of $R^s$ is optionally substituted with one or more halo or —C(O)—$C_{1-6}$alkoxy.

In some embodiments of a compound of formula (I'), (I-G), or a stereoisomer or tautomer thereof, or a pharmaceutically acceptable salt of any of the foregoing, $R^2$ is selected from the group consisting of

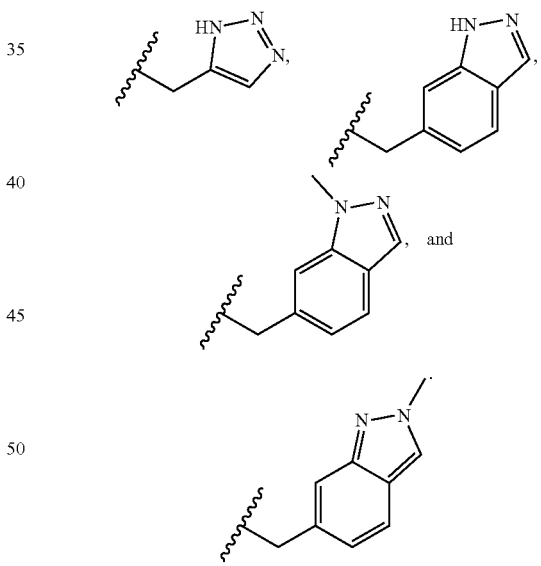

In some embodiments of a compound of formula (I') (I-G), or a stereoisomer or tautomer thereof, or a pharmaceutically acceptable salt of any of the foregoing, $R^2$ is methyl, wherein the methyl of $R^2$ is substituted with one or more $R^a$, wherein $R^a$ is —N($R^c$)($R^d$), wherein one of $R^c$ and $R^d$ is H, and the other of $R^c$ and $R^d$, —C(O)—$C_{1-6}$alkyl, —C(O)—N($C_{1-6}$alkyl)$_2$, or —C(O)-(3-15 membered heterocyclyl). In some embodiments, $R^2$ is

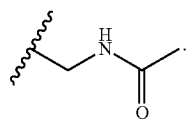 [SMILES: *CNC(C)=O]

In some embodiments of a compound of formula (I') (I-G), or a stereoisomer or tautomer thereof, or a pharmaceutically acceptable salt of any of the foregoing, ring A is (i) 3-15 membered heterocyclyl, wherein the 3-15 membered heterocyclyl of ring A is optionally substituted with one or more oxo, or $C_{1-6}$alkyl, (ii) 5-20 membered heteroaryl, wherein the 5-20 membered heteroaryl of ring A is optionally substituted with one or more halo, $C_{1-6}$alkyl, $C_{2-6}$alkenyl, $C_{1-6}$alkoxy, —$NH_2$, or $C_{3-10}$cycloalkyl, wherein, the $C_{1-6}$alkyl is optionally substituted with one or more halo, and the $C_{3-10}$cycloalkyl is optionally substituted with one or more halo or $C_{1-6}$alkyl, or (iii) $C_{3-10}$cycloalkyl.

In some embodiments of a compound of formula (I'), (I-G), or a stereoisomer or tautomer thereof, or a pharmaceutically acceptable salt of any of the foregoing, ring A is 3-15 membered heterocyclyl, wherein the 3-15 membered heterocyclyl of ring A is optionally substituted with one or more oxo, or $C_{1-6}$alkyl. In some embodiments ring A is selected from the group consisting of

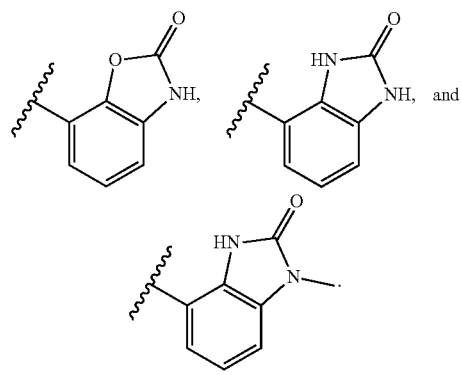

In some embodiments of a compound of formula (I'), (I-G), or a stereoisomer or tautomer thereof, or a pharmaceutically acceptable salt of any of the foregoing, ring A is 5-20 membered heteroaryl, wherein the 5-20 membered heteroaryl of ring A is optionally substituted with one or more halo, $C_{1-6}$alkyl, $C_{2-6}$alkenyl, $C_{1-6}$alkoxy, —$NH_2$, or $C_{3-10}$cycloalkyl, wherein, the $C_{1-6}$alkyl is optionally substituted with one or more halo, and the $C_{3-10}$cycloalkyl is optionally substituted with one or more halo or $C_{1-6}$alkyl. In some embodiments ring A is 5-20 membered heteroaryl, wherein the 5-20 membered heteroaryl of ring A is optionally substituted with one or more $C_{1-6}$alkyl. In some embodiments ring A is selected from the group consisting of

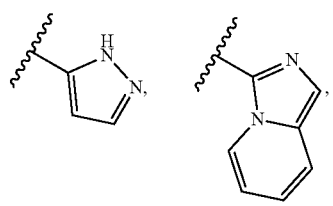

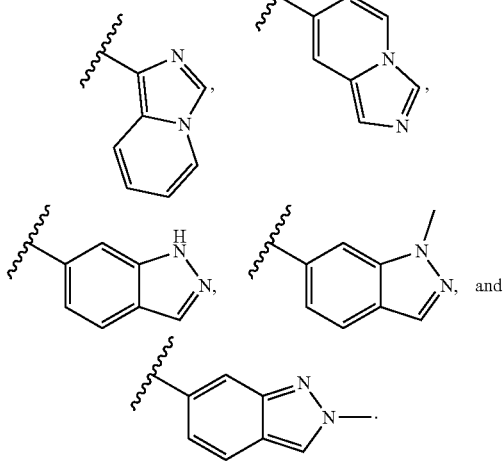

In some embodiments of a compound of formula (I'), (I-G), or a stereoisomer or tautomer thereof, or a pharmaceutically acceptable salt of any of the foregoing, ring A is $C_{3-10}$cycloalkyl. In some embodiments, ring A is $C_{3-6}$cycloalkyl. In some embodiments ring A is cyclopropyl.

In some embodiments, provided herein is a compound of formula (I'), or a stereoisomer or tautomer thereof, or a pharmaceutically acceptable salt thereof, wherein the compound is a compound of formula (I-H):

(I-H)

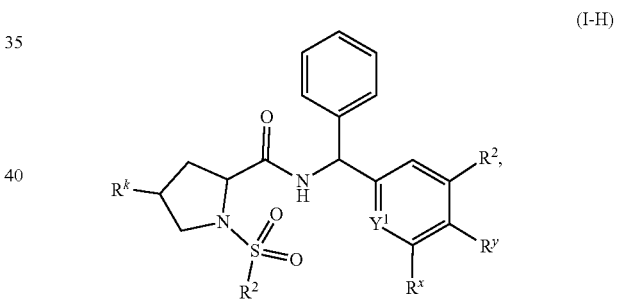

or a stereoisomer or tautomer thereof, or a pharmaceutically acceptable salt of any of the foregoing, wherein $Y^1$ is $CR^x$ or N; wherein, when the ring bearing $R^x$, $R^y$ and $R^z$ is phenyl, $R^x$, $R^y$ and $R^z$ is H, halo, $C_{1-6}$alkyl, $C_{2-6}$alkenyl, —$NH_2$, —NH—C(O)—($C_{1-6}$alkyl), —NH—C(O)-(3-15 membered heterocyclyl), $C_{3-10}$cycloalkyl, or 5-20 membered heteroaryl, wherein the $C_{1-6}$alkyl is optionally substituted with one or more halo, —NH—C(O)—NH($C_{1-6}$alkyl), —NH—C(O)—$C_{1-6}$alkyl, or —NH—C(O)—$C_{1-6}$alkoxy, the $C_{3-10}$cycloalkyl is optionally substituted with one or more halo or $C_{1-6}$alkyl, and the 5-20 membered heteroaryl is optionally substituted with one or more $C_{1-6}$alkyl; and wherein when the ring bearing $R^x$, $R^y$ and $R^z$ is pyridyl, $R^x$, $R^y$ and $R^z$ are each independently H, halo, $C_{1-6}$alkyl, $C_{2-6}$alkenyl, $C_{1-6}$alkoxy, —$NH_2$, or $C_{3-10}$cycloalkyl, wherein, the $C_{1-6}$alkyl is optionally substituted with one or more halo, and the $C_{3-10}$cycloalkyl is optionally substituted with one or more halo or $C_{1-6}$alkyl.

In some embodiments, provided herein is a compound of formula (I), such as a compound of formula (I), (I-A), (I-A1), (I-A2), (I-A3), (I-A4), (I-B), (I-B1), (I-B2), (I-C), (I-D), (I-E), or (I-F), or a stereoisomer or tautomer thereof, or a pharmaceutically acceptable salt of any of the foregoing, wherein $R^2$ is $C_{1-6}$alkyl, wherein the $C_{1-6}$alkyl of $R^2$ is optionally substituted with one or more $R^a$. In some embodiments, $R^2$ is $C_{3-10}$cycloalkyl, wherein the $C_{3-10}$cycloalkyl of $R^2$ is optionally substituted with one or more $R^q$. In other embodiments, $R^2$ is 3-15 membered heterocyclyl, wherein the 3-15 membered heterocyclyl of $R^2$ is optionally substituted with one or more halo, oxo, $C_{1-6}$alkyl, —C(O)—$C_{1-6}$alkyl, or 5-20 membered heteroaryl. In some embodiments, $R^2$ is 5-20 membered heteroaryl, wherein the 5-20 membered heteroaryl of $R^2$ is optionally substituted with one or more $R^s$. In some embodiments, $R^2$ is —N($R^g$)($R^h$), wherein $R^g$ and $R^h$ are independently H or $C_{1-6}$alkyl. In some embodiments, $R^2$ is —C(O)—$R^j$, wherein $R^j$ is $C_{3-10}$cycloalkyl, —NH($C_{1-6}$alkyl), —N($C_{1-6}$alkyl)$_2$, or —NH (5-20 membered heteroaryl). In some embodiments, $R^2$ is $C_{6-20}$aryl, wherein the $C_{6-20}$aryl of $R^2$ is optionally substituted with one or more 5-20 membered heteroaryl or —O($R^p$), wherein $R^p$ is 3-15 membered heterocyclyl, wherein the 3-15 membered heterocyclyl of $R^p$ is optionally substituted with one or more —C(O)—$C_{1-6}$alkyl.

In some embodiments, provided herein is a compound of formula (I'), such as a compound of formula (I), (I-A), (I-A1), (I-A2), (I-A3), (I-A4), (I-B), (I-B1), (I-B2), (I-C), (I-D), (I-D1), (I-D2), (I-E), (I-F), (I-G), or (I-H) or a stereoisomer or tautomer thereof, or a pharmaceutically acceptable salt of any of the foregoing, wherein $R^2$ is $C_{1-6}$alkyl, wherein the $C_{1-6}$alkyl of $R^2$ is optionally substituted with one or more $R^a$. In some embodiments, $R^2$ is $C_{3-10}$cycloalkyl, wherein the $C_{3-10}$cycloalkyl of $R^2$ is optionally substituted with one or more $R^q$. In other embodiments, $R^2$ is 3-15 membered heterocyclyl, wherein the 3-15 membered heterocyclyl of $R^2$ is optionally substituted with one or more halo, oxo, $C_{1-6}$alkyl, —C(O)—$C_{1-6}$alkyl, or 5-20 membered heteroaryl. In some embodiments, $R^2$ is 5-20 membered heteroaryl, or —($C_{1-4}$alkyl)(5-20 membered heteroaryl), wherein the $C_{1-4}$ alkyl is optionally substituted with one or more or more —OH, halo, —NH$_2$, —NH($C_{1-6}$alkyl), —N($C_{1-6}$alkyl)$_2$, and wherein the 5-20 membered heteroaryl is optionally substituted with one or more $R^s$. In some embodiments, $R^2$ is —N($R^g$)($R^h$), wherein $R^g$ and $R^h$ are independently H or $C_{1-6}$alkyl. In some embodiments, $R^2$ is —C(O)—$R^j$, wherein $R^j$ is $C_{3-10}$cycloalkyl, —NH($C_{1-6}$alkyl), —N($C_{1-6}$alkyl)$_2$, or —NH (5-20 membered heteroaryl). In some embodiments, $R^2$ is $C_{6-20}$aryl, wherein the $C_{6-20}$aryl of $R^2$ is optionally substituted with one or more 5-20 membered heteroaryl or —O($R^p$), wherein $R^p$ is 3-15 membered heterocyclyl, wherein the 3-15 membered heterocyclyl of $R^p$ is optionally substituted with one or more —C(O)—$C_{1-6}$alkyl.

In some embodiments of a compound of formula (I), or formula (I'), or any variation or embodiment thereof, or a stereoisomer or tautomer thereof, or a pharmaceutically acceptable salt of any of the foregoing, the compound, or a stereoisomer or tautomer thereof, or a pharmaceutically acceptable salt of any of the foregoing, is selected from Table 1.

Compound Names included in Table 1 and for all intermediates and compounds were generated using ChemDraw® Professional software version 17.1.1.0 or Collaborative Drug Discovery Inc. (CDD) CDD Vault update #3.

A Knime workflow was created to retrieve structures from an internal ChemAxon Compound Registry, generate the canonical smiles using RDKit Canon SMILES node, remove the stereochemistry using ChemAxon/Infocom MolConverter node, and name the structure using ChemAxon/Infocom Naming node. The following denotes the version of the Knime Analytics Platform and extensions utilized in the workflow:

Knime Analytics Platform 4.2.2
RDKit Knime Integration 4.0.1.v202006261025 (this extension includes the RDKit Canon SMILES node)
ChemAxon/Infocom Marvin Extensions Feature 4.3.0v202100 (this extension includes the MolConverter node)
ChemAxon/Infocom JChem Extensions Feature 4.3.0v202100 (this extension includes the Naming node)

TABLE 1

| Compound No. | Structure | IUPAC |
|---|---|---|
| 1 | 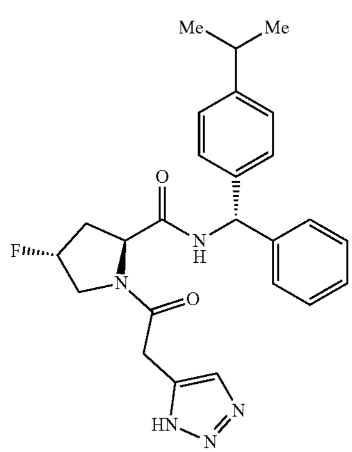 [SMILES: CC(C)c1ccc([C@@H](NC(=O)[C@@H]2C[C@@H](F)CN2C(=O)Cc2cnn[nH]2)c2ccccc2)cc1] | (2S,4R)-1-(2-(1H-1,2,3-triazol-5-yl)acetyl)-4-fluoro-N-((S)-(4-isopropylphenyl)(phenyl)methyl)pyrrolidine-2-carboxamide |

TABLE 1-continued

| Compound No. | Structure | IUPAC |
|---|---|---|
| 2 | 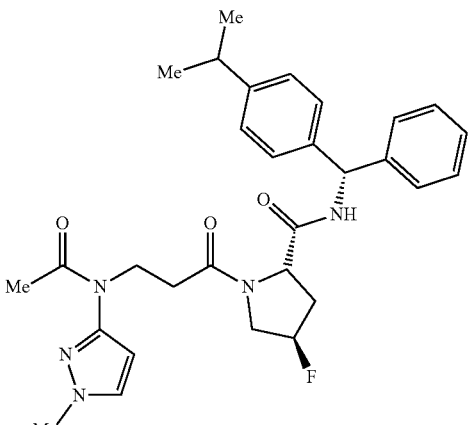 | (2S,4R)-4-fluoro-1-{3-[N-(1-methyl-1H-pyrazol-3-yl)acetamido)propanoyl}-N-[(S)-phenyl[4-(propan-2-yl)phenyl]methyl]pyrrolidine-2-carboxamide |
| 3 | 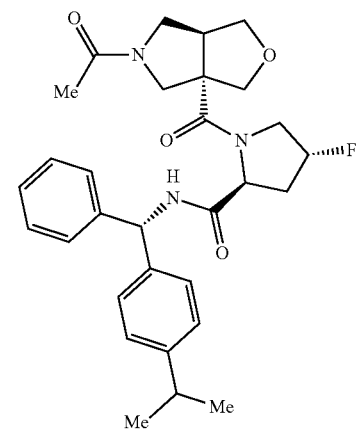 [SMILES: CC(=O)N1C[C@H]2COC[C@@]2(C(=O)N2C[C@H](F)C[C@H]2C(=O)N[C@@H](c2ccccc2)c2ccc(C(C)C)cc2)C1] | (2S,4R)-1-[(3aS,6aS)-5-acetyl-hexahydro-1H-furo[3,4-c]pyrrole-3a-carbonyl]-4-fluoro-N-[(S)-phenyl[4-(propan-2-yl)phenyl]methyl]pyrrolidine-2-carboxamide |
| 4 | 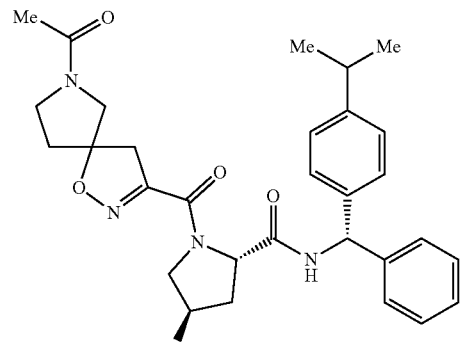 | (2S,4R)-{7-acetyl-1-oxa-2,7-diazaspiro[4.4]non-2-ene-3-carbonyl}-4-fluoro-N-[(S)-phenyl[4-(propan-2-yl)phenyl]methyl]pyrrolidine-2-carboxamide |

TABLE 1-continued

| Compound No. | Structure | IUPAC |
|---|---|---|
| 5 | 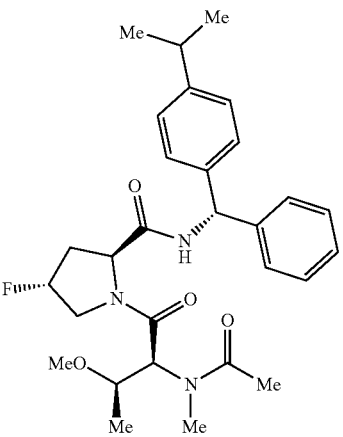 [SMILES: CO[C@H](C)[C@@H](C(=O)N1C[C@H](F)C[C@H]1C(=O)N[C@@H](c1ccccc1)c1ccc(C(C)C)cc1)N(C)C(C)=O] | (2S,4R)-4-fluoro-1-[(2S,3R)-3-methoxy-2-(N-methylacetamido)butanoyl]-N-[(S)-phenyl[4-(propan-2-yl)phenyl]methyl]pyrrolidine-2-carboxamide |
| 6 | 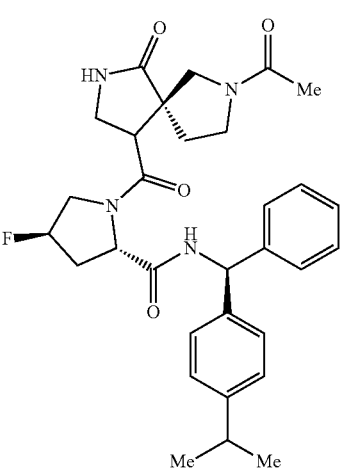 [SMILES: CC(=O)N1CC[C@@]2(C1)C(=O)NCC2C(=O)N1C[C@H](F)C[C@H]1C(=O)N[C@@H](c1ccccc1)c1ccc(C(C)C)cc1] | (2S,4R)-1-[(4S,5R)-7-acetyl-7-oxo-2,7-diazaspiro[4.4]nonane-4-carbonyl]-4-fluoro-N-[(S)-phenyl[4-(propan-2-yl)phenyl]methyl]pyrrolidine-2-carboxamide |
| 7 | 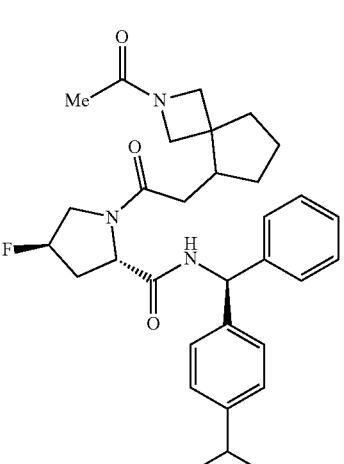 | (2S,4R)-1-(2-{2-acetyl-2-azaspiro[3.4]octan-5-yl}acetyl)-4-fluoro-N-[(S)-phenyl[4-(propan-2-yl)phenyl]methyl]pyrrolidine-2-carboxamide |

TABLE 1-continued
| Compound No. | Structure | IUPAC |
|---|---|---|
| 8 | 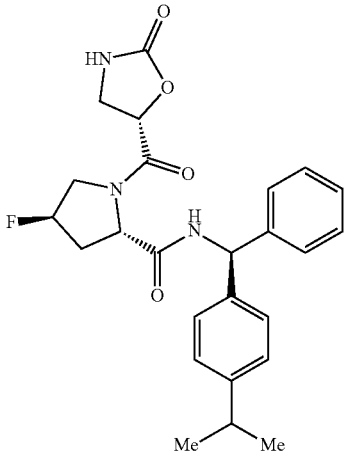 [SMILES: CC(C)c1ccc([C@@H](NC(=O)[C@@H]2C[C@@H](F)CN2C(=O)[C@@H]2CNC(=O)O2)c2ccccc2)cc1] | (2S,4R)-4-fluoro-1-[(5S)-2-oxo-1,3-oxazolidine-5-carbonyl]-N-[(S)-phenyl[4-(propan-2-yl)phenyl]methyl]pyrrolidine-2-carboxamide |
| 9 | 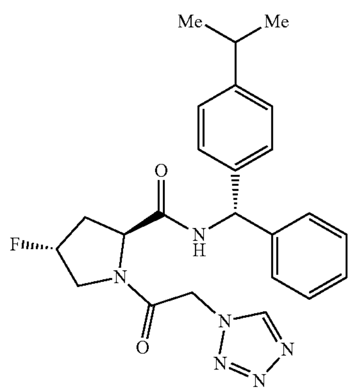 [SMILES: CC(C)c1ccc([C@@H](NC(=O)[C@@H]2C[C@@H](F)CN2C(=O)Cn2cnnn2)c2ccccc2)cc1] | (2S,4R)-4-fluoro-N-[(S)-phenyl[4-(propan-2-yl)phenyl]methyl]-1-[2-(1H-1,2,3-tetrazol-1-yl)acetyl]pyrrolidine-2-carboxamide |
| 10 | 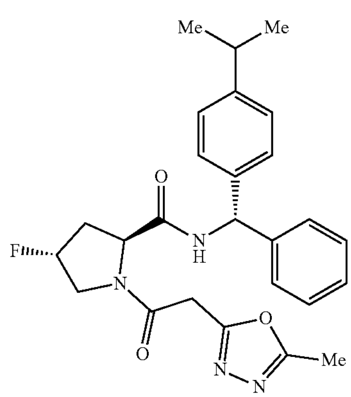 [SMILES: Cc1nnc(CC(=O)N2C[C@H](F)C[C@H]2C(=O)N[C@@H](c2ccccc2)c2ccc(C(C)C)cc2)o1] | (2S,4R)-4-fluoro-1-[2-(5-methyl-1,3,4-oxadiazol-2-yl)acetyl]-N-[(S)-phenyl[4-(propan-2-yl)phenyl]methyl]pyrrolidine-2-carboxamide |

TABLE 1-continued

| Compound No. | Structure | IUPAC |
|---|---|---|
| 11 | 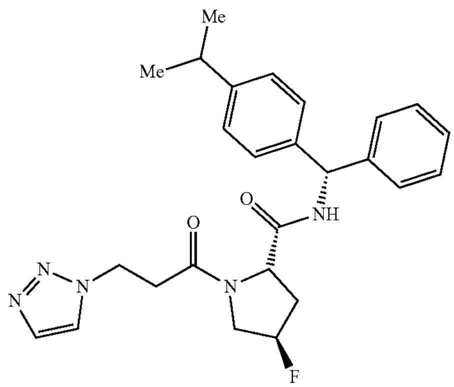 | (2S,4R)-4-fluoro-N-[(S)-phenyl[4-(propan-2-yl)phenyl]methyl]-1-[3-(1H-1,2,3-triazol-1-yl)propanoyl]pyrrolidine-2-carboxamide |
| 12 | 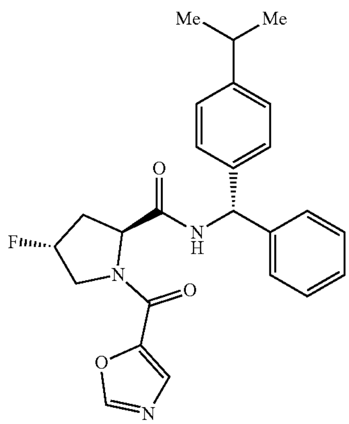 [SMILES: CC(C)c1ccc([C@@H](NC(=O)[C@@H]2C[C@@H](F)CN2C(=O)c2cnco2)c2ccccc2)cc1] | (2S,4R)-4-fluoro-1-(1,3-oxazole-5-carbonyl)-N-[(S)-phenyl[4-(propan-2-yl)phenyl]methyl]pyrrolidine-2-carboxamide |
| 13 | 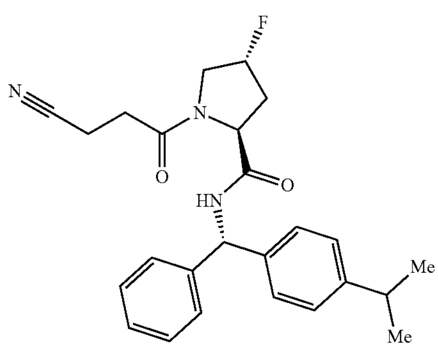 [SMILES: CC(C)c1ccc([C@@H](NC(=O)[C@@H]2C[C@@H](F)CN2C(=O)CCC#N)c2ccccc2)cc1] | (2S,4R)-1-(3-cyanopropanoyl)-4-fluoro-N-[(S)-phenyl[4-(propan-2-yl)phenyl]methyl]pyrrolidine-2-carboxamide |
| 14 | 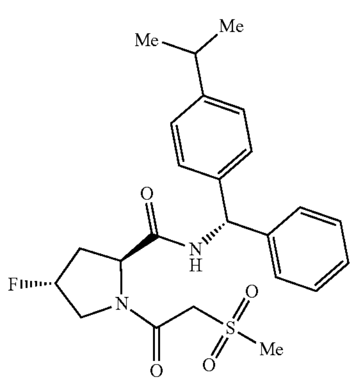 [SMILES: CC(C)c1ccc([C@@H](NC(=O)[C@@H]2C[C@@H](F)CN2C(=O)CS(C)(=O)=O)c2ccccc2)cc1] | (2S,4R)-4-fluoro-1-(2-methanesulfonylacetyl)-N-[(S)-phenyl[4-(propan-2-yl)phenyl]methyl]pyrrolidine-2-carboxamide |

TABLE 1-continued

| Compound No. | Structure | IUPAC |
|---|---|---|
| 15 | 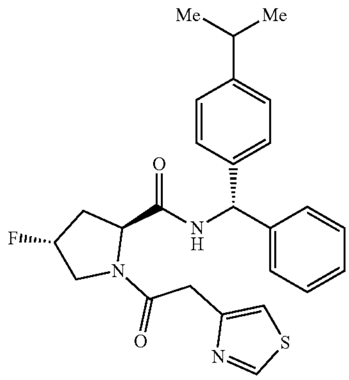 [SMILES: CC(C)c1ccc([C@@H](NC(=O)[C@@H]2C[C@@H](F)CN2C(=O)Cc2cscn2)c2ccccc2)cc1] | (2S,4R)-4-fluoro-N-[(S)-phenyl[4-(propan-2-yl)phenyl]methyl]-1-[2-(1,3-thiazol-4-yl)acetyl]pyrrolidine-2-carboxamide |
| 16 | 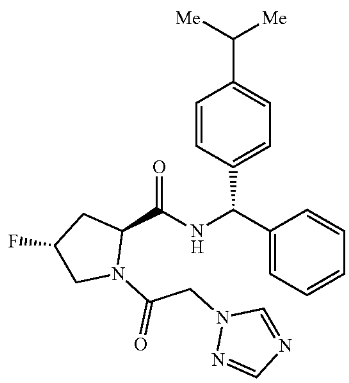 [SMILES: CC(C)c1ccc([C@@H](NC(=O)[C@@H]2C[C@@H](F)CN2C(=O)Cn2cncn2)c2ccccc2)cc1] | (2S,4R)-4-fluoro-N-[(S)-phenyl[4-(propan-2-yl)phenyl]methyl]-1-[2-(1H-1,2,4-triazol-1-yl)acetyl]pyrrolidine-2-carboxamide |
| 17 | 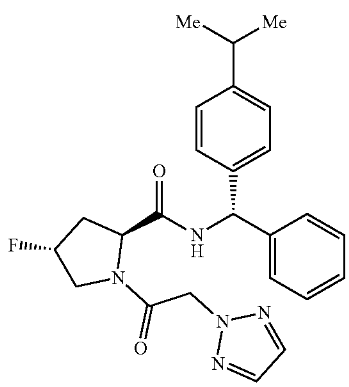 [SMILES: CC(C)c1ccc([C@@H](NC(=O)[C@@H]2C[C@@H](F)CN2C(=O)Cn2nccn2)c2ccccc2)cc1] | (2S,4R)-4-fluoro-N-[(S)-phenyl[4-(propan-2-yl)phenyl]methyl]-1-[2-(2H-1,2,3-triazol-2-yl)acetyl]pyrrolidine-2-carboxamide |
| 18 | 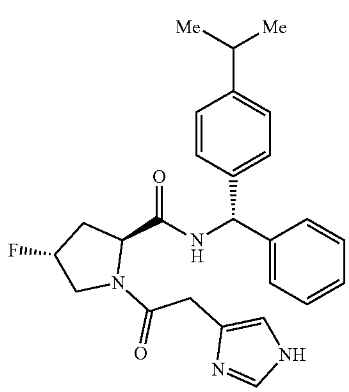 [SMILES: CC(C)c1ccc([C@@H](NC(=O)[C@@H]2C[C@@H](F)CN2C(=O)Cc2c[nH]cn2)c2ccccc2)cc1] | (2S,4R)-4-fluoro-1-[2-(1H-imidazol-4-yl)acetyl]-N-[(S)-phenyl[4-(propan-2-yl)phenyl]methyl]pyrrolidine-2-carboxamide |

TABLE 1-continued

| Compound No. | Structure | IUPAC |
|---|---|---|
| 19 | 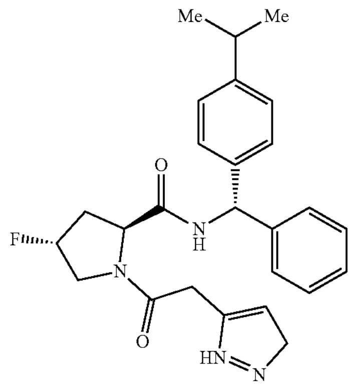 [SMILES: CC(C)c1ccc([C@@H](NC(=O)[C@@H]2C[C@@H](F)CN2C(=O)CC2=CCN=N2)c2ccccc2)cc1] | (2S,4R)-4-fluoro-N-[(S)-phenyl[4-(propan-2-yl)phenyl]methyl]-1-[2-(1H-pyrazol-5-yl)acetyl]pyrrolidine-2-carboxamide |
| 20 | 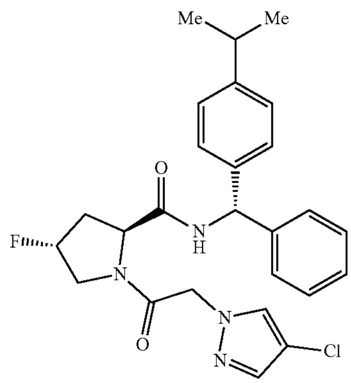 [SMILES: CC(C)c1ccc([C@@H](NC(=O)[C@@H]2C[C@@H](F)CN2C(=O)Cn2cc(Cl)cn2)c2ccccc2)cc1] | (2S,4R)-1-[2-(4-chloro-1H-pyrazol-1-yl)acetyl]-4-fluoro-N-[(S)-phenyl[4-(propan-2-yl)phenyl]methyl]pyrrolidine-2-carboxamide |
| 21 | 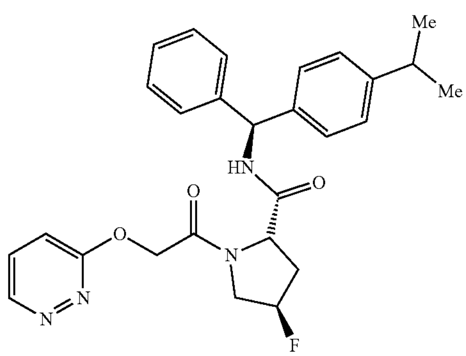 | (2S,4R)-4-fluoro-N-[(S)-phenyl[4-(propan-2-yl)phenyl]methyl]-1-[2-(pyridazin-3-yloxy)acetyl]pyrrolidine-2-carboxamide |
| 22 | 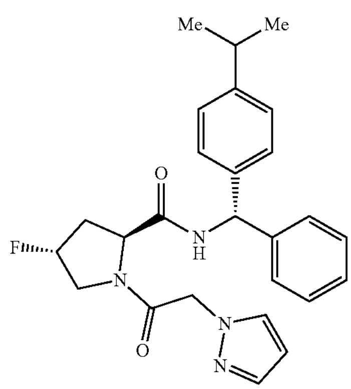 [SMILES: CC(C)c1ccc([C@@H](NC(=O)[C@@H]2C[C@@H](F)CN2C(=O)Cn2cccn2)c2ccccc2)cc1] | (2S,4R)-4-fluoro-N-[(S)-phenyl[4-(propan-2-yl)phenyl]methyl]-1-[2-(1H-pyrazol-1-yl)acetyl]pyrrolidine-2-carboxamide |

TABLE 1-continued

| Compound No. | Structure | IUPAC |
|---|---|---|
| 23 | 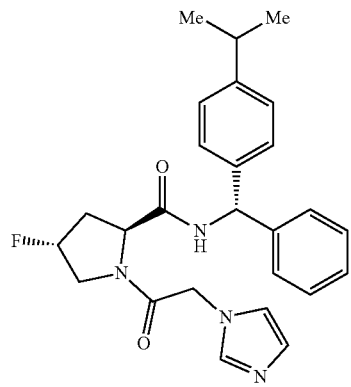 [SMILES: CC(C)c1ccc([C@@H](NC(=O)[C@@H]2C[C@@H](F)CN2C(=O)Cn2ccnc2)c2ccccc2)cc1] | (2S,4R)-4-fluoro-1-[2-(1H-imidazol-1-yl)acetyl]-N-[(S)-phenyl[4-(propan-2-yl)phenyl]methyl]pyrrolidine-2-carboxamide |
| 24 | 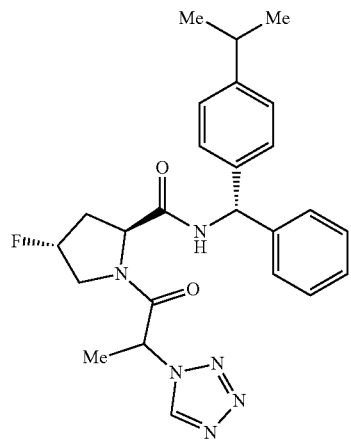 [SMILES: CC(C)c1ccc([C@@H](NC(=O)[C@@H]2C[C@@H](F)CN2C(=O)C(C)n2cnnn2)c2ccccc2)cc1] | (2S,4R)-4-fluoro-N-[(S)-phenyl[4-(propan-2-yl)phenyl]methyl]-1-[2-(1H-1,2,3,4-tetrazol-1-yl)propanoyl]pyrrolidine-2-carboxamide |
| 25 | 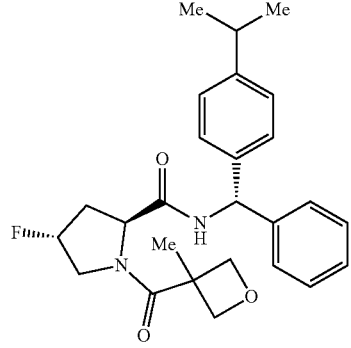 [SMILES: CC(C)c1ccc([C@@H](NC(=O)[C@@H]2C[C@@H](F)CN2C(=O)C2(C)COC2)c2ccccc2)cc1] | (2S,4R)-4-fluoro-1-(3-methyloxetane-3-carbonyl)-N-[(S)-phenyl[4-(propan-2-yl)phenyl]methyl]pyrrolidine-2-carboxamide |
| 26 | 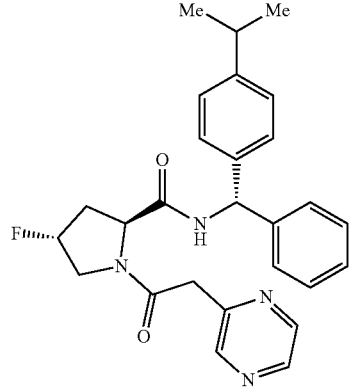 | (2S,4R)-4-fluoro-N-[(S)-phenyl[4-(propan-2-yl)phenyl]methyl]-1-[2-(pyrazin-2-yl)acetyl]pyrrolidine-2-carboxamide |

TABLE 1-continued

| Compound No. | Structure | IUPAC |
|---|---|---|
| 27 | 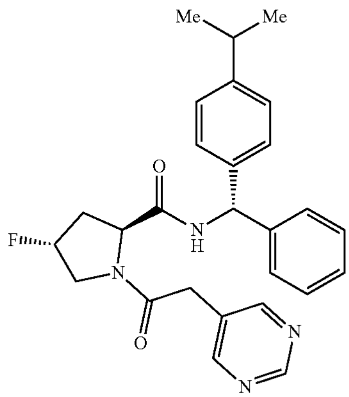 [SMILES: CC(C)c1ccc([C@@H](NC(=O)[C@@H]2C[C@@H](F)CN2C(=O)Cc2cncnc2)c2ccccc2)cc1] | (2S,4R)-4-fluoro-N-[(S)-phenyl[4-(propan-2-yl)phenyl]methyl]-1-[2-(pyrimidin-5-yl)acetyl]pyrrolidine-2-carboxamide |
| 28 | 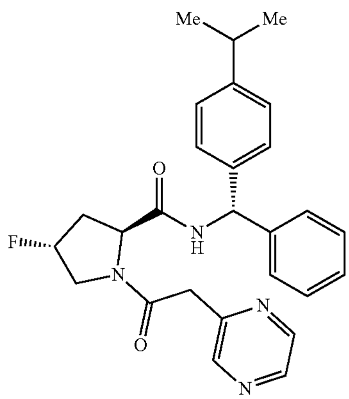 [SMILES: CC(C)c1ccc([C@@H](NC(=O)[C@@H]2C[C@@H](F)CN2C(=O)Cc2cnccn2)c2ccccc2)cc1] | (2S,4R)-4-fluoro-N-[(S)-phenyl[4-(propan-2-yl)phenyl]methyl]-1-[2-(pyrimidin-2-yl)acetyl]pyrrolidine-2-carboxamide |
| 29 | 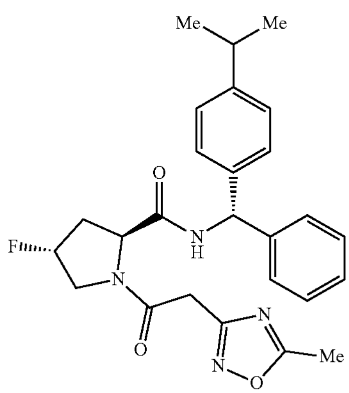 [SMILES: Cc1nc(CC(=O)N2C[C@H](F)C[C@H]2C(=O)N[C@@H](c2ccccc2)c2ccc(C(C)C)cc2)no1] | (2S,4R)-4-fluoro-1-[2-(5-methyl-1,2,4-oxadiazol-3-yl)acetyl]-N-[(S)-phenyl[4-(propan-2-yl)phenyl]methyl]pyrrolidine-2-carboxamide |
| 30 | 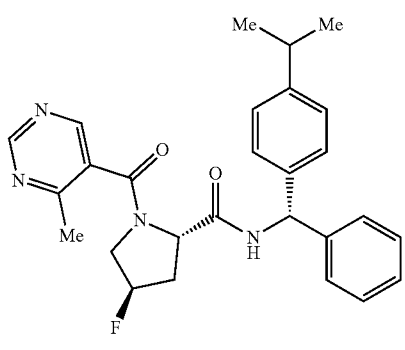 [SMILES: Cc1ncncc1C(=O)N1C[C@H](F)C[C@H]1C(=O)N[C@@H](c1ccccc1)c1ccc(C(C)C)cc1] | (2S,4R)-4-fluoro-1-(4-methylpyrimidine-5-carbonyl)-N-[(S)-phenyl[4-(propan-2-yl)phenyl]methyl]pyrrolidine-2-carboxamide |

TABLE 1-continued

| Compound No. | Structure | IUPAC |
|---|---|---|
| 31 | 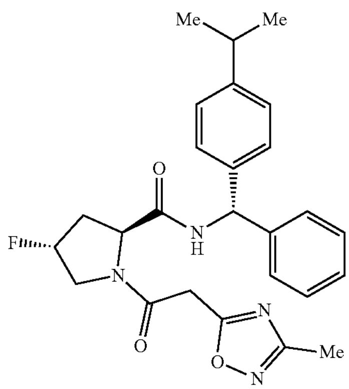 [SMILES: Cc1noc(CC(=O)N2C[C@H](F)C[C@H]2C(=O)N[C@@H](c2ccccc2)c2ccc(C(C)C)cc2)n1] | (2S,4R)-4-fluoro-1-[2-(3-methyl-1,2,4-oxadiazol-5-yl)acetyl]-N-[(S)-phenyl[4-(propan-2-yl)phenyl]methyl]pyrrolidine-2-carboxamide |
| 32 | 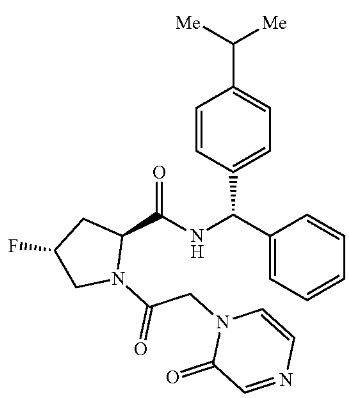 [SMILES: CC(C)c1ccc([C@@H](NC(=O)[C@@H]2C[C@@H](F)CN2C(=O)Cn2ccncc2=O)c2ccccc2)cc1] | (2S,4R)-4-fluoro-1-[2-(2-oxo-1,2-dihydropyrazin-1-yl)acetyl]-N-[(S)-phenyl[4-(propan-2-yl)phenyl]methyl]pyrrolidine-2-carboxamide |
| 33 | 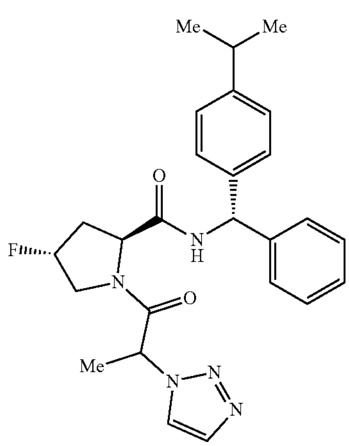 [SMILES: CC(C)c1ccc([C@@H](NC(=O)[C@@H]2C[C@@H](F)CN2C(=O)C(C)n2ccnn2)c2ccccc2)cc1] | (2S,4R)-4-fluoro-N-[(S)-phenyl[4-(propan-2-yl)phenyl]methyl]-1-[2-(1H-1,2,3-triazol-1-yl)propanoyl]pyrrolidine-2-carboxamide |

TABLE 1-continued
| Compound No. | Structure | IUPAC |
|---|---|---|
| 34 | 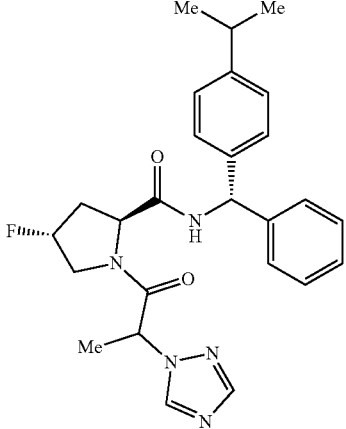 [SMILES: CC(C)c1ccc([C@@H](NC(=O)[C@@H]2C[C@@H](F)CN2C(=O)C(C)n2cncn2)c2ccccc2)cc1] | (2S,4R)-4-fluoro-N-[(S)-phenyl[4-(propan-2-yl)phenyl]methyl]-1-[2-(1H-1,2,4-triazol-1-yl)propanoyl]pyrrolidine-2-carboxamide |
| 35 | 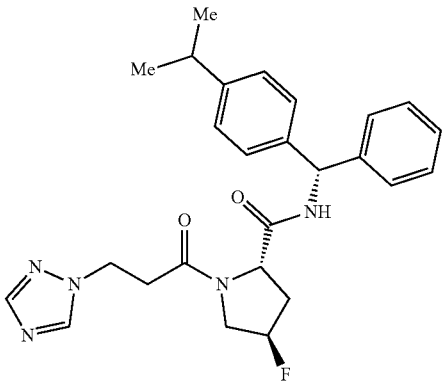 [SMILES: CC(C)c1ccc([C@@H](NC(=O)[C@@H]2C[C@@H](F)CN2C(=O)CCn2cncn2)c2ccccc2)cc1] | (2S,4R)-4-fluoro-N-[(S)-phenyl[4-(propan-2-yl)phenyl]methyl]-1-[3-(1H-1,2,4-triazol-1-yl)propanoyl]pyrrolidine-2-carboxamide |
| 36 | 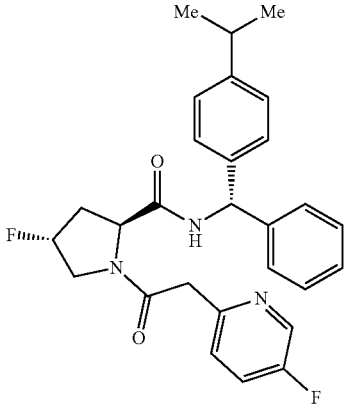 [SMILES: CC(C)c1ccc([C@@H](NC(=O)[C@@H]2C[C@@H](F)CN2C(=O)Cc2ccc(F)cn2)c2ccccc2)cc1] | (2S,4R)-4-fluoro-1-[2-(5-fluoropyridin-2-yl)acetyl]-N-[(S)-phenyl[4-(propan-2-yl)phenyl]methyl]pyrrolidine-2-carboxamide |

TABLE 1-continued

| Compound No. | Structure | IUPAC |
|---|---|---|
| 37 | 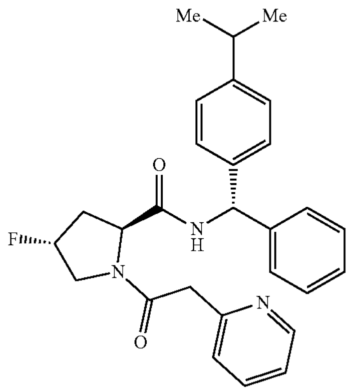 [SMILES: CC(C)c1ccc([C@@H](NC(=O)[C@@H]2C[C@@H](F)CN2C(=O)Cc2ccccn2)c2ccccc2)cc1] | (2S,4R)-4-fluoro-N-[(S)-phenyl[4-(propan-2-yl)phenyl]methyl]-1-[2-(pyridin-2-yl)acetyl]pyrrolidine-2-carboxamide |
| 38 | 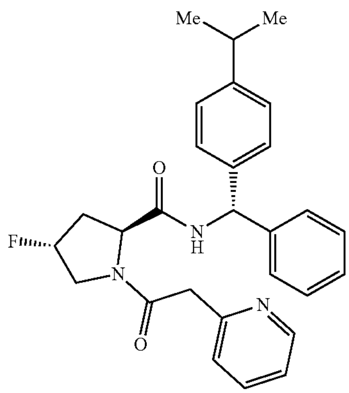 [SMILES: CC(C)c1ccc([C@@H](NC(=O)[C@@H]2C[C@@H](F)CN2C(=O)Cc2ccccn2)c2ccccc2)cc1] | (2S,4R)-4-fluoro-N-[(S)-phenyl[4-(propan-2-yl)phenyl]methyl]-1-[2-(pyridin-3-yl)acetyl]pyrrolidine-2-carboxamide |
| 39 | 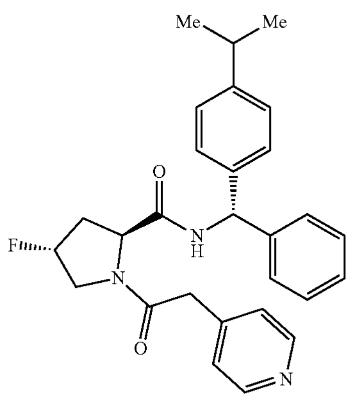 [SMILES: CC(C)c1ccc([C@@H](NC(=O)[C@@H]2C[C@@H](F)CN2C(=O)Cc2ccncc2)c2ccccc2)cc1] | (2S,4R)-4-fluoro-N-[(S)-phenyl[4-(propan-2-yl)phenyl]methyl]-1-[2-(pyridin-4-yl)acetyl]pyrrolidine-2-carboxamide |
| 40 | 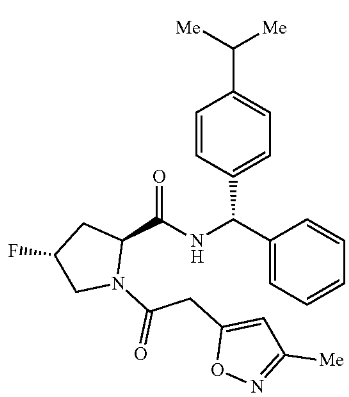 [SMILES: Cc1cc(CC(=O)N2C[C@H](F)C[C@H]2C(=O)N[C@@H](c2ccccc2)c2ccc(C(C)C)cc2)on1] | (2S,4R)-4-fluoro-1-[2-(3-methyl-1,2-oxazol-5-yl)acetyl]-N-[(S)-phenyl[4-(propan-2-yl)phenyl]methyl]pyrrolidine-2-carboxamide |

TABLE 1-continued
| Compound No. | Structure | IUPAC |
|---|---|---|
| 41 | 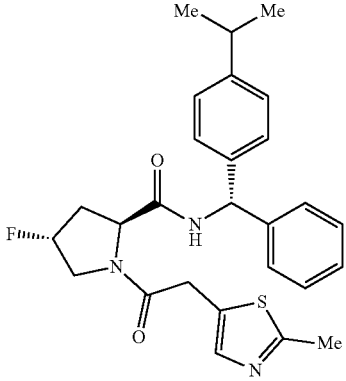 | (2S,4R)-4-fluoro-1-[2-(2-methyl-1,3-thiazol-5-yl)acetyl]-N-[(S)-phenyl[4-(propan-2-yl)phenyl]methyl]pyrrolidine-2-carboxamide |
| 42 | 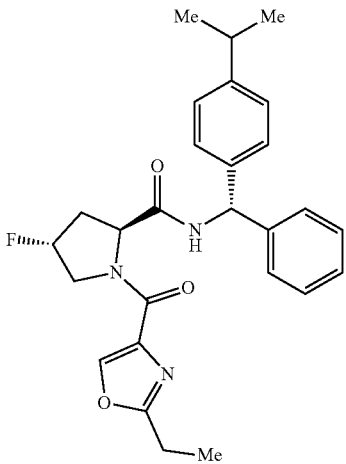 [SMILES: CCc1nc(C(=O)N2C[C@H](F)C[C@H]2C(=O)N[C@@H](c2ccccc2)c2ccc(C(C)C)cc2)co1] | (2S,4R)-1-(2-ethyl-1,3-oxazole-4-carbonyl)-4-fluoro-N-[(S)-phenyl[4-(propan-2-yl)phenyl]methyl]pyrrolidine-2-carboxamide |
| 43 | 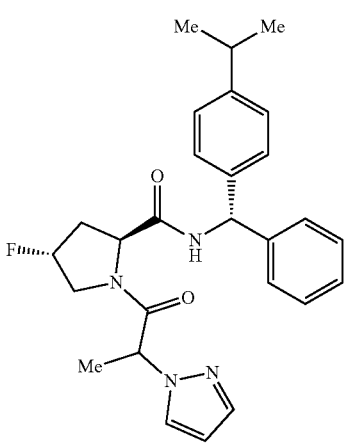 | (2S,4R)-4-fluoro-N-[(S)-phenyl[4-(propan-2-yl)phenyl]methyl]-1-[2-(1H-pyrazol-1-yl)propanoyl]pyrrolidine-2-carboxamide |

TABLE 1-continued

| Compound No. | Structure | IUPAC |
|---|---|---|
| 44 | 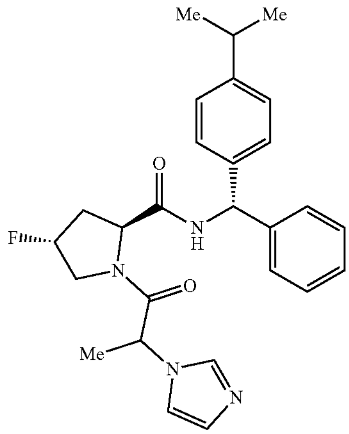 [SMILES: CC(C)c1ccc([C@@H](NC(=O)[C@@H]2C[C@@H](F)CN2C(=O)C(C)n2ccnc2)c2ccccc2)cc1] | (2S,4R)-4-fluoro-1-[2-(1H-imidazol-1-yl)propanoyl]-N-[(S)-phenyl[4-(propan-2-yl)phenyl]methyl]pyrrolidine-2-carboxamide |
| 45 | 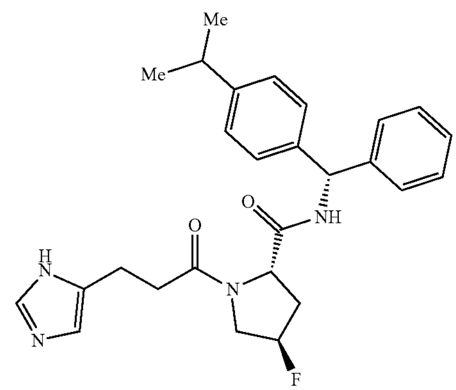 [SMILES: CC(C)c1ccc([C@@H](NC(=O)[C@@H]2C[C@@H](F)CN2C(=O)CCc2cnc[nH]2)c2ccccc2)cc1] | (2S,4R)-4-fluoro-1-[3-(1H-imidazol-5-yl)propanoyl]-N-[(S)-phenyl[4-(propan-2-yl)phenyl]methyl]pyrrolidine-2-carboxamide |
| 46 | 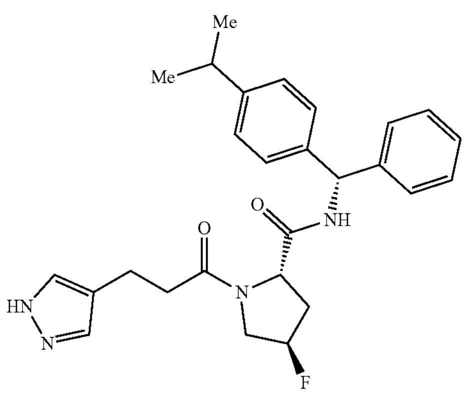 [SMILES: CC(C)c1ccc([C@@H](NC(=O)[C@@H]2C[C@@H](F)CN2C(=O)CCc2cn[nH]c2)c2ccccc2)cc1] | (2S,4R)-4-fluoro-N-[(S)-phenyl[4-(propan-2-yl)phenyl]methyl]-1-[3-(1H-pyrazol-4-yl)propanoyl]pyrrolidine-2-carboxamide |
| 47 | 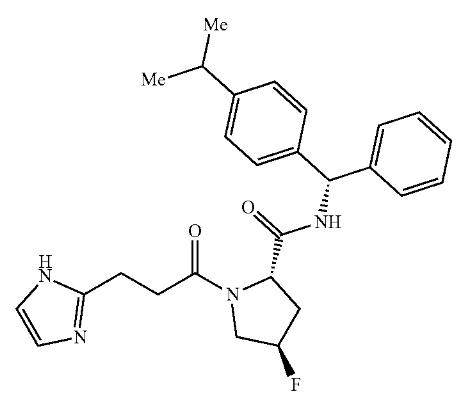 [SMILES: CC(C)c1ccc([C@@H](NC(=O)[C@@H]2C[C@@H](F)CN2C(=O)CCc2ncc[nH]2)c2ccccc2)cc1] | (2S,4R)-4-fluoro-1-[3-(1H-imidazol-2-yl)propanoyl]-N-[(S)-phenyl[4-(propan-2-yl)phenyl]methyl]pyrrolidine-2-carboxamide |

TABLE 1-continued

| Compound No. | Structure | IUPAC |
|---|---|---|
| 48 | 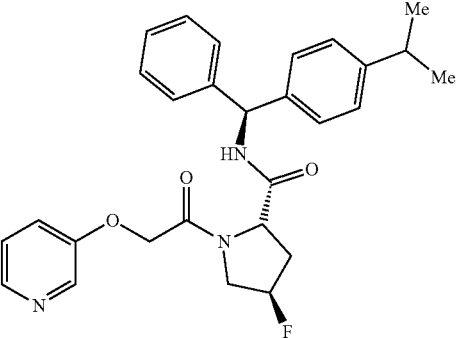 | (2S,4R)-4-fluoro-N-[(S)-phenyl[4-(propan-2-yl)phenyl]methyl]-1-[2-(pyridin-3-yloxy)acetyl]pyrrolidine-2-carboxamide |
| 49 | 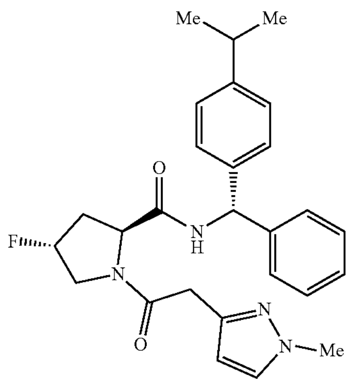 [SMILES: CC(C)c1ccc([C@@H](NC(=O)[C@@H]2C[C@@H](F)CN2C(=O)Cc2ccn(C)n2)c2ccccc2)cc1] | (2S,4R)-4-fluoro-1-[2-(1-methyl-1H-pyrazol-3-yl)acetyl]-N-[(S)-phenyl[4-(propan-2-yl)phenyl]methyl]pyrrolidine-2-carboxamide |
| 50 | 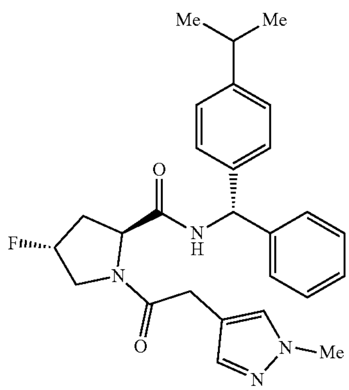 [SMILES: CC(C)c1ccc([C@@H](NC(=O)[C@@H]2C[C@@H](F)CN2C(=O)Cc2cnn(C)c2)c2ccccc2)cc1] | (2S,4R)-4-fluoro-1-[2-(1-methyl-1H-pyrazol-4-yl)acetyl]-N-[(S)-phenyl[4-(propan-2-yl)phenyl]methyl]pyrrolidine-2-carboxamide |
| 51 | 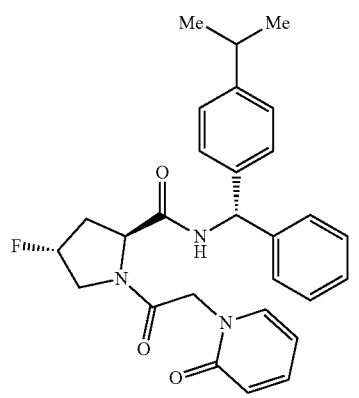 [SMILES: CC(C)c1ccc([C@@H](NC(=O)[C@@H]2C[C@@H](F)CN2C(=O)Cn2ccccc2=O)c2ccccc2)cc1] | (2S,4R)-4-fluoro-1-[2-(2-oxo-1,2-dihydropyridin-1-yl)acetyl]-N-[(S)-phenyl[4-(propan-2-yl)phenyl]methyl]pyrrolidine-2-carboxamide |

TABLE 1-continued

| Compound No. | Structure | IUPAC |
|---|---|---|
| 52 | 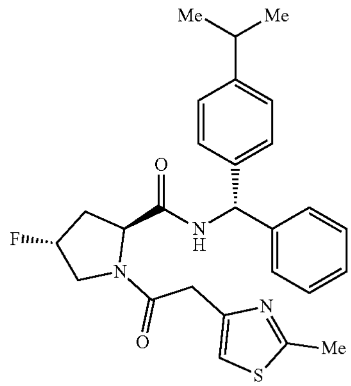 [SMILES: Cc1nc(CC(=O)N2C[C@H](F)C[C@H]2C(=O)N[C@@H](c2ccccc2)c2ccc(C(C)C)cc2)cs1] | (2S,4R)-4-fluoro-1-[2-(2-methyl-1,3-thiazol-4-yl)acetyl]-N-[(S)-phenyl[4-(propan-2-yl)phenyl]methyl]pyrrolidine-2-carboxamide |
| 53 | 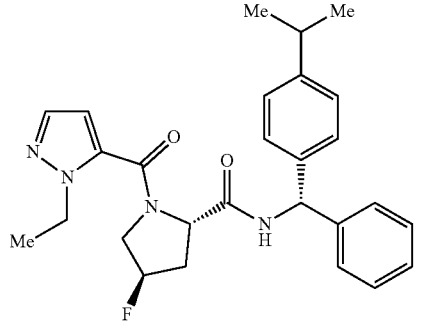 [SMILES: CCn1nccc1C(=O)N1C[C@H](F)C[C@H]1C(=O)N[C@@H](c1ccccc1)c1ccc(C(C)C)cc1] | (2S,4R)-1-(1-ethyl-1H-pyrazole-5-carbonyl)-4-fluoro-N-[(S)-phenyl[4-(propan-2-yl)phenyl]methyl]pyrrolidine-2-carboxamide |
| 54 | 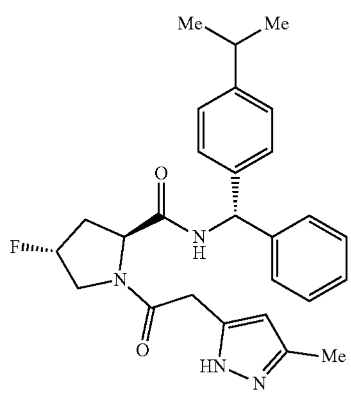 [SMILES: Cc1cc(CC(=O)N2C[C@H](F)C[C@H]2C(=O)N[C@@H](c2ccccc2)c2ccc(C(C)C)cc2)[nH]n1] | (2S,4R)-4-fluoro-1-[2-(3-methyl-1H-pyrazol-5-yl)acetyl]-N-[(S)-phenyl[4-(propan-2-yl)phenyl]methyl]pyrrolidine-2-carboxamide |
| 55 | 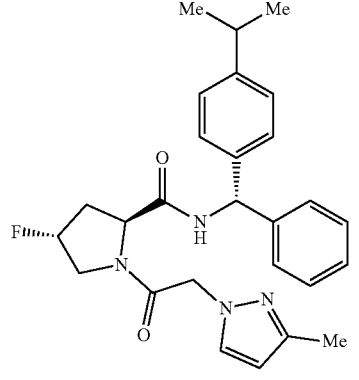 [SMILES: Cc1ccn(CC(=O)N2C[C@H](F)C[C@H]2C(=O)N[C@@H](c2ccccc2)c2ccc(C(C)C)cc2)n1] | (2S,4R)-4-fluoro-1-[2-(3-methyl-1H-pyrazol-1-yl)acetyl]-N-[(S)-phenyl[4-(propan-2-yl)phenyl]methyl]pyrrolidine-2-carboxamide |

TABLE 1-continued

| Compound No. | Structure | IUPAC |
|---|---|---|
| 56 | 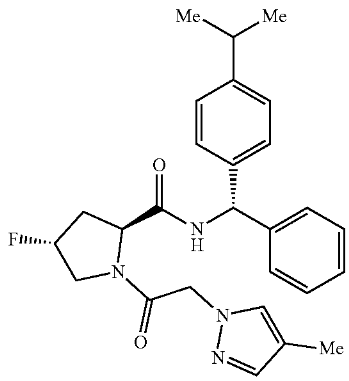 [SMILES: Cc1cnn(CC(=O)N2C[C@H](F)C[C@H]2C(=O)N[C@@H](c2ccccc2)c2ccc(C(C)C)cc2)c1] | (2S,4R)-4-fluoro-1-[2-(4-methyl-1H-pyrazol-1-yl)acetyl]-N-[(S)-phenyl[4-(propan-2-yl)phenyl]methyl]pyrrolidine-2-carboxamide |
| 57 | 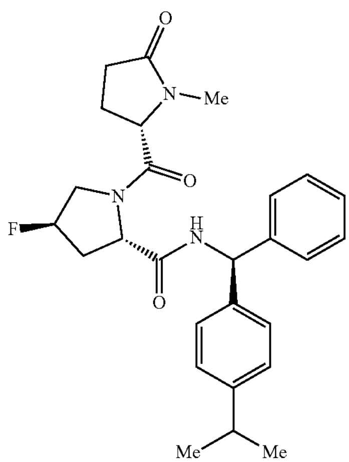 [SMILES: CC(C)c1ccc([C@@H](NC(=O)[C@@H]2C[C@@H](F)CN2C(=O)[C@@H]2CCC(=O)N2C)c2ccccc2)cc1] | (2S,4R)-4-fluoro-1-[(2S)-1-methyl-5-oxopyrrolidine-2-carbonyl]-N-[(S)-phenyl[4-(propan-2-yl)phenyl]methyl]pyrrolidine-2-carboxamide |
| 58 | 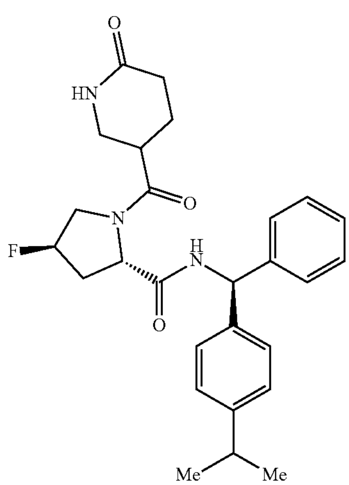 [SMILES: CC(C)c1ccc([C@@H](NC(=O)[C@@H]2C[C@@H](F)CN2C(=O)C2CCC(=O)NC2)c2ccccc2)cc1] | (2S,4R)-4-fluoro-1-(6-oxopiperidine-3-carbonyl)-N-[(S)-phenyl[4-(propan-2-yl)phenyl]methyl]pyrrolidine-2-carboxamide |

TABLE 1-continued

| Compound No. | Structure | IUPAC |
|---|---|---|
| 59 | 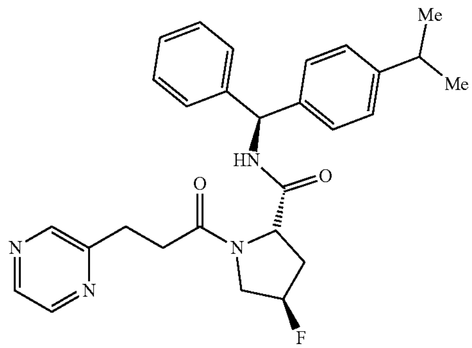 | (2S,4R)-4-fluoro-N-[(S)-phenyl[4-(propan-2-yl)phenyl]methyl]-1-[3-(pyrazin-2-yl)propanoyl]pyrrolidine-2-carboxamide |
| 60 | 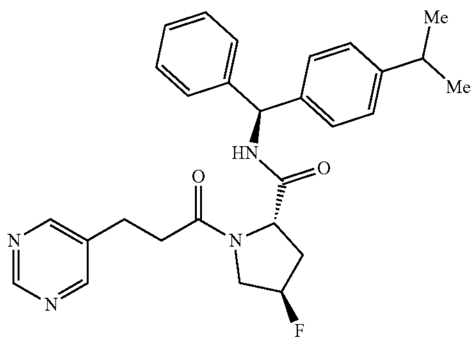 [SMILES: CC(C)c1ccc([C@@H](NC(=O)[C@@H]2C[C@@H](F)CN2C(=O)CCc2cncnc2)c2ccccc2)cc1] | (2S,4R)-4-fluoro-N-[(S)-phenyl[4-(propan-2-yl)phenyl]methyl]-1-[3-(pyrimidin-5-yl)propanoyl]pyrrolidine-2-carboxamide |
| 61 | 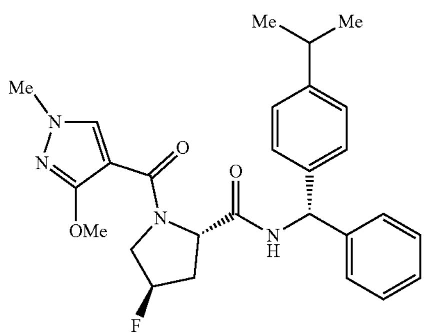 [SMILES: COc1nn(C)cc1C(=O)N1C[C@H](F)C[C@H]1C(=O)N[C@@H](c1ccccc1)c1ccc(C(C)C)cc1] | (2S,4R)-4-fluoro-1-(3-methoxy-1-methyl-1H-pyrazole-4-carbonyl)-N-[(S)-phenyl[4-(propan-2-yl)phenyl]methyl]pyrrolidine-2-carboxamide |
| 62 | 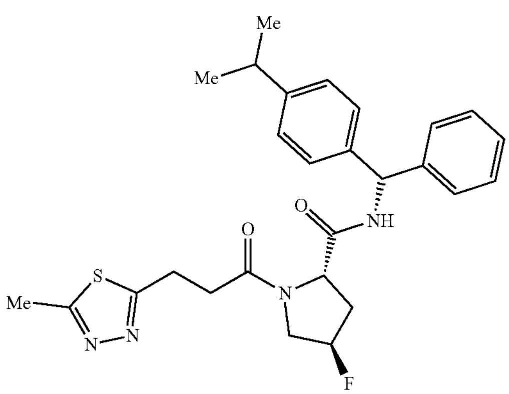 | (2S,4R)-4-fluoro-1-[3-(5-methyl-1,3,4-thiadiazol-2-yl)propanoyl]-N-[(S)-phenyl[4-(propan-2-yl)phenyl]methyl]pyrrolidine-2-carboxamide |

TABLE 1-continued

| Compound No. | Structure | IUPAC |
|---|---|---|
| 63 | 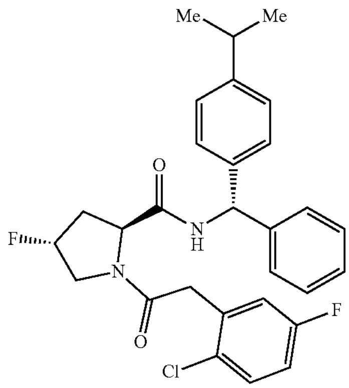 [SMILES: CC(C)c1ccc([C@@H](NC(=O)[C@@H]2C[C@@H](F)CN2C(=O)Cc2cc(F)ccc2Cl)c2ccccc2)cc1] | (2S,4R)-1-[2-(2-chloro-5-fluorophenyl]acetyl]-4-fluoro-N-[(S)-phenyl[4-(propan-2-yl)phenyl]methyl]pyrrolidine-2-carboxamide |
| 64 | 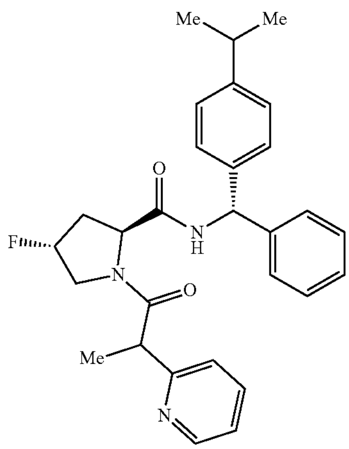 [SMILES: CC(C)c1ccc([C@@H](NC(=O)[C@@H]2C[C@@H](F)CN2C(=O)C(C)c2ccccn2)c2ccccc2)cc1] | (2S,4R)-4-fluoro-N-[(S)-phenyl[4-(propan-2-yl)phenyl]methyl]-1-[2-(pyridin-2-yl)propanoyl]pyrrolidine-2-carboxamide |
| 65 | 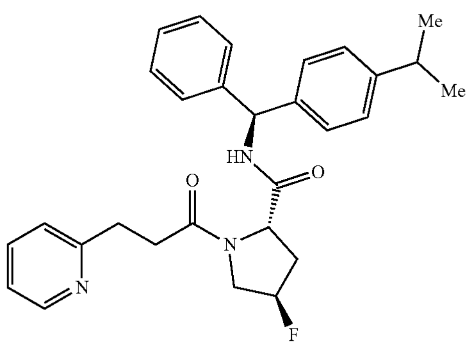 [SMILES: CC(C)c1ccc([C@@H](NC(=O)[C@@H]2C[C@@H](F)CN2C(=O)CCc2ccccn2)c2ccccc2)cc1] | (2S,4R)-4-fluoro-N-[(S)-phenyl[4-(propan-2-yl)phenyl]methyl]-1-[3-(pyridin-2-yl)propanoyl]pyrrolidine-2-carboxamide |
| 66 | 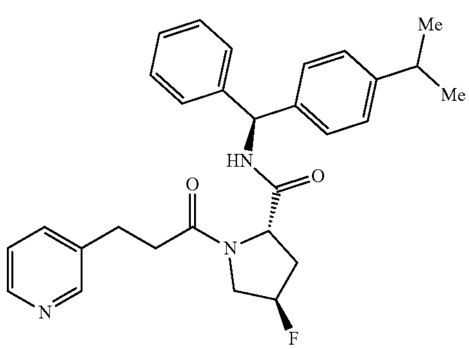 [SMILES: CC(C)c1ccc([C@@H](NC(=O)[C@@H]2C[C@@H](F)CN2C(=O)CCc2cccnc2)c2ccccc2)cc1] | (2S,4R)-4-fluoro-N-[(S)-phenyl[4-(propan-2-yl)phenyl]methyl]-1-[3-(pyridin-3-yl)propanoyl]pyrrolidine-2-carboxamide |

TABLE 1-continued

| Compound No. | Structure | IUPAC |
|---|---|---|
| 67 | 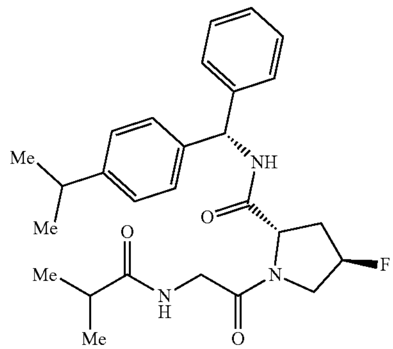 [SMILES: CC(C)C(=O)NCC(=O)N1C[C@H](F)C[C@H]1C(=O)N[C@@H](c1ccccc1)c1ccc(C(C)C)cc1] | (2S,4R)-1-{2-[(dimethylcarbamoyl)amino]acetyl}-4-fluoro-N-[(S)-phenyl[4-(propan-2-yl)phenyl]methyl]pyrrolidine-2-carboxamide |
| 68 | 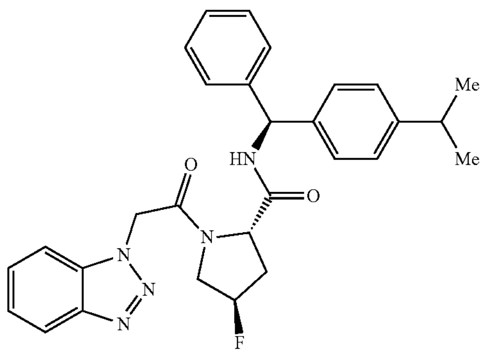 [SMILES: CC(C)c1ccc([C@@H](NC(=O)[C@@H]2C[C@@H](F)CN2C(=O)Cn2nnc3ccccc32)c2ccccc2)cc1] | (2S,4R)-1-[2-(1H-1,2,3-benzotriazol-1-yl)acetyl]-4-fluoro-N-[(S)-phenyl[4-(propan-2-yl)phenyl]methyl]pyrrolidine-2-carboxamide |
| 69 | 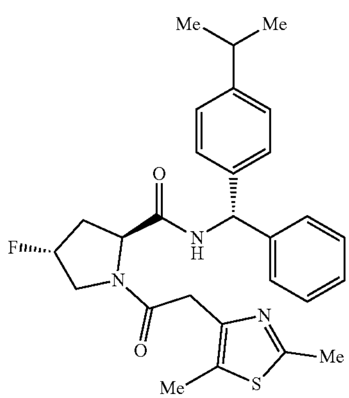 [SMILES: Cc1nc(CC(=O)N2C[C@H](F)C[C@H]2C(=O)N[C@@H](c2ccccc2)c2ccc(C(C)C)cc2)c(C)s1] | (2S,4R)-1-[2-(2,5-dimethyl-1,3-thiazol-4-yl)acetyl]-4-fluoro-N-[(S)-phenyl[4-(propan-2-yl)phenyl]methyl]pyrrolidine-2-carboxamide |
| 70 | 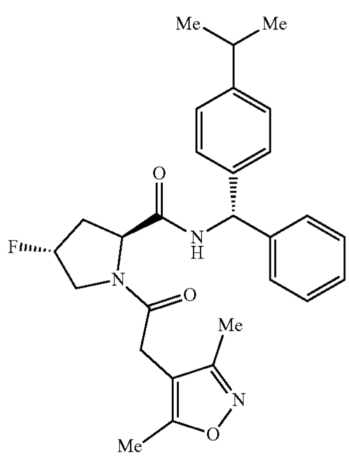 [SMILES: Cc1noc(C)c1CC(=O)N1C[C@H](F)C[C@H]1C(=O)N[C@@H](c1ccccc1)c1ccc(C(C)C)cc1] | (2S,4R)-1-[2-(3,5-dimethyl-1,2-oxazol-4-yl)acetyl]-4-fluoro-N-[(S)-phenyl[4-(propan-2-yl)phenyl]methyl]pyrrolidine-2-carboxamide |

TABLE 1-continued
| Compound No. | Structure | IUPAC |
|---|---|---|
| 71 | 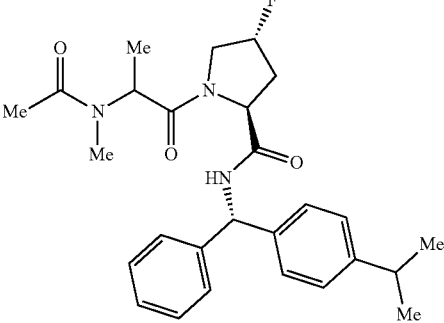 | (2S,4R)-4-fluoro-1-[2-(N-methylacetamido)propanoyl]-N-[(S)-phenyl[4-(propan-2-yl)phenyl]methyl]pyrrolidine-2-carboxamide |
| 72 | 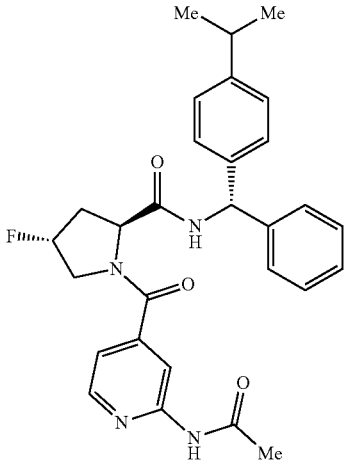 [SMILES: CC(=O)Nc1cc(C(=O)N2C[C@H](F)C[C@H]2C(=O)N[C@@H](c2ccccc2)c2ccc(C(C)C)cc2)ccn1] | (2S,4R)-1-(2-acetamidopyridine-4-carbonyl)-4-fluoro-N-[(S)-phenyl[4-(propan-2-yl)phenyl]methyl]pyrrolidine-2-carboxamide |
| 73 | 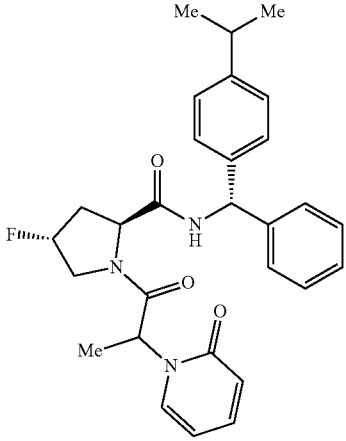 [SMILES: CC(C)c1ccc([C@@H](NC(=O)[C@@H]2C[C@@H](F)CN2C(=O)C(C)n2ccccc2=O)c2ccccc2)cc1] | (2S,4R)-4-fluoro-1-[2-(2-oxo-1,2-dihydropyridin-1-yl)propanoyl]-N-[(S)-phenyl[4-(propan-2-yl)phenyl]methyl]pyrrolidine-2-carboxamide |

TABLE 1-continued

| Compound No. | Structure | IUPAC |
|---|---|---|
| 74 | 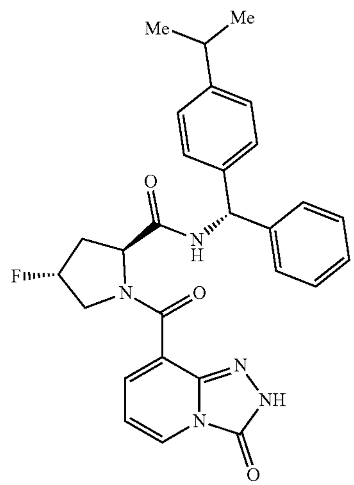 [SMILES: CC(C)c1ccc([C@@H](NC(=O)[C@@H]2C[C@@H](F)CN2C(=O)c2cccn3c(=O)[nH]nc23)c2ccccc2)cc1] | (2S,4R)-4-fluoro-1-{3-oxo-2H,3H-[1,2,4]triazolo[4,3-a]pyridine-8-carbonyl}-N-[(S)-phenyl[4-(propan-2-yl)phenyl]methyl]pyrrolidine-2-carboxamide |
| 75 | 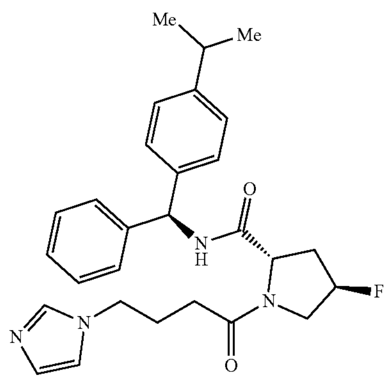 [SMILES: CC(C)c1ccc([C@@H](NC(=O)[C@@H]2C[C@@H](F)CN2C(=O)CCCn2ccnc2)c2ccccc2)cc1] | (2S,4R)-4-fluoro-1-[4-(1H-imidazol-1-yl)butanoyl]-N-[(S)-phenyl[4-(propan-2-yl)phenyl]methyl]pyrrolidine-2-carboxamide |
| 76 | 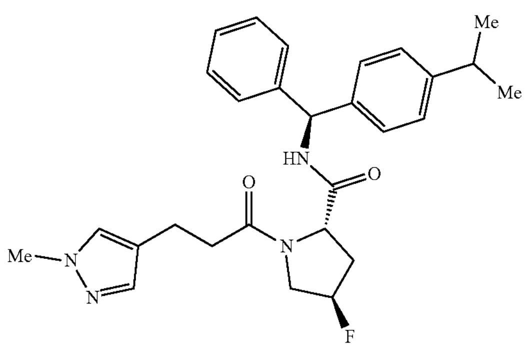 [SMILES: CC(C)c1ccc([C@@H](NC(=O)[C@@H]2C[C@@H](F)CN2C(=O)CCc2cnn(C)c2)c2ccccc2)cc1] | (2S,4R)-4-fluoro-1-[3-(1-methyl-1H-pyrazol-4-yl)propanoyl]-N-[(S)-phenyl[4-(propan-2-yl)phenyl]methyl]pyrrolidine-2-carboxamide |
| 77 | 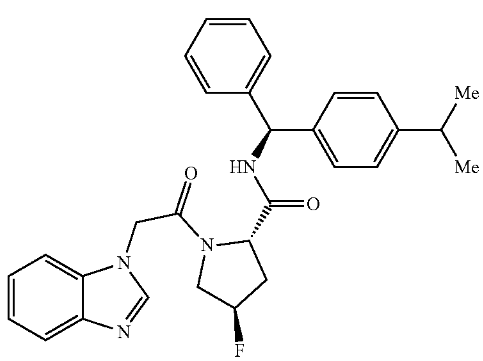 [SMILES: CC(C)c1ccc([C@@H](NC(=O)[C@@H]2C[C@@H](F)CN2C(=O)Cn2cnc3ccccc32)c2ccccc2)cc1] | (2S,4R)-1-[2-(1H-1,3-benzodiazol-1-yl)acetyl]-4-fluoro-N-[(S)-phenyl[4-(propan-2-yl)phenyl]methyl]pyrrolidine-2-carboxamide |

TABLE 1-continued

| Compound No. | Structure | IUPAC |
|---|---|---|
| 78 | 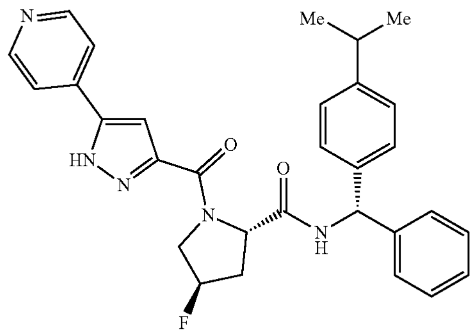 [SMILES: CC(C)c1ccc([C@@H](NC(=O)[C@@H]2C[C@@H](F)CN2C(=O)c2cc(-c3ccncc3)[nH]n2)c2ccccc2)cc1] | (2S,4R)-4-fluoro-N-[(S)-phenyl[4-(propan-2-yl)phenyl]methyl]-1-[5-(pyridin-4-yl)-1H-pyrazole-3-carbonyl]pyrrolidine-2-carboxamide |
| 79 | 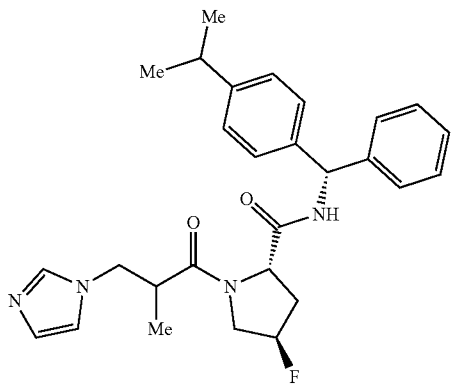 [SMILES: CC(Cn1ccnc1)C(=O)N1C[C@H](F)C[C@H]1C(=O)N[C@@H](c1ccccc1)c1ccc(C(C)C)cc1] | (2S,4R)-4-fluoro-1-[3-(1H-imidazol-1-yl)-2-methylpropanoyl]-N-[(S)-phenyl[4-(propan-2-yl)phenyl]methyl]pyrrolidine-2-carboxamide |
| 80 | 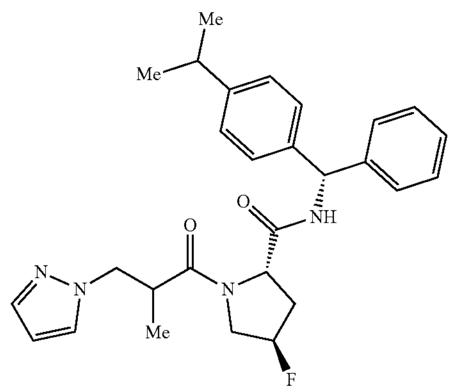 [SMILES: CC(Cn1cccn1)C(=O)N1C[C@H](F)C[C@H]1C(=O)N[C@@H](c1ccccc1)c1ccc(C(C)C)cc1] | (2S,4R)-4-fluoro-1-[2-methyl-3-(1H-pyrazol-1-yl)propanoyl]-N-[(S)-phenyl[4-(propan-2-yl)phenyl]methyl]pyrrolidine-2-carboxamide |
| 81 | 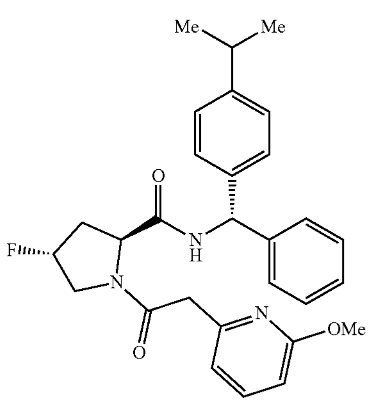 [SMILES: COc1cccc(CC(=O)N2C[C@H](F)C[C@H]2C(=O)N[C@@H](c2ccccc2)c2ccc(C(C)C)cc2)n1] | (2S,4R)-4-fluoro-1-[2-(6-methoxypyridin-2-yl)acetyl]-N-[(S)-phenyl[4-(propan-2-yl)phenyl]methyl]pyrrolidine-2-carboxamide |

TABLE 1-continued

| Compound No. | Structure | IUPAC |
|---|---|---|
| 82 | 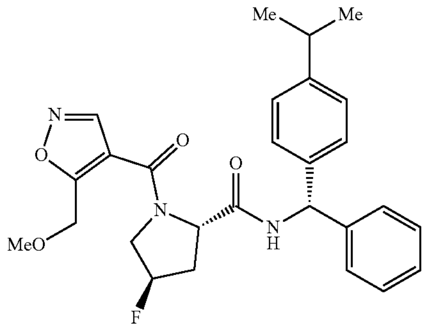 [SMILES: COCc1oncc1C(=O)N1C[C@H](F)C[C@H]1C(=O)N[C@@H](c1ccccc1)c1ccc(C(C)C)cc1] | (2S,4R)-4-fluoro-1-[5-(methoxymethyl)-1,2-oxazole-4-carbonyl]-N-[(S)-phenyl[4-(propan-2-yl)phenyl]methyl]pyrrolidine-2-carboxamide |
| 83 | 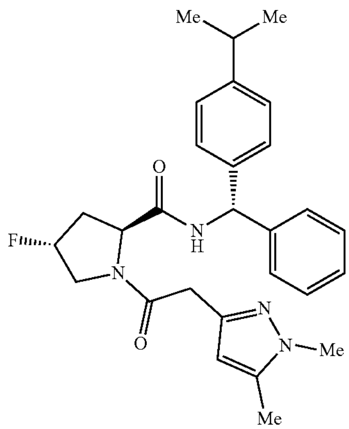 [SMILES: Cc1cc(CC(=O)N2C[C@H](F)C[C@H]2C(=O)N[C@@H](c2ccccc2)c2ccc(C(C)C)cc2)nn1C] | (2S,4R)-1-[2-(1,5-dimethyl-1H-pyrazol-3-yl)acetyl]-4-fluoro-N-[(S)-phenyl[4-(propan-2-yl)phenyl]methyl]pyrrolidine-2-carboxamide |
| 84 | 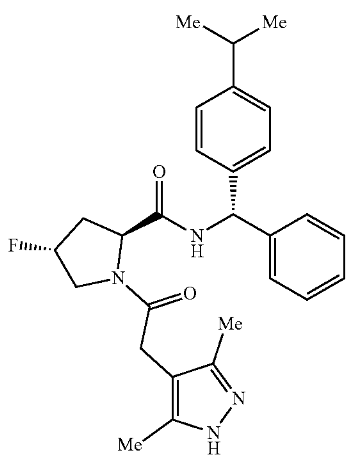 [SMILES: Cc1n[nH]c(C)c1CC(=O)N1C[C@H](F)C[C@H]1C(=O)N[C@@H](c1ccccc1)c1ccc(C(C)C)cc1] | (2S,4R)-1-[2-(3,5-dimethyl-1H-pyrazol-4-yl)acetyl]-4-fluoro-N-[(S)-phenyl[4-(propan-2-yl)phenyl]methyl]pyrrolidine-2-carboxamide |
| 85 | 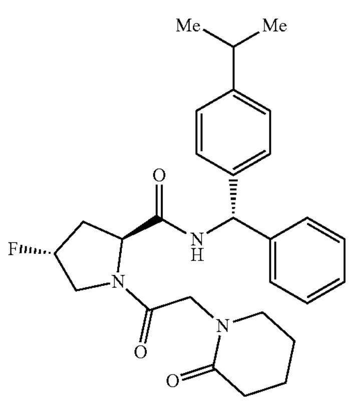 [SMILES: CC(C)c1ccc([C@@H](NC(=O)[C@@H]2C[C@@H](F)CN2C(=O)CN2CCCCC2=O)c2ccccc2)cc1] | (2S,4R)-4-fluoro-1-[2-(2-oxopiperidin-1-yl)acetyl]-N-[(S)-phenyl[4-(propan-2-yl)phenyl]methyl]pyrrolidine-2-carboxamide |

TABLE 1-continued

| Compound No. | Structure | IUPAC |
|---|---|---|
| 86 | 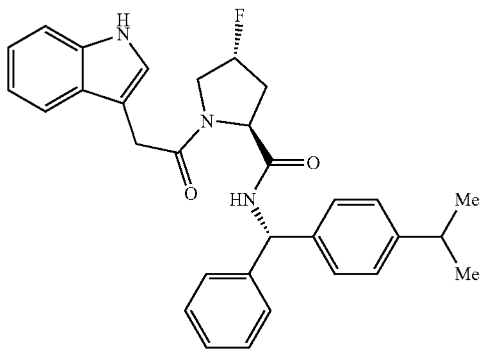 [SMILES: CC(C)c1ccc([C@@H](NC(=O)[C@@H]2C[C@@H](F)CN2C(=O)Cc2c[nH]c3ccccc23)c2ccccc2)cc1] | (2S,4R)-4-fluoro-1-[2-(1H-indol-3-yl)acetyl]-N-[(S)-phenyl[4-(propan-2-yl)phenyl]methyl]pyrrolidine-2-carboxamide |
| 87 | 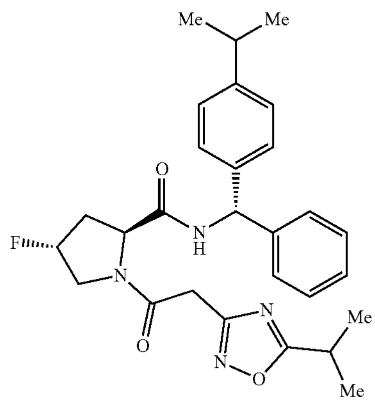 [SMILES: CC(C)c1ccc([C@@H](NC(=O)[C@@H]2C[C@@H](F)CN2C(=O)Cc2noc(C(C)C)n2)c2ccccc2)cc1] | (2S,4R)-4-fluoro-N-[(S)-phenyl[4-(propan-2-yl)phenyl]methyl]-1-{2-[5-(propan-2-yl)-1,2,4-oxadiazol-3-yl]acetyl}pyrrolidine-2-carboxamide |
| 88 | 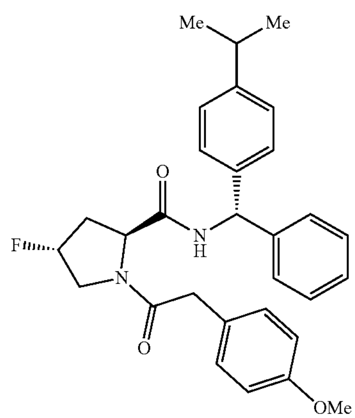 [SMILES: COc1ccc(CC(=O)N2C[C@H](F)C[C@H]2C(=O)N[C@@H](c2ccccc2)c2ccc(C(C)C)cc2)cc1] | (2S,4R)-4-fluoro-1-[2-(4-methoxyphenyl)acetyl]-N-[(S)-phenyl[4-(propan-2-yl)phenyl]methyl]pyrrolidine-2-carboxamide |
| 89 | 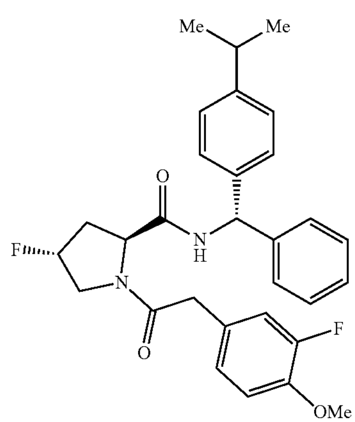 [SMILES: COc1ccc(CC(=O)N2C[C@H](F)C[C@H]2C(=O)N[C@@H](c2ccccc2)c2ccc(C(C)C)cc2)cc1F] | (2S,4R)-4-fluoro-1-[2-(3-fluoro-4-methoxyphenyl)acetyl]-N-[(S)-phenyl[4-(propan-2-yl)phenyl]methyl]pyrrolidine-2-carboxamide |

TABLE 1-continued
| Compound No. | Structure | IUPAC |
|---|---|---|
| 90 | 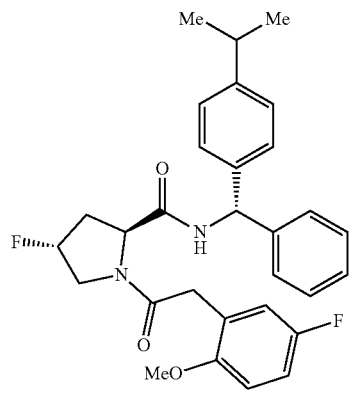 [SMILES: COc1ccc(F)cc1CC(=O)N1C[C@H](F)C[C@H]1C(=O)N[C@@H](c1ccccc1)c1ccc(C(C)C)cc1] | (2S,4R)-4-fluoro-1-[2-(5-fluoro-2-methoxyphenyl)acetyl]-N-[(S)-phenyl[4-(propan-2-yl)phenyl]methyl]pyrrolidine-2-carboxamide |
| 91 | 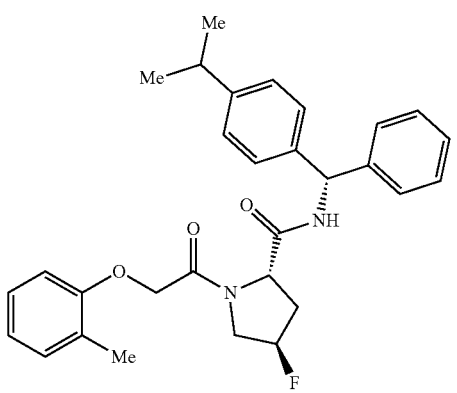 [SMILES: Cc1ccccc1OCC(=O)N1C[C@H](F)C[C@H]1C(=O)N[C@@H](c1ccccc1)c1ccc(C(C)C)cc1] | (2S,4R)-4-fluoro-1-[2-(2-methylphenoxy)acetyl]-N-[(S)-phenyl[4-(propan-2-yl)phenyl]methyl]pyrrolidine-2-carboxamide |
| 92 | 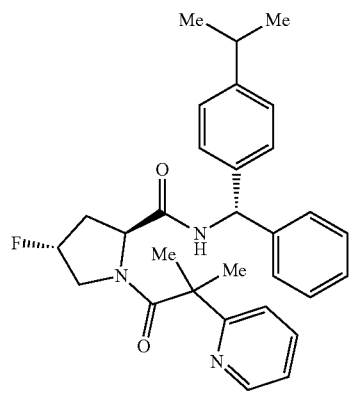 [SMILES: CC(C)c1ccc([C@@H](NC(=O)[C@@H]2C[C@@H](F)CN2C(=O)C(C)(C)c2ccccn2)c2ccccc2)cc1] | (2S,4R)-4-fluoro-1-[2-methyl-2-(pyridin-2-yl)propanoyl]-N-[(S)-phenyl[4-(propan-2-yl)phenyl]methyl]pyrrolidine-2-carboxamide |

| Compound No. | Structure | IUPAC |
|---|---|---|
| 93 | 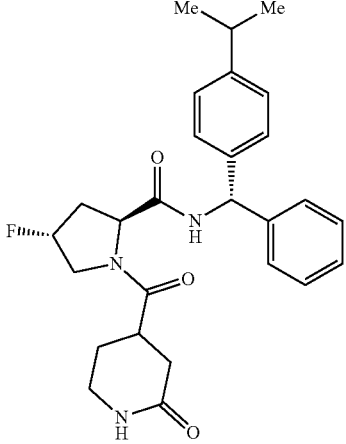 [SMILES: CC(C)c1ccc([C@@H](NC(=O)[C@@H]2C[C@@H](F)CN2C(=O)C2CCNC(=O)C2)c2ccccc2)cc1] | (2S,4R)-4-fluoro-1-(2-oxopiperidin-4-carbonyl)-N-[(S)-phenyl[4-(propan-2-yl)phenyl]methyl]pyrrolidine-2-carboxamide |
| 94 | 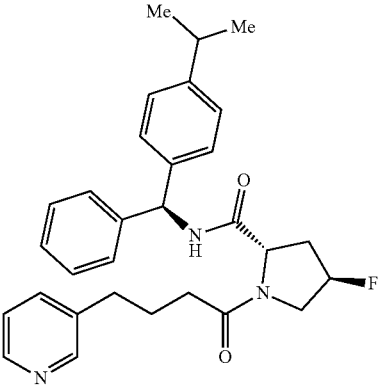 [SMILES: CC(C)c1ccc([C@@H](NC(=O)[C@@H]2C[C@@H](F)CN2C(=O)CCCc2cccnc2)c2ccccc2)cc1] | (2S,4R)-4-fluoro-N-[(S)-phenyl[4-(propan-2-yl)phenyl]methyl]-1-[4-(pyridin-3-yl)butanoyl]pyrrolidine-2-carboxamide |
| 95 | 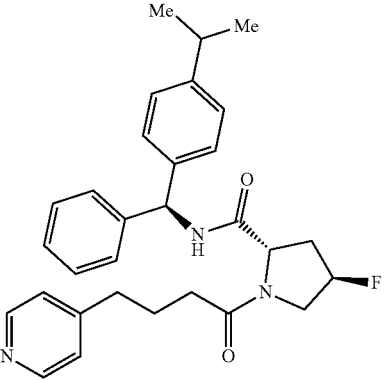 [SMILES: CC(C)c1ccc([C@@H](NC(=O)[C@@H]2C[C@@H](F)CN2C(=O)CCCc2ccncc2)c2ccccc2)cc1] | (2S,4R)-4-fluoro-N-[(S)-phenyl[4-(propan-2-yl)phenyl]methyl]-1-[4-(pyridin-4-yl)butanoyl]pyrrolidine-2-carboxamide |

TABLE 1-continued

| Compound No. | Structure | IUPAC |
|---|---|---|
| 96 | 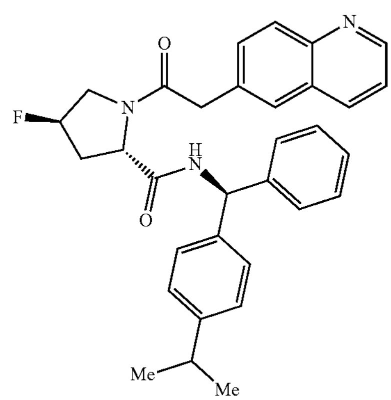 [SMILES: CC(C)c1ccc([C@@H](NC(=O)[C@@H]2C[C@@H](F)CN2C(=O)Cc2ccc3ncccc3c2)c2ccccc2)cc1] | (2S,4R)-4-fluoro-N-[(S)-phenyl[4-(propan-2-yl)phenyl]methyl]-1-[2-(quinolin-6-yl)acetyl]pyrrolidine-2-carboxamide |
| 97 | 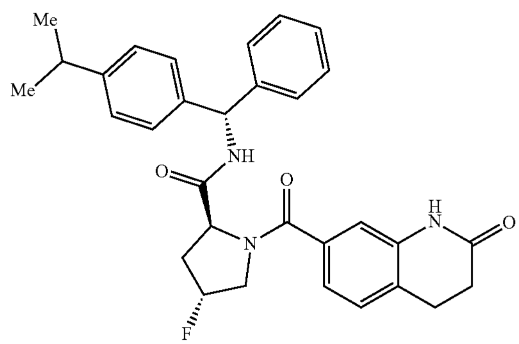 [SMILES: CC(C)c1ccc([C@@H](NC(=O)[C@@H]2C[C@@H](F)CN2C(=O)c2ccc3c(c2)NC(=O)CC3)c2ccccc2)cc1] | (2S,4R)-4-fluoro-1-(2-oxo-1,2,3,4-tetrahydroquinoline-7-carbonyl)-N-[(S)-phenyl[4-(propan-2-yl)phenyl]methyl]pyrrolidine-2-carboxamide |
| 98 | 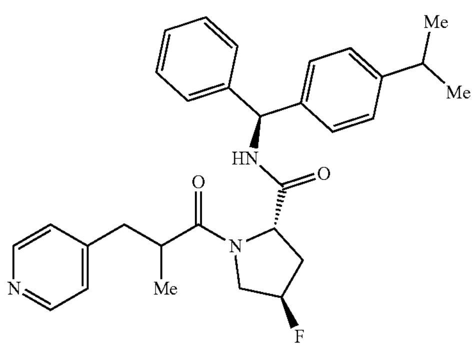 [SMILES: CC(Cc1ccncc1)C(=O)N1C[C@H](F)C[C@H]1C(=O)N[C@@H](c1ccccc1)c1ccc(C(C)C)cc1] | (2S,4R)-4-fluoro-1-[2-methyl-3-(pyridin-4-yl)propanoyl]-N-[(S)-phenyl[4-(propan-2-yl)phenyl]methyl]pyrrolidine-2-carboxamide |
| 99 | 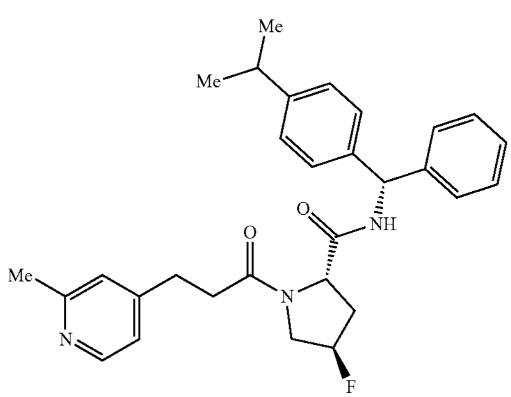 [SMILES: Cc1cc(CCC(=O)N2C[C@H](F)C[C@H]2C(=O)N[C@@H](c2ccccc2)c2ccc(C(C)C)cc2)ccn1] | (2S,4R)-4-fluoro-1-[3-(2-methylpyridin-4-yl)propanoyl]-N-[(S)-phenyl[4-(propan-2-yl)phenyl]methyl]pyrrolidine-2-carboxamide |

TABLE 1-continued

| Compound No. | Structure | IUPAC |
|---|---|---|
| 100 | 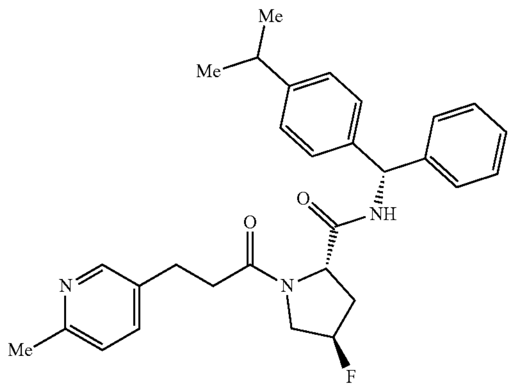 [SMILES: Cc1ccc(CCC(=O)N2C[C@H](F)C[C@H]2C(=O)N[C@@H](c2ccccc2)c2ccc(C(C)C)cc2)cn1] | (2S,4R)-4-fluoro-1-[3-(6-methylpyridin-3-yl)propanoyl]-N-[(S)-phenyl[4-(propan-2-yl)phenyl]methyl]pyrrolidine-2-carboxamide |
| 101 | 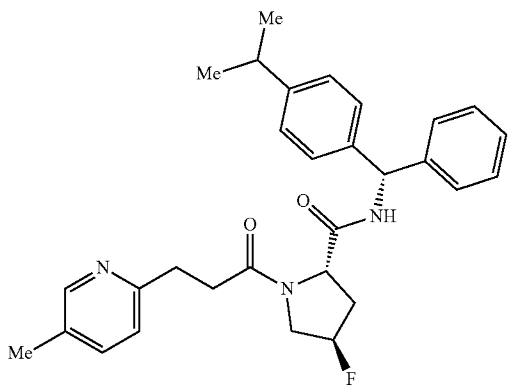 [SMILES: Cc1ccc(CCC(=O)N2C[C@H](F)C[C@H]2C(=O)N[C@@H](c2ccccc2)c2ccc(C(C)C)cc2)nc1] | (2S,4R)-4-fluoro-1-[3-(5-methylpyridin-2-yl)propanoyl]-N-[(S)-phenyl[4-(propan-2-yl)phenyl]methyl]pyrrolidine-2-carboxamide |
| 102 | 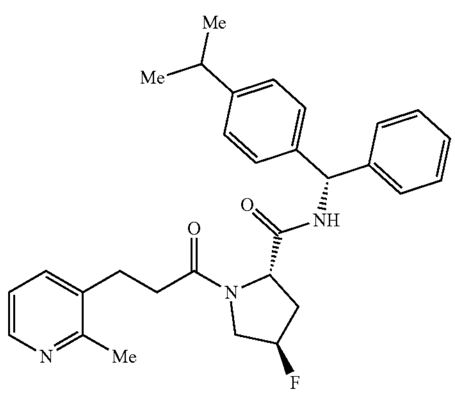 [SMILES: Cc1ncccc1CCC(=O)N1C[C@H](F)C[C@H]1C(=O)N[C@@H](c1ccccc1)c1ccc(C(C)C)cc1] | (2S,4R)-4-fluoro-1-[3-(2-methylpyridin-3-yl)propanoyl]-N-[(S)-phenyl[4-(propan-2-yl)phenyl]methyl]pyrrolidine-2-carboxamide |
| 103 | 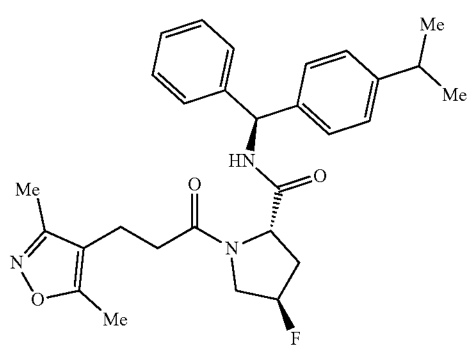 [SMILES: Cc1noc(C)c1CCC(=O)N1C[C@H](F)C[C@H]1C(=O)N[C@@H](c1ccccc1)c1ccc(C(C)C)cc1] | (2S,4R)-1-[3-(3,5-dimethyl-1,2-oxazol-4-yl)propanoyl]-4-fluoro-N-[(S)-phenyl[4-(propan-2-yl)phenyl]methyl]pyrrolidine-2-carboxamide |

TABLE 1-continued
| Compound No. | Structure | IUPAC |
|---|---|---|
| 104 | 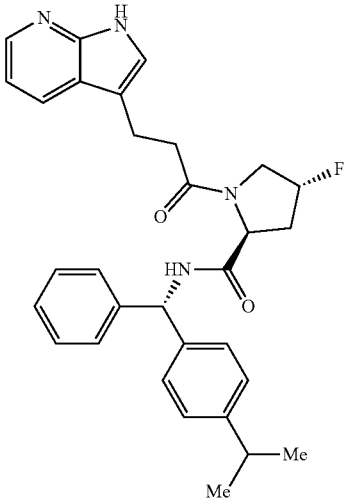 [SMILES: CC(C)c1ccc([C@@H](NC(=O)[C@@H]2C[C@@H](F)CN2C(=O)CCc2c[nH]c3ncccc23)c2ccccc2)cc1] | (2S,4R)-4-fluoro-N-[(S)-phenyl[4-(propan-2-yl)phenyl]methyl]-1-(3-{1H-pyrrolo[2,3-b]pyridin-3-yl}propanoyl)pyrrolidine-2-carboxamide |
| 105 | 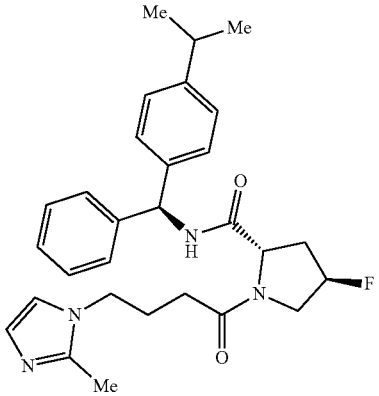 [SMILES: Cc1nccn1CCCC(=O)N1C[C@H](F)C[C@H]1C(=O)N[C@@H](c1ccccc1)c1ccc(C(C)C)cc1] | (2S,4R)-4-fluoro-1-[4-(2-methyl-1H-imidazol-1-yl)butanoyl]-N-[(S)-phenyl[4-(propan-2-yl)phenyl]methyl]pyrrolidine-2-carboxamide |
| 106 | 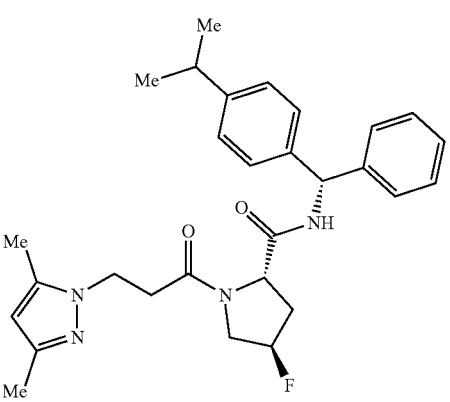 [SMILES: Cc1cc(C)n(CCC(=O)N2C[C@H](F)C[C@H]2C(=O)N[C@@H](c2ccccc2)c2ccc(C(C)C)cc2)n1] | (2S,4R)-1-[3-(3,5-dimethyl-1H-pyrazol-1-yl)propanoyl]-4-fluoro-N-[(S)-phenyl[4-(propan-2-yl)phenyl]methyl]pyrrolidine-2-carboxamide |

TABLE 1-continued
| Compound No. | Structure | IUPAC |
|---|---|---|
| 107 | 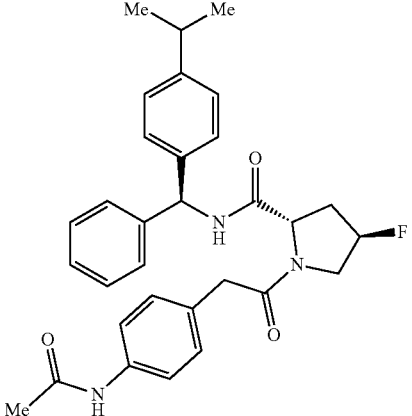 [SMILES: CC(=O)Nc1ccc(CC(=O)N2C[C@H](F)C[C@H]2C(=O)N[C@@H](c2ccccc2)c2ccc(C(C)C)cc2)cc1] | (2S,4R)-1-[2-(4-acetamidophenyl)acetyl]-4-fluoro-N-[(S)-phenyl[4-(propan-2-yl)phenyl]methyl]pyrrolidine-2-carboxamide |
| 108 | 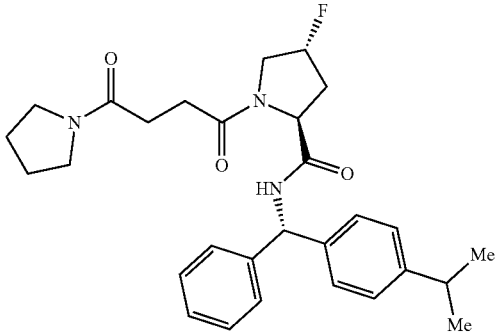 [SMILES: CC(C)c1ccc([C@@H](NC(=O)[C@@H]2C[C@@H](F)CN2C(=O)CCC(=O)N2CCCC2)c2ccccc2)cc1] | (2S,4R)-4-fluoro-1-[4-oxo-4-(pyrrolidin-1-yl)butanoyl]-N-[(S)-phenyl[4-(propan-2-yl)phenyl]methyl]pyrrolidine-2-carboxamide |
| 109 | 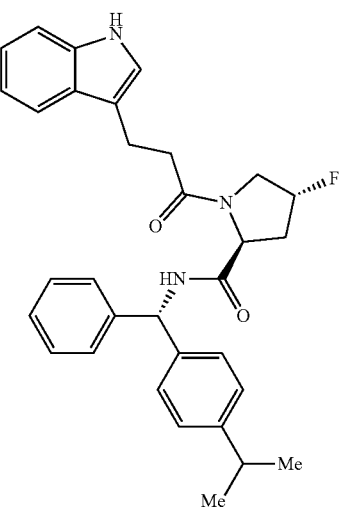 [SMILES: CC(C)c1ccc([C@@H](NC(=O)[C@@H]2C[C@@H](F)CN2C(=O)CCc2c[nH]c3ccccc23)c2ccccc2)cc1] | (2S,4R)-4-fluoro-1-[3-(1H-indol-3-yl)propanoyl]-N-[(S)-phenyl[4-(propan-2-yl)phenyl]methyl]pyrrolidine-2-carboxamide |

TABLE 1-continued

| Compound No. | Structure | IUPAC |
|---|---|---|
| 110 | 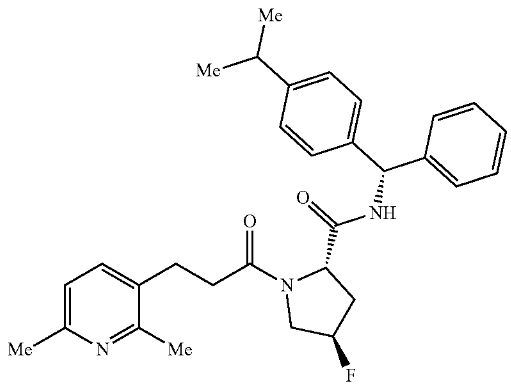 [SMILES: Cc1ccc(CCC(=O)N2C[C@H](F)C[C@H]2C(=O)N[C@@H](c2ccccc2)c2ccc(C(C)C)cc2)c(C)n1] | (2S,4R)-1-[3-(2,6-dimethylpyridin-3-yl)propanoyl]-4-fluoro-N-[(S)-phenyl[4-(propan-2-yl)phenyl]methyl]pyrrolidine-2-carboxamide |
| 111 | 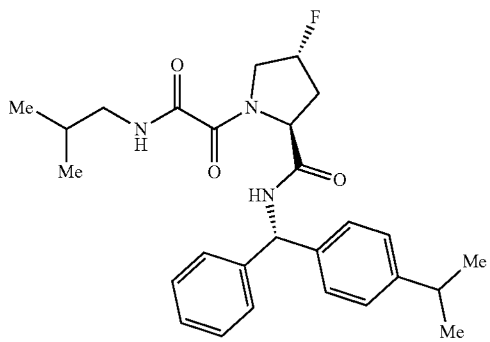 [SMILES: CC(C)CNC(=O)C(=O)N1C[C@H](F)C[C@H]1C(=O)N[C@@H](c1ccccc1)c1ccc(C(C)C)cc1] | (2S,4R)-4-fluoro-1-{[(2-methylpropyl)carbamoyl]carbonyl}-N-[(S)-phenyl[4-(propan-2-yl)phenyl]methyl]pyrrolidine-2-carboxamide |
| 112 | 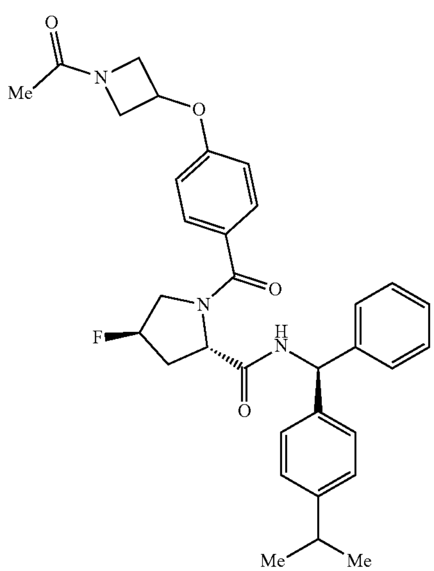 [SMILES: CC(=O)N1CC(Oc2ccc(C(=O)N3C[C@H](F)C[C@H]3C(=O)N[C@@H](c3ccccc3)c3ccc(C(C)C)cc3)cc2)C1] | (2S,4R)-1-{4-[(1-acetylazetidin-3-yl)oxy]benzoyl}-4-fluoro-N-[(S)-phenyl[4-(propan-2-yl)phenyl]methyl]pyrrolidine-2-carboxamide |

TABLE 1-continued

| Compound No. | Structure | IUPAC |
|---|---|---|
| 113 | 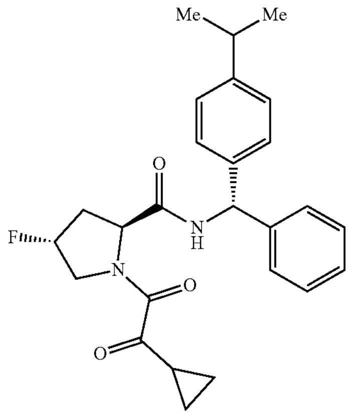 [SMILES: CC(C)c1ccc([C@@H](NC(=O)[C@@H]2C[C@@H](F)CN2C(=O)C(=O)C2CC2)c2ccccc2)cc1] | (2S,4R)-1-(2-cyclopropyl-2-oxoacetyl)-4-fluoro-N-[(S)-phenyl[4-(propan-2-yl)phenyl]methyl]pyrrolidine-2-carboxamide |
| 114 | 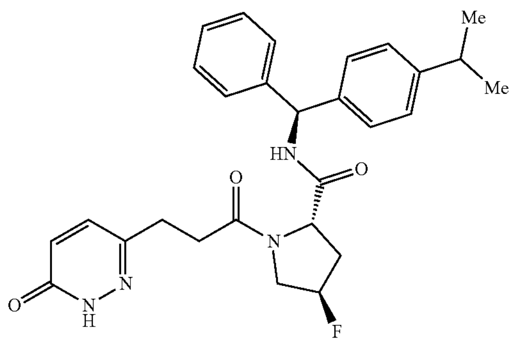 [SMILES: CC(C)c1ccc([C@@H](NC(=O)[C@@H]2C[C@@H](F)CN2C(=O)CCc2ccc(=O)[nH]n2)c2ccccc2)cc1] | (2S,4R)-4-fluoro-1-[3-(6-oxo-1,6-dihydropyridazin-3-yl)propanoyl]-N-[(S)-phenyl[4-(propan-2-yl)phenyl]methyl]pyrrolidine-2-carboxamide |
| 115 | 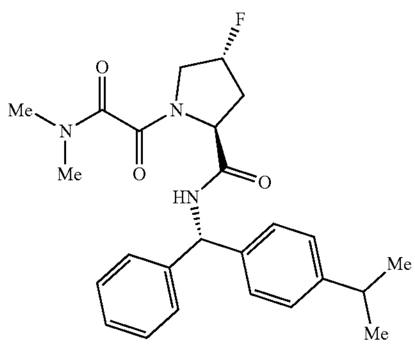 [SMILES: CC(C)c1ccc([C@@H](NC(=O)[C@@H]2C[C@@H](F)CN2C(=O)C(=O)N(C)C)c2ccccc2)cc1] | (2S,4R)-1-[(dimethylcarbamoyl)carbonyl]-4-fluoro-N-[(S)-phenyl[4-(propan-2-yl)phenyl]methyl]pyrrolidine-2-carboxamide |
| 116 | 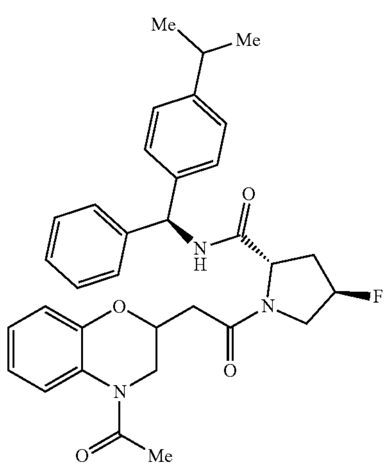 [SMILES: CC(=O)N1CC(CC(=O)N2C[C@H](F)C[C@H]2C(=O)N[C@@H](c2ccccc2)c2ccc(C(C)C)cc2)Oc2ccccc21] | (2S,4R)-1-[2-(4-acetyl-3,5-dihydro-2H-1,4-benzoxazin-2-yl)acetyl]-4-fluoro-N-[(S)-phenyl[4-(propan-2-yl)phenyl]methyl]pyrrolidine-2-carboxamide |

TABLE 1-continued

| Compound No. | Structure | IUPAC |
|---|---|---|
| 117 | 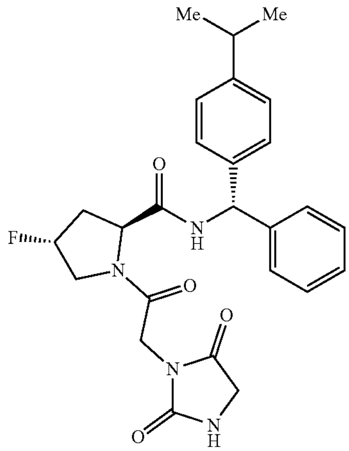 [SMILES: CC(C)c1ccc([C@@H](NC(=O)[C@@H]2C[C@@H](F)CN2C(=O)CN2C(=O)CNC2=O)c2ccccc2)cc1] | (2S,4R)-1-[2-(2,5-dioxoimidazolidin-1-yl)acetyl]-4-fluoro-N-[(S)-phenyl[4-(propan-2-yl)phenyl]methyl]pyrrolidine-2-carboxamide |
| 118 | 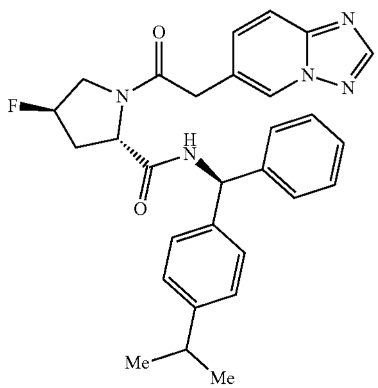 [SMILES: CC(C)c1ccc([C@@H](NC(=O)[C@@H]2C[C@@H](F)CN2C(=O)Cc2ccc3ncnn3c2)c2ccccc2)cc1] | (2S,4R)-4-fluoro-N-[(S)-phenyl[4-(propan-2-yl)phenyl]methyl]-1-(2-{[1,2,4]triazolo[1,5-a]pyridin-6-yl}acetyl)pyrrolidine-2-carboxamide |
| 119 | 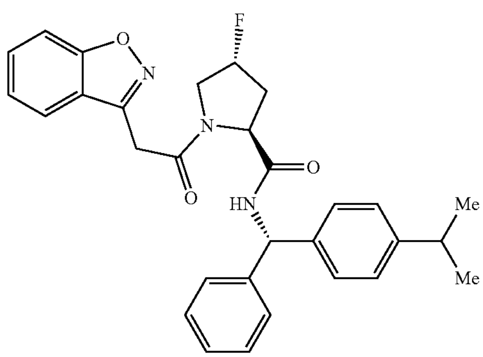 [SMILES: CC(C)c1ccc([C@@H](NC(=O)[C@@H]2C[C@@H](F)CN2C(=O)Cc2noc3ccccc23)c2ccccc2)cc1] | (2S,4R)-1-[2-(1,2-benzoxazol-3-yl)acetyl]-4-fluoro-N-[(S)-phenyl[4-(propan-2-yl)phenyl]methyl]pyrrolidine-2-carboxamide |
| 120 | 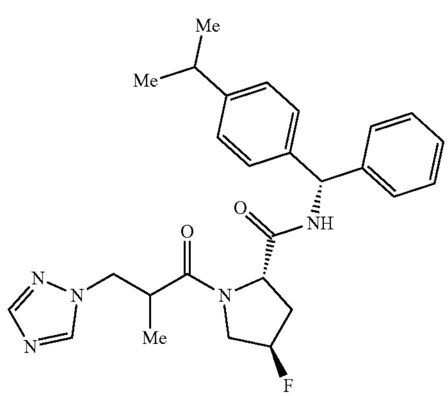 [SMILES: CC(Cn1cncn1)C(=O)N1C[C@H](F)C[C@H]1C(=O)N[C@@H](c1ccccc1)c1ccc(C(C)C)cc1] | (2S,4R)-4-fluoro-1-[2-methyl-3-(1H-1,2,4-triazol-1-yl)propanoyl]-N-[(S)-phenyl[4-(propan-2-yl)phenyl]methyl]pyrrolidine-2-carboxamide |

TABLE 1-continued

| Compound No. | Structure | IUPAC |
|---|---|---|
| 121 | 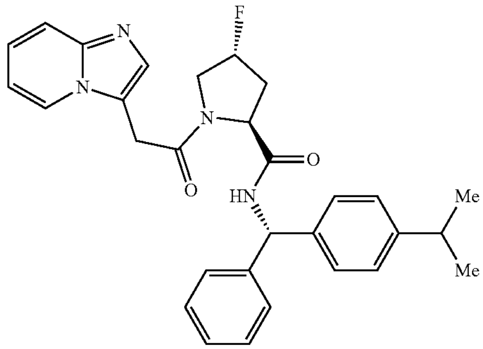 [SMILES: CC(C)c1ccc([C@@H](NC(=O)[C@@H]2C[C@@H](F)CN2C(=O)Cc2cnc3ccccn23)c2ccccc2)cc1] | (2S,4R)-4-fluoro-1-(2-{imidazo[1,2-a]pyridin-3-yl}acetyl-N-[(S)-phenyl[4-(propan-2-yl)phenyl]methyl]pyrrolidine-2-carboxamide |
| 122 | 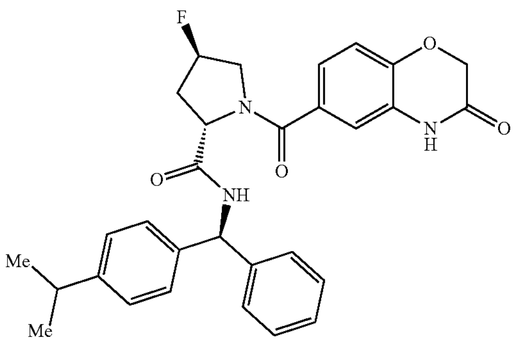 [SMILES: CC(C)c1ccc([C@@H](NC(=O)[C@@H]2C[C@@H](F)CN2C(=O)c2ccc3c(c2)NC(=O)CO3)c2ccccc2)cc1] | (2S,4R)-4-fluoro-1-(3-oxo-3,4-dihydro-2H-1,4-benzoxazine-6-carbonyl)-N-[(S)-phenyl[4-(propan-2-yl)phenyl]methyl]pyrrolidine-2-carboxamide |
| 123 | 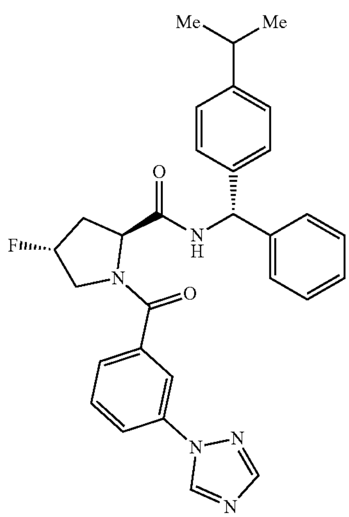 [SMILES: CC(C)c1ccc([C@@H](NC(=O)[C@@H]2C[C@@H](F)CN2C(=O)c2cccc(-n3cncn3)c2)c2ccccc2)cc1] | (2S,4R)-4-fluoro-N-[(S)-phenyl[4-(propan-2-yl)phenyl]methyl]-1-[3-(1H-1,2,4-triazol-1-yl)benzoyl]pyrrolidine-2-carboxamide |
| 124 | 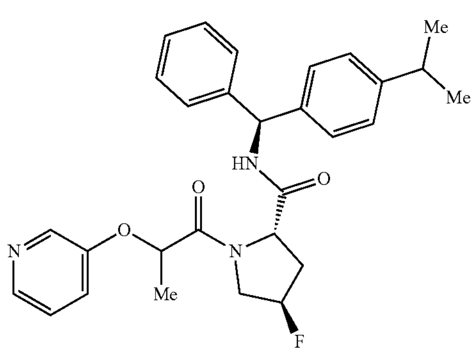 [SMILES: CC(Oc1cccnc1)C(=O)N1C[C@H](F)C[C@H]1C(=O)N[C@@H](c1ccccc1)c1ccc(C(C)C)cc1] | (2S,4R)-4-fluoro-N-[(S)-phenyl[4-(propan-2-yl)phenyl]methyl]-1-[2-(pyridin-3-yloxy)propanoyl]pyrrolidine-2-carboxamide |

TABLE 1-continued
| Compound No. | Structure | IUPAC |
|---|---|---|
| 125 | 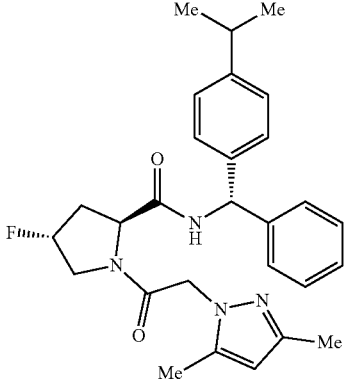 [SMILES: Cc1cc(C)n(CC(=O)N2C[C@H](F)C[C@H]2C(=O)N[C@@H](c2ccccc2)c2ccc(C(C)C)cc2)n1] | (2S,4R)-1-[2-(3,5-dimethyl-1H-pyrazol-1-yl)acetyl]-4-fluoro-N-[(S)-phenyl[4-(propan-2-yl)phenyl]methyl]pyrrolidine-2-carboxamide |
| 126 | 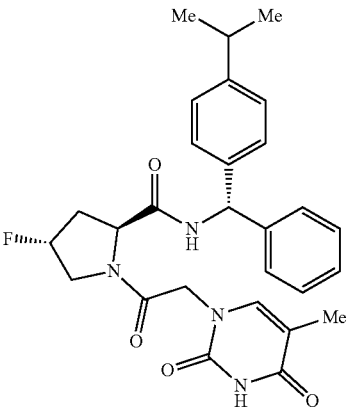 [SMILES: Cc1cn(CC(=O)N2C[C@H](F)C[C@H]2C(=O)N[C@@H](c2ccccc2)c2ccc(C(C)C)cc2)c(=O)[nH]c1=O] | (2S,4R)-4-fluoro-1-[2-(5-methyl-2,4-dioxo-1,2,3,4-tetrahydropyrimidin-1-yl)acetyl]-N-[(S)-phenyl[4-(propan-2-yl)phenyl]methyl]pyrrolidine-2-carboxamide |
| 127 | 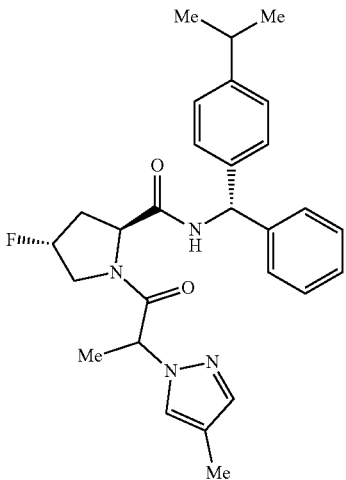 [SMILES: Cc1cnn(C(C)C(=O)N2C[C@H](F)C[C@H]2C(=O)N[C@@H](c2ccccc2)c2ccc(C(C)C)cc2)c1] | (2S,4R)-4-fluoro-1-[2-(4-methyl-1H-pyrazol-1-yl)propanoyl]-N-[(S)-phenyl[4-(propan-2-yl)phenyl]methyl]pyrrolidine-2-carboxamide |

TABLE 1-continued

| Compound No. | Structure | IUPAC |
|---|---|---|
| 128 | 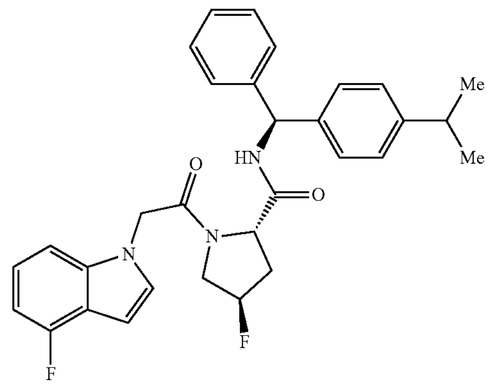 [SMILES: CC(C)c1ccc([C@@H](NC(=O)[C@@H]2C[C@@H](F)CN2C(=O)Cn2ccc3c(F)cccc32)c2ccccc2)cc1] | (2S,4R)-4-fluoro-1-[2-(4-fluoro-1H-indol-1-yl)acetyl]-N-[(S)-phenyl[4-(propan-2-yl)phenyl]methyl]pyrrolidine-2-carboxamide |
| 129 | 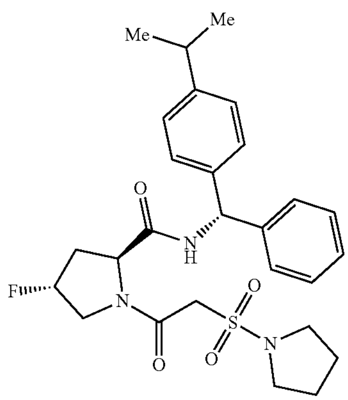 [SMILES: CC(C)c1ccc([C@@H](NC(=O)[C@@H]2C[C@@H](F)CN2C(=O)CS(=O)(=O)N2CCCC2)c2ccccc2)cc1] | (2S,4R)-4-fluoro-N-[(S)-phenyl[4-(propan-2-yl)phenyl]methyl]-1-[2-(pyrrolidine-1-sulfonyl)acetyl]pyrrolidine-2-carboxamide |
| 130 | 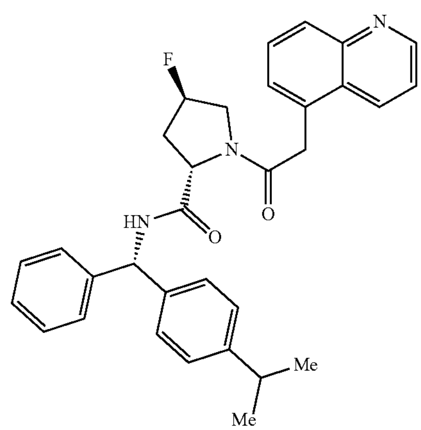 [SMILES: CC(C)c1ccc([C@@H](NC(=O)[C@@H]2C[C@@H](F)CN2C(=O)Cc2cccc3ncccc23)c2ccccc2)cc1] | (2S,4R)-4-fluoro-N-[(S)-phenyl[4-(propan-2-yl)phenyl]methyl]-1-[2-(quinolin-5-yl)acetyl]pyrrolidine-2-carboxamide |
| 131 | 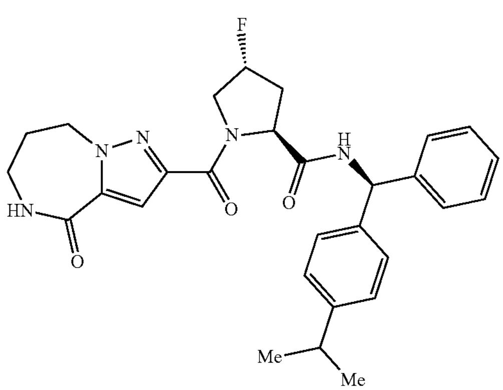 [SMILES: CC(C)c1ccc([C@@H](NC(=O)[C@@H]2C[C@@H](F)CN2C(=O)c2cc3n(n2)CCCNC3=O)c2ccccc2)cc1] | (2S,4R)-4-fluoro-1-{4-oxo-4H,5H,6H,7H,8H-pyrazolo[1,5-a][1,4]diazepine-2-carbonyl}-N-[(S)-phenyl[4-(propan-2-yl)phenyl]methyl]pyrrolidine-2-carboxamide |

TABLE 1-continued

| Compound No. | Structure | IUPAC |
|---|---|---|
| 132 | 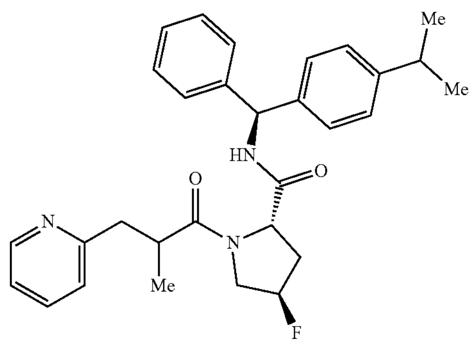 [SMILES: CC(Cc1ccccn1)C(=O)N1C[C@H](F)C[C@H]1C(=O)N[C@@H](c1ccccc1)c1ccc(C(C)C)cc1] | (2S,4R)-4-fluoro-1-[2-methyl-3-(pyridin-2-yl)propanoyl]-N-[(S)-phenyl[4-(propan-2-yl)phenyl]methyl]pyrrolidine-2-carboxamide |
| 133 | 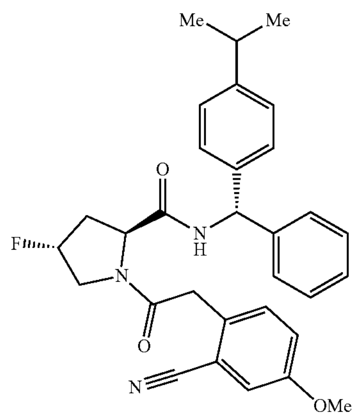 [SMILES: COc1ccc(CC(=O)N2C[C@H](F)C[C@H]2C(=O)N[C@@H](c2ccccc2)c2ccc(C(C)C)cc2)c(C#N)c1] | (2S,4R)-1-[2-(2-cyano-4-methoxyphenyl)acetyl]-4-fluoro-N-[(S)-phenyl[4-(propan-2-yl)phenyl]methyl]pyrrolidine-2-carboxamide |
| 134 | 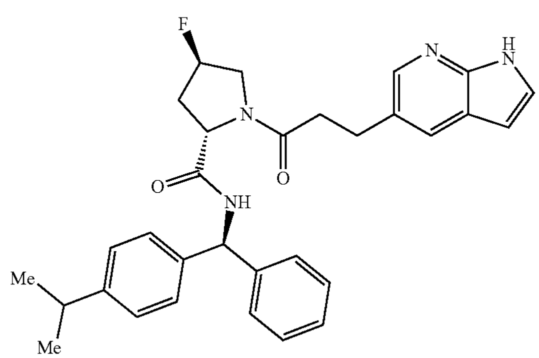 [SMILES: CC(C)c1ccc([C@@H](NC(=O)[C@@H]2C[C@@H](F)CN2C(=O)CCc2cnc3[nH]ccc3c2)c2ccccc2)cc1] | (2S,4R)-4-fluoro-N-[(S)-phenyl[4-(propan-2-yl)phenyl]methyl]-1-(3-{1H-pyrrolo[2,3-b]pyridin-5-yl}propanoyl)pyrrolidine-2-carboxamide |
| 135 | 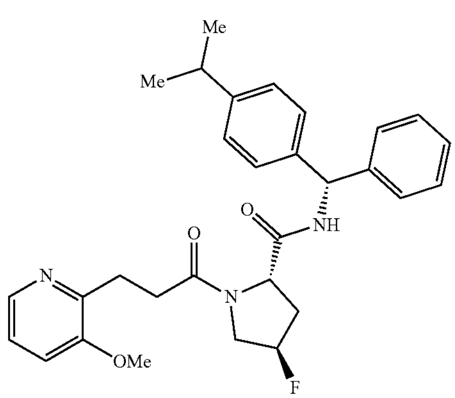 [SMILES: COc1cccnc1CCC(=O)N1C[C@H](F)C[C@H]1C(=O)N[C@@H](c1ccccc1)c1ccc(C(C)C)cc1] | (2S,4R)-4-fluoro-1-[3-(3-methoxypyridin-2-yl)propanoyl]-N-[(S)-phenyl[4-(propan-2-yl)phenyl]methyl]pyrrolidine-2-carboxamide |

TABLE 1-continued

| Compound No. | Structure | IUPAC |
|---|---|---|
| 136 | 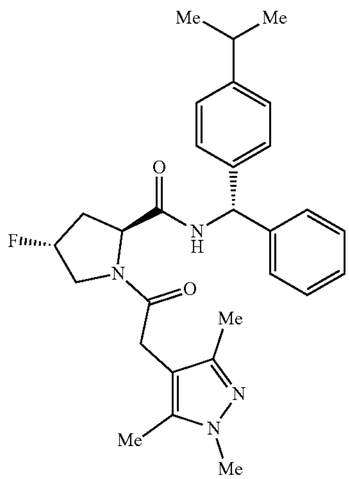 [SMILES: Cc1nn(C)c(C)c1CC(=O)N1C[C@H](F)C[C@H]1C(=O)N[C@@H](c1ccccc1)c1ccc(C(C)C)cc1] | (2S,4R)-4-fluoro-N-[(S)-phenyl[4-(propan-2-yl)phenyl]methyl]-1-[2-(1,3,5-trimethyl-1H-pyrazol-4-yl)acetyl]pyrrolidine-2-carboxamide |
| 137 | 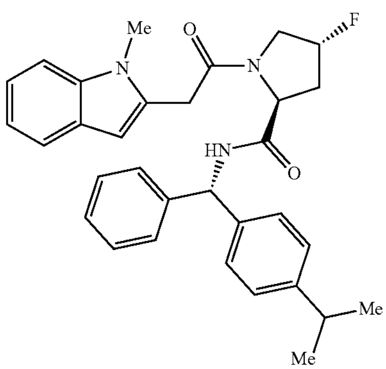 [SMILES: CC(C)c1ccc([C@@H](NC(=O)[C@@H]2C[C@@H](F)CN2C(=O)Cc2cc3ccccc3n2C)c2ccccc2)cc1] | (2S,4R)-4-fluoro-1-[2-(1-methyl-1H-indol-2-yl)acetyl]-N-[(S)-phenyl[4-(propan-2-yl)phenyl]methyl]pyrrolidine-2-carboxamide |
| 138 | 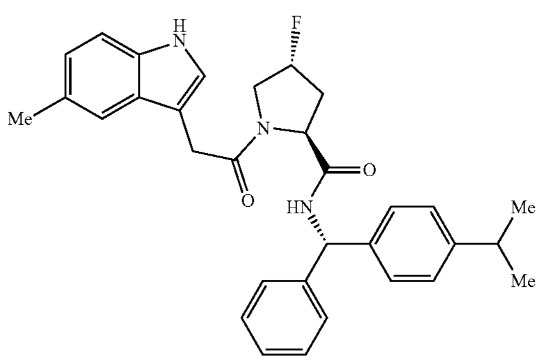 [SMILES: Cc1ccc2[nH]cc(CC(=O)N3C[C@H](F)C[C@H]3C(=O)N[C@@H](c3ccccc3)c3ccc(C(C)C)cc3)c2c1] | (2S,4R)-4-fluoro-1-[2-(5-methyl-1H-indol-3-yl)acetyl]-N-[(S)-phenyl[4-(propan-2-yl)phenyl]methyl]pyrrolidine-2-carboxamide |
| 139 | 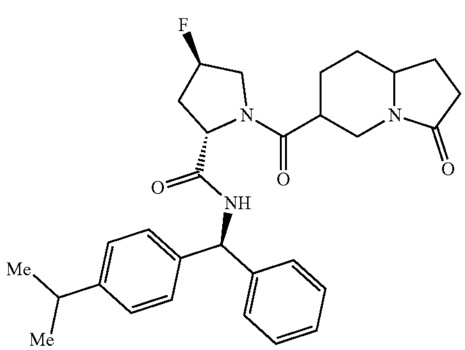 [SMILES: CC(C)c1ccc([C@@H](NC(=O)[C@@H]2C[C@@H](F)CN2C(=O)C2CCC3CCC(=O)N3C2)c2ccccc2)cc1] | (2S,4R)-4-fluoro-1-(3-oxo-octahydroindolizine-6-carbonyl)-N-[(S)-phenyl[4-(propan-2-yl)phenyl]methyl]pyrrolidine-2-carboxamide |

TABLE 1-continued

| Compound No. | Structure | IUPAC |
|---|---|---|
| 140 | 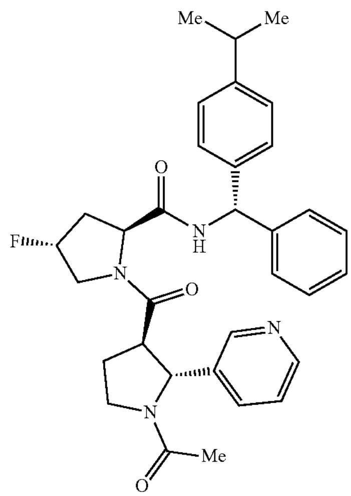 [SMILES: CC(=O)N1CC[C@@H](C(=O)N2C[C@H](F)C[C@H]2C(=O)N[C@@H](c2ccccc2)c2ccc(C(C)C)cc2)[C@@H]1c1cccnc1] | (2S,4R)-1-[(2R,3R)-1-acetyl-2-(pyridin-3-yl)pyrrolidine-3-carbonyl]-4-fluoro-N-[(S)-phenyl[4-(propan-2-yl)phenyl]methyl]pyrrolidine-2-carboxamide |
| 141 | 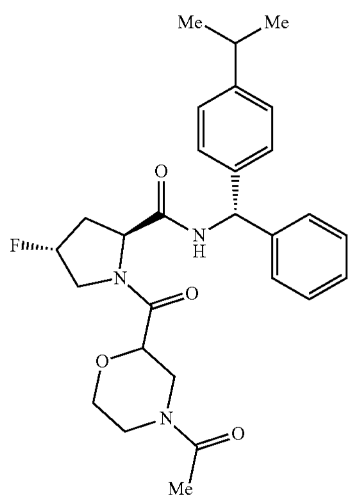 [SMILES: CC(=O)N1CCOC(C(=O)N2C[C@H](F)C[C@H]2C(=O)N[C@@H](c2ccccc2)c2ccc(C(C)C)cc2)C1] | (2S,4R)-1-(4-acetylmorpholine-2-carbonyl)-4-fluoro-N-[(S)-phenyl[4-(propan-2-yl)phenyl]methyl]pyrrolidine-2-carboxamide |
| 142 | 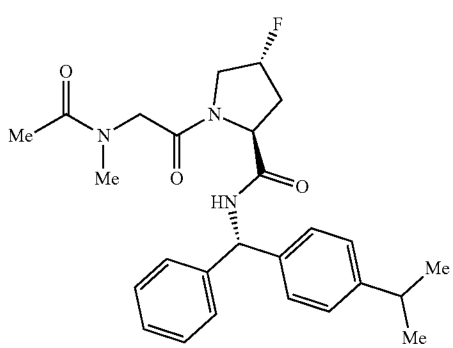 [SMILES: CC(=O)N(C)CC(=O)N1C[C@H](F)C[C@H]1C(=O)N[C@@H](c1ccccc1)c1ccc(C(C)C)cc1] | (2S,4R)-4-fluoro-1-[2-(N-methylacetamido)acetyl]-N-[(S)-phenyl[4-(propan-2-yl)phenyl]methyl]pyrrolidine-2-carboxamide |

TABLE 1-continued
| Compound No. | Structure | IUPAC |
|---|---|---|
| 143 | 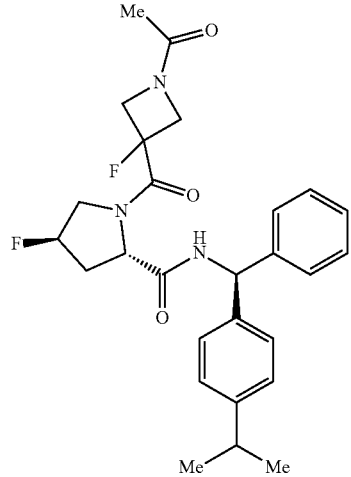 [SMILES: CC(=O)N1CC(F)(C(=O)N2C[C@H](F)C[C@H]2C(=O)N[C@@H](c2ccccc2)c2ccc(C(C)C)cc2)C1] | (2S,4R)-1-(1-acetyl-3-fluoroazetidine-3-carbonyl)-4-fluoro-N-[(S)-phenyl[4-(propan-2-yl)phenyl]methyl]pyrrolidine-2-carboxamide |
| 144 | 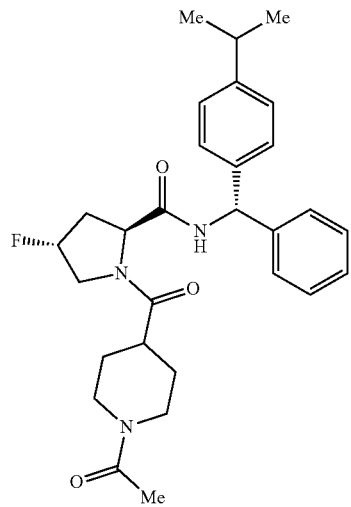 [SMILES: CC(=O)N1CCC(C(=O)N2C[C@H](F)C[C@H]2C(=O)N[C@@H](c2ccccc2)c2ccc(C(C)C)cc2)CC1] | (2S,4R)-1-(1-acetylpiperidine-4-carbonyl)-4-fluoro-N-[(S)-phenyl[4-(propan-2-yl)phenyl]methyl]pyrrolidine-2-carboxamide |
| 145 | 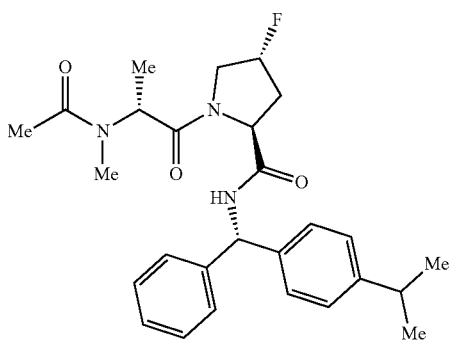 | (2S,4R)-4-fluoro-1-[(2R)-2-(N-methylacetamido)propanoyl]-N-[(S)-phenyl[4-(propan-2-yl)phenyl]methyl]pyrrolidine-2-carboxamide |

TABLE 1-continued

| Compound No. | Structure | IUPAC |
|---|---|---|
| 146 | 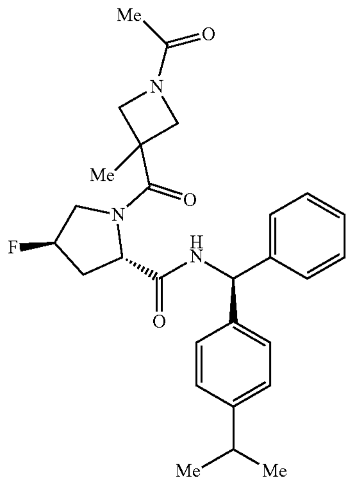 [SMILES: CC(=O)N1CC(C)(C(=O)N2C[C@H](F)C[C@H]2C(=O)N[C@@H](c2ccccc2)c2ccc(C(C)C)cc2)C1] | (2S,4R)-1-(1-acetyl-3-methylazetidine-3-carbonyl)-4-fluoro-N-[(S)-phenyl[4-(propan-2-yl)phenyl]methyl]pyrrolidine-2-carboxamide |
| 147 | 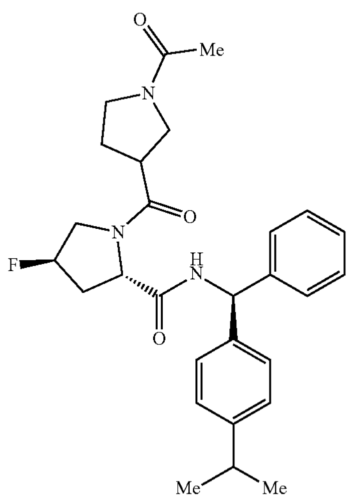 [SMILES: CC(=O)N1CCC(C(=O)N2C[C@H](F)C[C@H]2C(=O)N[C@@H](c2ccccc2)c2ccc(C(C)C)cc2)C1] | (2S,4R)-1-(1-acetylpyrrolidine-3-carbonyl)-4-fluoro-N-[(S)-phenyl[4-(propan-2-yl)phenyl]methyl]pyrrolidine-2-carboxamide |
| 148 | 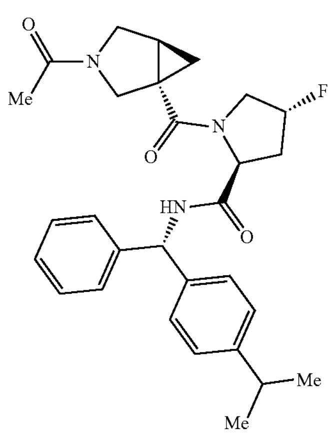 [SMILES: CC(=O)N1C[C@H]2C[C@@]2(C(=O)N2C[C@H](F)C[C@H]2C(=O)N[C@@H](c2ccccc2)c2ccc(C(C)C)cc2)C1] | (2S,4R)-1-[(1S,5S)-3-acetyl-3-azabicyclo[3.1.0]hexane-1-carbonyl]-4-fluoro-N-[(S)-phenyl[4-(propan-2-yl)phenyl]methyl]pyrrolidine-2-carboxamide |

TABLE 1-continued

| Compound No. | Structure | IUPAC |
|---|---|---|
| 149 | 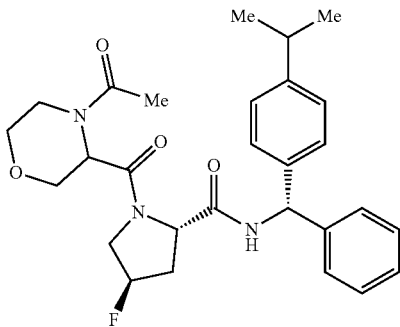 [SMILES: CC(=O)N1CCOCC1C(=O)N1C[C@H](F)C[C@H]1C(=O)N[C@@H](c1ccccc1)c1ccc(C(C)C)cc1] | (2S,4R)-1-(4-acetylmorpholine-3-carbonyl)-4-fluoro-N-[(S)-phenyl[4-(propan-2-yl)phenyl]methyl]pyrrolidine-2-carboxamide |
| 150 | 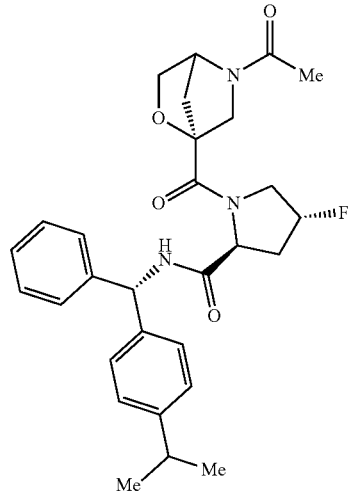 [SMILES: CC(=O)N1C[C@]2(C(=O)N3C[C@H](F)C[C@H]3C(=O)N[C@@H](c3ccccc3)c3ccc(C(C)C)cc3)CC1CO2] | (2S,4R)-1-[(1S)-5-acetyl-2-oxa-5-azabicyclo[2.2.1]heptane-1-carbonyl]-4-fluoro-N-[(S)-phenyl[4-(propan-2-yl)phenyl]methyl]pyrrolidine-2-carboxamide |
| 151 | 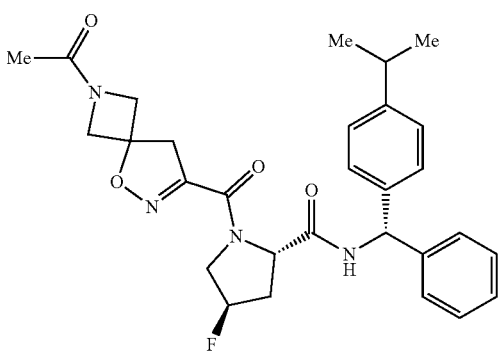 [SMILES: CC(=O)N1CC2(CC(C(=O)N3C[C@H](F)C[C@H]3C(=O)N[C@@H](c3ccccc3)c3ccc(C(C)C)cc3)=NO2)C1] | (2S,4R)-1-{2-acetyl-5-oxa-2,6-diazaspiro[3.4]oct-6-ene-7-carbonyl}-4-fluoro-N-[(S)-phenyl[4-(propan-2-yl)phenyl]methyl]pyrrolidine-2-carboxamide |

TABLE 1-continued
| Compound No. | Structure | IUPAC |
|---|---|---|
| 152 | 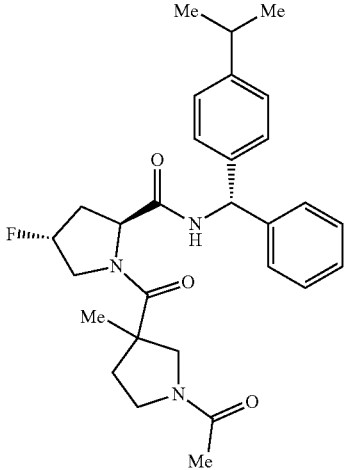 [SMILES: CC(=O)N1CCC(C)(C(=O)N2C[C@H](F)C[C@H]2C(=O)N[C@@H](c2ccccc2)c2ccc(C(C)C)cc2)C1] | (2S,4R)-1-(1-acetyl-3-methylpyrrolidine-3-carbonyl)-4-fluoro-N-[(S)-phenyl[4-(propan-2-yl)phenyl]methyl]pyrrolidine-2-carboxamide |
| 153 | 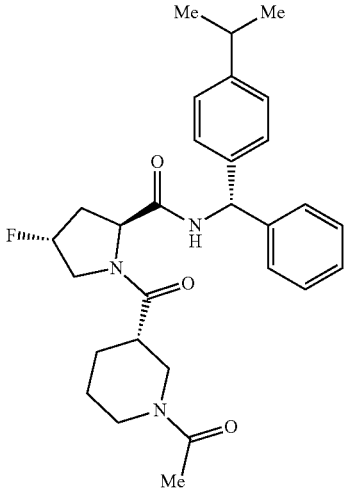 | (2S,4R)-1-[(3S)-1-acetylpiperidine-3-carbonyl]-4-fluoro-N-[(S)-phenyl[4-(propan-2-yl)phenyl]methyl]pyrrolidine-2-carboxamide |
| 154 | 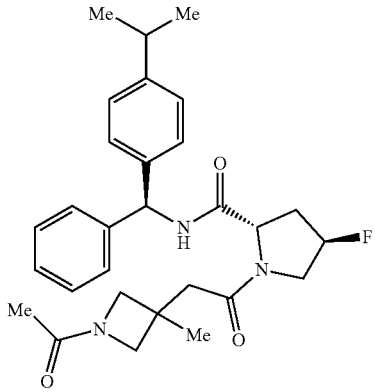 [SMILES: CC(=O)N1CC(C)(CC(=O)N2C[C@H](F)C[C@H]2C(=O)N[C@@H](c2ccccc2)c2ccc(C(C)C)cc2)C1] | (2S,4R)-1-[2-(1-acetyl-3-methylazetidin-3-yl)acetyl]-4-fluoro-N-[(S)-phenyl[4-(propan-2-yl)phenyl]methyl]pyrrolidine-2-carboxamide |

TABLE 1-continued

| Compound No. | Structure | IUPAC |
|---|---|---|
| 155 | 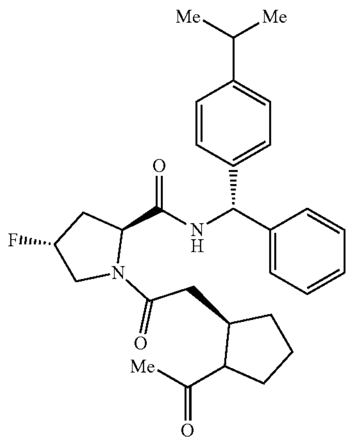 [SMILES: CC(=O)C1CCC[C@@H]1CC(=O)N1C[C@H](F)C[C@H]1C(=O)N[C@@H](c1ccccc1)c1ccc(C(C)C)cc1] | (2S,4R)-1-{2-[(2R)-1-acetylpyrrolidin-2-yl]acetyl}-4-fluoro-N-[(S)-phenyl[4-(propan-2-yl)phenyl]methyl]pyrrolidine-2-carboxamide |
| 156 | 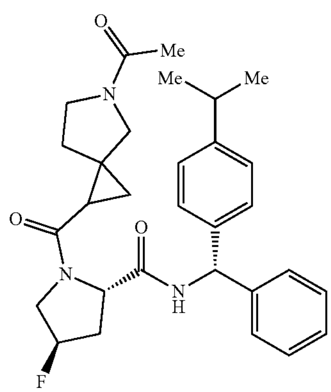 [SMILES: CC(=O)N1CCC2(CC2C(=O)N2C[C@H](F)C[C@H]2C(=O)N[C@@H](c2ccccc2)c2ccc(C(C)C)cc2)C1] | (2S,4R)-1-{5-acetyl-5-azaspiro[2.4]heptane-1-carbonyl}-4-fluoro-N-[(S)-phenyl[4-(propan-2-yl)phenyl]methyl]pyrrolidine-2-carboxamide |
| 157 | 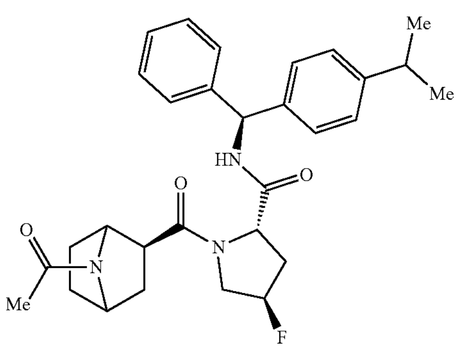 [SMILES: CC(=O)N1C2CCC1[C@@H](C(=O)N1C[C@H](F)C[C@H]1C(=O)N[C@@H](c1ccccc1)c1ccc(C(C)C)cc1)C2] | (2S,4R)-1-[(2S)-7-acetyl-7-azabicyclo[2.2.1]heptane-2-carbonyl]-4-fluoro-N-[(S)-phenyl[4-(propan-2-yl)phenyl]methyl]pyrrolidine-2-carboxamide |
| 158 | 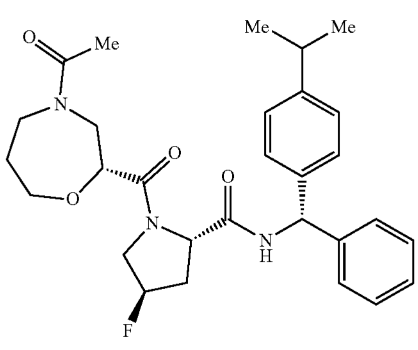 [SMILES: CC(=O)N1CCCO[C@@H](C(=O)N2C[C@H](F)C[C@H]2C(=O)N[C@@H](c2ccccc2)c2ccc(C(C)C)cc2)C1] | (2S,4R)-1-[(2R)-4-acetyl-1,4-oxazepane-2-carbonyl]-4-fluoro-N-[(S)-phenyl[4-(propan-2-yl)phenyl]methyl]pyrrolidine-2-carboxamide |

TABLE 1-continued

| Compound No. | Structure | IUPAC |
|---|---|---|
| 159 | 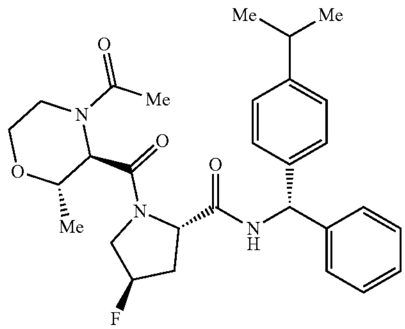 [SMILES: CC(=O)N1CCO[C@@H](C)[C@@H]1C(=O)N1C[C@H](F)C[C@H]1C(=O)N[C@@H](c1ccccc1)c1ccc(C(C)C)cc1] | (2S,4R)-1-[(2S,3R)-4-acetyl-2-methylmorpholine-3-carbonyl]-4-fluoro-N-[(S)-phenyl[4-(propan-2-yl)phenyl]methyl]pyrrolidine-2-carboxamide |
| 160 | 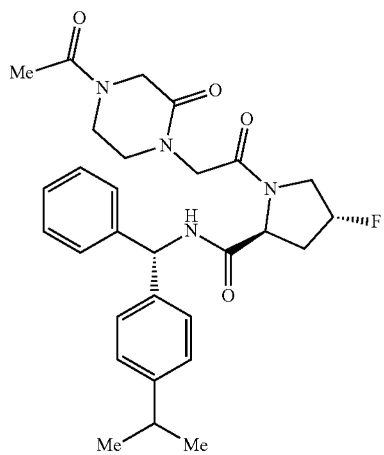 [SMILES: CC(=O)N1CCN(CC(=O)N2C[C@H](F)C[C@H]2C(=O)N[C@@H](c2ccccc2)c2ccc(C(C)C)cc2)C(=O)C1] | (2S,4R)-1-[2-(4-acetyl-2-oxopiperazin-1-yl)acetyl]-4-fluoro-N-[(S)-phenyl[4-(propan-2-yl)phenyl]methyl]pyrrolidine-2-carboxamide |
| 161 | 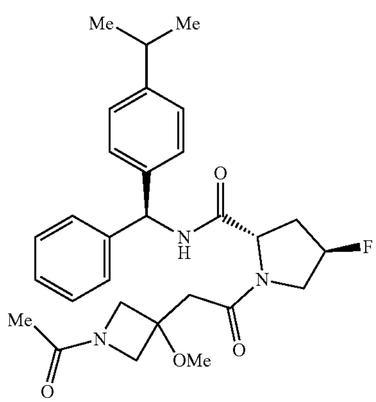 [SMILES: COC1(CC(=O)N2C[C@H](F)C[C@H]2C(=O)N[C@@H](c2ccccc2)c2ccc(C(C)C)cc2)CN(C(C)=O)C1] | (2S,4R)-1-[2-(1-acetyl-3-methoxyazetidin-3-yl)acetyl]-4-fluoro-N-[(S)-phenyl[4-(propan-2-yl)phenyl]methyl]pyrrolidine-2-carboxamide |
| 162 | 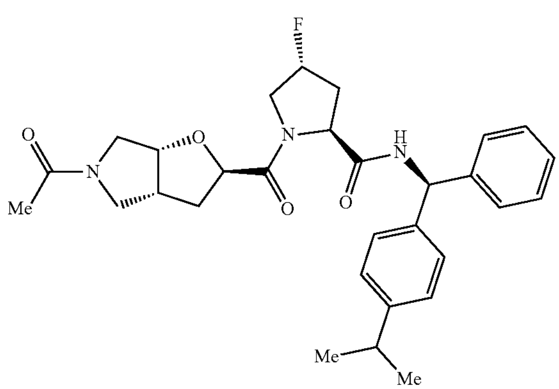 [SMILES: CC(=O)N1C[C@H]2C[C@H](C(=O)N3C[C@H](F)C[C@H]3C(=O)N[C@@H](c3ccccc3)c3ccc(C(C)C)cc3)O[C@H]2C1] | (2S,4R)-1-[(2R,3aR,6aR)-5-acetyl-hexahydro-2H-furo[2,3-c]pyrrole-2-carbonyl]-4-fluoro-N-[(S)-phenyl[4-(propan-2-yl)phenyl]methyl]pyrrolidine-2-carboxamide |

TABLE 1-continued

| Compound No. | Structure | IUPAC |
|---|---|---|
| 163 | 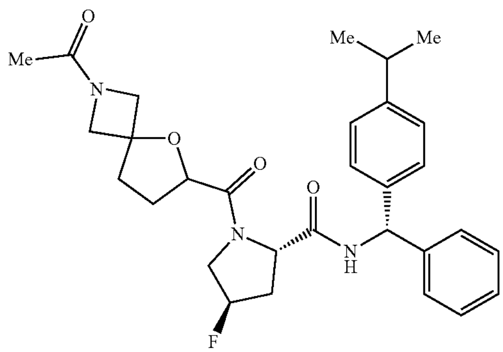 [SMILES: CC(=O)N1CC2(CCC(C(=O)N3C[C@H](F)C[C@H]3C(=O)N[C@@H](c3ccccc3)c3ccc(C(C)C)cc3)O2)C1] | (2S,4R)-1-{2-acetyl-5-oxa-2-azaspiro[3.4]octane-6-carbonyl}-4-fluoro-N-[(S)-phenyl[4-(propan-2-yl)phenyl]methyl]pyrrolidine-2-carboxamide |
| 164 | 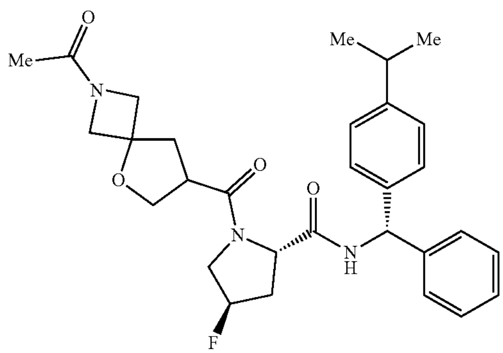 [SMILES: CC(=O)N1CC2(CC(C(=O)N3C[C@H](F)C[C@H]3C(=O)N[C@@H](c3ccccc3)c3ccc(C(C)C)cc3)CO2)C1] | (2S,4R)-1-{2-acetyl-5-oxa-2-azaspiro[3.4]octane-7-carbonyl}-4-fluoro-N-[(S)-phenyl[4-(propan-2-yl)phenyl]methyl]pyrrolidine-2-carboxamide |
| 165 | 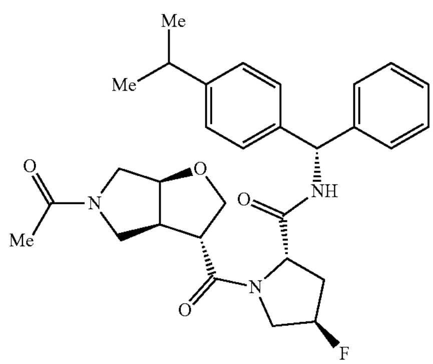 [SMILES: CC(=O)N1C[C@@H]2[C@@H](C(=O)N3C[C@H](F)C[C@H]3C(=O)N[C@@H](c3ccccc3)c3ccc(C(C)C)cc3)CO[C@@H]2C1] | (2S,4R)-1-[(3R,3aS,6aS)-5-acetyl-hexahydro-2H-furo[2,3-c]pyrrole-3-carbonyl]-4-fluoro-N-[(S)-phenyl[4-(propan-2-yl)phenyl]methyl]pyrrolidine-2-carboxamide |
| 166 | 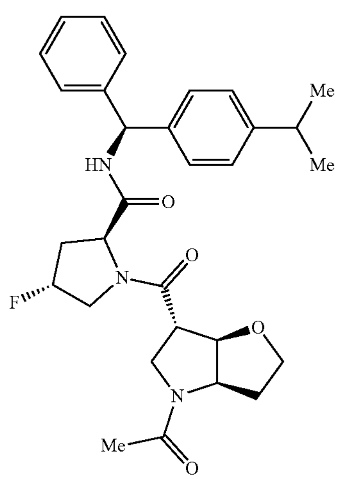 [SMILES: CC(=O)N1C[C@H](C(=O)N2C[C@H](F)C[C@H]2C(=O)N[C@@H](c2ccccc2)c2ccc(C(C)C)cc2)[C@H]2OCC[C@H]21] | (2S,4R)-1-[(3aR,6S,6aR)-4-acetyl-hexahydro-2H-furo[3,2-b]pyrrole-6-carbonyl]-4-fluoro-N-[(S)-phenyl[4-(propan-2-yl)phenyl]methyl]pyrrolidine-2-carboxamide |

TABLE 1-continued

| Compound No. | Structure | IUPAC |
|---|---|---|
| 167 | 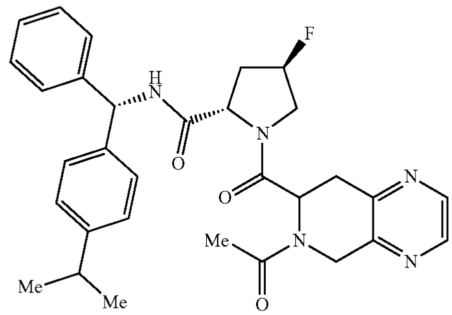 [SMILES: CC(=O)N1Cc2nccnc2CC1C(=O)N1C[C@H](F)C[C@H]1C(=O)N[C@@H](c1ccccc1)c1ccc(C(C)C)cc1] | (2S,4R)-1-{acetyl-5H,6H,7H,8H-pyrido[3,4-b]pyrazine-7-carbonyl}-4-fluoro-N-[(S)-phenyl[4-(propan-2-yl)phenyl]methyl]pyrrolidine-2-carboxamide |
| 168 | 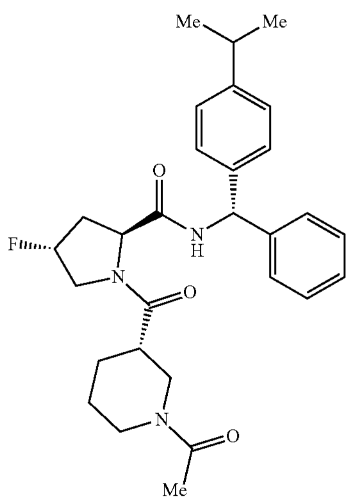 [SMILES: CC(=O)N1CCC[C@H](C(=O)N2C[C@H](F)C[C@H]2C(=O)N[C@@H](c2ccccc2)c2ccc(C(C)C)cc2)C1] | (2S,4R)-1-(1-acetyl-3-methylpiperidine-3-carbonyl)-4-fluoro-N-[(S)-phenyl[4-(propan-2-yl)phenyl]methyl]pyrrolidine-2-carboxamide |
| 169 | 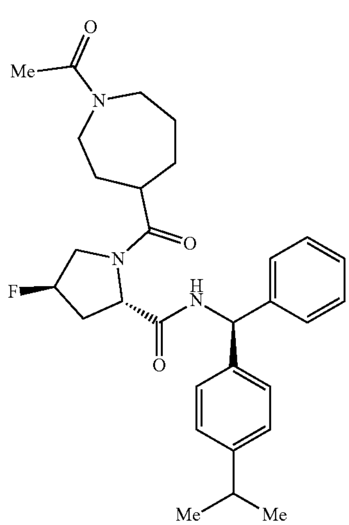 [SMILES: CC(=O)N1CCCC(C(=O)N2C[C@H](F)C[C@H]2C(=O)N[C@@H](c2ccccc2)c2ccc(C(C)C)cc2)CC1] | (2S,4R)-1-(1-acetylazepane-4-carbonyl)-4-fluoro-N-[(S)-phenyl[4-(propan-2-yl)phenyl]methyl]pyrrolidine-2-carboxamide |

TABLE 1-continued

| Compound No. | Structure | IUPAC |
|---|---|---|
| 170 | 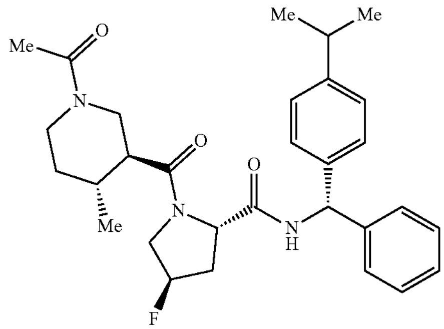 [SMILES: CC(=O)N1CC[C@@H](C)[C@H](C(=O)N2C[C@H](F)C[C@H]2C(=O)N[C@@H](c2ccccc2)c2ccc(C(C)C)cc2)C1] | (2S,4R)-1-[(3S,4R)-1-acetyl-4-methylpiperidine-3-carbonyl]-4-fluoro-N-[(S)-phenyl[4-(propan-2-yl)phenyl]methyl]pyrrolidine-2-carboxamide |
| 171 | 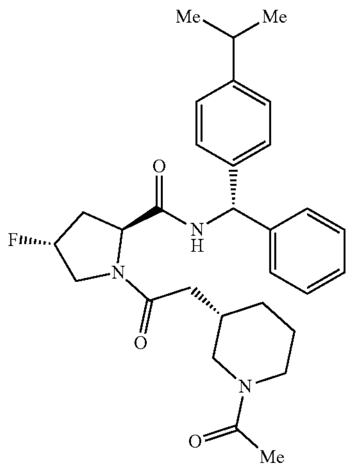 [SMILES: CC(=O)N1CCC[C@@H](CC(=O)N2C[C@H](F)C[C@H]2C(=O)N[C@@H](c2ccccc2)c2ccc(C(C)C)cc2)C1] | (2S,4R)-1-{2-[(3S)-1-acetylpiperidin-3-yl]acetyl}-4-fluoro-N-[(S)-phenyl[4-(propan-2-yl)phenyl]methyl]pyrrolidine-2-carboxamide |
| 172 | 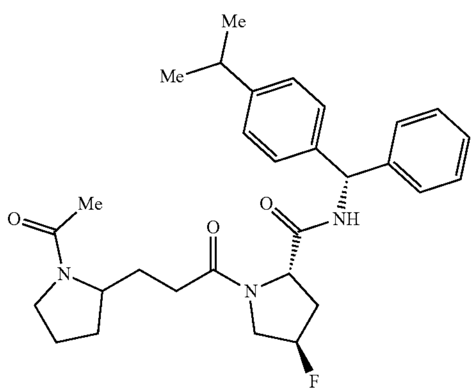 [SMILES: CC(=O)N1CCCC1CCC(=O)N1C[C@H](F)C[C@H]1C(=O)N[C@@H](c1ccccc1)c1ccc(C(C)C)cc1] | (2S,4R)-1-[3-(1-acetylpyrrolidin-2-yl)propanoyl]-4-fluoro-N-[(S)-phenyl[4-(propan-2-yl)phenyl]methyl]pyrrolidine-2-carboxamide |
| 173 | 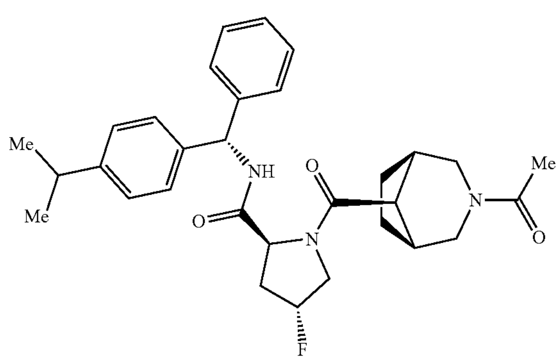 [SMILES: CC(=O)N1C[C@H]2CC[C@@H](C1)[C@@H]2C(=O)N1C[C@H](F)C[C@H]1C(=O)N[C@@H](c1ccccc1)c1ccc(C(C)C)cc1] | (2S,4R)-1-[(1R,5S,8S)-3-acetyl-3-azabicyclo[3.2.1]octane-8-carbonyl]-4-fluoro-N-[(S)-phenyl[4-(propan-2-yl)phenyl]methyl]pyrrolidine-2-carboxamide |

TABLE 1-continued

| Compound No. | Structure | IUPAC |
|---|---|---|
| 174 | 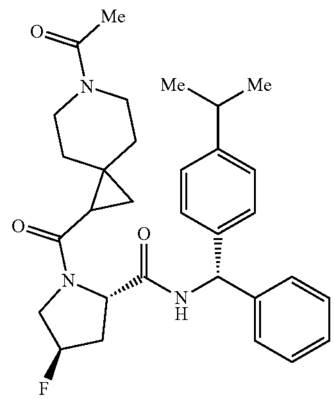 [SMILES: CC(=O)N1CCC2(CC1)CC2C(=O)N1C[C@H](F)C[C@H]1C(=O)N[C@@H](c1ccccc1)c1ccc(C(C)C)cc1] | (2S,4R)-1-{6-acetyl-6-azaspiro[2.5]octane-1-carbonyl}-4-fluoro-N-[(S)-phenyl[4-(propan-2-yl)phenyl]methyl]pyrrolidine-2-carboxamide |
| 175 | 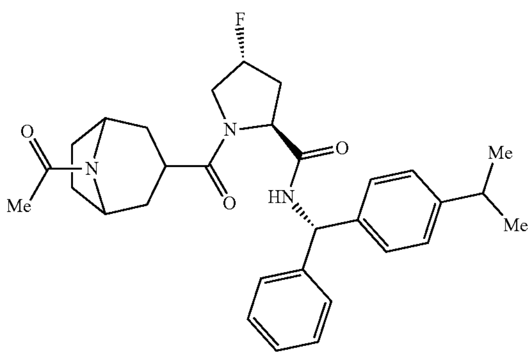 [SMILES: CC(=O)N1C2CCC1CC(C(=O)N1C[C@H](F)C[C@H]1C(=O)N[C@@H](c1ccccc1)c1ccc(C(C)C)cc1)C2] | (2S,4R)-1-{8-acetyl-8-azabicyclo[3.2.1]octane-3-carbonyl}-4-fluoro-N-[(S)-phenyl[4-(propan-2-yl)phenyl]methyl]pyrrolidine-2-carboxamide |
| 176 | 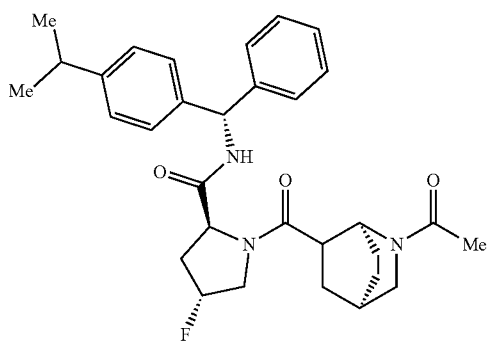 [SMILES: CC(=O)N1C[C@@H]2CC[C@H]1C(C(=O)N1C[C@H](F)C[C@H]1C(=O)N[C@@H](c1ccccc1)c1ccc(C(C)C)cc1)C2] | (2S,4R)-1-[(1S,4R)-2-acetyl-2-azabicyclo[2.2.2]octane-6-carbonyl]-4-fluoro-N-[(S)-phenyl[4-(propan-2-yl)phenyl]methyl]pyrrolidine-2-carboxamide |
| 177 | 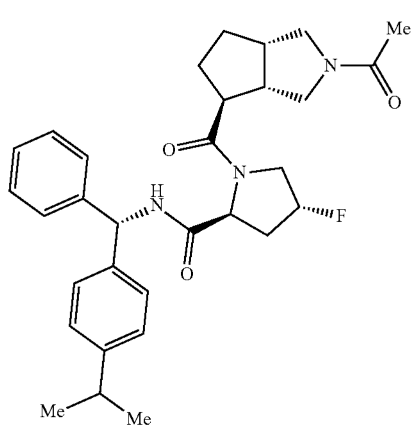 [SMILES: CC(=O)N1C[C@H]2CC[C@H](C(=O)N3C[C@H](F)C[C@H]3C(=O)N[C@@H](c3ccccc3)c3ccc(C(C)C)cc3)[C@H]2C1] | (2S,4R)-1-[(3aS,4S,6aS)-2-acetyl-octahydrocyclopenta[c]pyrrole-4-carbonyl]-4-fluoro-N-[(S)-phenyl[4-(propan-2-yl)phenyl]methyl]pyrrolidine-2-carboxamide |

TABLE 1-continued

| Compound No. | Structure | IUPAC |
|---|---|---|
| 178 | 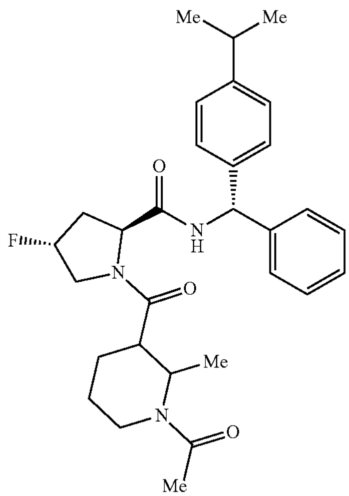 [SMILES: CC(=O)N1CCCC(C(=O)N2C[C@H](F)C[C@H]2C(=O)N[C@@H](c2ccccc2)c2ccc(C(C)C)cc2)C1C] | (2S,4R)-1-(1-acetyl-2-methylpiperidine-3-carbonyl)-4-fluoro-N-[(S)-phenyl[4-(propan-2-yl)phenyl]methyl]pyrrolidine-2-carboxamide |
| 179 | 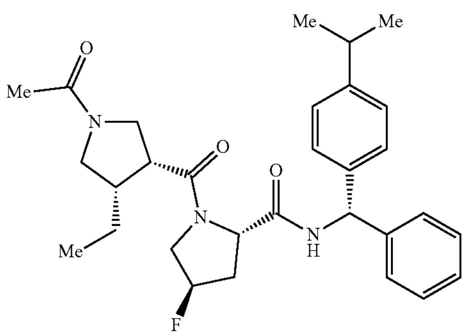 [SMILES: CC[C@@H]1CN(C(C)=O)C[C@@H]1C(=O)N1C[C@H](F)C[C@H]1C(=O)N[C@@H](c1ccccc1)c1ccc(C(C)C)cc1] | (2S,4R)-1-[(3R,4S)-1-acetyl-4-ethylpyrrolidine-3-carbonyl]-4-fluoro-N-[(S)-phenyl[4-(propan-2-yl)phenyl]methyl]pyrrolidine-2-carboxamide |
| 180 | 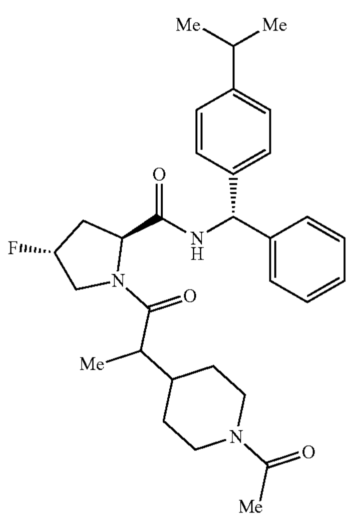 [SMILES: CC(=O)N1CCC(C(C)C(=O)N2C[C@H](F)C[C@H]2C(=O)N[C@@H](c2ccccc2)c2ccc(C(C)C)cc2)CC1] | (2S,4R)-1-[2-(1-acetylpiperidin-4-yl)propanoyl]-4-fluoro-N-[(S)-phenyl[4-(propan-2-yl)phenyl]methyl]pyrrolidine-2-carboxamide |

TABLE 1-continued

| Compound No. | Structure | IUPAC |
|---|---|---|
| 181 | 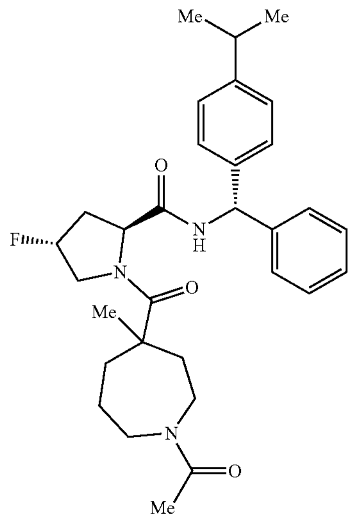 [SMILES: CC(=O)N1CCCC(C)(C(=O)N2C[C@H](F)C[C@H]2C(=O)N[C@@H](c2ccccc2)c2ccc(C(C)C)cc2)CC1] | (2S,4R)-1-(1-acetyl-4-methylazepane-4-carbonyl)-4-fluoro-N-[(S)-phenyl[4-(propan-2-yl)phenyl]methyl]pyrrolidine-2-carboxamide |
| 182 | 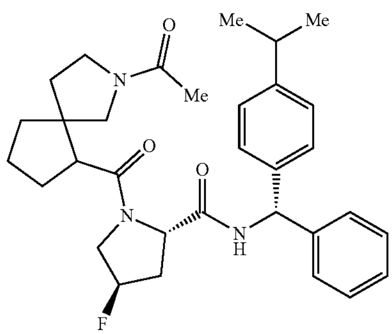 [SMILES: CC(=O)N1CCC2(CCCC2C(=O)N2C[C@H](F)C[C@H]2C(=O)N[C@@H](c2ccccc2)c2ccc(C(C)C)cc2)C1] | (2S,4R)-1-{2-acetyl-2-azaspiro[4.4]nonane-6-carbonyl}-4-fluoro-N-[(S)-phenyl[4-(propan-2-yl)phenyl]methyl]pyrrolidine-2-carboxamide |
| 183 | 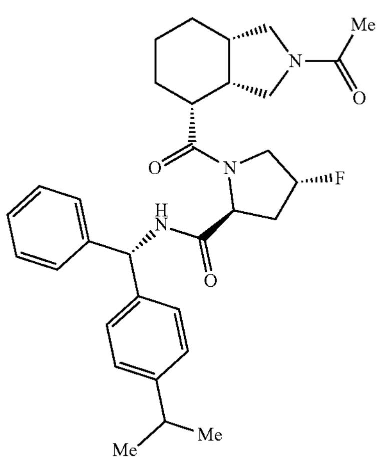 [SMILES: CC(=O)N1C[C@H]2CCC[C@@H](C(=O)N3C[C@H](F)C[C@H]3C(=O)N[C@@H](c3ccccc3)c3ccc(C(C)C)cc3)[C@H]2C1] | (2S,4R)-1-[(3aS,4R,7aS)-2-acetyl-octahydro-1H-isoindole-4-carbonyl]-4-fluoro-N-[(S)-phenyl[4-(propan-2-yl)phenyl]methyl]pyrrolidine-2-carboxamide |

TABLE 1-continued

| Compound No. | Structure | IUPAC |
|---|---|---|
| 184 | 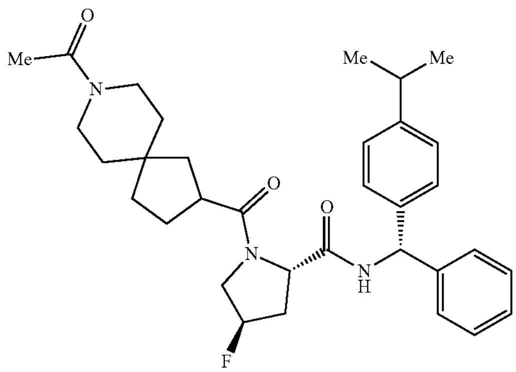 [SMILES: CC(=O)N1CCC2(CCC(C(=O)N3C[C@H](F)C[C@H]3C(=O)N[C@@H](c3ccccc3)c3ccc(C(C)C)cc3)C2)CC1] | (2S,4R)-1-{8-acetyl-8-azaspiro[4.5]decane-2-carbonyl}-4-fluoro-N-[(S)-phenyl[4-(propan-2-yl)phenyl]methyl]pyrrolidine-2-carboxamide |
| 185 | 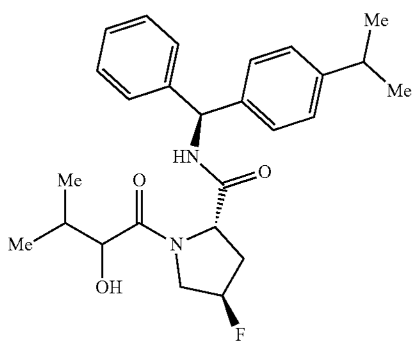 [SMILES: CC(C)c1ccc([C@@H](NC(=O)[C@@H]2C[C@@H](F)CN2C(=O)C(O)C(C)C)c2ccccc2)cc1] | (2S,4R)-4-fluoro-1-(2-hydroxy-3-methylbutanoyl)-N-[(S)-phenyl[4-(propan-2-yl)phenyl]methyl]pyrrolidine-2-carboxamide |
| 186 | 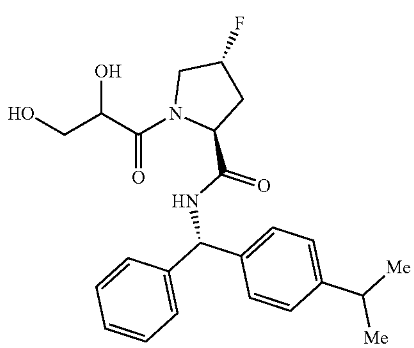 [SMILES: CC(C)c1ccc([C@@H](NC(=O)[C@@H]2C[C@@H](F)CN2C(=O)C(O)CO)c2ccccc2)cc1] | (2S,4R)-1-(2,3-dihydroxypropanoyl)-4-fluoro-N-[(S)-phenyl[4-(propan-2-yl)phenyl]methyl]pyrrolidine-2-carboxamide |
| 187 | 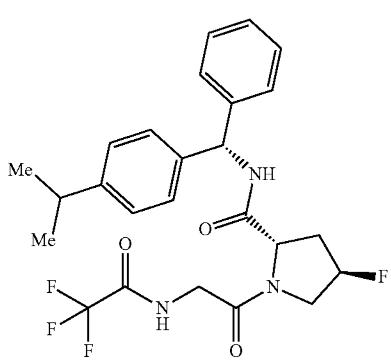 [SMILES: CC(C)c1ccc([C@@H](NC(=O)[C@@H]2C[C@@H](F)CN2C(=O)CNC(=O)C(F)(F)F)c2ccccc2)cc1] | (2S,4R)-4-fluoro-N-[(S)-phenyl[4-(propan-2-yl)phenyl]methyl]-1-[2-(2,2,2-trifluoroacetamido)acetyl]pyrrolidine-2-carboxamide |

TABLE 1-continued

| Compound No. | Structure | IUPAC |
|---|---|---|
| 188 | 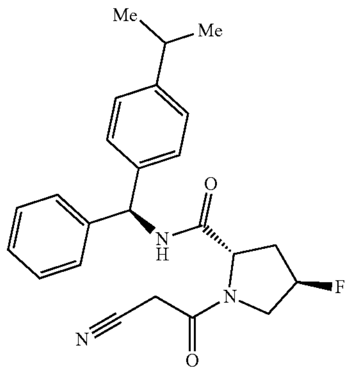 [SMILES: CC(C)c1ccc([C@@H](NC(=O)[C@@H]2C[C@@H](F)CN2C(=O)CC#N)c2ccccc2)cc1] | (2S,4R)-1-(2-cyanoacetyl)-4-fluoro-N-[(S)-phenyl[4-(propan-2-yl)phenyl]methyl]pyrrolidine-2-carboxamide |
| 189 | 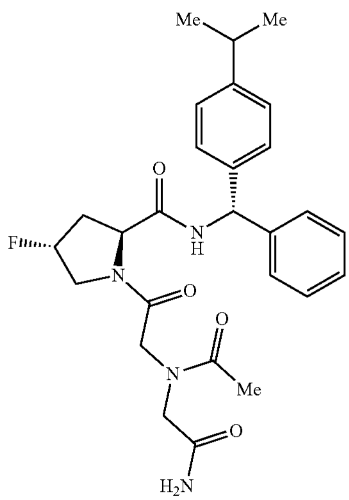 [SMILES: CC(=O)N(CC(N)=O)CC(=O)N1C[C@H](F)C[C@H]1C(=O)N[C@@H](c1ccccc1)c1ccc(C(C)C)cc1] | (2S,4R)-1-{2-[N-(carbamoylmethyl)acetamido]acetyl}-4-fluoro-N-[(S)-phenyl[4-(propan-2-yl)phenyl]methyl]pyrrolidine-2-carboxamide |
| 190 | 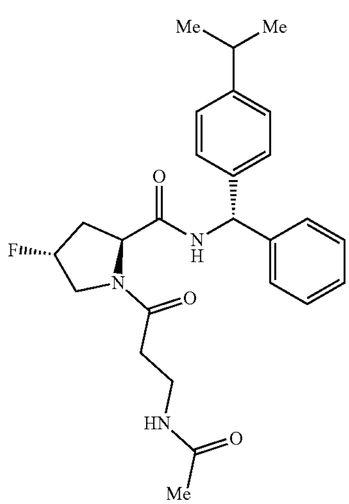 [SMILES: CC(=O)NCCC(=O)N1C[C@H](F)C[C@H]1C(=O)N[C@@H](c1ccccc1)c1ccc(C(C)C)cc1] | (2S,4R)-1-(3-acetamidopropanoyl)-4-fluoro-N-[(S)-phenyl[4-(propan-2-yl)phenyl]methyl]pyrrolidine-2-carboxamide |

TABLE 1-continued

| Compound No. | Structure | IUPAC |
|---|---|---|
| 191 | 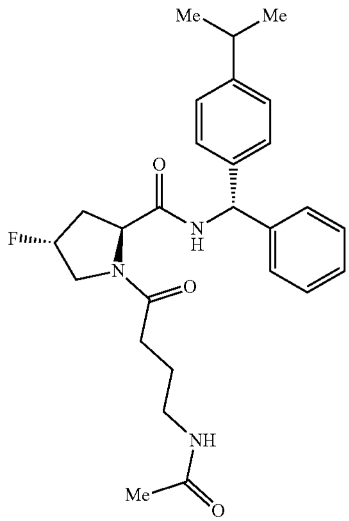 [SMILES: CC(=O)NCCCC(=O)N1C[C@H](F)C[C@H]1C(=O)N[C@@H](c1ccccc1)c1ccc(C(C)C)cc1] | (2S,4R)-1-(4-acetamidobutanoyl)-4-fluoro-N-[(S)-phenyl[4-(propan-2-yl)phenyl]methyl]pyrrolidine-2-carboxamide |
| 192 | 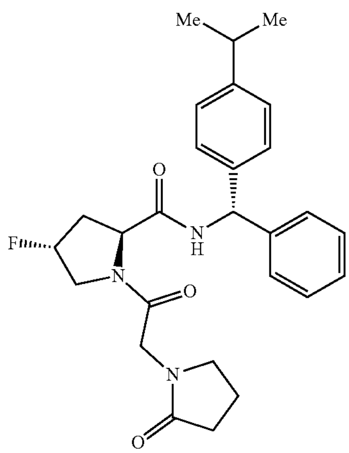 [SMILES: CC(C)c1ccc([C@@H](NC(=O)[C@@H]2C[C@@H](F)CN2C(=O)CN2CCCC2=O)c2ccccc2)cc1] | (2S,4R)-4-fluoro-1-[2-(2-oxopyrrolidin-1-yl)acetyl]-N-[(S)-phenyl[4-(propan-2-yl)phenyl]methyl]pyrrolidine-2-carboxamide |
| 193 | 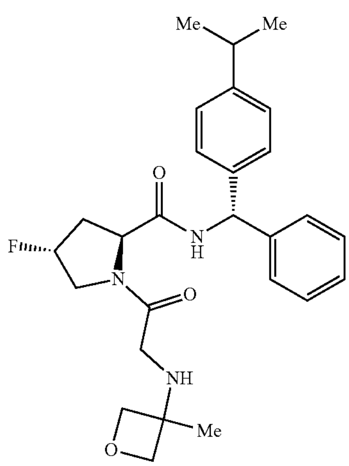 [SMILES: CC(C)c1ccc([C@@H](NC(=O)[C@@H]2C[C@@H](F)CN2C(=O)CNC2(C)COC2)c2ccccc2)cc1] | (2S,4R)-4-fluoro-1-{2-[(3-methyloxetan-3-yl)amino]acetyl}-N-[(S)-phenyl[4-(propan-2-yl)phenyl]methyl]pyrrolidine-2-carboxamide |

TABLE 1-continued
| Compound No. | Structure | IUPAC |
|---|---|---|
| 194 | 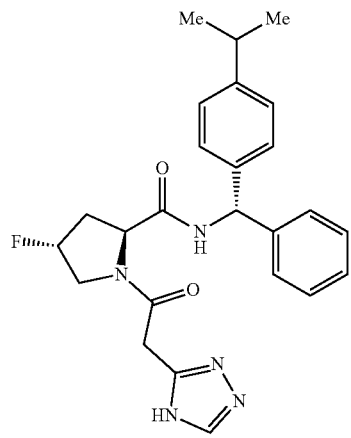 | (2S,4R)-4-fluoro-N-[(S)-phenyl[4-(propan-2-yl)phenyl]methyl]-1-[2-(4H-1,2,4-triazol-3-yl)acetyl]pyrrolidine-2-carboxamide |
| 195 | 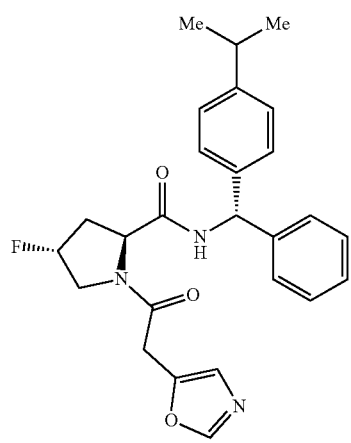 [SMILES: CC(C)c1ccc([C@@H](NC(=O)[C@@H]2C[C@@H](F)CN2C(=O)Cc2cnco2)c2ccccc2)cc1] | (2S,4R)-4-fluoro-1-[2-(1,3-oxazol-5-yl)acetyl]-N-[(S)-phenyl[4-(propan-2-yl)phenyl]methyl]pyrrolidine-2-carboxamide |
| 196 | 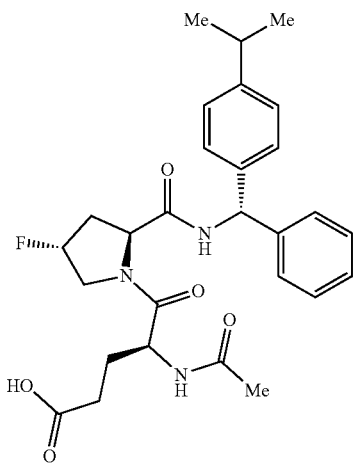 [SMILES: CC(=O)N[C@@H](CCC(=O)O)C(=O)N1C[C@H](F)C[C@H]1C(=O)N[C@@H](c1ccccc1)c1ccc(C(C)C)cc1] | (4S)-4-acetamido-5-[(2S,4R)-4-fluoro-2-{[(S)-phenyl[4-(propan-2-yl)phenyl]methyl]carbamoyl}pyrrolidin-1-yl]-5-oxopentanoic acid |

TABLE 1-continued

| Compound No. | Structure | IUPAC |
|---|---|---|
| 197 | 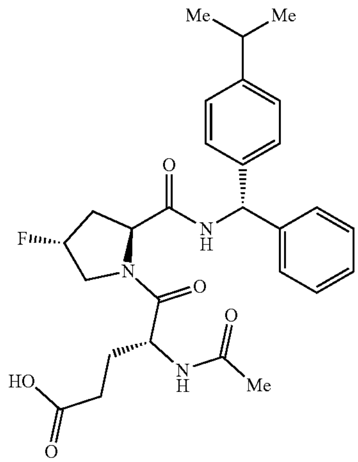 [SMILES: CC(=O)N[C@H](CCC(=O)O)C(=O)N1C[C@H](F)C[C@H]1C(=O)N[C@@H](c1ccccc1)c1ccc(C(C)C)cc1] | (4R)-4-acetamido-5-[(2S,4R)-4-fluoro-2-{[(S)-phenyl[4-(propan-2-yl)phenyl]methyl]carbamoyl}pyrrolidin-1-yl]-5-oxopentanoic acid |
| 198 | 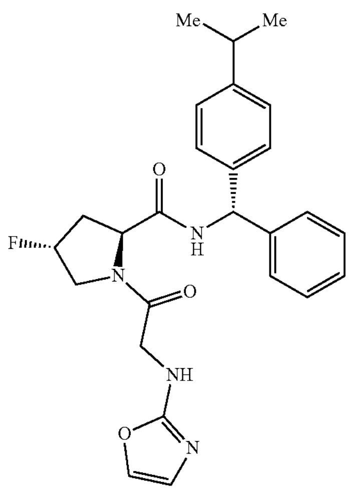 [SMILES: CC(C)c1ccc([C@@H](NC(=O)[C@@H]2C[C@@H](F)CN2C(=O)CNc2ncco2)c2ccccc2)cc1] | (2S,4R)-4-fluoro-1-{2-[(1,3-oxazol-2-yl)amino]acetyl}-N-[(S)-phenyl[4-(propan-2-yl)phenyl]methyl]pyrrolidine-2-carboxamide |
| 199 | 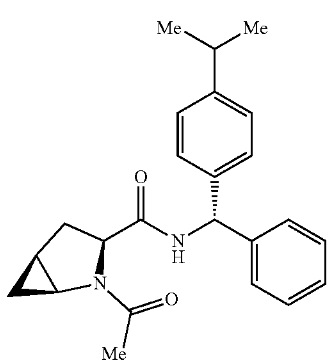 [SMILES: CC(=O)N1[C@H](C(=O)N[C@@H](c2ccccc2)c2ccc(C(C)C)cc2)C[C@@H]2C[C@@H]21] | (1S,3S,5S)-2-acetyl-N-[(S)-phenyl[4-(propan-2-yl)phenyl]methyl]-2-azabicyclo[3.1.0]hexane-3-carboxamide |

TABLE 1-continued

| Compound No. | Structure | IUPAC |
|---|---|---|
| 200 | 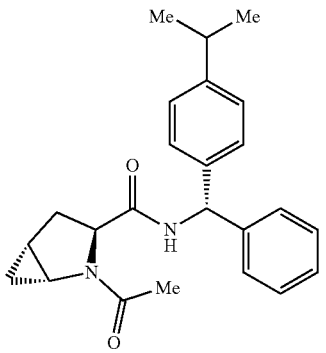 [SMILES: CC(=O)N1[C@@H]2C[C@@H]2C[C@H]1C(=O)N[C@@H](c1ccccc1)c1ccc(C(C)C)cc1] | (1R,3S,5R)-2-acetyl-N-[(S)-phenyl[4-(propan-2-yl)phenyl]methyl]-2-azabicyclo[3.1.0]hexane-3-carboxamide |
| 201 | 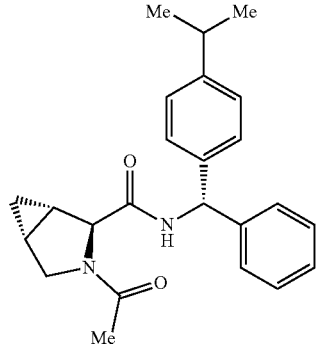 [SMILES: CC(=O)N1C[C@@H]2C[C@@H]2[C@H]1C(=O)N[C@@H](c1ccccc1)c1ccc(C(C)C)cc1] | (1S,2S,5R)-3-acetyl-N-[(S)-phenyl[4-(propan-2-yl)phenyl]methyl]-3-azabicycl[3.1.0]hexane-2-carboxamide |
| 202 | 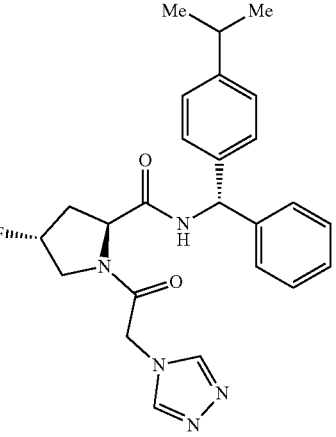 | (2S,4R)-4-fluoro-N-[(S)-phenyl[4-(propan-2-yl)phenyl]methyl]-1-[2-(4H-1,2,4-triazol-4-yl)acetyl]pyrrolidine-2-carboxamide |
| 203 | 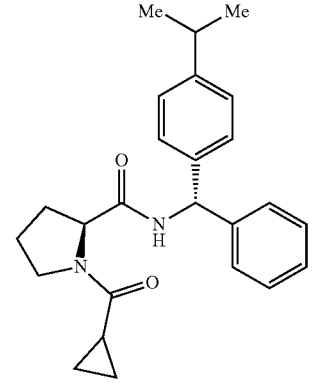 [SMILES: CC(C)c1ccc([C@@H](NC(=O)[C@@H]2CCCN2C(=O)C2CC2)c2ccccc2)cc1] | (2S)-1-cyclopropanecarbonyl-N-[(S)-phenyl[4-(propan-2-yl)phenyl]methyl]pyrrolidine-2-carboxamide |

TABLE 1-continued

| Compound No. | Structure | IUPAC |
|---|---|---|
| 204 | 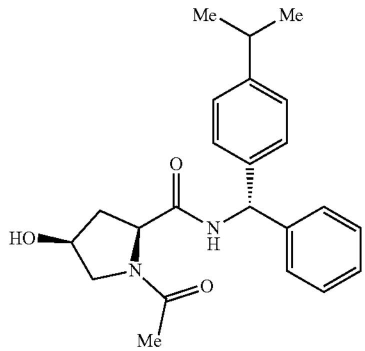 [SMILES: CC(=O)N1C[C@@H](O)C[C@H]1C(=O)N[C@@H](c1ccccc1)c1ccc(C(C)C)cc1] | (2S,4S)-1-acetyl-4-hydroxy-N-[(S)-phenyl[4-(propan-2-yl)phenyl]methyl]pyrrolidine-2-carboxamide |
| 205 | 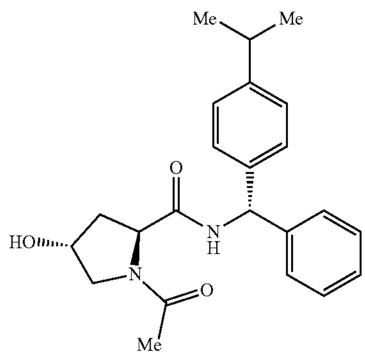 [SMILES: CC(=O)N1C[C@H](O)C[C@H]1C(=O)N[C@@H](c1ccccc1)c1ccc(C(C)C)cc1] | (2S,4R)-1-acetyl-4-hydroxy-N-[(S)-phenyl[4-(propan-2-yl)phenyl]methyl]pyrrolidine-2-carboxamide |
| 206 | 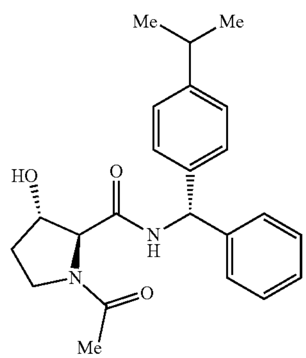 [SMILES: CC(=O)N1CC[C@H](O)[C@H]1C(=O)N[C@@H](c1ccccc1)c1ccc(C(C)C)cc1] | (2S,3S)-1-acetyl-3-hydroxy-N-[(S)-phenyl[4-(propan-2-yl)phenyl]methyl]pyrrolidine-2-carboxamide |
| 207 | 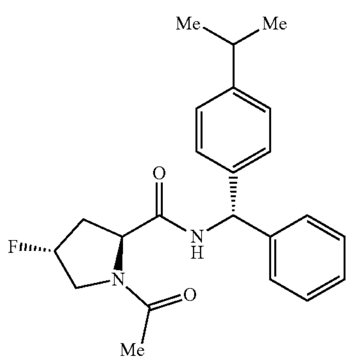 [SMILES: CC(=O)N1C[C@H](F)C[C@H]1C(=O)N[C@@H](c1ccccc1)c1ccc(C(C)C)cc1] | (2S,4R)-1-acetyl-4-fluoro-N-[(S)-phenyl[4-(propan-2-yl)phenyl]methyl]pyrrolidine-2-carboxamide |

TABLE 1-continued
| Compound No. | Structure | IUPAC |
|---|---|---|
| 208 | 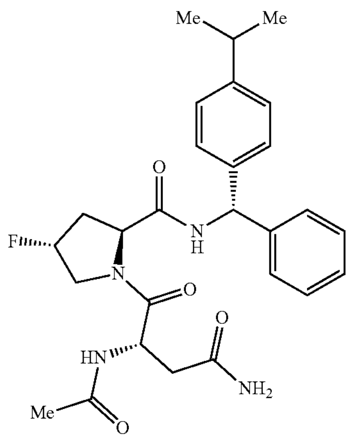 [SMILES: CC(=O)N[C@@H](CC(N)=O)C(=O)N1C[C@H](F)C[C@H]1C(=O)N[C@@H](c1ccccc1)c1ccc(C(C)C)cc1] | (2S,4R)-1-[(2S)-3-carbamoyl-2-acetamidopropanoyl]-4-fluoro-N-[(S)-phenyl[4-(propan-2-yl)phenyl]methyl]pyrrolidine-2-carboxamide |
| 209 | 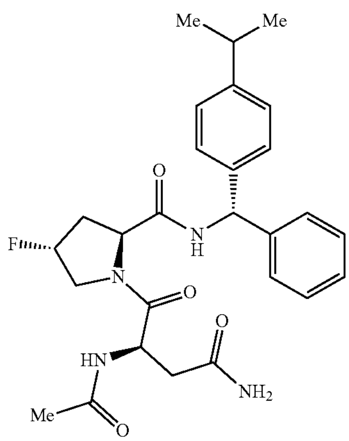 [SMILES: CC(=O)N[C@H](CC(N)=O)C(=O)N1C[C@H](F)C[C@H]1C(=O)N[C@@H](c1ccccc1)c1ccc(C(C)C)cc1] | (2S,4R)-1-[(2R)-3-carbamoyl-2-acetamidopropanoyl]-4-fluoro-N-[(S)-phenyl[4-(propan-2-yl)phenyl]methyl]pyrrolidine-2-carboxamide |
| 210 | 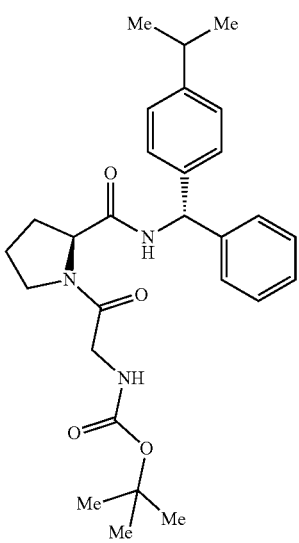 [SMILES: CC(C)c1ccc([C@@H](NC(=O)[C@@H]2CCCN2C(=O)CNC(=O)OC(C)(C)C)c2ccccc2)cc1] | tert-butyl N-{2-oxo-2-[(2S)-2-{[(S)-phenyl[4-(propan-2-yl)phenyl]methyl]carbamoyl}pyrrolidin-1-yl]ethyl}carbamate |

TABLE 1-continued
| Compound No. | Structure | IUPAC |
|---|---|---|
| 211 | 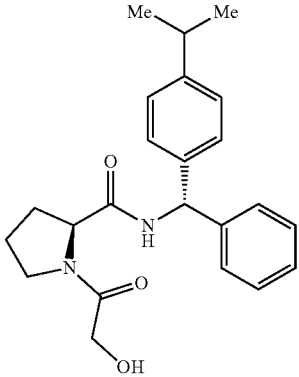 [SMILES: CC(C)c1ccc([C@@H](NC(=O)[C@@H]2CCCN2C(=O)CO)c2ccccc2)cc1] | (2S)-1-(2-hydroxyacetyl)-N-[(S)-phenyl[4-(propan-2-yl)phenyl]methyl]pyrrolidine-2-carboxamide |
| 212 | 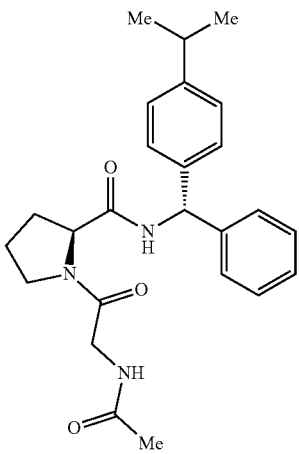 [SMILES: CC(=O)NCC(=O)N1CCC[C@H]1C(=O)N[C@@H](c1ccccc1)c1ccc(C(C)C)cc1] | (2S)-1-(2-acetamidoacetyl)-N-[(S)-phenyl[4-(propan-2-yl)phenyl]methyl]pyrrolidine-2-carboxamide |
| 213 | 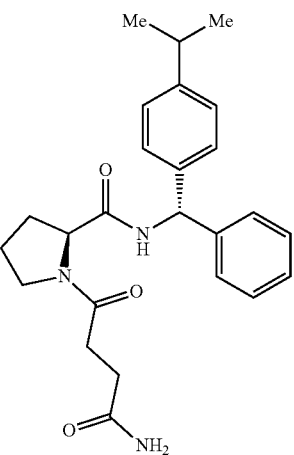 [SMILES: CC(C)c1ccc([C@@H](NC(=O)[C@@H]2CCCN2C(=O)CCC(N)=O)c2ccccc2)cc1] | (2S)-1-(3-carbamoylpropanoyl)-N-[(S)-phenyl[4-(propan-2-yl)phenyl]methyl]pyrrolidine-2-carboxamide |

TABLE 1-continued

| Compound No. | Structure | IUPAC |
|---|---|---|
| 214 | 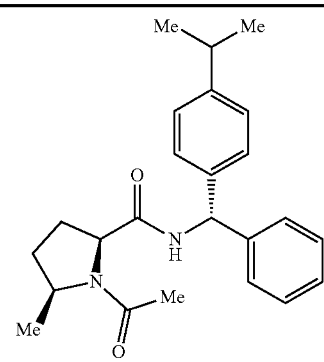 | (2S,5S)-1-acetyl-5-methyl-N-[(S)-phenyl[4-(propan-2-yl)phenyl]methyl]pyrrolidine-2-carboxamide |
| 215 | 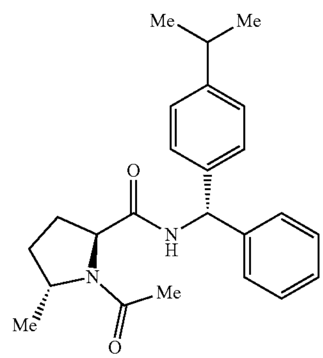 [SMILES: CC(=O)N1[C@H](C)CC[C@H]1C(=O)N[C@@H](c1ccccc1)c1ccc(C(C)C)cc1] | (2S,5R)-1-acetyl-5-methyl-N-[(S)-phenyl[4-(propan-2-yl)phenyl]methyl]pyrrolidine-2-carboxamide |
| 216 | 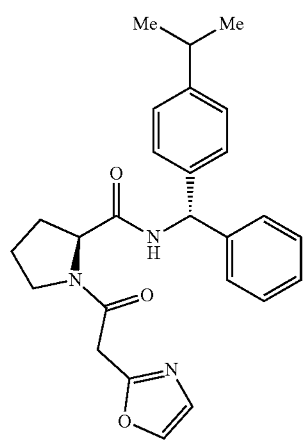 [SMILES: CC(C)c1ccc([C@@H](NC(=O)[C@@H]2CCCN2C(=O)Cc2ncco2)c2ccccc2)cc1] | (2S)-1-[2-(1,3-oxazol-2-yl)acetyl]-N-[(S)-phenyl[4-(propan-2-yl)phenyl]methyl]pyrrolidine-2-carboxamide |
| 217 | 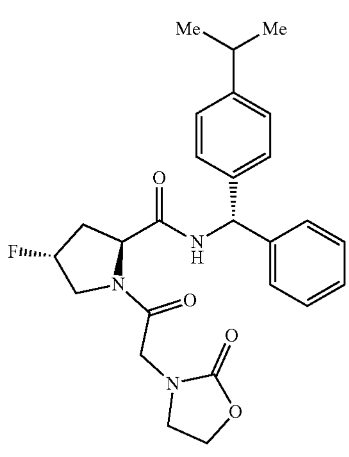 [SMILES: CC(C)c1ccc([C@@H](NC(=O)[C@@H]2C[C@@H](F)CN2C(=O)CN2CCOC2=O)c2ccccc2)cc1] | (2S,4R)-4-fluoro-1-[2-(2-oxo-1,3-oxazolidin-3-yl)acetyl-N-[(S)-phenyl[4-(propan-2-yl)phenyl]methyl]pyrrolidine-2-carboxamide |

TABLE 1-continued
| Compound No. | Structure | IUPAC |
|---|---|---|
| 218 | 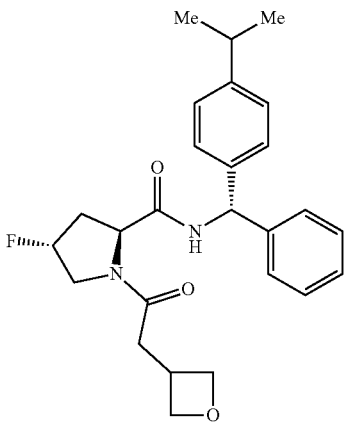 [SMILES: CC(C)c1ccc([C@@H](NC(=O)[C@@H]2C[C@@H](F)CN2C(=O)CC2COC2)c2ccccc2)cc1] | (2S,4R)-4-fluoro-1-[2-(oxetan-3-yl)acetyl]-[(S)-phenyl[4-(propan-2-yl)phenyl]methyl]pyrrolidine-2-carboxamide |
| 219 | 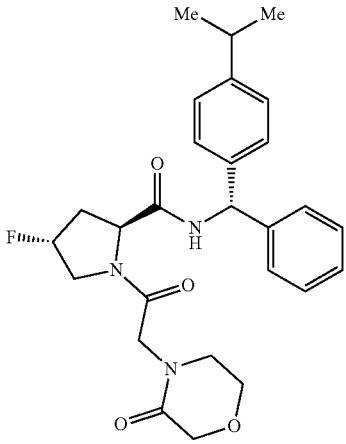 [SMILES: CC(C)c1ccc([C@@H](NC(=O)[C@@H]2C[C@@H](F)CN2C(=O)CN2CCOCC2=O)c2ccccc2)cc1] | (2S,4R)-4-fluoro-1-[2-(3-oxomorpholin-4-yl)acethyl]-N-[(S)-phenyl[4-(propan-2-yl)phenyl]methyl]pyrrolidine-2-carboxamide |
| 220 | 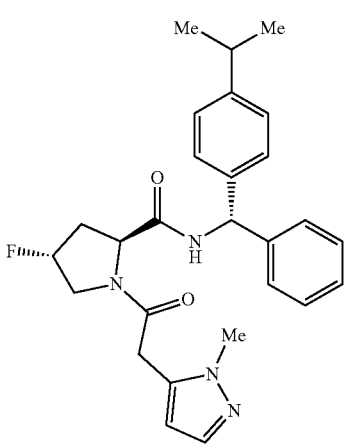 [SMILES: CC(C)c1ccc([C@@H](NC(=O)[C@@H]2C[C@@H](F)CN2C(=O)Cc2ccnn2C)c2ccccc2)cc1] | (2S,4RS)-4-fluoro-1-[2-(1-methyl-1H-pyrazol-5-yl)acetyl]-N-[(S)-phenyl[4-(propan-2-yl)phenyl]methyl]pyrrolidine-2-carboxamide |

TABLE 1-continued
| Compound No. | Structure | IUPAC |
|---|---|---|
| 221 | 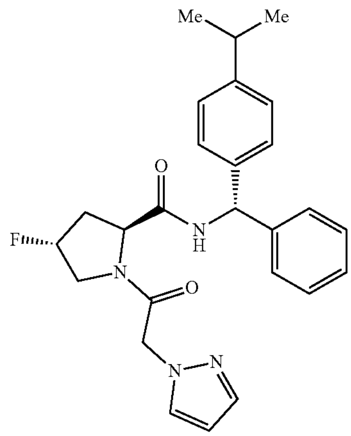 [SMILES: CC(C)c1ccc([C@@H](NC(=O)[C@@H]2C[C@@H](F)CN2C(=O)Cn2cccn2)c2ccccc2)cc1] | (2S,4RS)-4-fluoro-N-[(S)-phenyl[4-(propan-2-yl)phenyl]methyl]-1-[2-(1H-pyrazol-1-yl)acetyl]pyrrolidine-2-carboxamide |
| 222 | 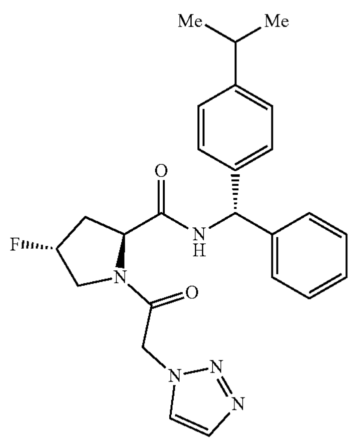 [SMILES: CC(C)c1ccc([C@@H](NC(=O)[C@@H]2C[C@@H](F)CN2C(=O)Cn2ccnn2)c2ccccc2)cc1] | (2RS,4R)-4-fluoro-N-[(S)-phenyl[4-(propan-2-yl)phenyl]methyl]-1-[2-(1H-1,2,3-triazol-1-yl)acetyl]pyrrolidine-2-carboxamide |
| 223 | 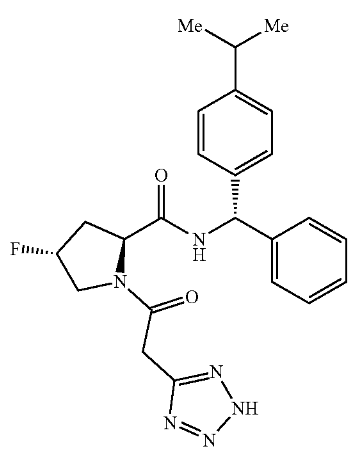 [SMILES: CC(C)c1ccc([C@@H](NC(=O)[C@@H]2C[C@@H](F)CN2C(=O)Cc2nn[nH]n2)c2ccccc2)cc1] | (2RS,4R)-4-fluoro-N-[(S)-phenyl[4-(propan-2-yl)phenyl]methyl]-1-[2-(2H-1,2,3,4-tetrazol-5-yl)acetyl]pyrrolidine-2-carboxamide |

TABLE 1-continued

| Compound No. | Structure | IUPAC |
|---|---|---|
| 224 | 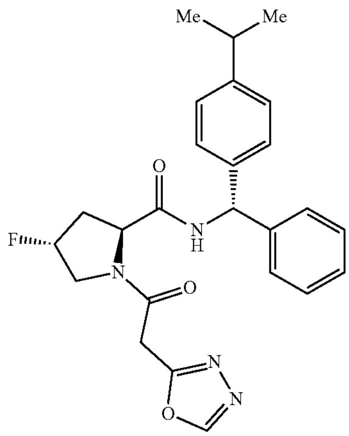 [SMILES: CC(C)c1ccc([C@@H](NC(=O)[C@@H]2C[C@@H](F)CN2C(=O)Cc2nnco2)c2ccccc2)cc1] | (2RS,4R)-4-fluoro-1-[2-(1,3,4-oxadiazol-2-yl)acetyl]-N-[(S)-phenyl[4-(propan-2-yl)phenyl]methyl]pyrrolidine-2-carboxamide |
| 225 | 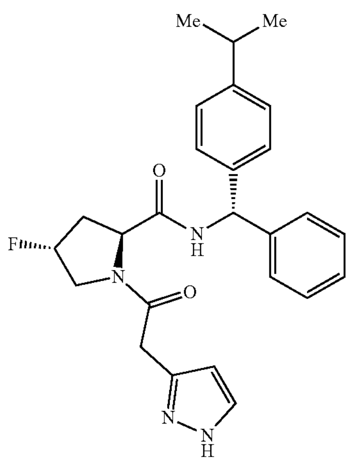 [SMILES: CC(C)c1ccc([C@@H](NC(=O)[C@@H]2C[C@@H](F)CN2C(=O)Cc2cc[nH]n2)c2ccccc2)cc1] | (2RS,4R)-4-fluoro-N-[(S)-phenyl[4-(propan-2-yl)phenyl]methyl]-1-[2-(1H-pyrazol-3-yl)acetyl]pyrrolidine-2-carboxamide |
| 226 | 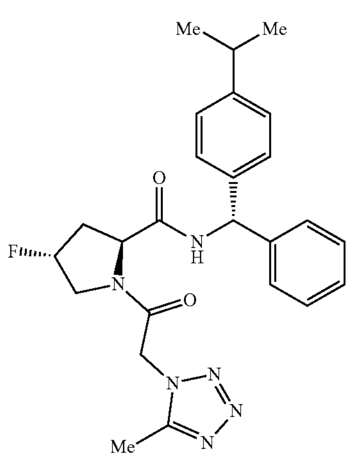 [SMILES: Cc1nnnn1CC(=O)N1C[C@H](F)C[C@H]1C(=O)N[C@@H](c1ccccc1)c1ccc(C(C)C)cc1] | (2RS,4R)-4-fluoro-1-[2-(5-methyl-1H-1,2,3-tetrazol-1-yl)acetyl]-N-[(S)-phenyl[4-(propan-2-yl)phenyl]methyl]pyrrolidine-2-carboxamide |

TABLE 1-continued
| Compound No. | Structure | IUPAC |
|---|---|---|
| 227 | 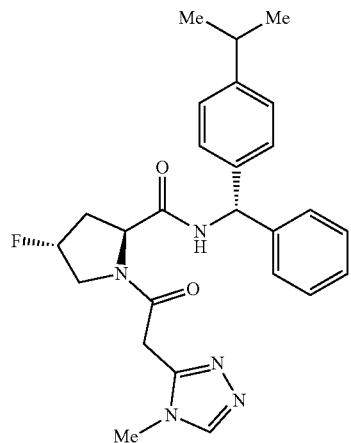 [SMILES: CC(C)c1ccc([C@@H](NC(=O)[C@@H]2C[C@@H](F)CN2C(=O)Cc2nncn2C)c2ccccc2)cc1] | (2RS,4R)-4-fluoro-1-[2-(4-methyl-4H-1,2,4-triazol-3-yl)acetyl]-N-[(S)-phenyl[4-(propan-2-yl)phenyl]methyl]pyrrolidine-2-carboxamide |
| 228 | 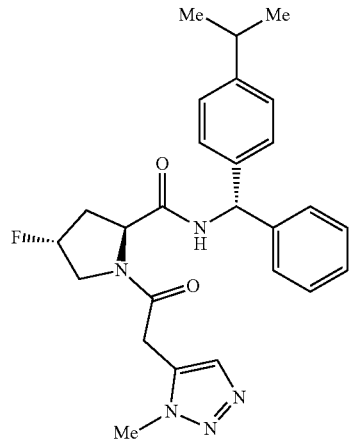 [SMILES: CC(C)c1ccc([C@@H](NC(=O)[C@@H]2C[C@@H](F)CN2C(=O)Cc2cnnn2C)c2ccccc2)cc1] | (2RS,4R)-4-fluoro-1-[2-(1-methyl-1H-1,2,3-triazol-5-yl)acetyl]-N-[(S)-phenyl[4-(propan-2-yl)phenyl]methyl]pyrrolidine-2-carboxamide |
| 229 | 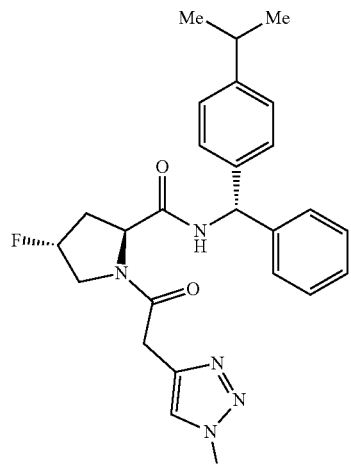 | (2RS,4R)-4-fluoro-1-[2-(1-methyl-1H-1,2,3-triazol-4-yl)acetyl]-N-[(S)-phenyl[4-(propan-2-yl)phenyl]methyl]pyrrolidine-2-carboxamide |

TABLE 1-continued
| Compound No. | Structure | IUPAC |
|---|---|---|
| 230 | 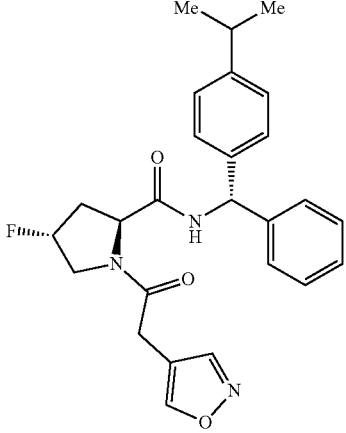 [SMILES: CC(C)c1ccc([C@@H](NC(=O)[C@@H]2C[C@@H](F)CN2C(=O)Cc2cnoc2)c2ccccc2)cc1] | (2S,4R)-4-fluoro-1-[2-(1,2-oxazol-4-yl)acetyl]-N-[(S)-phenyl[4-(propan-2-yl)phenyl]methyl]pyrrolidine-2-carboxamide |
| 231 | 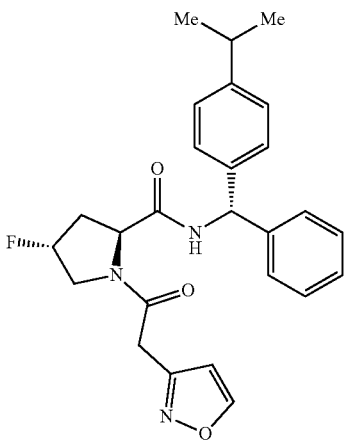 [SMILES: CC(C)c1ccc([C@@H](NC(=O)[C@@H]2C[C@@H](F)CN2C(=O)Cc2ccon2)c2ccccc2)cc1] | (2S,4R)-4-fluoro-1-[2-(1,2-oxazol-3-yl)acetyl]-N-[(S)-phenyl[4-(propan-2-yl)phenyl]methyl]pyrrolidine-2-carboxamide |
| 232 | 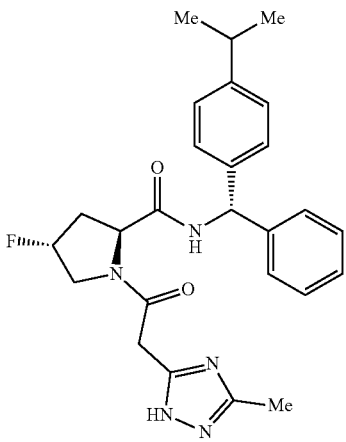 [SMILES: Cc1n[nH]c(CC(=O)N2C[C@H](F)C[C@H]2C(=O)N[C@@H](c2ccccc2)c2ccc(C(C)C)cc2)n1] | (2S,4R)-4-fluoro-1-[2-(3-methyl-1H-1,2,4-triazol-5-yl)acetyl]-N-[(S)-phenyl[4-(propan-2-yl)phenyl]methyl]pyrrolidine-2-carboxamide |

TABLE 1-continued
| Compound No. | Structure | IUPAC |
|---|---|---|
| 233 | 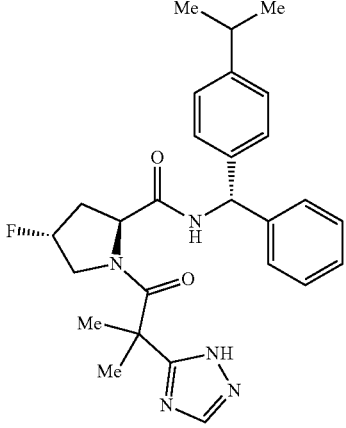 [SMILES: CC(C)c1ccc([C@@H](NC(=O)[C@@H]2C[C@@H](F)CN2C(=O)C(C)(C)c2ncn[nH]2)c2ccccc2)cc1] | (2S,4R)-4-fluoro-1-[2-methyl-2-(1H-1,2,4-triazol-5-yl)propanoyl]-N-[(S)-phenyl[4-(propan-2-yl)phenyl]methyl]pyrrolidine-2-carboxamide |
| 234 | 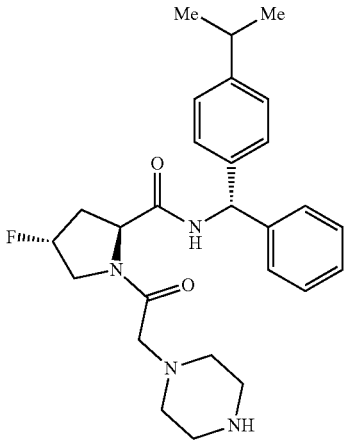 [SMILES: CC(C)c1ccc([C@@H](NC(=O)[C@@H]2C[C@@H](F)CN2C(=O)CN2CCNCC2)c2ccccc2)cc1] | (2S,4R)-4-fluoro-N-[(S)-phenyl[4-(propan-2-yl)phenyl]methyl]-1-[2-(piperazin-1-yl)acetyl]pyrrolidine-2-carboxamide |
| 235 | 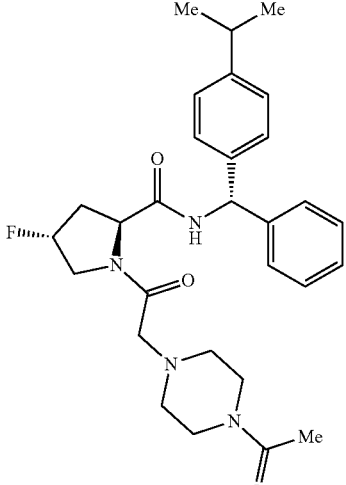 | (2S,4R)-1-[2-(4-acetylpiperazin-1-yl)acetyl]-4-fluoro-N-[(S)-phenyl[4-(propan-2-yl)phenyl]methyl]pyrrolidine-2-carboxamide |

TABLE 1-continued

| Compound No. | Structure | IUPAC |
|---|---|---|
| 236 | 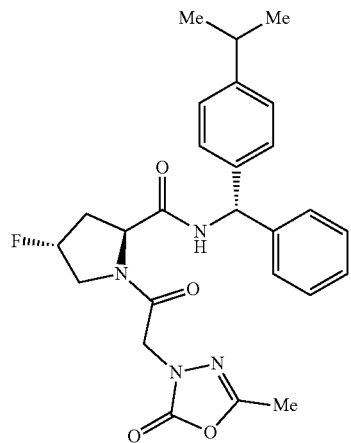 [SMILES: Cc1nn(CC(=O)N2C[C@H](F)C[C@H]2C(=O)N[C@@H](c2ccccc2)c2ccc(C(C)C)cc2)c(=O)o1] | (2S,4R)-4-fluoro-1-[2-(5-methyl-2-oxo-2,3-dihydro-1,3,4-oxadiazol-3-yl)acetyl]-N-[(S)-phenyl[4-(propan-2-yl)phenyl]methyl]pyrrolidine-2-carboxamide |
| 237 | 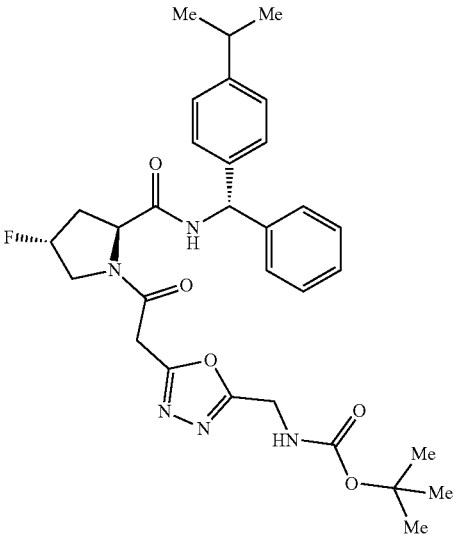 [SMILES: CC(C)c1ccc([C@@H](NC(=O)[C@@H]2C[C@@H](F)CN2C(=O)Cc2nnc(CNC(=O)OC(C)(C)C)o2)c2ccccc2)cc1] | tert-butyl N-[(5-{2-[(2S,4R)-4-fluoro-2-{[(S)-phenyl[4-(propan-2-yl)phenyl]methyl]carbamoyl}pyrrolidin-1-yl]-2-oxoethyl}-1,3,4-oxadiazol-2-yl)methyl]carbamate |
| 238 | 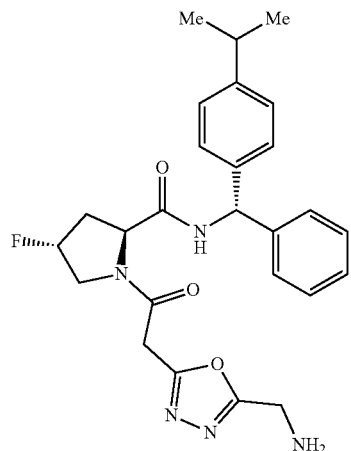 [SMILES: CC(C)c1ccc([C@@H](NC(=O)[C@@H]2C[C@@H](F)CN2C(=O)Cc2nnc(CN)o2)c2ccccc2)cc1] | (2S,4R)-1-{2-[5-(aminomethyl)-1,3,4-oxadiazol-2-yl]acetyl}-4-fluoro-N-[(S)-phenyl[4-(propan-2-yl)phenyl]methyl]pyrrolidine-2-carboxamide |

TABLE 1-continued

| Compound No. | Structure | IUPAC |
|---|---|---|
| 239 | 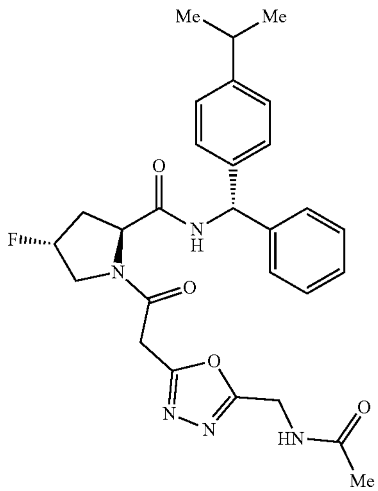 [SMILES: CC(=O)NCc1nnc(CC(=O)N2C[C@H](F)C[C@H]2C(=O)N[C@@H](c2ccccc2)c2ccc(C(C)C)cc2)o1] | (2S,4R)-1-{2-[5-(acetamidomethyl)-1,3,4-oxadiazol-2-yl]acetyl}-4-fluoro-N-[(S)-phenyl[4-(propan-2-yl)phenyl]methyl]pyrrolidine-2-carboxamide |
| 240 | 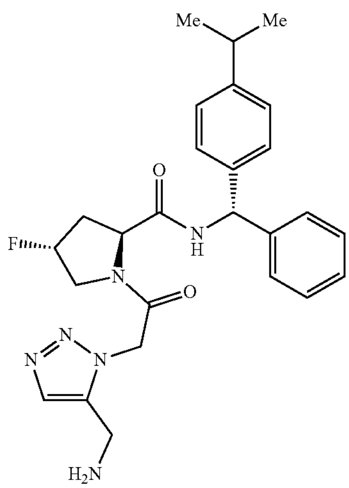 [SMILES: CC(C)c1ccc([C@@H](NC(=O)[C@@H]2C[C@@H](F)CN2C(=O)Cn2nncc2CN)c2ccccc2)cc1] | (2S,4R)-1-{2-[5-(aminomethyl)-1H-1,2,3-triazol-1-yl]acetyl}-4-fluoro-N-[(S)-phenyl[4-(propan-2-yl)phenyl]methyl]pyrrolidine-2-carboxamide |
| 241 | 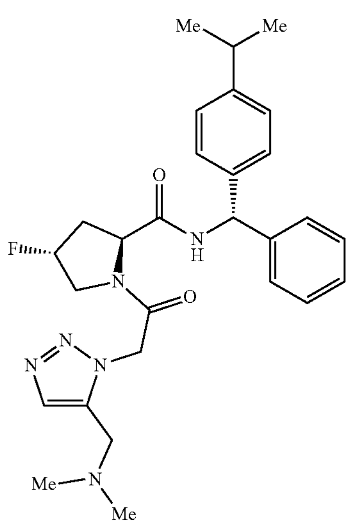 [SMILES: CC(C)c1ccc([C@@H](NC(=O)[C@@H]2C[C@@H](F)CN2C(=O)Cn2nncc2CN(C)C)c2ccccc2)cc1] | (2S,4R)-1-(2-{5-[(dimethylamino)methyl]-1H-1,2,3-triazol-1-yl}acetyl)-4-fluoro-N-[(S)-phenyl[4-(propan-2-yl)phenyl]methyl]pyrrolidine-2-carboxamide |

TABLE 1-continued

| Compound No. | Structure | IUPAC |
|---|---|---|
| 242 | 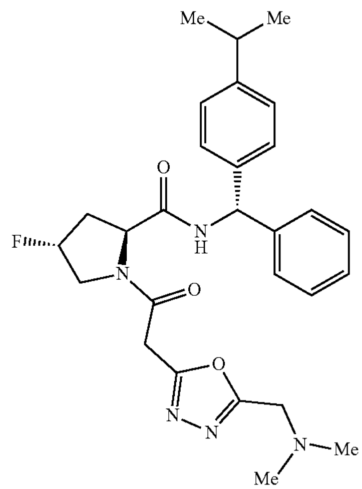 [SMILES: CC(C)c1ccc([C@@H](NC(=O)[C@@H]2C[C@@H](F)CN2C(=O)Cc2nnc(CN(C)C)o2)c2ccccc2)cc1] | (2S,4R)-1-(2-{5-[(dimethylamino)methyl]-1,3,4-oxadiazol-2-yl}acetyl)-4-fluoro-N-[(S)-phenyl[4-(propan-2-yl)phenyl]methyl]pyrrolidine-2-carboxamide |
| 243 | 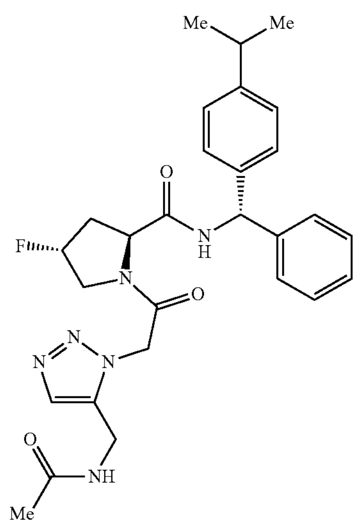 [SMILES: CC(=O)NCc1cnnn1CC(=O)N1C[C@H](F)C[C@H]1C(=O)N[C@@H](c1ccccc1)c1ccc(C(C)C)cc1] | (2S,4R)-1-{2-[5-(acetamidomethyl)-1H-1,2,3-triazol-1-yl]acetyl}-4-fluoro-N-[(S)-phenyl[4-(propan-2-yl)phenyl]methyl]pyrrolidine-2-carboxamide |
| 244 | 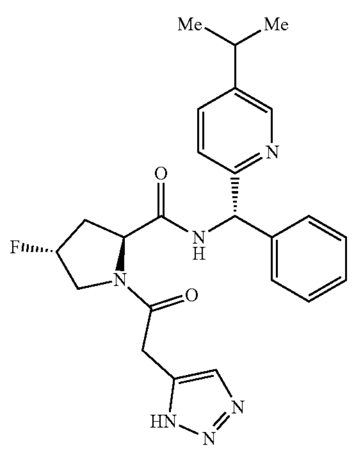 [SMILES: CC(C)c1ccc([C@@H](NC(=O)[C@@H]2C[C@@H](F)CN2C(=O)Cc2cnn[nH]2)c2ccccc2)nc1] | (2S,4R)-1-(2-(1H-1,2,3-triazol-5-yl)acetyl)-4-fluoro-N-((S)-(5-isopropylpyridin-2-yl)(phenyl)methyl)pyrrolidine-2-carboxamide |

TABLE 1-continued

| Compound No. | Structure | IUPAC |
|---|---|---|
| 245 | 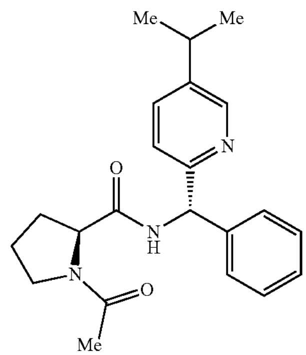 [SMILES: CC(=O)N1CCC[C@H]1C(=O)N[C@@H](c1ccccc1)c1ccc(C(C)C)cn1] | (2S)-1-acetyl-N-[(S)-phenyl[5-(propan-2-yl)pyridin-2-yl]methyl]pyrrolidine-2-carboxamide |
| 246 | 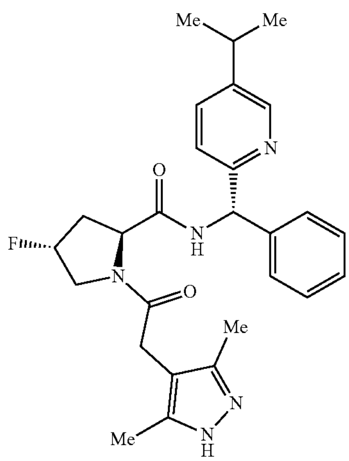 [SMILES: Cc1n[nH]c(C)c1CC(=O)N1C[C@H](F)C[C@H]1C(=O)N[C@@H](c1ccccc1)c1ccc(C(C)C)cn1] | (2S,4R)-1-[2-(3,5-dimethyl-1H-pyrazol-4-yl)acetyl]-4-fluoro-N-[(S)-phenyl[5-(propan-2-yl)pyridin-2-yl]methyl]pyrrolidine-2-carboxamide |
| 247 | 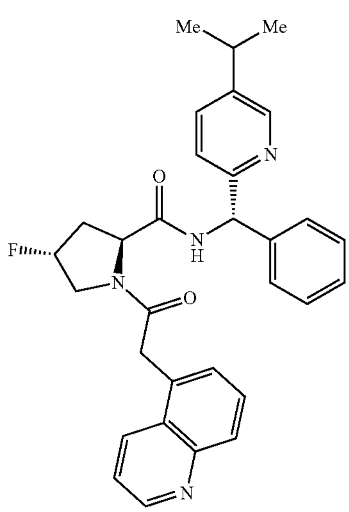 [SMILES: CC(C)c1ccc([C@@H](NC(=O)[C@@H]2C[C@@H](F)CN2C(=O)Cc2cccc3ncccc23)c2ccccc2)nc1] | (2S,4R)-4-fluoro-N-[(S)-phenyl[5-(propan-2-yl)pyridin-2-yl]methyl]-1-[2-(quinolin-5-yl)acetyl]pyrrolidine-2-carboxamide |

TABLE 1-continued

| Compound No. | Structure | IUPAC |
|---|---|---|
| 248 | 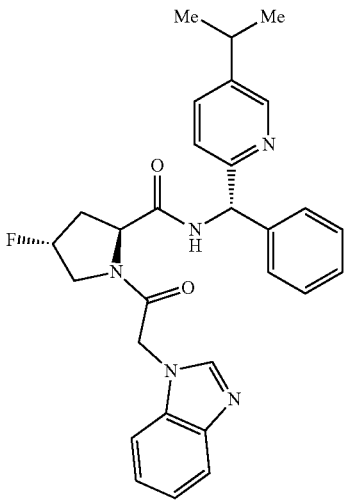 [SMILES: CC(C)c1ccc([C@@H](NC(=O)[C@@H]2C[C@@H](F)CN2C(=O)Cn2cnc3ccccc32)c2ccccc2)nc1] | (2S,4R)-1-[2-(1H-1,3-benzodiazol-1-yl)acetyl]-4-fluoro-N-[(S)-phenyl[5-(propan-2-yl)pyridin-2-yl]methyl]pyrrolidine-2-carboxamide |
| 249 | 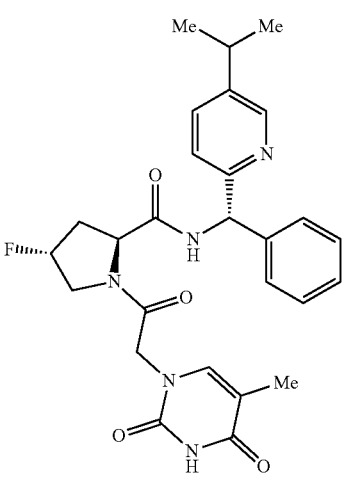 [SMILES: Cc1cn(CC(=O)N2C[C@H](F)C[C@H]2C(=O)N[C@@H](c2ccccc2)c2ccc(C(C)C)cn2)c(=O)[nH]c1=O] | (2S,4R)-4-fluoro-1-[2-(5-methyl-2,4-dioxo-1,2,3,4-tetrahydropyrimidin-1-yl)acetyl]-N-[(S)-phenyl[5-(propan-2-yl)pyridin-2-yl]methyl]pyrrolidine-2-carboxamide |
| 250 | 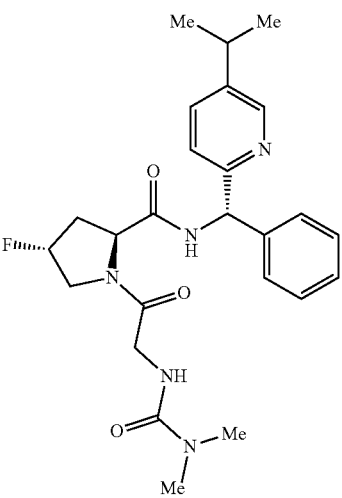 | (2S,4R)-1-{2-[(dimethylcarbamoyl)amino]acetyl}-4-fluoro-N-[(S)-phenyl[5-(propan-2-yl)pyridin-2-yl]methyl]pyrrolidine-2-carboxamide |

| Compound No. | Structure | IUPAC |
|---|---|---|
| 251 | 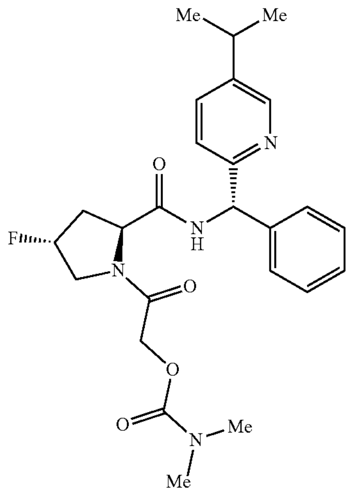 [SMILES: CC(C)c1ccc([C@@H](NC(=O)[C@@H]2C[C@@H](F)CN2C(=O)COC(=O)N(C)C)c2ccccc2)nc1] | 2-[(2S,4R)-4-fluoro-2-{[(S)-phenyl[5-(propan-2-yl)pyridin-2-yl]methyl]carbamoyl}pyrrolidin-1-yl]-2-oxoethyl-N,N-dimethylcarbamate |
| 252 | 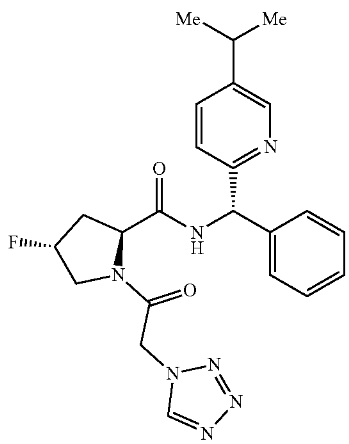 [SMILES: CC(C)c1ccc([C@@H](NC(=O)[C@@H]2C[C@@H](F)CN2C(=O)Cn2cnnn2)c2ccccc2)nc1] | (2S,4R)-4-fluoro-N-[(S)-phenyl[5-(propan-2-yl)pyridin-2-yl]methyl]-1-[2-(1H-1,2,3-tetrazol-1-yl)acetyl]pyrrolidine-2-carboxamide |
| 253 | 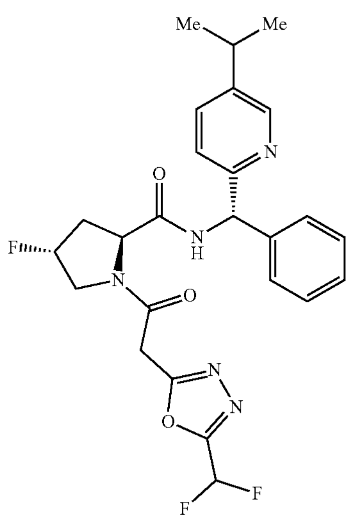 [SMILES: CC(C)c1ccc([C@@H](NC(=O)[C@@H]2C[C@@H](F)CN2C(=O)Cc2nnc(C(F)F)o2)c2ccccc2)nc1] | (2S,4R)-1-{2-[5-(difluoromethyl)-1,3,4-oxadiazol-2-yl]acetyl}-4-flouro-N-[(S)-phenyl[5-(propan-2-yl)pyridin-2-yl]methyl]pyrrolidine-2-carboxamide |

TABLE 1-continued

| Compound No. | Structure | IUPAC |
|---|---|---|
| 254 | 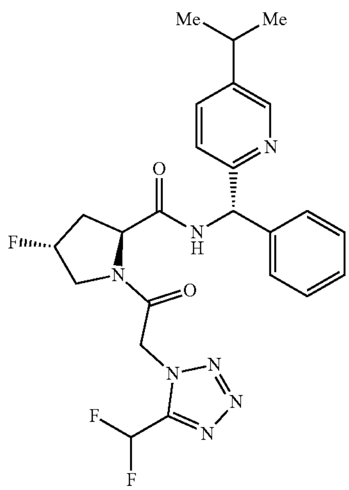 [SMILES: CC(C)c1ccc([C@@H](NC(=O)[C@@H]2C[C@@H](F)CN2C(=O)Cn2nnnc2C(F)F)c2ccccc2)nc1] | (2S,4R)-1-{2-[5-(difluoromethyl)-1H-1,2,3-tetrazol-1-yl]acetyl}-4-fluoro-N-[(S)-phenyl[5-(propan-2-yl)pyridin-2-yl]methyl]pyrrolidine-2-carboxamide |
| 255 | 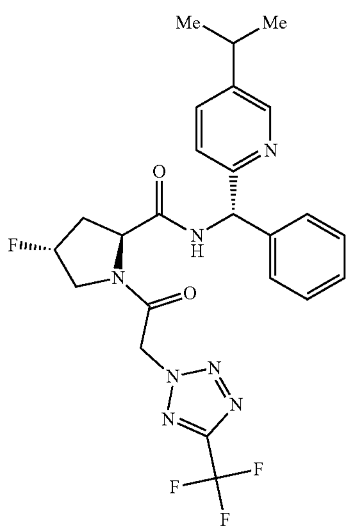 [SMILES: CC(C)c1ccc([C@@H](NC(=O)[C@@H]2C[C@@H](F)CN2C(=O)Cn2nnc(C(F)(F)F)n2)c2ccccc2)nc1] | (2S,4R)-4-fluoro-N-[(S)-phenyl[5-(propan-2-yl)pyridin-2-yl]methyl]-1-{2-[5-(trifluoromethyl)-2H-1,2,3,4-tetrazol-2-yl]acetyl}pyrrolidine-2-carboxamide |
| 256 | 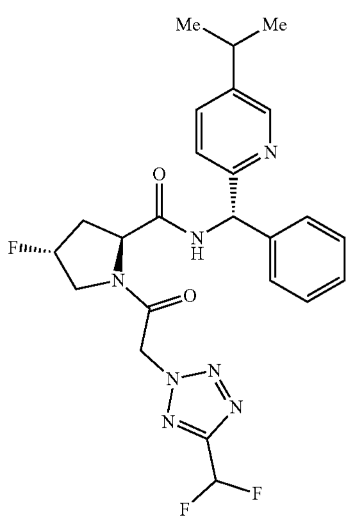 [SMILES: CC(C)c1ccc([C@@H](NC(=O)[C@@H]2C[C@@H](F)CN2C(=O)Cn2nnc(C(F)F)n2)c2ccccc2)nc1] | (2S,4R)-1-{2-[5-(difluoromethyl)-2H-1,2,3,4-tetrazol-2-yl]acetyl}-4-fluoro-N-[(S)-phenyl[5-(propan-2-yl)pyridin-2-yl]methyl]pyrrolidine-2-carboxamide |

TABLE 1-continued

| Compound No. | Structure | IUPAC |
|---|---|---|
| 257 | 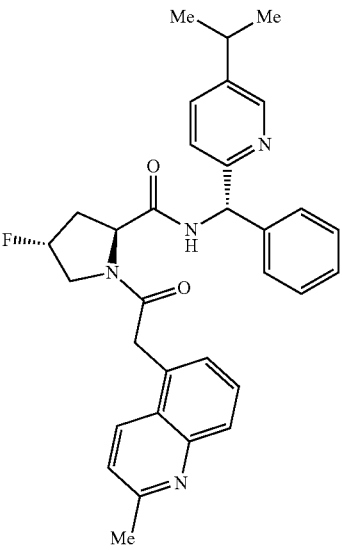 [SMILES: Cc1ccc2c(CC(=O)N3C[C@H](F)C[C@H]3C(=O)N[C@@H](c3ccccc3)c3ccc(C(C)C)cn3)cccc2n1] | (2S,4R)-4-fluoro-1-[2-(2-methylquinolin-5-yl)acetyl]-N-[(S)-phenyl[5-(propan-2-yl)pyridin-2-yl]methyl]pyrrolidine-2-carboxamide |
| 258 | 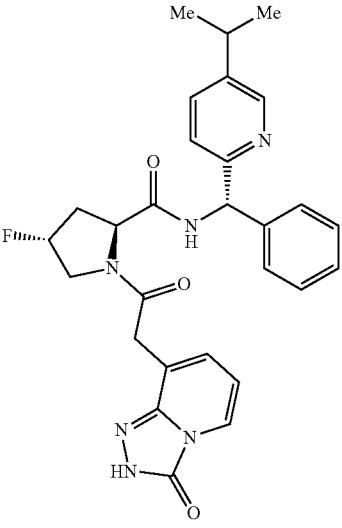 [SMILES: CC(C)c1ccc([C@@H](NC(=O)[C@@H]2C[C@@H](F)CN2C(=O)Cc2cccn3c(=O)[nH]nc23)c2ccccc2)nc1] | (2S,4R)-4-fluoro-1-(2-{3-oxo-2H,3H-[1,2,4]triazolo[4,3-a]pyridin-8-yl}acetyl)-N-[(S)-phenyl[5-(propan-2-yl)pyridin-2-yl]methyl]pyrrolidine-2-carboxamide |
| 259 | 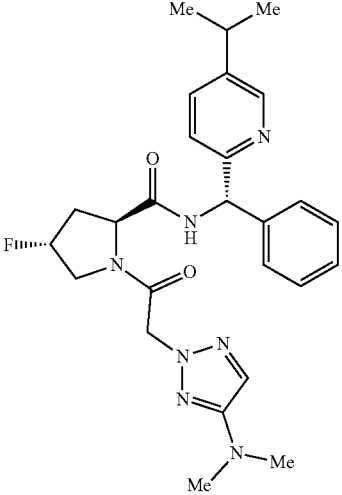 [SMILES: CC(C)c1ccc([C@@H](NC(=O)[C@@H]2C[C@@H](F)CN2C(=O)Cn2ncc(N(C)C)n2)c2ccccc2)nc1] | (2S,4R)-1-{2-[4-(dimethylamino)-2H-1,2,3-triazol-2-yl]acety}-4-fluoro-N-[(S)-phenyl[5-(propan-2-yl)pyridin-2-yl]methyl]pyrrolidine-2-carboxamide |

TABLE 1-continued
| Compound No. | Structure | IUPAC |
|---|---|---|
| 260 | 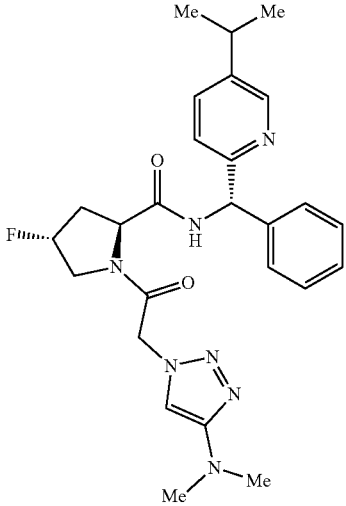 [SMILES: CC(C)c1ccc([C@@H](NC(=O)[C@@H]2C[C@@H](F)CN2C(=O)Cn2cc(N(C)C)nn2)c2ccccc2)nc1] | (2S,4R)-1-{2-[4-(dimethylamino)-1H-1,2,3-triazol-1-yl]acetyl}-4-fluoro-N-[(S)-phenyl[5-(propan-2-yl)pyridin-2-yl]methyl]pyrrolidine-2-carboxamide |
| 261 | 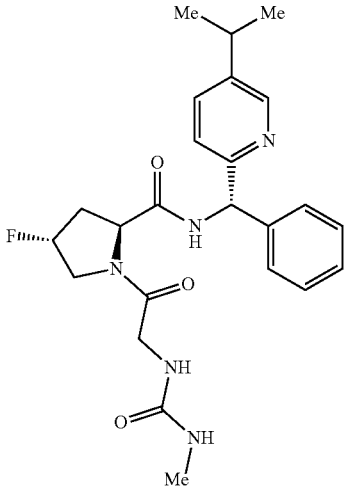 | (2S,4R)-4-fluoro-1-{2-[(methylcarbamoyl)amino]acetyl}-N-[(S)-phenyl[5-(propan-2-yl)pyridin-2-yl]methyl]pyrrolidine-2-carboxamide |
| 262 | 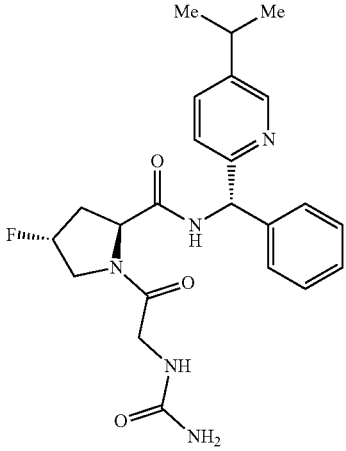 | (2S,4R)-1-[2-(carbamoylamino)acetyl]-4-fluoro-N-[(S)-phenyl[5-(propan-2-yl)pyridin-2-yl]methyl]pyrrolidine-2-carboxamide |

TABLE 1-continued

| Compound No. | Structure | IUPAC |
|---|---|---|
| 263 | 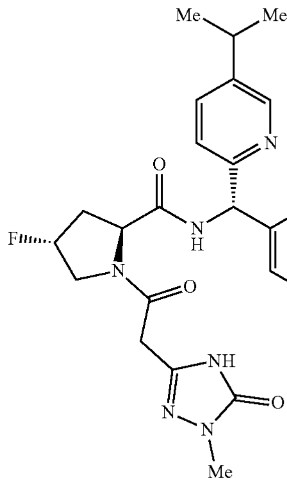 | (2S,4R)-4-fluoro-1-[2-(1-methyl-5-oxo-4,5-dihydro-1H-1,2,4-triazol-3-yl)acetyl]-N-[(S)-phenyl[5-(propan-2-yl)pyridin-2-yl]methyl]pyrrolidine-2-carboxamide |
| 264 | 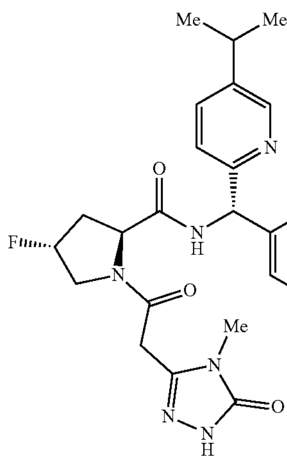 | (2S,4R)-4-fluoro-1-[2-(4-methyl-5-oxo-4,5-dihydro-1H-1,2,4-triazol-3-yl)acetyl]-N-[(S)-phenyl[5-(propan-2-yl)pyridin-2-yl]methyl]pyrrolidine-2-carboxamide |
| 265 | 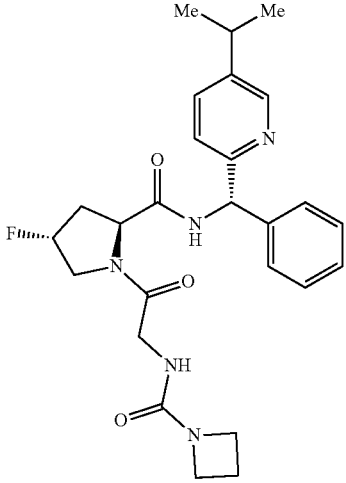 | (2S,4R)-1-{2-[(azetidine-1-carbonyl)amino]acetyl}-4-fluoro-N-[(S)-phenyl[5-(propan-2-yl)pyridin-2-yl]methyl]pyrrolidine-2-carboxamide |

TABLE 1-continued

| Compound No. | Structure | IUPAC |
|---|---|---|
| 266 | 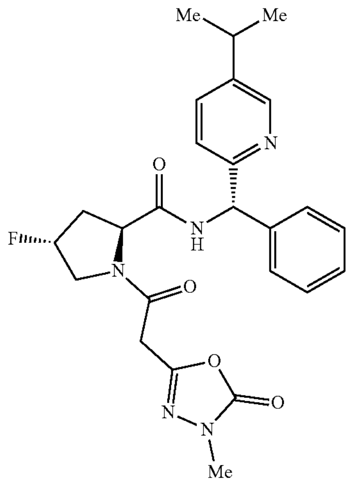 [SMILES: CC(C)c1ccc([C@@H](NC(=O)[C@@H]2C[C@@H](F)CN2C(=O)Cc2nn(C)c(=O)o2)c2ccccc2)nc1] | (2S,4R)-4-fluoro-1-[2-(4-methyl-5-oxo-4,5-dihydro-1,3,4-oxadiazol-2-yl)acetyl]-N-[(S)-phenyl[5-(propan-2-yl)pyridin-2-yl]methyl]pyrrolidine-2-carboxamide |
| 267 | 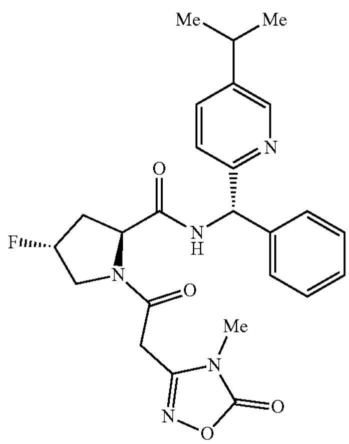 [SMILES: CC(C)c1ccc([C@@H](NC(=O)[C@@H]2C[C@@H](F)CN2C(=O)Cc2noc(=O)n2C)c2ccccc2)nc1] | (2S,4R)-4-fluoro-1-[2-(4-methyl-5-oxo-4,5-dihydro-1,2,4-oxadiazol-3-yl)acetyl]-N-[(S)-phenyl[5-(propan-2-yl)pyridin-2-yl]methyl]pyrrolidine-2-carboxamide |
| 268 | 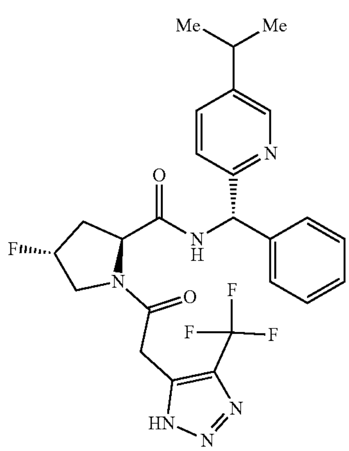 [SMILES: CC(C)c1ccc([C@@H](NC(=O)[C@@H]2C[C@@H](F)CN2C(=O)Cc2[nH]nnc2C(F)(F)F)c2ccccc2)nc1] | (2S,4R)-4-fluoro-N-[(S)-phenyl[5-(propan-2-yl)pyridin-2-yl]methyl]-1-{2-[4-(trifluoromethyl)-1H-1,2,3-triazol-5-yl]acetyl}pyrrolidine-2-carboxamide |

TABLE 1-continued
| Compound No. | Structure | IUPAC |
|---|---|---|
| 269 | 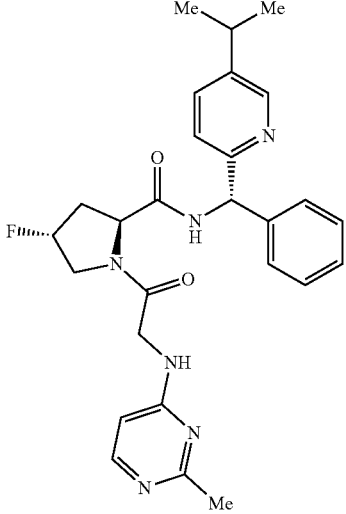 | (2S,4R)-4-fluoro-1-{2-[(2-methylpyrimidin-4-yl)amino]acetyl}-N-[(S)-phenyl[5-(propan-2-yl)pyridin-2-yl]methyl]pyrrolidine-2-carboxamide |
| 270 | 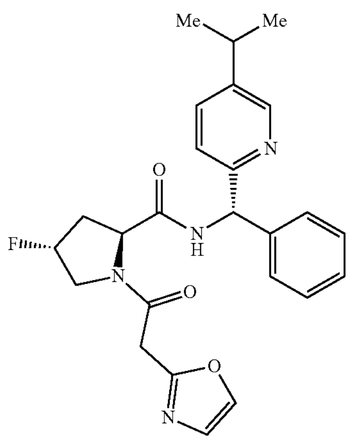 [SMILES: CC(C)c1ccc([C@@H](NC(=O)[C@@H]2C[C@@H](F)CN2C(=O)Cc2ncco2)c2ccccc2)nc1] | (2S,4R)-4-fluoro-1-[2-(1,3-oxazol-2-yl)acetyl]-N-[(S)-phenyl[5-(propan-2-yl)pyridin-2-yl]methyl]pyrrolidine-2-carboxamide |
| 271 | 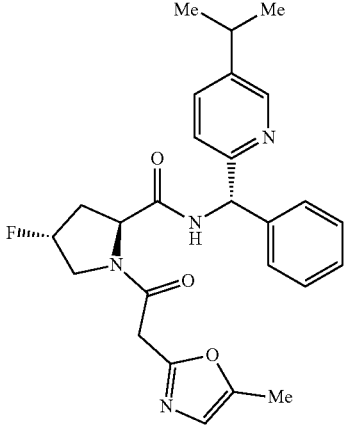 | (2S,4R)-4-fluoro-1-[2-(5-methyl-1,3-oxazol-2-yl)acetyl]-N-[(S)-phenyl[5-(propan-2-yl)pyridin-2-yl]methyl]pyrrolidine-2-carboxamide |

TABLE 1-continued

| Compound No. | Structure | IUPAC |
|---|---|---|
| 272 | 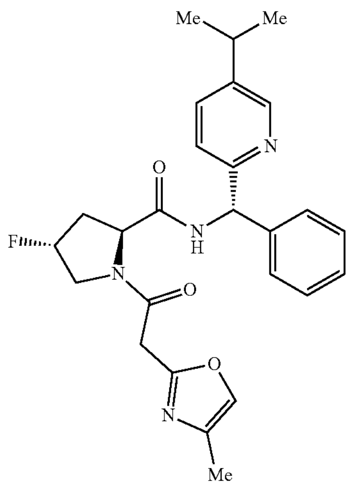 [SMILES: Cc1coc(CC(=O)N2C[C@H](F)C[C@H]2C(=O)N[C@@H](c2ccccc2)c2ccc(C(C)C)cn2)n1] | (2S,4R)-4-fluoro-1-[2-(5-methyl-1,3-oxazol-2-yl)methyl]-N-[(S)-phenyl[5-(propan-2-yl)pyridin-2-yl]methyl]pyrrolidine-2-carboxamide |
| 273 | 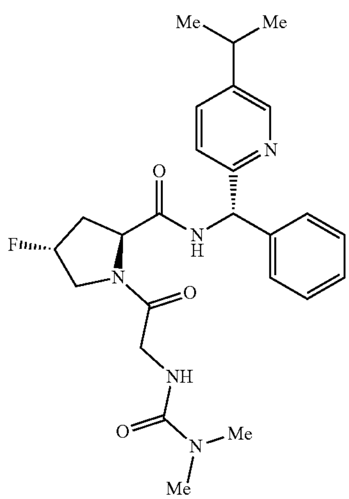 [SMILES: CC(C)c1ccc([C@@H](NC(=O)[C@@H]2C[C@@H](F)CN2C(=O)CNC(=O)N(C)C)c2ccccc2)nc1] | (2S,4R)-1-[(2S)-2-[(dimethylcarbamoyl)amino]propanoyl]-4-fluoro-N-[(S)-phenyl[5-(propan-2-yl)pyridin-2-yl]methyl]pyrrolidine-2-carboxamide |
| 274 | 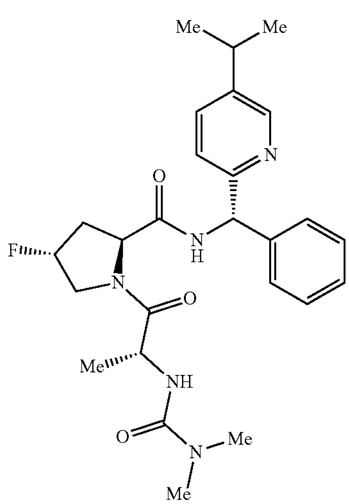 [SMILES: CC(C)c1ccc([C@@H](NC(=O)[C@@H]2C[C@@H](F)CN2C(=O)[C@@H](C)NC(=O)N(C)C)c2ccccc2)nc1] | (2S,4R)-1-[(2R)-2-[(dimethylcarbamoyl)amino]propanoyl]-4-fluoro-N-[(S)-phenyl[5-(propan-2-yl)pyridin-2-yl]methyl]pyrrolidine-2-carboxamide |

TABLE 1-continued

| Compound No. | Structure | IUPAC |
|---|---|---|
| 275 | 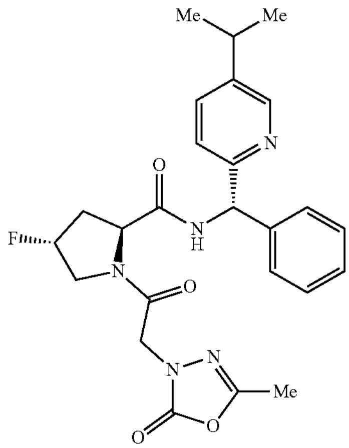 [SMILES: Cc1nn(CC(=O)N2C[C@H](F)C[C@H]2C(=O)N[C@@H](c2ccccc2)c2ccc(C(C)C)cn2)c(=O)o1] | (2S,4R)-4-fluoro-1-[2-(5-methyl-2-oxo-2,3-dihydro-1,3,4-oxadiazol-3-yl)acetyl]-N-N-[(S)-phenyl[5-(propan-2-yl)pyridin-2-yl]methyl]pyrrolidine-2-carboxamide |
| 276 | 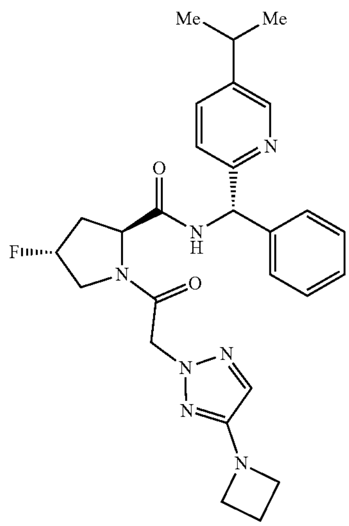 [SMILES: CC(C)c1ccc([C@@H](NC(=O)[C@@H]2C[C@@H](F)CN2C(=O)Cn2ncc(N3CCC3)n2)c2ccccc2)nc1] | (2S,4R)-1-{2-[4-(azetidin-1-yl)-2H-1,2,3-triazol-2-yl]acetyl}-4-fluoro-N-[(S)-phenyl[5-(propan-2-yl)pyridin-2-yl]methyl]pyrrolidine-2-carboxamide |
| 277 | 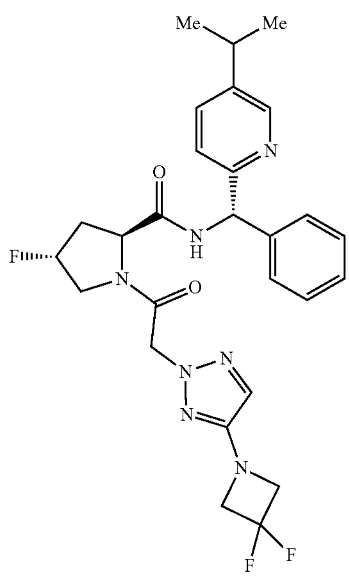 [SMILES: CC(C)c1ccc([C@@H](NC(=O)[C@@H]2C[C@@H](F)CN2C(=O)Cn2ncc(N3CC(F)(F)C3)n2)c2ccccc2)nc1] | (2S,4R)-1-{2-[4-(3,3-difluoroazetidin-1-yl)-2H-1,2,3-triazol-2-yl]acetyl}-4-fluoro-N-[(S)-phenyl[5-(propan-2-yl)pyridin-2-yl]methyl]pyrrolidine-2-carboxamide |

TABLE 1-continued

| Compound No. | Structure | IUPAC |
|---|---|---|
| 278 | 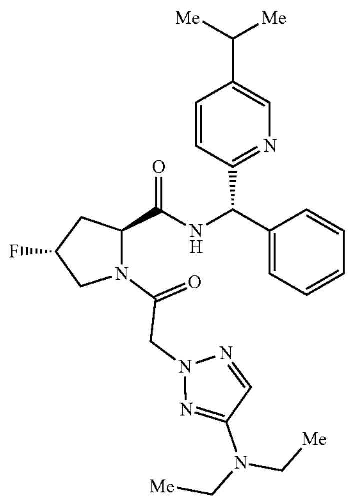 [SMILES: CCN(CC)c1cnn(CC(=O)N2C[C@H](F)C[C@H]2C(=O)N[C@@H](c2ccccc2)c2ccc(C(C)C)cn2)n1] | (2S,4R)-1-{2-[4-(diethylamino)-2H-1,2,3-triazol-2-yl]acety}-4-fluoro-N-N-[(S)-phenyl[5-(propan-2-yl)pyridin-2-yl]methyl]pyrrolidine-2-carboxamide |
| 279 | 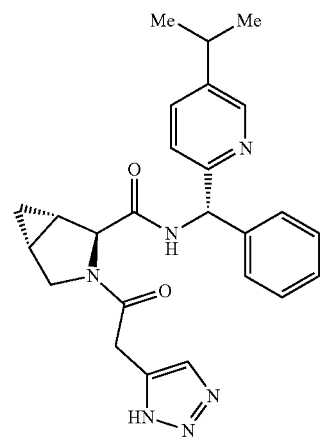 [SMILES: CC(C)c1ccc([C@@H](NC(=O)[C@@H]2[C@H]3C[C@H]3CN2C(=O)Cc2cnn[nH]2)c2ccccc2)nc1] | (1S,2S,5R)-N-[(S)-phenyl[5-(propan-2-yl)pyridin-2-yl]methyl]-3-[2-(1H-1,2,3-triazol-5-yl)acetyl]-3-azabicyclo[3.1.0]hexane-2-carboxamide |
| 280 | 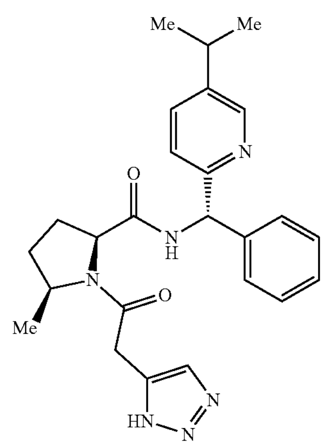 [SMILES: CC(C)c1ccc([C@@H](NC(=O)[C@@H]2CC[C@H](C)N2C(=O)Cc2cnn[nH]2)c2ccccc2)nc1] | (2S,5S)-5-methyl-N-[(S)-phenyl[5-(propan-2-yl)pyridin-2-yl]methyl]-1-[2-(1H-1,2,3-triazol-5-yl)acetyl]pyrrolidine-2-carboxamide |

TABLE 1-continued
| Compound No. | Structure | IUPAC |
|---|---|---|
| 281 | 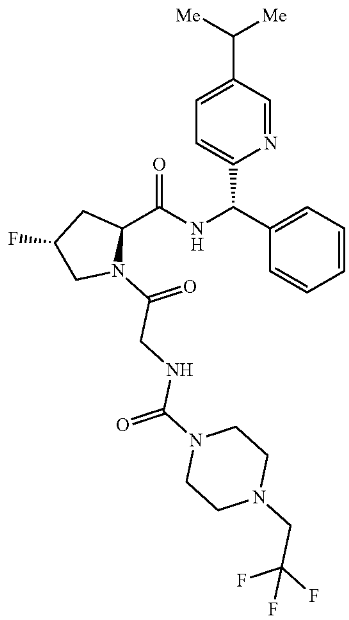 [SMILES: CC(C)c1ccc([C@@H](NC(=O)[C@@H]2C[C@@H](F)CN2C(=O)CNC(=O)N2CCN(CC(F)(F)F)CC2)c2ccccc2)nc1] | N-{2-[(2S,4R)-4-fluoro-2-{[(S)-phenyl[5-(propan-2-yl)pyridin-2-yl]methyl]carbamoyl}pyrrolidin-1-yl]-2-oxoethyl}-4-(2,2,2-trifluoroethyl)piperazine-1-carboxamide |
| 282 | 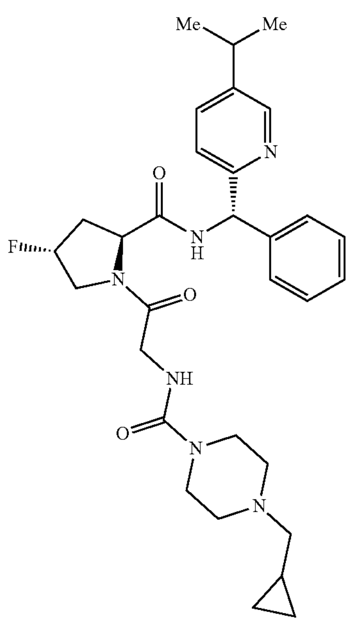 [SMILES: CC(C)c1ccc([C@@H](NC(=O)[C@@H]2C[C@@H](F)CN2C(=O)CNC(=O)N2CCN(CC3CC3)CC2)c2ccccc2)nc1] | 4-(cyclopropylmethyl)-N-{2-[(2S,4R)-4-fluoro-2-{[(S)-phenyl[5-(propan-2-yl)pyridin-2-yl]methyl]carbamoyl}pyrrolidin-1-yl]-2-oxoethyl}piperazine-1-carboxamide |

TABLE 1-continued

| Compound No. | Structure | IUPAC |
|---|---|---|
| 283 | 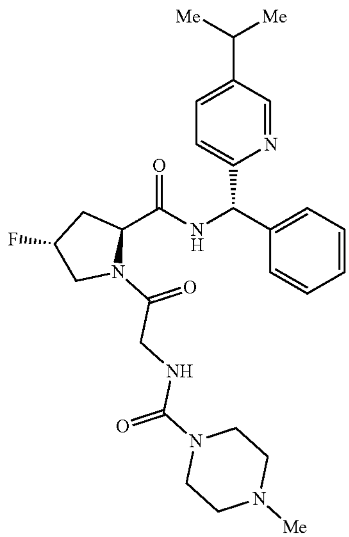 [SMILES: CC(C)c1ccc([C@@H](NC(=O)[C@@H]2C[C@@H](F)CN2C(=O)CNC(=O)N2CCN(C)CC2)c2ccccc2)nc1] | N-{2-[(2S,4R)-4-fluoro-2-{[(S)-phenyl[5-(propan-2-yl)pyridin-2-yl]methyl]carbamoyl}pyrrolidin-1-yl]-2-oxoethyl}-4-methylpiperazine-1-carboxamide |
| 284 | 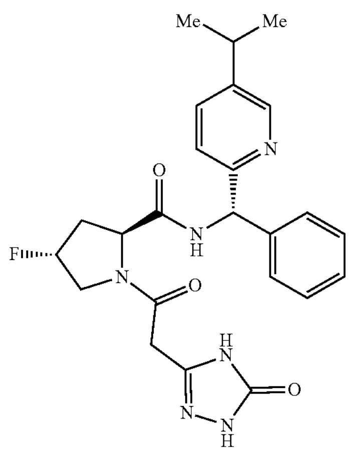 [SMILES: CC(C)c1ccc([C@@H](NC(=O)[C@@H]2C[C@@H](F)CN2C(=O)Cc2n[nH]c(=O)[nH]2)c2ccccc2)nc1] | (2S,4R)-4-fluoro-1-[2-(5-oxo-4,5-dihydro-1H-1,2,4-triazol-3-yl)acetyl]-N-[(S)-phenyl[5-(propan-2-yl)pyridin-2-yl]methyl]pyrrolidine-2-carboxamide |
| 285 | 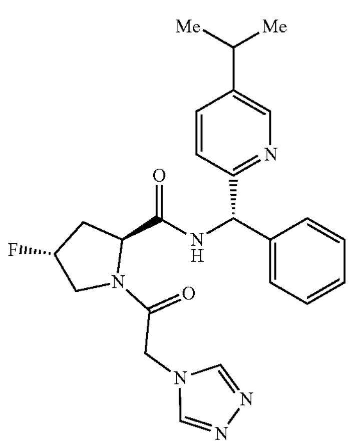 [SMILES: CC(C)c1ccc([C@@H](NC(=O)[C@@H]2C[C@@H](F)CN2C(=O)Cn2cnnc2)c2ccccc2)nc1] | (2S,4R)-4-fluoro-N-[(S)-phenyl[5-(propan-2-yl)pyridin-2-yl]methyl]-1-[2-(4H-1,2,4-triazol-4-yl)acetyl]pyrrolidine-2-carboxamide |

TABLE 1-continued

| Compound No. | Structure | IUPAC |
|---|---|---|
| 286 | 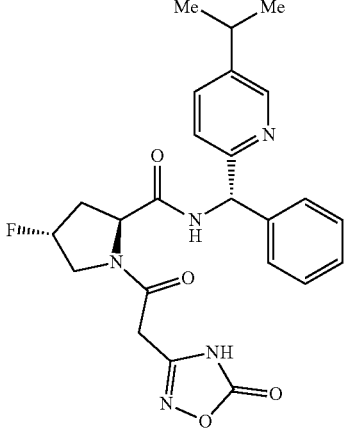 [SMILES: CC(C)c1ccc([C@@H](NC(=O)[C@@H]2C[C@@H](F)CN2C(=O)Cc2noc(=O)[nH]2)c2ccccc2)nc1] | (2S,4R)-4-fluoro-1-[2-(5-oxo-4,5-dihydro-1,2,4-oxadiazol-3-yl)acetyl]-N-[(S)-phenyl[5-(propan-2-yl)pyridin-2-yl]methyl]pyrrolidine-2-carboxamide |
| 287 | 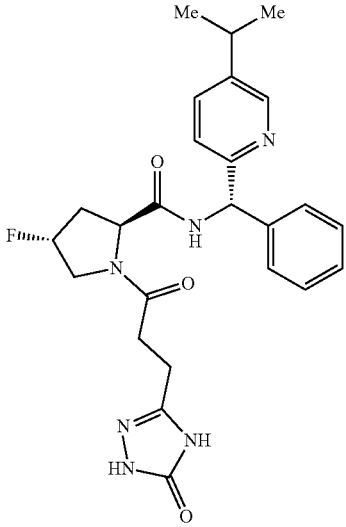 [SMILES: CC(C)c1ccc([C@@H](NC(=O)[C@@H]2C[C@@H](F)CN2C(=O)CCc2n[nH]c(=O)[nH]2)c2ccccc2)nc1] | (2S,4R)-4-fluoro-1-[3-(5-oxo-4,5-dihydro-1H-1,2,4-triazol-3-yl)propanoyl]-N-[(S)-phenyl[5-(propan-2-yl)pyridin-2-yl]methyl]pyrrolidine-2-carboxamide |
| 288 | 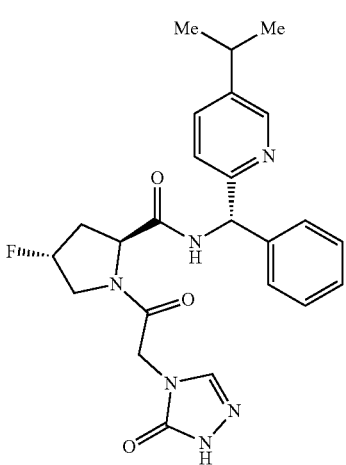 [SMILES: CC(C)c1ccc([C@@H](NC(=O)[C@@H]2C[C@@H](F)CN2C(=O)Cn2cn[nH]c2=O)c2ccccc2)nc1] | (2S,4R)-4-fluoro-1-[2-(5-oxo-4,5-dihydro-1H-1,2,4-triazol-4-yl)acetyl]-N-[(S)-phenyl[5-(propan-2-yl)pyridin-2-yl]methyl]pyrrolidine-2-carboxamide |

TABLE 1-continued
| Compound No. | Structure | IUPAC |
|---|---|---|
| 289 | 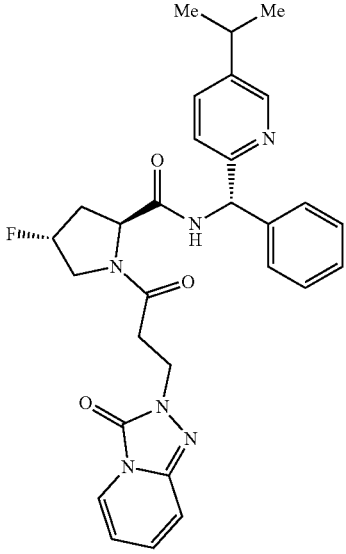 [SMILES: CC(C)c1ccc([C@@H](NC(=O)[C@@H]2C[C@@H](F)CN2C(=O)CCn2nc3ccccn3c2=O)c2ccccc2)nc1] | (2S,4R)-4-fluoro-1-(3-{3-oxo-2H,3H-[1,2,4]triazolo[4,3-a]pyridin-2-yl}propanoyl)-N-[(S)-phenyl[5-(propan-2-yl)pyridin-2-yl]methyl]pyrrolidine-2-carboxamide |
| 290 | 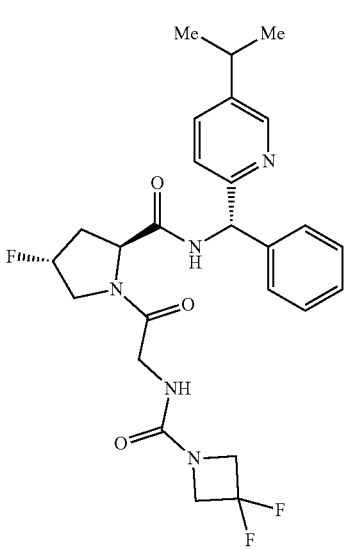 [SMILES: CC(C)c1ccc([C@@H](NC(=O)[C@@H]2C[C@@H](F)CN2C(=O)CNC(=O)N2CC(F)(F)C2)c2ccccc2)nc1] | (2S,4R)-1-{2-[(3,3-difluoroazetidine-1-carbonyl]amino]acetyl}-4-fluoro-N-[(S)-phenyl[5-(propan-2-yl)pyridin-2-yl]methyl]pyrrolidine-2-carboxamide |

TABLE 1-continued

| Compound No. | Structure | IUPAC |
|---|---|---|
| 291 | 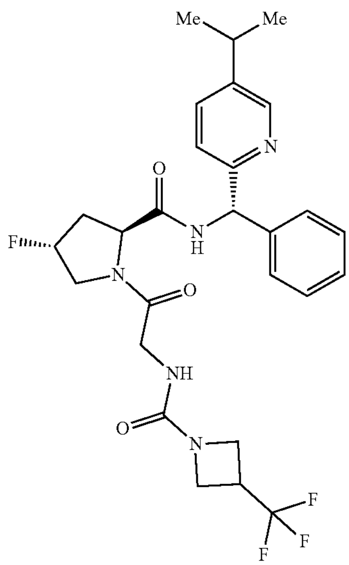 [SMILES: CC(C)c1ccc([C@@H](NC(=O)[C@@H]2C[C@@H](F)CN2C(=O)CNC(=O)N2CC(C(F)(F)F)C2)c2ccccc2)nc1] | (2S,4R)-4-fluoro-N-[(S)-phenyl[5-(propan-2-yl)pyridin-2-yl]methyl]-1-(2-{[3-(trifluoromethyl)azetidin-1-carbonyl]amino}acetyl)pyrrolidine-2-carboxamide |
| 292 | 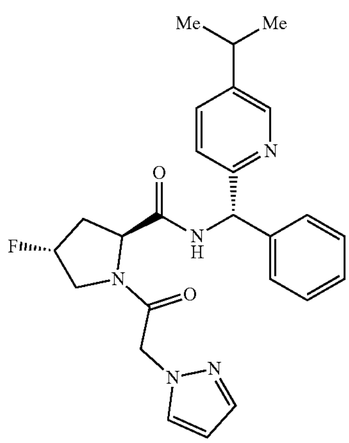 [SMILES: CC(C)c1ccc([C@@H](NC(=O)[C@@H]2C[C@@H](F)CN2C(=O)Cn2cccn2)c2ccccc2)nc1] | (2S,4R)-4-fluoro-N-[(S)-phenyl[5-(propan-2-yl)pyridin-2-yl]methyl]-1-[2-(1H-pyrazol-1-yl)acetyl]pyrrolidine-2-carboxamide |
| 293 | 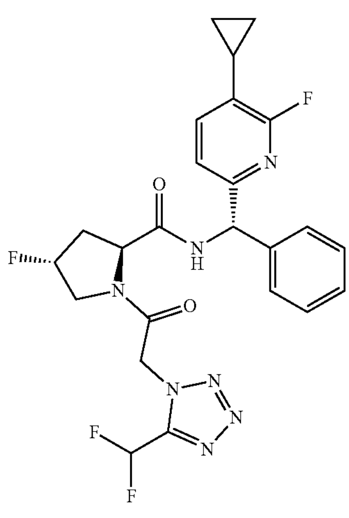 [SMILES: O=C(N[C@@H](c1ccccc1)c1ccc(C2CC2)c(F)n1)[C@@H]1C[C@@H](F)CN1C(=O)Cn1nnnc1C(F)F] | (2S,4R)-N-((S)-(5-cyclopropl-6-fluoropyridin-2-yl)(phenyl)methyl)-1-(2-(5-(difluoromethyl)-1H-tetrazol-1-yl)acetyl)-4-fluoropyrrolidine-2-carboxamide |

| Compound No. | Structure | IUPAC |
|---|---|---|
| 294 | 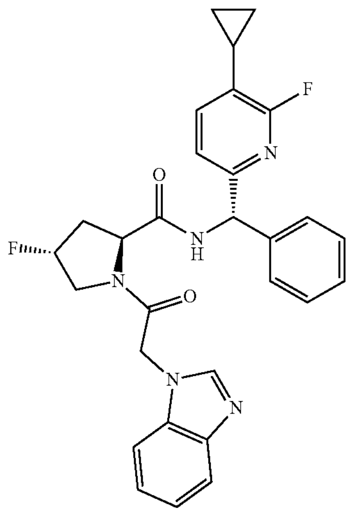 [SMILES: O=C(N[C@@H](c1ccccc1)c1ccc(C2CC2)c(F)n1)[C@@H]1C[C@@H](F)CN1C(=O)Cn1cnc2ccccc21] | (2S,4R)-1-[2-(1H-1,3-benzodiazol-1-yl)acetyl]-N-[(S)-(5-cyclopropyl-6-fluoropyridin-2-yl)(phenyl)methyl]-4-fluoropyrrolidine-2-carboxamide |
| 295 | 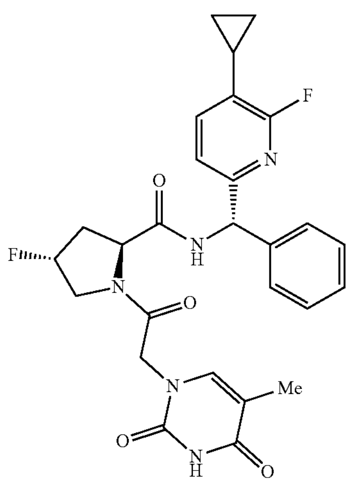 [SMILES: Cc1cn(CC(=O)N2C[C@H](F)C[C@H]2C(=O)N[C@@H](c2ccccc2)c2ccc(C3CC3)c(F)n2)c(=O)[nH]c1=O] | (2S,4R)-N-[(S)-(5-cyclopropyl-6-fluoropyridin-2-yl)(phenyl)methyl]-4-fluoro-1-[2-(5-methyl-2,4-dioxo-1,2,3,4-tetrahydropyrimidin-1-yl)acetyl]pyrrolidine-2-carboxamide |
| 296 | 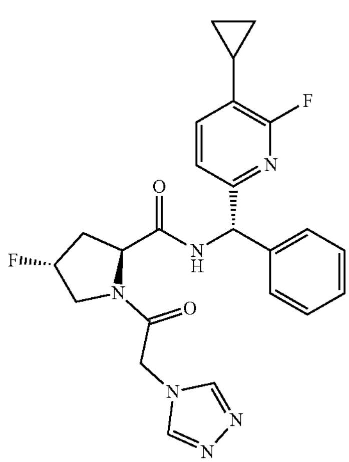 [SMILES: O=C(N[C@@H](c1ccccc1)c1ccc(C2CC2)c(F)n1)[C@@H]1C[C@@H](F)CN1C(=O)Cn1cnnc1] | (2S,4R)-N-[(S)-(5-cyclopropyl-6-fluoropyridin-2-yl)(phenyl)methyl]-4-fluoro-1-[2-(4H-1,2,4-triazol-4-yl)acetyl]pyrrolidine-2-carboxamide |

TABLE 1-continued

| Compound No. | Structure | IUPAC |
|---|---|---|
| 297 | 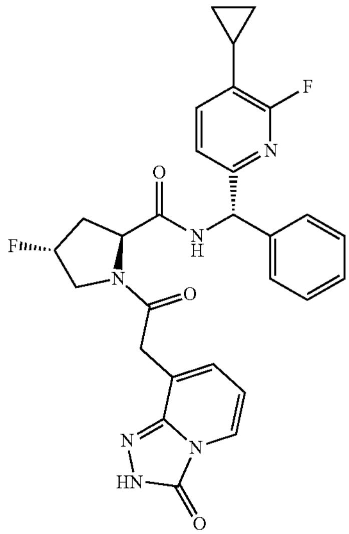 [SMILES: O=C(N[C@@H](c1ccccc1)c1ccc(C2CC2)c(F)n1)[C@@H]1C[C@@H](F)CN1C(=O)Cc1cccn2c(=O)[nH]nc12] | (2S,4R)-N-[(S)-(5-cyclopropyl-6-fluoropyridin-2-yl)(phenyl)methyl]-4-fluoro-1-(2-{3-oxo-2H,3H-[1,2,4]triazolo[4,3-a]pyridin-8-yl}acetyl)pyrrolidine-2-carboxamide |
| 298 | 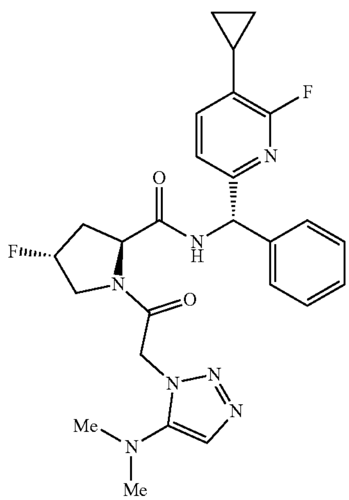 [SMILES: CN(C)c1cnnn1CC(=O)N1C[C@H](F)C[C@H]1C(=O)N[C@@H](c1ccccc1)c1ccc(C2CC2)c(F)n1] | (2S,4R)-N-[(S)-(5-cyclopropyl-6-fluoropyridin-2-yl)(phenyl)methyl]-1-{2-[5-(dimethylamino)-1H-1,2,3-triazol-1-yl]acetyl}-4-fluoropyrrolidine-2-carboxamide |
| 299 | 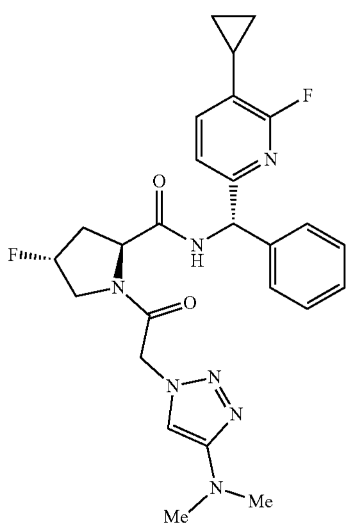 [SMILES: CN(C)c1cn(CC(=O)N2C[C@H](F)C[C@H]2C(=O)N[C@@H](c2ccccc2)c2ccc(C3CC3)c(F)n2)nn1] | (2S,4R)-N-[(S)-(5-cyclopropyl-6-fluoropyridin-2-yl)(phenyl)methyl]-1-{2-[4-(dimethylamino)-1H-1,2,3-triazol-1-yl]acetyl}-4-fluoropyrrolidine-2-carboxamide |

TABLE 1-continued

| Compound No. | Structure | IUPAC |
|---|---|---|
| 300 | 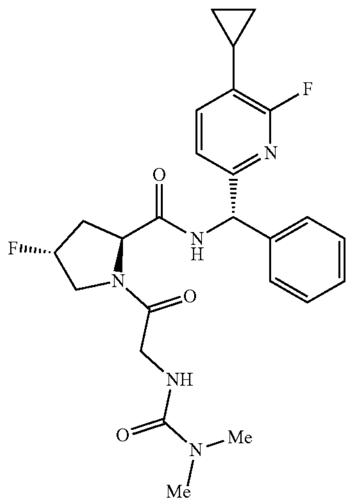 [SMILES: CN(C)C(=O)NCC(=O)N1C[C@H](F)C[C@H]1C(=O)N[C@@H](c1ccccc1)c1ccc(C2CC2)c(F)n1] | (2S,4R)-N-[(S)-(5-cyclopropyl-6-fluoropyridin-2-yl)(phenyl)methyl]-1-{2-[(dimethylcarbamoyl)amino]acetyl}-4-fluoropyrrolidine-2-carboxamide |
| 301 | 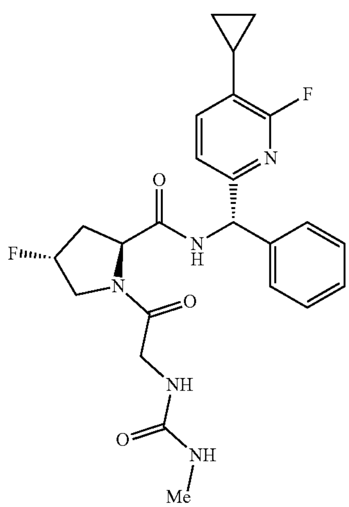 [SMILES: CNC(=O)NCC(=O)N1C[C@H](F)C[C@H]1C(=O)N[C@@H](c1ccccc1)c1ccc(C2CC2)c(F)n1] | (2S,4R)-N-[(S)-(5-cyclopropyl-6-fluoropyridin-2-yl)(phenyl)methyl]-4-fluoro-1-{2-[(methylcarbamoyl)amino]acetyl}pyrrolidine-2-carboxamide |
| 302 | 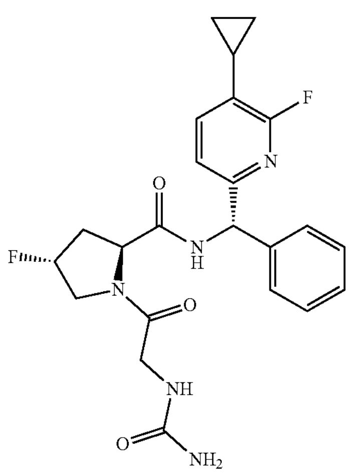 [SMILES: NC(=O)NCC(=O)N1C[C@H](F)C[C@H]1C(=O)N[C@@H](c1ccccc1)c1ccc(C2CC2)c(F)n1] | (2S,4R)-1-[2-(carbamoylamino)acetyl]-N-[(S)-(5-cyclopropyl-6-fluoropyridin-2-yl)(phenyl)methyl]-4-fluoropyrrolidine-2-carboxamide |

TABLE 1-continued

| Compound No. | Structure | IUPAC |
|---|---|---|
| 303 | 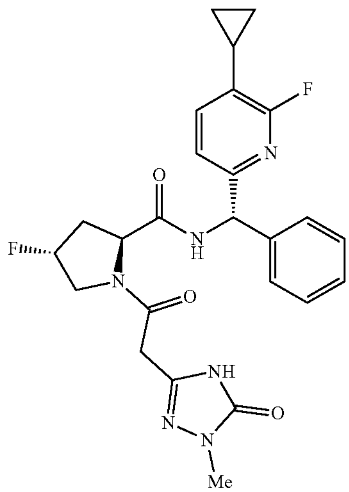 [SMILES: Cn1nc(CC(=O)N2C[C@H](F)C[C@H]2C(=O)N[C@@H](c2ccccc2)c2ccc(C3CC3)c(F)n2)[nH]c1=O] | (2S,4R)-N-[(S)-(5-cyclopropyl-6-fluoropyridin-2-yl)(phenyl)methyl]-4-fluoro-1-[2-(1-methyl-5-oxo-4,5-dihydro-1H-1,2,4-triazol-3-yl)acetyl]pyrrolidine-2-carboxamide |
| 304 | 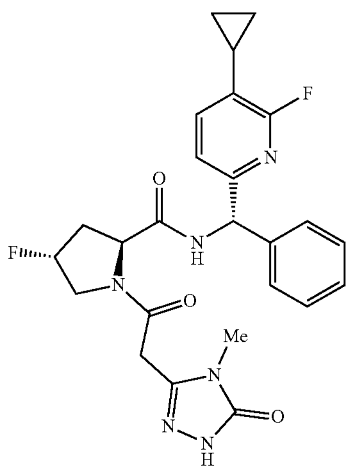 [SMILES: Cn1c(CC(=O)N2C[C@H](F)C[C@H]2C(=O)N[C@@H](c2ccccc2)c2ccc(C3CC3)c(F)n2)n[nH]c1=O] | (2S,4R)-N-[(S)-(5-cyclopropyl-6-fluoropyridin-2-yl)(phenyl)methyl]-4-fluoro-1-[2-(4-methyl-5-oxo-4,5-dihydro-1H-1,2,4-triazol-3-yl)acetyl]pyrrolidine-2-carboxamide |
| 305 | 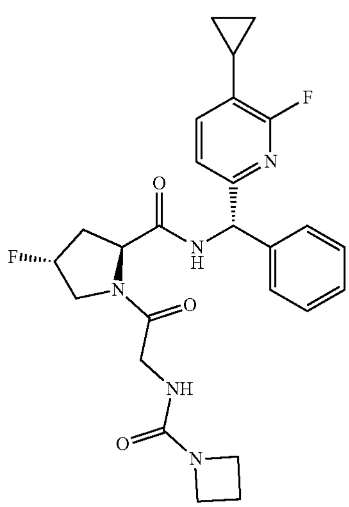 [SMILES: O=C(N[C@@H](c1ccccc1)c1ccc(C2CC2)c(F)n1)[C@@H]1C[C@@H](F)CN1C(=O)CNC(=O)N1CCC1] | (2S,4R)-1-{2-[(azetidine-1-carbonyl)amino]acetyl}-N-[(S)-(5-cyclopropyl-6-fluoropyridin-2-yl)(phenyl)methyl]-4-fluoropyrrolidine-2-carboxamide |

TABLE 1-continued

| Compound No. | Structure | IUPAC |
|---|---|---|
| 306 | 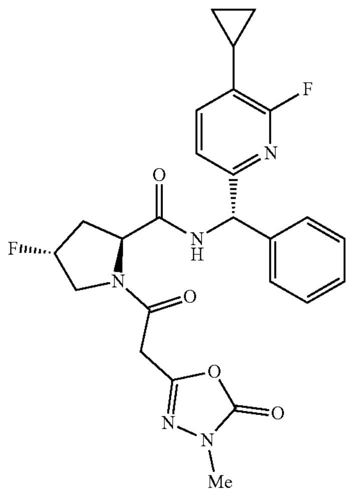 [SMILES: Cn1nc(CC(=O)N2C[C@H](F)C[C@H]2C(=O)N[C@@H](c2ccccc2)c2ccc(C3CC3)c(F)n2)oc1=O] | (2S,4R)-N-[(S)-(5-cyclopropyl-6-fluoropyridin-2-yl)(phenyl)methyl]-4-fluoro-1-[2-(4-methyl-5-oxo-4,5-dihydro-1,3,4-oxadiazol-2-yl)acetyl]pyrrolidine-2-carboxamide |
| 307 | 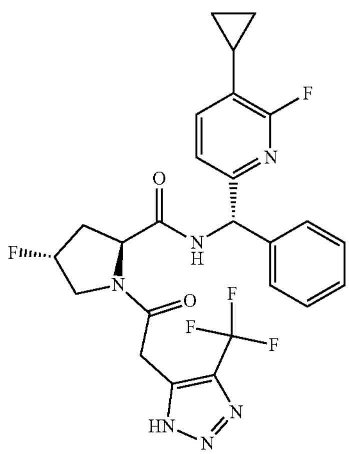 [SMILES: O=C(N[C@@H](c1ccccc1)c1ccc(C2CC2)c(F)n1)[C@@H]1C[C@@H](F)CN1C(=O)Cc1[nH]nnc1C(F)(F)F] | (2S,4R)-N-[(S)-(5-cyclopropyl-6-fluoropyridin-2-yl)(phenyl)methyl]-4-fluoro-1-{2-[4-(trifluoromethyl)-1H-1,2,3-triazol-5-yl]acetyl}pyrrolidine-2-carboxamide |
| 308 | 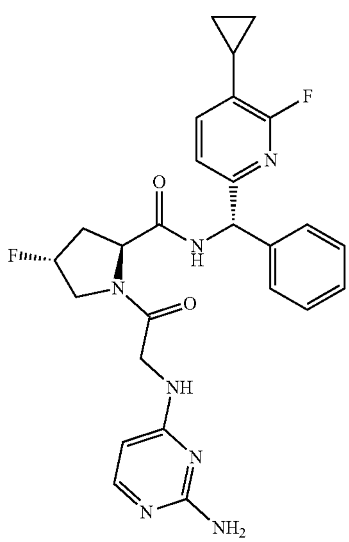 [SMILES: Nc1nccc(NCC(=O)N2C[C@H](F)C[C@H]2C(=O)N[C@@H](c2ccccc2)c2ccc(C3CC3)c(F)n2)n1] | (2S,4R)-N-[(S)-(5-cyclopropyl-6-fluoropyridin-2-yl)(phenyl)methyl]-4-fluoro-1-{2-[(2-methylpyrimidin-4-yl)amino]acetyl}pyrrolidine-2-carboxamide |

TABLE 1-continued

| Compound No. | Structure | IUPAC |
|---|---|---|
| 309 | 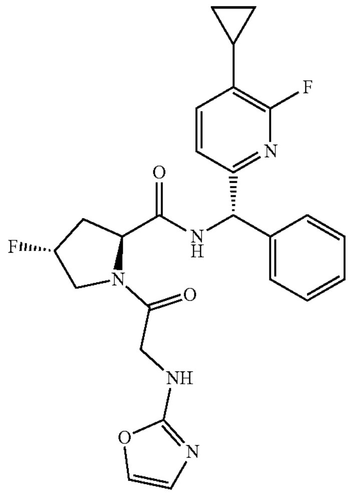 [SMILES: O=C(N[C@@H](c1ccccc1)c1ccc(C2CC2)c(F)n1)[C@@H]1C[C@@H](F)CN1C(=O)CNc1ncco1] | (2S,4R)-N-[(S)-(5-cyclopropyl-6-fluoropyridin-2-yl)(phenyl)methyl]-4-fluoro-1-{2-[(1,3-oxazol-2-yl)amino]acetyl}pyrrolidine-2-carboxamide |
| 310 | 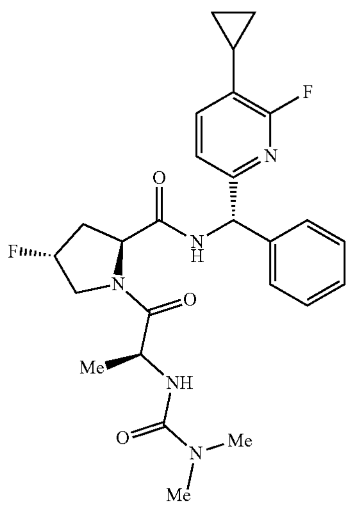 [SMILES: C[C@H](NC(=O)N(C)C)C(=O)N1C[C@H](F)C[C@H]1C(=O)N[C@@H](c1ccccc1)c1ccc(C2CC2)c(F)n1] | (2S,4R)-N-[(S)-(5-cyclopropyl-6-fluoropyridin-2-yl)(phenyl)methyl]-1-[(2S)-2-[(dimethylcarbamoyl)amino]propanoyl]-4-fluoropyrrolidine-2-carboxamide |
| 311 | 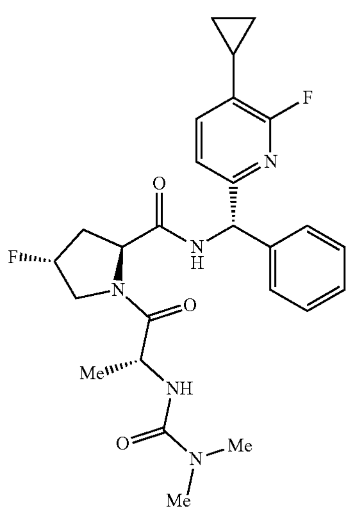 [SMILES: C[C@@H](NC(=O)N(C)C)C(=O)N1C[C@H](F)C[C@H]1C(=O)N[C@@H](c1ccccc1)c1ccc(C2CC2)c(F)n1] | (2S,4R)-N-[(S)-(5-cyclopropyl-6-fluoropyridin-2-yl)(phenyl)methyl]-1-[(2R)-2-[(dimethylcarbamoyl)amino]propanoyl]-4-fluoropyrrolidine-2-carboxamide |

TABLE 1-continued

| Compound No. | Structure | IUPAC |
|---|---|---|
| 312 | 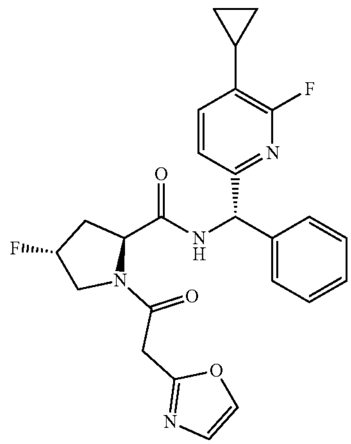 [SMILES: O=C(N[C@@H](c1ccccc1)c1ccc(C2CC2)c(F)n1)[C@@H]1C[C@@H](F)CN1C(=O)Cc1ncco1] | (2S,4R)-N-[(S)-(5-cyclopropyl-6-fluoropyridin-2-yl)(phenyl)methyl]-4-fluoro-1-[2-(1,3-oxazol-2-yl)acetyl]pyrrolidine-2-carboxamide |
| 313 | 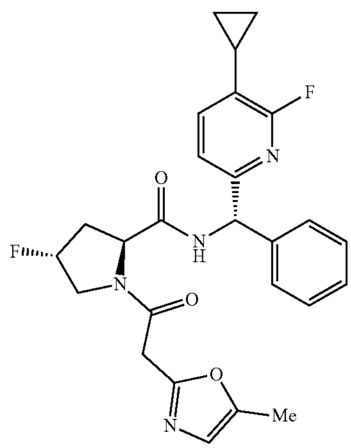 [SMILES: Cc1cnc(CC(=O)N2C[C@H](F)C[C@H]2C(=O)N[C@@H](c2ccccc2)c2ccc(C3CC3)c(F)n2)o1] | (2S,4R)-N-[(S)-(5-cyclopropyl-6-fluoropyridin-2-yl)(phenyl)methyl]-4-fluoro-1-[2-(5-methyl-1,3-oxazol-2-yl)acetyl]pyrrolidine-2-carboxamide |
| 314 | 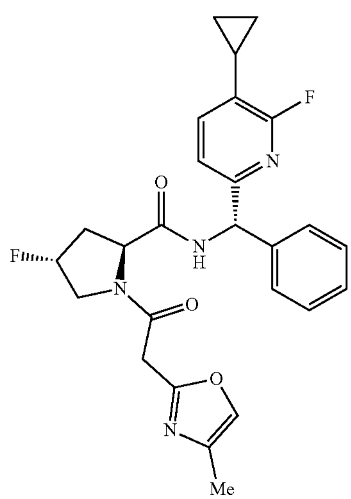 [SMILES: Cc1coc(CC(=O)N2C[C@H](F)C[C@H]2C(=O)N[C@@H](c2ccccc2)c2ccc(C3CC3)c(F)n2)n1] | (2S,4R)-N-[(S)-(5-cyclopropyl-6-fluoropyridin-2-yl)(phenyl)methyl]-4-fluoro-1-[2-(4-methyl-1,3-oxazol-2-yl)acetyl]pyrrolidine-2-carboxamide |

TABLE 1-continued

| Compound No. | Structure | IUPAC |
|---|---|---|
| 315 | 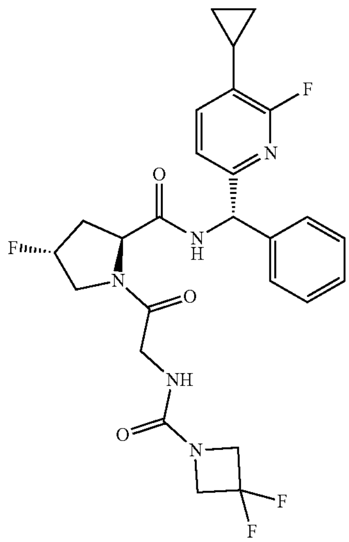 [SMILES: O=C(N[C@@H](c1ccccc1)c1ccc(C2CC2)c(F)n1)[C@@H]1C[C@@H](F)CN1C(=O)CNC(=O)N1CC(F)(F)C1] | (2S,4R)-N-[(S)-(5-cyclopropyl-6-fluoropyridin-2-yl)(phenyl)methyl]-1-{2-[(3,3-difluoroazetidine-1-carbonyl)amino]acetyl}-4-fluoropyrrolidine-2-carboxamide |
| 316 | 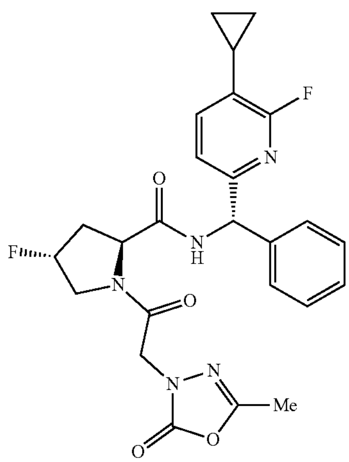 [SMILES: Cc1nn(CC(=O)N2C[C@H](F)C[C@H]2C(=O)N[C@@H](c2ccccc2)c2ccc(C3CC3)c(F)n2)c(=O)o1] | (2S,4R)-N-[(S)-(5-cyclopropyl-6-fluoropyridin-2-yl)(phenyl)methyl]-4-fluoro-1-[2-(5-methyl-2-oxo-2,3-dihydro-1,3,4-oxadiazol-3-yl)acetyl]pyrrolidine-2-carboxamide |
| 317 | 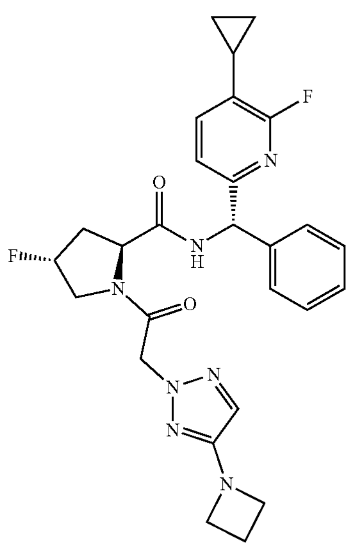 [SMILES: O=C(N[C@@H](c1ccccc1)c1ccc(C2CC2)c(F)n1)[C@@H]1C[C@@H](F)CN1C(=O)Cn1ncc(N2CCC2)n1] | (2S,4R)-1-{2-[4-(azetidin-1-yl)-2H-1,2,3-triazol-2-yl]acetyl}-N-[(S)-(5-cyclopropyl-6-fluoropyridin-2-yl)(phenyl)methyl]-4-fluoropyrrolidine-2-carboxamide |

TABLE 1-continued

| Compound No. | Structure | IUPAC |
|---|---|---|
| 318 | 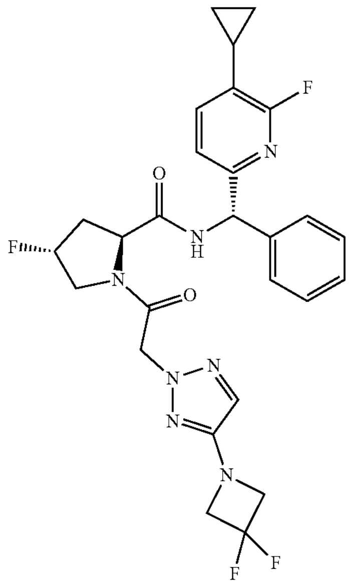 [SMILES: O=C(N[C@@H](c1ccccc1)c1ccc(C2CC2)c(F)n1)[C@@H]1C[C@@H](F)CN1C(=O)Cn1ncc(N2CC(F)(F)C2)n1] | (2S,4R)-N-[(S)-(5-cyclopropyl-6-fluoropyridin-2-yl)(phenyl)methyl]-1-{2-[4-(3,3-difluoroazetidin-1-yl)-2H-1,2,3-triazol-2-yl]acetyl}-4-fluoropyrrolidine-2-carboxamide |
| 319 | 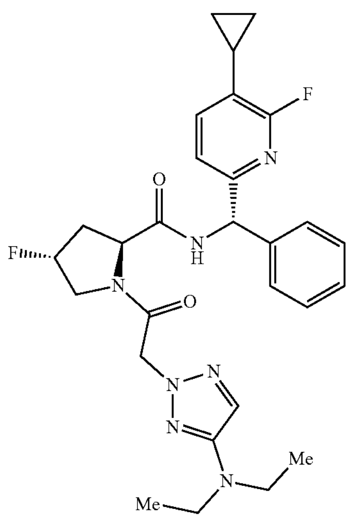 [SMILES: CCN(CC)c1cnn(CC(=O)N2C[C@H](F)C[C@H]2C(=O)N[C@@H](c2ccccc2)c2ccc(C3CC3)c(F)n2)n1] | (2S,4R)-N-[(S)-(5-cyclopropyl-6-fluoropyridin-2-yl)(phenyl)methyl]-1-{2-[4-(diethylamino)-2H-1,2,3-triazol-2-yl]acetyl}-4-fluoropyrrolidine-2-carboxamide |
| 320 | 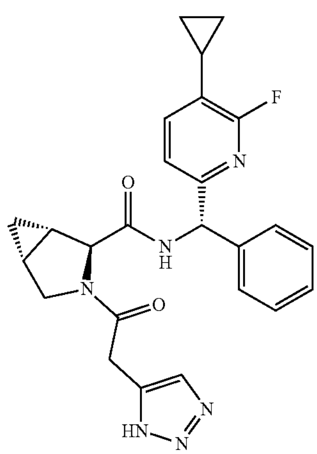 [SMILES: O=C(N[C@@H](c1ccccc1)c1ccc(C2CC2)c(F)n1)[C@@H]1[C@H]2C[C@H]2CN1C(=O)Cc1cnn[nH]1] | (1S,2S,5R)-N-[(S)-(5-cyclopropyl-6-fluoropyridin-2-yl)(phenyl)methyl]-3-[2-(1H-1,2,3-triazol-5-yl)acetyl]-3-azabicyclo[3.1.0]hexane-2-carboxamide |

TABLE 1-continued

| Compound No. | Structure | IUPAC |
|---|---|---|
| 321 | 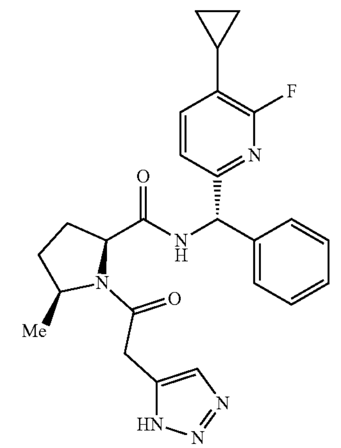 [SMILES: C[C@H]1CC[C@@H](C(=O)N[C@@H](c2ccccc2)c2ccc(C3CC3)c(F)n2)N1C(=O)Cc1cnn[nH]1] | (2S,5S)-N-[(S)-(5-cyclopropyl-6-fluoropyridin-2-yl)(phenyl)methyl]-5-methyl-1-[2-(1H-1,2,3-triazol-5-yl)acetyl]pyrrolidine-2-carboxamide |
| 322 | 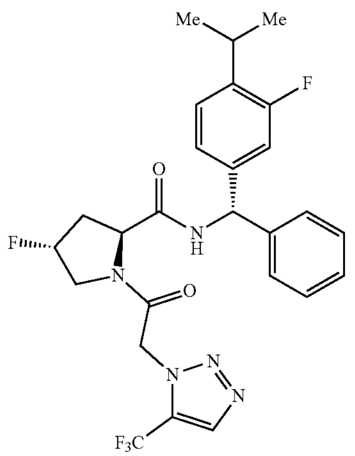 [SMILES: CC(C)c1ccc([C@@H](NC(=O)[C@@H]2C[C@@H](F)CN2C(=O)Cn2nncc2C(F)(F)F)c2ccccc2)cc1F] | (2S,4R)-4-fluoro-N-((S)-(3-fluoro-4-isopropylphenyl)(phenyl)methyl)-1-(2-(5-(trifluoromethyl)-1H-1,2,3-triazol-1-yl)acetyl)pyrrolidine-2-carboxamide |
| 323 | 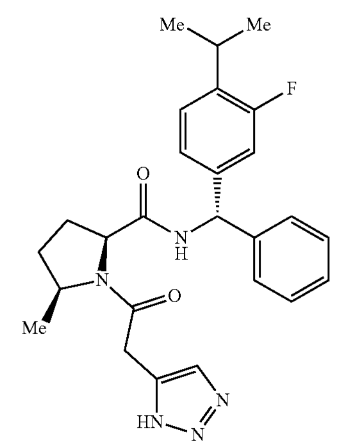 [SMILES: CC(C)c1ccc([C@@H](NC(=O)[C@@H]2CC[C@H](C)N2C(=O)Cc2cnn[nH]2)c2ccccc2)cc1F] | (2S,5S)-N-[(S)-[3-fluoro-4-(propan-2-yl)phenyl](phenyl)methyl]-5-methyl-1-[2-(1H-1,2,3-triazol-5-yl)acetyl]pyrrolidine-2-carboxamide |

US 11,814,367 B2
TABLE 1-continued
| Compound No. | Structure | IUPAC |
|---|---|---|
| 324 | 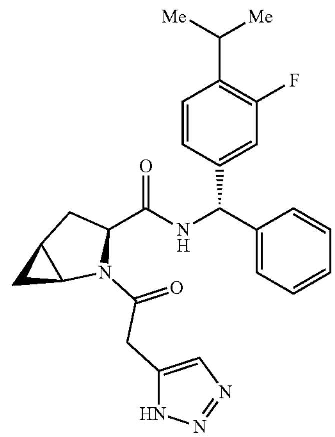 [SMILES: CC(C)c1ccc([C@@H](NC(=O)[C@@H]2C[C@@H]3C[C@@H]3N2C(=O)Cc2cnn[nH]2)c2ccccc2)cc1F] | (1S,3S,5S)-N-[(S)-[3-fluoro-4-(propan-2-yl)phenyl](phenyl)methyl]-2-[2-(1H-1,2,3-triazol-5-yl)acetyl]-2-azabicyclo[3.1.0]hexane-3-carboxamide |
| 325 | 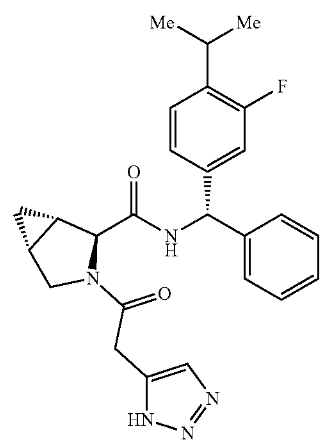 [SMILES: CC(C)c1ccc([C@@H](NC(=O)[C@@H]2[C@H]3C[C@H]3CN2C(=O)Cc2cnn[nH]2)c2ccccc2)cc1F] | (1S,2S,5R)-N-[(S)-[3-fluoro-4-(propan-2-yl)phenyl](phenyl)methyl]-3-[2-(1H-1,2,3-triazol-5-yl)acetyl]-3-azabicyclo[3.1.0]hexane-2-carboxamide |
| 326 | 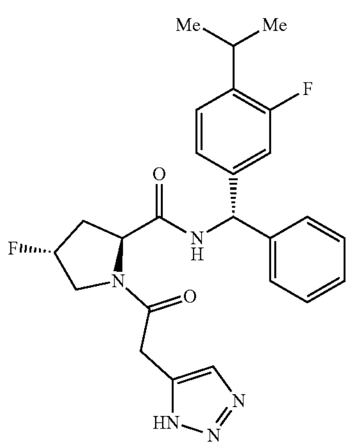 [SMILES: CC(C)c1ccc([C@@H](NC(=O)[C@@H]2C[C@@H](F)CN2C(=O)Cc2cnn[nH]2)c2ccccc2)cc1F] | (2S,4R)-4-fluoro-N-[(S)-[3-fluoro-4-(propan-2-yl)phenyl](phenyl)methyl]-1-[2-(1H-1,2,3-triazol-5-yl)acetyl]pyrrolidine-2-carboxamide |

TABLE 1-continued
| Compound No. | Structure | IUPAC |
|---|---|---|
| 327 | 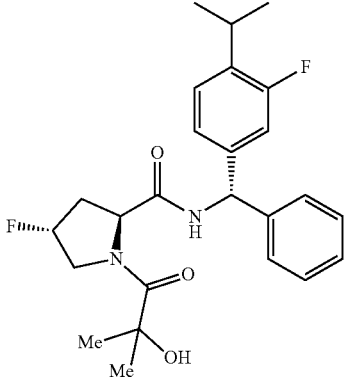 [SMILES: CC(C)c1ccc([C@@H](NC(=O)[C@@H]2C[C@@H](F)CN2C(=O)C(C)(C)O)c2ccccc2)cc1F] | (2S,4R)-4-fluoro-N-[(S)-[3-fluoro-4-(propan-2-yl)phenyl](phenyl)methyl]-1-(2-hydroxy-2-methylpropanoyl)pyrrolidine-2-carboxamide |
| 328 | 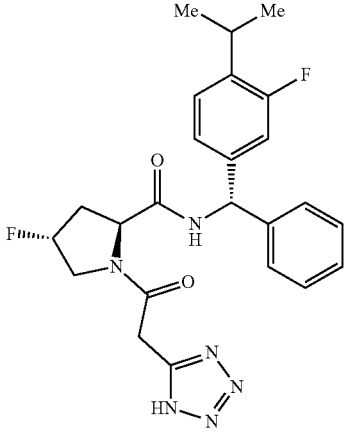 | (2S,4R)-4-fluoro-N-[(S)-[3-fluoro-4-(propan-2-yl)phenyl](phenyl)methyl]-1-[2-(1H-1,2,3-tetrazol-5-yl)acetyl]pyrrolidine-2-carboxamide |
| 329 | 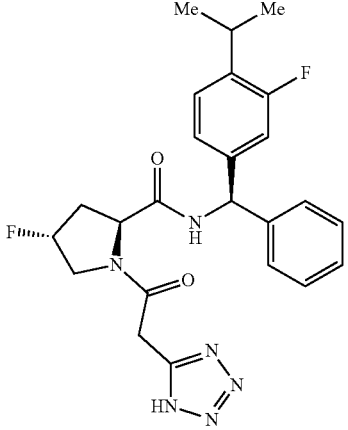 [SMILES: CC(C)c1ccc([C@H](NC(=O)[C@@H]2C[C@@H](F)CN2C(=O)Cc2nnn[nH]2)c2ccccc2)cc1F] | (2S,4R)-4-fluoro-N-[(R)-[3-fluoro-4-(propan-2-yl)phenyl](phenyl)methyl]-1-[2-(1H-1,2,3-tetrazol-5-yl)acetyl]pyrrolidine-2-carboxamide |

TABLE 1-continued
| Compound No. | Structure | IUPAC |
|---|---|---|
| 330 | 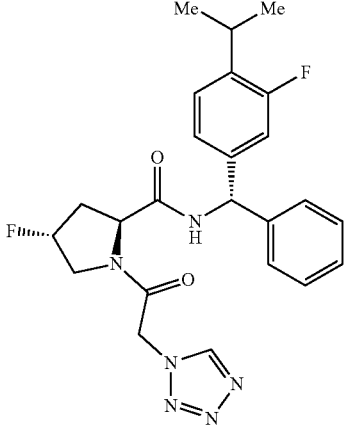 | (2S,4R)-4-fluoro-N-[(S)-[3-fluoro-4-(propan-2-yl)phenyl](phenyl)methyl]-1-[2-(1H-1,2,3,4-tetrazol-1-yl)acetyl]pyrrolidine-2-carboxamide |
| 331 | 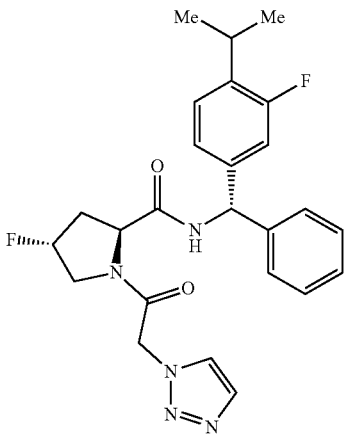 [SMILES: CC(C)c1ccc([C@@H](NC(=O)[C@@H]2C[C@@H](F)CN2C(=O)Cn2ccnn2)c2ccccc2)cc1F] | (2S,4R)-4-fluoro-N-[(S)-[3-fluoro-4-(propan-2-yl)phenyl](phenyl)methyl]-1-[2-(1H-1,2,3-triazol-1-yl)acetyl]pyrrolidine-2-carboxamide |
| 332 | 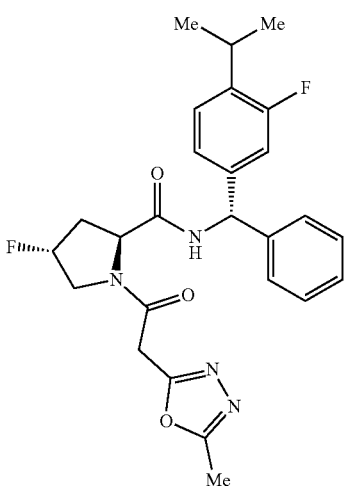 | (2S,4R)-4-fluoro-N-[(S)-[3-fluoro-4-(propan-2-yl)phenyl](phenyl)methyl]-1-[2-(5-methyl-1,3,4-oxadiazol-2-yl)acetyl]pyrrolidine-2-carboxamide |

TABLE 1-continued

| Compound No. | Structure | IUPAC |
|---|---|---|
| 333 | 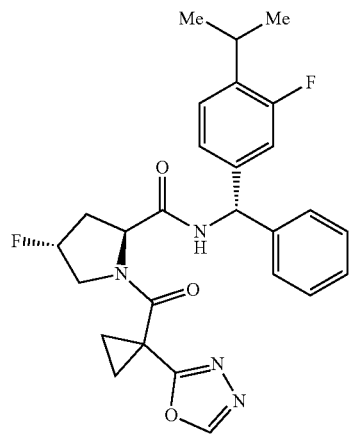 | (2S,4R)-4-fluoro-N-[(S)-[3-fluoro-4-(propan-2-yl)phenyl](phenyl)methyl]-1-[1-(1,3,4-oxadiazol-2-yl)cyclopropanecarbonyl]pyrrolidine-2-carboxamide |
| 334 | 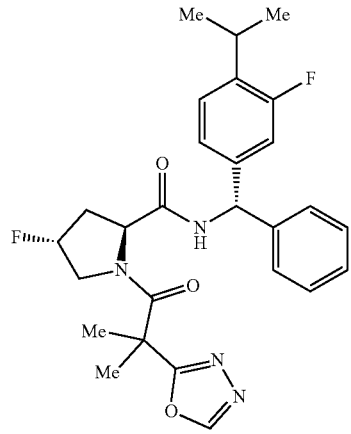 | (2S,4R)-4-fluoro-N-[(S)-[3-fluoro-4-(propan-2-yl)phenyl](phenyl)methyl]-1-[2-methyl-2-(1,3,4-oxadiazol-2-yl)propanoyl]pyrrolidine-2-carboxamide |
| 335 | 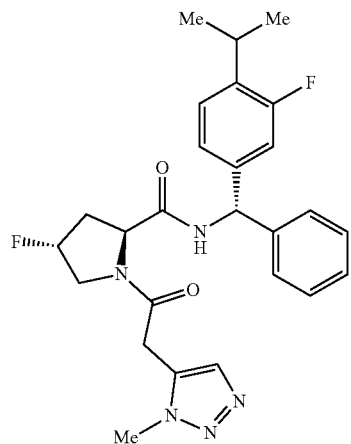 | (2S,4R)-4-fluoro-N-[(S)-[3-fluoro-4-(propan-2-yl)phenyl](phenyl)methyl]-1-[2-(1-methyl-1H-1,2,3-triazol-5-yl)acetyl]pyrrolidine-2-carboxamide |

| Compound No. | Structure | IUPAC |
|---|---|---|
| 336 | 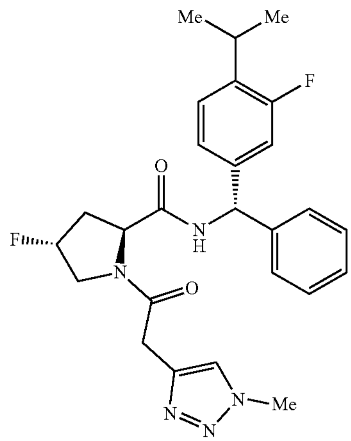 [SMILES: CC(C)c1ccc([C@@H](NC(=O)[C@@H]2C[C@@H](F)CN2C(=O)Cc2cn(C)nn2)c2ccccc2)cc1F] | (2S,4R)-4-fluoro-N-[(S)-[3-fluoro-4-(propan-2-yl)phenyl](phenyl)methyl]-1-[2-(1-methyl-1H-1,2,3-triazol-4-yl)acetyl]pyrrolidine-2-carboxamide |
| 337 | 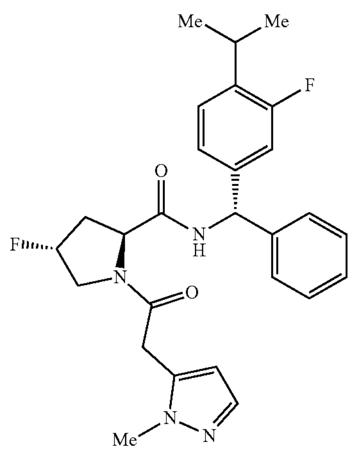 [SMILES: CC(C)c1ccc([C@@H](NC(=O)[C@@H]2C[C@@H](F)CN2C(=O)Cc2ccnn2C)c2ccccc2)cc1F] | (2S,4R)-4-fluoro-N-[(S)-[3-fluoro-4-(propan-2-yl)phenyl](phenyl)methyl]-1-[2-(1-methyl-1H-pyrazol-5-yl)acetyl]pyrrolidine-2-carboxamide |
| 338 | 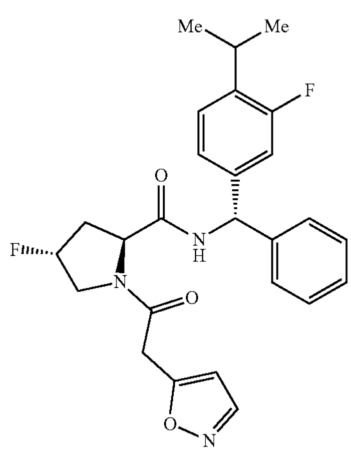 [SMILES: CC(C)c1ccc([C@@H](NC(=O)[C@@H]2C[C@@H](F)CN2C(=O)Cc2ccno2)c2ccccc2)cc1F] | (2S,4R)-4-fluoro-N-[(S)-[3-fluoro-4-(propan-2-yl)phenyl](phenyl)methyl]-1-[2-(1,2-oxazol-5-yl)acetyl]pyrrolidine-2-carboxamide |

TABLE 1-continued
| Compound No. | Structure | IUPAC |
|---|---|---|
| 339 | 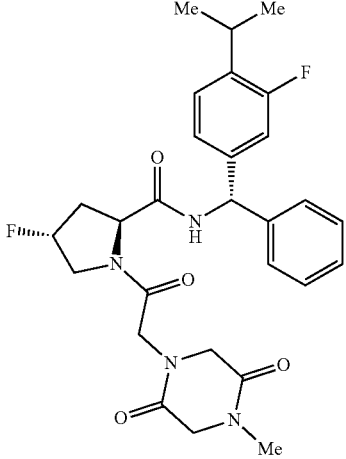 | (2S,4R)-4-fluoro-N-[(S)-[3-fluoro-4-(propan-2-yl)phenyl](phenyl)methyl]-1-[2-(4-methyl-2,5-dioxopiperazin-1-yl)acetyl]pyrrolidine-2-carboxamide |
| 340 | 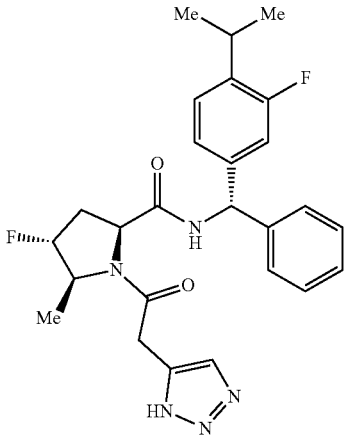 | (2S,4R,5S)-4-fluoro-N-[(S)-[3-fluoro-4-(propan-2-yl)phenyl](phenyl)methyl]-5-methyl-1-[2-(1H-1,2,3-triazol-5-yl)acetyl]pyrrolidine-2-carboxamide |
| 341 | 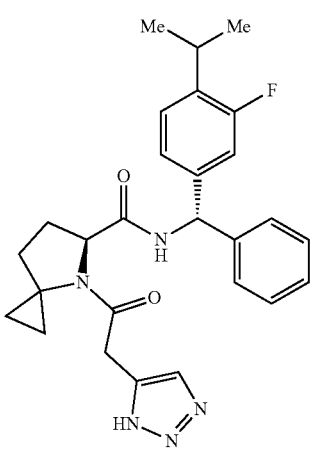 [SMILES: CC(C)c1ccc([C@@H](NC(=O)[C@@H]2CCC3(CC3)N2C(=O)Cc2cnn[nH]2)c2ccccc2)cc1F] | (5S)-N-[(S)-[3-fluoro-4-(propan-2-yl)phenyl](phenyl)methyl]-4-[2-(1H-1,2,3-triazol-5-yl)acetyl]-4-azaspiro[2.4]heptane-5-carboxamide |

TABLE 1-continued

| Compound No. | Structure | IUPAC |
|---|---|---|
| 342 | 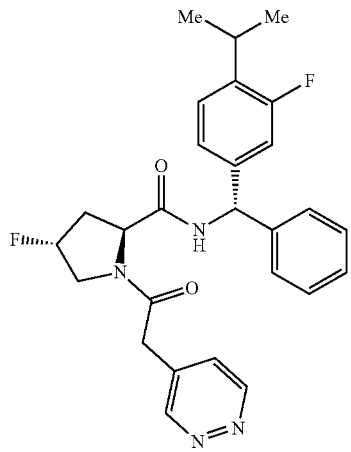 [SMILES: CC(C)c1ccc([C@@H](NC(=O)[C@@H]2C[C@@H](F)CN2C(=O)Cc2ccnnc2)c2ccccc2)cc1F] | (2S,4R)-4-fluoro-N-[(S)-[3-fluoro-4-(propan-2-yl)phenyl](phenyl)methyl]-1-[2-(pyridazin-4-yl)acetyl]pyrrolidine-2-carboxamide |
| 343 | 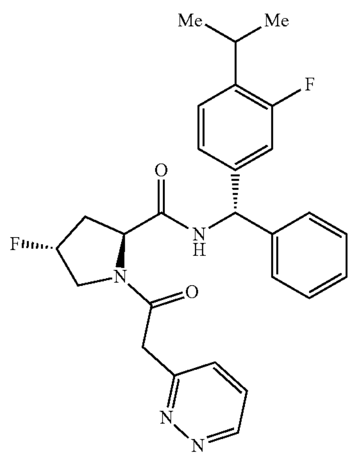 [SMILES: CC(C)c1ccc([C@@H](NC(=O)[C@@H]2C[C@@H](F)CN2C(=O)Cc2cccnn2)c2ccccc2)cc1F] | (2S,4R)-4-fluoro-N-[(S)-[3-fluoro-4-(propan-2-yl)phenyl](phenyl)methyl]-1-[2-(pyridazin-3-yl)acetyl]pyrrolidine-2-carboxamide |
| 344 | 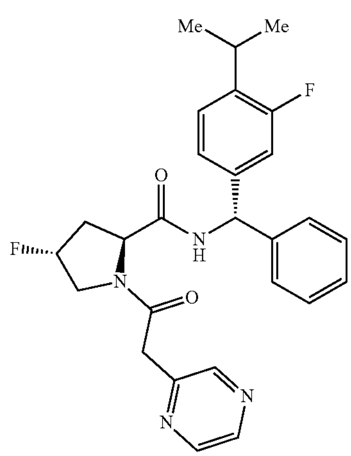 [SMILES: CC(C)c1ccc([C@@H](NC(=O)[C@@H]2C[C@@H](F)CN2C(=O)Cc2cnccn2)c2ccccc2)cc1F] | (2S,4R)-4-fluoro-N-[(S)-[3-fluoro-4-(propan-2-yl)phenyl](phenyl)methyl]-1-[2-(pyrazin-2-yl)acetyl]pyrrolidine-2-carboxamide |

TABLE 1-continued

| Compound No. | Structure | IUPAC |
|---|---|---|
| 345 | 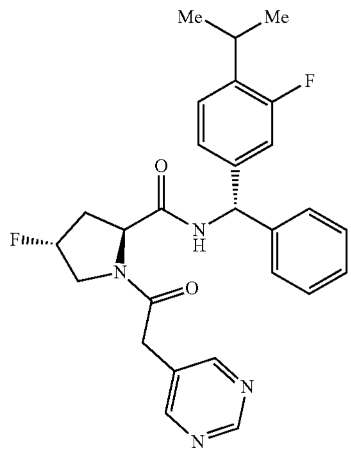 [SMILES: CC(C)c1ccc([C@@H](NC(=O)[C@@H]2C[C@@H](F)CN2C(=O)Cc2cncnc2)c2ccccc2)cc1F] | (2S,4R)-4-fluoro-N-[(S)-[3-fluoro-4-(propan-2-yl)phenyl](phenyl)methyl]-1-[2-(pyrimidin-5-yl)acetyl]pyrrolidine-2-carboxamide |
| 346 | 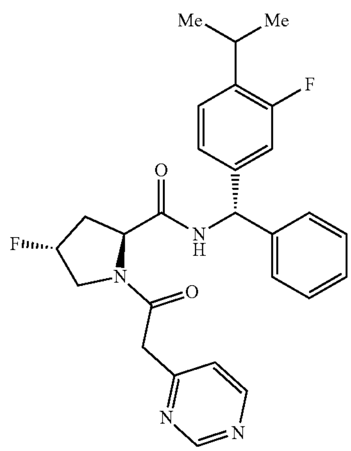 [SMILES: CC(C)c1ccc([C@@H](NC(=O)[C@@H]2C[C@@H](F)CN2C(=O)Cc2ccncn2)c2ccccc2)cc1F] | (2S,4R)-4-fluoro-N-[(S)-[3-fluoro-4-(propan-2-yl)phenyl](phenyl)methyl]-1-[2-(pyrimidin-4-yl)acetyl]pyrrolidine-2-carboxamide |
| 347 | 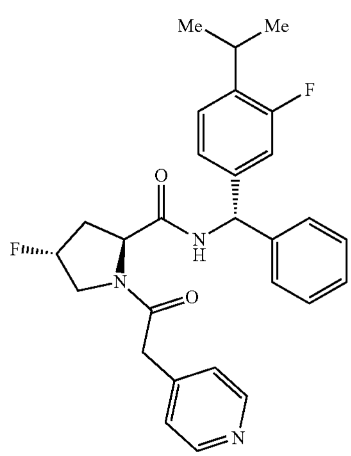 [SMILES: CC(C)c1ccc([C@@H](NC(=O)[C@@H]2C[C@@H](F)CN2C(=O)Cc2ccncc2)c2ccccc2)cc1F] | (2S,4R)-4-fluoro-N-[(S)-[3-fluoro-4-(propan-2-yl)phenyl](phenyl)methyl]-1-[2-(pyridin-4-yl)acetyl]pyrrolidine-2-carboxamide |

TABLE 1-continued

| Compound No. | Structure | IUPAC |
|---|---|---|
| 348 | 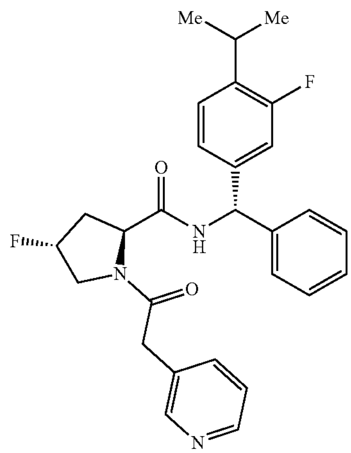 [SMILES: CC(C)c1ccc([C@@H](NC(=O)[C@@H]2C[C@@H](F)CN2C(=O)Cc2cccnc2)c2ccccc2)cc1F] | (2S,4R)-fluoro-N-[(S)-[3-fluoro-4-(propan-2-yl)phenyl](phenyl)methyl]-1-[2-(pyridin-3-yl)acetyl]pyrrolidine-2-carboxamide |
| 349 | 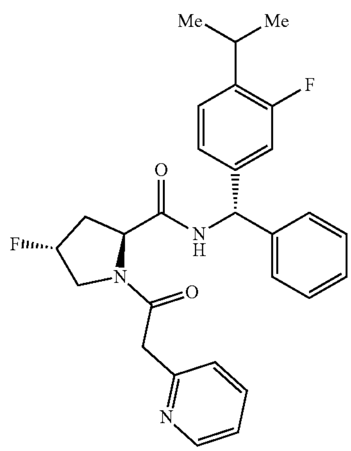 [SMILES: CC(C)c1ccc([C@@H](NC(=O)[C@@H]2C[C@@H](F)CN2C(=O)Cc2ccccn2)c2ccccc2)cc1F] | (2S,4R)-4-fluoro-N-[(S)-[3-fluoro-4-(propan-2-yl)phenyl](phenyl)methyl]-1-[2-(pyridin-2-yl)acetyl]pyrrolidine-2-carboxamide |
| 350 | 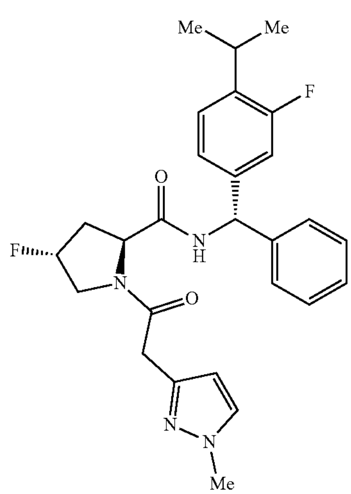 [SMILES: CC(C)c1ccc([C@@H](NC(=O)[C@@H]2C[C@@H](F)CN2C(=O)Cc2ccn(C)n2)c2ccccc2)cc1F] | (2S,4R)-4-fluoro-N-[(S)-[3-fluoro-4-(propan-2-yl)phenyl](phenyl)methyl]-1-[2-(1-methyl-1H-pyrazol-3-yl)acetyl]pyrrolidine-2-carboxamide |

TABLE 1-continued

| Compound No. | Structure | IUPAC |
|---|---|---|
| 351 | 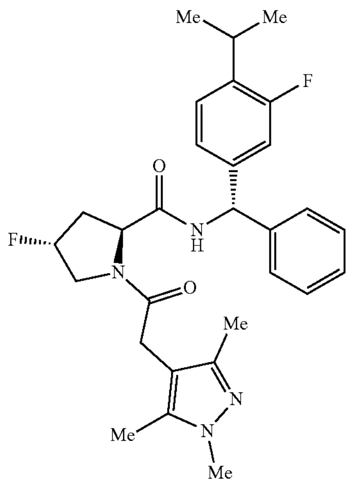 [SMILES: Cc1nn(C)c(C)c1CC(=O)N1C[C@H](F)C[C@H]1C(=O)N[C@@H](c1ccccc1)c1ccc(C(C)C)c(F)c1] | (2S,4R)-4-fluoro-N-[(S)-[3-fluoro-4-(propan-2-yl)phenyl](phenyl)methyl]-1-[2-(1,3,5-trimethyl-1H-pyrazol-4-yl)acetyl]pyrrolidine-2-carboxamide |
| 352 | 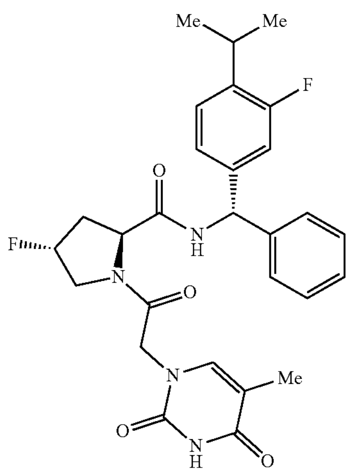 [SMILES: Cc1cn(CC(=O)N2C[C@H](F)C[C@H]2C(=O)N[C@@H](c2ccccc2)c2ccc(C(C)C)c(F)c2)c(=O)[nH]c1=O] | (2S,4R)-4-fluoro-N-[(S)-[3-fluoro-4-(propan-2-yl)phenyl](phenyl)methyl]-1-[2-(5-methyl-2,4-dioxo-1,2,3,4-tetrahydropyrimidin-1-yl)acetyl]pyrrolidine-2-carboxamide |
| 353 | 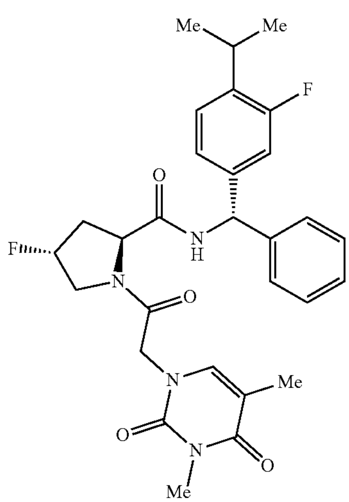 [SMILES: Cc1cn(CC(=O)N2C[C@H](F)C[C@H]2C(=O)N[C@@H](c2ccccc2)c2ccc(C(C)C)c(F)c2)c(=O)n(C)c1=O] | (2S,4R)-1-[2-(3,5-dimethyl-2,4-dioxo-1,2,3,4-tetrahydropyrimidin-1-yl)acetyl]-4-fluoro-N-[(S)-[3-fluoro-4-(propan-2-yl)phenyl](phenyl)methyl]pyrrolidine-2-carboxamide |

TABLE 1-continued

| Compound No. | Structure | IUPAC |
|---|---|---|
| 354 | 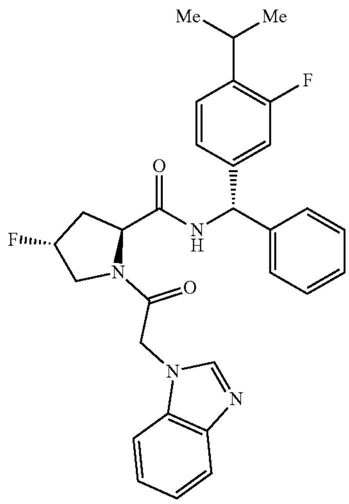 [SMILES: CC(C)c1ccc([C@@H](NC(=O)[C@@H]2C[C@@H](F)CN2C(=O)Cn2cnc3ccccc32)c2ccccc2)cc1F] | (2S,4R)-1-[2-(1H-1,3-benzodiazol-1-yl)acetyl]-4-fluoro-N-[(S)-[3-fluoro-4-(propan-2-yl)phenyl](phenyl)methyl]pyrrolidine-2-carboxamide |
| 355 | 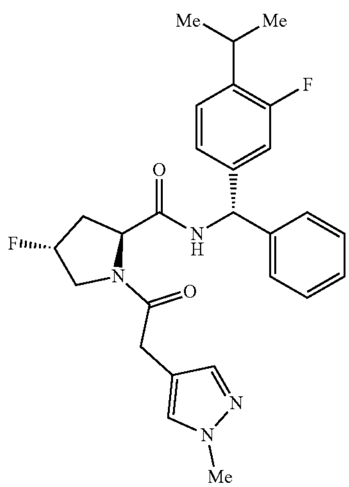 [SMILES: CC(C)c1ccc([C@@H](NC(=O)[C@@H]2C[C@@H](F)CN2C(=O)Cc2cnn(C)c2)c2ccccc2)cc1F] | (2S,4R)-4-fluoro-N-[(S)-[3-fluoro-4-(propan-2-yl)phenyl](phenyl)methyl]-1-[2-(1-methyl-1H-pyrazol-4-yl)acetyl]pyrrolidine-2-carboxamide |
| 356 | 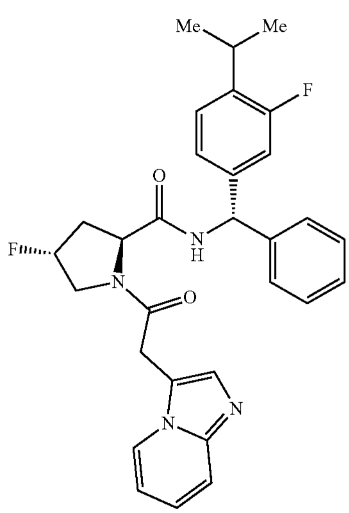 [SMILES: CC(C)c1ccc([C@@H](NC(=O)[C@@H]2C[C@@H](F)CN2C(=O)Cc2cnc3ccccn23)c2ccccc2)cc1F] | (2S,4R)-4-fluoro-N-[(S)-[3-fluoro-4-(propan-2-yl)phenyl](phenyl)methyl]-1-(2-{imidazo[1,2-a]pyridin-3-yl}acetyl)pyrrolidine-2-carboxamide |

TABLE 1-continued

| Compound No. | Structure | IUPAC |
|---|---|---|
| 357 | 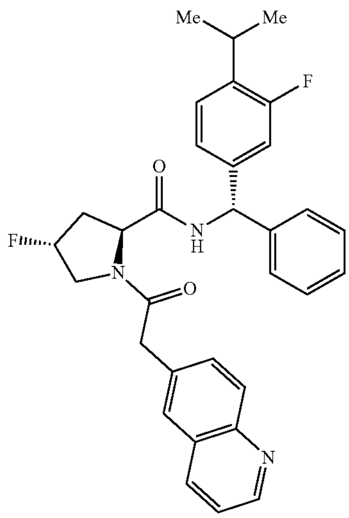 [SMILES: CC(C)c1ccc([C@@H](NC(=O)[C@@H]2C[C@@H](F)CN2C(=O)Cc2ccc3ncccc3c2)c2ccccc2)cc1F] | (2S,4R)-4-fluoro-N-[(S)-[3-fluoro-4-(propan-2-yl)phenyl](phenyl)methyl]-1-[2-(quinolin-6-yl)acetyl]pyrrolidine-2-carboxamide |
| 358 | 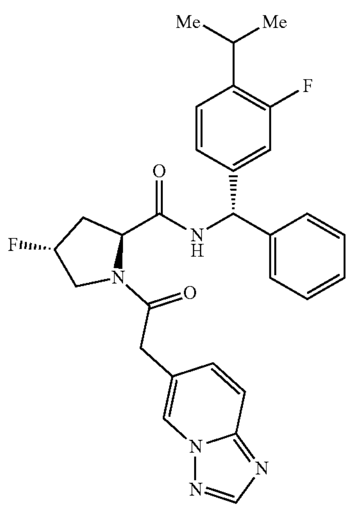 [SMILES: CC(C)c1ccc([C@@H](NC(=O)[C@@H]2C[C@@H](F)CN2C(=O)Cc2ccc3ncnn3c2)c2ccccc2)cc1F] | (2S,4R)-4-fluoro-N-[(S)-[3-fluoro-4-(propan-2-yl)phenyl](phenyl)methyl]-1-(2-{[1,2,4]triazolo[1,5-a]pyridin-6-yl}acetyl)pyrrolidine-2-carboxamide |
| 359 | 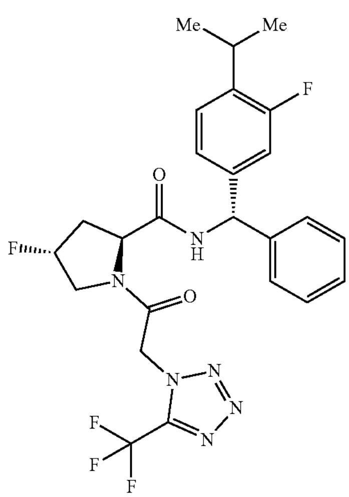 [SMILES: CC(C)c1ccc([C@@H](NC(=O)[C@@H]2C[C@@H](F)CN2C(=O)Cn2nnnc2C(F)(F)F)c2ccccc2)cc1F] | (2S,4R)-4-fluoro-N-[(S)-[3-fluoro-4-(propan-2-yl)phenyl](phenyl)methyl]-1-{2-[5-(trifluoromethyl)-1H-1,2,3,4-tetrazol-1-yl]acetyl}pyrrolidine-2-carboxamide |

TABLE 1-continued

| Compound No. | Structure | IUPAC |
|---|---|---|
| 360 | 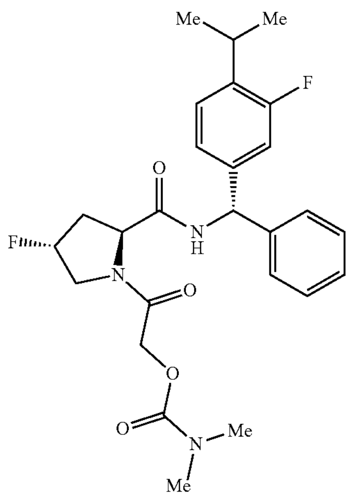 [SMILES: CC(C)c1ccc([C@@H](NC(=O)[C@@H]2C[C@@H](F)CN2C(=O)COC(=O)N(C)C)c2ccccc2)cc1F] | 2-[(2S,4R)-4-fluoro-2-{[(S)-[3-fluoro-4-(propan-2-yl)phenyl](phenyl)methyl]carbamoyl}pyrrolidin-1-yl]-2-oxoethyl-N,N-dimethylcarbamate |
| 361 | 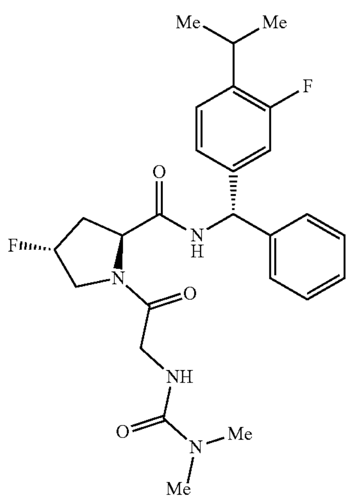 [SMILES: CC(C)c1ccc([C@@H](NC(=O)[C@@H]2C[C@@H](F)CN2C(=O)CNC(=O)N(C)C)c2ccccc2)cc1F] | (2S,4R)-1-{2-[(dimethylcarbamoyl)amino]acetyl}-4-fluoro-N-[(S)-[3-fluoro-4-(propan-2-yl)phenyl](phenyl)methyl]pyrrolidine-2-carboxamide |
| 362 | 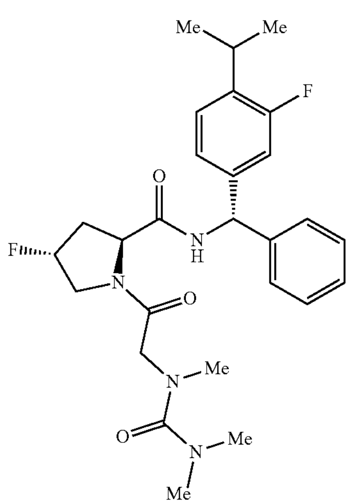 [SMILES: CC(C)c1ccc([C@@H](NC(=O)[C@@H]2C[C@@H](F)CN2C(=O)CN(C)C(=O)N(C)C)c2ccccc2)cc1F] | (2S,4R)-1-{2-[(dimethylcarbamoyl)(methyl)amino]acetyl}-4-fluoro-N-[(S)-[3-fluoro-4-(propan-2-yl)phenyl](phenyl)methyl]pyrrolidine-2-carboxamide |

TABLE 1-continued
| Compound No. | Structure | IUPAC |
|---|---|---|
| 363 | 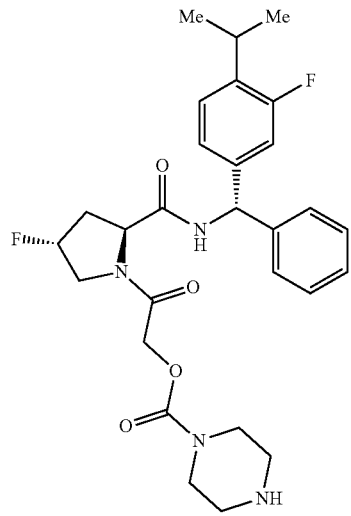 [SMILES: CC(C)c1ccc([C@@H](NC(=O)[C@@H]2C[C@@H](F)CN2C(=O)COC(=O)N2CCNCC2)c2ccccc2)cc1F] | 2-[(2S,4R)-4-fluoro-2-{[(S)-[3-fluoro-4-(propan-2-yl)phenyl](phenyl)methyl]carbamoyl}pyrrolidin-1-yl]-2-oxoethyl piperazine-1-carboxylate |
| 364 | 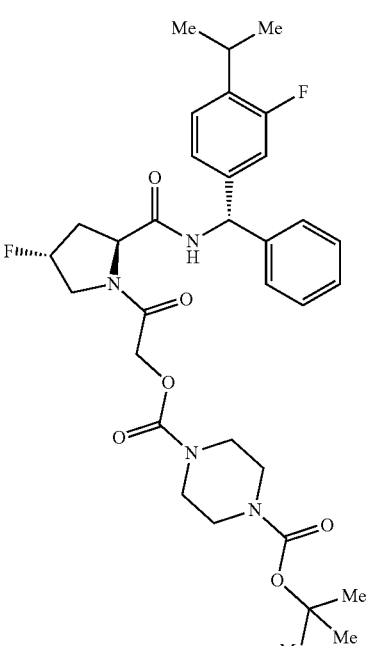 | 1-tert-butyl 4-{2-[(2S,4R)-4-fluoro-2-{[(S)-[3-fluoro-4-(propan-2-yl)phenyl](phenyl)methyl]carbamoyl}pyrrolidin-1-yl]-2-oxoethyl}piperazine-1,4-dicarboxylate |

TABLE 1-continued

| Compound No. | Structure | IUPAC |
|---|---|---|
| 365 | 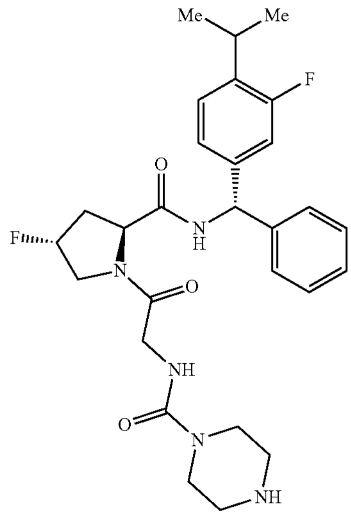 [SMILES: CC(C)c1ccc([C@@H](NC(=O)[C@@H]2C[C@@H](F)CN2C(=O)CNC(=O)N2CCNCC2)c2ccccc2)cc1F] | N-{2-(2S,4R)-4-fluoro-2-{[(S)-[3-fluoro-4-(propan-2-yl)phenyl](phenyl)methyl]carbamoyl}pyrrolidin-1-yl]-2-oxoethyl}piperazine-1-carboxamide |
| 366 | 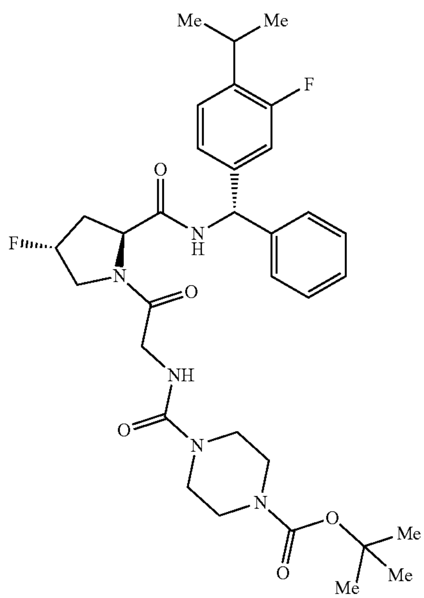 [SMILES: CC(C)c1ccc([C@@H](NC(=O)[C@@H]2C[C@@H](F)CN2C(=O)CNC(=O)N2CCN(C(=O)OC(C)(C)C)CC2)c2ccccc2)cc1F] | tert-butyl 4-({2-[(2S,4R)-4-fluoro-2-{[(S)-[3-fluoro-4-(propan-2-yl)phenyl](phenyl)methyl]carbamoyl}pyrrolidin-1-yl]-2-oxoethyl}carbamoyl)piperazine-1-carboxylate |
| 367 | 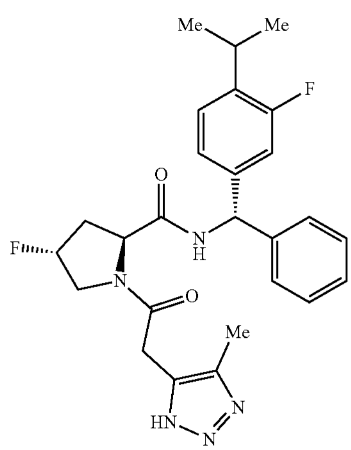 [SMILES: Cc1nn[nH]c1CC(=O)N1C[C@H](F)C[C@H]1C(=O)N[C@@H](c1ccccc1)c1ccc(C(C)C)c(F)c1] | (2S,4R)-4-fluoro-N-[(S)-[3-fluoro-4-(propan-2-yl)phenyl](phenyl)methyl]-1-[2-(4-methyl-1H-1,2,3-triazol-5-yl)acetyl]pyrrolidine-2-carboxamide |

TABLE 1-continued

| Compound No. | Structure | IUPAC |
|---|---|---|
| 368 | 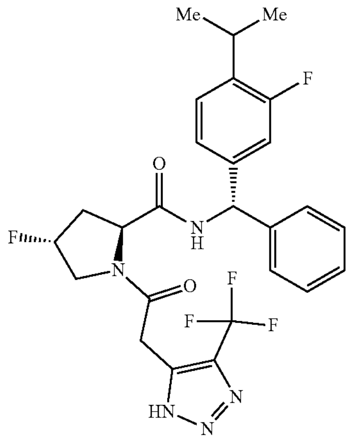 [SMILES: CC(C)c1ccc([C@@H](NC(=O)[C@@H]2C[C@@H](F)CN2C(=O)Cc2[nH]nnc2C(F)(F)F)c2ccccc2)cc1F] | (2S,4R)-4-fluoro-N-[(S)-[3-fluoro-4-(propan-2-yl)phenyl](phenyl)methyl]-1-{2-[4-(trifluoromethyl)-1H-1,2,3-triazol-5-yl]acetyl}pyrrolidine-2-carboxamide |
| 369 | 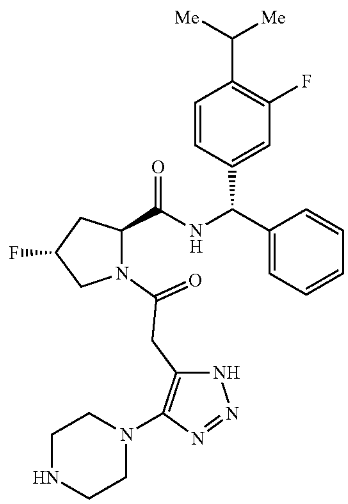 [SMILES: CC(C)c1ccc([C@@H](NC(=O)[C@@H]2C[C@@H](F)CN2C(=O)Cc2[nH]nnc2N2CCNCC2)c2ccccc2)cc1F] | (2S,4R)-4-fluoro-N-[(S)-[3-fluoro-4-(propan-2-yl)phenyl](phenyl)methyl]-1-{2-[4-(piperazin-1-yl)-1H-1,2,3-triazol-5-yl]acetyl}pyrrolidine-2-carboxamide |
| 370 | 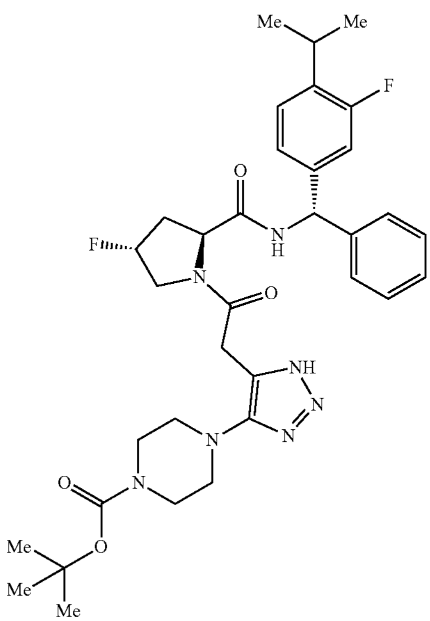 [SMILES: CC(C)c1ccc([C@@H](NC(=O)[C@@H]2C[C@@H](F)CN2C(=O)Cc2[nH]nnc2N2CCN(C(=O)OC(C)(C)C)CC2)c2ccccc2)cc1F] | tert-butyl 4-(5-{2-[(2S,4R)-4-fluoro-2-{[(S)-[3-fluoro-4-(propan-2-yl)phenyl](phenyl)methyl]carbamoyl}pyrrolidin-1-yl]-2-oxoethyl}-1H-1,2,3-triazol-4-yl)piperazine-1-carboxylate |

TABLE 1-continued

| Compound No. | Structure | IUPAC |
|---|---|---|
| 371 | 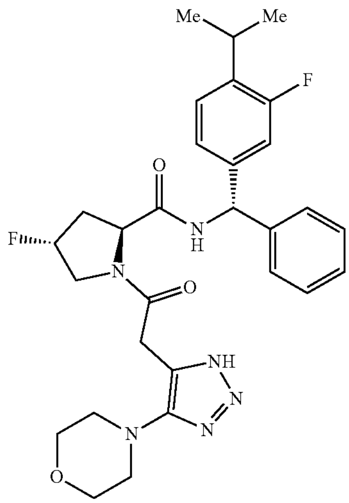 [SMILES: CC(C)c1ccc([C@@H](NC(=O)[C@@H]2C[C@@H](F)CN2C(=O)Cc2[nH]nnc2N2CCOCC2)c2ccccc2)cc1F] | (2S,4R)-4-fluoro-N-[(S)-[3-fluoro-4-(propan-2-yl)phenyl](phenyl)methyl]-1-{2-[4-(morpholin-4-yl)-1H-1,2,3-triazol-5-yl]acetyl}pyrrolidine-2-carboxamide |
| 372 | 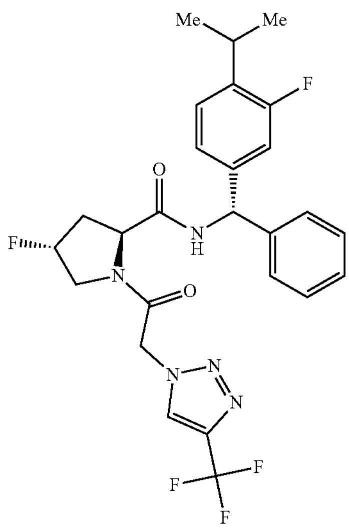 [SMILES: CC(C)c1ccc([C@@H](NC(=O)[C@@H]2C[C@@H](F)CN2C(=O)Cn2cc(C(F)(F)F)nn2)c2ccccc2)cc1F] | (2S,4R)-4-fluoro-N-[(S)-[3-fluoro-4-(propan-2-yl)phenyl](phenyl)methyl]-1-{2-[4-(trifluoromethyl)-1H-1,2,3-triazol-1-yl]acetyl}pyrrolidine-2-carboxamide |
| 373 | 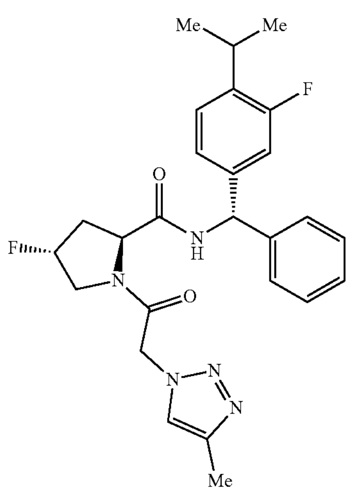 [SMILES: Cc1cn(CC(=O)N2C[C@H](F)C[C@H]2C(=O)N[C@@H](c2ccccc2)c2ccc(C(C)C)c(F)c2)nn1] | (2S,4R)-4-fluoro-N-[(S)-[3-fluoro-4-(propan-2-yl)phenyl](phenyl)methyl]-1-[2-(4-methyl-1H-1,2,3-triazol-1-yl)acetyl]pyrrolidine-2-carboxamide |

TABLE 1-continued

| Compound No. | Structure | IUPAC |
|---|---|---|
| 374 | 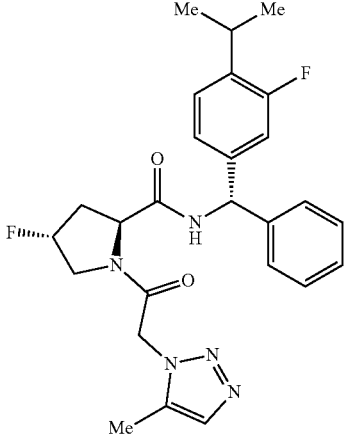 | (2S,4R)-4-fluoro-N-[(S)-[3-fluoro-4-(propan-2-yl)phenyl](phenyl)methyl]-1-[2-(5-methyl-1H-1,2,3-triazol-1-yl)acetyl]pyrrolidine-2-carboxamide |
| 375 | 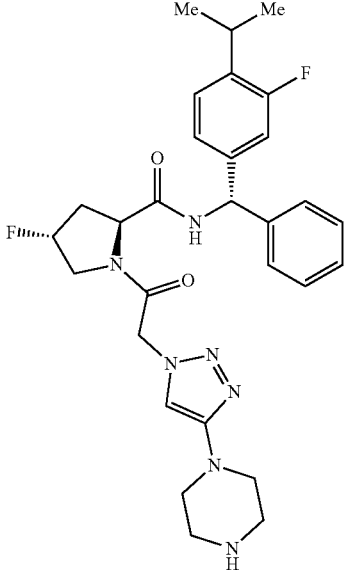 | (2S,4R)-4-fluoro-N-[(S)-[3-fluoro-4-(propan-2-yl)phenyl](phenyl)methyl]-1-{2-[4-(piperazin-1-yl)-1H-1,2,3-triazol-1-yl]acetyl}pyrrolidine-2-carboxamide |
| 376 | 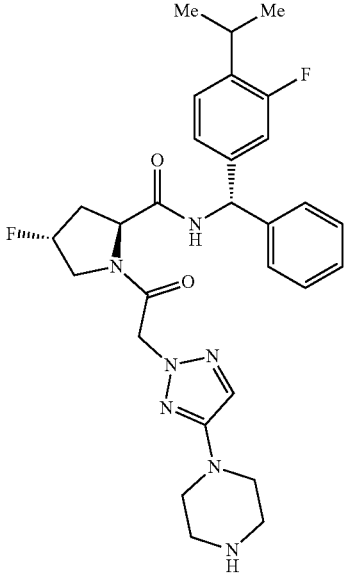 [SMILES: CC(C)c1ccc([C@@H](NC(=O)[C@@H]2C[C@@H](F)CN2C(=O)Cn2ncc(N3CCNCC3)n2)c2ccccc2)cc1F] | (2S,4R)-4-fluoro-N-[(S)-[3-fluoro-4-(propan-2-yl)phenyl](phenyl)methyl]-1-{2-[4-(piperazin-1-yl)-2H-1,2,3-triazol-2-yl]acetyl}pyrrolidine-2-carboxamide |

TABLE 1-continued

| Compound No. | Structure | IUPAC |
|---|---|---|
| 377 | 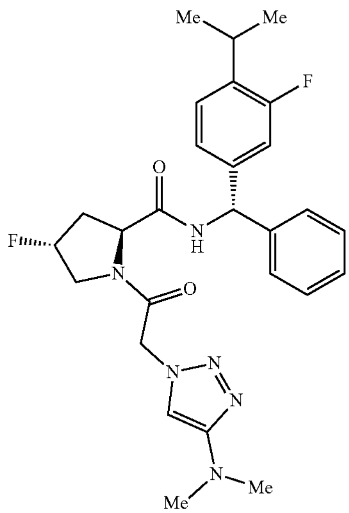 [SMILES: CC(C)c1ccc([C@@H](NC(=O)[C@@H]2C[C@@H](F)CN2C(=O)Cn2cc(N(C)C)nn2)c2ccccc2)cc1F] | (2S,4R)-1-{2-[4-(dimethylamino)-1H-1,2,3-triazol-1-yl]acetyl}-4-fluoro-N-[(S)-[3-fluoro-4-(propan-2-yl)phenyl](phenyl)methyl]pyrrolidine-2-carboxamide |
| 378 | 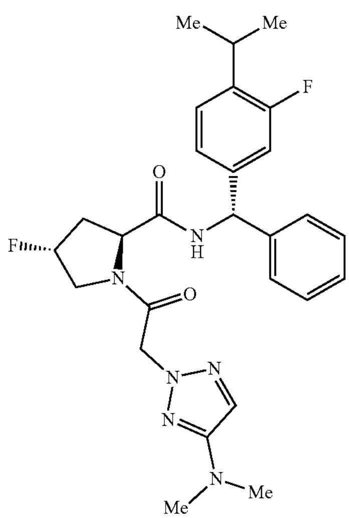 [SMILES: CC(C)c1ccc([C@@H](NC(=O)[C@@H]2C[C@@H](F)CN2C(=O)Cn2ncc(N(C)C)n2)c2ccccc2)cc1F] | (2S,4R)-1-{2-[4-(dimethylamino)-2H-1,2,3-triazol-2-yl]acetyl}-4-fluoro-N-[(S)-[3-fluoro-4-(propan-2-yl)phenyl](phenyl)methyl]pyrrolidine-2-carboxamide |
| 379 | 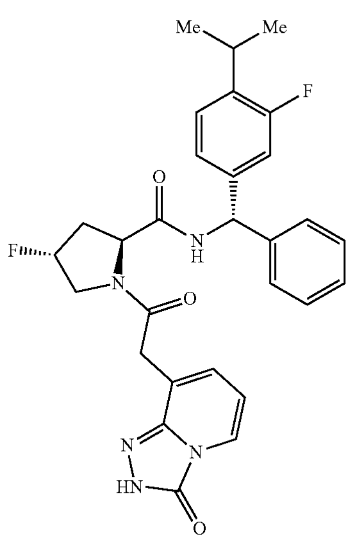 [SMILES: CC(C)c1ccc([C@@H](NC(=O)[C@@H]2C[C@@H](F)CN2C(=O)Cc2cccn3c(=O)[nH]nc23)c2ccccc2)cc1F] | (2S,4R)-4-fluoro-N-[(S)-[3-fluoro-4-(propan-2-yl)phenyl](phenyl)methyl]-1-(2-{3-oxo-2H,3H-[1,2,4]triazolo[4,3-a]pyridin-8-yl}acetyl)pyrrolidine-2-carboxamide |

TABLE 1-continued
| Compound No. | Structure | IUPAC |
|---|---|---|
| 380 | 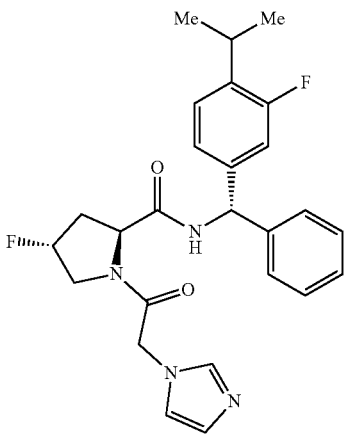 | (2S,4R)-4-fluoro-N-[(S)-[3-fluoro-4-(propan-2-yl)phenyl](phenyl)methyl]-1-[2-(1H-imidazol-1-yl)acetyl]pyrrolidine-2-carboxamide |
| 381 | 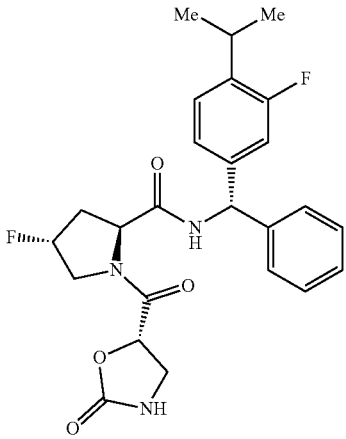 | (2S,4R)-4-fluoro-N-[(S)-[3-fluoro-4-(propan-2-yl)phenyl](phenyl)methyl]-1-[(5S)-2-oxo-1,3-oxazolidine-5-carbonyl]pyrrolidine-2-carboxamide |
| 382 | 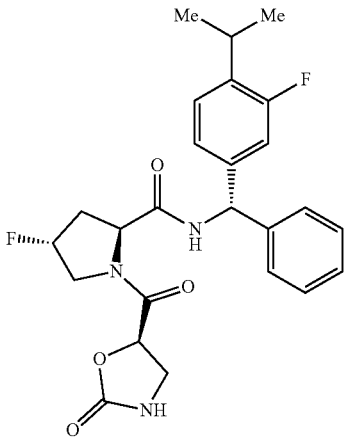 | (2S,4R)-4-fluoro-N-[(S)-[3-fluoro-4-(propan-2-yl)phenyl](phenyl)methyl]-1-[(5R)-2-oxo-1,3-oxazolidine-5-carbonyl]pyrrolidine-2-carboxamide |

TABLE 1-continued

| Compound No. | Structure | IUPAC |
|---|---|---|
| 383 | 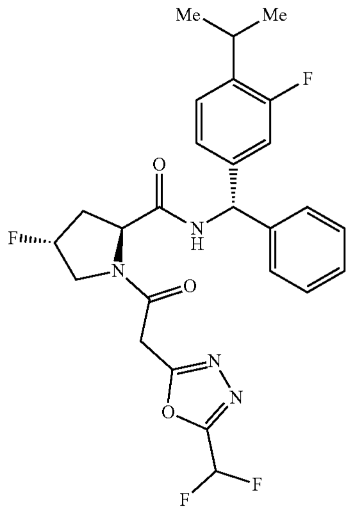 [SMILES: CC(C)c1ccc([C@@H](NC(=O)[C@@H]2C[C@@H](F)CN2C(=O)Cc2nnc(C(F)F)o2)c2ccccc2)cc1F] | (2S,4R)-1-{2-[5-(difluoromethyl)-1,3,4-oxadiazol-2-yl]acetyl}-4-fluoro-N-[(S)-[3-fluoro-4-(propan-2-yl)phenyl](phenyl)methyl]pyrrolidine-2-carboxamide |
| 384 | 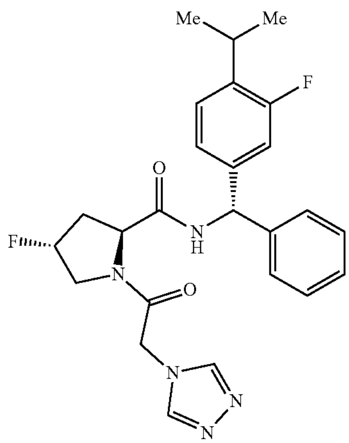 [SMILES: CC(C)c1ccc([C@@H](NC(=O)[C@@H]2C[C@@H](F)CN2C(=O)Cn2cnnc2)c2ccccc2)cc1F] | (2S,4R)-4-fluoro-N-[(1S)-[3-fluoro-4-(propan-2-yl)phenyl](phenyl)methyl]-1-[2-(4H-1,2,4-triazol-4-yl)acetyl]pyrrolidine-2-carboxamide |
| 385 | 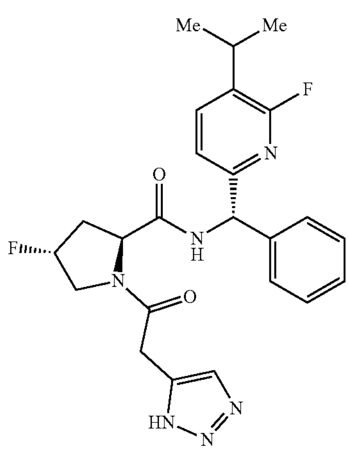 [SMILES: CC(C)c1ccc([C@@H](NC(=O)[C@@H]2C[C@@H](F)CN2C(=O)Cc2cnn[nH]2)c2ccccc2)nc1F] | (2S,4R)-1-(2-(1H-1,2,3-triazol-5-yl)acetyl)-4-fluoro-N-((S)-(6-fluoro-5-isopropylpyridin-2-yl)(phenyl)methyl)pyrrolidine-2-carboxamide |

TABLE 1-continued

| Compound No. | Structure | IUPAC |
|---|---|---|
| 386 | 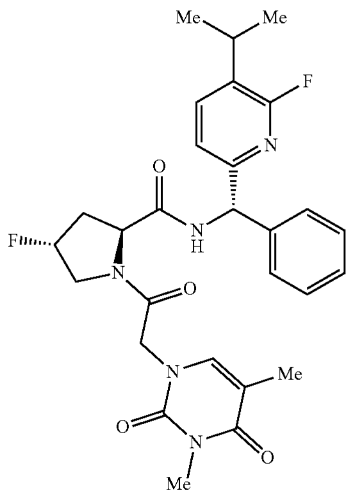 [SMILES: Cc1cn(CC(=O)N2C[C@H](F)C[C@H]2C(=O)N[C@@H](c2ccccc2)c2ccc(C(C)C)c(F)n2)c(=O)n(C)c1=O] | (2S,4R)-1-[2-(3,5-dimethyl-2,4-dioxo-1,2,3,4-tetrahydropyrimidin-1-yl)acetyl]-4-fluoro-N-[(S)-[6-fluoro-5-(propan-2-yl)pyridin-2-yl](phenyl)methyl]pyrrolidine-2-carboxamide |
| 387 | 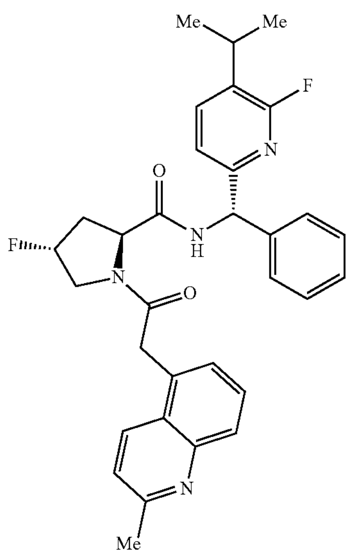 [SMILES: Cc1ccc2c(CC(=O)N3C[C@H](F)C[C@H]3C(=O)N[C@@H](c3ccccc3)c3ccc(C(C)C)c(F)n3)cccc2n1] | (2S,4R)-4-fluoro-N-[(S)-[6-fluoro-5-(propan-2-yl)pyridin-2-yl](phenyl)methyl]-1-[2-(2-methylquinolin-5-yl)acetyl]pyrrolidine-2-carboxamide |
| 388 | 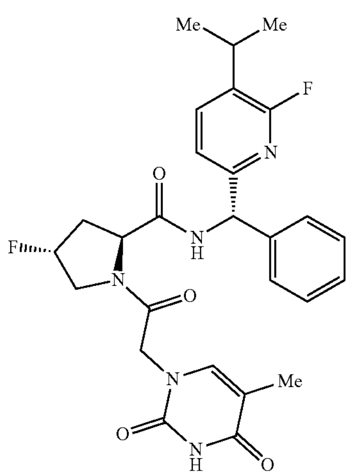 [SMILES: Cc1cn(CC(=O)N2C[C@H](F)C[C@H]2C(=O)N[C@@H](c2ccccc2)c2ccc(C(C)C)c(F)n2)c(=O)[nH]c1=O] | (2S,4R)-4-fluoro-N-[(S)-[6-fluoro-5-(propan-2-yl)pyridin-2-yl](phenyl)methyl]-1-[2-(5-methyl-2,4-dioxo-1,2,3,4-tetrahydropyrimidin-1-yl)acetyl]pyrrolidine-2-carboxamide |

TABLE 1-continued

| Compound No. | Structure | IUPAC |
|---|---|---|
| 389 | 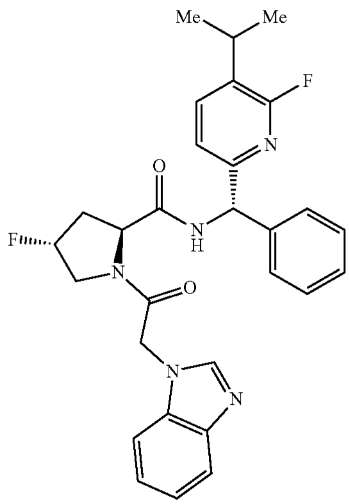 [SMILES: CC(C)c1ccc([C@@H](NC(=O)[C@@H]2C[C@@H](F)CN2C(=O)Cn2cnc3ccccc32)c2ccccc2)nc1F] | (2S,4R)-1-[2-(1H-1,3-benzodiazol-1-yl)acetyl]-4-fluoro-N-[(S)-[6-fluoro-5-(propan-2-yl)pyridin-2-yl](phenyl)methyl]pyrrolidine-2-carboxamide |
| 390 | 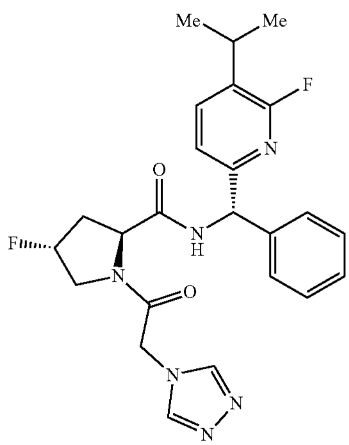 [SMILES: CC(C)c1ccc([C@@H](NC(=O)[C@@H]2C[C@@H](F)CN2C(=O)Cn2cnnc2)c2ccccc2)nc1F] | (2S,4R)-4-fluoro-N-[(S)-[6-fluoro-5-(propan-2-yl)pyridin-2-yl](phenyl)methyl]-1-[2-(4H-1,2,4-triazol-4-yl)acetyl]pyrrolidine-2-carboxamide |
| 391 | 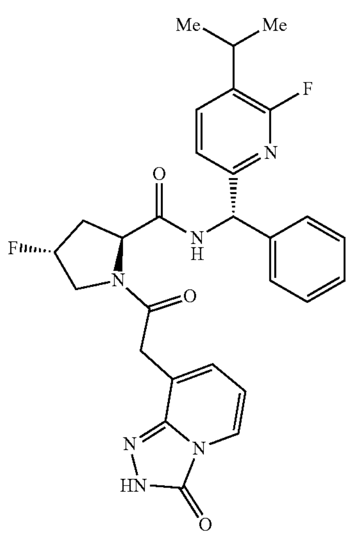 [SMILES: CC(C)c1ccc([C@@H](NC(=O)[C@@H]2C[C@@H](F)CN2C(=O)Cc2cccn3c(=O)[nH]nc23)c2ccccc2)nc1F] | (2S,4R)-4-fluoro-N-[(S)-[6-fluoro-5-(propan-2-yl)pyridin-2-yl](phenyl)methyl]-1-(2-{3-oxo-2H,3H-[1,2,4]triazolo[4,3-a]pyridin-8-yl}acetyl)pyrrolidine-2-carboxamide |

TABLE 1-continued

| Compound No. | Structure | IUPAC |
|---|---|---|
| 392 | 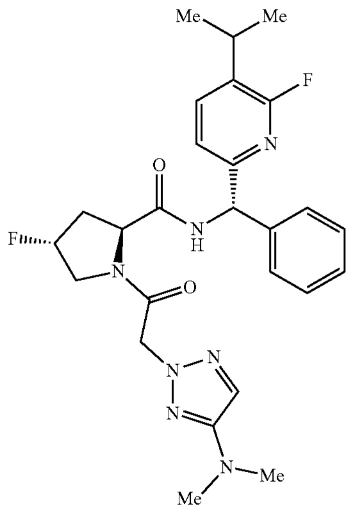 [SMILES: CC(C)c1ccc([C@@H](NC(=O)[C@@H]2C[C@@H](F)CN2C(=O)Cn2ncc(N(C)C)n2)c2ccccc2)nc1F] | (2S,4R)-1-{2-[4-(dimethylamino)-2H-1,2,3-triazol-2-yl]acetyl}-4-fluoro-N-[(S)-[6-fluoro-5-(propan-2-yl)pyridin-2-yl](phenyl)methyl]pyrrolidine-2-carboxamide |
| 393 | 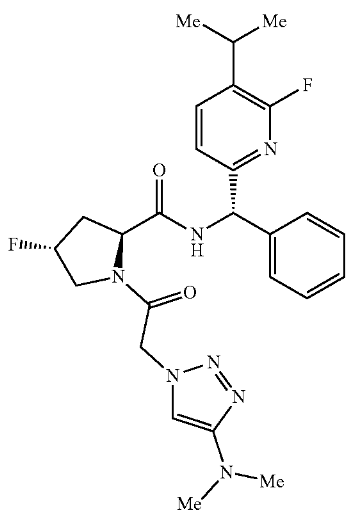 [SMILES: CC(C)c1ccc([C@@H](NC(=O)[C@@H]2C[C@@H](F)CN2C(=O)Cn2cc(N(C)C)nn2)c2ccccc2)nc1F] | (2S,4R)-1-{2-[4-(dimethylamino)-1H-1,2,3-triazol-1-yl]acetyl}-4-fluoro-N-[(S)-[6-fluoro-5-(propan-2-yl)pyridin-2-yl](phenyl)methyl]pyrrolidine-2-carboxamide |
| 394 | 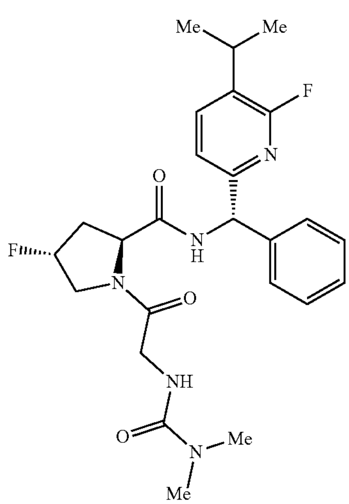 [SMILES: CC(C)c1ccc([C@@H](NC(=O)[C@@H]2C[C@@H](F)CN2C(=O)CNC(=O)N(C)C)c2ccccc2)nc1F] | (2S,4R)-1-{2-[(dimethylcarbamoyl)amino]acetyl}-4-fluoro-N-[(S)-[6-fluoro-5-(propan-2-yl)pyridin-2-yl](phenyl)methyl]pyrrolidine-2-carboxamide |

TABLE 1-continued

| Compound No. | Structure | IUPAC |
|---|---|---|
| 395 | 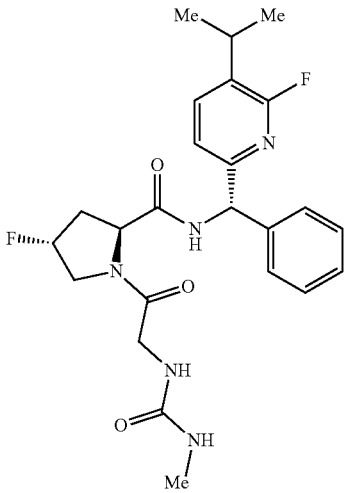 | (2S,4R)-4-fluoro-N-[(S)-[6-fluoro-5-(propan-2-yl)pyridin-2-yl](phenyl)methyl]-1-{2-[(methylcarbamoyl)amino]acetyl}pyrrolidine-2-carboxamide |
| 396 | 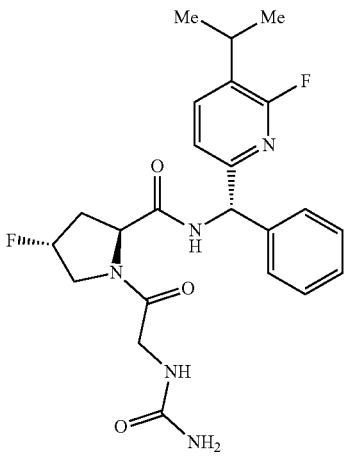 | (2S,4R)-1-[2-(carbamoylamino)acetyl]-4-fluoro-N-[(S)-[6-fluoro-5-(propan-2-yl)pyridin-2-yl](phenyl)methyl]pyrrolidine-2-carboxamide |
| 397 | 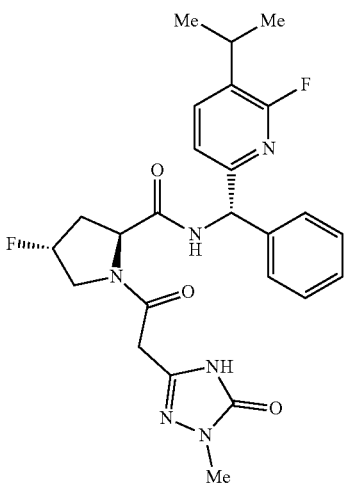 [SMILES: CC(C)c1ccc([C@@H](NC(=O)[C@@H]2C[C@@H](F)CN2C(=O)Cc2nn(C)c(=O)[nH]2)c2ccccc2)nc1F] | (2S,4R)-4-fluoro-N-[(S)-[6-fluoro-5-(propan-2-yl)pyridin-2-yl](phenyl)methyl]-1-[2-(1-methyl-5-oxo-4,5-dihydro-1H-1,2,4-triazol-3-yl)acetyl]pyrrolidine-2-carboxamide |

TABLE 1-continued

| Compound No. | Structure | IUPAC |
|---|---|---|
| 398 | 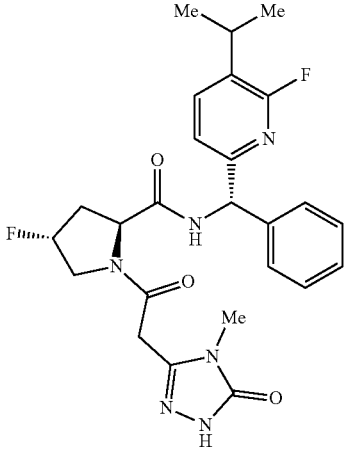 [SMILES: CC(C)c1ccc([C@@H](NC(=O)[C@@H]2C[C@@H](F)CN2C(=O)Cc2n[nH]c(=O)n2C)c2ccccc2)nc1F] | (2S,4R)-4-fluoro-N-[(S)-[6-fluoro-5-(propan-2-yl)pyridin-2-yl](phenyl)methyl]-1-[2-(4-methyl-5-oxo-4,5-dihydro-1H-1,2,4-triazol-3-yl)acetyl]pyrrolidine-2-carboxamide |
| 399 | 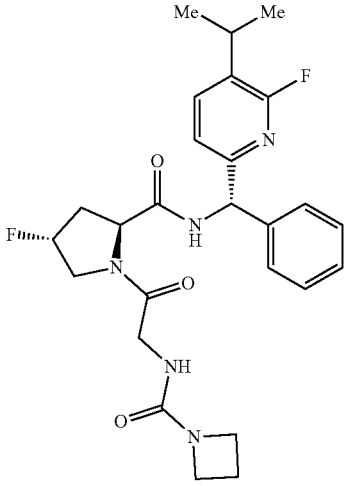 | (2S,4R)-1-{2-[(azetidine-1-carbonyl)amino]acetyl}-4-fluoro-N-[(S)-[6-fluoro-5-(propan-2-yl)pyridin-2-yl](phenyl)methyl]pyrrolidine-2-carboxamide |
| 400 | 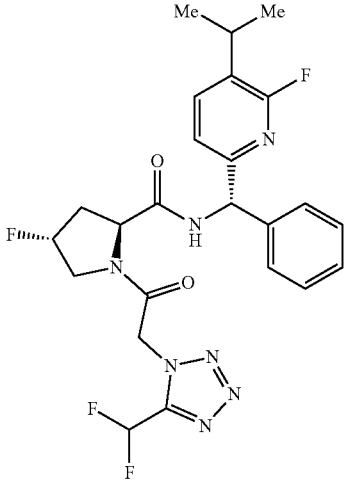 | (2S,4R)-1-{2-[5-(difluoromethyl)-1H-1,2,3-tetrazol-1-yl]acetyl}-4-fluoro-N-[(S)-[6-fluoro-5-(propan-2-yl)pyridin-2-yl](phenyl)methyl]pyrrolidine-2-carboxamide |

TABLE 1-continued

| Compound No. | Structure | IUPAC |
|---|---|---|
| 401 | 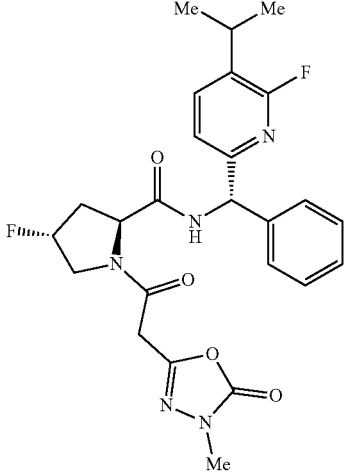 [SMILES: CC(C)c1ccc([C@@H](NC(=O)[C@@H]2C[C@@H](F)CN2C(=O)Cc2nn(C)c(=O)o2)c2ccccc2)nc1F] | (2S,4R)-4-fluoro-N-[(S)-[6-fluoro-5-(propan-2-yl)pyridin-2-yl](phenyl)methyl]-1-[2-(4-methyl-5-oxo-4,5-dihydro-1,3,4-oxadiazol-2-yl)acetyl]pyrrolidine-2-carboxamide |
| 402 | 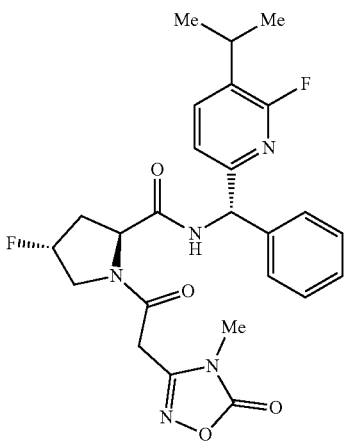 [SMILES: CC(C)c1ccc([C@@H](NC(=O)[C@@H]2C[C@@H](F)CN2C(=O)Cc2noc(=O)n2C)c2ccccc2)nc1F] | (2S,4R)-4-fluoro-N-[(S)-[6-fluoro-5-(propan-2-yl)pyridin-2-yl](phenyl)methyl]-1-[2-(4-methyl-5-oxo-4,5-dihydro-1,2,4-oxadiazol-3-yl)acetyl]pyrrolidine-2-carboxamide |
| 403 | 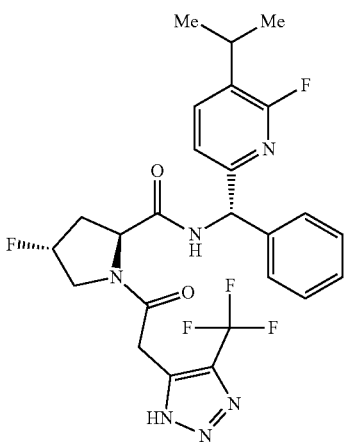 | (2S,4R)-4-fluoro-N-[(S)-[6-fluoro-5-(propan-2-yl)pyridin-2-yl](phenyl)methyl]-1-{2-[4-(trifluoromethyl)-1H-1,2,3-triazol-5-yl]acetyl}pyrrolidine-2-carboxamide |

TABLE 1-continued

| Compound No. | Structure | IUPAC |
|---|---|---|
| 404 | 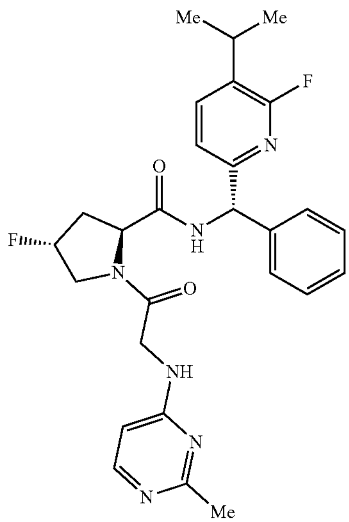 [SMILES: Cc1nccc(NCC(=O)N2C[C@H](F)C[C@H]2C(=O)N[C@@H](c2ccccc2)c2ccc(C(C)C)c(F)n2)n1] | (2S,4R)-4-fluoro-N-[(S)-[6-fluoro-5-(propan-2-yl)pyridin-2-yl](phenyl)methyl]-1-{2-[(2-methylpyrimidin-4-yl)amino]acetyl}pyrrolidine-2-carboxamide |
| 405 | 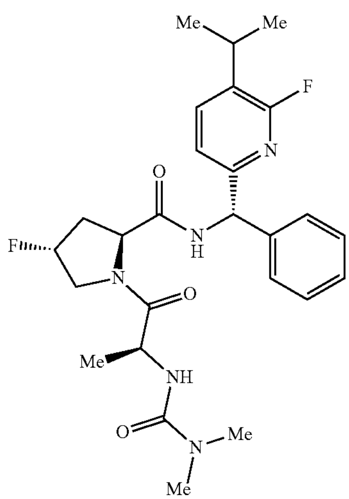 [SMILES: CC(C)c1ccc([C@@H](NC(=O)[C@@H]2C[C@@H](F)CN2C(=O)[C@H](C)NC(=O)N(C)C)c2ccccc2)nc1F] | (2S,4R)-1-[(2S)-2-[(dimethylcarbamoyl)amino]propanoyl]-4-fluoro-N-[(S)-[6-fluoro-5-(propan-2-yl)pyridin-2-yl](phenyl)methyl]pyrrolidine-2-carboxamide |
| 406 | 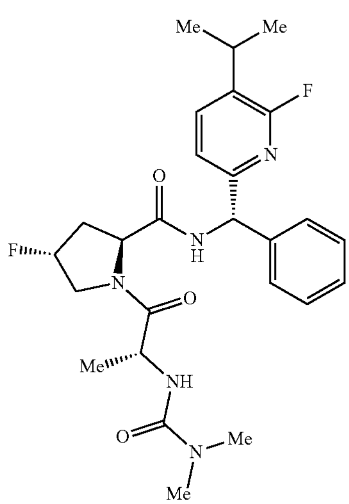 [SMILES: CC(C)c1ccc([C@@H](NC(=O)[C@@H]2C[C@@H](F)CN2C(=O)[C@@H](C)NC(=O)N(C)C)c2ccccc2)nc1F] | (2S,4R)-1-[(2R)-2-[(dimethylcarbamoyl)amino]propanoyl]-4-fluoro-N-[(S)-[6-fluoro-5-(propan-2-yl)pyridin-2-yl](phenyl)methyl]pyrrolidine-2-carboxamide |

TABLE 1-continued

| Compound No. | Structure | IUPAC |
|---|---|---|
| 407 | 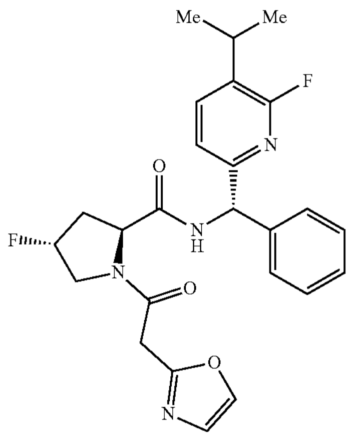 [SMILES: CC(C)c1ccc([C@@H](NC(=O)[C@@H]2C[C@@H](F)CN2C(=O)Cc2ncco2)c2ccccc2)nc1F] | (2S,4R)-4-fluoro-N-[(S)-[6-fluoro-5-(propan-2-yl)pyridin-2-yl](phenyl)methyl]-1-[2-(1,3-oxazol-2-yl)acetyl]pyrrolidine-2-carboxamide |
| 408 | 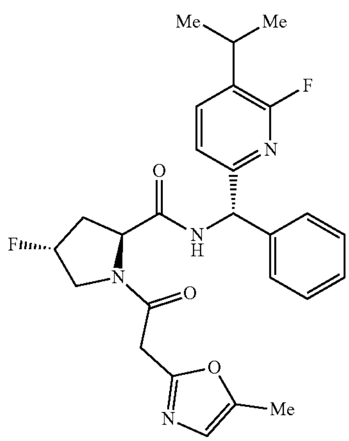 [SMILES: Cc1cnc(CC(=O)N2C[C@H](F)C[C@H]2C(=O)N[C@@H](c2ccccc2)c2ccc(C(C)C)c(F)n2)o1] | (2S,4R)-4-fluoro-N-[(S)-[6-fluoro-5-(propan-2-yl)pyridin-2-yl](phenyl)methyl]-1-[2-(5-methyl-1,3-oxazol-2-yl)acetyl]pyrrolidine-2-carboxamide |
| 409 | 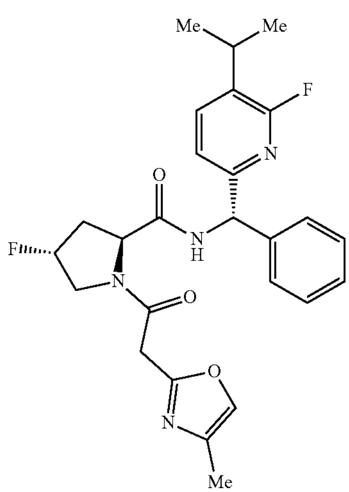 [SMILES: Cc1coc(CC(=O)N2C[C@H](F)C[C@H]2C(=O)N[C@@H](c2ccccc2)c2ccc(C(C)C)c(F)n2)n1] | (2S,4R)-4-fluoro-N-[(S)-[6-fluoro-5-(propan-2-yl)pyridin-2-yl](phenyl)methyl]-1-[2-(4-methyl-1,3-oxazol-2-yl)acetyl]pyrrolidine-2-carboxamide |

TABLE 1-continued

| Compound No. | Structure | IUPAC |
|---|---|---|
| 410 | 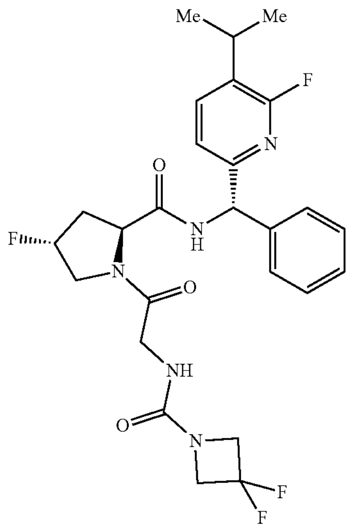 [SMILES: CC(C)c1ccc([C@@H](NC(=O)[C@@H]2C[C@@H](F)CN2C(=O)CNC(=O)N2CC(F)(F)C2)c2ccccc2)nc1F] | (2S,4R)-1-{2-[(3,3-difluoroazetidine-1-carbonyl)amino]acetyl}-4-fluoro-N-[(S)-[6-fluoro-5-(propan-2-yl)pyridin-2-yl](phenyl)methyl]pyrrolidine-2-carboxamide |
| 411 | 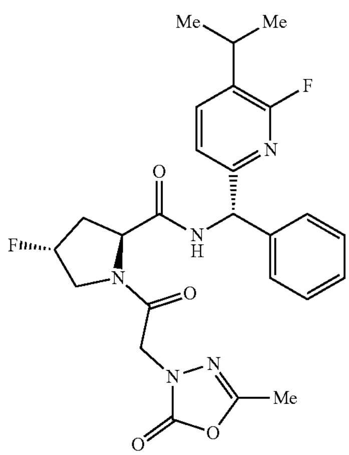 [SMILES: Cc1nn(CC(=O)N2C[C@H](F)C[C@H]2C(=O)N[C@@H](c2ccccc2)c2ccc(C(C)C)c(F)n2)c(=O)o1] | (2S,4R)-4-fluoro-N-[(S)-[6-fluoro-5-(propan-2-yl)pyridin-2-yl](phenyl)methyl]-1-[2-(5-methyl-2-oxo-2,3-dihydro-1,3,4-oxadiazol-3-yl)acetyl]pyrrolidine-2-carboxamide |
| 412 | 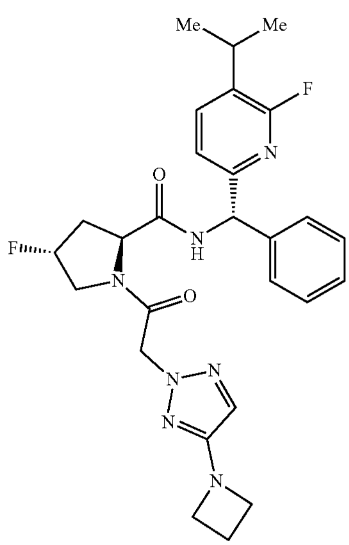 [SMILES: CC(C)c1ccc([C@@H](NC(=O)[C@@H]2C[C@@H](F)CN2C(=O)Cn2ncc(N3CCC3)n2)c2ccccc2)nc1F] | (2S,4R)-1-{2-[4-(azetidin-1-yl)-2H-1,2,3-triazol-2-yl]acetyl}-4-fluoro-N-[(S)-[6-fluoro-5-(propan-2-yl)pyridin-2-yl](phenyl)methyl]pyrrolidine-2-carboxamide |

TABLE 1-continued

| Compound No. | Structure | IUPAC |
|---|---|---|
| 413 | 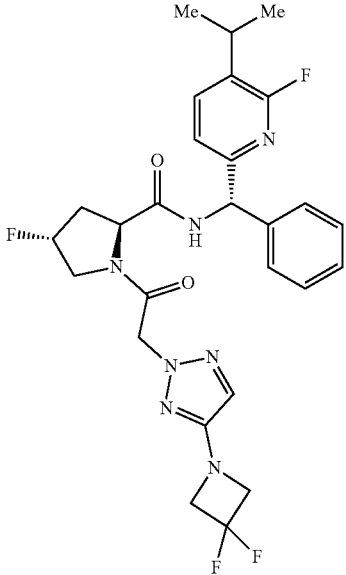 [SMILES: CC(C)c1ccc([C@@H](NC(=O)[C@@H]2C[C@@H](F)CN2C(=O)Cn2ncc(N3CC(F)(F)C3)n2)c2ccccc2)nc1F] | (2S,4R)-1-{2-[4-(3,3-difluoroazetidin-1-yl)-2H-1,2,3-triazol-2-yl]acetyl}-4-fluoro-N-[(S)-[6-fluoro-5-(propan-2-yl)pyridin-2-yl](phenyl)methyl]pyrrolidine-2-carboxamide |
| 414 | 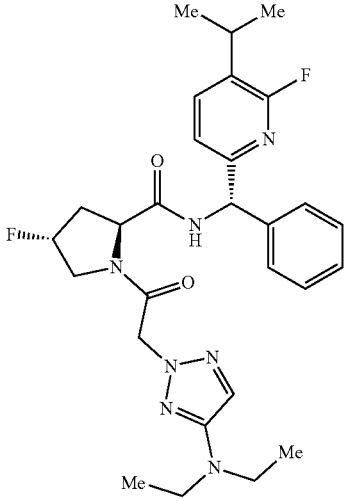 [SMILES: CCN(CC)c1cnn(CC(=O)N2C[C@H](F)C[C@H]2C(=O)N[C@@H](c2ccccc2)c2ccc(C(C)C)c(F)n2)n1] | (2S,4R)-1-{2-[4-(diethylamino)-2H-1,2,3-triazol-2-yl]acetyl}-4-fluoro-N-[(S)-[6-fluoro-5-(propan-2-yl)pyridin-2-yl](phenyl)methyl]pyrrolidine-2-carboxamide |
| 415 | 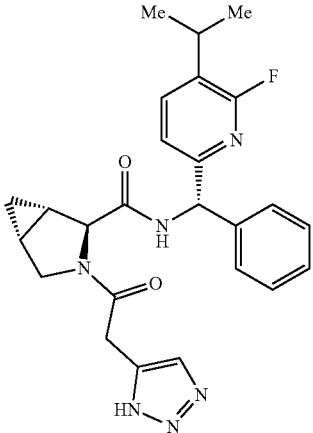 [SMILES: CC(C)c1ccc([C@@H](NC(=O)[C@@H]2[C@H]3C[C@H]3CN2C(=O)Cc2cnn[nH]2)c2ccccc2)nc1F] | (1S,2S,5R)-N-[(S)-[6-fluoro-5-(propan-2-yl)pyridin-2-yl](phenyl)methyl]-3-[2-(1H-1,2,3-triazol-5-yl)acetyl]-3-azabicyclo[3.1.0]hexane-2-carboxamide |

TABLE 1-continued

| Compound No. | Structure | IUPAC |
|---|---|---|
| 416 | 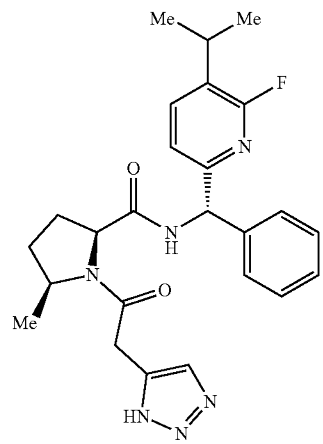 [SMILES: CC(C)c1ccc([C@@H](NC(=O)[C@@H]2CC[C@H](C)N2C(=O)Cc2cnn[nH]2)c2ccccc2)nc1F] | (2S,5S)-N-[(S)-[6-fluoro-5-(propan-2-yl)pyridin-2-yl](phenyl)methyl]-5-methyl-1-[2-(1H-1,2,3-triazol-5-yl)acetyl]pyrrolidine-2-carboxamide |
| 417 | 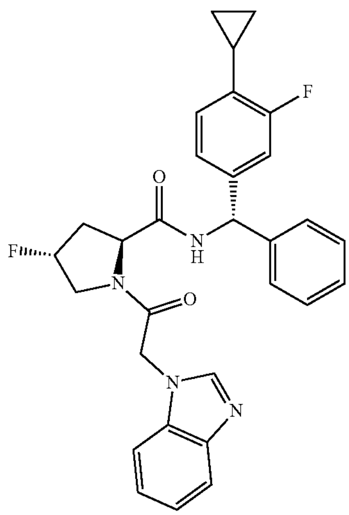 [SMILES: O=C(N[C@@H](c1ccccc1)c1ccc(C2CC2)c(F)c1)[C@@H]1C[C@@H](F)CN1C(=O)Cn1cnc2ccccc21] | (2S,4R)-1-(2-(1H-benzo[d]imidazol-1-yl)acetyl)-N-((S)-(4-cyclopropyl-3-fluorophenyl)(phenyl)methyl)-4-fluoropyrrolidine-2-carboxamide |
| 418 | 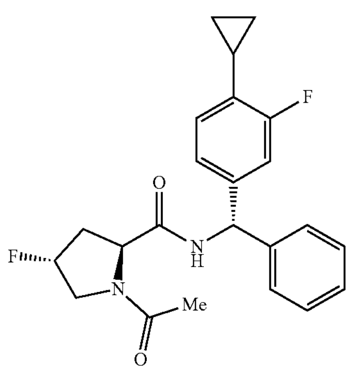 [SMILES: CC(=O)N1C[C@H](F)C[C@H]1C(=O)N[C@@H](c1ccccc1)c1ccc(C2CC2)c(F)c1] | (2S,4R)-1-acetyl-N-[(S)-(4-cyclopropyl-3-fluorophenyl)(phenyl)methyl]-4-fluoropyrrolidine-2-carboxamide |

| Compound No. | Structure | IUPAC |
|---|---|---|
| 419 | 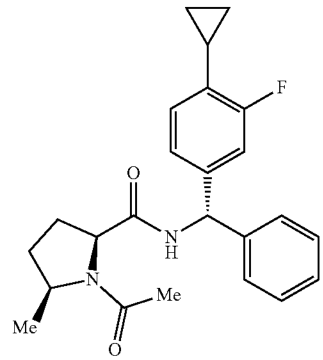 [SMILES: CC(=O)N1[C@@H](C)CC[C@H]1C(=O)N[C@@H](c1ccccc1)c1ccc(C2CC2)c(F)c1] | (2S,5S)-1-acetyl-N-[(S)-(4-cyclopropyl-3-fluorophenyl)(phenyl)methyl]-5-methylpyrrolidine-2-carboxamide |
| 420 | 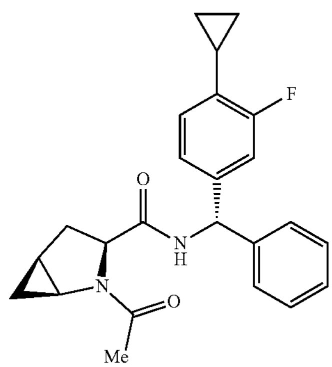 [SMILES: CC(=O)N1[C@H](C(=O)N[C@@H](c2ccccc2)c2ccc(C3CC3)c(F)c2)C[C@@H]2C[C@@H]21] | (1S,3S,5S)-2-acetyl-N-[(S)-(4-cyclopropyl-3-fluorophenyl)(phenyl)methyl]-2-azabicyclo[3.1.0]hexane-3-carboxamide |
| 421 | 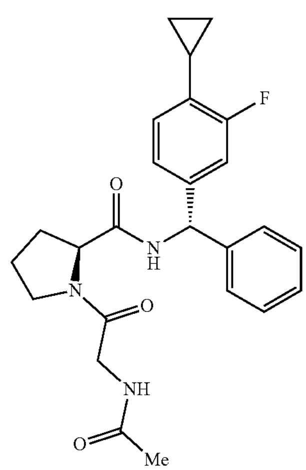 [SMILES: CC(=O)NCC(=O)N1CCC[C@H]1C(=O)N[C@@H](c1ccccc1)c1ccc(C2CC2)c(F)c1] | (2S)-N-[(S)-(4-cyclopropyl-3-fluorophenyl)(phenyl)methyl]-1-(2-acetamidoacetyl)pyrrolidine-2-carboxamide |

TABLE 1-continued

| Compound No. | Structure | IUPAC |
|---|---|---|
| 422 | 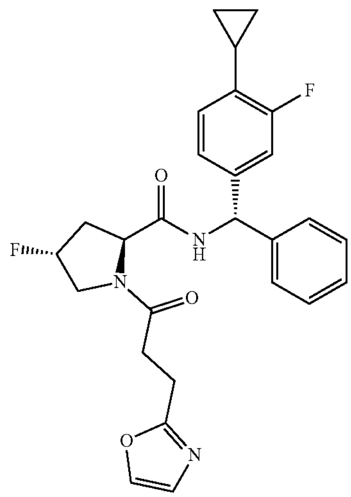 [SMILES: O=C(N[C@@H](c1ccccc1)c1ccc(C2CC2)c(F)c1)[C@@H]1C[C@@H](F)CN1C(=O)CCc1ncco1] | (2S,4R)-N-[(S)-(4-cyclopropyl-3-fluorophenyl)(phenyl)methyl]-4-fluoro-1-[3-(1,3-oxazol-2-yl)propanoyl]pyrrolidine-2-carboxamide |
| 423 | 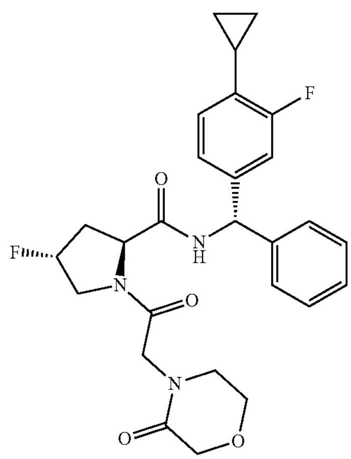 [SMILES: O=C(N[C@@H](c1ccccc1)c1ccc(C2CC2)c(F)c1)[C@@H]1C[C@@H](F)CN1C(=O)CN1CCOCC1=O] | (2S,4R)-N-[(S)-(4-cyclopropyl-3-fluorophenyl)(phenyl)methyl]-4-fluoro-1-[2-(3-oxomorpholin-4-yl)acetyl]pyrrolidine-2-carboxamide |
| 424 | 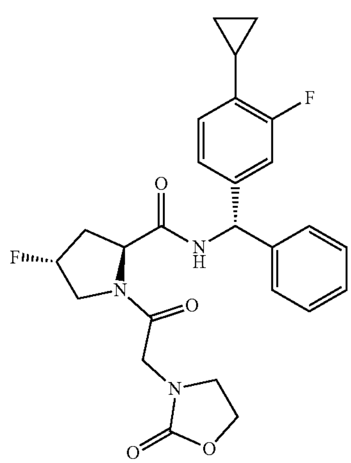 [SMILES: O=C(N[C@@H](c1ccccc1)c1ccc(C2CC2)c(F)c1)[C@@H]1C[C@@H](F)CN1C(=O)CN1CCOC1=O] | (2S,4R)-N-[(S)-(4-cyclopropyl-3-fluorophenyl)(phenyl)methyl]-4-fluoro-1-[2-(2-oxo-1,3-oxazolidin-3-yl)acetyl]pyrrolidine-2-carboxamide |

TABLE 1-continued

| Compound No. | Structure | IUPAC |
|---|---|---|
| 425 | 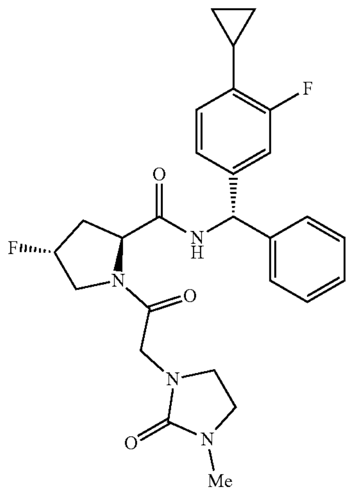 [SMILES: CN1CCN(CC(=O)N2C[C@H](F)C[C@H]2C(=O)N[C@@H](c2ccccc2)c2ccc(C3CC3)c(F)c2)C1=O] | (2S,4R)-N-[(S)-(4-cyclopropyl-3-fluorophenyl)(phenyl)methyl]-4-fluoro-1-[2-(3-methyl-2-oxoimidazolidin-1-yl)acetyl]pyrroldine-2-carboxamide |
| 426 | 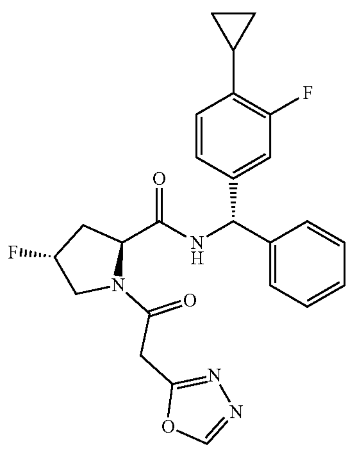 [SMILES: O=C(N[C@@H](c1ccccc1)c1ccc(C2CC2)c(F)c1)[C@@H]1C[C@@H](F)CN1C(=O)Cc1nnco1] | (2S,4R)-N-[(S)-(4-cyclopropyl-3-fluorophenyl)(phenyl)methyl]-4-fluoro-1-[2-(1,3,4-oxadiazol-2-yl)acetyl]pyrrolidine-2-carboxamide |
| 427 | 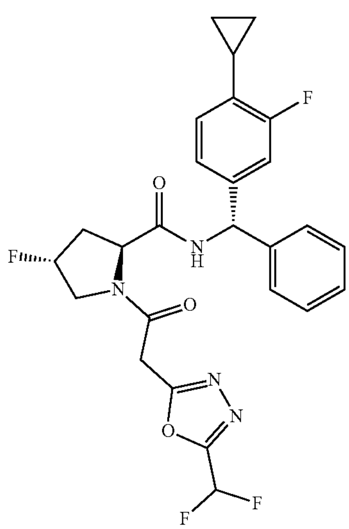 [SMILES: O=C(N[C@@H](c1ccccc1)c1ccc(C2CC2)c(F)c1)[C@@H]1C[C@@H](F)CN1C(=O)Cc1nnc(C(F)F)o1] | (2S,4R)-N-[(S)-(4-cyclopropyl-3-fluorophenyl)(phenyl)methyl]-1-{2-[5-(difluoromethyl)-1,3,4-oxadiazol-2-yl]acetyl}-4-fluoropyrrolidine-2-carboxamide |

TABLE 1-continued

| Compound No. | Structure | IUPAC |
|---|---|---|
| 428 | 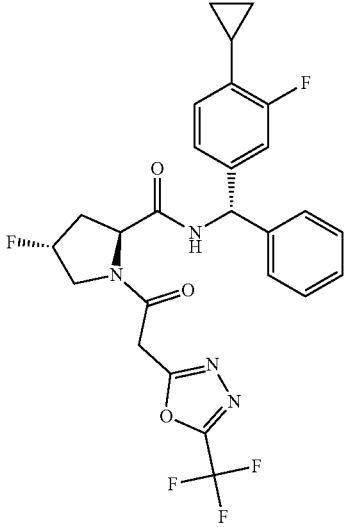 [SMILES: O=C(N[C@@H](c1ccccc1)c1ccc(C2CC2)c(F)c1)[C@@H]1C[C@@H](F)CN1C(=O)Cc1nnc(C(F)(F)F)o1] | (2S,4R)-N-[(S)-4-cyclopropyl-3-fluorophenyl)(phenyl)methyl]-4-fluoro-1-{2-[5-(trifluoromethyl)-1,3,4-oxadiazol-2-yl]acetyl}pyrrolidine-2-carboxamide |
| 429 | 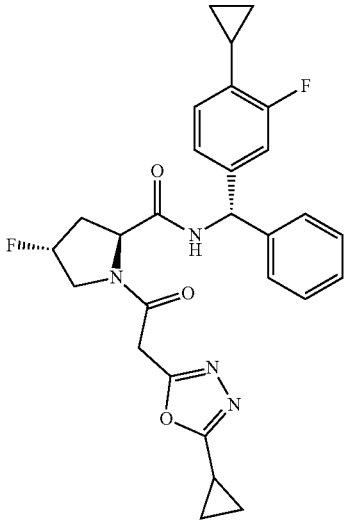 | (2S,4R)-1-[2-(5-cyclopropyl-1,3,4-oxadiazol-2-yl)acetyl]-N-[(S)-(4-cyclopropyl-3-fluorophenyl)(phenyl)methyl]-4-fluoropyrrolidine-2-carboxamide |
| 430 | 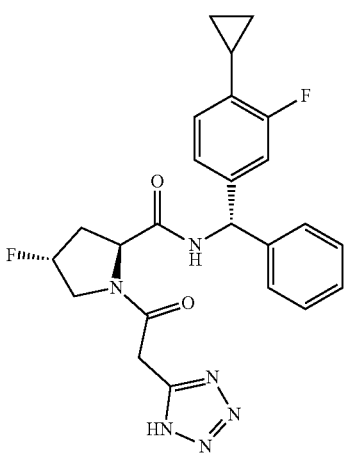 | (2S,4R)-N-[(S)-(4-cyclopropyl-3-fluorophenyl)(phenyl)methyl]-4-fluoro-1-[2-(1H-1,2,3-tetrazol-5-yl)acetyl]pyrrolidine-2-carboxamide |

TABLE 1-continued

| Compound No. | Structure | IUPAC |
|---|---|---|
| 431 | 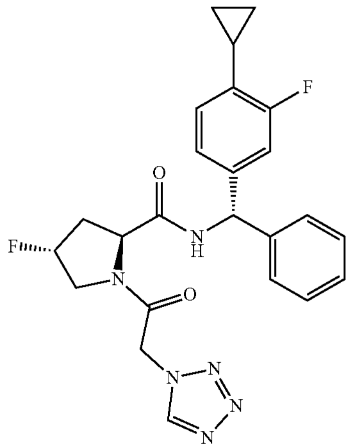 [SMILES: O=C(N[C@@H](c1ccccc1)c1ccc(C2CC2)c(F)c1)[C@@H]1C[C@@H](F)CN1C(=O)Cn1cnnn1] | (2S,4R)-N-[(S)-(4-cyclopropyl-3-fluorophenyl)(phenyl)methyl]-4-fluoro-1-[2-(1H-1,2,3,4-tetrazol-1-yl)acetyl]pyrrolidine-2-carboxamide |
| 432 | 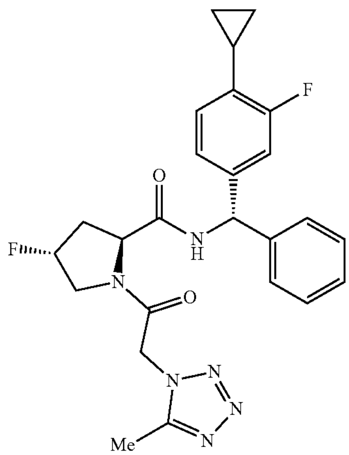 [SMILES: Cc1nnnn1CC(=O)N1C[C@H](F)C[C@H]1C(=O)N[C@@H](c1ccccc1)c1ccc(C2CC2)c(F)c1] | (2S,4R)-N-[(S)-(4-cyclopropyl-3-fluorophenyl)(phenyl)methyl]-4-fluoro-1-[2-(5-methyl-1H-1,3,4-tetrazol-1-yl)acetyl]pyrrolidine-2-carboxamide |
| 433 | 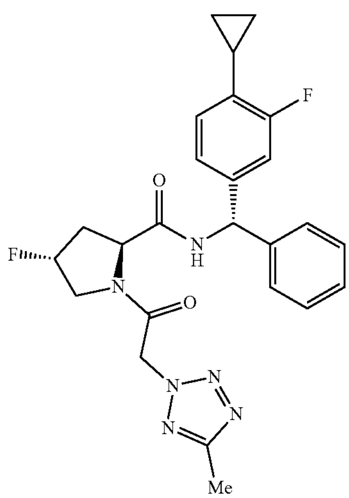 [SMILES: Cc1nnn(CC(=O)N2C[C@H](F)C[C@H]2C(=O)N[C@@H](c2ccccc2)c2ccc(C3CC3)c(F)c2)n1] | (2S,4R)-N-[(S)-(4-cyclopropyl-3-fluorophenyl)(phenyl)methyl]-4-fluoro-1-[2-(5-methyl-2H-1,3,4-tetrazol-2-yl)acetyl]pyrrolidine-2-carboxamide |

TABLE 1-continued

| Compound No. | Structure | IUPAC |
|---|---|---|
| 434 | 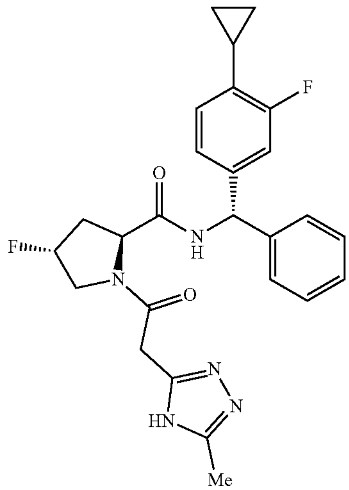 [SMILES: Cc1nnc(CC(=O)N2C[C@H](F)C[C@H]2C(=O)N[C@@H](c2ccccc2)c2ccc(C3CC3)c(F)c2)[nH]1] | (2S,4R)-N-[(S)-(4-cyclopropyl-3-fluorophenyl)(phenyl)methyl]-4-fluoro-1-[2-(5-methyl-4H-1,2,4-triazol-3-yl)acetyl]pyrrolidine-2-carboxamide |
| 435 | 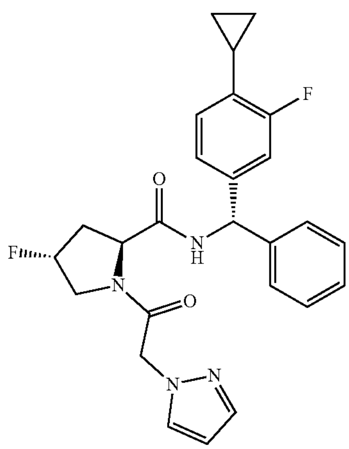 [SMILES: O=C(N[C@@H](c1ccccc1)c1ccc(C2CC2)c(F)c1)[C@@H]1C[C@@H](F)CN1C(=O)Cn1cccn1] | (2S,4R)-N-[(S)-(4-cyclopropyl-3-fluorophenyl)(phenyl)methyl]-4-fluoro-1-[2-(1H-pyrazol-1-yl)acetyl]pyrrolidine-2-carboxamide |
| 436 | 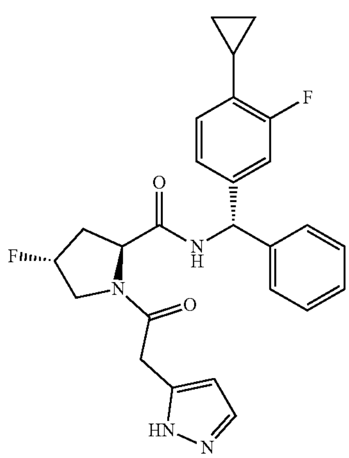 [SMILES: O=C(N[C@@H](c1ccccc1)c1ccc(C2CC2)c(F)c1)[C@@H]1C[C@@H](F)CN1C(=O)Cc1ccn[nH]1] | (2S,4R)-N-[(S)-(4-cyclopropyl-3-fluorophenyl)(phenyl)methyl]-4-fluoro-1-[2-(1H-pyrazol-5-yl)acetyl]pyrrolidine-2-carboxamide |

TABLE 1-continued

| Compound No. | Structure | IUPAC |
|---|---|---|
| 437 | 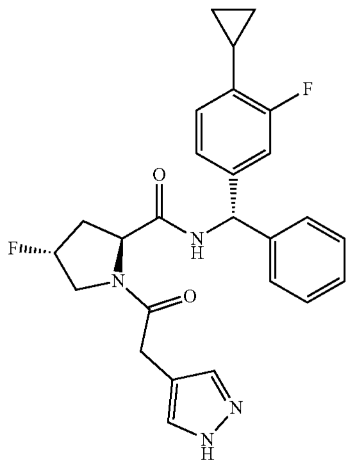 [SMILES: O=C(N[C@@H](c1ccccc1)c1ccc(C2CC2)c(F)c1)[C@@H]1C[C@@H](F)CN1C(=O)Cc1cn[nH]c1] | (2S,4R)-N-[(S)-(4-cyclopropyl-3-fluorophenyl)(phenyl)methyl]-4-fluoro-1-[2-(1H-pyrazol-4-yl)acetyl]pyrrolidine-2-carboxamide |
| 438 | 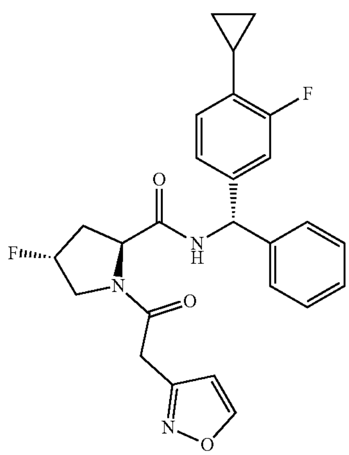 [SMILES: O=C(N[C@@H](c1ccccc1)c1ccc(C2CC2)c(F)c1)[C@@H]1C[C@@H](F)CN1C(=O)Cc1ccon1] | (2S,4R)-N-[(S)-(4-cyclopropyl-3-fluorophenyl)(phenyl)methyl]-4-fluoro-1-[2-(1,2-oxazol-3-yl)acetyl]pyrrolidine-2-carboxamide |
| 439 | 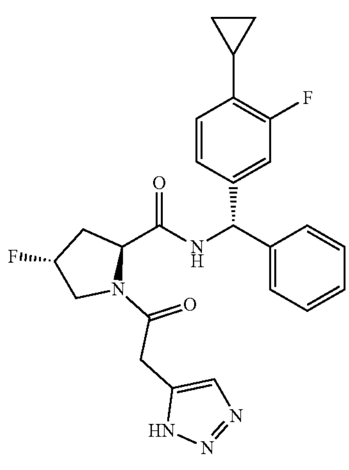 [SMILES: O=C(N[C@@H](c1ccccc1)c1ccc(C2CC2)c(F)c1)[C@@H]1C[C@@H](F)CN1C(=O)Cc1cnn[nH]1] | (2S,4R)-N-[(S)-(4-cyclopropyl-3-fluorophenyl)(phenyl)methyl]-4-fluoro-1-[2-(1H-1,2,3-triazol-5-yl)acetyl]pyrrolidine-2-carboxamide |

TABLE 1-continued

| Compound No. | Structure | IUPAC |
|---|---|---|
| 440 | 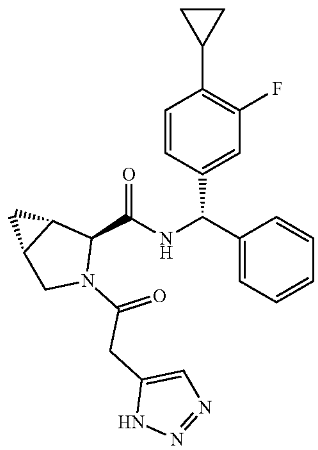 [SMILES: O=C(N[C@@H](c1ccccc1)c1ccc(C2CC2)c(F)c1)[C@@H]1[C@H]2C[C@H]2CN1C(=O)Cc1cnn[nH]1] | (1S,2S,5R)-N-[(S)-(4-cyclopropyl-3-fluorophenyl)(phenyl)methyl]-3-[2-(1H-1,2,3-triazol-5-yl)acetyl]-3-azabicyclo[3.1.0]hexane-2-carboxamide |
| 441 | 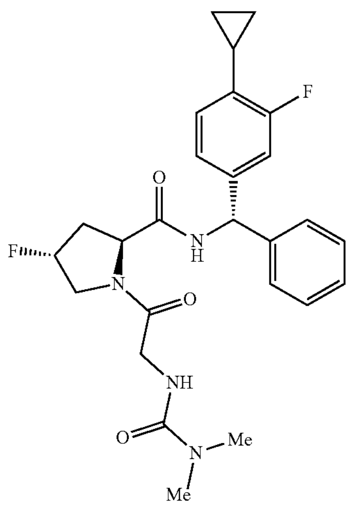 [SMILES: CN(C)C(=O)NCC(=O)N1C[C@H](F)C[C@H]1C(=O)N[C@@H](c1ccccc1)c1ccc(C2CC2)c(F)c1] | (2S,4R)-N-[(S)-(4-cyclopropyl-3-fluorophenyl)(phenyl)methyl]-1-{2-[(dimethylcarbamoyl)amino]acetyl}-4-fluoropyrrolidine-2-carboxamide |
| 442 | 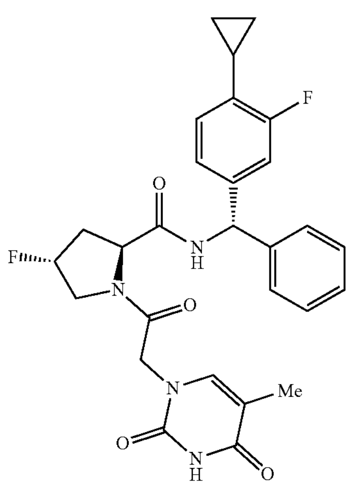 [SMILES: Cc1cn(CC(=O)N2C[C@H](F)C[C@H]2C(=O)N[C@@H](c2ccccc2)c2ccc(C3CC3)c(F)c2)c(=O)[nH]c1=O] | (2S,4R)-N-[(S)-(4-cyclopropyl-3-fluorophenyl)(phenyl)methyl]-4-fluoro-1-[2-(5-methyl-2,4-dioxo-1,2,3,4-tetrahydropyrimidin-1-yl)acetyl]pyrrolidine-2-carboxamide |

TABLE 1-continued

| Compound No. | Structure | IUPAC |
|---|---|---|
| 443 | 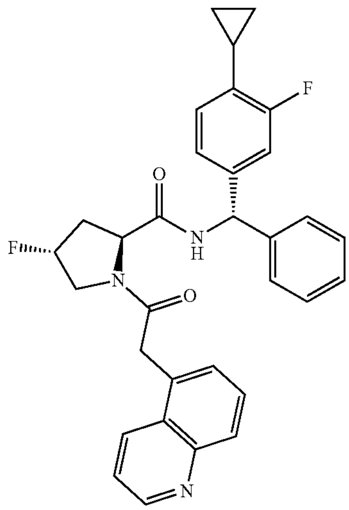 [SMILES: O=C(N[C@@H](c1ccccc1)c1ccc(C2CC2)c(F)c1)[C@@H]1C[C@@H](F)CN1C(=O)Cc1cccc2ncccc12] | (2S,4R)-N-[(S)-(4-cyclopropyl-3-fluorophenyl)(phenyl)methyl]-4-fluoro-1-[2-(quinolin-5-yl)acetyl]pyrrolidine-2-carboxamide |
| 444 | 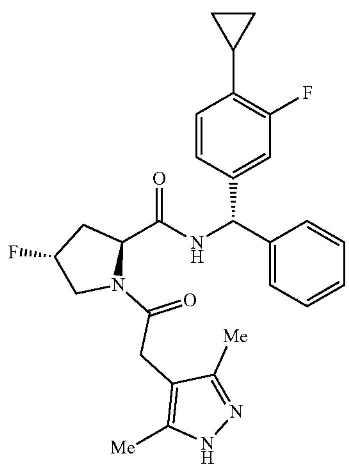 [SMILES: Cc1n[nH]c(C)c1CC(=O)N1C[C@H](F)C[C@H]1C(=O)N[C@@H](c1ccccc1)c1ccc(C2CC2)c(F)c1] | (2S,4R)-N-[(S)-(4-cyclopropyl-3-fluorophenyl)(phenyl)methyl]-1-[2-(3,5-dimethyl-1H-pyrazol-4-yl)acetyl]-4-fluoropyrrolidine-2-carboxamide |
| 445 | 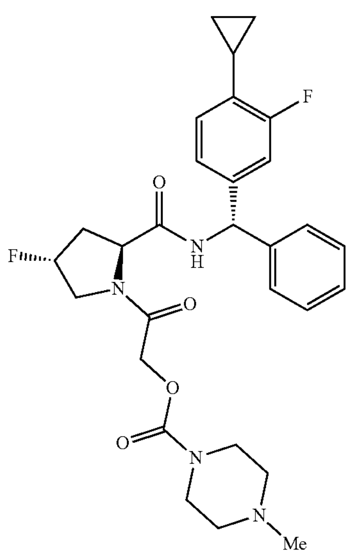 [SMILES: CN1CCN(C(=O)OCC(=O)N2C[C@H](F)C[C@H]2C(=O)N[C@@H](c2ccccc2)c2ccc(C3CC3)c(F)c2)CC1] | 2-[(2S,4R)-2-{[(S)-(4-cyclopropyl-3-fluorophenyl)(phenyl)methyl]carbamoyl}-4-fluoropyrrolidin-1-yl]-2-oxoethyl 4-methylpiperazine-1-carboxylate |

TABLE 1-continued
| Compound No. | Structure | IUPAC |
|---|---|---|
| 446 | 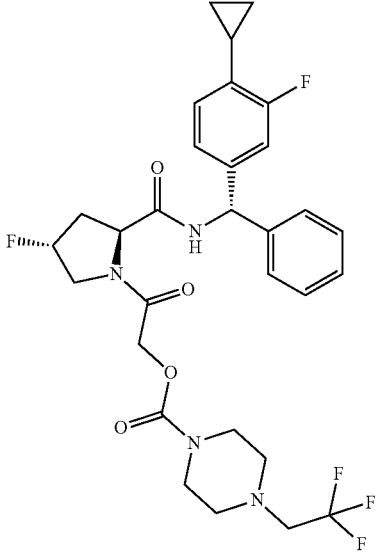 [SMILES: O=C(N[C@@H](c1ccccc1)c1ccc(C2CC2)c(F)c1)[C@@H]1C[C@@H](F)CN1C(=O)COC(=O)N1CCN(CC(F)(F)F)CC1] | 2-[(2S,4R)-2-{[(S)-(4-cyclopropyl-3-fluorophenyl)(phenyl)methyl]carbamoyl}-4-fluoropyrrolidin-1-yl]-2-oxoethyl 4-(2,2,2-trifluoroethyl)piperazine-1-carboxylate |
| 447 | 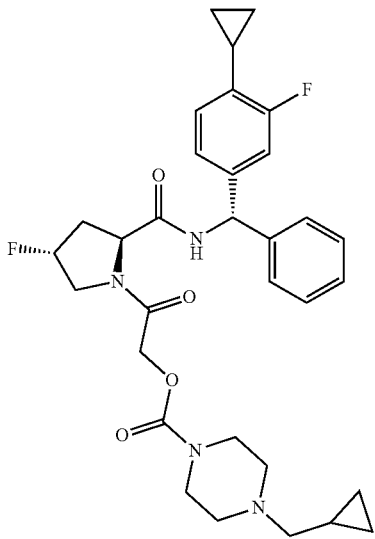 [SMILES: O=C(N[C@@H](c1ccccc1)c1ccc(C2CC2)c(F)c1)[C@@H]1C[C@@H](F)CN1C(=O)COC(=O)N1CCN(CC2CC2)CC1] | 2-[(2S,4R)-2-{[(S)-(4-cyclopropyl-3-fluorophenyl)(phenyl)methyl]carbamoyl}-4-fluoropyrrolidin-1-yl]-2-oxoethyl 4-(cyclopropylmethyl)piperazine-1-carboxylate |

TABLE 1-continued

| Compound No. | Structure | IUPAC |
|---|---|---|
| 448 | 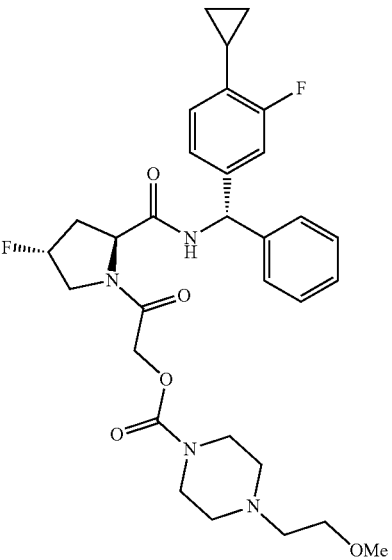 [SMILES: COCCN1CCN(C(=O)OCC(=O)N2C[C@H](F)C[C@H]2C(=O)N[C@@H](c2ccccc2)c2ccc(C3CC3)c(F)c2)CC1] | 2-[(2S,4R)-2-{[(S)-(4-cyclopropyl-3-fluorophenyl)(phenyl)methyl]carbamoyl}-4-fluoropyrrolidin-1-yl]-2-oxoethyl 4-(2-methoxyethyl)piperazine-1-carboxylate |
| 449 | 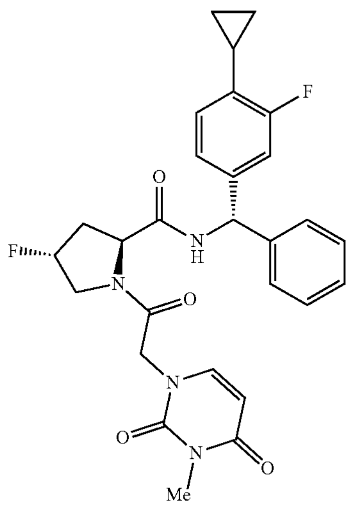 [SMILES: Cn1c(=O)ccn(CC(=O)N2C[C@H](F)C[C@H]2C(=O)N[C@@H](c2ccccc2)c2ccc(C3CC3)c(F)c2)c1=O] | (2S,4R)-N-[(S)-(4-cyclopropyl-3-fluorophenyl)(phenyl)methyl]-4-fluoro-1-[2-(3-methyl-2,4-dioxo-1,2,3,4-tetrahydropyrimidin-1-yl)acetyl]pyrrolidine-2-carboxamide |
| 450 | 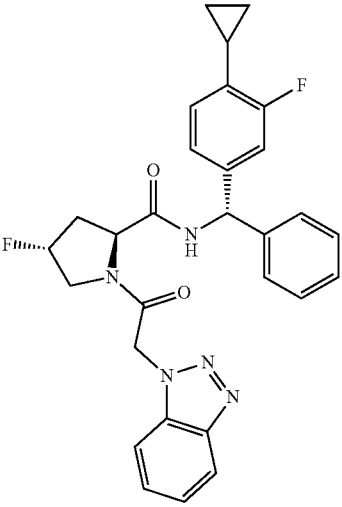 | (2S,4R)-1-[2-(1H-1,2,3-benzotriazol-1-yl)acetyl]-N-[(S)-(4-cyclopropyl-3-fluorophenyl)(phenyl)methyl]-4-fluoropyrrolidine-2-carboxamide |

TABLE 1-continued

| Compound No. | Structure | IUPAC |
|---|---|---|
| 451 | 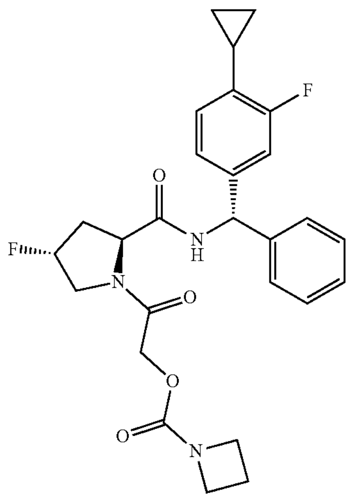 [SMILES: O=C(N[C@@H](c1ccccc1)c1ccc(C2CC2)c(F)c1)[C@@H]1C[C@@H](F)CN1C(=O)COC(=O)N1CCC1] | 2-[(2S,4R)-2-{[(S)-(4-cyclopropyl-3-fluorophenyl)(phenyl)methyl]carbamoyl}-4-fluoropyrrolidin-1-yl]-2-oxoethyl azetidine-1-carboxylate |
| 452 | 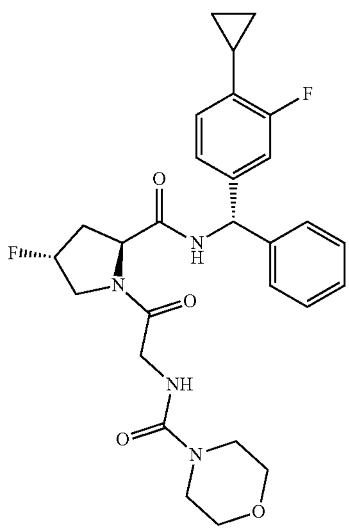 [SMILES: O=C(N[C@@H](c1ccccc1)c1ccc(C2CC2)c(F)c1)[C@@H]1C[C@@H](F)CN1C(=O)CNC(=O)N1CCOCC1] | N-{2-[(2S,4R)-2-{[(S)-(4-cyclopropyl-3-fluorophenyl)(phenyl)methyl]carbamoyl}-4-fluoropyrrolidin-1-yl]-2-oxoethyl}morpholine-4-carboxamide |
| 453 | 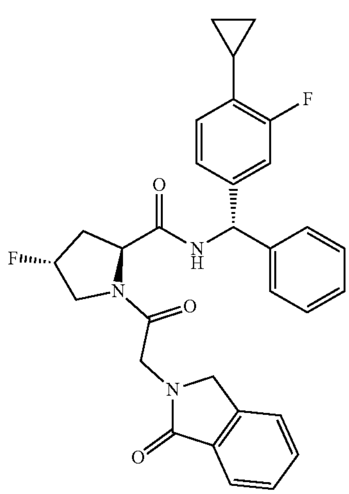 [SMILES: O=C(N[C@@H](c1ccccc1)c1ccc(C2CC2)c(F)c1)[C@@H]1C[C@@H](F)CN1C(=O)CN1Cc2ccccc2C1=O] | (2S,4R)-N-[(S)-(4-cyclopropyl-3-fluorophenyl)(phenyl)methyl]-4-fluoro-1-[2-(1-oxo-2,3-dihydro-1H-isoindol-2-yl)acetyl]pyrrolidine-2-carboxamide |

TABLE 1-continued

| Compound No. | Structure | IUPAC |
|---|---|---|
| 454 | 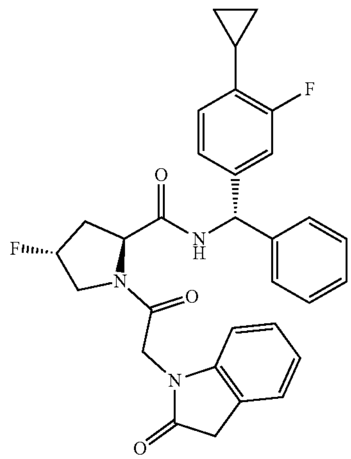 [SMILES: O=C(N[C@@H](c1ccccc1)c1ccc(C2CC2)c(F)c1)[C@@H]1C[C@@H](F)CN1C(=O)CN1C(=O)Cc2ccccc21] | (2S,4R)-N-[(S)-(4-cyclopropyl-3-fluorophenyl)(phenyl)methyl]-4-fluoro-1-[2-(2-oxo-2,3-dihydro-1H-indol-1-yl)acetyl]pyrrolidine-2-carboxamide |
| 455 | 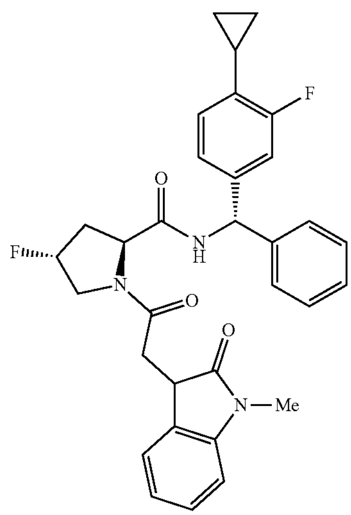 [SMILES: CN1C(=O)C(CC(=O)N2C[C@H](F)C[C@H]2C(=O)N[C@@H](c2ccccc2)c2ccc(C3CC3)c(F)c2)c2ccccc21] | (2S,4R)-N-[(S)-(4-cyclopropyl-3-fluorophenyl)(phenyl)methyl]-4-fluoro-1-[2-(1-methyl-2-oxo-2,3-dihydro-1H-indol-3-yl)acetyl]pyrrolidine-2-carboxamide |
| 456 | 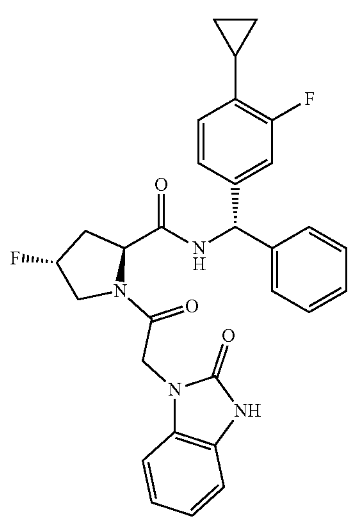 [SMILES: O=C(N[C@@H](c1ccccc1)c1ccc(C2CC2)c(F)c1)[C@@H]1C[C@@H](F)CN1C(=O)Cn1c(=O)[nH]c2ccccc21] | (2S,4R)-N-[(S)-(4-cyclopropyl-3-fluorophenyl)(phenyl)methyl]-4-fluoro-1-[2-(2-oxo-2,3-dihydro-1H-1,3-benzodiazol-1-yl)acetyl]pyrrolidine-2-carboxamide |

TABLE 1-continued

| Compound No. | Structure | IUPAC |
|---|---|---|
| 457 | 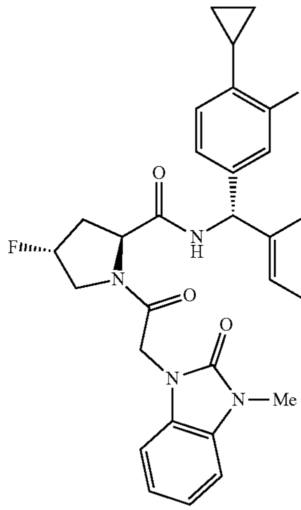 | (2S,4R)-N-[(S)-(4-cyclopropyl-3-fluorophenyl)(phenyl)methyl]-4-fluoro-1-[2-(3-methyl-2-oxo-2,3-dihydro-1H-1,3-benzodiazol-1-yl)acetyl]pyrrolidine-2-carboxamide |
| 458 | 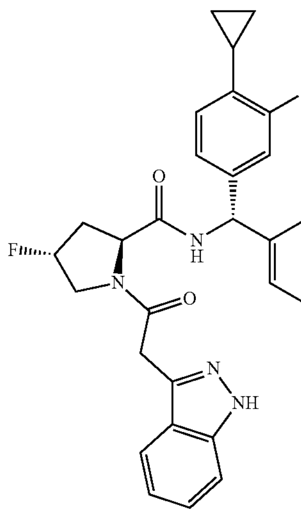 | (2S,4R)-N-[(S)-(4-cyclopropyl-3-fluorophenyl)(phenyl)methyl]-4-fluoro-1-[2-(1H-indazol-3-yl)acetyl]pyrrolidine-2-carboxamide |
| 459 | 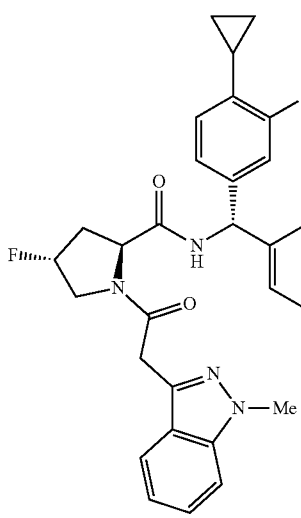 | (2S,4R)-N-[(S)-(4-cyclopropyl-3-fluorophenyl)(phenyl)methyl]-4-fluoro-1-[2-(1-methyl-1H-indazol-3-yl)acetyl]pyrrolidine-2-carboxamide |

TABLE 1-continued

| Compound No. | Structure | IUPAC |
|---|---|---|
| 460 | 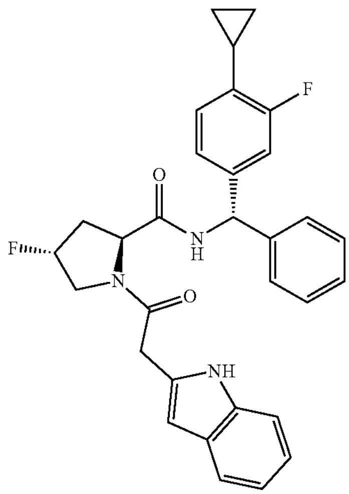 [SMILES: O=C(N[C@@H](c1ccccc1)c1ccc(C2CC2)c(F)c1)[C@@H]1C[C@@H](F)CN1C(=O)Cc1cc2ccccc2[nH]1] | (2S,4R)-N-[(S)-(4-cyclopropyl-3-fluorophenyl)(phenyl)methyl]-4-fluoro-1-[2-(1H-indol-2-yl)acetyl]pyrrolidine-2-carboxamide |
| 461 | 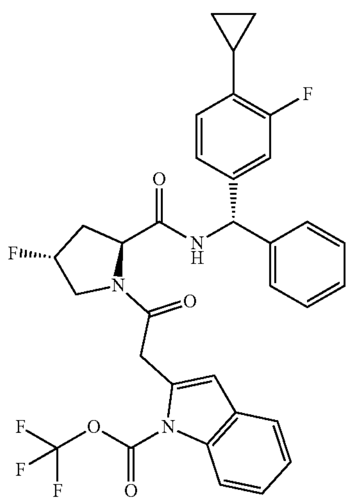 [SMILES: O=C(N[C@@H](c1ccccc1)c1ccc(C2CC2)c(F)c1)[C@@H]1C[C@@H](F)CN1C(=O)Cc1cc2ccccc2n1C(=O)OC(F)(F)F] | tert-butyl 2-{2-[(2S,4R)-2-{[(S)-(4-cyclopropyl-3-fluorophenyl)(phenyl)methyl]carbamoyl}-4-fluoropyridin-1-yl]-2-oxoethyl}-1H-indole-1-carboxylate |
| 462 | 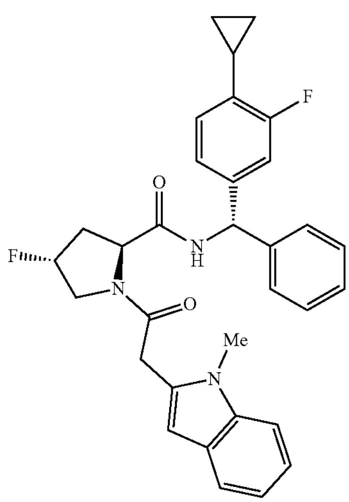 [SMILES: Cn1c(CC(=O)N2C[C@H](F)C[C@H]2C(=O)N[C@@H](c2ccccc2)c2ccc(C3CC3)c(F)c2)cc2ccccc21] | (2S,4R)-N-[(S)-(4-cyclopropyl-3-fluorophenyl)(phenyl)methyl]-4-fluoro-1-[2-(1-methyl-1H-indol-2-yl)acetyl]pyrrolidine-2-carboxamide |

TABLE 1-continued

| Compound No. | Structure | IUPAC |
|---|---|---|
| 463 | 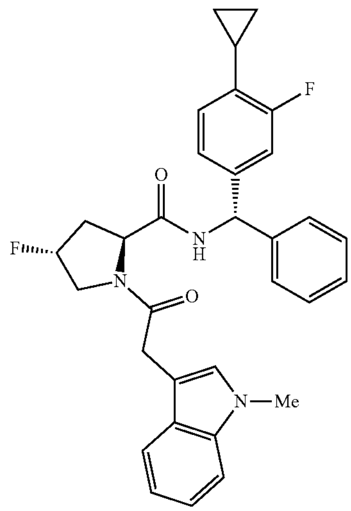 [SMILES: Cn1cc(CC(=O)N2C[C@H](F)C[C@H]2C(=O)N[C@@H](c2ccccc2)c2ccc(C3CC3)c(F)c2)c2ccccc21] | (2S,4R)-N-[(S)-(4-cyclopropyl-3-fluorophenyl)(phenyl)methyl]-4-fluoro-1-[2-(1-methyl-1H-indol-3-yl)acetyl]pyrrolidine-2-carboxamide |
| 464 | 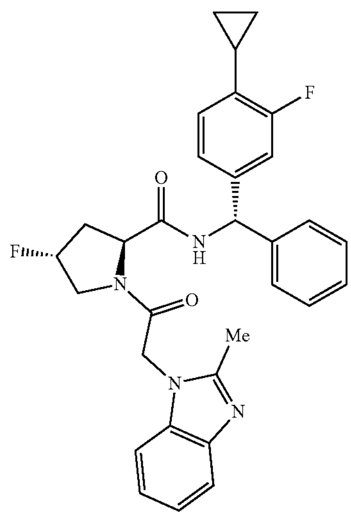 [SMILES: Cc1nc2ccccc2n1CC(=O)N1C[C@H](F)C[C@H]1C(=O)N[C@@H](c1ccccc1)c1ccc(C2CC2)c(F)c1] | (2S,4R)-N-[(S)-(4-cyclopropyl-3-fluorophenyl)(phenyl)methyl]-4-fluoro-1-[2-(2-methyl-1H-1,3-benzodiazol-1-yl)acetyl]pyrrolidine-2-carboxamide |
| 465 | 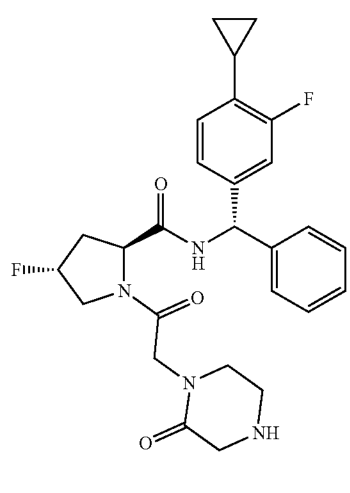 [SMILES: O=C(N[C@@H](c1ccccc1)c1ccc(C2CC2)c(F)c1)[C@@H]1C[C@@H](F)CN1C(=O)CN1CCNCC1=O] | (2S,4R)-N-[(S)-(4-cyclopropyl-3-fluorophenyl)(phenyl)methyl]-4-fluoro-1-[2-(2-oxopiperazin-1-yl)acetyl]pyrrolidine-2-carboxamide |

TABLE 1-continued

| Compound No. | Structure | IUPAC |
|---|---|---|
| 466 | 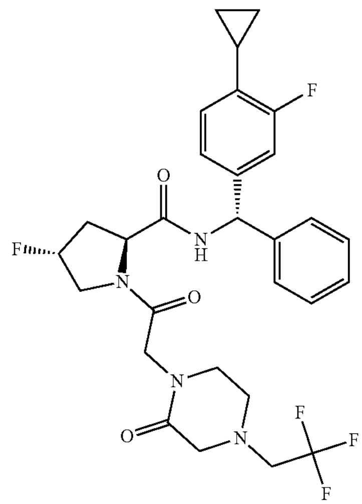 [SMILES: O=C(N[C@@H](c1ccccc1)c1ccc(C2CC2)c(F)c1)[C@@H]1C[C@@H](F)CN1C(=O)CN1CCN(CC(F)(F)F)CC1=O] | (2S,4R)-N-[(S)-(4-cyclopropyl-3-fluorophenyl)(phenyl)methyl]-4-fluoro-1-{2-[2-oxo-4-(2,2,2-trifluoroethyl)piperazin-1-yl]acetyl}pyrrolidine-2-carboxamide |
| 467 | 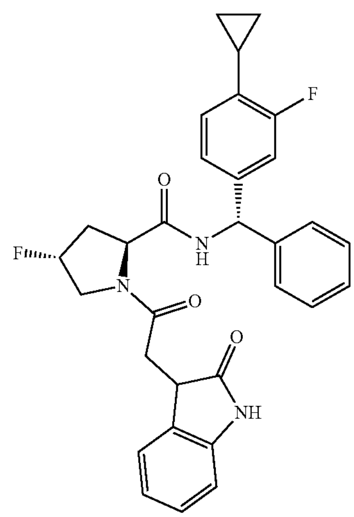 [SMILES: O=C1Nc2ccccc2C1CC(=O)N1C[C@H](F)C[C@H]1C(=O)N[C@@H](c1ccccc1)c1ccc(C2CC2)c(F)c1] | (2S,4R)-N-[(S)-(4-cyclopropyl-3-fluorophenyl)(phenyl)methyl]-4-fluoro-1-[2-(2-oxo-2,3-dihydro-1H-indol-3-yl)acetyl]pyrrolidine-2-carboxamide |
| 468 | 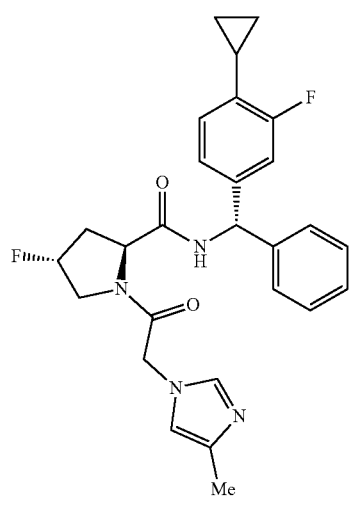 | (2S,4R)-N-[(S)-(4-cyclopropyl-3-fluorophenyl)(phenyl)methyl]-4-fluoro-1-[2-(4-methyl-1H-imidazol-1-yl)acetyl]pyrrolidine-2-carboxamide |

TABLE 1-continued
| Compound No. | Structure | IUPAC |
|---|---|---|
| 469 | 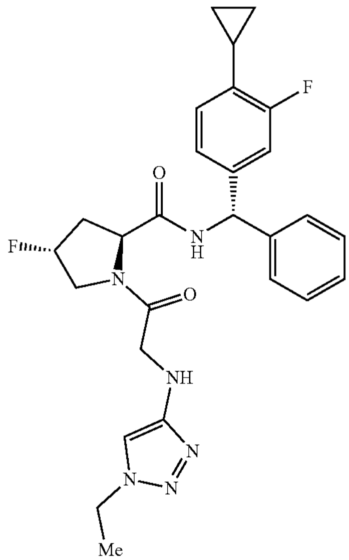 [SMILES: CCn1cc(NCC(=O)N2C[C@H](F)C[C@H]2C(=O)N[C@@H](c2ccccc2)c2ccc(C3CC3)c(F)c2)nn1] | (2S,4R)-N-[(S)-(4-cyclopropyl-3-fluorophenyl)(phenyl)methyl]-1-{2-[(1-ethyl-1H-1,2,3-triazol-4-yl)amino]acetyl}-4-fluoropyrrolidine-2-carboxamide |
| 470 | 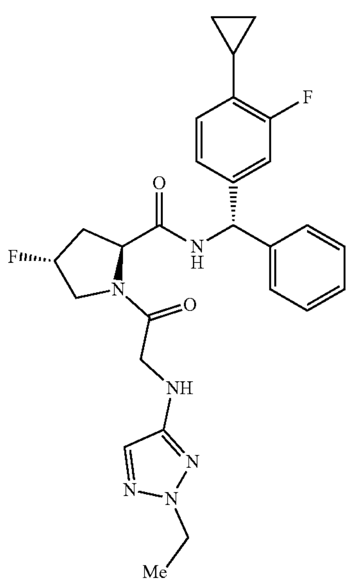 [SMILES: CCn1ncc(NCC(=O)N2C[C@H](F)C[C@H]2C(=O)N[C@@H](c2ccccc2)c2ccc(C3CC3)c(F)c2)n1] | (2S,4R)-N-[(S)-(4-cyclopropyl-3-fluorophenyl)(phenyl)methyl]-1-{2-[(2-ethyl-2H-1,2,3-triazol-4-yl)amino]acetyl}-4-fluoropyrrolidine-2-carboxamide |

TABLE 1-continued

| Compound No. | Structure | IUPAC |
|---|---|---|
| 471 | 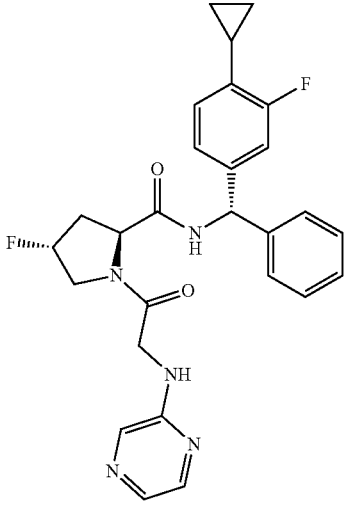 [SMILES: O=C(N[C@@H](c1ccccc1)c1ccc(C2CC2)c(F)c1)[C@@H]1C[C@@H](F)CN1C(=O)CNc1cnccn1] | (2S,4R)-N-[(S)-(4-cyclopropyl-3-fluorophenyl)(phenyl)methyl]-4-fluoro-1-{2-[(pyrazin-2-yl)amino]acetyl}pyrrolidine-2-carboxamide |
| 472 | 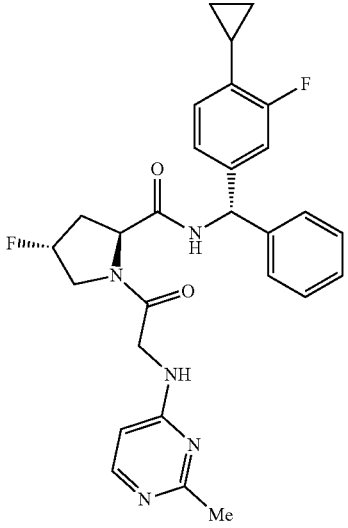 [SMILES: Cc1nccc(NCC(=O)N2C[C@H](F)C[C@H]2C(=O)N[C@@H](c2ccccc2)c2ccc(C3CC3)c(F)c2)n1] | (2S,4R)-N-[(S)-(4-cyclopropyl-3-fluorophenyl)(phenyl)methyl]-4-fluoro-1-{2-[(2-methylpyrimidin--4 yl)amino]acetyl}pyrrolidine-2-carboxamide |
| 473 | 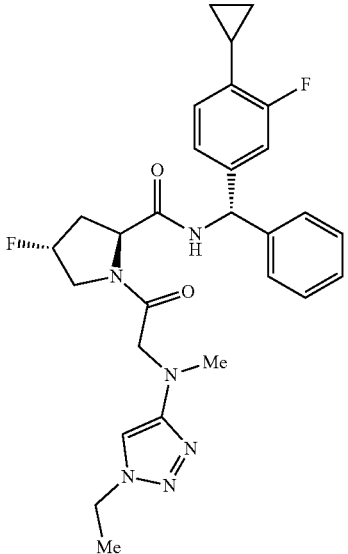 [SMILES: CCn1cc(N(C)CC(=O)N2C[C@H](F)C[C@H]2C(=O)N[C@@H](c2ccccc2)c2ccc(C3CC3)c(F)c2)nn1] | (2S,4R)-N-[(S)-(4-cyclopropyl-3-fluorophenyl)(phenyl)methyl]-1-{2-[(1-ethyl-1H-1,2,3-triazol-4-yl)(methyl)amino]acetyl}-4-fluoropyrrolidine-2-carboxamide |

TABLE 1-continued

| Compound No. | Structure | IUPAC |
|---|---|---|
| 474 | 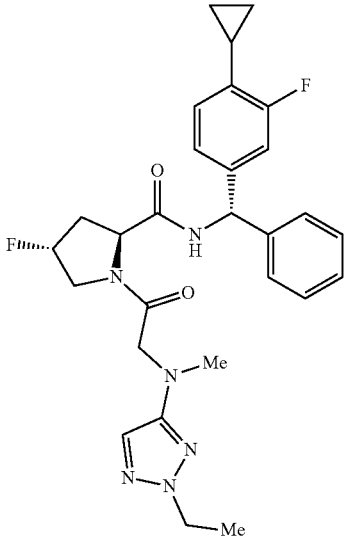 | (2S,4R)-N-[(S)-(4-cyclopropyl-3-fluorophenyl)(phenyl)methyl]-1-{2-[(2-ethyl-2H-1,2,3-triazol-4-yl)(methyl)amino]acetyl}-4-fluoropyrrolidine-2-carboxamide |
| 475 | 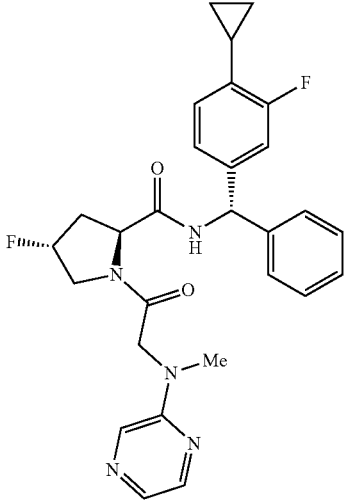 | (2S,4R)-N-[(S)-(4-cyclopropyl-3-fluorophenyl)(phenyl)methyl]-4-fluoro-1-{2-[methyl(pyrazin-2-yl)amino]acetyl}pyrrolidine-2-carboxamide |
| 476 | 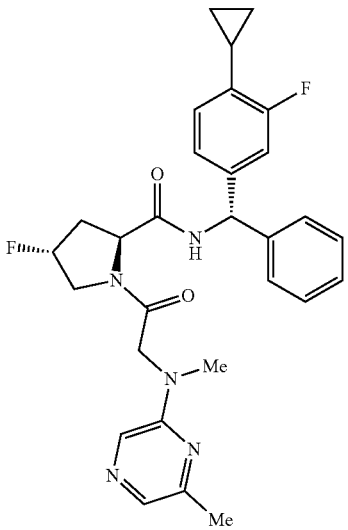 [SMILES: Cc1cncc(N(C)CC(=O)N2C[C@H](F)C[C@H]2C(=O)N[C@@H](c2ccccc2)c2ccc(C3CC3)c(F)c2)n1] | (2S,4R)-N-[(S)-(4-cyclopropyl-3-fluorophenyl)(phenyl)methyl]-4-fluoro-1-{2-[methyl(2-methylpyrimidin-4-yl)amino]acetyl}pyrrolidine-2-carboxamide |

TABLE 1-continued

| Compound No. | Structure | IUPAC |
|---|---|---|
| 477 | 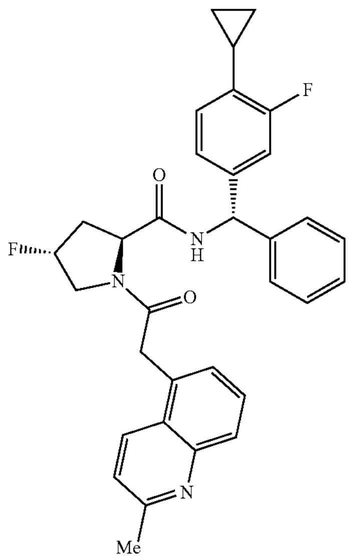 [SMILES: Cc1ccc2c(CC(=O)N3C[C@H](F)C[C@H]3C(=O)N[C@@H](c3ccccc3)c3ccc(C4CC4)c(F)c3)cccc2n1] | (2S,4R)-N-[(S)-(4-cyclopropyl-3-fluorophenyl)(phenyl)methyl]-4-fluoro-1-[2-(2-methylquinolin-5-yl)acetyl]pyrrolidine-2-carboxamide |
| 478 | 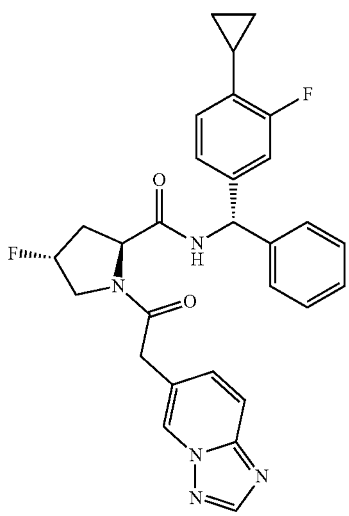 [SMILES: O=C(N[C@@H](c1ccccc1)c1ccc(C2CC2)c(F)c1)[C@@H]1C[C@@H](F)CN1C(=O)Cc1ccc2ncnn2c1] | (2S,4R)-N-[(S)-(4-cyclopropyl-3-fluorophenyl)(phenyl)methyl]-4-fluoro-1-(2-{[1,2,4]triazolo[1,5-a]pyridin-6-yl}acetyl)pyrrolidine-2-carboxamide |
| 479 | 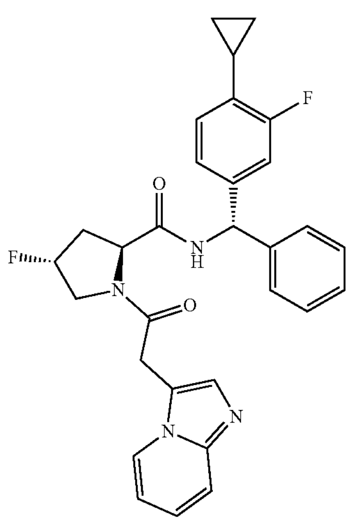 [SMILES: O=C(N[C@@H](c1ccccc1)c1ccc(C2CC2)c(F)c1)[C@@H]1C[C@@H](F)CN1C(=O)Cc1cnc2ccccn12] | (2S,4R)-N-[(S)-(4-cyclopropyl-3-fluorophenyl)(phenyl)methyl]-4-fluoro-1-(2-{imidazo[1,2-a]pyridin-3-yl}acetyl)pyrrolidine-2-carboxamide |

TABLE 1-continued

| Compound No. | Structure | IUPAC |
|---|---|---|
| 480 | 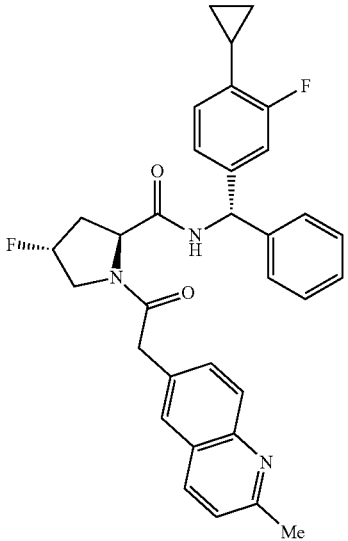 [SMILES: Cc1ccc2cc(CC(=O)N3C[C@H](F)C[C@H]3C(=O)N[C@@H](c3ccccc3)c3ccc(C4CC4)c(F)c3)ccc2n1] | (2S,4R)-N-[(S)-(4-cyclopropyl-3-fluorophenyl)(phenyl)methyl]-4-fluoro-1-[2-(2-methylquinolin-6-yl)acetyl]pyrrolidine-2-carboxamide |
| 481 | 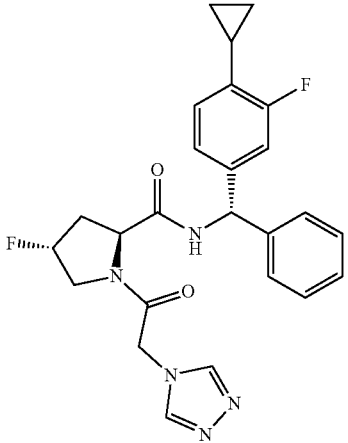 | (2S,4R)-N-[(S)-(4-cyclopropyl-3-fluorophenyl)(phenyl)methyl]-4-fluoro-1-[2-(4H-1,2,4-triazol-4-yl)acetyl]pyrrolidine-2-carboxamide |
| 482 | 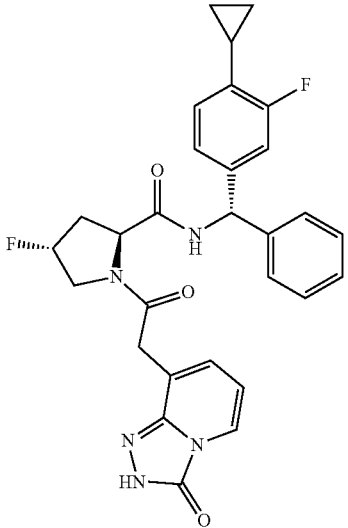 [SMILES: O=C(N[C@@H](c1ccccc1)c1ccc(C2CC2)c(F)c1)[C@@H]1C[C@@H](F)CN1C(=O)Cc1cccn2c(=O)[nH]nc12] | (2S,4R)-N-[(S)-(4-cyclopropyl-3-fluorophenyl)(phenyl)methyl]-4-fluoro-1-(2-{3-oxo-2H,3H-[1,2,4]triazolo[4,3-a]pyridin-8-yl}acetyl)pyrrolidine-2-carboxamide |

TABLE 1-continued

| Compound No. | Structure | IUPAC |
|---|---|---|
| 483 | 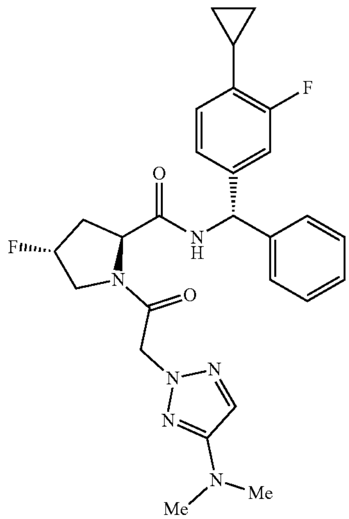 [SMILES: CN(C)c1cnn(CC(=O)N2C[C@H](F)C[C@H]2C(=O)N[C@@H](c2ccccc2)c2ccc(C3CC3)c(F)c2)n1] | (2S,4R)-N-[(S)-(4-cyclopropyl-3-fluorophenyl)(phenyl)methyl]-1-{2-[4-(dimethylamino)-2H-1,2,3-triazol-2-yl]acetyl}-4-fluoropyrrolidine-2-carboxamide |
| 484 | 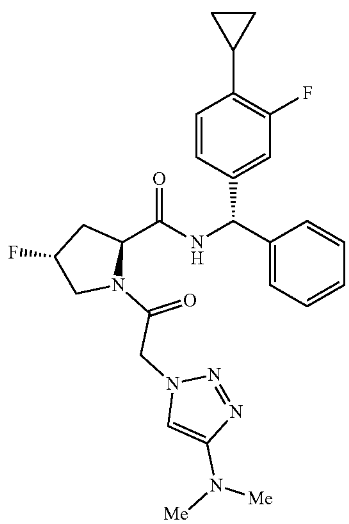 [SMILES: CN(C)c1cn(CC(=O)N2C[C@H](F)C[C@H]2C(=O)N[C@@H](c2ccccc2)c2ccc(C3CC3)c(F)c2)nn1] | (2S,4R)-N-[(S)-(4-cyclopropyl-3-fluorophenyl)(phenyl)methyl]-1-{2-[4-(dimethylamino)-1H-1,2,3-triazol-1-yl]acetyl}-4-fluoropyrrolidine-2-carboxamide |
| 485 | 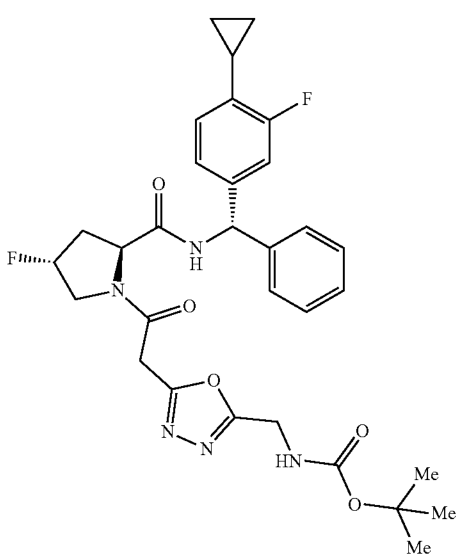 [SMILES: CC(C)(C)OC(=O)NCc1nnc(CC(=O)N2C[C@H](F)C[C@H]2C(=O)N[C@@H](c2ccccc2)c2ccc(C3CC3)c(F)c2)o1] | tert-butyl N-[(5-{2-[(2S,4R)-2-{[(S)-(4-cyclopropyl-3-fluorophenyl)(phenyl)methyl]carbamoyl}-4-fluoropyrrolidin-1-yl]-2-oxoethyl}-1,3,4-oxadiazol-2-yl)methyl]carbamate |

| Compound No. | Structure | IUPAC |
|---|---|---|
| 486 | 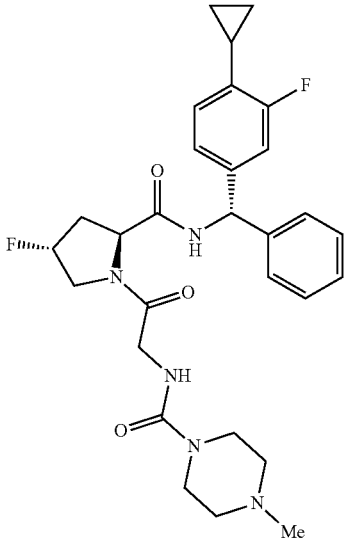 [SMILES: CN1CCN(C(=O)NCC(=O)N2C[C@H](F)C[C@H]2C(=O)N[C@@H](c2ccccc2)c2ccc(C3CC3)c(F)c2)CC1] | N-{2-[(2S,4R)-2-{[(S)-(4-cyclopropyl-3-fluorophenyl)(phenyl)methyl]carbamoyl}-4-fluoropyrrolidin-1-yl]-2-oxoethyl}-4-methylpiperazine-1-carboxamide |
| 487 | 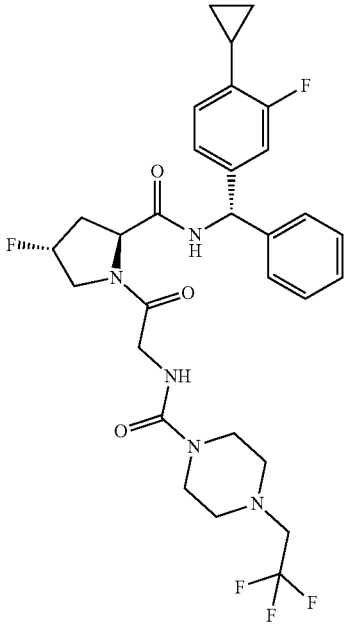 [SMILES: O=C(N[C@@H](c1ccccc1)c1ccc(C2CC2)c(F)c1)[C@@H]1C[C@@H](F)CN1C(=O)CNC(=O)N1CCN(CC(F)(F)F)CC1] | N-{2-[(2S,4R)-2-{[(S)-(4-cyclopropyl-3-fluorophenyl)(phenyl)methyl]carbamoyl}-4-fluoropyrrolidin-1-yl]-2-oxoethyl}-4-(2,2,2-trifluoroethyl)piperazine-1-carboxamide |

TABLE 1-continued
| Compound No. | Structure | IUPAC |
|---|---|---|
| 488 | 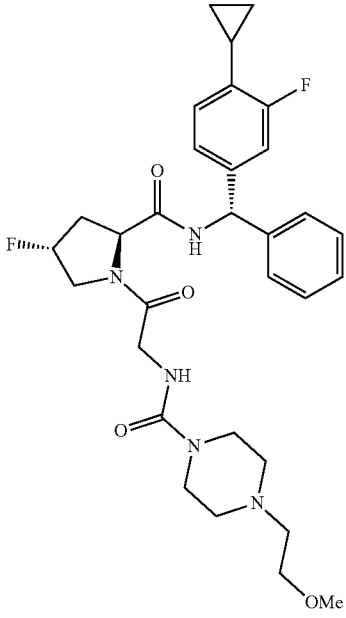 [SMILES: COCCN1CCN(C(=O)NCC(=O)N2C[C@H](F)C[C@H]2C(=O)N[C@@H](c2ccccc2)c2ccc(C3CC3)c(F)c2)CC1] | N-{2-[(2S,4R)-2-{[(S)-(4-cyclopropyl-3-fluorophenyl)(phenyl)methyl]carbamoyl}-4-fluoropyrrolidin-1-yl]-2-oxoethyl}-4-(2-methoxyethyl)piperazine-1-carboxamide |
| 489 | 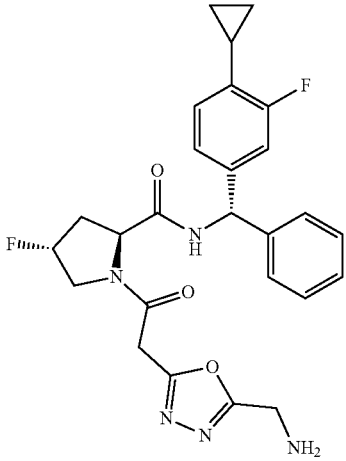 [SMILES: NCc1nnc(CC(=O)N2C[C@H](F)C[C@H]2C(=O)N[C@@H](c2ccccc2)c2ccc(C3CC3)c(F)c2)o1] | (2S,4R)-1-{2-[5-(aminomethyl)-1,3,4-oxadiazol-2-yl]acetyl}-N-[(S)-(4-cyclopropyl-3-fluorophenyl)(phenyl)methyl]-4-fluoropyrrolidine-2-carboxamide |

TABLE 1-continued

| Compound No. | Structure | IUPAC |
|---|---|---|
| 490 | 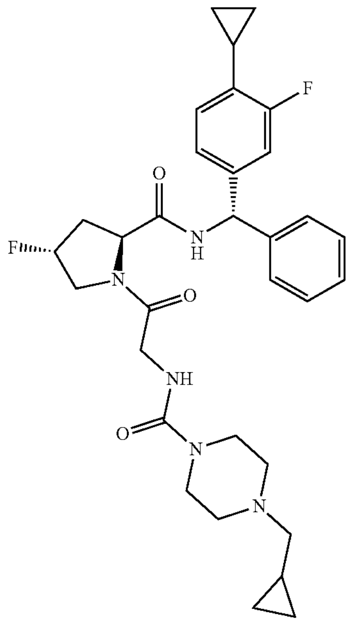 [SMILES: O=C(N[C@@H](c1ccccc1)c1ccc(C2CC2)c(F)c1)[C@@H]1C[C@@H](F)CN1C(=O)CNC(=O)N1CCN(CC2CC2)CC1] | N-{2-[(2S,4R)-2-{[(S)-(4-cyclopropyl-3-fluorophenyl)(phenyl)methyl]carbamoyl}-4-fluoropyrrolidin-1-yl]-2-oxoethyl}-4-(cyclopropylmethyl)piperazine-1-carboxamide |
| 491 | 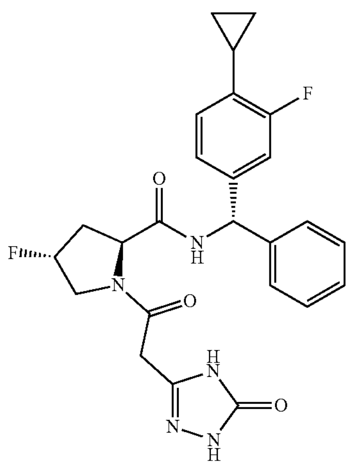 [SMILES: O=C(N[C@@H](c1ccccc1)c1ccc(C2CC2)c(F)c1)[C@@H]1C[C@@H](F)CN1C(=O)Cc1n[nH]c(=O)[nH]1] | (2S,4R)-N-[(S)-(4-cyclopropyl-3-fluorophenyl)(phenyl)methyl]-4-fluoro-1-[2-(5-oxo-4,5-dihydro-1H-1,2,4-triazol-3-yl)acetyl]pyrrolidine-2-carboxamide |
| 492 | 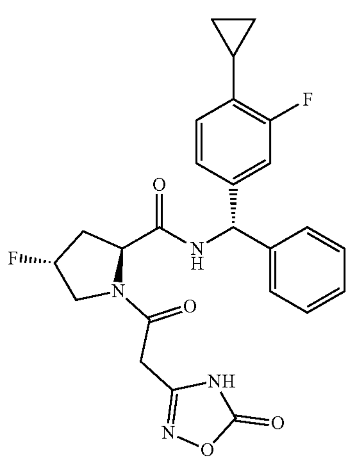 [SMILES: O=C(N[C@@H](c1ccccc1)c1ccc(C2CC2)c(F)c1)[C@@H]1C[C@@H](F)CN1C(=O)Cc1noc(=O)[nH]1] | (2S,4R)-N-[(S)-(4-cyclopropyl-3-fluorophenyl)(phenyl)methyl]-4-fluoro-1-[2-(5-oxo-4,5-dihydro-1,2,4-oxadiazol-3-yl)acetyl]pyrrolidine-3-carboxamide |

TABLE 1-continued

| Compound No. | Structure | IUPAC |
|---|---|---|
| 493 | 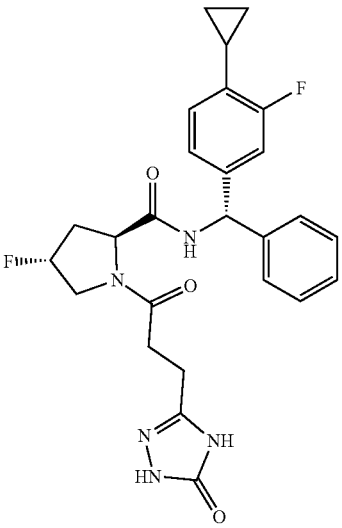 [SMILES: O=C(N[C@@H](c1ccccc1)c1ccc(C2CC2)c(F)c1)[C@@H]1C[C@@H](F)CN1C(=O)CCc1n[nH]c(=O)[nH]1] | (2S,4R)-N-[(S)-(4-cyclopropyl-3-fluorophenyl)(phenyl)methyl]-4-fluoro-1-[3-(5-oxo-4,5-dihydro-1H-1,2,4-triazol-3-yl)propanoyl]pyrrolidine-3-carboxamide |
| 494 | 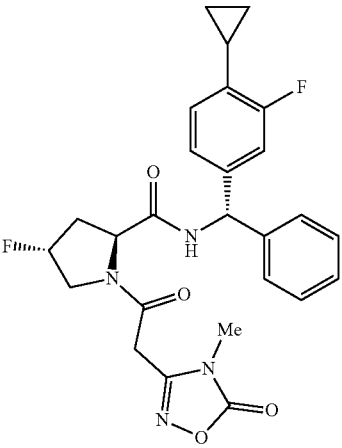 | (2S,4R)-N-[(S)-(4-cyclopropyl-3-fluorophenyl)(phenyl)methyl]-4-fluoro-1-[2-(4-methyl-5-oxo-4,5-dihydro-1,2,4-oxadiazol-3-yl)acetyl]pyrrolidine-2-carboxamide |
| 495 | 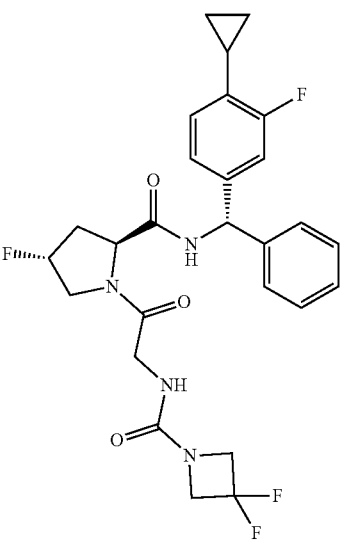 [SMILES: O=C(N[C@@H](c1ccccc1)c1ccc(C2CC2)c(F)c1)[C@@H]1C[C@@H](F)CN1C(=O)CNC(=O)N1CC(F)(F)C1] | (2S,4R)-N-[(S)-(4-cyclopropyl-3-fluorophenyl)(phenyl)methyl]-1-{2-[(3,3-difluoroazetidine-1-carbonyl)amino]acetyl}-4-fluoropyrrolidine-2-carboxamide |

TABLE 1-continued

| Compound No. | Structure | IUPAC |
|---|---|---|
| 496 | 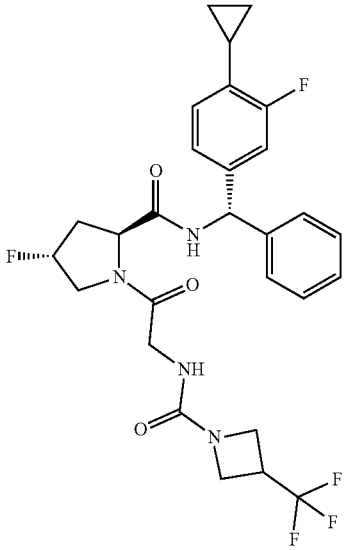 [SMILES: O=C(N[C@@H](c1ccccc1)c1ccc(C2CC2)c(F)c1)[C@@H]1C[C@@H](F)CN1C(=O)CNC(=O)N1CC(C(F)(F)F)C1] | (2S,4R)-N-[(S)-(4-cyclopropyl-3-fluorophenyl)(phenyl)methyl]-4-fluoro-1-(2-{[3-(trifluoromethyl)azetidine-1-carbonyl]amino}acetyl)pyrrolidine-2-carboxamide |
| 497 | 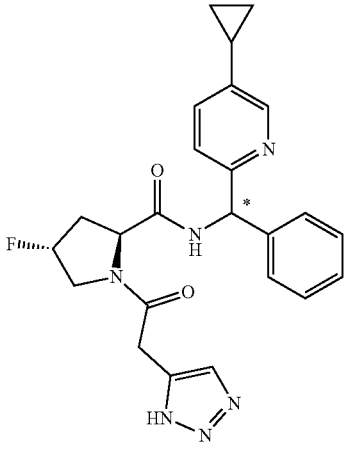 [SMILES: O=C(NC(c1ccccc1)c1ccc(C2CC2)cn1)[C@@H]1C[C@@H](F)CN1C(=O)Cc1cnn[nH]1] | (2S,4R)-1-(2-(1H-1,2,3-triazol-5-yl)acetyl)-N-((S) or (R)-(5-cyclopropylpyridin-2-yl)(phenyl)methyl)-4-fluoropyrrolidine-2-carboxamide |
| 498 | 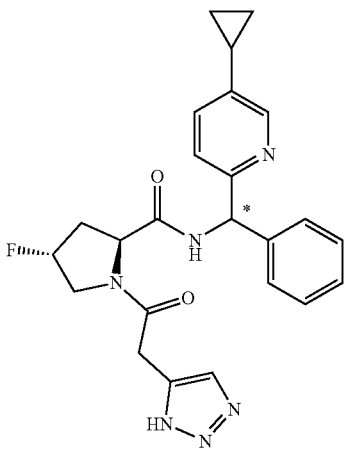 [SMILES: O=C(NC(c1ccccc1)c1ccc(C2CC2)cn1)[C@@H]1C[C@@H](F)CN1C(=O)Cc1cnn[nH]1] | (2S,4R)-1-(2-(1H-1,2,3-triazol-5-yl)acetyl)-N-((R) or (S)-(5-cyclopropylpyridin-2-yl)(phenyl)methyl)-4-fluoropyrrolidine-2-carboxamide |

TABLE 1-continued

| Compound No. | Structure | IUPAC |
|---|---|---|
| 499 | 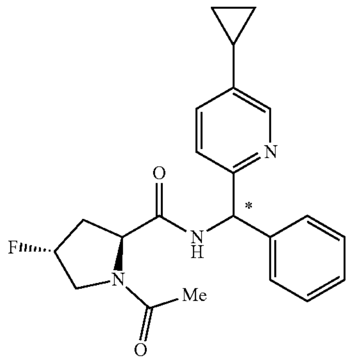 [SMILES: CC(=O)N1C[C@H](F)C[C@H]1C(=O)NC(c1ccccc1)c1ccc(C2CC2)cn1] | (2S,4R)-1-acetyl-N-[(S) or (R)-(5-cyclopropylpyridin-2-yl)(phenyl)methyl]-4-fluoropyrrolidine-2-carboxamide |
| 500 | 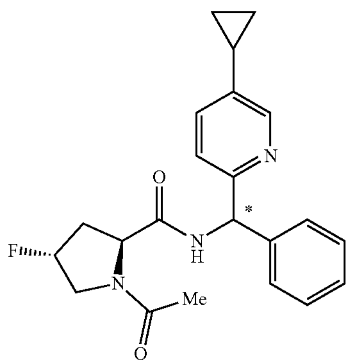 [SMILES: CC(=O)N1C[C@H](F)C[C@H]1C(=O)NC(c1ccccc1)c1ccc(C2CC2)cn1] | (2S,4R)-1-acetyl-N-[(R) or (S)-(5-cyclopropylpyridin-2-yl)(phenyl)methyl]-4-fluoropyrrolidine-2-carboxamide (second eluting isomer) |
| 501 | 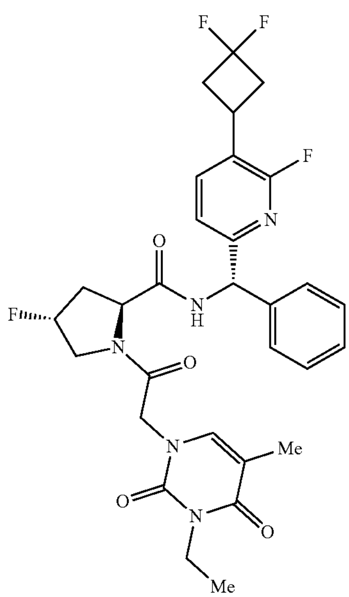 [SMILES: CCn1c(=O)c(C)cn(CC(=O)N2C[C@H](F)C[C@H]2C(=O)N[C@@H](c2ccccc2)c2ccc(C3CC(F)(F)C3)c(F)n2)c1=O] | (2S,4R)-N-((S)-(5-(3,3-difluorocyclobutyl)-6-fluoropyridin-2-y)(phenyl)methyl)-1-(2-(3-ethyl-5-methyl-2,4-dioxo-3,4-dihydropyrimidin-1(2H)-yl)acetyl)-4-fluoropyrrolidine-2-carboxamide |

TABLE 1-continued
| Compound No. | Structure | IUPAC |
|---|---|---|
| 502 | 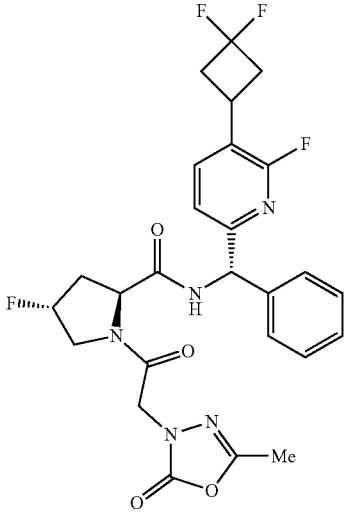 | (2S,4R)-N-[(S)-[5-(3,3-difluorocyclobutyl)-6-fluoropyridin-2-yl](phenyl)methyl]-4-fluoro-1-[2-(5-methyl-2-oxo-2,3-dihydro-1,3,4-oxadiazol-3-yl)acetyl]pyrrolidine-2-carboxamide |
| 503 | 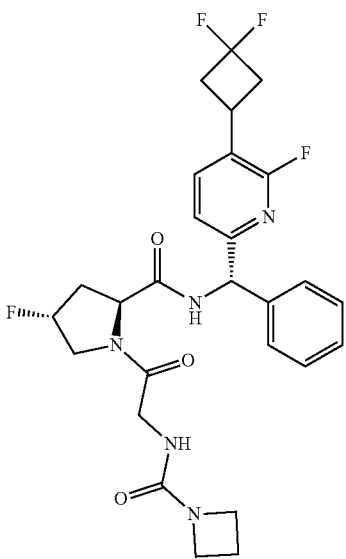 | (2S,4R)-1-{2-[(azetidine-1-carbonyl)amino]acetyl}-N-[(S)-[5-(3,3-difluorocyclobutyl)-6-fluoropyridin-2-yl](phenyl)methyl]-4-fluoropyrrolidine-2-carboxamide |

TABLE 1-continued

| Compound No. | Structure | IUPAC |
|---|---|---|
| 504 | 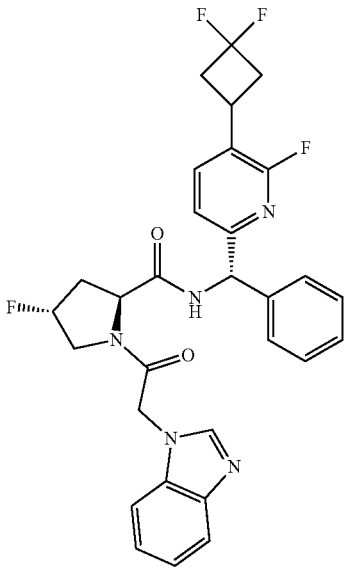 | (2S,4R)-1-[2-(1H-1,3-benzodiazol-1-yl)acetyl]-N-[(S)-[5-(3,3-difluorocyclobutyl)-6-fluoropyridin-2-yl](phenyl)methyl]-4-fluoropyrrolidine-2-carboxamide |
| 505 | 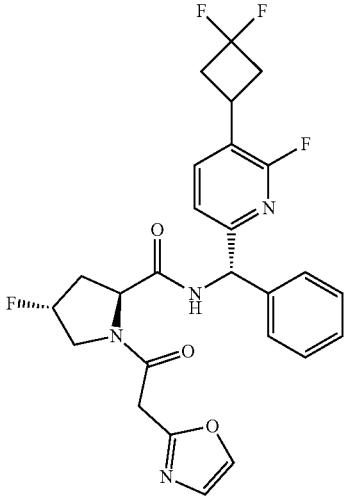 | (2S,4R)-N-[(S)-[5-(3,3-difluorocyclobutyl)-6-fluoropyridin-2-yl](phenyl)methyl]-4-fluoro-1-[2-(1,3-oxazol-2-yl)acetyl]pyrrolidine-2-carboxamide |
| 506 | 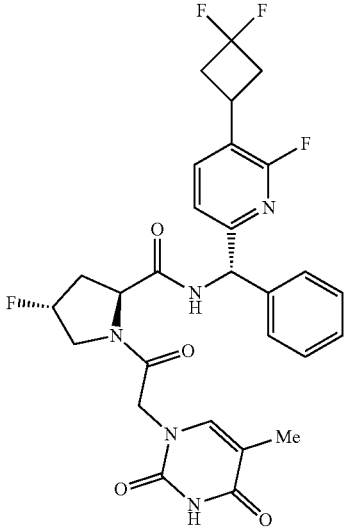 | (2S,4R)-N-[(S)-[5-(3,3-difluorocyclobutyl)-6-fluoropyridin-2-yl](phenyl)methyl]-4-fluoro-1-[2-(5-methyl-2,4-dioxo-1,2,3,4-tetrahydropyrimidin-1-yl)acetyl]pyrrolidine-2-carboxamide |

| Compound No. | Structure | IUPAC |
|---|---|---|
| 507 | 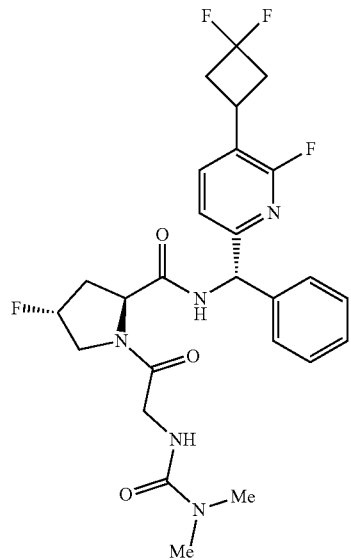 | (2S,4R)-N-[(S)-[5-(3,3-difluorocyclobutyl)-6-fluoropyridin-2-yl](phenyl)methyl]-1-{2-[(dimethylcarbamoyl)amino]acetyl}-4-fluoropyrrolidine-2-carboxamide |
| 508 | 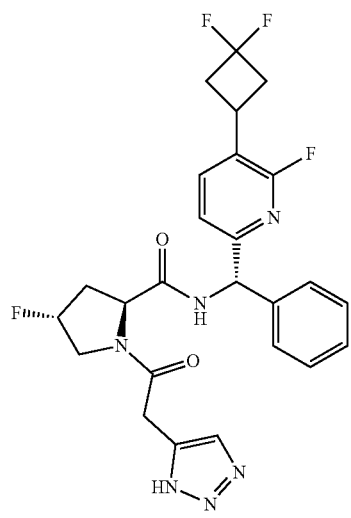 | (2S,4R)-N-[(S)-[5-(3,3-difluorocyclobutyl)-6-fluoropyridin-2-yl](phenyl)methyl]-4-fluoro-1-[2-(1H-1,2,3-triazol-5-yl)acetyl]pyrrolidine-2-carboxamide |
| 509 | 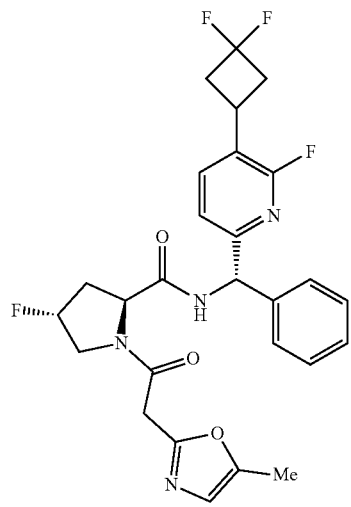 [SMILES: Cc1cnc(CC(=O)N2C[C@H](F)C[C@H]2C(=O)N[C@@H](c2ccccc2)c2ccc(C3CC(F)(F)C3)c(F)n2)o1] | (2S,4R)-N-[(S)-[5-(3,3-difluorocyclobutyl)-6-fluoropyridin-2-yl](phenyl)methyl]-4-fluoro-1-[2-(5-methyl-1,3-oxazol-2-yl)acetyl]pyrrolidine-2-carboxamide |

TABLE 1-continued
| Compound No. | Structure | IUPAC |
|---|---|---|
| 510 | 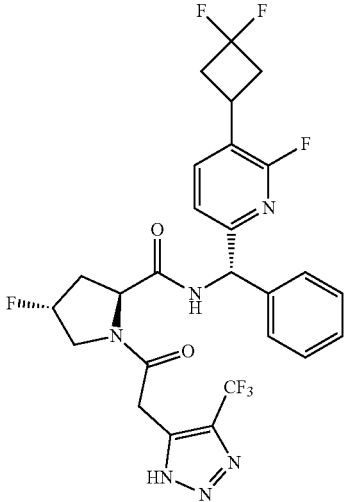 | (2S,4R)-N-[(S)-[5-(3,3-difluorocyclobutyl)-6-fluoropyridin-2-yl](phenyl)methyl]-4-fluoro-1-{2-[4-(trifluoromethyl)-1H-1,2,3-triazol-5-yl]acetyl}pyrrolidine-2-carboxamide |
| 511 | 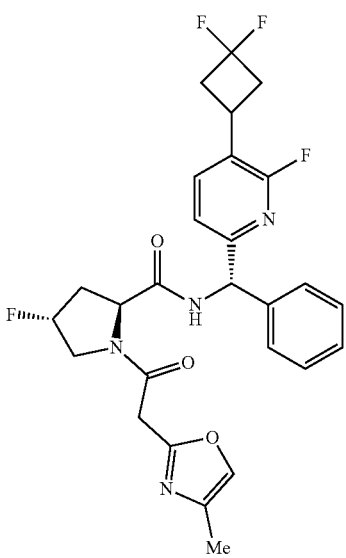 | (2S,4R)-N-[(S)-[5-(3,3-difluorocyclobutyl)-6-fluoropyridin-2-yl](phenyl)methyl]-4-fluoro-1-[2-(4-methyl-1,3-oxazol-2-yl)acetyl]pyrrolidine-2-carboxamide |

TABLE 1-continued

| Compound No. | Structure | IUPAC |
|---|---|---|
| 512 | 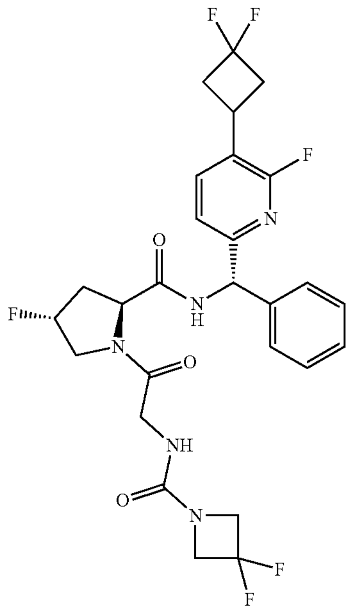 [SMILES: O=C(N[C@@H](c1ccccc1)c1ccc(C2CC(F)(F)C2)c(F)n1)[C@@H]1C[C@@H](F)CN1C(=O)CNC(=O)N1CC(F)(F)C1] | (2S,4R)-1-{2-[(3,3-difluoroazetidine-1-carbonyl)amino]acetyl}-N-[(S)-[5-(3,3-diflluorocyclobutyl)-6-fluoropyridin-2-yl](phenyl)methyl]-4-fluoropyrrolidine-2-carboxamide |
| 513 | 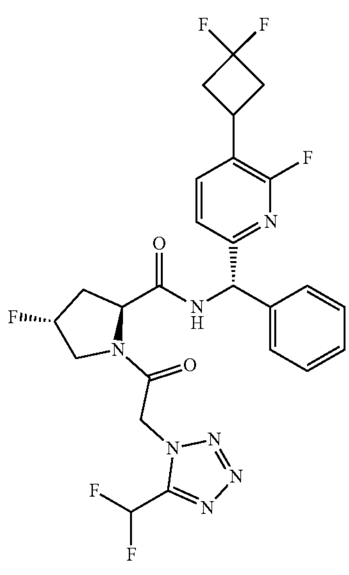 [SMILES: O=C(N[C@@H](c1ccccc1)c1ccc(C2CC(F)(F)C2)c(F)n1)[C@@H]1C[C@@H](F)CN1C(=O)Cn1nnnc1C(F)F] | (2S,4R)-N-[(S)-[5-(3,3-difluorocyclobutyl)-6-fluoropyridin-2-yl](phenyl)methyl]-1-{2-[5-(difluoromethyl)-1H-1,2,3,4-tetrazol-1-yl]acetyl}-4-fluoropyrrolidine-2-carboxamide |

TABLE 1-continued

| Compound No. | Structure | IUPAC |
|---|---|---|
| 514 | 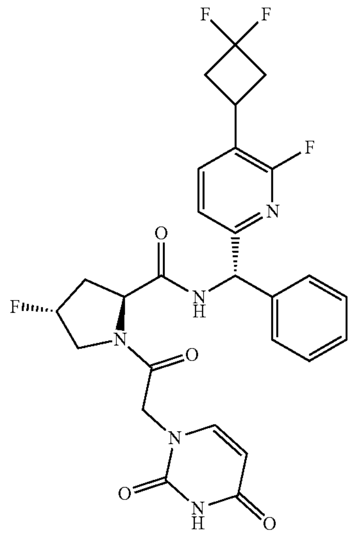 [SMILES: O=C(N[C@@H](c1ccccc1)c1ccc(C2CC(F)(F)C2)c(F)n1)[C@@H]1C[C@@H](F)CN1C(=O)Cn1ccc(=O)[nH]c1=O] | (2S,4R)-N-[(S)-[5-(3,3-difluorocyclobutyl)-6-fluoropyridin-2-yl](phenyl)methyl]-1-[2-(2,4-dioxo-1,2,3,4-tetrahydropyrimidin-1-yl)acetyl]-4-fluoropyrrolidine-2-carboxamide |
| 515 | 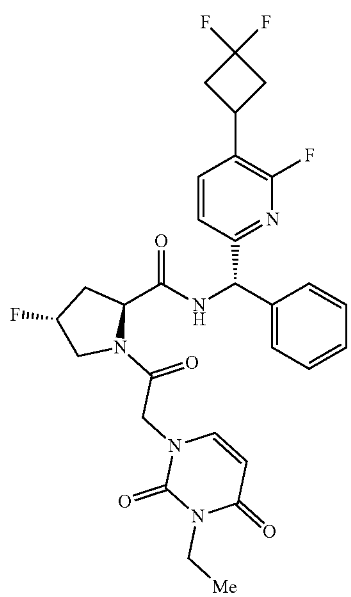 [SMILES: CCn1c(=O)ccn(CC(=O)N2C[C@H](F)C[C@H]2C(=O)N[C@@H](c2ccccc2)c2ccc(C3CC(F)(F)C3)c(F)n2)c1=O] | (2S,4R)-N-[(S)-[5-(3,3-difluorocyclobutyl)-6-fluoropyridin-2-yl](phenyl)methyl]-1-[2-(3-ethyl-2,4-dioxo-1,2,3,4-tetrahydropyrimidin-1-yl)acetyl]-4-fluoropyrrolidine-2-carboxamide |

TABLE 1-continued

| Compound No. | Structure | IUPAC |
|---|---|---|
| 516 | 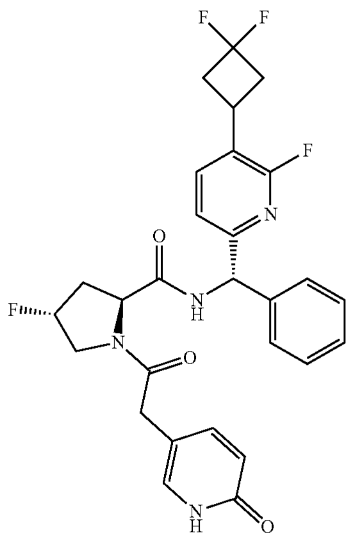 [SMILES: O=C(N[C@@H](c1ccccc1)c1ccc(C2CC(F)(F)C2)c(F)n1)[C@@H]1C[C@@H](F)CN1C(=O)Cc1ccc(=O)[nH]c1] | (2S,4R)-N-[(S)-[5-(3,3-difluorocyclobutyl)-6-fluoropyridin-2-yl](phenyl)methyl]-4-fluoro-1-[2-(6-oxo-1,6-dihydropyridin-3-yl)acetyl]pyrrolidine-2-carboxamide |
| 517 | 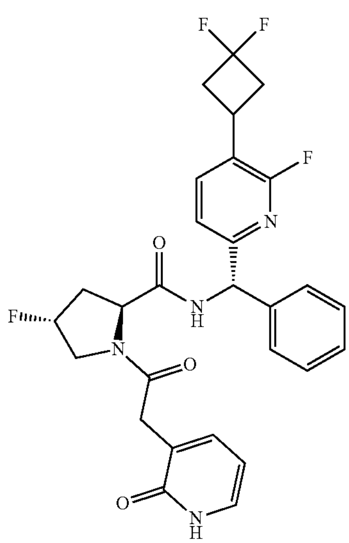 [SMILES: O=C(N[C@@H](c1ccccc1)c1ccc(C2CC(F)(F)C2)c(F)n1)[C@@H]1C[C@@H](F)CN1C(=O)Cc1ccc[nH]c1=O] | (2S,4R)-N-[(S)-[5-(3,3-difluorocyclobutyl)-6-fluoropyridin-2-yl](phenyl)methyl]-4-fluoro-1-[2-(2-oxo-1,2-dihydropyridin-3-yl)acetyl]pyrrolidine-2-carboxamide |

TABLE 1-continued

| Compound No. | Structure | IUPAC |
|---|---|---|
| 518 | 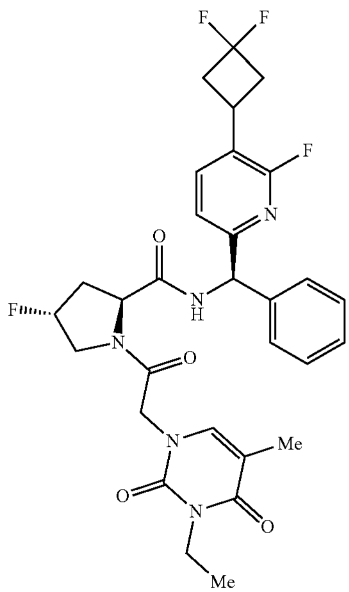 [SMILES: CCn1c(=O)c(C)cn(CC(=O)N2C[C@H](F)C[C@H]2C(=O)N[C@H](c2ccccc2)c2ccc(C3CC(F)(F)C3)c(F)n2)c1=O] | (2S,4R)-N-[(R)-[5-(3,3-difluorocyclobutyl)-6-fluoropyridin-2-yl](phenyl)methyl]-1-[2-(3-ethyl-5-methyl-2,4-dioxo-1,2,3,4-tetrahydropyrimidin-1-yl)acetyl]-4-fluoropyrrolidine-2-carboxamide |
| 519 | 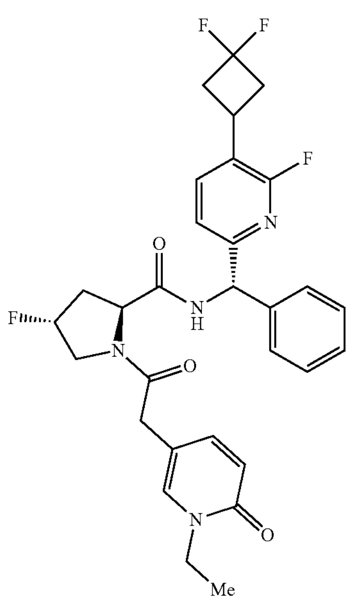 [SMILES: CCn1cc(CC(=O)N2C[C@H](F)C[C@H]2C(=O)N[C@@H](c2ccccc2)c2ccc(C3CC(F)(F)C3)c(F)n2)ccc1=O] | (2S,4R)-N-[(S)-[5-(3,3-difluorocyclobutyl)-6-fluoropyridin-2-yl](phenyl)methyl]-1-[2-(1-ethyl-6-oxo-1,6-dihydropyridin-3-yl)acetyl]-4-fluoropyrrolidine-2-carboxamide |

TABLE 1-continued

| Compound No. | Structure | IUPAC |
|---|---|---|
| 520 | 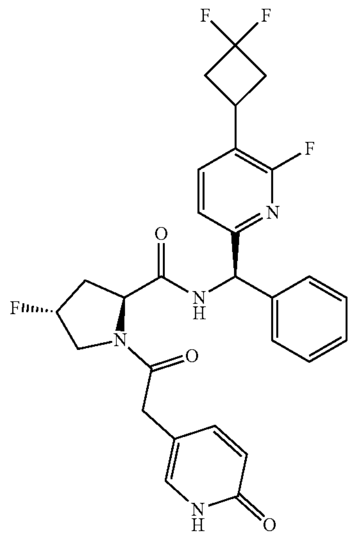 [SMILES: O=C(N[C@H](c1ccccc1)c1ccc(C2CC(F)(F)C2)c(F)n1)[C@@H]1C[C@@H](F)CN1C(=O)Cc1ccc(=O)[nH]c1] | (2S,4R)-N-[(R)-[5-(3,3-difluorocyclobutyl)-6-fluoropyridin-2-yl](phenyl)methyl]-4-fluoro-1-[2-(6-oxo-1,6-dihydropyridin-3-yl)acetyl]pyrrolidine-2-carboxamide |
| 521 | 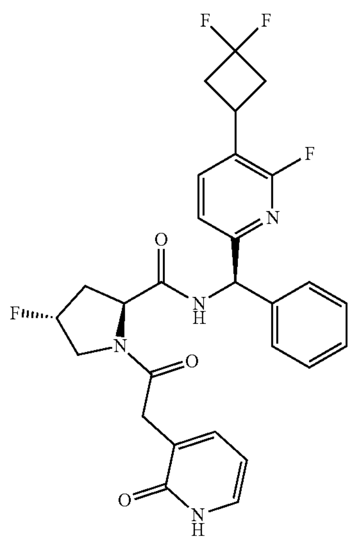 [SMILES: O=C(N[C@H](c1ccccc1)c1ccc(C2CC(F)(F)C2)c(F)n1)[C@@H]1C[C@@H](F)CN1C(=O)Cc1ccc[nH]c1=O] | (2S,4R)-N-[(R)-[5-(3,3-difluorocyclobutyl)-6-fluoropyridin-2-yl](phenyl)methyl]-4-fluoro-1-[2-(2-oxo-1,2-dihydropyridin-3-yl)acetyl]pyrrolidine-2-carboxamide |
| 522 | 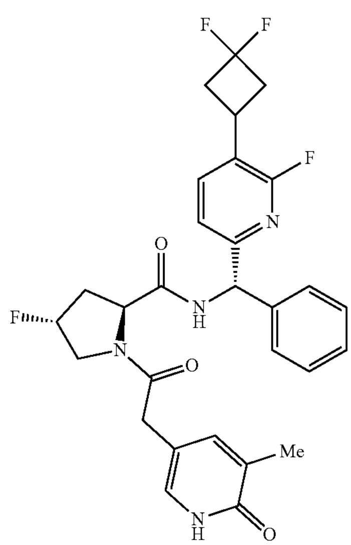 [SMILES: Cc1cc(CC(=O)N2C[C@H](F)C[C@H]2C(=O)N[C@@H](c2ccccc2)c2ccc(C3CC(F)(F)C3)c(F)n2)c[nH]c1=O] | (2S,4R)-N-[(S)-[5-(3,3-difluorocyclobutyl)-6-fluoropyridin-2-yl](phenyl)methyl]-4-fluoro-1-[2-(5-methyl-6-oxo-1,6-dihydropyridin-3-yl)acetyl]pyrrolidine-2-carboxamide |

TABLE 1-continued
| Compound No. | Structure | IUPAC |
|---|---|---|
| 523 | 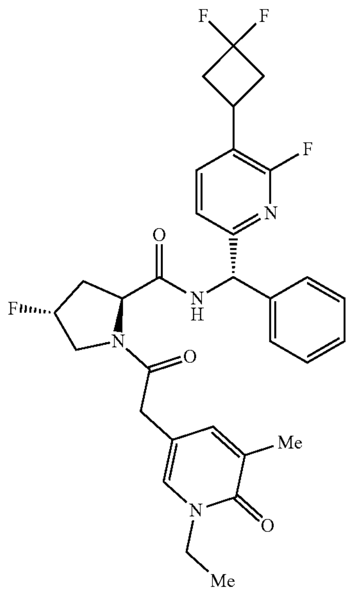 [SMILES: CCn1cc(CC(=O)N2C[C@H](F)C[C@H]2C(=O)N[C@@H](c2ccccc2)c2ccc(C3CC(F)(F)C3)c(F)n2)cc(C)c1=O] | (2S,4R)-N-[(S)-[5-(3,3-difluorocyclobutyl)-6-fluoropyridin-2-yl](phenyl)methyl]-1-[2-(1-ethyl-5-methyl-6-oxo-1,6-dihydropyridin-3-yl)acetyl]-4-fluoropyrrolidine-2-carboxamide |
| 524 | 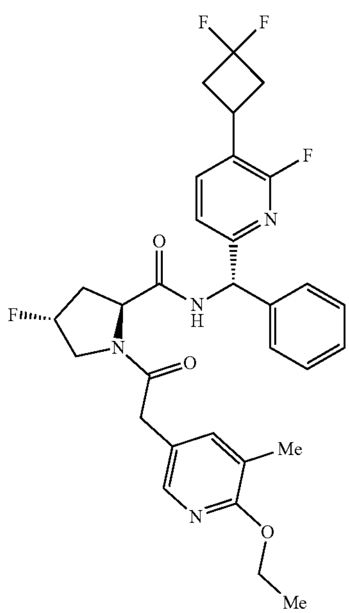 [SMILES: CCOc1ncc(CC(=O)N2C[C@H](F)C[C@H]2C(=O)N[C@@H](c2ccccc2)c2ccc(C3CC(F)(F)C3)c(F)n2)cc1C] | (2S,4R)-N-[(S)-[5-(3,3-difluorocyclobutyl)-6-fluoropyridin-2-yl](phenyl)methyl]-1-[2-(6-ethoxy-5-methylpyridin-3-yl)acetyl]-4-fluoropyrrolidine-2-carboxamide |

TABLE 1-continued

| Compound No. | Structure | IUPAC |
|---|---|---|
| 525 | 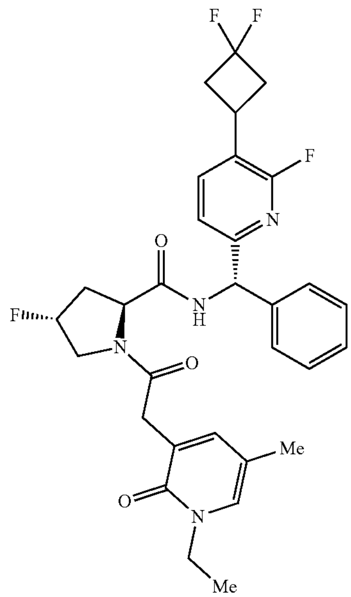 [SMILES: CCn1cc(C)cc(CC(=O)N2C[C@H](F)C[C@H]2C(=O)N[C@@H](c2ccccc2)c2ccc(C3CC(F)(F)C3)c(F)n2)c1=O] | (2S,4R)-N-[(S)-[5-(3,3-difluorocyclobutyl)-6-fluoropyridin-2-yl](phenyl)methyl]-1-[2-(1-ethyl-5-methyl-2-oxo-1,2-dihydropyridin-3-yl)acetyl]-4-fluoropyrrolidine-2-carboxamide |
| 526 | 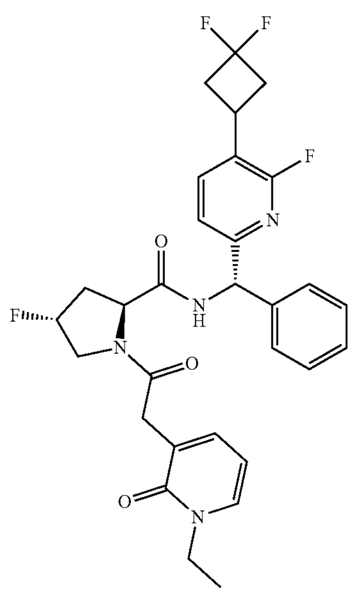 [SMILES: CCn1cccc(CC(=O)N2C[C@H](F)C[C@H]2C(=O)N[C@@H](c2ccccc2)c2ccc(C3CC(F)(F)C3)c(F)n2)c1=O] | (2S,4R)-N-[(S)-[5-(3,3-difluorocyclobutyl)-6-fluoropyridin-2-yl](phenyl)methyl]-1-[2-(1-ethyl-2-oxo-1,2-dihydropyridin-3-yl)acetyl]-4-fluoropyrrolidine-2-carboxamide |

TABLE 1-continued
| Compound No. | Structure | IUPAC |
|---|---|---|
| 527 | 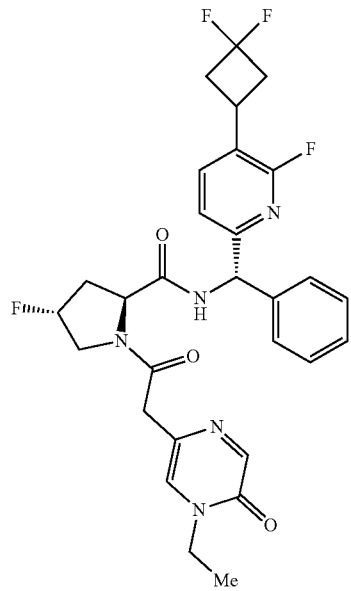 | (2S,4R)-N-[(S)-[5-(3,3-difluorocyclobutyl)-6-fluoropyridin-2-yl](phenyl)methyl]-1-[2-(4-ethyl-5-oxo-4,5-dihydropyrazin-2-yl)acetyl]-4-fluoropyrrrolidine-2-carboxamide |
| 528 | 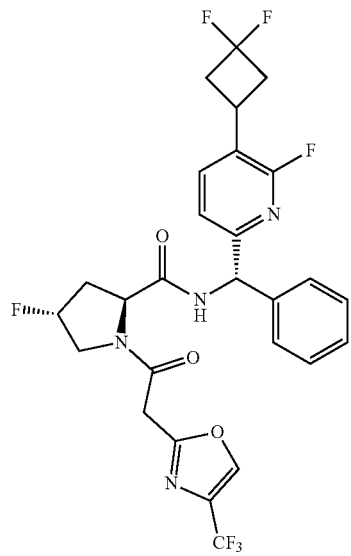 | (2S,4R)-N-[(S)-[5-(3,3-difluorocyclobutyl)-6-fluoropyridin-2-yl](phenyl)methyl]-4-fluoro-1-{2-[4-(trifluoromethyl)-1,3-oxazol-2-yl]acetyl}pyrrolidine-2-carboxamide |

TABLE 1-continued

| Compound No. | Structure | IUPAC |
|---|---|---|
| 529 | 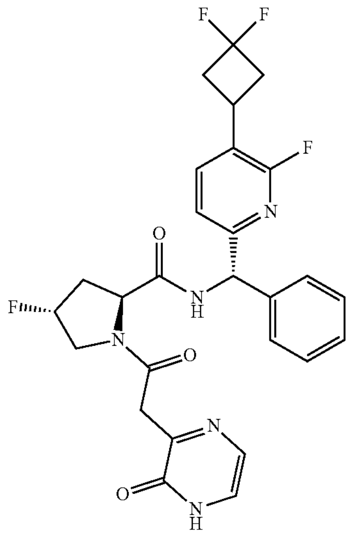 [SMILES: O=C(N[C@@H](c1ccccc1)c1ccc(C2CC(F)(F)C2)c(F)n1)[C@@H]1C[C@@H](F)CN1C(=O)Cc1ncc[nH]c1=O] | (2S,4R)-N-[(S)-[5-(3,3-difluorocyclobutyl)-6-fluoropyridin-2-yl](phenyl)methyl]-4-fluoro-1-[2-(3-oxo-3,4-dihydropyrazin-2-yl)acetyl]pyrrolidine-2-carboxamide |
| 530 | 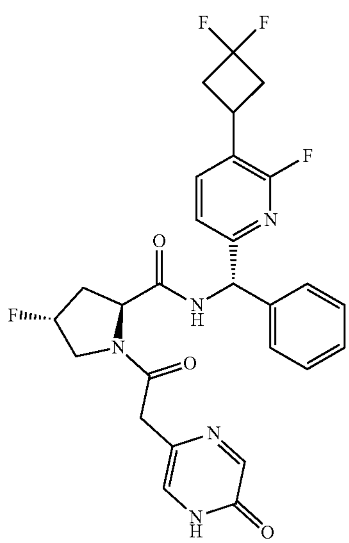 [SMILES: O=C(N[C@@H](c1ccccc1)c1ccc(C2CC(F)(F)C2)c(F)n1)[C@@H]1C[C@@H](F)CN1C(=O)Cc1c[nH]c(=O)cn1] | (2S,4R)-N-[(S)-[5-(3,3-difluorocyclobutyl)-6-fluoropyridin-2-yl](phenyl)methyl]-4-fluoro-1-[2-(5-oxo-4,5-dihydropyrazin-2-yl)acetyl]pyrrolidine-2-carboxamide |

| Compound No. | Structure | IUPAC |
|---|---|---|
| 531 | 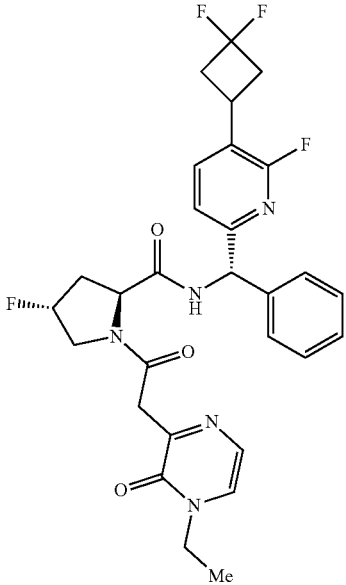 | (2S,4R)-N-[(S)-[5-(3,3-difluorocyclobutyl)-6-fluoropyridin-2-yl](phenyl)methyl]-1-[2-(4-ethyl-3-oxo-3,4-dihydropyrazin-2-yl)acetyl]-4-fluoropyrrolidine-2-carboxamide |
| 532 | 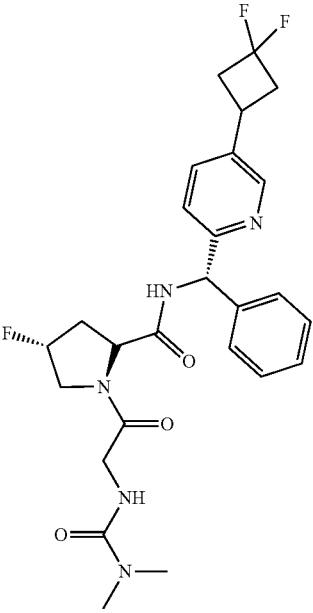 | (2S,4R)-N-((S)-(5-(3,3-difluorocyclobutyl)pyridin-2-yl)(phenyl)methyl)-1-((dimethylcarbamoyl)glycyl)-4-fluoropyrrolidine-2-carboxamide |

TABLE 1-continued

| Compound No. | Structure | IUPAC |
|---|---|---|
| 533 | 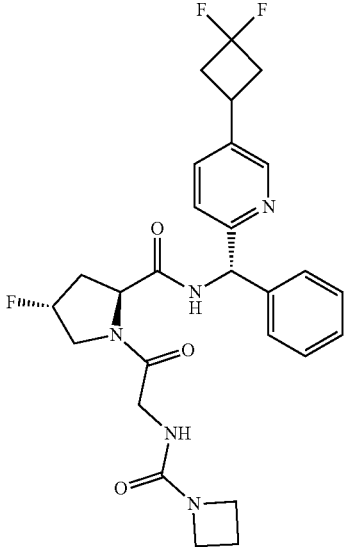 | (2S,4R)-1-{2-[(azetidine-1-carbonyl)amino]acetyl}-N-[(S)-[5-(3,3-difluorocyclobutyl)pyridin-2-yl](phenyl)methyl]-4-fluoropyrrolidine-2-carboxamide |
| 534 | 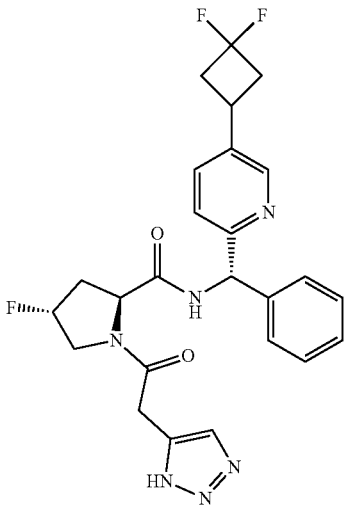 | (2S,4R)-N-[(S)-[5-(3,3-difluorocyclobutyl)pyridin-2-yl](phenyl)methyl]-4-fluoro-1-[2-(1H-1,2,3-triazol-5-yl)acetyl]pyrrolidine-2-carboxamide |
| 535 | 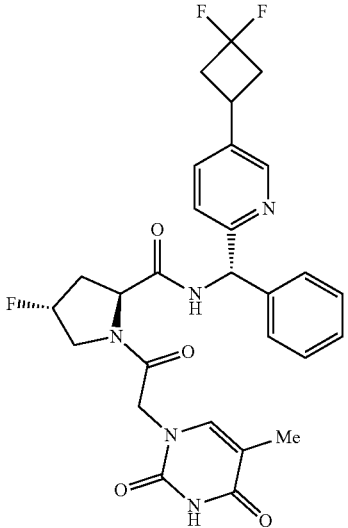 | (2S,4R)-N-[(S)-[5-(3,3-difluorocyclobutyl)pyridin-2-yl](phenyl)methyl]-4-fluoro-1-[2-(5-methyl-2,4-dioxo-1,2,3,4-tetrahydropyrimidin-1-yl)acetyl]pyrrolidine-2-carboxamide |

TABLE 1-continued

| Compound No. | Structure | IUPAC |
|---|---|---|
| 536 | 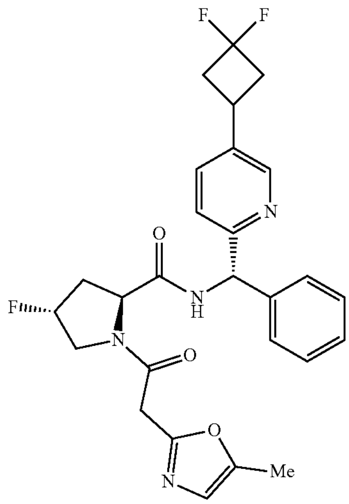 [SMILES: Cc1cnc(CC(=O)N2C[C@H](F)C[C@H]2C(=O)N[C@@H](c2ccccc2)c2ccc(C3CC(F)(F)C3)cn2)o1] | (2S,4R)-N-[(S)-[5-(3,3-difluorocyclobutyl)pyridin-2-yl](phenyl)methyl]-4-fluoro-1-[2-(5-methyl-1,3-oxazol-2-yl)acetyl]pyrrolidine-2-carboxamide |
| 537 | 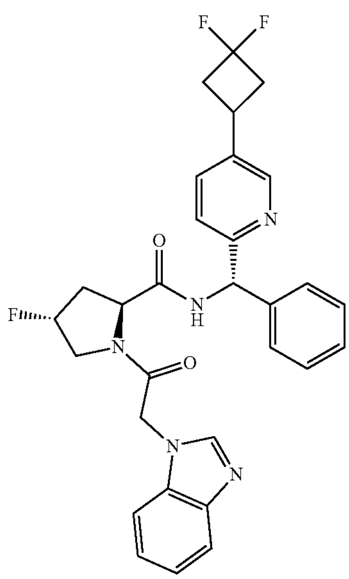 [SMILES: O=C(N[C@@H](c1ccccc1)c1ccc(C2CC(F)(F)C2)cn1)[C@@H]1C[C@@H](F)CN1C(=O)Cn1cnc2ccccc21] | (2S,4R)-1-[2-(1H-1,3-benzodiazol-1-yl)acetyl]-N-[(S)-[5-(3,3-difluorocyclobutyl)pyridin-2-yl](phenyl)methyl]-4-fluoropyrrolidine-2-carboxamide |

TABLE 1-continued
| Compound No. | Structure | IUPAC |
|---|---|---|
| 538 | 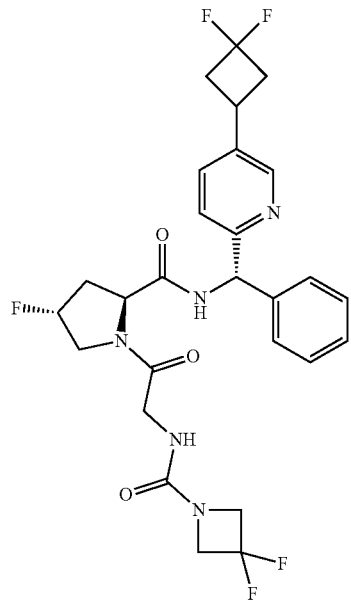 [SMILES: O=C(N[C@@H](c1ccccc1)c1ccc(C2CC(F)(F)C2)cn1)[C@@H]1C[C@@H](F)CN1C(=O)CNC(=O)N1CC(F)(F)C1] | (2S,4R)-1-{2-[(3,3-difluoroazetidine-1-carbonyl)amino]acetyl}-N-[(S)-[5-(3,3-difluorocyclobutyl)pyridin-2-yl](phenyl)methyl]-4-fluoropyrrolidine-2-carboxamide |
| 539 | 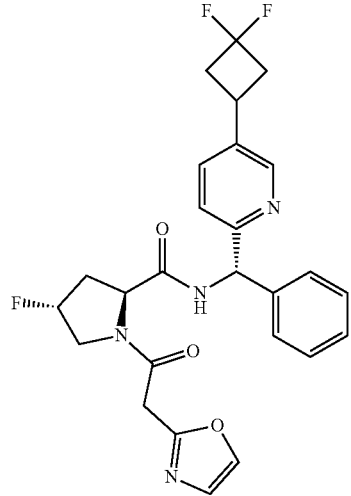 | (2S,4R)-N-[(S)-[5-(3,3-difluorocyclobutyl)pyridin-2-yl](phenyl)methyl]-4-fluoro-1-[2-(1,3-oxazol-2-yl)acetyl]pyrrolidine-2-carboxamide |

TABLE 1-continued

| Compound No. | Structure | IUPAC |
|---|---|---|
| 540 | 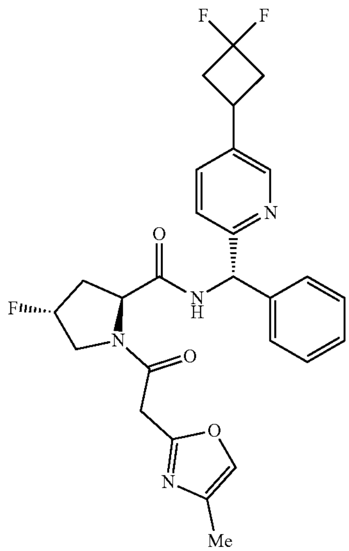 [SMILES: Cc1coc(CC(=O)N2C[C@H](F)C[C@H]2C(=O)N[C@@H](c2ccccc2)c2ccc(C3CC(F)(F)C3)cn2)n1] | (2S,4R)-N-[(S)-[5-(3,3-difluorocyclobutyl)pyridin-2-yl](phenyl)methyl]-4-fluoro-1-[2-(4-methyl-1,3-oxazol-2-yl)acetyl]pyrrolidine-2-carboxamide |
| 541 | 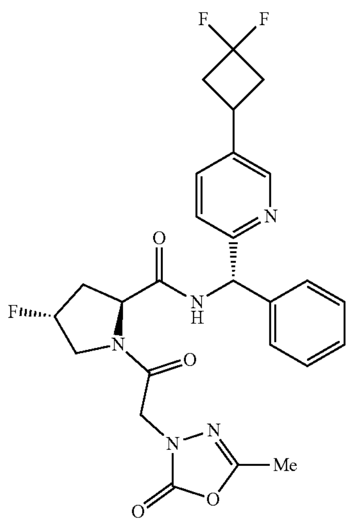 [SMILES: Cc1nn(CC(=O)N2C[C@H](F)C[C@H]2C(=O)N[C@@H](c2ccccc2)c2ccc(C3CC(F)(F)C3)cn2)c(=O)o1] | (2S,4R)-N-[(S)-[5-(3,3-difluorocyclobutyl)pyridin-2-yl](phenyl)methyl]-4-fluoro-1-[2-(5-methyl-2-oxo-2,3-dihydro-1,3,4-oxadiazol-3-yl)acetyl]pyrrolidine-2-carboxamide |
| 542 | 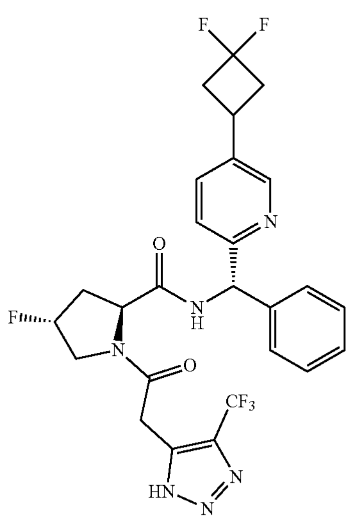 [SMILES: O=C(N[C@@H](c1ccccc1)c1ccc(C2CC(F)(F)C2)cn1)[C@@H]1C[C@@H](F)CN1C(=O)Cc1[nH]nnc1C(F)(F)F] | (2S,4R)-N-[(S)-[5-(3,3-difluorocyclobutyl)pyridin-2-yl](phenyl)methyl]-4-fluoro-1-{2-[4-(trifluoromethyl)-1H-1,2,3-triazol-5-yl]acetyl}pyrrolidine-2-carboxamide |

| Compound No. | Structure | IUPAC |
|---|---|---|
| 543 | 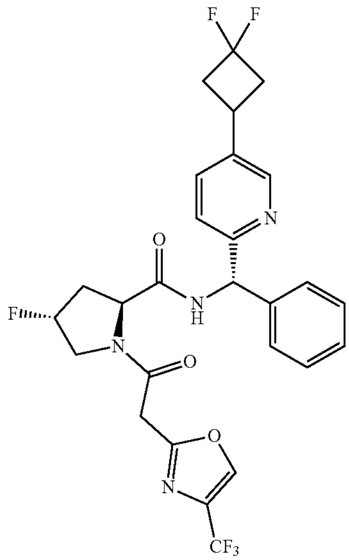 [SMILES: O=C(N[C@@H](c1ccccc1)c1ccc(C2CC(F)(F)C2)cn1)[C@@H]1C[C@@H](F)CN1C(=O)Cc1nc(C(F)(F)F)co1] | (2S,4R)-N-[(S)-[5-(3,3-difluorocyclobutyl)pyridin-2-yl](phenyl)methyl]-4-fluoro-1-{2-[4-(trifluoromethyl)-1,3-oxazol-2-yl]acetyl}pyrrolidine-2-carboxamide |
| 544 | 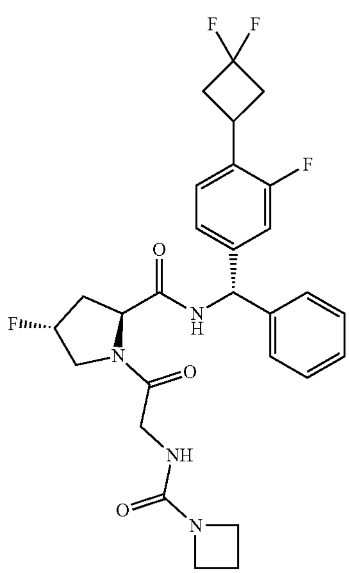 [SMILES: O=C(N[C@@H](c1ccccc1)c1ccc(C2CC(F)(F)C2)c(F)c1)[C@@H]1C[C@@H](F)CN1C(=O)CNC(=O)N1CCC1] | (2S,4R)-1-((azetidine-1-carbonyl)glycyl)-N-((S)-(4-(3,3-difluorocyclobutyl)-3-fluorophenyl)(phenyl)methyl)-4-fluoropyrrolidine-2-carboxamide |

TABLE 1-continued
| Compound No. | Structure | IUPAC |
|---|---|---|
| 545 | 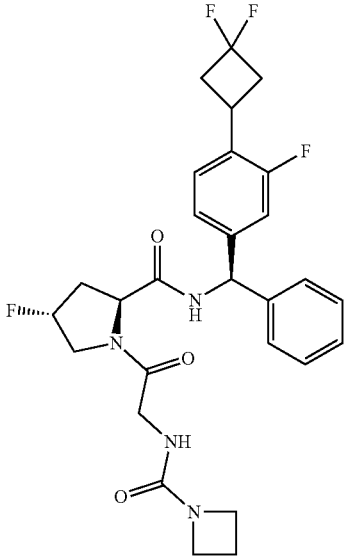 [SMILES: O=C(N[C@H](c1ccccc1)c1ccc(C2CC(F)(F)C2)c(F)c1)[C@@H]1C[C@@H](F)CN1C(=O)CNC(=O)N1CCC1] | (2S,4R)-1-((azetidine-1-carbonyl)glycyl)-N-((R)-(4-(3,3-difluorocyclobutyl)-3-fluorophenyl)(phenyl)methyl)-4-fluoropyrrolidine-2-carboxamide |
| 546 | 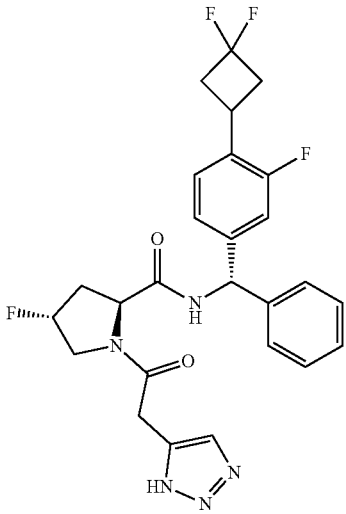 | (2S,4R)-N-[(S)-[4-(3,3-difluorocyclobutyl)-3-fluorophenyl](phenyl)methyl]-4-fluoro-1-[2-(1H-1,2,3-triazol-5-yl)acetyl]pyrrolidine-2-carboxamide |

TABLE 1-continued
| Compound No. | Structure | IUPAC |
|---|---|---|
| 547 | 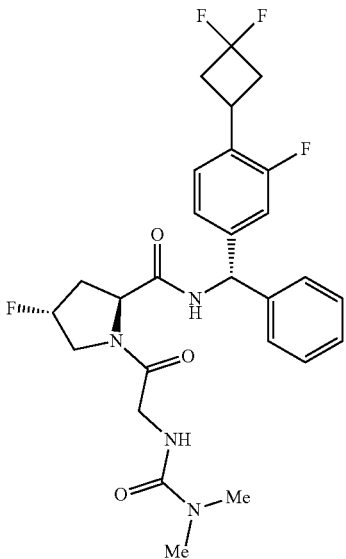 | (2S,4R)-N-[(S)-[4-(3,3-difluorocyclobutyl)-3-fluorophenyl](phenyl)methyl]-1-{2-[(dimethylcarbamoyl)amino]acetyl}-4-fluoropyrrolidine-2-carboxamide |
| 548 | 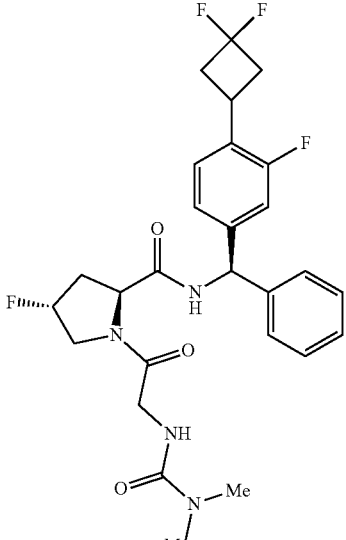 | (2S,4R)-N-[(R)-[4-(3,3-difluorocyclobutyl)-3-fluorophenyl](phenyl)methyl]-1-{2-[(dimethylcarbamoyl)amino]acetyl}-4-fluoropyrrolidine-2-carboxamide |

TABLE 1-continued

| Compound No. | Structure | IUPAC |
|---|---|---|
| 549 | 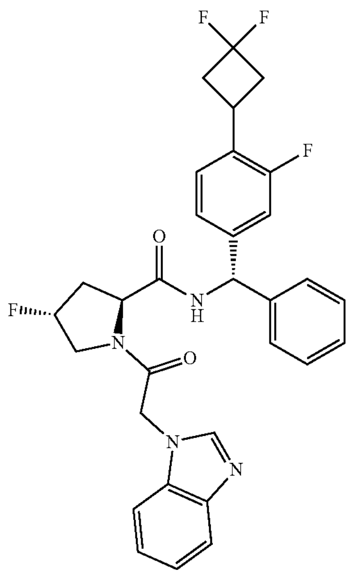 [SMILES: O=C(N[C@@H](c1ccccc1)c1ccc(C2CC(F)(F)C2)c(F)c1)[C@@H]1C[C@@H](F)CN1C(=O)Cn1cnc2ccccc21] | (2S,4R)-1-[2-(1H-1,3-benzodiazol-1-yl)acetyl]-N-[(S)-[4-(3,3-difluorocyclobutyl)-3-fluorophenyl](phenyl)methyl]-4-fluoropyrrolidine-2-carboxamide |
| 550 | 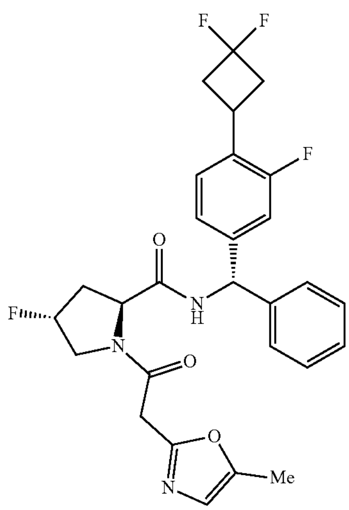 [SMILES: Cc1cnc(CC(=O)N2C[C@H](F)C[C@H]2C(=O)N[C@@H](c2ccccc2)c2ccc(C3CC(F)(F)C3)c(F)c2)o1] | (2S,4R)-N-[(S)-[4-(3,3-difluorocyclobutyl)-3-fluorophenyl](phenyl)methyl]-4-fluoro-1-[2-(5-methyl-1,3-oxazol-2-yl)acetyl]pyrrolidine-2-carboxamide |
| 551 | 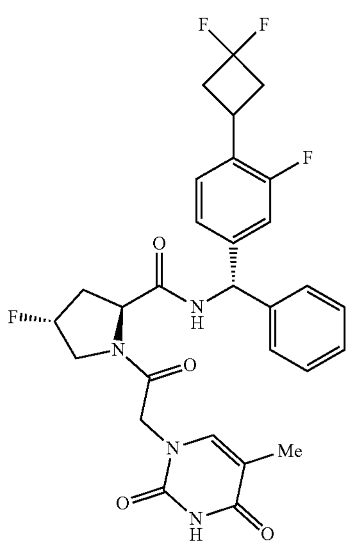 [SMILES: Cc1cn(CC(=O)N2C[C@H](F)C[C@H]2C(=O)N[C@@H](c2ccccc2)c2ccc(C3CC(F)(F)C3)c(F)c2)c(=O)[nH]c1=O] | (2S,4R)-N-[(S)-[4-(3,3-difluorocyclobutyl)-3-fluorophenyl](phenyl)methyl]-4-fluoro-1-[2-(5-methyl-2,4-dioxo-1,2,3,4-tetrahydropyrimidin-1-yl)acetyl]pyrrolidine-2-carboxamide |

TABLE 1-continued

| Compound No. | Structure | IUPAC |
|---|---|---|
| 552 | 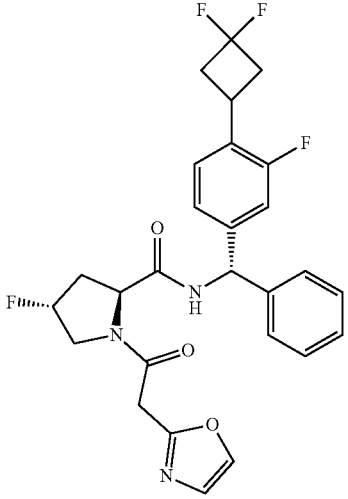 | (2S,4R)-N-[(S)-[4-(3,3-difluorocyclobutyl)-3-fluorophenyl](phenyl)methyl]-4-fluoro-1-[2-(1,3-oxazol-2-yl)acetyl]pyrrolidine-2-carboxamide |
| 553 | 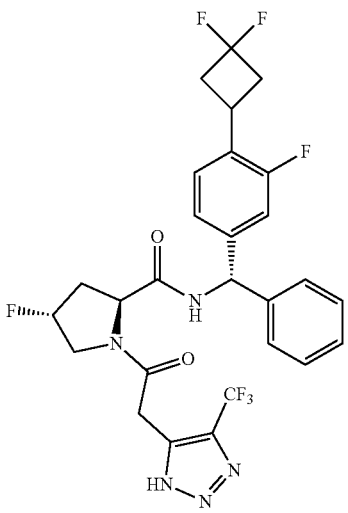 | (2S,4R)-N-[(S)-[4-(3,3-difluorocyclobutyl)-3-fluorophenyl](phenyl)methyl]-4-fluoro-1-{2-[4-(trifluoromethyl)-1H-1,2,3-triazol-5-yl]acetyl}pyrrolidine-2-carboxamide |
| 554 | 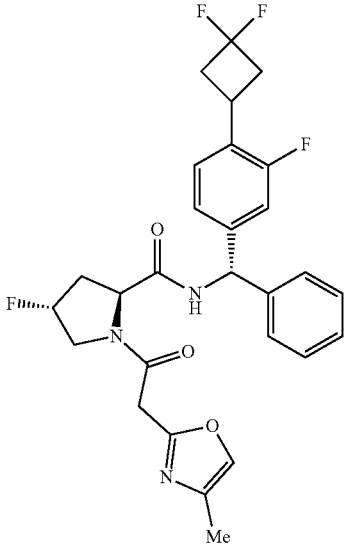 | (2S,4R)-N-[(S)-[4-(3,3-difluorocyclobutyl)-3-fluorophenyl](phenyl)methyl]-4-fluoro-1-[2-(4-methyl-1,3-oxazol-2-yl)acetyl]pyrrolidine-2-carboxamide |

TABLE 1-continued

| Compound No. | Structure | IUPAC |
|---|---|---|
| 555 | 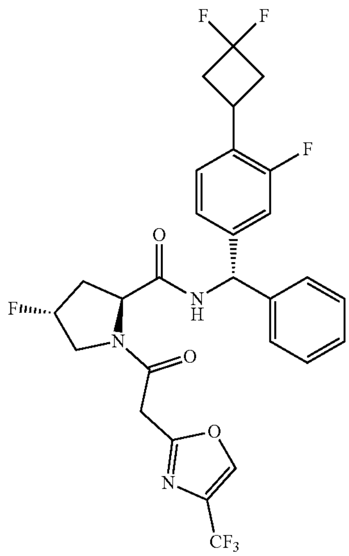 [SMILES: O=C(N[C@@H](c1ccccc1)c1ccc(C2CC(F)(F)C2)c(F)c1)[C@@H]1C[C@@H](F)CN1C(=O)Cc1nc(C(F)(F)F)co1] | (2S,4R)-N-[(S)-[4-(3,3-difluorocyclobutyl)-3-fluorophenyl](phenyl)methyl]-4-fluoro-1-{2-[4-(trifluoromethyl)-1,3-oxazol-2-yl]acetyl}pyrrolidine-2-carboxamide |
| 556 | 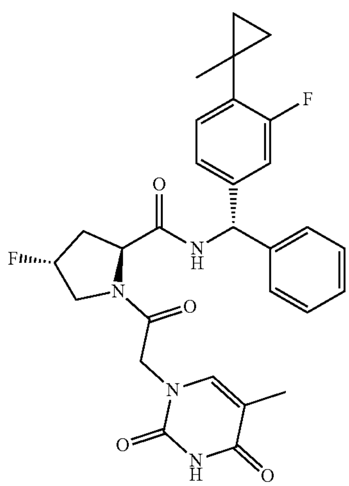 [SMILES: Cc1cn(CC(=O)N2C[C@H](F)C[C@H]2C(=O)N[C@@H](c2ccccc2)c2ccc(C3(C)CC3)c(F)c2)c(=O)[nH]c1=O] | (2S,4R)-4-fluoro-N-((S)-(3-fluoro-4-(1-methylcyclopropyl)phenyl)(phenyl)methyl)-1-(2-(5-methyl-2,4-dioxo-3,4-dihydropyrimidin-1(2H)-yl)acetyl)pyrrolidine-2-carboxamide |
| 557 | 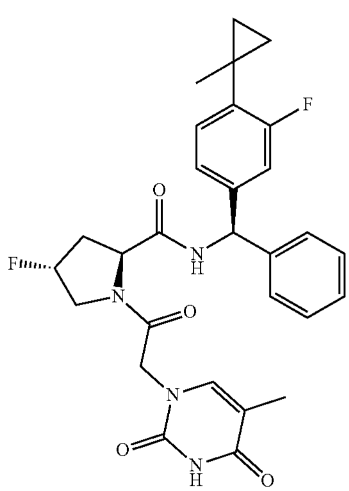 [SMILES: Cc1cn(CC(=O)N2C[C@H](F)C[C@H]2C(=O)N[C@H](c2ccccc2)c2ccc(C3(C)CC3)c(F)c2)c(=O)[nH]c1=O] | (2S,4R)-4-fluoro-N-((R)-(3-fluoro-4-(1-methylcyclopropyl)phenyl)(phenyl)methyl)-1-(2-(5-methyl-2,4-dioxo-3,4-dihydropyrimidin-1(2H)-yl)acetyl)pyrrolidine-2-carboxamide |

TABLE 1-continued

| Compound No. | Structure | IUPAC |
|---|---|---|
| 558 | 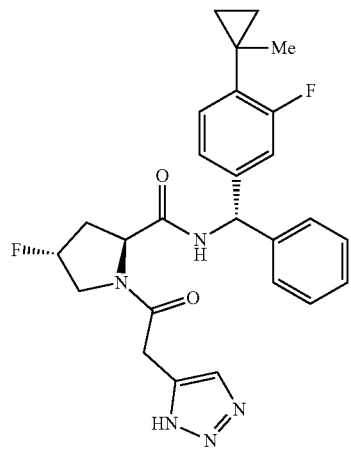 [SMILES: CC1(c2ccc([C@@H](NC(=O)[C@@H]3C[C@@H](F)CN3C(=O)Cc3cnn[nH]3)c3ccccc3)cc2F)CC1] | (2S,4R)-4-fluoro-N-[(S)-[3-fluoro-4-(1-methylcyclopropyl)phenyl](phenyl)methyl]-1-[2-(1H-1,2,3-triazol-5-yl)acetyl]pyrrolidine-2-carboxamide |
| 559 | 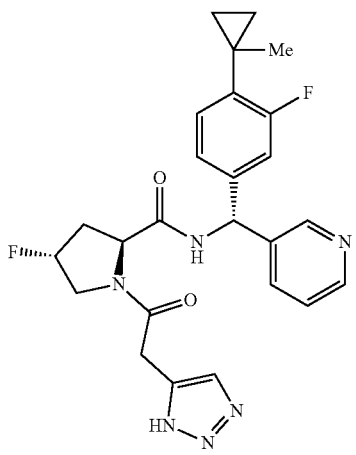 [SMILES: CC1(c2ccc([C@@H](NC(=O)[C@@H]3C[C@@H](F)CN3C(=O)Cc3cnn[nH]3)c3cccnc3)cc2F)CC1] | (2S,4R)-4-fluoro-N-[(R)-[3-fluoro-4-(1-methylcyclopropyl)phenyl](pyridin-3-yl)methyl]-1-[2-(1H-1,2,3-triazol-5-yl)acetyl]pyrrolidine-2-carboxamide |
| 560 | 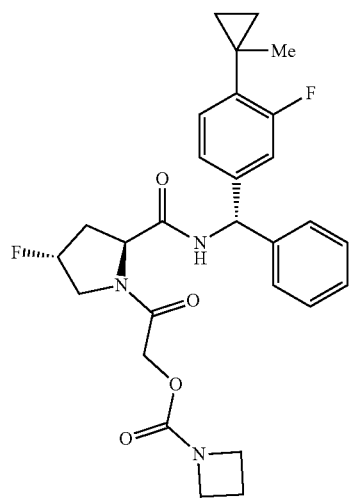 | 2-[(2S,4R)-4-fluoro-2-{[(S)-[3-fluoro-4-(1-methylcyclopropyl)phenyl](phenyl)methyl]carbamoyl}pyrrolidin-1-yl]-2-oxoethyl azetidine-1-carboxylate |

TABLE 1-continued

| Compound No. | Structure | IUPAC |
|---|---|---|
| 561 | 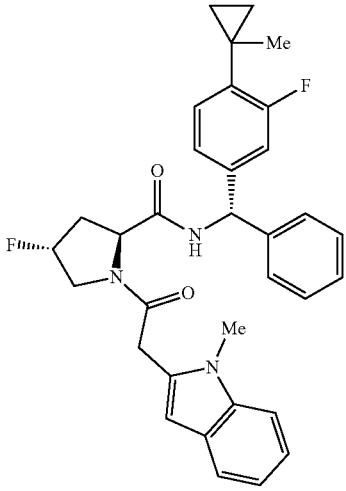 | (2S,4R)-4-fluoro-N-[(S)-[3-fluoro-4-(1-methylcyclopropyl)phenyl](phenyl)methyl]-1-[2-(1-methyl-1H-indol-2-yl)acetyl]pyrrolidine-2-carboxamide |
| 562 | 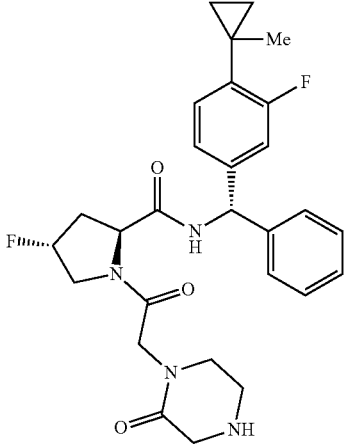 | (2S,4R)-4-fluoro-N-[(S)-[3-fluoro-4-(1-methylcyclopropyl)phenyl](phenyl)methyl]-1-[2-(2-oxopiperazin-1-yl)acetyl]pyrrolidine-2-carboxamide |
| 563 | 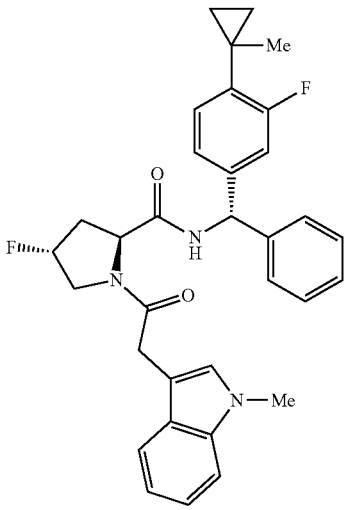 | (2S,4R)-4-fluoro-N-[(S)-[3-fluoro-4-(1-methylcyclopropyl)phenyl](phenyl)-methyl]-1-[2-(1-methyl-1H-indol-3-yl)acetyl]pyrrolidine-2-carboxamide |

TABLE 1-continued

| Compound No. | Structure | IUPAC |
|---|---|---|
| 564 | 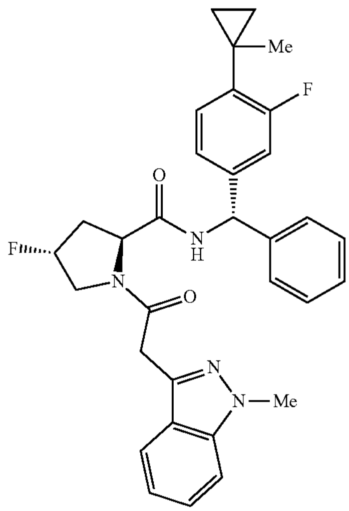 [SMILES: Cn1nc(CC(=O)N2C[C@H](F)C[C@H]2C(=O)N[C@@H](c2ccccc2)c2ccc(C3(C)CC3)c(F)c2)c2ccccc21] | (2S,4R)-4-fluoro-N-[(S)-[3-fluoro-4-(1-methylcyclopropyl)phenyl](phenyl)methyl]-1-[2-(1-methyl-1H-indazol-3-yl)acetyl]pyrrolidine-2-carboxamide |
| 565 | 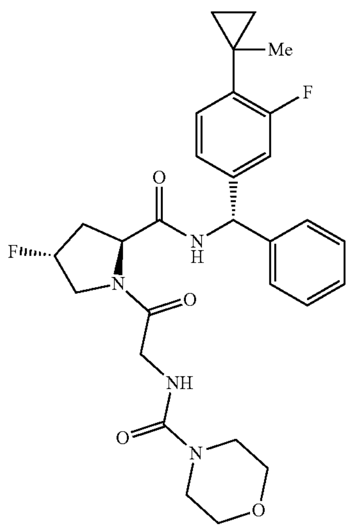 [SMILES: CC1(c2ccc([C@@H](NC(=O)[C@@H]3C[C@@H](F)CN3C(=O)CNC(=O)N3CCOCC3)c3ccccc3)cc2F)CC1] | N-{2-[(2S,4R)-4-fluoro-2-{[(S)-[3-fluoro-4-(1-methylcyclopropyl)phenyl](phenyl)methyl]carbamoyl}pyrrolidin-1-yl]-2-oxoethyl}morpholine-4-carboxamide |
| 566 | 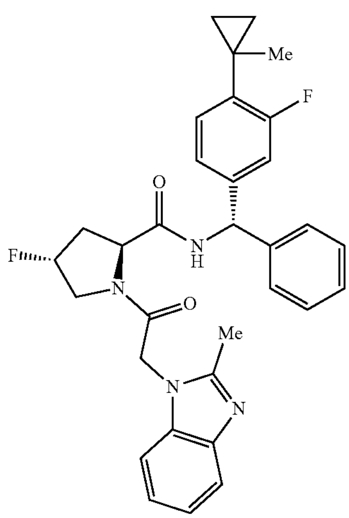 [SMILES: Cc1nc2ccccc2n1CC(=O)N1C[C@H](F)C[C@H]1C(=O)N[C@@H](c1ccccc1)c1ccc(C2(C)CC2)c(F)c1] | (2S,4R)-4-fluoro-N-[(S)-[3-fluoro-4-(1-methylcyclopropyl)phenyl](phenyl)methyl]-1-[2-(2-methyl-1H-1,3-benzodiazol-1-yl)acetyl]pyrrolidine-2-carboxamide |

| Compound No. | Structure | IUPAC |
|---|---|---|
| 567 | 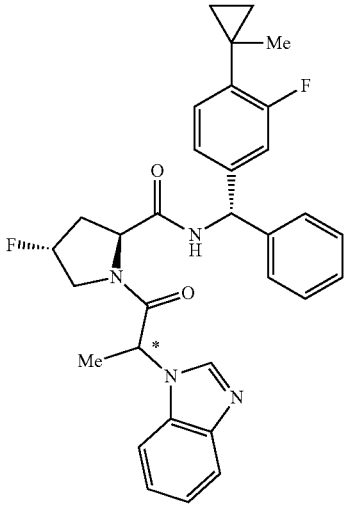 [SMILES: CC(C(=O)N1C[C@H](F)C[C@H]1C(=O)N[C@@H](c1ccccc1)c1ccc(C2(C)CC2)c(F)c1)n1cnc2ccccc21] | (2S,4R)-1-[(2R) or (2S)-2-(1H-1,3-benzodiazol-1-yl)propanoyl]-4-fluoro-N-[(S)-[3-fluoro-4-(1-methylcyclopropyl)phenyl](phenyl)methyl]pyrrolidine-2-carboxamide |
| 568 | 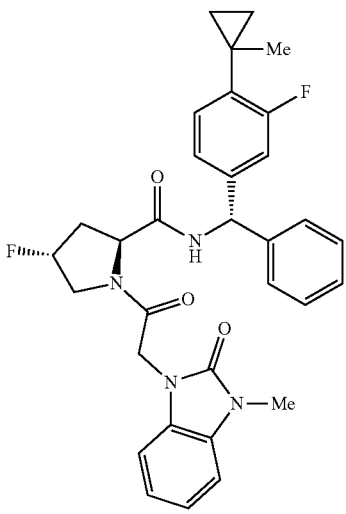 | (2S,4R)-4-fluoro-N-[(S)-[3-fluoro-4-(1-methylcyclopropyl)phenyl](phenyl)methyl]-1-[2-(3-methyl-2-oxo-2,3-dihydro-1H-1,3-benzodiazol-1-yl)acetyl]pyrrolidine-2-carboxamide |
| 569 | 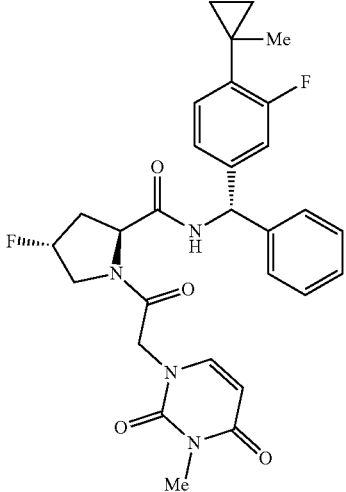 | (2S,4R)-4-fluoro-N-[(S)-[3-fluoro-4-(1-methylcyclopropyl)phenyl](phenyl)methyl]-1-[2-(3-methyl-2,4-dioxo-1,2,3,4-tetrahydropyrimidin-1-yl)acetyl]pyrrolidine-2-carboxamide |

TABLE 1-continued

| Compound No. | Structure | IUPAC |
|---|---|---|
| 570 | 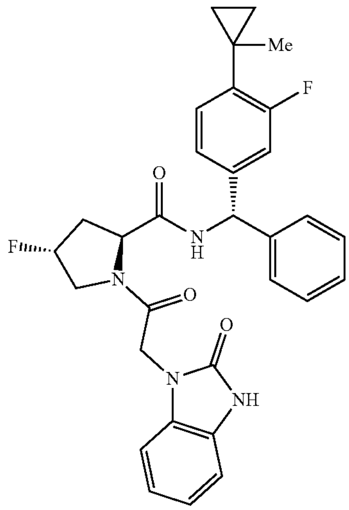 [SMILES: CC1(c2ccc([C@@H](NC(=O)[C@@H]3C[C@@H](F)CN3C(=O)Cn3c(=O)[nH]c4ccccc43)c3ccccc3)cc2F)CC1] | (2S,4R)-4-fluoro-N-[(S)-[3-fluoro-4-(1-methylcyclopropyl)phenyl](phenyl)methyl]-1-[2-(2-oxo-2,3-dihydro-1H-1,3-benzodiazol-1-yl)acetyl]pyrrolidine-2-carboxamide |
| 571 | 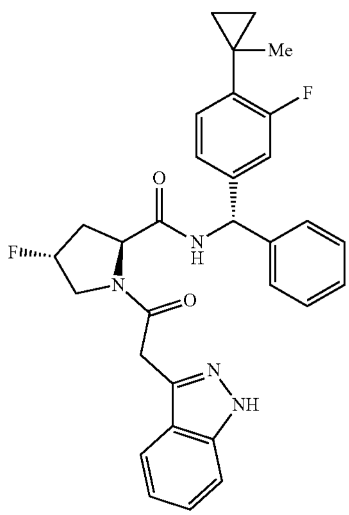 [SMILES: CC1(c2ccc([C@@H](NC(=O)[C@@H]3C[C@@H](F)CN3C(=O)Cc3n[nH]c4ccccc34)c3ccccc3)cc2F)CC1] | (2S,4R)-4-fluoro-N-[(S)-[3-fluoro-4-(1-methylcyclopropyl)phenyl](phenyl)methyl]-1-[2-(1H-indazol-3-yl)acetyl]pyrrolidine-2-carboxamide |
| 572 | 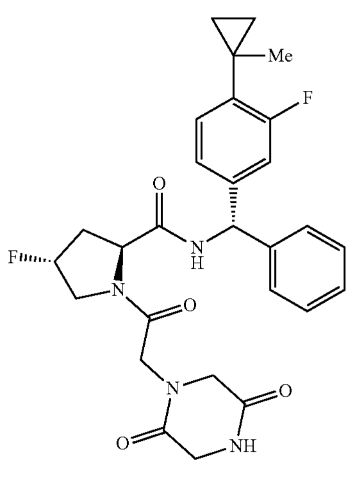 [SMILES: CC1(c2ccc([C@@H](NC(=O)[C@@H]3C[C@@H](F)CN3C(=O)CN3CC(=O)NCC3=O)c3ccccc3)cc2F)CC1] | (2S,4R)-1-[2-(2,5-dioxopiperazin-1-yl)acetyl]-4-fluoro-N-[(S)-[3-fluoro-1-(1-methylcyclopropyl)phenyl](phenyl)methyl]pyrrolidine-2-carboxamide |

TABLE 1-continued

| Compound No. | Structure | IUPAC |
|---|---|---|
| 573 | 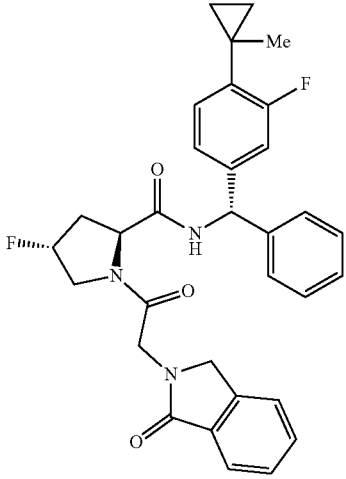 [SMILES: CC1(c2ccc([C@@H](NC(=O)[C@@H]3C[C@@H](F)CN3C(=O)CN3Cc4ccccc4C3=O)c3ccccc3)cc2F)CC1] | (2S,4R)-4-fluoro-N-[(S)-[3-fluoro-4-(1-methylcyclopropyl)phenyl](phenyl)methyl]-1-[2-(1-oxo-2,3-dihydro-1H-isoindol-2-yl)acetyl]pyrrolidine-2-carboxamide |
| 574 | 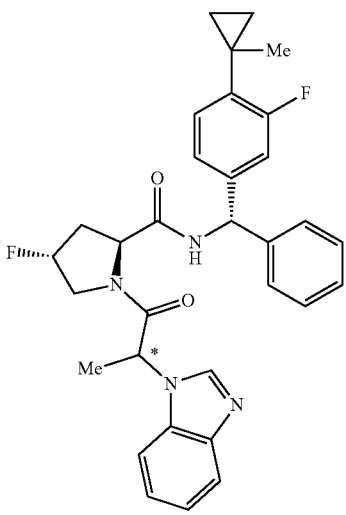 [SMILES: CC(C(=O)N1C[C@H](F)C[C@H]1C(=O)N[C@@H](c1ccccc1)c1ccc(C2(C)CC2)c(F)c1)n1cnc2ccccc21] | (2S,4R)-1-[(2S) or 2R)-2-(1H-1,3-benzodiazol-1-yl)propanoyl]-4-fluoro-N-[(S)-[3-fluoro-4-(1-methylcyclopropyl)phenyl](phenyl)methyl]pyrrolidine-2-carboxamide |
| 575 | 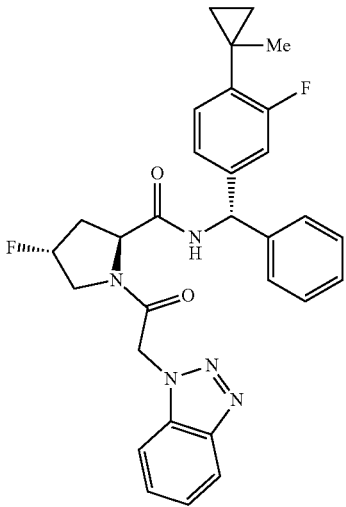 | (2S,4R)-1-[2-(1H-1,2,3-benzotriazol-1-yl)acetyl]-4-fluoro-N-[(S)-[3-fluoro-4-(1-methylcyclopropyl)phenyl](phenyl)methyl]pyrrolidine-2-carboxamide |

TABLE 1-continued

| Compound No. | Structure | IUPAC |
|---|---|---|
| 576 | 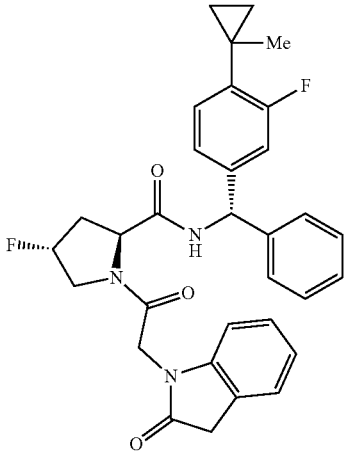 | (2S,4R)-4-fluoro-N-[(S)-[3-fluoro-4-(1-methylcyclopropyl)phenyl](phenyl)methyl]-1-[2-(2-oxo-2,3-dihydro-1H-indol-1-yl)acetyl]pyrrolidine-2-carboxamide |
| 577 | 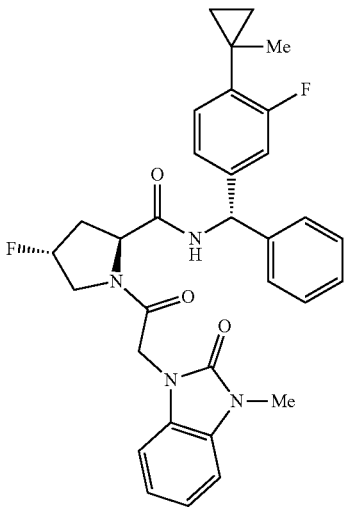 | (2S,4R)-4-fluoro-N-[(S)-[3-fluoro-4-(1-methylcyclopropyl)phenyl](phenyl)methyl]-1-[2-(1-methyl-2-oxo-2,3-dihydro-1H-indol-3-yl)acetyl]pyrrolidine-2-carboxamide |
| 578 | 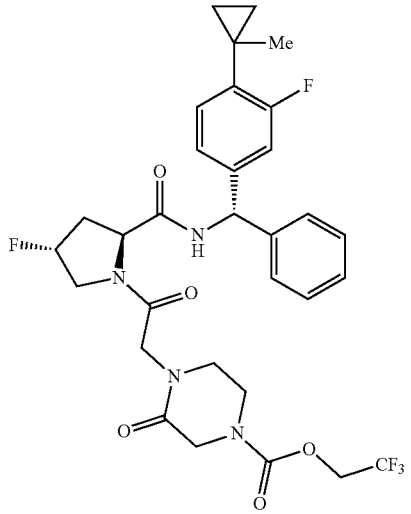 [SMILES: CC1(c2ccc([C@@H](NC(=O)[C@@H]3C[C@@H](F)CN3C(=O)CN3CCN(C(=O)OCC(F)(F)F)CC3=O)c3ccccc3)cc2F)CC1] | 2,2,2-trifluoroethyl 4-{2-[(2S,4R)-4-fluoro-2-{[(S)-[3-fluoro-4-(1-methylcyclopropyl)phenyl](phenyl)methyl]carbamoyl}pyrrolidin-1-yl]-2-oxoethyl}-3-oxopiperazine-1-carboxylate |

TABLE 1-continued

| Compound No. | Structure | IUPAC |
|---|---|---|
| 579 | 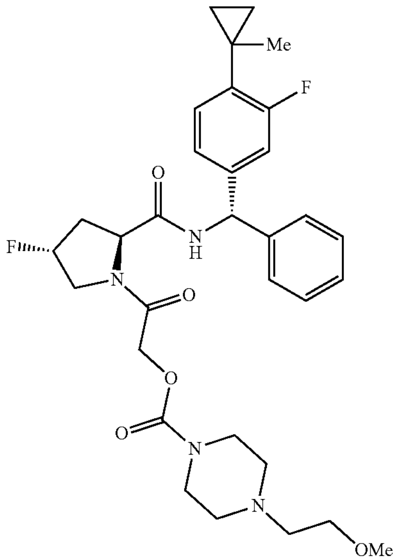 [SMILES: COCCN1CCN(C(=O)OCC(=O)N2C[C@H](F)C[C@H]2C(=O)N[C@@H](c2ccccc2)c2ccc(C3(C)CC3)c(F)c2)CC1] | 2-[(2S,4R)-4-fluoro-2-{[(S)-[3-fluoro-4-(1-methylcyclopropyl)phenyl](phenyl)methyl]carbamoyl}pyrrolidin-1-yl]-2-oxoethyl 4-(2-methoxyethyl)piperazine-1-carboxylate |
| 580 | 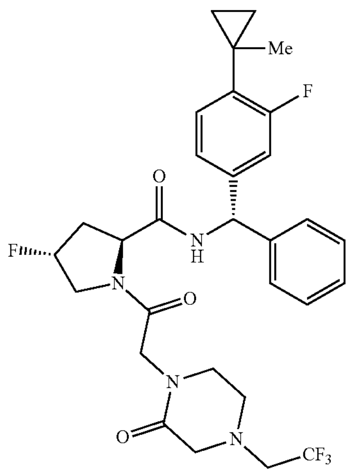 [SMILES: CC1(c2ccc([C@@H](NC(=O)[C@@H]3C[C@@H](F)CN3C(=O)CN3CCN(CC(F)(F)F)CC3=O)c3ccccc3)cc2F)CC1] | (2S,4R)-4-fluoro-N-[(S)-[3-fluoro-4-(1-methylcyclopropyl)phenyl](phenyl)methyl]-1-{2-[2-oxo-4-(2,2,2-trifluoroethyl)piperazin-1-yl]acetyl}pyrrolidine-2-carboxamide |
| 581 | 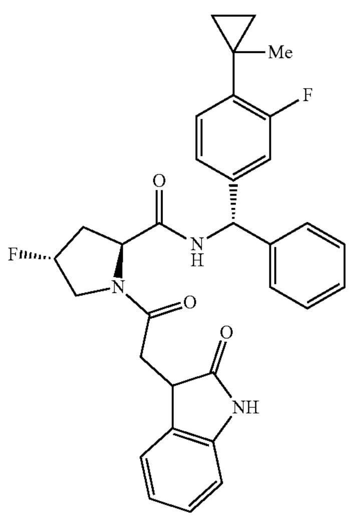 [SMILES: CC1(c2ccc([C@@H](NC(=O)[C@@H]3C[C@@H](F)CN3C(=O)CC3C(=O)Nc4ccccc43)c3ccccc3)cc2F)CC1] | (2S,4R)-4-fluoro-N-[(S)-[3-fluoro-4-(1-methylcyclopropyl)phenyl](phenyl)methyl]-1-[2-(2-oxo-2,3-dihydro-1H-indol-3-yl)acetyl]pyrrolidine-2-carboxamide |

TABLE 1-continued

| Compound No. | Structure | IUPAC |
|---|---|---|
| 582 | 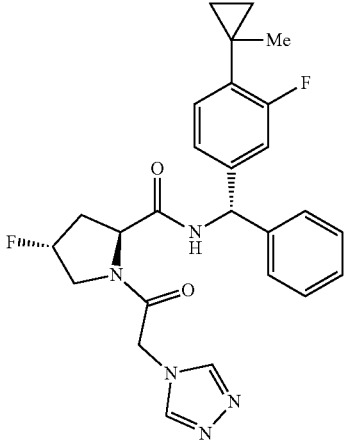 [SMILES: CC1(c2ccc([C@@H](NC(=O)[C@@H]3C[C@@H](F)CN3C(=O)Cn3cnnc3)c3ccccc3)cc2F)CC1] | (2S,4R)-4-fluoro-N-[(S)-[3-fluoro-4-(1-methylcyclopropyl)phenyl](phenyl)methyl]-1-[2-(4H-1,2,4-triazol-4-yl)acetyl]pyrrolidine-2-carboxamide |
| 583 | 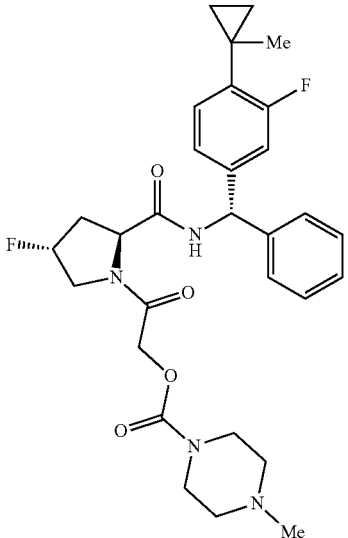 [SMILES: CN1CCN(C(=O)OCC(=O)N2C[C@H](F)C[C@H]2C(=O)N[C@@H](c2ccccc2)c2ccc(C3(C)CC3)c(F)c2)CC1] | 2-[(2S,4R)-4-fluoro-2-{[(S)-[3-fluoro-4-(1-methylcyclopropyl)phenyl](phenyl)methyl]carbamoyl}pyrrolidin-1-yl]-2-oxoethyl 4-methylpiperazine-1-carboxylate |
| 584 | 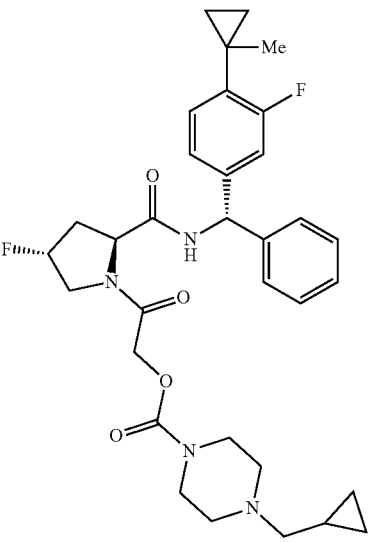 [SMILES: CC1(c2ccc([C@@H](NC(=O)[C@@H]3C[C@@H](F)CN3C(=O)COC(=O)N3CCN(CC4CC4)CC3)c3ccccc3)cc2F)CC1] | 2-[(2S,4R)-4-fluoro-2-{[(S)-[3-fluoro-4-(1-methylcyclopropyl)phenyl](phenyl)methyl]carbamoyl}pyrrolidin-1-yl]-2-oxoethyl-4-(cyclopropylmethyl)piperazine-1-carboxylate |

TABLE 1-continued

| Compound No. | Structure | IUPAC |
|---|---|---|
| 585 | 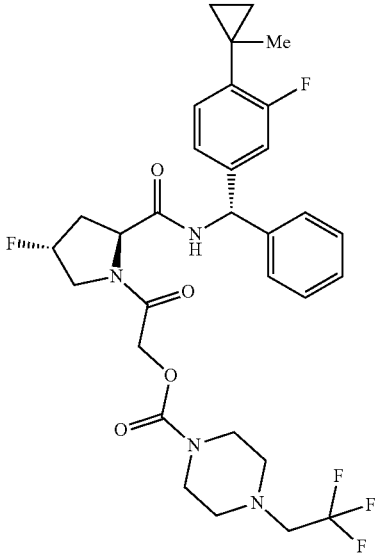 [SMILES: CC1(c2ccc([C@@H](NC(=O)[C@@H]3C[C@@H](F)CN3C(=O)COC(=O)N3CCN(CC(F)(F)F)CC3)c3ccccc3)cc2F)CC1] | 2-[(2S,4R)-4-fluoro-2-{[(S)-[3-fluoro-4-(1-methylcyclopropyl)phenyl](phenyl)methyl]carbamoyl}pyrrolidin-1-yl]-2-oxoethyl 4-(2,2,2-trifluoroethyl)piperazine-1-carboxylate |
| 586 | 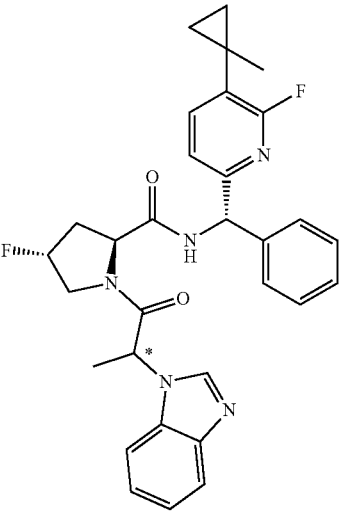 [SMILES: CC(C(=O)N1C[C@H](F)C[C@H]1C(=O)N[C@@H](c1ccccc1)c1ccc(C2(C)CC2)c(F)n1)n1cnc2ccccc21] | (2S,4R)-1-((R) or (S)-2-(1H-benzo[d]imidazol-1-yl)propanoyl)-4-fluoro-N-((S)-6-fluoro-5-(1-methylcyclopropyl)pyridin-2-yl)(phenyl)methyl)pyrrolidine-2-carboxamide |
| 587 | 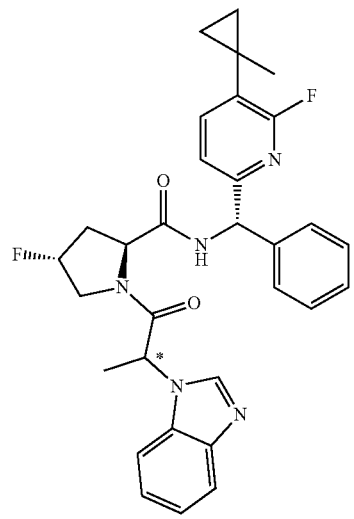 [SMILES: CC(C(=O)N1C[C@H](F)C[C@H]1C(=O)N[C@@H](c1ccccc1)c1ccc(C2(C)CC2)c(F)n1)n1cnc2ccccc21] | (2S,4R)-1-((S) or (R)-2-(1H-benzo[d]imidazol-1-yl)propanoyl)-4-fluoro-N-((S)-(6-fluoro-5-(1-methylcyclopropyl)pyridin-2-yl)(phenyl)methyl)pyrrolidine-2-carboxamide |

TABLE 1-continued

| Compound No. | Structure | IUPAC |
|---|---|---|
| 588 | 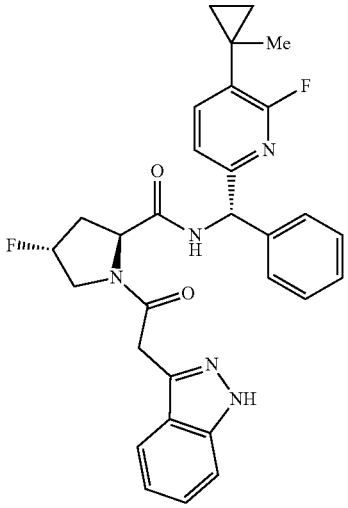 [SMILES: CC1(c2ccc([C@@H](NC(=O)[C@@H]3C[C@@H](F)CN3C(=O)Cc3n[nH]c4ccccc34)c3ccccc3)nc2F)CC1] | (2S,4R)-4-fluoro-N-[(S)-[6-fluoro-5-(1-methylcyclopropyl)pyridin-2-yl](phenyl)methyl]-1-[2-(1H-indazol-3-yl)acetyl]pyrrolidine-2-carboxamide |
| 589 | 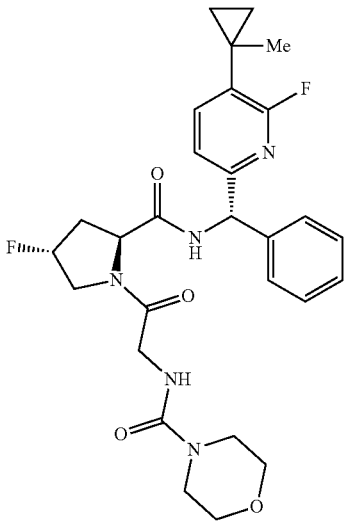 | N-{2-[(2S,4R)-4-fluoro-2-{[(S)-[6-fluoro-5-(1-methylcyclopropyl)pyridin-2-yl](phenyl)methyl]carbamoyl}pyrrolidin-1-yl]-2-oxoethyl}morpholine-4-carboxamide |
| 590 | 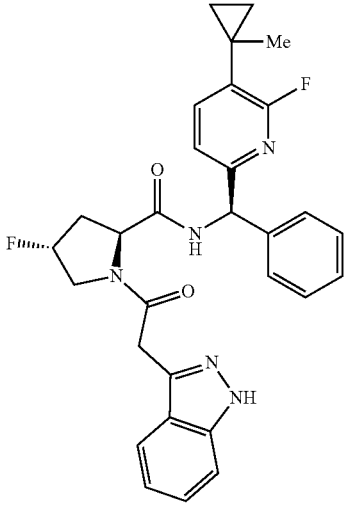 [SMILES: CC1(c2ccc([C@H](NC(=O)[C@@H]3C[C@@H](F)CN3C(=O)Cc3n[nH]c4ccccc34)c3ccccc3)nc2F)CC1] | (2S,4R)-4-fluoro-N-[(R)-[6-fluoro-5-(1-methylcyclopropyl)pyridin-2-yl](phenyl)methyl]-1-[2-(1H-indazol-3-yl)acetyl]pyrrolidine-2-carboxamide |

TABLE 1-continued

| Compound No. | Structure | IUPAC |
|---|---|---|
| 591 | 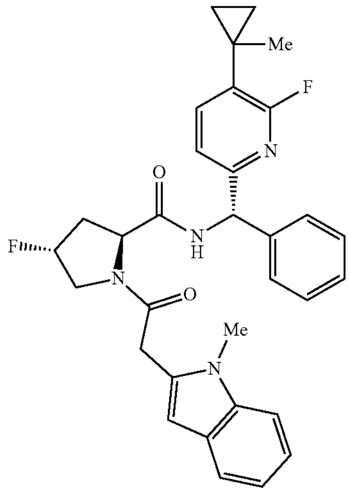 [SMILES: Cn1c(CC(=O)N2C[C@H](F)C[C@H]2C(=O)N[C@@H](c2ccccc2)c2ccc(C3(C)CC3)c(F)n2)cc2ccccc21] | (2S,4R)-4-fluoro-N-[(S)-[6-fluoro-5-(1-methylcyclopropyl)pyridin-2-yl](phenyl)methyl]-1-[2-(1-methyl-1H-indol-2-yl)acetyl]pyrrolidine-2-carboxamide |
| 592 | 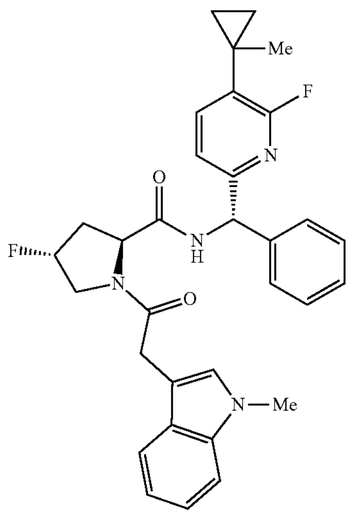 [SMILES: Cn1cc(CC(=O)N2C[C@H](F)C[C@H]2C(=O)N[C@@H](c2ccccc2)c2ccc(C3(C)CC3)c(F)n2)c2ccccc21] | (2S,4R)-4-fluoro-N-[(S)-[6-fluoro-5-(1-methylcyclopropyl)pyridin-2-yl](phenyl)methyl]-1-[2-(1-methyl-1H-indol-3-yl)acetyl]pyrrolidine-2-carboxamide |
| 593 | 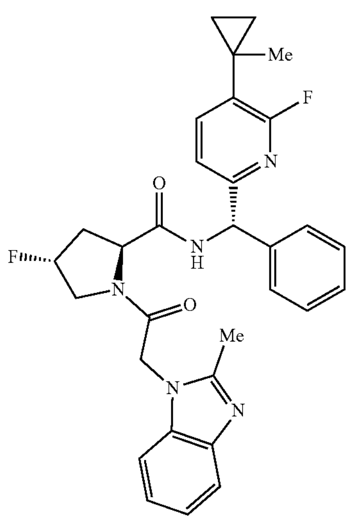 [SMILES: Cc1nc2ccccc2n1CC(=O)N1C[C@H](F)C[C@H]1C(=O)N[C@@H](c1ccccc1)c1ccc(C2(C)CC2)c(F)n1] | (2S,4R)-4-fluoro-N-[(S)-[6-fluoro-5-(1-methylcyclopropyl)pyridin-2-yl](phenyl)methyl]-1-[2-(2-methyl-1H-1,3-benzodiazol-1-yl)acetyl]pyrrolidine-2-carboxamide |

TABLE 1-continued

| Compound No. | Structure | IUPAC |
|---|---|---|
| 594 | 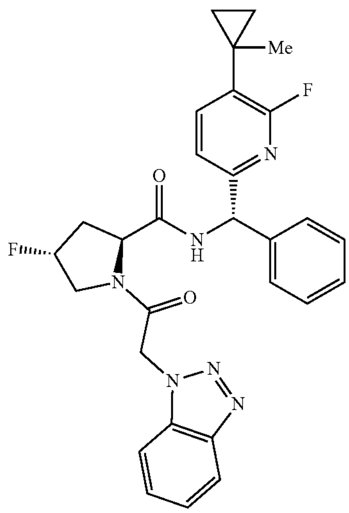 [SMILES: CC1(c2ccc([C@@H](NC(=O)[C@@H]3C[C@@H](F)CN3C(=O)Cn3nnc4ccccc43)c3ccccc3)nc2F)CC1] | (2S,4R)-1-[2-(1H-1,2,3-benzotriazol-1-yl)acetyl]-4-fluoro-N-[(S)-[6-fluoro-5-(1-methylcyclopropyl)pyridin-2-yl](phenyl)methyl]pyrrolidine-2-carboxamide |
| 595 | 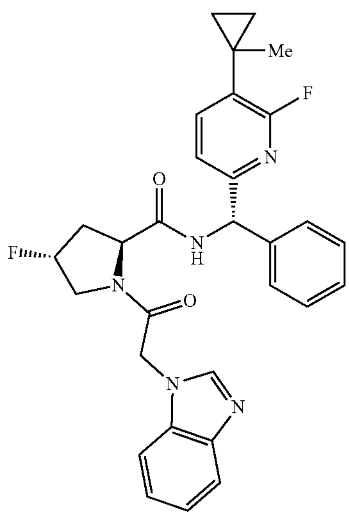 [SMILES: CC1(c2ccc([C@@H](NC(=O)[C@@H]3C[C@@H](F)CN3C(=O)Cn3cnc4ccccc43)c3ccccc3)nc2F)CC1] | (2S,4R)-1-[2-(1H-1,3-benzodiazol-1-yl)acetyl]-4-fluoro-N-[(S)-[6-fluoro-5-(1-methylcyclopropyl)pyridin-2-yl](phenyl)methyl]pyrrolidine-2-carboxamide |
| 596 | 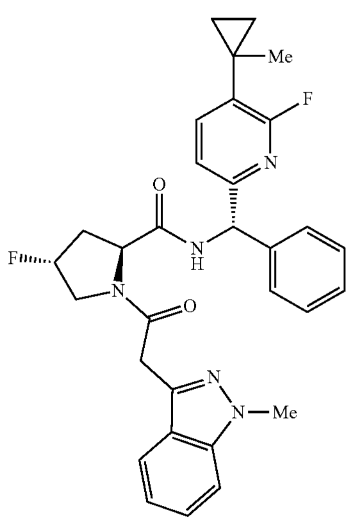 [SMILES: Cn1nc(CC(=O)N2C[C@H](F)C[C@H]2C(=O)N[C@@H](c2ccccc2)c2ccc(C3(C)CC3)c(F)n2)c2ccccc21] | (2S,4R)-4-fluoro-N-[(S)-[6-fluoro-5-(1-methylcyclopropyl)pyridin-2-yl](phenyl)methyl]-1-[2-(1-methyl-1H-indazol-3-yl)acetyl]pyrrolidine-2-carboxamide |

TABLE 1-continued

| Compound No. | Structure | IUPAC |
|---|---|---|
| 597 | 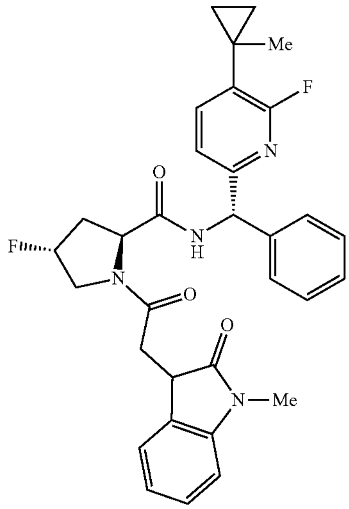 [SMILES: CN1C(=O)C(CC(=O)N2C[C@H](F)C[C@H]2C(=O)N[C@@H](c2ccccc2)c2ccc(C3(C)CC3)c(F)n2)c2ccccc21] | (2S,4R)-4-fluoro-N-[(S)-[6-fluoro-5-(1-methylcyclopropyl)pyridin-2-yl](phenyl)methyl]-1-[2-(1-methyl-2-oxo-2,3-dihydro-1H-indol-3-yl)acetyl]pyrrolidine-2-carboxamide |
| 598 | 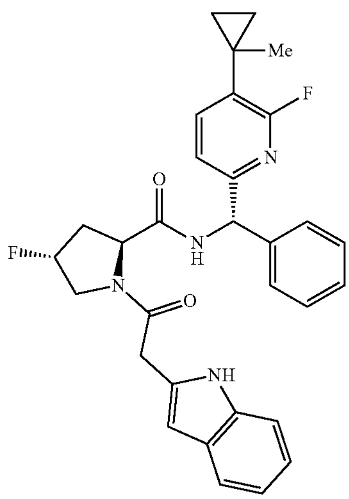 [SMILES: CC1(c2ccc([C@@H](NC(=O)[C@@H]3C[C@@H](F)CN3C(=O)Cc3cc4ccccc4[nH]3)c3ccccc3)nc2F)CC1] | (2S,4R)-4-fluoro-N-[(S)-[6-fluoro-5-(1-methylcyclopropyl)pyridin-2-yl](phenyl)methyl]-1-[2-(1H-indol-2-yl)acetyl]pyrrolidine-2-carboxamide |
| 599 | 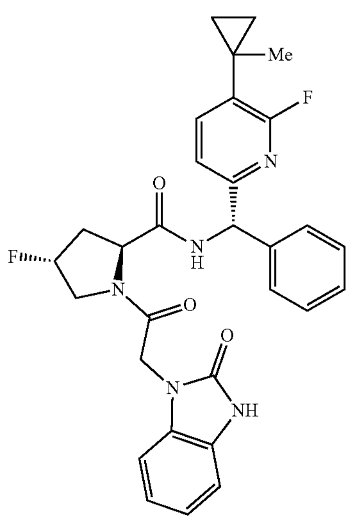 [SMILES: CC1(c2ccc([C@@H](NC(=O)[C@@H]3C[C@@H](F)CN3C(=O)Cn3c(=O)[nH]c4ccccc43)c3ccccc3)nc2F)CC1] | (2S,4R)-4-fluoro-N-[(S)-[6-fluoro-5-(1-methylcyclopropyl)pyridin-2-yl](phenyl)methyl]-1-[2-(2-oxo-2,3-dihydro-1H-1,3-benzodiazol-1-yl)acetyl]pyrrolidine-2-carboxamide |

TABLE 1-continued

| Compound No. | Structure | IUPAC |
|---|---|---|
| 600 | 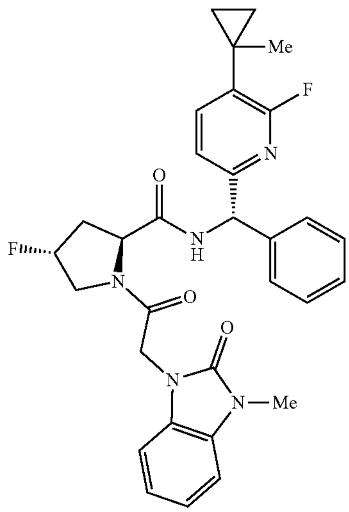 [SMILES: Cn1c(=O)n(CC(=O)N2C[C@H](F)C[C@H]2C(=O)N[C@@H](c2ccccc2)c2ccc(C3(C)CC3)c(F)n2)c2ccccc21] | (2S,4R)-4-fluoro-N-[(S)-[6-fluoro-5-(1-methylcyclopropyl)pyridin-2-yl](phenyl)methyl]-1-[2-(3-methyl-2-oxo-2,3-dihydro-1H-1,3-benzodiazol-1-yl)acetyl]pyrrolidine-2-carboxamide |
| 601 | 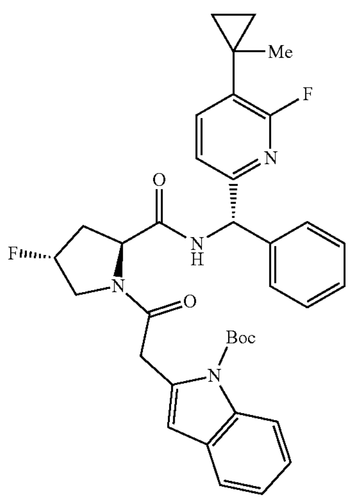 [SMILES: CC(C)(C)OC(=O)n1c(CC(=O)N2C[C@H](F)C[C@H]2C(=O)N[C@@H](c2ccccc2)c2ccc(C3(C)CC3)c(F)n2)cc2ccccc21] | tert-butyl 2-{2-[(2S,4R)-4-fluoro-2-{[(S)-[6-fluoro-5-(1-methylcyclopropyl)pyridin-2-yl](phenyl)methyl]carbamoyl}pyrrolidin-1-yl]-2-oxoethyl}-1H-indole-1-carboxylate |
| 602 | 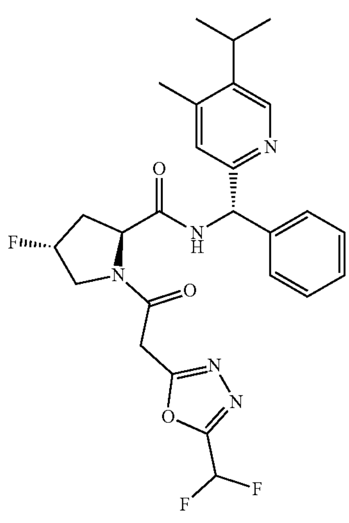 [SMILES: Cc1cc([C@@H](NC(=O)[C@@H]2C[C@@H](F)CN2C(=O)Cc2nnc(C(F)F)o2)c2ccccc2)ncc1C(C)C] | (2S,4R)-1-(2-(5-(difluoromethyl)-1,3,4-oxadiazol-2-yl)acetyl)-4-fluoro-N-((S)-(5-isopropyl-4-methylpyridin-2-yl)(phenyl)methyl)pyrrolidine-2-carboxamide |

TABLE 1-continued
| Compound No. | Structure | IUPAC |
|---|---|---|
| 603 | 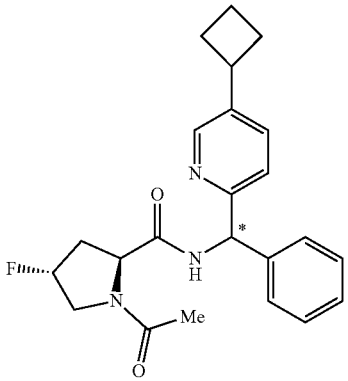 | (2S,4R)-1-acetyl-N-{(S) or (R)-(5-cyclobutylpyridin-2-yl)(phenyl)methyl}-4-fluoropyrrolidine-2-carboxamide |
| 604 | 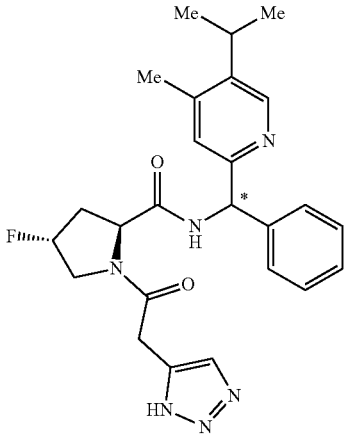 | (2S,4R)-4-fluoro-N-[(S) or (R)-[4-methyl-5-(propan-2-yl)pyridin-2-yl](phenyl)methyl]-1-[2-(1H-1,2,3-triazol-5-yl)acetyl]pyrrolidine-2-carboxamide |
| 605 | 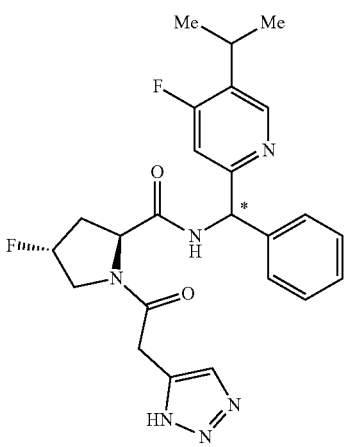 [SMILES: CC(C)c1cnc(C(NC(=O)[C@@H]2C[C@@H](F)CN2C(=O)Cc2cnn[nH]2)c2ccccc2)cc1F] | (2S,4R)-4-fluoro-N-[(S) or (R)-[4-fluoro-5-(propan-2-yl)pyridin-2-yl](phenyl)methyl]-1-[2-(1H-1,2,3-triazol-5-yl)acetyl]pyrrolidine-2-carboxamide |

TABLE 1-continued

| Compound No. | Structure | IUPAC |
|---|---|---|
| 606 | 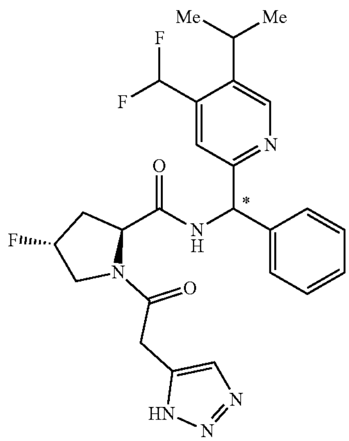 [SMILES: CC(C)c1cnc(C(NC(=O)[C@@H]2C[C@@H](F)CN2C(=O)Cc2cnn[nH]2)c2ccccc2)cc1C(F)F] | (2S,4R)-N-[(S) or (R)-[4-(difluoromethyl)-5-(propan-2-yl)pyridin-2-yl](phenyl)methyl]-4-fluoro-1-[2-(1H-1,2,3-triazol-4-yl)acetyl]pyrrolidine-5-carboxamide |
| 607 | 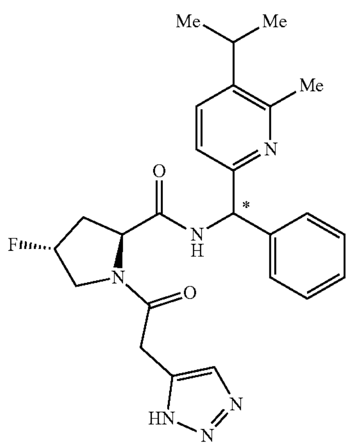 [SMILES: Cc1nc(C(NC(=O)[C@@H]2C[C@@H](F)CN2C(=O)Cc2cnn[nH]2)c2ccccc2)ccc1C(C)C] | (2S,4R)-4-fluoro-N-[(S) or (R)-[6-methyl-5-(propan-2-yl)pyridin-2-yl](phenyl)methyl]-1-[2-(1H-1,2,3-triazol-5-yl)acetyl]pyrrolidine-2-carboxamide |
| 608 | 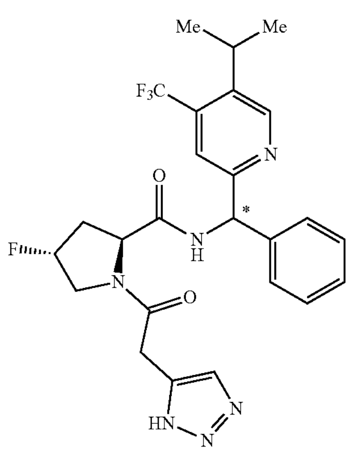 [SMILES: CC(C)c1cnc(C(NC(=O)[C@@H]2C[C@@H](F)CN2C(=O)Cc2cnn[nH]2)c2ccccc2)cc1C(F)(F)F] | (2S,4R)-4-fluoro-N-[(S) or (R)-phenyl[5-(propan-2-yl)-4-(trifluoromethyl)pyridin-2-yl]methyl]-1-[2-(1H-1,2,3-triazol-5-yl)acetyl]pyrrolidine-2-carboxamide |

TABLE 1-continued

| Compound No. | Structure | IUPAC |
|---|---|---|
| 609 | 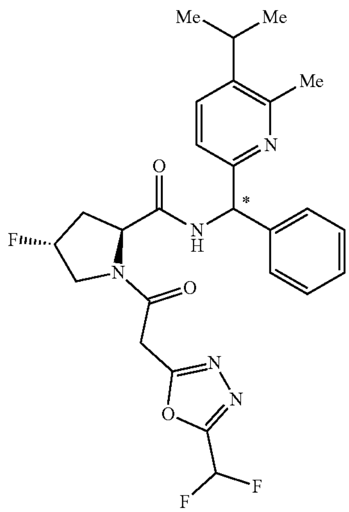 [SMILES: Cc1nc(C(NC(=O)[C@@H]2C[C@@H](F)CN2C(=O)Cc2nnc(C(F)F)o2)c2ccccc2)ccc1C(C)C] | (2S,4R)-1-{2-[5-(difluoromethyl)-1,3,4-oxadiazol-2-yl]acetyl}-4-fluoro-N-[(S) or (R)-[6-methyl-5-(propan-2-yl)pyridin-2-yl](phenyl)methyl]pyrrolidine-2-carboxamide |
| 610 | 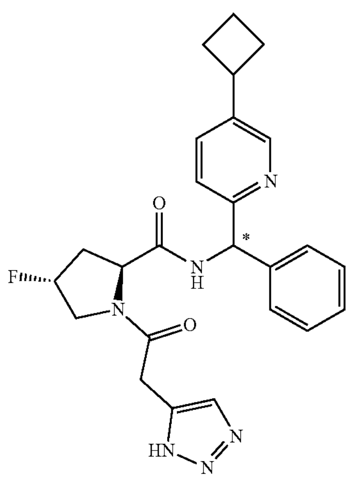 [SMILES: O=C(NC(c1ccccc1)c1ccc(C2CCC2)cn1)[C@@H]1C[C@@H](F)CN1C(=O)Cc1cnn[nH]1] | (2S,4R)-N-[(S) or (R)-(5-cyclobutylpyridin-2-yl)(phenyl)methyl]-4-fluoro-1-[2-(1H-1,2,3-triazol-5-yl)acetyl]pyrrolidine-2-carboxamide |
| 611 | 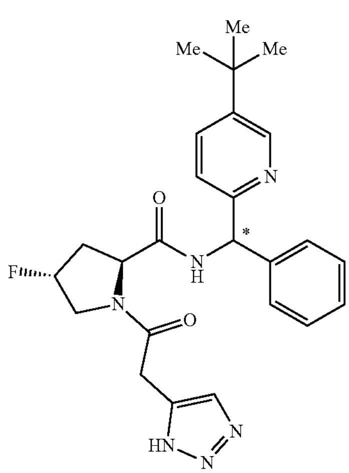 [SMILES: CC(C)(C)c1ccc(C(NC(=O)[C@@H]2C[C@@H](F)CN2C(=O)Cc2cnn[nH]2)c2ccccc2)nc1] | (2S,4R)-N-[(S) or (R)-(5-tert-butylpyridin-2-yl)(phenyl)methyl]-4-fluoro-1-[2-(1H-1,2,3-triazol-5-yl)acetyl]pyrrolidine-2-carboxamide |

TABLE 1-continued

| Compound No. | Structure | IUPAC |
|---|---|---|
| 612 | 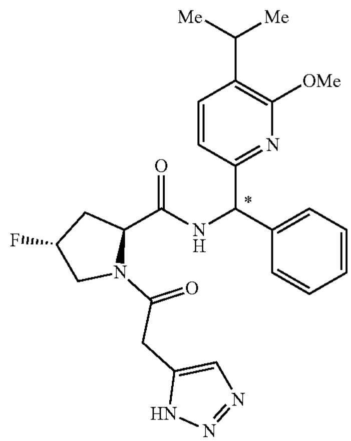 [SMILES: COc1nc(C(NC(=O)[C@@H]2C[C@@H](F)CN2C(=O)Cc2cnn[nH]2)c2ccccc2)ccc1C(C)C] | (2S,4R)-4-fluoro-N-[(S) or (R)-[6-methoxy-5-(propan-2-yl)pyridin-2-yl](phenyl)methyl]-1-[2-(1H-1,2,3-triazol-5-yl)acetyl]pyrrolidine-2-carboxamide |
| 613 | 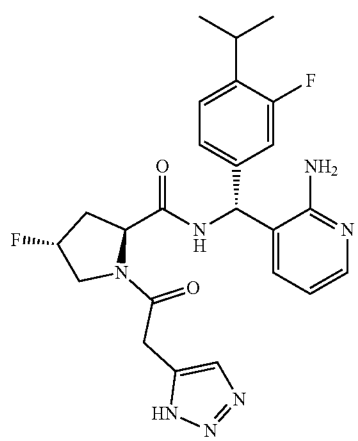 [SMILES: CC(C)c1ccc([C@@H](NC(=O)[C@@H]2C[C@@H](F)CN2C(=O)Cc2cnn[nH]2)c2cccnc2N)cc1F] | (2S,4R)-1-(2-(1H-1,2,3-triazol-5-yl)acetyl)-N-((R)-(2-aminopyridin-3-yl)(3-fluoro-4-isopropylphenyl)methyl)-4-fluoropyrrolidine-2-carboxamide |
| 614 | 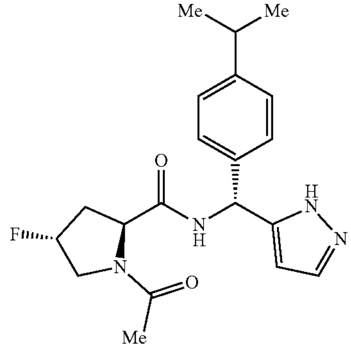 [SMILES: CC(=O)N1C[C@H](F)C[C@H]1C(=O)N[C@H](c1ccc(C(C)C)cc1)c1ccn[nH]1] | (2S,4R)-1-acetyl-4-fluoro-N-[(S)-[4-(propan-2-yl)phenyl](1H-pyrazol-5-yl)methyl]pyrrolidine-2-carboxamide |

TABLE 1-continued

| Compound No. | Structure | IUPAC |
|---|---|---|
| 615 | 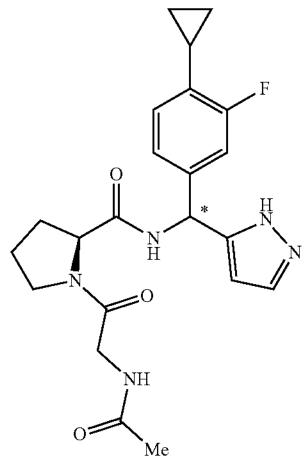 [SMILES: CC(=O)NCC(=O)N1CCC[C@H]1C(=O)NC(c1ccc(C2CC2)c(F)c1)c1ccn[nH]1] | (2S)-N-[(R) or (S)-(4-cyclopropyl-3-fluorophenyl)(1H-pyrazol-5-yl)methyl]-1-(2-acetamidoacetyl)pyrrolidine-2-carboxamide |
| 616 | 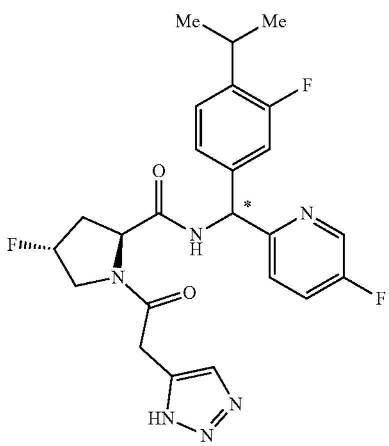 [SMILES: CC(C)c1ccc(C(NC(=O)[C@@H]2C[C@@H](F)CN2C(=O)Cc2cnn[nH]2)c2ccc(F)cn2)cc1F] | (2S,4R)-4-fluoro-N-[(R) or (S)-[3-fluoro-4-(propan-2-yl)phenyl](5-fluoropyridin-2-yl)methyl]-1-[2-(1H-1,2,3-triazol-5-yl)acetyl]pyrrolidine-2-carboxamide |
| 617 | 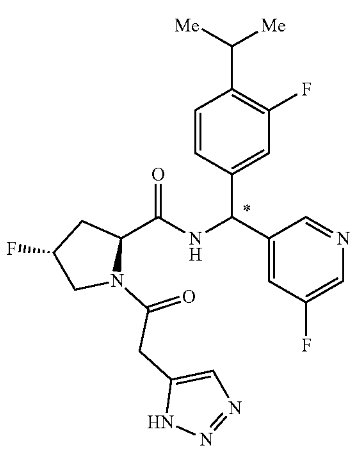 [SMILES: CC(C)c1ccc(C(NC(=O)[C@@H]2C[C@@H](F)CN2C(=O)Cc2cnn[nH]2)c2cncc(F)c2)cc1F] | (2S,4R)-4-fluoro-N-[(R) or (S)-[3-fluoro-4-(propan-2-yl)phenyl](5-fluoropyridin-3-yl)methyl]-1-[2-(1H-1,2,3-triazol-5-yl)acetyl]pyrrolidine-2-carboxamide |

TABLE 1-continued

| Compound No. | Structure | IUPAC |
|---|---|---|
| 618 | 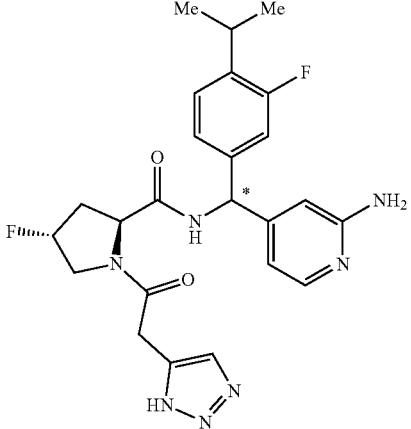 [SMILES: CC(C)c1ccc(C(NC(=O)[C@@H]2C[C@@H](F)CN2C(=O)Cc2cnn[nH]2)c2ccnc(N)c2)cc1F] | (2S,4R)-N-[(S) or (R)-(2-aminopyridin-4-yl](3-fluoro-4-(propan-2-yl)phenyl]methyl]-4-fluoro-1-[2-(1H-1,2,3-triazol-5-yl)acetyl]pyrrolidine-2-carboxamide |
| 619 | 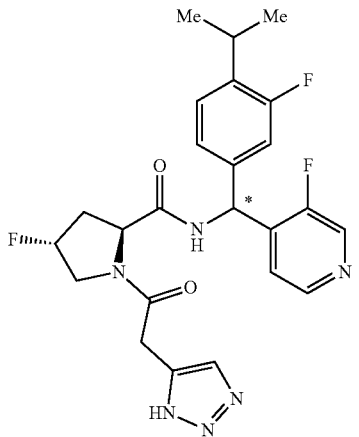 [SMILES: CC(C)c1ccc(C(NC(=O)[C@@H]2C[C@@H](F)CN2C(=O)Cc2cnn[nH]2)c2ccncc2F)cc1F] | (2S,4R)-4-fluoro-N-[(R) or (S)-[3-fluoro-4-(propan-2-yl)phenyl](3-fluoropyridin-4-yl)methyl]-1-[2-(1H-1,2,3-triazol-5-yl)acetyl]pyrrolidine-2-carboxamide |
| 620 | 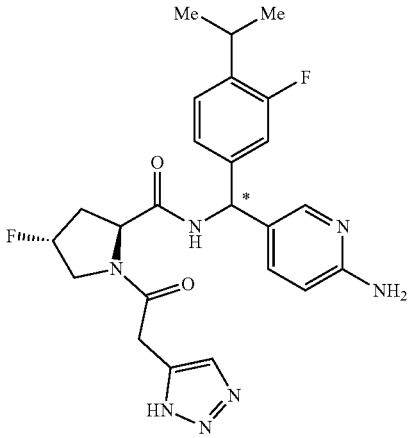 [SMILES: CC(C)c1ccc(C(NC(=O)[C@@H]2C[C@@H](F)CN2C(=O)Cc2cnn[nH]2)c2ccc(N)nc2)cc1F] | (2S,4R)-N-[(R) or (S)-(6-aminopyridin-3-yl)[3-fluoro-4-(propan-2-yl)phenyl]methyl]-4-fluoro-1-[2-(1H-1,2,3-triazol-5-yl)acetyl]pyrrolidine-2-carboxamide |

TABLE 1-continued

| Compound No. | Structure | IUPAC |
|---|---|---|
| 621 | 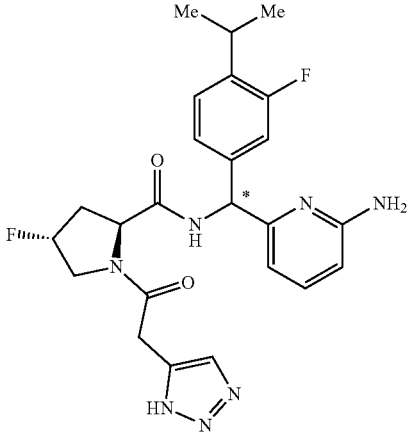 [SMILES: CC(C)c1ccc(C(NC(=O)[C@@H]2C[C@@H](F)CN2C(=O)Cc2cnn[nH]2)c2cccc(N)n2)cc1F] | (2S,4R)-N-[(R) or (S)-(6-aminopyridin-2-yl)[3-fluoro-4-(propan-2-yl)phenyl]methyl]-4-fluoro-1-[2-(1H-(1,2,3-triazol-5-yl)acetyl]pyrrolidine-2-carboxamide |
| 622 | 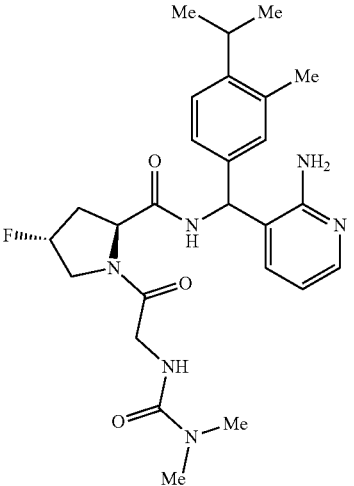 [SMILES: Cc1cc(C(NC(=O)[C@@H]2C[C@@H](F)CN2C(=O)CNC(=O)N(C)C)c2cccnc2N)ccc1C(C)C] | (2S,4R)-N-[(R) or (S)-(2-aminopyridin-3-yl)[3-methyl-4-(propan-2-yl)phenyl]methyl]-1-{2-[(dimethylcarbamoyl)amino]acetyl}-4-fluoropyrrolidine-2-carboxamide |
| 623 | 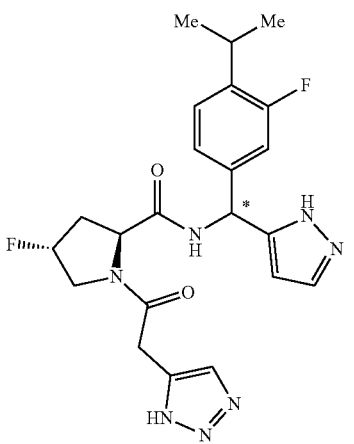 | (2S,4R)-4-fluoro-N-[(R) or (S)-[3-fluoro-4-(propan-2-yl)phenyl](1H-pyrazol-5-yl)methyl]-1-[2-(1H-1,2,3-triazol-5-yl)acetyl]pyrrolidine-2-carboxamide |

TABLE 1-continued

| Compound No. | Structure | IUPAC |
|---|---|---|
| 624 | 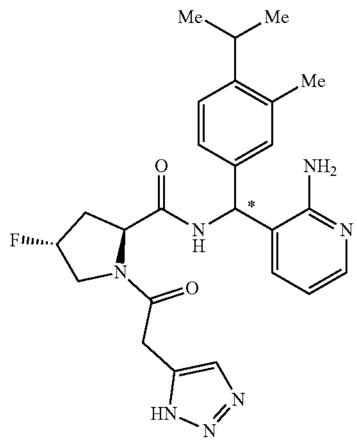 [SMILES: Cc1cc(C(NC(=O)[C@@H]2C[C@@H](F)CN2C(=O)Cc2cnn[nH]2)c2cccnc2N)ccc1C(C)C] | (2S,4R)-N-[(R) or (S)-(2-aminopyridin-3-yl)[3-methyl-4-(propan-2-yl)phenyl]methyl]-4-fluoro-1-[2-(1H-1,2,3-triazol-5-yl)acetyl]pyrrolidine-2-carboxamide |
| 625 | 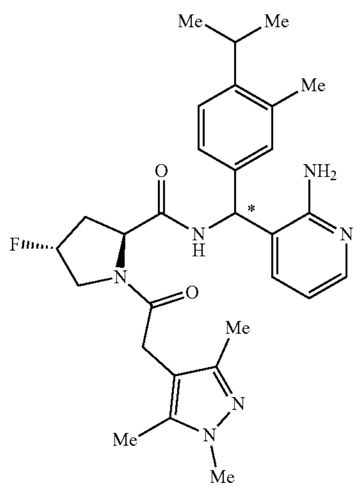 [SMILES: Cc1cc(C(NC(=O)[C@@H]2C[C@@H](F)CN2C(=O)Cc2c(C)nn(C)c2C)c2cccnc2N)ccc1C(C)C] | (2S,4R)-N-[(R) or (S)-(2-aminopyridin-3-yl)[3-methyl-4-(propan-2-yl)phenyl]methyl]-4-fluoro-1-[2-(1,3,5-trimethyl-1H-pyrazol-4-yl)acetyl]pyrrolidine-2-carboxamide |
| 626 | 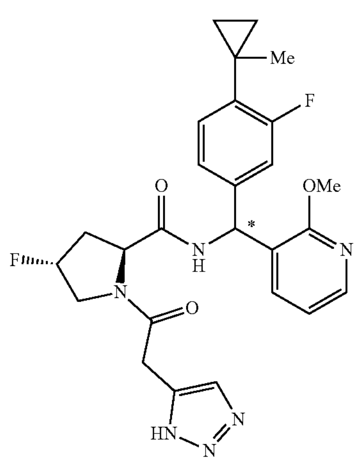 [SMILES: COc1ncccc1C(NC(=O)[C@@H]1C[C@@H](F)CN1C(=O)Cc1cnn[nH]1)c1ccc(C2(C)CC2)c(F)c1] | (2S,4R)-4-fluoro-N-[(R) or (S)-[3-fluoro-4-(1-methylcyclopropyl)phenyl](2-methoxypyridin-3-yl)methyl]-1-[2-(1H-1,2,3-triazol-5-yl)acetyl]pyrrolidine-2-carboxamide |

TABLE 1-continued

| Compound No. | Structure | IUPAC |
|---|---|---|
| 627 | 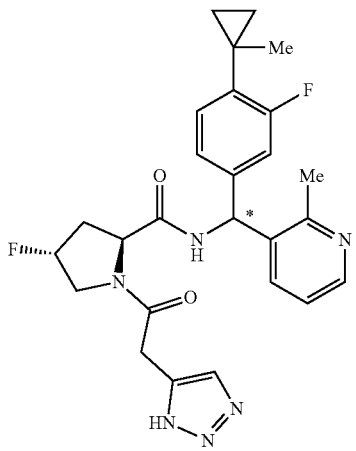 [SMILES: Cc1ncccc1C(NC(=O)[C@@H]1C[C@@H](F)CN1C(=O)Cc1cnn[nH]1)c1ccc(C2(C)CC2)c(F)c1] | (2S,4R)-4-fluoro-N-[(R) or (S)-[3-fluoro-4-(1-methylcyclopropyl)phenyl](2-methylpyridin-3-yl)methyl]-1-[2-(1H-1,2,3-triazol-5-yl)acetyl]pyrrolidine-2-carboxamide |
| 628 | 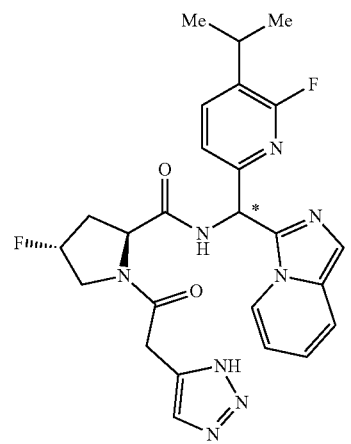 [SMILES: CC(C)c1ccc(C(NC(=O)[C@@H]2C[C@@H](F)CN2C(=O)Cc2cnn[nH]2)c2ncc3ccccn23)nc1F] | (2S,4R)-4-fluoro-N-[(R) or (S)-[6-fluoro-5-(propan-2-yl)pyridin-2-yl]({imidazo[1,5-a]pyridin-3-yl})methyl]-1-[2-(1H-1,2,3-triazol-5-yl)acetyl]pyrrolidine-2-carboxamide |
| 629 | 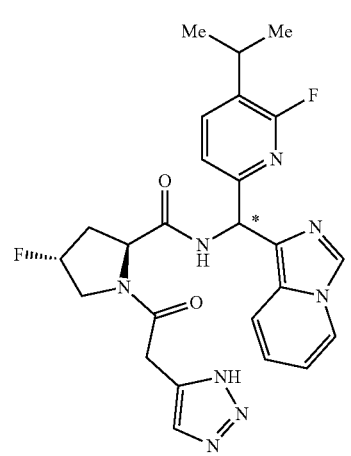 [SMILES: CC(C)c1ccc(C(NC(=O)[C@@H]2C[C@@H](F)CN2C(=O)Cc2cnn[nH]2)c2ncn3ccccc23)nc1F] | (2S,4R)-4-fluoro-N-[(S) or (R)-[6-fluoro-5-(propan-2-yl)pyridin-2-yl]({imidazo[1,5-a]pyridin-1-yl})methyl]-1-[2-(1H-1,2,3-triazol-5-yl)acetyl]pyrrolidine-2-carboxamide |

| Compound No. | Structure | IUPAC |
|---|---|---|
| 630 | 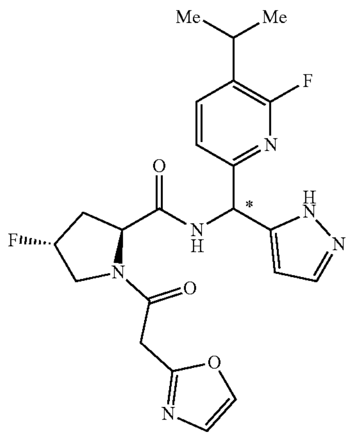 [SMILES: CC(C)c1ccc(C(NC(=O)[C@@H]2C[C@@H](F)CN2C(=O)Cc2ncco2)c2ccn[nH]2)nc1F] | (2S,4R)-4-fluoro-N-[(S) or (R)-[6-fluoro-5-(propan-2-yl)pyridin-2-yl](1H-pyrazol-5-yl)methyl]-1-[2-(1,3-oxazol-2-yl)acetyl]pyrrolidine-2-carboxamide |
| 631 | 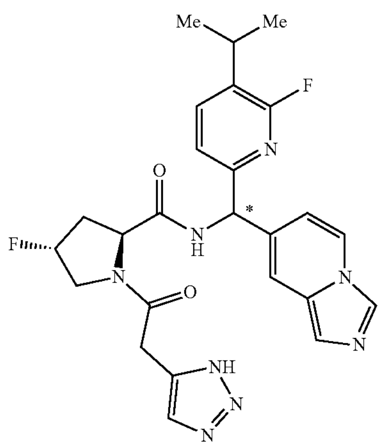 [SMILES: CC(C)c1ccc(C(NC(=O)[C@@H]2C[C@@H](F)CN2C(=O)Cc2cnn[nH]2)c2ccn3cncc3c2)nc1F] | (2S,4R)-4-fluoro-N-[(S) or (R)-[6-fluoro-5-(propan-2-yl)pyridin-2-yl]({imidazo[1,5-a]pyridin-7-yl})methyl]-1-[2-(1H-1,2,3-triazol-5-yl)acetyl]pyrrolidine-2-carboxamide |
| 632 | 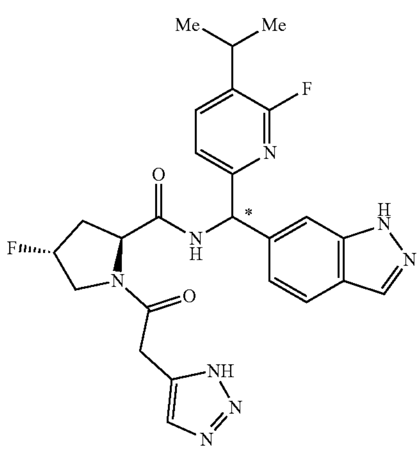 [SMILES: CC(C)c1ccc(C(NC(=O)[C@@H]2C[C@@H](F)CN2C(=O)Cc2cnn[nH]2)c2ccc3cn[nH]c3c2)nc1F] | (2S,4R)-4-fluoro-N-[(S) or (R)-[6-fluoro-5-(propan-2-yl)pyridin-2-yl](1H-indazol-6-yl)methyl]-1-[2-(1H-1,2,3-triazol-5-yl)acetyl]pyrrolidine-2-carboxamide |

TABLE 1-continued

| Compound No. | Structure | IUPAC |
|---|---|---|
| 633 | 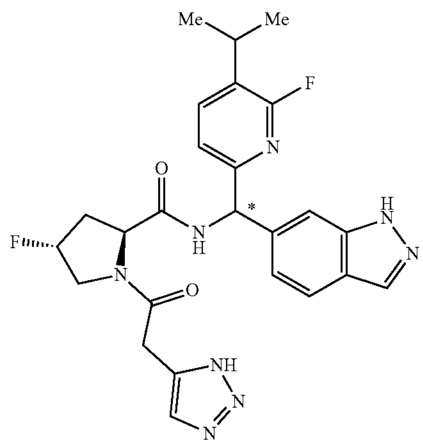 [SMILES: CC(C)c1ccc(C(NC(=O)[C@@H]2C[C@@H](F)CN2C(=O)Cc2cnn[nH]2)c2ccc3cn[nH]c3c2)nc1F] | (2S,4R)-4-fluoro-N-[(R) or (S)-[6-fluoro-5-(propan-2-yl)pyridin-2-yl](1H-indazol-6-yl)methyl]-1-[2-(1H-1,2,3-triazol-5-yl)acetyl]pyrrolidine-2-carboxamide |
| 634 | 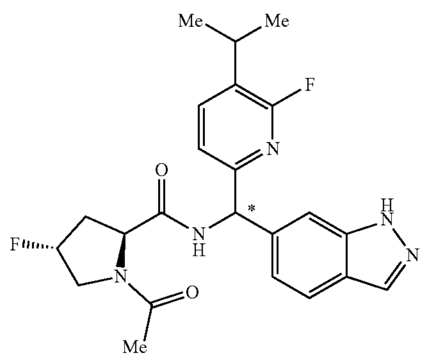 [SMILES: CC(=O)N1C[C@H](F)C[C@H]1C(=O)NC(c1ccc2cn[nH]c2c1)c1ccc(C(C)C)c(F)n1] | (2S,4R)-1-acetyl-4-fluoro-N-[(S) or (R)-[6-fluoro-5-(propan-2-yl)pyridin-2-yl](1H-indazol-6-yl)methyl]pyrrolidine-2-carboxamidee |
| 635 | 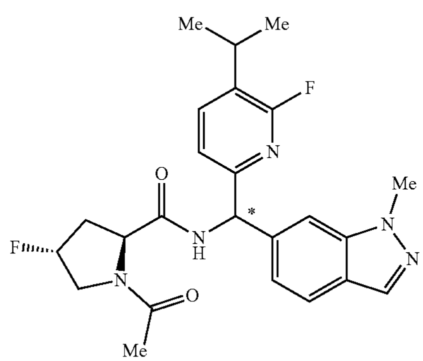 [SMILES: CC(=O)N1C[C@H](F)C[C@H]1C(=O)NC(c1ccc2cnn(C)c2c1)c1ccc(C(C)C)c(F)n1] | (2S,4R)-1-acetyl-4-fluoro-N-[(S) or (R)-[6-fluoro-5-(propan-2-yl)pyridin-2-yl](1-methyl-1H-indazol-6-yl)methyl]pyrrolidine-2-carboxamide |
| 636 | 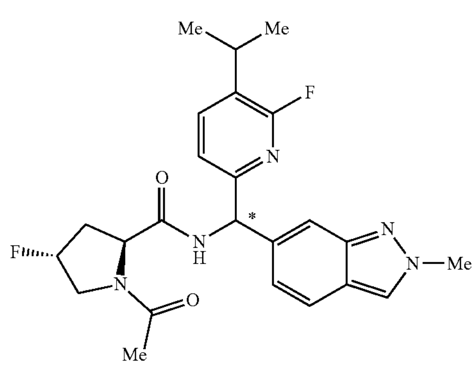 [SMILES: CC(=O)N1C[C@H](F)C[C@H]1C(=O)NC(c1ccc2cn(C)nc2c1)c1ccc(C(C)C)c(F)n1] | (2S,4R)-1-acetyl-4-fluoro-N-[(S) or (R)-[6-fluoro-5-(propan-2-yl)pyridin-2-yl](2-methyl-2H-indazol-6-yl)methyl]pyrrolidine-2-carboxamide |

TABLE 1-continued

| Compound No. | Structure | IUPAC |
|---|---|---|
| 637 | 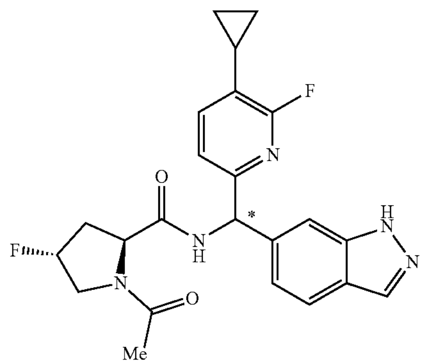 [SMILES: CC(=O)N1C[C@H](F)C[C@H]1C(=O)NC(c1ccc2cn[nH]c2c1)c1ccc(C2CC2)c(F)n1] | (2S,4R)-1-acetyl-N-[(S) or (R)-(5-cyclopropyl-6-fluoropyridin-2-yl)(1H-indazol-6-yl)methyl]-4-fluoropyrrolidine-2-carboxamide |
| 638 | 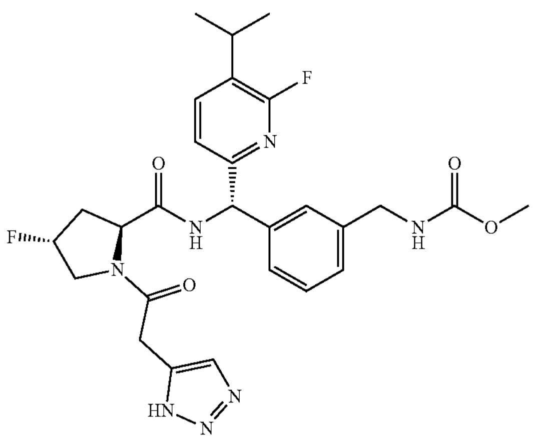 [SMILES: COC(=O)NCc1cccc([C@H](NC(=O)[C@@H]2C[C@@H](F)CN2C(=O)Cc2cnn[nH]2)c2ccc(C(C)C)c(F)n2)c1] | methyl (3-((S)-((2S,4R)-1-(2-(1H-1,2,3-triazol-6-yl)acetyl)-4-fluoropyrrolidine-2-carboxamido)(6-fluoro-5-isopropylpyridin-2-yl)methyl)benzyl)carbamate |
| 639 | 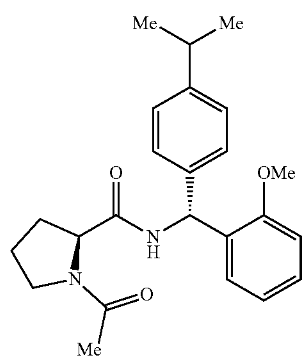 | (2S)-1-acetyl-N-[(R)-(2-methoxyphenyl)[4-(propan-2-yl)phenyl]methyl]pyrrolidine-2-carboxamide |
| 640 | 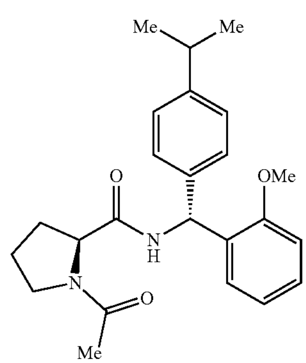 | (2S)-1-acetyl-N-[(R)-(2-methylphenyl)[4-(propan-2-yl)phenyl]methyl]pyrrolidine-2-carboxamide |

TABLE 1-continued

| Compound No. | Structure | IUPAC |
|---|---|---|
| 641 | 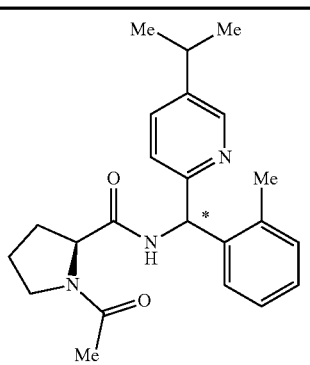 | (2S)-1-acetyl-N-[(S) or (R)-(2-methylphenyl)[5-(propan-2-yl)pyridin-2-yl]methyl]pyrrolidine-2-carboxamide |
| 642 | 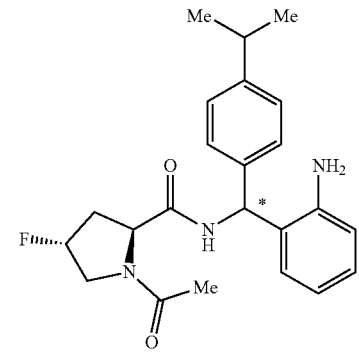 | (2S,4R)-1-acetyl-N-[(R) or (S)-(2-aminophenyl)[4-(propan-2-yl)phenyl]methyl]-4-fluoropyrrolidine-2-carboxamide |
| 643 | 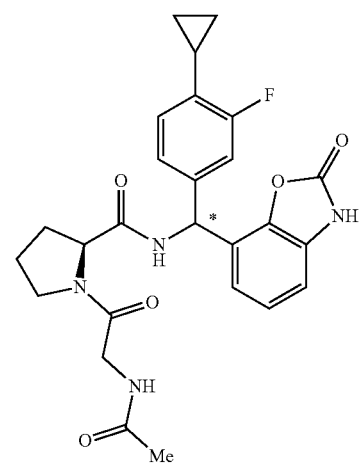 [SMILES: CC(=O)NCC(=O)N1CCC[C@H]1C(=O)NC(c1ccc(C2CC2)c(F)c1)c1cccc2[nH]c(=O)oc12] | (2S)-N-[(R) or (S)-(4-cyclopropyl-3-fluorophenyl)(2-oxo-2,3-dihydro-1,3-benzoxazol-7-yl)methyl]-1-(2-acetamidoacetyl)pyrrolidine-2-carboxamide |
| 644 | 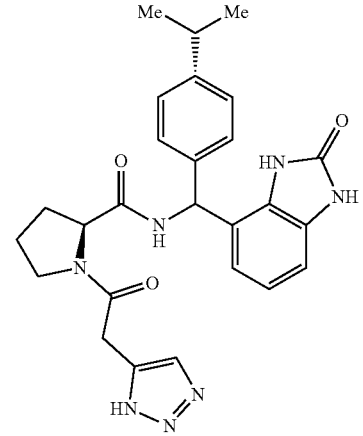 | (2S)-N-[(R) or (2-oxo-2,3-dihydro-1H-1,3-benzodiazol-4-yl)[4-(propan-2-yl)phenyl]methyl]-1-[2-(1H-1,2,3-triazol-5-yl)acetyl]pyrrolidine-2-carboxamide |

TABLE 1-continued

| Compound No. | Structure | IUPAC |
|---|---|---|
| 645 | 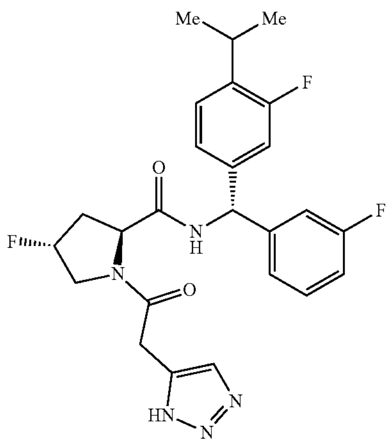 [SMILES: CC(C)c1ccc([C@@H](NC(=O)[C@@H]2C[C@@H](F)CN2C(=O)Cc2cnn[nH]2)c2cccc(F)c2)cc1F] | (2S,4R)-4-fluoro-N-[(S)-[3-fluoro-4-(propan-2-yl)phenyl](3-fluorophenyl)methyl]-1-[2-(1H-1,2,3-triazol-5-yl)acetyl]pyrrolidine-2-carboxamide |
| 646 | 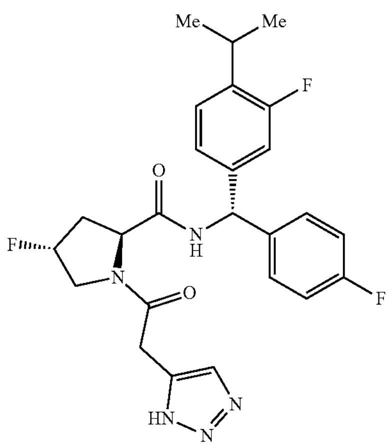 [SMILES: CC(C)c1ccc([C@@H](NC(=O)[C@@H]2C[C@@H](F)CN2C(=O)Cc2cnn[nH]2)c2ccc(F)cc2)cc1F] | (2S,4R)-4-fluoro-N-[(S)-[3-fluoro-4-(propan-2-yl)phenyl](4-fluorophenyl)methyl]-1-[2-(1H-1,2,3-triazol-5-yl)acetyl]pyrrolidine-2-carboxamide |
| 647 | 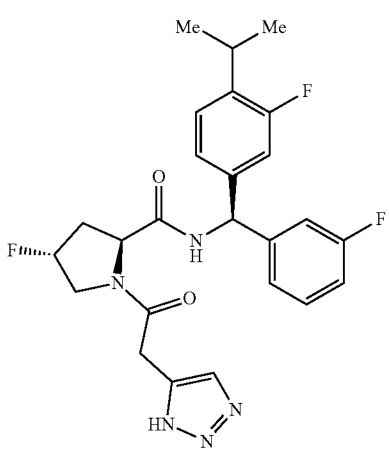 [SMILES: CC(C)c1ccc([C@H](NC(=O)[C@@H]2C[C@@H](F)CN2C(=O)Cc2cnn[nH]2)c2cccc(F)c2)cc1F] | (2S,4R)-4-fluoro-N-[(R)-[3-fluoro-4-(propan-2-yl)phenyl](3-fluorophenyl)methyl]-1-[2-(1H-1,2,3-triazol-5-yl)acetyl]pyrrolidine-2-carboxamide |

TABLE 1-continued

| Compound No. | Structure | IUPAC |
|---|---|---|
| 648 | 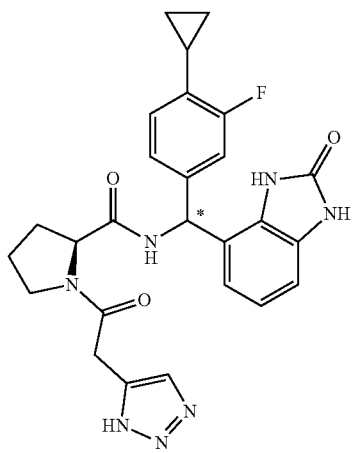 [SMILES: O=C(NC(c1ccc(C2CC2)c(F)c1)c1cccc2[nH]c(=O)[nH]c12)[C@@H]1CCCN1C(=O)Cc1cnn[nH]1] | (2S)-N-[(S)-(4-cyclopropyl-3-fluorophenyl)(2-oxo-2,3-dihydro-1H-1,3-benzodiazol-4-yl)methyl]-1-[2-(1H-1,2,3-triazol-5-yl)acetyl]pyrrolidine-2-carboxamide |
| 649 | 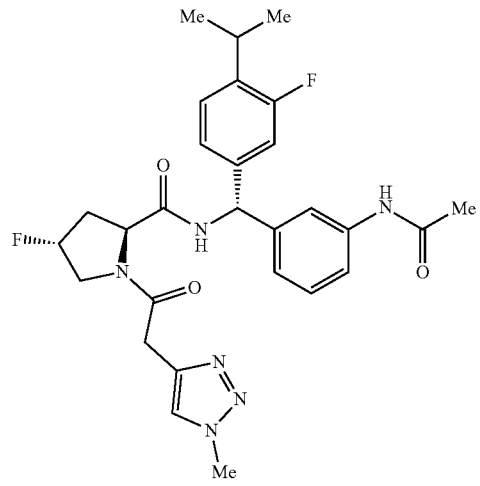 [SMILES: CC(=O)Nc1cccc([C@H](NC(=O)[C@@H]2C[C@@H](F)CN2C(=O)Cc2cn(C)nn2)c2ccc(C(C)C)c(F)c2)c1] | (2S,4R)-N-[(R)-(3-acetamidophenyl)[4-(propan-2-yl)phenyl]methyl]-4-fluoro-1-[2-(1-methyl-1H-1,2,3-triazol-4-yl)acetyl]pyrrolidine-2-carboxamide |
| 650 | 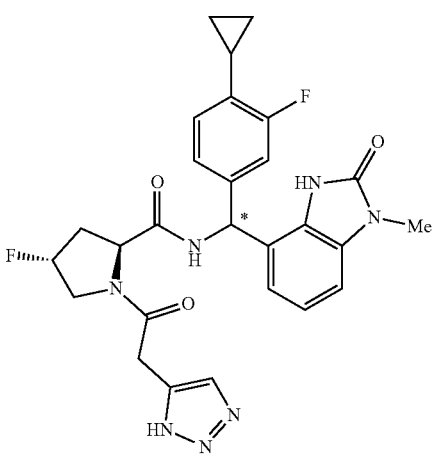 [SMILES: Cn1c(=O)[nH]c2c(C(NC(=O)[C@@H]3C[C@@H](F)CN3C(=O)Cc3cnn[nH]3)c3ccc(C4CC4)c(F)c3)cccc21] | (2S,4R)-N-[(R) or (S)-(4-cyclopropyl-3-fluorophenyl)(1-methyl-2-oxo-2,3-dihydro-1H-1,3-benzodiazol-4-yl)methyl]-4-fluoro-1-[2-(1H-1,2,3-triazol-5-yl)acetyl]pyrrolidine-2-carboxamide |

TABLE 1-continued

| Compound No. | Structure | IUPAC |
|---|---|---|
| 651 | 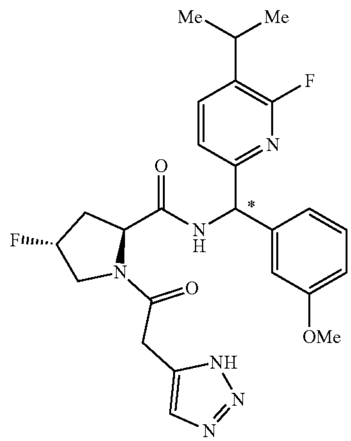 [SMILES: COc1cccc(C(NC(=O)[C@@H]2C[C@@H](F)CN2C(=O)Cc2cnn[nH]2)c2ccc(C(C)C)c(F)n2)c1] | (2S,4R)-4-fluoro-N-[(S) or (R)-[6-fluoro-5-(propan-2-yl)pyridin-2-yl](3-methoxyphenyl)methyl]-1-[2-(1H-1,2,3-triazol-5-yl)acetyl]pyrrolidine-2-carboxamide |
| 652 | 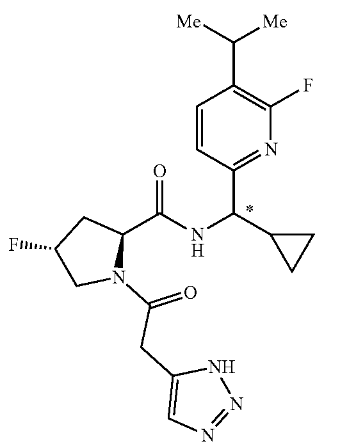 [SMILES: CC(C)c1ccc(C(NC(=O)[C@@H]2C[C@@H](F)CN2C(=O)Cc2cnn[nH]2)C2CC2)nc1F] | (2S,4R)-N-[(S) or (R)-cyclopropyl[3-fluoro-4-(propan-2-yl)phenyl]methyl]-4-fluoro-1-[2-(1H-1,2,3-triazol-5-yl)acetyl]pyrrolidine-2-carboxamide |
| 653 | 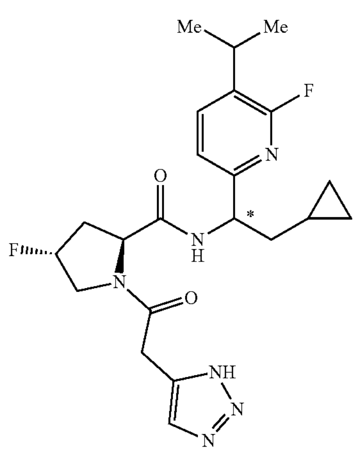 [SMILES: CC(C)c1ccc(C(CC2CC2)NC(=O)[C@@H]2C[C@@H](F)CN2C(=O)Cc2cnn[nH]2)nc1F] | (2S,4R)-N-[(1S) or (1R)-2-cyclopropyl-1-[3-fluoro-4-(propan-2-yl)phenyl]ethyl]-4-fluoro-1-[2-(1H-1,2,3-triazol-5-yl)acetyl]pyrrolidine-2-carboxamide |

| Compound No. | Structure | IUPAC |
|---|---|---|
| 654 | 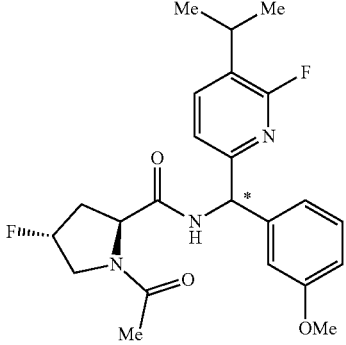 | (2S,4R)-1-acetyl-4-fluoro-N-[(S) or (R)-[6-fluoro-5-(propan-2-yl)pyridin-2-yl](3-methoxyphenyl)methyl]pyrrolidine-2-carboxamide |
| 655 | 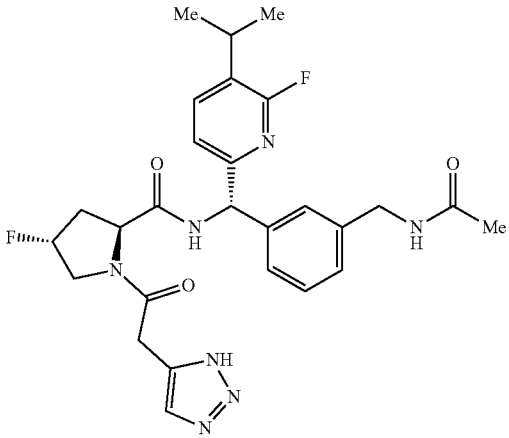 [SMILES: CC(=O)NCc1cccc([C@H](NC(=O)[C@@H]2C[C@@H](F)CN2C(=O)Cc2cnn[nH]2)c2ccc(C(C)C)c(F)n2)c1] | (2S,4R)-N-[(S)-[3-(acetamidomethyl)phenyl][6-fluoro-5-(propan-2-yl)pyridin-2-yl]methyl]-4-fluoro-1-[2-(1H-1,2,3-triazol-5-yl)acetyl]pyrrolidine-2-carboxamide |
| 656 | 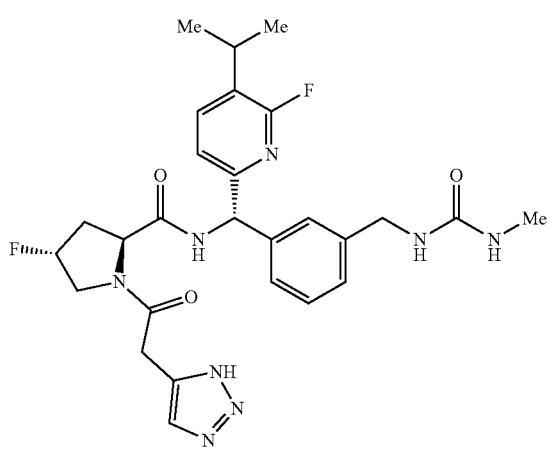 [SMILES: CNC(=O)NCc1cccc([C@H](NC(=O)[C@@H]2C[C@@H](F)CN2C(=O)Cc2cnn[nH]2)c2ccc(C(C)C)c(F)n2)c1] | (2S,4R)-4-fluoro-N-[(S)-[6-fluoro-5-(propan-2-yl)pyridin-2-yl](3-{[(methylcarbamoyl)amino]methyl}phenyl)methyl]-1-[2-(1H-1,2,3-triazol-5-yl)acetyl]pyrrolidine-2-carboxamide |

TABLE 1-continued

| Compound No. | Structure | IUPAC |
|---|---|---|
| 657 | 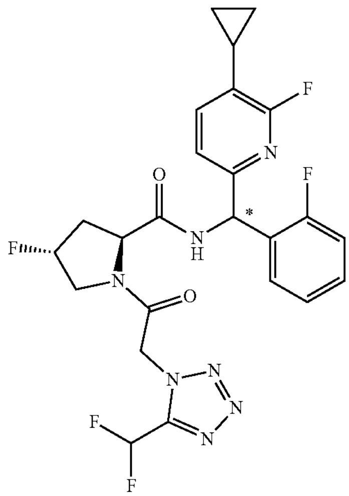 [SMILES: O=C(NC(c1ccc(C2CC2)c(F)n1)c1ccccc1F)[C@@H]1C[C@@H](F)CN1C(=O)Cn1nnnc1C(F)F] | (2S,4R)-N-[(S) or (R)-(5-cyclopropyl-6-fluoropyridin-2-yl)(2-fluorophenyl)methyl]-1-{2-[5-(difluoromethyl)-1H-1,2,3,4-tetrazol-1-yl]acetyl}-4-fluoropyrroldine-2-carboxamide |
| 658 | 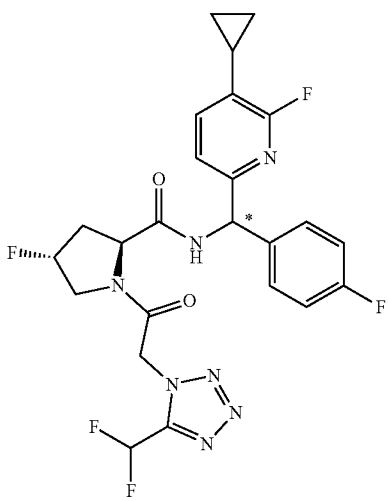 [SMILES: O=C(NC(c1ccc(F)cc1)c1ccc(C2CC2)c(F)n1)[C@@H]1C[C@@H](F)CN1C(=O)Cn1nnnc1C(F)F] | (2S,4R)-N-[(S) or (R)-(5-cyclopropyl-6-fluoropyridin-2-yl)(4-fluorophenyl)methyl]-1-{2-[5-(difluoromethyl)-1H-1,2,3,4-tetrazol-1-yl]acetyl}-4-fluoropyrrolidine-2-carboxamide |
| 659 | 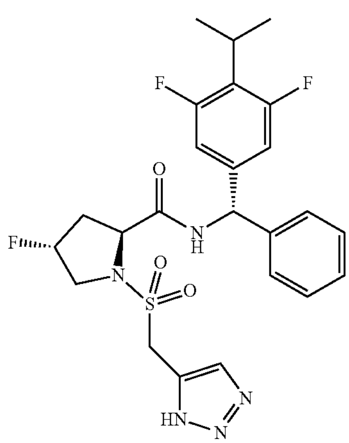 [SMILES: CC(C)c1c(F)cc([C@@H](NC(=O)[C@@H]2C[C@@H](F)CN2S(=O)(=O)Cc2cnn[nH]2)c2ccccc2)cc1F] | (2S,4R)-1-(((1H-1,2,3-triazol-5-yl)methyl)sulfonyl)-N-((S)-(3,5-difluoro-4-isopropylphenyl)(phenyl)methyl)-4-fluoropyrrolidine-2-carboxamide |

TABLE 1-continued
| Compound No. | Structure | IUPAC |
|---|---|---|
| 660 | 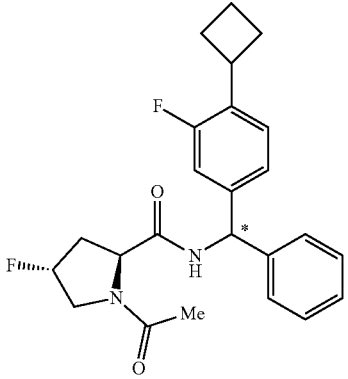 | (2S,4R)-1-acetyl-N-[(S) or (R)-(4-cyclobutyl-3-fluorophenyl)(phenyl)methyl]-4-fluoropyrrolidine-2-carboxamide |
| 661 | 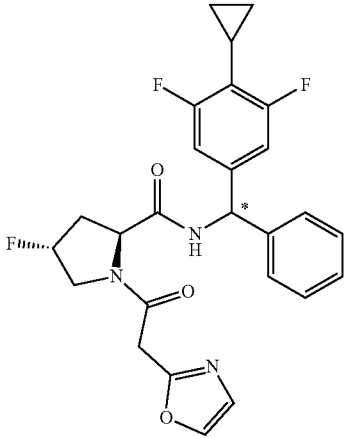 [SMILES: O=C(NC(c1ccccc1)c1cc(F)c(C2CC2)c(F)c1)[C@@H]1C[C@@H](F)CN1C(=O)Cc1ncco1] | (2S,4R)-N-[(S) or (R)-[3,5-difluoro-4-(propan-2-yl)(phenyl](phenyl)methyl]-4-fluoro-1-[2-(1,3-oxazol-2-yl)acetyl]pyrrolidine-2-carboxamide |
| 662 | 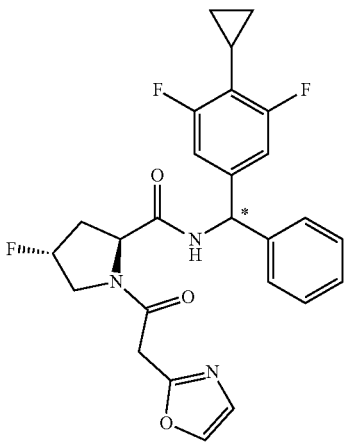 [SMILES: O=C(NC(c1ccccc1)c1cc(F)c(C2CC2)c(F)c1)[C@@H]1C[C@@H](F)CN1C(=O)Cc1ncco1] | (2S,4R)-N-[(S)-(4-cyclopropyl-3,5-difluorophenyl)(phenyl)methyl]-4-fluoro-1-[2-(1,3-oxazol-2-yl)acetyl]pyrrolidine-2-carboxamide |

TABLE 1-continued

| Compound No. | Structure | IUPAC |
|---|---|---|
| 663 | 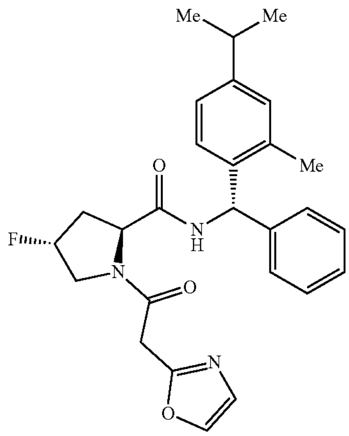 [SMILES: Cc1cc(C(C)C)ccc1[C@@H](NC(=O)[C@@H]1C[C@@H](F)CN1C(=O)Cc1ncco1)c1ccccc1] | (2S,4R)-4-fluoro-N-[(S)-[2-methyl-4-(propan-2-yl)phenyl](phenyl)methyl]-1-[2-(1,3-oxazol-2-yl)acetyl]pyrrolidine-2-carboxamide |
| 664 | 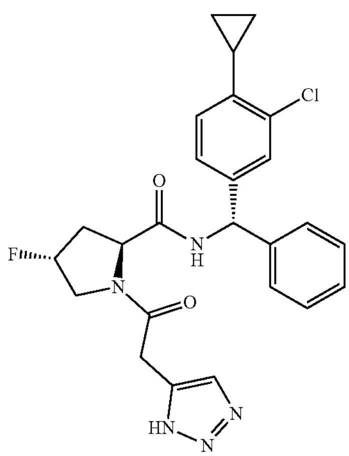 [SMILES: O=C(N[C@@H](c1ccccc1)c1ccc(C2CC2)c(Cl)c1)[C@@H]1C[C@@H](F)CN1C(=O)Cc1cnn[nH]1] | (2S,4R)-N-[(S)-(3-chloro-4-cyclopropylphenyl)(phenyl)methyl]-4-fluoro-1-[2-(1H-1,2,3-triazol-5-yl)acetyl]pyrrolidine-2-carboxamide |
| 665 | 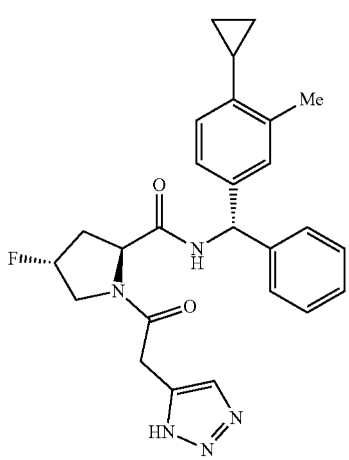 [SMILES: Cc1cc([C@@H](NC(=O)[C@@H]2C[C@@H](F)CN2C(=O)Cc2cnn[nH]2)c2ccccc2)ccc1C1CC1] | (2S,4R)-N-[(S)-(4-cyclopropyl-3-methylphenyl)(phenyl)methyl]-4-fluoro-1-[2-(1H-1,2,3-triazol-5-yl)acetyl]pyrrolidine-2-carboxamide |

TABLE 1-continued

| Compound No. | Structure | IUPAC |
|---|---|---|
| 666 | 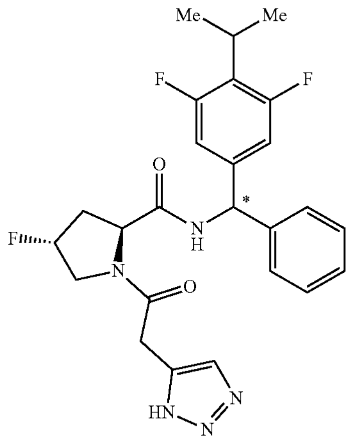 [SMILES: CC(C)c1c(F)cc(C(NC(=O)[C@@H]2C[C@@H](F)CN2C(=O)Cc2cnn[nH]2)c2ccccc2)cc1F] | (2S,4R)-N-[(R) or (S)-[3,5-difluoro-4-(propan-2-yl)phenyl](phenyl)methyl]-4-fluoro-1-[2-(1H-1,2,3-triazol-5-yl)acetyl]pyrrolidine-2-carboxamide |
| 667 | 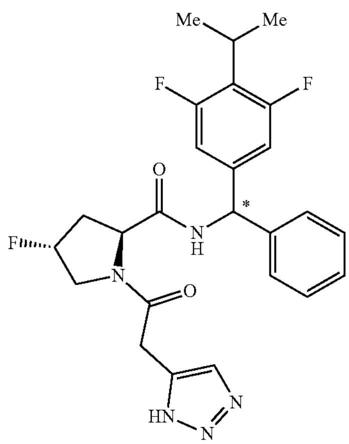 [SMILES: CC(C)c1c(F)cc(C(NC(=O)[C@@H]2C[C@@H](F)CN2C(=O)Cc2cnn[nH]2)c2ccccc2)cc1F] | (2S,4R)-N-[(S) or (R)-[3,5-difluoro-4-(propan-2-yl)phenyl](phenyl)methyl]-4-fluoro-1-[2-(1H-1,2,3-triazol-5-yl)acetyl]pyrrolidine-2-carboxamide |
| 668 | 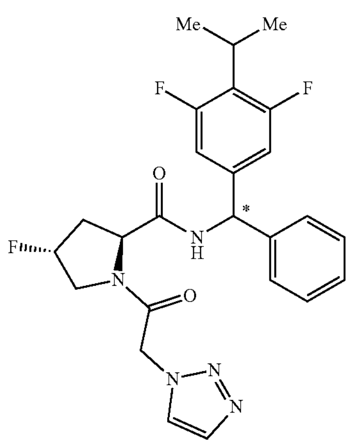 [SMILES: CC(C)c1c(F)cc(C(NC(=O)[C@@H]2C[C@@H](F)CN2C(=O)Cn2ccnn2)c2ccccc2)cc1F] | (2S,4R)-N-[(S) or (R)-[3,5-difluoro-4-(propan-2-yl)phenyl](phenyl)methyl]-4-fluoro-1-[2-(1H-1,2,3-triazol-1-yl)acetyl]pyrrolidine-2-carboxamide |

TABLE 1-continued
| Compound No. | Structure | IUPAC |
|---|---|---|
| 669 | 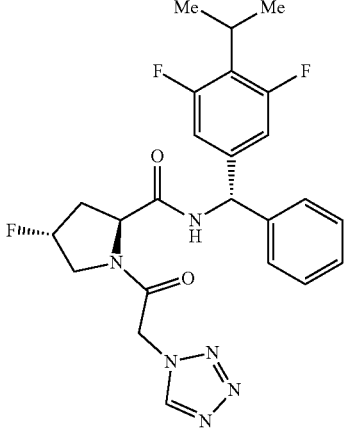 [SMILES: CC(C)c1c(F)cc([C@@H](NC(=O)[C@@H]2C[C@@H](F)CN2C(=O)Cn2cnnn2)c2ccccc2)cc1F] | (2S,4R)-N-[(S)-[3,5-difluoro-4-(propan-2-yl)phenyl](phenyl)methyl]-4-fluoro-1-[2-(1H-1,2,3-tetrazol-1-yl)acetyl]pyrrolidine-2-carboxamide |
| 670 | 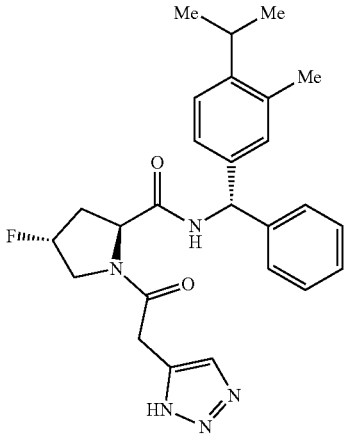 [SMILES: Cc1cc([C@@H](NC(=O)[C@@H]2C[C@@H](F)CN2C(=O)Cc2cnn[nH]2)c2ccccc2)ccc1C(C)C] | (2S,4R)-4-fluoro-N-[(S)-[3-methyl-4-(propan-2-yl)phenyl](phenyl)methyl]-1-[2-(1H-1,2,3-triazol-5-yl)acetyl]pyrrolidine-2-carboxamide |
| 671 | 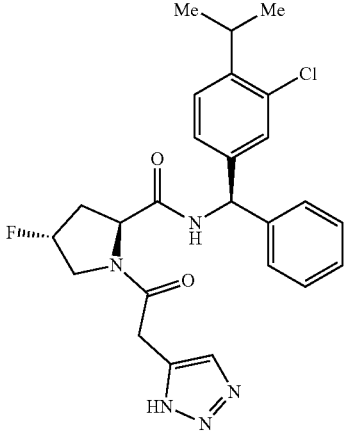 | (2S,4R)-N-[(R)-[3-chloro-4-(propan-2-yl)phenyl](phenyl)methyl]-4-fluoro-1-[2-(1H-1,2,3-triazol-5-yl)acetyl]pyrrolidine-2-carboxamide |

TABLE 1-continued
| Compound No. | Structure | IUPAC |
|---|---|---|
| 672 | 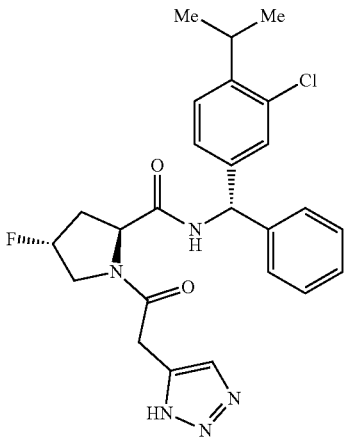 [SMILES: CC(C)c1ccc([C@@H](NC(=O)[C@@H]2C[C@@H](F)CN2C(=O)Cc2cnn[nH]2)c2ccccc2)cc1Cl] | (2S,4R)-N-[(S)-[3-chloro-4-(propan-2-yl)phenyl](phenyl)methyl]-4-fluoro-1-[2-(1H-1,2,3-triazol-5-yl)acetyl]pyrrolidine-2-carboxamide |
| 673 | 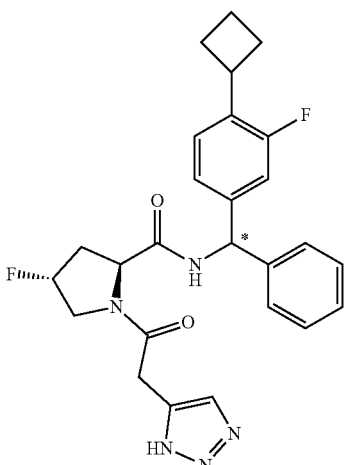 | (2S,4R)-N-[(R) or (S)-(4-cyclobutyl-3-fluorophenyl)(phenyl)methyl]-4-fluoro-1-[2-(1H-1,2,3-triazol-5-yl)acetyl]pyrrolidine-2-carboxamide |
| 674 | 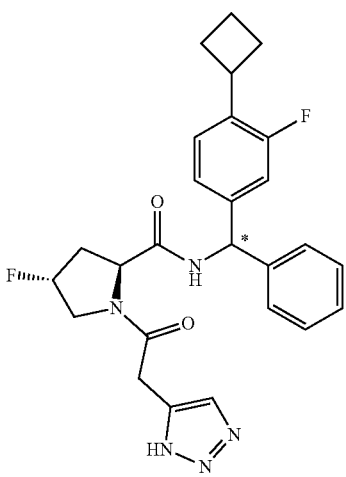 [SMILES: O=C(NC(c1ccccc1)c1ccc(C2CCC2)c(F)c1)[C@@H]1C[C@@H](F)CN1C(=O)Cc1cnn[nH]1] | (2S,4R)-N-[(S) or (R)-(4-cyclobutyl-3-fluorophenyl)(phenyl)methyl]-4-fluoro-1-[2-(1H-1,2,3-triazol-5-yl)acetyl]pyrrolidine-2-carboxamide |

TABLE 1-continued

| Compound No. | Structure | IUPAC |
|---|---|---|
| 675 | 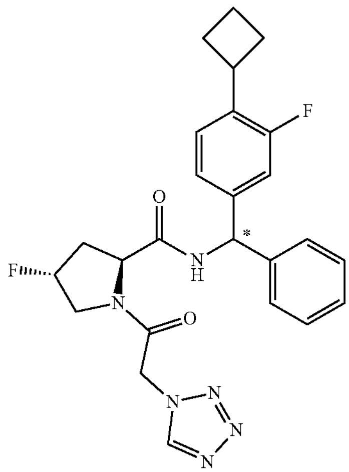 [SMILES: O=C(NC(c1ccccc1)c1ccc(C2CCC2)c(F)c1)[C@@H]1C[C@@H](F)CN1C(=O)Cn1cnnn1] | (2S,4R)-N-[(S) or (R)-(4-cyclobutyl-3-fluorophenyl)(phenyl)methyl]-4-fluoro-1-[2-(1H-1,2,3,4-tetrazol-1-yl)acetyl]pyrrolidine-2-carboxamide |
| 676 | 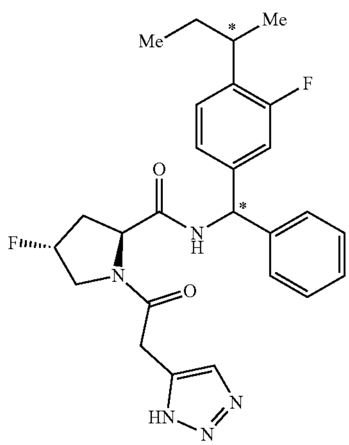 [SMILES: CCC(C)c1ccc(C(NC(=O)[C@@H]2C[C@@H](F)CN2C(=O)Cc2cnn[nH]2)c2ccccc2)cc1F] | (2S,4R)-N-[(R) or (S)-{4-[(2R) or (2S)-butan-2-yl]-3-fluorophenyl}(phenyl)methyl]-4-fluoro-1-[2-(1H-1,2,3-triazol-5-yl)acetyl]pyrrolidine-2-carboxamide |
| 677 | 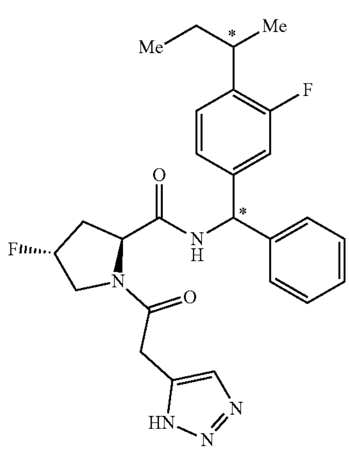 [SMILES: CCC(C)c1ccc(C(NC(=O)[C@@H]2C[C@@H](F)CN2C(=O)Cc2cnn[nH]2)c2ccccc2)cc1F] | (2S,4R)-N-[(S) or (R)-{4-[(2R) or (2S)-butan-2-yl]-3-fluorophenyl}(phenyl)methyl]-4-fluoro-1-(2-(1H-1,2,3-triazol-5-yl)acetyl]pyrrolidine-2-carboxamide |

TABLE 1-continued

| Compound No. | Structure | IUPAC |
|---|---|---|
| 678 | 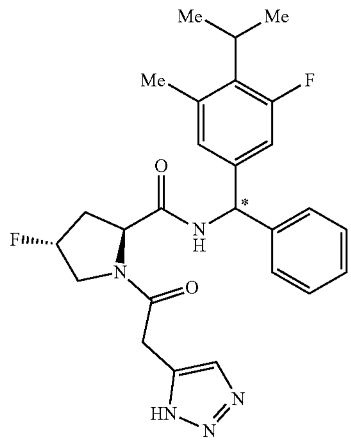 [SMILES: Cc1cc(C(NC(=O)[C@@H]2C[C@@H](F)CN2C(=O)Cc2cnn[nH]2)c2ccccc2)cc(F)c1C(C)C] | (2S,4R)-4-fluoro-N-[(R) or (S)-[3-fluoro-5-methyl-4-(propan-2-yl)phenyl](phenyl)methyl]-1-[2-(1H-1,2,3-triazol-5-yl)acetyl]pyrrolidine-2-carboxamide |
| 679 | 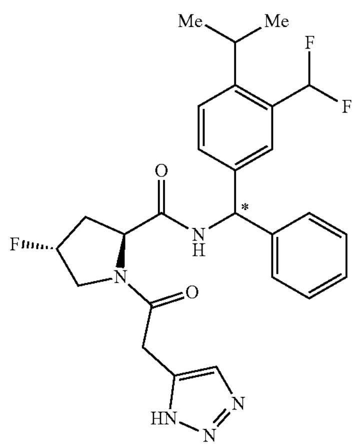 [SMILES: CC(C)c1ccc(C(NC(=O)[C@@H]2C[C@@H](F)CN2C(=O)Cc2cnn[nH]2)c2ccccc2)cc1C(F)F] | (2S,4R)-N-[(S)-[3-(difluoromethyl)-4-(propan-2-yl)phenyl](phenyl)methyl]-4-fluoro-1-[2-(1H-1,2,3-triazol-5-yl)acetyl]pyrrolidine-2-carboxamide |
| 680 | 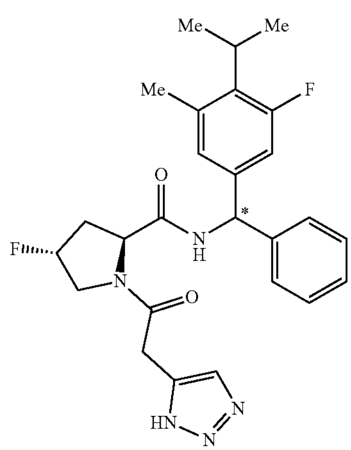 [SMILES: Cc1cc(C(NC(=O)[C@@H]2C[C@@H](F)CN2C(=O)Cc2cnn[nH]2)c2ccccc2)cc(F)c1C(C)C] | (2S,4R)-4-fluoro-N-[(S) or (R)-[3-fluoro-5-methyl-4-(propan-2-yl)phenyl](phenyl)methyl]-1-[2-(1H-1,2,3-triazol-5-yl)acetyl]pyrrolidine-2-carboxamide |

TABLE 1-continued

| Compound No. | Structure | IUPAC |
|---|---|---|
| 681 | 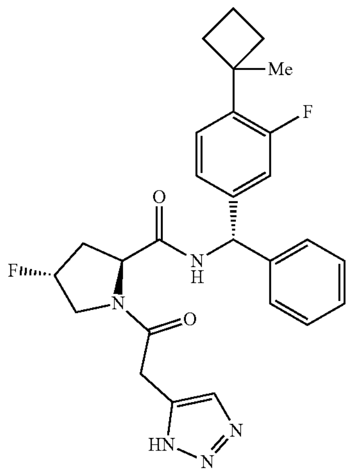 [SMILES: CC1(c2ccc([C@@H](NC(=O)[C@@H]3C[C@@H](F)CN3C(=O)Cc3cnn[nH]3)c3ccccc3)cc2F)CCC1] | (2S,4R)-4-fluoro-N-[(S)-[3-fluoro-4-(1-methylcyclobutyl)phenyl](phenyl)methyl]-1-[2-(1H-1,2,3-triazol-5-yl)acetyl]pyrrolidine-2-carboxamide |
| 682 | 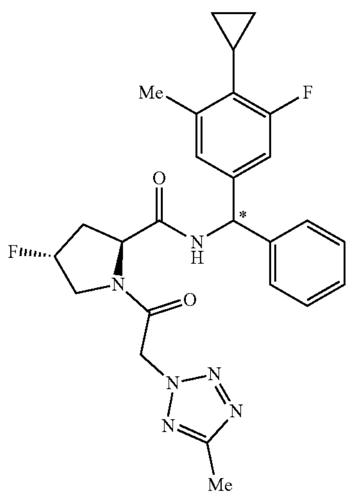 [SMILES: Cc1nnn(CC(=O)N2C[C@H](F)C[C@H]2C(=O)NC(c2ccccc2)c2cc(C)c(C3CC3)c(F)c2)n1] | (2S,4R)-N-[(S) or (R)-(4-cyclopropyl-3-fluoro-5-methylphenyl)(phenyl)methyl]-4-fluoro-1-[2-(5-methyl-2H-1,2,3-tetrazol-2-yl)acetyl]pyrrolidine-2-carboxamide |
| 683 | 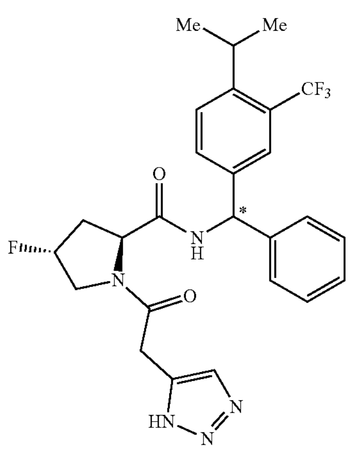 [SMILES: CC(C)c1ccc(C(NC(=O)[C@@H]2C[C@@H](F)CN2C(=O)Cc2cnn[nH]2)c2ccccc2)cc1C(F)(F)F] | (2S,4R)-4-fluoro-N-[(S) or (R)-phenyl[4-(propan-2-yl)-3-(trifluoromethyl)phenyl]methyl]-1-[2-(1H-1,2,3-triazol-5-yl)acetyl]pyrrolidine-2-carboxamide |

TABLE 1-continued

| Compound No. | Structure | IUPAC |
|---|---|---|
| 684 | 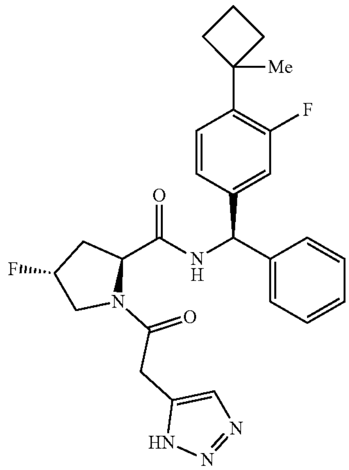 [SMILES: CC1(c2ccc([C@H](NC(=O)[C@@H]3C[C@@H](F)CN3C(=O)Cc3cnn[nH]3)c3ccccc3)cc2F)CCC1] | (2S,4R)-4-fluoro-N-[(R)-[3-fluoro-4-(1-methylcyclobutyl)phenyl](phenyl)methyl]-1-[2-(1H-1,2,3-triazol-5-yl)acetyl]pyrrolidine-2-carboxamide |
| 685 | 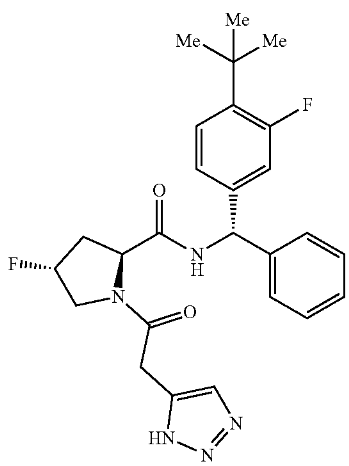 [SMILES: CC(C)(C)c1ccc([C@@H](NC(=O)[C@@H]2C[C@@H](F)CN2C(=O)Cc2cnn[nH]2)c2ccccc2)cc1F] | (2S,4R)-N-[(S)-(4-tert-butyl-3-fluorophenyl)(phenyl)methyl]-4-fluoro-1-[2-(1H-1,2,3-triazol-5-yl)acetyl]pyrrolidine-2-carboxamide |
| 686 | 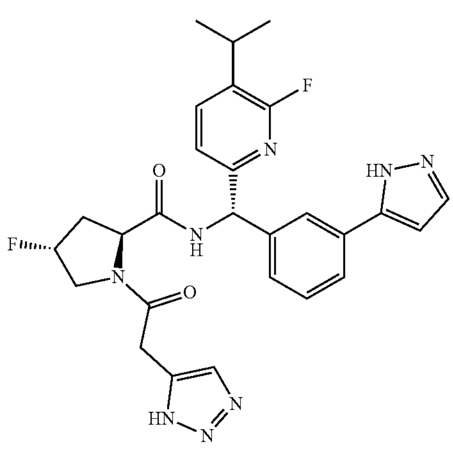 [SMILES: CC(C)c1ccc([C@@H](NC(=O)[C@@H]2C[C@@H](F)CN2C(=O)Cc2cnn[nH]2)c2cccc(-c3ccn[nH]3)c2)nc1F] | (2S,4R)-1-(2-(1H-1,2,3-triazol-5-yl)acetyl)-N-((S)-(3-(1H-pyrazol-5-yl)phenyl)(6-fluoro-5-isopropylpyridin-2-yl)methyl)-4-fluoropyrrolidine-2-carboxamide |

TABLE 1-continued

| Compound No. | Structure | IUPAC |
|---|---|---|
| 687 | 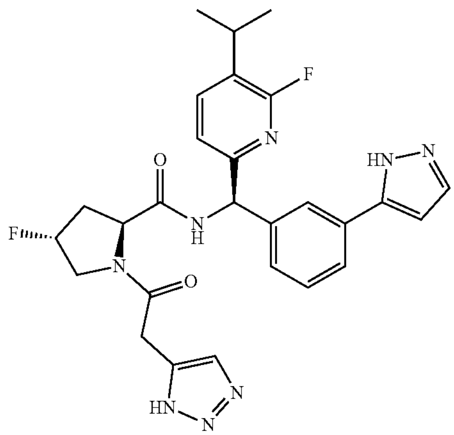 [SMILES: CC(C)c1ccc([C@H](NC(=O)[C@@H]2C[C@@H](F)CN2C(=O)Cc2cnn[nH]2)c2cccc(-c3ccn[nH]3)c2)nc1F] | (2S,4R)-1-(2-(1H-1,2,3-triazol-5-yl)acetyl)-N-((R)-(3-(1H-pyrazol-5-yl)phenyl)(6-fluoro-5-isopropylpyridin-2-yl)methyl)-4-fluoropyrrolidine-2-carboxamide |
| 688 | 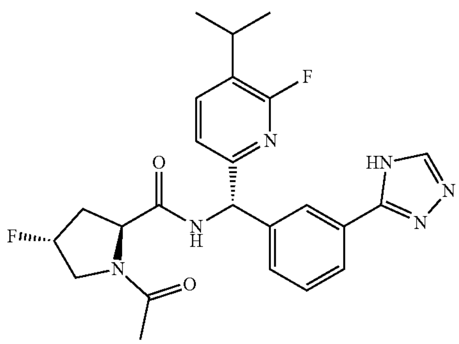 [SMILES: CC(=O)N1C[C@H](F)C[C@H]1C(=O)N[C@@H](c1cccc(-c2nnc[nH]2)c1)c1ccc(C(C)C)c(F)n1] | (2S,4R)-N-((S) or (R)-(3-(4H-1,2,4-triazol-3-yl)phenyl)(6-fluoro-5-isopropylpyridin-2-yl)methyl)-1-acetyl-4-fluoropyrrolidine-2-carboxamide |
| 689 | 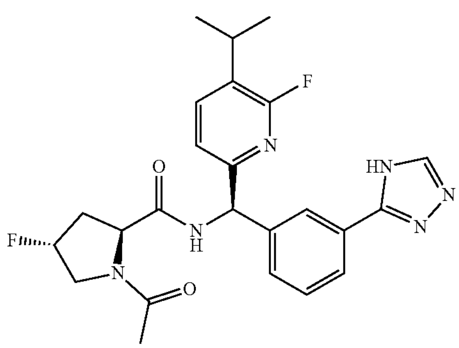 [SMILES: CC(=O)N1C[C@H](F)C[C@H]1C(=O)N[C@H](c1cccc(-c2nnc[nH]2)c1)c1ccc(C(C)C)c(F)n1] | (2S,4R)-N-((R) or (S)-(3-(4H-1,2,4-triazol-3-yl)(phenyl)(6-fluoro-5-isopropylpyridin-2-yl)methyl)-1-acetyl-4-fluoropyrrolidine-2-carboxamide |
| 690 | 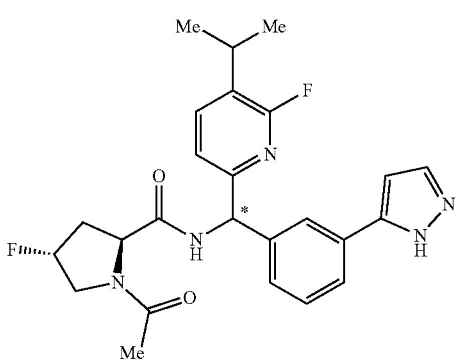 [SMILES: CC(=O)N1C[C@H](F)C[C@H]1C(=O)NC(c1cccc(-c2ccn[nH]2)c1)c1ccc(C(C)C)c(F)n1] | (2S,4R)-1-acetyl-4-fluoro-N-[(S) or (R)-[6-fluoro-5-(propan-2-yl)pyridin-2-yl][3-(1H-pyrazol-5-yl)phenyl]methyl]pyrrolidine-2-carboxamide |

TABLE 1-continued

| Compound No. | Structure | IUPAC |
|---|---|---|
| 691 | 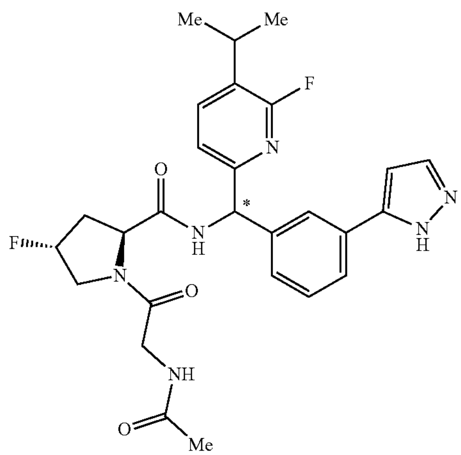 [SMILES: CC(=O)NCC(=O)N1C[C@H](F)C[C@H]1C(=O)NC(c1cccc(-c2ccn[nH]2)c1)c1ccc(C(C)C)c(F)n1] | (2S,4R)-1-(2-acetamidoacetyl)-4-fluoro-N-[(S) or (R)-[6-fluoro-5-(propan-2-yl)pyridin-2-yl][3-(1H-pyrazol-5-yl)phenyl]methyl]pyrrolidine-2-carboxamide |
| 692 | 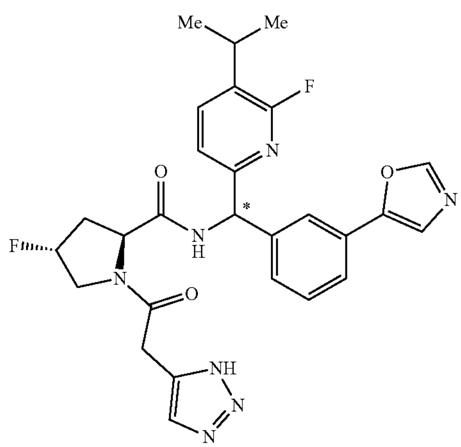 [SMILES: CC(C)c1ccc(C(NC(=O)[C@@H]2C[C@@H](F)CN2C(=O)Cc2cnn[nH]2)c2cccc(-c3cnco3)c2)nc1F] | (2S,4R)-4-fluoro-N-[(R) or (S)-[6-fluoro-5-(propan-2-yl)pyridin-2-yl][3-(1,3-oxazol-5-yl)phenyl]methyl]-1-[2-(1H-1,2,3-triazol-5-yl)acetyl]pyrrolidine-2-carboxamide |
| 693 | 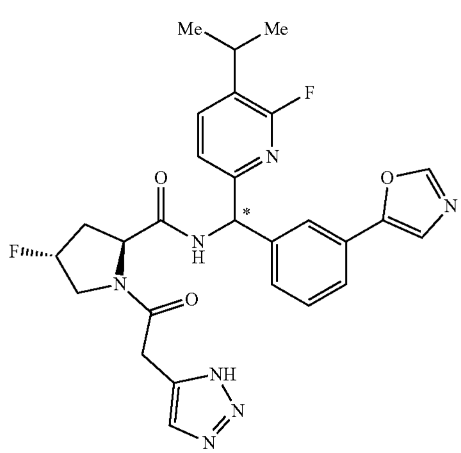 [SMILES: CC(C)c1ccc(C(NC(=O)[C@@H]2C[C@@H](F)CN2C(=O)Cc2cnn[nH]2)c2cccc(-c3cnco3)c2)nc1F] | (2S,4R)-4-fluoro-N-[(S) or (R)-[6-fluoro-5-(propan-2-yl)pyridin-2-yl][3-(1,3-oxazol-5-yl)phenyl]methyl]-1-[2-(1H-1,2,3-triazol-5-yl)acetyl]pyrrolidine-2-carboxamide |

TABLE 1-continued

| Compound No. | Structure | IUPAC |
|---|---|---|
| 694 | 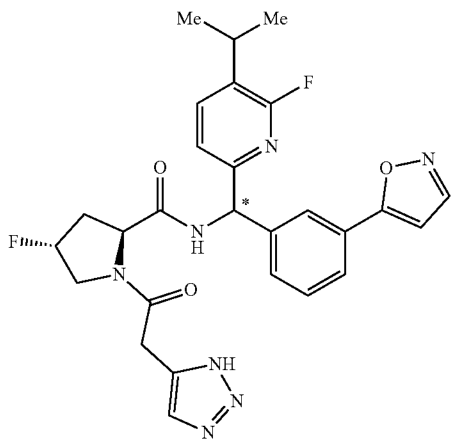 [SMILES: CC(C)c1ccc(C(NC(=O)[C@@H]2C[C@@H](F)CN2C(=O)Cc2cnn[nH]2)c2cccc(-c3ccno3)c2)nc1F] | (2S,4R)-4-fluoro-N-[(S) or (R)-[6-fluoro-5-(propan-2-yl)pyridin-2-yl][3-(1,2-oxazol-5-yl)phenyl]methyl]-1-[2-(1H-1,2,3-triazol-5-yl)acetyl]pyrrolidine-2-carboxamide |
| 695 | 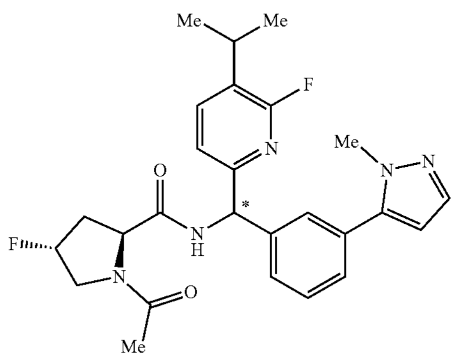 [SMILES: CC(=O)N1C[C@H](F)C[C@H]1C(=O)NC(c1cccc(-c2ccnn2C)c1)c1ccc(C(C)C)c(F)n1] | (2S,4R)-1-acetyl-4-fluoro-N-[(S) or (R)-[6-fluoro-5-(propan-2-yl)pyridin-2-yl][3-(1-methyl-1H-pyrazol-5-yl)phenyl]methyl]pyrrolidine-2-carboxamide |
| 696 | 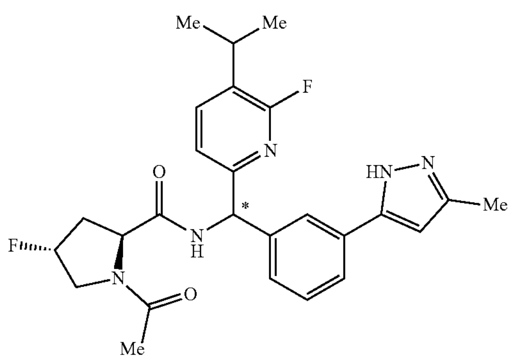 [SMILES: CC(=O)N1C[C@H](F)C[C@H]1C(=O)NC(c1cccc(-c2cc(C)n[nH]2)c1)c1ccc(C(C)C)c(F)n1] | (2S,4R)-1-acetyl-4-fluoro-N-[(S) or (R)-[6-fluoro-5-(propan-2-yl)pyridin-2-yl][3-(3-methyl-1H-pyrazol-5-yl)phenyl]methyl]pyrrolidine-2-carboxamide |
| 697 | 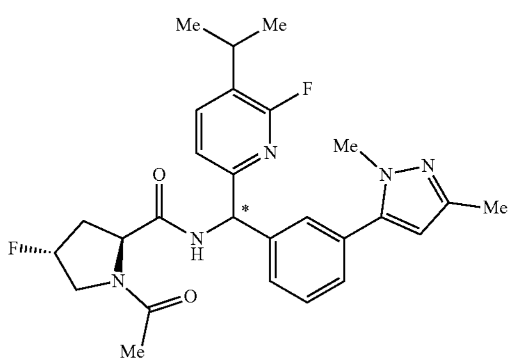 [SMILES: CC(=O)N1C[C@H](F)C[C@H]1C(=O)NC(c1cccc(-c2cc(C)nn2C)c1)c1ccc(C(C)C)c(F)n1] | (2S,4R)-1-acetyl-N-[(S) or (R)-[3-(1,3-dimethyl-1H-pyrazol-5-yl)phenyl][6-fluoro-5-(propan-2-yl)pyridin-2-yl]methyl]-4-fluoropyrrolidine-2-carboxamide |

TABLE 1-continued
| Compound No. | Structure | IUPAC |
|---|---|---|
| 698 | 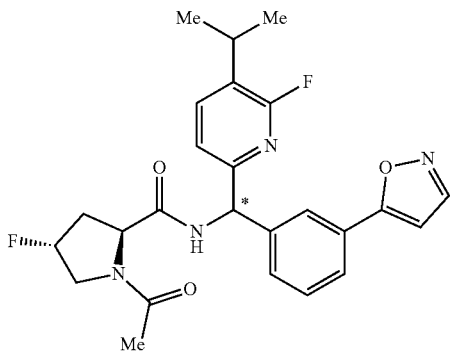 [SMILES: CC(=O)N1C[C@H](F)C[C@H]1C(=O)NC(c1cccc(-c2ccno2)c1)c1ccc(C(C)C)c(F)n1] | (2S,4R)-1-acetyl-4-fluoro-N-[(S) or (R)-[6-fluoro-5-(propan-2-yl)pyridin-2-yl][3-(1,2-oxazol-5-yl)phenyl]methyl]pyrrolidine-2-carboxamide |
| 699 | 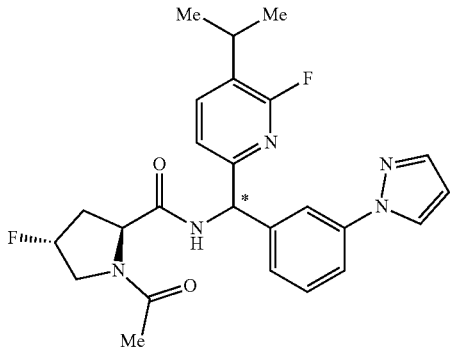 [SMILES: CC(=O)N1C[C@H](F)C[C@H]1C(=O)NC(c1cccc(-n2cccn2)c1)c1ccc(C(C)C)c(F)n1] | (2S,4R)-1-acetyl-4-fluoro-N-[(S) or (R)-[6-fluoro-5-(propan-2-yl)pyridin-2-yl][3-(1H-pyrazol-1-yl)phenyl]methyl]pyrrolidine-2-carboxamide |
| 700 | 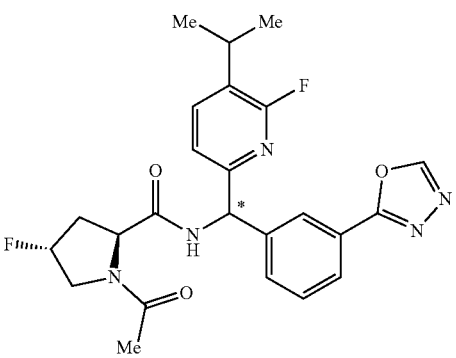 [SMILES: CC(=O)N1C[C@H](F)C[C@H]1C(=O)NC(c1cccc(-c2nnco2)c1)c1ccc(C(C)C)c(F)n1] | (2S,4R)-1-acetyl-4-fluoro-N-[(S) or (R)-[6-fluoro-5-(propan-2-yl)pyridin-2-yl][3-(1,3,4-oxadiazol-2-yl)phenyl]methyl]pyrrolidine-2-carboxamide |

TABLE 1-continued

| Compound No. | Structure | IUPAC |
|---|---|---|
| 701 | 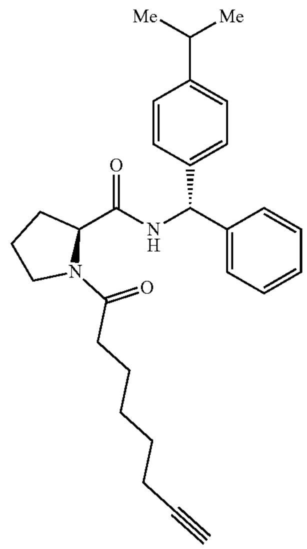 [SMILES: C#CCCCCCC(=O)N1CCC[C@H]1C(=O)N[C@@H](c1ccccc1)c1ccc(C(C)C)cc1] | (2S)-1-(oct-7-ynoyl)-N-[(S)-phenyl[4-(propan-2-yl)phenyl]methyl]pyrrolidine-2-carboxamide |
| 702 | 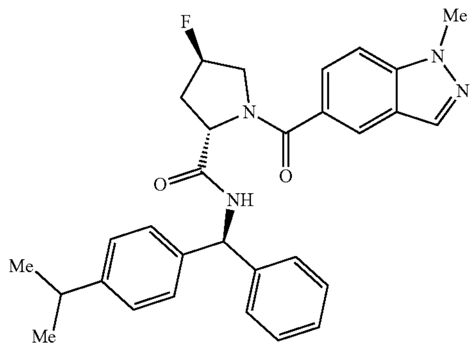 [SMILES: CC(C)c1ccc([C@@H](NC(=O)[C@@H]2C[C@@H](F)CN2C(=O)c2ccc3c(cnn3C)c2)c2ccccc2)cc1] | (2S,4R)-4-fluoro-1-(1-methyl-1H-indazole-5-carbonyl)-N-[(S)-phenyl[4-(propan-2-yl)phenyl]methyl]pyrrolidine-2-carboxamide |
| 703 | 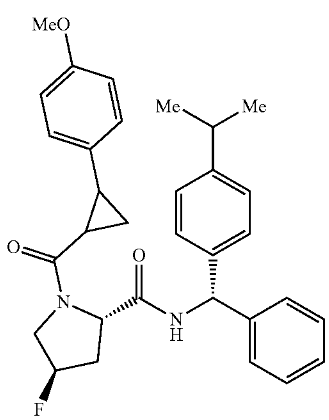 [SMILES: COc1ccc(C2CC2C(=O)N2C[C@H](F)C[C@H]2C(=O)N[C@@H](c2ccccc2)c2ccc(C(C)C)cc2)cc1] | (2S,4R)-4-fluoro-1-[2-(4-methoxyphenyl)cyclopropane-carbonyl]-N-[(S)-phenyl[4-(propan-2-yl)phenyl]methyl]pyrrolidine-2-carboxamide |

TABLE 1-continued

| Compound No. | Structure | IUPAC |
|---|---|---|
| 704 | 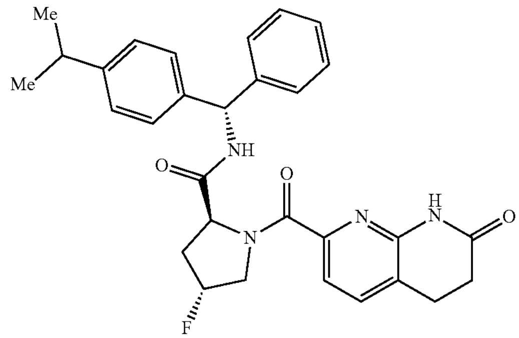 [SMILES: CC(C)c1ccc([C@@H](NC(=O)[C@@H]2C[C@@H](F)CN2C(=O)c2ccc3c(n2)NC(=O)CC3)c2ccccc2)cc1] | (2S,4R)-4-fluoro-1-(7-oxo-5,6,7,8-tetrahydro-1,8-naphthyridine-2-carbonyl)-N-[(S)-phenyl[4-(propan-2-yl)phenyl]methyl]pyrrolidine-2-carboxamide |
| 705 | 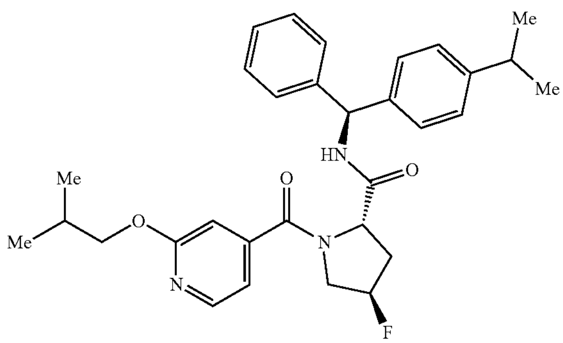 [SMILES: CC(C)COc1cc(C(=O)N2C[C@H](F)C[C@H]2C(=O)N[C@@H](c2ccccc2)c2ccc(C(C)C)cc2)ccn1] | (2S,4R)-4-fluoro-1-[2-(2-methylpropoxy)pyridine-4-carbonyl]-N-[(S)-phenyl[4-(propan-2-yl)phenyl]methyl]pyrrolidine-2-carboxamide |
| 707 | 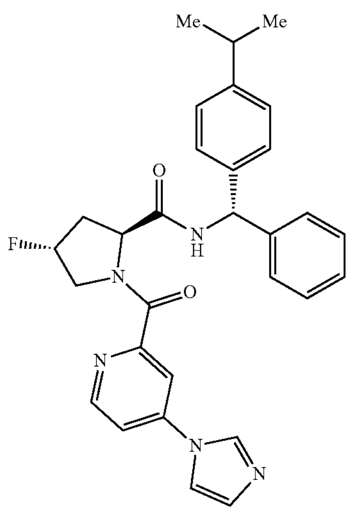 [SMILES: CC(C)c1ccc([C@@H](NC(=O)[C@@H]2C[C@@H](F)CN2C(=O)c2cc(-n3ccnc3)ccn2)c2ccccc2)cc1] | (2S,4R)-4-fluoro-1-[4-(1H-imidazol-1-yl)pyridine-2-carbonyl]-N-[(S)-phenyl[4-(propan-2-yl)phenyl]methyl]pyrrolidine-2-carboxamide |
| 708 | 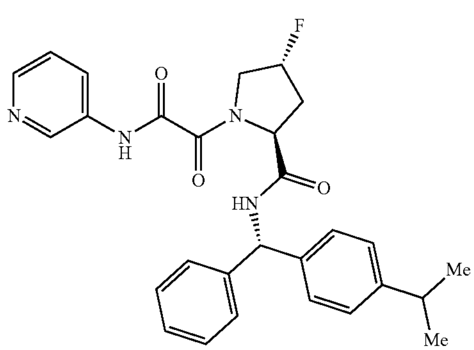 [SMILES: CC(C)c1ccc([C@@H](NC(=O)[C@@H]2C[C@@H](F)CN2C(=O)C(=O)Nc2cccnc2)c2ccccc2)cc1] | (2S,4R)-4-fluoro-N-[(S)-phenyl[4-(propan-2-yl)phenyl]methyl]-1-{[(pyridin-3-yl)carbamoyl]carbonyl}pyrrolidine-2-carboxamide |

TABLE 1-continued

| Compound No. | Structure | IUPAC |
|---|---|---|
| 709 | 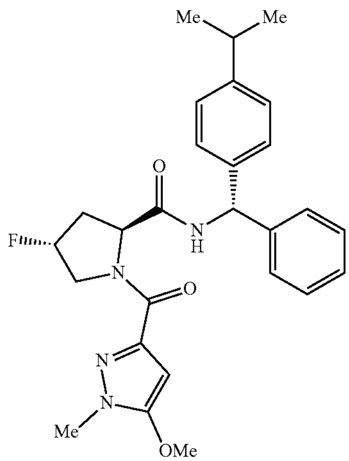 [SMILES: COc1cc(C(=O)N2C[C@H](F)C[C@H]2C(=O)N[C@@H](c2ccccc2)c2ccc(C(C)C)cc2)nn1C] | (2S,4R)-4-fluoro-1-(5-methoxy-1-methyl-1H-pyrazole-3-carbonyl)-N-[(S)-phenyl[4-(propan-2-yl)phenyl]methyl]pyrrolidine-2-carboxamide |
| 710 | 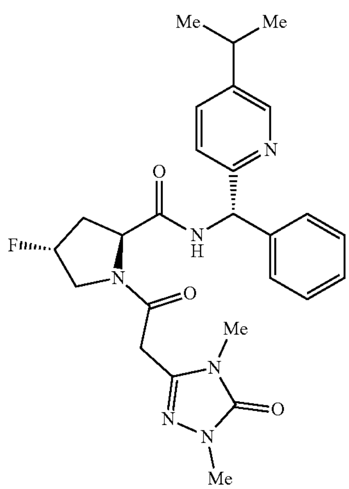 [SMILES: CC(C)c1ccc([C@@H](NC(=O)[C@@H]2C[C@@H](F)CN2C(=O)Cc2nn(C)c(=O)n2C)c2ccccc2)nc1] | (2S,4R)-1-[2-(1,4-dimethyl-5-oxo-4,5-dihydro-1H-1,2,4-triazol-3-yl)acetyl]-4-fluoro-N-[(S)-phenyl[5-(propan-2-yl)pyridin-2-yl]methyl]pyrrolidine-2-carboxamide |
| 711 | 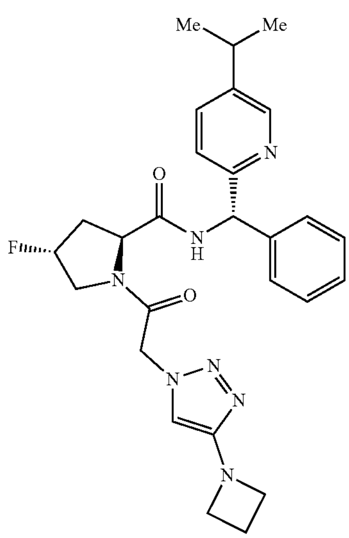 [SMILES: CC(C)c1ccc([C@@H](NC(=O)[C@@H]2C[C@@H](F)CN2C(=O)Cn2cc(N3CCC3)nn2)c2ccccc2)nc1] | (2S,4R)-1-{2-[4-(azetidin-1-yl)-1H-1,2,3-triazol-1-yl]acetyl}-4-fluoro-N-[(S)-phenyl[5-(propan-2-yl)pyridin-2-yl]methyl]pyrrolidine-2-carboxamide |

TABLE 1-continued

| Compound No. | Structure | IUPAC |
|---|---|---|
| 712 | 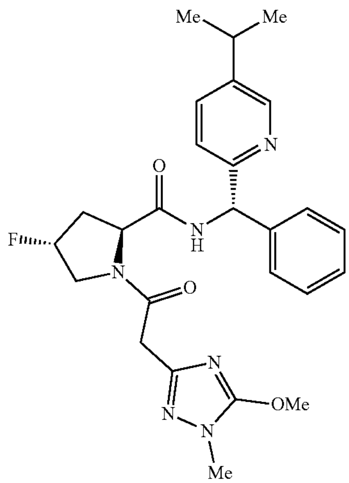 [SMILES: COc1nc(CC(=O)N2C[C@H](F)C[C@H]2C(=O)N[C@@H](c2ccccc2)c2ccc(C(C)C)cn2)nn1C] | (2S,4R)-4-fluoro-1-[2-(5-methoxy-1-methyl-1H-1,2,4-triazol-3-yl)acetyl]-N-[(S)-phenyl[5-(propan-2-yl)pyridin-2-yl]methyl]pyrrolidine-2-carboxamide |
| 713 | 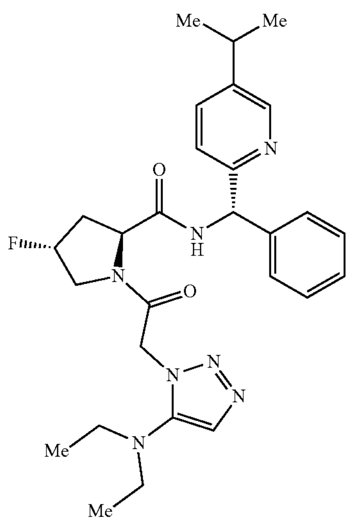 [SMILES: CCN(CC)c1cnnn1CC(=O)N1C[C@H](F)C[C@H]1C(=O)N[C@@H](c1ccccc1)c1ccc(C(C)C)cn1] | (2S,4R)-1-{2-[5-(diethylamino)-1H-1,2,3-triazol-1-yl]acetyl}-4-fluoro-N-[(S)-phenyl[5-(propan-2-yl)pyridin-2-yl]methyl]pyrrolidine-2-carboxamide |
| 714 | 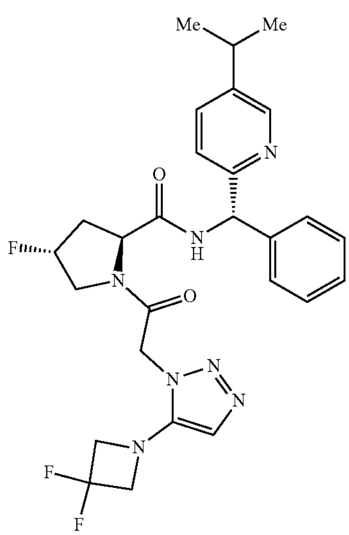 [SMILES: CC(C)c1ccc([C@@H](NC(=O)[C@@H]2C[C@@H](F)CN2C(=O)Cn2nncc2N2CC(F)(F)C2)c2ccccc2)nc1] | (2S,4R)-1-{2-[5-(3,3-difluoroazetidin-1-yl)-1H-1,2,3-triazol-1-yl]acetyl}-4-fluoro-N-[(S)-phenyl[5-(propan-2-yl)pyridin-2-yl]methyl]pyrrolidine-2-carboxamide |

TABLE 1-continued

| Compound No. | Structure | IUPAC |
|---|---|---|
| 715 | 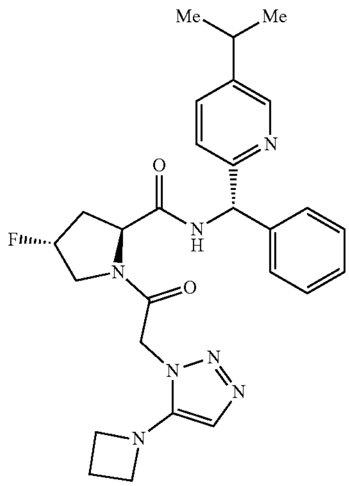 [SMILES: CC(C)c1ccc([C@@H](NC(=O)[C@@H]2C[C@@H](F)CN2C(=O)Cn2nncc2N2CCC2)c2ccccc2)nc1] | (2S,4R)-1-{2-[5-(azetidin-1-yl)-1H-1,2,3-triazol-1-yl]acetyl}-4-fluoro-N-[(S)-phenyl[5-(propan-2-yl)pyridin-2-yl]methyl]pyrrolidine-2-carboxamide |
| 716 | 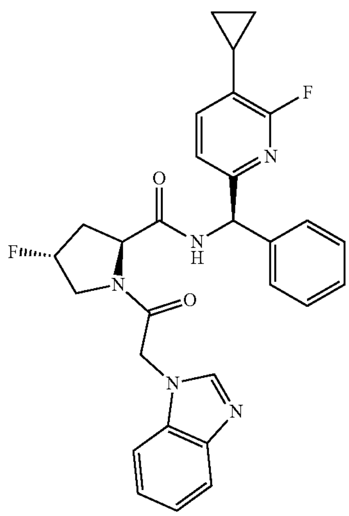 [SMILES: O=C(N[C@H](c1ccccc1)c1ccc(C2CC2)c(F)n1)[C@@H]1C[C@@H](F)CN1C(=O)Cn1cnc2ccccc21] | (2S,4R)-1-[2-(1H-1,3-benzodiazol-1-yl)acetyl]-N-[(R)-(5-cyclopropyl-6-fluoropyridin-2-yl)(phenyl)methyl]-4-fluoropyrrolidine-2-carboxamide |
| 717 | 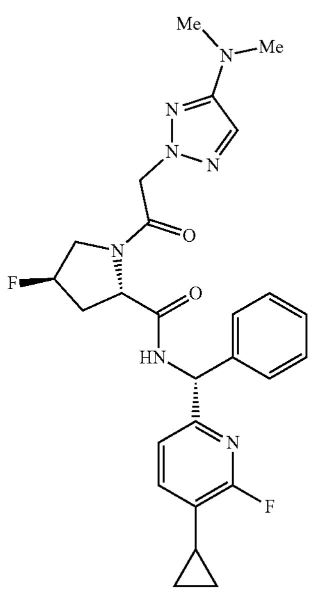 [SMILES: CN(C)c1cnn(CC(=O)N2C[C@H](F)C[C@H]2C(=O)N[C@H](c2ccccc2)c2ccc(C3CC3)c(F)n2)n1] | (2S,4R)-N-[(R)-(5-cyclopropyl-6-fluoropyridin-2-yl)(phenyl)methyl]-1-{2-[4-(dimethylamino)-2H-1,2,3-triazol-2-yl]acetyl}-4-fluoropyrrolidine-2-carboxamide |

TABLE 1-continued

| Compound No. | Structure | IUPAC |
|---|---|---|
| 718 | 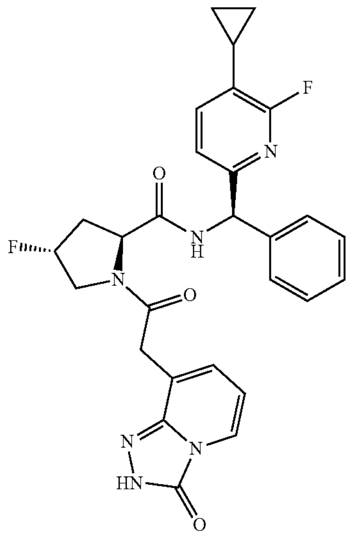 [SMILES: O=C(N[C@H](c1ccccc1)c1ccc(C2CC2)c(F)n1)[C@@H]1C[C@@H](F)CN1C(=O)Cc1cccn2c(=O)[nH]nc12] | (2S,4R)-N-[(R)-(5-cyclopropyl-6-fluoropyridin-2-yl)(phenyl)methyl]-4-fluoro-1-(2-{3-oxo-2H,3H-[1,2,4]triazolo[4,3-a]pyridin-8-yl}acetyl)pyrrolidine-2-carboxamide |
| 719 | 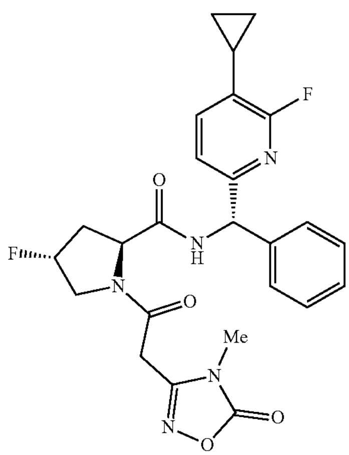 [SMILES: Cn1c(CC(=O)N2C[C@H](F)C[C@H]2C(=O)N[C@@H](c2ccccc2)c2ccc(C3CC3)c(F)n2)noc1=O] | (2S,4R)-N-[(S)-(5-cyclopropyl-6-fluoropyridin-2-yl)(phenyl)methyl]-4-fluoro-1-[2-(4-methyl-5-oxo-4,5-dihydro-1,2,4-oxadiazol-3-yl)acetyl]pyrrolidine-2-carboxamide |
| 720 | 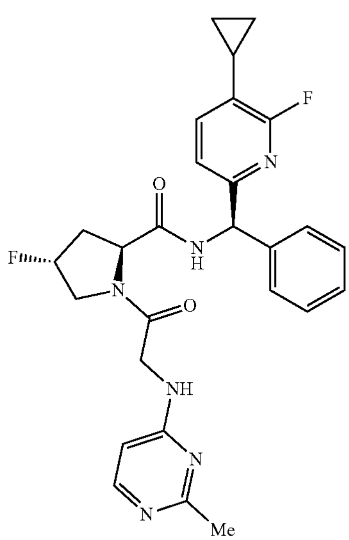 [SMILES: Cc1nccc(NCC(=O)N2C[C@H](F)C[C@H]2C(=O)N[C@H](c2ccccc2)c2ccc(C3CC3)c(F)n2)n1] | (2S,4R)-N-[(R)-(5-cyclopropyl-6-fluoropyridin-2-yl)(phenyl)methyl]-4-fluoro-1-{2-[(2-methylpyrimidin-4-yl)amino]acetyl}pyrrolidine-2-carboxamide |

TABLE 1-continued

| Compound No. | Structure | IUPAC |
|---|---|---|
| 721 | 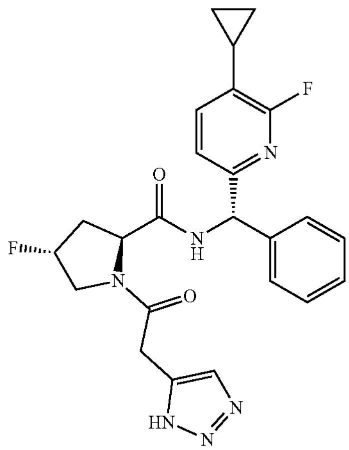 [SMILES: O=C(N[C@@H](c1ccccc1)c1ccc(C2CC2)c(F)n1)[C@@H]1C[C@@H](F)CN1C(=O)Cc1cnn[nH]1] | (2S,4R)-N-[(S)-(5-cyclopropyl-6-fluoropyridin-2-yl)(phenyl)methyl]-4-fluoro-1-{2-(1H-1,2,3-triazol-5-yl)acetyl]pyrrolidine-2-carboxamide |
| 722 | 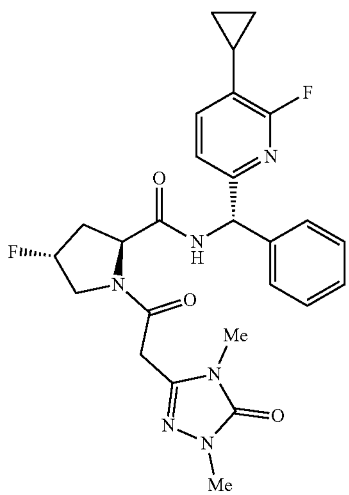 [SMILES: Cn1nc(CC(=O)N2C[C@H](F)C[C@H]2C(=O)N[C@@H](c2ccccc2)c2ccc(C3CC3)c(F)n2)n(C)c1=O] | (2S,4R)-N-[(S)-(5-cyclopropyl-6-fluoropyridin-2-yl)(phenyl)methyl]-1-[2-(1,4-dimethyl-5-oxo-4,5-dihydro-1H-1,2,4-triazol-3-yl)acetyl]-4-fluoropyrrolidine-2-carboxamide |
| 723 | 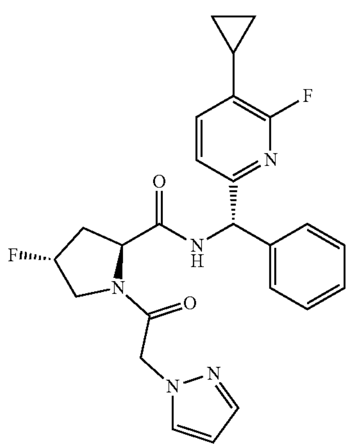 [SMILES: O=C(N[C@@H](c1ccccc1)c1ccc(C2CC2)c(F)n1)[C@@H]1C[C@@H](F)CN1C(=O)Cn1cccn1] | (2S,4R)-N-[(S)-(5-cyclopropyl-6-fluoropyridin-2-yl)(phenyl)methyl]-4-fluoro-1-[2-(1H-pyrazol-1-yl)acetyl]pyrrolidine-2-carboxamide |

TABLE 1-continued

| Compound No. | Structure | IUPAC |
|---|---|---|
| 724 | 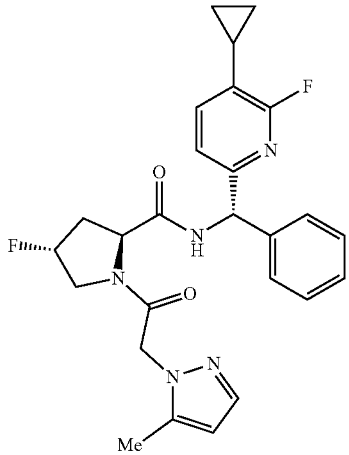 [SMILES: Cc1ccnn1CC(=O)N1C[C@H](F)C[C@H]1C(=O)N[C@@H](c1ccccc1)c1ccc(C2CC2)c(F)n1] | (2S,4R)-N-[(S)-(5-cyclopropyl-6-fluoropyridin-2-yl)(phenyl)methyl]-4-fluoro-1-[2-(5-methyl-1H-pyrazol-1-yl)acetyl]pyrrolidine-2-carboxamide |
| 725 | 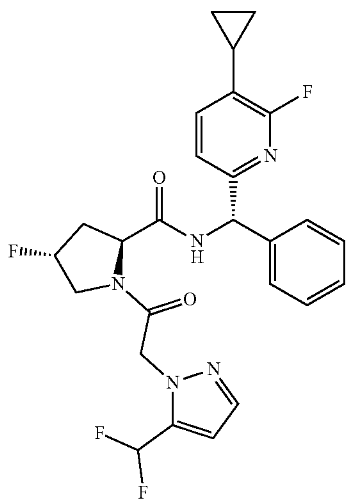 [SMILES: O=C(N[C@@H](c1ccccc1)c1ccc(C2CC2)c(F)n1)[C@@H]1C[C@@H](F)CN1C(=O)Cn1nccc1C(F)F] | (2S,4R)-N-[(S)-(5-cyclopropyl-6-fluoropyridin-2-yl)(phenyl)methyl]-1-{2-[5-(difluoromethyl)-1H-pyrazol-1-yl]acetyl}-4-fluoropyrrolidine-2-carboxamide |
| 726 | 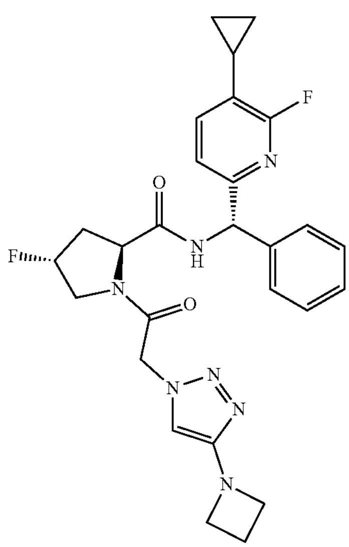 [SMILES: O=C(N[C@@H](c1ccccc1)c1ccc(C2CC2)c(F)n1)[C@@H]1C[C@@H](F)CN1C(=O)Cn1cc(N2CCC2)nn1] | (2S,4R)-1-{2-[4-(azetidin-1-yl)-1H-1,2,3-triazol-1-yl]acetyl}-N-[(S)-(5-cyclopropyl-6-fluoropyridin-2-yl)(phenyl)methyl]-4-fluoropyrrolidine-2-carboxamide |

TABLE 1-continued

| Compound No. | Structure | IUPAC |
|---|---|---|
| 727 | 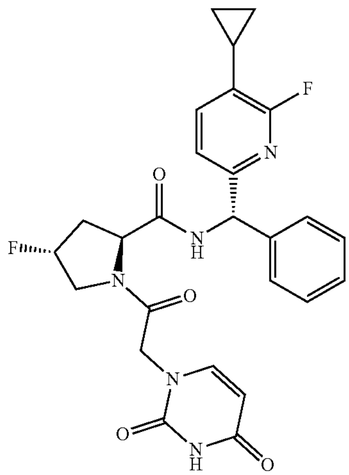 [SMILES: O=C(N[C@@H](c1ccccc1)c1ccc(C2CC2)c(F)n1)[C@@H]1C[C@@H](F)CN1C(=O)Cn1ccc(=O)[nH]c1=O] | (2S,4R)-N-[(S)-(5-cyclopropyl-6-fluoropyridin-2-yl)(phenyl)methyl]-1-[2-(2,4-dioxo-1,2,3,4-tetrahydropyrimidin-1-yl)acetyl]-4-fluoropyrrolidine-2-carboxamide |
| 728 | 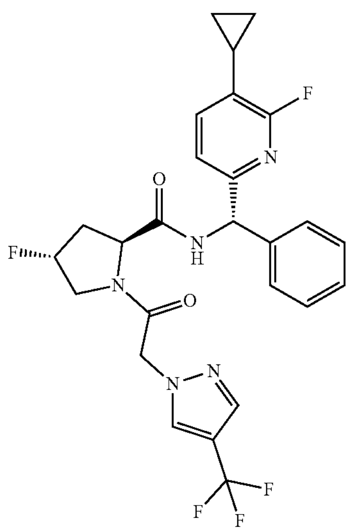 [SMILES: O=C(N[C@@H](c1ccccc1)c1ccc(C2CC2)c(F)n1)[C@@H]1C[C@@H](F)CN1C(=O)Cn1cc(C(F)(F)F)cn1] | (2S,4R)-N-[(S)-(5-cyclopropyl-6-fluoropyridin-2-yl)(phenyl)methyl]-4-fluoro-1-{2-[4-(trifluoromethyl)-1H-pyrazol-1-yl]acetyl}pyrrolidine-2-carboxamide |
| 729 | 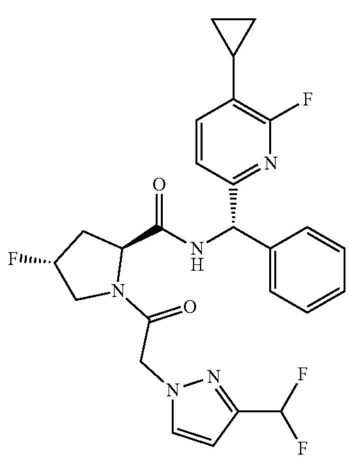 [SMILES: O=C(N[C@@H](c1ccccc1)c1ccc(C2CC2)c(F)n1)[C@@H]1C[C@@H](F)CN1C(=O)Cn1ccc(C(F)F)n1] | (2S,4R)-N-[(S)-(5-cyclopropyl-6-fluoropyridin-2-yl)(phenyl)methyl]-1-{2-[3-(difluoromethyl)-1H-pyrazol-1-yl]acetyl}-4-fluoropyrrolidine-2-carboxamide |

TABLE 1-continued

| Compound No. | Structure | IUPAC |
|---|---|---|
| 730 | 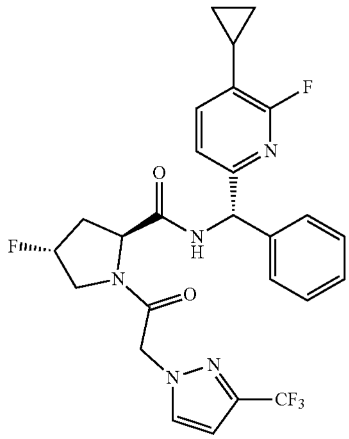 [SMILES: O=C(N[C@@H](c1ccccc1)c1ccc(C2CC2)c(F)n1)[C@@H]1C[C@@H](F)CN1C(=O)Cn1ccc(C(F)(F)F)n1] | (2S,4R)-N-[(S)-(5-cyclopropyl-6-fluoropyridin-2-yl)(phenyl)methyl]-4-fluoro-1-{2-[3-(trifluoromethyl)-1H-pyrazol-1-yl]acetyl}pyrrolidine-2-carboxamide |
| 731 | 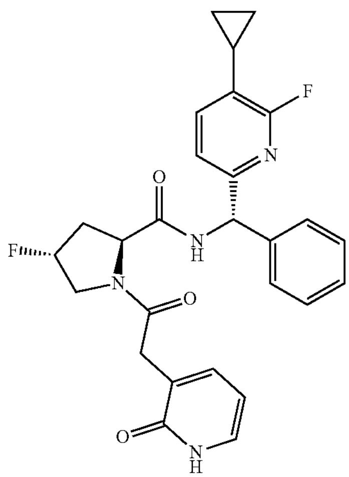 [SMILES: O=C(N[C@@H](c1ccccc1)c1ccc(C2CC2)c(F)n1)[C@@H]1C[C@@H](F)CN1C(=O)Cc1ccc[nH]c1=O] | (2S,4R)-N-[(S)-(5-cyclopropyl-6-fluoropyridin-2-yl)(phenyl)methyl]-4-fluoro-1-[2-(2-oxo-1,2-dihydropyridin-3-yl)acetyl]pyrrolidine-2-carboxamide |
| 732 | 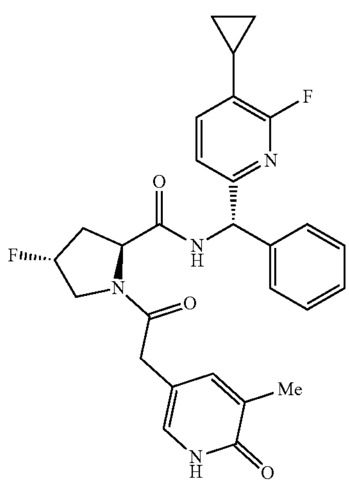 [SMILES: Cc1cc(CC(=O)N2C[C@H](F)C[C@H]2C(=O)N[C@@H](c2ccccc2)c2ccc(C3CC3)c(F)n2)c[nH]c1=O] | (2S,4R)-N-[(S)-(5-cyclopropyl-6-fluoropyridin-2-yl)(phenyl)methyl]-4-fluoro-1-[2-(5-methyl-6-oxo-1,6-dihydropyridin-3-yl)aceyl]pyrrolidine-2-carboxamide |

TABLE 1-continued

| Compound No. | Structure | IUPAC |
|---|---|---|
| 733 | 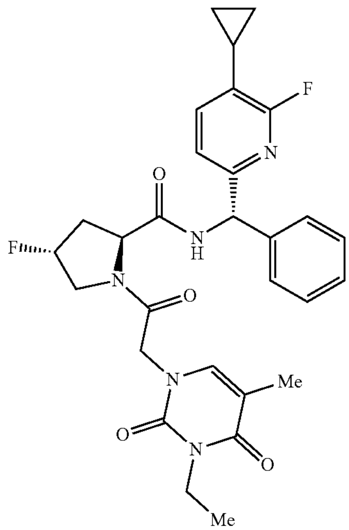 [SMILES: CCn1c(=O)c(C)cn(CC(=O)N2C[C@H](F)C[C@H]2C(=O)N[C@@H](c2ccccc2)c2ccc(C3CC3)c(F)n2)c1=O] | (2S,4R)-N-[(S)-(5-cyclopropyl-6-fluoropyridin-2-yl)(phenyl)methyl]-1-[2-(3-ethyl-5-methyl-2,4-dioxo-1,2,3,4-tetrahydropyrimidin-1-yl)acetyl]-4-fluoropyrrolidine-2-carboxamide |
| 734 | 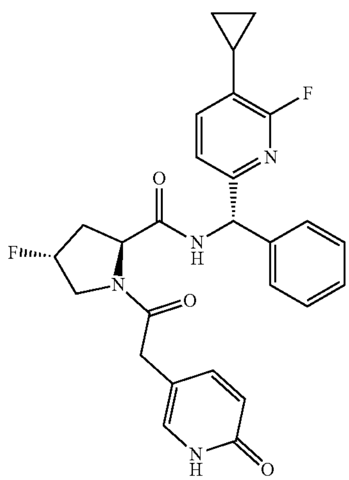 [SMILES: O=C(N[C@@H](c1ccccc1)c1ccc(C2CC2)c(F)n1)[C@@H]1C[C@@H](F)CN1C(=O)Cc1ccc(=O)[nH]c1] | (2S,4R)-N-[(S)-(5-cyclopropyl-6-fluoropyridin-2-yl)(phenyl)methyl]-4-fluoro-1-[2-(6-oxo-1,6-dihydropyridin-3-yl)acetyl]pyrrolidine-2-carboxamide |
| 735 | 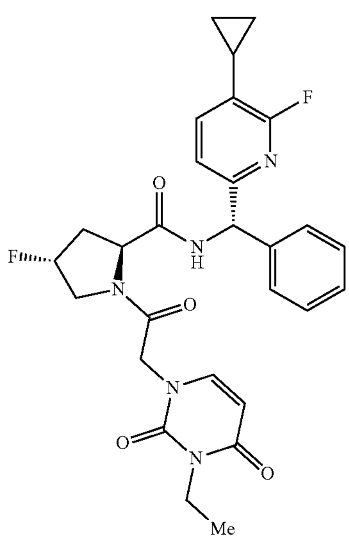 [SMILES: CCn1c(=O)ccn(CC(=O)N2C[C@H](F)C[C@H]2C(=O)N[C@@H](c2ccccc2)c2ccc(C3CC3)c(F)n2)c1=O] | (2S,4R)-N-[(S)-(5-cyclopropyl-6-fluoropyridin-2-yl)(phenyl)methyl]-1-[2-(3-ethyl-2,4-dioxo-1,2,3,4-tetrahydropyrimidin-1-yl)acetyl]-4-fluoropyrrolidine-2-carboxamide |

TABLE 1-continued

| Compound No. | Structure | IUPAC |
|---|---|---|
| 736 | 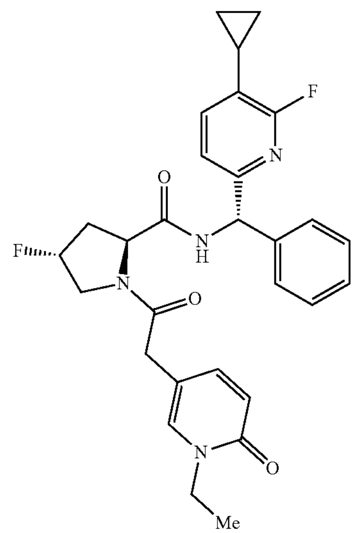 [SMILES: CCn1cc(CC(=O)N2C[C@H](F)C[C@H]2C(=O)N[C@@H](c2ccccc2)c2ccc(C3CC3)c(F)n2)ccc1=O] | (2S,4R)-N-[(S)-(5-cyclopropyl-6-fluoropyridin-2-yl)(phenyl)methyl]-1-[2-(1-ethyl-6-oxo-1,6-dihydropyridin-3-yl)acetyl]-4-fluoropyrrolidine-2-carboxamide |
| 737 | 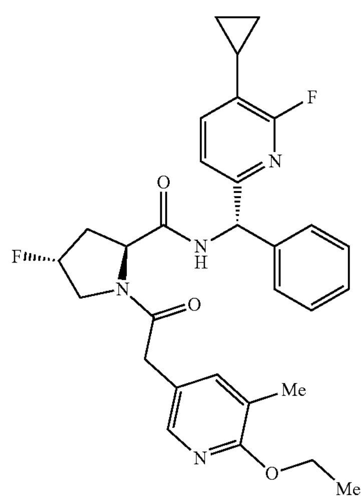 [SMILES: CCOc1ncc(CC(=O)N2C[C@H](F)C[C@H]2C(=O)N[C@@H](c2ccccc2)c2ccc(C3CC3)c(F)n2)cc1C] | (2S,4R)-N-[(S)-(5-cyclopropyl-6-fluoropyridin-2-yl)(phenyl)methyl]-1-[2-(6-ethoxy-5-methylpyridin-3-yl)acetyl]-4-fluoropyrrolidine-2-carboxamide |
| 738 | 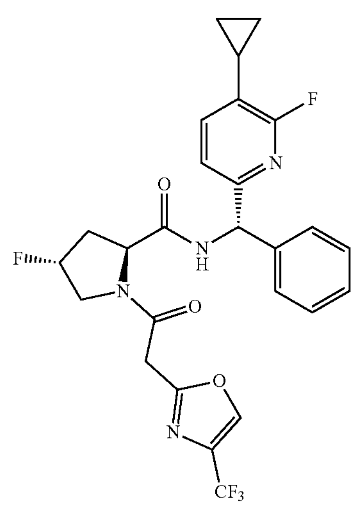 [SMILES: O=C(N[C@@H](c1ccccc1)c1ccc(C2CC2)c(F)n1)[C@@H]1C[C@@H](F)CN1C(=O)Cc1nc(C(F)(F)F)co1] | (2S,4R)-N-[(S)-(5-cyclopropyl-6-fluoropyridin-2-yl)(phenyl)methyl]-4-fluoro-1-{2-[4-(trifluoromethyl)-1,3-oxazol-2-yl]acetyl}pyrrolidine-2-carboxamide |

TABLE 1-continued

| Compound No. | Structure | IUPAC |
|---|---|---|
| 739 | 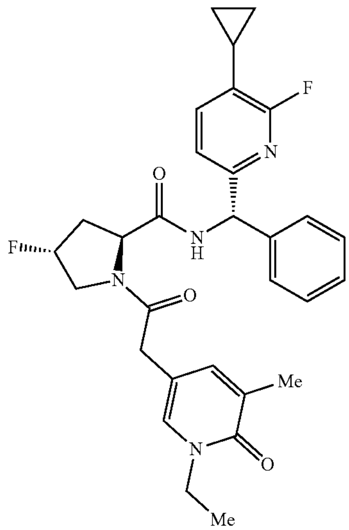 [SMILES: CCn1cc(CC(=O)N2C[C@H](F)C[C@H]2C(=O)N[C@@H](c2ccccc2)c2ccc(C3CC3)c(F)n2)cc(C)c1=O] | (2S,4R)-N-[(S)-(5-cyclopropyl-6-fluoropyridin-2-yl)(phenyl)methyl]-1-[2-(1-ethyl-5-methyl-6-oxo-1,6-dihydropyridin-3-yl)acetyl]-4-fluoropyrrolidine-2-carboxamide |
| 740 | 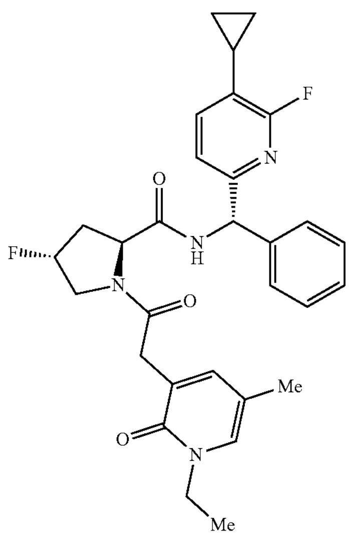 [SMILES: CCn1cc(C)cc(CC(=O)N2C[C@H](F)C[C@H]2C(=O)N[C@@H](c2ccccc2)c2ccc(C3CC3)c(F)n2)c1=O] | (2S,4R)-N-[(S)-(5-cyclopropyl-6-fluoropyridin-2-yl)(phenyl)methyl]-1-[2-(1-ethyl-5-methyl-2-oxo-1,2-dihydropyridin-3-yl)acetyl]-4-fluoropyrrolidine-2-carboxamide |
| 741 | 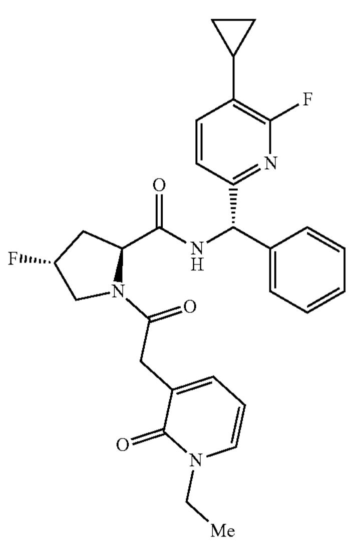 [SMILES: CCn1cccc(CC(=O)N2C[C@H](F)C[C@H]2C(=O)N[C@@H](c2ccccc2)c2ccc(C3CC3)c(F)n2)c1=O] | (2S,4R)-N-[(S)-(5-cyclopropyl-6-fluoropyridin-2-yl)(phenyl)methyl]-1-[2-(1-ethyl-2-oxo-1,2-dihydropyridin-3-yl)acetyl]-4-fluoropyrrolidine-2-carboxamide |

TABLE 1-continued

| Compound No. | Structure | IUPAC |
|---|---|---|
| 742 | 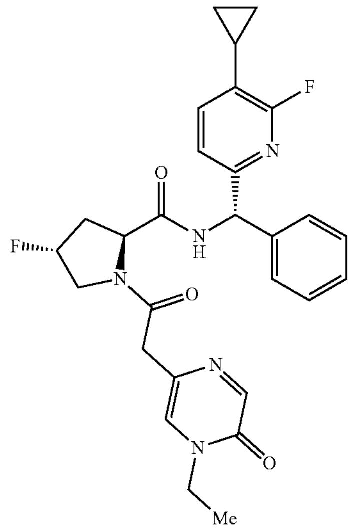 [SMILES: CCn1cc(CC(=O)N2C[C@H](F)C[C@H]2C(=O)N[C@@H](c2ccccc2)c2ccc(C3CC3)c(F)n2)ncc1=O] | (2S,4R)-N-[(S)-(5-cyclopropyl-6-fluoropyridin-2-yl)(phenyl)methyl]-1-[2-(4-ethyl-5-oxo-4,5-dihydropyrazin-2-yl)acetyl]-4-fluoropyrrolidine-2-carboxamide |
| 743 | 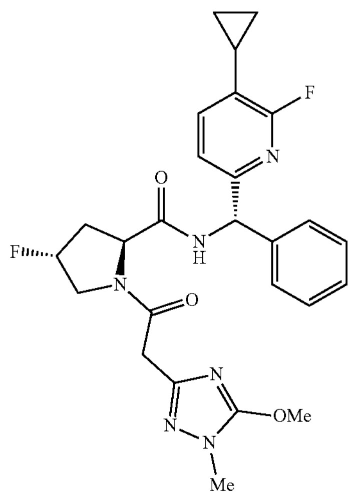 [SMILES: COc1nc(CC(=O)N2C[C@H](F)C[C@H]2C(=O)N[C@@H](c2ccccc2)c2ccc(C3CC3)c(F)n2)nn1C] | (2S,4R)-N-[(S)-(5-cyclopropyl-6-fluoropyridin-2-yl)(phenyl)methyl]-4-fluoro-1-[2-(5-methoxy-1-methyl-1H-1,2,4-triazol-3-yl)acetyl]pyrrolidine-2-carboxamide |
| 744 | 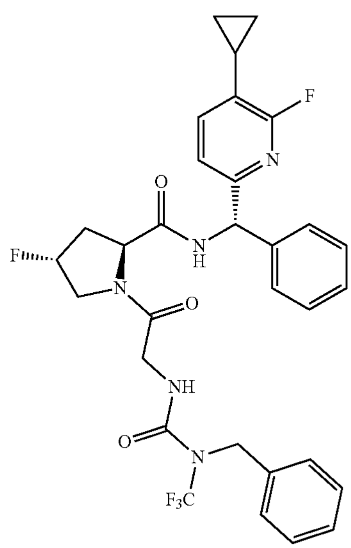 [SMILES: O=C(N[C@@H](c1ccccc1)c1ccc(C2CC2)c(F)n1)[C@@H]1C[C@@H](F)CN1C(=O)CNC(=O)N(Cc1ccccc1)C(F)(F)F] | (2S,4R)-1-(2-{[benzyl(trifluoromethyl)carbamoyl]amino}acetyl)-N-[(S)-(5-cyclopropyl-6-fluoropyridin-2-yl)(phenyl)methyl]-4-fluoropyrroldine-2-carboxamide |

| Compound No. | Structure | IUPAC |
|---|---|---|
| 745 | 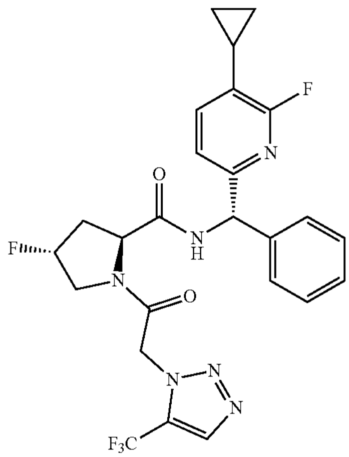 [SMILES: O=C(N[C@@H](c1ccccc1)c1ccc(C2CC2)c(F)n1)[C@@H]1C[C@@H](F)CN1C(=O)Cn1nncc1C(F)(F)F] | (2S,4R)-N-[(S)-(5-cyclopropyl-6-fluoropyridin-2-yl)(phenyl)methyl]-4-fluoro-1-{2-[5-(trifluoromethyl)-1H-1,2,3-triazol-1-yl]acetyl}pyrrolidine-2-carboxamide |
| 746 | 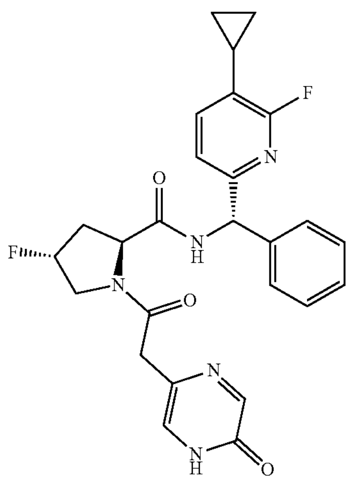 [SMILES: O=C(N[C@@H](c1ccccc1)c1ccc(C2CC2)c(F)n1)[C@@H]1C[C@@H](F)CN1C(=O)Cc1c[nH]c(=O)cn1] | (2S,4R)-N-[(S)-(5-cyclopropyl-6-fluoropyridin-2-yl)(phenyl)methyl]-4-fluoro-1-[2-(5-oxo-4,5-dihydropyrazin-2-yl)acetyl]pyrrolidine-2-carboxamide |
| 747 | 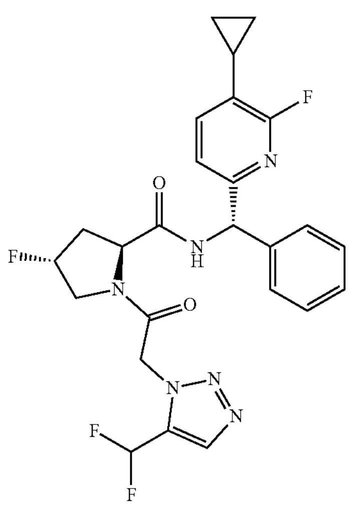 [SMILES: O=C(N[C@@H](c1ccccc1)c1ccc(C2CC2)c(F)n1)[C@@H]1C[C@@H](F)CN1C(=O)Cn1nncc1C(F)F] | (2S,4R)-N-[(S)-(5-cyclopropyl-6-fluoropyridin-2-yl)(phenyl)methyl]-1-{2-[5-(difluoromethyl)-1H-1,2,3-triazol-1-yl]acetyl}-4-fluoropyrrolidine-2-carboxamide |

TABLE 1-continued

| Compound No. | Structure | IUPAC |
|---|---|---|
| 748 | 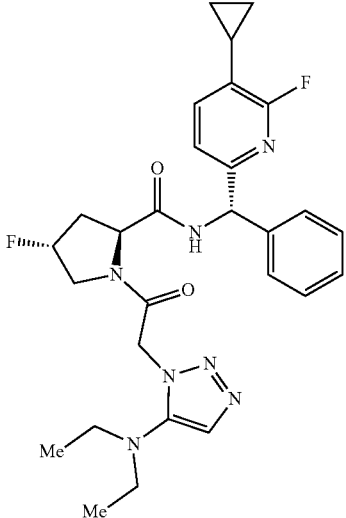 [SMILES: CCN(CC)c1cnnn1CC(=O)N1C[C@H](F)C[C@H]1C(=O)N[C@@H](c1ccccc1)c1ccc(C2CC2)c(F)n1] | (2S,4R)-N-[(S)-(5-cyclopropyl-6-fluoropyridin-2-yl)(phenyl)methyl]-1-{2-[5-(diethylamino)-1H-1,2,3-triazol-1-yl]acetyl}-4-fluoropyrrolidine-2-carboxamide |
| 749 | 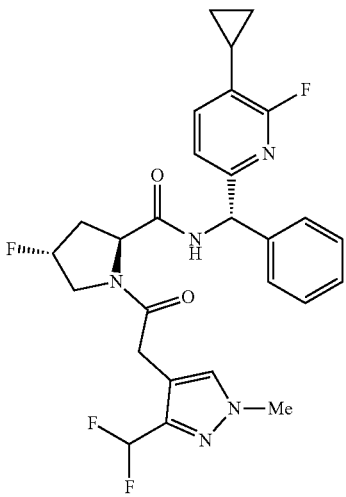 | (2S,4R)-N-[(S)-(5-cyclopropyl-6-fluoropyridin-2-yl)(phenyl)methyl]-1-{2-[3-(difluoromethyl)-1-methyl-1H-pyrazol-4-yl]acetyl}-4-fluoropyrrolidine-2-carboxamide |
| 750 | 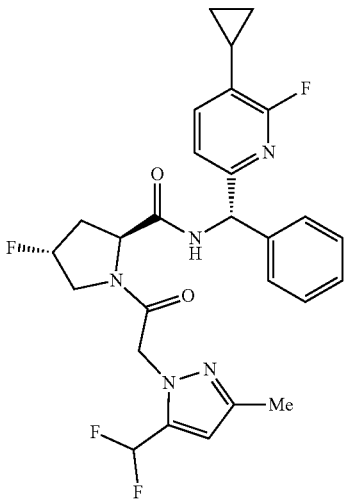 [SMILES: Cc1cc(C(F)F)n(CC(=O)N2C[C@H](F)C[C@H]2C(=O)N[C@@H](c2ccccc2)c2ccc(C3CC3)c(F)n2)n1] | (2S,4R)-N-[(S)-(5-cyclopropyl-6-fluoropyridin-2-yl)phenyl)methyl]-1-{2-[5-(difluoromethyl)-3-methyl-1H-pyrazol-1-yl]acetyl}-4-fluoropyrrolidine-2-carboxamide |

TABLE 1-continued

| Compound No. | Structure | IUPAC |
|---|---|---|
| 751 | 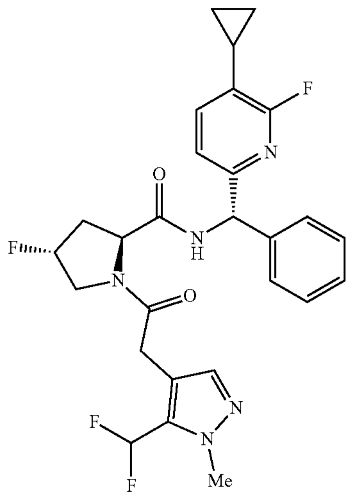 [SMILES: Cn1ncc(CC(=O)N2C[C@H](F)C[C@H]2C(=O)N[C@@H](c2ccccc2)c2ccc(C3CC3)c(F)n2)c1C(F)F] | (2S,4R)-N-[(S)-(5-cyclopropyl-6-fluoropyridin-2-yl)(phenyl)methyl]-1-{2-[5-(difluoromethyl)-1-methyl-1H-pyrazol-4-yl]acetyl}-4-fluoropyrrolidine-2-carboxamide |
| 752 | 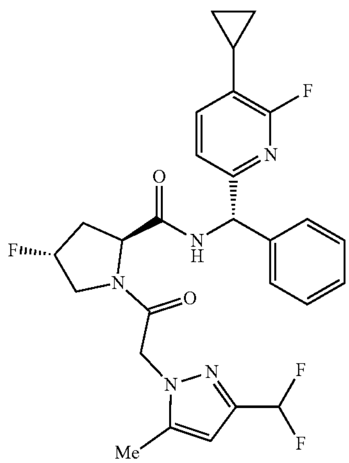 [SMILES: Cc1cc(C(F)F)nn1CC(=O)N1C[C@H](F)C[C@H]1C(=O)N[C@@H](c1ccccc1)c1ccc(C2CC2)c(F)n1] | (2S,4R)-N-[(S)-(5-cyclopropyl-6-fluoropyridin-2-yl)(phenyl)methyl]-1-{2-[3-(difluoromethyl)-5-methyl-1H-pyrazol-1-yl]aceetyl}-4-fluoropyrrolidine-2-carboxamide |
| 753 | 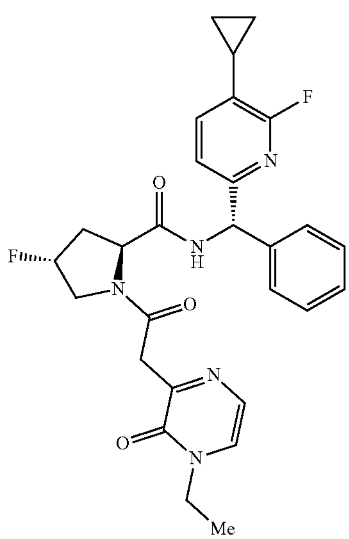 [SMILES: CCn1ccnc(CC(=O)N2C[C@H](F)C[C@H]2C(=O)N[C@@H](c2ccccc2)c2ccc(C3CC3)c(F)n2)c1=O] | (2S,4R)-N-[(S)-(5-cyclopropyl-6-fluoropyridin-2-yl)(phenyl)methyl]-1-[2-(4-ethyl-3-oxo-3,4-dihydropyrazin-2-yl)acetyl]-4-fluoropyrrolidine-2-carboxamide |

TABLE 1-continued

| Compound No. | Structure | IUPAC |
|---|---|---|
| 754 | 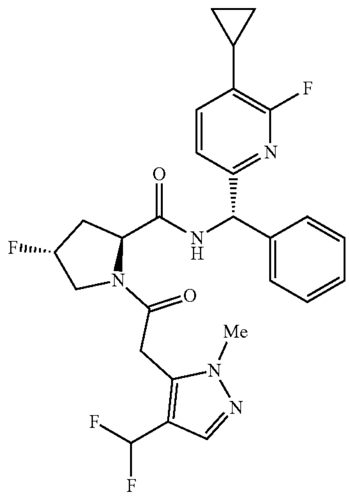 [SMILES: Cn1ncc(C(F)F)c1CC(=O)N1C[C@H](F)C[C@H]1C(=O)N[C@@H](c1ccccc1)c1ccc(C2CC2)c(F)n1] | (2S,4R)-N-[(S)-(5-cyclopropyl-6-fluoropyridin-2-yl)(phenyl)methyl]-1-{2-[4-(difluoromethyl)-1-methyl-1H-pyrazol-5-yl]acetyl}-4-fluoropyrrolidine-2-carboxamide |
| 755 | 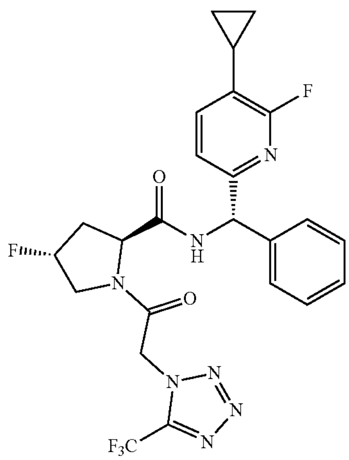 [SMILES: O=C(N[C@@H](c1ccccc1)c1ccc(C2CC2)c(F)n1)[C@@H]1C[C@@H](F)CN1C(=O)Cn1nnnc1C(F)(F)F] | (2S,4R)-N-[(S)-(5-cyclopropyl-6-fluoropyridin-2-yl)(phenyl)methyl]-4-fluoro-1-{2-[5-(trifluoromethyl)-1H-1,2,3,4-tetrazol-1-yl]acetyl}pyrrolidine-2-carboxamide |
| 756 | 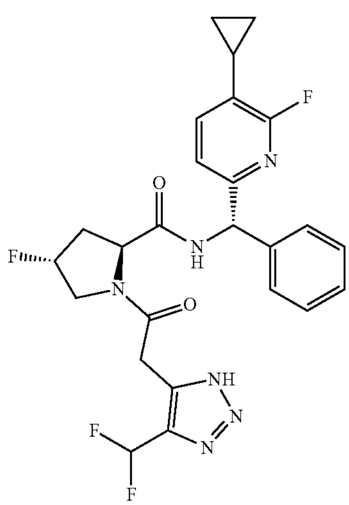 [SMILES: O=C(N[C@@H](c1ccccc1)c1ccc(C2CC2)c(F)n1)[C@@H]1C[C@@H](F)CN1C(=O)Cc1[nH]nnc1C(F)F] | (2S,4R)-N-[(S)-(5-cyclopropyl-6-fluoropyridin-2-yl)(phenyl)methyl]-1-{2-[4-(difluoromethyl)-1H-1,2,3-triazol-5-yl]acetyl}-4-fluoropyrrolidine-2-carboxamide |

TABLE 1-continued

| Compound No. | Structure | IUPAC |
|---|---|---|
| 757 | 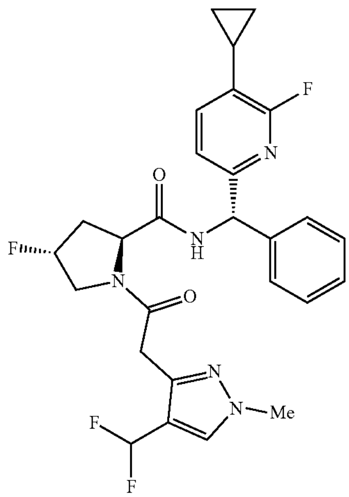 [SMILES: Cn1cc(C(F)F)c(CC(=O)N2C[C@H](F)C[C@H]2C(=O)N[C@@H](c2ccccc2)c2ccc(C3CC3)c(F)n2)n1] | (2S,4R)-N-[(S)-(5-cyclopropyl-6-fluoropyridin-2-yl)(phenyl)methyl]-1-{2-[4-(difluoromethyl)-1-methyl-1H-pyrazol-3-yl]acetyl}-4-fluoropyrrolidine-2-carboxamide |
| 758 | 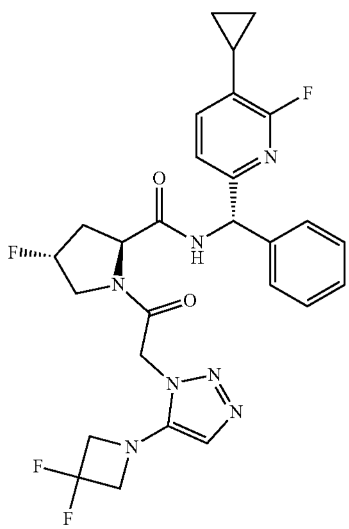 [SMILES: O=C(N[C@@H](c1ccccc1)c1ccc(C2CC2)c(F)n1)[C@@H]1C[C@@H](F)CN1C(=O)Cn1nncc1N1CC(F)(F)C1] | (2S,4R)-N-[(S)-(5-cyclopropyl-6-fluoropyridin-2-yl)(phenyl)methyl]-1-{2-[5-(3,3-difluoroazetidin-1-yl)-1H-1,2,3-triazol-1-yl]acetyl}-4-fluoropyrrolidine-2-carboxamide |
| 759 | 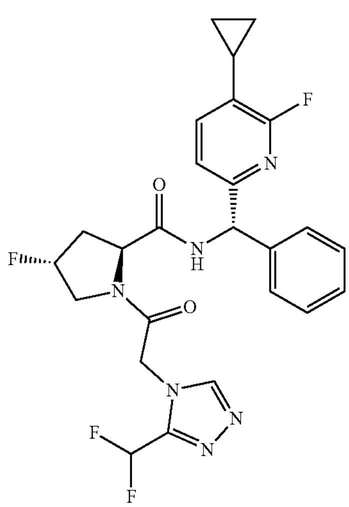 [SMILES: O=C(N[C@@H](c1ccccc1)c1ccc(C2CC2)c(F)n1)[C@@H]1C[C@@H](F)CN1C(=O)Cn1cnnc1C(F)F] | (2S,4R)-N-[(S)-(5-cyclopropyl-6-fluoropyridin-2-yl)(phenyl)methyl]-1-{2-[3-(difluoromethyl)-4H-1,2,4-triazol-4-yl]acetyl}-4-fluoropyrrolidine-2-carboxamide |

TABLE 1-continued

| Compound No. | Structure | IUPAC |
|---|---|---|
| 760 | 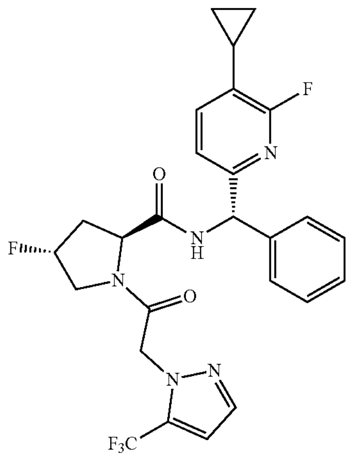 [SMILES: O=C(N[C@@H](c1ccccc1)c1ccc(C2CC2)c(F)n1)[C@@H]1C[C@@H](F)CN1C(=O)Cn1nccc1C(F)(F)F] | (2S,4R)-N-[(S)-(5-cyclopropyl-6-fluoropyridin-2-yl)(phenyl)methyl]-4-fluoro-1-{2-[5-(trifluoromethyl)-1H-pyrazol-1-yl]acetyl}pyrrolidine-2-carboxamide |
| 761 | 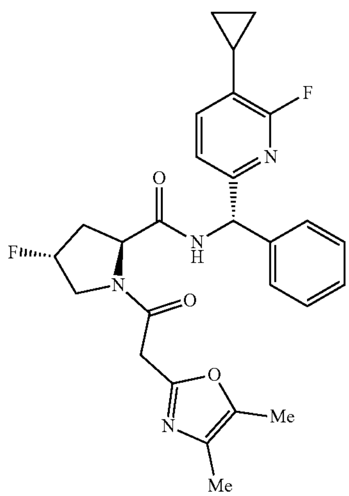 [SMILES: Cc1nc(CC(=O)N2C[C@H](F)C[C@H]2C(=O)N[C@@H](c2ccccc2)c2ccc(C3CC3)c(F)n2)oc1C] | (2S,4R)-N-[(S)-(5-cyclopropyl-6-fluoropyridin-2-yl)(phenyl)methyl]-1-[2-(4,5-dimethyl-1,3-oxazol-2-yl)acetyl]-4-fluoropyrrolidine-2-carboxamide |
| 762 | 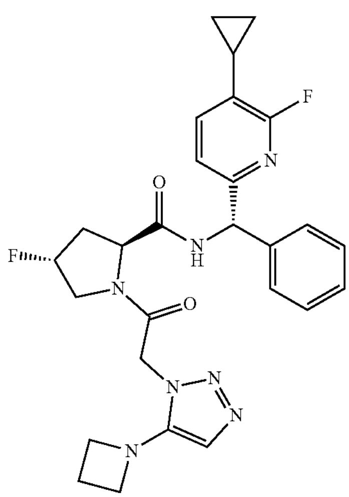 [SMILES: O=C(N[C@@H](c1ccccc1)c1ccc(C2CC2)c(F)n1)[C@@H]1C[C@@H](F)CN1C(=O)Cn1nncc1N1CCC1] | (2S,4R)-1-{2-[5-(azetidin-1-yl)-1H-1,2,3-triazol-1-yl]acetyl}-N-[(S)-(5-cyclopropyl-6-fluoropyridin-2-yl)(phenyl)methyl]-4-fluoropyrrolidine-2-carboxamide |

TABLE 1-continued

| Compound No. | Structure | IUPAC |
|---|---|---|
| 763 | 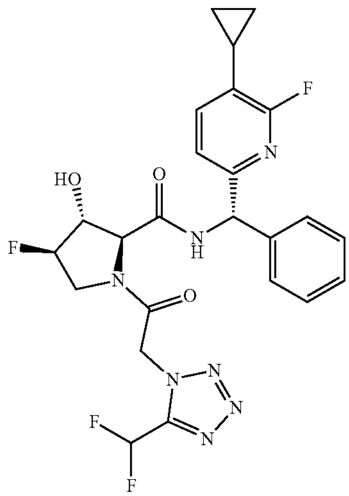 [SMILES: O=C(N[C@@H](c1ccccc1)c1ccc(C2CC2)c(F)n1)[C@@H]1[C@@H](O)[C@H](F)CN1C(=O)Cn1nnnc1C(F)F] | (2S,3R,4R)-N-[(S)-(5-cyclopropyl-6-fluoropyridin-2-yl)(phenyl)methyl]-1-{2-[5-(difluoromethyl)-1H-1,2,3,4-tetrazol-1-yl]acetyl}-4-fluoro-3-hydroxypyrrolidine-2-carboxamide |
| 764 | 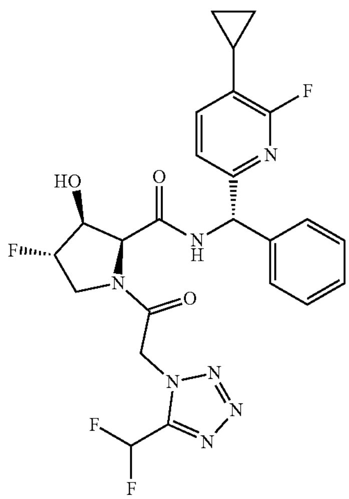 [SMILES: O=C(N[C@@H](c1ccccc1)c1ccc(C2CC2)c(F)n1)[C@@H]1[C@H](O)[C@@H](F)CN1C(=O)Cn1nnnc1C(F)F] | (2S,3S,4S)-N-[(S)-(5-cyclopropyl-6-fluoropyridin-2-yl)(phenyl)methyl]-1-{2-[5-(difluoromethyl)-1H-1,2,3,4-tetrazol-1-yl]acetyl}-4-fluoro-3-hydroxypyrrolidine-2-carboxamide |
| 765 | 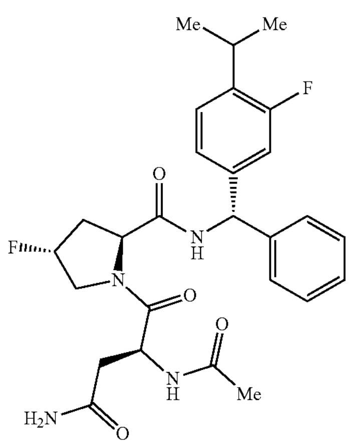 [SMILES: CC(=O)N[C@@H](CC(N)=O)C(=O)N1C[C@H](F)C[C@H]1C(=O)N[C@@H](c1ccccc1)c1ccc(C(C)C)c(F)c1] | (2S,4R)-1-[(2S)-3-carbamoyl-2-acetamidopropanoyl]-4-fluoro-N-[(S)-[3-fluoro-4-(propan-2-yl)phenyl](phenyl)methyl]pyrrolidine-2-carboxamide |

TABLE 1-continued

| Compound No. | Structure | IUPAC |
|---|---|---|
| 766 | 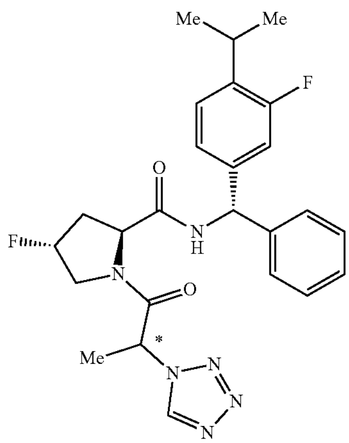 [SMILES: CC(C)c1ccc([C@@H](NC(=O)[C@@H]2C[C@@H](F)CN2C(=O)C(C)n2cnnn2)c2ccccc2)cc1F] | (2S,4R)-4-fluoro-N-[(S)-[3-fluoro-4-(propan-2-yl)phenyl](phenyl)methyl]-1-[(2R) or (2S)-2-(1H-1,2,3,4-tetrazol-1-yl)propanoyl]pyrroldine-2-carboxamide |
| 767 | 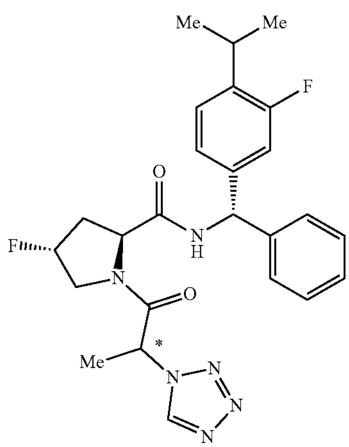 [SMILES: CC(C)c1ccc([C@@H](NC(=O)[C@@H]2C[C@@H](F)CN2C(=O)C(C)n2cnnn2)c2ccccc2)cc1F] | (2S,4R)-4-fluoro-N-[(S)-[3-fluoro-4-(propan-2-yl)phenyl](phenyl)methyl]-[(2S)- or (2R)-2-(1H-1,2,3,4-tetrazol-1-yl)propanoyl]pyrrolidine-2-carboxamide |
| 768 | 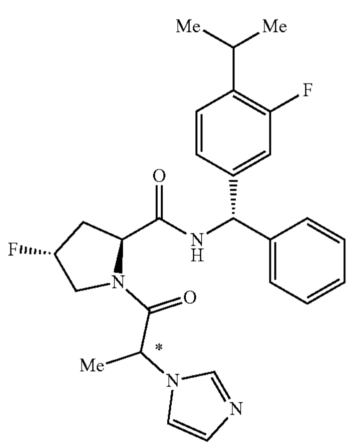 [SMILES: CC(C)c1ccc([C@@H](NC(=O)[C@@H]2C[C@@H](F)CN2C(=O)C(C)n2ccnc2)c2ccccc2)cc1F] | (2S,4R)-4-fluoro-N-[(S)-[3-fluoro-4-(propan-2-yl)phenyl](phenyl)methyl]-1-[(2R) or (2S)-2-(1H-imidazol-1-yl)propanoyl]pyrrolidine-2-carboxamide |

TABLE 1-continued

| Compound No. | Structure | IUPAC |
|---|---|---|
| 769 | 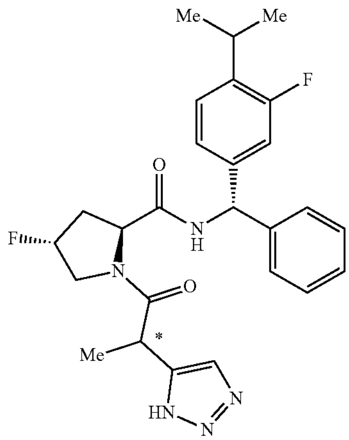 [SMILES: CC(C)c1ccc([C@@H](NC(=O)[C@@H]2C[C@@H](F)CN2C(=O)C(C)c2cnn[nH]2)c2ccccc2)cc1F] | (2S,4R)-4-fluoro-N-[(S)-[3-fluoro-4-(propan-2-yl)phenyl](phenyl)methyl]-1-[(2R) or (2S)-2-(1H-1,2,3-triazol-5-yl)propanoyl]pyrrolidine-2-carboxamide |
| 770 | 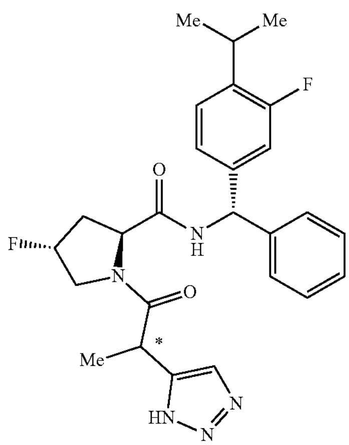 [SMILES: CC(C)c1ccc([C@@H](NC(=O)[C@@H]2C[C@@H](F)CN2C(=O)C(C)c2cnn[nH]2)c2ccccc2)cc1F] | (2S,4R)-4-fluoro-N-[(S)-[3-fluoro-4-(propan-2-yl)phenyl](phenyl)methyl]-1-[(2S) or (2R)-2-(1H-1,2,3-triazol-5-yl)propanoyl]pyrrolidine-2-carboxamide |
| 771 | 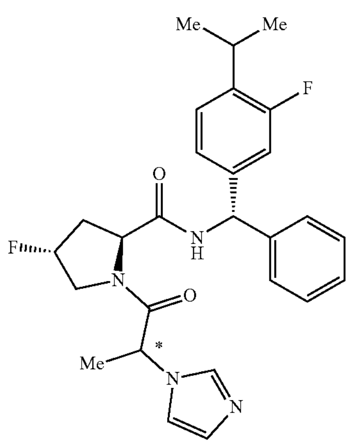 [SMILES: CC(C)c1ccc([C@@H](NC(=O)[C@@H]2C[C@@H](F)CN2C(=O)C(C)n2ccnc2)c2ccccc2)cc1F] | (2S,4R)-4-fluoro-N-[(S)-[3-fluoro-4-(propan-2-yl)phenyl](phenyl)methyl]-1-[(2S)- or (2R)-2-(1H-imidazol-1-yl)propanoyl]pyrrolidine-2-carboxamide |

TABLE 1-continued

| Compound No. | Structure | IUPAC |
|---|---|---|
| 772 | 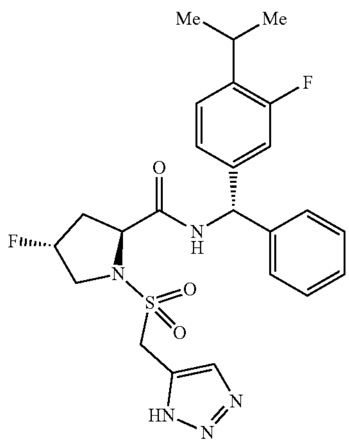 [SMILES: CC(C)c1ccc([C@@H](NC(=O)[C@@H]2C[C@@H](F)CN2S(=O)(=O)Cc2cnn[nH]2)c2ccccc2)cc1F] | (2S,4R)-4-fluoro-N-[(S)-[3-fluoro-4-(propan-2-yl)phenyl](phenyl)methyl]-1-[(1H-1,2,3-triazol-5-yl)methanesulfonyl]pyrrolidine-2-carboxamide |
| 773 | 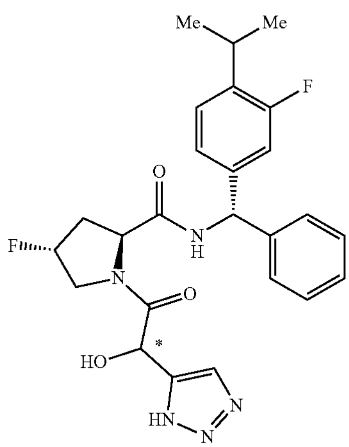 [SMILES: CC(C)c1ccc([C@@H](NC(=O)[C@@H]2C[C@@H](F)CN2C(=O)C(O)c2cnn[nH]2)c2ccccc2)cc1F] | (2S,4R)-4-fluoro-N-[(S)-[3-fluoro-4-(propan-2-yl)phenyl](phenyl)methyl]-1-[(2R)- or (2S)-2-hydroxy-2-(1H-1,2,3-triazol-5-yl)acetyl]pyrrolidine-2-carboxamide |
| 774 | 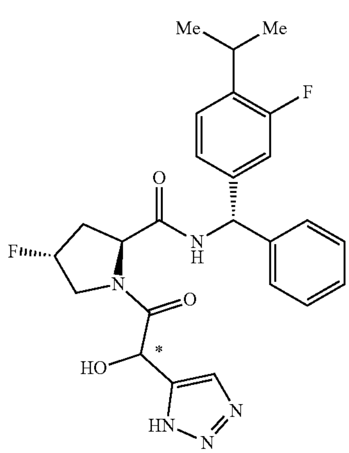 [SMILES: CC(C)c1ccc([C@@H](NC(=O)[C@@H]2C[C@@H](F)CN2C(=O)C(O)c2cnn[nH]2)c2ccccc2)cc1F] | (2S,4R)-4-fluoro-N-[(S)-[3-fluoro-4-(propan-2-yl)phenyl](phenyl)methyl]-1-[(2S) or (2R)-2-hydroxy-2-(1H-1,2,3-triazol-5-yl)acetyl]pyrrolidine-2-carboxamide |

TABLE 1-continued

| Compound No. | Structure | IUPAC |
|---|---|---|
| 775 | 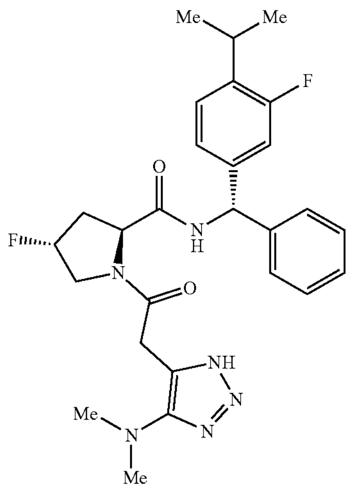 [SMILES: CC(C)c1ccc([C@@H](NC(=O)[C@@H]2C[C@@H](F)CN2C(=O)Cc2[nH]nnc2N(C)C)c2ccccc2)cc1F] | (2S,4R)-1-{2-[4-(dimethylamino)-1H-1,2,3-triazol-5-yl]acetyl}-4-fluoro-N-[(S)-[3-fluoro-4-(propan-2-yl)phenyl](phenyl)methyl]pyrrolidine-2-carboxamide |
| 776 | 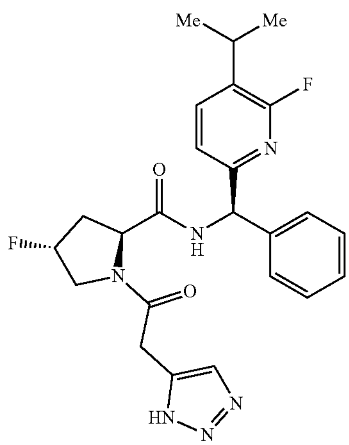 [SMILES: CC(C)c1ccc([C@H](NC(=O)[C@@H]2C[C@@H](F)CN2C(=O)Cc2cnn[nH]2)c2ccccc2)nc1F] | (2S,4R)-4-fluoro-N-[(R*)-[6-fluoro-5-(propan-2-yl)pyridin-2-yl](phenyl)methyl]-1-[2-(1H-1,2,3-triazol-5-yl)acetyl]pyrroldine-2-carboxamide |
| 777 | 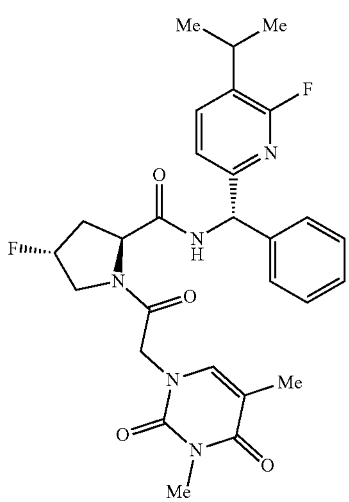 [SMILES: Cc1cn(CC(=O)N2C[C@H](F)C[C@H]2C(=O)N[C@@H](c2ccccc2)c2ccc(C(C)C)c(F)n2)c(=O)n(C)c1=O] | (2S,4R)-1-[2-(3,5-dimethyl-2,4-dioxo-1,2,3,4-tetrahydropyrimidin-1-yl)acetyl]-4-fluoro-N-[(R*)-[6-fluoro-5-(propan-2-yl)pyridin-2-yl](phenyl)methyl]pyrrolidine-2-carboxamide |

TABLE 1-continued

| Compound No. | Structure | IUPAC |
|---|---|---|
| 778 | 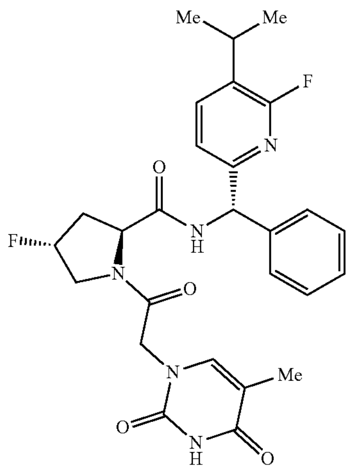 [SMILES: Cc1cn(CC(=O)N2C[C@H](F)C[C@H]2C(=O)N[C@@H](c2ccccc2)c2ccc(C(C)C)c(F)n2)c(=O)[nH]c1=O] | (2S,4R)-4-fluoro-N-[(R*)-[6-fluoro-5-(propan-2-yl)pyridin-2-yl](phenyl)methyl]-1-[2-(5-methyl-2,4-dioxo-1,2,3,4-tetrahydropyrimidin-1-yl)acetyl]pyrrolidine-2-carboxamide |
| 779 | 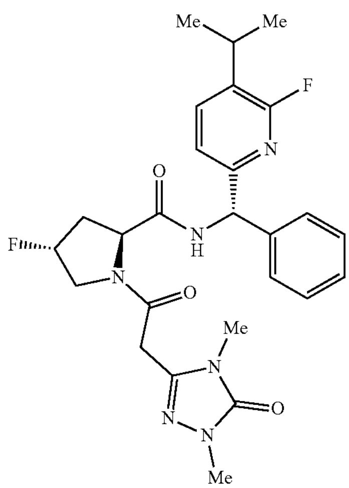 [SMILES: CC(C)c1ccc([C@@H](NC(=O)[C@@H]2C[C@@H](F)CN2C(=O)Cc2nn(C)c(=O)n2C)c2ccccc2)nc1F] | (2S,4R)-1-[2-(1,4-dimethyl-5-oxo-4,5-dihydro-1H-1,2,4-triazol-3-yl)acetyl]-4-fluoro-N-[(S)-[6-fluoro-5-(propan-2-yl)pyridin-2-yl](phenyl)methyl]pyrrolidine-2-carboxamide |
| 780 | 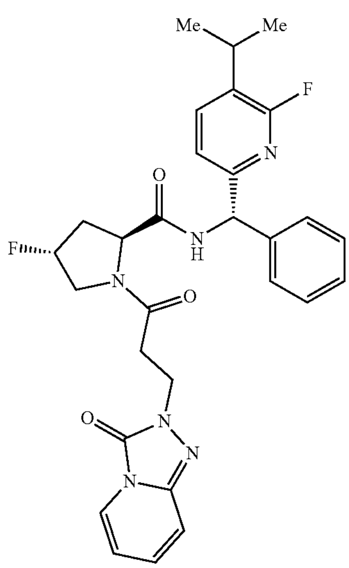 [SMILES: CC(C)c1ccc([C@@H](NC(=O)[C@@H]2C[C@@H](F)CN2C(=O)CCn2nc3ccccn3c2=O)c2ccccc2)nc1F] | (2S,4R)-4-fluoro-N-[(S)-[6-fluoro-5-(propan-2-yl)pyridin-2-yl](phenyl)methyl]-1-(3-{3-oxo-2H,3H-[1,2,4]triazolo[4,3-a]pyridin-2-yl}propanoyl)pyrrolidine-2-carboxamide |

TABLE 1-continued

| Compound No. | Structure | IUPAC |
|---|---|---|
| 781 | 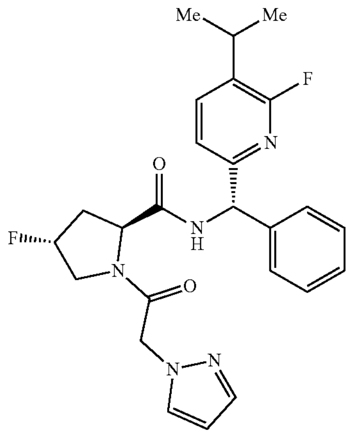 [SMILES: CC(C)c1ccc([C@@H](NC(=O)[C@@H]2C[C@@H](F)CN2C(=O)Cn2cccn2)c2ccccc2)nc1F] | (2S,4R)-4-fluoro-N-[(S)-[6-fluoro-5-(propan-2-yl)pyridin-2-yl](phenyl)methyl]-1-[2-(1H-pyrazol-1-yl)acetyl]pyrrolidine-2-carboxamide |
| 782 | 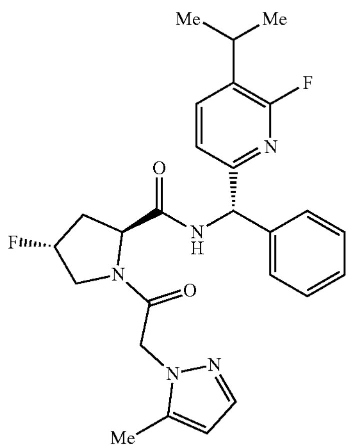 [SMILES: Cc1ccnn1CC(=O)N1C[C@H](F)C[C@H]1C(=O)N[C@@H](c1ccccc1)c1ccc(C(C)C)c(F)n1] | (2S,4R)-4-fluoro-N-[(S)-[6-fluoro-5-(propan-2-yl)pyridin-2-yl](phenyl)methyl]-1-[2-(5-methyl-1H-pyrazol-1-yl)acetyl]pyrrolidine-2-carboxamide |
| 783 | 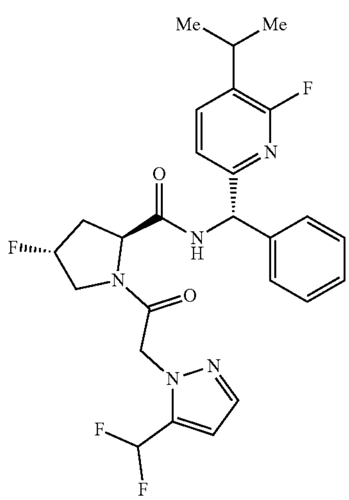 [SMILES: CC(C)c1ccc([C@@H](NC(=O)[C@@H]2C[C@@H](F)CN2C(=O)Cn2nccc2C(F)F)c2ccccc2)nc1F] | (2S,4R)-1-{2-[5-(difluoromethyl)-1H-pyrazol-1-yl]acetyl}-4-fluoro-N-[(S)-[6-fluoro-5-(propan-2-yl)pyridin-2-yl](phenyl)methyl]pyrrolidine-2-carboxamide |

TABLE 1-continued

| Compound No. | Structure | IUPAC |
|---|---|---|
| 784 | 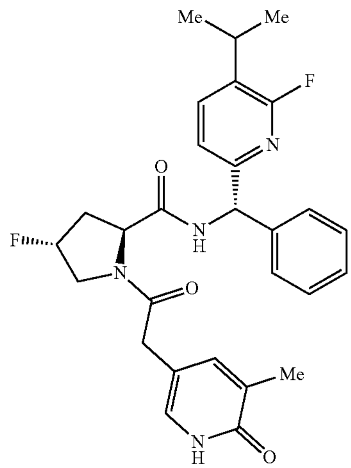 [SMILES: Cc1cc(CC(=O)N2C[C@H](F)C[C@H]2C(=O)N[C@@H](c2ccccc2)c2ccc(C(C)C)c(F)n2)c[nH]c1=O] | (2S,4R)-4-fluoro-N-[(S)-[6-fluoro-5-(propan-2-yl)pyridin-2-yl](phenyl)methyl]-1-[2-(5-methyl-6-oxo-1,6-dihydropyridin-3-yl)acetyl]pyrrolidine-2-carboxamide |
| 785 | 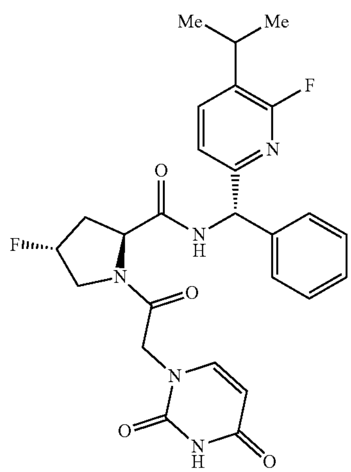 [SMILES: CC(C)c1ccc([C@@H](NC(=O)[C@@H]2C[C@@H](F)CN2C(=O)Cn2ccc(=O)[nH]c2=O)c2ccccc2)nc1F] | (2S,4R)-1-[2-(2,4-dioxo-1,2,3,4-tetrahydropyrimidin-1-yl)acetyl]-4-fluoro-N-[(S)-[6-fluoro-5-(propan-2-yl)pyridin-2-yl](phenyl)methyl]pyrrolidine-2-carboxamide |
| 786 | 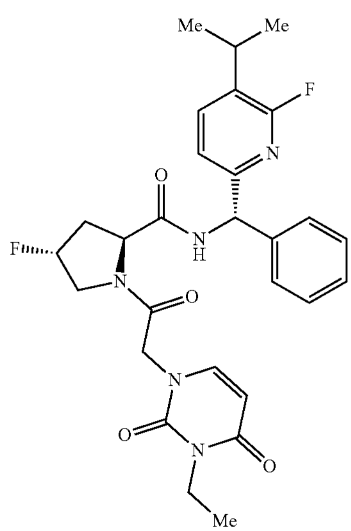 [SMILES: CCn1c(=O)ccn(CC(=O)N2C[C@H](F)C[C@H]2C(=O)N[C@@H](c2ccccc2)c2ccc(C(C)C)c(F)n2)c1=O] | (2S,4R)-1-[2-(3-ethyl-2,4-dioxo-1,2,3,4-tetrahydropyrimidin-1-yl)acetyl-4-fluoro-N-[(S)-[6-fluoro-5-(propan-2-yl)pyridin-2-yl](phenyl)methyl]pyrrolidine-2-carboxamide |

TABLE 1-continued

| Compound No. | Structure | IUPAC |
|---|---|---|
| 787 | 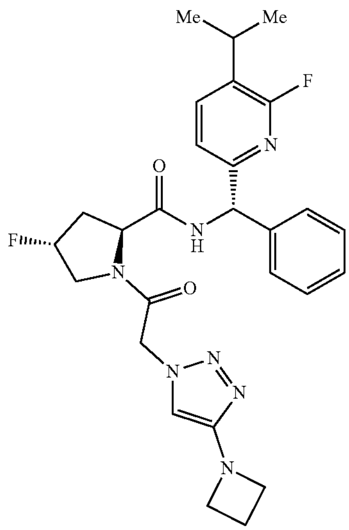 [SMILES: CC(C)c1ccc([C@@H](NC(=O)[C@@H]2C[C@@H](F)CN2C(=O)Cn2cc(N3CCC3)nn2)c2ccccc2)nc1F] | (2S,4R)-1-{2-[4-(azetidin-1-yl)-1H-1,2,3-triazol-1-yl]acetyl}-4-fluoro-N-[(S)-[6-fluoro-5-(propan-2-yl)pyridin-2-yl](phenyl)methyl]pyrrolidine-2-carboxamide |
| 788 | 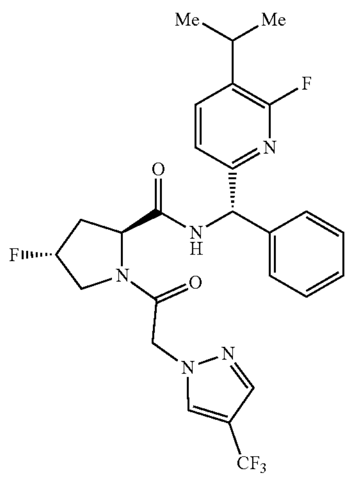 [SMILES: CC(C)c1ccc([C@@H](NC(=O)[C@@H]2C[C@@H](F)CN2C(=O)Cn2cc(C(F)(F)F)cn2)c2ccccc2)nc1F] | (2S,4R)-4-fluoro-N-[(S)-[6-fluoro-5-(propan-2-yl)pyridin-2-yl](phenyl)methyl]-1-{2-[4-(trifluoromethyl)-1H-pyrazol-1-yl]acetyl}pyrrolidine-2-carboxamide |
| 789 | 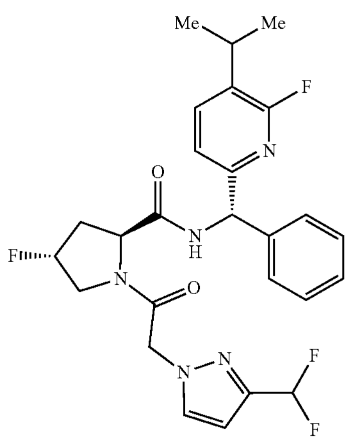 [SMILES: CC(C)c1ccc([C@@H](NC(=O)[C@@H]2C[C@@H](F)CN2C(=O)Cn2ccc(C(F)F)n2)c2ccccc2)nc1F] | (2S,4R)-1-{2-[3-(difluoromethyl)-1H-pyrazol-1-yl]acetyl}-4-fluoro-N-[(S)-[6-fluoro-5-(propan-2-yl)pyridin-2-yl](phenyl)methyl]pyrrolidine-2-carboxamide |

TABLE 1-continued

| Compound No. | Structure | IUPAC |
|---|---|---|
| 790 | 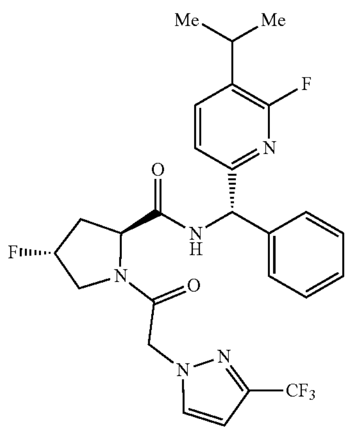 [SMILES: CC(C)c1ccc([C@@H](NC(=O)[C@@H]2C[C@@H](F)CN2C(=O)Cn2ccc(C(F)(F)F)n2)c2ccccc2)nc1F] | (2S,4R)-4-fluoro-N-[(S)-[6-fluoro-5-(propan-2-yl)pyridin-2-yl](phenyl)methyl]-1-{2-[3-(trifluoromethyl)-1H-pyrazol-1-yl]acetyl}pyrrolidine-2-carboxamide |
| 791 | 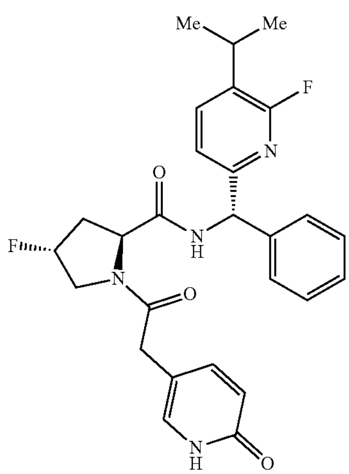 [SMILES: CC(C)c1ccc([C@@H](NC(=O)[C@@H]2C[C@@H](F)CN2C(=O)Cc2ccc(=O)[nH]c2)c2ccccc2)nc1F] | (2S,4R)-4-fluoro-N-[(S)-[6-fluoro-5-(propan-2-yl)pyridin-2-yl](phenyl)methyl]-1-[2-(6-oxo-1,6-dihydropyridin-3-yl)acetyl]pyrrolidine-2-carboxamide |
| 792 | 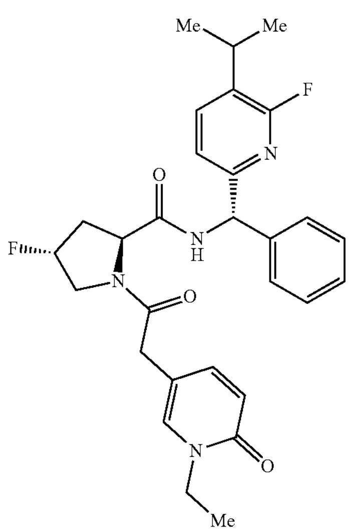 [SMILES: CCn1cc(CC(=O)N2C[C@H](F)C[C@H]2C(=O)N[C@@H](c2ccccc2)c2ccc(C(C)C)c(F)n2)ccc1=O] | (2S,4R)-1-[2-(1-ethyl-6-oxo-1,6-dihydropyridin-3-yl)acetyl]-4-fluoro-N-[(S)-[6-fluoro-5-(propan-2-yl)pyridin-2-yl](phenyl)methyl]pyrrolidine-2-carboxamide |

TABLE 1-continued

| Compound No. | Structure | IUPAC |
|---|---|---|
| 793 | 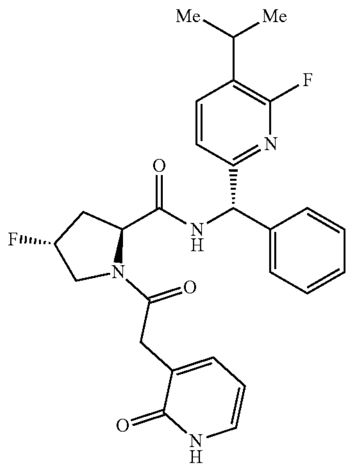 [SMILES: CC(C)c1ccc([C@@H](NC(=O)[C@@H]2C[C@@H](F)CN2C(=O)Cc2ccc[nH]c2=O)c2ccccc2)nc1F] | (2S,4R)-4-fluoro-N-[(S)-[6-fluoro-5-(propan-2-yl)pyridin-2-yl](phenyl)methyl]-1-[2-(2-oxo-1,2-dihydropyridin-3-yl)acetyl]pyrrolidine-2-carboxamide |
| 794 | 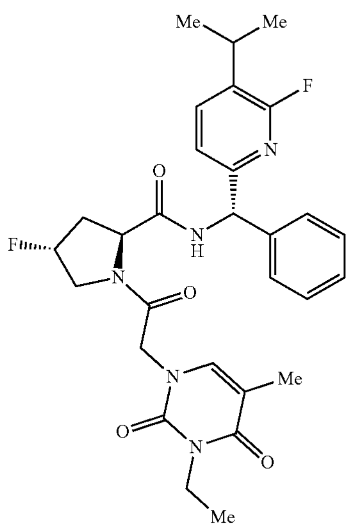 [SMILES: CCn1c(=O)c(C)cn(CC(=O)N2C[C@H](F)C[C@H]2C(=O)N[C@@H](c2ccccc2)c2ccc(C(C)C)c(F)n2)c1=O] | (2S,4R)-1-[2-(3-ethyl-5-methyl-2,4-dioxo-1,2,3,4-tetrahydropyrimidin-1-yl)acetyl]-4-fluoro-N-[(S)-[6-fluoro-5-(propan-2-yl)pyridin-2-yl](phenyl)methyl]pyrrolidine-2-carboxamide |
| 795 | 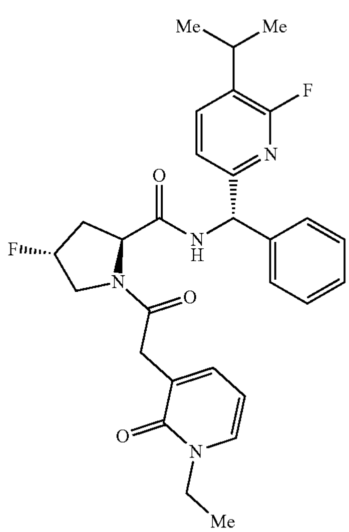 [SMILES: CCn1cccc(CC(=O)N2C[C@H](F)C[C@H]2C(=O)N[C@@H](c2ccccc2)c2ccc(C(C)C)c(F)n2)c1=O] | (2S,4R)-1-[2-(1-ethyl-2-oxo-1,2-dihydropyridin-3-yl)acetyl]-4-fluoro-N-[(S)-[6-fluoro-5-(propan-2-yl)pyridin-2-yl](phenyl)methyl]pyrrolidine-2-carboxamide |

TABLE 1-continued

| Compound No. | Structure | IUPAC |
|---|---|---|
| 796 | 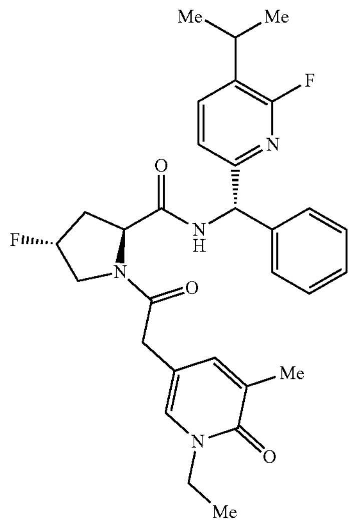 [SMILES: CCn1cc(CC(=O)N2C[C@H](F)C[C@H]2C(=O)N[C@@H](c2ccccc2)c2ccc(C(C)C)c(F)n2)cc(C)c1=O] | (2S,4R)-1-[2-(1-ethyl-5-methyl-6-oxo-1,6-dihydropyridin-3-yl)acetyl]-4-fluoro-N-[(S)-[6-fluoro-5-(propan-2-yl)pyridin-2-yl](phenyl)methyl]pyrrolidine-2-carboxamide |
| 797 | 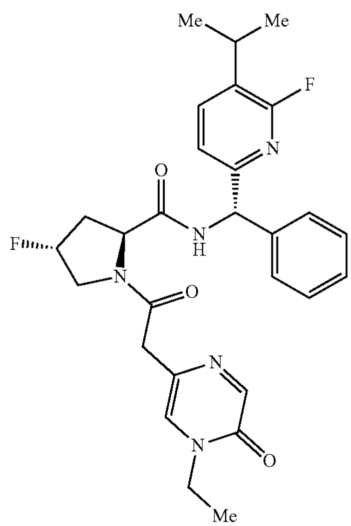 [SMILES: CCn1cc(CC(=O)N2C[C@H](F)C[C@H]2C(=O)N[C@@H](c2ccccc2)c2ccc(C(C)C)c(F)n2)ncc1=O] | (2S,4R)-1-[2-(4-ethyl-5-oxo-4,5-dihydropyrazin-2-yl)acetyl]-4-fluoro-N-[(S)-[6-fluoro-5-(propan-2-yl)pyridin-2-yl](phenyl)methyl]pyrrolidine-2-carboxamide |
| 798 | 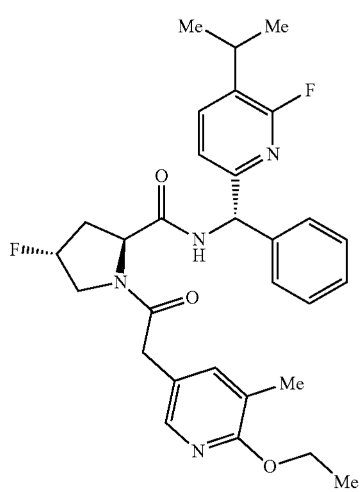 [SMILES: CCOc1ncc(CC(=O)N2C[C@H](F)C[C@H]2C(=O)N[C@@H](c2ccccc2)c2ccc(C(C)C)c(F)n2)cc1C] | (2S,4R)-1-[2-(6-ethoxy-5-methylpyridin-3-yl)acetyl]-4-fluoro-N-[(S)-[6-fluoro-5-(propan-2-yl)pyridin-2-yl](phenyl)methyl]pyrrolidine-2-carboxamide |

TABLE 1-continued

| Compound No. | Structure | IUPAC |
|---|---|---|
| 799 | 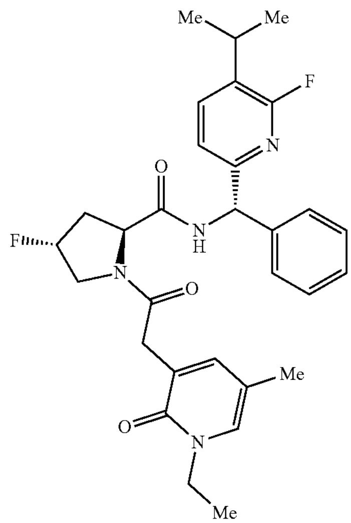 [SMILES: CCn1cc(C)cc(CC(=O)N2C[C@H](F)C[C@H]2C(=O)N[C@@H](c2ccccc2)c2ccc(C(C)C)c(F)n2)c1=O] | (2S,4R)-1-[2-(1-ethyl-5-methyl-2-oxo-1,2-dihydropyridin-3-yl)acetyl]-4-fluoro-N-[(S)-[6-fluoro-5-(propan-2-yl)pyridin-2-yl](phenyl)methyl]pyrrolidine-2-carboxamide |
| 800 | 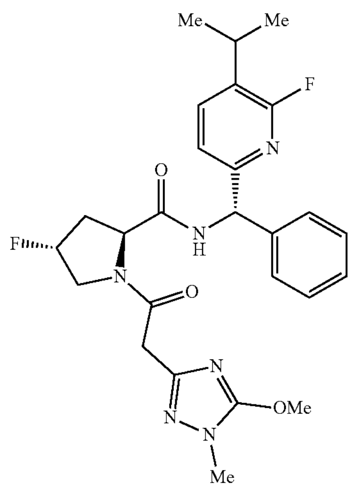 [SMILES: COc1nc(CC(=O)N2C[C@H](F)C[C@H]2C(=O)N[C@@H](c2ccccc2)c2ccc(C(C)C)c(F)n2)nn1C] | (2S,4R)-4-fluoro-N-[(S)-[6-fluoro-5-(propan-2-yl)pyridin-2-yl](phenyl)methyl]-1-[2-(5-methoxy-1-methyl-1H-1,2,4-triazol-3-yl)acetyl]pyrrolidine-2-carboxamide |
| 801 | 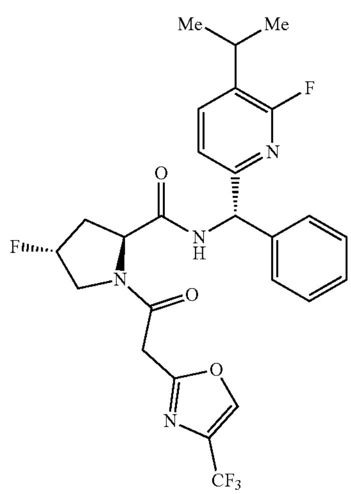 [SMILES: CC(C)c1ccc([C@@H](NC(=O)[C@@H]2C[C@@H](F)CN2C(=O)Cc2nc(C(F)(F)F)co2)c2ccccc2)nc1F] | (2S,4R)-4-fluoro-N-[(S)-[6-fluoro-5-(propan-2-yl)pyridin-2-yl](phenyl)methyl]-1-{2-[4-(trifluoromethyl)-1,3-oxazol-2-yl]acetyl}pyrrolidine-2-carboxamide |

TABLE 1-continued

| Compound No. | Structure | IUPAC |
|---|---|---|
| 802 | 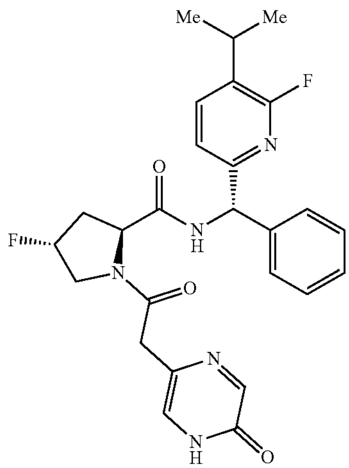 [SMILES: CC(C)c1ccc([C@@H](NC(=O)[C@@H]2C[C@@H](F)CN2C(=O)Cc2c[nH]c(=O)cn2)c2ccccc2)nc1F] | (2S,4R)-4-fluoro-N-[(S)-[6-fluoro-5-(propan-2-yl)pyridin-2-yl](phenyl)methyl]-1-[2-(5-oxo-4,5-dihydropyrazin-2-yl)acetyl]pyrrolidine-2-carboxamide |
| 803 | 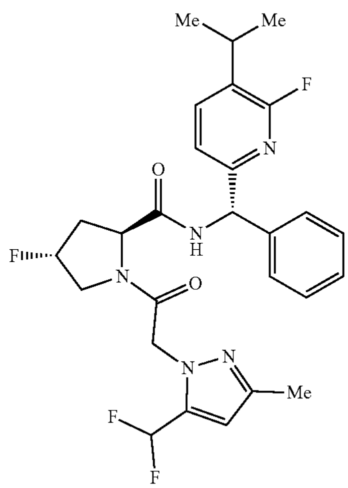 [SMILES: Cc1cc(C(F)F)n(CC(=O)N2C[C@H](F)C[C@H]2C(=O)N[C@@H](c2ccccc2)c2ccc(C(C)C)c(F)n2)n1] | (2S,4R)-1-{2-[5-(difluoromethyl)-3-methyl-1H-pyrazol-1-yl]acetyl}-4-fluoro-N-[(S)-[6-fluoro-5-(propan-2-yl)pyridin-2-yl](phenyl)methyl]pyrrolidine-2-carboxamide |
| 804 | 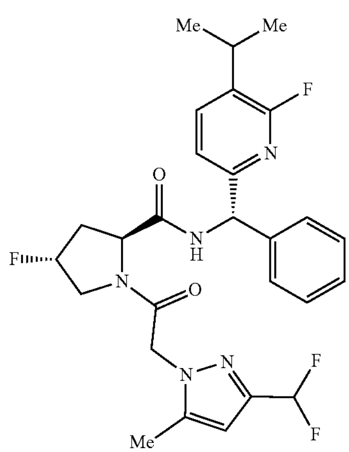 [SMILES: Cc1cc(C(F)F)nn1CC(=O)N1C[C@H](F)C[C@H]1C(=O)N[C@@H](c1ccccc1)c1ccc(C(C)C)c(F)n1] | (2S,4R)-1-{2-[3-(difluoromethyl)-5-methyl-1H-pyrazol-1-yl]acetyl}-4-fluoro-N-[(S)-[6-fluoro-5-(propan-2-yl)pyridin-2-yl](phenyl)methyl]pyrrolidine-2-carboxamide |

TABLE 1-continued

| Compound No. | Structure | IUPAC |
|---|---|---|
| 805 | 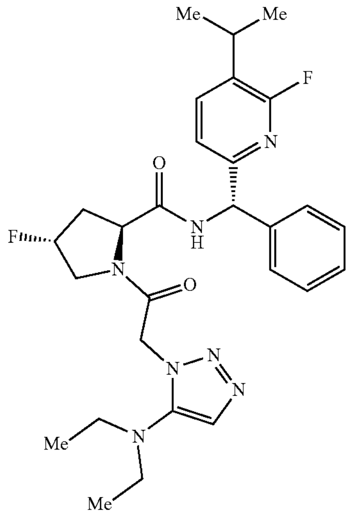 [SMILES: CCN(CC)c1cnnn1CC(=O)N1C[C@H](F)C[C@H]1C(=O)N[C@@H](c1ccccc1)c1ccc(C(C)C)c(F)n1] | (2S,4R)-1-{2-[5-(diethylamino)-1H-1,2,3-triazol-1-yl]acetyl}-4-fluoro-N-[(S)-[6-fluoro-5-(propan-2-yl)pyridin-2-yl](phenyl)methyl]pyrrolidine-2-carboxamide |
| 806 | 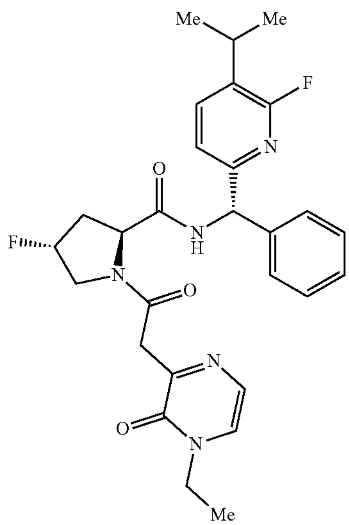 [SMILES: CCn1ccnc(CC(=O)N2C[C@H](F)C[C@H]2C(=O)N[C@@H](c2ccccc2)c2ccc(C(C)C)c(F)n2)c1=O] | (2S,4R)-1-[2-(4-ethyl-3-oxo-3,4-dihydropyrazin-2-yl)acetyl]-4-fluoro-N-[(S)-[6-fluoro-5-(propan-2-yl)pyridin-2-yl](phenyl)methyl]pyrrolidine-2-carboxamide |
| 807 | 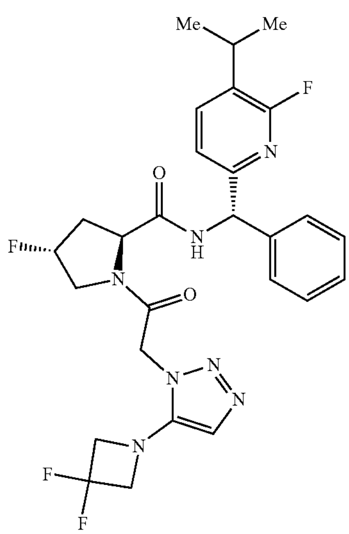 [SMILES: CC(C)c1ccc([C@@H](NC(=O)[C@@H]2C[C@@H](F)CN2C(=O)Cn2nncc2N2CC(F)(F)C2)c2ccccc2)nc1F] | (2S,4R)-1-{2-[5-(3,3-difluoroazetidin-1-yl)-1H-1,2,3-triazol-1-yl]acetyl}-4-fluoro-N-[(S)-[6-fluoro-5-(propan-2-yl)pyridin-2-yl](phenyl)methyl]pyrrolidine-2-carboxamide |

TABLE 1-continued

| Compound No. | Structure | IUPAC |
|---|---|---|
| 808 | 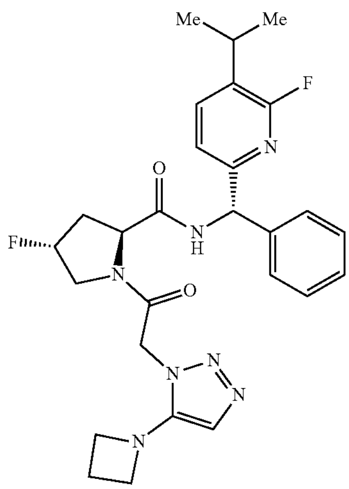 [SMILES: CC(C)c1ccc([C@@H](NC(=O)[C@@H]2C[C@@H](F)CN2C(=O)Cn2nncc2N2CCC2)c2ccccc2)nc1F] | (2S,4R)-1-{2-[5-(azetidin-1-yl)-1H-1,2,3-triazol-1-yl]acetyl}-4-fluoro-N-[(S)-[6-fluoro-5-(propan-2-yl)pyridin-2-yl](phenyl)methyl]pyrrolidine-2-carboxamide |
| 809 | 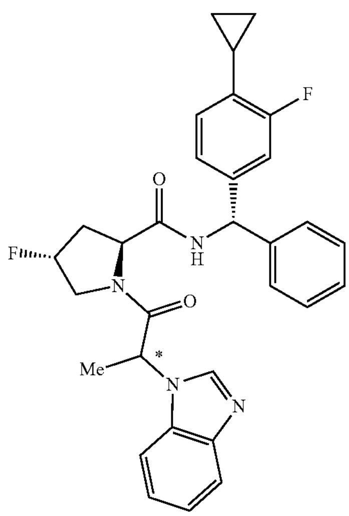 [SMILES: CC(C(=O)N1C[C@H](F)C[C@H]1C(=O)N[C@@H](c1ccccc1)c1ccc(C2CC2)c(F)c1)n1cnc2ccccc21] | (2S,4R)-1-[(2S) or (2R)-2-(1H-1,3-benzodiazol-1-yl)propanoyl]-N-[(S)-(4-cyclopropyl-3-fluorophenyl)(phenyl)methyl]-4-fluoropyrrolidine-2-carboxamide |
| 810 | 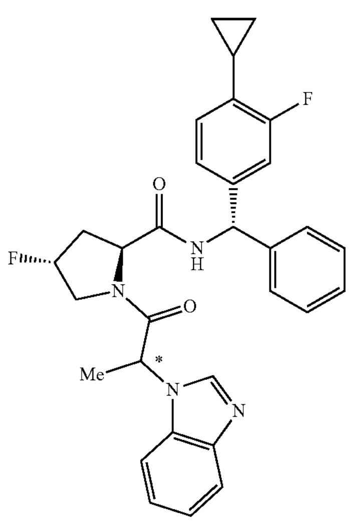 [SMILES: CC(C(=O)N1C[C@H](F)C[C@H]1C(=O)N[C@@H](c1ccccc1)c1ccc(C2CC2)c(F)c1)n1cnc2ccccc21] | (2S,4R)-1-[(2R) or (2S)-2-(1H-1,3-benzodiazol-1-yl)propanoyl]-N-[(S)-(4-cyclopropyl-3-fluorophenyl)(phenyl)methyl]-4-fluoropyrrolidine-2-carboxamide |

In some embodiments, provided herein is a compound of formula (I), or any variation or embodiment thereof, or a stereoisomer or tautomer thereof, or a pharmaceutically acceptable salt of any of the foregoing, the compound, or a stereoisomer or tautomer thereof, or a pharmaceutically acceptable salt of any of the foregoing, is selected from the group consisting of:

1-cyclopropanecarbonyl-N-{phenyl[4-(propan-2-yl)phenyl]methyl}pyrrolidine-2-carboxamide;

1-acetyl-4-hydroxy-N-{phenyl[4-(propan-2-yl)phenyl]methyl}pyrrolidine-2-carboxamide;

1-acetyl-3-hydroxy-N-{phenyl[4-(propan-2-yl)phenyl]methyl}pyrrolidine-2-carboxamide;

1-acetyl-4-fluoro-N-{phenyl[4-(propan-2-yl)phenyl]methyl}pyrrolidine-2-carboxamide;

1-acetyl-N-{phenyl[5-(propan-2-yl)pyridin-2-yl]methyl}pyrrolidine-2-carboxamide;

1-(3-carbamoyl-2-acetamidopropanoyl)-4-fluoro-N-{phenyl[4-(propan-2-yl)phenyl]methyl}pyrrolidine-2-carboxamide;

tert-butyl N-{2-oxo-2-[2-({phenyl[4-(propan-2-yl)phenyl]methyl}carbamoyl)pyrrolidin-1-yl]ethyl}carbamate;

1-(2-hydroxyacetyl)-N-{phenyl[4-(propan-2-yl)phenyl]methyl}pyrrolidine-2-carboxamide;

1-(2-acetamidoacetyl)-N-{phenyl[4-(propan-2-yl)phenyl]methyl}pyrrolidine-2-carboxamide;

1-acetyl-N-[(4-cyclopropyl-3-fluorophenyl)(phenyl)methyl]-4-fluoropyrrolidine-2-carboxamide;

1-(3-carbamoylpropanoyl)-N-{phenyl[4-(propan-2-yl)phenyl]methyl}pyrrolidine-2-carboxamide;

1-acetyl-N-[(5-cyclopropylpyridin-2-yl)(phenyl)methyl]-4-fluoropyrrolidine-2-carboxamide;

2-acetyl-N-{phenyl[4-(propan-2-yl)phenyl]methyl}-2-azabicyclo[3.1.0]hexane-3-carboxamide;

1-{2-[N-(carbamoylmethyl)acetamido]acetyl}-4-fluoro-N-{phenyl[4-(propan-2-yl)phenyl]methyl}pyrrolidine-2-carboxamide;

1-acetyl-5-methyl-N-{phenyl[4-(propan-2-yl)phenyl]methyl}pyrrolidine-2-carboxamide;

1-[2-(1,3-oxazol-2-yl)acetyl]-N-{phenyl[4-(propan-2-yl)phenyl]methyl}pyrrolidine-2-carboxamide;

4-fluoro-N-{phenyl[4-(propan-2-yl)phenyl]methyl}-1-[2-(4H-1,2,4-triazol-3-yl)acetyl]pyrrolidine-2-carboxamide;

4-fluoro-1-{2-[(3-methyloxetan-3-yl)amino]acetyl}-N-{phenyl[4-(propan-2-yl)phenyl]methyl}pyrrolidine-2-carboxamide;

4-acetamido-5-[4-fluoro-2-({phenyl[4-(propan-2-yl)phenyl]methyl}carbamoyl)pyrrolidin-1-yl]-5-oxopentanoic acid;

4-fluoro-N-{phenyl[4-(propan-2-yl)phenyl]methyl}-1-[2-(1H-1,2,3-triazol-5-yl)acetyl]pyrrolidine-2-carboxamide;

1-(3-acetamidopropanoyl)-4-fluoro-N-{phenyl[4-(propan-2-yl)phenyl]methyl}pyrrolidine-2-carboxamide;

4-fluoro-1-[2-(2-oxopyrrolidin-1-yl)acetyl]-N-{phenyl[4-(propan-2-yl)phenyl]methyl}pyrrolidine-2-carboxamide;

4-fluoro-1-[2-(1,3-oxazol-5-yl)acetyl]-N-{phenyl[4-(propan-2-yl)phenyl]methyl}pyrrolidine-2-carboxamide;

1-(4-acetamidobutanoyl)-4-fluoro-N-{phenyl[4-(propan-2-yl)phenyl]methyl}pyrrolidine-2-carboxamide;

2-acetyl-N-[(4-cyclopropyl-3-fluorophenyl)(phenyl)methyl]-2-azabicyclo[3.1.0]hexane-3-carboxamide;

N-[(4-cyclopropyl-3-fluorophenyl)(phenyl)methyl]-1-(2-acetamidoacetyl)pyrrolidine-2-carboxamide;

3-acetyl-N-{phenyl[4-(propan-2-yl)phenyl]methyl}-3-azabicyclo[3.1.0]hexane-2-carboxamide;

4-fluoro-1-[2-(2-oxo-1,3-oxazolidin-3-yl)acetyl]-N-{phenyl[4-(propan-2-yl)phenyl]methyl}pyrrolidine-2-carboxamide;

4-fluoro-1-[2-(oxetan-3-yl)acetyl]-N-{phenyl[4-(propan-2-yl)phenyl]methyl}pyrrolidine-2-carboxamide;

4-fluoro-1-[2-(3-oxomorpholin-4-yl)acetyl]-N-{phenyl[4-(propan-2-yl)phenyl]methyl}pyrrolidine-2-carboxamide;

1-acetyl-N-[(4-cyclopropyl-3-fluorophenyl)(phenyl)methyl]-5-methylpyrrolidine-2-carboxamide;

4-fluoro-1-[2-(1-methyl-1H-pyrazol-5-yl)acetyl]-N-{phenyl[4-(propan-2-yl)phenyl]methyl}pyrrolidine-2-carboxamide;

N-[(4-cyclopropyl-3-fluorophenyl)(phenyl)methyl]-4-fluoro-1-[2-(1H-pyrazol-1-yl)acetyl]pyrrolidine-2-carboxamide;

N-[(4-cyclopropyl-3-fluorophenyl)(phenyl)methyl]-4-fluoro-1-[2-(3-oxomorpholin-4-yl)acetyl]pyrrolidine-2-carboxamide;

N-[(4-cyclopropyl-3-fluorophenyl)(phenyl)methyl]-4-fluoro-1-[2-(5-methyl-4H-1,2,4-triazol-3-yl)acetyl]pyrrolidine-2-carboxamide;

N-[(4-cyclopropyl-3-fluorophenyl)(phenyl)methyl]-4-fluoro-1-[3-(1,3-oxazol-2-yl)propanoyl]pyrrolidine-2-carboxamide;

N-[(4-cyclopropyl-3-fluorophenyl)(phenyl)methyl]-4-fluoro-1-[2-(1H-1,2,3,4-tetrazol-1-yl)acetyl]pyrrolidine-2-carboxamide;

N-[(4-cyclopropyl-3-fluorophenyl)(phenyl)methyl]-4-fluoro-1-[2-(2-oxo-1,3-oxazolidin-3-yl)acetyl]pyrrolidine-2-carboxamide;

N-[(4-cyclopropyl-3-fluorophenyl)(phenyl)methyl]-4-fluoro-1-[2-(1H-pyrazol-5-yl)acetyl]pyrrolidine-2-carboxamide;

N-[(4-cyclopropyl-3-fluorophenyl)(phenyl)methyl]-4-fluoro-1-[2-(1H-1,2,3,4-tetrazol-5-yl)acetyl]pyrrolidine-2-carboxamide;

N-[(4-cyclopropyl-3-fluorophenyl)(phenyl)methyl]-4-fluoro-1-[2-(1,2-oxazol-3-yl)acetyl]pyrrolidine-2-carboxamide;

4-fluoro-N-{phenyl[4-(propan-2-yl)phenyl]methyl}-1-[2-(1H-pyrazol-1-yl)acetyl]pyrrolidine-2-carboxamide;

4-fluoro-N-{phenyl[4-(propan-2-yl)phenyl]methyl}-1-[2-(1H-1,2,3-triazol-1-yl)acetyl]pyrrolidine-2-carboxamide;

4-fluoro-N-{phenyl[4-(propan-2-yl)phenyl]methyl}-1-[2-(2H-1,2,3,4-tetrazol-5-yl)acetyl]pyrrolidine-2-carboxamide;

4-fluoro-1-[2-(1,3,4-oxadiazol-2-yl)acetyl]-N-{phenyl[4-(propan-2-yl)phenyl]methyl}pyrrolidine-2-carboxamide;

N-[(4-cyclopropyl-3-fluorophenyl)(phenyl)methyl]-4-fluoro-1-[2-(1H-pyrazol-4-yl)acetyl]pyrrolidine-2-carboxamide;

4-fluoro-1-{2-[(1,3-oxazol-2-yl)amino]acetyl}-N-{phenyl[4-(propan-2-yl)phenyl]methyl}pyrrolidine-2-carboxamide;

N-[(4-cyclopropyl-3-fluorophenyl)(phenyl)methyl]-4-fluoro-1-[2-(3-methyl-2-oxoimidazolidin-1-yl)acetyl]pyrrolidine-2-carboxamide;

1-[2-(5-cyclopropyl-1,3,4-oxadiazol-2-yl)acetyl]-N-[(4-cyclopropyl-3-fluorophenyl)(phenyl)methyl]-4-fluoropyrrolidine-2-carboxamide;

N-[(4-cyclopropyl-3-fluorophenyl)(phenyl)methyl]-4-fluoro-1-{2-[5-(trifluoromethyl)-1,3,4-oxadiazol-2-yl]acetyl}pyrrolidine-2-carboxamide;

N-[(4-cyclopropyl-3-fluorophenyl)(phenyl)methyl]-4-fluoro-1-[2-(1H-1,2,3-triazol-5-yl)acetyl]pyrrolidine-2-carboxamide;

N-[(4-cyclopropyl-3-fluorophenyl)(phenyl)methyl]-1-{2-[5-(difluoromethyl)-1,3,4-oxadiazol-2-yl]acetyl}-4-fluoropyrrolidine-2-carboxamide;
4-fluoro-N-{phenyl[4-(propan-2-yl)phenyl]methyl}-1-[3-(1H-1,2,4-triazol-1-yl)propanoyl]pyrrolidine-2-carboxamide;
4-fluoro-1-[2-(1-methyl-1H-pyrazol-4-yl)acetyl]-N-{phenyl[4-(propan-2-yl)phenyl]methyl}pyrrolidine-2-carboxamide;
4-fluoro-N-{phenyl[4-(propan-2-yl)phenyl]methyl}-1-[2-(1H-1,2,3,4-tetrazol-1-yl)acetyl]pyrrolidine-2-carboxamide;
4-fluoro-N-{phenyl[4-(propan-2-yl)phenyl]methyl}-1-[2-(pyridazin-3-yloxy)acetyl]pyrrolidine-2-carboxamide;
4-fluoro-1-(1-methyl-5-oxopyrrolidine-2-carbonyl)-N-{phenyl[4-(propan-2-yl)phenyl]methyl}pyrrolidine-2-carboxamide;
1-[2-(2-chloro-5-fluorophenyl)acetyl]-4-fluoro-N-{phenyl[4-(propan-2-yl)phenyl]methyl}pyrrolidine-2-carboxamide;
4-fluoro-N-{phenyl[4-(propan-2-yl)phenyl]methyl}-1-[4-(pyridin-3-yl)butanoyl]pyrrolidine-2-carboxamide;
4-fluoro-1-(3-oxo-octahydroindolizine-6-carbonyl)-N-{phenyl[4-(propan-2-yl)phenyl]methyl}pyrrolidine-2-carboxamide;
4-fluoro-1-(2-oxopiperidine-4-carbonyl)-N-{phenyl[4-(propan-2-yl)phenyl]methyl}pyrrolidine-2-carboxamide;
1-[2-(2-cyano-4-methoxyphenyl)acetyl]-4-fluoro-N-{phenyl[4-(propan-2-yl)phenyl]methyl}pyrrolidine-2-carboxamide;
4-fluoro-1-{3-oxo-2H,3H-[1,2,4]triazolo[4,3-a]pyridine-8-carbonyl}-N-{phenyl[4-(propan-2-yl)phenyl]methyl}pyrrolidine-2-carboxamide;
4-fluoro-1-[4-(1H-imidazol-1-yl)butanoyl]-N-{phenyl[4-(propan-2-yl)phenyl]methyl}pyrrolidine-2-carboxamide;
4-fluoro-N-{phenyl[4-(propan-2-yl)phenyl]methyl}-1-[2-(pyrimidin-5-yl)acetyl]pyrrolidine-2-carboxamide;
4-fluoro-1-(4-methylpyrimidine-5-carbonyl)-N-{phenyl[4-(propan-2-yl)phenyl]methyl}pyrrolidine-2-carboxamide;
4-fluoro-1-[2-(2-oxo-1,2-dihydropyridin-1-yl)acetyl]-N-{phenyl[4-(propan-2-yl)phenyl]methyl}pyrrolidine-2-carboxamide;
1-[3-(3,5-dimethyl-1,2-oxazol-4-yl)propanoyl]-4-fluoro-N-{phenyl[4-(propan-2-yl)phenyl]methyl}pyrrolidine-2-carboxamide;
4-fluoro-1-[2-(3-fluoro-4-methoxyphenyl)acetyl]-N-{phenyl[4-(propan-2-yl)phenyl]methyl}pyrrolidine-2-carboxamide;
4-fluoro-1-(1,3-oxazole-5-carbonyl)-N-{phenyl[4-(propan-2-yl)phenyl]methyl}pyrrolidine-2-carboxamide;
4-fluoro-N-{phenyl[4-(propan-2-yl)phenyl]methyl}-1-[4-(pyridin-4-yl)butanoyl]pyrrolidine-2-carboxamide;
1-[(dimethylcarbamoyl)carbonyl]-4-fluoro-N-{phenyl[4-(propan-2-yl)phenyl]methyl}pyrrolidine-2-carboxamide;
4-fluoro-1-[2-(5-methyl-2,4-dioxo-1,2,3,4-tetrahydropyrimidin-1-yl)acetyl]-N-{phenyl[4-(propan-2-yl)phenyl]methyl}pyrrolidine-2-carboxamide;
4-fluoro-1-[2-(1H-imidazol-1-yl)acetyl]-N-{phenyl[4-(propan-2-yl)phenyl]methyl}pyrrolidine-2-carboxamide;
4-fluoro-N-{phenyl[4-(propan-2-yl)phenyl]methyl}-1-[2-(1H-pyrazol-5-yl)acetyl]pyrrolidine-2-carboxamide;
4-fluoro-1-[2-methyl-3-(1H-1,2,4-triazol-1-yl)propanoyl]-N-{phenyl[4-(propan-2-yl)phenyl]methyl}pyrrolidine-2-carboxamide;
4-fluoro-1-[2-(5-fluoropyridin-2-yl)acetyl]-N-{phenyl[4-(propan-2-yl)phenyl]methyl}pyrrolidine-2-carboxamide;
4-fluoro-1-[2-(5-methyl-1H-indol-3-yl)acetyl]-N-{phenyl[4-(propan-2-yl)phenyl]methyl}pyrrolidine-2-carboxamide;
1-[2-(4-acetamidophenyl)acetyl]-4-fluoro-N-{phenyl[4-(propan-2-yl)phenyl]methyl}pyrrolidine-2-carboxamide;
4-fluoro-1-[2-(1H-imidazol-4-yl)acetyl]-N-{phenyl[4-(propan-2-yl)phenyl]methyl}pyrrolidine-2-carboxamide;
4-fluoro-N-{phenyl[4-(propan-2-yl)phenyl]methyl}-1-[3-(pyridin-3-yl)propanoyl]pyrrolidine-2-carboxamide;
4-fluoro-1-[2-(4-methoxyphenyl)acetyl]-N-{phenyl[4-(propan-2-yl)phenyl]methyl}pyrrolidine-2-carboxamide;
1-[2-(1,5-dimethyl-1H-pyrazol-3-yl)acetyl]-4-fluoro-N-{phenyl[4-(propan-2-yl)phenyl]methyl}pyrrolidine-2-carboxamide;
4-fluoro-1-[3-(2-methylpyridin-3-yl)propanoyl]-N-{phenyl[4-(propan-2-yl)phenyl]methyl}pyrrolidine-2-carboxamide;
4-fluoro-N-{phenyl[4-(propan-2-yl)phenyl]methyl}-1-[2-(pyrimidin-2-yl)acetyl]pyrrolidine-2-carboxamide;
4-fluoro-N-{phenyl[4-(propan-2-yl)phenyl]methyl}-1-[3-(pyrazin-2-yl)propanoyl]pyrrolidine-2-carboxamide;
4-fluoro-N-{phenyl[4-(propan-2-yl)phenyl]methyl}-1-[2-(2H-1,2,3-triazol-2-yl)acetyl]pyrrolidine-2-carboxamide;
1-[3-(2,6-dimethylpyridin-3-yl)propanoyl]-4-fluoro-N-{phenyl[4-(propan-2-yl)phenyl]methyl}pyrrolidine-2-carboxamide;
1-[2-(1H-1,2,3-benzotriazol-1-yl)acetyl]-4-fluoro-N-{phenyl[4-(propan-2-yl)phenyl]methyl}pyrrolidine-2-carboxamide;
4-fluoro-N-{phenyl[4-(propan-2-yl)phenyl]methyl}-1-[2-(1,3,5-trimethyl-1H-pyrazol-4-yl)acetyl]pyrrolidine-2-carboxamide;
4-fluoro-N-{phenyl[4-(propan-2-yl)phenyl]methyl}-1-[2-(pyridin-3-yloxy)acetyl]pyrrolidine-2-carboxamide;
4-fluoro-1-[3-(1H-imidazol-5-yl)propanoyl]-N-{phenyl[4-(propan-2-yl)phenyl]methyl}pyrrolidine-2-carboxamide;
4-fluoro-1-[3-(5-methyl-1,3,4-thiadiazol-2-yl)propanoyl]-N-{phenyl[4-(propan-2-yl)phenyl]methyl}pyrrolidine-2-carboxamide;
1-[3-(3,5-dimethyl-1H-pyrazol-1-yl)propanoyl]-4-fluoro-N-{phenyl[4-(propan-2-yl)phenyl]methyl}pyrrolidine-2-carboxamide;
1-(3-cyanopropanoyl)-4-fluoro-N-{phenyl[4-(propan-2-yl)phenyl]methyl}pyrrolidine-2-carboxamide;
1-{2-[(dimethylcarbamoyl)amino]acetyl}-4-fluoro-N-{phenyl[4-(propan-2-yl)phenyl]methyl}pyrrolidine-2-carboxamide;
4-fluoro-1-[2-(5-methyl-1,2,4-oxadiazol-3-yl)acetyl]-N-{phenyl[4-(propan-2-yl)phenyl]methyl}pyrrolidine-2-carboxamide;
4-fluoro-1-[2-(1-methyl-1H-indol-2-yl)acetyl]-N-{phenyl[4-(propan-2-yl)phenyl]methyl}pyrrolidine-2-carboxamide;
4-fluoro-1-[3-(5-methylpyridin-2-yl)propanoyl]-N-{phenyl[4-(propan-2-yl)phenyl]methyl}pyrrolidine-2-carboxamide;
1-(2-ethyl-1,3-oxazole-4-carbonyl)-4-fluoro-N-{phenyl[4-(propan-2-yl)phenyl]methyl}pyrrolidine-2-carboxamide;
4-fluoro-1-[2-(2-methyl-1,3-thiazol-4-yl)acetyl]-N-{phenyl[4-(propan-2-yl)phenyl]methyl}pyrrolidine-2-carboxamide;
4-fluoro-N-{phenyl[4-(propan-2-yl)phenyl]methyl}-1-[2-(pyrazin-2-yl)acetyl]pyrrolidine-2-carboxamide;
4-fluoro-1-[2-methyl-3-(1H-pyrazol-1-yl)propanoyl]-N-{phenyl[4-(propan-2-yl)phenyl]methyl}pyrrolidine-2-carboxamide;

4-fluoro-1-[3-(1H-indol-3-yl)propanoyl]-N-{phenyl[4-(propan-2-yl)phenyl]methyl}pyrrolidine-2-carboxamide;
4-fluoro-1-[2-methyl-3-(pyridin-4-yl)propanoyl]-N-{phenyl[4-(propan-2-yl)phenyl]methyl}pyrrolidine-2-carboxamide;
4-fluoro-1-[2-(4-fluoro-1H-indol-1-yl)acetyl]-N-{phenyl[4-(propan-2-yl)phenyl]methyl}pyrrolidine-2-carboxamide;
4-fluoro-1-{4-oxo-4H,5H,6H,7H,8H-pyrazolo[1,5-a][1,4]diazepine-2-carbonyl}-N-{phenyl[4-(propan-2-yl)phenyl]methyl}pyrrolidine-2-carboxamide;
4-fluoro-N-{phenyl[4-(propan-2-yl)phenyl]methyl}-1-{2-[5-(propan-2-yl)-1,2,4-oxadiazol-3-yl]acetyl}pyrrolidine-2-carboxamide;
4-fluoro-1-(6-oxopiperidine-3-carbonyl)-N-{phenyl[4-(propan-2-yl)phenyl]methyl}pyrrolidine-2-carboxamide;
4-fluoro-N-{phenyl[4-(propan-2-yl)phenyl]methyl}-1-[2-(pyrrolidine-1-sulfonyl)acetyl]pyrrolidine-2-carboxamide;
1-[2-(1,2-benzoxazol-3-yl)acetyl]-4-fluoro-N-{phenyl[4-(propan-2-yl)phenyl]methyl}pyrrolidine-2-carboxamide;
4-fluoro-N-{phenyl[4-(propan-2-yl)phenyl]methyl}-1-(2-{[1,2,4]triazolo[1,5-a]pyridin-6-yl}acetyl)pyrrolidine-2-carboxamide;
1-[2-(1H-1,3-benzodiazol-1-yl)acetyl]-4-fluoro-N-{phenyl[4-(propan-2-yl)phenyl]methyl}pyrrolidine-2-carboxamide;
4-fluoro-N-{phenyl[4-(propan-2-yl)phenyl]methyl}-1-[2-(1H-pyrazol-1-yl)propanoyl]pyrrolidine-2-carboxamide;
4-fluoro-1-[3-(3-methoxypyridin-2-yl)propanoyl]-N-{phenyl[4-(propan-2-yl)phenyl]methyl}pyrrolidine-2-carboxamide;
4-fluoro-1-[2-(1H-imidazol-1-yl)propanoyl]-N-{phenyl[4-(propan-2-yl)phenyl]methyl}pyrrolidine-2-carboxamide;
1-[2-(3,5-dimethyl-1,2-oxazol-4-yl)acetyl]-4-fluoro-N-{phenyl[4-(propan-2-yl)phenyl]methyl}pyrrolidine-2-carboxamide;
4-fluoro-1-[2-(1-methyl-1H-pyrazol-3-yl)acetyl]-N-{phenyl[4-(propan-2-yl)phenyl]methyl}pyrrolidine-2-carboxamide;
4-fluoro-N-{phenyl[4-(propan-2-yl)phenyl]methyl}-1-[3-(1H-1,2,3-triazol-1-yl)propanoyl]pyrrolidine-2-carboxamide;
4-fluoro-1-[3-(1H-imidazol-2-yl)propanoyl]-N-{phenyl[4-(propan-2-yl)phenyl]methyl}pyrrolidine-2-carboxamide;
4-fluoro-1-[2-(2-methylphenoxy)acetyl]-N-{phenyl[4-(propan-2-yl)phenyl]methyl}pyrrolidine-2-carboxamide;
4-fluoro-1-[2-(3-methyl-1,2-oxazol-5-yl)acetyl]-N-{phenyl[4-(propan-2-yl)phenyl]methyl}pyrrolidine-2-carboxamide;
4-fluoro-1-(3-methyloxetane-3-carbonyl)-N-{phenyl[4-(propan-2-yl)phenyl]methyl}pyrrolidine-2-carboxamide;
1-[2-(4-chloro-1H-pyrazol-1-yl)acetyl]-4-fluoro-N-{phenyl[4-(propan-2-yl)phenyl]methyl}pyrrolidine-2-carboxamide;
1-(1-ethyl-1H-pyrazole-5-carbonyl)-4-fluoro-N-{phenyl[4-(propan-2-yl)phenyl]methyl}pyrrolidine-2-carboxamide;
4-fluoro-N-{phenyl[4-(propan-2-yl)phenyl]methyl}-1-[2-(pyridin-2-yl)propanoyl]pyrrolidine-2-carboxamide;
4-fluoro-N-{phenyl[4-(propan-2-yl)phenyl]methyl}-1-[3-(pyrimidin-5-yl)propanoyl]pyrrolidine-2-carboxamide;
4-fluoro-1-(3-methoxy-1-methyl-1H-pyrazole-4-carbonyl)-N-{phenyl[4-(propan-2-yl)phenyl]methyl}pyrrolidine-2-carboxamide;
4-fluoro-1-[2-(5-methyl-1,3,4-oxadiazol-2-yl)acetyl]-N-{phenyl[4-(propan-2-yl)phenyl]methyl}pyrrolidine-2-carboxamide;
4-fluoro-N-{phenyl[4-(propan-2-yl)phenyl]methyl}-1-[3-(1H-pyrazol-4-yl)propanoyl]pyrrolidine-2-carboxamide;
4-fluoro-N-{phenyl[4-(propan-2-yl)phenyl]methyl}-1-[2-(1,3-thiazol-4-yl)acetyl]pyrrolidine-2-carboxamide;
4-fluoro-1-[4-(2-methyl-1H-imidazol-1-yl)butanoyl]-N-{phenyl[4-(propan-2-yl)phenyl]methyl}pyrrolidine-2-carboxamide;
4-fluoro-1-(2-{imidazo[1,2-a]pyridin-3-yl}acetyl)-N-{phenyl[4-(propan-2-yl)phenyl]methyl}pyrrolidine-2-carboxamide;
4-fluoro-N-{phenyl[4-(propan-2-yl)phenyl]methyl}-1-[3-(pyridin-2-yl)propanoyl]pyrrolidine-2-carboxamide;
4-fluoro-1-[2-(3-methyl-1,2,4-oxadiazol-5-yl)acetyl]-N-{phenyl[4-(propan-2-yl)phenyl]methyl}pyrrolidine-2-carboxamide;
1-[2-(3,5-dimethyl-1H-pyrazol-1-yl)acetyl]-4-fluoro-N-{phenyl[4-(propan-2-yl)phenyl]methyl}pyrrolidine-2-carboxamide;
4-fluoro-1-[3-(6-methylpyridin-3-yl)propanoyl]-N-{phenyl[4-(propan-2-yl)phenyl]methyl}pyrrolidine-2-carboxamide;
4-fluoro-N-{phenyl[4-(propan-2-yl)phenyl]methyl}-1-(3-{1H-pyrrolo[2,3-b]pyridin-3-yl}propanoyl)pyrrolidine-2-carboxamide;
4-fluoro-1-(2-oxo-1,3-oxazolidine-5-carbonyl)-N-{phenyl[4-(propan-2-yl)phenyl]methyl}pyrrolidine-2-carboxamide;
4-fluoro-1-[2-(4-methyl-1H-pyrazol-1-yl)acetyl]-N-{phenyl[4-(propan-2-yl)phenyl]methyl}pyrrolidine-2-carboxamide;
4-fluoro-1-[3-(1-methyl-1H-pyrazol-4-yl)propanoyl]-N-{phenyl[4-(propan-2-yl)phenyl]methyl}pyrrolidine-2-carboxamide;
4-fluoro-N-{phenyl[4-(propan-2-yl)phenyl]methyl}-1-[2-(1H-1,2,4-triazol-1-yl)acetyl]pyrrolidine-2-carboxamide;
4-fluoro-N-{phenyl[4-(propan-2-yl)phenyl]methyl}-1-[5-(pyridin-4-yl)-1H-pyrazole-3-carbonyl]pyrrolidine-2-carboxamide;
4-fluoro-1-[3-(2-methylpyridin-4-yl)propanoyl]-N-{phenyl[4-(propan-2-yl)phenyl]methyl}pyrrolidine-2-carboxamide;
4-fluoro-1-(2-hydroxy-3-methylbutanoyl)-N-{phenyl[4-(propan-2-yl)phenyl]methyl}pyrrolidine-2-carboxamide;
4-fluoro-N-{phenyl[4-(propan-2-yl)phenyl]methyl}-1-(3-{1H-pyrrolo[2,3-b]pyridin-5-yl}propanoyl)pyrrolidine-2-carboxamide;
4-fluoro-1-[4-oxo-4-(pyrrolidin-1-yl)butanoyl]-N-{phenyl[4-(propan-2-yl)phenyl]methyl}pyrrolidine-2-carboxamide;
4-fluoro-N-{phenyl[4-(propan-2-yl)phenyl]methyl}-1-[2-(quinolin-6-yl)acetyl]pyrrolidine-2-carboxamide;
4-fluoro-N-{phenyl[4-(propan-2-yl)phenyl]methyl}-1-[2-(pyridin-4-yl)acetyl]pyrrolidine-2-carboxamide;
4-fluoro-N-{phenyl[4-(propan-2-yl)phenyl]methyl}-1-[2-(2,2,2-trifluoroacetamido)acetyl]pyrrolidine-2-carboxamide;
4-fluoro-N-{phenyl[4-(propan-2-yl)phenyl]methyl}-1-[2-(pyridin-3-yloxy)propanoyl]pyrrolidine-2-carboxamide;
4-fluoro-1-[2-(1H-indol-3-yl)acetyl]-N-{phenyl[4-(propan-2-yl)phenyl]methyl}pyrrolidine-2-carboxamide;
1-(2-cyclopropyl-2-oxoacetyl)-4-fluoro-N-{phenyl[4-(propan-2-yl)phenyl]methyl}pyrrolidine-2-carboxamide;
4-fluoro-1-[2-(5-fluoro-2-methoxyphenyl)acetyl]-N-{phenyl[4-(propan-2-yl)phenyl]methyl}pyrrolidine-2-carboxamide;
4-fluoro-1-[2-(6-methoxypyridin-2-yl)acetyl]-N-{phenyl[4-(propan-2-yl)phenyl]methyl}pyrrolidine-2-carboxamide;

4-fluoro-1-[2-(2-oxo-1,2-dihydropyridin-1-yl)propanoyl]-N-{phenyl[4-(propan-2-yl)phenyl]methyl}pyrrolidine-2-carboxamide;

4-fluoro-N-{phenyl[4-(propan-2-yl)phenyl]methyl}-1-[2-(pyridin-3-yl)acetyl]pyrrolidine-2-carboxamide;

1-[2-(3,5-dimethyl-1H-pyrazol-4-yl)acetyl]-4-fluoro-N-{phenyl[4-(propan-2-yl)phenyl]methyl}pyrrolidine-2-carboxamide;

1-[2-(2,5-dioxoimidazolidin-1-yl)acetyl]-4-fluoro-N-{phenyl[4-(propan-2-yl)phenyl]methyl}pyrrolidine-2-carboxamide;

1-[2-(2,5-dimethyl-1,3-thiazol-4-yl)acetyl]-4-fluoro-N-{phenyl[4-(propan-2-yl)phenyl]methyl}pyrrolidine-2-carboxamide;

4-fluoro-1-[2-methyl-3-(pyridin-2-yl)propanoyl]-N-{phenyl[4-(propan-2-yl)phenyl]methyl}pyrrolidine-2-carboxamide;

4-fluoro-1-[2-(2-oxo-1,2-dihydropyrazin-1-yl)acetyl]-N-{phenyl[4-(propan-2-yl)phenyl]methyl}pyrrolidine-2-carboxamide;

4-fluoro-1-[2-(N-methylacetamido)propanoyl]-N-{phenyl[4-(propan-2-yl)phenyl]methyl}pyrrolidine-2-carboxamide;

4-fluoro-1-[2-methyl-2-(pyridin-2-yl)propanoyl]-N-{phenyl[4-(propan-2-yl)phenyl]methyl}pyrrolidine-2-carboxamide;

4-fluoro-1-[2-(2-oxopiperidin-1-yl)acetyl]-N-{phenyl[4-(propan-2-yl)phenyl]methyl}pyrrolidine-2-carboxamide;

4-fluoro-N-{phenyl[4-(propan-2-yl)phenyl]methyl}-1-[2-(quinolin-5-yl)acetyl]pyrrolidine-2-carboxamide;

4-fluoro-N-{phenyl[4-(propan-2-yl)phenyl]methyl}-1-[3-(1H-1,2,4-triazol-1-yl)benzoyl]pyrrolidine-2-carboxamide;

4-fluoro-1-{[(2-methylpropyl)carbamoyl]carbonyl}-N-{phenyl[4-(propan-2-yl)phenyl]methyl}pyrrolidine-2-carboxamide;

4-fluoro-N-{phenyl[4-(propan-2-yl)phenyl]methyl}-1-[2-(1H-1,2,3,4-tetrazol-1-yl)propanoyl]pyrrolidine-2-carboxamide;

4-fluoro-1-(2-oxo-1,2,3,4-tetrahydroquinoline-7-carbonyl)-N-{phenyl[4-(propan-2-yl)phenyl]methyl}pyrrolidine-2-carboxamide;

4-fluoro-1-[2-(2-methyl-1,3-thiazol-5-yl)acetyl]-N-{phenyl[4-(propan-2-yl)phenyl]methyl}pyrrolidine-2-carboxamide;

4-fluoro-1-[3-(6-oxo-1,6-dihydropyridazin-3-yl)propanoyl]-N-{phenyl[4-(propan-2-yl)phenyl]methyl}pyrrolidine-2-carboxamide;

4-fluoro-1-[2-(4-methyl-1H-pyrazol-1-yl)propanoyl]-N-{phenyl[4-(propan-2-yl)phenyl]methyl}pyrrolidine-2-carboxamide;

4-fluoro-N-{phenyl[4-(propan-2-yl)phenyl]methyl}-1-[2-(pyridin-2-yl)acetyl]pyrrolidine-2-carboxamide;

4-fluoro-1-[2-(3-methyl-1H-pyrazol-1-yl)acetyl]-N-{phenyl[4-(propan-2-yl)phenyl]methyl}pyrrolidine-2-carboxamide;

4-fluoro-1-(3-oxo-3,4-dihydro-2H-1,4-benzoxazine-6-carbonyl)-N-{phenyl[4-(propan-2-yl)phenyl]methyl}pyrrolidine-2-carboxamide;

1-(2-acetamidopyridine-4-carbonyl)-4-fluoro-N-{phenyl[4-(propan-2-yl)phenyl]methyl}pyrrolidine-2-carboxamide;

4-fluoro-N-{phenyl[4-(propan-2-yl)phenyl]methyl}-1-[2-(1H-pyrazol-3-yl)acetyl]pyrrolidine-2-carboxamide;

N-{[3-fluoro-4-(propan-2-yl)phenyl](phenyl)methyl}-3-[2-(1H-1,2,3-triazol-5-yl)acetyl]-3-azabicyclo[3.1.0]hexane-2-carboxamide;

N-[(4-cyclopropyl-3-fluorophenyl)(phenyl)methyl]-4-fluoro-1-[2-(5-methyl-1H-1,2,3,4-tetrazol-1-yl)acetyl]pyrrolidine-2-carboxamide;

N-[(4-cyclopropyl-3-fluorophenyl)(phenyl)methyl]-4-fluoro-1-[2-(1,3,4-oxadiazol-2-yl)acetyl]pyrrolidine-2-carboxamide;

4-fluoro-N-{phenyl[5-(propan-2-yl)pyridin-2-yl]methyl}-1-[2-(1H-1,2,3-triazol-5-yl)acetyl]pyrrolidine-2-carboxamide;

4-fluoro-N-{[3-fluoro-4-(propan-2-yl)phenyl](phenyl)methyl}-1-[2-(1H-1,2,3-triazol-5-yl)acetyl]pyrrolidine-2-carboxamide;

N-{[3-fluoro-4-(propan-2-yl)phenyl](phenyl)methyl}-2-[2-(1H-1,2,3-triazol-5-yl)acetyl]-2-azabicyclo[3.1.0]hexane-3-carboxamide;

N-{[3-fluoro-4-(propan-2-yl)phenyl](phenyl)methyl}-5-methyl-1-[2-(1H-1,2,3-triazol-5-yl)acetyl]pyrrolidine-2-carboxamide;

4-fluoro-N-{[3-fluoro-4-(propan-2-yl)phenyl](phenyl)methyl}-1-(2-hydroxy-2-methylpropanoyl)pyrrolidine-2-carboxamide;

4-fluoro-1-[2-(5-methyl-1H-1,2,3,4-tetrazol-1-yl)acetyl]-N-{phenyl[4-(propan-2-yl)phenyl]methyl}pyrrolidine-2-carboxamide;

4-fluoro-N-{[3-fluoro-4-(propan-2-yl)phenyl](phenyl)methyl}-1-[2-(1H-1,2,3,4-tetrazol-5-yl)acetyl]pyrrolidine-2-carboxamide;

N-[(4-cyclopropyl-3-fluorophenyl)(phenyl)methyl]-4-fluoro-1-[2-(5-methyl-2H-1,2,3,4-tetrazol-2-yl)acetyl]pyrrolidine-2-carboxamide;

N-[(4-cyclopropyl-3-fluorophenyl)(phenyl)methyl]-3-[2-(1H-1,2,3-triazol-5-yl)acetyl]-3-azabicyclo[3.1.0]hexane-2-carboxamide;

4-fluoro-N-{[3-fluoro-4-(propan-2-yl)phenyl](phenyl)methyl}-1-[2-(1H-1,2,3-triazol-1-yl)acetyl]pyrrolidine-2-carboxamide;

4-fluoro-N-{[3-fluoro-4-(propan-2-yl)phenyl](phenyl)methyl}-1-[2-(1H-1,2,3,4-tetrazol-1-yl)acetyl]pyrrolidine-2-carboxamide;

4-fluoro-N-{phenyl[4-(propan-2-yl)phenyl]methyl}-1-[2-(4H-1,2,4-triazol-4-yl)acetyl]pyrrolidine-2-carboxamide;

4-fluoro-1-[2-(4-methyl-4H-1,2,4-triazol-3-yl)acetyl]-N-{phenyl[4-(propan-2-yl)phenyl]methyl}pyrrolidine-2-carboxamide;

4-fluoro-1-[2-(1-methyl-1H-1,2,3-triazol-5-yl)acetyl]-N-{phenyl[4-(propan-2-yl)phenyl]methyl}pyrrolidine-2-carboxamide;

4-fluoro-1-[2-(1-methyl-1H-1,2,3-triazol-4-yl)acetyl]-N-{phenyl[4-(propan-2-yl)phenyl]methyl}pyrrolidine-2-carboxamide;

4-fluoro-1-[2-(1,2-oxazol-4-yl)acetyl]-N-{phenyl[4-(propan-2-yl)phenyl]methyl}pyrrolidine-2-carboxamide;

4-fluoro-1-[2-(1,2-oxazol-3-yl)acetyl]-N-{phenyl[4-(propan-2-yl)phenyl]methyl}pyrrolidine-2-carboxamide;

4-fluoro-1-[2-(3-methyl-1H-1,2,4-triazol-5-yl)acetyl]-N-{phenyl[4-(propan-2-yl)phenyl]methyl}pyrrolidine-2-carboxamide;

4-fluoro-N-{[3-fluoro-4-(propan-2-yl)phenyl](phenyl)methyl}-1-[2-(1-methyl-1H-pyrazol-5-yl)acetyl]pyrrolidine-2-carboxamide;

4-fluoro-N-{[3-fluoro-4-(propan-2-yl)phenyl](phenyl)methyl}-1-[2-(1-methyl-1H-pyrazol-3-yl)acetyl]pyrrolidine-2-carboxamide;

4-fluoro-N-{[3-fluoro-4-(propan-2-yl)phenyl](phenyl)methyl}-1-[2-(1-methyl-1H-1,2,3-triazol-5-yl)acetyl]pyrrolidine-2-carboxamide;

4-fluoro-N-{[3-fluoro-4-(propan-2-yl)phenyl](phenyl)methyl}-1-[2-(pyridin-2-yl)acetyl]pyrrolidine-2-carboxamide;
4-fluoro-N-{[3-fluoro-4-(propan-2-yl)phenyl](phenyl)methyl}-1-[2-(5-methyl-1,3,4-oxadiazol-2-yl)acetyl]pyrrolidine-2-carboxamide;
4-fluoro-N-{[3-fluoro-4-(propan-2-yl)phenyl](phenyl)methyl}-1-[2-(pyridin-3-yl)acetyl]pyrrolidine-2-carboxamide;
4-fluoro-N-{[3-fluoro-4-(propan-2-yl)phenyl](phenyl)methyl}-1-[2-(pyrimidin-4-yl)acetyl]pyrrolidine-2-carboxamide;
4-fluoro-N-{[3-fluoro-4-(propan-2-yl)phenyl](phenyl)methyl}-1-[2-(pyrimidin-5-yl)acetyl]pyrrolidine-2-carboxamide;
4-fluoro-N-{[3-fluoro-4-(propan-2-yl)phenyl](phenyl)methyl}-1-[2-(pyrazin-2-yl)acetyl]pyrrolidine-2-carboxamide;
4-fluoro-N-{[3-fluoro-4-(propan-2-yl)phenyl](phenyl)methyl}-1-[2-(4-methyl-2,5-dioxopiperazin-1-yl)acetyl]pyrrolidine-2-carboxamide;
1-(2-cyanoacetyl)-4-fluoro-N-{phenyl[4-(propan-2-yl)phenyl]methyl}pyrrolidine-2-carboxamide;
4-fluoro-1-(2-methanesulfonylacetyl)-N-{phenyl[4-(propan-2-yl)phenyl]methyl}pyrrolidine-2-carboxamide;
4-fluoro-N-{phenyl[4-(propan-2-yl)phenyl]methyl}-1-[2-(1H-1,2,3-triazol-1-yl)propanoyl]pyrrolidine-2-carboxamide;
1-(4-acetylmorpholine-2-carbonyl)-4-fluoro-N-{phenyl[4-(propan-2-yl)phenyl]methyl}pyrrolidine-2-carboxamide;
1-[2-(4-acetyl-3,4-dihydro-2H-1,4-benzoxazin-2-yl)acetyl]-4-fluoro-N-{phenyl[4-(propan-2-yl)phenyl]methyl}pyrrolidine-2-carboxamide;
1-[2-(4-acetyl-2-oxopiperazin-1-yl)acetyl]-4-fluoro-N-{phenyl[4-(propan-2-yl)phenyl]methyl}pyrrolidine-2-carboxamide;
1-(1-acetylpiperidine-4-carbonyl)-4-fluoro-N-{phenyl[4-(propan-2-yl)phenyl]methyl}pyrrolidine-2-carboxamide;
1-(2,3-dihydroxypropanoyl)-4-fluoro-N-{phenyl[4-(propan-2-yl)phenyl]methyl}pyrrolidine-2-carboxamide;
1-{8-acetyl-8-azaspiro[4.5]decane-2-carbonyl}-4-fluoro-N-{phenyl[4-(propan-2-yl)phenyl]methyl}pyrrolidine-2-carboxamide;
4-fluoro-1-[3-(1H-imidazol-1-yl)-2-methylpropanoyl]-N-{phenyl[4-(propan-2-yl)phenyl]methyl}pyrrolidine-2-carboxamide;
1-{6-acetyl-6-azaspiro[2.5]octane-1-carbonyl}-4-fluoro-N-{phenyl[4-(propan-2-yl)phenyl]methyl}pyrrolidine-2-carboxamide;
1-(1-acetyl-3-methylpyrrolidine-3-carbonyl)-4-fluoro-N-{phenyl[4-(propan-2-yl)phenyl]methyl}pyrrolidine-2-carboxamide;
4-fluoro-1-[2-(N-methylacetamido)acetyl]-N-{phenyl[4-(propan-2-yl)phenyl]methyl}pyrrolidine-2-carboxamide;
1-{2-acetyl-5-oxa-2,6-diazaspiro[3.4]oct-6-ene-7-carbonyl}-4-fluoro-N-{phenyl[4-(propan-2-yl)phenyl]methyl}pyrrolidine-2-carboxamide;
1-[1-acetyl-2-(pyridin-3-yl)pyrrolidine-3-carbonyl]-4-fluoro-N-{phenyl[4-(propan-2-yl)phenyl]methyl}pyrrolidine-2-carboxamide;
4-fluoro-1-[5-(methoxymethyl)-1,2-oxazole-4-carbonyl]-N-{phenyl[4-(propan-2-yl)phenyl]methyl}pyrrolidine-2-carboxamide;
1-{6-acetyl-5H,6H,7H,8H-pyrido[3,4-b]pyrazine-7-carbonyl}-4-fluoro-N-{phenyl[4-(propan-2-yl)phenyl]methyl}pyrrolidine-2-carboxamide;
4-fluoro-N-{phenyl[4-(propan-2-yl)phenyl]methyl}-1-[2-(1H-1,2,4-triazol-1-yl)propanoyl]pyrrolidine-2-carboxamide;
1-{5-acetyl-5-azaspiro[2.4]heptane-1-carbonyl}-4-fluoro-N-{phenyl[4-(propan-2-yl)phenyl]methyl}pyrrolidine-2-carboxamide;
1-[3-(1-acetylpyrrolidin-2-yl)propanoyl]-4-fluoro-N-{phenyl[4-(propan-2-yl)phenyl]methyl}pyrrolidine-2-carboxamide;
1-{4-[(1-acetylazetidin-3-yl)oxy]benzoyl}-4-fluoro-N-{phenyl[4-(propan-2-yl)phenyl]methyl}pyrrolidine-2-carboxamide;
4-fluoro-1-[3-methoxy-2-(N-methylacetamido)butanoyl]-N-{phenyl[4-(propan-2-yl)phenyl]methyl}pyrrolidine-2-carboxamide;
1-[2-(1-acetylpyrrolidin-2-yl)acetyl]-4-fluoro-N-{phenyl[4-(propan-2-yl)phenyl]methyl}pyrrolidine-2-carboxamide;
1-{7-acetyl-1-oxa-2,7-diazaspiro[4.4]non-2-ene-3-carbonyl}-4-fluoro-N-{phenyl[4-(propan-2-yl)phenyl]methyl}pyrrolidine-2-carboxamide;
1-{5-acetyl-hexahydro-1H-furo[3,4-c]pyrrole-3a-carbonyl}-4-fluoro-N-{phenyl[4-(propan-2-yl)phenyl]methyl}pyrrolidine-2-carboxamide;
1-(1-acetylpyrrolidine-3-carbonyl)-4-fluoro-N-{phenyl[4-(propan-2-yl)phenyl]methyl}pyrrolidine-2-carboxamide;
4-fluoro-1-[2-(3-methyl-1H-pyrazol-5-yl)acetyl]-N-{phenyl[4-(propan-2-yl)phenyl]methyl}pyrrolidine-2-carboxamide;
1-{5-acetyl-2-oxa-5-azabicyclo[2.2.1]heptane-1-carbonyl}-4-fluoro-N-{phenyl[4-(propan-2-yl)phenyl]methyl}pyrrolidine-2-carboxamide;
1-[2-(1-acetylpiperidin-4-yl)propanoyl]-4-fluoro-N-{phenyl[4-(propan-2-yl)phenyl]methyl}pyrrolidine-2-carboxamide;
4-fluoro-1-[2-methyl-2-(1H-1,2,4-triazol-5-yl)propanoyl]-N-{phenyl[4-(propan-2-yl)phenyl]methyl}pyrrolidine-2-carboxamide;
4-fluoro-N-{[3-fluoro-4-(propan-2-yl)phenyl](phenyl)methyl}-1-[2-methyl-2-(1,3,4-oxadiazol-2-yl)propanoyl]pyrrolidine-2-carboxamide;
4-fluoro-N-{[3-fluoro-4-(propan-2-yl)phenyl](phenyl)methyl}-1-[2-(pyridin-4-yl)acetyl]pyrrolidine-2-carboxamide;
4-fluoro-N-{[3-fluoro-4-(propan-2-yl)phenyl](phenyl)methyl}-1-(2-{imidazo[1,2-a]pyridin-3-yl}acetyl)pyrrolidine-2-carboxamide;
4-fluoro-N-{[3-fluoro-4-(propan-2-yl)phenyl](phenyl)methyl}-1-[2-(1H-imidazol-1-yl)acetyl]pyrrolidine-2-carboxamide;
4-fluoro-N-{[3-fluoro-4-(propan-2-yl)phenyl](phenyl)methyl}-1-[2-(1,3,5-trimethyl-1H-pyrazol-4-yl)acetyl]pyrrolidine-2-carboxamide;
4-fluoro-N-{[3-fluoro-4-(propan-2-yl)phenyl](phenyl)methyl}-1-[2-(1,2-oxazol-5-yl)acetyl]pyrrolidine-2-carboxamide;
1-{2-[(dimethylcarbamoyl)amino]acetyl}-4-fluoro-N-{[3-fluoro-4-(propan-2-yl)phenyl](phenyl)methyl}pyrrolidine-2-carboxamide;
N-{[3-fluoro-4-(propan-2-yl)phenyl](phenyl)methyl}-4-[2-(1H-1,2,3-triazol-5-yl)acetyl]-4-azaspiro[2.4]heptane-5-carboxamide;
4-fluoro-N-{[3-fluoro-4-(propan-2-yl)phenyl](phenyl)methyl}-1-(2-{[1,2,4]triazolo[1,5-a]pyridin-6-yl}acetyl)pyrrolidine-2-carboxamide;
4-fluoro-N-{[3-fluoro-4-(propan-2-yl)phenyl](phenyl)methyl}-1-[2-(quinolin-6-yl)acetyl]pyrrolidine-2-carboxamide;

4-fluoro-N-{[3-fluoro-4-(propan-2-yl)phenyl](phenyl)methyl}-1-[2-(1-methyl-1H-pyrazol-4-yl)acetyl]pyrrolidine-2-carboxamide;

4-fluoro-N-{phenyl[4-(propan-2-yl)phenyl]methyl}-1-[2-(piperazin-1-yl)acetyl]pyrrolidine-2-carboxamide;

1-(1-acetyl-3-methylpiperidine-3-carbonyl)-4-fluoro-N-{phenyl[4-(propan-2-yl)phenyl]methyl}pyrrolidine-2-carboxamide;

1-(1-acetyl-4-methylazepane-4-carbonyl)-4-fluoro-N-{phenyl[4-(propan-2-yl)phenyl]methyl}pyrrolidine-2-carboxamide;

1-(1-acetylazepane-4-carbonyl)-4-fluoro-N-{phenyl[4-(propan-2-yl)phenyl]methyl}pyrrolidine-2-carboxamide;

1-(1-acetylpiperidine-3-carbonyl)-4-fluoro-N-{phenyl[4-(propan-2-yl)phenyl]methyl}pyrrolidine-2-carboxamide;

1-(4-acetylmorpholine-3-carbonyl)-4-fluoro-N-{phenyl[4-(propan-2-yl)phenyl]methyl}pyrrolidine-2-carboxamide;

1-(2-{2-acetyl-2-azaspiro[3.4]octan-5-yl}acetyl)-4-fluoro-N-{phenyl[4-(propan-2-yl)phenyl]methyl}pyrrolidine-2-carboxamide;

1-{2-acetyl-2-azaspiro[4.4]nonane-6-carbonyl}-4-fluoro-N-{phenyl[4-(propan-2-yl)phenyl]methyl}pyrrolidine-2-carboxamide;

1-{2-acetyl-2-azabicyclo[2.2.2]octane-6-carbonyl}-4-fluoro-N-{phenyl[4-(propan-2-yl)phenyl]methyl}pyrrolidine-2-carboxamide;

1-[2-(1-acetylpiperidin-3-yl)acetyl]-4-fluoro-N-{phenyl[4-(propan-2-yl)phenyl]methyl}pyrrolidine-2-carboxamide;

1-(4-acetyl-1,4-oxazepane-2-carbonyl)-4-fluoro-N-{phenyl[4-(propan-2-yl)phenyl]methyl}pyrrolidine-2-carboxamide;

1-(1-acetyl-4-methylpiperidine-3-carbonyl)-4-fluoro-N-{phenyl[4-(propan-2-yl)phenyl]methyl}pyrrolidine-2-carboxamide;

1-(4-acetyl-2-methylmorpholine-3-carbonyl)-4-fluoro-N-{phenyl[4-(propan-2-yl)phenyl]methyl}pyrrolidine-2-carboxamide;

1-{5-acetyl-hexahydro-2H-furo[2,3-c]pyrrole-3-carbonyl}-4-fluoro-N-{phenyl[4-(propan-2-yl)phenyl]methyl}pyrrolidine-2-carboxamide;

1-{3-acetyl-3-azabicyclo[3.1.0]hexane-1-carbonyl}-4-fluoro-N-{phenyl[4-(propan-2-yl)phenyl]methyl}pyrrolidine-2-carboxamide;

1-{2-acetyl-octahydrocyclopenta[c]pyrrole-4-carbonyl}-4-fluoro-N-{phenyl[4-(propan-2-yl)phenyl]methyl}pyrrolidine-2-carboxamide;

1-{8-acetyl-8-azabicyclo[3.2.1]octane-3-carbonyl}-4-fluoro-N-{phenyl[4-(propan-2-yl)phenyl]methyl}pyrrolidine-2-carboxamide;

1-(1-acetyl-3-methylazetidine-3-carbonyl)-4-fluoro-N-{phenyl[4-(propan-2-yl)phenyl]methyl}pyrrolidine-2-carboxamide;

1-{5-acetyl-hexahydro-2H-furo[2,3-c]pyrrole-2-carbonyl}-4-fluoro-N-{phenyl[4-(propan-2-yl)phenyl]methyl}pyrrolidine-2-carboxamide;

1-{3-acetyl-3-azabicyclo[3.2.1]octane-8-carbonyl}-4-fluoro-N-{phenyl[4-(propan-2-yl)phenyl]methyl}pyrrolidine-2-carboxamide;

1-(2-acetyl-octahydro-1H-isoindole-4-carbonyl)-4-fluoro-N-{phenyl[4-(propan-2-yl)phenyl]methyl}pyrrolidine-2-carboxamide;

1-{7-acetyl-7-azabicyclo[2.2.1]heptane-2-carbonyl}-4-fluoro-N-{phenyl[4-(propan-2-yl)phenyl]methyl}pyrrolidine-2-carboxamide;

1-{2-acetyl-5-oxa-2-azaspiro[3.4]octane-7-carbonyl}-4-fluoro-N-{phenyl[4-(propan-2-yl)phenyl]methyl}pyrrolidine-2-carboxamide;

1-[2-(1-acetyl-3-methylazetidin-3-yl)acetyl]-4-fluoro-N-{phenyl[4-(propan-2-yl)phenyl]methyl}pyrrolidine-2-carboxamide;

1-{2-acetyl-5-oxa-2-azaspiro[3.4]octane-6-carbonyl}-4-fluoro-N-{phenyl[4-(propan-2-yl)phenyl]methyl}pyrrolidine-2-carboxamide;

1-(1-acetyl-2-methylpiperidine-3-carbonyl)-4-fluoro-N-{phenyl[4-(propan-2-yl)phenyl]methyl}pyrrolidine-2-carboxamide;

4-fluoro-1-{3-[N-(1-methyl-1H-pyrazol-3-yl)acetamido]propanoyl}-N-{phenyl[4-(propan-2-yl)phenyl]methyl}pyrrolidine-2-carboxamide;

1-(1-acetyl-3-fluoroazetidine-3-carbonyl)-4-fluoro-N-{phenyl[4-(propan-2-yl)phenyl]methyl}pyrrolidine-2-carboxamide;

1-[2-(1-acetyl-3-methoxyazetidin-3-yl)acetyl]-4-fluoro-N-{phenyl[4-(propan-2-yl)phenyl]methyl}pyrrolidine-2-carboxamide;

1-{4-acetyl-hexahydro-2H-furo[3,2-b]pyrrole-6-carbonyl}-4-fluoro-N-{phenyl[4-(propan-2-yl)phenyl]methyl}pyrrolidine-2-carboxamide;

1-(1-acetyl-4-ethylpyrrolidine-3-carbonyl)-4-fluoro-N-{phenyl[4-(propan-2-yl)phenyl]methyl}pyrrolidine-2-carboxamide;

1-{7-acetyl-1-oxo-2,7-diazaspiro[4.4]nonane-4-carbonyl}-4-fluoro-N-{phenyl[4-(propan-2-yl)phenyl]methyl}pyrrolidine-2-carboxamide;

4-fluoro-N-{[3-fluoro-4-(propan-2-yl)phenyl](phenyl)methyl}-1-[1-(1,3,4-oxadiazol-2-yl)cyclopropanecarbonyl]pyrrolidine-2-carboxamide;

2-[4-fluoro-2-({[3-fluoro-4-(propan-2-yl)phenyl](phenyl)methyl}carbamoyl)pyrrolidin-1-yl]-2-oxoethyl N,N-dimethylcarbamate;

1-[2-(1H-1,3-benzodiazol-1-yl)acetyl]-4-fluoro-N-{[3-fluoro-4-(propan-2-yl)phenyl](phenyl)methyl}pyrrolidine-2-carboxamide;

1-[2-(1H-1,3-benzodiazol-1-yl)acetyl]-N-[(4-cyclopropyl-3-fluorophenyl)(phenyl)methyl]-4-fluoropyrrolidine-2-carboxamide;

2-[4-fluoro-2-({phenyl[5-(propan-2-yl)pyridin-2-yl]methyl}carbamoyl)pyrrolidin-1-yl]-2-oxoethyl N,N-dimethylcarbamate;

4-fluoro-N-{[3-fluoro-4-(propan-2-yl)phenyl](phenyl)methyl}-1-[2-(1-methyl-1H-1,2,3-triazol-4-yl)acetyl]pyrrolidine-2-carboxamide;

N-[(4-cyclopropyl-3-fluorophenyl)(phenyl)methyl]-4-fluoro-1-[2-(5-methyl-2,4-dioxo-1,2,3,4-tetrahydropyrimidin-1-yl)acetyl]pyrrolidine-2-carboxamide;

4-fluoro-N-{[3-fluoro-4-(propan-2-yl)phenyl](phenyl)methyl}-1-[2-(5-methyl-2,4-dioxo-1,2,3,4-tetrahydropyrimidin-1-yl)acetyl]pyrrolidine-2-carboxamide;

1-{2-[(dimethylcarbamoyl)amino]acetyl}-4-fluoro-N-{phenyl[5-(propan-2-yl)pyridin-2-yl]methyl}pyrrolidine-2-carboxamide;

N-[(4-cyclopropyl-3-fluorophenyl)(phenyl)methyl]-1-{2-[(dimethylcarbamoyl)amino]acetyl}-4-fluoropyrrolidine-2-carboxamide;

4-fluoro-1-[2-(5-methyl-2,4-dioxo-1,2,3,4-tetrahydropyrimidin-1-yl)acetyl]-N-{phenyl[5-(propan-2-yl)pyridin-2-yl]methyl}pyrrolidine-2-carboxamide;

4-fluoro-N-{phenyl[5-(propan-2-yl)pyridin-2-yl]methyl}-1-[2-(quinolin-5-yl)acetyl]pyrrolidine-2-carboxamide;

tert-butyl 4-({2-[4-fluoro-2-({[3-fluoro-4-(propan-2-yl)phenyl](phenyl)methyl}carbamoyl)pyrrolidin-1-yl]-2-oxoethyl}carbamoyl)piperazine-1-carboxylate;

N-[(4-cyclopropyl-3-fluorophenyl)(phenyl)methyl]-1-[2-(3,5-dimethyl-1H-pyrazol-4-yl)acetyl]-4-fluoropyrrolidine-2-carboxamide;

N-{2-[4-fluoro-2-({[3-fluoro-4-(propan-2-yl)phenyl](phenyl)methyl}carbamoyl)pyrrolidin-1-yl]-2-oxoethyl}piperazine-1-carboxamide;

N-[(4-cyclopropyl-3-fluorophenyl)(phenyl)methyl]-4-fluoro-1-[2-(quinolin-5-yl)acetyl]pyrrolidine-2-carboxamide;

4-fluoro-N-{phenyl[5-(propan-2-yl)pyridin-2-yl]methyl}-1-[2-(1H-1,2,3,4-tetrazol-1-yl)acetyl]pyrrolidine-2-carboxamide;

1-[2-(4-acetylpiperazin-1-yl)acetyl]-4-fluoro-N-{phenyl[4-(propan-2-yl)phenyl]methyl}pyrrolidine-2-carboxamide;

4-fluoro-1-[2-(5-methyl-2-oxo-2,3-dihydro-1,3,4-oxadiazol-3-yl)acetyl]-N-{phenyl[4-(propan-2-yl)phenyl]methyl}pyrrolidine-2-carboxamide;

1-[2-(3,5-dimethyl-2,4-dioxo-1,2,3,4-tetrahydropyrimidin-1-yl)acetyl]-4-fluoro-N-{[3-fluoro-4-(propan-2-yl)phenyl](phenyl)methyl}pyrrolidine-2-carboxamide;

4-fluoro-N-{[6-fluoro-5-(propan-2-yl)pyridin-2-yl](phenyl)methyl}-1-[2-(1H-1,2,3-triazol-5-yl)acetyl]pyrrolidine-2-carboxamide;

1-{2-[(dimethylcarbamoyl)(methyl)amino]acetyl}-4-fluoro-N-{[3-fluoro-4-(propan-2-yl)phenyl](phenyl)methyl}pyrrolidine-2-carboxamide;

4-fluoro-N-{[3-fluoro-4-(propan-2-yl)phenyl](phenyl)methyl}-1-(2-oxo-1,3-oxazolidine-5-carbonyl)pyrrolidine-2-carboxamide;

2-[4-fluoro-2-({[3-fluoro-4-(propan-2-yl)phenyl](phenyl)methyl}carbamoyl)pyrrolidin-1-yl]-2-oxoethyl piperazine-1-carboxylate;

1-[2-(3,5-dimethyl-1H-pyrazol-4-yl)acetyl]-4-fluoro-N-{phenyl[5-(propan-2-yl)pyridin-2-yl]methyl}pyrrolidine-2-carboxamide;

1-tert-butyl 4-{2-[4-fluoro-2-({[3-fluoro-4-(propan-2-yl)phenyl](phenyl)methyl}carbamoyl)pyrrolidin-1-yl]-2-oxoethyl} piperazine-1,4-dicarboxylate;

1-{2-[5-(difluoromethyl)-1,3,4-oxadiazol-2-yl]acetyl}-4-fluoro-N-{phenyl[5-(propan-2-yl)pyridin-2-yl]methyl}pyrrolidine-2-carboxamide;

1-[2-(1H-1,3-benzodiazol-1-yl)acetyl]-4-fluoro-N-{phenyl[5-(propan-2-yl)pyridin-2-yl]methyl}pyrrolidine-2-carboxamide;

1-{2-[5-(difluoromethyl)-1,3,4-oxadiazol-2-yl]acetyl}-4-fluoro-N-{[3-fluoro-4-(propan-2-yl)phenyl](phenyl)methyl}pyrrolidine-2-carboxamide;

tert-butyl N-({5-[2-(2-{[(4-cyclopropyl-3-fluorophenyl)(phenyl)methyl]carbamoyl}-4-fluoropyrrolidin-1-yl)-2-oxoethyl]-1,3,4-oxadiazol-2-yl}methyl)carbamate;

4-fluoro-N-{[3-fluoro-4-(propan-2-yl)phenyl](phenyl)methyl}-1-[2-(pyridazin-4-yl)acetyl]pyrrolidine-2-carboxamide;

4-fluoro-N-{phenyl[5-(propan-2-yl)pyridin-2-yl]methyl}-1-{2-[5-(trifluoromethyl)-2H-1,2,3,4-tetrazol-2-yl]acetyl}pyrrolidine-2-carboxamide;

4-fluoro-N-{[3-fluoro-4-(propan-2-yl)phenyl](phenyl)methyl}-5-methyl-1-[2-(1H-1,2,3-triazol-5-yl)acetyl]pyrrolidine-2-carboxamide;

4-fluoro-N-{[3-fluoro-4-(propan-2-yl)phenyl](phenyl)methyl}-1-[2-(pyridazin-3-yl)acetyl]pyrrolidine-2-carboxamide;

N-[(5-cyclopropylpyridin-2-yl)(phenyl)methyl]-4-fluoro-1-[2-(1H-1,2,3-triazol-5-yl)acetyl]pyrrolidine-2-carboxamide;

N-[(4-cyclopropyl-3-fluorophenyl)(phenyl)methyl]-4-fluoro-1-[2-(2-oxopiperazin-1-yl)acetyl]pyrrolidine-2-carboxamide;

N-[2-(2-{[(4-cyclopropyl-3-fluorophenyl)(phenyl)methyl]carbamoyl}-4-fluoropyrrolidin-1-yl)-2-oxoethyl]-4-methylpiperazine-1-carboxamide;

N-[2-(2-{[(4-cyclopropyl-3-fluorophenyl)(phenyl)methyl]carbamoyl}-4-fluoropyrrolidin-1-yl)-2-oxoethyl]-4-(2,2,2-trifluoroethyl)piperazine-1-carboxamide;

N-{2-[4-fluoro-2-({phenyl[5-(propan-2-yl)pyridin-2-yl]methyl}carbamoyl)pyrrolidin-1-yl]-2-oxoethyl}-4-(2,2,2-trifluoroethyl)piperazine-1-carboxamide;

N-[2-(2-{[(4-cyclopropyl-3-fluorophenyl)(phenyl)methyl]carbamoyl}-4-fluoropyrrolidin-1-yl)-2-oxoethyl]-4-(2-methoxyethyl)piperazine-1-carboxamide;

1-{2-[5-(aminomethyl)-1,3,4-oxadiazol-2-yl]acetyl}-N-[(4-cyclopropyl-3-fluorophenyl)(phenyl)methyl]-4-fluoropyrrolidine-2-carboxamide;

4-fluoro-N-{[3-fluoro-4-(propan-2-yl)phenyl](phenyl)methyl}-1-[2-(5-methyl-1H-1,2,3-triazol-1-yl)acetyl]pyrrolidine-2-carboxamide;

4-fluoro-N-{[3-fluoro-4-(propan-2-yl)phenyl](phenyl)methyl}-1-[2-(4-methyl-1H-1,2,3-triazol-1-yl)acetyl]pyrrolidine-2-carboxamide;

4-fluoro-N-{[3-fluoro-4-(propan-2-yl)phenyl](phenyl)methyl}-1-{2-[4-(piperazin-1-yl)-2H-1,2,3-triazol-2-yl]acetyl}pyrrolidine-2-carboxamide;

N-[2-(2-{[(4-cyclopropyl-3-fluorophenyl)(phenyl)methyl]carbamoyl}-4-fluoropyrrolidin-1-yl)-2-oxoethyl]-4-(cyclopropylmethyl)piperazine-1-carboxamide;

4-(cyclopropylmethyl)-N-{2-[4-fluoro-2-({phenyl[5-(propan-2-yl)pyridin-2-yl]methyl}carbamoyl)pyrrolidin-1-yl]-2-oxoethyl}piperazine-1-carboxamide;

N-{2-[4-fluoro-2-({phenyl[5-(propan-2-yl)pyridin-2-yl]methyl}carbamoyl)pyrrolidin-1-yl]-2-oxoethyl}-4-methylpiperazine-1-carboxamide;

4-fluoro-N-{[3-fluoro-4-(propan-2-yl)phenyl](phenyl)methyl}-1-[2-(4-methyl-1H-1,2,3-triazol-5-yl)acetyl]pyrrolidine-2-carboxamide;

4-fluoro-N-{[3-fluoro-4-(propan-2-yl)phenyl](phenyl)methyl}-1-{2-[4-(trifluoromethyl)-1H-1,2,3-triazol-1-yl]acetyl}pyrrolidine-2-carboxamide;

4-fluoro-1-[2-(2-methylquinolin-5-yl)acetyl]-N-{phenyl[5-(propan-2-yl)pyridin-2-yl]methyl}pyrrolidine-2-carboxamide;

tert-butyl N-[(5-{2-[4-fluoro-2-({phenyl[4-(propan-2-yl)phenyl]methyl}carbamoyl)pyrrolidin-1-yl]-2-oxoethyl}-1,3,4-oxadiazol-2-yl)methyl]carbamate;

1-{2-[5-(aminomethyl)-1,3,4-oxadiazol-2-yl]acetyl}-4-fluoro-N-{phenyl[4-(propan-2-yl)phenyl]methyl}pyrrolidine-2-carboxamide;

1-{2-[4-(dimethylamino)-1H-1,2,3-triazol-1-yl]acetyl}-4-fluoro-N-{[3-fluoro-4-(propan-2-yl)phenyl](phenyl)methyl}pyrrolidine-2-carboxamide;

tert-butyl 4-(5-{2-[4-fluoro-2-({[3-fluoro-4-(propan-2-yl)phenyl](phenyl)methyl}carbamoyl)pyrrolidin-1-yl]-2-oxoethyl}-1H-1,2,3-triazol-4-yl)piperazine-1-carboxylate;

4-fluoro-N-{[3-fluoro-4-(propan-2-yl)phenyl](phenyl)methyl}-1-(2-{3-oxo-2H,3H-[1,2,4]triazolo[4,3-a]pyridin-8-yl}acetyl)pyrrolidine-2-carboxamide;

4-fluoro-N-{[3-fluoro-4-(propan-2-yl)phenyl](phenyl)methyl}-1-{2-[5-(trifluoromethyl)-1H-1,2,3-triazol-1-yl]acetyl}pyrrolidine-2-carboxamide;

1-{2-[4-(dimethylamino)-2H-1,2,3-triazol-2-yl]acetyl}-4-fluoro-N-{[3-fluoro-4-(propan-2-yl)phenyl](phenyl)methyl}pyrrolidine-2-carboxamide;

1-[2-(3,5-dimethyl-2,4-dioxo-1,2,3,4-tetrahydropyrimidin-1-yl)acetyl]-4-fluoro-N-{[6-fluoro-5-(propan-2-yl)pyridin-2-yl](phenyl)methyl}pyrrolidine-2-carboxamide;

1-{2-[5-(difluoromethyl)-2H-1,2,3,4-tetrazol-2-yl]acetyl}-4-fluoro-N-{phenyl[5-(propan-2-yl)pyridin-2-yl]methyl}pyrrolidine-2-carboxamide;

1-{2-[5-(acetamidomethyl)-1,3,4-oxadiazol-2-yl]acetyl}-4-fluoro-N-{phenyl[4-(propan-2-yl)phenyl]methyl}pyrrolidine-2-carboxamide;

1-{2-[5-(aminomethyl)-1H-1,2,3-triazol-1-yl]acetyl}-4-fluoro-N-{phenyl[4-(propan-2-yl)phenyl]methyl}pyrrolidine-2-carboxamide;

1-(2-{5-[(dimethylamino)methyl]-1H-1,2,3-triazol-1-yl}acetyl)-4-fluoro-N-{phenyl[4-(propan-2-yl)phenyl]methyl}pyrrolidine-2-carboxamide;

4-fluoro-N-{[3-fluoro-4-(propan-2-yl)phenyl](phenyl)methyl}-1-{2-[4-(piperazin-1-yl)-1H-1,2,3-triazol-5-yl]acetyl}pyrrolidine-2-carboxamide;

4-fluoro-N-{[3-fluoro-4-(propan-2-yl)phenyl](phenyl)methyl}-1-{2-[4-(morpholin-4-yl)-1H-1,2,3-triazol-5-yl]acetyl}pyrrolidine-2-carboxamide;

1-(2-{5-[(dimethylamino)methyl]-1,3,4-oxadiazol-2-yl}acetyl)-4-fluoro-N-{phenyl[4-(propan-2-yl)phenyl]methyl}pyrrolidine-2-carboxamide;

4-fluoro-N-{[3-fluoro-4-(propan-2-yl)phenyl](phenyl)methyl}-1-[2-(4H-1,2,4-triazol-4-yl)acetyl]pyrrolidine-2-carboxamide;

N-[(4-cyclopropyl-3-fluorophenyl)(phenyl)methyl]-4-fluoro-1-[2-(4H-1,2,4-triazol-4-yl)acetyl]pyrrolidine-2-carboxamide;

N-[(4-cyclopropyl-3-fluorophenyl)(phenyl)methyl]-4-fluoro-1-[2-(1H-indazol-3-yl)acetyl]pyrrolidine-2-carboxamide;

4-fluoro-N-{[3-fluoro-4-(propan-2-yl)phenyl](phenyl)methyl}-1-{2-[5-(trifluoromethyl)-1H-1,2,3,4-tetrazol-1-yl]acetyl}pyrrolidine-2-carboxamide;

1-[2-(1H-1,2,3-benzotriazol-1-yl)acetyl]-N-[(4-cyclopropyl-3-fluorophenyl)(phenyl)methyl]-4-fluoropyrrolidine-2-carboxamide;

N-[(4-cyclopropyl-3-fluorophenyl)(phenyl)methyl]-4-fluoro-1-[2-(3-methyl-2-oxo-2,3-dihydro-1H-1,3-benzodiazol-1-yl)acetyl]pyrrolidine-2-carboxamide;

N-[(4-cyclopropyl-3-fluorophenyl)(phenyl)methyl]-4-fluoro-1-[2-(3-methyl-2,4-dioxo-1,2,3,4-tetrahydropyrimidin-1-yl)acetyl]pyrrolidine-2-carboxamide;

N-[(4-cyclopropyl-3-fluorophenyl)(phenyl)methyl]-4-fluoro-1-[2-(2-oxo-2,3-dihydro-1H-1,3-benzodiazol-1-yl)acetyl]pyrrolidine-2-carboxamide;

N-[(4-cyclopropyl-3-fluorophenyl)(phenyl)methyl]-4-fluoro-1-[2-(1-oxo-2,3-dihydro-1H-isoindol-2-yl)acetyl]pyrrolidine-2-carboxamide;

N-[2-(2-{[(4-cyclopropyl-3-fluorophenyl)(phenyl)methyl]carbamoyl}-4-fluoropyrrolidin-1-yl)-2-oxoethyl]morpholine-4-carboxamide;

N-[(4-cyclopropyl-3-fluorophenyl)(phenyl)methyl]-4-fluoro-1-[2-(1-methyl-1H-indol-3-yl)acetyl]pyrrolidine-2-carboxamide;

N-[(4-cyclopropyl-3-fluorophenyl)(phenyl)methyl]-4-fluoro-1-[2-(1-methyl-1H-indol-2-yl)acetyl]pyrrolidine-2-carboxamide;

2-(2-{[(4-cyclopropyl-3-fluorophenyl)(phenyl)methyl]carbamoyl}-4-fluoropyrrolidin-1-yl)-2-oxoethyl azetidine-1-carboxylate;

N-[(4-cyclopropyl-3-fluorophenyl)(phenyl)methyl]-4-fluoro-1-[2-(1-methyl-1H-indazol-3-yl)acetyl]pyrrolidine-2-carboxamide;

N-[(4-cyclopropyl-3-fluorophenyl)(phenyl)methyl]-4-fluoro-1-[2-(2-oxo-2,3-dihydro-1H-indol-1-yl)acetyl]pyrrolidine-2-carboxamide;

N-[(4-cyclopropyl-3-fluorophenyl)(phenyl)methyl]-4-fluoro-1-[2-(2-methyl-1H-1,3-benzodiazol-1-yl)acetyl]pyrrolidine-2-carboxamide;

1-{2-[5-(acetamidomethyl)-1H-1,2,3-triazol-1-yl]acetyl}-4-fluoro-N-{phenyl[4-(propan-2-yl)phenyl]methyl}pyrrolidine-2-carboxamide;

4-fluoro-1-[2-(5-oxo-4,5-dihydro-1H-1,2,4-triazol-3-yl)acetyl]-N-{phenyl[5-(propan-2-yl)pyridin-2-yl]methyl}pyrrolidine-2-carboxamide;

N-[(4-cyclopropyl-3-fluorophenyl)(phenyl)methyl]-4-fluoro-1-[2-(5-oxo-4,5-dihydro-1H-1,2,4-triazol-3-yl)acetyl]pyrrolidine-2-carboxamide;

N-[(4-cyclopropyl-3-fluorophenyl)(phenyl)methyl]-4-fluoro-1-[2-(5-oxo-4,5-dihydro-1,2,4-oxadiazol-3-yl)acetyl]pyrrolidine-2-carboxamide;

N-[(4-cyclopropyl-3-fluorophenyl)(phenyl)methyl]-4-fluoro-1-[2-(1-methyl-2-oxo-2,3-dihydro-1H-indol-3-yl)acetyl]pyrrolidine-2-carboxamide;

N-[(4-cyclopropyl-3-fluorophenyl)(phenyl)methyl]-4-fluoro-1-[2-(4-methyl-1H-imidazol-1-yl)acetyl]pyrrolidine-2-carboxamide;

1-{2-[5-(difluoromethyl)-1H-1,2,3,4-tetrazol-1-yl]acetyl}-4-fluoro-N-{phenyl[5-(propan-2-yl)pyridin-2-yl]methyl}pyrrolidine-2-carboxamide;

2-(2-{[(4-cyclopropyl-3-fluorophenyl)(phenyl)methyl]carbamoyl}-4-fluoropyrrolidin-1-yl)-2-oxoethyl 4-(cyclopropylmethyl)piperazine-1-carboxylate;

2-(2-{[(4-cyclopropyl-3-fluorophenyl)(phenyl)methyl]carbamoyl}-4-fluoropyrrolidin-1-yl)-2-oxoethyl 4-methylpiperazine-1-carboxylate;

N-[(4-cyclopropyl-3-fluorophenyl)(phenyl)methyl]-4-fluoro-1-[2-(2-oxo-2,3-dihydro-1H-indol-3-yl)acetyl]pyrrolidine-2-carboxamide;

N-[(4-cyclopropyl-3-fluorophenyl)(phenyl)methyl]-4-fluoro-1-(2-{imidazo[1,2-a]pyridin-3-yl}acetyl)pyrrolidine-2-carboxamide;

N-[(4-cyclopropyl-3-fluorophenyl)(phenyl)methyl]-4-fluoro-1-(2-{[1,2,4]triazolo[1,5-a]pyridin-6-yl}acetyl)pyrrolidine-2-carboxamide;

4-fluoro-N-{[3-fluoro-4-(propan-2-yl)phenyl](phenyl)methyl}-1-{2-[4-(trifluoromethyl)-1H-1,2,3-triazol-5-yl]acetyl}pyrrolidine-2-carboxamide;

N-[(4-cyclopropyl-3-fluorophenyl)(phenyl)methyl]-4-fluoro-1-{2-[(pyrazin-2-yl)amino]acetyl}pyrrolidine-2-carboxamide;

4-fluoro-N-{[3-fluoro-4-(propan-2-yl)phenyl](phenyl)methyl}-1-{2-[4-(piperazin-1-yl)-1H-1,2,3-triazol-1-yl]acetyl}pyrrolidine-2-carboxamide;

N-[(4-cyclopropyl-3-fluorophenyl)(phenyl)methyl]-1-{2-[(2-ethyl-2H-1,2,3-triazol-4-yl)amino]acetyl}-4-fluoropyrrolidine-2-carboxamide;

4-fluoro-N-{[6-fluoro-5-(propan-2-yl)pyridin-2-yl](phenyl)methyl}-1-[2-(5-methyl-2,4-dioxo-1,2,3,4-tetrahydropyrimidin-1-yl)acetyl]pyrrolidine-2-carboxamide;

N-[(4-cyclopropyl-3-fluorophenyl)(phenyl)methyl]-1-{2-[(1-ethyl-1H-1,2,3-triazol-4-yl)amino]acetyl}-4-fluoropyrrolidine-2-carboxamide;

N-[(4-cyclopropyl-3-fluorophenyl)(phenyl)methyl]-4-fluoro-1-[2-(2-methylquinolin-6-yl)acetyl]pyrrolidine-2-carboxamide;

2-(2-{[(4-cyclopropyl-3-fluorophenyl)(phenyl)methyl]carbamoyl}-4-fluoropyrrolidin-1-yl)-2-oxoethyl 4-(2-methoxyethyl)piperazine-1-carboxylate;

N-[(4-cyclopropyl-3-fluorophenyl)(phenyl)methyl]-4-fluoro-1-{2-[2-oxo-4-(2,2,2-trifluoroethyl)piperazin-1-yl]acetyl}pyrrolidine-2-carboxamide;

N-[(4-cyclopropyl-3-fluorophenyl)(phenyl)methyl]-4-fluoro-1-{2-[methyl(2-methylpyrimidin-4-yl)amino]acetyl}pyrrolidine-2-carboxamide;

N-[(4-cyclopropyl-3-fluorophenyl)(phenyl)methyl]-4-fluoro-1-[2-(2-methylquinolin-5-yl)acetyl]pyrrolidine-2-carboxamide;

N-[(4-cyclopropyl-3-fluorophenyl)(phenyl)methyl]-4-fluoro-1-{2-[(2-methylpyrimidin-4-yl)amino]acetyl}pyrrolidine-2-carboxamide;

4-fluoro-1-[2-(4-methyl-5-oxo-4,5-dihydro-1,2,4-oxadiazol-3-yl)acetyl]-N-{phenyl[5-(propan-2-yl)pyridin-2-yl]methyl}pyrrolidine-2-carboxamide;

N-[(4-cyclopropyl-3-fluorophenyl)(phenyl)methyl]-4-fluoro-1-{2-[methyl(pyrazin-2-yl)amino]acetyl}pyrrolidine-2-carboxamide;

4-fluoro-1-(2-{3-oxo-2H,3H-[1,2,4]triazolo[4,3-a]pyridin-8-yl}acetyl)-N-{phenyl[5-(propan-2-yl)pyridin-2-yl]methyl}pyrrolidine-2-carboxamide;

2-(2-{[(4-cyclopropyl-3-fluorophenyl)(phenyl)methyl]carbamoyl}-4-fluoropyrrolidin-1-yl)-2-oxoethyl 4-(2,2,2-trifluoroethyl)piperazine-1-carboxylate;

N-[(5-cyclopropyl-6-fluoropyridin-2-yl)(phenyl)methyl]-4-fluoro-1-[2-(4H-1,2,4-triazol-4-yl)acetyl]pyrrolidine-2-carboxamide;

4-fluoro-N-{[6-fluoro-5-(propan-2-yl)pyridin-2-yl](phenyl)methyl}-1-[2-(4H-1,2,4-triazol-4-yl)acetyl]pyrrolidine-2-carboxamide;

1-[2-(1H-1,3-benzodiazol-1-yl)acetyl]-N-[(5-cyclopropyl-6-fluoropyridin-2-yl)(phenyl)methyl]-4-fluoropyrrolidine-2-carboxamide;

1-[2-(1H-1,3-benzodiazol-1-yl)acetyl]-4-fluoro-N-{[6-fluoro-5-(propan-2-yl)pyridin-2-yl](phenyl)methyl}pyrrolidine-2-carboxamide;

N-[(4-cyclopropyl-3-fluorophenyl)(phenyl)methyl]-1-{2-[4-(dimethylamino)-2H-1,2,3-triazol-2-yl]acetyl}-4-fluoropyrrolidine-2-carboxamide;

N-[(4-cyclopropyl-3-fluorophenyl)(phenyl)methyl]-1-{2-[4-(dimethylamino)-1H-1,2,3-triazol-1-yl]acetyl}-4-fluoropyrrolidine-2-carboxamide;

1-{2-[4-(dimethylamino)-1H-1,2,3-triazol-1-yl]acetyl}-4-fluoro-N-{phenyl[5-(propan-2-yl)pyridin-2-yl]methyl}pyrrolidine-2-carboxamide;

N-[(4-cyclopropyl-3-fluorophenyl)(phenyl)methyl]-4-fluoro-1-(2-{3-oxo-2H,3H-[1,2,4]triazolo[4,3-a]pyridin-8-yl}acetyl)pyrrolidine-2-carboxamide;

4-fluoro-N-{[6-fluoro-5-(propan-2-yl)pyridin-2-yl](phenyl)methyl}-1-(2-{3-oxo-2H,3H-[1,2,4]triazolo[4,3-a]pyridin-8-yl}acetyl)pyrrolidine-2-carboxamide;

4-fluoro-N-{[6-fluoro-5-(propan-2-yl)pyridin-2-yl](phenyl)methyl}-1-[2-(2-methylquinolin-5-yl)acetyl]pyrrolidine-2-carboxamide;

tert-butyl 2-[2-(2-{[(4-cyclopropyl-3-fluorophenyl)(phenyl)methyl]carbamoyl}-4-fluoropyrrolidin-1-yl)-2-oxoethyl]-1H-indole-1-carboxylate;

1-{2-[4-(dimethylamino)-2H-1,2,3-triazol-2-yl]acetyl}-4-fluoro-N-{phenyl[5-(propan-2-yl)pyridin-2-yl]methyl}pyrrolidine-2-carboxamide;

N-[(4-cyclopropyl-3-fluorophenyl)(phenyl)methyl]-4-fluoro-1-[2-(1H-indol-2-yl)acetyl]pyrrolidine-2-carboxamide;

1-[2-(carbamoylamino)acetyl]-4-fluoro-N-{[6-fluoro-5-(propan-2-yl)pyridin-2-yl](phenyl)methyl}pyrrolidine-2-carboxamide;

1-{2-[4-(dimethylamino)-1H-1,2,3-triazol-1-yl]acetyl}-4-fluoro-N-{[6-fluoro-5-(propan-2-yl)pyridin-2-yl](phenyl)methyl}pyrrolidine-2-carboxamide;

N-[(4-cyclopropyl-3-fluorophenyl)(phenyl)methyl]-1-{2-[(2-ethyl-2H-1,2,3-triazol-4-yl)(methyl)amino]acetyl}-4-fluoropyrrolidine-2-carboxamide;

N-[(4-cyclopropyl-3-fluorophenyl)(phenyl)methyl]-1-{2-[(1-ethyl-1H-1,2,3-triazol-4-yl)(methyl)amino]acetyl}-4-fluoropyrrolidine-2-carboxamide;

N-[(5-cyclopropyl-6-fluoropyridin-2-yl)(phenyl)methyl]-4-fluoro-1-[2-(5-methyl-2,4-dioxo-1,2,3,4-tetrahydropyrimidin-1-yl)acetyl]pyrrolidine-2-carboxamide;

N-[(5-cyclopropyl-6-fluoropyridin-2-yl)(phenyl)methyl]-1-{2-[4-(dimethylamino)-1H-1,2,3-triazol-1-yl]acetyl}-4-fluoropyrrolidine-2-carboxamide;

1-{2-[4-(dimethylamino)-2H-1,2,3-triazol-2-yl]acetyl}-4-fluoro-N-{[6-fluoro-5-(propan-2-yl)pyridin-2-yl](phenyl)methyl}pyrrolidine-2-carboxamide;

N-[(5-cyclopropyl-6-fluoropyridin-2-yl)(phenyl)methyl]-1-{2-[5-(dimethylamino)-1H-1,2,3-triazol-1-yl]acetyl}-4-fluoropyrrolidine-2-carboxamide;

4-fluoro-N-{phenyl[5-(propan-2-yl)pyridin-2-yl]methyl}-1-[2-(4H-1,2,4-triazol-4-yl)acetyl]pyrrolidine-2-carboxamide;

N-[(4-cyclopropyl-3-fluorophenyl)(phenyl)methyl]-4-fluoro-1-[3-(5-oxo-4,5-dihydro-1H-1,2,4-triazol-3-yl)propanoyl]pyrrolidine-2-carboxamide;

N-[(4-cyclopropyl-3-fluorophenyl)(phenyl)methyl]-4-fluoro-1-[2-(4-methyl-5-oxo-4,5-dihydro-1,2,4-oxadiazol-3-yl)acetyl]pyrrolidine-2-carboxamide;

4-fluoro-1-[2-(5-oxo-4,5-dihydro-1,2,4-oxadiazol-3-yl)acetyl]-N-{phenyl[5-(propan-2-yl)pyridin-2-yl]methyl}pyrrolidine-2-carboxamide;

1-{2-[(dimethylcarbamoyl)amino]acetyl}-4-fluoro-N-{[6-fluoro-5-(propan-2-yl)pyridin-2-yl](phenyl)methyl}pyrrolidine-2-carboxamide;

4-fluoro-1-{2-[(methylcarbamoyl)amino]acetyl}-N-{phenyl[5-(propan-2-yl)pyridin-2-yl]methyl}pyrrolidine-2-carboxamide;

4-fluoro-N-{[6-fluoro-5-(propan-2-yl)pyridin-2-yl](phenyl)methyl}-1-{2-[(2-methylpyrimidin-4-yl)amino]acetyl}pyrrolidine-2-carboxamide;

4-fluoro-N-{[6-fluoro-5-(propan-2-yl)pyridin-2-yl](phenyl)methyl}-1-{2-[(methylcarbamoyl)amino]acetyl}pyrrolidine-2-carboxamide;

4-fluoro-N-{[6-fluoro-5-(propan-2-yl)pyridin-2-yl](phenyl)methyl}-1-[2-(4-methyl-5-oxo-4,5-dihydro-1,3,4-oxadiazol-2-yl)acetyl]pyrrolidine-2-carboxamide;

1-{2-[(azetidine-1-carbonyl)amino]acetyl}-4-fluoro-N-{phenyl[5-(propan-2-yl)pyridin-2-yl]methyl}pyrrolidine-2-carboxamide;

1-{2-[(azetidine-1-carbonyl)amino]acetyl}-4-fluoro-N-{[6-fluoro-5-(propan-2-yl)pyridin-2-yl](phenyl)methyl}pyrrolidine-2-carboxamide;

4-fluoro-1-{2-[(2-methylpyrimidin-4-yl)amino]acetyl}-N-{phenyl[5-(propan-2-yl)pyridin-2-yl]methyl}pyrrolidine-2-carboxamide;

N-[(5-cyclopropyl-6-fluoropyridin-2-yl)(phenyl)methyl]-1-{2-[(dimethylcarbamoyl)amino]acetyl}-4-fluoropyrrolidine-2-carboxamide;

1-[2-(carbamoylamino)acetyl]-4-fluoro-N-{phenyl[5-(propan-2-yl)pyridin-2-yl]methyl}pyrrolidine-2-carboxamide;

4-fluoro-1-[2-(4-methyl-5-oxo-4,5-dihydro-1,3,4-oxadiazol-2-yl)acetyl]-N-{phenyl[5-(propan-2-yl)pyridin-2-yl]methyl}pyrrolidine-2-carboxamide;

4-fluoro-1-[3-(5-oxo-4,5-dihydro-1H-1,2,4-triazol-3-yl) propanoyl]-N-{phenyl[5-(propan-2-yl)pyridin-2-yl] methyl}pyrrolidine-2-carboxamide;

1-[2-(carbamoylamino)acetyl]-N-[(5-cyclopropyl-6-fluoropyridin-2-yl)(phenyl)methyl]-4-fluoropyrrolidine-2-carboxamide;

1-{2-[(azetidine-1-carbonyl)amino]acetyl}-N-[(5-cyclopropyl-6-fluoropyridin-2-yl)(phenyl)methyl]-4-fluoropyrrolidine-2-carboxamide;

N-[(5-cyclopropyl-6-fluoropyridin-2-yl)(phenyl)methyl]-4-fluoro-1-{2-[(methylcarbamoyl)amino] acetyl}pyrrolidine-2-carboxamide;

4-fluoro-1-[2-(1-methyl-5-oxo-4,5-dihydro-1H-1,2,4-triazol-3-yl)acetyl]-N-{phenyl[5-(propan-2-yl)pyridin-2-yl] methyl}pyrrolidine-2-carboxamide;

4-fluoro-N-{[6-fluoro-5-(propan-2-yl)pyridin-2-yl](phenyl) methyl}-1-[2-(4-methyl-5-oxo-4,5-dihydro-1,2,4-oxadiazol-3-yl)acetyl]pyrrolidine-2-carboxamide;

N-[(5-cyclopropyl-6-fluoropyridin-2-yl)(phenyl)methyl]-4-fluoro-1-{2-[(2-methylpyrimidin-4-yl)amino] acetyl}pyrrolidine-2-carboxamide;

N-[(5-cyclopropyl-6-fluoropyridin-2-yl)(phenyl)methyl]-4-fluoro-1-[2-(4-methyl-5-oxo-4,5-dihydro-1,3,4-oxadiazol-2-yl)acetyl]pyrrolidine-2-carboxamide;

N-[(5-cyclopropyl-6-fluoropyridin-2-yl)(phenyl)methyl]-4-fluoro-1-[2-(1,3-oxazol-2-yl)acetyl]pyrrolidine-2-carboxamide;

4-fluoro-1-[2-(1,3-oxazol-2-yl)acetyl]-N-{phenyl[5-(propan-2-yl)pyridin-2-yl]methyl}pyrrolidine-2-carboxamide;

N-[(5-cyclopropyl-6-fluoropyridin-2-yl)(phenyl)methyl]-1-{2-[5-(difluoromethyl)-1H-1,2,3,4-tetrazol-1-yl]acetyl}-4-fluoropyrrolidine-2-carboxamide;

1-{2-[5-(difluoromethyl)-1H-1,2,3,4-tetrazol-1-yl]acetyl}-4-fluoro-N-{[6-fluoro-5-(propan-2-yl)pyridin-2-yl](phenyl)methyl}pyrrolidine-2-carboxamide;

N-[(5-cyclopropyl-6-fluoropyridin-2-yl)(phenyl)methyl]-4-fluoro-1-[2-(1-methyl-5-oxo-4,5-dihydro-1H-1,2,4-triazol-3-yl)acetyl]pyrrolidine-2-carboxamide;

4-fluoro-N-{[6-fluoro-5-(propan-2-yl)pyridin-2-yl](phenyl) methyl}-1-[2-(1-methyl-5-oxo-4,5-dihydro-1H-1,2,4-triazol-3-yl)acetyl]pyrrolidine-2-carboxamide;

4-fluoro-N-{[6-fluoro-5-(propan-2-yl)pyridin-2-yl](phenyl) methyl}-1-{2-[4-(trifluoromethyl)-1H-1,2,3-triazol-5-yl] acetyl}pyrrolidine-2-carboxamide;

4-fluoro-N-{phenyl[5-(propan-2-yl)pyridin-2-yl]methyl}-1-{2-[4-(trifluoromethyl)-1H-1,2,3-triazol-5-yl] acetyl}pyrrolidine-2-carboxamide;

1-{2-[(dimethylcarbamoyl)amino]propanoyl}-4-fluoro-N-{[6-fluoro-5-(propan-2-yl)pyridin-2-yl](phenyl) methyl}pyrrolidine-2-carboxamide;

N-[(4-cyclopropyl-3-fluorophenyl)(phenyl)methyl]-1-{2-[(3,3-difluoroazetidine-1-carbonyl)amino]acetyl}-4-fluoropyrrolidine-2-carboxamide;

N-[(4-cyclopropyl-3-fluorophenyl)(phenyl)methyl]-4-fluoro-1-(2-{[3-(trifluoromethyl)azetidine-1-carbonyl] amino}acetyl)pyrrolidine-2-carboxamide;

N-[(5-cyclopropyl-6-fluoropyridin-2-yl)(phenyl)methyl]-4-fluoro-1-{2-[4-(trifluoromethyl)-1H-1,2,3-triazol-5-yl] acetyl}pyrrolidine-2-carboxamide;

N-[(5-cyclopropyl-6-fluoropyridin-2-yl)(phenyl)methyl]-1-{2-[(dimethylcarbamoyl)amino]propanoyl}-4-fluoropyrrolidine-2-carboxamide;

4-fluoro-1-[2-(5-methyl-1,3-oxazol-2-yl)acetyl]-N-{phenyl [5-(propan-2-yl)pyridin-2-yl]methyl}pyrrolidine-2-carboxamide;

1-{2-[(dimethylcarbamoyl)amino]propanoyl}-4-fluoro-N-{phenyl[5-(propan-2-yl)pyridin-2-yl]methyl}pyrrolidine-2-carboxamide;

4-fluoro-N-{[6-fluoro-5-(propan-2-yl)pyridin-2-yl](phenyl) methyl}-1-[2-(5-methyl-1,3-oxazol-2-yl)acetyl]pyrrolidine-2-carboxamide;

N-[(5-cyclopropyl-6-fluoropyridin-2-yl)(phenyl)methyl]-4-fluoro-1-[2-(5-methyl-1,3-oxazol-2-yl)acetyl]pyrrolidine-2-carboxamide;

4-fluoro-N-{[6-fluoro-5-(propan-2-yl)pyridin-2-yl](phenyl) methyl}-1-[2-(1,3-oxazol-2-yl)acetyl]pyrrolidine-2-carboxamide;

4-fluoro-1-[2-(5-oxo-4,5-dihydro-1H-1,2,4-triazol-4-yl) acetyl]-N-{phenyl[5-(propan-2-yl)pyridin-2-yl] methyl}pyrrolidine-2-carboxamide;

4-fluoro-1-(3-{3-oxo-2H,3H-[1,2,4]triazolo[4,3-a]pyridin-2-yl}propanoyl)-N-{phenyl[5-(propan-2-yl)pyridin-2-yl] methyl}pyrrolidine-2-carboxamide;

1-{2-[(3,3-difluoroazetidine-1-carbonyl)amino]acetyl}-4-fluoro-N-{phenyl[5-(propan-2-yl)pyridin-2-yl] methyl}pyrrolidine-2-carboxamide;

4-fluoro-N-{phenyl[5-(propan-2-yl)pyridin-2-yl]methyl}-1-(2-{[3-(trifluoromethyl)azetidine-1-carbonyl] amino}acetyl)pyrrolidine-2-carboxamide;

4-fluoro-N-{[6-fluoro-5-(propan-2-yl)pyridin-2-yl](phenyl) methyl}-1-[2-(4-methyl-5-oxo-4,5-dihydro-1H-1,2,4-triazol-3-yl)acetyl]pyrrolidine-2-carboxamide;

1-{2-[(3,3-difluoroazetidine-1-carbonyl)amino]acetyl}-4-fluoro-N-{[6-fluoro-5-(propan-2-yl)pyridin-2-yl](phenyl)methyl}pyrrolidine-2-carboxamide;

4-fluoro-1-[2-(4-methyl-5-oxo-4,5-dihydro-1H-1,2,4-triazol-3-yl)acetyl]-N-{phenyl[5-(propan-2-yl)pyridin-2-yl] methyl}pyrrolidine-2-carboxamide;

N-[(5-cyclopropyl-6-fluoropyridin-2-yl)(phenyl)methyl]-1-{2-[(3,3-difluoroazetidine-1-carbonyl)amino]acetyl}-4-fluoropyrrolidine-2-carboxamide;

N-{phenyl[5-(propan-2-yl)pyridin-2-yl]methyl}-3-[2-(1H-1,2,3-triazol-5-yl)acetyl]-3-azabicyclo[3.1.0]hexane-2-carboxamide;

5-methyl-N-{phenyl[5-(propan-2-yl)pyridin-2-yl]methyl}-1-[2-(1H-1,2,3-triazol-5-yl)acetyl]pyrrolidine-2-carboxamide;

N-[(5-cyclopropyl-6-fluoropyridin-2-yl)(phenyl)methyl]-4-fluoro-1-[2-(4-methyl-1,3-oxazol-2-yl)acetyl]pyrrolidine-2-carboxamide;

N-[(5-cyclopropyl-6-fluoropyridin-2-yl)(phenyl)methyl]-4-fluoro-1-(2-{3-oxo-2H,3H-[1,2,4]triazolo[4,3-a]pyridin-8-yl}acetyl)pyrrolidine-2-carboxamide;

4-fluoro-1-[2-(4-methyl-1,3-oxazol-2-yl)acetyl]-N-{phenyl [5-(propan-2-yl)pyridin-2-yl]methyl}pyrrolidine-2-carboxamide;

N-[(5-cyclopropyl-6-fluoropyridin-2-yl)(phenyl)methyl]-4-fluoro-1-[2-(4-methyl-5-oxo-4,5-dihydro-1H-1,2,4-triazol-3-yl)acetyl]pyrrolidine-2-carboxamide;

4-fluoro-N-{[6-fluoro-5-(propan-2-yl)pyridin-2-yl](phenyl) methyl}-1-[2-(4-methyl-1,3-oxazol-2-yl)acetyl]pyrrolidine-2-carboxamide;

4-fluoro-N-{phenyl[5-(propan-2-yl)pyridin-2-yl]methyl}-1-[2-(1H-pyrazol-1-yl)acetyl]pyrrolidine-2-carboxamide;

1-{2-[4-(3,3-difluoroazetidin-1-yl)-2H-1,2,3-triazol-2-yl] acetyl}-4-fluoro-N-{[6-fluoro-5-(propan-2-yl)pyridin-2-yl](phenyl)methyl}pyrrolidine-2-carboxamide;

1-{2-[4-(diethylamino)-2H-1,2,3-triazol-2-yl]acetyl}-4-fluoro-N-{[6-fluoro-5-(propan-2-yl)pyridin-2-yl](phenyl)methyl}pyrrolidine-2-carboxamide;

N-{[6-fluoro-5-(propan-2-yl)pyridin-2-yl](phenyl)methyl}-5-methyl-1-[2-(1H-1,2,3-triazol-5-yl)acetyl]pyrrolidine-2-carboxamide;

1-{2-[4-(3,3-difluoroazetidin-1-yl)-2H-1,2,3-triazol-2-yl]acetyl}-4-fluoro-N-{phenyl[5-(propan-2-yl)pyridin-2-yl]methyl}pyrrolidine-2-carboxamide;

N-[(5-cyclopropyl-6-fluoropyridin-2-yl)(phenyl)methyl]-4-fluoro-1-{2-[(1,3-oxazol-2-yl)amino]acetyl}pyrrolidine-2-carboxamide;

N-{[6-fluoro-5-(propan-2-yl)pyridin-2-yl](phenyl)methyl}-3-[2-(1H-1,2,3-triazol-5-yl)acetyl]-3-azabicyclo[3.1.0]hexane-2-carboxamide;

N-[(5-cyclopropyl-6-fluoropyridin-2-yl)(phenyl)methyl]-1-{2-[4-(3,3-difluoroazetidin-1-yl)-2H-1,2,3-triazol-2-yl]acetyl}-4-fluoropyrrolidine-2-carboxamide;

1-{2-[4-(diethylamino)-2H-1,2,3-triazol-2-yl]acetyl}-4-fluoro-N-{phenyl[5-(propan-2-yl)pyridin-2-yl]methyl}pyrrolidine-2-carboxamide;

N-[(5-cyclopropyl-6-fluoropyridin-2-yl)(phenyl)methyl]-1-{2-[4-(diethylamino)-2H-1,2,3-triazol-2-yl]acetyl}-4-fluoropyrrolidine-2-carboxamide;

N-[(5-cyclopropyl-6-fluoropyridin-2-yl)(phenyl)methyl]-5-methyl-1-[2-(1H-1,2,3-triazol-5-yl)acetyl]pyrrolidine-2-carboxamide;

1-{2-[4-(azetidin-1-yl)-2H-1,2,3-triazol-2-yl]acetyl}-4-fluoro-N-{phenyl[5-(propan-2-yl)pyridin-2-yl]methyl}pyrrolidine-2-carboxamide;

1-{2-[4-(azetidin-1-yl)-2H-1,2,3-triazol-2-yl]acetyl}-N-[(5-cyclopropyl-6-fluoropyridin-2-yl)(phenyl)methyl]-4-fluoropyrrolidine-2-carboxamide;

1-{2-[4-(azetidin-1-yl)-2H-1,2,3-triazol-2-yl]acetyl}-4-fluoro-N-{[6-fluoro-5-(propan-2-yl)pyridin-2-yl](phenyl)methyl}pyrrolidine-2-carboxamide;

4-fluoro-1-[2-(5-methyl-2-oxo-2,3-dihydro-1,3,4-oxadiazol-3-yl)acetyl]-N-{phenyl[5-(propan-2-yl)pyridin-2-yl]methyl}pyrrolidine-2-carboxamide;

N-[(5-cyclopropyl-6-fluoropyridin-2-yl)(phenyl)methyl]-4-fluoro-1-[2-(5-methyl-2-oxo-2,3-dihydro-1,3,4-oxadiazol-3-yl)acetyl]pyrrolidine-2-carboxamide;

4-fluoro-N-{[6-fluoro-5-(propan-2-yl)pyridin-2-yl](phenyl)methyl}-1-[2-(5-methyl-2-oxo-2,3-dihydro-1,3,4-oxadiazol-3-yl)acetyl]pyrrolidine-2-carboxamide; and N-[(5-cyclopropyl-6-fluoropyridin-2-yl)(phenyl)methyl]-3-[2-(1H-1,2,3-triazol-5-yl)acetyl]-3-azabicyclo[3.1.0]hexane-2-carboxamide, N-{[5-(3,3-difluorocyclobutyl)-6-fluoropyridin-2-yl](phenyl)methyl}-4-fluoro-1-[2-(5-methyl-2-oxo-2,3-dihydro-1,3,4-oxadiazol-3-yl)acetyl]pyrrolidine-2-carboxamide 1-{2-[(azetidine-1-carbonyl)amino]acetyl}-N-{[5-(3,3-difluorocyclobutyl)-6-fluoropyridin-2-yl](phenyl)methyl}-4-fluoropyrrolidine-2-carboxamide 1-[2-(1H-1,3-benzodiazol-1-yl)acetyl]-N-{[5-(3,3-difluorocyclobutyl)-6-fluoropyridin-2-yl](phenyl)methyl}-4-fluoropyrrolidine-2-carboxamide N-{[5-(3,3-difluorocyclobutyl)-6-fluoropyridin-2-yl](phenyl)methyl}-4-fluoro-1-[2-(1,3-oxazol-2-yl)acetyl]pyrrolidine-2-carboxamide N-{[5-(3,3-difluorocyclobutyl)-6-fluoropyridin-2-yl](phenyl)methyl}-4-fluoro-1-[2-(5-methyl-2,4-dioxo-1,2,3,4-tetrahydropyrimidin-1-yl)acetyl]pyrrolidine-2-carboxamide N-{[5-(3,3-difluorocyclobutyl)-6-fluoropyridin-2-yl](phenyl)methyl}-1-{2-[(dimethylcarbamoyl)amino]acetyl}-4-fluoropyrrolidine-2-carboxamide N-{[5-(3,3-difluorocyclobutyl)-6-fluoropyridin-2-yl](phenyl)methyl}-4-fluoro-1-[2-(1H-1,2,3-triazol-5-yl)acetyl]pyrrolidine-2-carboxamide N-{[5-(3,3-difluorocyclobutyl)-6-fluoropyridin-2-yl](phenyl)methyl}-4-fluoro-1-[2-(5-methyl-1,3-oxazol-2-yl)acetyl]pyrrolidine-2-carboxamide N-{[5-(3,3-difluorocyclobutyl)-6-fluoropyridin-2-yl](phenyl)methyl}-4-fluoro-1-{2-[4-(trifluoromethyl)-1H-1,2,3-triazol-5-yl]acetyl}pyrrolidine-2-carboxamide N-{[5-(3,3-difluorocyclobutyl)-6-fluoropyridin-2-yl](phenyl)methyl}-4-fluoro-1-[2-(4-methyl-1,3-oxazol-2-yl)acetyl]pyrrolidine-2-carboxamide 1-{2-[(3,3-difluoroazetidine-1-carbonyl)amino]acetyl}-N-{[5-(3,3-difluorocyclobutyl)-6-fluoropyridin-2-yl](phenyl)methyl}-4-fluoropyrrolidine-2-carboxamide N-{[5-(3,3-difluorocyclobutyl)-6-fluoropyridin-2-yl](phenyl)methyl}-1-{2-[5-(difluoromethyl)-1H-1,2,3,4-tetrazol-1-yl]acetyl}-4-fluoropyrrolidine-2-carboxamide N-{[5-(3,3-difluorocyclobutyl)-6-fluoropyridin-2-yl](phenyl)methyl}-1-[2-(2,4-dioxo-1,2,3,4-tetrahydropyrimidin-1-yl)acetyl]-4-fluoropyrrolidine-2-carboxamide N-{[5-(3,3-difluorocyclobutyl)-6-fluoropyridin-2-yl](phenyl)methyl}-1-[2-(3-ethyl-2,4-dioxo-1,2,3,4-tetrahydropyrimidin-1-yl)acetyl]-4-fluoropyrrolidine-2-carboxamide N-{[5-(3,3-difluorocyclobutyl)-6-fluoropyridin-2-yl](phenyl)methyl}-4-fluoro-1-[2-(6-oxo-1,6-dihydropyridin-3-yl)acetyl]pyrrolidine-2-carboxamide N-{[5-(3,3-difluorocyclobutyl)-6-fluoropyridin-2-yl](phenyl)methyl}-4-fluoro-1-[2-(2-oxo-1,2-dihydropyridin-3-yl)acetyl]pyrrolidine-2-carboxamide N-{[5-(3,3-difluorocyclobutyl)-6-fluoropyridin-2-yl](phenyl)methyl}-1-[2-(3-ethyl-5-methyl-2,4-dioxo-1,2,3,4-tetrahydropyrimidin-1-yl)acetyl]-4-fluoropyrrolidine-2-carboxamide N-{[5-(3,3-difluorocyclobutyl)-6-fluoropyridin-2-yl](phenyl)methyl}-1-[2-(1-ethyl-6-oxo-1,6-dihydropyridin-3-yl)acetyl]-4-fluoropyrrolidine-2-carboxamide N-{[5-(3,3-difluorocyclobutyl)-6-fluoropyridin-2-yl](phenyl)methyl}-4-fluoro-1-[2-(5-methyl-6-oxo-1,6-dihydropyridin-3-yl)acetyl]pyrrolidine-2-carboxamide N-{[5-(3,3-difluorocyclobutyl)-6-fluoropyridin-2-yl](phenyl)methyl}-1-[2-(1-ethyl-5-methyl-6-oxo-1,6-dihydropyridin-3-yl)acetyl]-4-fluoropyrrolidine-2-carboxamide N-{[5-(3,3-difluorocyclobutyl)-6-fluoropyridin-2-yl](phenyl)methyl}-1-[2-(6-ethoxy-5-methylpyridin-3-yl)acetyl]-4-fluoropyrrolidine-2-carboxamide N-{[5-(3,3-difluorocyclobutyl)-6-fluoropyridin-2-yl](phenyl)methyl}-1-[2-(1-ethyl-5-methyl-2-oxo-1,2-dihydropyridin-3-yl)acetyl]-4-fluoropyrrolidine-2-carboxamide N-{[5-(3,3-difluorocyclobutyl)-6-fluoropyridin-2-yl](phenyl)methyl}-1-[2-(1-ethyl-2-oxo-1,2-dihydropyridin-3-yl)acetyl]-4-fluoropyrrolidine-2-carboxamide N-{[5-(3,3-difluorocyclobutyl)-6-fluoropyridin-2-yl](phenyl)methyl}-1-[2-(4-ethyl-5-oxo-4,5-dihydropyrazin-2-yl)acetyl]-4-fluoropyrrolidine-2-carboxamide N-{[5-(3,3-difluorocyclobutyl)-6-fluoropyridin-2-yl](phenyl)methyl}-4-fluoro-1-{2-[4-(trifluoromethyl)-1,3-oxazol-2-yl]acetyl}pyrrolidine-2-carboxamide N-{[5-(3,3-difluorocyclobutyl)-6-fluoropyridin-2-yl](phenyl)methyl}-4-fluoro-1-[2-(3-oxo-3,4-dihydropyrazin-2-yl)acetyl]pyrrolidine-2-carboxamide N-{[5-(3,3-difluorocyclobutyl)-6-fluoropyridin-2-yl](phenyl)methyl}-4-fluoro-1-[2-(5-oxo-4,5-dihydropyrazin-2-yl)acetyl]pyrrolidine-2-carboxamide N-{[5-(3,3-difluorocyclobutyl)-6-fluoropyridin-2-yl](phenyl)methyl}-1-[2-(4-ethyl-3-oxo-3,4-dihydropyrazin-2-yl)acetyl]-4-fluoropyrrolidine-2-carboxamide N-{[5-(3,3-difluorocyclobutyl)pyridin-2-yl](phenyl)
methyl}-1-{2-[(dimethylcarbamoyl)amino]acetyl}-4-
fluoropyrrolidine-2-carboxamide
1-{2-[(azetidine-1-carbonyl)amino]acetyl}-N-{[5-(3,3-dif-
luorocyclobutyl)pyridin-2-yl](phenyl)methyl}-4-fluoro-
pyrrolidine-2-carboxamide
N-{[5-(3,3-difluorocyclobutyl)pyridin-2-yl](phenyl)
methyl}-4-fluoro-1-[2-(1H-1,2,3-triazol-5-yl)acetyl]pyr-
rolidine-2-carboxamide
N-{[5-(3,3-difluorocyclobutyl)pyridin-2-yl](phenyl)
methyl}-4-fluoro-1-[2-(5-methyl-2,4-dioxo-1,2,3,4-tetra-
hydropyrimidin-1-yl)acetyl]pyrrolidine-2-carboxamide
N-{[5-(3,3-difluorocyclobutyl)pyridin-2-yl](phenyl)
methyl}-4-fluoro-1-[2-(5-methyl-1,3-oxazol-2-yl)acetyl]
pyrrolidine-2-carboxamide
1-[2-(1H-1,3-benzodiazol-1-yl)acetyl]-N-{[5-(3,3-difluoro-
cyclobutyl)pyridin-2-yl](phenyl)methyl}-4-fluoropyrro-
lidine-2-carboxamide
1-{2-[(3,3-difluoroazetidine-1-carbonyl)amino]acetyl}-N-
{[5-(3,3-difluorocyclobutyl)pyridin-2-yl](phenyl)
methyl}-4-fluoropyrrolidine-2-carboxamide
N-{[5-(3,3-difluorocyclobutyl)pyridin-2-yl](phenyl)
methyl}-4-fluoro-1-[2-(1,3-oxazol-2-yl)acetyl]pyrroli-
dine-2-carboxamide
N-{[5-(3,3-difluorocyclobutyl)pyridin-2-yl](phenyl)
methyl}-4-fluoro-1-[2-(4-methyl-1,3-oxazol-2-yl)acetyl]
pyrrolidine-2-carboxamide
N-{[5-(3,3-difluorocyclobutyl)pyridin-2-yl](phenyl)
methyl}-4-fluoro-1-[2-(5-methyl-2-oxo-2,3-dihydro-1,3,
4-oxadiazol-3-yl)acetyl]pyrrolidine-2-carboxamide
N-{[5-(3,3-difluorocyclobutyl)pyridin-2-yl](phenyl)
methyl}-4-fluoro-1-{2-[4-(trifluoromethyl)-1H-1,2,3-tri-
azol-5-yl]acetyl}pyrrolidine-2-carboxamide
N-{[5-(3,3-difluorocyclobutyl)pyridin-2-yl](phenyl)
methyl}-4-fluoro-1-{2-[4-(trifluoromethyl)-1,3-oxazol-
2-yl]acetyl}pyrrolidine-2-carboxamide
1-{2-[(azetidine-1-carbonyl)amino]acetyl}-N-{[4-(3,3-dif-
luorocyclobutyl)-3-fluorophenyl](phenyl)methyl}-4-
fluoropyrrolidine-2-carboxamide
N-{[4-(3,3-difluorocyclobutyl)-3-fluorophenyl](phenyl)
methyl}-1-{2-[(dimethylcarbamoyl)amino]acetyl}-4-
fluoropyrrolidine-2-carboxamide
1-[2-(1H-1,3-benzodiazol-1-yl)acetyl]-N-{[4-(3,3-difluoro-
cyclobutyl)-3-fluorophenyl](phenyl)methyl}-4-fluoropy-
rrolidine-2-carboxamide
N-{[4-(3,3-difluorocyclobutyl)-3-fluorophenyl](phenyl)
methyl}-4-fluoro-1-[2-(5-methyl-1,3-oxazol-2-yl)acetyl]
pyrrolidine-2-carboxamide
N-{[4-(3,3-difluorocyclobutyl)-3-fluorophenyl](phenyl)
methyl}-4-fluoro-1-[2-(5-methyl-2,4-dioxo-1,2,3,4-tetra-
hydropyrimidin-1-yl)acetyl]pyrrolidine-2-carboxamide
N-{[4-(3,3-difluorocyclobutyl)-3-fluorophenyl](phenyl)
methyl}-4-fluoro-1-[2-(1,3-oxazol-2-yl)acetyl]pyrroli-
dine-2-carboxamide
N-{[4-(3,3-difluorocyclobutyl)-3-fluorophenyl](phenyl)
methyl}-4-fluoro-1-{2-[4-(trifluoromethyl)-1H-1,2,3-tri-
azol-5-yl]acetyl}pyrrolidine-2-carboxamide
N-{[4-(3,3-difluorocyclobutyl)-3-fluorophenyl](phenyl)
methyl}-4-fluoro-1-[2-(4-methyl-1,3-oxazol-2-yl)acetyl]
pyrrolidine-2-carboxamide
N-{[4-(3,3-difluorocyclobutyl)-3-fluorophenyl](phenyl)
methyl}-4-fluoro-1-{2-[4-(trifluoromethyl)-1,3-oxazol-
2-yl]acetyl}pyrrolidine-2-carboxamide
4-fluoro-N-{[3-fluoro-4-(1-methylcyclopropyl)phenyl]
(phenyl)methyl}-1-[2-(5-methyl-2,4-dioxo-1,2,3,4-tetra-
hydropyrimidin-1-yl)acetyl]pyrrolidine-2-carboxamide
4-fluoro-N-{[3-fluoro-4-(1-methylcyclopropyl)phenyl]
(phenyl)methyl}-1-[2-(1H-1,2,3-triazol-5-yl)acetyl]pyr-
rolidine-2-carboxamide
4-fluoro-N-{[3-fluoro-4-(1-methylcyclopropyl)phenyl]
(pyridin-3-yl)methyl}-1-[2-(1H-1,2,3-triazol-5-yl)acetyl]
pyrrolidine-2-carboxamide
2-[4-fluoro-2-({[3-fluoro-4-(1-methylcyclopropyl)phenyl]
(phenyl)methyl}carbamoyl)pyrrolidin-1-yl]-2-oxoethyl
azetidine-1-carboxylate
4-fluoro-N-{[3-fluoro-4-(1-methylcyclopropyl)phenyl]
(phenyl)methyl}-1-[2-(1-methyl-1H-indol-2-yl)acetyl]
pyrrolidine-2-carboxamide
4-fluoro-N-{[3-fluoro-4-(1-methylcyclopropyl)phenyl]
(phenyl)methyl}-1-[2-(2-oxopiperazin-1-yl)acetyl]pyrro-
lidine-2-carboxamide
4-fluoro-N-{[3-fluoro-4-(1-methylcyclopropyl)phenyl]
(phenyl)methyl}-1-[2-(1-methyl-1H-indol-3-yl)acetyl]
pyrrolidine-2-carboxamide
4-fluoro-N-{[3-fluoro-4-(1-methylcyclopropyl)phenyl]
(phenyl)methyl}-1-[2-(1-methyl-1H-indazol-3-yl)acetyl]
pyrrolidine-2-carboxamide
N-{2-[4-fluoro-2-({[3-fluoro-4-(1-methylcyclopropyl)phe-
nyl](phenyl)methyl}carbamoyl)pyrrolidin-1-yl]-2-
oxoethyl}morpholine-4-carboxamide
4-fluoro-N-{[3-fluoro-4-(1-methylcyclopropyl)phenyl]
(phenyl)methyl}-1-[2-(2-methyl-1H-1,3-benzodiazol-1-
yl)acetyl]pyrrolidine-2-carboxamide
1-[2-(1H-1,3-benzodiazol-1-yl)propanoyl]-4-fluoro-N-{[3-
fluoro-4-(1-methylcyclopropyl)phenyl](phenyl)
methyl}pyrrolidine-2-carboxamide
4-fluoro-N-{[3-fluoro-4-(1-methylcyclopropyl)phenyl]
(phenyl)methyl}-1-[2-(3-methyl-2-oxo-2,3-dihydro-1H-
1,3-benzodiazol-1-yl)acetyl]pyrrolidine-2-carboxamide
4-fluoro-N-{[3-fluoro-4-(1-methylcyclopropyl)phenyl]
(phenyl)methyl}-1-[2-(3-methyl-2,4-dioxo-1,2,3,4-tetra-
hydropyrimidin-1-yl)acetyl]pyrrolidine-2-carboxamide
4-fluoro-N-{[3-fluoro-4-(1-methylcyclopropyl)phenyl]
(phenyl)methyl}-1-[2-(2-oxo-2,3-dihydro-1H-1,3-benzo-
diazol-1-yl)acetyl]pyrrolidine-2-carboxamide
4-fluoro-N-{[3-fluoro-4-(1-methylcyclopropyl)phenyl]
(phenyl)methyl}-1-[2-(1H-indazol-3-yl)acetyl]pyrroli-
dine-2-carboxamide
1-[2-(2,5-dioxopiperazin-1-yl)acetyl]-4-fluoro-N-{[3-
fluoro-4-(1-methylcyclopropyl)phenyl](phenyl)
methyl}pyrrolidine-2-carboxamide
4-fluoro-N-{[3-fluoro-4-(1-methylcyclopropyl)phenyl]
(phenyl)methyl}-1-[2-(1-oxo-2,3-dihydro-1H-isoindol-2-
yl)acetyl]pyrrolidine-2-carboxamide
1-[2-(1H-1,2,3-benzotriazol-1-yl)acetyl]-4-fluoro-N-{[3-
fluoro-4-(1-methylcyclopropyl)phenyl](phenyl)
methyl}pyrrolidine-2-carboxamide
4-fluoro-N-{[3-fluoro-4-(1-methylcyclopropyl)phenyl]
(phenyl)methyl}-1-[2-(2-oxo-2,3-dihydro-1H-indol-1-yl)
acetyl]pyrrolidine-2-carboxamide
4-fluoro-N-{[3-fluoro-4-(1-methylcyclopropyl)phenyl]
(phenyl)methyl}-1-[2-(1-methyl-2-oxo-2,3-dihydro-1H-
indol-3-yl)acetyl]pyrrolidine-2-carboxamide
2,2,2-trifluoroethyl 4-{2-[4-fluoro-2-({[3-fluoro-4-(1-meth-
ylcyclopropyl)phenyl](phenyl)methyl}carbamoyl)pyrro-
lidin-1-yl]-2-oxoethyl}-3-oxopiperazine-1-carboxylate
2-[4-fluoro-2-({[3-fluoro-4-(1-methylcyclopropyl)phenyl]
(phenyl)methyl}carbamoyl)pyrrolidin-1-yl]-2-oxoethyl
4-(2-methoxyethyl)piperazine-1-carboxylate
4-fluoro-N-{[3-fluoro-4-(1-methylcyclopropyl)phenyl]
(phenyl)methyl}-1-{2-[2-oxo-4-(2,2,2-trifluoroethyl)pip-
erazin-1-yl]acetyl}pyrrolidine-2-carboxamide 4-fluoro-N-{[3-fluoro-4-(1-methylcyclopropyl)phenyl](phenyl)methyl}-1-[2-(2-oxo-2,3-dihydro-1H-indol-3-yl)acetyl]pyrrolidine-2-carboxamide 4-fluoro-N-{[3-fluoro-4-(1-methylcyclopropyl)phenyl](phenyl)methyl}-1-[2-(4H-1,2,4-triazol-4-yl)acetyl]pyrrolidine-2-carboxamide 2-[4-fluoro-2-({[3-fluoro-4-(1-methylcyclopropyl)phenyl](phenyl)methyl}carbamoyl)pyrrolidin-1-yl]-2-oxoethyl 4-methylpiperazine-1-carboxylate 2-[4-fluoro-2-({[3-fluoro-4-(1-methylcyclopropyl)phenyl](phenyl)methyl}carbamoyl)pyrrolidin-1-yl]-2-oxoethyl 4-(cyclopropylmethyl)piperazine-1-carboxylate 2-[4-fluoro-2-({[3-fluoro-4-(1-methylcyclopropyl)phenyl](phenyl)methyl}carbamoyl)pyrrolidin-1-yl]-2-oxoethyl 4-(2,2,2-trifluoroethyl)piperazine-1-carboxylate 1-[2-(1H-1,3-benzodiazol-1-yl)propanoyl]-4-fluoro-N-{[6-fluoro-5-(1-methylcyclopropyl)pyridin-2-yl](phenyl)methyl}pyrrolidine-2-carboxamide 4-fluoro-N-{[6-fluoro-5-(1-methylcyclopropyl)pyridin-2-yl](phenyl)methyl}-1-[2-(1H-indazol-3-yl)acetyl]pyrrolidine-2-carboxamide N-{2-[4-fluoro-2-({[6-fluoro-5-(1-methylcyclopropyl)pyridin-2-yl](phenyl)methyl}carbamoyl)pyrrolidin-1-yl]-2-oxoethyl}morpholine-4-carboxamide 4-fluoro-N-{[6-fluoro-5-(1-methylcyclopropyl)pyridin-2-yl](phenyl)methyl}-1-[2-(1-methyl-1H-indol-2-yl)acetyl]pyrrolidine-2-carboxamide 4-fluoro-N-{[6-fluoro-5-(1-methylcyclopropyl)pyridin-2-yl](phenyl)methyl}-1-[2-(1-methyl-1H-indol-3-yl)acetyl]pyrrolidine-2-carboxamide 4-fluoro-N-{[6-fluoro-5-(1-methylcyclopropyl)pyridin-2-yl](phenyl)methyl}-1-[2-(2-methyl-1H-1,3-benzodiazol-1-yl)acetyl]pyrrolidine-2-carboxamide 1-[2-(1H-1,2,3-benzotriazol-1-yl)acetyl]-4-fluoro-N-{[6-fluoro-5-(1-methylcyclopropyl)pyridin-2-yl](phenyl)methyl}pyrrolidine-2-carboxamide 1-[2-(1H-1,3-benzodiazol-1-yl)acetyl]-4-fluoro-N-{[6-fluoro-5-(1-methylcyclopropyl)pyridin-2-yl](phenyl)methyl}pyrrolidine-2-carboxamide 4-fluoro-N-{[6-fluoro-5-(1-methylcyclopropyl)pyridin-2-yl](phenyl)methyl}-1-[2-(1-methyl-1H-indazol-3-yl)acetyl]pyrrolidine-2-carboxamide 4-fluoro-N-{[6-fluoro-5-(1-methylcyclopropyl)pyridin-2-yl](phenyl)methyl}-1-[2-(1-methyl-2-oxo-2,3-dihydro-1H-indol-3-yl)acetyl]pyrrolidine-2-carboxamide 4-fluoro-N-{[6-fluoro-5-(1-methylcyclopropyl)pyridin-2-yl](phenyl)methyl}-1-[2-(1H-indol-2-yl)acetyl]pyrrolidine-2-carboxamide 4-fluoro-N-{[6-fluoro-5-(1-methylcyclopropyl)pyridin-2-yl](phenyl)methyl}-1-[2-(2-oxo-2,3-dihydro-1H-1,3-benzodiazol-1-yl)acetyl]pyrrolidine-2-carboxamide 4-fluoro-N-{[6-fluoro-5-(1-methylcyclopropyl)pyridin-2-yl](phenyl)methyl}-1-[2-(3-methyl-2-oxo-2,3-dihydro-1H-1,3-benzodiazol-1-yl)acetyl]pyrrolidine-2-carboxamide tert-butyl 2-{2-[4-fluoro-2-({[6-fluoro-5-(1-methylcyclopropyl)pyridin-2-yl](phenyl)methyl}carbamoyl)pyrrolidin-1-yl]-2-oxoethyl}-1H-indole-1-carboxylate 1-{2-[5-(difluoromethyl)-1,3,4-oxadiazol-2-yl]acetyl}-4-fluoro-N-{[4-methyl-5-(propan-2-yl)pyridin-2-yl](phenyl)methyl}pyrrolidine-2-carboxamide 1-acetyl-N-[(5-cyclobutylpyridin-2-yl)(phenyl)methyl]-4-fluoropyrrolidine-2-carboxamide 4-fluoro-N-{[4-methyl-5-(propan-2-yl)pyridin-2-yl](phenyl)methyl}-1-[2-(1H-1,2,3-triazol-5-yl)acetyl]pyrrolidine-2-carboxamide 4-fluoro-N-{[4-fluoro-5-(propan-2-yl)pyridin-2-yl](phenyl)methyl}-1-[2-(1H-1,2,3-triazol-5-yl)acetyl]pyrrolidine-2-carboxamide N-{[4-(difluoromethyl)-5-(propan-2-yl)pyridin-2-yl](phenyl)methyl}-4-fluoro-1-[2-(1H-1,2,3-triazol-5-yl)acetyl]pyrrolidine-2-carboxamide 4-fluoro-N-{[6-methyl-5-(propan-2-yl)pyridin-2-yl](phenyl)methyl}-1-[2-(1H-1,2,3-triazol-5-yl)acetyl]pyrrolidine-2-carboxamide 4-fluoro-N-{phenyl[5-(propan-2-yl)-4-(trifluoromethyl)pyridin-2-yl]methyl}-1-[2-(1H-1,2,3-triazol-5-yl)acetyl]pyrrolidine-2-carboxamide 1-{2-[5-(difluoromethyl)-1,3,4-oxadiazol-2-yl]acetyl}-4-fluoro-N-{[6-methyl-5-(propan-2-yl)pyridin-2-yl](phenyl)methyl}pyrrolidine-2-carboxamide N-[(5-cyclobutylpyridin-2-yl)(phenyl)methyl]-4-fluoro-1-[2-(1H-1,2,3-triazol-5-yl)acetyl]pyrrolidine-2-carboxamide N-[(5-tert-butylpyridin-2-yl)(phenyl)methyl]-4-fluoro-1-[2-(1H-1,2,3-triazol-5-yl)acetyl]pyrrolidine-2-carboxamide 4-fluoro-N-{[6-methoxy-5-(propan-2-yl)pyridin-2-yl](phenyl)methyl}-1-[2-(1H-1,2,3-triazol-5-yl)acetyl]pyrrolidine-2-carboxamide N-[(2-aminopyridin-3-yl)[3-fluoro-4-(propan-2-yl)phenyl]methyl]-4-fluoro-1-[2-(1H-1,2,3-triazol-5-yl)acetyl]pyrrolidine-2-carboxamide N-[(4-cyclopropyl-3-fluorophenyl)(1H-pyrazol-5-yl)methyl]-1-(2-acetamidoacetyl)pyrrolidine-2-carboxamide 4-fluoro-N-{[3-fluoro-4-(propan-2-yl)phenyl](5-fluoropyridin-2-yl)methyl}-1-[2-(1H-1,2,3-triazol-5-yl)acetyl]pyrrolidine-2-carboxamide 4-fluoro-N-{[3-fluoro-4-(propan-2-yl)phenyl](5-fluoropyridin-3-yl)methyl}-1-[2-(1H-1,2,3-triazol-5-yl)acetyl]pyrrolidine-2-carboxamide N-[(2-aminopyridin-4-yl)[3-fluoro-4-(propan-2-yl)phenyl]methyl]-4-fluoro-1-[2-(1H-1,2,3-triazol-5-yl)acetyl]pyrrolidine-2-carboxamide 4-fluoro-N-{[3-fluoro-4-(propan-2-yl)phenyl](3-fluoropyridin-4-yl)methyl}-1-[2-(1H-1,2,3-triazol-5-yl)acetyl]pyrrolidine-2-carboxamide N-[(6-aminopyridin-3-yl)[3-fluoro-4-(propan-2-yl)phenyl]methyl]-4-fluoro-1-[2-(1H-1,2,3-triazol-5-yl)acetyl]pyrrolidine-2-carboxamide N-[(6-aminopyridin-2-yl)[3-fluoro-4-(propan-2-yl)phenyl]methyl]-4-fluoro-1-[2-(1H-1,2,3-triazol-5-yl)acetyl]pyrrolidine-2-carboxamide N-[(2-aminopyridin-3-yl)[3-methyl-4-(propan-2-yl)phenyl]methyl]-1-{2-[(dimethylcarbamoyl)amino]acetyl}-4-fluoropyrrolidine-2-carboxamide 4-fluoro-N-{[3-fluoro-4-(propan-2-yl)phenyl](1H-pyrazol-5-yl)methyl}-1-[2-(1H-1,2,3-triazol-5-yl)acetyl]pyrrolidine-2-carboxamide N-[(2-aminopyridin-3-yl)[3-methyl-4-(propan-2-yl)phenyl]methyl]-4-fluoro-1-[2-(1H-1,2,3-triazol-5-yl)acetyl]pyrrolidine-2-carboxamide N-[(2-aminopyridin-3-yl)[3-methyl-4-(propan-2-yl)phenyl]methyl]-4-fluoro-1-[2-(1,3,5-trimethyl-1H-pyrazol-4-yl)acetyl]pyrrolidine-2-carboxamide 4-fluoro-N-{[3-fluoro-4-(1-methylcyclopropyl)phenyl](2-methoxypyridin-3-yl)methyl}-1-[2-(1H-1,2,3-triazol-5-yl)acetyl]pyrrolidine-2-carboxamide 4-fluoro-N-{[3-fluoro-4-(1-methylcyclopropyl)phenyl](2-methylpyridin-3-yl)methyl}-1-[2-(1H-1,2,3-triazol-5-yl)acetyl]pyrrolidine-2-carboxamide 4-fluoro-N-{[6-fluoro-5-(propan-2-yl)pyridin-2-yl]({imidazo[1,5-a]pyridin-3-yl})methyl}-1-[2-(1H-1,2,3-triazol-5-yl)acetyl]pyrrolidine-2-carboxamide 4-fluoro-N-{[6-fluoro-5-(propan-2-yl)pyridin-2-yl]({imidazo[1,5-a]pyridin-1-yl})methyl}-1-[2-(1H-1,2,3-triazol-5-yl)acetyl]pyrrolidine-2-carboxamide 4-fluoro-N-{[6-fluoro-5-(propan-2-yl)pyridin-2-yl](1H-pyrazol-5-yl)methyl}-1-[2-(1,3-oxazol-2-yl)acetyl]pyrrolidine-2-carboxamide 4-fluoro-N-{[6-fluoro-5-(propan-2-yl)pyridin-2-yl]({imidazo[1,5-a]pyridin-7-yl})methyl}-1-[2-(1H-1,2,3-triazol-5-yl)acetyl]pyrrolidine-2-carboxamide 4-fluoro-N-{[6-fluoro-5-(propan-2-yl)pyridin-2-yl](1H-indazol-6-yl)methyl}-1-[2-(1H-1,2,3-triazol-5-yl)acetyl]pyrrolidine-2-carboxamide 1-acetyl-4-fluoro-N-{[6-fluoro-5-(propan-2-yl)pyridin-2-yl](1H-indazol-6-yl)methyl}pyrrolidine-2-carboxamide 1-acetyl-4-fluoro-N-{[6-fluoro-5-(propan-2-yl)pyridin-2-yl](1-methyl-1H-indazol-6-yl)methyl}pyrrolidine-2-carboxamide 1-acetyl-4-fluoro-N-{[6-fluoro-5-(propan-2-yl)pyridin-2-yl](2-methyl-2H-indazol-6-yl)methyl}pyrrolidine-2-carboxamide 1-acetyl-N-[(5-cyclopropyl-6-fluoropyridin-2-yl)(1H-indazol-6-yl)methyl]-4-fluoropyrrolidine-2-carboxamide methyl N-({3-[({4-fluoro-1-[2-(1H-1,2,3-triazol-5-yl)acetyl]pyrrolidin-2-yl}formamido)[6-fluoro-5-(propan-2-yl)pyridin-2-yl]methyl]phenyl}methyl)carbamate 1-acetyl-N-[(2-methoxyphenyl)[4-(propan-2-yl)phenyl]methyl]pyrrolidine-2-carboxamide 1-acetyl-N-[(2-methylphenyl)[4-(propan-2-yl)phenyl]methyl]pyrrolidine-2-carboxamide 1-acetyl-N-[(2-methylphenyl)[5-(propan-2-yl)pyridin-2-yl]methyl]pyrrolidine-2-carboxamide N-[(4-cyclopropyl-3-fluorophenyl)(2-oxo-2,3-dihydro-1,3-benzoxazol-7-yl)methyl]-1-(2-acetamidoacetyl)pyrrolidine-2-carboxamide N-[(2-oxo-2,3-dihydro-1H-1,3-benzodiazol-4-yl)[4-(propan-2-yl)phenyl]methyl]-1-[2-(1H-1,2,3-triazol-5-yl)acetyl]pyrrolidine-2-carboxamide 4-fluoro-N-{[3-fluoro-4-(propan-2-yl)phenyl](3-fluorophenyl)methyl}-1-[2-(1H-1,2,3-triazol-5-yl)acetyl]pyrrolidine-2-carboxamide 4-fluoro-N-{[3-fluoro-4-(propan-2-yl)phenyl](4-fluorophenyl)methyl}-1-[2-(1H-1,2,3-triazol-5-yl)acetyl]pyrrolidine-2-carboxamide N-[(4-cyclopropyl-3-fluorophenyl)(2-oxo-2,3-dihydro-1H-1,3-benzodiazol-4-yl)methyl]-1-[2-(1H-1,2,3-triazol-5-yl)acetyl]pyrrolidine-2-carboxamide N-[(3-acetamidophenyl)[4-(propan-2-yl)phenyl]methyl]-4-fluoro-1-[2-(1-methyl-1H-1,2,3-triazol-4-yl)acetyl]pyrrolidine-2-carboxamide N-[(4-cyclopropyl-3-fluorophenyl)(1-methyl-2-oxo-2,3-dihydro-1H-1,3-benzodiazol-4-yl)methyl]-4-fluoro-1-[2-(1H-1,2,3-triazol-5-yl)acetyl]pyrrolidine-2-carboxamide 4-fluoro-N-{[6-fluoro-5-(propan-2-yl)pyridin-2-yl](3-methoxyphenyl)methyl}-1-[2-(1H-1,2,3-triazol-5-yl)acetyl]pyrrolidine-2-carboxamide N-{cyclopropyl[3-fluoro-4-(propan-2-yl)phenyl]methyl}-4-fluoro-1-[2-(1H-1,2,3-triazol-5-yl)acetyl]pyrrolidine-2-carboxamide N-{2-cyclopropyl-1-[3-fluoro-4-(propan-2-yl)phenyl]ethyl}-4-fluoro-1-[2-(1H-1,2,3-triazol-5-yl)acetyl]pyrrolidine-2-carboxamide 1-acetyl-4-fluoro-N-{[6-fluoro-5-(propan-2-yl)pyridin-2-yl](3-methoxyphenyl)methyl}pyrrolidine-2-carboxamide N-{[3-(acetamidomethyl)phenyl][6-fluoro-5-(propan-2-yl)pyridin-2-yl]methyl}-4-fluoro-1-[2-(1H-1,2,3-triazol-5-yl)acetyl]pyrrolidine-2-carboxamide 4-fluoro-N-{[6-fluoro-5-(propan-2-yl)pyridin-2-yl](3-{[(methylcarbamoyl)amino]methyl}phenyl)methyl}-1-[2-(1H-1,2,3-triazol-5-yl)acetyl]pyrrolidine-2-carboxamide N-[(5-cyclopropyl-6-fluoropyridin-2-yl)(2-fluorophenyl)methyl]-1-{2-[5-(difluoromethyl)-1H-1,2,3,4-tetrazol-1-yl]acetyl}-4-fluoropyrrolidine-2-carboxamide N-[(5-cyclopropyl-6-fluoropyridin-2-yl)(4-fluorophenyl)methyl]-1-{2-[5-(difluoromethyl)-1H-1,2,3,4-tetrazol-1-yl]acetyl}-4-fluoropyrrolidine-2-carboxamide N-{[3,5-difluoro-4-(propan-2-yl)phenyl](phenyl)methyl}-4-fluoro-1-[(1H-1,2,3-triazol-5-yl)methanesulfonyl]pyrrolidine-2-carboxamide 1-acetyl-N-[(4-cyclobutyl-3-fluorophenyl)(phenyl)methyl]-4-fluoropyrrolidine-2-carboxamide N-{[3,5-difluoro-4-(propan-2-yl)phenyl](phenyl)methyl}-4-fluoro-1-[2-(1,3-oxazol-2-yl)acetyl]pyrrolidine-2-carboxamide N-[(4-cyclopropyl-3,5-difluorophenyl)(phenyl)methyl]-4-fluoro-1-[2-(1,3-oxazol-2-yl)acetyl]pyrrolidine-2-carboxamide 4-fluoro-N-{[2-methyl-4-(propan-2-yl)phenyl](phenyl)methyl}-1-[2-(1,3-oxazol-2-yl)acetyl]pyrrolidine-2-carboxamide N-[(3-chloro-4-cyclopropylphenyl)(phenyl)methyl]-4-fluoro-1-[2-(1H-1,2,3-triazol-5-yl)acetyl]pyrrolidine-2-carboxamide N-[(4-cyclopropyl-3-methylphenyl)(phenyl)methyl]-4-fluoro-1-[2-(1H-1,2,3-triazol-5-yl)acetyl]pyrrolidine-2-carboxamide N-{[3,5-difluoro-4-(propan-2-yl)phenyl](phenyl)methyl}-4-fluoro-1-[2-(1H-1,2,3-triazol-5-yl)acetyl]pyrrolidine-2-carboxamide N-{[3,5-difluoro-4-(propan-2-yl)phenyl](phenyl)methyl}-4-fluoro-1-[2-(1H-1,2,3-triazol-1-yl)acetyl]pyrrolidine-2-carboxamide N-{[3,5-difluoro-4-(propan-2-yl)phenyl](phenyl)methyl}-4-fluoro-1-[2-(1H-1,2,3,4-tetrazol-1-yl)acetyl]pyrrolidine-2-carboxamide 4-fluoro-N-{[3-methyl-4-(propan-2-yl)phenyl](phenyl)methyl}-1-[2-(1H-1,2,3-triazol-5-yl)acetyl]pyrrolidine-2-carboxamide N-{[3-chloro-4-(propan-2-yl)phenyl](phenyl)methyl}-4-fluoro-1-[2-(1H-1,2,3-triazol-5-yl)acetyl]pyrrolidine-2-carboxamide N-[(4-cyclobutyl-3-fluorophenyl)(phenyl)methyl]-4-fluoro-1-[2-(1H-1,2,3-triazol-5-yl)acetyl]pyrrolidine-2-carboxamide N-[(4-cyclobutyl-3-fluorophenyl)(phenyl)methyl]-4-fluoro-1-[2-(1H-1,2,3,4-tetrazol-1-yl)acetyl]pyrrolidine-2-carboxamide N-{[4-(butan-2-yl)-3-fluorophenyl](phenyl)methyl}-4-fluoro-1-[2-(1H-1,2,3-triazol-5-yl)acetyl]pyrrolidine-2-carboxamide 4-fluoro-N-{[3-fluoro-5-methyl-4-(propan-2-yl)phenyl](phenyl)methyl}-1-[2-(1H-1,2,3-triazol-5-yl)acetyl]pyrrolidine-2-carboxamide N-{[3-(difluoromethyl)-4-(propan-2-yl)phenyl](phenyl)methyl}-4-fluoro-1-[2-(1H-1,2,3-triazol-5-yl)acetyl]pyrrolidine-2-carboxamide 4-fluoro-N-{[3-fluoro-4-(1-methylcyclobutyl)phenyl](phenyl)methyl}-1-[2-(1H-1,2,3-triazol-5-yl)acetyl]pyrrolidine-2-carboxamide N-[(4-cyclopropyl-3-fluoro-5-methylphenyl)(phenyl)methyl]-4-fluoro-1-[2-(5-methyl-2H-1,2,3,4-tetrazol-2-yl)acetyl]pyrrolidine-2-carboxamide 4-fluoro-N-{phenyl[4-(propan-2-yl)-3-(trifluoromethyl)phenyl]methyl}-1-[2-(1H-1,2,3-triazol-5-yl)acetyl]pyrrolidine-2-carboxamide N-[(4-tert-butyl-3-fluorophenyl)(phenyl)methyl]-4-fluoro-1-[2-(1H-1,2,3-triazol-5-yl)acetyl]pyrrolidine-2-carboxamide 4-fluoro-N-{[6-fluoro-5-(propan-2-yl)pyridin-2-yl][3-(1H-pyrazol-5-yl)phenyl]methyl}-1-[2-(1H-1,2,3-triazol-5-yl)acetyl]pyrrolidine-2-carboxamide 1-acetyl-4-fluoro-N-{[6-fluoro-5-(propan-2-yl)pyridin-2-yl][3-(4H-1,2,4-triazol-3-yl)phenyl]methyl}pyrrolidine-2-carboxamide 1-acetyl-4-fluoro-N-{[6-fluoro-5-(propan-2-yl)pyridin-2-yl][3-(1H-pyrazol-5-yl)phenyl]methyl}pyrrolidine-2-carboxamide 1-(2-acetamidoacetyl)-4-fluoro-N-{[6-fluoro-5-(propan-2-yl)pyridin-2-yl][3-(1H-pyrazol-5-yl)phenyl]methyl}pyrrolidine-2-carboxamide 4-fluoro-N-{[6-fluoro-5-(propan-2-yl)pyridin-2-yl][3-(1,3-oxazol-5-yl)phenyl]methyl}-1-[2-(1H-1,2,3-triazol-5-yl)acetyl]pyrrolidine-2-carboxamide 4-fluoro-N-{[6-fluoro-5-(propan-2-yl)pyridin-2-yl][3-(1,2-oxazol-5-yl)phenyl]methyl}-1-[2-(1H-1,2,3-triazol-5-yl)acetyl]pyrrolidine-2-carboxamide 1-acetyl-4-fluoro-N-{[6-fluoro-5-(propan-2-yl)pyridin-2-yl][3-(1-methyl-1H-pyrazol-5-yl)phenyl]methyl}pyrrolidine-2-carboxamide 1-acetyl-4-fluoro-N-{[6-fluoro-5-(propan-2-yl)pyridin-2-yl][3-(3-methyl-1H-pyrazol-5-yl)phenyl]methyl}pyrrolidine-2-carboxamide 1-acetyl-N-{[3-(1,3-dimethyl-1H-pyrazol-5-yl)phenyl][6-fluoro-5-(propan-2-yl)pyridin-2-yl]methyl}-4-fluoropyrrolidine-2-carboxamide 1-acetyl-4-fluoro-N-{[6-fluoro-5-(propan-2-yl)pyridin-2-yl][3-(1,2-oxazol-5-yl)phenyl]methyl}pyrrolidine-2-carboxamide 1-acetyl-4-fluoro-N-{[6-fluoro-5-(propan-2-yl)pyridin-2-yl][3-(1H-pyrazol-1-yl)phenyl]methyl}pyrrolidine-2-carboxamide 1-acetyl-4-fluoro-N-{[6-fluoro-5-(propan-2-yl)pyridin-2-yl][3-(1,3,4-oxadiazol-2-yl)phenyl]methyl}pyrrolidine-2-carboxamide 1-(oct-7-ynoyl)-N-{phenyl[4-(propan-2-yl)phenyl]methyl}pyrrolidine-2-carboxamide 4-fluoro-1-(1-methyl-1H-indazole-5-carbonyl)-N-{phenyl[4-(propan-2-yl)phenyl]methyl}pyrrolidine-2-carboxamide 4-fluoro-1-[2-(4-methoxyphenyl)cyclopropanecarbonyl]-N-{phenyl[4-(propan-2-yl)phenyl]methyl}pyrrolidine-2-carboxamide 4-fluoro-1-(7-oxo-5,6,7,8-tetrahydro-1,8-naphthyridine-2-carbonyl)-N-{phenyl[4-(propan-2-yl)phenyl]methyl}pyrrolidine-2-carboxamide 4-fluoro-1-[2-(2-methylpropoxy)pyridine-4-carbonyl]-N-{phenyl[4-(propan-2-yl)phenyl]methyl}pyrrolidine-2-carboxamide 4-fluoro-1-[3-(1H-imidazol-4-yl)propanoyl]-N-{phenyl[4-(propan-2-yl)phenyl]methyl}pyrrolidine-2-carboxamide 4-fluoro-1-[4-(1H-imidazol-1-yl)pyridine-2-carbonyl]-N-{phenyl[4-(propan-2-yl)phenyl]methyl}pyrrolidine-2-carboxamide 4-fluoro-N-{phenyl[4-(propan-2-yl)phenyl]methyl}-1-{[(pyridin-3-yl)carbamoyl]carbonyl}pyrrolidine-2-carboxamide 4-fluoro-1-(5-methoxy-1-methyl-1H-pyrazole-3-carbonyl)-N-{phenyl[4-(propan-2-yl)phenyl]methyl}pyrrolidine-2-carboxamide 1-[2-(1,4-dimethyl-5-oxo-4,5-dihydro-1H-1,2,4-triazol-3-yl)acetyl]-4-fluoro-N-{phenyl[5-(propan-2-yl)pyridin-2-yl]methyl}pyrrolidine-2-carboxamide 1-{2-[4-(azetidin-1-yl)-1H-1,2,3-triazol-1-yl]acetyl}-4-fluoro-N-{phenyl[5-(propan-2-yl)pyridin-2-yl]methyl}pyrrolidine-2-carboxamide 4-fluoro-1-[2-(5-methoxy-1-methyl-1H-1,2,4-triazol-3-yl)acetyl]-N-{phenyl[5-(propan-2-yl)pyridin-2-yl]methyl}pyrrolidine-2-carboxamide 1-{2-[5-(diethylamino)-1H-1,2,3-triazol-1-yl]acetyl}-4-fluoro-N-{phenyl[5-(propan-2-yl)pyridin-2-yl]methyl}pyrrolidine-2-carboxamide 1-{2-[5-(3,3-difluoroazetidin-1-yl)-1H-1,2,3-triazol-1-yl]acetyl}-4-fluoro-N-{phenyl[5-(propan-2-yl)pyridin-2-yl]methyl}pyrrolidine-2-carboxamide 1-{2-[5-(azetidin-1-yl)-1H-1,2,3-triazol-1-yl]acetyl}-4-fluoro-N-{phenyl[5-(propan-2-yl)pyridin-2-yl]methyl}pyrrolidine-2-carboxamide N-[(5-cyclopropyl-6-fluoropyridin-2-yl)(phenyl)methyl]-4-fluoro-1-(2-{3-oxo-2H,3H-[1,2,4]triazolo[4,3-a]pyridin-8-yl}acetyl)pyrrolidine-2-carboxamide N-[(5-cyclopropyl-6-fluoropyridin-2-yl)(phenyl)methyl]-4-fluoro-1-[2-(4-methyl-5-oxo-4,5-dihydro-1,2,4-oxadiazol-3-yl)acetyl]pyrrolidine-2-carboxamide N-[(5-cyclopropyl-6-fluoropyridin-2-yl)(phenyl)methyl]-4-fluoro-1-[2-(1H-1,2,3-triazol-5-yl)acetyl]pyrrolidine-2-carboxamide N-[(5-cyclopropyl-6-fluoropyridin-2-yl)(phenyl)methyl]-1-[2-(1,4-dimethyl-5-oxo-4,5-dihydro-1H-1,2,4-triazol-3-yl)acetyl]-4-fluoropyrrolidine-2-carboxamide N-[(5-cyclopropyl-6-fluoropyridin-2-yl)(phenyl)methyl]-4-fluoro-1-[2-(1H-pyrazol-1-yl)acetyl]pyrrolidine-2-carboxamide N-[(5-cyclopropyl-6-fluoropyridin-2-yl)(phenyl)methyl]-4-fluoro-1-[2-(5-methyl-1H-pyrazol-1-yl)acetyl]pyrrolidine-2-carboxamide N-[(5-cyclopropyl-6-fluoropyridin-2-yl)(phenyl)methyl]-1-{2-[5-(difluoromethyl)-1H-pyrazol-1-yl]acetyl}-4-fluoropyrrolidine-2-carboxamide 1-{2-[4-(azetidin-1-yl)-1H-1,2,3-triazol-1-yl]acetyl}-N-[(5-cyclopropyl-6-fluoropyridin-2-yl)(phenyl)methyl]-4-fluoropyrrolidine-2-carboxamide N-[(5-cyclopropyl-6-fluoropyridin-2-yl)(phenyl)methyl]-1-[2-(2,4-dioxo-1,2,3,4-tetrahydropyrimidin-1-yl)acetyl]-4-fluoropyrrolidine-2-carboxamide N-[(5-cyclopropyl-6-fluoropyridin-2-yl)(phenyl)methyl]-4-fluoro-1-{2-[4-(trifluoromethyl)-1H-pyrazol-1-yl]acetyl}pyrrolidine-2-carboxamide N-[(5-cyclopropyl-6-fluoropyridin-2-yl)(phenyl)methyl]-1-{2-[3-(difluoromethyl)-1H-pyrazol-1-yl]acetyl}-4-fluoropyrrolidine-2-carboxamide N-[(5-cyclopropyl-6-fluoropyridin-2-yl)(phenyl)methyl]-4-fluoro-1-{2-[3-(trifluoromethyl)-1H-pyrazol-1-yl]acetyl}pyrrolidine-2-carboxamide N-[(5-cyclopropyl-6-fluoropyridin-2-yl)(phenyl)methyl]-4-fluoro-1-[2-(2-oxo-1,2-dihydropyridin-3-yl)acetyl]pyrrolidine-2-carboxamide N-[(5-cyclopropyl-6-fluoropyridin-2-yl)(phenyl)methyl]-4-fluoro-1-[2-(5-methyl-6-oxo-1,6-dihydropyridin-3-yl)acetyl]pyrrolidine-2-carboxamide N-[(5-cyclopropyl-6-fluoropyridin-2-yl)(phenyl)methyl]-1-[2-(3-ethyl-5-methyl-2,4-dioxo-1,2,3,4-tetrahydropyrimidin-1-yl)acetyl]-4-fluoropyrrolidine-2-carboxamide N-[(5-cyclopropyl-6-fluoropyridin-2-yl)(phenyl)methyl]-4-fluoro-1-[2-(6-oxo-1,6-dihydropyridin-3-yl)acetyl]pyrrolidine-2-carboxamide
N-[(5-cyclopropyl-6-fluoropyridin-2-yl)(phenyl)methyl]-1-[2-(3-ethyl-2,4-dioxo-1,2,3,4-tetrahydropyrimidin-1-yl)acetyl]-4-fluoropyrrolidine-2-carboxamide
N-[(5-cyclopropyl-6-fluoropyridin-2-yl)(phenyl)methyl]-1-[2-(1-ethyl-6-oxo-1,6-dihydropyridin-3-yl)acetyl]-4-fluoropyrrolidine-2-carboxamide
N-[(5-cyclopropyl-6-fluoropyridin-2-yl)(phenyl)methyl]-1-[2-(6-ethoxy-5-methylpyridin-3-yl)acetyl]-4-fluoropyrrolidine-2-carboxamide
N-[(5-cyclopropyl-6-fluoropyridin-2-yl)(phenyl)methyl]-4-fluoro-1-{2-[4-(trifluoromethyl)-1,3-oxazol-2-yl]acetyl}pyrrolidine-2-carboxamide
N-[(5-cyclopropyl-6-fluoropyridin-2-yl)(phenyl)methyl]-1-[2-(1-ethyl-5-methyl-6-oxo-1,6-dihydropyridin-3-yl)acetyl]-4-fluoropyrrolidine-2-carboxamide
N-[(5-cyclopropyl-6-fluoropyridin-2-yl)(phenyl)methyl]-1-[2-(1-ethyl-5-methyl-2-oxo-1,2-dihydropyridin-3-yl)acetyl]-4-fluoropyrrolidine-2-carboxamide
N-[(5-cyclopropyl-6-fluoropyridin-2-yl)(phenyl)methyl]-1-[2-(1-ethyl-2-oxo-1,2-dihydropyridin-3-yl)acetyl]-4-fluoropyrrolidine-2-carboxamide
N-[(5-cyclopropyl-6-fluoropyridin-2-yl)(phenyl)methyl]-1-[2-(4-ethyl-5-oxo-4,5-dihydropyrazin-2-yl)acetyl]-4-fluoropyrrolidine-2-carboxamide
N-[(5-cyclopropyl-6-fluoropyridin-2-yl)(phenyl)methyl]-4-fluoro-1-[2-(5-methoxy-1-methyl-1H-1,2,4-triazol-3-yl)acetyl]pyrrolidine-2-carboxamide
1-(2-{[benzyl(trifluoromethyl)carbamoyl]amino}acetyl)-N-[(5-cyclopropyl-6-fluoropyridin-2-yl)(phenyl)methyl]-4-fluoropyrrolidine-2-carboxamide
N-[(5-cyclopropyl-6-fluoropyridin-2-yl)(phenyl)methyl]-4-fluoro-1-{2-[5-(trifluoromethyl)-1H-1,2,3-triazol-1-yl]acetyl}pyrrolidine-2-carboxamide
N-[(5-cyclopropyl-6-fluoropyridin-2-yl)(phenyl)methyl]-4-fluoro-1-[2-(5-oxo-4,5-dihydropyrazin-2-yl)acetyl]pyrrolidine-2-carboxamide
N-[(5-cyclopropyl-6-fluoropyridin-2-yl)(phenyl)methyl]-1-{2-[5-(difluoromethyl)-1H-1,2,3-triazol-1-yl]acetyl}-4-fluoropyrrolidine-2-carboxamide
N-[(5-cyclopropyl-6-fluoropyridin-2-yl)(phenyl)methyl]-1-{2-[5-(diethylamino)-1H-1,2,3-triazol-1-yl]acetyl}-4-fluoropyrrolidine-2-carboxamide
N-[(5-cyclopropyl-6-fluoropyridin-2-yl)(phenyl)methyl]-1-{2-[3-(difluoromethyl)-1-methyl-1H-pyrazol-4-yl]acetyl}-4-fluoropyrrolidine-2-carboxamide
N-[(5-cyclopropyl-6-fluoropyridin-2-yl)(phenyl)methyl]-1-{2-[5-(difluoromethyl)-3-methyl-1H-pyrazol-1-yl]acetyl}-4-fluoropyrrolidine-2-carboxamide
N-[(5-cyclopropyl-6-fluoropyridin-2-yl)(phenyl)methyl]-1-{2-[5-(difluoromethyl)-1-methyl-1H-pyrazol-4-yl]acetyl}-4-fluoropyrrolidine-2-carboxamide
N-[(5-cyclopropyl-6-fluoropyridin-2-yl)(phenyl)methyl]-1-{2-[3-(difluoromethyl)-5-methyl-1H-pyrazol-1-yl]acetyl}-4-fluoropyrrolidine-2-carboxamide
N-[(5-cyclopropyl-6-fluoropyridin-2-yl)(phenyl)methyl]-1-[2-(4-ethyl-3-oxo-3,4-dihydropyrazin-2-yl)acetyl]-4-fluoropyrrolidine-2-carboxamide
N-[(5-cyclopropyl-6-fluoropyridin-2-yl)(phenyl)methyl]-1-{2-[4-(difluoromethyl)-1-methyl-1H-pyrazol-5-yl]acetyl}-4-fluoropyrrolidine-2-carboxamide
N-[(5-cyclopropyl-6-fluoropyridin-2-yl)(phenyl)methyl]-4-fluoro-1-{2-[5-(trifluoromethyl)-1H-1,2,3,4-tetrazol-1-yl]acetyl}pyrrolidine-2-carboxamide
N-[(5-cyclopropyl-6-fluoropyridin-2-yl)(phenyl)methyl]-1-{2-[4-(difluoromethyl)-1H-1,2,3-triazol-5-yl]acetyl}-4-fluoropyrrolidine-2-carboxamide
N-[(5-cyclopropyl-6-fluoropyridin-2-yl)(phenyl)methyl]-1-{2-[4-(difluoromethyl)-1-methyl-1H-pyrazol-3-yl]acetyl}-4-fluoropyrrolidine-2-carboxamide
N-[(5-cyclopropyl-6-fluoropyridin-2-yl)(phenyl)methyl]-1-{2-[5-(3,3-difluoroazetidin-1-yl)-1H-1,2,3-triazol-1-yl]acetyl}-4-fluoropyrrolidine-2-carboxamide
N-[(5-cyclopropyl-6-fluoropyridin-2-yl)(phenyl)methyl]-1-{2-[3-(difluoromethyl)-4H-1,2,4-triazol-4-yl]acetyl}-4-fluoropyrrolidine-2-carboxamide
N-[(5-cyclopropyl-6-fluoropyridin-2-yl)(phenyl)methyl]-4-fluoro-1-{2-[5-(trifluoromethyl)-1H-pyrazol-1-yl]acetyl}pyrrolidine-2-carboxamide
N-[(5-cyclopropyl-6-fluoropyridin-2-yl)(phenyl)methyl]-1-[2-(4,5-dimethyl-1,3-oxazol-2-yl)acetyl]-4-fluoropyrrolidine-2-carboxamide
1-{2-[5-(azetidin-1-yl)-1H-1,2,3-triazol-1-yl]acetyl}-N-[(5-cyclopropyl-6-fluoropyridin-2-yl)(phenyl)methyl]-4-fluoropyrrolidine-2-carboxamide
N-[(5-cyclopropyl-6-fluoropyridin-2-yl)(phenyl)methyl]-1-{2-[5-(difluoromethyl)-1H-1,2,3,4-tetrazol-1-yl]acetyl}-4-fluoro-3-hydroxypyrrolidine-2-carboxamide
1-(3-carbamoyl-2-acetamidopropanoyl)-4-fluoro-N-{[3-fluoro-4-(propan-2-yl)phenyl](phenyl)methyl}pyrrolidine-2-carboxamide
4-fluoro-N-{[3-fluoro-4-(propan-2-yl)phenyl](phenyl)methyl}-1-[2-(1H-1,2,3,4-tetrazol-1-yl)propanoyl]pyrrolidine-2-carboxamide
4-fluoro-N-{[3-fluoro-4-(propan-2-yl)phenyl](phenyl)methyl}-1-[2-(1H-imidazol-1-yl)propanoyl]pyrrolidine-2-carboxamide
4-fluoro-N-{[3-fluoro-4-(propan-2-yl)phenyl](phenyl)methyl}-1-[2-(1H-1,2,3-triazol-5-yl)propanoyl]pyrrolidine-2-carboxamide
4-fluoro-N-{[3-fluoro-4-(propan-2-yl)phenyl](phenyl)methyl}-1-[(1H-1,2,3-triazol-5-yl)methanesulfonyl]pyrrolidine-2-carboxamide
4-fluoro-N-{[3-fluoro-4-(propan-2-yl)phenyl](phenyl)methyl}-1-[2-hydroxy-2-(1H-1,2,3-triazol-5-yl)acetyl]pyrrolidine-2-carboxamide
1-{2-[4-(dimethylamino)-1H-1,2,3-triazol-5-yl]acetyl}-4-fluoro-N-{[3-fluoro-4-(propan-2-yl)phenyl](phenyl)methyl}pyrrolidine-2-carboxamide
4-fluoro-N-{[6-fluoro-5-(propan-2-yl)pyridin-2-yl](phenyl)methyl}-1-[2-(1H-1,2,3-triazol-5-yl)acetyl]pyrrolidine-2-carboxamide
1-[2-(3,5-dimethyl-2,4-dioxo-1,2,3,4-tetrahydropyrimidin-1-yl)acetyl]-4-fluoro-N-{[6-fluoro-5-(propan-2-yl)pyridin-2-yl](phenyl)methyl}pyrrolidine-2-carboxamide
4-fluoro-N-{[6-fluoro-5-(propan-2-yl)pyridin-2-yl](phenyl)methyl}-1-[2-(5-methyl-2,4-dioxo-1,2,3,4-tetrahydropyrimidin-1-yl)acetyl]pyrrolidine-2-carboxamide
1-[2-(1,4-dimethyl-5-oxo-4,5-dihydro-1H-1,2,4-triazol-3-yl)acetyl]-4-fluoro-N-{[6-fluoro-5-(propan-2-yl)pyridin-2-yl](phenyl)methyl}pyrrolidine-2-carboxamide
4-fluoro-N-{[6-fluoro-5-(propan-2-yl)pyridin-2-yl](phenyl)methyl}-1-(3-{3-oxo-2H,3H-[1,2,4]triazolo[4,3-a]pyridin-2-yl}propanoyl)pyrrolidine-2-carboxamide
4-fluoro-N-{[6-fluoro-5-(propan-2-yl)pyridin-2-yl](phenyl)methyl}-1-[2-(1H-pyrazol-1-yl)acetyl]pyrrolidine-2-carboxamide
4-fluoro-N-{[6-fluoro-5-(propan-2-yl)pyridin-2-yl](phenyl)methyl}-1-[2-(5-methyl-1H-pyrazol-1-yl)acetyl]pyrrolidine-2-carboxamide 1-{2-[5-(difluoromethyl)-1H-pyrazol-1-yl]acetyl}-4-fluoro-N-{[6-fluoro-5-(propan-2-yl)pyridin-2-yl](phenyl)methyl}pyrrolidine-2-carboxamide 4-fluoro-N-{[6-fluoro-5-(propan-2-yl)pyridin-2-yl](phenyl)methyl}-1-[2-(5-methyl-6-oxo-1,6-dihydropyridin-3-yl)acetyl]pyrrolidine-2-carboxamide 1-[2-(2,4-dioxo-1,2,3,4-tetrahydropyrimidin-1-yl)acetyl]-4-fluoro-N-{[6-fluoro-5-(propan-2-yl)pyridin-2-yl](phenyl)methyl}pyrrolidine-2-carboxamide 1-[2-(3-ethyl-2,4-dioxo-1,2,3,4-tetrahydropyrimidin-1-yl)acetyl]-4-fluoro-N-{[6-fluoro-5-(propan-2-yl)pyridin-2-yl](phenyl)methyl}pyrrolidine-2-carboxamide 1-{2-[4-(azetidin-1-yl)-1H-1,2,3-triazol-1-yl]acetyl}-4-fluoro-N-{[6-fluoro-5-(propan-2-yl)pyridin-2-yl](phenyl)methyl}pyrrolidine-2-carboxamide 4-fluoro-N-{[6-fluoro-5-(propan-2-yl)pyridin-2-yl](phenyl)methyl}-1-{2-[4-(trifluoromethyl)-1H-pyrazol-1-yl]acetyl}pyrrolidine-2-carboxamide 1-{2-[3-(difluoromethyl)-1H-pyrazol-1-yl]acetyl}-4-fluoro-N-{[6-fluoro-5-(propan-2-yl)pyridin-2-yl](phenyl)methyl}pyrrolidine-2-carboxamide 4-fluoro-N-{[6-fluoro-5-(propan-2-yl)pyridin-2-yl](phenyl)methyl}-1-{2-[3-(trifluoromethyl)-1H-pyrazol-1-yl]acetyl}pyrrolidine-2-carboxamide 4-fluoro-N-{[6-fluoro-5-(propan-2-yl)pyridin-2-yl](phenyl)methyl}-1-[2-(6-oxo-1,6-dihydropyridin-3-yl)acetyl]pyrrolidine-2-carboxamide 1-[2-(1-ethyl-6-oxo-1,6-dihydropyridin-3-yl)acetyl]-4-fluoro-N-{[6-fluoro-5-(propan-2-yl)pyridin-2-yl](phenyl)methyl}pyrrolidine-2-carboxamide 4-fluoro-N-{[6-fluoro-5-(propan-2-yl)pyridin-2-yl](phenyl)methyl}-1-[2-(2-oxo-1,2-dihydropyridin-3-yl)acetyl]pyrrolidine-2-carboxamide 1-[2-(3-ethyl-5-methyl-2,4-dioxo-1,2,3,4-tetrahydropyrimidin-1-yl)acetyl]-4-fluoro-N-{[6-fluoro-5-(propan-2-yl)pyridin-2-yl](phenyl)methyl}pyrrolidine-2-carboxamide 1-[2-(1-ethyl-2-oxo-1,2-dihydropyridin-3-yl)acetyl]-4-fluoro-N-{[6-fluoro-5-(propan-2-yl)pyridin-2-yl](phenyl)methyl}pyrrolidine-2-carboxamide 1-[2-(1-ethyl-5-methyl-6-oxo-1,6-dihydropyridin-3-yl)acetyl]-4-fluoro-N-{[6-fluoro-5-(propan-2-yl)pyridin-2-yl](phenyl)methyl}pyrrolidine-2-carboxamide 1-[2-(4-ethyl-5-oxo-4,5-dihydropyrazin-2-yl)acetyl]-4-fluoro-N-{[6-fluoro-5-(propan-2-yl)pyridin-2-yl](phenyl)methyl}pyrrolidine-2-carboxamide 1-[2-(6-ethoxy-5-methylpyridin-3-yl)acetyl]-4-fluoro-N-{[6-fluoro-5-(propan-2-yl)pyridin-2-yl](phenyl)methyl}pyrrolidine-2-carboxamide 1-[2-(1-ethyl-5-methyl-2-oxo-1,2-dihydropyridin-3-yl)acetyl]-4-fluoro-N-{[6-fluoro-5-(propan-2-yl)pyridin-2-yl](phenyl)methyl}pyrrolidine-2-carboxamide 4-fluoro-N-{[6-fluoro-5-(propan-2-yl)pyridin-2-yl](phenyl)methyl}-1-[2-(5-methoxy-1-methyl-1H-1,2,4-triazol-3-yl)acetyl]pyrrolidine-2-carboxamide 4-fluoro-N-{[6-fluoro-5-(propan-2-yl)pyridin-2-yl](phenyl)methyl}-1-{2-[4-(trifluoromethyl)-1,3-oxazol-2-yl]acetyl}pyrrolidine-2-carboxamide 4-fluoro-N-{[6-fluoro-5-(propan-2-yl)pyridin-2-yl](phenyl)methyl}-1-[2-(5-oxo-4,5-dihydropyrazin-2-yl)acetyl]pyrrolidine-2-carboxamide 1-{2-[5-(difluoromethyl)-3-methyl-1H-pyrazol-1-yl]acetyl}-4-fluoro-N-{[6-fluoro-5-(propan-2-yl)pyridin-2-yl](phenyl)methyl}pyrrolidine-2-carboxamide 1-{2-[3-(difluoromethyl)-5-methyl-1H-pyrazol-1-yl]acetyl}-4-fluoro-N-{[6-fluoro-5-(propan-2-yl)pyridin-2-yl](phenyl)methyl}pyrrolidine-2-carboxamide 1-{2-[5-(diethylamino)-1H-1,2,3-triazol-1-yl]acetyl}-4-fluoro-N-{[6-fluoro-5-(propan-2-yl)pyridin-2-yl](phenyl)methyl}pyrrolidine-2-carboxamide 1-[2-(4-ethyl-3-oxo-3,4-dihydropyrazin-2-yl)acetyl]-4-fluoro-N-{[6-fluoro-5-(propan-2-yl)pyridin-2-yl](phenyl)methyl}pyrrolidine-2-carboxamide 1-{2-[5-(3,3-difluoroazetidin-1-yl)-1H-1,2,3-triazol-1-yl]acetyl}-4-fluoro-N-{[6-fluoro-5-(propan-2-yl)pyridin-2-yl](phenyl)methyl}pyrrolidine-2-carboxamide 1-{2-[5-(azetidin-1-yl)-1H-1,2,3-triazol-1-yl]acetyl}-4-fluoro-N-{[6-fluoro-5-(propan-2-yl)pyridin-2-yl](phenyl)methyl}pyrrolidine-2-carboxamide 1-[2-(1H-1,3-benzodiazol-1-yl)propanoyl]-N-[(4-cyclopropyl-3-fluorophenyl)(phenyl)methyl]-4-fluoropyrrolidine-2-carboxamide or a stereoisomer or tautomer thereof, or a pharmaceutically acceptable salt of any of the foregoing.

Methods of Treatment

Provided herein is a method of modulating GYS1 in a cell, comprising exposing the cell to (i) a composition comprising an effective amount of a GYS1 inhibitor, or (ii) a pharmaceutical composition, comprising an effective amount of a GYS1 inhibitor, and one or more pharmaceutically acceptable excipients. In some embodiments, the GYS1 inhibitor is a small molecule. In some embodiments, the GYS1 inhibitor is selective for GYS1 over GYS2. In some embodiments, the GYS1 inhibitor is greater than 500 or 1,000 or 1,500 or 1,700-fold selective for GYS1 over GYS2.

Provided herein is a method of modulating GYS1 in a cell, comprising exposing the cell to (i) a composition comprising an effective amount of a compound of formula (I), or any variation or embodiment thereof, or a stereoisomer or tautomer thereof, or a pharmaceutically acceptable salt of any of the foregoing, or (ii) a pharmaceutical composition, comprising an effective amount of a compound of formula (I), or any variation or embodiment thereof, or a stereoisomer or tautomer thereof, or a pharmaceutically acceptable salt of any of the foregoing, and one or more pharmaceutically acceptable excipients.

Provided herein is a method of inhibiting GYS1 in a cell, comprising exposing the cell to (i) a composition comprising an effective amount of a GYS1 inhibitor, or (ii) a pharmaceutical composition, comprising an effective amount of a GYS1 inhibitor, and one or more pharmaceutically acceptable excipients. In some embodiments, the GYS1 inhibitor is a small molecule. In some embodiments, the GYS1 inhibitor is selective for GYS1 over GYS2. In some embodiments, the GYS1 inhibitor is greater than 500 or 1,000 or 1,500 or 1,700-fold selective for GYS1 over GYS2.

Provided herein is a method of inhibiting GYS1 in a cell, comprising exposing the cell to (i) a composition comprising an effective amount of a compound of formula (I), or any variation or embodiment thereof, or a stereoisomer or tautomer thereof, or a pharmaceutically acceptable salt of any of the foregoing, or (ii) a pharmaceutical composition, comprising an effective amount of a compound of formula (I), or any variation or embodiment thereof, or a stereoisomer or tautomer thereof, or a pharmaceutically acceptable salt of any of the foregoing, and one or more pharmaceutically acceptable excipients.

Provided herein is a method of reducing tissue glycogen stores in an individual in need thereof, comprising administering to the individual an effective amount of (i) a GYS1 inhibitor, or (ii) a pharmaceutical composition, comprising a GYS1 inhibitor, and one or more pharmaceutically acceptable excipients. In some embodiments, the GYS1 inhibitor is a small molecule. In some embodiments, the GYS1 inhibitor is selective for GYS1 over GYS2. In some embodiments, the GYS1 inhibitor is greater than 500 or 1,000 or 1,500 or 1,700-fold selective for GYS1 over GYS2. In some embodiments, the individual has a GYS1-mediated disease, disorder, or condition is selected from the group consisting of Pompe disease, Cori disease (GSD III), adult polyglucosan body disease (APBD), and Lafora disease. In some embodiments, the GYS1-mediated disease, disorder, or condition is cancer. In some embodiments, the GYS1-mediated disease, disorder, or condition is selected from the group consisting of Ewing sarcoma (ES), clear cell renal cell carcinoma (ccRCC), glycogen rich clear cell carcinoma (GRCC) breast cancer, non-small-cell lung carcinoma (NSCLC), and acute myeloid leukemia (AML). In some embodiments, the GYS1-mediated disease, disorder, or condition is Pompe disease. In some embodiments, the GYS1-mediated disease, disorder, or condition is late-onset Pompe disease (LOPD).

Provided herein is a method of reducing tissue glycogen stores in an individual in need thereof, comprising administering to the individual (i) a composition comprising an effective amount of a compound of formula (I), or any variation or embodiment thereof, or a stereoisomer or tautomer thereof, or a pharmaceutically acceptable salt of any of the foregoing, or (ii) a pharmaceutical composition, comprising an effective amount of a compound of formula (I), or any variation or embodiment thereof, or a stereoisomer or tautomer thereof, or a pharmaceutically acceptable salt of any of the foregoing, and one or more pharmaceutically acceptable excipients.

Provided herein is a method of reducing tissue glycogen stores in an individual in need thereof, comprising administering to the individual (i) a composition comprising an effective amount of a compound of formula (I'), or any variation or embodiment thereof, or a stereoisomer or tautomer thereof, or a pharmaceutically acceptable salt of any of the foregoing, or (ii) a pharmaceutical composition, comprising an effective amount of a compound of formula (I'), or any variation or embodiment thereof, or a stereoisomer or tautomer thereof, or a pharmaceutically acceptable salt of any of the foregoing, and one or more pharmaceutically acceptable excipients.

Provided herein is a method of inhibiting glycogen synthesis in an individual in need thereof, comprising administering to the individual an effective amount of (i) a GYS1 inhibitor, or (ii) a pharmaceutical composition, comprising a GYS1 inhibitor, and one or more pharmaceutically acceptable excipients. In certain embodiments the GYS1 inhibitor is a compound of formula (I'), (I) or any variation or embodiment thereof, or a stereoisomer or tautomer thereof, or a pharmaceutically acceptable salt of any of the foregoing, and one or more pharmaceutically acceptable excipients. In some embodiments, the pharmaceutical composition is (i) a composition comprising an effective amount of a compound of formula (I'), (I), or any variation or embodiment thereof, or a stereoisomer or tautomer thereof, or a pharmaceutically acceptable salt of any of the foregoing, or (ii) a pharmaceutical composition, comprising an effective amount of a compound of formula (I'), (I), or any variation or embodiment thereof, or a stereoisomer or tautomer thereof, or a pharmaceutically acceptable salt of any of the foregoing, and one or more pharmaceutically acceptable excipients. In some embodiments, the compounds and/or compositions inhibit the hGYS enzyme, and subsequently, the glycogen synthesis in cells.

Provided herein is a method of treating a GYS1-mediated disease, disorder, or condition in an individual in need thereof, comprising subjecting the individual to glycogen substrate reduction therapy. In some embodiments, glycogen substrate reduction therapy reduces glycogen stores. In some embodiments, glycogen substrate reduction therapy comprises administering to the individual an effective amount of (i) a GYS1 inhibitor, or (ii) a pharmaceutical composition comprising a GYS1 inhibitor, and one or more pharmaceutically acceptable excipients. In some embodiments, the GYS1 inhibitor is a small molecule. In some embodiments, the GYS1 inhibitor is selective for GYS1 over GYS2. In some embodiments, the GYS1 inhibitor is greater than 500 or 1,000 or 1,500 or 1,700-fold selective for GYS1 over GYS2. In some embodiments, the GYS1-mediated disease, disorder, or condition is selected from the group consisting of Pompe disease, Cori disease (GSD III), adult polyglucosan body disease (APBD), and Lafora disease. In some embodiments, the GYS1-mediated disease, disorder, or condition is cancer. In some embodiments, the GYS1-mediated disease, disorder, or condition is selected from the group consisting of Ewing sarcoma (ES), clear cell renal cell carcinoma (ccRCC), glycogen rich clear cell carcinoma (GRCC) breast cancer, non-small-cell lung carcinoma (NSCLC), and acute myeloid leukemia (AML). In some embodiments, the GYS1-mediated disease, disorder, or condition is Pompe disease.

Provided herein is a method of treating a GYS1-mediated disease, disorder, or condition in an individual in need thereof, comprising administering to the individual (i) a composition comprising an effective amount of a compound of formula (I), or any variation or embodiment thereof, or a stereoisomer or tautomer thereof, or a pharmaceutically acceptable salt of any of the foregoing, or (ii) a pharmaceutical composition, comprising an effective amount of a compound of formula (I), or any variation or embodiment thereof, or a stereoisomer or tautomer thereof, or a pharmaceutically acceptable salt of any of the foregoing, and one or more pharmaceutically acceptable excipients. In some embodiments, the GYS1-mediated disease, disorder, or condition is selected from the group consisting of Pompe disease, Cori disease (GSD III), adult polyglucosan body disease (APBD), and Lafora disease. In some embodiments, the GYS1-mediated disease, disorder, or condition is cancer. In some embodiments, the GYS1-mediated disease, disorder, or condition is selected from the group consisting of Ewing sarcoma (ES), clear cell renal cell carcinoma (ccRCC), glycogen rich clear cell carcinoma (GRCC) breast cancer, non-small-cell lung carcinoma (NSCLC), and acute myeloid leukemia (AML).

Provided herein is a method of treating a glycogen storage disease, disorder, or condition in an individual in need thereof, comprising subjecting the individual to glycogen substrate reduction therapy. In some embodiments, glycogen substrate reduction therapy reduces glycogen stores. In some embodiments, glycogen substrate reduction therapy comprises administering to the individual an effective amount of (i) a GYS1 inhibitor, or (ii) a pharmaceutical composition comprising a GYS1 inhibitor, and one or more pharmaceutically acceptable excipients. In some embodiments, the GYS1 inhibitor is a small molecule. In some embodiments, the GYS1 inhibitor is selective for GYS1 over GYS2. In some embodiments, the GYS1 inhibitor is greater than 500 or 1,000 or 1,500 or 1,700-fold selective for GYS1 over GYS2. In some embodiments, the level of glycogen in the individual is reduced upon treatment. In some embodiments, the level of glycogen in muscle is reduced. In some embodiments, the level of glycogen is skeletal muscle is reduced. In some embodiments, the level of glycogen is reduced at least 10%, at least 20%, at least 30% or at least 50% upon administration of the compound. In some embodiments, the compounds provided herein are effective for treating a lysosomal disorder. In some embodiments, the glycogen storage disease, disorder, or condition is selected from the group consisting of Pompe disease, Cori disease (GSD III), adult polyglucosan body disease (APBD), and Lafora disease. In some embodiments, the glycogen storage disease, disorder, or condition is Pompe disease. In some embodiments, the individual has late onset Pompe Disease. In some embodiments, the GYS1 inhibitor comprises a compound of formula (I), or any variation or embodiment thereof, or a stereoisomer or tautomer thereof, or a pharmaceutically acceptable salt thereof.

Provided herein is a method of treating a glycogen storage disease, disorder, or condition in an individual in need thereof, comprising administering to the individual (i) a composition comprising an effective amount of a compound of formula (I), or any variation or embodiment thereof, or a stereoisomer or tautomer thereof, or a pharmaceutically acceptable salt of any of the foregoing, or (ii) a pharmaceutical composition, comprising an effective amount of a compound of formula (I), or any variation or embodiment thereof, or a stereoisomer or tautomer thereof, or a pharmaceutically acceptable salt of any of the foregoing, and one or more pharmaceutically acceptable excipients. In some embodiments, the level of glycogen in the individual is reduced upon treatment. In some embodiments, the level of glycogen in muscle is reduced. In some embodiments, the level of glycogen is skeletal muscle is reduced. In some embodiments, the level of glycogen is reduced at least 10%, at least 20%, at least 30% or at least 50% upon administration of the compound. In some embodiments, the compounds provided herein are effective for treating a lysosomal disorder. In some embodiments, the glycogen storage disease, disorder, or condition is selected from the group consisting of Pompe disease, Cori disease (GSD III), adult polyglucosan body disease (APBD), and Lafora disease.

Provided herein is a method of treating Pompe disease in an individual in need thereof, comprising administering to the individual (i) a composition comprising an effective amount of a compound of formula (I), or any variation or embodiment thereof, or a stereoisomer or tautomer thereof, or a pharmaceutically acceptable salt of any of the foregoing, or (ii) a pharmaceutical composition, comprising an effective amount of a compound of formula (I), or any variation or embodiment thereof, or a stereoisomer or tautomer thereof, or a pharmaceutically acceptable salt of any of the foregoing, and one or more pharmaceutically acceptable excipients. In some embodiments, the individual has infant onset Pompe disease. In some embodiments, the individual has non-classic infant-onset Pompe disease. In some embodiments, the individual has late-onset Pompe disease. In some embodiments, the individual has a deficiency in acid alfa glucosidase (GAA). In some embodiments, the individual has reduced expression of GAA.

In some embodiments, the compounds provided herein reduce and/or eliminate one or more symptoms associated with Pompe disease. In some embodiments, the compounds reduce and/or eliminate weak muscles, poor muscle tone, enlarged liver, failure to grow and gain weight, trouble breathing, feeding problems, infections in the respiratory system, problems with hearing, motor skill delay, heart enlargement, tiredness, lung infection, frequent falling, or irregular heartbeat. In some embodiments, the compounds herein delay progression of Pompe disease.

In some embodiments, the compounds provided herein increase the lifespan of the individual. In some embodiments, the lifespan is increased at least 5, at least 10, or at least 20 years upon treatment.

In some embodiments, the compounds provided herein prevent, reduce, or delay muscle weakness. In some embodiments, muscle weakness is determined by manual muscle testing, sit to stand test, heel-raise test, hand-held dynamometry, or hand grip dynamometry. In some embodiments, strength is graded according to the following scale: 0: No visible muscle contraction; 1: Visible muscle contraction with no or trace movement; 2: Limb movement, but not against gravity; 3: Movement against gravity but not resistance; 4: Movement against at least some resistance supplied by the examiner; 5: Full strength.

Also provided herein is a method of inhibiting a GYS1 enzyme in an individual comprising administering an effective amount of a compound of formula (I) or a pharmaceutically acceptable salt thereof to the individual. In some embodiments the GYS1 enzyme is human GYS1 (hGYS1). In some embodiments, the compounds provided herein are inhibit GYS1 at a concentration of less than 10 µM, less than 1 µM, less than 0.5 µM, or less than 0.1 µM. In some embodiments, the compounds provided herein inhibit GYS1 at a concentration of 1-10 µM, 0.01 to 1 µM, or 0.01 to 10 µM.

In some embodiments, the compounds have an $IC_{50}$ of less than 10 nM, less than 10 µM, less than 1 µM, less than 0.5 µM, or less than 0.1 µM. In some embodiments, the compounds provided herein have an $IC_{50}$ of 1 to 10 nM, 1 to 10 µM, 0.01 to 1 µM, 0.01 to 10 µM, or 0.001 to 0.01 µM.

In some embodiments, glycogen synthesis is inhibited upon administration of a compound provided herein. In some embodiments, glycogen synthesis is reduced at least 10%, at least 20%, at least 40% or at least 50% upon administration.

In some embodiments, the individual receiving treatment is a juvenile human or an infant. In some embodiments, the individual is less than 10 years old, less than 9 years old, less than 8 years old, less than 7 years old, less than 6 years old, less than 5 years old, less than 4 years old, less than 3 years old, less than 2 years old, or less than one year old.

In some embodiments, the methods further comprise enzyme replacement therapy (ERT). Exemplary ERTs include alglucosidase alfa (human recombinant alpha-glucosidase (human GAA)) and those described in Byrne B J et al (2011). Pompe disease: design, methodology, and early findings from the Pompe Registry. Mol Genet Metab 103: 1-11 (herein incorporated by reference in its entirety). In some embodiments, the ERT is selected from the group consisting of Myozyme and Lumizyme. In some embodiments, the ERT is Myozyme. In some embodiments, the ERT is Lumizyme. In some embodiments, the individual has an advanced glycogen storage disease. In some embodiments, the individual has late onset Pompe Disease. Thus, provided herein is a method of treating a GYS1-mediated disease, disorder, or condition in an individual in need thereof, comprising subjecting the individual to (a) glycogen substrate reduction therapy, such as administering to the individual an effective amount of (i) a GYS1 inhibitor, or (ii) a pharmaceutical composition comprising a GYS1 inhibitor, and one or more pharmaceutically acceptable excipients and (b) enzyme replacement therapy. In some embodiments, the GYS1-mediated disease, disorder, or condition is Pompe disease, such as late-onset Pompe disease. In some embodiments, the GYS1 inhibitor is a small molecule. In some embodiments, the GYS1 inhibitor is selective for GYS1 over GYS2. In some embodiments, the GYS1 inhibitor is greater than 500 or 1,000 or 1,500 or 1,700-fold selective for GYS1 over GYS2. In some embodiments, the GYS1 inhibitor is a compound of formula (I) or a pharmaceutically acceptable salt thereof.

In some embodiments, the individual has a mutation in the GAA gene. In some embodiments, the mutation reduces the level of GAA protein. In some embodiments, the mutation is a loss-of-function mutation. In some embodiments, the mutation is a missense mutation. In some embodiments, the mutation is a deletion. In some embodiments, the mutation is a recessive mutation. In some embodiments, the mutation is a splicing variant.

In some embodiments of the foregoing, the administration is oral administration.

Kits

The present disclosure further provides kits for carrying out the methods of the invention. The kits may comprise a compound or pharmaceutically acceptable salt thereof as described herein and suitable packaging. The kits may comprise one or more containers comprising any compound described herein. In one aspect, a kit includes a compound of the disclosure or a pharmaceutically acceptable salt thereof, and a label and/or instructions for use of the compound in the treatment of a disease or disorder described herein. The kits may comprise a unit dosage form of the compound.

Provided herein are kits, comprising (i) a composition comprising an effective amount of a compound of formula (I), or any variation or embodiment thereof, or a stereoisomer or tautomer thereof, or a pharmaceutically acceptable salt of any of the foregoing, and (ii) instructions for use in treating an GYS1-mediated disease, disorder, or condition in an individual in need thereof. Also provided herein are kits, comprising (i) a pharmaceutical composition comprising an effective amount of a compound of formula (I), or any variation or embodiment thereof, or a stereoisomer or tautomer thereof, or a pharmaceutically acceptable salt of any of the foregoing, and one or more pharmaceutically acceptable excipients; and (ii) instructions for use in treating an GYS1-mediated disease, disorder, or condition in an individual in need thereof Articles of manufacture are also provided, wherein the article of manufacture comprises a compound of formula (I), or any variation or embodiment thereof, as described elsewhere herein, or a stereoisomer or tautomer thereof, or a pharmaceutically acceptable salt of any of the foregoing, in a suitable container. Also provided herein are articles of manufacture, comprising a pharmaceutical composition comprising a compound of formula (I), or any variation or embodiment thereof, as described elsewhere herein, or a stereoisomer or tautomer thereof, or a pharmaceutically acceptable salt of any of the foregoing, in a suitable container. The container may be a vial, jar, ampoule, preloaded syringe, or intravenous bag.

ENUMERATED EMBODIMENTS

The following enumerated embodiments are also contemplated:

Embodiment 1. A Compound of Formula (I)

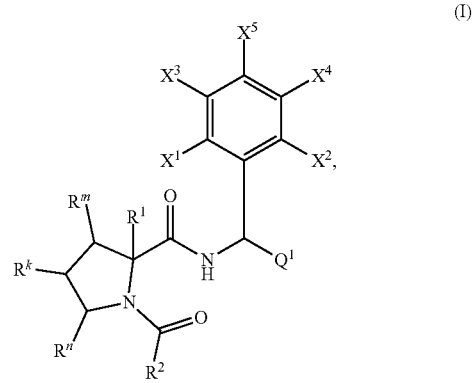

or a stereoisomer or tautomer thereof, or a pharmaceutically acceptable salt of any of the foregoing, wherein:
  $X^1$ and $X^2$ are each independently H, $C_{1-6}$alkyl, or $C_{1-6}$alkoxy;
  $X^3$ and $X^4$ are each independently H, halo, $C_{1-6}$alkyl, $C_{1-6}$alkoxy, or 5-20 membered heteroaryl;
  $X^5$ is H, $C_{1-6}$alkyl, $C_{1-6}$alkoxy, or $C_{3-10}$cycloalkyl;
  $Q^1$ is selected from (i) to (iii):
  (i) phenyl, wherein the phenyl of $Q^1$ is substituted with one or more halo, $C_{1-6}$alkyl, $C_{2-6}$alkenyl, —$NH_2$, —NH—C(O)—($C_{1-6}$alkyl), —NH—C(O)-(3-15 membered heterocyclyl), or $C_{3-10}$cycloalkyl, wherein the $C_{1-6}$alkyl is optionally substituted with one or more halo, and the $C_{3-10}$cycloalkyl is optionally substituted with one or more halo or $C_{1-6}$alkyl,
  (ii) 3-15 membered heterocyclyl, wherein the 3-15 membered heterocyclyl of $Q^1$ is optionally substituted with one or more oxo, and
  (iii) 5-20 membered heteroaryl, wherein the 5-20 membered heteroaryl of $Q^1$ is optionally substituted with one or more halo, $C_{1-6}$alkyl, $C_{2-6}$alkenyl, $C_{1-6}$alkoxy, —$NH_2$, or $C_{3-10}$cycloalkyl, wherein the $C_{3-10}$cycloalkyl is optionally substituted with one or more halo or $C_{1-6}$alkyl;
  $R^1$ is H or $C_{1-6}$alkyl;
  $R^k$ is H, halo, —OH, —$NH_2$, or —NH—C(O)$C_{1-6}$alkyl;
  $R^m$ is H, —OH, or $C_{1-6}$alkyl;
  $R^n$ is H, $C_{1-6}$alkyl, or $C_{3-10}$cycloalkyl;
  or $R^k$ is taken together with either $R^m$ or $R^n$, and the atoms to which they are attached, to form cyclopropyl; and
  $R^2$ is selected from (i) to (vii):
  (i) $C_{1-6}$alkyl, wherein the $C_{1-6}$alkyl of $R^2$ is optionally substituted with one or more $R^a$, wherein $R^a$ is:
    (a) —OH,
    (b) cyano,
    (c) $C_{2-6}$alkynyl,
    (d) $C_{6-20}$aryl, wherein the $C_{6-20}$aryl of $R^a$ is optionally substituted with one or more halo, cyano, $C_{1-6}$alkoxy, or —NH—C(O)—$C_{1-6}$alkyl,
    (e) 5-20 membered heteroaryl, wherein the 5-20 membered heteroaryl of $R^a$ is optionally substituted with one or more $R^b$, wherein
      $R^b$ is halo, $C_{1-6}$alkyl, $C_{1-6}$alkoxy, —$NH_2$, —NH($C_{1-6}$alkyl), —N($C_{1-6}$alkyl)$_2$, $C_{3-10}$cycloalkyl, 3-15 membered heterocyclyl, or —C(O)—$C_{1-6}$alkoxy, wherein the $C_{1-6}$alkyl of $R^b$ is optionally substituted with one or more halo, —$NH_2$, —$NH(C_{1-6}alkyl)$, —$N(C_{1-6}alkyl)_2$, —NH—$C(O)C_{1-6}alkyl$, or —NH—$C(O)$—$C_{1-6}$alkoxy, and the 3-15-membered heterocyclyl of $R^b$ is optionally substituted with one or more halo or —$C(O)$—$C_{1-6}$alkoxy, (f) 3-15 membered heterocyclyl, wherein the 3-15 membered heterocyclyl of $R^a$ is optionally substituted with one or more $R^c$, wherein $R^c$ is halo, oxo, $C_{1-6}$alkyl, $C_{1-6}$alkoxy, —$C(O)$—$C_{1-6}$alkyl, or —$C(O)$—$C_{1-6}$alkoxy, wherein the $C_{1-6}$alkyl of $R^c$ is optionally substituted with one or more halo or $C_{2-6}$alkynyl, and the —$C(O)$—$C_{1-6}$alkoxy of $R^c$ is optionally substituted with one or more halo, (g) —$N(R^c)(R^d)$, wherein $R^c$ and $R^d$ are, independently of each other, H, $C_{1-6}$alkyl,
—$C(O)$—$C_{1-6}$alkyl, —$C(O)$—$C_{1-6}$alkoxy, —$C(O)$—$NH_2$, —$C(O)$—$NH(C_{1-6}alkyl)$, —$C(O)$—$N(C_{1-6}alkyl)_2$, —$C(O)$-(3-15 membered heterocyclyl), —$CH_2$—$C(O)$—$NH_2$, 3-15 membered heterocyclyl, or 5-20 membered heteroaryl, wherein the —$C(O)$—$C_{1-6}$alkyl of $R^c$ or $R^d$ is optionally substituted with one or more halo, the 3-15 membered heterocyclyl and the 5-20 membered heteroaryl of $R^c$ or $R^d$ are independently optionally substituted with one or more $C_{1-6}$alkyl, and the —$C(O)$-(3-15 membered heterocyclyl) of $R^c$ or $R^d$ is optionally substituted with one or more halo, —$C(O)$—$C_{1-6}$alkoxy, or $C_{1-6}$alkyl, wherein the $C_{1-6}$alkyl is optionally substituted with one or more halo, $C_{1-6}$alkoxy, or $C_{3-10}$cycloalkyl, (h) —O—$R^e$, wherein $R^e$ is $C_{1-6}$alkyl, $C_{6-20}$aryl, —$C(O)$-(3-15 membered heterocyclyl), —$C(O)$—N—$(C_{1-6}alkyl)_2$, or 5-20 membered heteroaryl, wherein the $C_{1-6}$alkyl of $R^e$ is optionally substituted with one or more $C_{1-6}$alkoxy, wherein the $C_{1-6}$alkoxy is optionally substituted with one or more $C_{2-6}$alkynyl, the $C_{6-20}$aryl of $R^e$ is optionally substituted with one or more $C_{1-6}$alkyl, and the —$C(O)$-(3-15 membered heterocyclyl) of $R^e$ is optionally substituted with one or more $C_{1-6}$alkyl, $C_{1-6}$alkoxy, or —$C(O)$—$C_{1-6}$alkoxy, wherein the $C_{1-6}$alkyl is optionally substituted with one or more halo, $C_{1-6}$alkoxy, or $C_{3-10}$cycloalkyl, (i) —$C(O)$—$R^e$, wherein $R^e$ is —$NH_2$, —OH, or 3-15 membered heterocyclyl, or (j) —$S(O)_2$—$R^f$, wherein $R^f$ is $C_{1-6}$alkyl or 3-15 membered heterocyclyl, provided that, when $R^2$ is unsubstituted methyl, then either (1) $Q^1$ is 5-20 membered heteroaryl, wherein the 5-20 membered heteroaryl of $Q^1$ is substituted with one or more halo, $C_{1-6}$alkyl, $C_{2-6}$alkenyl, $C_{1-6}$alkoxy, —$NH_2$, $C_{3-10}$cycloalkyl, or —OH, or (2) $Q^1$ is phenyl, wherein the phenyl of $Q^1$ is substituted with at least one $C_{3-6}$alkyl or at least one $C_{3-10}$cycloalkyl, wherein the at least one $C_{3-6}$alkyl is optionally substituted with one or more halo, and the at least one $C_{3-10}$cycloalkyl is optionally substituted with one or more halo or $C_{1-6}$alkyl, (ii) $C_{3-10}$cycloalkyl, wherein the $C_{3-10}$cycloalkyl of $R^2$ is optionally substituted with one or more $R^q$, wherein $R^q$ is 5-20 membered heteroaryl or $C_{6-20}$aryl, wherein the $C_{6-20}$aryl of $R^q$ is optionally substituted with one or more $C_{1-6}$alkoxy, (iii) 3-15 membered heterocyclyl, wherein the 3-15 membered heterocyclyl of $R^2$ is optionally substituted with one or more halo, oxo, $C_{1-6}$alkyl, —$C(O)$—$C_{1-6}$alkyl, or 5-20 membered heteroaryl, (iv) 5-20 membered heteroaryl, wherein the 5-20 membered heteroaryl of $R^2$ is optionally substituted with one or more $R^s$, wherein $R^s$ is $C_{1-6}$alkyl, $C_{1-6}$alkoxy, —NH—$C(O)$—$C_{1-6}$alkyl, $C_{6-20}$aryl, or 5-20 membered heteroaryl, wherein the $C_{1-6}$alkyl of $R^s$ is optionally substituted with one or more $C_{1-6}$alkoxy, (v) —$N(R^g)(R^h)$, wherein $R^g$ and $R^h$ are independently H or $C_{1-6}$alkyl, (vi) —$C(O)$—$R^j$, wherein $R^j$ is $C_{3-10}$cycloalkyl, —NH($C_{1-6}$alkyl), —$N(C_{1-6}alkyl)_2$, or —NH (5-20 membered heteroaryl), and (vii) $C_{6-20}$aryl, wherein the $C_{6-20}$aryl of $R^2$ is optionally substituted with one or more 5-20 membered heteroaryl or —O—$R^p$, wherein $R^p$ is 3-15 membered heterocyclyl, wherein the 3-15 membered heterocyclyl of $R^p$ is optionally substituted with one or more —$C(O)$—$C_{1-6}$alkyl.

Embodiment 2. The compound of embodiment 1, or a stereoisomer or tautomer thereof, or a pharmaceutically acceptable salt of any of the foregoing, wherein $Q^1$ is 5-20 membered heteroaryl, wherein the 5-20 membered heteroaryl of $Q^1$ is optionally substituted with one or more halo, $C_{1-6}$alkyl, $C_{2-6}$alkenyl, $C_{1-6}$alkoxy, —$NH_2$, or $C_{3-10}$cycloalkyl, wherein the $C_{3-10}$cycloalkyl is optionally substituted with one or more $C_{1-6}$alkyl or halo.

Embodiment 3. The compound of embodiment 1 or embodiment 2, or a stereoisomer or tautomer thereof, or a pharmaceutically acceptable salt of any of the foregoing, wherein $Q^1$ is 5-6 membered heteroaryl, wherein the 5-6 membered heteroaryl of $Q^1$ is optionally substituted with one or more halo, $C_{1-6}$alkyl, $C_{2-6}$alkenyl, $C_{1-6}$alkoxy, —$NH_2$, or $C_{3-10}$cycloalkyl, wherein the $C_{3-10}$cycloalkyl is optionally substituted with one or more $C_{1-6}$alkyl or halo.

Embodiment 4. The compound of any one of embodiments 1-3, or a stereoisomer or tautomer thereof, or a pharmaceutically acceptable salt of any of the foregoing, wherein $Q^1$ is pyridinyl, wherein the pyridinyl of $Q^1$ is optionally substituted with one or more halo, $C_{1-6}$alkyl, $C_{2-6}$alkenyl, $C_{1-6}$alkoxy, —$NH_2$, or $C_{3-10}$cycloalkyl, wherein the $C_{3-10}$cycloalkyl is optionally substituted with one or more $C_{1-6}$alkyl or halo.

Embodiment 5. The compound of any one of embodiments 1-4, or a stereoisomer or tautomer thereof, or a pharmaceutically acceptable salt of any of the foregoing, wherein $Q^1$ is 2-pyridinyl or 3-pyridinyl, wherein the 2-pyridinyl or 3-pyridinyl of $Q^1$ is optionally substituted with one or more halo, $C_{1-6}$alkyl, $C_{2-6}$alkenyl, $C_{1-6}$alkoxy, —$NH_2$, or $C_{3-10}$cycloalkyl, wherein the $C_{3-10}$cycloalkyl is optionally substituted with one or more $C_{1-6}$alkyl or halo.

Embodiment 6. The compound of any one of embodiments 1-5, or a stereoisomer or tautomer thereof, or a pharmaceutically acceptable salt of any of the foregoing, wherein $Q^1$ is 2-pyridinyl, wherein the 2-pyridinyl of $Q^1$ is optionally substituted with one or more halo, $C_{1-6}$alkyl, $C_{2-6}$alkenyl, $C_{1-6}$alkoxy, —$NH_2$, or $C_{3-10}$cycloalkyl, wherein the $C_{3-10}$cycloalkyl is optionally substituted with one or more $C_{1-6}$alkyl or halo.

Embodiment 7. The compound of any one of embodiments 1-6, or a stereoisomer or tautomer thereof, or a pharmaceutically acceptable salt of any of the foregoing, wherein $Q^1$ is 2-pyridinyl, wherein the 2-pyridinyl of $Q^1$ is optionally substituted with one or more halo, $C_{1-6}$alkyl, or $C_{3-10}$cycloalkyl, wherein the $C_{3-10}$cycloalkyl is optionally substituted with one or more $C_{1-6}$alkyl or halo.

Embodiment 8. The compound of any one of embodiments 1-7, or a stereoisomer or tautomer thereof, or a pharmaceutically acceptable salt of any of the foregoing, wherein $Q^1$ is 2-pyridinyl, wherein the 2-pyridinyl of $Q^1$ is optionally substituted with one or more fluoro, chloro, methyl, iso-propyl, tert-butyl, cyclopropyl, or cyclobutyl, wherein the cyclopropyl and cyclobutyl are independently optionally substituted with one or more methyl or fluoro.

Embodiment 9. The compound of any one of embodiments 1-8, or a stereoisomer or tautomer thereof, or a pharmaceutically acceptable salt of any of the foregoing, wherein $Q^1$ is selected from the group consisting of

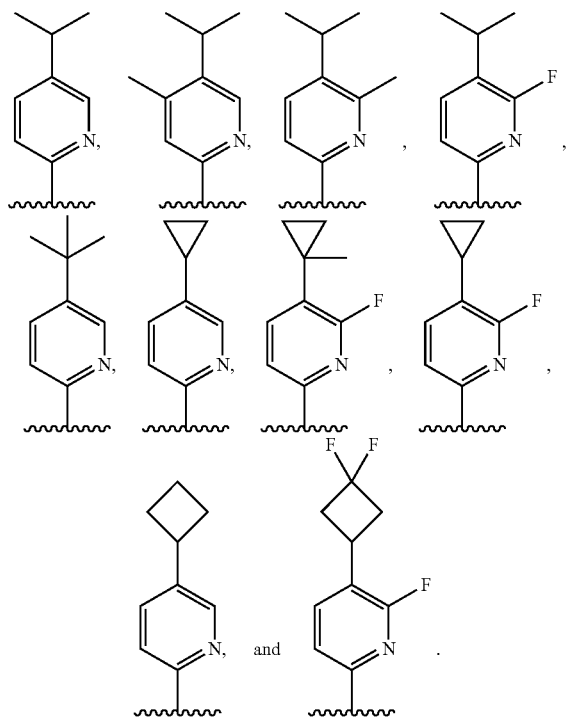

Embodiment 10. The compound of any one of embodiments 1-9, or a stereoisomer or tautomer thereof, or a pharmaceutically acceptable salt of any of the foregoing, wherein $Q^1$ is selected from the group consisting of

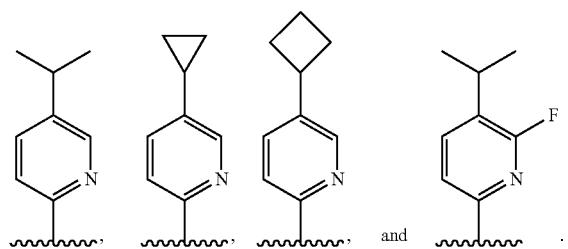

Embodiment 11. The compound of embodiment 1, or a stereoisomer or tautomer thereof, or a pharmaceutically acceptable salt of any of the foregoing, wherein $Q^1$ is phenyl, wherein the phenyl of $Q^1$ is substituted with one or more halo, $C_{1-6}$alkyl, $C_{2-6}$ alkenyl, —$NH_2$, —NH—C(O)—($C_{1-6}$alkyl), —NH—C(O)-(3-15 membered heterocyclyl), or $C_{3-10}$cycloalkyl, wherein the $C_{1-6}$alkyl is optionally substituted with one or more halo, and the $C_{3-10}$cycloalkyl is optionally substituted with one or more halo or $C_{1-6}$alkyl.

Embodiment 12. The compound of embodiment 1 or embodiment 11, or a stereoisomer or tautomer thereof, or a pharmaceutically acceptable salt of any of the foregoing, wherein $Q^1$ is phenyl, wherein the phenyl of $Q^1$ is substituted with one or more halo, $C_{1-6}$alkyl, $C_{2-6}$ alkenyl, or $C_{3-10}$cycloalkyl, wherein the $C_{1-6}$alkyl is optionally substituted with one or more halo, and the $C_{3-10}$cycloalkyl is optionally substituted with one or more halo or $C_{1-6}$alkyl.

Embodiment 13. The compound of any one of embodiments 1, 11 and 12, or a stereoisomer or tautomer thereof, or a pharmaceutically acceptable salt of any of the foregoing, wherein $Q^1$ is phenyl, wherein the phenyl of $Q^1$ is substituted with one or more fluoro, chloro, methyl, iso-propyl, sec-butyl, tert-butyl, prop-1-en-2-yl, cyclopropyl, or cyclobutyl, wherein the methyl, iso-propyl, sec-butyl, and tert-butyl are independently optionally substituted with one or more halo, and the cyclopropyl and cyclobutyl are independently optionally substituted with one or more fluoro or methyl.

Embodiment 14. The compound of any one of embodiments 1 and 11-13, or a stereoisomer or tautomer thereof, or a pharmaceutically acceptable salt of any of the foregoing, wherein $Q^1$ is selected from the group consisting of

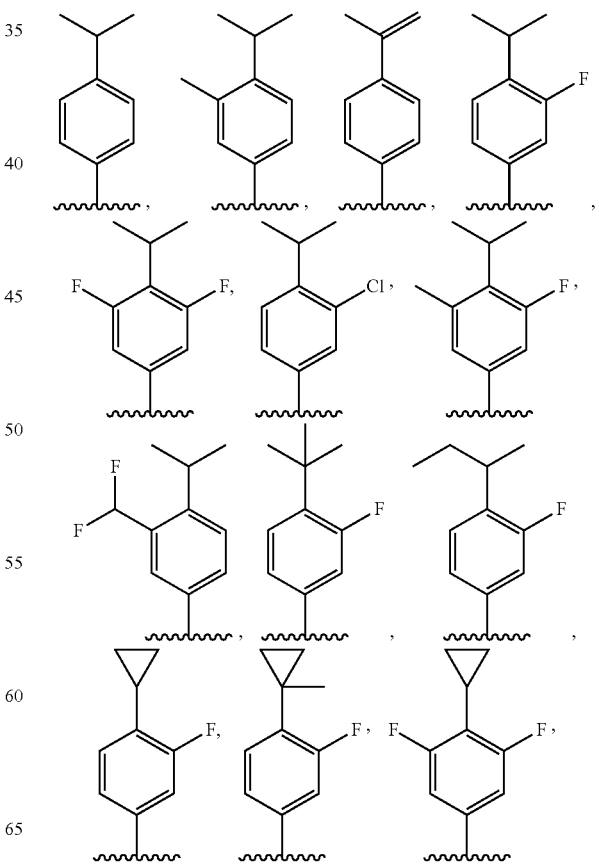

-continued

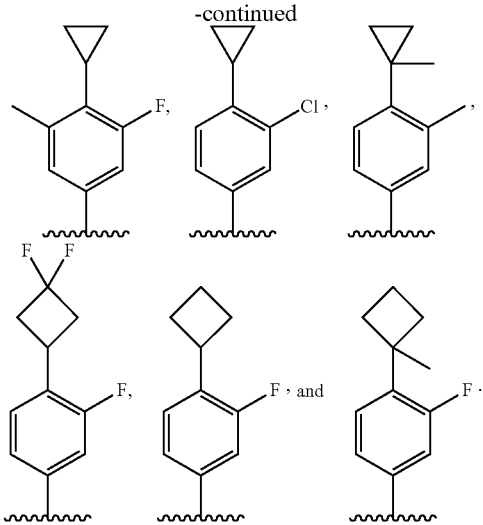

Embodiment 15. The compound of any one of embodiments 1 and 11-13, or a stereoisomer or tautomer thereof, or a pharmaceutically acceptable salt of any of the foregoing, wherein $Q^1$ is selected from the group consisting of

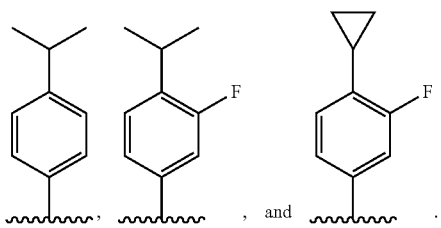

Embodiment 16. The compound of embodiment 1, or a stereoisomer or tautomer thereof, or a pharmaceutically acceptable salt of any of the foregoing, wherein $Q^1$ is 3-15 membered heterocyclyl, wherein the 3-15 membered heterocyclyl of $Q^1$ is optionally substituted with one or more oxo.

Embodiment 17. The compound of embodiment 1 or embodiment 16, or a stereoisomer or tautomer thereof, or a pharmaceutically acceptable salt of any of the foregoing, wherein $Q^1$ is

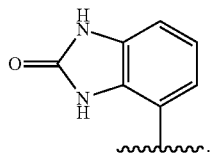

Embodiment 18. The compound of any one of embodiments 1-17, or a stereoisomer or tautomer thereof, or a pharmaceutically acceptable salt of any of the foregoing, wherein $X^1$, $X^2$, $X^3$, $X^4$, and $X^5$ are each H.

Embodiment 19. The compound of any one of embodiments 1-18, or a stereoisomer or tautomer thereof, or a pharmaceutically acceptable salt of any of the foregoing, wherein $R^m$ is H, $R^n$ is H, and $R^k$ is H, halo, —OH, —NH$_2$, or —NH—C(O)C$_{1-6}$alkyl.

Embodiment 20. The compound of any one of embodiments 1-19, or a stereoisomer or tautomer thereof, or a pharmaceutically acceptable salt of any of the foregoing, wherein $R^m$ is H, $R^n$ is H, and $R^k$ is halo, —OH, or —NH$_2$.

Embodiment 21. The compound of any one of embodiments 1-20, or a stereoisomer or tautomer thereof, or a pharmaceutically acceptable salt of any of the foregoing, wherein $R^m$ is H, $R^n$ is H, and $R^k$ is halo.

Embodiment 22. The compound of any one of embodiments 1-21, or a stereoisomer or tautomer thereof, or a pharmaceutically acceptable salt of any of the foregoing, wherein $R^m$ is H, $R^n$ is H, and $R^k$ is fluoro.

Embodiment 23. The compound of any one of embodiments 1-18, or a stereoisomer or tautomer thereof, or a pharmaceutically acceptable salt of any of the foregoing, wherein $R^k$ is taken together with either $R^m$ or $R^n$, and the atoms to which they are attached, to form cyclopropyl.

Embodiment 24. The compound of any one of embodiments 1-23, or a stereoisomer or tautomer thereof, or a pharmaceutically acceptable salt of any of the foregoing, wherein $R^1$ is H.

Embodiment 25. The compound of any one of embodiments 1-24, or a stereoisomer or tautomer thereof, or a pharmaceutically acceptable salt of any of the foregoing, wherein $R^2$ is C$_{1-6}$alkyl, wherein the C$_{1-6}$alkyl of $R^2$ is optionally substituted with one or more $R^a$.

Embodiment 26. The compound of any one of embodiments 1-25, or a stereoisomer or tautomer thereof, or a pharmaceutically acceptable salt of any of the foregoing, wherein $R^2$ is C$_{1-6}$alkyl, wherein the C$_{1-6}$alkyl of $R^2$ is substituted with one or more $R^a$, wherein $R^a$ is —OH or 5-20 membered heteroaryl, wherein the 5-20 membered heteroaryl of $R^a$ is optionally substituted with one or more $R^b$.

Embodiment 27. The compound of any one of embodiments 1-26, or a stereoisomer or tautomer thereof, or a pharmaceutically acceptable salt of any of the foregoing, wherein $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more $R^b$.

Embodiment 28. The compound of any one of embodiments 1-27, or a stereoisomer or tautomer thereof, or a pharmaceutically acceptable salt of any of the foregoing, wherein $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more C$_{1-6}$alkyl, wherein the C$_{1-6}$alkyl is optionally substituted with one or more halo, —NH$_2$, —NH(C$_{1-6}$alkyl), —N(C$_{1-6}$alkyl)$_2$, —NH—C(O)C$_{1-6}$alkyl, or —NH—C(O)—C$_{1-6}$alkoxy.

Embodiment 29. The compound of any one of embodiments 1-28, or a stereoisomer or tautomer thereof, or a pharmaceutically acceptable salt of any of the foregoing, wherein $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more methyl, wherein the methyl is optionally substituted with one or more fluoro.

Embodiment 30. The compound of any one of embodiments 1-29, or a stereoisomer or tautomer thereof, or a pharmaceutically acceptable salt of any of the foregoing, wherein $R^2$ is selected from the group consisting of

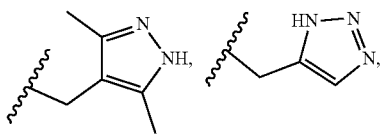

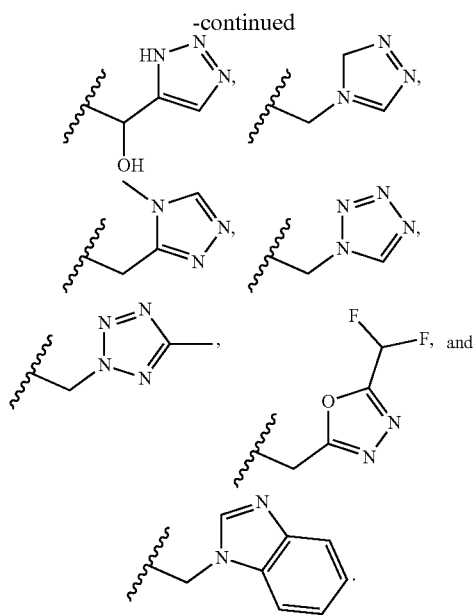

Embodiment 31. The compound of any one of embodiments 1-30, or a stereoisomer or tautomer thereof, or a pharmaceutically acceptable salt of any of the foregoing, wherein $R^2$ is

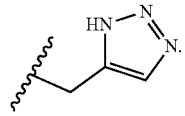 [SMILES: *Cc1cnn[nH]1]

Embodiment 32. The compound of any one of embodiments 1-25, or a stereoisomer or tautomer thereof, or a pharmaceutically acceptable salt of any of the foregoing, wherein $R^2$ is $C_{1-6}$alkyl, wherein the $C_{1-6}$alkyl of $R^2$ is substituted with one or more $R^a$, wherein $R^a$ is 3-15 membered heterocyclyl, wherein the 3-15 membered heterocyclyl of $R^a$ is optionally substituted with one or more $R^c$.

Embodiment 33. The compound of any one of embodiments 1-25 and 32, or a stereoisomer or tautomer thereof, or a pharmaceutically acceptable salt of any of the foregoing, wherein $R^2$ is methyl, wherein the methyl of $R^2$ is substituted with one or more $R^a$, wherein $R^a$ is 3-15 membered heterocyclyl, wherein the 3-15 membered heterocyclyl of $R^a$ is optionally substituted with one or more $R^c$.

Embodiment 34. The compound of any one of embodiments 1-25, 32, and 33, or a stereoisomer or tautomer thereof, or a pharmaceutically acceptable salt of any of the foregoing, wherein $R^2$ is methyl, wherein the methyl of $R^2$ is substituted with one or more $R^a$, wherein $R^a$ is 3-8 membered heterocyclyl, wherein the 3-8 membered heterocyclyl of $R^a$ is optionally substituted with one or more $R^c$.

Embodiment 35. The compound of any one of embodiments 1-25 and 32-34, or a stereoisomer or tautomer thereof, or a pharmaceutically acceptable salt of any of the foregoing, wherein $R^2$ is methyl, wherein the methyl of $R^2$ is substituted with one or more $R^a$, wherein $R^a$ is 3-8 membered heterocyclyl, wherein the 3-8 membered heterocyclyl of $R^a$ is optionally substituted with one or more oxo or $C_{1-6}$alkyl.

Embodiment 36. The compound of any one of embodiments 1-25 and 32-35, or a stereoisomer or tautomer thereof, or a pharmaceutically acceptable salt of any of the foregoing, wherein $R^2$ is

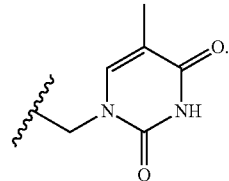 [SMILES: *Cn1cc(C)c(=O)[nH]c1=O]

Embodiment 37. The compound of any one of embodiments 1-25, or a stereoisomer or tautomer thereof, or a pharmaceutically acceptable salt of any of the foregoing, wherein $R^2$ is $C_{1-6}$alkyl, wherein the $C_{1-6}$alkyl of $R^2$ is substituted with one or more $R^a$, wherein $R^a$ is —O—$R^e$.

Embodiment 38. The compound of any one of embodiments 1-25 and 37, or a stereoisomer or tautomer thereof, or a pharmaceutically acceptable salt of any of the foregoing, wherein $R^2$ is methyl, wherein the methyl of $R^2$ is substituted with one or more $R^a$, wherein $R^a$ is —O—$R^e$.

Embodiment 39. The compound of any one of embodiments 1-25, 37, and 38, or a stereoisomer or tautomer thereof, or a pharmaceutically acceptable salt of any of the foregoing, wherein $R^2$ is methyl, wherein the methyl of $R^2$ is substituted with one or more $R^a$, wherein $R^a$ is —O—$R^e$, wherein $R^e$ is —C(O)-(3-15 membered heterocyclyl).

Embodiment 40. The compound of any one of embodiments 1-25 and 37-39, or a stereoisomer or tautomer thereof, or a pharmaceutically acceptable salt of any of the foregoing, wherein $R^2$ is

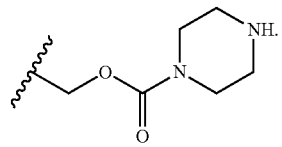

Embodiment 41. The compound of any one of embodiments 1-25, or a stereoisomer or tautomer thereof, or a pharmaceutically acceptable salt of any of the foregoing, wherein $R^2$ is $C_{1-6}$alkyl, wherein the $C_{1-6}$alkyl of $R^2$ is substituted with one or more $R^a$, wherein $R^a$ is —N($R^c$)($R^d$).

Embodiment 42. The compound of any one of embodiments 1-25 and 41, or a stereoisomer or tautomer thereof, or a pharmaceutically acceptable salt of any of the foregoing, wherein $R^2$ is methyl, wherein the methyl of $R^2$ is substituted with one or more $R^a$, wherein $R^a$ is —N($R^c$)($R^d$).

Embodiment 43. The compound of any one of embodiments 1-25, 41, and 42, or a stereoisomer or tautomer thereof, or a pharmaceutically acceptable salt of any of the foregoing, wherein $R^2$ is methyl, wherein the methyl of $R^2$ is substituted with one or more $R^a$, wherein $R^a$ is —N($R^c$)($R^d$), wherein one of $R^c$ and $R^d$ is H, and the other of $R^c$ and $R^d$ is —C(O)—N($C_{1-6}$alkyl)$_2$.

Embodiment 44. The compound of any one of embodiments 1-25 and 41-43, or a stereoisomer or tautomer thereof, or a pharmaceutically acceptable salt of any of the foregoing, wherein $R^2$ is

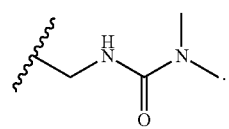 [SMILES: *CNC(=O)N(C)C]

Embodiment 45. The compound of embodiment 1, or a stereoisomer or tautomer thereof, or a pharmaceutically acceptable salt of any of the foregoing, wherein the compound is of formula (I-A):

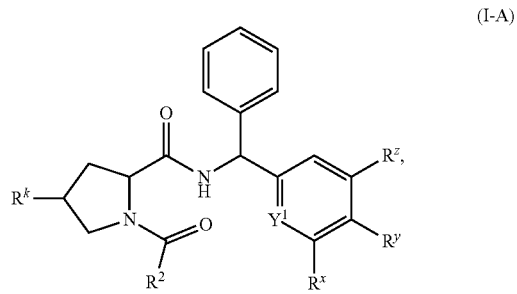

(I-A)

or a stereoisomer or tautomer thereof, or a pharmaceutically acceptable salt of any of the foregoing, wherein
$Y^1$ is CH or N;
$R^x$ and $R^z$ are independently H, halo, $C_{1-6}$alkyl, or —$NH_2$, wherein, when $Y^1$ is CH, the $C_{1-6}$alkyl of $R^x$ or $R^z$ may be optionally substituted with one or more halo; and
$R^y$ is (i) $C_{1-6}$alkyl, (ii) $C_{2-6}$alkenyl, or (iii) $C_{3-10}$cycloalkyl, wherein the $C_{3-10}$cycloalkyl is optionally substituted with one or more halo or $C_{1-6}$alkyl.

Embodiment 46. The compound of embodiment 1 or embodiment 45, or a stereoisomer or tautomer thereof, or a pharmaceutically acceptable salt of any of the foregoing, wherein $R^x$ is H, fluoro, or methyl, and
$R^y$ is (i) isopropyl, or (ii) $C_{3-4}$cycloalkyl, wherein the $C_{3-4}$cycloalkyl is optionally substituted with one or more fluoro or methyl.

Embodiment 47. The compound of any one of embodiments 1, 45, and 46, or a stereoisomer or tautomer thereof, or a pharmaceutically acceptable salt of any of the foregoing, wherein $R^k$ is H or halo.

Embodiment 48. The compound of any one of embodiments 1-24, or a stereoisomer or tautomer thereof, or a pharmaceutically acceptable salt of any of the foregoing, wherein $R^2$ is $C_{1-6}$alkyl, wherein the $C_{1-6}$alkyl of $R^2$ is optionally substituted with one or more $R^a$.

Embodiment 49. The compound of any one of embodiments 1 and 45-48, or a stereoisomer or tautomer thereof, or a pharmaceutically acceptable salt of any of the foregoing, wherein $R^2$ is $C_{1-6}$alkyl, wherein the $C_{1-6}$alkyl of $R^2$ is substituted with one or more $R^a$, wherein $R^a$ is —OH or 5-20 membered heteroaryl, wherein the 5-20 membered heteroaryl of $R^a$ is optionally substituted with one or more $R^b$.

Embodiment 50. The compound of any one of embodiments 1 and 45-49, or a stereoisomer or tautomer thereof, or a pharmaceutically acceptable salt of any of the foregoing, wherein $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more $R^b$.

Embodiment 51. The compound of any one of embodiments 1 and 45-50, or a stereoisomer or tautomer thereof, or a pharmaceutically acceptable salt of any of the foregoing, wherein $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more $C_{1-6}$alkyl, wherein the $C_{1-6}$alkyl is optionally substituted with one or more halo, —$NH_2$, —$NH(C_{1-6}$alkyl), —$N(C_{1-6}$alkyl$)_2$, —NH—C(O) $C_{1-6}$alkyl, or —NH—C(O)—$C_{1-6}$alkoxy.

Embodiment 52. The compound of any one of embodiments 1 and 45-51, or a stereoisomer or tautomer thereof, or a pharmaceutically acceptable salt of any of the foregoing, wherein $R^2$ is methyl, wherein the methyl of $R^2$ is substituted with one or more $R^a$, wherein $R^a$ is —OH or 5-10 membered heteroaryl, wherein the 5-10 membered heteroaryl of $R^a$ is optionally substituted with one or more methyl, wherein the methyl is optionally substituted with one or more fluoro.

Embodiment 53. The compound of any one of embodiments 1 and 45-52, or a stereoisomer or tautomer thereof, or a pharmaceutically acceptable salt of any of the foregoing, wherein $R^2$ is selected from the group consisting of

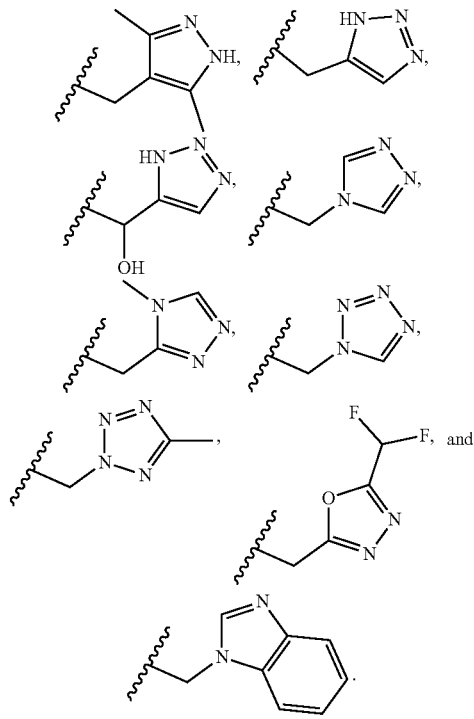

Embodiment 54. The compound of any one of embodiments 1 and 45-53, or a stereoisomer or tautomer thereof, or a pharmaceutically acceptable salt of any of the foregoing, wherein $R^2$ is

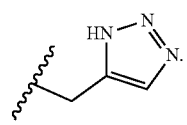 [SMILES: *Cc1cnn[nH]1]

Embodiment 55. The compound of any one of embodiments 1 and 45-48, or a stereoisomer or tautomer thereof, or a pharmaceutically acceptable salt of any of the foregoing, wherein $R^2$ is $C_{1-6}$alkyl, wherein the $C_{1-6}$alkyl of $R^2$ is substituted with one or more $R^a$, wherein $R^a$ is 3-15 membered heterocyclyl, wherein the 3-15 membered heterocyclyl of $R^a$ is optionally substituted with one or more $R^c$.

Embodiment 56. The compound of any one of embodiments 1, 45-48, and 55, or a stereoisomer or tautomer thereof, or a pharmaceutically acceptable salt of any of the foregoing, wherein $R^2$ is methyl, wherein the methyl of $R^2$ is substituted with one or more $R^a$, wherein $R^a$ is 3-15 membered heterocyclyl, wherein the 3-15 membered heterocyclyl of $R^a$ is optionally substituted with one or more $R^c$.

Embodiment 57. The compound of any one of embodiments 1, 45-48, 55, and 56, or a stereoisomer or tautomer thereof, or a pharmaceutically acceptable salt of any of the foregoing, wherein $R^2$ is methyl, wherein the methyl of $R^2$ is substituted with one or more $R^a$, wherein $R^a$ is 3-8 membered heterocyclyl, wherein the 3-8 membered heterocyclyl of $R^a$ is optionally substituted with one or more $R^c$.

Embodiment 58. The compound of any one of embodiments 1, 45-48, and 55-57, or a stereoisomer or tautomer thereof, or a pharmaceutically acceptable salt of any of the foregoing, wherein $R^2$ is methyl, wherein the methyl of $R^2$ is substituted with one or more $R^a$, wherein $R^a$ is 3-8 membered heterocyclyl, wherein the 3-8 membered heterocyclyl of $R^a$ is optionally substituted with one or more oxo or $C_{1-6}$alkyl.

Embodiment 59. The compound of any one of embodiments 1, 45-48, and 55-58, or a stereoisomer or tautomer thereof, or a pharmaceutically acceptable salt of any of the foregoing, wherein $R^2$ is

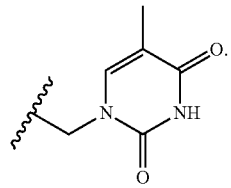 [SMILES: *Cn1cc(C)c(=O)[nH]c1=O]

Embodiment 60. The compound of any one of embodiments 1 and 45-48, or a stereoisomer or tautomer thereof, or a pharmaceutically acceptable salt of any of the foregoing, wherein $R^2$ is $C_{1-6}$alkyl, wherein the $C_{1-6}$alkyl of $R^2$ is substituted with one or more $R^a$, wherein $R^a$ is —O—$R^e$.

Embodiment 61. The compound of any one of embodiments 1, 45-48, and 60, or a stereoisomer or tautomer thereof, or a pharmaceutically acceptable salt of any of the foregoing, wherein $R^2$ is methyl, wherein the methyl of $R^2$ is substituted with one or more $R^a$, wherein $R^a$ is —O—$R^e$.

Embodiment 62. The compound of any one of embodiments 1, 45-48, 60, and 61, or a stereoisomer or tautomer thereof, or a pharmaceutically acceptable salt of any of the foregoing, wherein $R^2$ is methyl, wherein the methyl of $R^2$ is substituted with one or more $R^a$, wherein $R^a$ is —O—$R^e$, wherein $R^e$ is —C(O)-(3-15 membered heterocyclyl).

Embodiment 63. The compound of any one of embodiments 1, 45-48, and 60-62, or a stereoisomer or tautomer thereof, or a pharmaceutically acceptable salt of any of the foregoing, wherein $R^2$ is

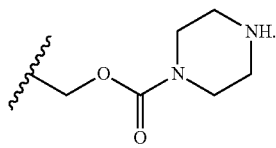 [SMILES: *COC(=O)N1CCNCC1]

Embodiment 64. The compound of any one of embodiments 1, 45-48, and 60-63, or a stereoisomer or tautomer thereof, or a pharmaceutically acceptable salt of any of the foregoing, wherein $R^2$ is $C_{1-6}$alkyl, wherein the $C_{1-6}$alkyl of $R^2$ is substituted with one or more $R^a$, wherein $R^a$ is —N($R^c$)($R^d$).

Embodiment 65. The compound of any one of embodiments 1, 45-48, and 60-64, or a stereoisomer or tautomer thereof, or a pharmaceutically acceptable salt of any of the foregoing, wherein $R^2$ is methyl, wherein the methyl of $R^2$ is substituted with one or more $R^a$, wherein $R^a$ is —N($R^c$)($R^d$).

Embodiment 66. The compound of any one of embodiments 1, 45-48, and 60-65, or a stereoisomer or tautomer thereof, or a pharmaceutically acceptable salt of any of the foregoing, wherein $R^2$ is methyl, wherein the methyl of $R^2$ is substituted with one or more $R^a$, wherein $R^a$ is —N(R)($R^d$), wherein one of $R^c$ and $R^d$ is H, and the other of $R^c$ and $R^d$ is —C(O)—N($C_{1-6}$alkyl)$_2$.

Embodiment 67. The compound of any one of embodiments 1, 45-48, and 60-66, or a stereoisomer or tautomer thereof, or a pharmaceutically acceptable salt of any of the foregoing, wherein $R^2$ is

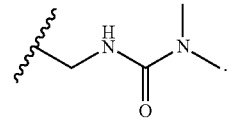 [SMILES: *CNC(=O)N(C)C]

Embodiment 68. The compound of embodiment 1, or a stereoisomer or tautomer thereof, or a pharmaceutically acceptable salt of any of the foregoing, wherein the compound, or a stereoisomer or tautomer thereof, or a pharmaceutically acceptable salt of any of the foregoing, is selected from Table 1.

Embodiment 69. A pharmaceutical composition comprising (i) a compound of any one of embodiments 1-68, or a stereoisomer or tautomer thereof, or a pharmaceutically acceptable salt of any of the foregoing, and (ii) one or more pharmaceutically acceptable excipients.

Embodiment 70. A method of modulating GYS1 in a cell, comprising exposing the cell to a composition comprising an effective amount of a compound of any one or embodiments 1-68, or a stereoisomer or tautomer thereof, or a pharmaceutically acceptable salt of any of the foregoing, or a pharmaceutical composition of embodiment 69.

Embodiment 71. A method of inhibiting GYS1 in a cell, comprising exposing the cell to a composition comprising an effective amount of a compound of any one or embodiments 1-68, or a stereoisomer or tautomer thereof, or a pharmaceutically acceptable salt of any of the foregoing, or a pharmaceutical composition of embodiment 69.

Embodiment 72. A method of reducing tissue glycogen stores in an individual in need thereof, comprising administering to the individual an effective amount of a compound of any one of embodiments 1-68, or a stereoisomer or tautomer thereof, or a pharmaceutically acceptable salt of any of the foregoing, or a pharmaceutical composition of embodiment 69.

Embodiment 73. A method of treating a GYS1-mediated disease, disorder, or condition in an individual in need thereof, comprising administering to the individual an effective amount of a compound of any one of embodiments 1-68, or a stereoisomer or tautomer thereof, or a pharmaceutically acceptable salt of any of the foregoing, or a pharmaceutical composition of embodiment 69.

Embodiment 74. The method of embodiment 73, wherein the disease, disorder, or condition is a glycogen storage disorder (GSD).

Embodiment 75. The method of embodiment 73 or embodiment 74, wherein the disease, disorder, or condition is selected from the group consisting of Pompe disease, Cori disease (GSD III), adult polyglucosan body disease (APBD), and Lafora disease.

Embodiment 76. The method of any one of embodiments 73-75, wherein the disease, disorder, or condition is Pompe disease.

Embodiment 77. The method of embodiment 73, wherein the disease, disorder, or condition is cancer.

Embodiment 78. The method of embodiment 73 or embodiment 77, wherein the disease, disorder, or condition is selected from the group consisting of Ewing sarcoma (ES), clear cell renal cell carcinoma (ccRCC), glycogen rich clear cell carcinoma (GRCC) breast cancer, non-small-cell lung carcinoma (NSCLC), and acute myeloid leukemia (AML).

Embodiment 79. The method of embodiment 73, wherein the individual has a GAA mutation.

Embodiment 80. The method of embodiment 79, wherein the GAA mutation is a loss-of-function mutation.

Embodiment 81. A kit, comprising (i) a compound of any one of embodiments 1-68, or a stereoisomer or tautomer thereof, or a pharmaceutically acceptable salt of any of the foregoing, or a pharmaceutical composition of embodiment 69, and (ii) instructions for use in treating an GYS1-mediated disease, disorder, or condition in an individual in need thereof.

Embodiment 82. The kit of embodiment 81, wherein the disease, disorder, or condition is a glycogen storage disorder (GSD).

Embodiment 83. The kit of embodiment 81 or embodiment 82, wherein the disease, disorder, or condition is selected from the group consisting of Pompe disease, Cori disease (GSD III), adult polyglucosan body disease (APBD), and Lafora disease.

Embodiment 84. The kit of any one of embodiments 81-83, wherein the disease, disorder, or condition is Pompe disease.

Embodiment 85. The kit of embodiment 81, wherein the disease, disorder, or condition is cancer.

Embodiment 86. The kit of embodiment 81 or embodiment 85, wherein the disease, disorder, or condition is selected from the group consisting of Ewing sarcoma (ES), clear cell renal cell carcinoma (ccRCC), glycogen rich clear cell carcinoma (GRCC) breast cancer, non-small-cell lung carcinoma (NSCLC), and acute myeloid leukemia (AML).

Embodiment 87. The kit of embodiment 81, wherein the individual has a GAA mutation.

Embodiment 88. The kit of embodiment 87, wherein the GAA mutation is a loss-of-function mutation.

Embodiment 89. A method of modulating GYS1 in a cell, comprising exposing the cell to a composition comprising an effective amount of a GYS1 modulator, or a pharmaceutical composition comprising a GYS1 modulator.

Embodiment 90. A method of inhibiting GYS1 in a cell, comprising exposing the cell to a composition comprising an effective amount of a GYS1 inhibitor, or a pharmaceutical composition comprising a GYS1 inhibitor.

Embodiment 91. A method of reducing tissue glycogen stores in an individual in need thereof, comprising administering to the individual an effective amount of a GYS1 inhibitor, or a pharmaceutical composition comprising a GYS1 inhibitor.

Embodiment 92. A method of treating a GYS1-mediated disease, disorder, or condition in an individual in need thereof, comprising subjecting the individual to glycogen substrate reduction therapy.

Embodiment 93. The method of embodiment 92, wherein the disease, disorder, or condition is a glycogen storage disorder (GSD).

Embodiment 94. The method of embodiment 92 or embodiment 93, wherein the disease, disorder, or condition is selected from the group consisting of Pompe disease, Cori disease (GSD III), adult polyglucosan body disease (APBD), and Lafora disease.

Embodiment 95. The method of any one of embodiments 92-94, wherein the disease, disorder, or condition is Pompe disease.

Embodiment 96. The method of embodiment 92, wherein the disease, disorder, or condition is cancer.

Embodiment 97. The method of embodiment 92 or embodiment 96, wherein the disease, disorder, or condition is selected from the group consisting of Ewing sarcoma (ES), clear cell renal cell carcinoma (ccRCC), glycogen rich clear cell carcinoma (GRCC) breast cancer, non-small-cell lung carcinoma (NSCLC), and acute myeloid leukemia (AML).

Embodiment 98. The method of embodiment 92, wherein the individual has a GAA mutation.

Embodiment 99. The method of embodiment 98, wherein the GAA mutation is a loss-of-function mutation.

Embodiment 100. The method of any one of embodiments 89-91 wherein the GYS1 inhibitor is selective for GYS1 over GYS2.

Embodiment 101. The method of embodiment 100, wherein the GYS1 inhibitor is greater than 500 or 1,000 or 1,500 or 1,700-fold selective for GYS1 over GYS2.

Embodiment 102. The method of any one of embodiments 92-99 wherein the glycogen substrate reduction therapy comprises administering to the individual a GYS1 inhibitor.

Embodiment 103. The method of embodiment 102, wherein the GYS1 inhibitor is a small molecule.

Embodiment 104. The method of embodiment 103, wherein the GYS1 inhibitor is selective for GYS1 over GYS2.

Embodiment 105. The method of embodiment 104, wherein the GYS1 inhibitor is greater than 500 or 1,000 or 1,500 or 1,700-fold selective for GYS1 over GYS2.

Methods of Preparing

The present disclosure further provides processes for preparing the compounds of present invention. In some aspect, provided herein are processes of preparing a compound of formula (I') or formula (I), or any embodiment or variation thereof, such as a compound of formula (I-A), (I-B), (I-C), (I-D), (I-D1), (I-D2), (I-E), (I-F), (I-G), (I-H) or a stereoisomer or tautomer thereof, or a pharmaceutically acceptable salt of any of the foregoing.

In some embodiments, a process for preparing a compound of formula (I') or formula (I), or a stereoisomer or tautomer thereof, or a pharmaceutically acceptable salt of any of the foregoing, comprises reacting a compound of formula (I'-1):

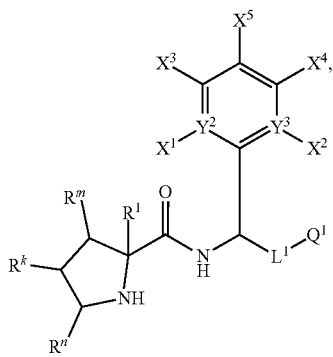

(I'-1)

or a salt thereof, with a compound of formula R²COOH in the presence of a coupling reagent.

In some embodiments, the coupling reagent comprises EDCCl, TCFH, or T3P. In some embodiments, the process further comprises the presence of a base. In some embodiments, the base comprises an amine. In some embodiments, the amine is DMAP, NMM, or a trialkylamine.

In some embodiments, a process for preparing a compound of formula (I'), or a stereoisomer or tautomer thereof, or a pharmaceutically acceptable salt of any of the foregoing, comprises (a) reacting a compound of formula (I'-2):

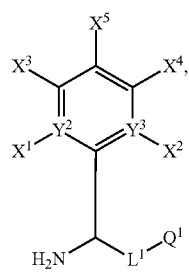

(I'-2)

or a salt thereof, with a compound of formula (I'-3):

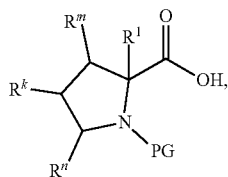

(I'-3)

wherein PG is a protecting group,
in the presence of a coupling reagent to provide a compound of formula I'-4:

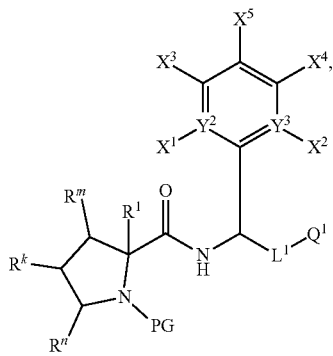

(I'-4)

followed by
(b) contacting the compound of formula (I'-4) with an acid to provide a compound of formula (I').

In some embodiments, the protecting group is an oxycarbonyl group. In some embodiments the protecting group is a tert-butoxycarbonyl.

In some embodiments, the coupling reagent comprises EDCCl, TCFH, or T3P. In some embodiments, the process further comprises the presence of a base. In some embodiments, the base comprises an amine. In some embodiments, the amine is DMAP, NMM, or a trialkylamine.

In some embodiments the acid is HCl or TFA.

EXAMPLES

The following synthetic reaction schemes, which are detailed in the Schemes and Examples, are merely illustrative of some of the methods by which the compounds of the present disclosure, or an embodiment or aspect thereof, can be synthesized. Various modifications to these synthetic reaction schemes can be made, as will be apparent to those of ordinary skill in the art.

The starting materials and the intermediates of the synthetic reaction schemes can be isolated and purified if desired using conventional techniques, including, but not limited to, filtration, distillation, crystallization, chromatography, and the like. Such materials can be characterized using conventional means, including physical constants and spectral data.

Although certain exemplary embodiments are depicted and described herein, the compounds of the present disclosure, or any variation or embodiment thereof, may be prepared using appropriate starting materials according to the methods described generally herein and/or by methods available to one of ordinary skill in the art.

Synthetic Examples

As depicted in the Schemes and Examples below, in certain exemplary embodiments, compounds of formula (I), or any variation or embodiment thereof, as described elsewhere herein, or a stereoisomer or tautomer thereof, or a pharmaceutically acceptable salt of any of the foregoing, are prepared according to the general procedures. The general methods below, and other methods known to synthetic chemists of ordinary skill in the art, can be applied to all formulae, variations, embodiments, and species described herein.

Schemes

Scheme 1

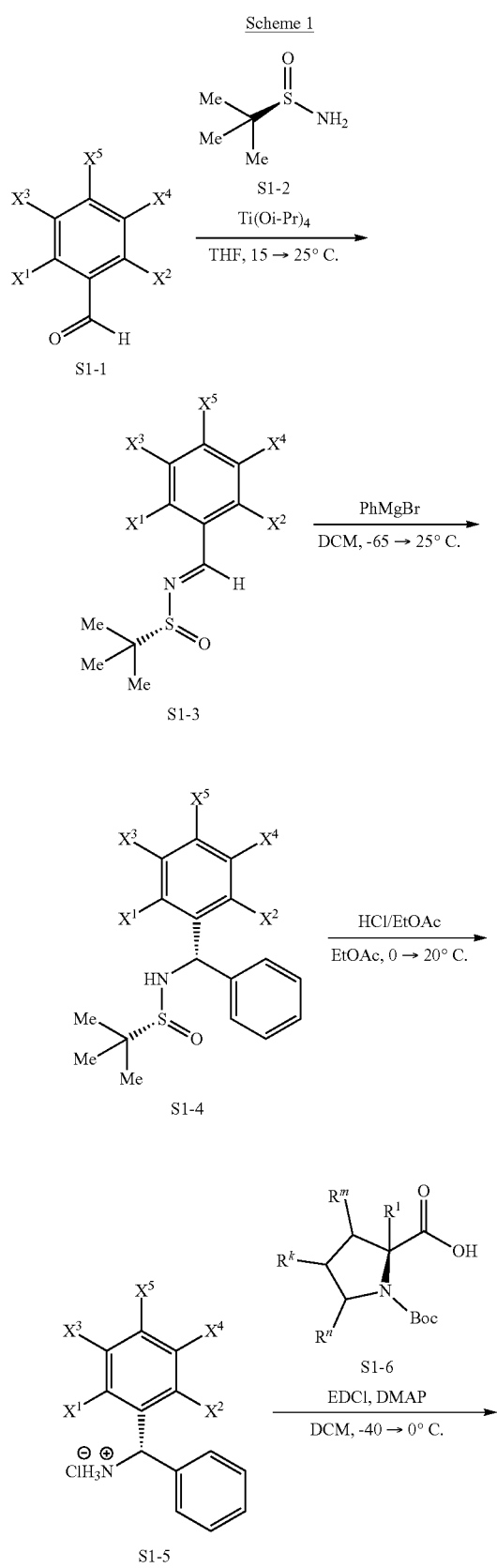

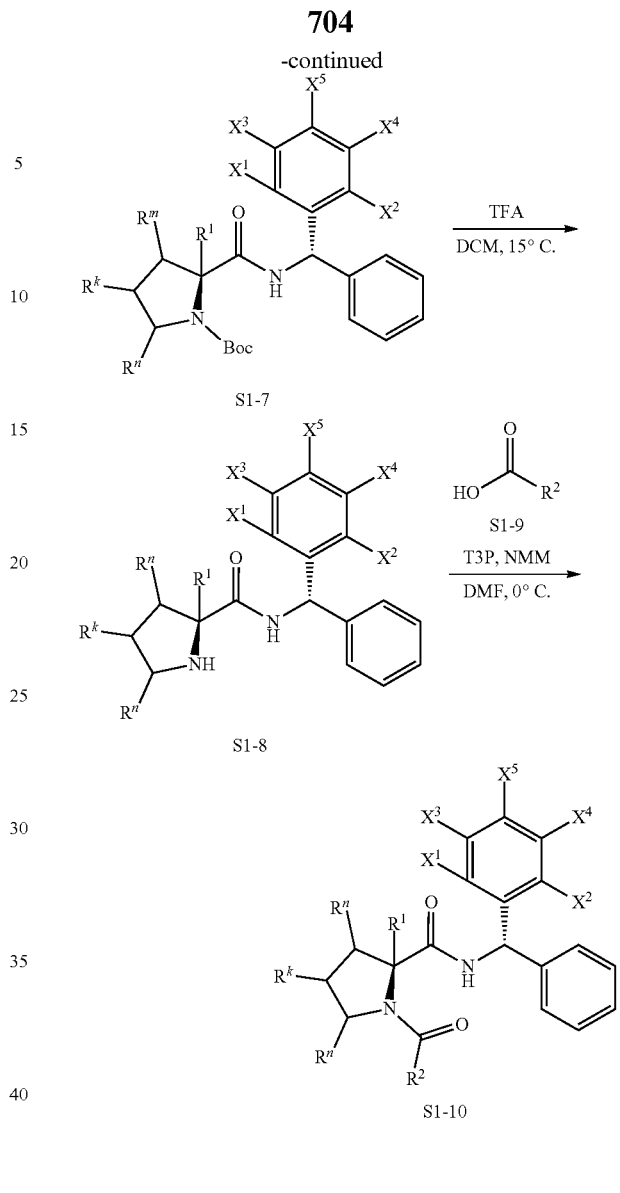

Compounds of the formula S1-10 may be prepared according to the general synthetic scheme outlined in Scheme 1.

Condensation of a chiral sulfinamide such as S1-2 with an aldehyde such as S1-1 provides sulfinimine S1-3. Addition of a reagent such as phenylmagnesium bromide at low temperature, followed by warming to ambient temperature provides benzhydryl sulfinamide S1-4. Sulfinamide S1-3 can be converted to the corresponding amine hydrochloride salt upon treatment with HCl in a solvent such as EtOAc. Amide bond formation between S1-5 and a substituted proline analog such as S1-6 may be achieved with a carbodiimide reagent such as EDCI and DMAP as a catalyst. Removal of the N-Boc group of S1-7 via treatment with a protic acid such as trifluoroacetic acid gives rise to amines such as S1-8. Proline amides such as S1-10 may then be generated by coupling with a carboxylic acid such as S1-9 using a coupling agent such as T3P and NMM as a base.

Scheme 2
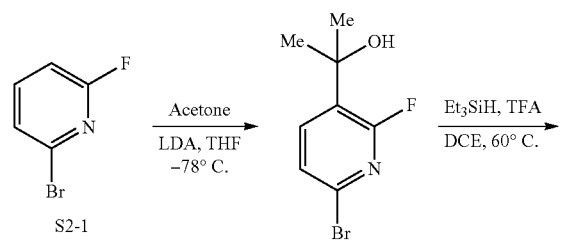
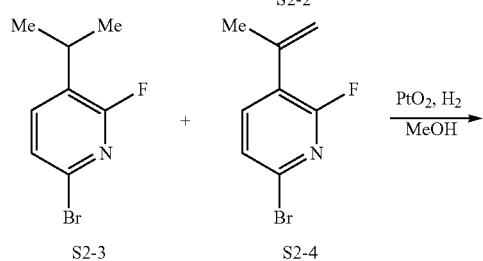
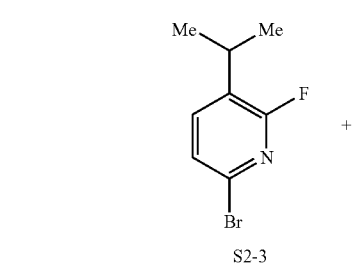
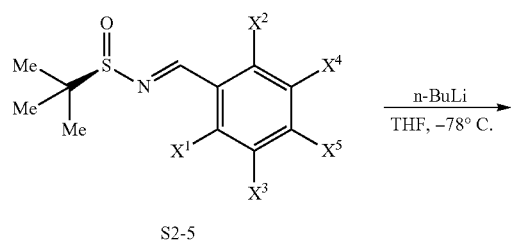
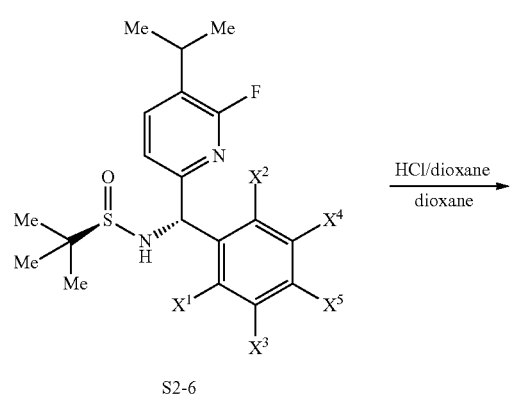
-continued
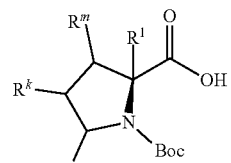
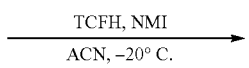
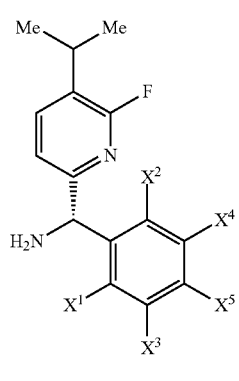
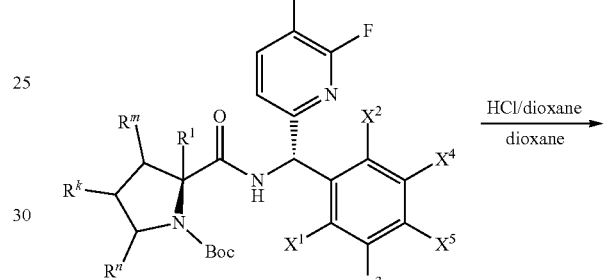
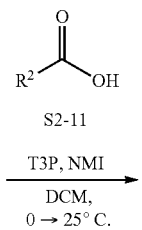
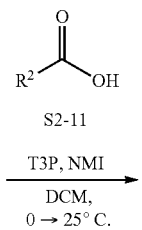

Compounds of the formula S2-12 may be prepared according to the general synthetic scheme outlined in Scheme 2.

Directed ortho-metalation of pyridine S2-1 with an amide base such as LDA in an aprotic solvent such as THF at −78° C. followed by reaction with a ketone such as acetone can generate pyridine S2-2. Treatment of S2-2 with a reducing agent such as triethyl silane and a protic acid such as trifluoroacetic acid generates a mixture of compounds, S2-3 and S2-4. This mixture can be converted to S2-3 by reduction with hydrogen gas and a metal catalyst such as $PtO_2$. Metal-halogen exchange can be affected by treatment of S2-3 at −78° C. with n-butyllithium, and the pyridyllithium intermediate may then be reacted with sulfinimine S2-5 to generate S2-6. Treatment with a protic acid such as HCl generates the amine S2-7. Coupling of amine S2-7 with proline derivative S2-8 using TCFH and N-methylimidazole base gives rise to S2-9. Removal of the proline N-Boc group by treatment with a protic acid such as HCl, in an aprotic solvent such as 1,4-dioxane, provides amine S2-10. Amine S2-10 may then be reacted with carboxylic acid S2-11 to generate S2-12, using methods described in Scheme 1.

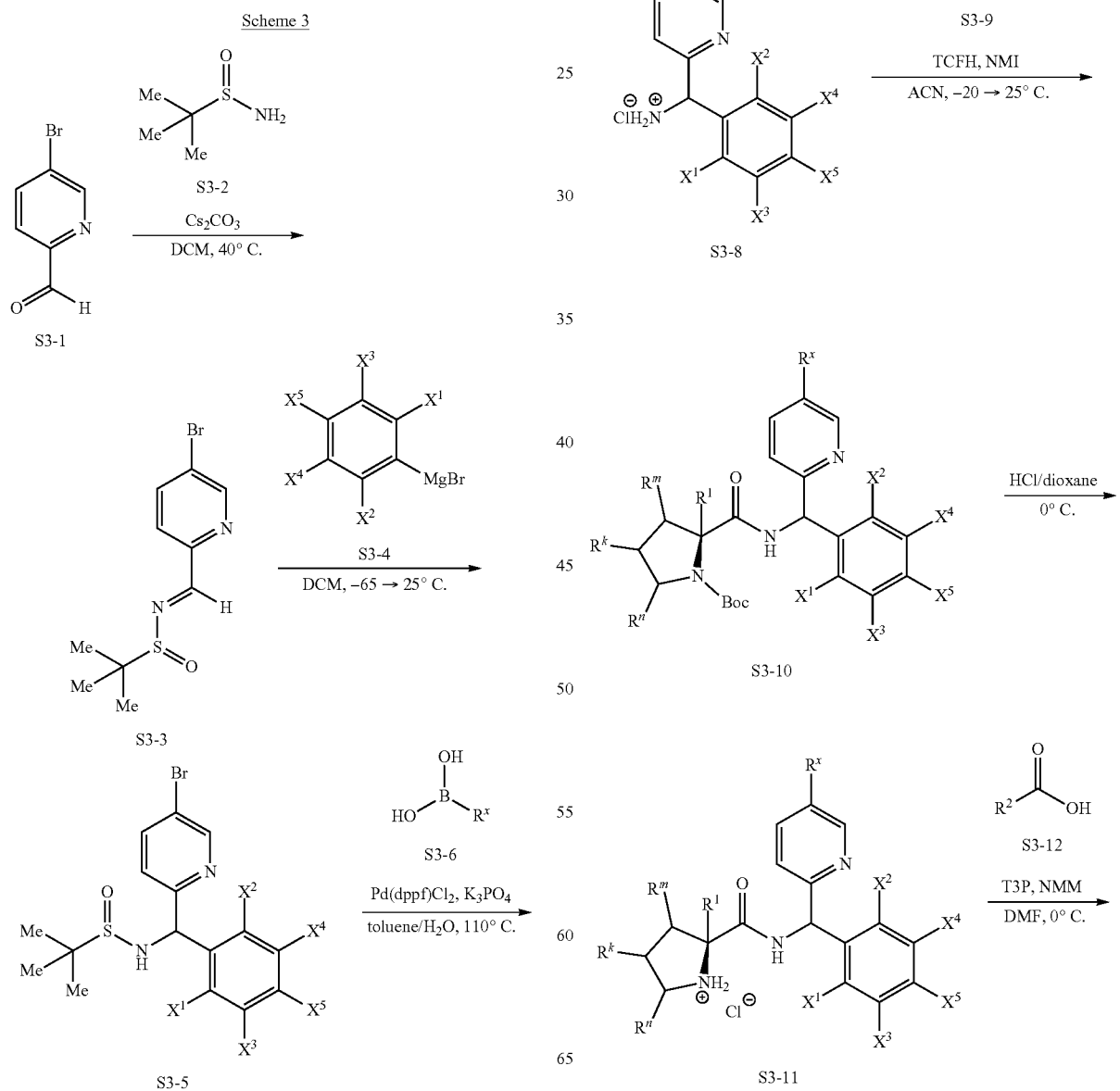

-continued

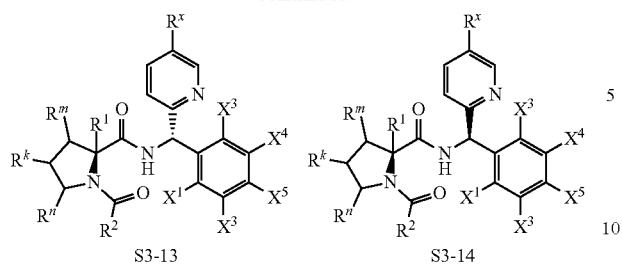

S3-13   S3-14

Compounds of the formulae S3-13 and S3-14 may be prepared according to the general synthetic scheme outlined in Scheme 3.

Condensation of racemic sulfinimide S3-2 with pyridyl aldehyde S3-1 generates sulfinimine S3-3. Reaction with arylmagnesium bromide S3-4 generates S3-5, as a racemate. A Suzuki cross-coupling of S3-5 with a boronic acid such as S3-6 using a palladium catalyst such as Pd(dppf)Cl$_2$ and an inorganic base such as K$_3$PO$_4$ generates compound S3-7. Treatment of S3-7 with a protic acid such as HCl in an aprotic solvent mixture such as EtOAc/DCM provides amine S3-8. S3-8 may then be coupled with carboxylic acid S3-9 and processed to compounds S3-13 and S3-14 using methods outlined in Scheme 1. If desired, mixtures of stereoisomers may be further purified to provide S3-13 and S3-14 as single isomers, using methods such as reverse-phase HPLC or chiral SFC.

Scheme 4

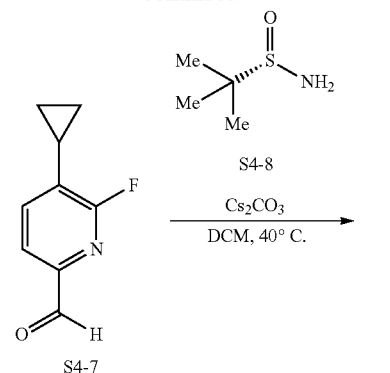

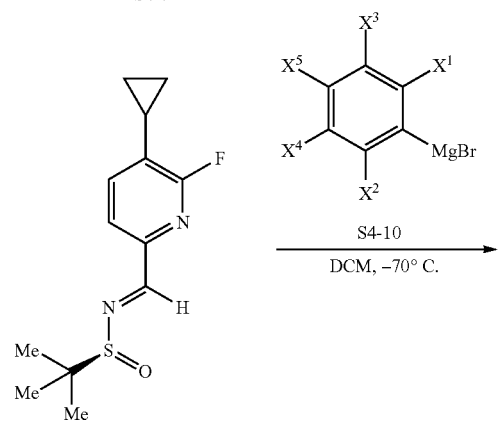

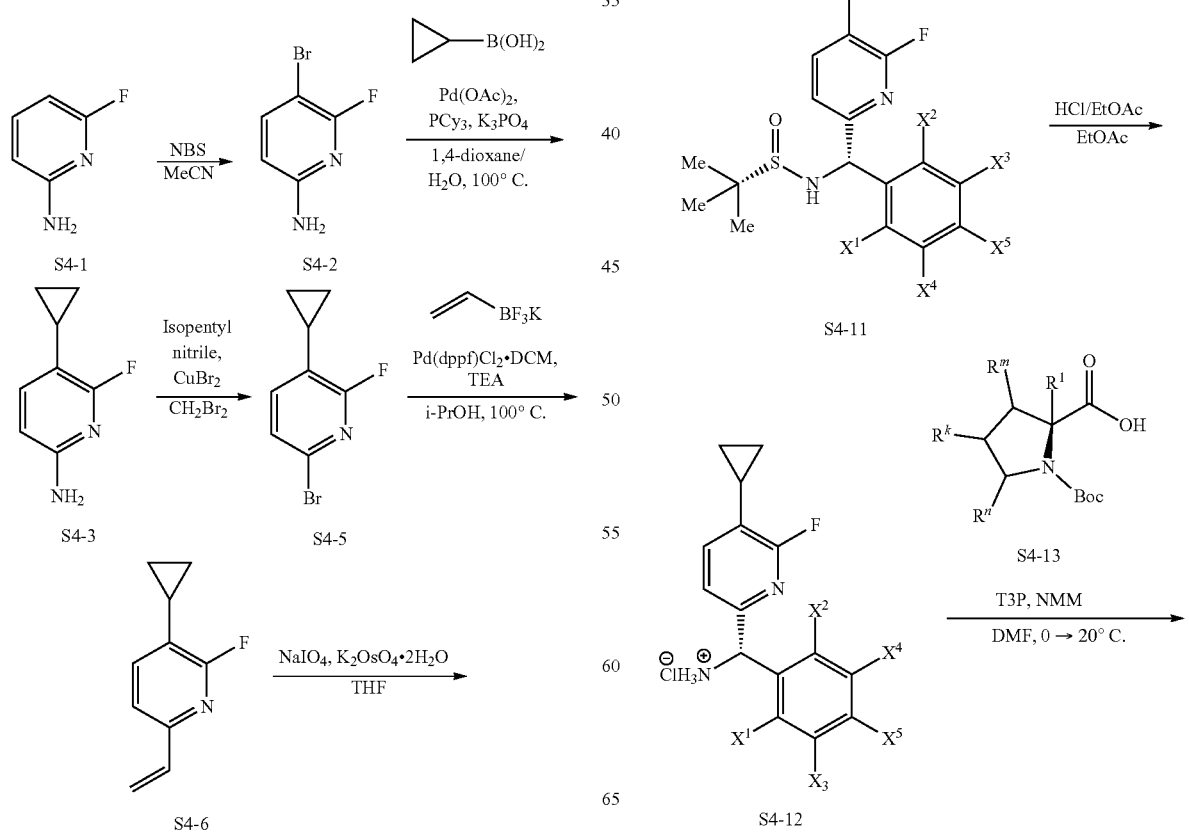

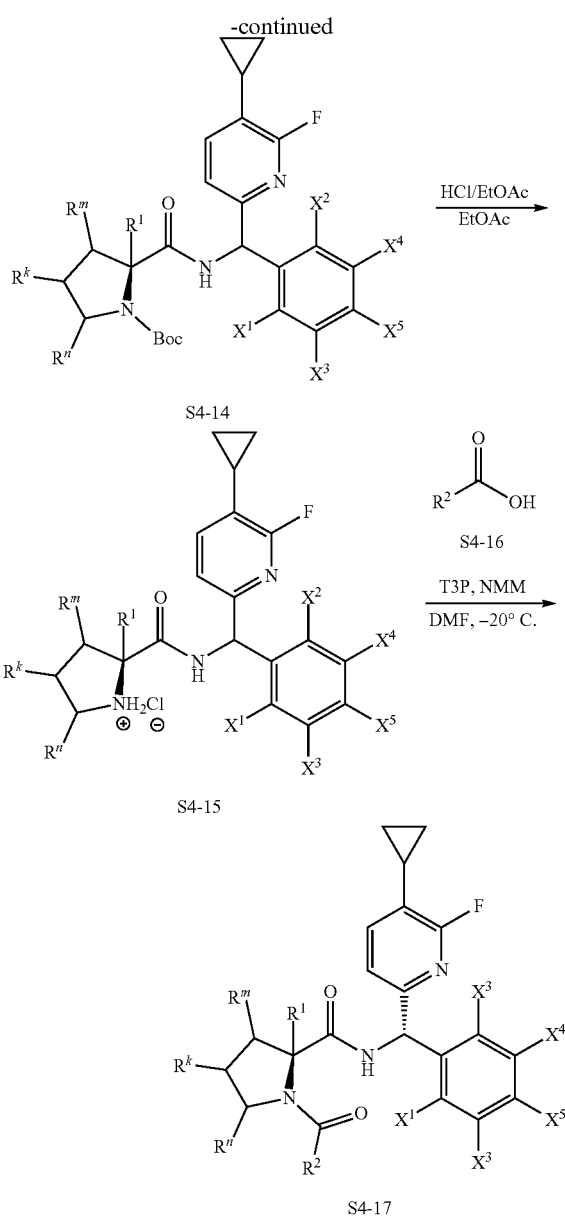

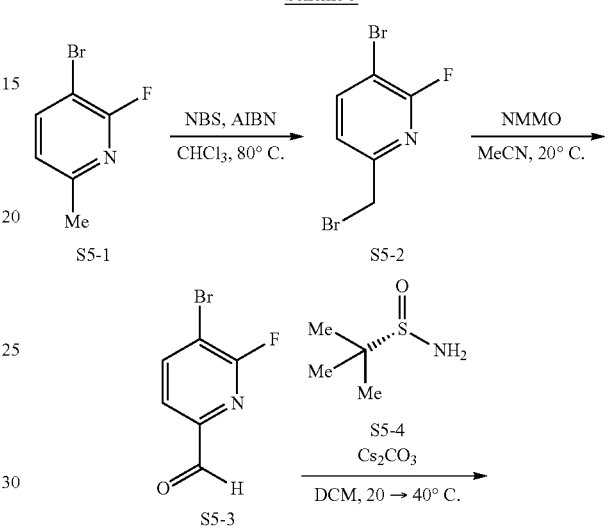

temperature gives rise to S4-11. Cleavage of sulfinimide S4-11 with a HCl in EtOAc generates amine salt S4-12. S4-12 may then be joined with carboxylic acid S4-13 using a coupling agent such as T3P and a base such as NMM in DMF to produce S4-14. Removal of the N-Boc group with HCl in EtOAc generates amine S4-15, which may then be processed to S4-17 using the procedure described in Scheme 3.

Scheme 5

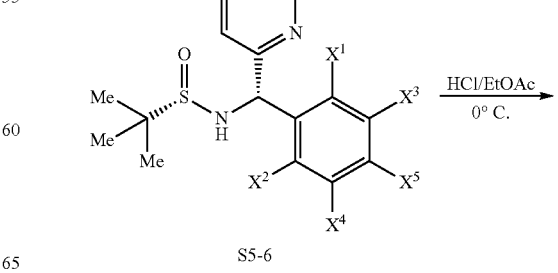

Compounds of the formula S4-17 may be prepared according to the general synthetic scheme outlined in Scheme 4.

Reaction of pyridine S3-1 with an electrophilic brominating agent such as NBS gives pyridine S4-2. Suzuki cross-coupling with cyclopropylboronic acid, using a catalyst such as palladium acetate, a ligand such as tricyclohexyl phosphine, and an inorganic base such $K_3PO_4$ in a mixed solvent system such as 1,4-dioxane and water, provides S4-3. Conversion of S4-3 to pyridyl bromide S4-5 can be achieved with a Sandmeyer reaction under the action of isopentyl nitrite and cupric bromide in dibromomethane solvent. Suzuki cross coupling of potassium vinyltrifluoroborate with S4-6 using a palladium catalyst such as Pd(dppf)Cl$_2$ and an inorganic base such as $K_3PO_4$. Oxidative cleavage of olefin S4-6 with NaIO$_4$ and K$_2$OsO$_4$·2H$_2$O in a THF generates aldehyde S4-7. Condensation with sulfinimide S4-8 generates sulfinimine S4-9. Reaction of S4-9 with aryl Grignard reagent S4-10 in a solvent such as DCM at low

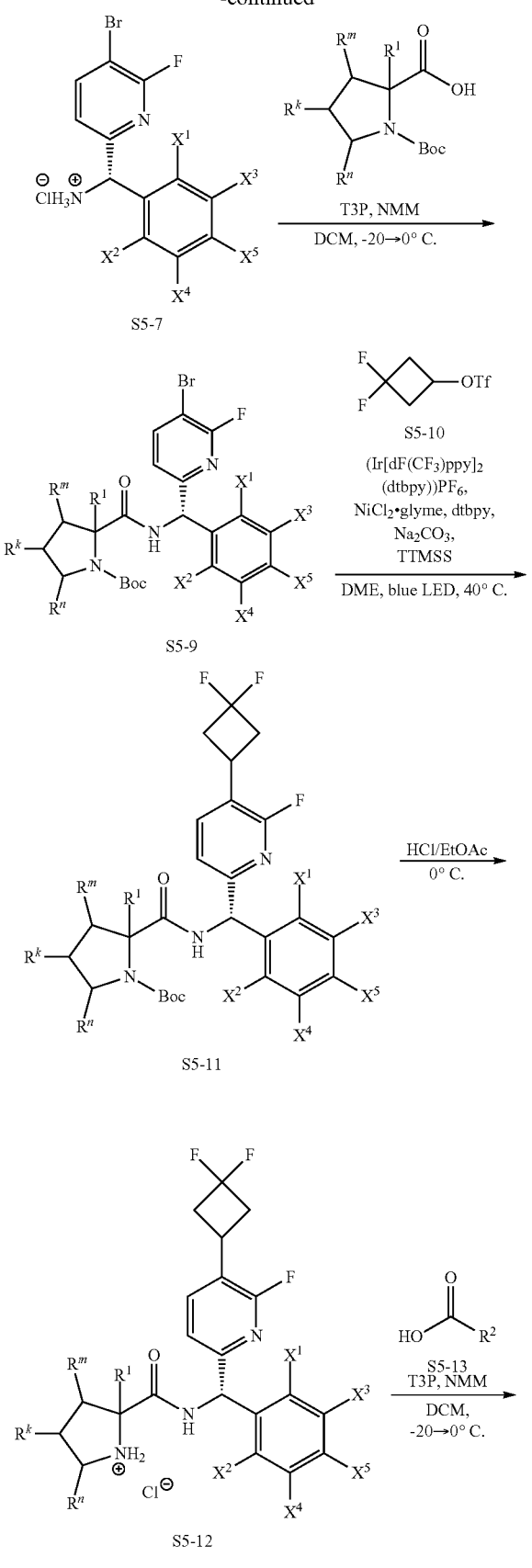
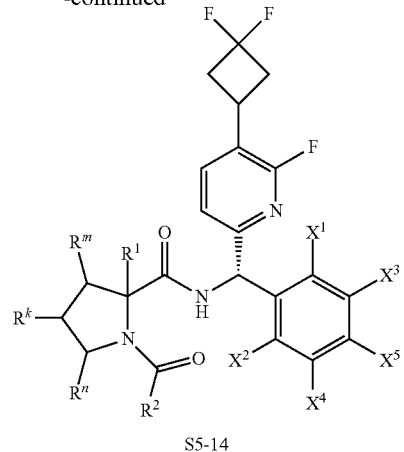

Compounds of the general formula S5-14 can be prepared according to the general scheme outlined in Scheme 5.

Radical bromination of S5-1 with NBS and catalytic AIBN provides S5-2. Oxidation under the action NMMO gives aldehyde S5-3. Condensation of aldehyde with sulfinimide S5-4 using an inorganic base such as cesium carbonate provide sulfinimine S5-5. Addition of an aryl Grignard reagent such as phenylmagnesium bromide at low temperature provides S5-6. Cleavage of the sulfinimide to generate a primary amine salt can be achieved upon treatment with a protic acid such as HCl in a solvent such as EtOAc. Amide bond formation with proline derivative S5-8 proceeds as previously described to give S5-9. Photoredox coupling of triflate S5-10 with S5-9 using an iridium photocatalyst such as (Ir[dF(CF$_3$)ppy]$_2$(dtbpy))PF$_6$, a nickel co-catalyst such as NiCl$_2$·glyme, a ligand such as 4,4-di-tert-butyl-2,2-bipyridyl, sodium carbonate as base, and tris(trimethylsilyl)silane and blue LED gives cyclobutyl adduct S5-11. Removal of the proline Boc protecting group with HCl in EtOAc, followed by amide bond formation under the action of T3P and NMM in DCM gives compounds of formula S5-14.

Scheme 6

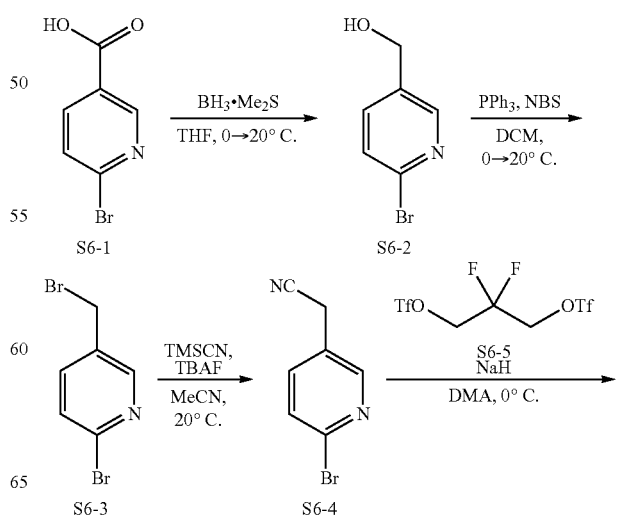

715
-continued
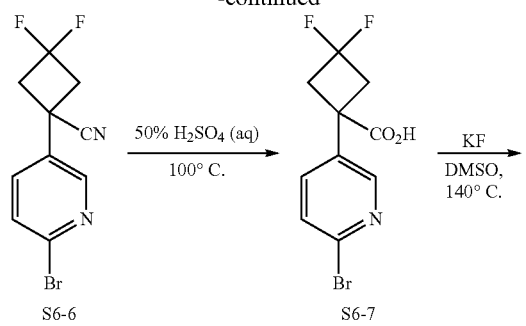
716
-continued
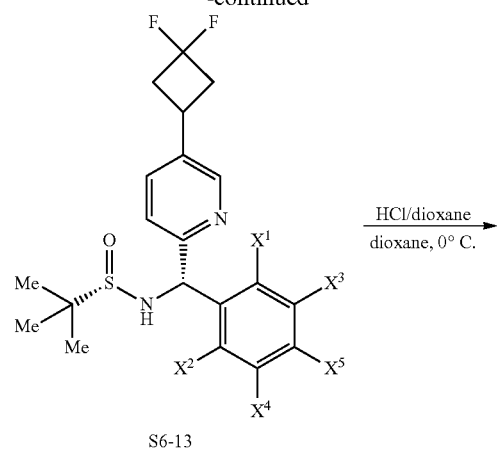
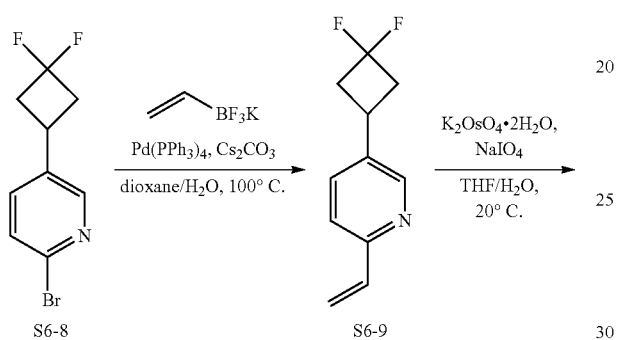
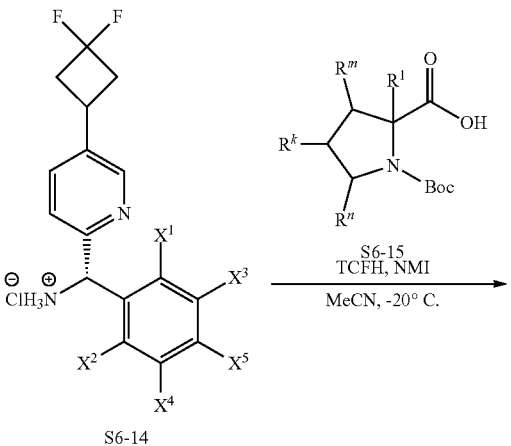
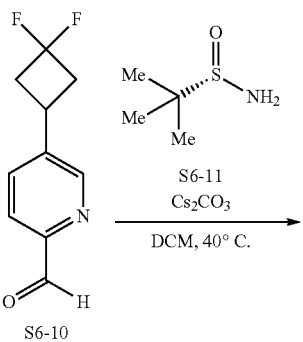
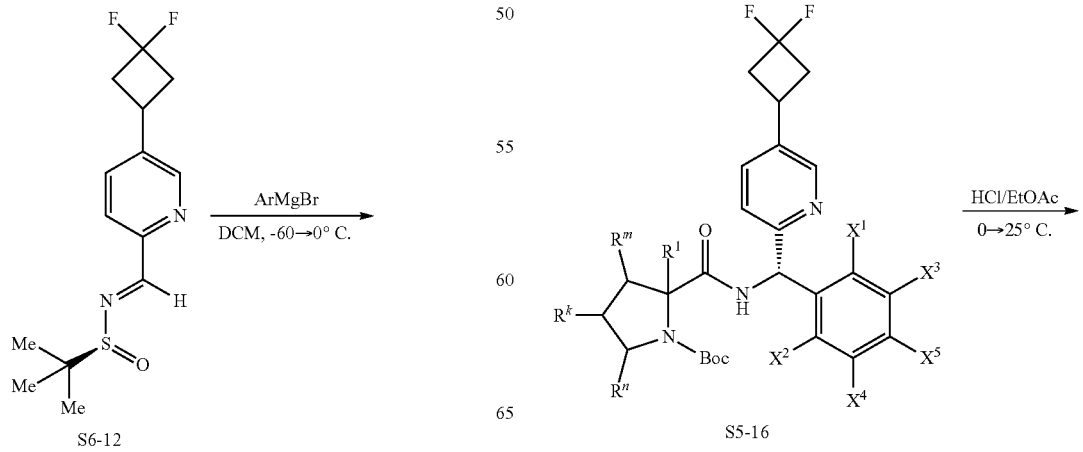

-continued

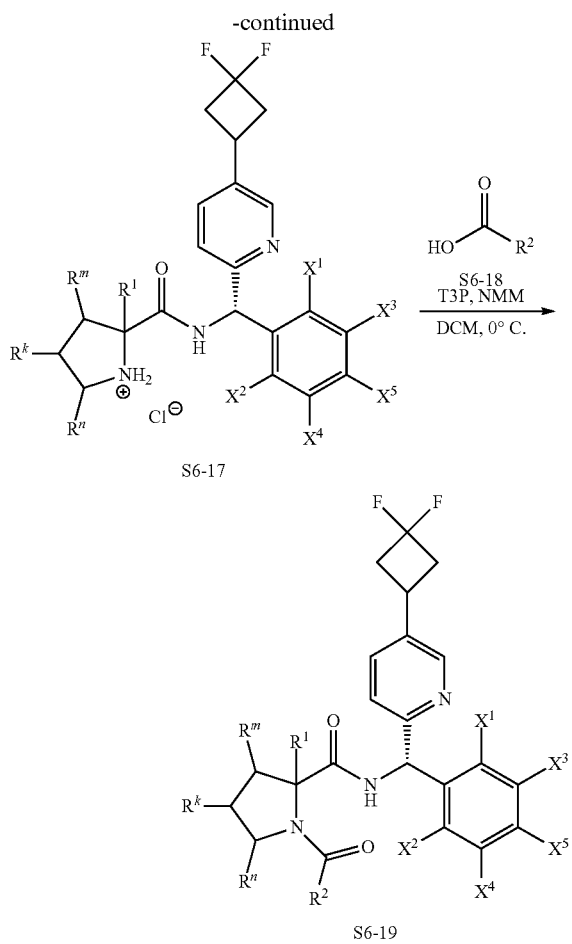

Compounds of the general formula S6-19 can be prepared according to the general scheme outlined in Scheme 6.

Reduction of carboxylic acid S6-1 with borane-methylsulfide complex gives alcohol S6-2. Conversion of S6-2 to alkyl bromide S6-3 is achieved by treatment with triphenylphosphine and NBS in a solvent such as DCM. Selective displacement of the primary bromide can be achieved upon reaction with TMSCN and TBAF in acetonitrile to provide S6-4. Double alkylation of nitrile S6-4 with a di-triflate such as S6-5 gives rise to cyclobutane S6-6. Hydrolysis of the nitrile on treatment with sulfuric acid at elevated temperature gives acid S6-7. Decarboxylation can be achieved by reaction with KF in DMSO at high temperature to provide S6-8. Suzuki-type cross coupling with potassium vinyltrifluoroborate, a palladium catalyst such as tetrakis triphenylphosphine palladium(0) and a base such as cesium carbonate generates S6-9. Lemieux-Johnson oxidation of S6-9 gives aldehyde S6-10, which may then be condensed with sulfinimide S6-11 under conditions previously described to give S6-12. Addition of an aryl Grignard reagent such as phenylmagnesium bromide to S6-12 gives S6-13. Generation of primary amine salt S6-14 may occur upon treatment with HCl in dioxane. Coupling of S6-14 with proline derivative S6-15 using chloro-N,N,N',N'-tetramethylformamidinium hexafluorophosphate (TCFH) and N-methylimidazole (NMI) gives S6-16. Boc deprotection and proline amide bond formation as described in Scheme 5 gives compounds of formula S6-19.

Scheme 7

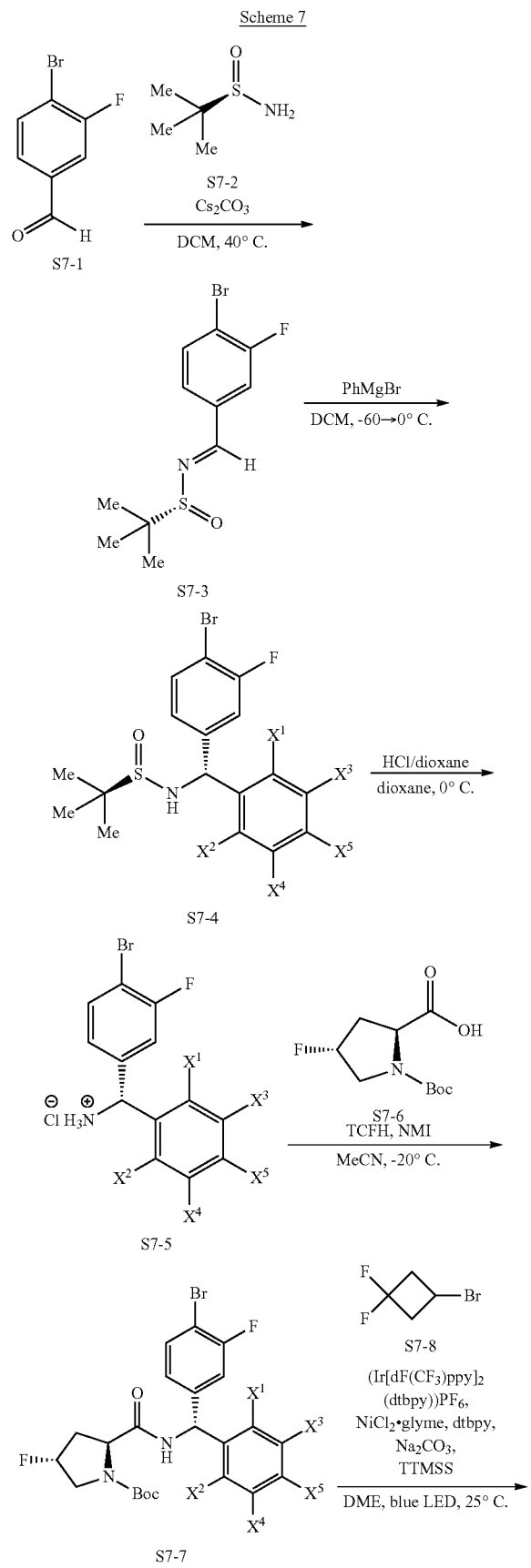

719

-continued

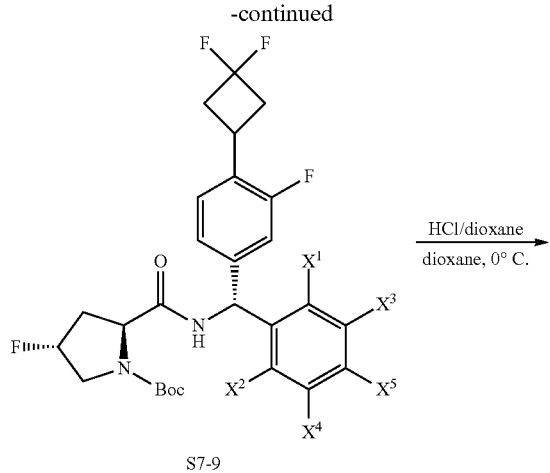

S7-9

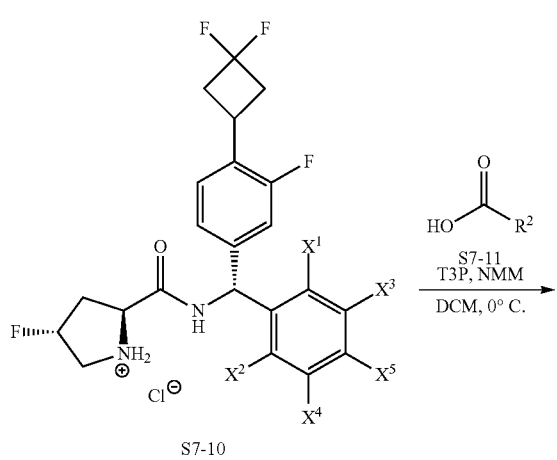

S7-10

720

-continued

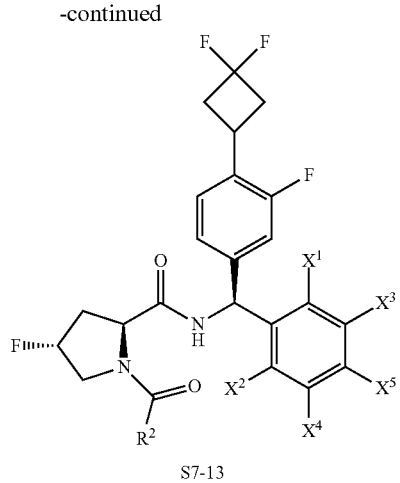

S7-13

Compounds of the general formulae S7-12 and S7-13 can be prepared according to the general scheme outlined in Scheme 7.

Condensation of sulfinimide S7-2 with aldehyde S7-1 as previously described, followed by addition of an aryl Grignard reagent such as phenylmagnesium bromide, gives S7-4. Generation of the amine salt and coupling with proline derivative S7-6 may be achieved under conditions previously described. Photoredox coupling of cyclobutyl bromide S7-8 under conditions like those described in Scheme 5 gives S7-9. As previously described, Boc deprotection and amide bond formation generates compounds of formula S7-12. A minor stereoisomer such as S7-13 may also be isolated at this stage.

Scheme 8

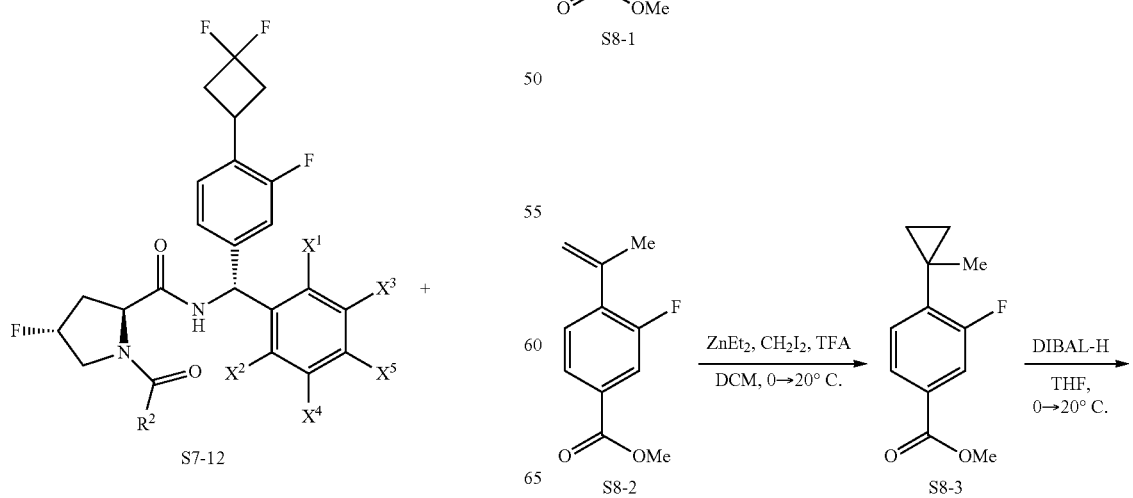

721
-continued
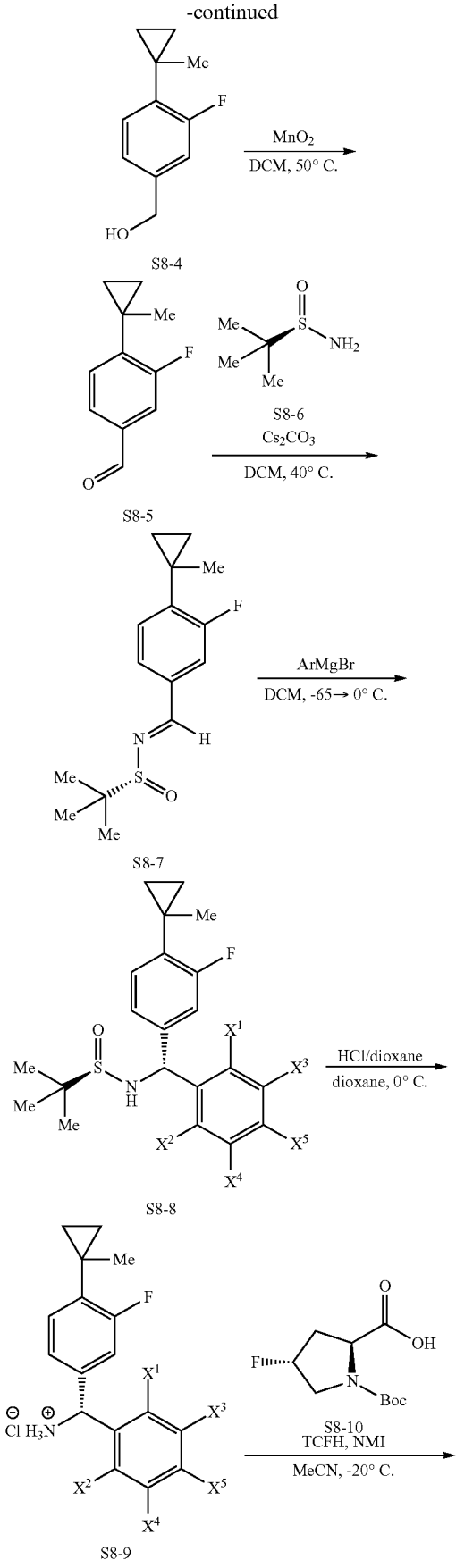
722
-continued
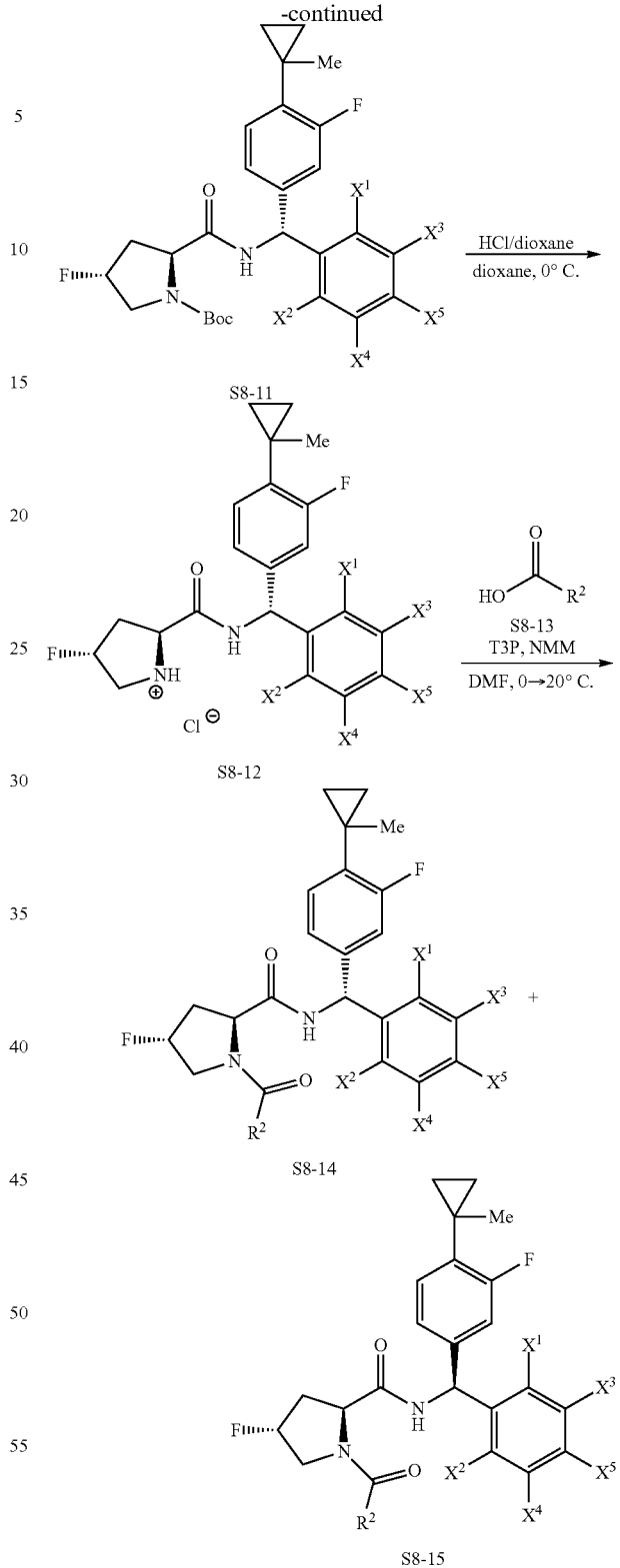
Compounds of the general formula 3 S8-14 and S8-15 can be prepared according to the general scheme outlined in Scheme 8.
An alternative generation of benzhydryl fragments begins with cross-coupling of S8-1 with isopropenylboronic acid pinacol ester with a catalyst such as [1,1'-bis(diphenylphosphino)ferrocene]palladium(II) dichloride and potassium carbonate as base in a mixed dioxane/water solvent at elevated temperature gives S8-2. Simmons-Smith cyclopropanation gives S8-3. Reduction of ester S8-3 with DIBAL-H, followed by oxidation with MnO₂ gives aldehyde S8-5. Aldehyde S8-5 may then be processed over several steps previously described to give compounds of formula S8-14. Minor diastereomers which could not be separated in previous steps may be isolated at this stage, giving S8-15.

Scheme 9

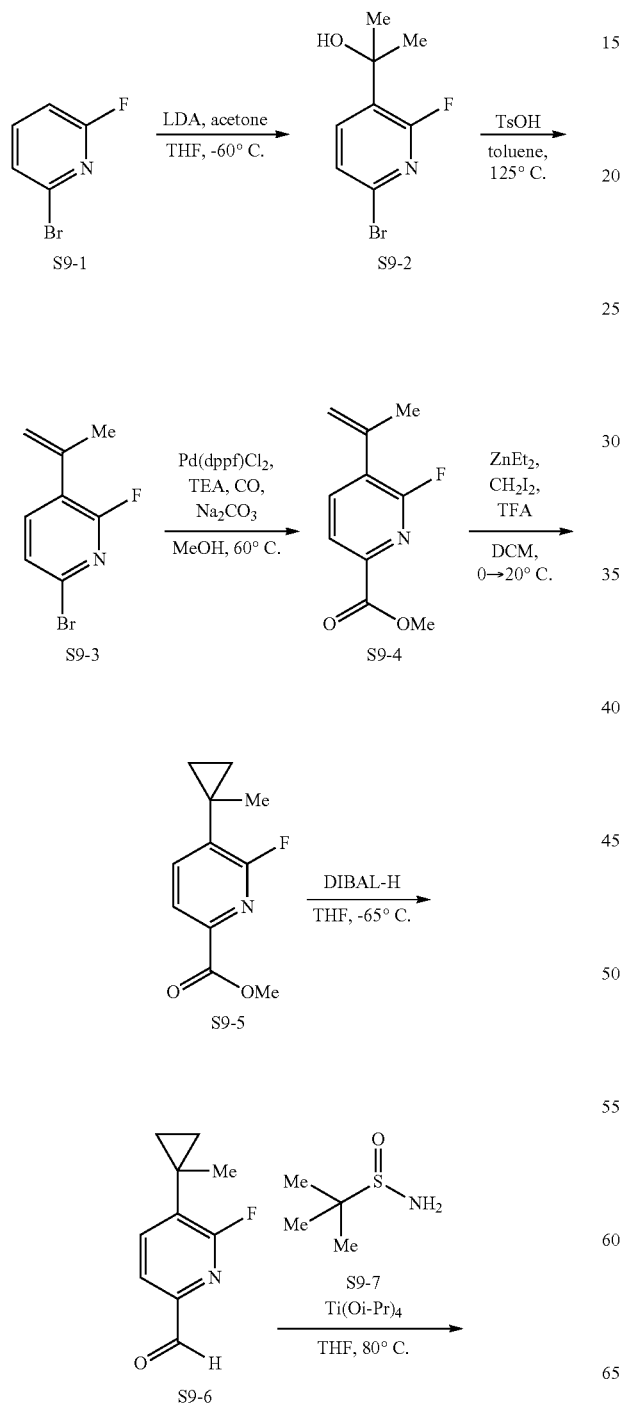

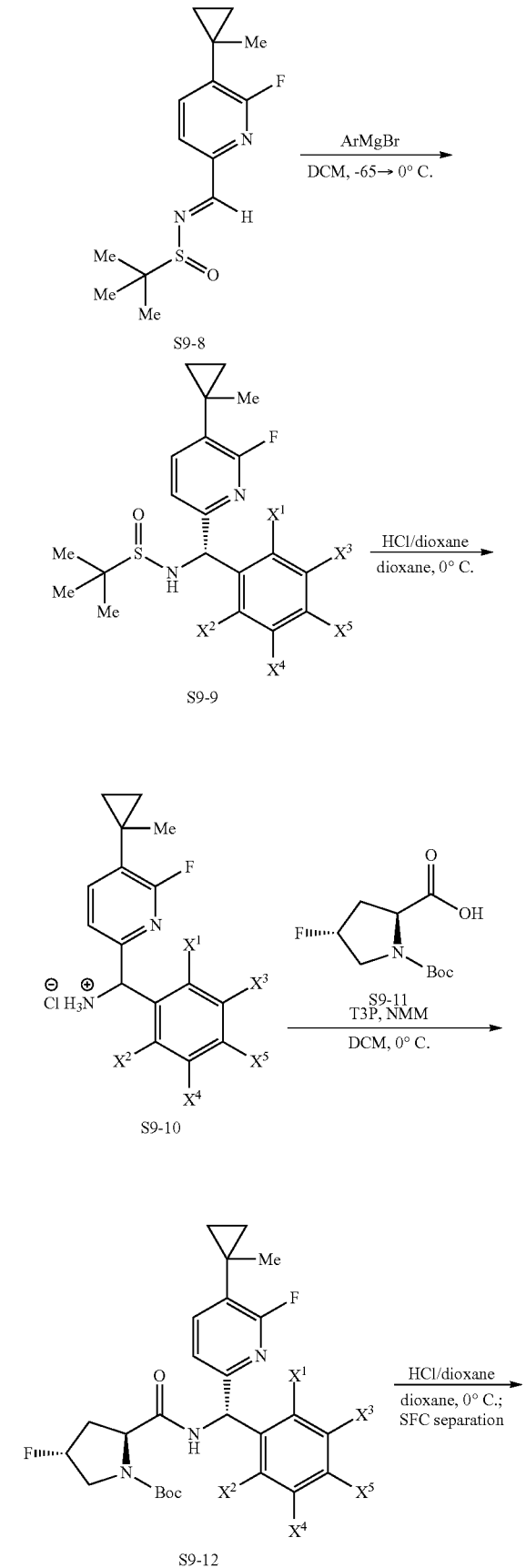

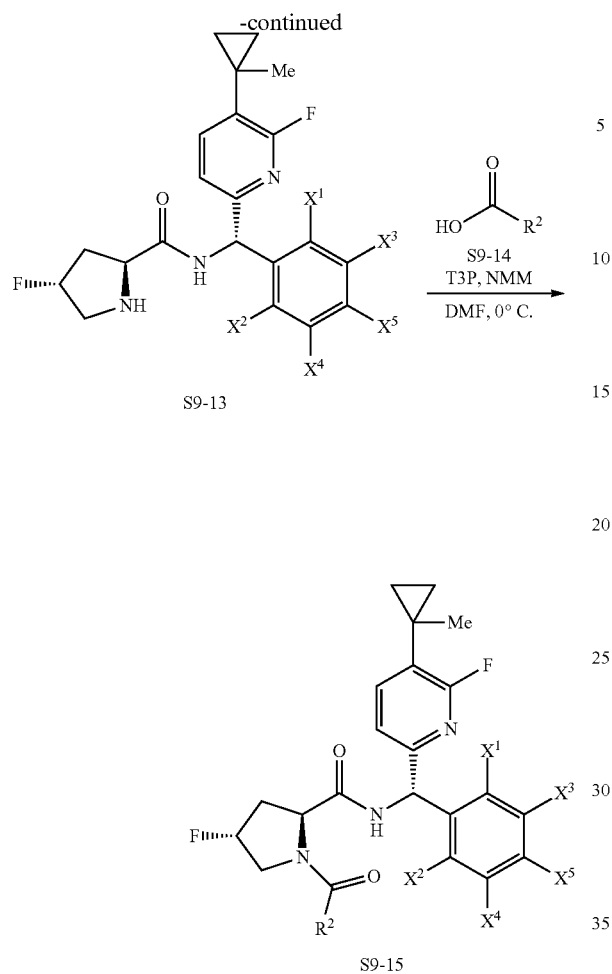

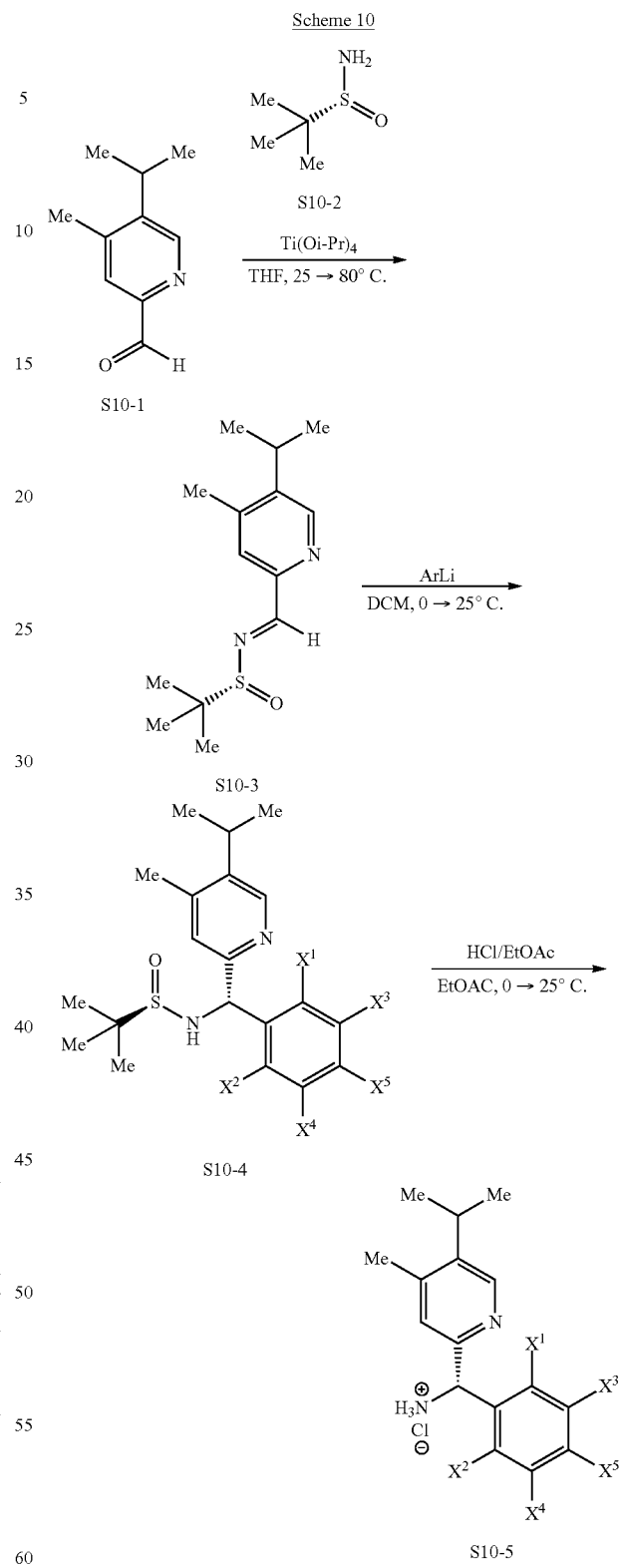

Compounds of the general formula S9-15 can be prepared according to the general scheme outlined in Scheme 9.

An alternative approach to cyclopropane containing analogs begins with directed metalation of S9-1 with LDA and reaction with acetone to generate S9-2. Dehydration under the action of a protic acid such asp-toluene sulfonic acid in toluene at elevated temperature generates olefin S9-3. Cyclopropanation under conditions described in Scheme 8 gives S9-5. Partial reduction of S9-5 to aldehyde S9-6 can be achieved with DIBAL-H in THF at low temperature. Condensation of aldehyde S9-6 with racemic sulfinimide S9-7 gives S9-8. Addition of a Grignard reagent and deprotection under conditions previously described gives amine salt S9-10 as a racemate. Coupling with proline derivative S9-11 under standard conditions and Boc deprotection generates an intermediate which can be further purified by chiral SFC to give amine S9-13 as a single isomer. Conversion to compounds of formula S9-15 occurs under conditions previous described. If the R² substituent bears stereogenic atoms that are mixtures, additional purification by chiral SFC may be utilized to generate single isomer analogs.

Compounds of the general formula S10-5 can be prepared according to the general scheme outlined in Scheme 10.

An alternative approach to compounds of formula S10-5 starts with condensation of pyridine S10-1 with sulfinimide S10-2. Addition of an aryllithium reagent such as phenyl-lithium provides S10-4. Deprotection under standard conditions gives amine salts of formula S10-5, which may be further elaborated as described in the Schemes 1-9 and Schemes 11-15.

Scheme 11

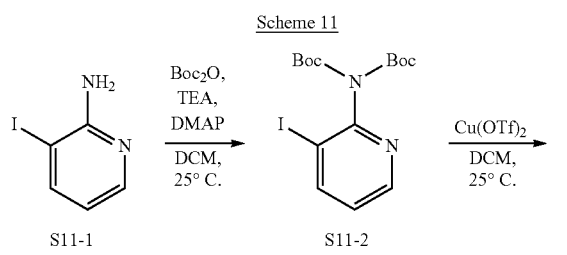

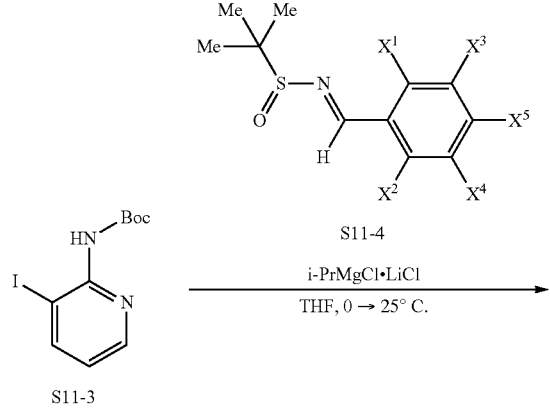

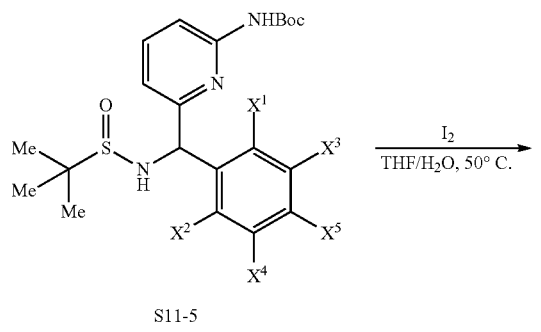

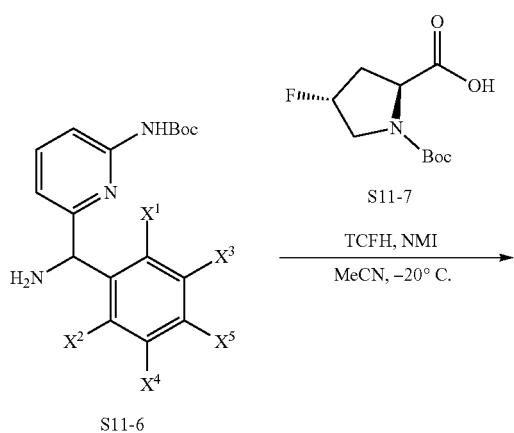

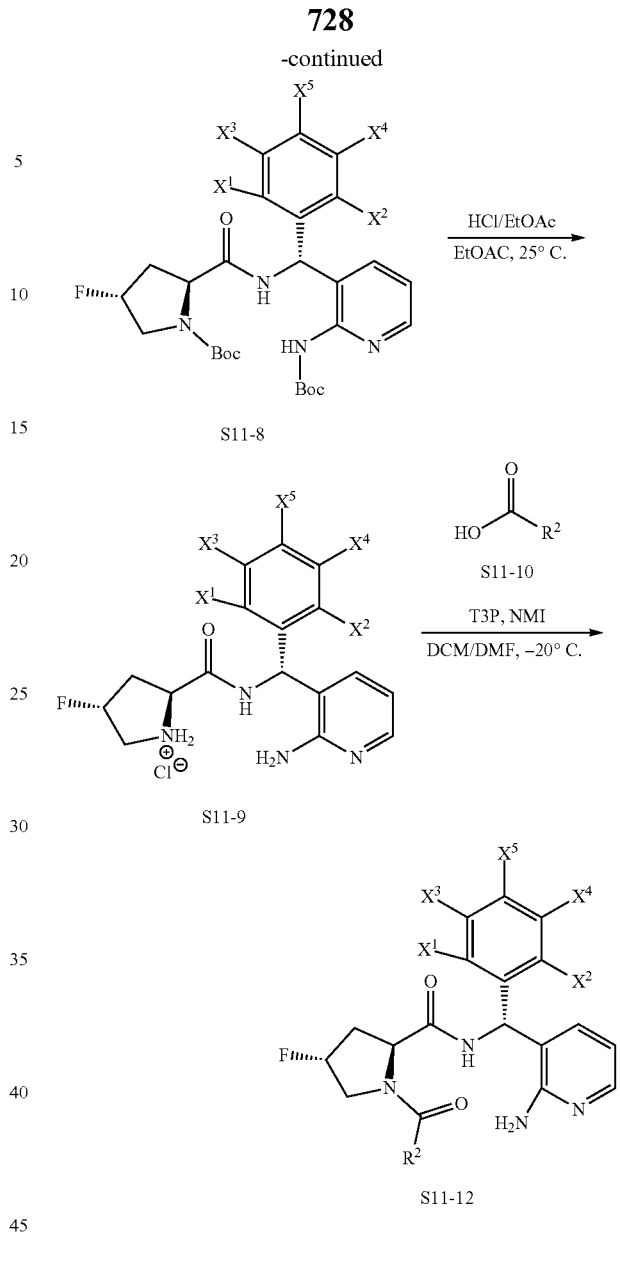

Compounds of the general formula S11-12 can be prepared according to the general scheme outlined in Scheme 11.

Yet another alternative approach to amine intermediates such as S11-6 starts with pyridine S11-1. Bis-carbamate formation, followed by treatment copper (II) triflate gives pyridine S11-3. Conversion of S11-3 to the corresponding Grignard reagent with isopropylmagnesium chloride-lithium chloride complex followed by addition to a racemic sulfinimine such as S11-4 gives S11-5. Selective cleavage of the sulfinamide may occur on reaction with iodine at elevated temperature. Coupling with proline derivative S11-7 and further processing to generate compounds of formula S11-12 occurs as previously described. If necessary, mixtures of stereoisomers may be further purified using chiral SFC, to generate compounds as single isomers.

Scheme 12

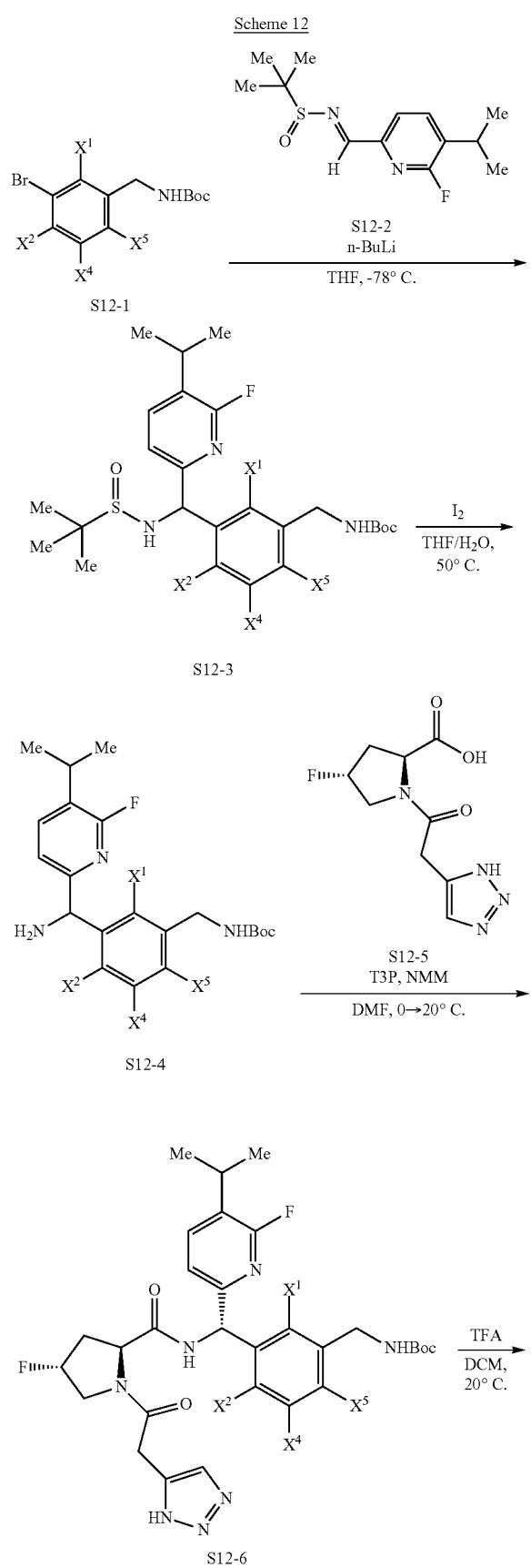

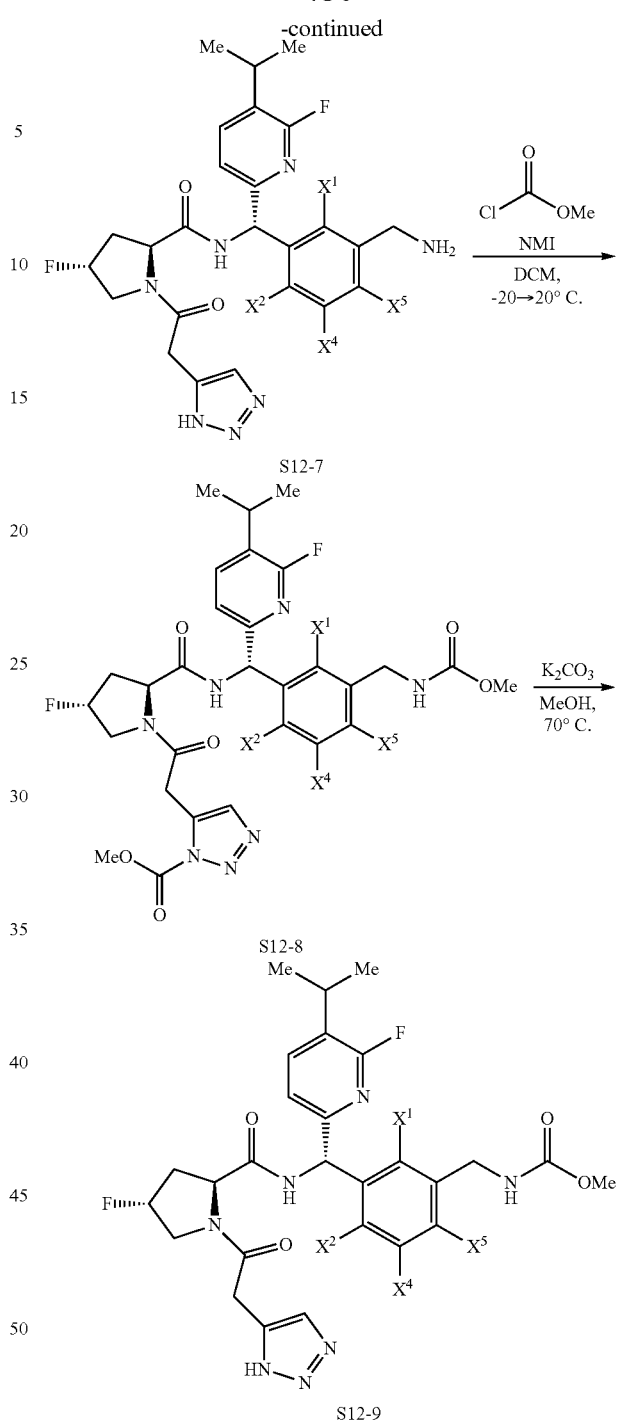

Compounds of the general formula S12-9 can be prepared according to the general scheme outlined in Scheme 12.

An alternative sequence enabling late-stage elaboration of the benzhydryl moieties begins with lithiation of S12-1 and addition of sulfinimine S12-2. Oxidative cleavage with iodine generates S12-4. Coupling with proline derivative S12-5 generates S12-6. Cleavage of the Boc group with TFA generates amine S12-7. Treatment with an acylating agent such as methyl chloroformate and NMI as base gives bis-carbamate S12-8. Selective cleavage of the triazole carbamate moiety can be achieved by reaction with potassium carbonate and methanol at elevated temperature, to generate compounds of formula S12-9.

Scheme 13

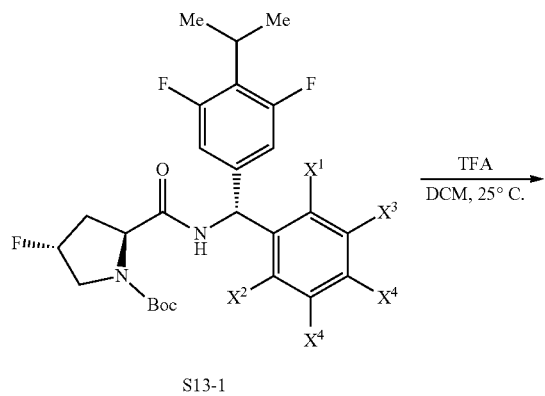

S13-1

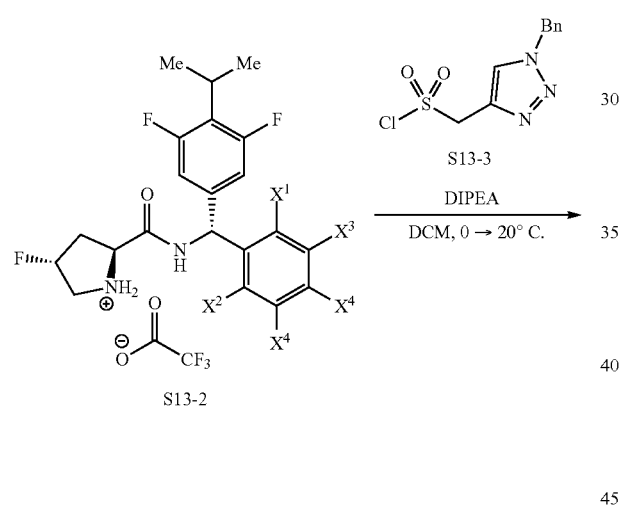

S13-2

S13-3

S13-4

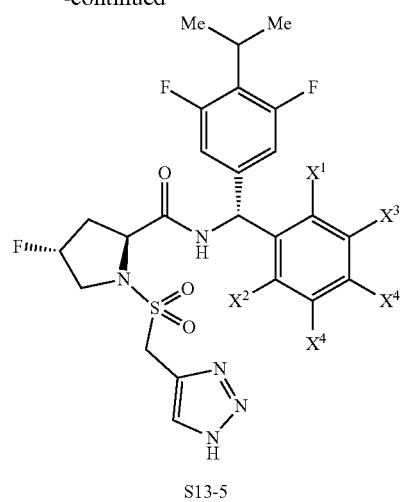

S13-5

Compounds of the general formula S13-5 can be prepared according to the general scheme outlined in Scheme 13.

Sulfonamides of formula S13-5 can be generated starting from 513-1. Boc cleavage as previously described gives S13-2. Reaction of S13-2 with sulfonyl chloride S13-3 using a tertiary amine base such as DIPEA gives S13-4. Cleavage of the triazole N-benzyl group occurs under standard hydrogenation conditions to give 513-5.

Scheme 14

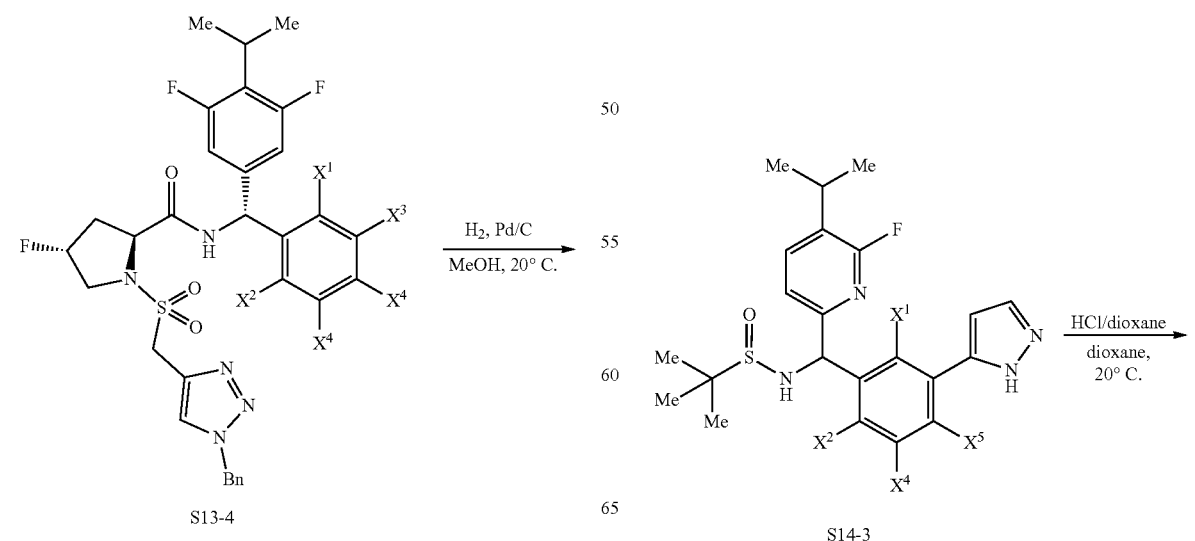

S14-1

S14-2

S14-3

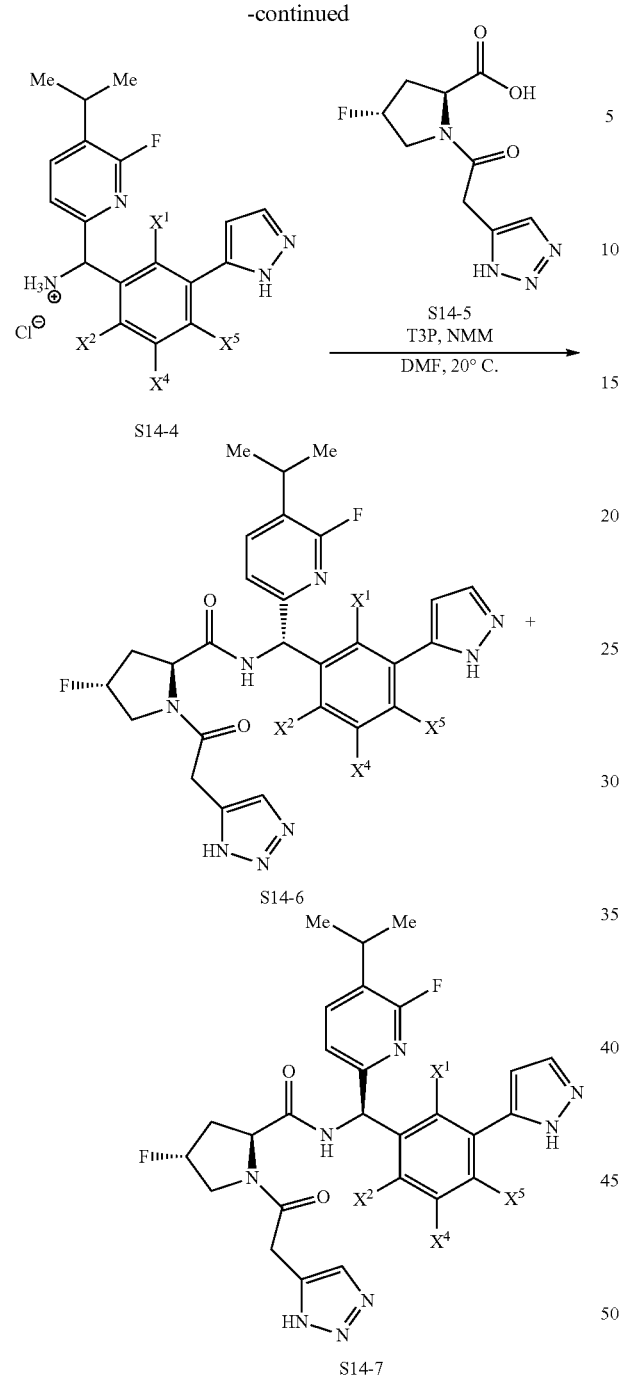

S14-4

S14-6

S14-7

Compounds of the general formulae S14-6 and S14-7 can be prepared according to the general scheme outlined in Scheme 14.

Bromobenzene analogs bearing heterocycles such as pyrazoles can undergo metalation using an excess of n-BuLi and addition to sulfinimines such as S14-2 to give adducts such as S14-3. Conversion to the amine HCl salt can occur under previously described conditions. Coupling with proline derivative S14-5 under previously described conditions gives compounds of formulae S14-6 and S14-7, which can be isolated as single isomers using methods such as reverse phase prep-HPLC or chiral SFC.

Scheme 15

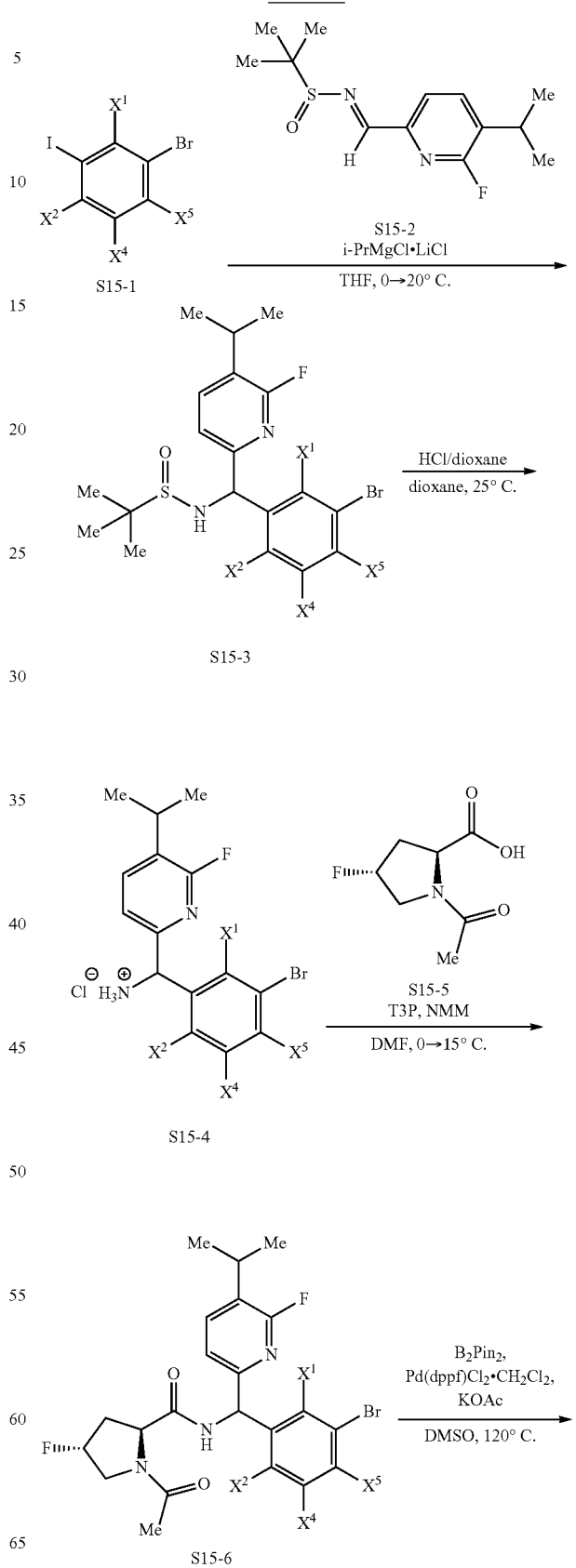

S15-1

S15-3

S15-4

S15-6

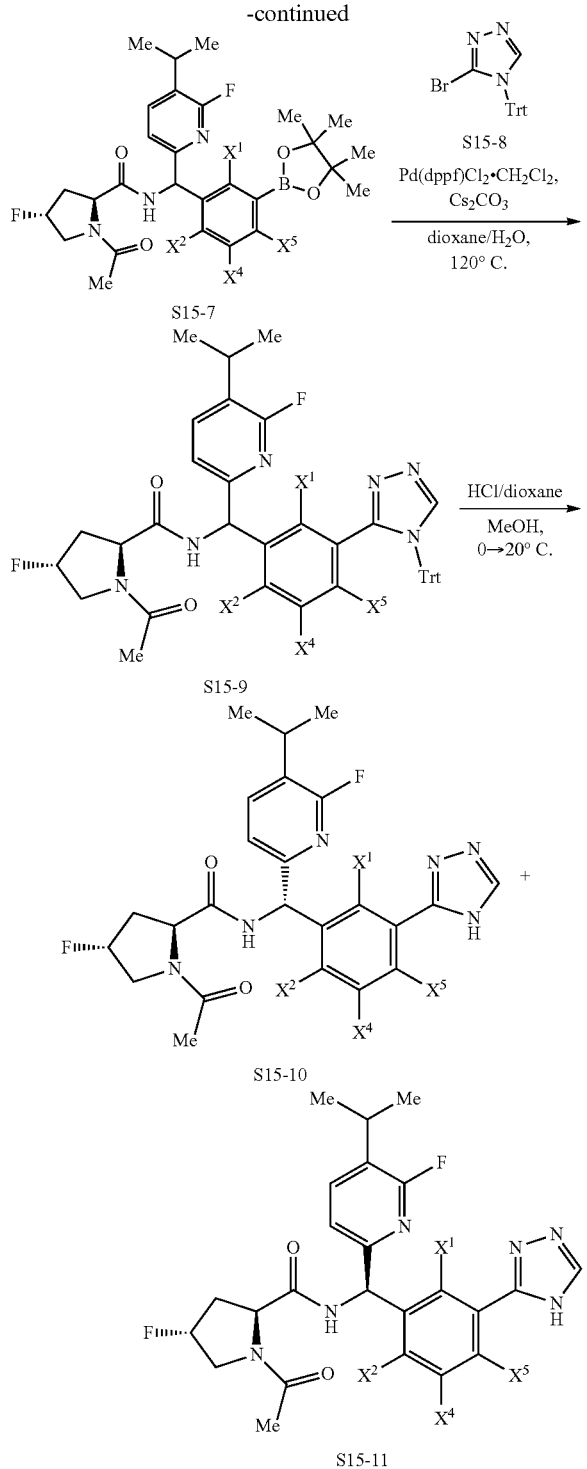

generate boronate ester S15-7. Suzuki-type cross coupling under conditions previously described, using an aryl or heteroaryl bromide such as S15-8 gives S15-9. Cleavage of the trityl protecting from the triazole moiety under protic acid conditions gives compounds of formula S15-10 and S15-11, which can be isolated as single isomers using methods such as flash column chromatography, reverse phase HPLC, or chiral SFC.

Abbreviations used are those conventional in the art and are in accordance with the Periodic Table of the Elements, CAS version, *Handbook of Chemistry and Physics*, 75th Ed. The following examples are intended to be illustrative only and not limiting in any way.

| | |
|---|---|
| ° C. | degrees Celsius |
| µL | microliter |
| [M + XX]$^+$ | observed mass |
| AC$_{50}$ | half-maximal activity concentration |
| ACN | acetonitrile |
| app | apparent (NMR) |
| BH$_3$•THF | borane-tetrahydrofuran complex |
| BBr$_3$ | boron tribromide |
| Calc'd | calculated |
| Cbz-Cl | benzyl chloroformate |
| CO$_2$ | carbon dioxide |
| Cs$_2$CO$_3$ | cesium carbonate |
| d | deuterated (NMR solvents) |
| d | doublet (NMR) |
| dd | doublet of doublets (NMR) |
| DCM | dichloromethane |
| DIAD | diisopropyl azodicarboxylate |
| DMF | N,N-dimethylformamide |
| EC$_{50}$ | half-maximal effective concentration |
| EDCI | 1-Ethyl-3-(3-dimethylaminopropyl)carbodiimide |
| ESI | electrospray ionization |
| EtOAc | ethyl acetate |
| EtOH | ethanol |
| eq | equivalents |
| g | grams |
| h | hours |
| H | hydrogen |
| HCl | hydrochloric acid |
| HPLC | high-performance liquid chromatography |
| IC$_{50}$ | half-maximal inhibitory concentration |
| In vacuo | in a vacuum |
| IUPAC | International Union of Pure and Applied Chemistry |
| MHz | megahertz |
| J | J-coupling value (NMR) |
| K$_2$CO$_3$ | potassium carbonate |
| LDA | lithium diisopropylamide |
| LiHMDS | lithium bis(trimethylsilyl)amide |
| MeOH | Methanol |
| MeCN | acetonitrile |
| m | multiplet (NMR) |
| mg | milligrams |
| min | minutes |
| mL | milliliter |
| mmol | millimole |
| mM | millimolar |
| M | molarity or molar |
| MS | mass spectrometry |
| MsCl | methanesulfonyl chloride |
| MTBE | methyl tert-butyl ether |
| n/a | not applicable |
| NBS | N-bromosuccinimide |
| NH$_4$ | ammonium |
| NH$_4$OH | ammonium hydroxide |
| NH$_4$HCO$_3$ | ammonium bicarbonate |
| Na$_2$SO$_4$ | sodium sulfate |
| NaBH$_3$CN | sodium cyanoborohydride |
| NMI | N-methylimidazole |
| NMM | N-methylmorpholine |
| NMR | nuclear magnetic resonance |
| NaOH | sodium hydroxide |
| PCy$_3$ | Tricyclohexylphosphine |
| PdCl$_2$(dppf) | [1,1'- |

Compounds of the general formula S15-10 and S15-11 can be prepared according to the general scheme outlined in Scheme 15.

An alternative strategy that enables late-stage elaboration to generate compounds of formulae 515-10 and 515-11 begins by selective metal-halogen exchange with 515-1 and addition to sulfinimine S15-2 to generate S15-3. Generation of the amine HCl salt and coupling to proline derivative S15-5 under conditions previously described gives S15-6. S16-6 may then undergo palladium catalyzed borylation to

| | |
|---|---|
| | Bis(diphenylphosphino)ferrocene]dichloropalladium(II) |
| pH | potential of hydrogen |
| PPh₃ | triphenyl phosphine |
| s | singlet (NMR) |
| SFC | super fluid chromatography |
| t | triplet (NMR) |
| T3P | Propanephosphonic acid anhydride |
| TBAB | tetrabutylammonium bromide |
| TEA | triethylamine |
| TFA | trifluoroacetic acid |
| TFCH | N,N,N',N'-tetramethylchloroformamidinium hexafluorophosphate |
| THF | tetrahydrofuran |
| TMSCl | trimethylsilyl chloride |
| wt. % | weight percent |

Intermediate A-1: Synthesis of
2-(1H-1,2,3-triazol-5-yl)acetic acid

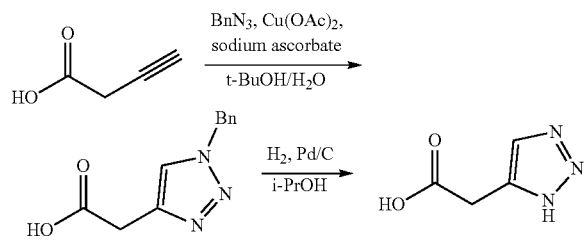

Step a: To a mixture of but-3-ynoic acid (7.5 g, 89.2 mmol, 1 eq), Cu(OAc)₂ (1.62 g, 8.92 mmol, 0.1 eq) and sodium ascorbate (3.53 g, 17.8 mmol, 0.2 eq) in H₂O (75 mL) and t-BuOH (75 mL) at 0° C. was added, in portions, benzyl azide (BnN₃, 13.9 g, 93.7 mmol, 90% purity, 1.05 eq). The resulting mixture was warmed to 25° C. and stirred for 12 h. The mixture was then filtered and the solids were washed with water (2×20 mL) and dried under reduced pressure to afford 2-(1-benzyl-1H-1,2,3-triazol-4-yl)acetic acid. LC-MS (ESI): m/z: [M+H]⁺ calculated for C₁₁H₁₁N₃O₂: 218.1; found 218.1.

Step b: A suspension of 2-(1-benzyl-1H-1,2,3-triazol-4-yl)acetic acid (5 g, 23 mmol, 1 eq) and Pd/C (2.45 g, 10% wt. %) in i-PrOH (300 mL) was stirred under H₂ (50 psi) at 25° C. for 5 h. The reaction mixture was then filtered through a pad of Celite, and the filter cake was washed with CH₂Cl₂ (3×30 mL). The filtrate was concentrated under reduced pressure to give 2-(1H-1,2,3-triazol-5-yl)acetic acid. LC-MS (ESI): m/z: [M+H]⁺ calculated for C₄H₅N₃O₂: 128.1; found 128.1.

Intermediate A-2: Synthesis of 2-(5-(difluoromethyl)-1H-tetrazol-1-yl)acetic acid

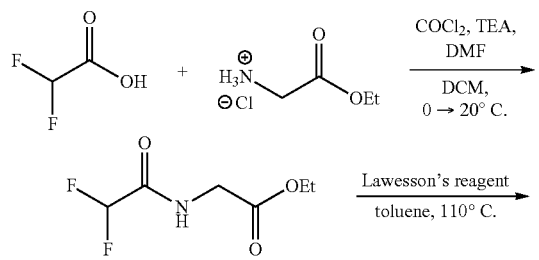

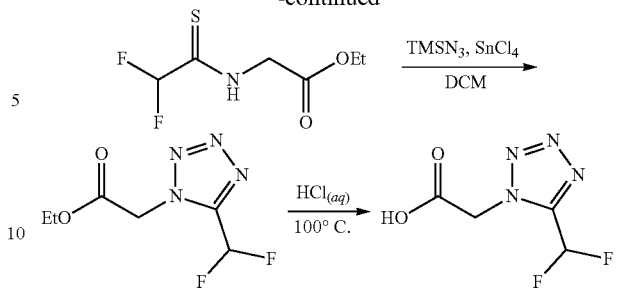

Step a: To a solution of 2,2-difluoroacetic acid (50.0 g, 520 mmol, 1.00 eq) in dry DCM (200 mL) at 0° C. was added a catalytic amount of DMF (4 mL) and oxalyl dichloride (66.1 g, 520 mmol, 45.6 mL, 1.00 eq), sequentially. The resulting mixture was warmed to 20° C. and stirred for 1 h. The reaction mixture was then cooled to 0° C. and a solution of 2-ethoxy-2-oxoethan-1-aminium chloride (80.0 g, 573 mmol, 1.10 eq), TEA (105 g, 1.04 mol, 2.00 eq) and DMAP (7.37 g, 52.1 mmol, 0.10 eq) in DCM (500 mL) was added. The reaction mixture was warmed to 20° C. and stirred for 1 h. The reaction mixture was then quenched with water (100 mL) and extracted with dichloromethane (3×200 mL). The combined organic extracts were washed with brine (500 mL), dried over anhydrous Na₂SO₄, filtered, and concentrated under reduced pressure. The resulting crude residue was purified by column chromatography to give ethyl (2,2-difluoroacetyl)glycinate. This compound was carried forward to the next step without further characterization.

Step b: To a solution of ethyl (2,2-difluoroacetyl)glycinate (25.0 g, 138 mmol, 1.00 eq) in toluene (250 mL) at 25° C. was added 2,4-bis(4-methoxyphenyl)-2,4-dithioxo-1,3,2λ⁵, 4λ⁵-dithiadiphosphetane (Lawesson's reagent, 67.0 g, 165 mmol, 1.20 eq) under N₂. The resulting mixture was warmed to 110° C. and stirred for 1 h. The reaction mixture was then cooled to 25° C., and poured into water (300 mL) and NaOCl (~10% aqueous, 100 mL). The resulting mixture was extracted with ethyl acetate (3×200 mL). The combined organic extracts were washed with brine (2×200 mL), dried over anhydrous Na₂SO₄, filtered, and concentrated under reduced pressure. The resulting crude residue was purified by column chromatography to give ethyl (2,2-difluoroethanethioyl)glycinate. This compound was carried forward to the next step without further characterization.

Step c: To a mixture of ethyl (2,2-difluoroethanethioyl) glycinate (12.5 g, 63.4 mmol, 1.00 eq) and azido(trimethyl) silane (14.6 g, 127 mmol, 2.00 eq) in DCM (120 mL) at 0° C. under N₂ was added SnCl₄ (41.2 g, 158 mmol, 2.50 eq). The resulting mixture was warmed to 25° C. and stirred for 2 h. The reaction mixture was then cooled to 0° C. and quenched by addition of saturated aqueous NaHCO₃ (200 mL). The resulting biphasic mixture was extracted with DCM (2×100 mL). The combined organic extracts were dried over anhydrous Na₂SO₄, filtered, and concentrated under reduced pressure. The resulting crude residue was purified by silica gel chromatography to give ethyl 2-(5-(difluoromethyl)-1H-tetrazol-1-yl)acetate. This compound was carried forward to the next step without further characterization.

Step d: Ethyl 2-(5-(difluoromethyl)-1H-tetrazol-1-yl)acetate (6.50 g, 31.5 mmol, 1.00 eq) was dissolved in aqueous HCl (6 M, 65 mL) at 20° C. The resulting mixture was warmed to 100° C. and stirred for 20 h. The reaction mixture was then concentrated under reduced pressure to give 2-(5-(difluoromethyl)-1H-tetrazol-1-yl)acetic acid. LC-MS (ESI): m/z: [M+H]+ calculated for $C_4H_4F_2N_4O_2$: 179.0; found 179.0.

Intermediate A-3: Synthesis of 2-(5-(trifluoromethyl)-1H-1,2,3-triazol-1-yl)acetic acid

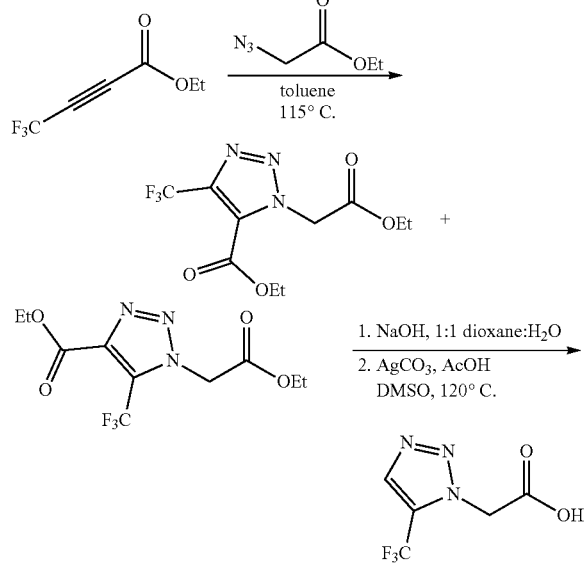

Step a: To a solution of ethyl 2-azidoacetate (200 mg, 94% purity, 1.5 mmol, 1 eq) in toluene (5 mL) was added ethyl 4,4,4-trifluorobut-2-ynoate (500 mg, 3.0 mmol, 2 eq). The mixture was warmed to 115° C. and stirred for 16 h. The reaction mixture was then cooled to 0° C., quenched with MeOH (10 mL) and concentrated under reduced pressure. The resulting crude residue was purified by column chromatography to give a mixture of ethyl 1-(2-ethoxy-2-oxoethyl)-4-(trifluoromethyl)-1H-1,2,3-triazole-5-carboxylate and ethyl 1-(2-ethoxy-2-oxoethyl)-5-(trifluoromethyl)-1H-1,2,3-triazole-4-carboxylate. This compound was carried forward to the next step without further characterization.

Step b: To a mixture of ethyl 1-(2-ethoxy-2-oxoethyl)-4-(trifluoromethyl)-1H-1,2,3-triazole-5-carboxylate and ethyl 1-(2-ethoxy-2-oxoethyl)-5-(trifluoromethyl)-1H-1,2,3-triazole-4-carboxylate (220.00 mg, 745 μmol, 1 eq) in 1:1 dioxane:H₂O (4 mL) at 25° C. was added NaOH (60 mg, 1.1 mmol, 1.5 eq). The resulting mixture was stirred at for 16 h. The reaction mixture was then quenched with HCl (6 M, 1 mL) in H₂O (10 mL) and extracted with DCM (3×20 mL). The aqueous phase was lyophilized to afford a crude solid, which was immediately dissolved in DMSO (3 mL). To the resulting mixture was added Ag₂CO₃ (140 mg, 508 μmol, 0.5 eq), followed by AcOH (6 mg, 100 μmol, 0.1 eq). The mixture was warmed to 130° C. and stirred for 16 h. The reaction mixture was then quenched with H₂O (30 mL) and extracted with EtOAc (3×10 mL). The combined organic extracts were washed with brine (2×15 mL), dried over anhydrous Na₂SO₄, filtered, and concentrated under reduced pressure. The resulting crude residue was purified by prep-HPLC to give 2-(5-(trifluoromethyl)-1H-1,2,3-triazol-1-yl) acetic acid. LC-MS (ESI): m/z: [M−H]− calculated for $C_5H_4F_3N_3O_2$: 194.0; found 194.1.

Intermediate A-4: Synthesis of 2-(1H-benzo[d]imidazol-1-yl)acetic acid

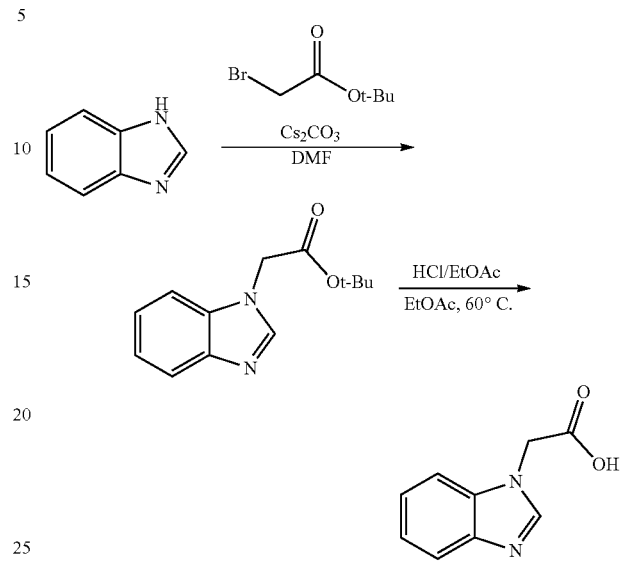

Step a: To a solution of 1H-benzo[d]imidazole (10.0 g, 84.6 mmol, 1 eq) in DMF (100 mL) was added Cs₂CO₃ (33.1 g, 102 mmol, 1.2 eq) and tert-butyl 2-bromoacetate (18.2 g, 93.1 mmol, 1.1 eq). The mixture was stirred at 25° C. for 2 h. The reaction mixture was then filtered and the filtrate was diluted with EtOAc (200 mL). The combined organic extracts were washed with brine (100 mL), dried over Na₂SO₄, filtered, and concentrated under reduced pressure. The resulting crude residue was purified by column chromatography to give compound tert-butyl 2-(1H-benzo [d]imidazol-1-yl)acetate. LC-MS (ESI): m/z: [M+H]+ calculated for $C_{13}H_{16}N_2O_2$: 233.1; found 233.1.

Step b: To a solution of tert-butyl 2-(1H-benzo[d]imidazol-1-yl)acetate (16.8 g, 72.3 mmol, 1 eq) in EtOAc (100 mL) was added HCl/EtOAc (4 M, 200 mL). The mixture was warmed to 60° C. and stirred for 2 h. The reaction mixture was then concentrated under reduced pressure. The resulting crude product was triturated with petroleum ether at 25° C. for 10 min and filtered to give 2-(1H-benzo[d] imidazol-1-yl)acetic acid. LC-MS (ESI): m/z: [M+H]+ calculated for $C_9H_8N_2O_2$: 177.1; found 177.0.

Intermediate A-5: Synthesis of 2-(3-ethyl-5-methyl-2,4-dioxo-3,4-dihydropyrimidin-1(2H)-yl)acetic acid

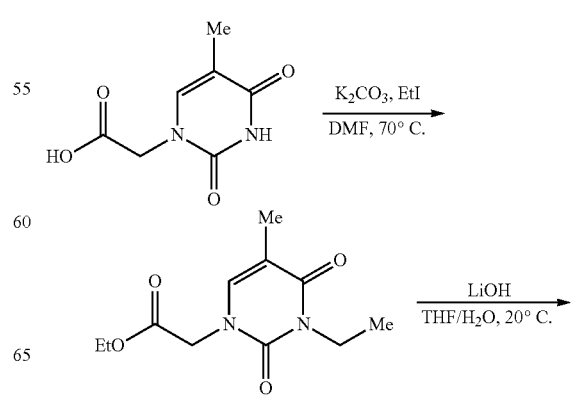

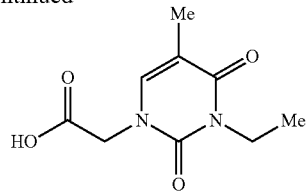

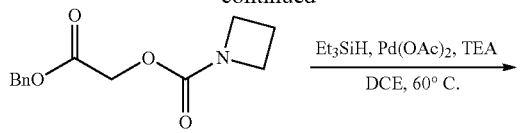

Step a: To a mixture of iodoethane (1.27 g, 8.15 mmol, 3 eq) and 2-(5-methyl-2,4-dioxo-3,4-dihydropyrimidin-1(2H)-yl)acetic acid (500 mg, 2.72 mmol, 1 eq) in DMF (6 mL) at 20° C. under $N_2$ was added $K_2CO_3$ (1.88 g, 13.5 mmol, 5 eq) in one portion. The resulting mixture was warmed to 70° C. and stirred for 2 h. After this time, the reaction mixture was cooled to 0° C., and the reaction was quenched by addition $H_2O$ (30 mL). The resulting biphasic mixture was then extracted with EtOAc (3×30 mL). The combined organic extracts were washed with brine (20 mL), dried over $Na_2SO_4$, filtered, and concentrated under reduced pressure to give a crude residue that was purified by column chromatography to obtain ethyl 2-(3-ethyl-5-methyl-2,4-dioxo-3,4-dihydropyrimidin-1(2H)-yl)acetate. LC-MS (ESI): m/z: [M+H]$^+$ calculated for $C_{11}H_{16}N_2O_4$: 241.1; found 241.1.

Step b: To a solution of ethyl 2-(3-ethyl-5-methyl-2,4-dioxo-3,4-dihydropyrimidin-1(2H)-yl)acetate (450 mg, 1.87 mmol, 1 eq) in THF (5 mL) and $H_2O$ (5 mL) at 20° C. under $N_2$ was added LiOH (89.7 mg, 3.75 mmol, 2 eq) in one portion. The resulting mixture was stirred at 20° C. for 2 h. After this time, the reaction mixture was diluted with $H_2O$ (20 mL), and the pH of the solution was adjusted to pH=3 by addition of aqueous HCl (2M). The resulting mixture was then extracted with EtOAc (3×10 mL). The combined organic extracts were then washed with brine (20 mL), dried over $Na_2SO_4$, filtered, and concentrated under reduced pressure to obtain 2-(3-ethyl-5-methyl-2,4-dioxo-3,4-dihydropyrimidin-1(2H)-yl)acetic acid. LC-MS (ESI): m/z: [M+H]$^+$ calculated for $C_9H_{12}N_2O_4$: 213.1; found 213.1.

Intermediate A-6: Synthesis of 2-((azetidine-1-carbonyl)oxy)acetic acid

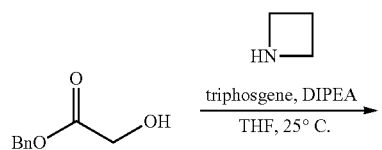

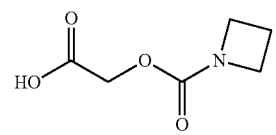

Step a: To a solution of benzyl 2-hydroxyacetate (0.96 g, 5.78 mmol, 821 µL, 1 eq) in THF (10 mL) at 0° C. was added triphosgene (686 mg, 2.31 mmol, 0.4 eq) followed by DIPEA (2.09 g, 16.2 mmol, 2.82 mL, 2.8 eq), and the resulting mixture was stirred at 0° C. for 0.5 h before it was warmed to 25° C. and stirred for 0.5 h. A solution of azetidine (330 mg, 5.78 mmol, 390 µL, 1 eq) in THF (10 mL) and DIPEA (1.05 g, 8.09 mmol, 1.41 mL, 1.4 eq) were then added, and the resulting mixture was stirred at 25° C. for 12 h. The reaction mixture was then diluted with saturated aqueous $NaHCO_3$ (20 mL), and the resulting biphasic mixture was extracted with EtOAc (3×10 mL). The combined organic extracts were washed with brine (10 mL), dried over anhydrous $Na_2SO_4$, filtered, and concentrated under reduced pressure. The crude residue obtained was purified by column chromatography to give 2-(benzyloxy)-2-oxoethyl azetidine-1-carboxylate. LC-MS (ESI): m/z: [M+H]$^+$ calculated for $C_{13}H_{15}NO_4$: 250.1; found 250.2.

Step b: To a mixture of 2-(benzyloxy)-2-oxoethyl azetidine-1-carboxylate (250 mg, 1.00 mmol, 1 eq) in DCE (5 mL) at 25° C. under $N_2$ was added TEA (20.3 mg, 200 µmol, 27.9 µL, 0.2 eq), Pd(OAc)$_2$ (56.3 mg, 251 µmol, 0.25 eq) and Et$_3$SiH (233 mg, 2.01 mmol, 320 µL, 2 eq). The resulting mixture was stirred at 60° C. for 2 h before it was filtered through a pad of Celite. The filtrate was then concentrated under reduced pressure to give 2-((azetidine-1-carbonyl)oxy)acetic acid. LC-MS (ESI): m/z: [M−H]$^−$ calculated for $C_6H_9NO_4$: 158.0; found 158.1.

The following compounds in Table B-1 were synthesized using procedures similar to Intermediate A-6 using the appropriate starting materials.

TABLE B-1

| Intermediate No. | Structure | IUPAC | Exact mass (g/mol) | LCMS, Found [M + H]$^+$ |
|---|---|---|---|---|
| B-1-1 | 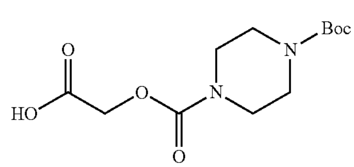 [SMILES: CC(C)(C)OC(=O)N1CCN(C(=O)OCC(=O)O)CC1] | 2-((4-(tert-butoxycarbonyl)piperazine-1-carbonyl)oxy)acetic acid | 288.1 | 189.1 [M − Boc + H]$^+$ |

Intermediate A-7: Synthesis of 2-(1-benzyl-4-(4-(tert-butoxycarbonyl)piperazin-1-yl)-1H-1,2,3-triazol-5-yl)acetic acid

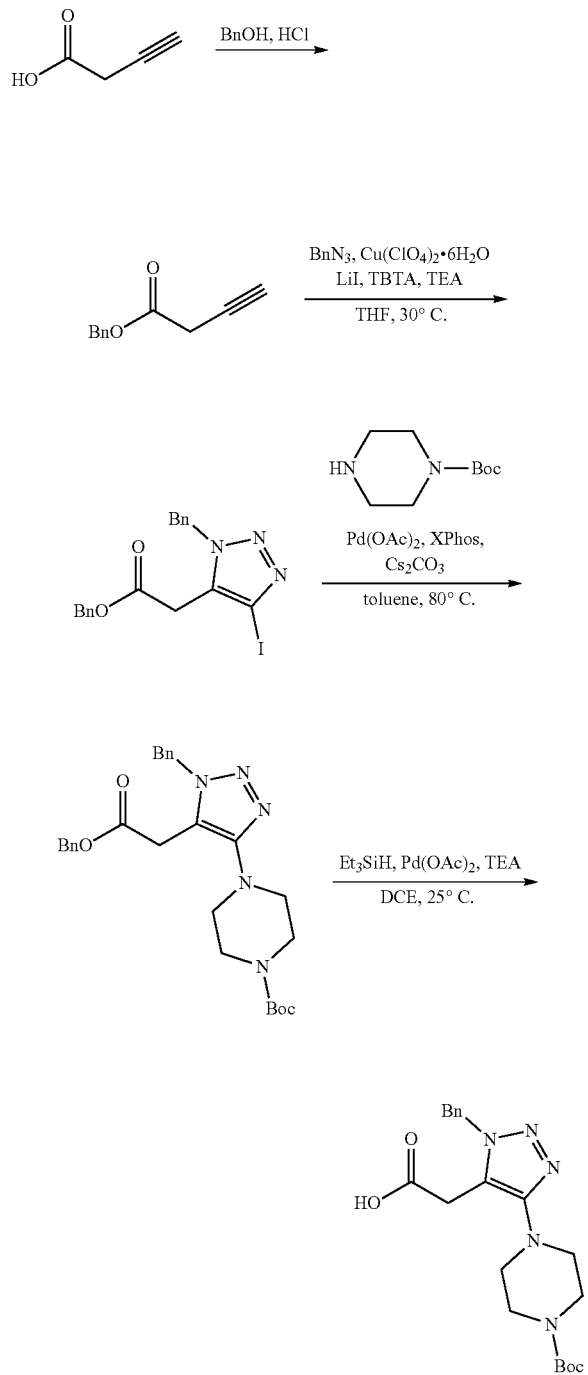

Step a: To a mixture of but-3-ynoic acid (5.00 g, 59.5 mmol, 1.00 eq) in benzyl alcohol (19.3 g, 178 mmol, 18.6 mL, 3.00 eq) at 25° C. was added aqueous HCl (12 M, 297 µL, 37.0% purity, 0.06 eq) in one portion. The resulting mixture was stirred at 25° C. for 16 h. The reaction mixture was then quenched by addition of H$_2$O (30 mL) at 25° C., and the resulting biphasic mixture was extracted with EtOAc (3×10 mL). The combined organic extracts were dried over anhydrous Na$_2$SO$_4$, filtered, and concentrated under reduced pressure. The crude residue obtained was purified by column chromatography to give benzyl but-3-ynoate. This compound was carried forward to the next step without further characterization.

Step b: To a mixture of benzyl azide (3.00 g, 22.5 mmol, 1.00 eq) in THF (45 mL) at 25° C. under N$_2$ was added LiI (12.1 g, 90.1 mmol, 3.46 mL, 4.00 eq), copper (II) perchlorate hexahydrate (16.7 g, 45.1 mmol, 2.00 eq), and tris[(1-benzyl-1H-1,2,3-triazol-4-yl)methyl]amine (TBTA, 1.20 g, 2.25 mmol, 0.100 eq) in one portion. The resulting mixture was stirred at 25° C. for 5 min before TEA (2.28 g, 22.5 mmol, 3.14 mL, 1.00 eq) and benzyl but-3-ynoate (4.32 g, 24.8 mmol, 1.10 eq) were added, and the resulting mixture was stirred at 30° C. for 6 h. The reaction mixture was then quenched by addition H$_2$O (30 mL), and the resulting biphasic mixture was extracted with EtOAc (3×10 mL). The combined organic extracts were dried over anhydrous Na$_2$SO$_4$, filtered, and concentrated under reduced pressure. The crude residue obtained was purified by column chromatography to give benzyl 2-(1-benzyl-4-iodo-1H-1,2,3-triazol-5-yl)acetate. LC-MS (ESI): m/z: [M+H]$^+$ calculated for C$_{18}$H$_{16}$IN$_3$O$_2$: 434.0; found 434.1.

Step c: To a mixture of tert-butyl piperazine-1-carboxylate (645 mg, 3.46 mmol, 5.00 eq) and benzyl 2-(1-benzyl-4-iodo-1H-1,2,3-triazol-5-yl)acetate (300 mg, 693 µmol, 1.00 eq) in toluene (10 mL) at 25° C. under N$_2$ was added XPhos (83.0 mg, 173 µmol, 0.250 eq), Pd(OAc)$_2$ (34.0 mg, 152 µmol, 0.220 eq) and Cs$_2$CO$_3$ (677 mg, 2.08 mmol, 3.00 eq) in one portion. The resulting mixture was stirred at 80° C. for 6 h. The reaction mixture was then filtered, and the filtrate was concentrated under reduced pressure. The crude residue obtained was purified by column chromatography to give tert-butyl 4-(1-benzyl-5-(2-(benzyloxy)-2-oxoethyl)-1H-1,2,3-triazol-4-yl)piperazine-1-carboxylate. LC-MS (ESI): m/z: [M+H]$^+$ calculated for C$_{27}$H$_{33}$N$_5$O$_4$: 492.2; found 492.3.

Step d: To a mixture of tert-butyl 4-(1-benzyl-5-(2-(benzyloxy)-2-oxoethyl)-1H-1,2,3-triazol-4-yl)piperazine-1-carboxylate (200 mg, 406 µmol, 1.00 eq) in DCE (5 mL) at 25° C. under N$_2$ were added TEA (8.0 mg, 81.3 µmol, 11.3 µL, 0.2 eq), Et$_3$SiH (95.0 mg, 813 µmol, 130 µL, 2.00 eq), Pd(OAc)$_2$ (23.0 mg, 102 µmol, 0.250 eq) in one portion. The resulting mixture was stirred at 25° C. for 60 min before it was quenched by addition H$_2$O (10 mL). The resulting biphasic mixture was then extracted with EtOAc (3×10 mL). The combined organic extracts were dried over anhydrous Na$_2$SO$_4$, filtered, and concentrated under reduced pressure to give 2-(1-benzyl-4-(4-(tert-butoxycarbonyl)piperazin-1-yl)-1H-1,2,3-triazol-5-yl)acetic acid. LC-MS (ESI): m/z: [M+H]$^+$ calculated for C$_{20}$H$_{27}$N$_5$O$_4$: 402.2; found 402.3.

The following compounds in Table B-2 were synthesized using procedures similar to Intermediate A-7 using the appropriate starting materials.

TABLE B-2

| Intermediate No. | Structure | IUPAC | Exact mass (g/mol) | LCMS, Found [M + H]+ |
|---|---|---|---|---|
| B-2-1 | ![structure] | 2-(1-benzyl-4-morpholino-1H-1,2,3-triazol-5-yl)acetic acid | 302.1 | 303.2 |

Intermediate A-8: Synthesis of 2-(1-benzyl-1H-1,2,3-triazol-4-yl)-2-hydroxyacetic acid

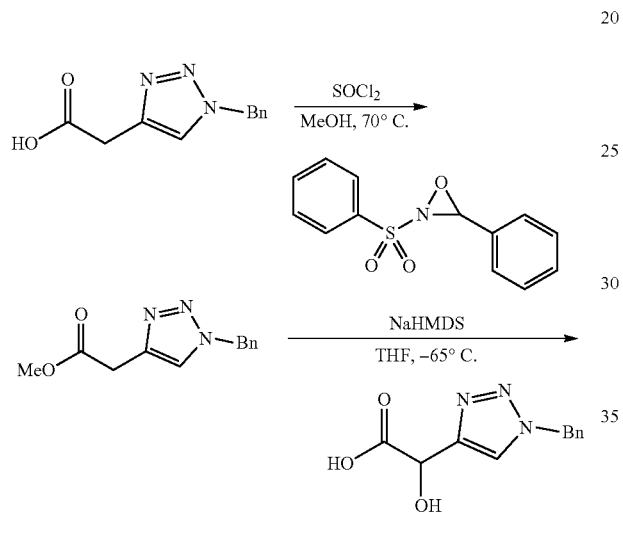

Step a: To a solution of 2-(1-benzyl-1H-1,2,3-triazol-4-yl)acetic acid (2.00 g, 9.21 mmol, 1 eq) in MeOH (20 mL) at 25° C. was added SOCl$_2$ (109.54 mg, 920.71 μmol, 66.79 μL, 0.1 eq). The resulting mixture was warmed to 70° C. and stirred for 3 h. The reaction mixture was then quenched with water (20 mL), and the resulting biphasic mixture was extracted with EtOAc (3×20 mL). The combined organic extracts were dried over anhydrous Na$_2$SO$_4$, filtered, and concentrated under reduced pressure to give methyl 2-(1-benzyl-1H-1,2,3-triazol-4-yl)acetate. LC-MS (ESI): m/z: [M+H]+ calculated for C$_{12}$H$_{13}$N$_3$O$_2$: 232.1; found 232.1.

Step b: To a solution of methyl 2-(1-benzyl-1H-1,2,3-triazol-4-yl)acetate (500 mg, 2.16 mmol, 1 eq) and 3-phenyl-2-(phenylsulfonyl)-1,2-oxaziridine (847.45 mg, 3.24 mmol, 1.5 eq) in THF (5 mL) at −65° C. under N$_2$ was added NaHMDS (1 M in THF, 3.24 mL, 1.5 eq) in THF (5 mL) in a dropwise manner. The resulting mixture was stirred at −65° C. for 2 h. The reaction mixture was adjusted to pH=7 by addition of saturated aqueous NH$_4$Cl solution. The resulting biphasic solution was extracted with EtOAc (3×10 mL). The combined organic extracts were dried over anhydrous Na$_2$SO$_4$, filtered, and concentrated under reduced pressure. The crude residue obtained was purified by prep-HPLC to give 2-(1-benzyl-1H-1,2,3-triazol-4-yl)-2-hydroxyacetic acid. LC-MS (ESI): m/z: [M+H]+ calculated for C$_{11}$H$_{11}$N$_3$O$_3$: 234.1; found 234.1.

Intermediate A-9: Synthesis of 2-(3-oxo-2,3-dihydro-[1,2,4]triazolo[4,3-a]pyridin-8-yl)acetic acid

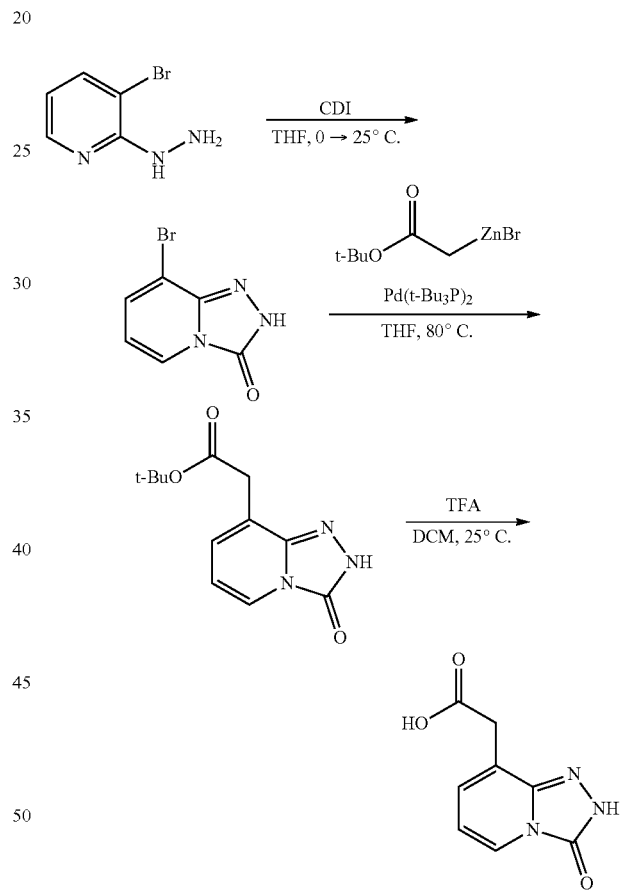

Step a: To a solution of 3-bromo-2-hydrazineylpyridine (2 g, 10.6 mmol, 1 eq) in THF (20 mL) at 0° C. was added CDI (2.24 g, 13.8 mmol, 1.3 eq). The resulting mixture was warmed to 25° C. and stirred for 2 h. The mixture was then poured into water (20 mL), resulting in the precipitation of a solid. The mixture was then filtered, and the filter cake was washed with water. The washed solid was then dried under reduced pressure to give 8-bromo-[1,2,4]triazolo[4,3-a]pyridin-3(2H)-one. LC-MS (ESI): m/z: [M+H]+ calculated for C$_6$H$_4$BrN$_3$O: 214.0; found 213.9.

Step b: To a mixture of 8-bromo-[1,2,4]triazolo[4,3-a]pyridin-3(2H)-one (500 mg, 2.34 mmol, 1 eq) and Pd(t-Bu$_3$P)$_2$ (239 mg, 467 μmol, 0.2 eq) in THF (30 mL) was added (2-(tert-butoxy)-2-oxoethyl)zinc(II) bromide (1 M in THF, 14.02 mL, 6 eq). The resulting mixture was degassed and purged with $N_2$, and then the mixture was warmed to 80° C. and stirred for 2 h under $N_2$ atmosphere. The mixture was then filtered, and $H_2O$ (10 mL) was added to the filtrate. The resulting biphasic mixture was extracted with EtOAc (2×10 mL). The combined organic extracts were washed with brine (2×15 mL), dried over anhydrous $Na_2SO_4$, filtered, and concentrated under reduced pressure. The crude residue obtained was purified by column chromatography to give tert-butyl 2-(3-oxo-2,3-dihydro-[1,2,4]triazolo[4,3-a]pyridin-8-yl)acetate. LC-MS (ESI): m/z: [M−H]⁻ calculated for $C_{12}H_{15}N_3O_3$: 248.1; found 248.1.

Step c: To a solution of tert-butyl 2-(3-oxo-2,3-dihydro-[1,2,4]triazolo[4,3-a]pyridin-8-yl)acetate (50 mg, 201 µmol, 1 eq) in DCM (2 mL) was added TFA (1.54 g, 13.5 mmol, 1 mL, 67.3 eq). The resulting mixture was stirred at 25° C. for 15 h. The mixture was then concentrated under reduced pressure to give 2-(3-oxo-2,3-dihydro-[1,2,4]triazolo[4,3-a]pyridin-8-yl)acetic acid. LC-MS (ESI): m/z: [M−CO₂H−H]⁻ calculated for $C_8H_7N_3O_3$: 148.1; found 148.2.

Intermediate A-10: Synthesis of 2-(2-methylquinolin-5-yl)acetic acid

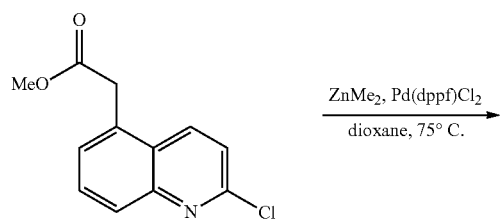

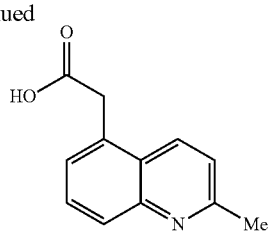

Step a: To a mixture of methyl 2-(2-chloroquinolin-5-yl)acetate (200 mg, 849 µmol, 1 eq) and dimethylzinc (1 M in toluene, 2.55 mL, 3.00 eq) in dioxane (2 mL) at 25° C. under $N_2$ was added Pd(dppf)Cl₂ (124 mg, 170 µmol, 0.20 eq) in one portion. The mixture was then degassed and charged with $N_2$. The reaction mixture was then warmed to 75° C. and stirred for 1 h. The reaction mixture was then cooled to 25° C. and poured into water (10 mL). The resulting biphasic mixture was extracted with ethyl acetate (3×50 mL). The combined organic extracts were dried over anhydrous $Na_2SO_4$, filtered, and concentrated under reduced pressure. The crude residue obtained was purified by column chromatography to give methyl 2-(2-methylquinolin-5-yl)acetate. LC-MS (ESI): m/z: [M+H]⁺ calculated for $C_{13}H_{13}NO_2$: 216.1; found 216.1.

Step b: Methyl 2-(2-methylquinolin-5-yl)acetate (90 mg, 418 µmol, 1.00 eq) was added to aqueous HCl (6 M, 0.5 mL) in one portion at 25° C. The reaction mixture was then warmed to 100° C. and stirred for 16 h. The reaction mixture was then concentrated under reduced pressure to give 2-(2-methylquinolin-5-yl)acetic acid. LC-MS (ESI): m/z: [M+H]⁺ calculated for $C_{12}H_{11}NO_2$: 202.1; found 202.1.

The following compounds in Table B-3 were synthesized using procedures similar to Intermediate A-10 using the appropriate starting materials.

TABLE B-3

| Intermediate No. | Structure | IUPAC | Exact mass (g/mol) | LCMS, Found [M + H]⁺ |
| --- | --- | --- | --- | --- |
| B-3-1 | 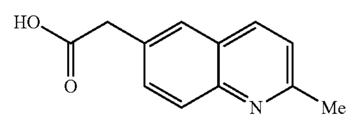 [SMILES: Cc1ccc2cc(CC(=O)O)ccc2n1] | 2-(2-methylquinolin-6-yl)acetic acid | 201.1 | 202.2 |

Intermediate A-11: Synthesis of 2-(5-(difluoromethyl)-2H-tetrazol-2-yl)acetic acid

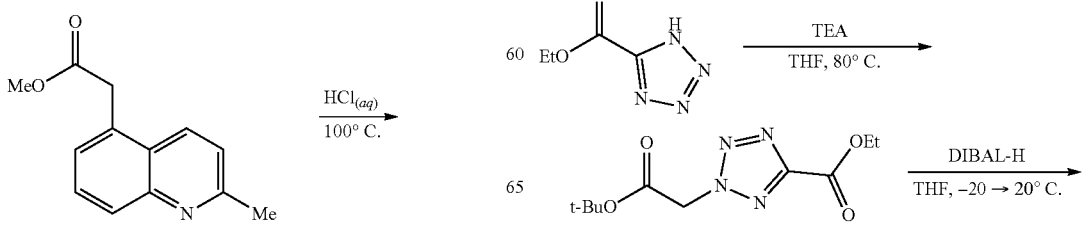

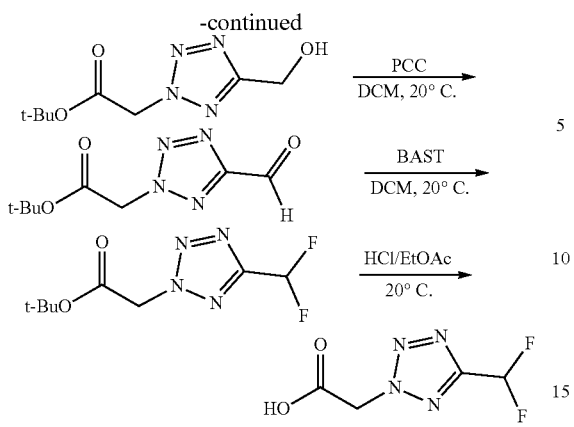

Step a: A mixture of ethyl 1H-tetrazole-5-carboxylate (25.0 g, 175 mmol, 1.00 eq), tert-butyl 2-bromoacetate (37.7 g, 193 mmol, 28.5 mL, 1.10 eq) and TEA (26.7 g, 263 mmol, 36.7 mL, 1.50 eq) in THF (250 mL) was warmed to 80° C. and stirred for 1 h. The reaction mixture was then cooled and quenched with water (200 mL), and the resulting biphasic mixture was extracted with ethyl acetate (3×200 mL). The combined organic extracts were washed with brine (400 mL), dried over anhydrous $Na_2SO_4$, filtered, and concentrated under reduced pressure to give ethyl 2-(2-(tert-butoxy)-2-oxoethyl)-2H-tetrazole-5-carboxylate. LC-MS (ESI): m/z: $[M+H]^+$ calculated for $C_{10}H_{16}N_4O_4$: 257.1; found 257.1.

Step b: To a solution of ethyl 2-(2-(tert-butoxy)-2-oxoethyl)-2H-tetrazole-5-carboxylate (35.0 g, 136 mmol, 1.00 eq) in THF (180 mL) at −20° C. under $N_2$ was added DIBAL-H (1 M in THF, 273 mL, 2.00 eq) in a dropwise manner. The mixture was then warmed to 20° C. and stirred for 1 h. The mixture was then cooled to 0° C. and quenched with water (300 mL) before it was stirred for 10 min. The resulting biphasic mixture was extracted with ethyl acetate (2×100 mL). The combined organic extracts were washed with brine (200 mL), dried over anhydrous $Na_2SO_4$, filtered, and concentrated under reduced pressure. The crude residue obtained was purified by column chromatography to give tert-butyl 2-(5-(hydroxymethyl)-2H-tetrazol-2-yl)acetate. LC-MS (ESI): m/z: $[M+H]^+$ calculated for $C_8H_{14}N_4O_3$: 215.1; found 215.1.

Step c: To a solution of tert-butyl 2-(5-(hydroxymethyl)-2H-tetrazol-2-yl)acetate (2.00 g, 9.34 mmol, 1.00 eq) in DCM (20 mL) at 20° C. was added PCC (4.02 g, 18.6 mmol, 2.00 eq) and silica gel (4.00 g). The resulting mixture was stirred at 20° C. for 40 h. The reaction mixture was then diluted with water (20 mL), and the resulting biphasic mixture was extracted with ethyl acetate (2×20 mL). The combined organic extracts were washed with brine (30 mL), dried over anhydrous $Na_2SO_4$, filtered, and concentrated under reduced pressure. The crude residue obtained was purified by column chromatography to give tert-butyl 2-(5-formyl-2H-tetrazol-2-yl)acetate. LC-MS (ESI): m/z: $[M+H]^+$ calculated for $C_8H_{12}N_4O_3$: 213.1; found 213.1.

Step d: To a solution of tert-butyl 2-(5-formyl-2H-tetrazol-2-yl)acetate (400 mg, 1.88 mmol, 1.00 eq) in DCM (4 mL) at 20° C. was added BAST (1.25 g, 5.64 mmol, 1.24 mL, 3.00 eq). The resulting mixture was stirred for 1 h. The mixture was then diluted with water (10 mL), and the resulting biphasic mixture was extracted with ethyl acetate (2×10 mL). The combined organic extracts were washed with brine (20 mL), dried over anhydrous $Na_2SO_4$, filtered, and concentrated under reduced pressure. The crude residue obtained was purified by column chromatography to give tert-butyl 2-(5-(difluoromethyl)-2H-tetrazol-2-yl)acetate. LC-MS (ESI): m/z: $[M+H]^+$ calculated for $C_8H_{12}F_2N_4O_2$: 235.1; found 235.1.

Step e: A solution of tert-butyl 2-(5-(difluoromethyl)-2H-tetrazol-2-yl)acetate (200 mg, 853 μmol, 1.00 eq) in HCl/EtOAc (4 M, 3 mL) was stirred at 20° C. for 16 h. The reaction mixture was then concentrated under reduced pressure to give 2-(5-(difluoromethyl)-2H-tetrazol-2-yl)acetic acid. LC-MS (ESI): m/z: $[M+H]^+$ calculated for $C_4H_4F_2N_4O_2$: 179.0; found 179.0.

Intermediate A-12: Synthesis of 2-methyl-2-(1,3,4-oxadiazol-2-yl)propanoic acid

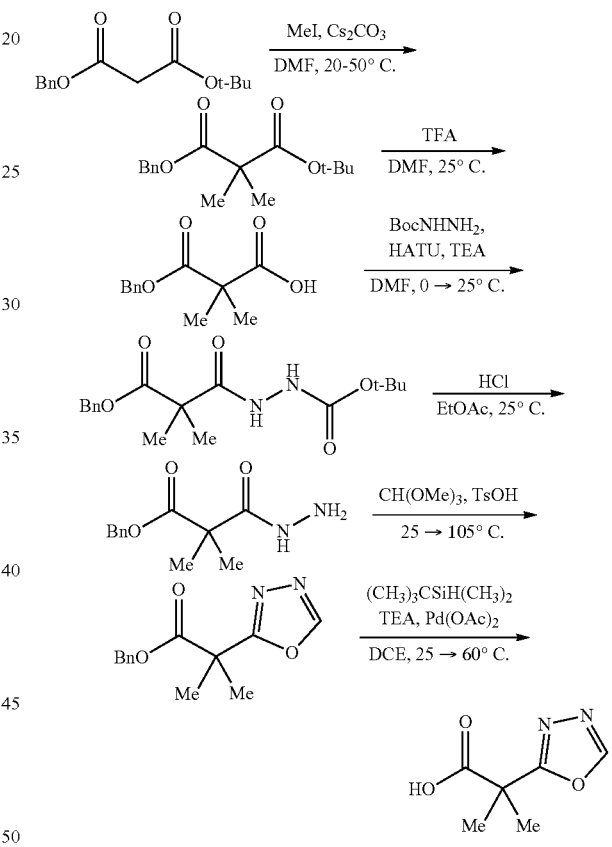

Step a: To a solution of benzyl tert-butyl malonate (4.5 g, 17.9 mmol, 1 eq) in DMF (40 mL) at 20° C. was added $Cs_2CO_3$ (14.6 g, 44.9 mmol, 2.5 eq) and iodomethane (10.2 g, 71.9 mmol, 4.48 mL, 4 eq). The resulting mixture was then warmed to 50° C. and stirred for 2 h. The reaction mixture was then cooled to 0° C. and quenched by addition of $H_2O$ (30 mL). The resulting biphasic mixture was then extracted with EtOAc (3×30 mL). The combined organic extracts were washed with brine (3×50 mL), dried over anhydrous $Na_2SO_4$, filtered, and concentrated under reduced pressure. The crude residue obtained was purified by column chromatography to give 1-benzyl 3-(tert-butyl) 2,2-dimethylmalonate, which was carried forward to the next step without further characterization.

Step b: To a solution of 1-benzyl 3-(tert-butyl) 2,2-dimethylmalonate (4.6 g, 16.5 mmol, 1 eq) in DCM (40 mL)

at 25° C. was added TFA (15.0 g, 132 mmol, 9.8 mL, 8.00 eq), and the resulting mixture was stirred at 25° C. for 2 h. The reaction mixture was then concentrated under reduced pressure to give 3-(benzyloxy)-2,2-dimethyl-3-oxopropanoic acid. LC-MS (ESI): m/z: [M+H]+ calculated for $C_{12}H_{14}O_4$: 223.1; found 223.1.

Step c: To a solution of 3-(benzyloxy)-2,2-dimethyl-3-oxopropanoic acid (1 g, 4.50 mmol, 1 eq) and tert-butyl hydrazinecarboxylate (654 mg, 4.95 mmol, 1.1 eq) in DMF (10 mL) at 0° C. was added triethylamine (1.37 g, 13.5 mmol, 1.88 mL, 3 eq) and HATU (1.88 g, 4.95 mmol, 1.1 eq). The resulting mixture was warmed to 25° C. and stirred for 2 h. The reaction mixture was then quenched by addition of $H_2O$ (30 mL), and the resulting biphasic mixture was then extracted with EtOAc (3×20 mL). The combined organic extracts were washed with brine (40 mL), dried over anhydrous $Na_2SO_4$, filtered, and concentrated under reduced pressure. The crude residue obtained was purified by column chromatography to give tert-butyl 2-(3-(benzyloxy)-2,2-dimethyl-3-oxopropanoyl)hydrazine-1-carboxylate, which was carried forward to the next step without further characterization.

Step d: To a solution of tert-butyl 2-(3-(benzyloxy)-2,2-dimethyl-3-oxopropanoyl)hydrazine-1-carboxylate (1 g, 2.97 mmol, 1 eq) in EtOAc (20 mL) at 25° C. was added HCl in EtOAc (4 M, 17.4 mL, 23.6 eq). The resulting mixture was stirred at 25° C. for 2 h. The reaction mixture was then concentrated under reduced pressure to give benzyl 3-hydrazineyl-2,2-dimethyl-3-oxopropanoate, which was carried forward to the next step without further characterization.

Step e: To a solution of benzyl 3-hydrazineyl-2,2-dimethyl-3-oxopropanoate (0.7 g, 2.50 mmol, 1 eq) in trimethoxymethane (10 mL) at 25° C. was added 4-methylbenzenesulfonic acid (43.0 mg, 249 μmol, 0.1 eq). The resulting mixture was warmed to 105° C. and stirred for 12 h. The reaction mixture was then cooled and concentrated under reduced pressure. The crude residue obtained was purified by column chromatography to give benzyl 2-methyl-2-(1,3,4-oxadiazol-2-yl)propanoate, which was carried forward to the next step without further characterization.

Step f: To a solution of benzyl 2-methyl-2-(1,3,4-oxadiazol-2-yl)propanoate (0.4 g, 1.62 mmol, 1 eq), TEA (32.8 mg, 324 μmol, 45.2 μL, 0.2 eq) and tert-butyldimethylsilane (378 mg, 3.25 mmol, 2 eq) in DCE (5 mL) at 25° C. under $N_2$ was added Pd(OAc)$_2$ (91.2 mg, 406 μmol, 0.25 eq). The resulting mixture was warmed to 60° C. and stirred for 4 h. The reaction mixture was then filtered through a pad of Celite, and the pad was washed with EtOAc (2×200 mL). The combined filtrates were concentrated under reduced pressure, and the crude residue obtained was purified by prep-HPLC to give 2-methyl-2-(1,3,4-oxadiazol-2-yl)propanoic acid. LC-MS (ESI): m/z: [M+H]+ calculated for $C_6H_8N_2O_3$: 157.0; found 157.1.

Intermediate A-13: Synthesis of 2-(5-(4-(tert-butoxycarbonyl)piperazin-1-yl)-1H-1,2,3-triazol-1-yl)acetic acid

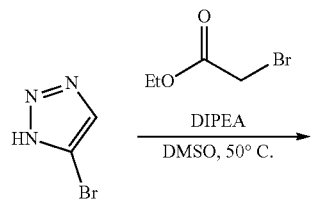

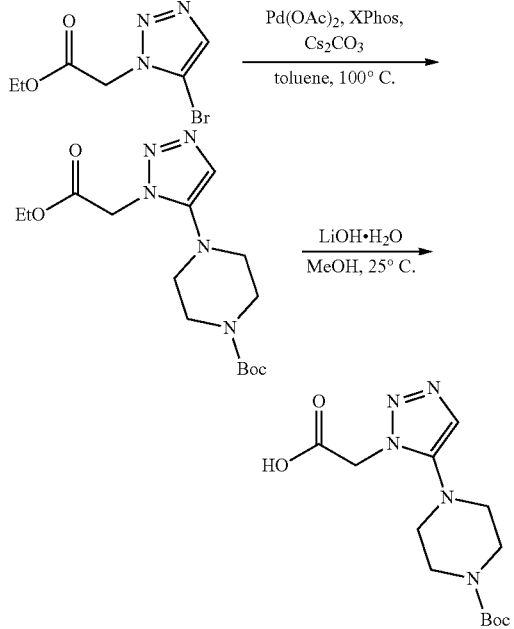

Step a: To a solution of 5-bromo-1H-1,2,3-triazole (2.0 g, 13.5 mmol, 1 eq) and ethyl 2-bromoacetate (3.39 g, 20.3 mmol, 2.2 mL, 1.5 eq) in DMSO (15 mL) was added DIPEA (5.24 g, 40.6 mmol, 7.06 mL, 3 eq). The resulting mixture was warmed to 50° C. and stirred for 4 h. The reaction mixture was then cooled to 0° C. and quenched by addition of $H_2O$ (20 mL), and the resulting biphasic mixture was then extracted with EtOAc (2×20 mL). The combined organic extracts were washed with $H_2O$ (20 mL) and brine (20 mL), dried over anhydrous $Na_2SO_4$, filtered, and concentrated under reduced pressure. The crude residue obtained was purified by column chromatography to give ethyl 2-(5-bromo-1H-1,2,3-triazol-1-yl)acetate. LC-MS (ESI): m/z: [M+H]+ calculated for $C_6H_8BrN_3O_2$: 234.0; found 234.0.

Step b: To a mixture of ethyl 2-(5-bromo-1H-1,2,3-triazol-1-yl)acetate (250 mg, 1.07 mmol, 1 eq), tert-butyl piperazine-1-carboxylate (1 g, 5.4 mmol, 5 eq), $Cs_2CO_3$ (1.1 g, 3.2 mmol, 3 eq), and XPhos (113 mg, 0.12 eq) in toluene (10 mL) was added Pd(OAc)$_2$ (60 mg, 0.12 eq). The resulting mixture was then degassed and placed under an $N_2$ atmosphere. The reaction mixture was then warmed to 100° C. and stirred for 16 h. The reaction mixture was then cooled to room temperature and filtered through a pad of Celite, and the filter cake was washed with toluene (2×10 mL). The combined filtrates were then concentrated under reduced pressure, and the crude residue obtained was purified by column chromatography to give tert-butyl 4-(1-(2-ethoxy-2-oxoethyl)-1H-1,2,3-triazol-5-yl)piperazine-1-carboxylate. LC-MS (ESI): m/z: [M+H]+ calculated for $C_{15}H_{25}N_5O_4$: 340.2; found 340.1.

Step c: To a solution of tert-butyl 4-(1-(2-ethoxy-2-oxoethyl)-1H-1,2,3-triazol-5-yl)piperazine-1-carboxylate (95 mg, 280 μmol, 1 eq) in MeOH (4 mL) was added LiOH·$H_2O$ (23.5 mg, 560 μmol, 2 eq), and the resulting mixture was stirred at 25° C. for 2 h. The reaction mixture was then concentrated under reduced pressure, and the residue obtained was dissolved in $H_2O$ (5 mL). The resulting aqueous solution was extracted with EtOAc (2×5 mL), and then the aqueous phase was adjusted to pH 5-6 with aqueous HCl (3 M). The resulting aqueous solution was then extracted with EtOAc (2×6 mL), and the combined organic extracts were washed with brine (5 mL), dried over anhydrous $Na_2SO_4$, filtered, and concentrated under reduced pressure to give 2-(5-(4-(tert-butoxycarbonyl)piperazin-1-yl)-1H-1,2,3-triazol-1-yl)acetic acid. LC-MS (ESI): m/z: $[M-t-Bu+H]^+$ calculated for $C_{13}H_{21}N_5O_4$: 256.1; found 256.0.

The following compounds in Table B-4 were synthesized using procedures similar to Intermediate A-13 using the appropriate starting materials.

Step a: To a mixture of 5-nitro-1H-1,2,3-triazole (11.3 g, 99.1 mmol, 1 eq) and ethyl 2-bromoacetate (24.8 g, 149 mmol, 16.4 mL, 1.5 eq) in DMSO (100 mL) at 25° C. was added DIPEA (38.4 g, 297 mmol, 51.8 mL, 3 eq), and the resulting mixture was stirred at 25° C. for 3 h. The reaction mixture was then cooled to 0° C. and quenched by addition of $H_2O$ (100 mL), and the resulting biphasic mixture was then extracted with EtOAc (2×70 mL). The combined organic extracts were washed with $H_2O$ (50 mL) and brine (2×50 mL), dried over anhydrous $Na_2SO_4$, filtered, and concentrated under reduced pressure. The crude residue obtained was purified by column chromatography to give

TABLE B-4

| Intermediate No. | Structure | IUPAC | Exact mass (g/mol) | LCMS, Found [M + H]+ |
|---|---|---|---|---|
| B-4-1 | 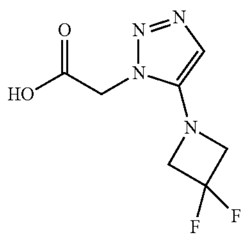 [SMILES: O=C(O)Cn1nncc1N1CC(F)(F)C1] | 2-(5-(3,3-difluoroazetidin-1-yl)-1H-1,2,3-triazol-1-yl)acetic acid | 218.1 | 219.0 |
| B-4-2 | 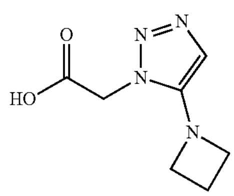 [SMILES: O=C(O)Cn1nncc1N1CCC1] | 2-(5-(azetidin-1-yl)-1H-1,2,3-triazol-1-yl)acetic acid | 182.1 | 183.2 |

Intermediate A-14: Synthesis of 2-(4-(dimethylamino)-1H-1,2,3-triazol-1-yl)acetic acid

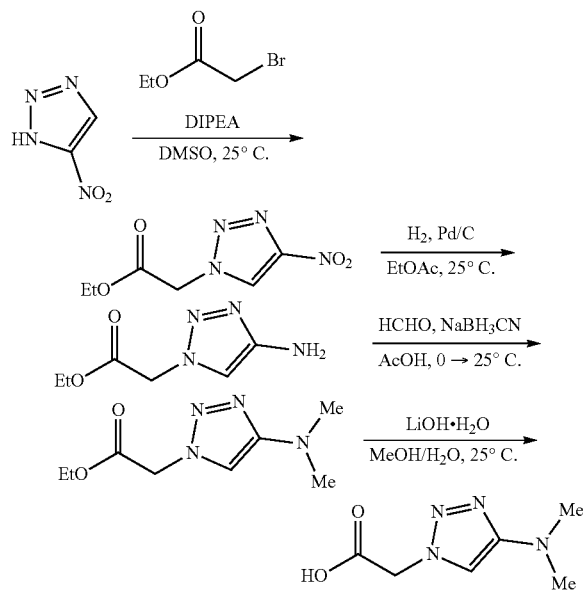

ethyl 2-(4-nitro-1H-1,2,3-triazol-1-yl)acetate. LC-MS (ESI): m/z: $[M+H]^+$ calculated for $C_6H_8N_4O_4$: 201.0; found 201.0.

Step b: To a solution of ethyl 2-(4-nitro-1H-1,2,3-triazol-1-yl)acetate (11 g, 54.9 mmol, 1 eq) in EtOAc (300 mL) was added Pd/C (1.5 g, 10% purity) under $N_2$. The suspension was then degassed under vacuum and placed under an $H_2$ atmosphere. The resulting mixture was then stirred under $H_2$ (15 psi) at 25° C. for 8 h. The mixture was then filtered, and the filtrate was concentrated under reduced pressure to give ethyl 2-(4-amino-1H-1,2,3-triazol-1-yl)acetate. LC-MS (ESI): m/z: $[M+H]^+$ calculated for $C_6H_{10}N_4O_2$: 171.1; found 171.1.

Step c: A mixture of ethyl 2-(4-amino-1H-1,2,3-triazol-1-yl)acetate (8 g, 47.0 mmol, 1 eq) and paraformaldehyde (14.1 g, 470 mmol, 10 eq) in AcOH (100 mL) was stirred at 25° C. for 60 min. The reaction mixture was then cooled to 0° C. before $NaBH_3CN$ (8.86 g, 141 mmol, 3 eq) was added in one portion. The resulting mixture was warmed to 25° C. and stirred for 15 h. The reaction mixture was then cooled to 0° C. and quenched by addition $H_2O$ (100 mL). The pH of the resulting mixture was adjusted to pH=6 using aqueous NaOH (4 M) before it was filtered. The filtrate was then extracted with EtOAc (2×150 mL). The combined organic extracts were washed with brine (2×100 mL), dried over anhydrous $Na_2SO_4$, filtered, and concentrated under reduced pressure. The crude residue obtained was purified by column chromatography to give ethyl 2-(4-(dimethylamino)-1H-1, 2,3-triazol-1-yl)acetate, which was carried forward to the next step without further characterization.

Step d: To a solution of ethyl 2-(4-(dimethylamino)-1H-1,2,3-triazol-1-yl)acetate (7 g, 35.3 mmol, 1 eq) in MeOH (70 mL) and H$_2$O (20 mL) at 25° C. was added LiOH·H$_2$O (2.96 g, 70.6 mmol, 2 eq). The resulting mixture was stirred at 25° C. for 2 h. The reaction mixture was then concentrated under reduced pressure. The aqueous solution obtained was then adjusted to pH 5-6 using aqueous HCl (3 M), and the resulting mixture was concentrated under reduced pressure. The crude residue obtained was purified by prep-HPLC to give 2-(4-(dimethylamino)-1H-1,2,3-triazol-1-yl)acetic acid. LC-MS (ESI): m/z: [M+H]$^+$ calculated for C$_6$H$_{10}$N$_4$O$_2$: 171.1; found 171.1.

The following compounds in Table B-5 were synthesized using procedures similar to Intermediate A-14 using the appropriate starting materials.

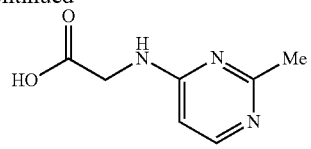

Step a: To a solution of 4-chloro-2-methylpyrimidine (300 mg, 2.33 mmol, 1 eq) in i-PrOH (3.00 mL) at 25° C. was added TEA (708 mg, 7.00 mmol, 3 eq) and tert-butyl 2-aminoacetate (367 mg, 2.80 mmol, 1.2 eq). The resulting mixture was warmed to 80° C. and stirred for 2 h. The reaction mixture was then quenched by addition H$_2$O (10 mL), and the resulting biphasic mixture was then extracted with EtOAc (3×10 mL). The combined organic extracts were washed with brine (2×10 mL), dried over anhydrous Na$_2$SO$_4$, filtered, and concentrated under reduced pressure. The crude residue obtained was purified by column chromatography to give tert-butyl (2-methylpyrimidin-4-yl)glycinate. LC-MS (ESI): m/z: [M+H]$^+$ calculated for C$_{11}$H$_{17}$N$_3$O$_2$: 224.1; found 224.1.

Step b: To a solution of tert-butyl (2-methylpyrimidin-4-yl)glycinate (310 mg, 1.39 mmol, 1 eq) in EtOAc (1.00 mL) was added HCl in EtOAc (4 M, 3 mL, 8.64 eq). The resulting mixture was stirred at 25° C. for 4 h. The reaction mixture was then concentrated under reduced pressure to give (2-methylpyrimidin-4-yl)glycine. LC-MS (ESI): m/z: [M+H]$^+$ calculated for C$_7$H$_9$N$_3$O$_2$: 168.1; found 168.1.

The following compounds in Table B-6 were synthesized using procedures similar to Intermediate A-15 using the appropriate starting materials.

TABLE B-5

| Intermediate No. | Structure | IUPAC | Exact mass (g/mol) | LCMS, Found [M + H]$^+$ |
|---|---|---|---|---|
| B-5-1 | 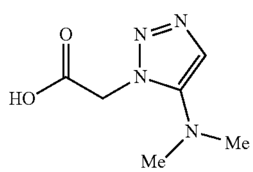 [SMILES: CN(C)c1cnnn1CC(=O)O] | 2-(5-(dimethylamino)-1H-1,2,3-triazol-1-yl)acetic acid | 170.1 | 171.1 |
| B-5-2 | 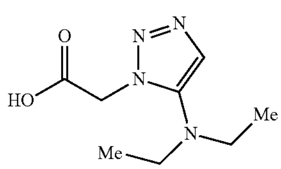 [SMILES: CCN(CC)c1cnnn1CC(=O)O] | 2-(5-(diethylamino)-1H-1,2,3-triazol-1-yl)acetic acid | 198.1 | 199.0 |

Intermediate A-15: Synthesis of (2-methylpyrimidin-4-yl)glycine

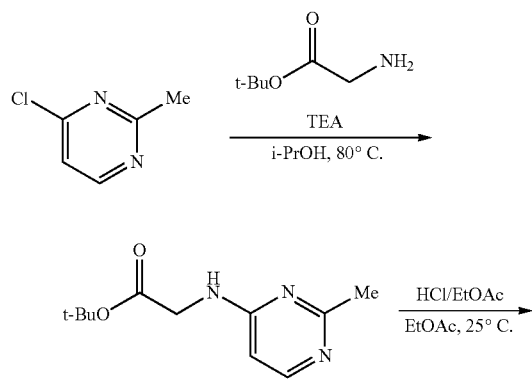

TABLE B-6

| Intermediate No. | Structure | IUPAC | Exact mass (g/mol) | LCMS, Found [M + H]+ |
|---|---|---|---|---|
| B-6-1 | ![structure] | N-methyl-N-(2-methylpyrimidin-4-yl)glycine | 181.1 | 182.1 |

Intermediate A-16: Synthesis of (3,3-difluoroazetidine-1-carbonyl)glycine

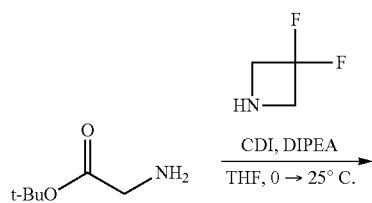

Step a: To a solution of tert-butyl 2-aminoacetate (1.00 g, 7.62 mmol, 1 eq) in THF (10 mL) at 0° C. under $N_2$ was added CDI (1.36 g, 8.39 mmol, 1.1 eq) and DIPEA (2.96 g, 22.9 mmol, 3 eq). The resulting mixture was stirred at 0° C. for 1 h. 3,3-difluoroazetidine (987 mg, 7.62 mmol, 1 eq, HCl salt) was then added, and the resulting mixture was warmed to 60° C. and stirred for 1 h. The reaction mixture was then diluted with $H_2O$ (50 mL) and filtered. The filter cake was washed with $H_2O$ (20 mL), and the washed solid was dried under reduced pressure to give tert-butyl (3,3-difluoroazetidine-1-carbonyl)glycinate. LC-MS (ESI): m/z: [M−t-Bu+H+H]+ calculated for $C_{10}H_{16}F_2N_2O_3$: 195.0; found 195.0.

Step b: A solution tert-butyl (3,3-difluoroazetidine-1-carbonyl)glycinate (1.3 g, 5.19 mmol, 1 eq) in HCl in dioxane (4 M, 30 mL) was stirred at 20° C. for 1 h. The reaction mixture was then concentrated under reduced pressure, and the crude residue obtained was triturated with MTBE (20 mL) to give (3,3-difluoroazetidine-1-carbonyl)glycine. LC-MS (ESI): m/z: [M+H]+ calculated for $C_6H_8F_2N_2O_3$: 195.0; found 195.0.

The following compounds in Table B-7 were synthesized using procedures similar to Intermediate A-16 using the appropriate starting materials.

TABLE B-7

| Intermediate No. | Structure | IUPAC | Exact mass (g/mol) | LCMS, Found [M + H]+ |
|---|---|---|---|---|
| B-7-1 | ![structure] | (azetidine-1-carbonyl)glycine | 158.1 | 159.1 |

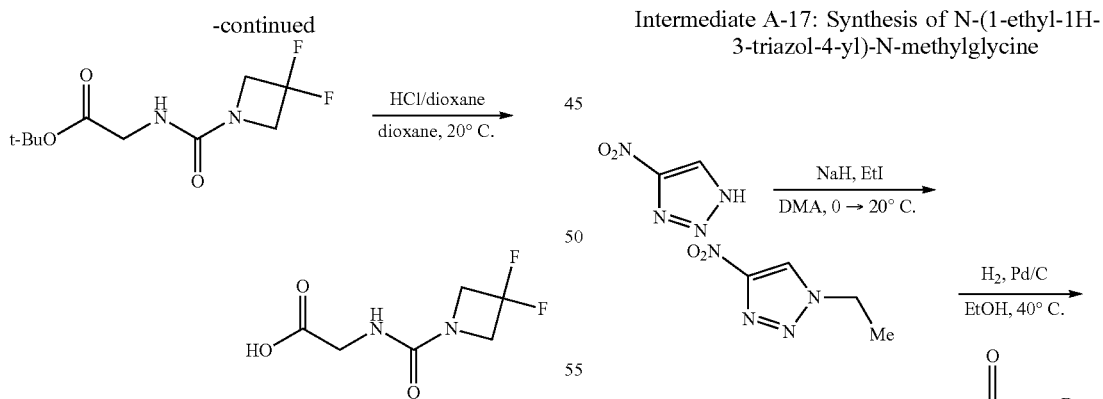

Intermediate A-17: Synthesis of N-(1-ethyl-1H-1,2,3-triazol-4-yl)-N-methylglycine

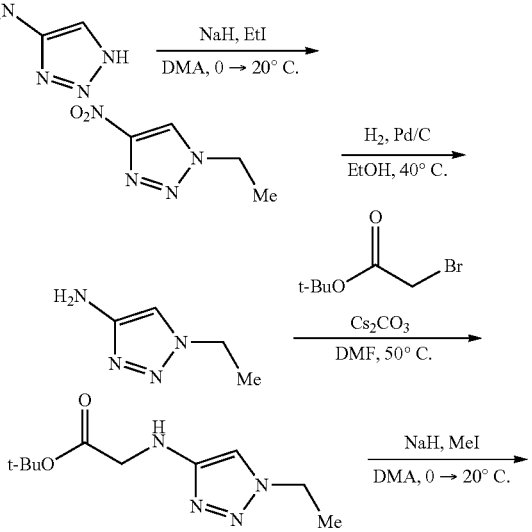

-continued

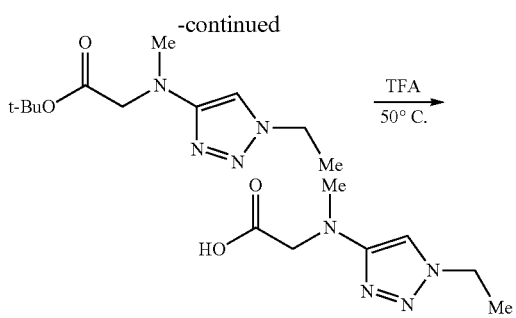

Step a: To a solution of 4-nitro-1H-1,2,3-triazole (4.00 g, 35.1 mmol, 1 eq) in DMA (80 mL) at 0° C. was added NaH (1.47 g, 36.8 mmol, 60% purity, 1.05 eq). The resulting mixture was stirred at 0° C. for 0.5 h. EtI (8.20 g, 52.6 mmol, 4.21 mL, 1.5 eq) was then added in one portion, and the resulting mixture was warmed to 20° C. and stirred for 3 h. The reaction mixture was then quenched with H$_2$O (150 mL), and the resulting biphasic mixture was extracted with EtOAc (2×50 mL). The combined organic extracts were concentrated under reduced pressure. The crude residue obtained was purified by column chromatography to give 1-ethyl-4-nitro-1H-1,2,3-triazole. LC-MS (ESI): m/z: [M+H]$^+$ calculated for C$_4$H$_6$N$_4$O$_2$: 143.0; found 143.1.

Step b: A mixture of 1-ethyl-4-nitro-1H-1,2,3-triazole 1.6 g, 11.3 mmol, 1 eq) and Pd/C (400 mg, 10% purity) in EtOH (20 mL) was degassed with H$_2$. The degassed mixture was then warmed to 40° C. and stirred under H$_2$ (50 psi) for 3 h. The reaction mixture was then cooled and filtered, and the filtrate was concentrated under reduced pressure to give 1-ethyl-1H-1,2,3-triazol-4-amine, which was carried forward to the next step without further purification or characterization.

Step c: A mixture of 1-ethyl-1H-1,2,3-triazol-4-amine (600 mg, 5.35 mmol, 1 eq) and Cs$_2$CO$_3$ (1.74 g, 5.35 mmol, 1 eq) in DMF (3 mL) was stirred at 25° C. for 0.5 h before tert-butyl 2-bromoacetate (1.15 g, 5.89 mmol, 1.1 eq) was added in one portion, and the resulting mixture was warmed to 50° C. and stirred for 12 h. The reaction mixture was then quenched with H$_2$O (10 mL) and extracted with EtOAc (2×20 mL). The organic extracts were concentrated under reduced pressure, and the crude residue obtained was purified by column chromatography to give tert-butyl (1-ethyl-1H-1,2,3-triazol-4-yl)glycinate. LC-MS (ESI): m/z: [M−t-Bu+H+H]$^+$ calculated for C$_{10}$H$_{18}$N$_4$O$_2$: 171.1; found 171.1.

Step d: To a solution of tert-butyl (1-ethyl-1H-1,2,3-triazol-4-yl)glycinate (280 mg, 1.24 mmol, 1 eq) in DMA (2 mL) at 0° C. was added NaH (49 mg, 1.24 mmol, 60% purity, 1 eq), and the resulting mixture was stirred at 0° C. for 0.5 h. CH$_3$I (175 mg, 1.24 mmol, 1 eq) was then added, and the resulting mixture was warmed to 20° C. and stirred for 3 h. The mixture was then quenched with H$_2$O (10 mL), and the biphasic mixture was extracted with EtOAc (2×10 mL). The organic extracts were concentrated under reduced pressure, and the crude residue obtained was purified by prep-TLC to give tert-butyl N-(1-ethyl-1H-1,2,3-triazol-4-yl)-N-methylglycinate. LC-MS (ESI): m/z: [M−t-Bu+H+H]$^+$ calculated for C$_{11}$H$_{20}$N$_4$O$_2$: 185.1; found 185.1.

Step e: A solution of tert-butyl N-(1-ethyl-1H-1,2,3-triazol-4-yl)-N-methylglycinate (130 mg, 541 μmol, 1 eq) in TFA (2.00 g, 17.56 mmol, 32.5 eq) was stirred at 50° C. for 1 h. The reaction mixture was then cooled and concentrated under reduced pressure to give N-(1-ethyl-1H-1,2,3-triazol-4-yl)-N-methylglycine, which was used without any additional purification. LC-MS (ESI): m/z: [M+H]$^+$ calculated for C$_7$H$_{12}$N$_4$O$_2$: 185.1; found 185.2.

The following compounds in Table B-8 were synthesized using procedures similar to Intermediate A-17 using the appropriate starting materials.

TABLE B-8

| Intermediate No. | Structure | IUPAC | Exact mass (g/mol) | LCMS, Found [M + H]$^+$ |
| --- | --- | --- | --- | --- |
| B-8-1 | 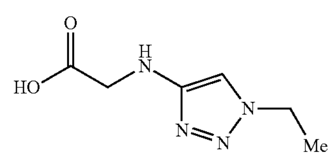 [SMILES: CCn1cc(NCC(=O)O)nn1] | (1-ethyl-1H-1,2,3-triazol-4-yl)glycine | 170.1 | 171.1 |
| B-8-2 | 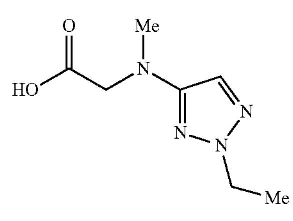 [SMILES: CCn1ncc(N(C)CC(=O)O)n1] | N-(2-ethyl-2H-1,2,3-triazol-4-yl)-N-methylglycine | 184.1 | 185.1 |
| B-8-3 | 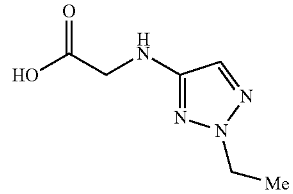 [SMILES: CCn1ncc(NCC(=O)O)n1] | (2-ethyl-2H-1,2,3-triazol-4-yl)glycine | 170.1 | 171.1 |

Intermediate A-18: Synthesis of 2-(4-methyl-5-oxo-4,5-dihydro-1H-1,2,4-triazol-3-yl)acetic acid

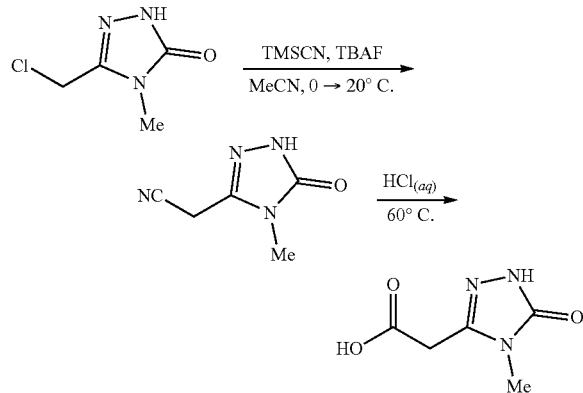

Step a: To a solution of 5-(chloromethyl)-4-methyl-2,4-dihydro-3H-1,2,4-triazol-3-one (100 mg, 678 μmol, 1 eq) in MeCN (2 mL) at 0° C. was added TMSCN (100 mg, 1.02 mmol, 127 μL, 1.5 eq) and TBAF (1 M in THF, 1.02 mL, 1.5 eq). The resulting mixture was warmed to 20° C. and stirred for 3 h. The reaction mixture was then quenched with $H_2O$ (5 mL) and extracted with EtOAc (2×10 mL). The organic extracts were then concentrated under reduced pressure to give 2-(4-methyl-5-oxo-4,5-dihydro-1H-1,2,4-triazol-3-yl)acetonitrile. LC-MS (ESI): m/z: [M–H]⁻ calculated for $C_5H_6N_4O$: 137.0; found 137.2.

Step b: A mixture of 2-(4-methyl-5-oxo-4,5-dihydro-1H-1,2,4-triazol-3-yl)acetonitrile (30 mg, 217 μmol, 1 eq) in aqueous HCl (12 M, 7.60 mL) was stirred at 60° C. for 1 h. The mixture was then concentrated under reduced pressure to give 2-(4-methyl-5-oxo-4,5-dihydro-1H-1,2,4-triazol-3-yl)acetic acid. LC-MS (ESI): m/z: [M–H]⁻ calculated for $C_5H_7N_3O_3$: 156.0; found 156.2.

The following compounds in Table B-9 were synthesized using procedures similar to Intermediate A-18 using the appropriate starting materials.

TABLE B-9

| Intermediate No. | Structure | IUPAC | Exact mass (g/mol) | LCMS, Found [M + H]⁺ |
|---|---|---|---|---|
| B-9-1 | ![structure] | 2-(1-methyl-5-oxo-4,5-dihydro-1H-1,2,4-triazol-3-yl)acetic acid | 157.0 | 156.1 [M – H]⁻ |

Intermediate A-19: Synthesis of 1-trityl-1H-indazole-6-carbaldehyde

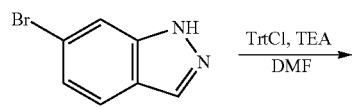

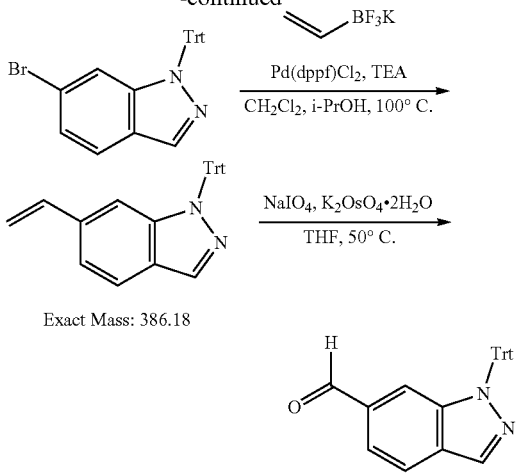

Step a: To a solution of 6-bromo-1H-indazole (8 g, 40.6 mmol, 1 eq) in DMF (50 mL) was added trityl chloride (TrtCl, 12.4 g, 44.6 mmol, 1.1 eq) and TEA (7.06 mL, 50.7 mmol, 1.25 eq). The resulting mixture was stirred at 25° C. for 16 h. The reaction mixture was then diluted with water, and the resulting biphasic mixture was extracted with ethyl acetate (3×50 mL). The combined organic extracts were dried over anhydrous $Na_2SO_4$, filtered, and concentrated under reduced pressure. The crude residue obtained was triturated with MTBE (30 mL) and filtered to give 6-bromo-1-trityl-1H-indazole, which was carried forward to the next step without further purification or characterization.

Step b: To a mixture of 6-bromo-1-trityl-1H-indazole (16.7 g, 38.0 mmol, 1 eq), potassium vinyltrifluoroborate (10.1 g, 76.0 mmol, 2 eq) and TEA (15.8 mL, 14.0 mmol, 3 eq) in i-PrOH (160 mL), was added Pd(dppf)Cl₂·CH₂Cl₂ (1.55 g, 1.90 mmol, 0.05 eq) under $N_2$. The resulting mixture was then degassed and placed under an $N_2$ atmosphere. The reaction mixture was then warmed to 100° C. and stirred for 2 h under $N_2$. After cooling, the mixture was filtered, and the filter cake was washed with ethyl acetate (3×100 mL). The combined filtrates were concentrated, and the crude residue obtained was purified by column chromatography to give 1-trityl-6-vinyl-1H-indazole LC-MS (ESI): m/z: [2M+Na]⁺ calculated for $C_{28}H_{22}N_2$: 795.4; found 795.3.

Step c: To a solution of 1-trityl-6-vinyl-1H-indazole (14.2 g, 36.7 mmol, 1 eq) in THF:$H_2O$ (5:1) (300 mL) at 0° C. was added $NaIO_4$ (31.4 g, 146 mmol, 4 eq) and $K_2OsO_4·2H_2O$ (676 mg, 1.84 mmol, 0.05 eq). The resulting mixture was warmed to 50° C. and stirred for 1 h. The reaction mixture was then cooled to 25° C. and quenched with sat. aq. $Na_2S_2O_3$ (100 mL). The resulting mixture was extracted with ethyl acetate (3×100 mL), and the combined extracts were dried over Na$_2$SO$_4$, filtered, and concentrated under reduced pressure. The resulting residue was purified by column chromatography to give 1-trityl-1H-indazole-6-carbaldehyde.

Intermediate A-20: Synthesis of 3-(isoxazol-5-yl)benzaldehyde

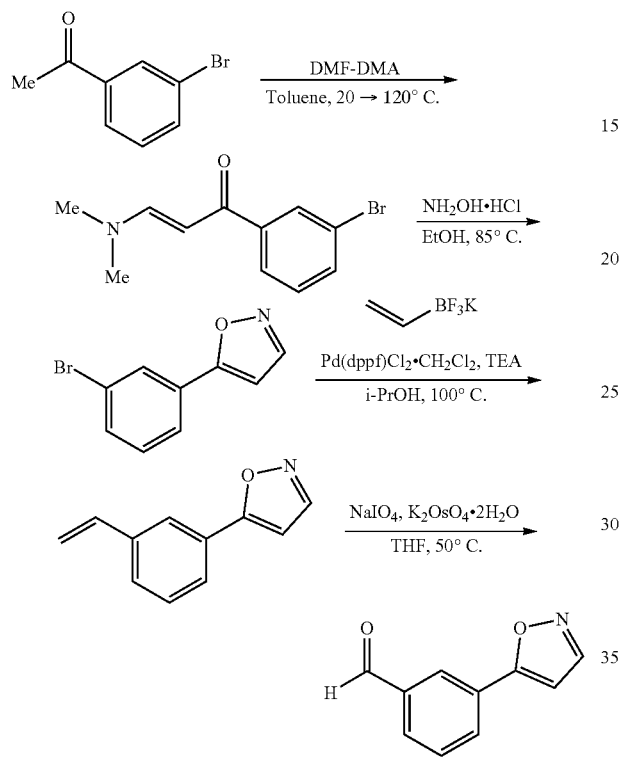

Step a: To a solution of 1-(3-bromophenyl)ethan-1-one (18.5 g, 92.9 mmol, 1 eq) in toluene (150 mL) was added N,N-dimethylformamide dimethyl acetal (37 mL, 346 mmol, 3.7 eq) at 20° C. The resulting mixture was warmed to 120° C. and stirred for 1 h. The reaction mixture was then cooled to 20° C. and quenched with water (100 mL), and the resulting biphasic mixture was extracted with ethyl acetate (3×100 mL). The combined organic extracts were washed with brine (100 mL), dried over anhydrous Na$_2$SO$_4$, filtered, and concentrated under reduced pressure. The crude residue obtained was purified by column chromatography to give (E)-1-(3-bromophenyl)-3-(dimethylamino)prop-2-en-1-one. LC-MS (ESI): m/z: [M+H]$^+$ calculated for C$_{11}$H$_{12}$BrNO: 254.1; found 254.1.

Step b: To a solution of (E)-1-(3-bromophenyl)-3-(dimethylamino)prop-2-en-1-one (8 g, 31.4 mmol, 1 eq) in EtOH (50 mL) was added NH$_2$OH·HCl (2.63 g, 37.7 mmol, 1.2 eq). The resulting mixture was warmed to 85° C. and stirred for 2 h. The reaction mixture was then cooled to 25° C. and quenched with water (50 mL), and the resulting biphasic mixture was extracted with ethyl acetate (3×50 mL). The combined organic extracts were dried over anhydrous Na$_2$SO$_4$, filtered, and concentrated under reduced pressure. The crude residue obtained was purified by column chromatography to give 5-(3-bromophenyl)isoxazole. LC-MS (ESI): m/z: [M+H]$^+$ calculated for C$_9$H$_6$BrNO: 224.0; found 224.1.

Step c: To a mixture of 5-(3-bromophenyl)isoxazole (8 g, 28.5 mmol, 1 eq), potassium vinyltrifluoroborate (7.65 g, 57.1 mmol, 2 eq) and TEA (11.9 mL, 85.6 mmol, 3 eq) in i-PrOH (50 mL) was added Pd(dppf)Cl$_2$·CH$_2$Cl$_2$ (1.17 g, 1.43 mmol, 0.05 eq) under N$_2$. The resulting mixture was degassed and placed under N$_2$, and the reaction mixture was then warmed to 100° C. and stirred for 1 h. The reaction mixture was then cooled, quenched with water (50 mL) and extracted with ethyl acetate (3×50 mL). The combined organic extracts were washed with brine (50 mL), dried over anhydrous Na$_2$SO$_4$, filtered, and concentrated under reduced pressure. The crude residue obtained was purified by column chromatography to give 5-(3-vinylphenyl)isoxazole. LC-MS (ESI): m/z: [M+H]$^+$ calculated for C$_{11}$H$_9$NO: 172.1; found 172.1.

Step d: To a solution of 5-(3-vinylphenyl)isoxazole (1.8 g, 10.5 mmol, 1 eq) in THF (50 mL) and H$_2$O (10 mL) was added NaIO$_4$ (9.00 g, 42.0 mmol, 4 eq) and potassium osmate dihydrate (194 mg, 525 μmol, 0.05 eq). The resulting mixture was warmed to 50° C. and stirred for 1 h. The reaction mixture was then cooled and quenched with water (50 mL), and the resulting biphasic mixture was extracted with ethyl acetate (3×50 mL). The combined organic layers were washed with brine (50 mL), dried over anhydrous Na$_2$SO$_4$, filtered, and concentrated under reduced pressure. The crude residue obtained was purified by column chromatography to give 3-(isoxazol-5-yl)benzaldehyde. LC-MS (ESI): m/z: [M+H]$^+$ calculated for C$_{10}$H$_7$NO$_2$: 174.0; found 174.0.

Intermediate A-21: Synthesis of 2-(5-(diethylamino)-1H-1,2,3-triazol-1-yl)acetic acid

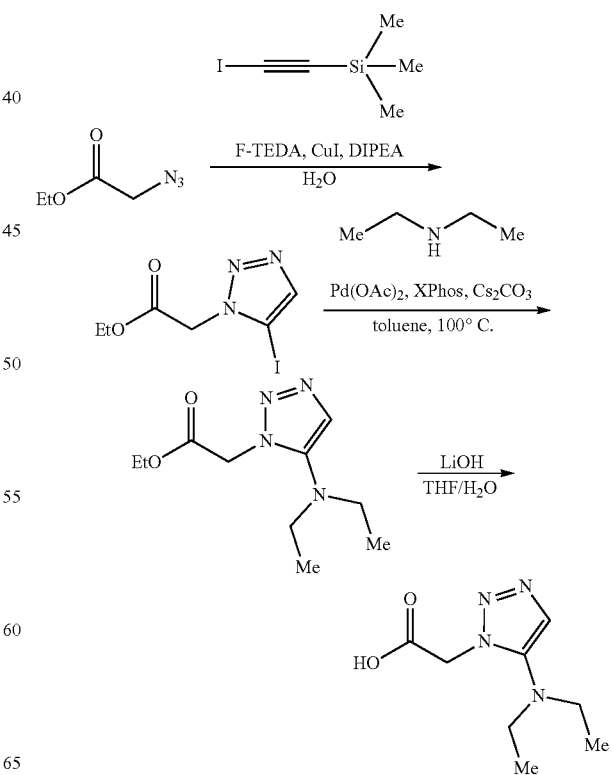

Step a: A mixture of ethyl 2-azidoacetate (8 g, 61.9 mmol, 7.08 mL, 1 eq), (iodoethynyl)trimethylsilane (15.2 g, 68.1 mmol, 1.1 eq), copper iodide (1.18 g, 6.20 mmol, 0.1 eq), DIPEA (16.0 g, 123 mmol, 21.5 mL, 2 eq) and 1-(chloromethyl)-4-fluoro-1,4-diazabicyclo[2.2.2]octane-1,4-diium ditetrafluoroborate (F-TEDA, 32.9 g, 92.9 mmol, 1.5 eq) in H$_2$O (80 mL) was degassed and placed under an N$_2$ atmosphere. The reaction mixture was then stirred for 16 h. The reaction mixture was then diluted with water and extracted with EtOAc (2×200 mL). The combined organic extracts were washed with brine (300 mL), dried over anhydrous Na$_2$SO$_4$, filtered, and concentrated under reduced pressure. The crude residue obtained was purified by column chromatography to give ethyl 2-(5-iodo-1H-1,2,3-triazol-1-yl)acetate. LC-MS (ESI): m/z: [M+H]$^+$ calculated for C$_6$H$_8$IN$_3$O$_2$: 282.0; found 281.9.

Step b: To a solution of ethyl 2-(5-iodo-1H-1,2,3-triazol-1-yl)acetate (700 mg, 2.49 mmol, 1 eq) in toluene (5 mL) was added N-ethylethanamine (911 mg, 12.4 mmol, 5 eq) and Cs$_2$CO$_3$ (1.62 g, 4.98 mmol, 2 eq). The resulting mixture was degassed and placed under an N$_2$ atmosphere, and then XPhos (949 mg, 1.99 mmol, 0.8 eq) and Pd(OAc)$_2$ (112 mg, 498 µmol, 0.2 eq) were added. The resulting mixture was then degassed and placed under an N$_2$ atmosphere, warmed to 100° C., and stirred for 16 h. After cooling, the reaction mixture was concentrated under reduced pressure. Water (15 mL) was added, and the resulting mixture was extracted with ethyl acetate (3×15 mL). The combined organic layers were washed with brine (3×10 mL), dried over anhydrous Na$_2$SO$_4$, filtered, and concentrated under reduced pressure. The crude residue obtained was purified by column chromatography to give ethyl 2-(5-(diethylamino)-1H-1,2,3-triazol-1-yl)acetate. LC-MS (ESI): m/z: [M+H]$^+$ calculated for C$_{10}$H$_{18}$N$_4$O$_2$: 227.1; found 227.2.

Step c: To a solution of ethyl 2-(5-(diethylamino)-1H-1,2,3-triazol-1-yl)acetate (200 mg, 883 µmol, 1 eq) in THF (2 mL) at 0° C. was added LiOH (23.3 mg, 972 µmol, 4.85 mL, 1.1 eq) in water (0.5 mL), and the resulting mixture was warmed to 25° C. and stirred for 1 h. The reaction mixture was then concentrated under reduced pressure. The crude residue obtained was purified by prep-HPLC to give 2-(5-(diethylamino)-1H-1,2,3-triazol-1-yl)acetic acid. LC-MS (ESI): m/z: [M+H]$^+$ calculated for C$_8$H$_{14}$N$_4$O$_2$: 199.1; found 199.2.

Intermediate A-22: Synthesis of 2-(5-(difluoromethyl)-1H-1,2,3-triazol-1-yl)acetic acid

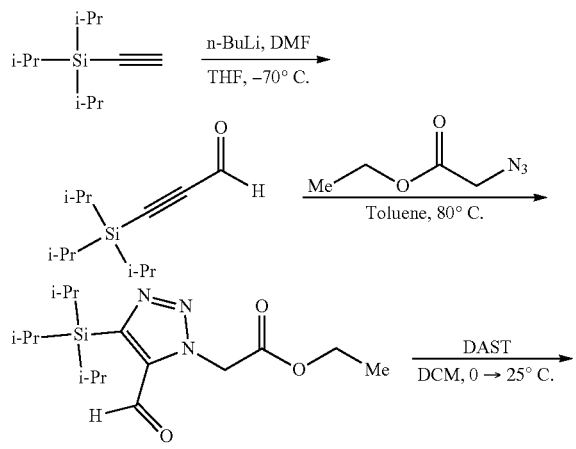

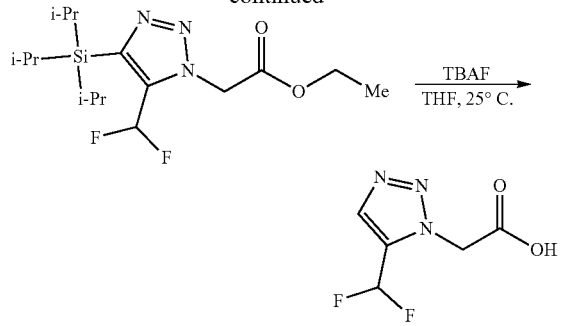

Step a: To a solution of ethynyltriisopropylsilane (15 g, 82.3 mmol, 18.5 mL, 1 eq) in THF (200 mL) at −70° C. was added n-BuLi (2.5 M in hexane, 29.6 mL, 0.9 eq) in a dropwise manner. After 30 min, DMF (10.8 g, 148 mmol, 11.39 mL, 1.8 eq) was added in a dropwise manner, and the resulting mixture was warmed to room temperature and stirred for 30 min. The reaction mixture was then quenched with water (100 mL) and extracted with EtOAc (3×100 mL). The combined organic extracts were dried over anhydrous Na$_2$SO$_4$, filtered, and concentrated under reduced pressure. The crude residue obtained was purified by column chromatography to give 3-(triisopropylsilyl)propiolaldehyde.

Step b: To a solution of ethyl 2-azidoacetate (2.56 g, 19.8 mmol, 1 eq) in toluene (60 mL) was added 3-(triisopropylsilyl)propiolaldehyde (5 g, 23.8 mmol, 1.2 eq). The resulting mixture was then warmed to 80° C. and stirred for 16 h. After cooling, the reaction mixture was concentrated under reduced pressure. The crude residue obtained was purified by column chromatography to give ethyl 2-(5-formyl-4-(triisopropylsilyl)-1H-1,2,3-triazol-1-yl)acetate. LC-MS (ESI): m/z: [M+H]$^+$ calculated for C$_{16}$H$_{29}$N$_3$O$_3$Si: 340.2; found 340.3.

Step c: To a solution of ethyl 2-(5-formyl-4-(triisopropylsilyl)-1H-1,2,3-triazol-1-yl)acetate (4.5 g, 13.3 mmol, 1 eq) in DCM (40 mL) at 0° C. was added DAST (5.34 g, 33.1 mmol, 2.5 eq) dropwise in a dropwise manner. The resulting mixture was warmed to room temperature and stirred for 16 h. The reaction mixture was then slowly added into ice-water (50 mL), and the resulting biphasic mixture was extracted with DCM (3×50 mL). The combined organic extracts were dried over anhydrous Na$_2$SO$_4$ and filtered, concentrated under reduced pressure. The crude residue obtained was purified by column chromatography to give ethyl 2-(5-(difluoromethyl)-4-(triisopropylsilyl)-1H-1,2,3-triazol-1-yl)acetate. LC-MS (ESI): m/z: [M+H]$^+$ calculated for C$_{16}$H$_{29}$F$_2$N$_3$O$_2$Si: 362.2; found 362.3.

Step d: To a solution of 2-(5-(difluoromethyl)-4-(triisopropylsilyl)-1H-1,2,3-triazol-1-yl)acetate (1 g, 2.77 mmol, 1 eq) in THF (20 mL) was added TBAF (1.45 g, 5.53 mmol, 2 eq). The resulting mixture was stirred at 25° C. for 16 h. The reaction mixture was then poured into ice-water (20 mL), and the resulting biphasic mixture was extracted with EtOAc (2×20 mL). The water phase was adjusted to pH 3-4 with aqueous HCl (2N) and then extracted with EtOAc (3×30 mL). The combined organic extracts were dried over anhydrous Na$_2$SO$_4$, filtered, concentrated under reduced pressure to give 2-(5-(difluoromethyl)-1H-1,2,3-triazol-1-yl)acetic acid. LC-MS (ESI): m/z: [M+H]$^+$ calculated for C$_5$H$_5$F$_2$N$_3$O$_2$: 178.0; found 178.0.

Intermediate A-23: Synthesis of 2-(1-ethyl-5-methyl-2-oxo-1,2-dihydropyridin-3-yl)acetic acid

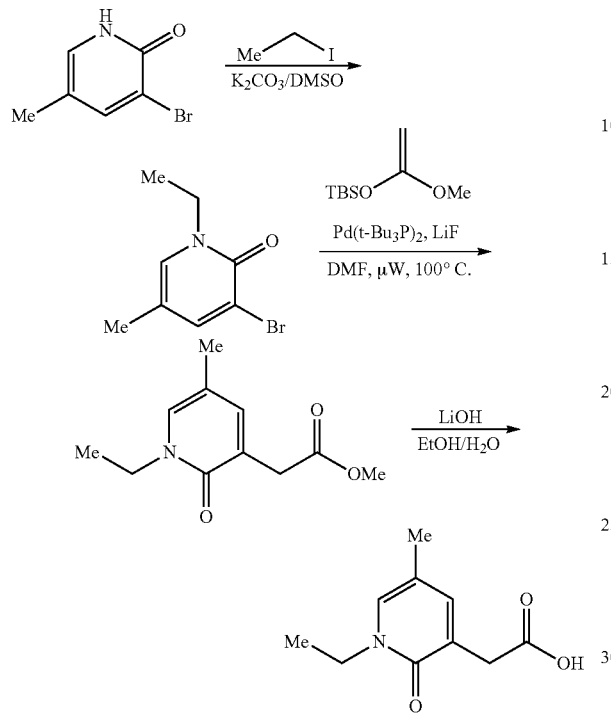

Step a: To a solution of 3-bromo-5-methylpyridin-2(1H)-one (5 g, 26.6 mmol, 1 eq) and K$_2$CO$_3$ (7.35 g, 53.2 mmol, 2 eq) in DMSO (30 mL) was added iodoethane (5.39 g, 34.6 mmol, 1.3 eq). The resulting mixture was warmed to 40° C. and stirred for 4 h. The reaction mixture was then cooled and quenched with H$_2$O (30 mL), and the resulting biphasic mixture was then extracted with EtOAc (3×30 mL). The combined organic extracts were washed with brine (20 mL), dried over anhydrous Na$_2$SO$_4$, filtered, and concentrated under reduced pressure. The crude residue obtained was purified by column chromatography to give 3-bromo-1-ethyl-5-methylpyridin-2(1H)-one. LC-MS (ESI): m/z: [M+H]$^+$ calculated for C$_8$H$_{10}$BrNO: 216.0; found 216.1.

Step b: A mixture of 3-bromo-1-ethyl-5-methylpyridin-2(1H)-one (0.1 g, 462 μmol, 1 eq), tert-butyl((1-methoxyvinyl)oxy)dimethylsilane (261 mg, 1.39 mmol, 3 eq), LiF (72.0 mg, 2.78 mmol, 6 eq), and bis(tri-tert-butylphosphine)palladium(0) (23.6 mg, 46.2 μmol, 0.1 eq) in DMF (4 mL) was degassed and placed under an N$_2$ atmosphere. The reaction mixture was then warmed to 100° C. under in a microwave and stirred for 2 h. The reaction mixture was then cooled and quenched with H$_2$O (10 mL), and the resulting biphasic mixture was extracted with EtOAc (3×20 mL). The combined organic extracts were washed with brine (10 mL), dried over anhydrous Na$_2$SO$_4$, filtered, and concentrated under reduced pressure. The crude residue obtained was purified by column chromatography to give methyl 2-(1-ethyl-5-methyl-2-oxo-1,2-dihydropyridin-3-yl)acetate. LC-MS (ESI): m/z: [M+H]$^+$ calculated for C$_{11}$H$_{15}$NO$_3$: 210.1; found 210.1.

Step c: To a solution of methyl 2-(1-ethyl-5-methyl-2-oxo-1,2-dihydropyridin-3-yl)acetate (0.25 g, 1.19 mmol, 1 eq) in EtOH (3 mL) was added a solution of LiOH·H$_2$O (100 mg, 2.39 mmol, 2 eq) in H$_2$O (1 mL). The resulting mixture was stirred for 2 h and then concentrated under reduced pressure. The crude residue obtained was purified by prep-HPLC to give 2-(1-ethyl-5-methyl-2-oxo-1,2-dihydropyridin-3-yl)acetic acid. LC-MS (ESI): m/z: [M+H]$^+$ calculated for C$_{10}$H$_{13}$NO$_3$: 196.1; found 196.2.

Intermediate A-24: Synthesis of 2-(5-oxo-4,5-dihydropyrazin-2-yl)acetic acid

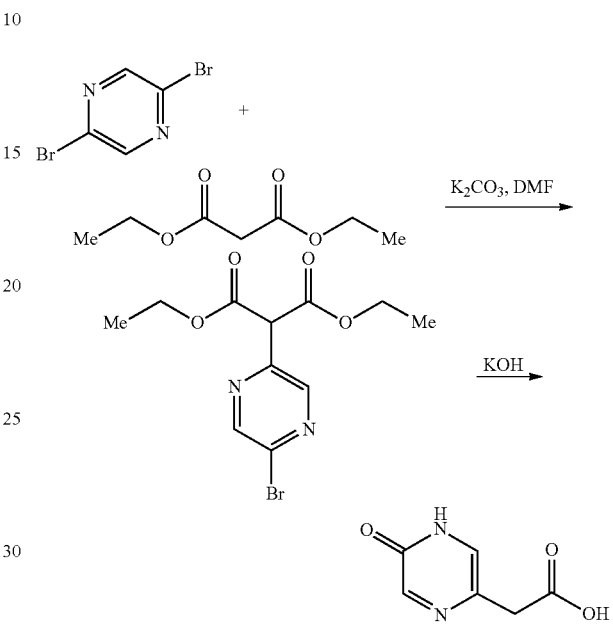

Step a: To a solution of 2,5-dibromopyrazine (2 g, 8.41 mmol, 1 eq) in DMF (20 mL) was added K$_2$CO$_3$ (1.51 g, 10.9 mmol, 1.3 eq) and diethyl propanedioate (1.62 g, 10.1 mmol, 1.52 mL, 1.2 eq). The resulting mixture was warmed to 110° C. and stirred for 4 h. The reaction mixture was then cooled and diluted with H$_2$O (10 mL). The resulting biphasic mixture was extracted with EtOAc (3×20 mL). The combined organic extracts were washed with brine (2×20 mL), dried over anhydrous Na$_2$SO$_4$, filtered, and concentrated under reduced pressure. The crude residue obtained was purified by column chromatography to give diethyl 2-(5-bromopyrazin-2-yl)malonate. LC-MS (ESI): m/z: [M+H]$^+$ calculated for C$_{11}$H$_{13}$BrN$_2$O$_4$: 317.0; found 317.0.

Step b: Diethyl 2-(5-bromopyrazin-2-yl)malonate (700 mg, 2.21 mmol, 1 eq) was added to aqueous KOH (10 M, 7 mL), and the resulting mixture was warmed to 120° C. and stirred for 16 h. The reaction mixture was then cooled to room temperature, and the pH was adjusted to pH=1 with aqueous HCl (6 N). The reaction mixture was then concentrated under reduced pressure, and the crude residue obtained was purified by prep-HPLC to give 2-(5-oxo-4,5-dihydropyrazin-2-yl)acetic acid. LC-MS (ESI): m/z: [M−H]$^−$ calculated for C$_6$H$_6$N$_2$O$_3$: 153.0; found 153.1.

Intermediate A-25: Synthesis of 2-(4-(azetidin-1-yl)-2H-1,2,3-triazol-2-yl)acetic acid

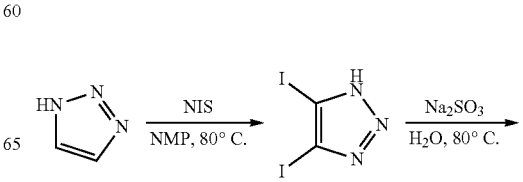

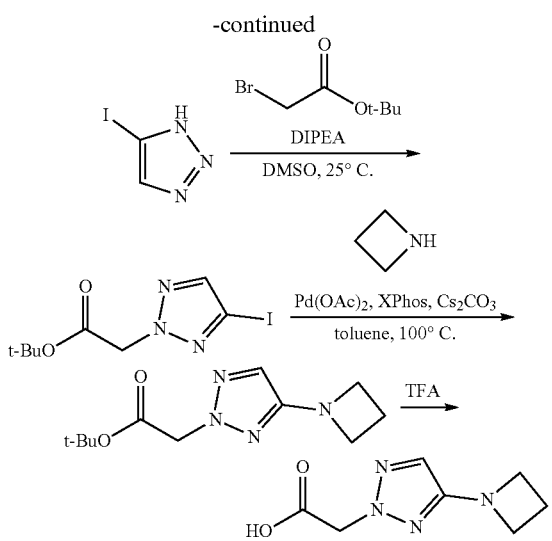

Step a: A mixture of 1H-1,2,3-triazole (10 g, 144 mmol, 1 eq) and N-iodosuccinimide (81.4 g, 361 mmol, 2.5 eq) in NMP (100 mL) under $N_2$ atmosphere was warmed to 80° C. and stirred for 1 h. The reaction mixture was then cooled to 0° C. and quenched with saturated aqueous $Na_2SO_3$ (15 mL). The resulting precipitate was collected by filtration. The solid was then diluted with $H_2O$ (50 mL), and the resulting mixture was extracted with EtOAc (2×50 mL). The combined organic extracts were dried over anhydrous $Na_2SO_4$, filtered, and concentrated under reduced pressure to give 4,5-diiodo-1H-1,2,3-triazole. LC-MS (ESI): m/z: $[M+H]^+$ calculated for $C_2H_{12}N_3$: 321.8; found 321.8.

Step b: A mixture of 5-diiodo-1H-1,2,3-triazole (4 g, 12.4 mmol, 1 eq) and $Na_2SO_3$ (4.71 g, 37.4 mmol, 3 eq) in $H_2O$ (40 mL) under $N_2$ atmosphere was warmed to 80° C. and stirred for 2 h. The reaction mixture was then cooled and diluted with $H_2O$ (20 mL). The resulting biphasic mixture was extracted with EtOAc (2×20 mL). The combined organic extracts were washed with brine, dried over anhydrous $Na_2SO_4$, filtered, and concentrated under reduced pressure to give 4-iodo-1H-1,2,3-triazole, which was carried forward without further purification. LC-MS (ESI): m/z: $[M+H]^+$ calculated for $C_2H_{21}N_3$: 195.9; found 195.9.

Step c: To a mixture of 4-iodo-1H-1,2,3-triazole (2 g, 10.2 mmol, 1 eq) and tert-butyl 2-bromoacetate (5 g, 25.6 mmol, 2.50 eq) in DMSO (20 mL) under $N_2$ atmosphere was added DIPEA (3.98 g, 30.7 mmol, 3 eq). The resulting mixture was stirred at 25° C. for 16 h. The reaction mixture was then quenched with $H_2O$ (30 mL), and the resulting biphasic mixture was extracted with EtOAc (3×30 mL). The combined organic extracts were washed with brine (30 mL), dried over $Na_2SO_4$, filtered, and concentrated under reduced pressure. The crude residue obtained was purified by column chromatography to give tert-butyl 2-(4-iodo-2H-1,2,3-triazol-2-yl)acetate, which was carried forward to the next step without further characterization.

Step d: To a solution of tert-butyl 2-(4-iodo-2H-1,2,3-triazol-2-yl)acetate (1 g, 3.24 mmol, 1 eq) in dry toluene (25 mL) was added azetidine (923 mg, 16.2 mmol, 5 eq), $Cs_2CO_3$ (3.16 g, 9.71 mmol, 3 eq), and XPhos (1.23 g, 2.59 mmol, 0.8 eq) at 25° C., The resulting mixture was then degassed and placed under an $N_2$ atmosphere before $Pd(OAc)_2$ (145 mg, 647 µmol, 0.2 eq) was added. The resulting mixture was then degassed, placed under an $N_2$ atmosphere, warmed to 100° C., and stirred for 16 h. The reaction mixture was then cooled, and water (30 mL) was added. The resulting biphasic mixture was then extracted with ethyl acetate (3×30 mL). The combined organic extracts were washed with brine (30 mL), dried over anhydrous $Na_2SO_4$, filtered, and concentrated under reduced pressure. The crude residue obtained was purified by column chromatography to give tert-butyl 2-(4-(azetidin-1-yl)-2H-1,2,3-triazol-2-yl)acetate. LC-MS (ESI): m/z: $[M+H]^+$ calculated for $C_{11}H_{18}N_4O_2$: 239.1; found 239.2.

Step e: A solution of tert-butyl 2-(4-(azetidin-1-yl)-2H-1,2,3-triazol-2-yl)acetate (370 mg, 1.55 mmol, 1 eq) in TFA (3 mL, 40.5 mmol) was stirred at 25° C. for 1 h. The mixture was then concentrated under reduced pressure, and the crude residue obtained was triturated with MTBE (3 mL) to give 2-(4-(azetidin-1-yl)-2H-1,2,3-triazol-2-yl)acetic acid. LC-MS (ESI): m/z: $[M+H]^+$ calculated for $C_7H_{10}N_4O_2$: 183.1; found 183.2.

The following compounds in Table B-10 were synthesized using procedures similar to Intermediate A-25 using the appropriate starting materials.

TABLE B-10

| Intermediate No. | Structure | IUPAC | Exact mass (g/mol) | LCMS, Found [M + ]+ |
| --- | --- | --- | --- | --- |
| B-10-1 | 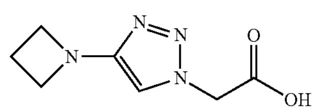 [SMILES: O=C(O)Cn1cc(N2CCC2)nn1] | 2-(4-(azetidin-1-yl)-1H-1,2,3-triazol-1-yl)acetic acid | 182.1 | 183.2 |

Intermediate A-26: Synthesis of 2-(3-(difluoromethyl)-4H-1,2,4-triazol-4-yl)acetic acid

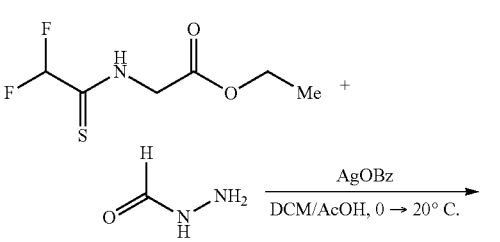

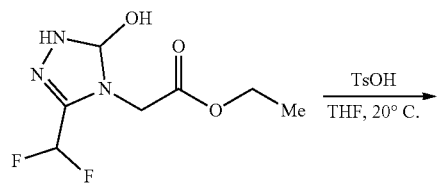

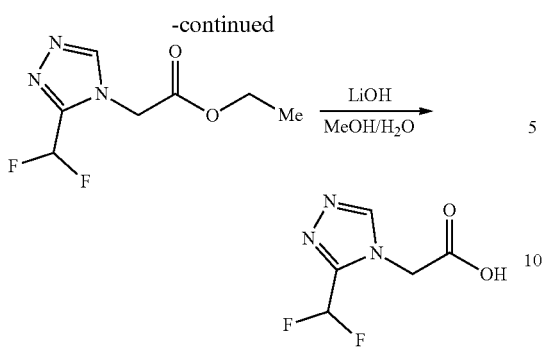

Step a: To a solution of ethyl (2,2-difluoroethanethioyl) glycinate (2 g, 9.29 mmol, 1 eq) and formic hydrazide (669 mg, 11.1 mmol, 1.2 eq) in DCM (100 mL) at 0° C. was added silver benzoate (4.26 g, 18.5 mmol, 2 eq) and AcOH (1.67 g, 27.8 mmol, 3 eq). The resulting mixture was then warmed to 20° C. and stirred for 16 h. The reaction mixture was then filtered, and the filtrate was quenched by addition of ice-water (100 mL). The resulting biphasic mixture was then extracted with DCM (3×50 mL). The combined organic extracts were washed with brine (50 mL), dried over anhydrous Na$_2$SO$_4$, filtered, and concentrated under reduced pressure. The crude residue obtained was purified by column chromatography to give ethyl 2-(3-(difluoromethyl)-5-hydroxy-1,5-dihydro-4H-1,2,4-triazol-4-yl)acetate. LC-MS (ESI): m/z: [M+H]$^+$ calculated for C$_7$H$_{11}$F$_2$N$_3$O$_3$: 224.1; found 224.0.

Step b: A mixture of ethyl 2-(3-(difluoromethyl)-5-hydroxy-1,5-dihydro-4H-1,2,4-triazol-4-yl)acetate (1 g, 4.48 mmol, 1 eq) and 4-methylbenzenesulfonic acid (77.1 mg, 448 μmol, 0.1 eq) in THF (20 mL) was stirred at 20° C. for 16 hours under N$_2$. The reaction mixture was then concentrated under reduced pressure. The crude residue obtained was purified by column chromatography to give ethyl 2-(3-(difluoromethyl)-4H-1,2,4-triazol-4-yl)acetate. LC-MS (ESI): m/z: [M+H]$^+$ calculated for C$_7$H$_9$F$_2$N$_3$O$_2$: 206.1; found 206.0.

Step c: To a solution of ethyl 2-(3-(difluoromethyl)-4H-1,2,4-triazol-4-yl)acetate (100 mg, 487 μmol, 1 eq) in H$_2$O (1 mL) and MeOH (5 mL) was added LiOH·H$_2$O (40.9 mg, 974 μmol, 2 eq) at 20° C. The resulting mixture was then stirred at 20° C. for 2 h. The reaction mixture was then concentrated under reduced pressure to remove MeOH. The resulting mixture was then adjusted to pH 3-4 using aqueous HCl (1 M), and the aqueous mixture was then extracted with EtOAc (3×10 mL). The combined organic extracts were washed with brine (50 mL), dried over with anhydrous Na$_2$SO$_4$, filtered, and concentrated under reduced pressure to give 2-(3-(difluoromethyl)-4H-1,2,4-triazol-4-yl)acetic acid. LC-MS (ESI): m/z: [M+H]$^+$ calculated for C$_5$H$_5$F$_2$N$_3$O$_2$: 178.0; found 178.1.

Intermediate A-27: Synthesis of 2-(4-(difluoromethyl)-1-methyl-1H-pyrazol-5-yl)acetic acid

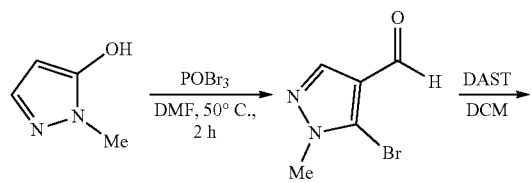

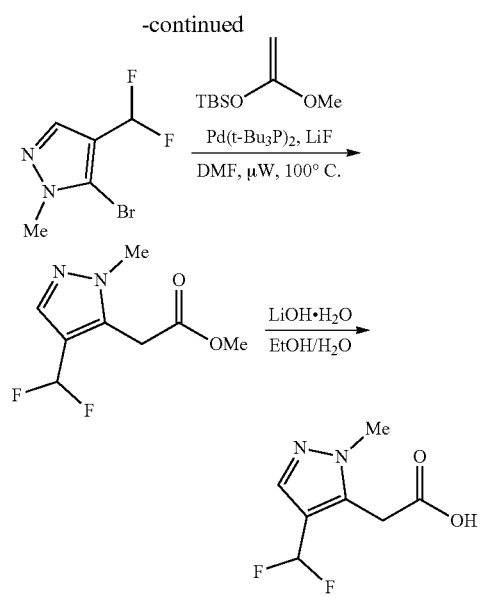

Step a: To a solution of POBr$_3$ (81.8 g, 285 mmol, 29.0 mL, 7 eq) in DMF (40 mL) at 0° C. was added 1-methyl-1H-pyrazol-5-ol (4 g, 40.7 mmol, 1 eq). The resulting mixture was warmed to 50° C. and stirred for 2 h. After cooling, the reaction mixture was quenched by addition saturated aq. Na$_2$CO$_3$ (100 mL) at 0° C. The resulting biphasic mixture was extracted with EtOAc (2×250 mL). The combined organic extracts were washed with brine (100 mL), dried over anhydrous Na$_2$SO$_4$, filtered, and concentrated under reduced pressure. The crude residue obtained was purified by column chromatography to give 5-bromo-1-methyl-1H-pyrazole-4-carbaldehyde. LC-MS (ESI): m/z: [M+H]$^+$ calculated for C$_5$H$_5$BrN$_2$O: 189.0; found 188.9.

Step b: To a solution of 5-bromo-1-methyl-pyrazole-4-carbaldehyde (2.5 g, 13.2 mmol, 1 eq) in DCM (20 mL) at 0° C. was added DAST (8.53 g, 52.9 mmol, 4 eq) in a dropwise manner. The resulting mixture was warmed to 20° C. and stirred for 12 h. The reaction mixture was then cooled to 0° C. and quenched by addition H$_2$O (30 mL). The resulting biphasic mixture was extracted with DCM (3×10 mL). The combined organic extracts were washed with brine (30 mL), dried over with anhydrous Na$_2$SO$_4$, filtered, and concentrated under reduced pressure. The crude residue obtained was purified by column chromatography to give 5-bromo-4-(difluoromethyl)-1-methyl-1H-pyrazole. LC-MS (ESI): m/z: [M+H]$^+$ calculated for C$_5$H$_5$BrF$_2$N$_2$: 211.0; found 210.9.

Step c: To a solution of 5-bromo-4-(difluoromethyl)-1-methyl-1H-pyrazole (200 mg, 947 μmol, 1 eq) in DMF (2 mL) was added lithium fluoride (147 mg, 5.69 mmol, 6 eq) and tert-tert-butyl((1-methoxyvinyl)oxy)dimethylsilane (535 mg, 2.84 mmol, 3 eq). The resulting mixture was then degassed and placed under an N$_2$ atmosphere. Bis(tri-tert-butylphosphine)palladium(0) (48.4 mg, 94.7 μmol, 0.1 eq) was then added, and the resulting mixture was warmed to 100° C. using a microwave and stirred for 1.5 h. After cooling, the reaction mixture was then quenched by addition of H$_2$O (15 mL). The resulting biphasic mixture was then filtered and extracted with EtOAc (3×10 mL). The combined organic extracts were washed with brine (10 mL), dried over anhydrous Na$_2$SO$_4$, filtered, and concentrated under reduced pressure. The crude residue obtained was purified by column chromatography to give methyl 2-(4-(difluoromethyl)-1- methyl-1H-pyrazol-5-yl)acetate. LC-MS (ESI): m/z: [M+H]+ calculated for $C_8H_{10}F_2N_2O_2$: 205.1; found 205.1.

Step d: To a solution of methyl 2-(4-(difluoromethyl)-1-methyl-1H-pyrazol-5-yl)acetate (75 mg, 367 μmol, 1 eq) in EtOH (1 mL) and $H_2O$ (0.5 mL) was added LiOH·$H_2O$ (30.8 mg, 734 μmol, 2 eq), and the resulting mixture was stirred at 20° C. for 1 h. The reaction mixture was then quenched by addition of $H_2O$ (5 mL), and the resulting biphasic mixture was extracted with EtOAc (2×5 mL). The aqueous phase pH was then adjusted to pH 3-4 with aqueous HCl (1M), and the aqueous phase was extracted with EtOAc (2×5 mL). The second set of organic extracts were dried over anhydrous $Na_2SO_4$, filtered, and concentrated under reduced pressure to give 2-(4-(difluoromethyl)-1-methyl-1H-pyrazol-5-yl)acetic acid. LC-MS (ESI): m/z: [M+H]+ calculated for $C_7H_8F_2N_2O_2$: 190.0; found 190.1.

Intermediate A-28: Synthesis of 2-(4-(difluoromethyl)-1H-1,2,3-triazol-5-yl)acetic acid

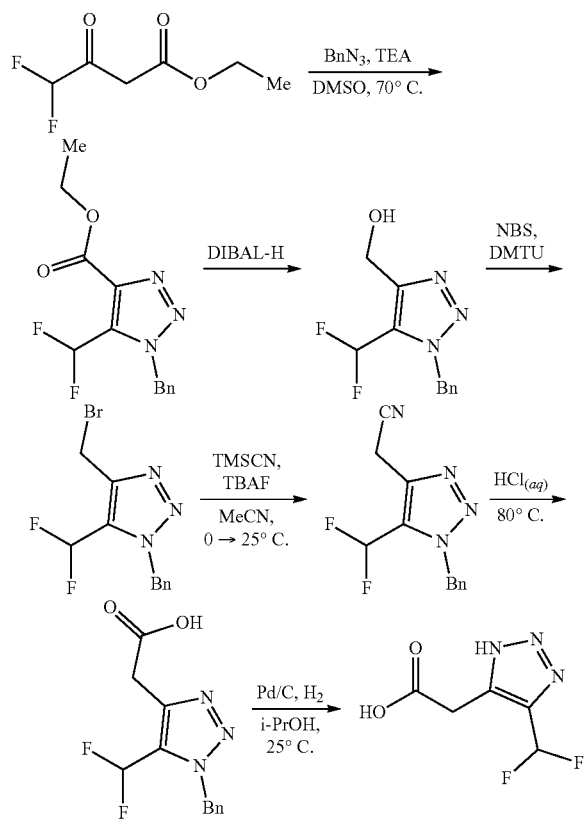

Step a: A mixture of compound ethyl 4,4-difluoro-3-oxobutanoate (12.0 g, 72.2 mmol, 1 eq), TEA (21.9 g, 217 mmol, 30.1 mL, 3 eq) and azidomethylbenzene (9.62 g, 72.2 mmol, 1 eq) in DMSO (100 mL) was heated and stirred at 70° C. for 16 h. After cooling the mixture was poured into ice-water (100 mL) and extracted with EtOAc (2×200 mL). The combined organic layers were washed with aqueous HCl (0.5 M, 100 mL) and brine (200 mL), dried over anhydrous $Na_2SO_4$ filtered and concentrated under reduced pressure. The resulting residue was purified by column chromatography to give ethyl 1-benzyl-5-(difluoromethyl)-1H-1,2,3-triazole-4-carboxylate. LC-MS (ESI): m/z: [M+H]+ calculated for $C_{13}H_{13}F_2N_3O_2$: 282.2; found 282.2.

Step b: To a mixture of ethyl 1-benzyl-5-(difluoromethyl)-1H-1,2,3-triazole-4-carboxylate (3.00 g, 10.7 mmol, 1 eq) in THF (100 mL) was added DIBAL-H (1 M in THF, 64.0 mL, 6 eq) at 0° C. The resulting mixture was warmed to 25° C. and stirred for 1 h. The mixture was quenched by addition of sat. aq. $NH_4Cl$ (10 mL), and the pH was adjusted to 5 with aqueous HCl (4M) and extracted with EtOAc (2×50 mL). The combined organic layers were washed with brine (30 mL), dried over with anhydrous $Na_2SO_4$, filtered and concentrated under reduced pressure. The resulting residue was purified by flash silica gel chromatography to give (1-benzyl-5-(difluoromethyl)-1H-1,2,3-triazol-4-yl)methanol LC-MS (ESI): m/z: [M+H]+ calculated for $C_{11}H_{11}F_2N_3O$: 240.1; found 240.1.

Step c: To a solution of compound (1-benzyl-5-(difluoromethyl)-1H-1,2,3-triazol-4-yl)methanol (2.00 g, 8.36 mmol, 1 eq) and 1,3-dimethylthiourea (DMTU, 392 mg, 3.76 mmol, 0.45 eq) in DCM (20 mL) was added NBS (2.23 g, 12.5 mmol, 1.5 eq) at 0° C. The resulting mixture was warmed to 25° C. and stirred for 2 h. The mixture was quenched with $H_2O$ (50 mL) and extracted with DCM (2×50 mL). The combined organic layers were washed with brine (80 mL), dried over with anhydrous $Na_2SO_4$, filtered and concentrated under reduced pressure. The resulting residue was purified by column chromatography to give 1-benzyl-4-(bromomethyl)-5-(difluoromethyl)-1H-1,2,3-triazole. LC-MS (ESI): m/z: [M+H]+ calculated for $C_{11}H_{10}BrN_3$: 301.9; found 301.9.

Step d: To a solution of compound 1-benzyl-4-(bromomethyl)-5-(difluoromethyl)-1H-1,2,3-triazole (800 mg, 2.65 mmol, 1 eq) and TMSCN (276 mg, 2.78 mmol, 1.05 eq) in MeCN (20 mL) was added TBAF (1 M, 3.97 mL, 1.5 eq) at 0° C. The resulting mixture was warmed to 25° C. and stirred for 30 min. The mixture was quenched by addition of sat. aq. $NaHCO_3$ (30 mL) and extracted with EtOAc (2×30 mL). The combined organic layers were washed with brine (20 mL), dried over with anhydrous $Na_2SO_4$, filtered and concentrated under reduced pressure. The residue was purified by column chromatography to obtain 2-(1-benzyl-5-(difluoromethyl)-1H-1,2,3-triazol-4-yl)acetonitrile. LC-MS (ESI): m/z: [M+H]+ calculated for $C_{12}H_{10}F_2N_4$: 249.0; found 249.0.

Step e: A mixture of 2-(1-benzyl-5-(difluoromethyl)-1H-1,2,3-triazol-4-yl)acetonitrile (880 mg, 3.55 mmol, 1 eq) in concentrated HCl (20 mL) was stirred at 80° C. for 2 h. After cooling, the mixture was concentrated under reduced pressure. The resulting residue was washed with THF (40 mL) and filtered. The filtrate was dried over anhydrous $Na_2SO_4$, filtered and concentrated under reduced pressure to give 2-(1-benzyl-5-(difluoromethyl)-1H-1,2,3-triazol-4-yl)acetic acid. LC-MS (ESI): m/z: [M+H]+ calculated for $C_{12}H_{11}F_2N_3O_2$: 268.0; found 268.0.

Step f: To a solution of 2-(1-benzyl-5-(difluoromethyl)-1H-1,2,3-triazol-4-yl)acetic acid (300 mg, 1.12 mmol, 1 eq) and concentrated HCl (11.4 mg, 112 μmol, 0.1 eq) in i-PrOH (10 mL) was added Pd/C (100 mg, 10% purity) under $N_2$. The suspension was degassed under vacuum and purged with $H_2$ several times. The mixture was stirred under $H_2$ (50 psi) at 25° C. for 16 h. The reaction mixture was filtered through a pad of celite and concentrated under reduced pressure to give 2-(4-(difluoromethyl)-1H-1,2,3-triazol-5-yl)acetic acid. LC-MS (ESI): m/z: [M+H]+ calculated for $C_5H_5F_2N_3O_2$: 178.0; found 178.0.

Intermediate A-29: Synthesis of 2-(5-(trifluoromethyl)-1H-tetrazol-1-yl)acetic acid

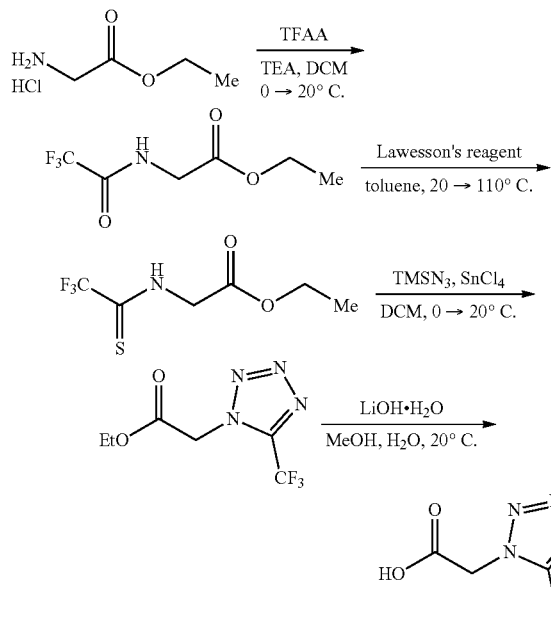

Step a: To a solution of ethyl glycinate hydrochloride (10 g, 71.6 mmol, 1 eq) in DCM (100 mL) at 0° C. was added trifluoroacetic anhydride (22.5 g, 107 mmol, 14.9 mL, 1.5 eq) and TEA (36.2 g, 358 mmol, 5 eq). The mixture was then warmed to 20° C. and stirred for 3 h. The reaction mixture was then poured into $H_2O$ (100 mL), and the resulting biphasic mixture was extracted with EtOAc (3×100 mL). The combined organic extracts were dried over with anhydrous $Na_2SO_4$, filtered, and concentrated under reduced pressure. The crude residue obtained was purified by column chromatography to give ethyl (2,2,2-trifluoroacetyl)glycinate. LC-MS (ESI): m/z: $[M+H]^+$ calculated for $C_6H_8F_3NO_3$: 200.0; found 200.0.

Step b: To a solution of ethyl (2,2,2-trifluoroacetyl)glycinate (11 g, 55.2 mmol, 1 eq) in toluene (200 mL) at 20° C. was added Lawesson's reagent (26.8 g, 66.2 mmol, 1.2 eq). The reaction mixture was then warmed to 110° C. and stirred for 1 h. After cooling to 20° C., the reaction mixture was poured into $H_2O$ (100 mL), and the resulting biphasic mixture was extracted with EtOAc (3×100 mL). The combined organic extracts were dried over with anhydrous $Na_2SO_4$, filtered, and concentrated under reduced pressure. The crude residue obtained was purified by column chromatography to give ethyl (2,2,2-trifluoroethanethioyl)glycinate. LC-MS (ESI): m/z: $[M+H]^+$ calculated for $C_6H_8F_3NO_2S$: 216.0; found 215.9.

Step c: To a mixture of ethyl (2,2,2-trifluoroethanethioyl) glycinate (2 g, 9.29 mmol, 1 eq) and $TMSN_3$ (2.14 g, 18.5 mmol, 2.44 mL, 2 eq) in DCM (40 mL) at 0° C. under a $N_2$ atmosphere was added $SnCl_4$ (6.05 g, 23.2 mmol, 2.71 mL, 2.5 eq). The reaction mixture was then warmed to 20° C. and stirred for 16 h. The reaction mixture was then cooled to 0° C. and quenched by slow addition of saturated aq. $NaHCO_3$ (200 mL). The resulting biphasic mixture was extracted with EtOAc (2×200 mL). The combined organic extracts were dried over anhydrous $Na_2SO_4$, filtered, and concentrated under reduced pressure. The crude residue obtained was purified by column chromatography to give ethyl 2-(5-(trifluoromethyl)-1H-tetrazol-1-yl)acetate. LC-MS (ESI): m/z: $[M+H]^+$ calculated for $C_6H_7F_3N_4O_2$: 225.0; found 225.0.

Step d: To a solution of ethyl 2-(5-(trifluoromethyl)-1H-tetrazol-1-yl)acetate (500 mg, 2.23 mmol, 1 eq) in MeOH (10 mL) and $H_2O$ (1 mL) at 20° C. was added $LiOH·H_2O$ (187 mg, 4.46 mmol, 2 eq). The resulting mixture was stirred at 20° C. for 16 h. The reaction mixture was then adjusted to pH 3-4 with aqueous HCl (1M) and stirred for 5 min. The resulting mixture was then filtered and concentrated under reduced pressure to give 2-(5-(trifluoromethyl)-1H-tetrazol-1-yl)acetic acid which was used without further purification. LC-MS (ESI): m/z: $[M+H]^+$ calculated for $C_4H_3F_3N_4O_2$: 197.0; found 196.9.

Intermediate A-30: Synthesis of 2-(5-(trifluoromethyl)-1H-1,2,3-triazol-1-yl)acetic acid

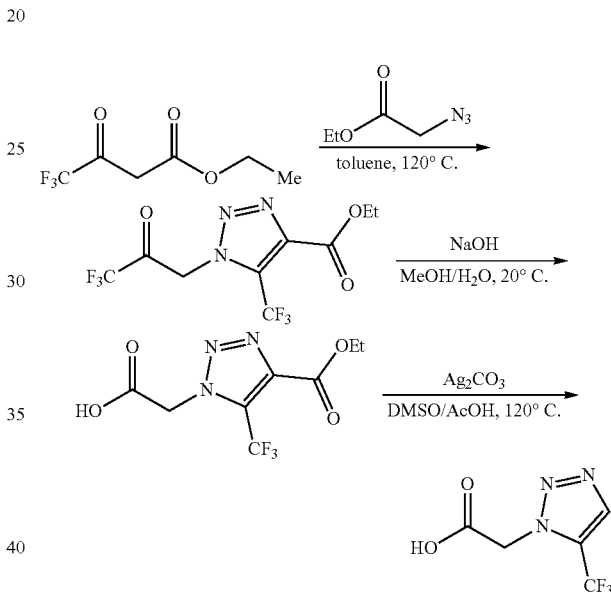

Step a: A mixture of ethyl 4,4,4-trifluoro-3-oxobutanoate (1.00 g, 5.43 mmol, 1 eq) and ethyl 2-azidoacetate (701 mg, 5.43 mmol, 1 eq) in toluene (10 mL) was warmed to 120° C. and stirred for 16 h. After cooling, the reaction mixture was concentrated under reduced pressure. The crude residue obtained was purified by column chromatography to give ethyl 1-(2-ethoxy-2-oxoethyl)-5-(trifluoromethyl)-1H-1,2,3-triazole-4-carboxylate. LC-MS (ESI): m/z: $[M+H]^+$ calculated for $C_{10}H_{12}F_3N_3O_4$: 296.1; found 296.1.

Step b: A mixture of ethyl 1-(2-ethoxy-2-oxoethyl)-5-(trifluoromethyl)-1H-1,2,3-triazole-4-carboxylate (300 mg, 1.02 mmol, 1 eq) and NaOH (203 mg, 5.08 mmol, 5 eq) in $H_2O$ (1 mL) and MeOH (10 mL) was stirred at 20° C. for 2 h. The reaction mixture was then acidified to pH=2 with concentrated aq. HCl (12 N). The reaction mixture was concentrated under reduced pressure to give 1-(carboxymethyl)-5-(trifluoromethyl)-1H-1,2,3-triazole-4-carboxylic acid. LC-MS (ESI): m/z: $[M+H]^+$ calculated for $C_6H_4F_3N_3O_4$: 240.0; found 240.1.

Step c: A mixture of 1-(carboxymethyl)-5-(trifluoromethyl)-1H-1,2,3-triazole-4-carboxylic acid (250 mg, 1.05 mmol, 1 eq) and $Ag_2CO_3$ (28.8 mg, 104 μmol, 0.1 eq) in DMSO (1 mL) and AcOH (6.28 mg, 104 μmol, 0.1 eq) was warmed to 120° C. and stirred for 16 h. After cooling, the reaction mixture was acidified to pH=2 with concentrated aq. HCl (12 N). The reaction mixture was then concentrated under reduced pressure. The crude residue obtained was purified by prep-HPLC to give 2-(5-(trifluoromethyl)-1H-1,2,3-triazol-1-yl)acetic acid. LC-MS (ESI): m/z: [M+H]+ calculated for $C_5H_4F_3N_3O_2$: 196.0; found 196.1.

Intermediate A-31: Synthesis of (benzyl(trifluoromethyl)carbamoyl)glycine

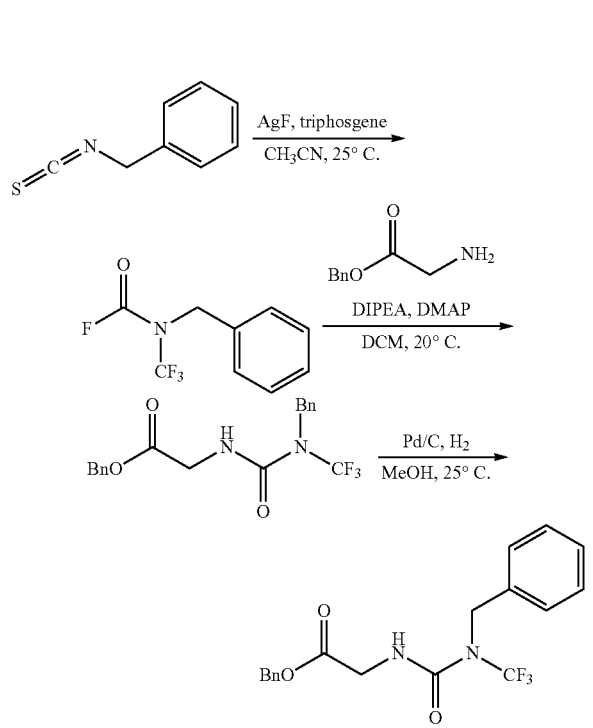

Step a. To a solution of AgF (1.02 g, 8.04 mmol, 6 eq) in CH₃CN (10 mL) at 0° C. under an atmosphere of N₂ was added (isothiocyanatomethyl)benzene (0.2 g, 1.34 mmol, 177 μL, 1 eq) in a dropwise manner. Triphosgene (199 mg, 670 μmol, 0.5 eq) was then added. The resulting reaction mixture was warmed to 25° C. and stirred for 16 h. The reaction mixture was then added to MTBE (20 mL) and stirred for 10 min. The precipitate generated was filtered to give benzyl (trifluoromethyl)carbamic fluoride, which was carried forward to the next step without further purification or characterization.

Step b. To as solution of benzyl (trifluoromethyl)carbamic fluoride (0.3 g, 1.36 mmol, 1 eq) in DCM (5 mL) was added benzyl glycinate (448 mg, 2.71 mmol, 2 eq), DIPEA (526 mg, 4.07 mmol, 3 eq), and DMAP (16 mg, 136 μmol, 0.1 eq). The resulting reaction mixture was stirred at 20° C. for 16 h. The reaction was then quenched with water (20 mL), and the resulting biphasic mixture was extracted with DCM (3×20 mL). The combined organic extracts were washed with brine (2×10 mL), dried over anhydrous Na₂SO₄, filtered, and concentrated under reduced pressure. The crude residue obtained was purified by column chromatography to give benzyl (benzyl(trifluoromethyl)carbamoyl)glycinate. LC-MS (ESI): m/z: [M+H]+ calculated for $C_{18}H_{17}F_3N_2O_3$: 367.1; found 367.1.

Step c. To a solution of benzyl (benzyl(trifluoromethyl) carbamoyl)glycinate (150 mg, 409 μmol, 1 eq) in MeOH (3 mL) was added Pd/C (50 mg, 40.9 μmol, 10% purity, 0.1 eq). The resulting mixture was stirred at 25° C. for 16 h under H₂ (15 psi). The reaction mixture was then filtered and concentrated under reduced pressure to give (benzyl(trifluoromethyl)carbamoyl)glycine. LC-MS (ESI): m/z: [M+H]+ calculated for $C_{11}H_{11}F_3N_2O_3$: 277.1; found 277.1.

Intermediate A-32: Synthesis of 2-(5-(trifluoromethyl)-1H-pyrazol-1-yl)acetic acid

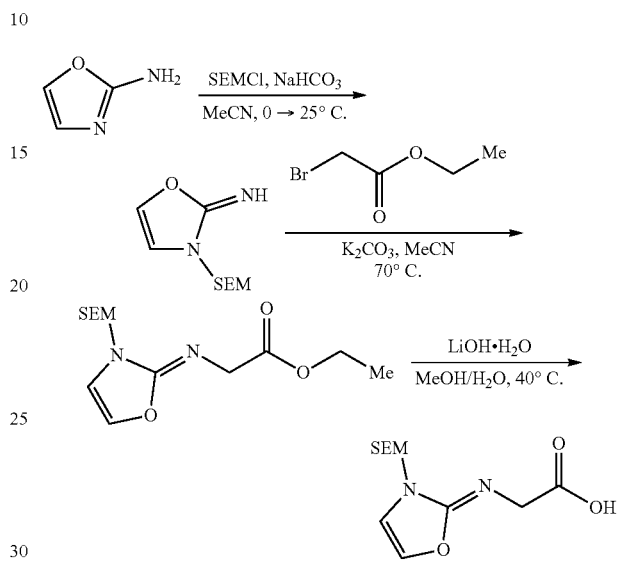

Step a: To a solution of ethyl aminoglycinate hydrochloride (3 g, 19.4 mmol, 1 eq) in EtOH (30 mL) was added NaOH (776 mg, 19.4 mmol, 1 eq) and ethyl (Z)-2-(ethoxymethylene)-4,4,4-trifluoro-3-oxobutanoate (5.13 g, 21.4 mmol, 254 μL, 1.1 eq). The reaction was then stirred at 25° C. for 2 h. The reaction mixture was then concentrated under reduced pressure. The crude residue obtained was purified by column chromatography to give ethyl 1-(2-ethoxy-2-oxoethyl)-5-(trifluoromethyl)-1H-pyrazole-4-carboxylate. LC-MS (ESI): m/z: [M+H]+ calculated for $C_{11}H_{13}F_3N_2O_4$: 295.1; found 295.2.

Step b: A mixture of ethyl 1-(2-ethoxy-2-oxoethyl)-5-(trifluoromethyl)-1H-pyrazole-4-carboxylate (3.5 g, 11.9 mmol, 1 eq) and LiOH·H₂O (3.49 g, 83.2 mmol, 7 eq) in THF (20 mL) and H₂O (20 mL) at 25° C. was stirred for 12 h. The reaction mixture was then extracted with EtOAc (50 mL). The combined organic extracts were washed with water (50 mL), dried over anhydrous Na₂SO₄, filtered, and concentrated under reduced pressure. The crude residue obtained was purified by column chromatography to give 1-(carboxymethyl)-5-(trifluoromethyl)-1H-pyrazole-4-carboxylic acid. LC-MS (ESI): m/z: [M+H]+ calculated for $C_7H_5F_3N_2O_4$: 239.0; found 239.1.

Step c: A mixture of 1-(carboxymethyl)-5-(trifluoromethyl)-1H-pyrazole-4-carboxylic acid (400 mg, 1.68 mmol, 1 eq), Cu₂O (24.0 mg, 168 μmol, 17.2 μL, 0.1 eq) and 1,10-phenantholine (30.3 mg, 168 μmol, 0.1 eq) in NMP (3 mL) were warmed to 150° C. and stirred for 3 h. The reaction mixture was then concentrated under reduced pressure. The crude residue obtained was purified by prep-HPLC to give 2-(5-(trifluoromethyl)-1H-pyrazol-1-yl)acetic acid. LC-MS (ESI): m/z: [M+H]+ calculated for $C_6H_5F_3N_2O_2$: 195.0; found 195.0.

Intermediate A-33: Synthesis of (Z)-2-((3-((2-(trimethylsilyl)ethoxy)methyl)oxazol-2(3H)-ylidene)amino)acetic acid

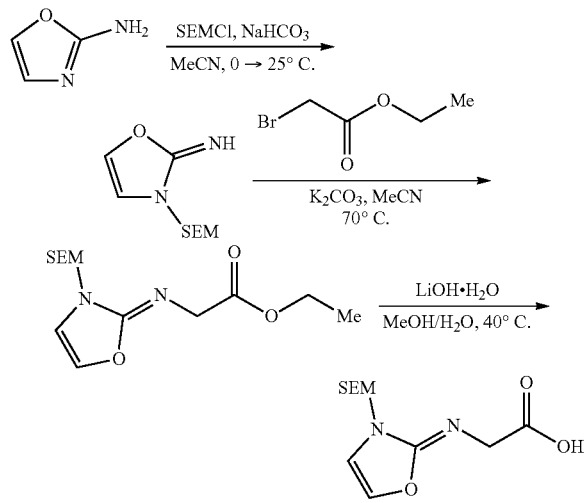

Step a: To a mixture of oxazol-2-amine (640 mg, 7.61 mmol, 1 eq) and NaHCO$_3$ (639 mg, 7.61 mmol, 296 μL, 1 eq) in MeCN (20 mL) at 0° C. under N$_2$ was added SEMCl (1.27 g, 7.61 mmol, 1.35 mL, 1 eq). The resulting mixture was warmed to 25° C. and stirred for 16 h. The reaction mixture was then quenched with H$_2$O (10 mL), and resulting biphasic mixture was extracted with EtOAc (2×30 mL). The combined organic extracts were washed with brine (20 mL), dried over with anhydrous Na$_2$SO$_4$, filtered, and concentrated under reduced pressure to give 3-((2-(trimethylsilyl)ethoxy)methyl)oxazol-2(3H)-imine, which was carried forward to the next step without further purification or characterization.

Step b: A mixture of 3-((2-(trimethylsilyl) ethoxy)methyl) oxazol-2(3H)-imine (1.4 g, 6.53 mmol, 1 eq), K$_2$CO$_3$ (1.81 g, 13 mmol, 2 eq) and ethyl 2-bromoacetate (1.64 g, 9.80 mmol, 1.08 mL, 1.5 eq) in MeCN (50 mL) was warmed to 70° C. and stirred for 3 h. After cooling, the reaction was quenched with H$_2$O (20 mL), and the resulting biphasic mixture was extracted with EtOAc (2×30 mL). The combined organic extracts were dried over anhydrous Na$_2$SO$_4$, filtered, and concentrated under reduced pressure. The crud residue obtained was purified by column chromatography to give ethyl (Z)-2-((3-((2-(trimethylsilyl)ethoxy)methyl)oxazol-2(3H)-ylidene)amino)acetate, which was carried forward to the next step without further characterization.

Step 3: A mixture of ethyl (Z)-2-((3-((2-(trimethylsilyl)ethoxy)methyl)oxazol-2(3H)-ylidene)amino)acetate (500 mg, 1.66 mmol, 1 eq) and LiOH·H$_2$O (210 mg, 4.99 mmol, 3 eq) in MeOH (8 mL) and H$_2$O (1 mL) was stirred at 40° C. for 1 h. After cooling, the reaction was diluted with H$_2$O (10 mL). The pH of the resulting solution was adjusted to pH=5 using aqueous HCl (4M). The resulting mixture was extracted with EtOAc (2×30 mL). The combined organic extracts were washed with brine (10 mL), dried over with anhydrous Na$_2$SO$_4$, filtered, and concentrated under reduced pressure to give (Z)-2-((3-((2-(trimethylsilyl)ethoxy)methyl)oxazol-2(3H)-ylidene)amino)acetic acid. LC-MS (ESI): m/z: [M+H]$^+$ calculated for C$_{11}$H$_{20}$N$_2$O$_4$Si: 273.1; found 273.1.

Intermediate A-34: Synthesis of 3-(difluoromethyl)-4-isopropylbenzaldehyde

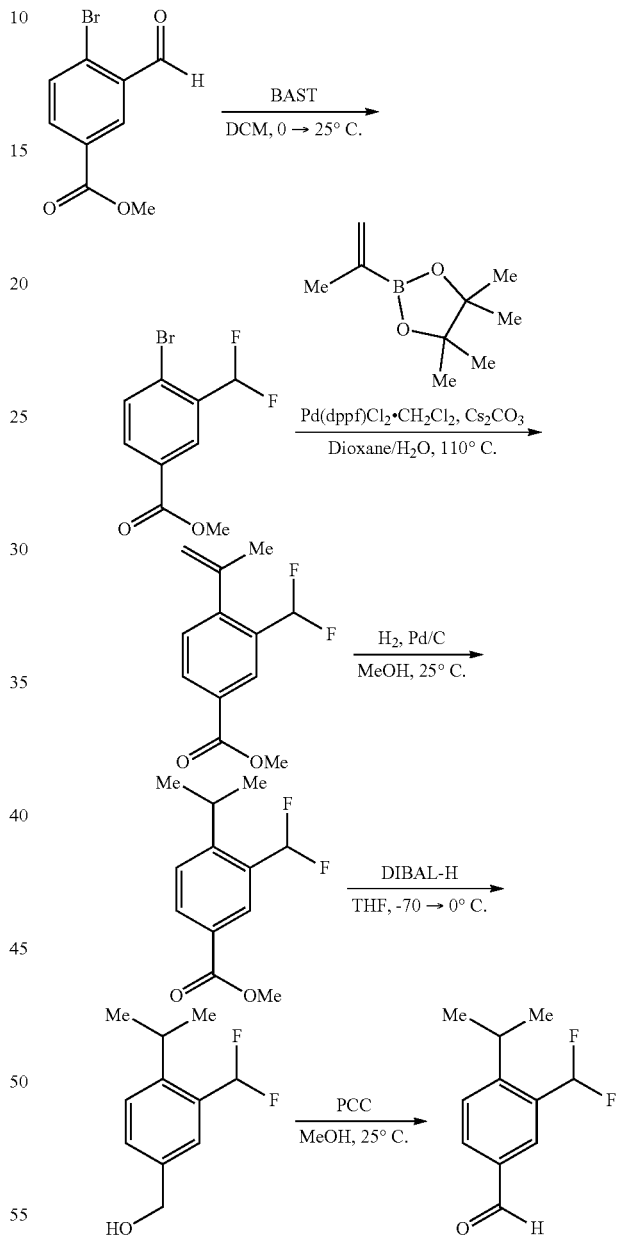

Step a: To a solution of methyl 4-bromo-3-formylbenzoate (4.50 g, 18.5 mmol, 1 eq) in DCM (45 mL) at 0° C. was added 1,1,1-trifluoro-N,N-bis(2-methoxyethyl)-λ$^4$-sulfanamine (BAST, 10.5 mL, 48.1 mmol, 2.6 eq). The mixture was warmed to 25° C. and stirred for 40 min. The mixture was then poured into ice-water (50 mL) and stirred for 5 min. Saturated aqueous NaHCO$_3$ was then added to adjust the pH to 8. The resulting biphasic mixture was extracted with ethyl acetate (3×50 mL). The combined organic extracts were washed with brine (3×30 mL), dried over anhydrous Na$_2$SO$_4$, filtered, and concentrated under reduced pressure. The crude residue obtained was purified by column chromatography to give methyl 4-bromo-3-(difluoromethyl)benzoate. LC-MS (ESI): m/z: [M+H]$^+$ calculated for C$_9$H$_7$BrF$_2$O$_2$: 265.0; found 264.9.

Step b: To a mixture of methyl 4-bromo-3-(difluoromethyl)benzoate (4.30 g, 16.2 mmol, 1 eq), 4,4,5,5-tetramethyl-2-(prop-1-en-2-yl)-1,3,2-dioxaborolane (3.27 g, 19.5 mmol, 1.20 eq), and Cs$_2$CO$_3$ (10.6 g, 32.5 mmol, 2.00 eq) in dioxane (43 mL) and H$_2$O (4 mL) at 25° C. under N$_2$ was added Pd(dppf)Cl$_2$·CH$_2$Cl$_2$ (1.32 g, 1.62 mmol, 0.10 eq). The resulting mixture was then degassed and then charged with N$_2$. The mixture was then warmed to 110° C. and stirred for 30 min. After cooling to room temperature, the mixture was poured into water (20 mL) and stirred for 5 min. The resulting biphasic mixture was extracted with ethyl acetate (3×50 mL). The combined organic extracts were washed with brine (2×50 mL), dried over Na$_2$SO$_4$, filtered, and concentrated under reduce pressure. The crude residue obtained was purified by column chromatography to give methyl 3-(difluoromethyl)-4-(prop-1-en-2-yl)benzoate. LC-MS (ESI): m/z: [M+H]$^+$ calculated for C$_{12}$H$_{12}$F$_2$O$_2$: 227.1; found 227.1.

Step c: To a solution of methyl 3-(difluoromethyl)-4-(prop-1-en-2-yl)benzoate (2.40 g, 10.6 mmol, 1.00 eq) in MeOH (30 mL) at 25° C. was added Pd/C (1.12 g, 1.06 mmol, 10% purity, 0.1 eq) under N$_2$. The suspension was then degassed under vacuum and purged with H$_2$. The reaction mixture was then stirred under H$_2$ (15 psi) at 25° C. for 1 h. The reaction mixture was then filtered and concentrated under reduced pressure to give methyl 3-(difluoromethyl)-4-isopropylbenzoate. LC-MS (ESI): m/z: [M+H]$^+$ calculated for C$_{12}$H$_{14}$F$_2$O$_2$: 229.1; found 229.1.

Step d: To a solution of methyl 3-(difluoromethyl)-4-isopropylbenzoate (2.35 g, 10.3 mmol, 1 eq) in THF (30 mL) at −70° C. under N$_2$ was added DIBAL-H (1 M in THF, 20.6 mL, 2.00 eq) dropwise. The reaction mixture was then stirred at −70° C. for 2 h under N$_2$. The reaction mixture was the warmed to 0° C. and quenched by addition of water (20 mL). The resulting biphasic mixture was then filtered and extracted with ethyl acetate (2×20 mL). The combined organic extracts were washed with brine (2×20 mL), dried over Na$_2$SO$_4$, filtered, and concentrated under reduced pressure. The crude residue obtained was purified by column chromatography to give (3-(difluoromethyl)-4-isopropylphenyl)methanol. LC-MS (ESI): m/z: [M−OH]$^+$ calculated for C$_{11}$H$_{14}$F$_2$O: 183.1; found 183.1.

Step e: To a mixture of (3-(difluoromethyl)-4-isopropylphenyl)methanol (1.80 g, 8.99 mmol, 1.00 eq) and silica gel (2.91 g) in DCM (20 mL) at 25° C. under N$_2$ was added PCC (2.91 g, 13.48 mmol, 1.50 eq). The resulting mixture was stirred at 25° C. for 30 min. The reaction mixture was then filtered and concentrated under reduced pressure. The crude residue obtained was purified by column chromatography to give 3-(difluoromethyl)-4-isopropylbenzaldehyde. LC-MS (ESI): m/z: [M+H]$^+$ calculated for C$_{11}$H$_{12}$F$_2$O: 199.1; found 199.1.

Intermediate A-35: Synthesis of 4-isopropyl-3-methylbenzaldehyde

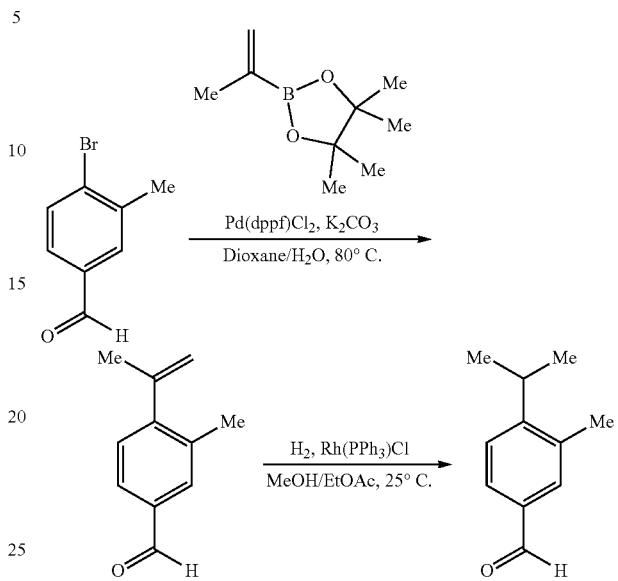

Step a: To a mixture of 4-bromo-3-methylbenzaldehyde (5 g, 25.1 mmol, 1 eq), 4,4,5,5-tetramethyl-2-(prop-1-en-2-yl)-1,3,2-dioxaborolane (8.44 g, 50.2 mmol, 2 eq), and K$_2$CO$_3$ (10.4 g, 75.4 mmol, 3 eq) in dioxane (60 mL) and H$_2$O (6 mL) was added Pd(dppf)Cl$_2$ (551 mg, 754 μmol, 0.03 eq). The resulting mixture was degassed and purged with N$_2$, and then the mixture was warmed to 80° C. and stirred for 16 h under N$_2$ atmosphere. The reaction mixture was then filtered, and the filtrate was concentrated under reduced pressure. The crude residue obtained was purified by column chromatography to give 3-methyl-4-(prop-1-en-2-yl)benzaldehyde (4 g, crude). LC-MS (ESI): m/z: [M+H]$^+$ calculated for C$_{11}$H$_{12}$O: 161.1; found 161.1.

Step b: To a solution of 3-methyl-4-(prop-1-en-2-yl)benzaldehyde (4 g, 25.0 mmol, 1 eq) in EtOAc (40 mL) and MeOH (20 mL) was added Rh(PPh$_3$)Cl (1.15 g, 1.25 mmol, 0.05 eq) under argon. The resulting suspension was then degassed under vacuum and placed under an H$_2$ atmosphere. The resulting mixture was then stirred under H$_2$ (15 psi) at 25° C. for 16 h. The mixture was then filtered, and the filtrate was concentrated under reduced pressure to give 4-isopropyl-3-methylbenzaldehyde. LC-MS (ESI): m/z: [M+H]$^+$ calculated for C$_{11}$H$_{14}$O: 163.1; found 163.1.

Intermediate A-36: Synthesis of 4-fluoro-2-iodo-5-isopropylpyridine

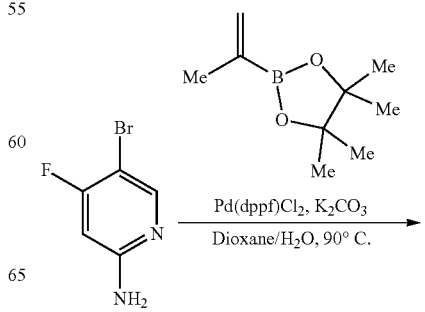

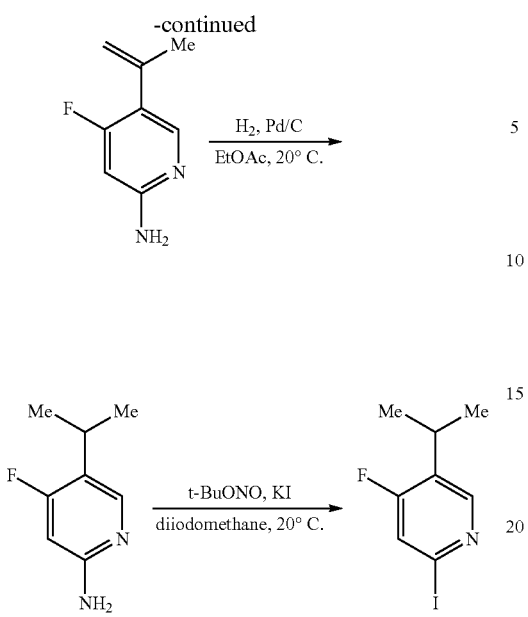

Step a: To a mixture of 5-bromo-4-fluoropyridin-2-amine (3 g, 15.7 mmol, 1 eq), 4,4,5,5-tetramethyl-2-(prop-1-en-2-yl)-1,3,2-dioxaborolane (3.96 g, 23.5 mmol, 1.5 eq), and $K_2CO_3$ (6.51 g, 47.1 mmol, 3 eq) in $H_2O$ (3 mL) and dioxane (30 mL) was added Pd(dppf)$Cl_2$ (460 mg, 629 μmol, 0.04). The resulting mixture was degassed and purged with $N_2$, and then the mixture was warmed to 90° C. and stirred for 16 h under $N_2$ atmosphere. The reaction mixture was then filtered, and the filtrate was concentrated under reduced pressure. The crude residue obtained was purified by column chromatography to give 4-fluoro-5-(prop-1-en-2-yl)pyridin-2-amine. LC-MS (ESI): m/z: $[M+H]^+$ calculated for $C_8H_9FN_2$: 153; found 153.2.

Step b: To a solution of 4-fluoro-5-(prop-1-en-2-yl)pyridin-2-amine (2.2 g, 14.4 mmol, 1 eq) in EtOAc (50 mL) was added Pd/C (1 g, 10% purity) under $N_2$. The suspension was then degassed under vacuum and placed under an $H_2$ atmosphere. The resulting mixture was then stirred under $H_2$ (20 psi) at 20° C. for 16 h. The mixture was then filtered, and the filtrate was concentrated under reduced pressure to give 4-fluoro-5-isopropylpyridin-2-amine. LC-MS (ESI): m/z: $[M+H]^+$ calculated for $C_8H_{11}FN_2$: 155.1; found 155.0.

Step c: To a mixture of 4-fluoro-5-isopropylpyridin-2-amine (2 g, 12.9 mmol, 1 eq) and KI (21.5 g, 129 mmol, 10 eq) in diiodomethane (69.4 g, 259 mmol, 20.9 mL, 20 eq) was added t-BuONO (6.69 g, 64.8 mmol, 5 eq). The resulting mixture was degassed and purged with $N_2$, and then the mixture was stirred for 16 h under $N_2$ atmosphere at 20° C. The reaction mixture was then filtered, and the filtrate was concentrated under reduced pressure. The crude residue was purified by column chromatography to give 4-fluoro-2-iodo-5-isopropylpyridine. LC-MS (ESI): m/z: $[M+H]^+$ calculated for $C_8H_9FIN$: 266.0; found 265.9.

Intermediate A-37:
3-chloro-4-cyclopropylbenzaldehyde

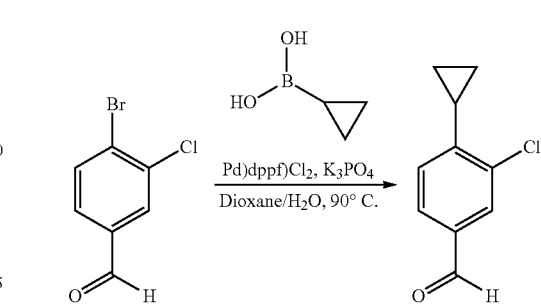

Step a: To a mixture of cyclopropylboronic acid (2.30 g, 26.7 mmol, 1.30 eq), 4-bromo-3-chlorobenzaldehyde (4.5 g, 20.5 mmol, 1.00 eq), and $K_3PO_4$ (10.0 g, 47.1 mmol, 2.30 eq) in dioxane (40.0 mL) and $H_2O$ (4.00 mL) was added Pd(dppf)$Cl_2$ (750 mg, 1.02 mmol, 0.05 eq). The resulting mixture was degassed and purged with $N_2$, and then the mixture was warmed to 90° C. and stirred for 16 h under $N_2$ atmosphere. The reaction mixture was then dried over $Na_2SO_4$, filtered, and concentrated under reduced pressure. The crude residue obtained was purified by column chromatography to give 3-chloro-4-cyclopropylbenzaldehyde. LC-MS (ESI): m/z: $[M+H]^+$ calculated for $C_{10}H_9ClO$: 181.0; found 181.1.

Intermediate A-38:
4-cyclopropyl-3,5-difluorobenzaldehyde

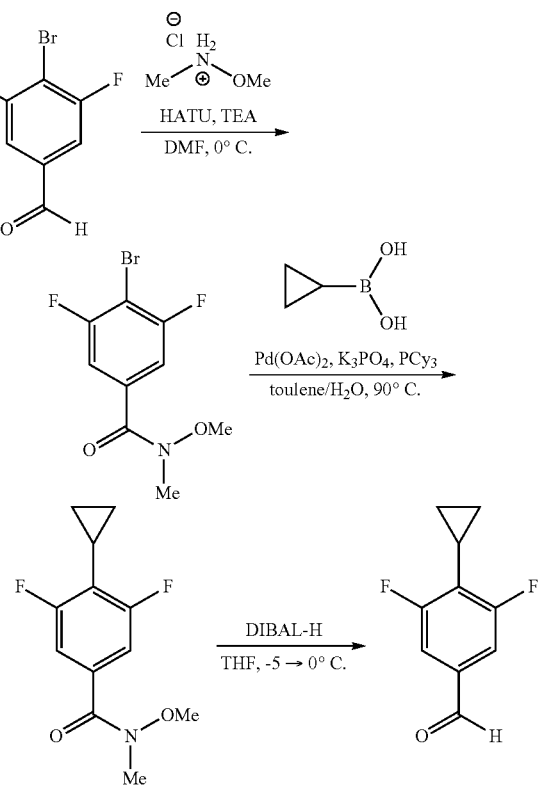

Step a: To a solution of 4-bromo-3,5-difluorobenzoic acid (2.7 g, 11.4 mmol, 1 eq), Et₃N (3.46 g, 34.2 mmol, 4.76 mL, 3 eq) and N,O-dimethylhydroxylammonium chloride (1.33 g, 13.7 mmol, 1.2 eq) in DMF (25 mL) at 0° C. was added HATU (4.55 g, 11.9 mmol, 1.05 eq). The resulting mixture was stirred at 0° C. for 1 h. The reaction was then quenched by addition of H₂O (80 mL) at 0° C., and the resulting biphasic mixture was then extracted with EtOAc (3×50 mL). The combined organic extracts were washed with brine (80 mL), dried over anhydrous Na₂SO₄, filtered, and concentrated under reduced pressure. The crude residue obtained was purified by column chromatography to give 4-bromo-3,5-difluoro-N-methoxy-N-methylbenzamide. This compound was carried forward to the next step without further characterization.

Step b: To a mixture of 4-bromo-3,5-difluoro-N-methoxy-N-methylbenzamide (3.15 g, 11.3 mmol, 1 eq), cyclopropylboronic acid (1.45 g, 16.8 mmol, 1.5 eq), K₃PO₄ (7.16 g, 33.7 mmol, 3 eq), and PCy₃ (315 mg, 1.12 mmol, 0.1 eq) in toluene (60 mL) and H₂O (6 mL) was added Pd(OAc)₂ (253 mg, 1.12 mmol, 0.1 eq). The resulting mixture was degassed and purged with N₂, and the resulting mixture was warmed to 90° C. and stirred for 12 h under N₂ atmosphere. The reaction mixture was then filtered, and the filtrate was concentrated under reduced pressure. The crude residue obtained was purified by column chromatography to give 4-cyclopropyl-3,5-difluoro-N-methoxy-N-methylbenzamide. This compound was carried forward to the next step without further characterization.

Step c: To a solution of 4-cyclopropyl-3,5-difluoro-N-methoxy-N-methylbenzamide (2.50 g, 10.4 mmol, 1 eq) in THF (20 mL) at −5° C. under N₂ was added DIBAL-H (1 M in THF, 13.47 mL, 1.3 eq). The resulting mixture was then warmed to 0° C. and stirred for 3 h. The reaction mixture was then poured into ice-water (20 mL), adjusted to pH=7 with aq. HCl (4M), and extracted with Et₂₀ (3×20 mL). The combined organic extracts were washed with brine (40 mL), dried over anhydrous Na₂SO₄, filtered, and concentrated under reduced pressure. The crude residue obtained was purified by column chromatography to give 4-cyclopropyl-3,5-difluorobenzaldehyde.

Intermediate A-39:
2-cyclopropyl-1-fluoro-5-iodo-3-methylbenzene

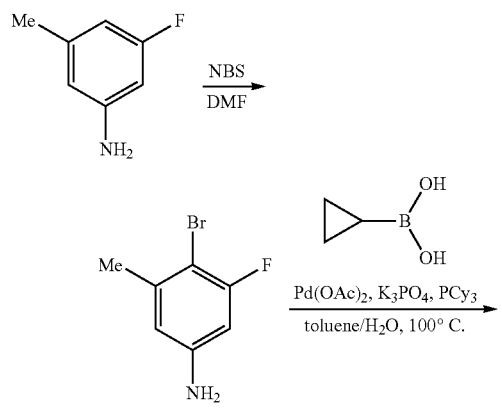

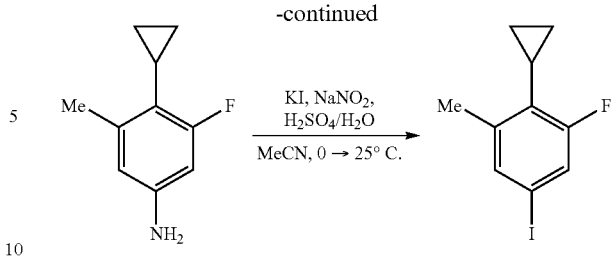

Step a: To a solution of 3-fluoro-5-methylaniline (15.0 g, 120 mmol, 1.00 eq) in DMF (100 mL) at 0° C. was added NBS (21.5 g, 121 mmol, 1.01 eq). The resulting mixture was stirred at 0° C. for 0.5 h. The reaction mixture was then warmed to 25° C. and stirred for 1 h. The reaction mixture was then diluted with water (100 mL) and extracted with ethyl acetate (3×100 mL). The combined organic extracts were washed with saturated aqueous NaHCO₃, dried over anhydrous Na₂SO₄, filtered, and concentrated under reduced pressure. The crude residue obtained was purified by column chromatography to give 4-bromo-3-fluoro-5-methylaniline. LC-MS (ESI): m/z: [M+H]⁺ calculated for C₇H₇BrFN: 204.0; found 204.0.

Step b: To a solution of 4-bromo-3-fluoro-5-methylaniline (8.0 g, 39.2 mmol, 1.00 eq), tricyclohexylphosphine (2.20 g, 7.84 mmol, 0.20 eq), cyclopropylboronic acid (4.04 g, 47.0 mmol, 1.20 eq), and K₃PO₄ (25.0 g, 118 mmol, 3.00 eq) in toluene (160 mL) and H₂O (32 mL) was added Pd(OAc)₂ (880 mg, 3.92 mmol, 0.10 eq). The resulting mixture was degassed and purged with N₂. The reaction mixture was then warmed to 100° C. and stirred for 16 h under N₂. After cooling to the room temperature, the reaction mixture was extracted with ethyl acetate (3×80 mL). The combined organic extracts were washed with saturated aqueous NaHCO₃, dried over anhydrous Na₂SO₄, filtered, and concentrated under reduced pressure. The crude residue obtained was purified by column chromatography to give 4-cyclopropyl-3-fluoro-5-methylaniline. LC-MS (ESI): m/z: [M+H]⁺ calculated for C₁₀H₁₂FN: 166.1; found 166.1.

Step c: To a solution of 4-cyclopropyl-3-fluoro-5-methylaniline (4.00 g, 24.21 mmol, 1 eq) in MeCN (40 mL) was added a solution of H₂SO₄ (18 M, 3.36 mL, 98% purity, 2.50 eq) in H₂O (40 mL). After stirring 10 min, the reaction mixture was cooled to 0° C., and a solution of NaNO₂ (3.34 g, 48.4 mmol, 2.00 eq) in H₂O (40 mL) was added over 20 min. A solution of KI (16.1 g, 96.8 mmol, 4.00 eq) in H₂O (40 mL) was then added to the reaction mixture at 0° C. The reaction mixture was then warmed to 25° C. and stirred under N₂ atmosphere or 0.5 h. The reaction mixture was then extracted with ethyl acetate (3×600 mL). The combined organic extracts were washed with saturated aqueous NaHCO₃, dried over anhydrous Na₂SO₄, filtered, and concentrated under reduced pressure. The crude residue obtained was purified by column chromatography to give 2-cyclopropyl-1-fluoro-5-iodo-3-methylbenzene.

Intermediate A-40:
3-fluoro-4-(1-methylcyclopropyl)benzaldehyde

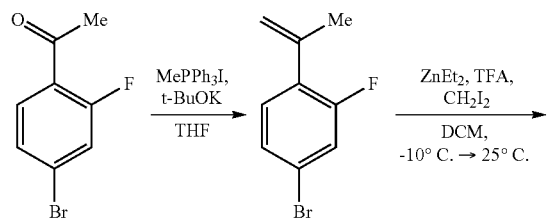

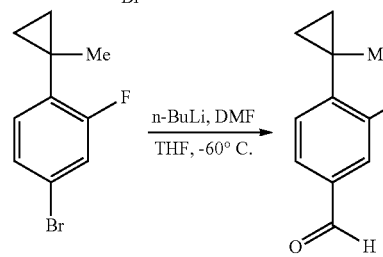

Step a: To a solution of methyltriphenylphosphonium iodide (14.0 g, 34.6 mmol, 1.5 eq) in THF (50.0 mL) was added t-BuOK (3.88 g, 34.6 mmol, 1.5 eq). The resulting mixture was stirred at 25° C. for 30 min. To this mixture was added a solution of 1-(4-bromo-2-fluorophenyl)ethan-1-one (5.00 g, 23.0 mmol, 1 eq) in THF (5.00 mL) at 25° C. The resulting mixture was stirred at 25° C. for 16 h. The reaction mixture was then cooled to 0° C. and quenched by addition H$_2$O (100 mL), and the resulting biphasic mixture was extracted with EtOAc (3×100 mL). The combined organic extracts were washed with brine (100 mL), dried over anhydrous Na$_2$SO$_4$, filtered, and concentrated under reduced pressure. The crude residue obtained was purified by column chromatography to give 4-bromo-2-fluoro-1-(prop-1-en-2-yl)benzene, which was carried forward to the next step without further characterization.

Step b: To a solution of ZnEt$_2$ (1 M in hexane, 18.6 mL, 4 eq) in DCM (5.00 mL) at 0° C. under N$_2$ atmosphere was added TFA (2.12 g, 18.6 mmol, 1.38 mL, 4 eq). The resulting mixture was stirred at 0° C. for 30 min before CH$_2$I$_2$ (4.98 g, 18.6 mmol, 1.50 mL, 4 eq) in DCM (5.00 mL) was added dropwise at 0° C. The resulting mixture was stirred at 0° C. for 30 min before 4-bromo-2-fluoro-1-(prop-1-en-2-yl)benzene (1.00 g, 4.65 mmol, 1 eq) in DCM (5.00 mL) was added dropwise at 0° C. The resulting mixture was then warmed to 25° C. and stirred for 16 h. The reaction mixture was then cooled to 0° C. and quenched by addition of aq. HCl (1N, 50 mL). The resulting biphasic mixture was extracted with EtOAc (3×30 mL). The combined organic extracts were washed with brine (2×50 mL), dried over anhydrous Na$_2$SO$_4$, filtered, and concentrated under reduced pressure. The crude residue obtained was purified by column chromatography to give 4-bromo-2-fluoro-1-(1-methylcyclopropyl)benzene, which was carried forward to the next step without further characterization.

Step c: To a solution of 4-bromo-2-fluoro-1-(1-methylcyclopropyl)benzene (5 g, 21.8 mmol, 1 eq) in THF (80 mL) at −60° C. under N$_2$ atmosphere was added n-BuLi (2.5 M in hexane, 8.72 mL, 1 eq). After 30 min, DMF (4.79 g, 65.4 mmol, 3 eq) was added dropwise at −60° C. The resulting mixture was allowed to warm to 25° C. and stirred for 2 h. The reaction mixture was then cooled to 0° C. and quenched by addition saturated aqueous NH$_4$Cl (150 mL). The resulting biphasic mixture was extracted with EtOAc (3×50 mL). The combined organic extracts were washed with brine (2×50 mL), dried over anhydrous Na$_2$SO$_4$, filtered, and concentrated under reduced pressure. The crude residue was purified by column chromatography to give 3-fluoro-4-(1-methylcyclopropyl)benzaldehyde. LC-MS (ESI): m/z: [M+H]$^+$ calculated for C$_{11}$H$_{11}$FO: 179.1; found 179.1.

Intermediate A-41:
6-fluoro-5-(1-methylcyclopropyl)picolinaldehyde

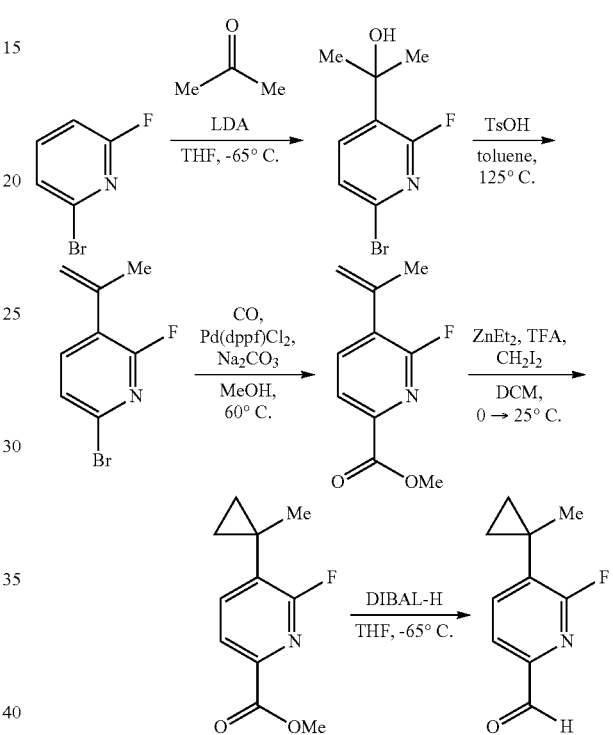

Step a: To a solution of 2-bromo-6-fluoropyridine (12.5 g, 71.0 mmol, 1.00 eq) in THF (125 mL) at −65° C. under N$_2$ atmosphere was added LDA (2 M in THF, 35.5 mL, 1.00 eq) in a dropwise manner. The reaction mixture was stirred at −65° C. for 0.5 h before acetone (6.19 g, 106 mmol, 1.50 eq) was added in a dropwise manner at −65° C. The reaction mixture was then stirred at −65° C. for 0.5 h before it was warmed to 0° C., quenched by addition of H$_2$O (60 mL), and stirred for 5 min. The resulting biphasic mixture was extracted with ethyl acetate (3×100 mL). The combined organic extracts were dried over anhydrous Na$_2$SO$_4$, filtered, and concentrated under reduced pressure. The crude residue obtained was purified by column chromatography to give 2-(6-bromo-2-fluoropyridin-3-yl)propan-2-ol. LC-MS (ESI): m/z: [M+H]$^+$ calculated for C$_8$H$_9$BrFNO: 234.0; found 234.0.

Step b: To a solution of 2-(6-bromo-2-fluoropyridin-3-yl)propan-2-ol (13.5 g, 57.7 mmol, 1.00 eq) in toluene (135 mL) was added TsOH (1.99 g, 11.5 mmol, 0.2 eq). The reaction mixture was then warmed to 125° C. and stirred for 16 h. The reaction mixture was then filtered and concentrated under reduced pressure. The crude residue obtained was purified by column chromatography to give 6-bromo-2-fluoro-3-(prop-1-en-2-yl)pyridine. LC-MS (ESI): m/z: [M+H]$^+$ calculated for C$_8$H$_7$BrFN: 216.0; found 215.9.

Step c: To a solution of 6-bromo-2-fluoro-3-(prop-1-en-2-yl)pyridine (6.50 g, 30.1 mmol, 1.00 eq) in MeOH (65 mL) was added TEA (6.09 g, 60.1 mmol, 2.00 eq) and Pd(dppf)Cl$_2$·CH$_2$Cl$_2$ (2.46 g, 3.01 mmol, 0.10 eq). The reaction mixture was then placed under a CO atmosphere (50 psi), warmed to 60° C., and stirred for 1.5 h. The reaction mixture was then concentrated under reduced pressure. The crude residue obtained was purified by column chromatography to give methyl 6-fluoro-5-(prop-1-en-2-yl)picolinate. LC-MS (ESI): m/z: [M+H]$^+$ calculated for C$_{10}$H$_{10}$FNO$_2$: 196.1; found 196.1.

Step d: To a solution of ZnEt$_2$ (1 M in hexane, 102 mL, 5.00 eq) at 0° C. was added TFA (102 mmol, 7.6 mL, 5.00 eq) in DCM (24 mL) in a dropwise manner. The resulting mixture was stirred at 0° C. for 30 min before CH$_2$I$_2$ (27.4 g, 102 mmol, 5.0 eq) in DCM (22 mL) was added in a dropwise manner. The resulting mixture was stirred at 0° C. for 30 min before methyl 6-fluoro-5-(prop-1-en-2-yl)picolinate (4 g, 20 mmol, 1.0 eq) in DCM (12 mL) was added in a dropwise manner at 0° C. The resulting mixture was then warmed to 25° C. and stirred for 15 h. The reaction mixture was then cooled to 0° C. and quenched by addition of saturated aq. NH$_4$Cl (100 ml). The resulting biphasic mixture was then extracted with ethyl acetate (3×500 mL). The combined organic extracts were dried over anhydrous Na$_2$SO$_4$, filtered, and concentrated under reduced pressure. The crude residue obtained was purified by prep-HPLC to give methyl 6-fluoro-5-(1-methylcyclopropyl)picolinate. LC-MS (ESI): m/z: [M+H]$^+$ calculated for C$_{11}$H$_{12}$FNO$_2$: 210.1; found 210.1.

Step e: A solution of methyl 6-fluoro-5-(1-methylcyclopropyl)picolinate (1.25 g, 5.97 mmol, 1 eq) in THF (12.5 mL) was degassed and purged with N$_2$. The resulting solution was cooled to −65° C., and then DIBAL-H (1 M in THF, 11.95 mL, 2 eq) was added in a dropwise manner. The resulting mixture was stirred at −65° C. for 2 h. The reaction mixture was then warmed to 0° C. and quenched by addition of water (20 mL). The resulting biphasic mixture was then filtered and extracted with ethyl acetate (2×20 mL). The combined organic extracts were washed with brine (2×20 mL), dried over anhydrous Na$_2$SO$_4$, filtered, and concentrated under reduced pressure. The crude residue obtained was purified by column chromatography to give 6-fluoro-5-(1-methylcyclopropyl)picolinaldehyde. LC-MS (ESI): m/z: [M+H]$^+$ calculated for C$_{10}$H$_{10}$FNO: 180.1; found 180.1.

Intermediate A-42:
4-(tert-butyl)-3-fluorobenzaldehyde

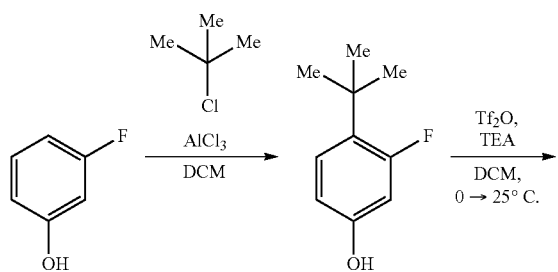

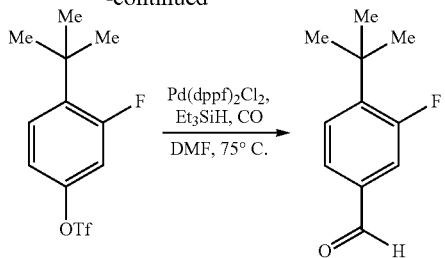

Step a: To a mixture of 3-fluorophenol (10.0 g, 89.20 mmol, 8.20 mL, 1 eq) and AlCl$_3$ (4.76 g, 35.7 mmol, 1.95 mL, 0.4 eq) in DCM (150 mL) under N$_2$ was added 2-chloro-2-methyl-propane (12.4 g, 134 mmol, 14.8 mL, 1.5 eq) in a dropwise manner. The resulting mixture was stirred at 25° C. for 16 h. The reaction mixture was then quenched with water (50 mL), and the resulting biphasic mixture was extracted with ethyl acetate (3×50 mL). The combined organic extracts were washed with water (3×50 mL), dried over anhydrous Na$_2$SO$_4$, filtered, and concentrated under reduced pressure. The crude residue obtained was purified by column chromatography to give 4-(tert-butyl)-3-fluorophenol. LC-MS (ESI): m/z: [M+H]$^+$ calculated for C$_{10}$H$_{13}$FO: 169.1; found 169.1.

Step b: To a solution of 4-(tert-butyl)-3-fluorophenol (3.80 g, 22.6 mmol, 1 eq) and TEA (6.86 g, 67.8 mmol, 9.43 mL, 3 eq) in DCM (15 mL) at 0° C. was added Tf$_2$O (3.19 g, 11.3 mmol, 1.86 mL, 0.5 eq) in a dropwise manner. The resulting mixture was warmed to 25° C. and stirred for 2 h. The reaction was then diluted with H$_2$O (5 mL) and extracted with ethyl acetate (3×10 mL). The combined organic extracts were washed with brine (5 mL), dried over anhydrous Na$_2$SO$_4$, filtered, and concentrated under reduced pressure. The crude residue obtained was purified by column chromatography to give 4-(tert-butyl)-3-fluorophenyl trifluoromethanesulfonate. LC-MS (ESI): m/z: [M+H]$^+$ calculated for C$_{11}$H$_{12}$F$_4$O$_3$S: 301.0; found 301.1.

Step c: To a solution of 4-(tert-butyl)-3-fluorophenyl trifluoromethanesulfonate (2.00 g, 6.66 mmol, 1 eq), Et$_3$SiH (1.55 g, 13.3 mmol, 2.13 mL, 2 eq), and Na$_2$CO$_3$ (1.41 g, 13.3 mmol, 2 eq) in DMF (15 mL) under N$_2$ atmosphere was added Pd(dppf)Cl$_2$ (487 mg, 666 μmol, 0.1 eq). The resulting mixture was placed under CO atmosphere (50 psi), warmed to 75° C., and stirred for 5 h. The reaction mixture was then diluted with H$_2$O (20 mL) and extracted with ethyl acetate (3×10 mL). The combined organic extracts were washed with brine (3×10 mL), dried over anhydrous Na$_2$SO$_4$, filtered, and concentrated under reduced pressure. The crude residue obtained was purified by column chromatography to give 4-(tert-butyl)-3-fluorobenzaldehyde. LC-MS (ESI): m/z: [M+H]$^+$ calculated for C$_{11}$H$_{13}$FO: 181.1; found 181.1.

Intermediate A-43:
3-fluoro-4-(1-methylcyclobutyl)benzaldehyde

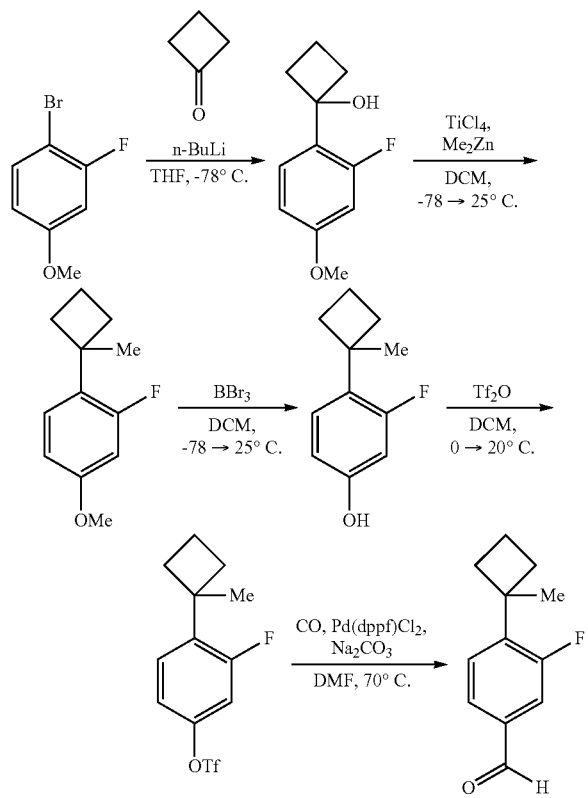

Step a: To a solution of 1-bromo-2-fluoro-4-methoxybenzene (23.0 g, 112 mmol, 1 eq) in THF (200 mL) at −78° C. under N₂ atmosphere was added n-BuLi (2.5 M in hexane, 50 mL, 125.0 mmol, 1.1 eq). The resulting mixture was stirred at −78° C. for 1 h before cyclobutanone (7.86 g, 112 mmol, 8.3 mL, 1 eq) was added in a dropwise manner. The resulting mixture was stirred at −78° C. for 2 h. The reaction was then quenched by addition of saturated aqueous NH₄Cl (200 mL), and the resulting biphasic mixture was extracted with ethyl acetate (2×300 mL). The combined organic extracts were washed with water (50 mL) and brine (3×250 mL), dried over Na₂SO₄, filtered, and concentrated under reduced pressure. The crude residue obtained was purified by column chromatography to give 1-(2-fluoro-4-methoxyphenyl)cyclobutan-1-ol. This compound was carried forward to the next step without further characterization.

Step b: To a solution of 1-(2-fluoro-4-methoxyphenyl)cyclobutan-1-ol (5 g, 25.4 mmol, 1 eq) in DCM (40 mL) at −78° C. was added titanium tetrachloride (9.6 g, 50.9 mmol, 9.67 mL, 2 eq), and the resulting mixture was stirred at −78° C. for 1 h. A solution of dimethylzinc (1 M in heptane, 76.45 mL, 3 eq) was added at −78° C. in a dropwise manner. The resulting mixture was warmed to 25° C. and stirred for 1 h. The reaction mixture was then poured into ice-water (30 mL), and the resulting biphasic mixture was extracted with DCM (50 mL). The organic extracts were then washed with brine (50 mL), dried over anhydrous Na₂SO₄, filtered, and concentrated under reduced pressure. The crude residue obtained was purified by column chromatography to give 2-fluoro-4-methoxy-1-(1-methylcyclobutyl)benzene. This compound was carried forward to the next step without further characterization.

Step c: To a solution of 2-fluoro-4-methoxy-1-(1-methylcyclobutyl)benzene (1.5 g, 7.7 mmol, 1 eq) in DCM (2 mL) at −78° C. was added BBr₃ (1 M, 23.17 mL, 3 eq). The resulting mixture was stirred at −78° C. for 0.5 h. The reaction mixture was then warmed to 25° C. and stirred for 1 h. The reaction mixture was then quenched by addition of H₂O (100 mL), and the resulting biphasic mixture was extracted with DCM (2×50 mL). The combined organic extracts were dried over anhydrous Na₂SO₄, filtered, and concentrated under reduced pressure. The crude residue obtained was purified by column chromatography to give 3-fluoro-4-(1-methylcyclobutyl)phenol. This compound was carried forward to the next step without further characterization.

Step d: To a solution of 3-fluoro-4-(1-methylcyclobutyl)phenol (1.3 g, 7.2 mmol, 1 eq) and TEA (1.4 g, 14.4 mmol, 2.01 mL, 2 eq) in DCM (15 mL) at 0° C. was added Tf₂O (2.44 g, 8.66 mmol, 1.43 mL, 1.2 eq). The resulting mixture was stirred at 0° C. for 1 h. The reaction mixture was then warmed to 20° C. and stirred for 1 h. The reaction mixture was then diluted with DCM (22 ml) and washed with H₂O (20 mL). The organic solution was then dried over anhydrous Na₂SO₄, filtered, and concentrated under reduced pressure. The crude residue obtained was purified by column chromatography to give 3-fluoro-4-(1-methylcyclobutyl)phenyl trifluoromethanesulfonate. This compound was carried forward to the next step without further characterization.

Step e: To a solution of 3-fluoro-4-(1-methylcyclobutyl)phenyl trifluoromethanesulfonate (2.2 g, 7.0 mmol, 1 eq), Na₂CO₃ (1.49 g, 14.09 mmol, 2 eq), and TESH (1.64 g, 14.1 mmol, 2.25 mL, 2 eq) in DMF (40 mL) was added Pd(dppf)Cl₂ (515 mg, 704 μmol, 0.1 eq). The resulting mixture was then placed under CO atmosphere (50 psi), warmed to 70° C., and stirred for 4 h. The reaction mixture was then cooled to 20° C. and diluted with ethyl acetate (50 mL). The organic solution was then washed with H₂O (20 mL), dried over anhydrous Na₂SO₄, filtered, and concentrated under reduced pressure. The crude residue obtained was purified by column chromatography to give 3-fluoro-4-(1-methylcyclobutyl)benzaldehyde.

Intermediate A-44:
4-cyclobutyl-3-fluorobenzaldehyde

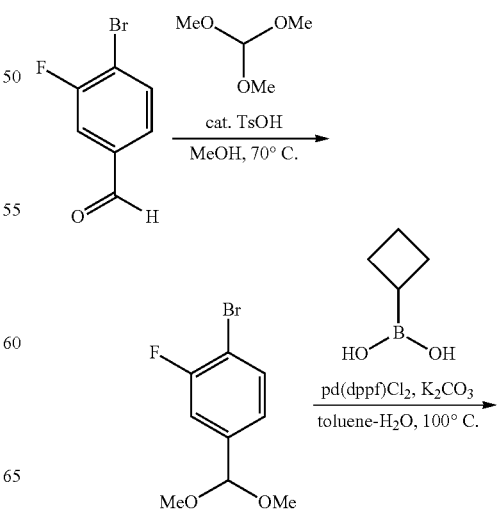

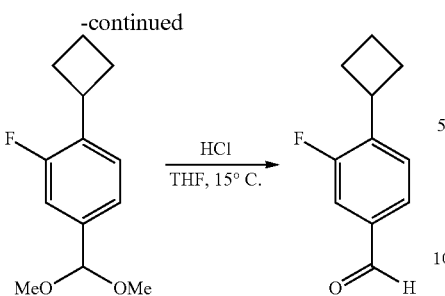

Step a: To a solution of 4-bromo-3-fluorobenzaldehyde (5 g, 24.63 mmol, 1 eq) and 4-methylbenzenesulfonic acid (848 mg, 4.93 mmol, 0.2 eq) in MeOH (50 mL) was added trimethyl orthoformate (5.23 g, 49.3 mmol, 5.40 mL, 2 eq). The resulting mixture was warmed to 70° C. and stirred for 1 h. The reaction mixture was then poured into ice-water (150 mL) and stirred for 3 min. The resulting biphasic mixture was extracted with ethyl acetate (3×80 mL). The combined organic extracts were washed with brine (100 mL), dried over anhydrous $Na_2SO_4$, filtered, and concentrated under reduced pressure to give 1-bromo-4-(dimethoxymethyl)-2-fluorobenzene. LC-MS (ESI): m/z: [M–OMe]+ calculated for $C_9H_{10}BrFO_2$: 217.0; found 217.0.

Step b: To a solution of 1-bromo-4-(dimethoxymethyl)-2-fluorobenzene (1.4 g, 5.62 mmol, 1 eq), cyclobutylboronic acid (5.62 g, 56.2 mmol, 10 eq), and $K_2CO_3$ (1.55 g, 11.2 mmol, 2 eq) in toluene (12 mL) and $H_2O$ (3 mL) under $N_2$ was added Pd(dppf)Cl$_2$·CH$_2$Cl$_2$ (918 mg, 1.12 mmol, 0.2 eq). The resulting mixture was warmed to 100° C. and stirred for 1 h. The reaction mixture was then poured into ice-water and stirred for 3 min. The resulting biphasic mixture was extracted with ethyl acetate (3×80 mL). The combined organic extracts were washed with brine (100 mL), dried over anhydrous $Na_2SO_4$, filtered, and concentrated under reduced pressure. The crude residue obtained was purified by column chromatography to give 1-cyclobutyl-4-(dimethoxymethyl)-2-fluorobenzene, which was carried forward to the next step without further characterization.

Step c: To a solution of 1-cyclobutyl-4-(dimethoxymethyl)-2-fluorobenzene (1 g, 4.46 mmol, 1 eq) in THF (5 mL) at 15° C. was added aq. HCl (1 M, 10.00 mL, 2.24 eq). The resulting mixture was stirred at 15° C. for 1 h. The mixture was poured into ice-water (30 mL) and stirred for 2 min. The resulting biphasic mixture was extracted with ethyl acetate (3×20 mL). The combined organic extracts were washed with brine (20 mL), dried over anhydrous $Na_2SO_4$, filtered, and concentrated under reduced pressure to give 4-cyclobutyl-3-fluorobenzaldehyde, which was used without further purification. LC-MS (ESI): m/z: [M+H]+ calculated for $C_{11}H_{11}FO$: 179.1; found 179.1.

Intermediate A-45:
4-(sec-butyl)-3-fluorobenzaldehyde

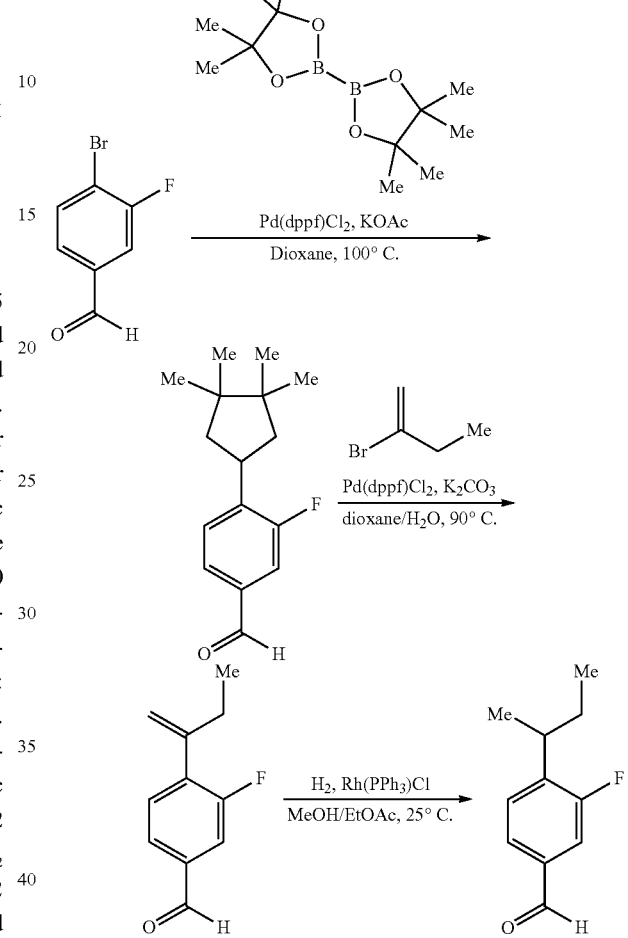

Step a: To a mixture of 4-bromo-3-fluorobenzaldehyde (5.00 g, 24.6 mmol, 1 eq), KOAc (6.04 g, 61.6 mmol, 2.5 eq), and bis(pinacolato)diboron (7.51 g, 29.6 mmol, 1.2 eq) in dioxane (50 mL) was added Pd(dppf)Cl$_2$ (1.80 g, 2.46 mmol, 0.1 eq). The resulting mixture was degassed and purged with $N_2$. The reaction mixture was then warmed to 100° C. and stirred for 3 h. The reaction mixture was then filtered, and the filter cake was washed with 10:1 EtOAc/MeOH (3×200 mL). The combined filtrate and washes were concentrated under reduced pressure. The crude residue obtained was poured into $H_2O$ (100 mL), adjusted to pH=10 with sat. aqueous $Na_2CO_3$, and extracted with ethyl acetate (3×100 mL). The organic extracts were discarded. The aqueous phase was then adjusted to pH=4 with aq. HCl (4M) and extracted with EtOAc (3×100 mL). The combined organic extracts were dried over anhydrous $Na_2SO_4$, filtered, and concentrated under reduced pressure to give 3-fluoro-4-(4,4,5,5-tetramethyl-1,3,2-dioxaborolan-2-yl)benzaldehyde, which was carried forward to the next step without further characterization.

Step b: To a mixture of 3-fluoro-4-(4,4,5,5-tetramethyl-1,3,2-dioxaborolan-2-yl)benzaldehyde (3.00 g, 12.0 mmol, 1 eq), 2-bromobut-1-ene (1.62 g, 12.0 mmol, 1 eq), and K₂CO₃ (3.32 g, 24.0 mmol, 2 eq) in dioxane (60 mL) and H₂O (6 mL) was added Pd(dppf)Cl₂ (439 mg, 600 µmol, 0.05 eq). The reaction was degassed and purged with N₂. The resulting mixture was then warmed to 90° C. and stirred for 16 h. The reaction mixture was then cooled, filtered, and concentrated under reduced pressure. The crude residue obtained was purified by column chromatography to give 4-(but-1-en-2-yl)-3-fluorobenzaldehyde, which was carried forward to the next step without further characterization.

Step c: To a solution of 4-(but-1-en-2-yl)-3-fluorobenzaldehyde (1.70 g, 9.54 mmol, 1 eq) in MeOH (20 mL) and ethyl acetate (20 mL) was added Rh(PPh₃)₃Cl (883 mg, 954 µmol, 0.1 eq) under N₂. The resulting suspension was degassed under vacuum and purged with H₂. The resulting mixture was then stirred under H₂ (15 psi) at 25° C. for 2 h. The reaction mixture was then filtered through a pad of Celite, and the filtrate was concentrated under reduced pressure. The crude residue obtained was purified by column chromatography to give 4-(sec-butyl)-3-fluorobenzaldehyde. LC-MS (ESI): m/z: [M+H]⁺ calculated for C₁₁H₁₃FO: 181.1; found 181.1.

Intermediate A-46: 5-cyclobutylpicolinaldehyde

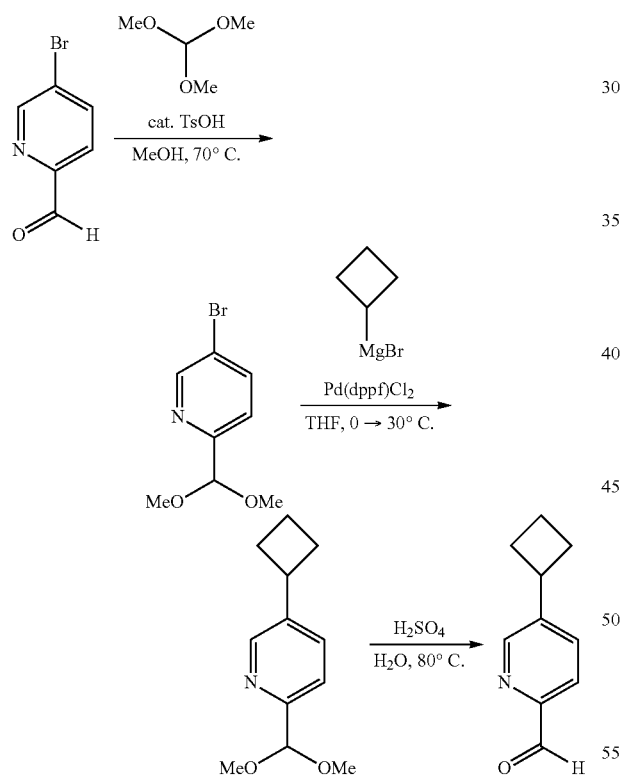

Step a: To a solution of 5-bromopicolinaldehyde (20 g, 107.52 mmol, 1 eq) and trimethyl orthoformate (22.8 g, 215.05 mmol, 23.6 mL, 2 eq) in MeOH (50 mL) at 0° C. was added 4-methylbenzenesulfonic acid (3.70 g, 21.50 mmol, 0.2 eq) in MeOH (5 mL). The resulting mixture was warmed to 70° C. and stirred for 1 h. The reaction solution was then cooled and quenched with sat. aqueous NaHCO₃ to reach pH=7. The resulting biphasic mixture was then extracted with EtOAc (2×200 mL). The combined organic extracts were washed with brine (100 mL), dried over anhydrous Na₂SO₄, filtered, and concentrated under reduced pressure to give 5-bromo-2-(dimethoxymethyl)pyridine. LC-MS (ESI): m/z: [M−OMe]⁺ calculated for C₈H₁₀BrNO₂: 200.0; found 200.1.

Step b: To a mixture of 5-bromo-2-(dimethoxymethyl)pyridine (2.5 g, 10.77 mmol, 1 eq) and Pd(dppf)Cl₂ (394 mg, 538.62 µmol, 0.05 eq) in THF (2 mL) at 0° C. was added cyclobutylmagnesium bromide (0.5 M, 86.2 mL, 4 eq). The resulting mixture was warmed to 30° C. and stirred for 16 h. The reaction mixture was then diluted with water and extracted with EtOAc (150 mL). The organic extracts were washed with brine (150 mL), dried over anhydrous Na₂SO₄, filtered, and concentrated under reduced pressure. The crude residue obtained was purified by column chromatography to give 5-cyclobutyl-2-(dimethoxymethyl)pyridine, which was carried forward to the next step without further characterization.

Step c: To a solution of 5-cyclobutyl-2-(dimethoxymethyl)pyridine (0.9 g, 4.34 mmol, 1 eq) in H₂O (9 mL) was added H₂SO₄ (5 M, 1.04 mL, 1.2 eq). The resulting mixture was warmed to 80° C. and stirred for 2 h. The reaction mixture was then adjusted to pH=7 with sat. aqueous NaHCO₃. The resulting biphasic mixture was then extracted with EtOAc (80 mL). The organic extracts were washed with brine (100 mL), dried over anhydrous Na₂SO₄, filtered, and concentrated under reduced pressure to give 5-cyclobutylpicolinaldehyde. LC-MS (ESI): m/z: [M+H]⁺ calculated for C₁₀H₁₁NO: 162.1; found 162.1.

Intermediate A-47: (2S,4R,5S)-1-(tert-butoxycarbonyl)-4-fluoro-5-methylpyrrolidine-2-carboxylic acid

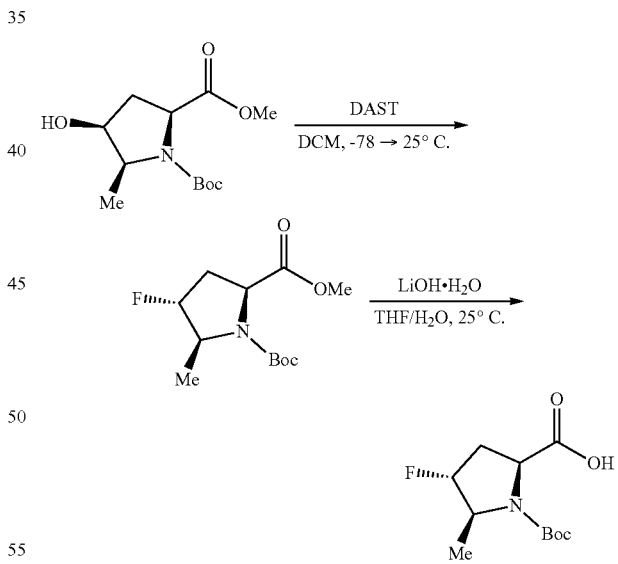

Step a: To a mixture of 1-(tert-butyl) 2-methyl (2S,4S,5S)-4-hydroxy-5-methylpyrrolidine-1,2-dicarboxylate (150 mg, 0.57 mmol, 1 eq) in DCM (4 mL) at −78° C. under N₂ atmosphere was added DAST (466 mg, 2.89 mmol, 5 eq) in a dropwise manner. The resulting mixture was warmed to 25° C. and stirred for 16 h. The reaction mixture was then diluted with H₂O (10 mL) and extracted with EtOAc (3×10 mL). The combined organic extracts were washed with brine (5 mL), dried over anhydrous Na₂SO₄, filtered, and concentrated under reduced pressure to give 1-(tert-butyl) 2-methyl (2S,4R,5S)-4-fluoro-5-methylpyrrolidine-1,2-dicarboxylate, which was carried forward to the next step without further characterization.

Step b: To a mixture of 1-(tert-butyl) 2-methyl (2S,4R,5S)-4-fluoro-5-methylpyrrolidine-1,2-dicarboxylate (40 mg, 0.15 mmol, 1 eq) in THF (2 mL) at 25° C. was added a solution of LiOH·H$_2$O (7 mg, 0.16 mmol, 1.1 eq) in H$_2$O (2 mL). The resulting mixture was stirred at 25° C. for 1 hr. The reaction mixture was then concentrated under reduced pressure. The crude residue was then diluted with water (3 mL) and washed with MTBE (3×5 mL). The aqueous phase was then adjusted to pH=4 with aq. HCl (1 N) and extracted with EtOAc (3×5 mL). The combined organic extracts were washed with brine (5 mL), dried over anhydrous Na$_2$SO$_4$, filtered, and concentrated under reduced pressure to give (2S,4R,5S)-1-(tert-butoxycarbonyl)-4-fluoro-5-methylpyrrolidine-2-carboxylic acid. LC-MS (ESI): m/z: [M−H]$^-$ calculated for C$_{11}$H$_{18}$FNO$_4$: 246.1; found 246.2.

Intermediate A-48: (2S,3RS,4RS)—N—((S)-(5-cyclopropyl-6-fluoropyridin-2-yl)(phenyl)methyl)-4-fluoro-3-hydroxypyrrolidine-2-carboxamide

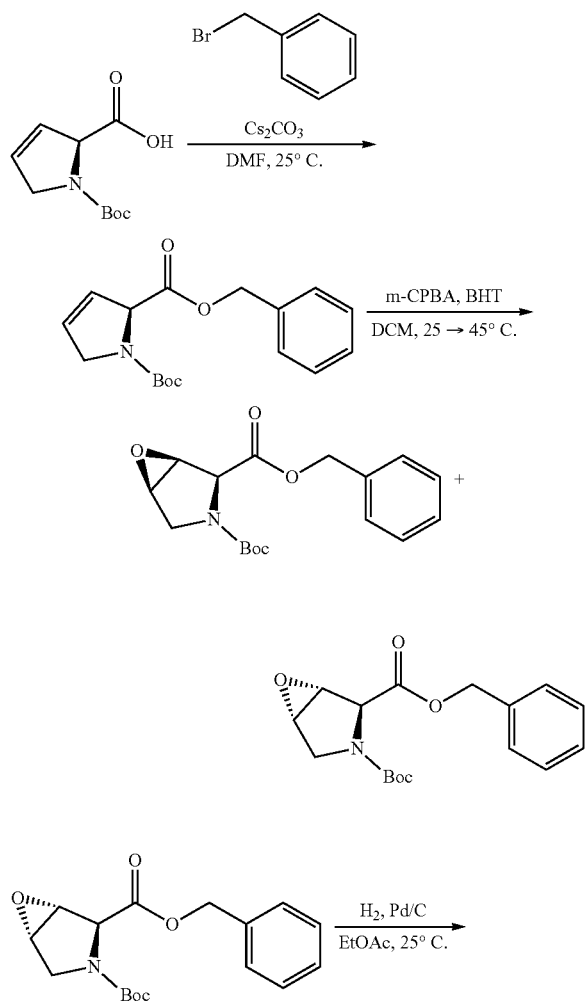

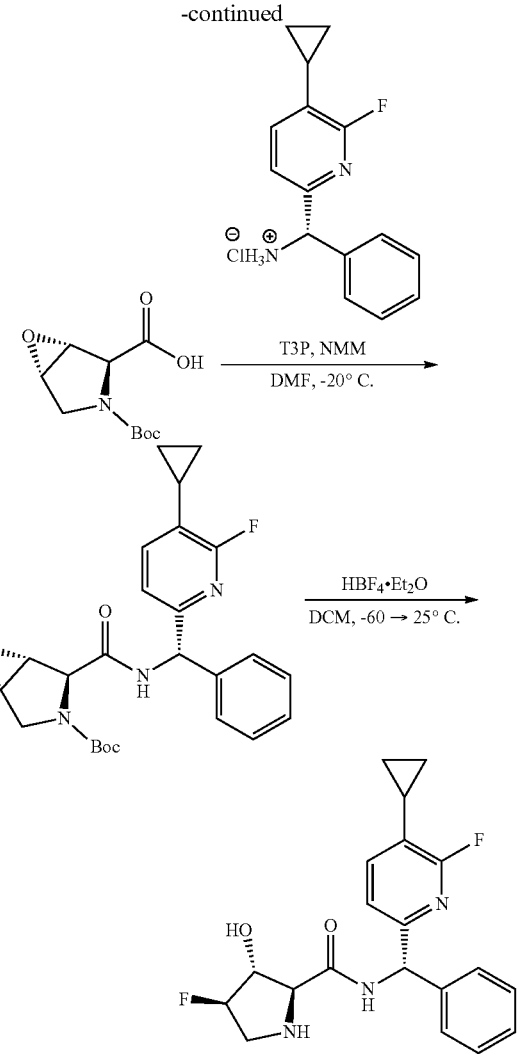

Step a: To a mixture of (S)-1-(tert-butoxycarbonyl)-2,5-dihydro-1H-pyrrole-2-carboxylic acid (9 g, 42.2 mmol, 1 eq) and Cs$_2$CO$_3$ (15.1 g, 46.4 mmol, 1.1 eq) in DMF (100 mL) at 0° C. was added BnBr (8.66 g, 50.6 mmol, 1.2 eq) in a dropwise manner. The resulting suspension was degassed under vacuum and purged with N$_2$. The reaction mixture was then warmed to 25° C. and stirred for 12 h. The reaction mixture was then quenched with H$_2$O (100 mL) and extracted with EtOAc (3×50 mL). The combined organic extracts were washed with brine (50 mL), dried over anhydrous Na$_2$SO$_4$, filtered, and concentrated under reduced pressure. The crude residue obtained was purified by column chromatography to give 2-benzyl 1-(tert-butyl) (S)-2,5-dihydro-1H-pyrrole-1,2-dicarboxylate. LC-MS (ESI): m/z: [M−t-Bu+H+H]$^+$ calculated for C$_{17}$H$_{21}$NO$_4$: 248.1; found 248.1.

Step b: To a solution of 2-benzyl 1-(tert-butyl) (S)-2,5-dihydro-1H-pyrrole-1,2-dicarboxylate (4.7 g, 15.5 mmol, 1 eq) and BHT (341 mg, 1.55 mmol, 0.1 eq) in DCM (200 mL) at 25° C. was added 3-chloroperbenzoic acid (31.5 g, 154 mmol, 85% purity, 10 eq). The reaction was warmed to 45° C. and stirred for 12 h. After cooling to 25° C., the reaction was quenched with saturated aqueous Na$_2$S2O$_3$, and the resulting biphasic mixture extracted with DCM (2×200 mL). The combined organic extracts were washed with brine, dried over anhydrous Na₂SO₄, filtered, and concentrated under reduced pressure. The crude residue obtained was purified by column chromatography and prep-HPLC to give 2-benzyl 3-(tert-butyl) (1S,2S,5R)-6-oxa-3-azabicyclo[3.1.0]hexane-2,3-dicarboxylate and 2-benzyl 3-(tert-butyl) (1R,2S,5S)-6-oxa-3-azabicyclo[3.1.0]hexane-2,3-dicarboxylate as separate diastereomers. LC-MS (ESI): m/z: [M−t-Bu+H+H]⁺ calculated for $C_{17}H_{21}NO_5$: 264.1; found 264.0.

Step c: To a solution of 2-benzyl 3-(tert-butyl) (1R,2S,5S)-6-oxa-3-azabicyclo[3.1.0]hexane-2,3-dicarboxylate (600 mg, 1.88 mmol, 1 eq) in EtOAc (15 mL) was added Pd/C (500 mg, 1.88 mmol, 10% purity, 1.00 eq) under N₂. The resulting suspension was degassed under vacuum and purged with H₂. The resulting mixture was stirred under H₂ (15 psi) at 25° C. for 2 h. The reaction mixture was then filtered and concentrated under reduced pressure to give (1R,2S,5S)-3-(tert-butoxycarbonyl)-6-oxa-3-azabicyclo[3.1.0]hexane-2-carboxylic acid. LC-MS (ESI): m/z: [M−t-Bu+H+H]⁺ calculated for $C_{10}H_{15}NO_5$ 174.0; found 174.1.

Step d: To a solution of (1R,2S,5S)-3-(tert-butoxycarbonyl)-6-oxa-3-azabicyclo[3.1.0]hexane-2-carboxylic acid (430 mg, 1.88 mmol, 1 eq), (S)-(5-cyclopropyl-6-fluoropyridin-2-yl)(phenyl)methanaminium chloride (522 mg, 1.88 mmol, 1 eq), and N-methylmorpholine (NMM, 948 mg, 9.38 mmol, 5 eq) in DMF (5 mL) at −20° C. was added 2,4,6-tripropyl-1,3,5,2,4,6-trioxatriphosphorinane-2,4,6-trioxide (T3P, 1.43 g, 2.25 mmol, 50% purity, 1.2 eq). The resulting mixture was stirred at −20° C. for 1 h. The reaction mixture was then quenched with H₂O (10 mL), and the resulting biphasic mixture was extracted with EtOAc (3×20 mL). The combined organic extracts were washed with brine (5 mL), dried over anhydrous Na₂SO₄, filtered, and concentrated under reduced pressure. The crude residue obtained was purified by column chromatography to give tert-butyl (1R,2S,5S)-2-(((S)-(5-cyclopropyl-6-fluoropyridin-2-yl)(phenyl)methyl)carbamoyl)-6-oxa-3-azabicyclo[3.1.0]hexane-3-carboxylate. LC-MS (ESI): m/z: [M+H]⁺ calculated for $C_{25}H_{28}FN_3O_4$: 454.2; found 454.2.

Step e: To a solution of tert-butyl (1R,2S,5S)-2-(((S)-(5-cyclopropyl-6-fluoropyridin-2-yl)(phenyl)methyl)carbamoyl)-6-oxa-3-azabicyclo[3.1.0]hexane-3-carboxylate (430 mg, 0.95 mmol, 1 eq) in DCM (12 mL) at −60° C. was added tetrafluoroboric acid diethyl ether complex (2.15 g, 6.64 mmol, 50% purity, 7 eq) in a dropwise manner. The resulting mixture was allowed to warm to 25° C. and stirred for 12 h. The mixture was adjusted to pH=7 with saturated aqueous NaHCO₃ and extracted with EtOAc (3×15 mL). The combined organic extracts were washed with brine (15 mL), dried over anhydrous Na₂SO₄, filtered, and concentrated under reduced pressure. The crude residue obtained was purified by prep-TLC to give (2S,3RS,4RS)—N—((S)-(5-cyclopropyl-6-fluoropyridin-2-yl)(phenyl)methyl)-4-fluoro-3-hydroxypyrrolidine-2-carboxamide. LC-MS (ESI): m/z: [M+H]⁺ calculated for $C_{20}H_{21}F_2N_3O_2$: 374.2; found 374.3.

The following compounds in Table B-11 were synthesized using procedures similar to Intermediate A-48 using the appropriate starting materials.

TABLE B-11

| Intermediate No. | Structure | IUPAC | Exact mass (g/mol) | LCMS, Found [M + H]⁺ |
|---|---|---|---|---|
| B-11-1 | 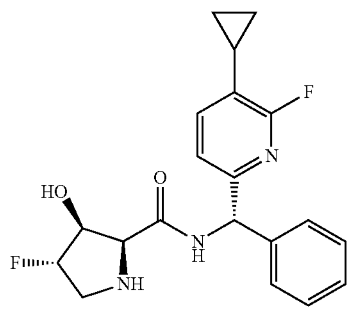 [SMILES: O=C(N[C@@H](c1ccccc1)c1ccc(C2CC2)c(F)n1)[C@H]1NC[C@H](F)[C@H]1O] | (2S,3RS,4RS)-N-((S)-(5-cyclopropyl-6-fluoropyridin-2-yl)(phenyl)methyl)-4-fluoro-3-hydroxypyrrolidine-2-carboxamide | 373.2 | 374.1 |

Intermediate A-49: (3-methyloxetan-3-yl)glycine

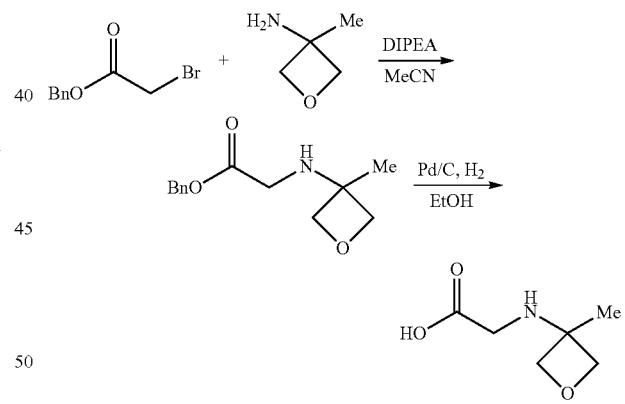

Step a: To a solution of 3-methyloxetan-3-amine (500 mg, 5.74 mmol, 1 eq) in MeCN (10 mL) at 30° C. was added benzyl 2-bromoacetate (2.63 g, 11.5 mmol, 2 eq) and DIPEA (1.48 g, 11.5 mmol, 2 eq) in a dropwise manner. The resulting mixture was stirred at 30° C. for 16 h under N₂. The reaction mixture was then diluted with H₂O (20 mL), and the resulting biphasic mixture was extracted with ethyl acetate (3×20 mL). The combined organic extracts were washed with brine (10 mL), dried over anhydrous Na₂SO₄, filtered, and concentrated under reduced pressure. The crude residue obtained was purified by column chromatography to give benzyl (3-methyloxetan-3-yl)glycinate. LC-MS (ESI): m/z: [M+H]⁺ calculated for $C_{13}H_{17}NO_3$: 236.1; found 236.1.

Step b: To a solution of benzyl (3-methyloxetan-3-yl) glycinate (100 mg, 425 μmol, 1 eq) in EtOH (2 mL) at 20°

C. was added Pd/C (452 mg, 10% purity). The resulting mixture was stirred at 20° C. for 5 h under H₂ (15 Psi). The reaction mixture was then filtered, and the filtrate was concentrated under reduced pressure to give (3-methyloxetan-3-yl)glycine. LC-MS (ESI): m/z: [M–H]⁻ calculated for $C_6H_{11}NO_3$: 144.1; found 144.1.

Intermediate A-50: (1-benzyl-1H-1,2,3-triazol-4-yl)methanesulfonyl chloride

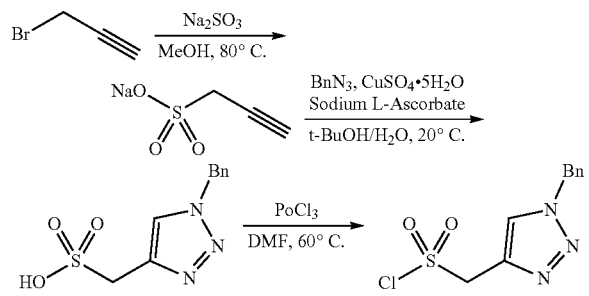

Step a: A mixture of 3-bromoprop-1-yne (25 g, 168 mmol, 80% purity, 1 eq) and Na₂SO₃ (25.4 g, 201 mmol, 1.2 eq) in MeOH (200 mL) was warmed to 80° C. and stirred for 16 h. The reaction mixture was then filtered, and the filtrate was concentrated under reduced pressure. The crude residue obtained was purified by re-crystallization from acetone to obtain sodium prop-2-yne-1-sulfonate, which was carried forward to the next step without further characterization.

Step b: To a mixture of sodium prop-2-yne-1-sulfonate (2 g, 14.0 mmol, 1 eq), sodium L-ascorbate (557 mg, 2.81 mmol, 0.2 eq), and CuSO₄·5H₂O (351 mg, 1.41 mmol, 0.1 eq) in H₂O (10 mL) and t-BuOH (10 mL) at 20° C. was added benzyl azide (BnN₃, 1.97 g, 14.7 mmol, 1.05 eq). The resulting mixture was stirred at 20° C. for 16 h. The reaction mixture was then filtered, and the filtrate was concentrated under reduced pressure. The crude residue obtained was purified by prep-HPLC to give (1-benzyl-1H-1,2,3-triazol-4-yl)methanesulfonic acid. LC-MS (ESI): m/z: [M–H]⁻ calculated for $C_{10}H_{11}N_3O_3S$: 254.0; found 254.0.

Step c: To a mixture of (1-benzyl-1H-1,2,3-triazol-4-yl)methanesulfonic acid (300 mg, 947 µmol, 80% purity, 1 eq) in POCl₃ (7.26 g, 47.4 mmol, 4.4 mL, 50 eq) was added DMF (6.93 mg, 94.8 µmol, 0.1 eq). The resulting mixture was the warmed to 60° C. and stirred for 2 h. The mixture was then concentrated under reduced pressure to give (1-benzyl-1H-1,2,3-triazol-4-yl)methanesulfonyl chloride, which was used without further purification or characterization.

Intermediate A-51: 2-(5-(difluoromethyl)-1,3,4-oxadiazol-2-yl)acetic acid

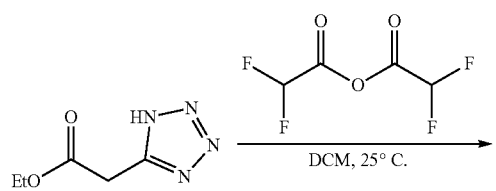

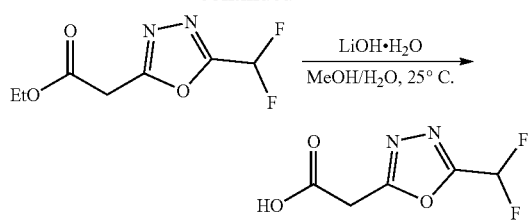

Step a: To a solution of ethyl 2-(1H-tetrazol-5-yl)acetate (1.0 g, 6.40 mmol, 1 eq) in DCM (10 mL) was added 2,2-difluoroacetic anhydride (1.45 g, 8.33 mmol, 1.3 eq). The resulting mixture was stirred at 25° C. for 16 h before it was poured into ice water (20 mL). The resulting biphasic mixture was extracted with EtOAc (3×30 mL). The combined organic extracts were washed with brine (20 mL), dried over anhydrous Na₂SO₄, filtered, and concentrated under reduced pressure. The crude residue obtained was purified by column chromatography to give ethyl 2-(5-(difluoromethyl)-1,3,4-oxadiazol-2-yl)acetate. LC-MS (ESI): m/z: [M+H]⁺ calculated for $C_7H_8F_2N_2O_3$: 207.0; found 207.0.

Step b: To a solution of ethyl 2-(5-(difluoromethyl)-1,3,4-oxadiazol-2-yl)acetate (60 mg, 291 µmol, 1 eq) in MeOH (1 mL) and H₂O (1 mL) was added LiOH·H₂O (13.4 mg, 320 µmol, 1.1 eq). The resulting mixture was stirred at 25° C. for 3 h. The reaction mixture was then poured into ice-water (5 mL), and the pH was adjusted to pH=3 with aqueous HCl (3M). The resulting biphasic mixture was extracted with EtOAc (3×5 mL). The combined organic extracts were dried over anhydrous Na₂SO₄, filtered, and concentrated under reduced pressure to give 2-(5-(difluoromethyl)-1,3,4-oxadiazol-2-yl)acetic acid. LC-MS (ESI): m/z: [M–H]⁻ calculated for $C_5H_4F_2N_2O_3$: 177.0; found 177.1.

Intermediate A-52: (2S,4R)-1-(2-(1H-1,2,3-triazol-5-yl)acetyl)-4-fluoropyrrolidine-2-carboxylic acid

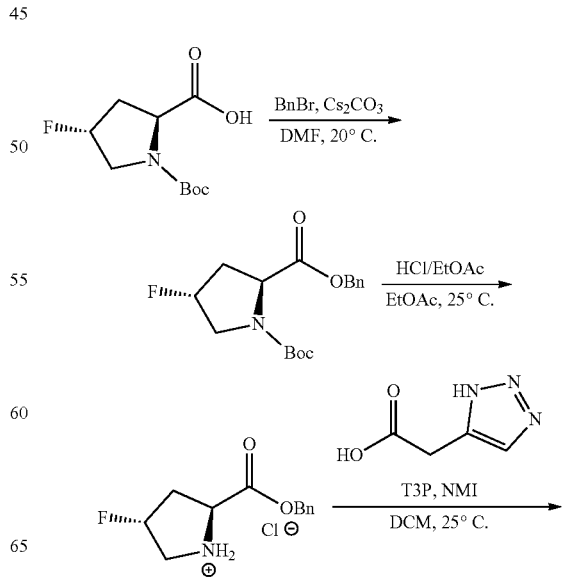

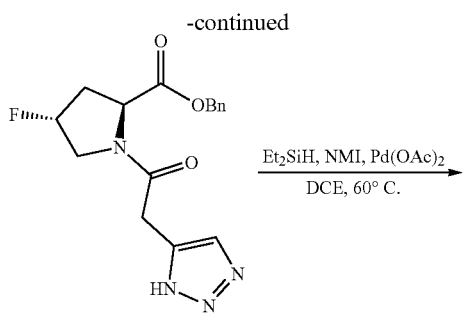

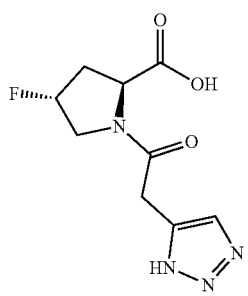

Step a: To a solution of (2S,4R)-1-(tert-butoxycarbonyl)-4-fluoropyrrolidine-2-carboxylic acid (10.0 g, 42.9 mmol, 1 eq) and benzyl bromide (8.80 g, 51.5 mmol, 6.11 mL, 1.2 eq) in DMF (50 mL) at 20° C. was added $Cs_2CO_3$ (21.0 g, 64.3 mmol, 1.5 eq). The resulting mixture was stirred at 20° C. for 12 h before the reaction was quenched by addition of ice-water (100 mL). The resulting biphasic mixture was extracted with EtOAc (3×100 mL). The combined organic extracts were washed with brine (100 mL), dried over anhydrous $Na_2SO_4$, filtered, and concentrated under reduced pressure. The crude residue obtained was triturated with petroleum ether to give 2-benzyl 1-(tert-butyl) (2S,4R)-4-fluoropyrrolidine-1,2-dicarboxylate. LC-MS (ESI): m/z: $[M+Na]^+$ calculated for $C_{17}H_{22}FNO_4$: 346.1; found 346.2.

Step b: To a solution of 2-benzyl 1-(tert-butyl) (2S,4R)-4-fluoropyrrolidine-1,2-dicarboxylate (12.7 g, 39.3 mmol, 1 eq) in EtOAc (50 mL) at 0° C. was added HCl in EtOAc (4 M, 180 mL). The resulting mixture was warmed to 25° C. and stirred for 30 min. The reaction mixture was then filtered, and the filter cake was washed with petroleum ether (3×50 mL) to give (2S,4R)-2-((benzyloxy)carbonyl)-4-fluoropyrrolidin-1-ium chloride. LC-MS (ESI): m/z: $[M+H]^+$ calculated for $C_{12}H_{14}FNO_2$: 224.1; found 224.1.

Step c: To a mixture of (2S,4R)-2-((benzyloxy)carbonyl)-4-fluoropyrrolidin-1-ium chloride (9.55 g, 36.8 mmol, 1 eq), 2-(1H-1,2,3-triazol-5-yl)acetic acid (5.61 g, 44.1 mmol, 1.2 eq) and N-methylimidazole (NMI, 15.1 g, 184 mmol, 5 eq) in DCM (45 mL) at 0° C. was added T3P (35.1 g, 55.1 mmol, 50% purity, 1.5 eq). The resulting mixture was warmed to 25° C. and stirred for 2 h. The reaction mixture was then quenched by addition of $H_2O$ (80 mL), and the resulting biphasic mixture was extracted with EtOAc (3×80 mL). The combined organic extracts were washed with brine (100 mL), dried over anhydrous $Na_2SO_4$, filtered, and concentrated under reduced pressure. The crude residue obtained was triturated with EtOAc to give benzyl (2S,4R)-1-(2-(1H-1,2,3-triazol-5-yl)acetyl)-4-fluoropyrrolidine-2-carboxylate. LC-MS (ESI): m/z: $[M+H]^+$ calculated for $C_{16}H_{17}FN_4O_3$: 333.1; found 333.1.

Step d: To a mixture of benzyl (2S,4R)-1-(2-(1H-1,2,3-triazol-5-yl)acetyl)-4-fluoropyrrolidine-2-carboxylate (6.60 g, 19.9 mmol, 1 eq), $Et_3SiH$ (4.62 g, 39.7 mmol, 6.34 mL, 2 eq), and N-methylimidazole (NMI, 326 mg, 3.97 mmol, 0.2 eq) in DCE (132 mL) at 25° C. under $N_2$ was added $Pd(OAc)_2$ (1.11 g, 4.96 mmol, 0.25 eq). The resulting mixture was warmed to 60° C. and stirred for 6 h. The reaction mixture was then filtered, and the filter cake was washed with EtOAc (3×50 mL). The combined filtrates were concentrated under reduced pressure to give (2S,4R)-1-(2-(1H-1,2,3-triazol-5-yl)acetyl)-4-fluoropyrrolidine-2-carboxylic acid. LC-MS (ESI): m/z: $[M+H]^+$ calculated for $C_9H_{11}FN_4O_3$: 243.1; found 243.1.

The following compounds in Table B-12 were synthesized using procedures similar to Intermediate A-52 using the appropriate starting materials.

TABLE B-12

| Intermediate No. | Structure | IUPAC | Exact mass (g/mol) | LCMS, Found [M + H]+ |
|---|---|---|---|---|
| B-12-1 | 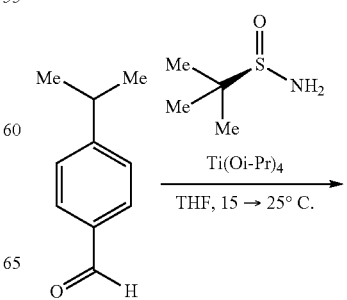 | (2S,4R)-1-acetyl-4-fluoropyrrolidine-2-carboxylic acid | 175.1 | 176.0 |

Example S-1: Synthesis of (2S,4R)-1-(2-(1H-1,2,3-triazol-5-yl)acetyl)-4-fluoro-N—((S)-(4-isopropylphenyl)(phenyl)methyl)pyrrolidine-2-carboxamide Compound 1

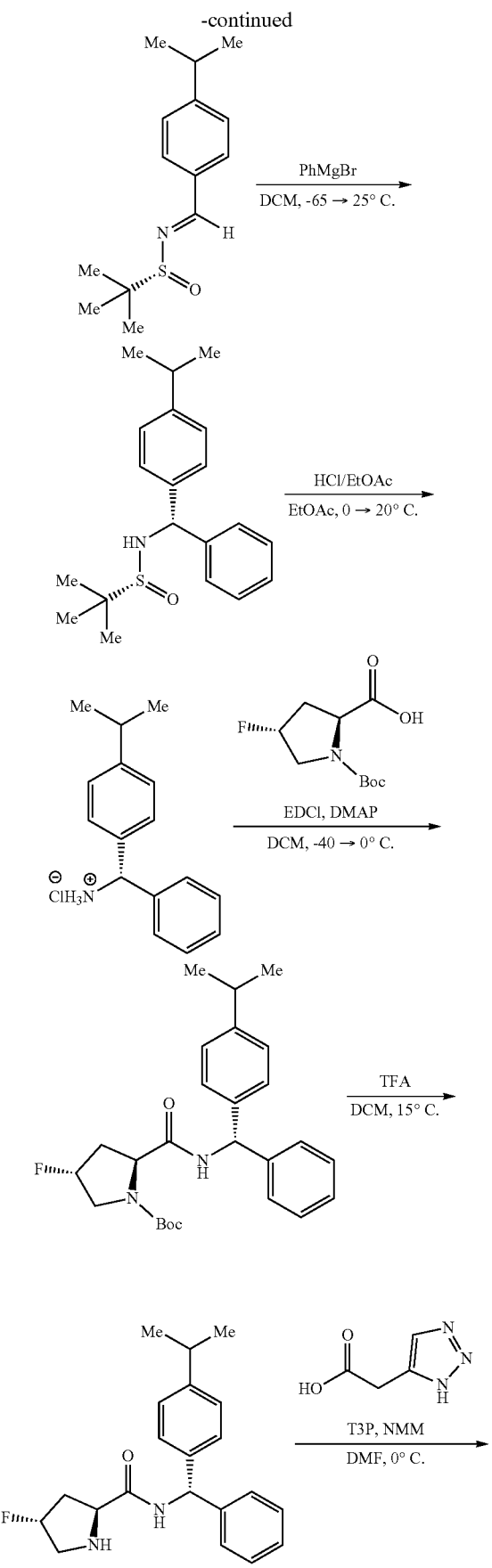

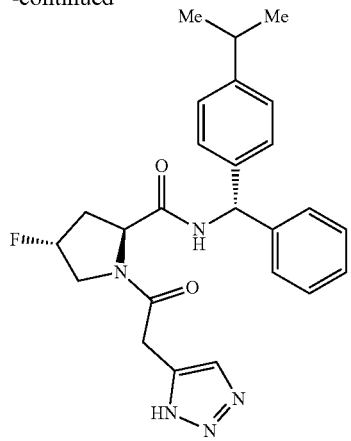

Step a: To a mixture of 4-isopropylbenzaldehyde (25 g, 169 mmol, 25.6 mL, 1 eq) and (R)-2-methylpropane-2-sulfinamide (22.5 g, 186 mmol, 1.1 eq) in THF (150 mL) at 15° C. under $N_2$ was added Ti(OiPr)$_4$ (76.9 g, 337 mmol, 2 eq). The system was degassed and then charged with nitrogen three times. The mixture was then warmed to 25° C. and stirred for 16 h under $N_2$. The reaction was then quenched by addition of $H_2O$ (200 mL) at 0° C. and stirred for 20 min. The resulting mixture was then filtered, and the filter cake was washed with ethyl acetate (2×200 mL). The filtrate was then extracted with ethyl acetate (2×200 mL). The combined organic extracts were washed with saturated aqueous $NH_4Cl$ (200 mL) and brine (200 mL), dried over anhydrous $Na_2SO_4$, filtered, and concentrated under reduced pressure. The resulting residue was purified by column chromatography to give (R,E)-N-(4-isopropylbenzylidene)-2-methylpropane-2-sulfinamide. LC-MS (ESI): m/z: [M+H]$^+$ calculated for $C_{14}H_{21}NOS$: 252.1; found 252.1.

Step b: To a solution of (R,E)-N-(4-isopropylbenzylidene)-2-methylpropane-2-sulfinamide (150 g, 596 mmol, 1.00 eq) in DCM (1500 mL) at −65° C. was added phenylmagnesium bromide (3.00 M in Et$_2$O, 358 mL, 1073 mmol, 1.80 eq). The reaction mixture was warmed to 25° C. and stirred for 30 h. The reaction mixture was then cooled to 0° C. and quenched with saturated aqueous $NH_4Cl$ (2000 mL). The organic phase was isolated and the solvent was removed under reduced pressure to give (R)—N—((S)-(4-isopropylphenyl)(phenyl)methyl)-2-methylpropane-2-sulfinamide, which was used in the next step without further purification. LC-MS (ESI): m/z: [M+H]$^+$ calculated for $C_{20}H_{27}NOS$: 330.2; found 330.3.

Step c: To a solution of (R)—N—((S)-(4-isopropylphenyl)(phenyl)methyl)-2-methylpropane-2-sulfinamide (15 g, 45.5 mmol, 1 eq) in EtOAc (100 mL) at 0° C. was added HCl/EtOAc (4 M, 100 mL). The resulting mixture was then warmed to 20° C. and stirred for 1 h. The reaction mixture was then concentrated under reduced pressure. The resulting crude residue was washed with MTBE (2×80 mL), and the resulting solid was collected by filtration. The solid obtained was dried under reduced pressure to give (S)-(4-isopropylphenyl)(phenyl)methanaminium chloride. LC-MS (ESI): m/z: [M-NH$_2$]$^+$ calculated for $C_{16}H_{19}N$: 209.1; found 209.1.

Step d: To a solution of (S)-(4-isopropylphenyl)(phenyl) methanaminium chloride (15 g, 57.4 mmol, 1 eq) in DCM (150 mL) was added (2S,4R)-1-tert-butoxycarbonyl-4-fluoro-pyrrolidine-2-carboxylic acid (14.7 g, 63.1 mmol, 1.1 eq), DMAP (7.0 g, 57.4 mmol, 1 eq), and EDCI (11.0 g, 57.3 mmol, 1 eq) sequentially at −40° C. The reaction mixture was warmed over 30 min and stirred at 0° C. for 2 h. The reaction was then quenched with H₂O (50 mL) and extracted with ethyl acetate (3×100 mL). The combined organic extracts were washed with brine (100 mL), dried over anhydrous Na₂SO₄, filtered, and concentrated under reduced pressure. The crude residue obtained was purified by column chromatography to give tert-butyl (2S,4R)-4-fluoro-2-(((S)-(4-isopropylphenyl)(phenyl)methyl)carbamoyl)pyrrolidine-1-carboxylate. LC-MS (ESI): m/z: [M+H]⁺ calculated for $C_{26}H_{33}FN_2O_3$: 441.3; found 441.3.

Step e: To a solution of tert-butyl (2S,4R)-4-fluoro-2-(((S)-(4-isopropylphenyl)(phenyl)methyl)carbamoyl)pyrrolidine-1-carboxylate (24 g, 54.47 mmol, 1 eq) in DCM (240 mL) at 15° C. was added TFA (120 mL) in a dropwise manner. The resulting mixture was stirred at 15° C. for 1 h before the reaction mixture was adjusted to pH 5-6 with aq. NaHCO₃ (1 M) and extracted with ethyl acetate (3×150 mL). The combined organic extracts were washed with brine (100 mL), dried over anhydrous Na₂SO₄, filtered, and concentrated under reduced pressure to give (2S,4R)-4-fluoro-N—((S)-(4-isopropylphenyl)(phenyl)methyl)pyrrolidine-2-carboxamide. LC-MS (ESI): m/z: [M+H]⁺ calculated for $C_{21}H_{25}FN_2O$: 341.2; found 341.1.

Step f: To a solution of (2S,4R)-4-fluoro-N—((S)-(4-isopropylphenyl)(phenyl)methyl)pyrrolidine-2-carboxamide (6.5 g, 19.1 mmol, 1 eq) and 2-(1H-1,2,3-triazol-5-yl)acetic acid (Intermediate A-1, 3.64 g, 28.6 mmol, 1.5 eq) in DMF (65 mL) at 0° C. was added NMM (5.79 g, 57.3 mmol, 3 eq) and T3P (18.2 g, 28.6 mmol, 50% in EtOAc, 1.5 eq). The resulting mixture was stirred at 0° C. for 1 h. The reaction mixture was then poured into H₂O (200 mL) and extracted with EtOAc (2×200 mL). The combined organic extracts were washed with brine (200 mL), dried over Na₂SO₄, filtered, and concentrated under reduced pressure. The resulting residue was purified by column chromatography and SFC to give (2S,4R)-1-(2-(1H-1,2,3-triazol-5-yl)acetyl)-4-fluoro-N—((S)-(4-isopropylphenyl)(phenyl)methyl)pyrrolidine-2-carboxamide. ¹H NMR (3:1 rotamer ratio, asterisk denotes distinct minor rotamer peaks, obscured peaks not reported, 400 MHz, DMSO-d6) δ 14.77 (br s, 1H), 9.25*(d, J=8.2 Hz, 1H), 8.87 (d, J=8.4 Hz, 1H), 7.98-7.41 (m, 1H), 7.35-7.26 (m, 4H), 7.26-7.11 (m, 5H), 6.11*(d, J=8.1 Hz, 1H), 6.03 (d, J=8.3 Hz, 1H), 5.48-5.22 (m, 1H), 4.82*(t, J=8.1 Hz, 1H), 4.58 (t, J=8.4 Hz, 1H), 4.13-3.88 (m, 1H), 3.88-3.66 (m, 3H), 3.55-3.38*(m, 1H), 2.92-2.62 (m, 1H), 2.47-2.35 (m, 1H), 2.28-1.89 (m, 1H), 1.18 (d, J=7.0, 1.4 Hz, 6H). LC-MS (ESI): m/z: [M+H]⁺ calculated for $C_{25}H_{28}FN_5O_2$: 450.2; found 450.1.

The following compounds in Table T-1 were synthesized using procedures similar to Compound 1 using the appropriate starting materials.

TABLE T-1

| Compound No. | Structure | IUPAC | Exact mass (g/mol) | LCMS, Found [M + H]⁺ |
|---|---|---|---|---|
| 2 | 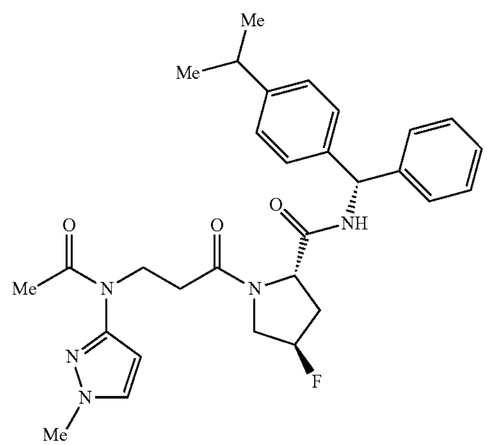 [SMILES: CC(=O)N(CCC(=O)N1C[C@H](F)C[C@H]1C(=O)N[C@@H](c1ccccc1)c1ccc(C(C)C)cc1)c1ccn(C)n1] | (2S,4R)-4-fluoro-1-{3-[N-(1-methyl-1H-pyrazol-3-yl)acetamido]propanoyl}-N-[(2S)-phenyl[4-(propan-2-yl)phenyl]methyl]pyrrolidine-2-carboxamide | 533.3 | 534.3 |
| 3 | 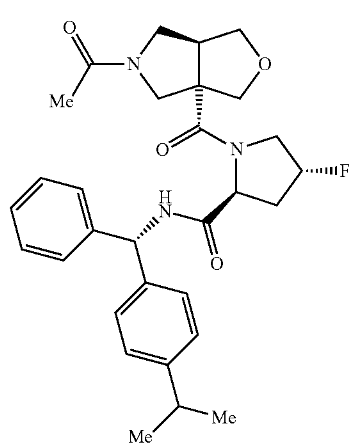 | (2S,4R)-1-[(3aS,6aS)-5-acetyl-hexahydro-1H-furo[3,4-c]pyrrole-3a-carbonyl]-4-fluoro-N-[(S)-phenyl[4-(propan-2-yl)phenyl]methyl]pyrrolidine-2-carboxamide | 521.3 | 522.3 |

TABLE T-1-continued

| Compound No. | Structure | IUPAC | Exact mass (g/mol) | LCMS, Found [M + H]+ |
|---|---|---|---|---|
| 4 | 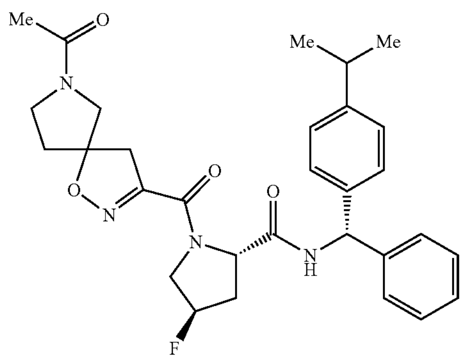 [SMILES: CC(=O)N1CCC2(CC(C(=O)N3C[C@H](F)C[C@H]3C(=O)N[C@@H](c3ccccc3)c3ccc(C(C)C)cc3)=NO2)C1] | (2S,4R)-1-{7-acetyl-1-oxa-2,7-diazaspiro[4.4]non-2-ene-3-carbonyl}-4-fluoro-N-[(S)-phenyl[4-(propan-2-yl)phenyl]methyl]pyrrolidine-2-carboxamide | 534.3 | 535.2 |
| 5 | 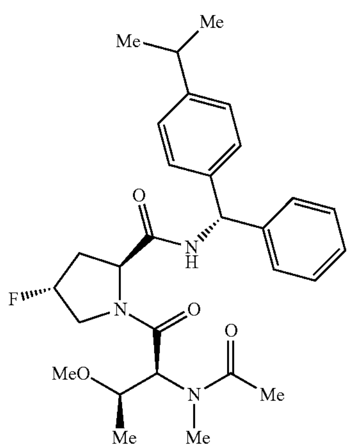 [SMILES: CO[C@H](C)[C@@H](C(=O)N1C[C@H](F)C[C@H]1C(=O)N[C@@H](c1ccccc1)c1ccc(C(C)C)cc1)N(C)C(C)=O] | (2S,4R)-4-fluoro-1-[(2S,3R)-3-methoxy-2-(N-methylacetamido)butanoyl]-N-[(2S)-phenyl[4-(propan-2-yl)phenyl]methyl]pyrrolidine-2-carboxamide | 511.3 | 512.3 |
| 6 | 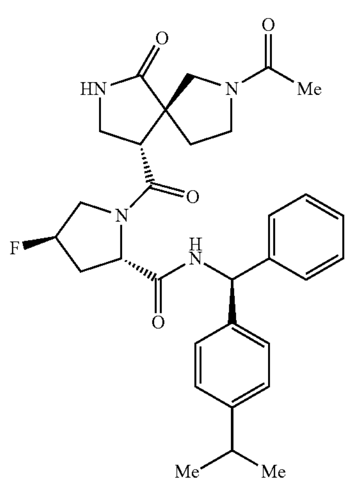 [SMILES: CC(=O)N1CC[C@@]2(C1)C(=O)NC[C@H]2C(=O)N1C[C@H](F)C[C@H]1C(=O)N[C@@H](c1ccccc1)c1ccc(C(C)C)cc1] | (2S,4R)-1-[(4S,5R)-7-acetyl-1-oxo-2,7-diazaspiro[4.4]nonane-4-carbonyl]-4-fluoro-N-[(S)-phenyl[4-(propan-2-yl)phenyl]methyl]pyrrolidine-2-carboxamide | 548.3 | 549.3 |

TABLE T-1-continued

| Compound No. | Structure | IUPAC | Exact mass (g/mol) | LCMS, Found [M + H]+ |
| --- | --- | --- | --- | --- |
| 7 | 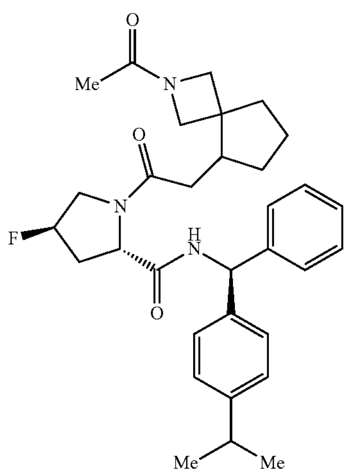 [SMILES: CC(=O)N1CC2(CCCC2CC(=O)N2C[C@H](F)C[C@H]2C(=O)N[C@@H](c2ccccc2)c2ccc(C(C)C)cc2)C1] | (2S,4R)-1-(2-{2-acetyl-2-azaspiro[3.4]octan-5-yl}acetyl)-4-fluoro-N-[(S)-phenyl[4-(propan-2-yl)phenyl]methyl]pyrrolidine-2-carboxamide | 533.3 | 534.3 |
| 8 | 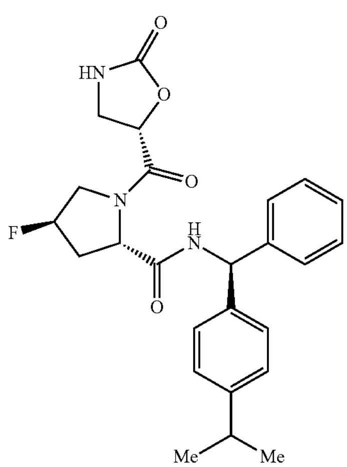 [SMILES: CC(C)c1ccc([C@@H](NC(=O)[C@@H]2C[C@@H](F)CN2C(=O)[C@@H]2CNC(=O)O2)c2ccccc2)cc1] | (2S,4R)-4-fluoro-1-[(5S)-2-oxo-1,3-oxazolidine-5-carbonyl]-N-[(S)-phenyl[4-(propan-2-yl)phenyl]methyl]pyrrolidine-2-carboxamide | 453.2 | 454.3 |
| 9 | 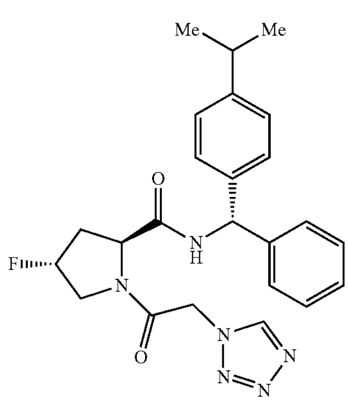 [SMILES: CC(C)c1ccc([C@@H](NC(=O)[C@@H]2C[C@@H](F)CN2C(=O)Cn2cnnn2)c2ccccc2)cc1] | (2S,4R)-4-fluoro-N-[(2S)-phenyl[4-(propan-2-yl)phenyl]methyl]-1-[2-(1H-1,2,3,4-tetrazol-1-yl)acetyl]pyrrolidine-2-carboxamide | 450.2 | 451.3 |

TABLE T-1-continued

| Compound No. | Structure | IUPAC | Exact mass (g/mol) | LCMS, Found [M + H]+ |
| --- | --- | --- | --- | --- |
| 10 | 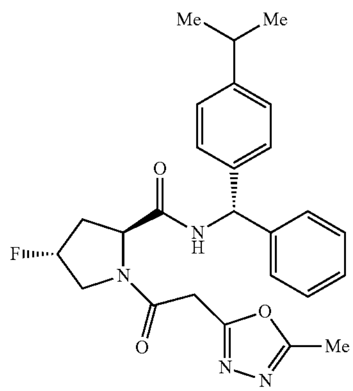 [SMILES: Cc1nnc(CC(=O)N2C[C@H](F)C[C@H]2C(=O)N[C@@H](c2ccccc2)c2ccc(C(C)C)cc2)o1] | (2S,4R)-4-fluoro-1-[2-(5-methyl-1,3,4-oxadiazol-2-yl)acetyl]-N-[(S)-phenyl[4-(propan-2-yl)phenyl]methyl]pyrrolidine-2-carboxamide | 464.2 | 465.2 |
| 11 | 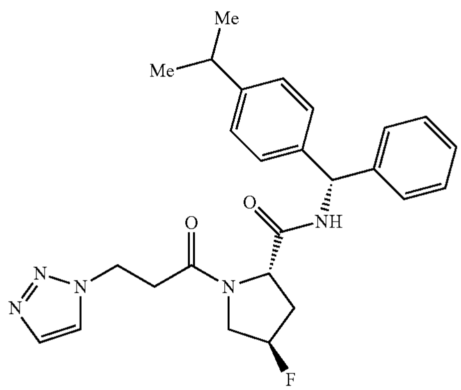 [SMILES: CC(C)c1ccc([C@@H](NC(=O)[C@@H]2C[C@@H](F)CN2C(=O)CCn2ccnn2)c2ccccc2)cc1] | (2S,4R)-4-fluoro-N-[(S)-phenyl[4-(propan-2-yl)phenyl]methyl]-1-[3-(1H-1,2,3-triazol-1-yl)propanoyl]pyrrolidine-2-carboxamide | 463.2 | 464.3 |
| 12 | 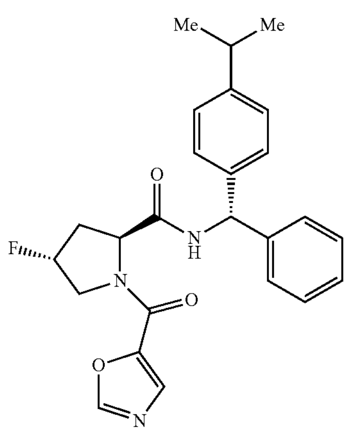 [SMILES: CC(C)c1ccc([C@@H](NC(=O)[C@@H]2C[C@@H](F)CN2C(=O)c2cnco2)c2ccccc2)cc1] | (2S,4R)-4-fluoro-1-(1,3-oxazole-5-carbonyl)-N-[(S)-phenyl[4-(propan-2-yl)phenyl]methyl]pyrrolidine-2-carboxamide | 435.2 | 436.1 |
| 13 | 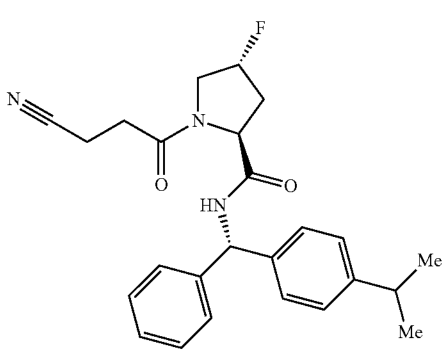 [SMILES: CC(C)c1ccc([C@@H](NC(=O)[C@@H]2C[C@@H](F)CN2C(=O)CCC#N)c2ccccc2)cc1] | (2S,4R)-1-(3-cyanopropanoyl)-4-fluoro-N-[(S)-phenyl[4-(propan-2-yl)phenyl]methyl]pyrrolidine-2-carboxamide | 421.2 | 422.3 |

TABLE T-1-continued

| Compound No. | Structure | IUPAC | Exact mass (g/mol) | LCMS, Found [M + H]+ |
| --- | --- | --- | --- | --- |
| 14 | 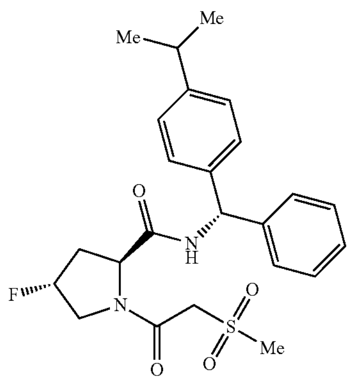 [SMILES: CC(C)c1ccc([C@@H](NC(=O)[C@@H]2C[C@@H](F)CN2C(=O)CS(C)(=O)=O)c2ccccc2)cc1] | (2S,4R)-4-fluoro-1-(2-methanesulfonylacetyl)-N-[(S)-phenyl[4-(propan-2-yl)phenyl]methyl]pyrrolidine-2-carboxamide | 460.2 | 461.1 |
| 15 | 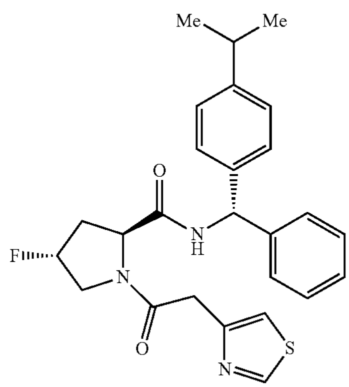 [SMILES: CC(C)c1ccc([C@@H](NC(=O)[C@@H]2C[C@@H](F)CN2C(=O)Cc2cscn2)c2ccccc2)cc1] | (2S,4R)-4-fluoro-N-[(S)-phenyl[4-(propan-2-yl)phenyl]methyl]-1-[2-(1,3-thiazol-4-yl)acetyl]pyrrolidine-2-carboxamide | 465.2 | 466.2 |
| 16 | 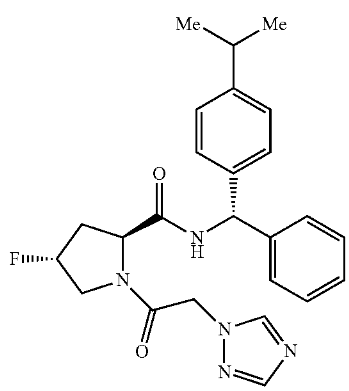 [SMILES: CC(C)c1ccc([C@@H](NC(=O)[C@@H]2C[C@@H](F)CN2C(=O)Cn2cncn2)c2ccccc2)cc1] | (2S,4R)-4-fluoro-N-[(S)-phenyl[4-(propan-2-yl)phenyl]methyl]-1-[2-(1H-1,2,4-triazol-1-yl)acetyl]pyrrolidine-2-carboxamide | 449.2 | 450.2 |
| 17 | 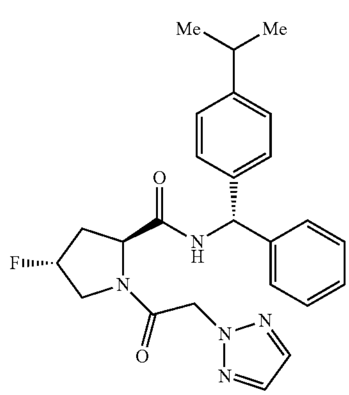 [SMILES: CC(C)c1ccc([C@@H](NC(=O)[C@@H]2C[C@@H](F)CN2C(=O)Cn2nccn2)c2ccccc2)cc1] | (2S,4R)-4-fluoro-N-[(S)-phenyl[4-(propan-2-yl)phenyl]methyl]-1-[2-(2H-1,2,3-triazol-2-yl)acetyl]pyrrolidine-2-carboxamide | 449.2 | 450.3 |

TABLE T-1-continued

| Compound No. | Structure | IUPAC | Exact mass (g/mol) | LCMS, Found [M + H]+ |
|---|---|---|---|---|
| 18 | 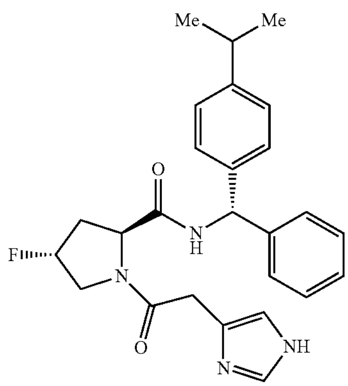 [SMILES: CC(C)c1ccc([C@@H](NC(=O)[C@@H]2C[C@@H](F)CN2C(=O)Cc2c[nH]cn2)c2ccccc2)cc1] | (2S,4R)-4-fluoro-1-[2-(1H-imidazol-4-yl)acetyl]-N-[(S)-phenyl[4-(propan-2-yl)phenyl]methyl]pyrrolidine-2-carboxamide | 448.2 | 449.2 |
| 19 | 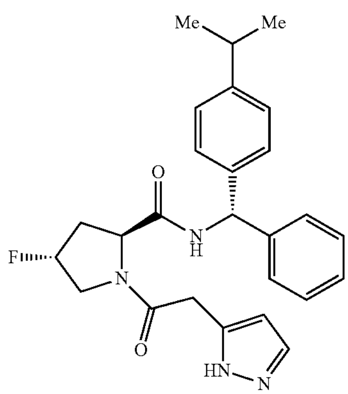 [SMILES: CC(C)c1ccc([C@@H](NC(=O)[C@@H]2C[C@@H](F)CN2C(=O)Cc2ccn[nH]2)c2ccccc2)cc1] | (2S,4R)-4-fluoro-N-[(S)-phenyl[4-(propan-2-yl)phenyl]methyl]-1-[2-(1H-pyrazol-5-yl)acetyl]pyrrolidine-2-carboxamide | 448.2 | 449.3 |
| 20 | 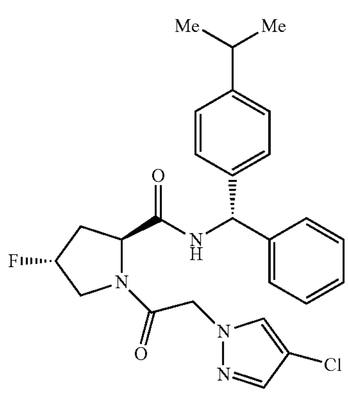 [SMILES: CC(C)c1ccc([C@@H](NC(=O)[C@@H]2C[C@@H](F)CN2C(=O)Cn2cc(Cl)cn2)c2ccccc2)cc1] | (2S,4R)-1-[2-(4-chloro-1H-pyrazol-1-yl)acetyl]-4-fluoro-N-[(S)-phenyl[4-(propan-2-yl)phenyl]methyl]pyrrolidine-2-carboxamide | 482.2 | 483.2 |
| 21 | 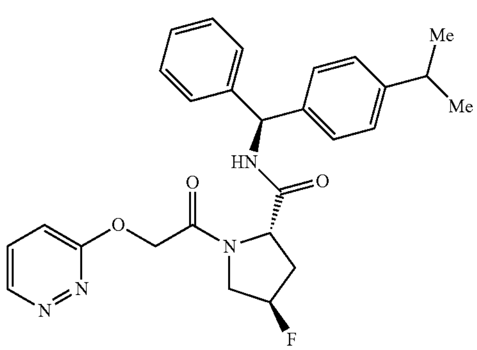 [SMILES: CC(C)c1ccc([C@@H](NC(=O)[C@@H]2C[C@@H](F)CN2C(=O)COc2cccnn2)c2ccccc2)cc1] | (2S,4R)-4-fluoro-N-[(S)-phenyl[4-(propan-2-yl)phenyl]methyl]-1-[2-(pyridazin-3-yloxy)acetyl]pyrrolidine-2-carboxamide | 476.2 | 477.1 |

TABLE T-1-continued

| Compound No. | Structure | IUPAC | Exact mass (g/mol) | LCMS, Found [M + H]+ |
|---|---|---|---|---|
| 22 | 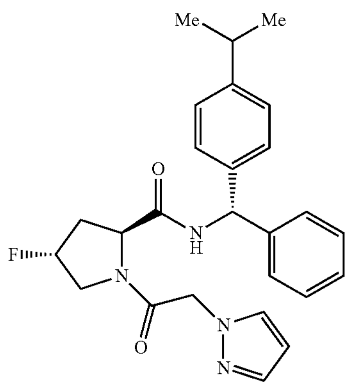 [SMILES: CC(C)c1ccc([C@@H](NC(=O)[C@@H]2C[C@@H](F)CN2C(=O)Cn2cccn2)c2ccccc2)cc1] | (2S,4R)-4-fluoro-N-[(S)-phenyl[4-(propan-2-yl)phenyl]methyl]-1-[2-(1H-pyrazol-1-yl)acetyl]pyrrolidine-2-carboxamide | 448.2 | 449.3 |
| 23 | 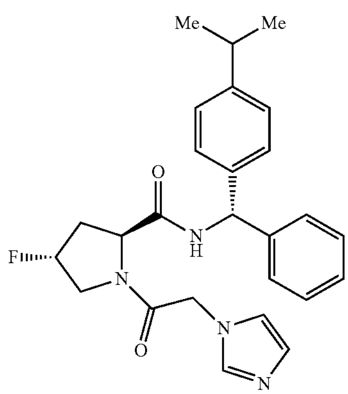 [SMILES: CC(C)c1ccc([C@@H](NC(=O)[C@@H]2C[C@@H](F)CN2C(=O)Cn2ccnc2)c2ccccc2)cc1] | (2S,4R)-4-fluoro-1-[2-(1H-imidazol-1-yl)acetyl]-N-[(S)-phenyl[4-(propan-2-yl)phenyl]methyl]pyrrolidine-2-carboxamide | 448.2 | 449.3 |
| 24 | 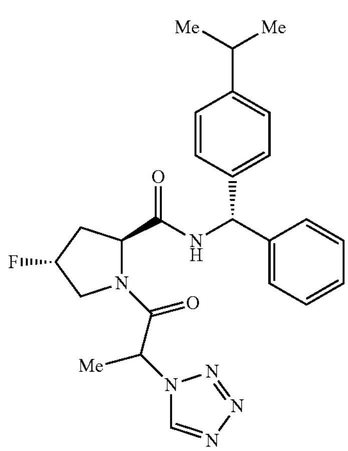 [SMILES: CC(C)c1ccc([C@@H](NC(=O)[C@@H]2C[C@@H](F)CN2C(=O)C(C)n2cnnn2)c2ccccc2)cc1] | (2S,4R)-4-fluoro-N-[(S)-phenyl[4-(propan-2-yl)phenyl]methyl]-1-[2-(1H-1,2,3,4-tetrazol-1-yl)propanoyl]pyrrolidine-2-carboxamide | 464.2 | 465.3 |

TABLE T-1-continued

| Compound No. | Structure | IUPAC | Exact mass (g/mol) | LCMS, Found [M + H]+ |
| --- | --- | --- | --- | --- |
| 25 | 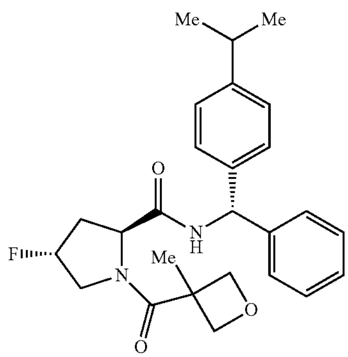 [SMILES: CC(C)c1ccc([C@@H](NC(=O)[C@@H]2C[C@@H](F)CN2C(=O)C2(C)COC2)c2ccccc2)cc1] | (2S,4R)-4-fluoro-1-(3-methyloxetane-3-carbonyl)-N-[(S)-phenyl[4-(propan-2-yl)phenyl]methyl]pyrrolidine-2-carboxamide | 438.2 | 439.3 |
| 26 | 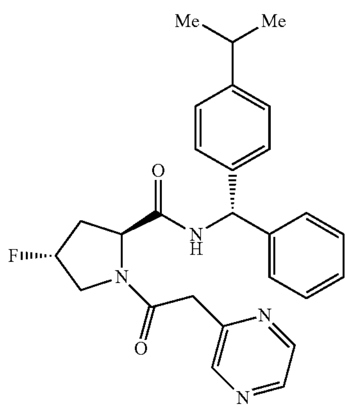 [SMILES: CC(C)c1ccc([C@@H](NC(=O)[C@@H]2C[C@@H](F)CN2C(=O)Cc2cnccn2)c2ccccc2)cc1] | (2S,4R)-4-fluoro-N-[(S)-phenyl[4-(propan-2-yl)phenyl]methyl]-1-[2-(pyrazin-2-yl)acetyl]pyrrolidine-2-carboxamide | 460.2 | 461.2 |
| 27 | 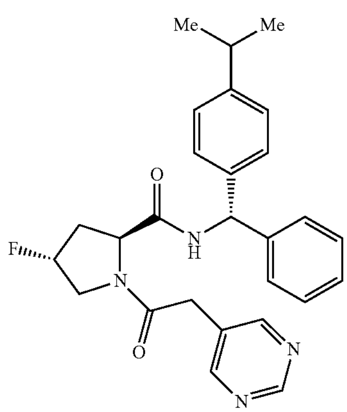 [SMILES: CC(C)c1ccc([C@@H](NC(=O)[C@@H]2C[C@@H](F)CN2C(=O)Cc2cncnc2)c2ccccc2)cc1] | (2S,4R)-4-fluoro-N-[(S)-phenyl[4-(propan-2-yl)phenyl]methyl]-1-[2-(pyrimidin-5-yl)acetyl]pyrrolidine-2-carboxamide | 460.2 | 461.2 |
| 28 | 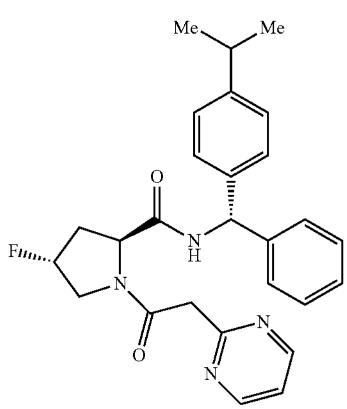 [SMILES: CC(C)c1ccc([C@@H](NC(=O)[C@@H]2C[C@@H](F)CN2C(=O)Cc2ncccn2)c2ccccc2)cc1] | (2S,4R)-4-fluoro-N-[(S)-phenyl[4-(propan-2-yl)phenyl]methyl]-1-[2-(pyrimidin-2-yl)acetyl]pyrrolidine-2-carboxamide | 460.2 | 461.2 |

TABLE T-1-continued

| Compound No. | Structure | IUPAC | Exact mass (g/mol) | LCMS, Found [M + H]+ |
| --- | --- | --- | --- | --- |
| 29 | 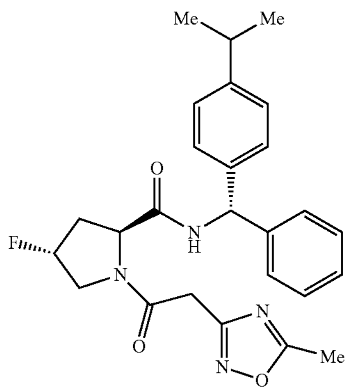 [SMILES: Cc1nc(CC(=O)N2C[C@H](F)C[C@H]2C(=O)N[C@@H](c2ccccc2)c2ccc(C(C)C)cc2)no1] | (2S,4R)-4-fluoro-1-[2-(5-methyl-1,2,4-oxadiazol-3-yl)acetyl]-N-[(S)-phenyl[4-(propan-2-yl)phenyl]methyl]pyrrolidine-2-carboxamide | 464.2 | 465.2 |
| 30 | 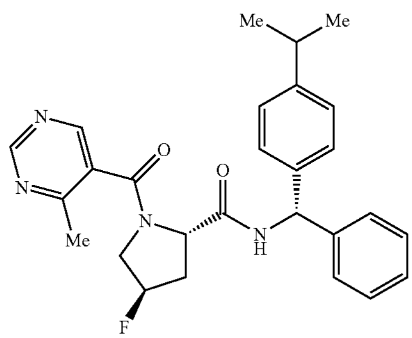 [SMILES: Cc1ncncc1C(=O)N1C[C@H](F)C[C@H]1C(=O)N[C@@H](c1ccccc1)c1ccc(C(C)C)cc1] | (2S,4R)-4-fluoro-1-(4-methylpyrimidine-5-carbonyl)-N-[(S)-phenyl[4-(propan-2-yl)phenyl]methyl]pyrrolidine-2-carboxamide | 460.2 | 461.1 |
| 31 | 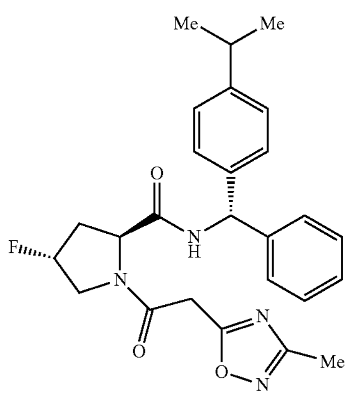 [SMILES: Cc1noc(CC(=O)N2C[C@H](F)C[C@H]2C(=O)N[C@@H](c2ccccc2)c2ccc(C(C)C)cc2)n1] | (2S,4R)-4-fluoro-1-[2-(3-methyl-1,2,4-oxadiazol-5-yl)acetyl]-N-[(S)-phenyl[4-(propan-2-yl)phenyl]methyl]pyrrolidine-2-carboxamide | 464.2 | 465.2 |
| 32 | 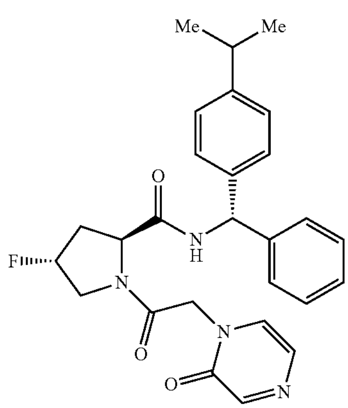 [SMILES: CC(C)c1ccc([C@@H](NC(=O)[C@@H]2C[C@@H](F)CN2C(=O)Cn2ccncc2=O)c2ccccc2)cc1] | (2S,4R)-4-fluoro-1-[2-(2-oxo-1,2-dihydropyrazin-1-yl)acetyl]-N-[(S)-phenyl[4-(propan-2-yl)phenyl]methyl]pyrrolidine-2-carboxamide | 476.2 | 477.0 |

TABLE T-1-continued

| Compound No. | Structure | IUPAC | Exact mass (g/mol) | LCMS, Found [M + H]+ |
| --- | --- | --- | --- | --- |
| 33 | 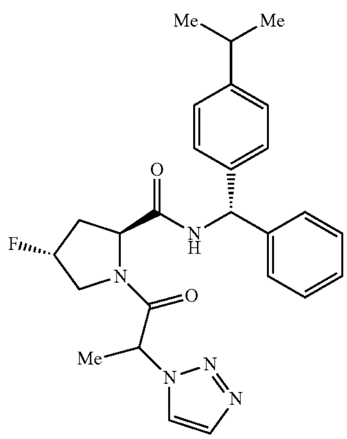 [SMILES: CC(C)c1ccc([C@@H](NC(=O)[C@@H]2C[C@@H](F)CN2C(=O)C(C)n2ccnn2)c2ccccc2)cc1] | (2S,4R)-4-fluoro-N-[(S)-phenyl[4-(propan-2-yl)phenyl]methyl]-1-[2-(1H-1,2,3-triazol-1-yl)propanoyl]pyrrolidine-2-carboxamide | 463.2 | 464.1 |
| 34 | 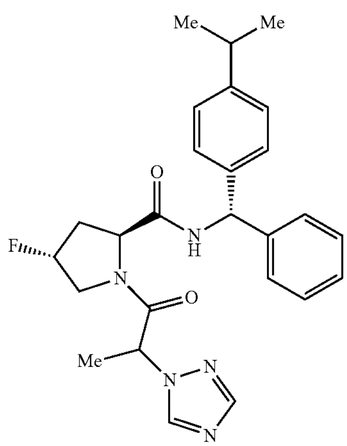 [SMILES: CC(C)c1ccc([C@@H](NC(=O)[C@@H]2C[C@@H](F)CN2C(=O)C(C)n2cncn2)c2ccccc2)cc1] | (2S,4R)-4-fluoro-N-[(S)-phenyl[4-(propan-2-yl)phenyl]methyl]-1-[2-(1H-1,2,4-triazol-1-yl)propanoyl]pyrrolidine-2-carboxamide | 463.2 | 464.3 |
| 35 | 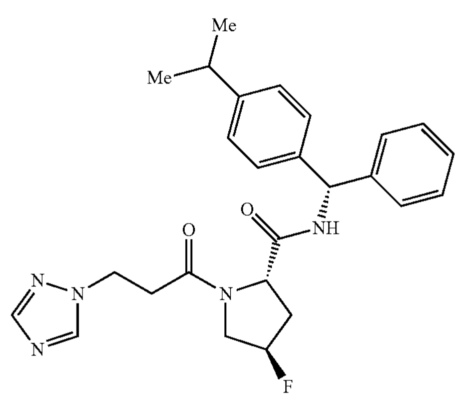 [SMILES: CC(C)c1ccc([C@@H](NC(=O)[C@@H]2C[C@@H](F)CN2C(=O)CCn2cncn2)c2ccccc2)cc1] | (2S,4R)-4-fluoro-N-[(S)-phenyl[4-(propan-2-yl)phenyl]methyl]-1-[3-(1H-1,2,4-triazol-1-yl)propanoyl]pyrrolidine-2-carboxamide | 463.2 | 464.2 |

TABLE T-1-continued

| Compound No. | Structure | IUPAC | Exact mass (g/mol) | LCMS, Found [M + H]+ |
| --- | --- | --- | --- | --- |
| 36 | 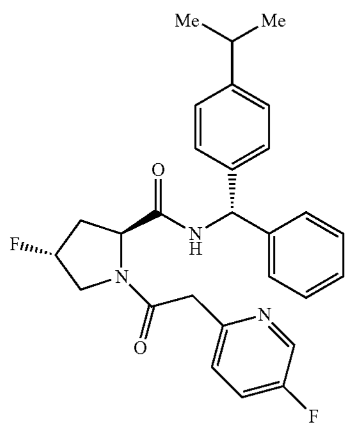 [SMILES: CC(C)c1ccc([C@@H](NC(=O)[C@@H]2C[C@@H](F)CN2C(=O)Cc2ccc(F)cn2)c2ccccc2)cc1] | (2S,4R)-4-fluoro-1-[2-(5-fluoropyridin-2-yl)acetyl]-N-[(S)-phenyl[4-(propan-2-yl)phenyl]methyl]pyrrolidine-2-carboxamide | 477.2 | 478.3 |
| 37 | 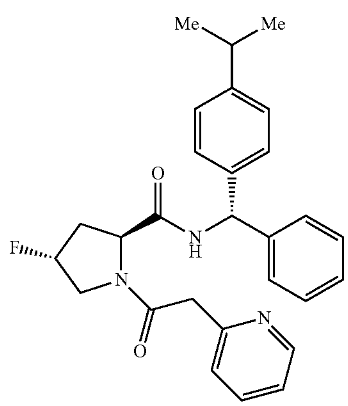 [SMILES: CC(C)c1ccc([C@@H](NC(=O)[C@@H]2C[C@@H](F)CN2C(=O)Cc2ccccn2)c2ccccc2)cc1] | (2S,4R)-4-fluoro-N-[(S)-phenyl[4-(propan-2-yl)phenyl]methyl]-1-[2-(pyridin-2-yl)acetyl]pyrrolidine-2-carboxamide | 459.2 | 460.3 |
| 38 | 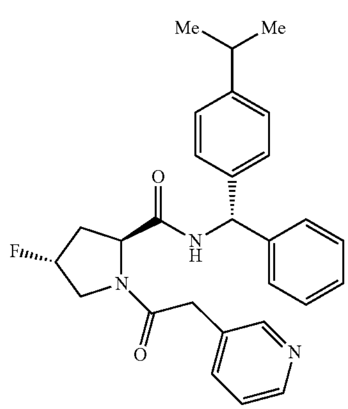 [SMILES: CC(C)c1ccc([C@@H](NC(=O)[C@@H]2C[C@@H](F)CN2C(=O)Cc2cccnc2)c2ccccc2)cc1] | (2S,4R)-4-fluoro-N-[(S)-phenyl[4-(propan-2-yl)phenyl]methyl]-1-[2-(pyridin-3-yl)acetyl]pyrrolidine-2-carboxamide | 459.2 | 460.3 |

TABLE T-1-continued

| Compound No. | Structure | IUPAC | Exact mass (g/mol) | LCMS, Found [M + H]+ |
| --- | --- | --- | --- | --- |
| 39 | 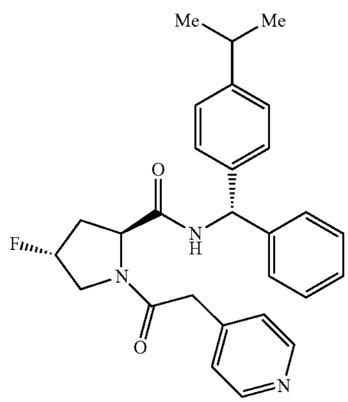 [SMILES: CC(C)c1ccc([C@@H](NC(=O)[C@@H]2C[C@@H](F)CN2C(=O)Cc2ccncc2)c2ccccc2)cc1] | (2S,4R)-4-fluoro-N-[(S)-phenyl[4-(propan-2-yl)phenyl]methyl]-1-[2-(pyridin-4-yl)acetyl]pyrrolidine-2-carboxamide | 459.2 | 460.3 |
| 40 | 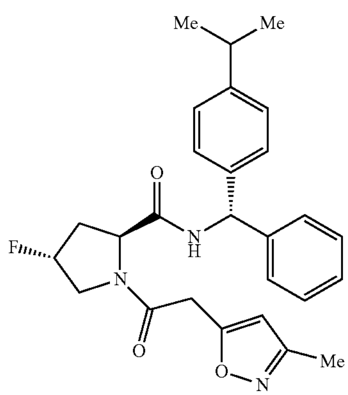 [SMILES: Cc1cc(CC(=O)N2C[C@H](F)C[C@H]2C(=O)N[C@@H](c2ccccc2)c2ccc(C(C)C)cc2)on1] | (2S,4R)-4-fluoro-1-[2-(3-methyl-1,2-oxazol-5-yl)acetyl]-N-[(S)-phenyl[4-(propan-2-yl)phenyl]methyl]pyrrolidine-2-carboxamide | 463.2 | 464.4 |
| 41 | 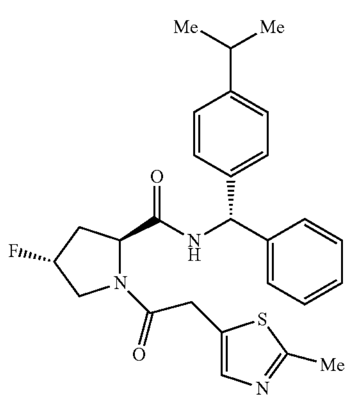 [SMILES: Cc1ncc(CC(=O)N2C[C@H](F)C[C@H]2C(=O)N[C@@H](c2ccccc2)c2ccc(C(C)C)cc2)s1] | (2S,4R)-4-fluoro-1-[2-(2-methyl-1,3-thiazol-5-yl)acetyl]-N-[(S)-phenyl[4-(propan-2-yl)phenyl]methyl]pyrrolidine-2-carboxamide | 479.2 | 480.3 |

TABLE T-1-continued

| Compound No. | Structure | IUPAC | Exact mass (g/mol) | LCMS, Found [M + H]+ |
|---|---|---|---|---|
| 42 | 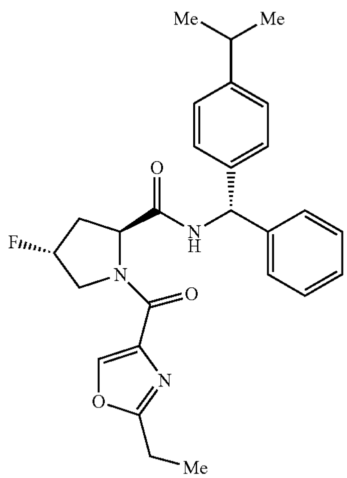 [SMILES: CCc1nc(C(=O)N2C[C@H](F)C[C@H]2C(=O)N[C@@H](c2ccccc2)c2ccc(C(C)C)cc2)co1] | (2S,4R)-1-(2-ethyl-1,3-oxazole-4-carbonyl)-4-fluoro-N-[(S)-phenyl[4-(propan-2-yl)phenyl]methyl]pyrrolidine-2-carboxamide | 463.2 | 464.3 |
| 43 | 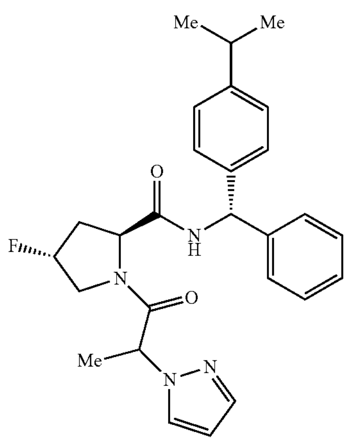 [SMILES: CC(C)c1ccc([C@@H](NC(=O)[C@@H]2C[C@@H](F)CN2C(=O)C(C)n2cccn2)c2ccccc2)cc1] | (2S,4R)-4-fluoro-N-[(S)-phenyl[4-(propan-2-yl)phenyl]methyl]-1-[2-(1H-pyrazol-1-yl)propanoyl]pyrrolidine-2-carboxamide | 462.2 | 463.3 |
| 44 | 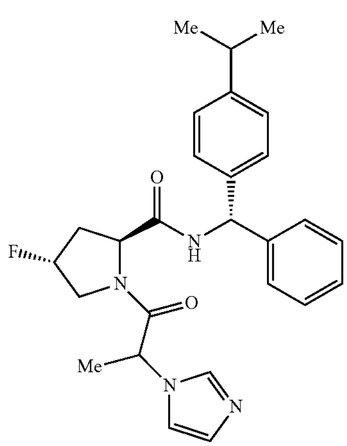 [SMILES: CC(C)c1ccc([C@@H](NC(=O)[C@@H]2C[C@@H](F)CN2C(=O)C(C)n2ccnc2)c2ccccc2)cc1] | (2S,4R)-4-fluoro-1-[2-(1H-imidazol-1-yl)propanoyl]-N-[(S)-phenyl[4-(propan-2-yl)phenyl]methyl]pyrrolidine-2-carboxamide | 462.2 | 463.3 |

TABLE T-1-continued

| Compound No. | Structure | IUPAC | Exact mass (g/mol) | LCMS, Found [M + H]+ |
| --- | --- | --- | --- | --- |
| 45 | 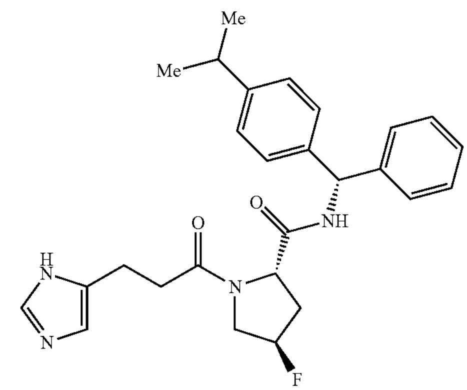 [SMILES: CC(C)c1ccc([C@@H](NC(=O)[C@@H]2C[C@@H](F)CN2C(=O)CCc2cnc[nH]2)c2ccccc2)cc1] | (2S,4R)-4-fluoro-1-[3-(1H-imidazol-5-yl)propanoyl]-N-[(S)-phenyl[4-(propan-2-yl)phenyl]methyl]pyrrolidine-2-carboxamide | 462.2 | 463.2 |
| 46 | 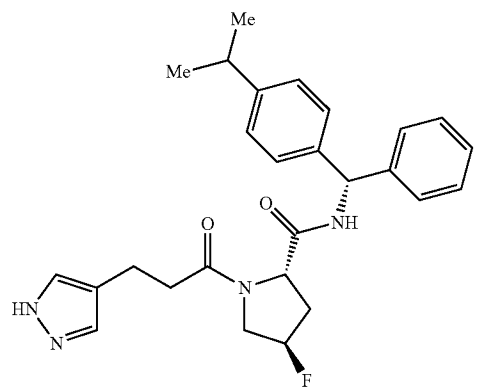 [SMILES: CC(C)c1ccc([C@@H](NC(=O)[C@@H]2C[C@@H](F)CN2C(=O)CCc2cn[nH]c2)c2ccccc2)cc1] | (2S,4R)-4-fluoro-N-[(S)-phenyl[4-(propan-2-yl)phenyl]methyl]-1-[3-(1H-pyrazol-4-yl)propanyl]pyrrolidine-2-carboxamide | 462.2 | 463.3 |
| 47 | 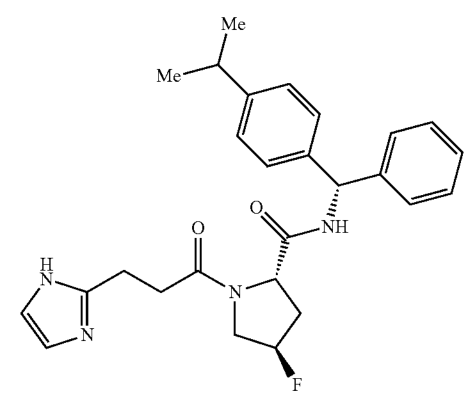 [SMILES: CC(C)c1ccc([C@@H](NC(=O)[C@@H]2C[C@@H](F)CN2C(=O)CCc2ncc[nH]2)c2ccccc2)cc1] | (2S,4R)-4-fluoro-1-[3-(1H-imidazol-2-yl)propanoyl]-N-[(S)-phenyl[4-(propan-2-yl)phenyl]methyl]pyrrolidine-2-carboxamide | 462.2 | 463.2 |
| 48 | 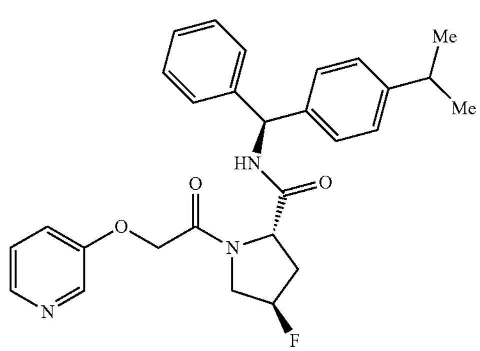 [SMILES: CC(C)c1ccc([C@@H](NC(=O)[C@@H]2C[C@@H](F)CN2C(=O)COc2cccnc2)c2ccccc2)cc1] | (2S,4R)-4-fluoro-N-[(S)-phenyl[4-(propan-2-yl)phenyl]methyl]-1-[2-(pyridin-3-yloxy)acetyl]pyrrolidine-2-carboxamide | 475.2 | 476.3 |

TABLE T-1-continued

| Compound No. | Structure | IUPAC | Exact mass (g/mol) | LCMS, Found [M + H]+ |
| --- | --- | --- | --- | --- |
| 49 | 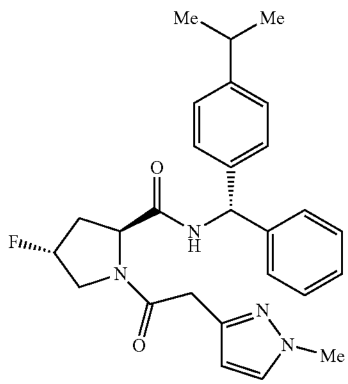 [SMILES: CC(C)c1ccc([C@@H](NC(=O)[C@@H]2C[C@@H](F)CN2C(=O)Cc2ccn(C)n2)c2ccccc2)cc1] | (2S,4R)-4-fluoro-1-[2-(1-methyl-1H-pyrazol-3-yl)acetyl]-N-[(S)-phenyl[4-(propan-2-yl)phenyl]methyl]pyrrolidine-2-carboxamide | 462.2 | 463.3 |
| 50 | 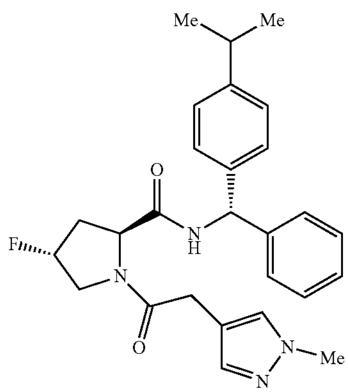 [SMILES: CC(C)c1ccc([C@@H](NC(=O)[C@@H]2C[C@@H](F)CN2C(=O)Cc2cnn(C)c2)c2ccccc2)cc1] | (2S,4R)-4-fluoro-1-[2-(1-methyl-1H-pyrazol-4-yl)acetyl]-N-[(S)-phenyl[4-(propan-2-yl)phenyl]methyl]pyrrolidine-2-carboxamide | 462.2 | 463.3 |
| 51 | 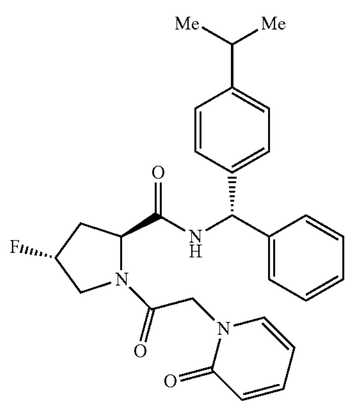 [SMILES: CC(C)c1ccc([C@@H](NC(=O)[C@@H]2C[C@@H](F)CN2C(=O)Cn2ccccc2=O)c2ccccc2)cc1] | (2S,4R)-4-fluoro-1-[2-(2-oxo-1,2-dihydropyridin-1-yl)acetyl]-N-[(S)-phenyl[4-(propan-2-yl)phenyl]methyl]pyrrolidine-2-carboxamide | 475.2 | 476.3 |
| 52 | 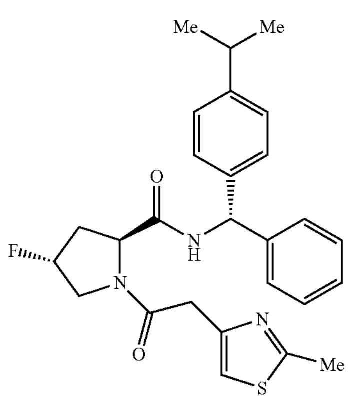 | (2S,4R)-4-fluoro-1-[2-(2-methyl-1,3-thiazol-4-yl)acetyl]-N-[(S)-phenyl[4-(propan-2-yl)phenyl]methyl]pyrrolidine-2-carboxamide | 479.2 | 480.3 |

TABLE T-1-continued

| Compound No. | Structure | IUPAC | Exact mass (g/mol) | LCMS, Found [M + H]+ |
| --- | --- | --- | --- | --- |
| 53 | 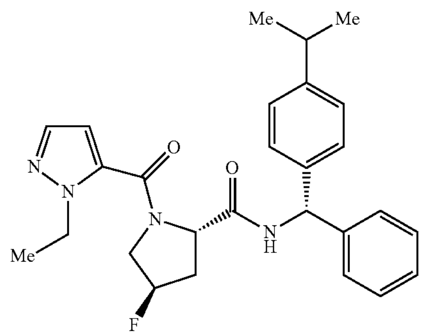 [SMILES: CCn1nccc1C(=O)N1C[C@H](F)C[C@H]1C(=O)N[C@@H](c1ccccc1)c1ccc(C(C)C)cc1] | (2S,4R)-1-(1-ethyl-1H-pyrazole-5-carbonyl)-4-fluoro-N-[(S)-phenyl[4-(propan-2-yl)phenyl]methyl]pyrrolidine-2-carboxamide | 462.2 | 463.3 |
| 54 | 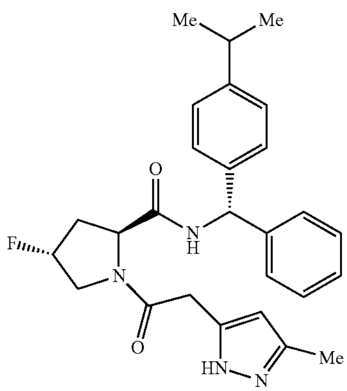 [SMILES: Cc1cc(CC(=O)N2C[C@H](F)C[C@H]2C(=O)N[C@@H](c2ccccc2)c2ccc(C(C)C)cc2)[nH]n1] | (2S,4R)-4-fluoro-1-[2-(3-methyl-1H-pyrazol-5-yl)acetyl]-N-[(S)-phenyl[4-(propan-2-yl)phenyl]methyl]pyrrolidine-2-carboxamide | 462.2 | 463.3 |
| 55 | 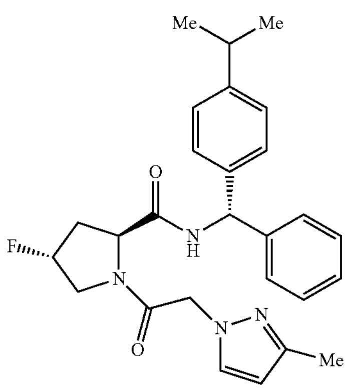 [SMILES: Cc1ccn(CC(=O)N2C[C@H](F)C[C@H]2C(=O)N[C@@H](c2ccccc2)c2ccc(C(C)C)cc2)n1] | (2S,4R)-4-fluoro-1-[2-(3-methyl-1H-pyrazol-1-yl)acetyl]-N-[(S)-phenyl[4-(propan-2-yl)phenyl]methyl]pyrrolidine-2-carboxamide | 462.2 | 463.3 |
| 56 | 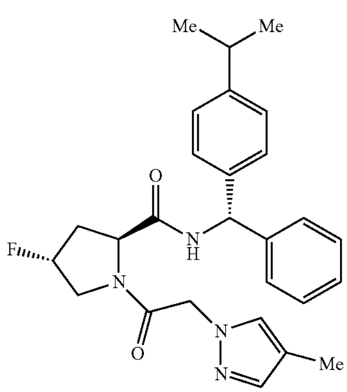 [SMILES: Cc1cnn(CC(=O)N2C[C@H](F)C[C@H]2C(=O)N[C@@H](c2ccccc2)c2ccc(C(C)C)cc2)c1] | (2S,4R)-4-fluoro-1-[2-(4-methyl-1H-pyrazol-1-yl)acetyl]-N-[(S)-phenyl[4-(propan-2-yl)phenyl]methyl]pyrrolidine-2-carboxamide | 462.2 | 463.3 |

TABLE T-1-continued

| Compound No. | Structure | IUPAC | Exact mass (g/mol) | LCMS, Found [M + H]+ |
|---|---|---|---|---|
| 57 | 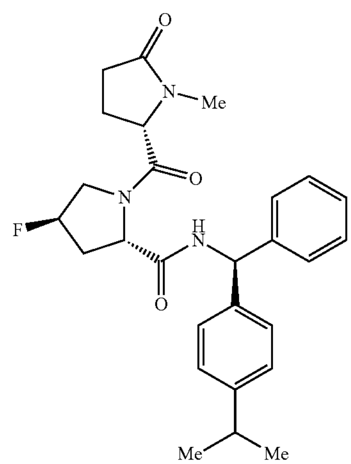 [SMILES: CC(C)c1ccc([C@@H](NC(=O)[C@@H]2C[C@@H](F)CN2C(=O)[C@@H]2CCC(=O)N2C)c2ccccc2)cc1] | (2S,4R)-4-fluoro-1-[(2S)-1-methyl-5-oxopyrrolidine-2-carbonyl]-N-[(S)-phenyl[4-(propan-2-yl)phenyl]methyl]pyrrolidine-2-carboxamide | 465.2 | 466.3 |
| 58 | 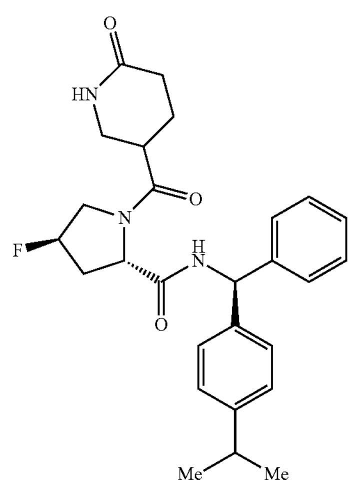 [SMILES: CC(C)c1ccc([C@@H](NC(=O)[C@@H]2C[C@@H](F)CN2C(=O)C2CCC(=O)NC2)c2ccccc2)cc1] | (2S,4R)-4-fluoro-1-(6-oxopiperidine-3-carbonyl)-N-[(S)-phenyl[4-(propan-2-yl)phenyl]methyl]pyrrolidine-2-carboxamide | 465.2 | 466.2 |
| 59 | 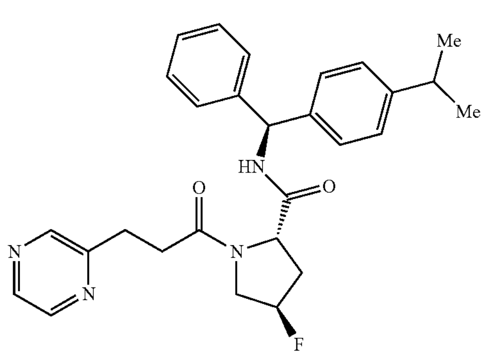 [SMILES: CC(C)c1ccc([C@@H](NC(=O)[C@@H]2C[C@@H](F)CN2C(=O)CCc2cnccn2)c2ccccc2)cc1] | (2S,4R)-4-fluoro-N-[(S)-phenyl[4-(propan-2-yl)phenyl]methyl]-1-[3-(pyrazin-2-yl)propanoyl]pyrrolidine-2-carboxamide | 474.2 | 475.2 |

TABLE T-1-continued

| Compound No. | Structure | IUPAC | Exact mass (g/mol) | LCMS, Found [M + H]+ |
|---|---|---|---|---|
| 60 | 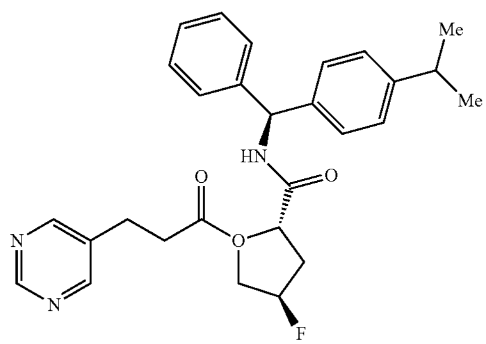 | (2S,4R)-4-fluoro-N-[(S)-phenyl[4-(propan-2-yl)phenyl]methyl]-1-[3-(pyrimidin-5-yl)propanoyl]pyrrolidine-2-carboxamide | 474.2 | 475.2 |
| 61 | 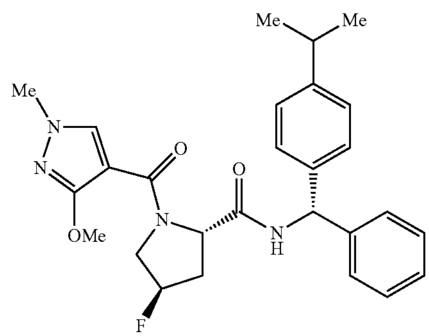 [SMILES: COc1nn(C)cc1C(=O)N1C[C@H](F)C[C@H]1C(=O)N[C@@H](c1ccccc1)c1ccc(C(C)C)cc1] | (2S,4R)-4-fluoro-1-(3-methoxy-1-methyl-1H-pyrazole-4-carbonyl)-N-[(S)-phenyl[4-(propan-2-yl)phenyl]methyl]pyrrolidine-2-carboxamide | 478.2 | 479.3 |
| 62 | 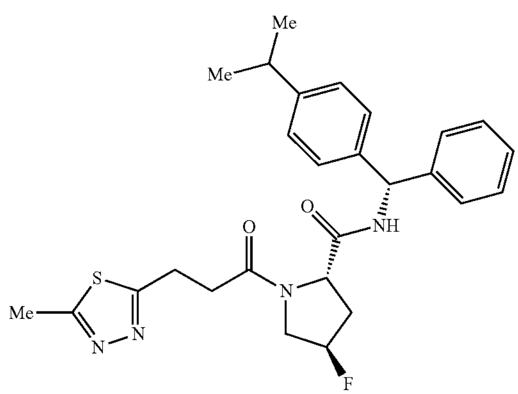 [SMILES: Cc1nnc(CCC(=O)N2C[C@H](F)C[C@H]2C(=O)N[C@@H](c2ccccc2)c2ccc(C(C)C)cc2)s1] | (2S,4R)-4-fluoro-1-[3-(5-methyl-1,3,4-thiadiazol-2-yl)propanoyl]-N-[(S)-phenyl[4-(propan-2-yl)phenyl]methyl]pyrrolidine-2-carboxamide | 494.2 | 495.2 |
| 63 | 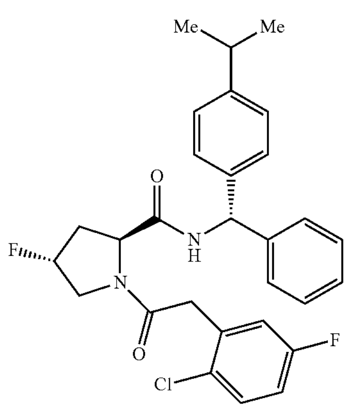 [SMILES: CC(C)c1ccc([C@@H](NC(=O)[C@@H]2C[C@@H](F)CN2C(=O)Cc2cc(F)ccc2Cl)c2ccccc2)cc1] | (2S,4R)-1-[2-(2-chloro-5-fluorophenyl)acetyl]-4-fluoro-N-[(S)-phenyl[4-(propan-2-yl)phenyl]methyl]pyrrolidine-2-carboxamide | 510.2 | 511.3 |

TABLE T-1-continued

| Compound No. | Structure | IUPAC | Exact mass (g/mol) | LCMS, Found [M + H]+ |
|---|---|---|---|---|
| 64 | 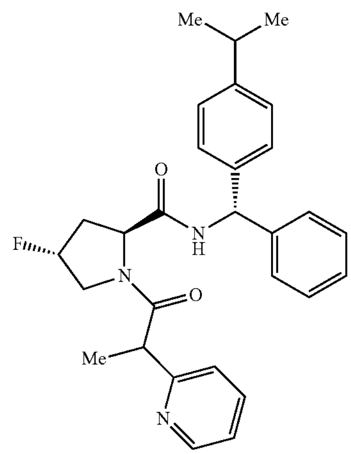 [SMILES: CC(C)c1ccc([C@@H](NC(=O)[C@@H]2C[C@@H](F)CN2C(=O)C(C)c2ccccn2)c2ccccc2)cc1] | (2S,4R)-4-fluoro-N-[(S)-phenyl[4-(propan-2-yl)phenyl]methyl]-1-[2-(pyridin-2-yl)propanoyl]pyrrolidine-2-carboxamide | 473.2 | 474.3 |
| 65 | 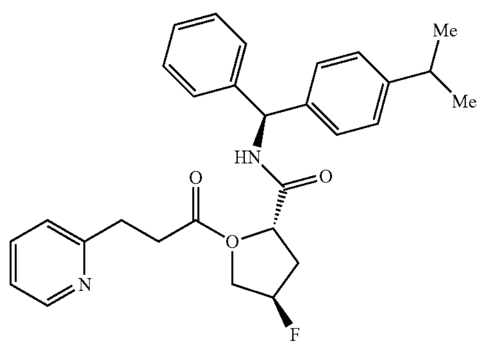 | (2S,4R)-4-fluoro-N-[(S)-phenyl[4-(propan-2-yl)phenyl]methyl]-1-[3-(pyridin-2-yl)propanoyl]pyrrolidine-2-carboxamide | 473.2 | 474.3 |
| 66 | 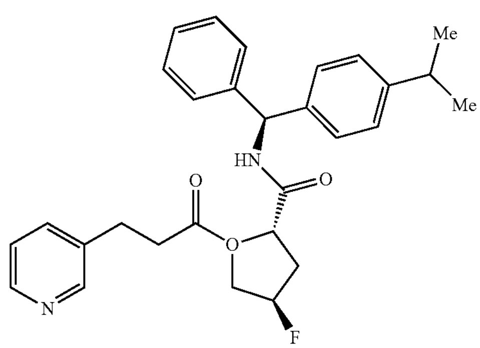 | (2S,4R)-4-fluoro-N-[(S)-phenyl[4-(propan-2-yl)phenyl]methyl]-1-[3-(pyridin-3-yl)propanoyl]pyrrolidine-2-carboxamide | 473.2 | 474.3 |
| 67 | 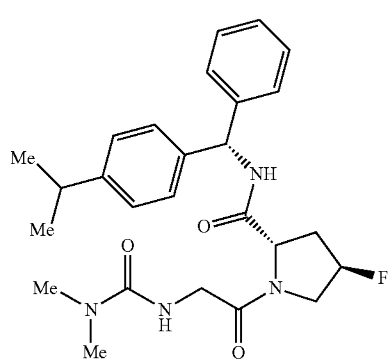 [SMILES: CC(C)c1ccc([C@@H](NC(=O)[C@@H]2C[C@@H](F)CN2C(=O)CNC(=O)N(C)C)c2ccccc2)cc1] | (2S,4R)-1-{2-[(dimethylcarbamoyl)amino]acetyl}-4-fluoro-N-[(S)-phenyl[4-(propan-2-yl)phenyl]methyl]pyrrolidine-2-carboxamide | 468.3 | 469.3 |

TABLE T-1-continued

| Compound No. | Structure | IUPAC | Exact mass (g/mol) | LCMS, Found [M + H]+ |
|---|---|---|---|---|
| 68 | 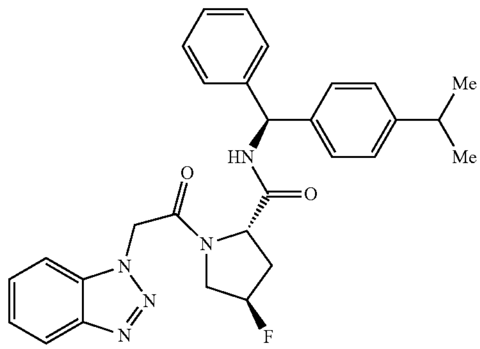 [SMILES: CC(C)c1ccc([C@@H](NC(=O)[C@@H]2C[C@@H](F)CN2C(=O)Cn2nnc3ccccc32)c2ccccc2)cc1] | (2S,4R)-1-[2-(1H-1,2,3-benzotriazol-1-yl)acetyl]-4-fluoro-N-[(S)-phenyl[4-(propan-2-yl)phenyl]methyl]pyrrolidine-2-carboxamide | 499.2 | 500.3 |
| 69 | 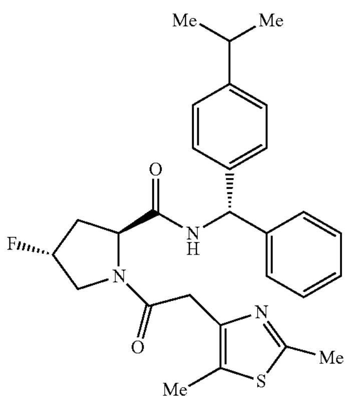 [SMILES: Cc1nc(CC(=O)N2C[C@H](F)C[C@H]2C(=O)N[C@@H](c2ccccc2)c2ccc(C(C)C)cc2)c(C)s1] | (2S,4R)-1-[2-(2,5-dimethyl-1,3-thiazol-4-yl)acetyl]-4-fluoro-N-[(S)-phenyl[4-(propan-2-yl)phenyl]methyl]pyrrolidine-2-carboxamide | 493.2 | 494.3 |
| 70 | 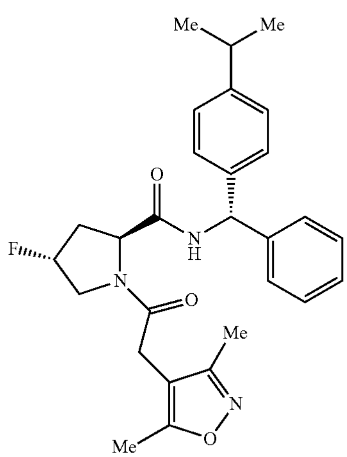 [SMILES: Cc1noc(C)c1CC(=O)N1C[C@H](F)C[C@H]1C(=O)N[C@@H](c1ccccc1)c1ccc(C(C)C)cc1] | (2S,4R)-1-[2-(3,5-dimethyl-1,2-oxazol-4-yl)acetyl]-4-fluoro-N-[(S)-phenyl[4-(propan-2-yl)phenyl]methyl]pyrrolidine-2-carboxamide | 477.2 | 478.3 |
| 71 | 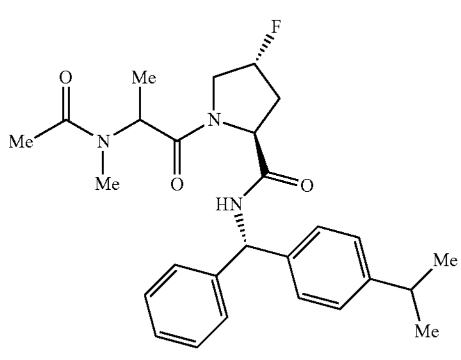 [SMILES: CC(=O)N(C)C(C)C(=O)N1C[C@H](F)C[C@H]1C(=O)N[C@@H](c1ccccc1)c1ccc(C(C)C)cc1] | (2S,4R)-4-fluoro-1-[2-(N-methylacetamido)propanoyl]-N-[(S)-phenyl[4-(propan-2-yl)phenyl]methyl]pyrrolidine-2-carboxamide | 467.3 | 468.3 |

TABLE T-1-continued

| Compound No. | Structure | IUPAC | Exact mass (g/mol) | LCMS, Found [M + H]+ |
|---|---|---|---|---|
| 72 | 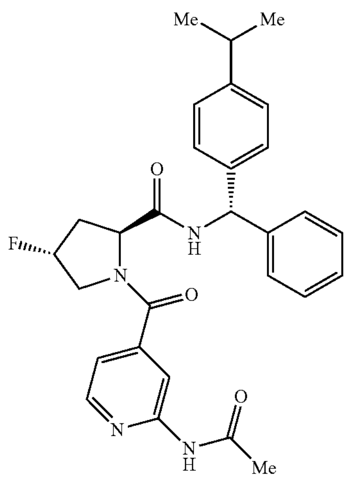 [SMILES: CC(=O)Nc1cc(C(=O)N2C[C@H](F)C[C@H]2C(=O)N[C@@H](c2ccccc2)c2ccc(C(C)C)cc2)ccn1] | (2S,4R)-1-(2-acetamidopyridine-4-carbonyl)-4-fluoro-N-[(S)-phenyl[4-(propan-2-yl)phenyl]methyl]pyrrolidine-2-carboxamide | 502.2 | 503.3 |
| 73 | 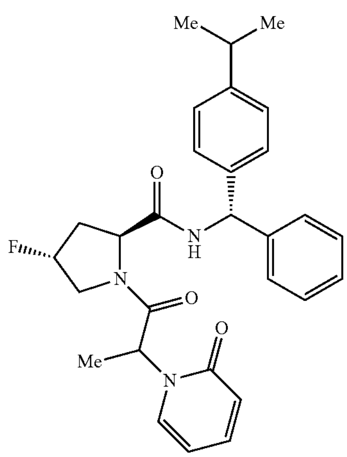 [SMILES: CC(C)c1ccc([C@@H](NC(=O)[C@@H]2C[C@@H](F)CN2C(=O)C(C)n2ccccc2=O)c2ccccc2)cc1] | (2S,4R)-4-fluoro-1-[2-(2-oxo-1,2-dihydropyridin-1-yl)propanoyl]-N-[(S)-phenyl[4-(propan-2-yl)phenyl]methyl]pyrrolidine-2-carboxamide | 489.2 | 490.3 |
| 74 | 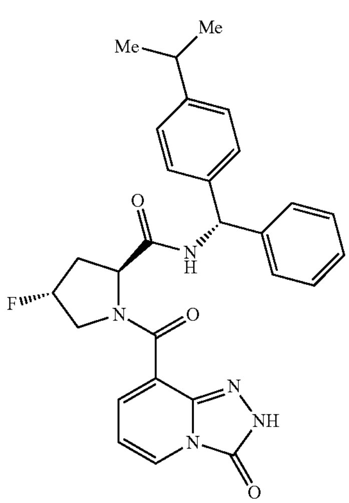 [SMILES: CC(C)c1ccc([C@@H](NC(=O)[C@@H]2C[C@@H](F)CN2C(=O)c2cccn3c(=O)[nH]nc23)c2ccccc2)cc1] | (2S,4R)-4-fluoro-1-{3-oxo-2H,3H-[1,2,4]triazolo[4,3-a]pyridine-8-carbonyl}-N-[(S)-phenyl[4-(propan-2-yl)phenyl]methyl]pyrrolidine-2-carboxamide | 501.2 | 502.2 |

TABLE T-1-continued

| Compound No. | Structure | IUPAC | Exact mass (g/mol) | LCMS, Found [M + H]+ |
|---|---|---|---|---|
| 75 | 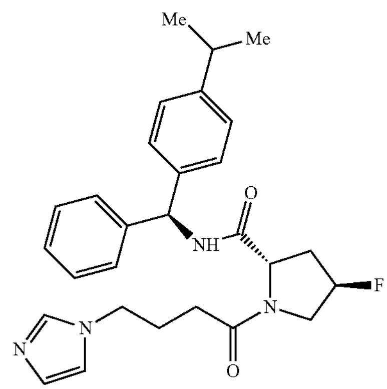 [SMILES: CC(C)c1ccc([C@@H](NC(=O)[C@@H]2C[C@@H](F)CN2C(=O)CCCn2ccnc2)c2ccccc2)cc1] | (2S,4R)-4-fluoro-1-[4-(1H-imidazol-1-yl)butanoyl]-N-[(S)-phenyl[4-(propan-2-yl)phenyl]methyl]pyrrolidine-2-carboxamide | 476.3 | 477.4 |
| 76 | 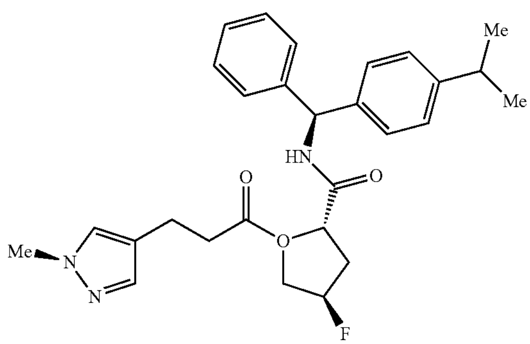 | (2S,4R)-4-fluoro-1-[3-(1-methyl-1H-pyrazol-4-yl)propanoyl]-N-[(S)-phenyl[4-(propan-2-yl)phenyl]methyl]pyrrolidine-2-carboxamide | 476.3 | 477.3 |
| 77 | 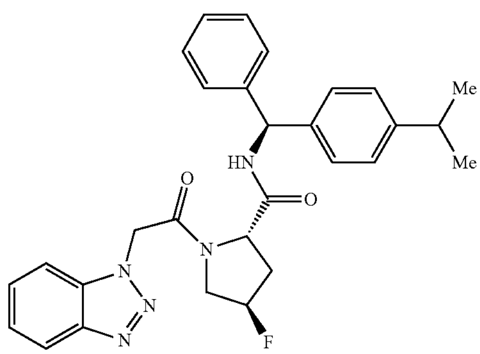 [SMILES: CC(C)c1ccc([C@@H](NC(=O)[C@@H]2C[C@@H](F)CN2C(=O)Cn2nnc3ccccc32)c2ccccc2)cc1] | (2S,4R)-1-[2-(1H-1,3-benzodiazol-1-yl)acetyl]-4-fluoro-N-[(S)-phenyl[4-(propan-2-yl)phenyl]methyl]pyrrolidine-2-carboxamide | 498.2 | 499.3 |
| 78 | 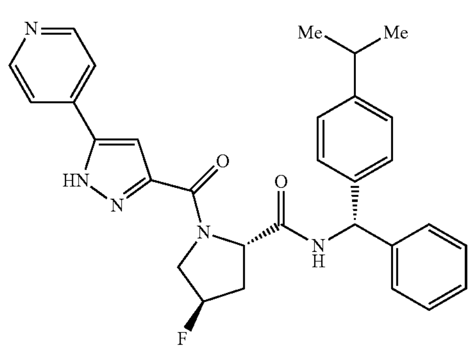 [SMILES: CC(C)c1ccc([C@@H](NC(=O)[C@@H]2C[C@@H](F)CN2C(=O)c2cc(-c3ccncc3)[nH]n2)c2ccccc2)cc1] | (2S,4R)-4-fluoro-N-[(S)-phenyl[4-(propan-2-yl)phenyl]methyl]-1-[5-(pyridin-4-yl)-1H-pyrazole-3-carbonyl]pyrrolidine-2-carboxamide | 511.2 | 512.3 |

TABLE T-1-continued

| Compound No. | Structure | IUPAC | Exact mass (g/mol) | LCMS, Found [M + H]+ |
|---|---|---|---|---|
| 79 | 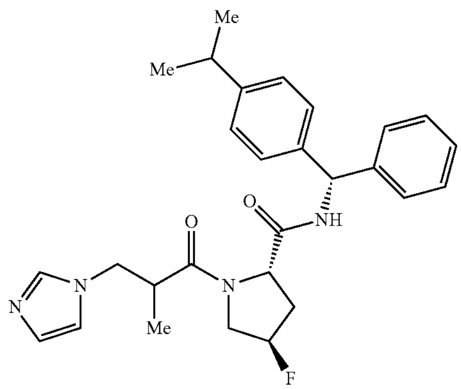 [SMILES: CC(Cn1ccnc1)C(=O)N1C[C@H](F)C[C@H]1C(=O)N[C@@H](c1ccccc1)c1ccc(C(C)C)cc1] | (2S,4R)-4-fluoro-1-[3-(1H-imidazol-1-yl)-2-methylpropanoyl]-N-[(S)-phenyl[4-(propan-2-yl)phenyl]methyl]pyrrolidine-2-carboxamide | 476.3 | 477.3 |
| 80 | 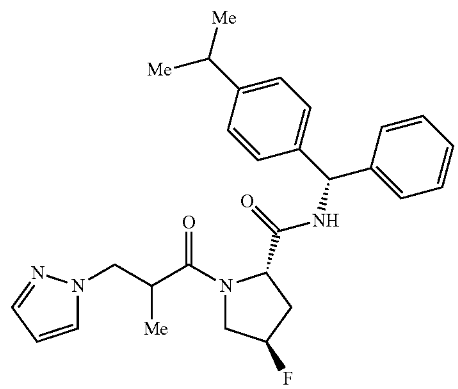 [SMILES: CC(Cn1cccn1)C(=O)N1C[C@H](F)C[C@H]1C(=O)N[C@@H](c1ccccc1)c1ccc(C(C)C)cc1] | (2S,4R)-4-fluoro-1-[2-methyl-3-(1H-pyrazol-1-yl)propanoyl]-N-[(S)-phenyl[4-(propan-2-yl)phenyl]methyl]pyrrolidine-2-carboxamide | 476.3 | 477.3 |
| 81 | 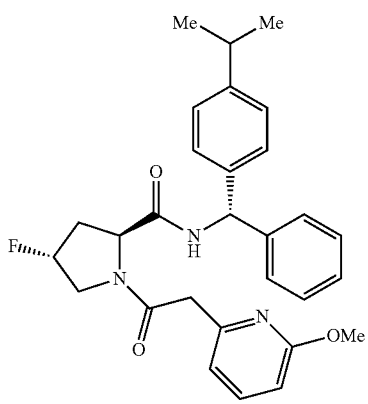 [SMILES: COc1cccc(CC(=O)N2C[C@H](F)C[C@H]2C(=O)N[C@@H](c2ccccc2)c2ccc(C(C)C)cc2)n1] | (2S,4R)-4-fluoro-1-[2-(6-methoxypyridin-2-yl)acetyl]-N-[(S)-phenyl[4-(propan-2-yl)phenyl]methyl]pyrrolidine-2-carboxamide | 489.2 | 490.3 |
| 82 | 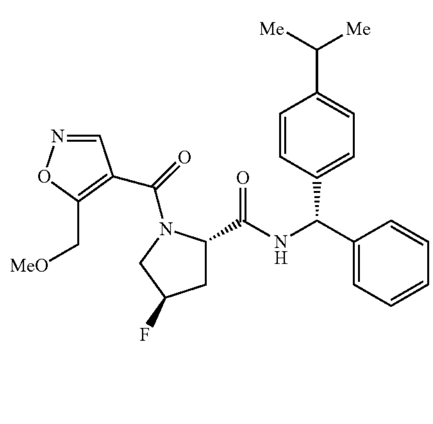 [SMILES: COCc1oncc1C(=O)N1C[C@H](F)C[C@H]1C(=O)N[C@@H](c1ccccc1)c1ccc(C(C)C)cc1] | (2S,4R)-4-fluoro-1-[5-(methoxymethyl)-1,2-oxazole-4-carbonyl]-N-[(S)-phenyl[4-(propan-2-yl)phenyl]methyl]pyrrolidine-2-carboxamide | 479.2 | 480.2 |

TABLE T-1-continued

| Compound No. | Structure | IUPAC | Exact mass (g/mol) | LCMS, Found [M + H]+ |
| --- | --- | --- | --- | --- |
| 83 | 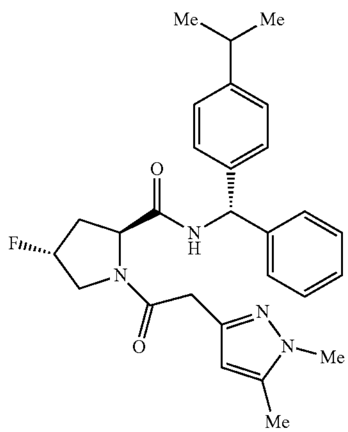 [SMILES: Cc1cc(CC(=O)N2C[C@H](F)C[C@H]2C(=O)N[C@@H](c2ccccc2)c2ccc(C(C)C)cc2)nn1C] | (2S,4R)-1-[2-(1,5-dimethyl-1H-pyrazol-3-yl)acetyl]-4-fluoro-N-[(S)-phenyl[4-(propan-2-yl)phenyl]methyl]pyrrolidine-2-carboxamide | 476.3 | 477.3 |
| 84 | 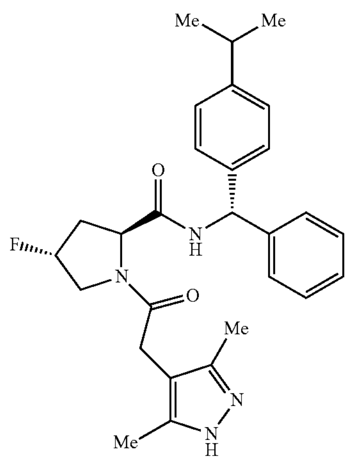 [SMILES: Cc1n[nH]c(C)c1CC(=O)N1C[C@H](F)C[C@H]1C(=O)N[C@@H](c1ccccc1)c1ccc(C(C)C)cc1] | (2S,4R)-1-[2-(3,5-dimethyl-1H-pyrazol-4-yl)acetyl]-4-fluoro-N-[(S)-phenyl[4-(propan-2-yl)phenyl]methyl]pyrrolidine-2-carboxamide | 476.3 | 477.3 |
| 85 | 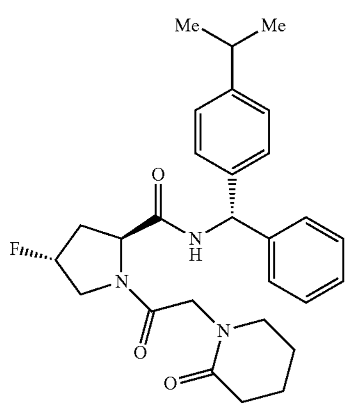 [SMILES: CC(C)c1ccc([C@@H](NC(=O)[C@@H]2C[C@@H](F)CN2C(=O)CN2CCCCC2=O)c2ccccc2)cc1] | (2S,4R)-4-fluoro-1-[2-(2-oxopiperidin-1-yl)acetyl]-N-[(S)-phenyl[4-(propan-2-yl)phenyl]methyl]pyrrolidine-2-carboxamide | 479.3 | 480.3 |

TABLE T-1-continued

| Compound No. | Structure | IUPAC | Exact mass (g/mol) | LCMS, Found [M + H]+ |
|---|---|---|---|---|
| 86 | 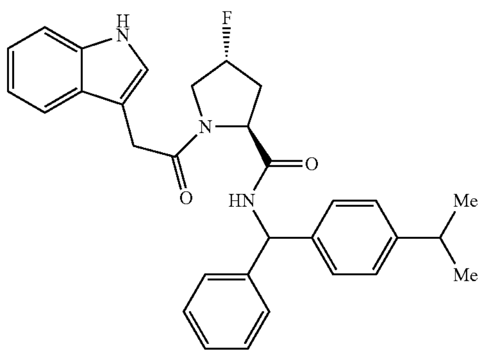 [SMILES: CC(C)c1ccc(C(NC(=O)[C@@H]2C[C@@H](F)CN2C(=O)Cc2c[nH]c3ccccc23)c2ccccc2)cc1] | (2S,4R)-4-fluoro-1-[2-(1H-indol-3-yl)acetyl]-N-[(S)-phenyl[4-(propan-2-yl)phenyl]methyl]pyrrolidine-2-carboxamide | 497.2 | 498.3 |
| 87 | 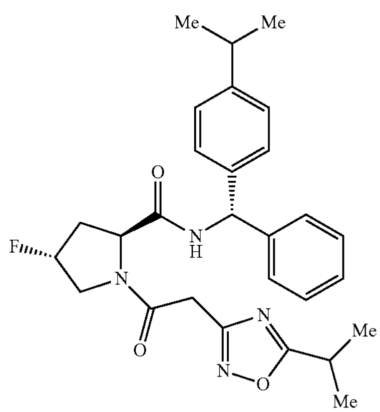 [SMILES: CC(C)c1ccc([C@@H](NC(=O)[C@@H]2C[C@@H](F)CN2C(=O)Cc2noc(C(C)C)n2)c2ccccc2)cc1] | (2S,4R)-4-fluoro-N-[(S)-phenyl[4-(propan-2-yl)phenyl]methyl]-1-{2-[5-(propan-2-yl)-1,2,4-oxadiazol-3-yl]acetyl}pyrrolidine-2-carboxamide | 492.3 | 493.3 |
| 88 | 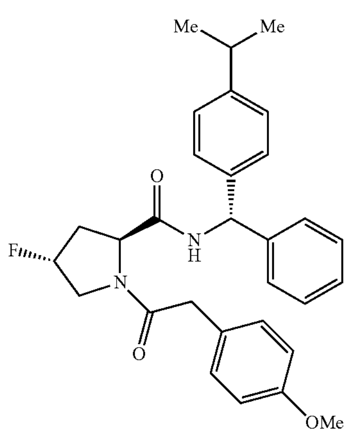 [SMILES: COc1ccc(CC(=O)N2C[C@H](F)C[C@H]2C(=O)N[C@@H](c2ccccc2)c2ccc(C(C)C)cc2)cc1] | (2S,4R)-4-fluoro-1-[2-(4-methoxyphenyl)acetyl]-N-[(S)-phenyl[4-(propan-2-yl)phenyl]methyl]pyrrolidine-2-carboxamide | 488.2 | 489.3 |

TABLE T-1-continued

| Compound No. | Structure | IUPAC | Exact mass (g/mol) | LCMS, Found [M + H]+ |
|---|---|---|---|---|
| 89 | 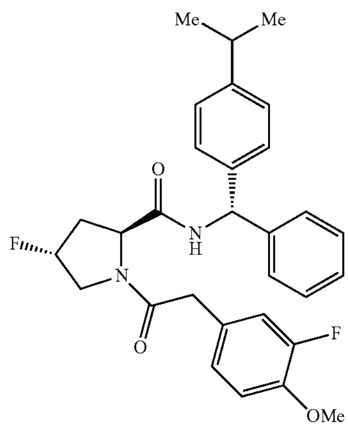 [SMILES: COc1ccc(CC(=O)N2C[C@H](F)C[C@H]2C(=O)N[C@@H](c2ccccc2)c2ccc(C(C)C)cc2)cc1F] | (2S,4R)-4-fluoro-1-[2-(3-fluoro-4-methoxyphenyl)acetyl]-N-[(S)-phenyl[4-(propan-2-yl)phenyl]methyl]pyrrolidine-2-carboxamide | 506.2 | 507.3 |
| 90 | 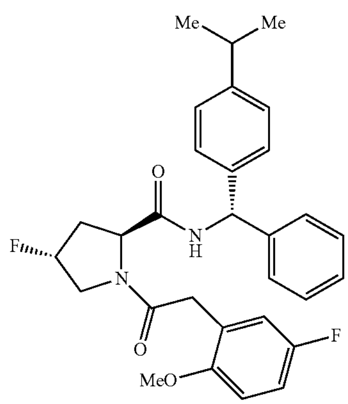 [SMILES: COc1ccc(F)cc1CC(=O)N1C[C@H](F)C[C@H]1C(=O)N[C@@H](c1ccccc1)c1ccc(C(C)C)cc1] | (2S,4R)-4-fluoro-1-[2-(5-fluoro-2-methoxyphenyl)acetyl]-N-[(S)-phenyl[4-(propan-2-yl)phenyl]methyl]pyrrolidine-2-carboxamide | 506.2 | 507.3 |
| 91 | 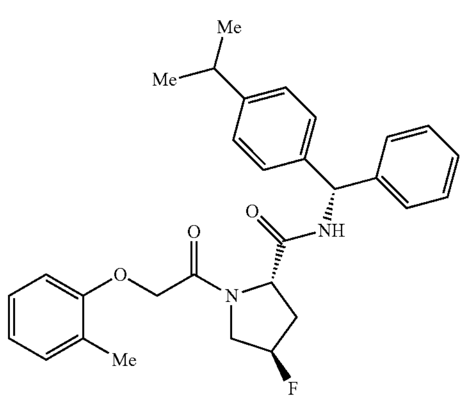 [SMILES: Cc1ccccc1OCC(=O)N1C[C@H](F)C[C@H]1C(=O)N[C@@H](c1ccccc1)c1ccc(C(C)C)cc1] | (2S,4R)-4-fluoro-1-[2-(2-methylphenoxy)acetyl]-N-[(S)-phenyl[4-(propan-2-yl)phenyl]methyl]pyrrolidine-2-carboxamide | 488.2 | 489.3 |

TABLE T-1-continued

| Compound No. | Structure | IUPAC | Exact mass (g/mol) | LCMS, Found [M + H]+ |
|---|---|---|---|---|
| 92 | 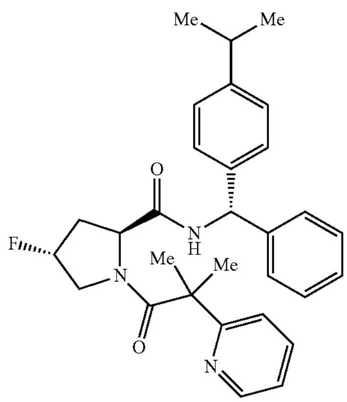 [SMILES: CC(C)c1ccc([C@@H](NC(=O)[C@@H]2C[C@@H](F)CN2C(=O)C(C)(C)c2ccccn2)c2ccccc2)cc1] | (2S,4R)-4-fluoro-1-[2-methyl-2-(pyridin-2-yl)propanoyl]-N-[(S)-phenyl[4-(propan-2-yl)phenyl]methyl]pyrrolidine-2-carboxamide | 487.3 | 488.3 |
| 93 | 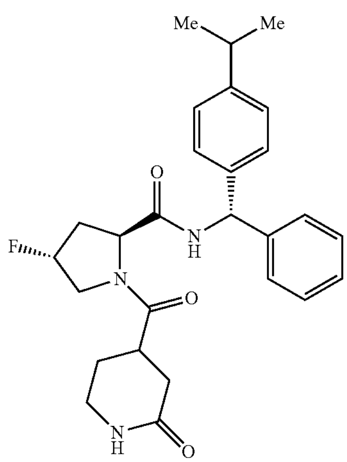 [SMILES: CC(C)c1ccc([C@@H](NC(=O)[C@@H]2C[C@@H](F)CN2C(=O)C2CCNC(=O)C2)c2ccccc2)cc1] | (2S,4R)-4-fluoro-1-(2-oxopiperidine-4-carbonyl)-N-[(S)-phenyl[4-(propan-2-yl)phenyl]methyl]pyrrolidine-2-carboxamide | 465.2 | 466.1 |
| 94 | 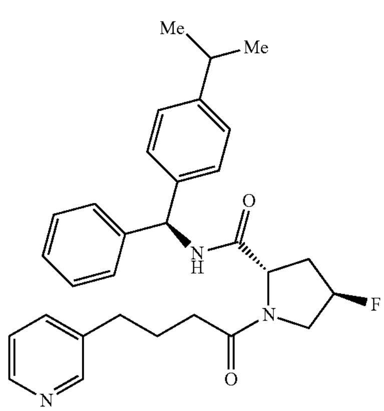 [SMILES: CC(C)c1ccc([C@@H](NC(=O)[C@@H]2C[C@@H](F)CN2C(=O)CCCc2cccnc2)c2ccccc2)cc1] | (2S,4R)-4-fluoro-N-[(S)-phenyl[4-(propan-2-yl)phenyl]methyl]-1-[4-(pyridin-3-yl)butanoyl]pyrrolidine-2-carboxamide | 487.3 | 488.3 |

TABLE T-1-continued

| Compound No. | Structure | IUPAC | Exact mass (g/mol) | LCMS, Found [M + H]+ |
| --- | --- | --- | --- | --- |
| 95 | 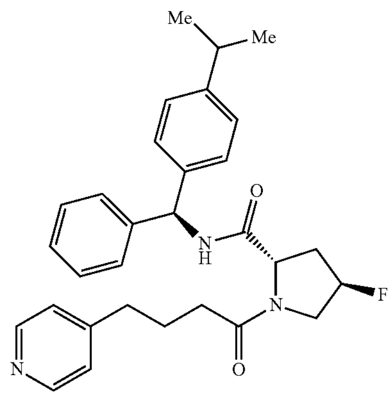 [SMILES: CC(C)c1ccc([C@@H](NC(=O)[C@@H]2C[C@@H](F)CN2C(=O)CCCc2ccncc2)c2ccccc2)cc1] | (2S,4R)-4-fluoro-N-[(S)-phenyl[4-(propan-2-yl)phenyl]methyl]-1-[4-(pyridin-4-yl)butanoyl]pyrrolidine-2-carboxamide | 487.3 | 488.3 |
| 96 | 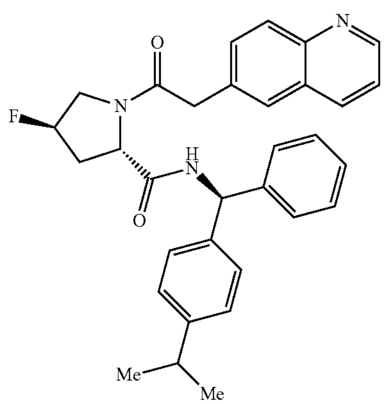 [SMILES: CC(C)c1ccc([C@@H](NC(=O)[C@@H]2C[C@@H](F)CN2C(=O)Cc2ccc3ncccc3c2)c2ccccc2)cc1] | (2S,4R)-4-fluoro-N-[(S)-phenyl[4-(propan-2-yl)phenyl]methyl]-1-[2-(quinolin-6-yl)acetyl]pyrrolidine-2-carboxamide | 509.2 | 510.3 |
| 97 | 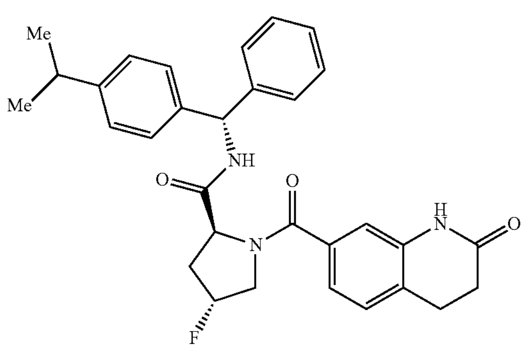 [SMILES: CC(C)c1ccc([C@@H](NC(=O)[C@@H]2C[C@@H](F)CN2C(=O)c2ccc3c(c2)NC(=O)CC3)c2ccccc2)cc1] | (2S,4R)-4-fluoro-1-(2-oxo-1,2,3,4-tetrahydroquinoline-7-carbonyl)-N-[(S)-phenyl[4-(propan-2-yl)phenyl]methyl]pyrrolidine-2-carboxamide | 513.2 | 514.3 |
| 98 | 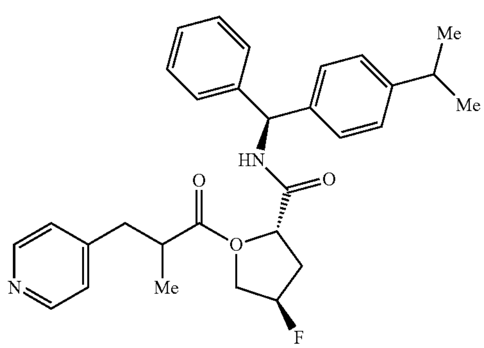 | (2S,4R)-4-fluoro-1-[2-methyl-3-(pyridin-4-yl)propanoyl]-N-[(S)-phenyl[4-(propan-2-yl)phenyl]methyl]pyrrolidine-2-carboxamide | 487.3 | 488.3 |

TABLE T-1-continued

| Compound No. | Structure | IUPAC | Exact mass (g/mol) | LCMS, Found [M + H]+ |
| --- | --- | --- | --- | --- |
| 99 | 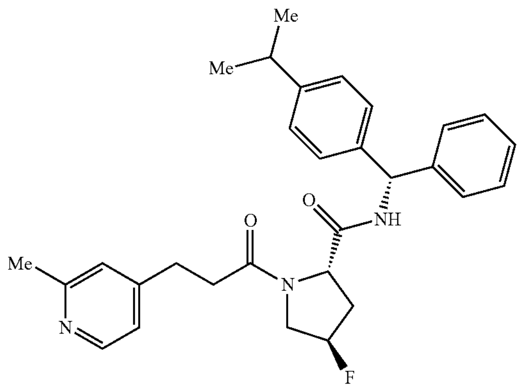 [SMILES: Cc1cc(CCC(=O)N2C[C@H](F)C[C@H]2C(=O)N[C@@H](c2ccccc2)c2ccc(C(C)C)cc2)ccn1] | (2S,4R)-4-fluoro-1-[3-(2-methylpyridin-4-yl)propanoyl]-N-[(S)-phenyl[4-(propan-2-yl)phenyl]methyl]pyrrolidine-2-carboxamide | 487.3 | 488.3 |
| 100 | 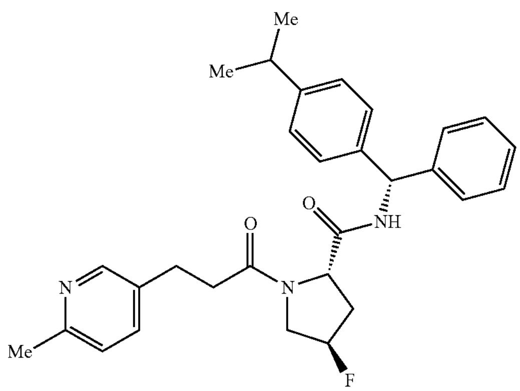 [SMILES: Cc1ccc(CCC(=O)N2C[C@H](F)C[C@H]2C(=O)N[C@@H](c2ccccc2)c2ccc(C(C)C)cc2)cn1] | (2S,4R)-4-fluoro-1-[3-(6-methylpyridin-3-yl)propanoyl]-N-[(S)-phenyl[4-(propan-2-yl)phenyl]methyl]pyrrolidine-2-carboxamide | 487.3 | 488.3 |
| 101 | 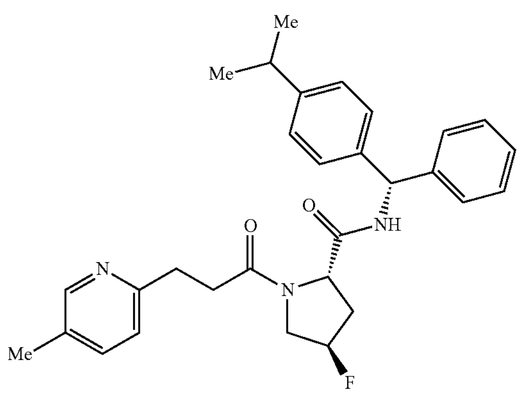 [SMILES: Cc1ccc(CCC(=O)N2C[C@H](F)C[C@H]2C(=O)N[C@@H](c2ccccc2)c2ccc(C(C)C)cc2)nc1] | (2S,4R)-4-fluoro-1-[3-(5-methylpyridin-2-yl)propanoyl]-N-[(S)-phenyl[4-(propan-2-yl)phenyl]methyl]pyrrolidine-2-carboxamide | 487.3 | 488.3 |
| 102 | 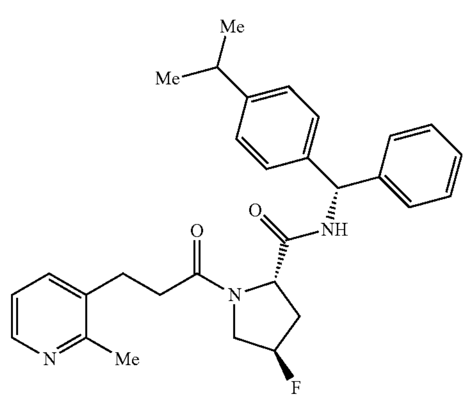 [SMILES: Cc1ncccc1CCC(=O)N1C[C@H](F)C[C@H]1C(=O)N[C@@H](c1ccccc1)c1ccc(C(C)C)cc1] | (2S,4R)-4-fluoro-1-[3-(2-methylpyridin-3-yl)propanoyl]-N-[(S)-phenyl[4-(propan-2-yl)phenyl]methyl]pyrrolidine-2-carboxamide | 487.3 | 488.3 |

TABLE T-1-continued

| Compound No. | Structure | IUPAC | Exact mass (g/mol) | LCMS, Found [M + H]+ |
| --- | --- | --- | --- | --- |
| 103 | 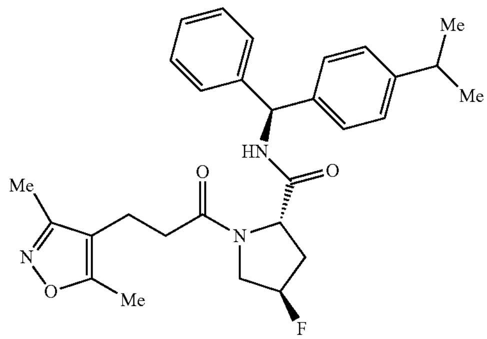 [SMILES: Cc1noc(C)c1CCC(=O)N1C[C@H](F)C[C@H]1C(=O)N[C@@H](c1ccccc1)c1ccc(C(C)C)cc1] | (2S,4R)-1-[3-(3,5-dimethyl-1,2-oxazol-4-yl)propanoyl]-4-fluoro-N-[(S)-phenyl[4-(propan-2-yl)phenyl]methyl]pyrrolidine-2-carboxamide | 491.3 | 492.3 |
| 104 | 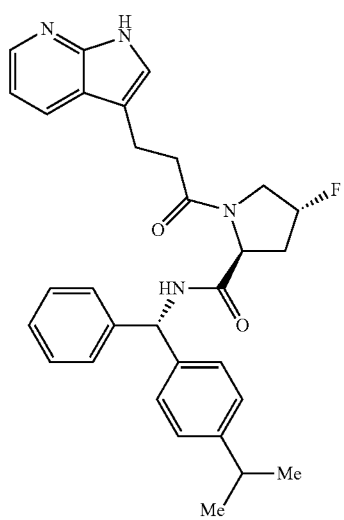 [SMILES: CC(C)c1ccc([C@@H](NC(=O)[C@@H]2C[C@@H](F)CN2C(=O)CCc2c[nH]c3ncccc23)c2ccccc2)cc1] | (2S,4R)-4-fluoro-N-[(S)-phenyl[4-(propan-2-yl)phenyl]methyl]-1-(3-{1H-pyrrolo[2,3-b]pyridin-3-yl}propanoyl)pyrrolidine-2-carboxamide | 512.3 | 513.3 |
| 105 | 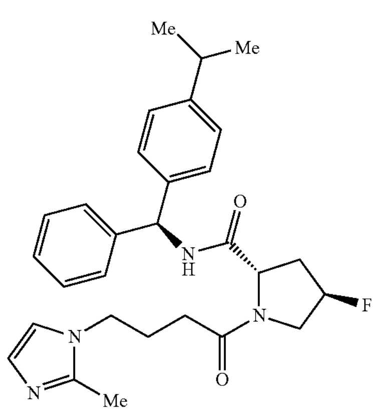 [SMILES: Cc1nccn1CCCC(=O)N1C[C@H](F)C[C@H]1C(=O)N[C@@H](c1ccccc1)c1ccc(C(C)C)cc1] | (2S,4R)-4-fluoro-1-[4-(2-methyl-1H-imidazol-1-yl)butanoyl]-N-[(S)-phenyl[4-(propan-2-yl)phenyl]methyl]pyrrolidine-2-carboxamide | 490.3 | 491.3 |

TABLE T-1-continued

| Compound No. | Structure | IUPAC | Exact mass (g/mol) | LCMS, Found [M + H]+ |
| --- | --- | --- | --- | --- |
| 106 | 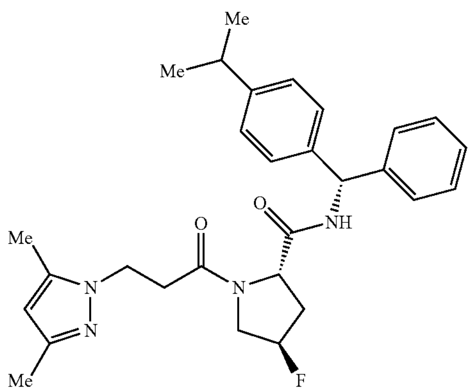 [SMILES: Cc1cc(C)n(CCC(=O)N2C[C@H](F)C[C@H]2C(=O)N[C@@H](c2ccccc2)c2ccc(C(C)C)cc2)n1] | (2S,4R)-1-[3-(3,5-dimethyl-1H-pyrazol-1-yl)propanoyl]-4-fluoro-N-[(S)-phenyl[4-(propan-2-yl)phenyl]methyl]pyrrolidine-2-carboxamide | 490.3 | 491.3 |
| 107 | 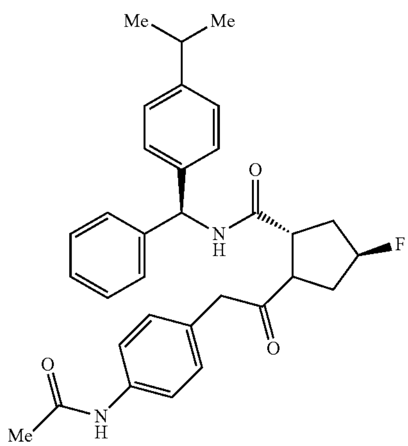 [SMILES: CC(=O)Nc1ccc(CC(=O)C2C[C@H](F)C[C@H]2C(=O)N[C@@H](c2ccccc2)c2ccc(C(C)C)cc2)cc1] | (2S,4R)-1-[2-(4-acetamidophenyl)acetyl]-4-fluoro-N-[(S)-phenyl[4-(propan-2-yl)phenyl]methyl]pyrrolidine-2-carboxamide | 515.3 | 516.3 |
| 108 | 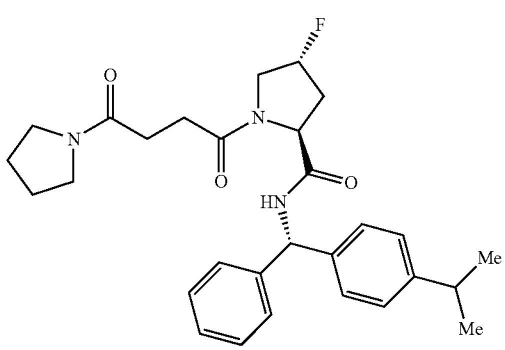 [SMILES: CC(C)c1ccc([C@@H](NC(=O)[C@@H]2C[C@@H](F)CN2C(=O)CCC(=O)N2CCCC2)c2ccccc2)cc1] | (2S,4R)-4-fluoro-1-[4-oxo-4-(pyrrolidin-1-yl)butanoyl]-N-[(S)-phenyl[4-(propan-2-yl)phenyl]methyl]pyrrolidine-2-carboxamide | 493.3 | 494.3 |

TABLE T-1-continued

| Compound No. | Structure | IUPAC | Exact mass (g/mol) | LCMS, Found [M + H]+ |
|---|---|---|---|---|
| 109 | 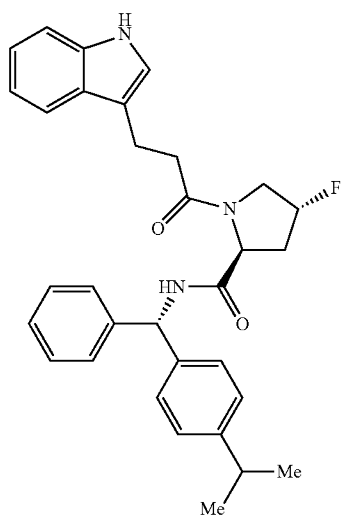 [SMILES: CC(C)c1ccc([C@@H](NC(=O)[C@@H]2C[C@@H](F)CN2C(=O)CCc2c[nH]c3ccccc23)c2ccccc2)cc1] | (2S,4R)-4-fluoro-1-[3-(1H-indol-3-yl)propanoyl]-N-[(S)-phenyl[4-(propan-2-yl)phenyl]methyl]pyrrolidine-2-carboxamide | 511.3 | 512.3 |
| 110 | 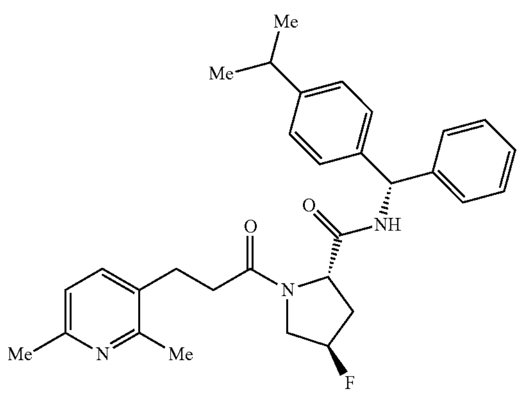 [SMILES: Cc1ccc(CCC(=O)N2C[C@H](F)C[C@H]2C(=O)N[C@@H](c2ccccc2)c2ccc(C(C)C)cc2)c(C)n1] | (2S,4R)-1-[3-(2,6-dimethylpyridin-3-yl)propanoyl]-4-fluoro-N-[(S)-phenyl[4-(propan-2-yl)phenyl]methyl]pyrrolidine-2-carboxamide | 501.3 | 502.3 |
| 111 | 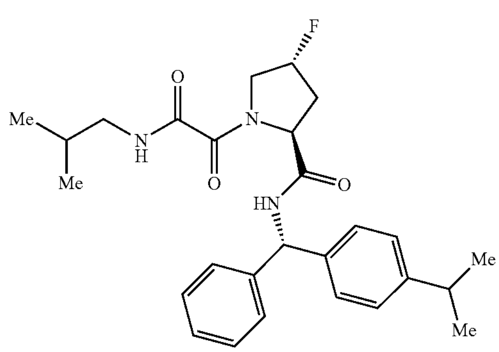 [SMILES: CC(C)CNC(=O)C(=O)N1C[C@H](F)C[C@H]1C(=O)N[C@@H](c1ccccc1)c1ccc(C(C)C)cc1] | (2S,4R)-4-fluoro-1-{[(2-methylpropyl)carbamoyl]carbonyl}-N-[(S)-phenyl[4-(propan-2-yl)phenyl]methyl]pyrrolidine-2-carboxamide | 467.3 | 468.3 |

TABLE T-1-continued

| Compound No. | Structure | IUPAC | Exact mass (g/mol) | LCMS, Found [M + H]+ |
|---|---|---|---|---|
| 112 | 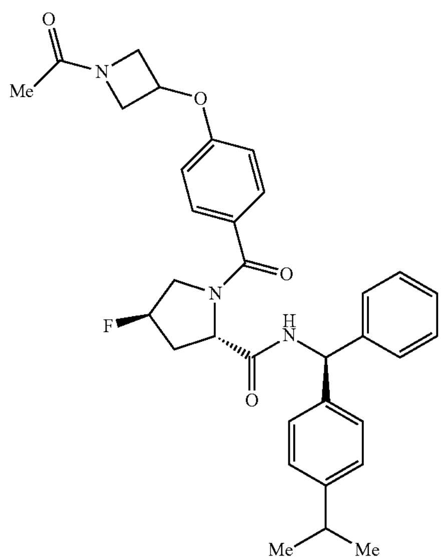 [SMILES: CC(=O)N1CC(Oc2ccc(C(=O)N3C[C@H](F)C[C@H]3C(=O)N[C@@H](c3ccccc3)c3ccc(C(C)C)cc3)cc2)C1] | (2S,4R)-1-{4-[(1-acetylazetidin-3-yl)oxy]benzoyl}-4-fluoro-N-[(S)-phenyl[4-(propan-2-yl)phenyl]methyl]pyrrolidine-2-carboxamide | 557.3 | 558.3 |
| 113 | 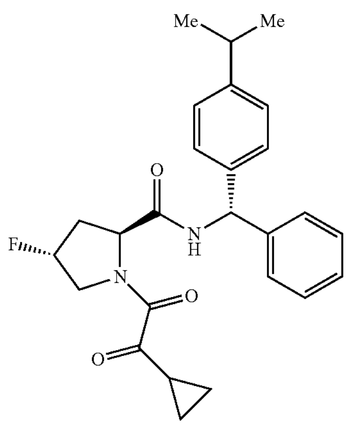 [SMILES: CC(C)c1ccc([C@@H](NC(=O)[C@@H]2C[C@@H](F)CN2C(=O)C(=O)C2CC2)c2ccccc2)cc1] | (2S,4R)-1-(2-cyclopropyl-2-oxoacetyl)-4-fluoro-N-[(S)-phenyl[4-(propan-2-yl)phenyl]methyl]pyrrolidine-2-carboxamide | 436.2 | 437.3 |
| 114 | 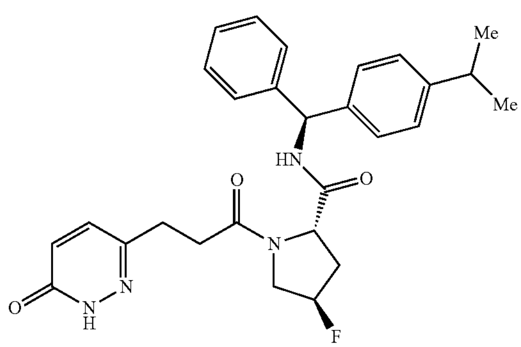 [SMILES: CC(C)c1ccc([C@@H](NC(=O)[C@@H]2C[C@@H](F)CN2C(=O)CCc2ccc(=O)[nH]n2)c2ccccc2)cc1] | (2S,4R)-4-fluoro-1-[3-(6-oxo-1,6-dihydropyridazin-3-yl)propanoyl]-N-[(S)-phenyl[4-(propan-2-yl)phenyl]methyl]pyrrolidine-2-carboxamide | 490.2 | 491.2 |

TABLE T-1-continued

| Compound No. | Structure | IUPAC | Exact mass (g/mol) | LCMS, Found [M + H]+ |
|---|---|---|---|---|
| 115 | 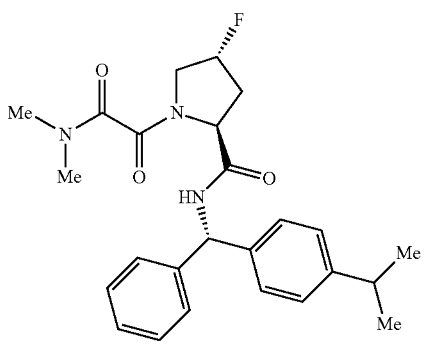 [SMILES: CC(C)c1ccc([C@@H](NC(=O)[C@@H]2C[C@@H](F)CN2C(=O)C(=O)N(C)C)c2ccccc2)cc1] | (2S,4R)-1-[(dimethylcarbamoyl)carbonyl]-4-fluoro-N-[(S)-phenyl[4-(propan-2-yl)phenyl]methyl]pyrrolidine-2-carboxamide | 439.2 | 440.2 |
| 116 | 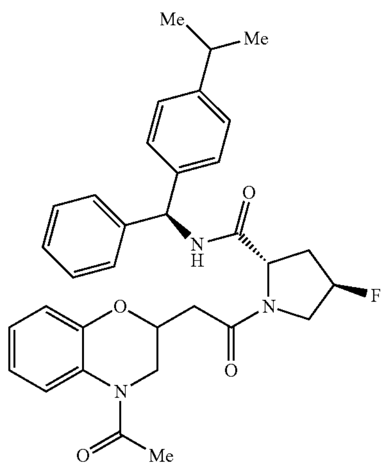 [SMILES: CC(=O)N1CC(CC(=O)N2C[C@H](F)C[C@H]2C(=O)N[C@@H](c2ccccc2)c2ccc(C(C)C)cc2)Oc2ccccc21] | (2S,4R)-1-[2-(4-acetyl-3,4-dihydro-2H-1,4-benzoxazin-2-yl)acetyl]-4-fluoro-N-[(S)-phenyl[4-(propan-2-yl)phenyl]methyl]pyrrolidine-2-carboxamide | 557.3 | 558.3 |
| 117 | 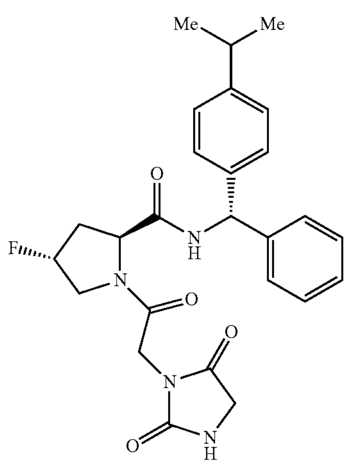 [SMILES: CC(C)c1ccc([C@@H](NC(=O)[C@@H]2C[C@@H](F)CN2C(=O)CN2C(=O)CNC2=O)c2ccccc2)cc1] | (2S,4R)-1-[2-(2,5-dioxoimidazolidin-1-yl)acetyl]-4-fluoro-N-[(S)-phenyl[4-(propan-2-yl)phenyl]methyl]pyrrolidine-2-carboxamide | 480.2 | 481.1 |

TABLE T-1-continued

| Compound No. | Structure | IUPAC | Exact mass (g/mol) | LCMS, Found [M + H]+ |
| --- | --- | --- | --- | --- |
| 118 | 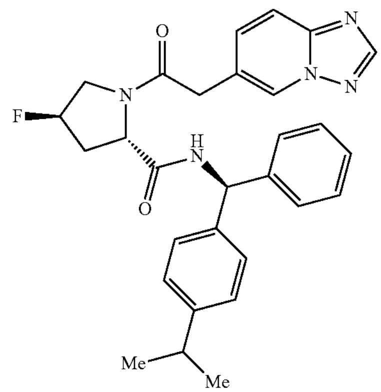 [SMILES: CC(C)c1ccc([C@@H](NC(=O)[C@@H]2C[C@@H](F)CN2C(=O)Cc2ccc3ncnn3c2)c2ccccc2)cc1] | (2S,4R)-4-fluoro-N-[(S)-phenyl[4-(propan-2-yl)phenyl]methyl]-1-(2-{[1,2,4]triazolo[1,5-a]pyridin-6-yl}acetyl)pyrrolidine-2-carboxamide | 499.2 | 500.3 |
| 119 | 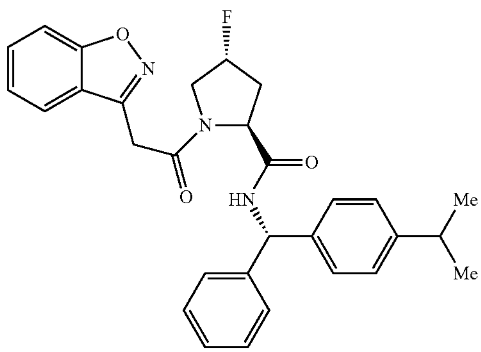 [SMILES: CC(C)c1ccc([C@@H](NC(=O)[C@@H]2C[C@@H](F)CN2C(=O)Cc2noc3ccccc23)c2ccccc2)cc1] | (2S,4R)-1-[2-(1,2-benzoxazol-3-yl)acetyl]-4-fluoro-N-[(S)-phenyl[4-(propan-2-yl)phenyl]methyl]pyrrolidine-2-carboxamide | 499.2 | 500.3 |
| 120 | 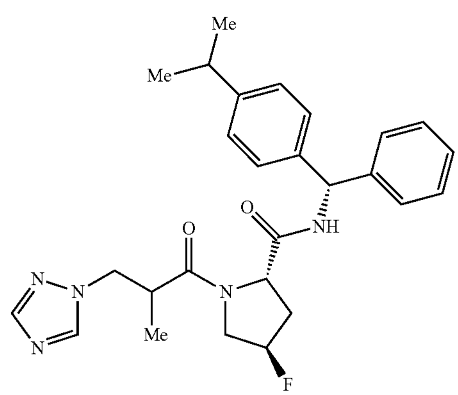 | (2S,4R)-4-fluoro-1-[2-methyl-3-(1H-1,2,4-triazol-1-yl)propanoyl]-N-[(S)-phenyl[4-(propan-2-yl)phenyl]methyl]pyrrolidine-2-carboxamide | 477.3 | 478.1 |
| 121 | 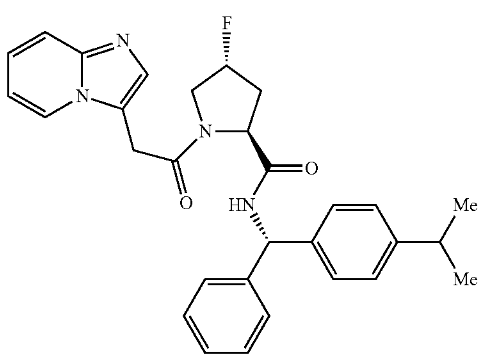 [SMILES: CC(C)c1ccc([C@@H](NC(=O)[C@@H]2C[C@@H](F)CN2C(=O)Cc2cnc3ccccn23)c2ccccc2)cc1] | (2S,4R)-4-fluoro-1-(2-{imidazo[1,2-a]pyridin-3-yl}acetyl)-N-[(S)-phenyl[4-(propan-2-yl)phenyl]methyl]pyrrolidine-2-carboxamide | 498.2 | 499.3 |

TABLE T-1-continued

| Compound No. | Structure | IUPAC | Exact mass (g/mol) | LCMS, Found [M + H]+ |
|---|---|---|---|---|
| 122 | 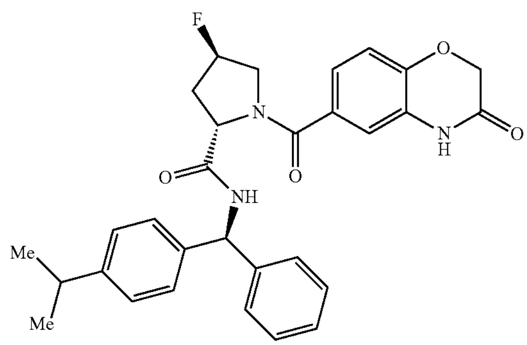 [SMILES: CC(C)c1ccc([C@@H](NC(=O)[C@@H]2C[C@@H](F)CN2C(=O)c2ccc3c(c2)NC(=O)CO3)c2ccccc2)cc1] | (2S,4R)-4-fluoro-1-(3-oxo-3,4-dihydro-2H-1,4-benzoxazine-6-carbonyl)-N-[(S)-phenyl[4-(propan-2-yl)phenyl]methyl]pyrrolidine-2-carboxamide | 515.2 | 516.3 |
| 123 | 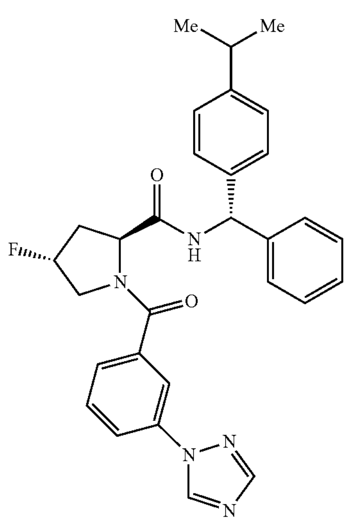 [SMILES: CC(C)c1ccc([C@@H](NC(=O)[C@@H]2C[C@@H](F)CN2C(=O)c2cccc(-n3cncn3)c2)c2ccccc2)cc1] | (2S,4R)-4-fluoro-N-[(S)-phenyl[4-(propan-2-yl)phenyl]methyl]-1-[3-(1H-1,2,4-triazol-1-yl)benzoyl]pyrrolidine-2-carboxamide | 511.2 | 512.3 |
| 124 | 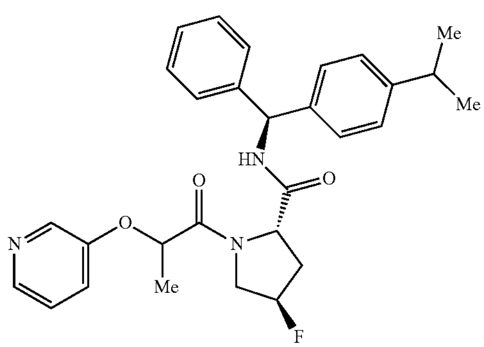 [SMILES: CC(Oc1cccnc1)C(=O)N1C[C@H](F)C[C@H]1C(=O)N[C@@H](c1ccccc1)c1ccc(C(C)C)cc1] | (2S,4R)-4-fluoro-N-[(S)-phenyl[4-(propan-2-yl)phenyl]methyl]-1-[2-(pyridin-3-yloxy)propanoyl]pyrrolidine-2-carboxamide | 489.2 | 490.3 |

TABLE T-1-continued

| Compound No. | Structure | IUPAC | Exact mass (g/mol) | LCMS, Found [M + H]+ |
|---|---|---|---|---|
| 125 | 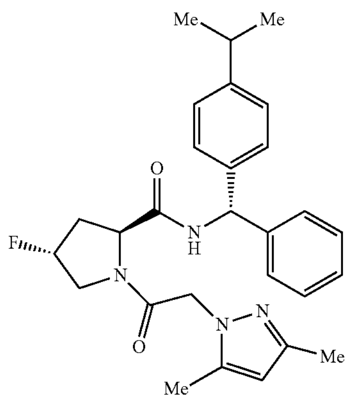 [SMILES: Cc1cc(C)n(CC(=O)N2C[C@H](F)C[C@H]2C(=O)N[C@@H](c2ccccc2)c2ccc(C(C)C)cc2)n1] | (2S,4R)-1-[2-(3,5-dimethyl-1H-pyrazol-1-yl)acetyl]-4-fluoro-N-[(S)-phenyl[4-(propan-2-yl)phenyl]methyl]pyrrolidine-2-carboxamide | 476.3 | 477.4 |
| 126 | 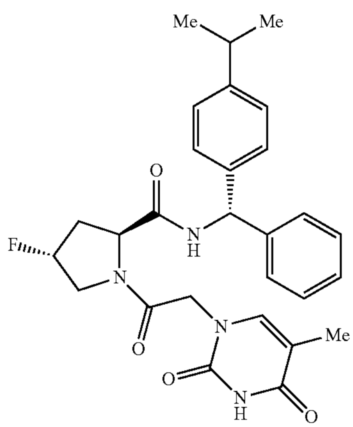 [SMILES: Cc1cn(CC(=O)N2C[C@H](F)C[C@H]2C(=O)N[C@@H](c2ccccc2)c2ccc(C(C)C)cc2)c(=O)[nH]c1=O] | (2S,4R)-4-fluoro-1-[2-(5-methyl-2,4-dioxo-1,2,3,4-tetrahydropyrimidin-1-yl)acetyl]-N-[(S)-phenyl[4-(propan-2-yl)phenyl]methyl]pyrrolidine-2-carboxamide | 506.2 | 507.3 |
| 127 | 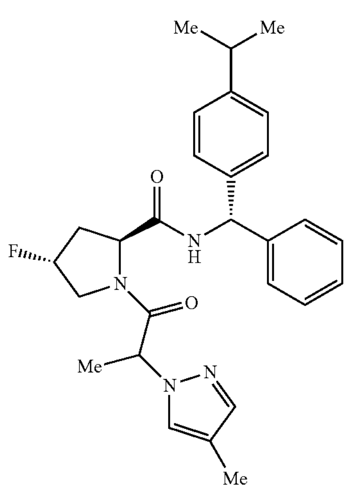 [SMILES: Cc1cnn(C(C)C(=O)N2C[C@H](F)C[C@H]2C(=O)N[C@@H](c2ccccc2)c2ccc(C(C)C)cc2)c1] | (2S,4R)-4-fluoro-1-[2-(4-methyl-1H-pyrazol-1-yl)propanoyl]-N-[(S)-phenyl[4-(propan-2-yl)phenyl]methyl]pyrrolidine-2-carboxamide | 476.3 | 477.4 |

TABLE T-1-continued

| Compound No. | Structure | IUPAC | Exact mass (g/mol) | LCMS, Found [M + H]+ |
|---|---|---|---|---|
| 128 | 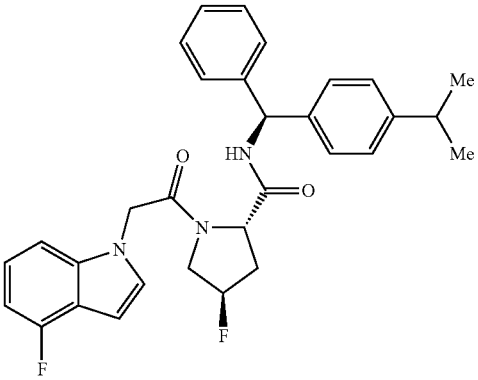 [SMILES: CC(C)c1ccc([C@@H](NC(=O)[C@@H]2C[C@@H](F)CN2C(=O)Cn2ccc3c(F)cccc32)c2ccccc2)cc1] | (2S,4R)-4-fluoro-1-[2-(4-fluoro-1H-indol-1-yl)acetyl]-N-[(S)-phenyl[4-(propan-2-yl)phenyl]methyl]pyrrolidine-2-carboxamide | 515.2 | 516.3 |
| 129 | 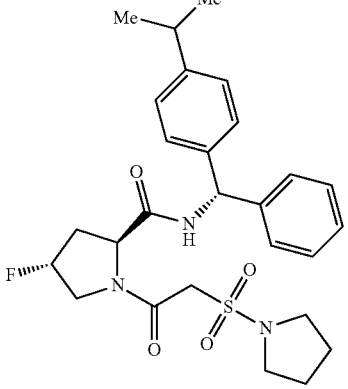 | (2S,4R)-4-fluoro-N-[(S)-phenyl[4-(propan-2-yl)phenyl]methyl]-1-[2-(pyrrolidine-1-sulfonyl)acetyl]pyrrolidine-2-carboxamide | 515.2 | 516.3 |
| 130 | 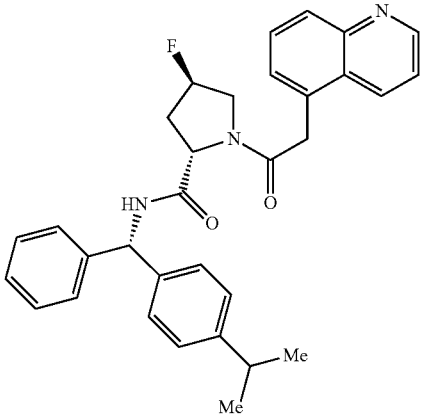 [SMILES: CC(C)c1ccc([C@@H](NC(=O)[C@@H]2C[C@@H](F)CN2C(=O)Cc2cccc3ncccc23)c2ccccc2)cc1] | (2S,4R)-4-fluoro-N-[(S)-phenyl[4-(propan-2-yl)phenyl]methyl]-1-[2-(quinolin-5-yl)acetyl]pyrrolidine-2-carboxamide | 509.2 | 510.3 |

TABLE T-1-continued

| Compound No. | Structure | IUPAC | Exact mass (g/mol) | LCMS, Found [M + H]+ |
|---|---|---|---|---|
| 131 | 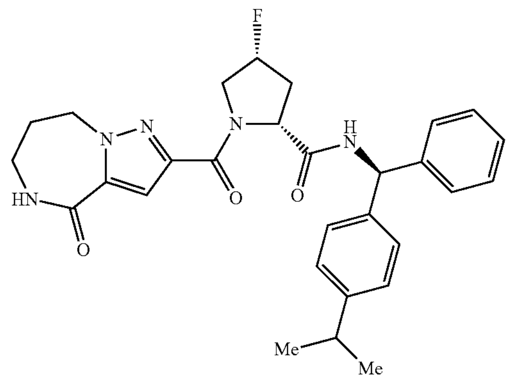 [SMILES: CC(C)c1ccc([C@@H](NC(=O)[C@H]2C[C@@H](F)CN2C(=O)c2cc3n(n2)CCCNC3=O)c2ccccc2)cc1] | (2S,4R)-4-fluoro-1-{4-oxo-4H,5H,6H,7H,8H-pyrazolo[1,5-a][1,4]diazepine-2-carbonyl}-N-[(S)-phenyl[4-(propan-2-yl)phenyl]methyl]pyrrolidine-2-carboxamide | 517.2 | 518.2 |
| 132 | 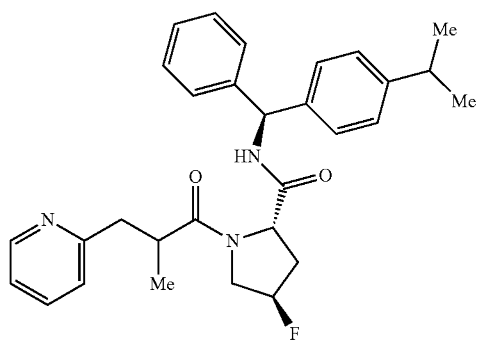 [SMILES: CC(Cc1ccccn1)C(=O)N1C[C@H](F)C[C@H]1C(=O)N[C@@H](c1ccccc1)c1ccc(C(C)C)cc1] | (2S,4R)-4-fluoro-1-[2-methyl-3-(pyridin-2-yl)propanoyl]-N-[(S)-phenyl[4-(propan-2-yl)phenyl]methyl]pyrrolidine-2-carboxamide | 487.3 | 488.3 |
| 133 | 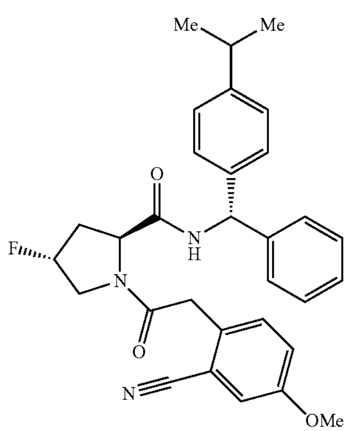 [SMILES: COc1ccc(CC(=O)N2C[C@H](F)C[C@H]2C(=O)N[C@@H](c2ccccc2)c2ccc(C(C)C)cc2)c(C#N)c1] | (2S,4R)-1-[2-(2-cyano-4-methoxyphenyl)acetyl]-4-fluoro-N-[(S)-phenyl[4-(propan-2-yl)phenyl]methyl]pyrrolidine-2-carboxamide | 513.2 | 514.3 |
| 134 | 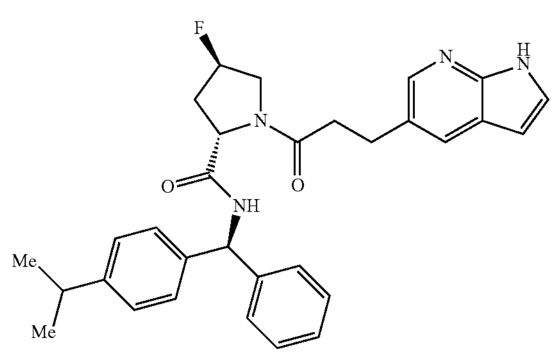 [SMILES: CC(C)c1ccc([C@@H](NC(=O)[C@@H]2C[C@@H](F)CN2C(=O)CCc2cnc3[nH]ccc3c2)c2ccccc2)cc1] | (2S,4R)-4-fluoro-N-[(S)-phenyl[4-(propan-2-yl)phenyl]methyl]-1-(3-{1H-pyrrolo[2,3-b]pyridin-5-yl}propanoyl)pyrrolidine-2-carboxamide | 512.3 | 513.3 |

TABLE T-1-continued

| Compound No. | Structure | IUPAC | Exact mass (g/mol) | LCMS, Found [M + H]+ |
|---|---|---|---|---|
| 135 | 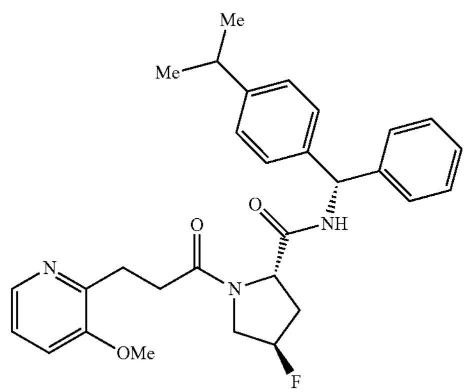 [SMILES: COc1cccnc1CCC(=O)N1C[C@H](F)C[C@H]1C(=O)N[C@@H](c1ccccc1)c1ccc(C(C)C)cc1] | (2S,4R)-4-fluoro-1-[3-(3-methoxypyridin-2-yl)propanoyl]-N-[(S)-phenyl[4-(propan-2-yl)phenyl]methyl]pyrrolidine-2-carboxamide | 503.3 | 504.3 |
| 136 | 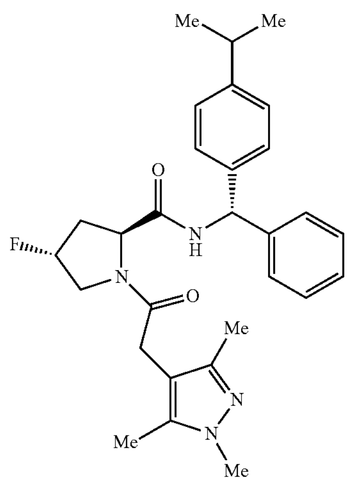 [SMILES: Cc1nn(C)c(C)c1CC(=O)N1C[C@H](F)C[C@H]1C(=O)N[C@@H](c1ccccc1)c1ccc(C(C)C)cc1] | (2S,4R)-4-fluoro-N-[(S)-phenyl[4-(propan-2-yl)phenyl]methyl]-1-[2-(1,3,5-trimethyl-1H-pyrazol-4-yl)acetyl]pyrrolidine-2-carboxamide | 490.3 | 491.3 |
| 137 | 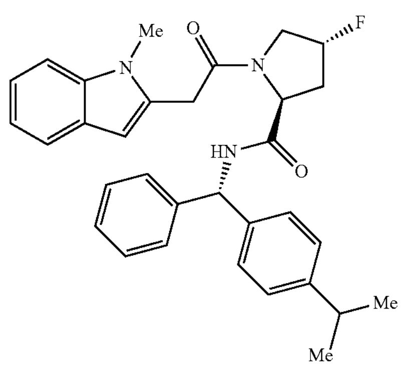 [SMILES: CC(C)c1ccc([C@@H](NC(=O)[C@@H]2C[C@@H](F)CN2C(=O)Cc2cc3ccccc3n2C)c2ccccc2)cc1] | (2S,4R)-4-fluoro-1-[2-(1-methyl-1H-indol-2-yl)acetyl]-N-[(S)-phenyl[4-(propan-2-yl)phenyl]methyl]pyrrolidine-2-carboxamide | 511.3 | 512.3 |

TABLE T-1-continued

| Compound No. | Structure | IUPAC | Exact mass (g/mol) | LCMS, Found [M + H]+ |
|---|---|---|---|---|
| 138 | 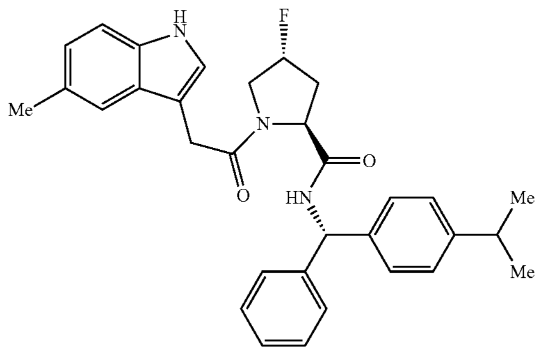 [SMILES: Cc1ccc2[nH]cc(CC(=O)N3C[C@H](F)C[C@H]3C(=O)N[C@@H](c3ccccc3)c3ccc(C(C)C)cc3)c2c1] | (2S,4R)-4-fluoro-1-[2-(5-methyl-1H-indol-3-yl)acetyl]-N-[(S)-phenyl[4-(propan-2-yl)phenyl]methyl]pyrrolidine-2-carboxamide | 511.3 | 512.3 |
| 139 | 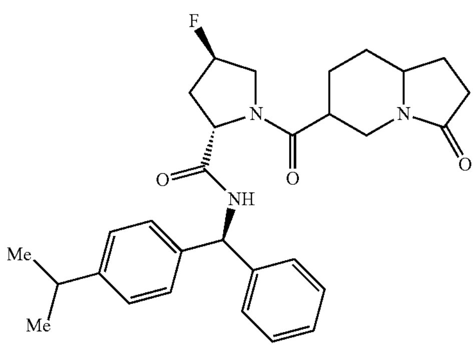 [SMILES: CC(C)c1ccc([C@@H](NC(=O)[C@@H]2C[C@@H](F)CN2C(=O)C2CCC3CCC(=O)N3C2)c2ccccc2)cc1] | (2S,4R)-4-fluoro-1-(3-oxo-octahydroindolizine-6-carbonyl)-N-[(S)-phenyl[4-(propan-2-yl)phenyl]methyl]pyrrolidine-2-carboxamide | 505.3 | 506.3 |
| 140 | 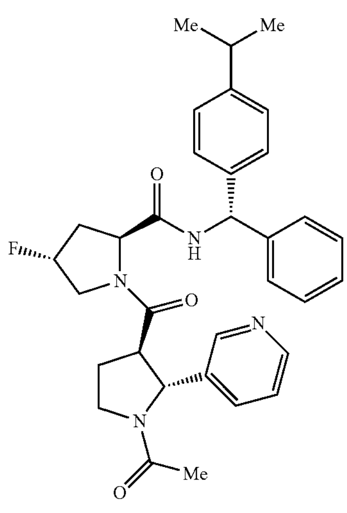 [SMILES: CC(=O)N1CC[C@@H](C(=O)N2C[C@H](F)C[C@H]2C(=O)N[C@@H](c2ccccc2)c2ccc(C(C)C)cc2)[C@@H]1c1cccnc1] | (2S,4R)-1-[(2R,3R)-1-acetyl-2-(pyridin-3-yl)pyrrolidine-3-carbonyl]-4-fluoro-N-[(S)-phenyl[4-(propan-2-yl)phenyl]methyl]pyrrolidine-2-carboxamide | 556.3 | 557.2 |

TABLE T-1-continued

| Compound No. | Structure | IUPAC | Exact mass (g/mol) | LCMS, Found [M + H]+ |
| --- | --- | --- | --- | --- |
| 141 | 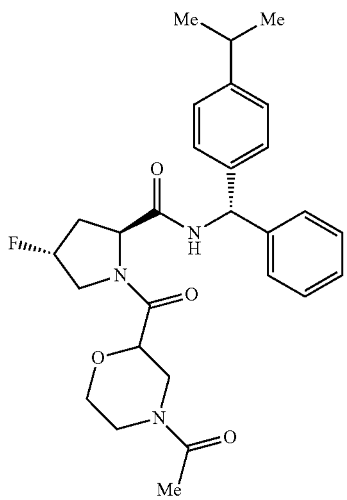 [SMILES: CC(=O)N1CCOC(C(=O)N2C[C@H](F)C[C@H]2C(=O)N[C@@H](c2ccccc2)c2ccc(C(C)C)cc2)C1] | (2S,4R)-1-(4-acetylmorpholine-2-carbonyl)-4-fluoro-N-[(S)-phenyl[4-(propan-2-yl)phenyl]methyl]pyrrolidine-2-carboxamide | 495.3 | 496.3 |
| 142 | 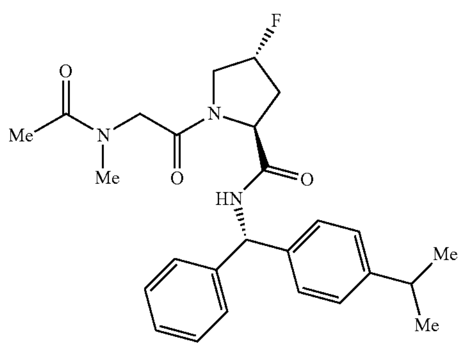 [SMILES: CC(=O)N(C)CC(=O)N1C[C@H](F)C[C@H]1C(=O)N[C@@H](c1ccccc1)c1ccc(C(C)C)cc1] | (2S,4R)-4-fluoro-1-[2-(N-methylacetamido)acetyl]-N-[(S)-phenyl[4-(propan-2-yl)phenyl]methyl]pyrrolidine-2-carboxamide | 453.2 | 454.3 |
| 143 | 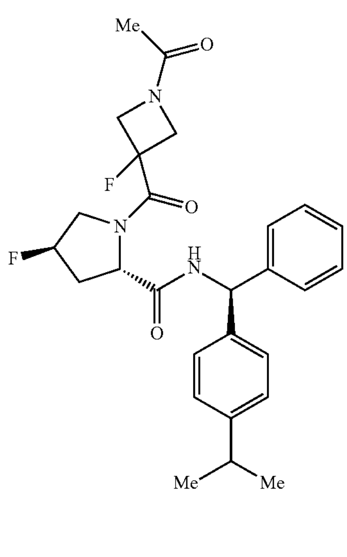 [SMILES: CC(=O)N1CC(F)(C(=O)N2C[C@H](F)C[C@H]2C(=O)N[C@@H](c2ccccc2)c2ccc(C(C)C)cc2)C1] | (2S,4R)-1-(1-acetyl-3-fluoroazetidine-3-carbonyl)-4-fluoro-N-[(S)-phenyl[4-(propan-2-yl)phenyl]methyl]pyrrolidine-2-carboxamide | 483.2 | 484.3 |

TABLE T-1-continued

| Compound No. | Structure | IUPAC | Exact mass (g/mol) | LCMS, Found [M + H]+ |
|---|---|---|---|---|
| 144 | 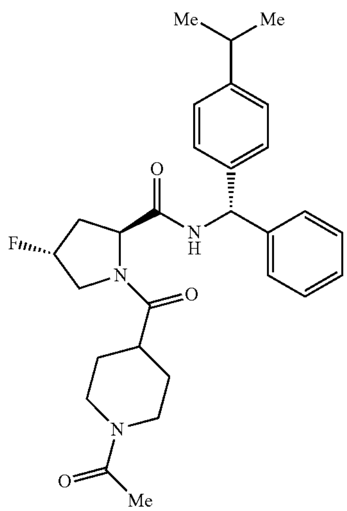 [SMILES: CC(=O)N1CCC(C(=O)N2C[C@H](F)C[C@H]2C(=O)N[C@@H](c2ccccc2)c2ccc(C(C)C)cc2)CC1] | (2S,4R)-1-(1-acetylpiperidine-4-carbonyl)-4-fluoro-N-[(S)-phenyl[4-(propan-2-yl)phenyl]methyl]pyrrolidine-2-carboxamide | 493.3 | 494.2 |
| 145 | 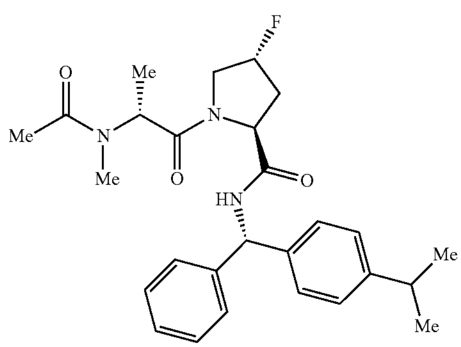 [SMILES: CC(=O)N(C)[C@H](C)C(=O)N1C[C@H](F)C[C@H]1C(=O)N[C@@H](c1ccccc1)c1ccc(C(C)C)cc1] | (2S,4R)-4-fluoro-1-[(2R)-2-(N-methylacetamido)propanoyl]-N-[(S)-phenyl[4-(propan-2-yl)phenyl]methyl]pyrrolidine-2-carboxamide | 467.3 | 468.3 |
| 146 | 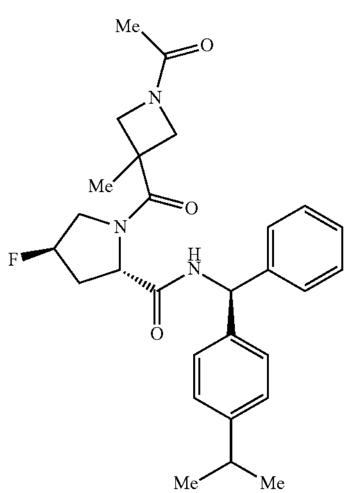 [SMILES: CC(=O)N1CC(C)(C(=O)N2C[C@H](F)C[C@H]2C(=O)N[C@@H](c2ccccc2)c2ccc(C(C)C)cc2)C1] | (2S,4R)-1-(1-acetyl-3-methylazetidine-3-carbonyl)-4-fluoro-N-[(S)-phenyl[4-(propan-2-yl)phenyl]methyl]pyrrolidine-2-carboxamide | 479.3 | 480.3 |

TABLE T-1-continued

| Compound No. | Structure | IUPAC | Exact mass (g/mol) | LCMS, Found [M + H]+ |
| --- | --- | --- | --- | --- |
| 147 | 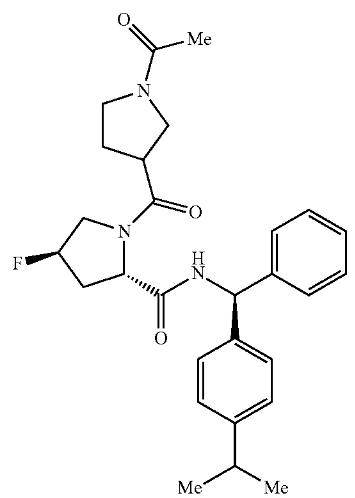 [SMILES: CC(=O)N1CCC(C(=O)N2C[C@H](F)C[C@H]2C(=O)N[C@@H](c2ccccc2)c2ccc(C(C)C)cc2)C1] | (2S,4R)-1-(1-acetylpyrrolidine-3-carbonyl)-4-fluoro-N-[(S)-phenyl[4-(propan-2-yl)phenyl]methyl]pyrrolidine-2-carboxamide | 479.3 | 480.2 |
| 148 | 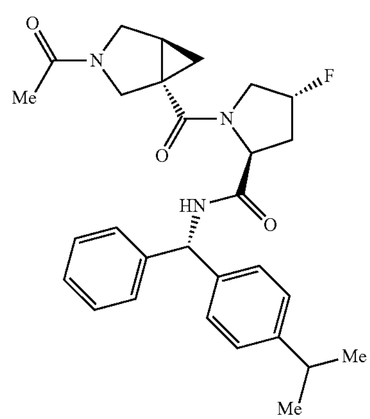 [SMILES: CC(=O)N1C[C@H]2C[C@@]2(C(=O)N2C[C@H](F)C[C@H]2C(=O)N[C@@H](c2ccccc2)c2ccc(C(C)C)cc2)C1] | (2S,4R)-1-[(1S,5S)-3-acetyl-3-azabicyclo[3.1.0]hexane-1-carbonyl]-4-fluoro-N-[(S)-phenyl[4-(propan-2-yl)phenyl]methyl]pyrrolidine-2-carboxamide | 491.3 | 492.3 |
| 149 | 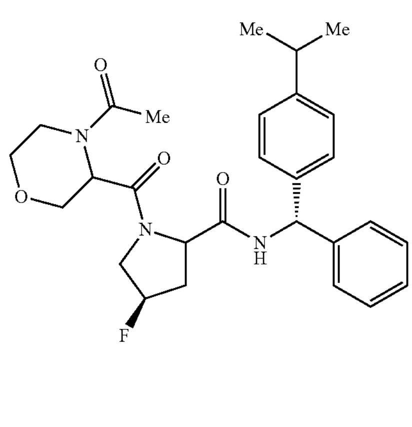 [SMILES: CC(=O)N1CCOCC1C(=O)N1C[C@H](F)CC1C(=O)N[C@@H](c1ccccc1)c1ccc(C(C)C)cc1] | (2S,4R)-1-(4-acetylmorpholine-3-carbonyl)-4-fluoro-N-[(S)-phenyl[4-(propan-2-yl)phenyl]methyl]pyrrolidine-2-carboxamide | 495.3 | 496.3 |

TABLE T-1-continued

| Compound No. | Structure | IUPAC | Exact mass (g/mol) | LCMS, Found [M + H]+ |
| --- | --- | --- | --- | --- |
| 150 | 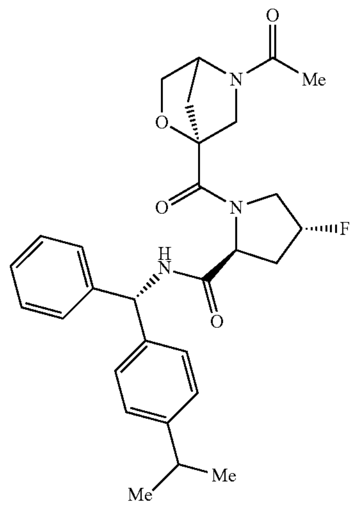 [SMILES: CC(=O)N1C[C@]2(C(=O)N3C[C@H](F)C[C@H]3C(=O)N[C@@H](c3ccccc3)c3ccc(C(C)C)cc3)CC1CO2] | (2S,4R)-1-[(1S)-5-acetyl-2-oxa-5-azabicyclo[2.2.1]heptane-1-carbonyl]-4-fluoro-N-[(S)-phenyl[4-(propan-2-yl)phenyl]methyl]pyrrolidine-2-carboxamide | 507.3 | 508.3 |
| 151 | 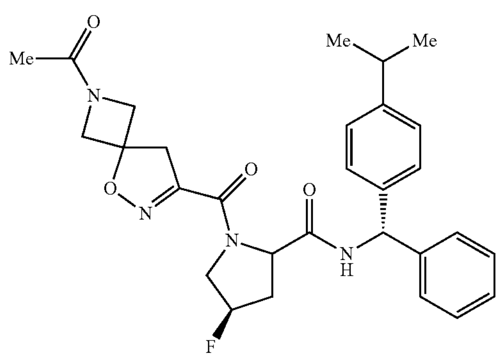 [SMILES: CC(=O)N1CC2(CC(C(=O)N3C[C@H](F)CC3C(=O)N[C@@H](c3ccccc3)c3ccc(C(C)C)cc3)=NO2)C1] | (2S,4R)-1-{2-acetyl-5-oxa-2,6-diazaspiro[3.4]oct-6-ene-7-carbonyl}-4-fluoro-N-[(S)-phenyl[4-(propan-2-yl)phenyl]methyl]pyrrolidine-2-carboxamide | 520.2 | 521.3 |
| 152 | 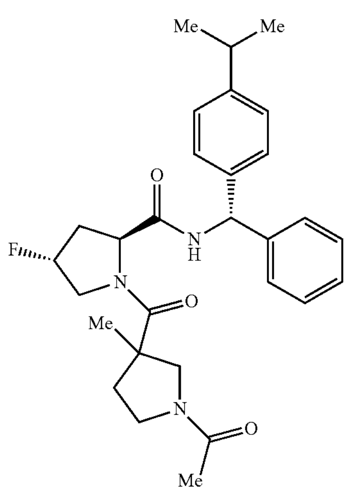 [SMILES: CC(=O)N1CCC(C)(C(=O)N2C[C@H](F)C[C@H]2C(=O)N[C@@H](c2ccccc2)c2ccc(C(C)C)cc2)C1] | (2S,4R)-1-(1-acetyl-3-methylpyrrolidine-3-carbonyl)-4-fluoro-N-[(S)-phenyl[4-(propan-2-yl)phenyl]methyl]pyrrolidine-2-carboxamide | 493.3 | 494.3 |

TABLE T-1-continued

| Compound No. | Structure | IUPAC | Exact mass (g/mol) | LCMS, Found [M + H]+ |
|---|---|---|---|---|
| 153 | 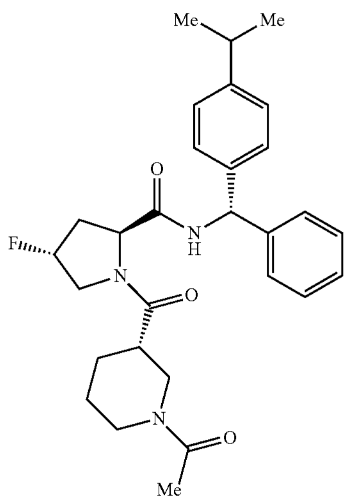 [SMILES: CC(=O)N1CCC[C@H](C(=O)N2C[C@H](F)C[C@H]2C(=O)N[C@@H](c2ccccc2)c2ccc(C(C)C)cc2)C1] | (2S,4R)-1-[(3S)-1-acetylpiperidine-3-carbonyl]-4-fluoro-N-[(S)-phenyl[4-(propan-2-yl)phenyl]methyl]pyrrolidine-2-carboxamide | 493.3 | 494.3 |
| 154 | 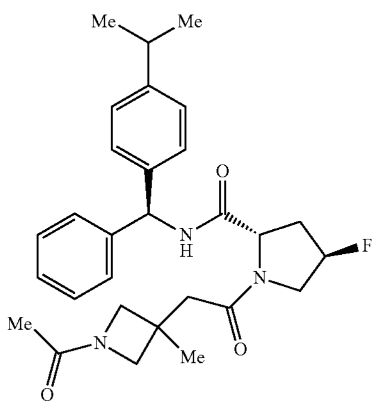 [SMILES: CC(=O)N1CC(C)(CC(=O)N2C[C@H](F)C[C@H]2C(=O)N[C@@H](c2ccccc2)c2ccc(C(C)C)cc2)C1] | (2S,4R)-1-[2-(1-acetyl-3-methylazetidin-3-yl)acetyl]-4-fluoro-N-[(S)-phenyl[4-(propan-2-yl)phenyl]methyl]pyrrolidine-2-carboxamide | 493.3 | 494.1 |
| 155 | 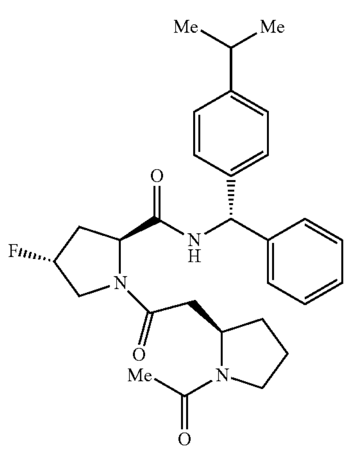 [SMILES: CC(=O)N1CCC[C@@H]1CC(=O)N1C[C@H](F)C[C@H]1C(=O)N[C@@H](c1ccccc1)c1ccc(C(C)C)cc1] | (2S,4R)-1-{2-[(2R)-1-acetylpyrrolidin-2-yl]acetyl}-4-fluoro-N-[(S)-phenyl[4-(propan-2-yl)phenyl]methyl]pyrrolidine-2-carboxamide | 493.3 | 494.3 |

| Compound No. | Structure | IUPAC | Exact mass (g/mol) | LCMS, Found [M + H]+ |
|---|---|---|---|---|
| 156 | 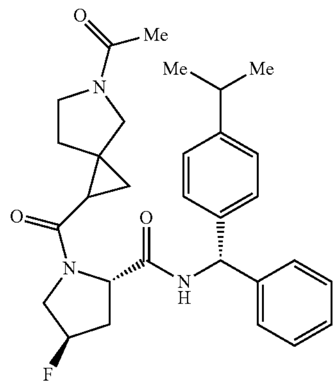 [SMILES: CC(=O)N1CCC2(CC2C(=O)N2C[C@H](F)C[C@H]2C(=O)N[C@@H](c2ccccc2)c2ccc(C(C)C)cc2)C1] | (2S,4R)-1-{5-acetyl-5-azaspiro[2.4]heptane-1-carbonyl}-4-fluoro-N-[(S)-phenyl[4-(propan-2-yl)phenyl]methyl]pyrrolidine-2-carboxamide | 505.3 | 506.2 |
| 157 | 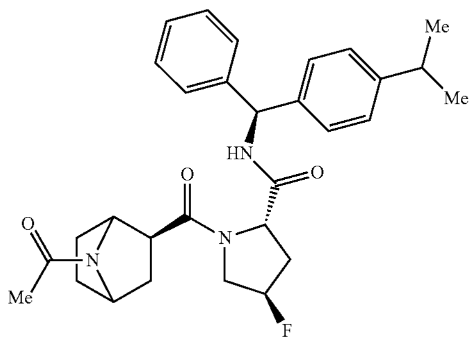 [SMILES: CC(=O)N1C2CCC1[C@@H](C(=O)N1C[C@H](F)C[C@H]1C(=O)N[C@@H](c1ccccc1)c1ccc(C(C)C)cc1)C2] | (2S,4R)-1-[(2S)-7-acetyl-7-azabicyclo[2.2.1]heptane-2-carbonyl]-4-fluoro-N-[(S)-phenyl[4-(propan-2-yl)phenyl]methyl]pyrrolidine-2-carboxamide | 505.3 | 506.3 |
| 158 | 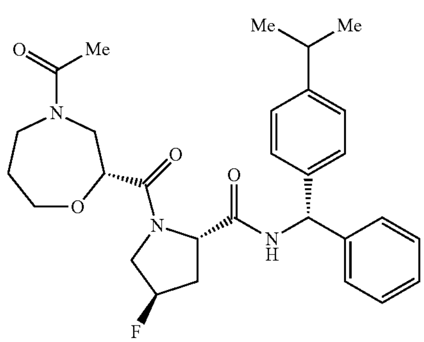 [SMILES: CC(=O)N1CCCO[C@@H](C(=O)N2C[C@H](F)C[C@H]2C(=O)N[C@@H](c2ccccc2)c2ccc(C(C)C)cc2)C1] | (2S,4R)-1-[(2R)-4-acetyl-1,4-oxazepane-2-carbonyl]-4-fluoro-N-[(S)-phenyl[4-(propan-2-yl)phenyl]methyl]pyrrolidine-2-carboxamide | 509.3 | 510.2 |
| 159 | 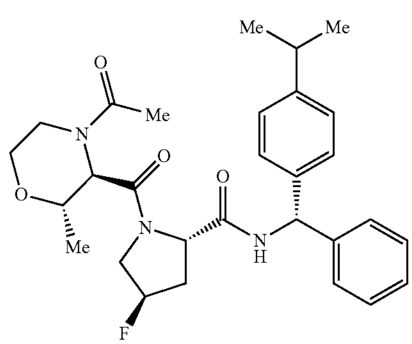 [SMILES: CC(=O)N1CCO[C@@H](C)[C@@H]1C(=O)N1C[C@H](F)C[C@H]1C(=O)N[C@@H](c1ccccc1)c1ccc(C(C)C)cc1] | (2S,4R)-1-[(2S,3R)-4-acetyl-2-methylmorpholine-3-carbonyl]-4-fluoro-N-[(S)-phenyl[4-(propan-2-yl)phenyl]methyl]pyrrolidine-2-carboxamide | 509.3 | 510.3 |

TABLE T-1-continued

| Compound No. | Structure | IUPAC | Exact mass (g/mol) | LCMS, Found [M + H]+ |
| --- | --- | --- | --- | --- |
| 160 | 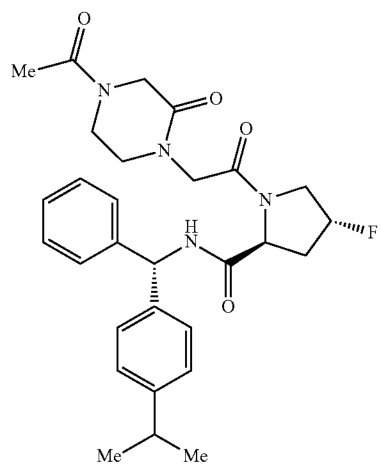 [SMILES: CC(=O)N1CCN(CC(=O)N2C[C@H](F)C[C@H]2C(=O)N[C@@H](c2ccccc2)c2ccc(C(C)C)cc2)C(=O)C1] | (2S,4R)-1-[2-(4-acetyl-2-oxopiperazin-1-yl)acetyl]-4-fluoro-N-[(S)-phenyl[4-(propan-2-yl)phenyl]methyl]pyrrolidine-2-carboxamide | 522.3 | 523.3 |
| 161 | 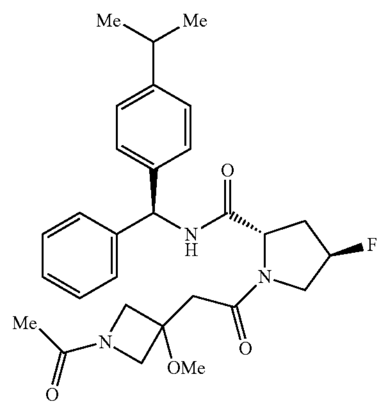 [SMILES: COC1(CC(=O)N2C[C@H](F)C[C@H]2C(=O)N[C@@H](c2ccccc2)c2ccc(C(C)C)cc2)CN(C(C)=O)C1] | (2S,4R)-1-[2-(1-acetyl-3-methoxyazetidin-3-yl)acetyl]-4-fluoro-N-[(S)-phenyl[4-(propan-2-yl)phenyl]methyl]pyrrolidine-2-carboxamide | 509.3 | 510.3 |
| 162 | 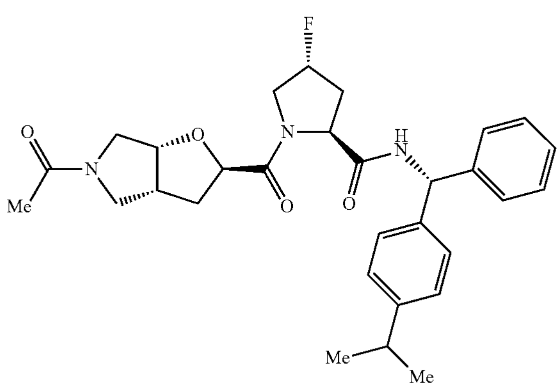 [SMILES: CC(=O)N1C[C@H]2C[C@H](C(=O)N3C[C@H](F)C[C@H]3C(=O)N[C@H](c3ccccc3)c3ccc(C(C)C)cc3)O[C@H]2C1] | (2S,4R)-1-[(2R,3aR,6aR)-5-acetyl-hexahydro-2H-furo[2,3-c]pyrrole-2-carbonyl]-4-fluoro-N-[(S)-phenyl[4-(propan-2-yl)phenyl]methyl]pyrrolidine-2-carboxamide | 521.3 | 522.2 |

TABLE T-1-continued

| Compound No. | Structure | IUPAC | Exact mass (g/mol) | LCMS, Found [M + H]+ |
|---|---|---|---|---|
| 163 | 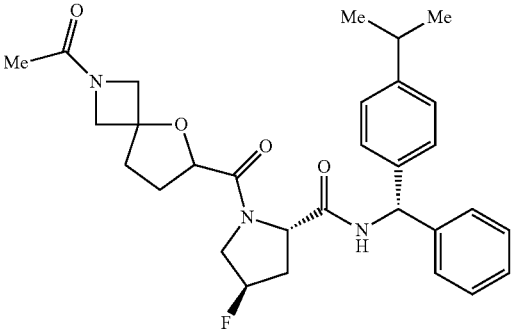 [SMILES: CC(=O)N1CC2(CCC(C(=O)N3C[C@H](F)C[C@H]3C(=O)N[C@@H](c3ccccc3)c3ccc(C(C)C)cc3)O2)C1] | (2S,4R)-1-{2-acetyl-5-oxa-2-oazaspiro[3.4]octane-6-carbonyl}-4-fluoro-N-[(S)-phenyl[4-(propan-2-yl)phenyl]methyl]pyrrolidine-2-carboxamide | 521.3 | 522.2 |
| 164 | 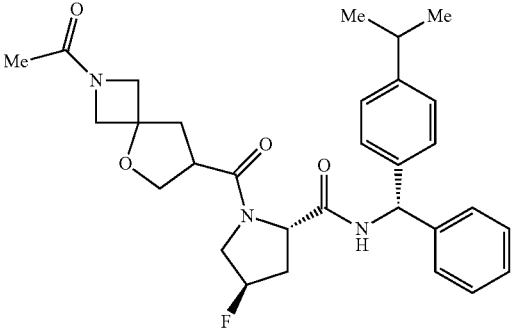 [SMILES: CC(=O)N1CC2(CC(C(=O)N3C[C@H](F)C[C@H]3C(=O)N[C@@H](c3ccccc3)c3ccc(C(C)C)cc3)CO2)C1] | (2S,4R)-1-{2-acetyl-5-oxa-2-azaspiro[3.4]octane-7-carbonyl}-4-fluoro-N-[(S)-phenyl[4-(propan-2-yl)phenyl]methyl]pyrrolidine-2-carboxamide | 521.3 | 522.2 |
| 165 | 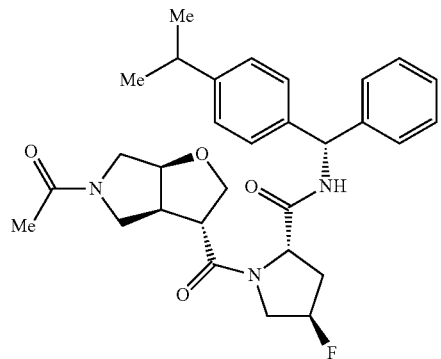 [SMILES: CC(=O)N1C[C@@H]2[C@@H](C(=O)N3C[C@H](F)C[C@H]3C(=O)N[C@@H](c3ccccc3)c3ccc(C(C)C)cc3)CO[C@@H]2C1] | (2S,4R)-1-[(3R,3aS,6aS)-5-acetyl-hexahydro-2H-furo[2,3-c]pyrrole-3-carbonyl]-4-fluoro-N-[(S)-phenyl[4-(propan-2-yl)phenyl]methyl]pyrrolidine-2-carboxamide | 521.3 | 522.3 |
| 166 | 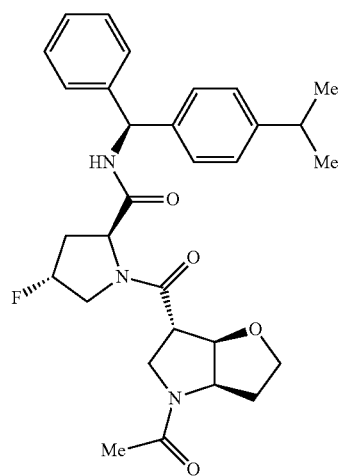 [SMILES: CC(=O)N1C[C@H](C(=O)N2C[C@H](F)C[C@H]2C(=O)N[C@@H](c2ccccc2)c2ccc(C(C)C)cc2)[C@H]2OCC[C@H]21] | (2S,4R)-1-[(3aR,6S,6aR)-4-acetyl-hexahydro-2H-furo[3,2-b]pyrrole-6-carbonyl]-4-fluoro-N-[(S)-phenyl[4-(propan-2-yl)phenyl]methyl]pyrrolidine-2-carboxamide | 521.3 | 522.3 |

TABLE T-1-continued

| Compound No. | Structure | IUPAC | Exact mass (g/mol) | LCMS, Found [M + H]+ |
|---|---|---|---|---|
| 167 | 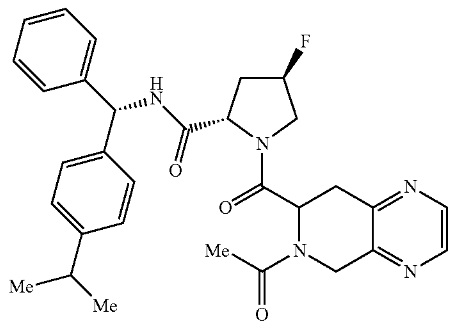 [SMILES: CC(=O)N1Cc2nccnc2CC1C(=O)N1C[C@H](F)C[C@H]1C(=O)N[C@@H](c1ccccc1)c1ccc(C(C)C)cc1] | (2S,4R)-1-{6-acetyl-5H,6H,7H,8H-pyrido[3,4-b]pyrazine-7-carbonyl}-4-fluoro-N-[(S)-phenyl[4-(propan-2-yl)phenyl]methyl]pyrrolidine-2-carboxamide | 543.3 | 544.2 |
| 168 | 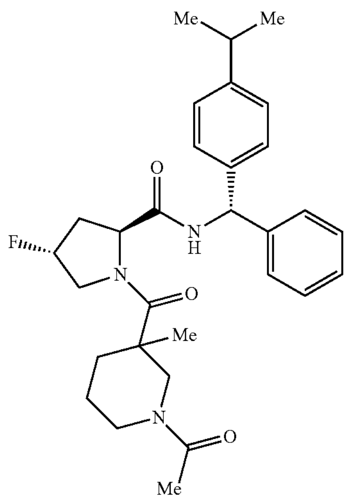 [SMILES: CC(=O)N1CCCC(C)(C(=O)N2C[C@H](F)C[C@H]2C(=O)N[C@@H](c2ccccc2)c2ccc(C(C)C)cc2)C1] | (2S,4R)-1-(1-acetyl-3-methylpiperidine-3-carbonyl)-4-fluoro-N-[(S)-phenyl[4-(propan-2-yl)phenyl]methyl]pyrrolidine-2-carboxamide | 507.3 | 508.3 |
| 169 | 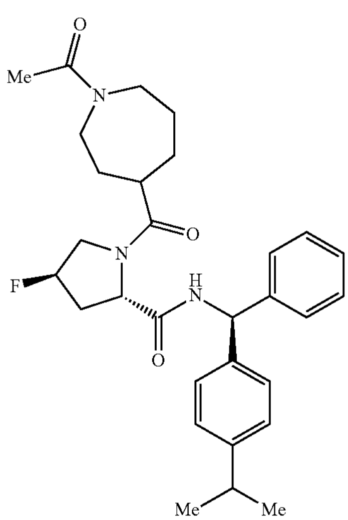 [SMILES: CC(=O)N1CCCC(C(=O)N2C[C@H](F)C[C@H]2C(=O)N[C@@H](c2ccccc2)c2ccc(C(C)C)cc2)CC1] | (2S,4R)-1-(1-acetylazepane-4-carbonyl)-4-fluoro-N-[(S)-phenyl[4-(propan-2-yl)phenyl]methyl]pyrrolidine-2-carboxamide | 507.3 | 508.2 |

TABLE T-1-continued

| Compound No. | Structure | IUPAC | Exact mass (g/mol) | LCMS, Found [M + H]+ |
| --- | --- | --- | --- | --- |
| 170 | 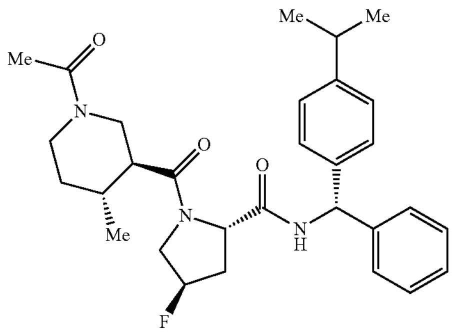 [SMILES: CC(=O)N1CC[C@@H](C)[C@H](C(=O)N2C[C@H](F)C[C@H]2C(=O)N[C@@H](c2ccccc2)c2ccc(C(C)C)cc2)C1] | (2S,4R)-1-[(3S,4R)-1-acetyl-4-methylpiperidine-3-carbonyl]-4-fluoro-N-[(S)-phenyl[4-(propan-2-yl)phenyl]methyl]pyrrolidine-2-carboxamide | 507.3 | 508.3 |
| 171 | 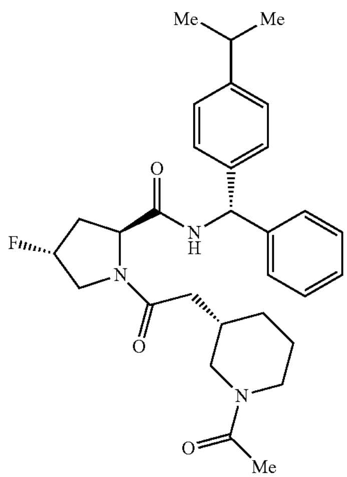 [SMILES: CC(=O)N1CCC[C@@H](CC(=O)N2C[C@H](F)C[C@H]2C(=O)N[C@@H](c2ccccc2)c2ccc(C(C)C)cc2)C1] | (2S,4R)-1-{2-[(3S)-1-acetylpiperidin-3-yl]acetyl}-4-fluoro-N-[(S)-phenyl[4-(propan-2-yl)phenyl]methyl]pyrrolidine-2-carboxamide | 507.3 | 508.2 |
| 172 | 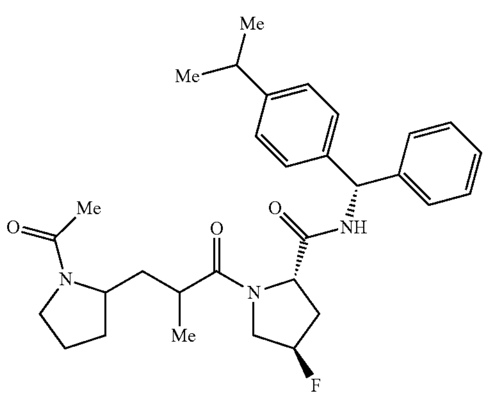 [SMILES: CC(=O)N1CCCC1CC(C)C(=O)N1C[C@H](F)C[C@H]1C(=O)N[C@@H](c1ccccc1)c1ccc(C(C)C)cc1] | (2S,4R)-1-[3-(1-acetylpyrrolidin-2-yl)propanoyl]-4-fluoro-N-[(S)-phenyl[4-(propan-2-yl)phenyl]methyl]pyrrolidine-2-carboxamide | 507.3 | 508.3 |
| 173 | 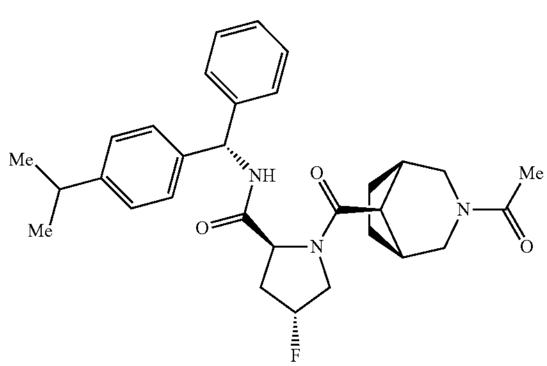 [SMILES: CC(=O)N1C[C@H]2CC[C@@H](C1)[C@@H]2C(=O)N1C[C@H](F)C[C@H]1C(=O)N[C@@H](c1ccccc1)c1ccc(C(C)C)cc1] | (2S,4R)-1-[(1R,5S,8S)-3-acetyl-3-azabicyclo[3.2.1]octane-8-carbonyl]-4-fluoro-N-[(S)-phenyl[4-(propan-2-yl)phenyl]methyl]pyrrolidine-2-carboxamide | 519.3 | 520.3 |

TABLE T-1-continued

| Compound No. | Structure | IUPAC | Exact mass (g/mol) | LCMS, Found [M + H]+ |
|---|---|---|---|---|
| 174 | 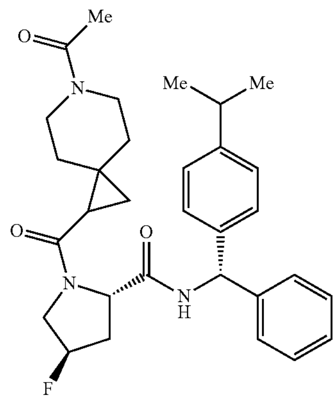 [SMILES: CC(=O)N1CCC2(CC1)CC2C(=O)N1C[C@H](F)C[C@H]1C(=O)N[C@@H](c1ccccc1)c1ccc(C(C)C)cc1] | (2S,4R)-1-{6-acetyl-6-azaspiro[2.5]octane-1-carbonyl}-4-fluoro-N-[(S)-phenyl[4-(propan-2-yl)phenyl]methyl]pyrrolidine-2-carboxamide | 519.3 | 520.2 |
| 175 | 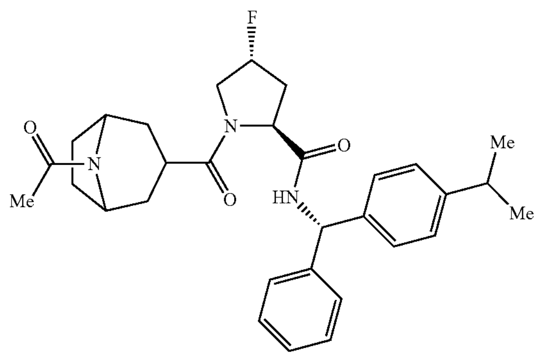 [SMILES: CC(=O)N1C2CCC1CC(C(=O)N1C[C@H](F)C[C@H]1C(=O)N[C@@H](c1ccccc1)c1ccc(C(C)C)cc1)C2] | (2S,4R)-1-{8-acetyl-8-azabicyclo[3.2.1]octane-3-carbonyl}-4-fluoro-N-[(S)-phenyl[4-(propan-2-yl)phenyl]methyl]pyrrolidine-2-carboxamide | 519.3 | 520.2 |
| 176 | 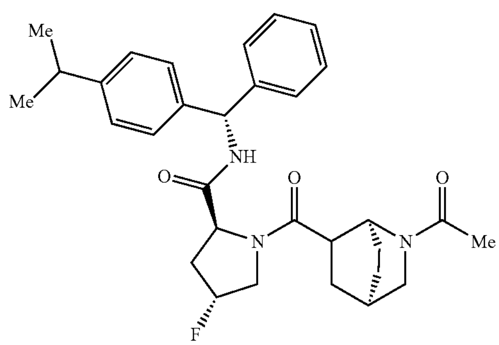 [SMILES: CC(=O)N1C[C@@H]2CC[C@H]1C(C(=O)N1C[C@H](F)C[C@H]1C(=O)N[C@@H](c1ccccc1)c1ccc(C(C)C)cc1)C2] | (2S,4R)-1-[(1S,4R)-2-acetyl-2-azabicyclo[2.2.2]octane-6-carbonyl]-4-fluoro-N-[(S)-phenyl[4-(propan-2-yl)phenyl]methyl]pyrrolidine-2-carboxamide | 519.3 | 520.3 |
| 177 | 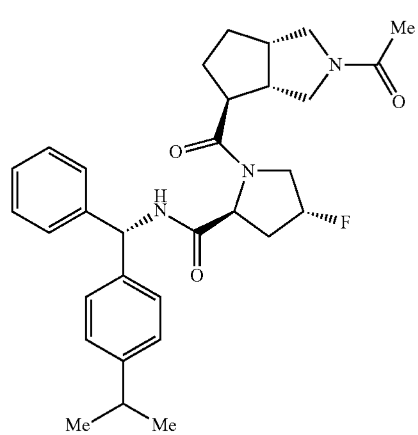 [SMILES: CC(=O)N1C[C@H]2CC[C@H](C(=O)N3C[C@H](F)C[C@H]3C(=O)N[C@@H](c3ccccc3)c3ccc(C(C)C)cc3)[C@H]2C1] | (2S,4R)-1-[(3aS,4S,6aS)-2-acetyl-octahydrocyclopenta[c]pyrrole-4-carbonyl]-4-fluoro-N-[(S)-phenyl[4-(propan-2-yl)phenyl]methyl]pyrrolidine-2-carboxamide | 519.3 | 520.3 |

TABLE T-1-continued

| Compound No. | Structure | IUPAC | Exact mass (g/mol) | LCMS, Found [M + H]+ |
|---|---|---|---|---|
| 178 | 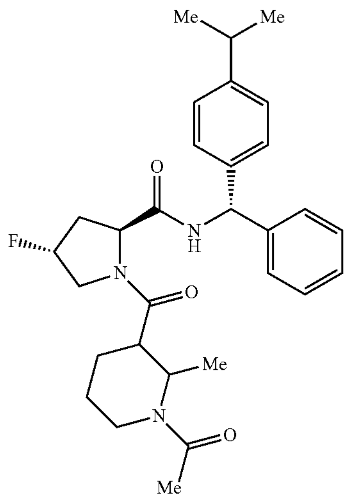 [SMILES: CC(=O)N1CCCC(C(=O)N2C[C@H](F)C[C@H]2C(=O)N[C@@H](c2ccccc2)c2ccc(C(C)C)cc2)C1C] | (2S,4R)-1-(1-acetyl-2-methylpiperidine-3-carbonyl)-4-fluoro-N-[(S)-phenyl[4-(propan-2-yl)phenyl]methyl]pyrrolidine-2-carboxamide | 507.3 | 508.3 |
| 179 | 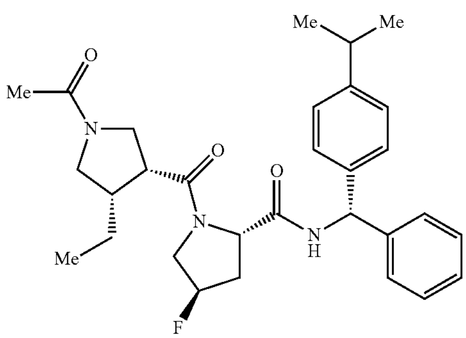 [SMILES: CC[C@@H]1CN(C(C)=O)C[C@@H]1C(=O)N1C[C@H](F)C[C@H]1C(=O)N[C@@H](c1ccccc1)c1ccc(C(C)C)cc1] | (2S,4R)-1-[(3R,4S)-1-acetyl-4-ethylpyrrolidine-3-carbonyl]-4-fluoro-N-[(S)-phenyl[4-(propan-2-yl)phenyl]methyl]pyrrolidine-2-carboxamide | 507.3 | 508.3 |
| 180 | 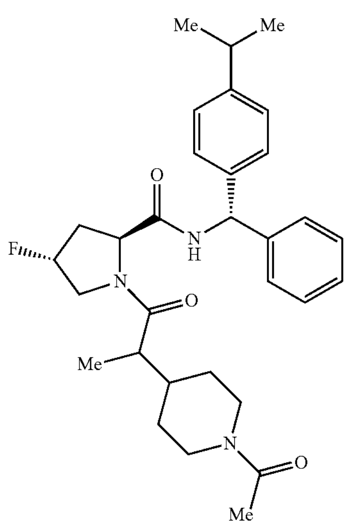 [SMILES: CC(=O)N1CCC(C(C)C(=O)N2C[C@H](F)C[C@H]2C(=O)N[C@@H](c2ccccc2)c2ccc(C(C)C)cc2)CC1] | (2S,4R)-1-[2-(1-acetylpiperidin-4-yl)propanoyl]-4-fluoro-N-[(S)-phenyl[4-(propan-2-yl)phenyl]methyl]pyrrolidine-2-carboxamide | 521.3 | 522.3 |

TABLE T-1-continued

| Compound No. | Structure | IUPAC | Exact mass (g/mol) | LCMS, Found [M + H]+ |
|---|---|---|---|---|
| 181 | 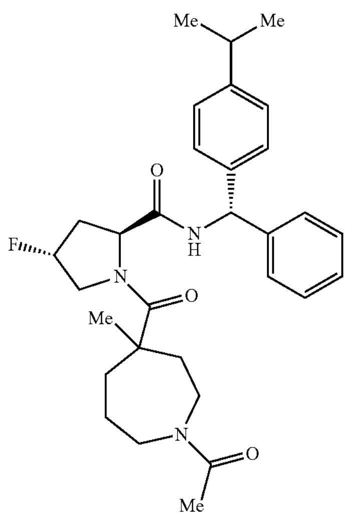 [SMILES: CC(=O)N1CCCC(C)(C(=O)N2C[C@H](F)C[C@H]2C(=O)N[C@@H](c2ccccc2)c2ccc(C(C)C)cc2)CC1] | (2S,4R)-1-(1-acetyl-4-methylazepane-4-carbonyl)-4-fluoro-N-[(S)-phenyl[4-(propan-2-yl)phenyl]methyl]pyrrolidine-2-carboxamide | 521.3 | 522.2 |
| 182 | 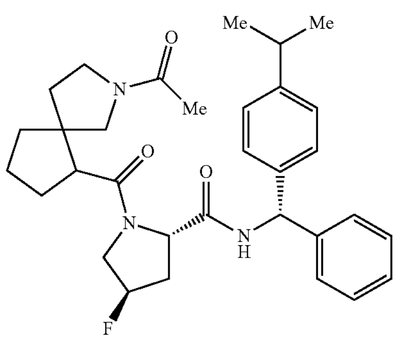 [SMILES: CC(=O)N1CCC2(CCCC2C(=O)N2C[C@H](F)C[C@H]2C(=O)N[C@@H](c2ccccc2)c2ccc(C(C)C)cc2)C1] | (2S,4R)-1-{2-acetyl-2-azaspiro[4.4]nonane-6-carbonyl}-4-fluoro-N-[(S)-phenyl[4-(propan-2-yl)phenyl]methyl]pyrrolidine-2-carboxamide | 533.3 | 534.3 |
| 183 | 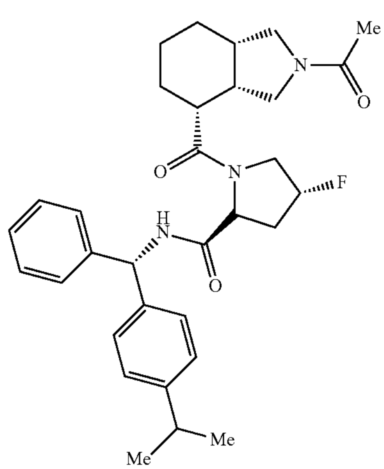 | (2S,4R)-1-[(3aS,4R,7aS)-2-acetyl-octahydro-1H-isoindole-4-carbonyl]-4-fluoro-N-[(S)-phenyl[4-(propan-2-yl)phenyl]methyl]pyrrolidine-2-carboxamide | 533.3 | 534.0 |

TABLE T-1-continued

| Compound No. | Structure | IUPAC | Exact mass (g/mol) | LCMS, Found [M + H]+ |
|---|---|---|---|---|
| 184 | 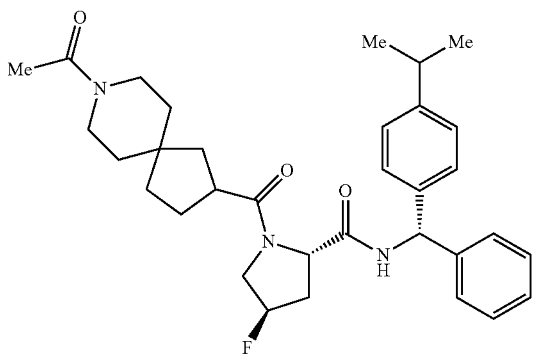 [SMILES: CC(=O)N1CCC2(CCC(C(=O)N3C[C@H](F)C[C@H]3C(=O)N[C@@H](c3ccccc3)c3ccc(C(C)C)cc3)C2)CC1] | (2S,4R)-1-{8-acetyl-8-azaspiro[4.5]decane-2-carbonyl}-4-fluoro-N-[(S)-phenyl[4-(propan-2-yl)phenyl]methyl]pyrrolidine-2-carboxamide | 547.3 | 548.3 |
| 185 | 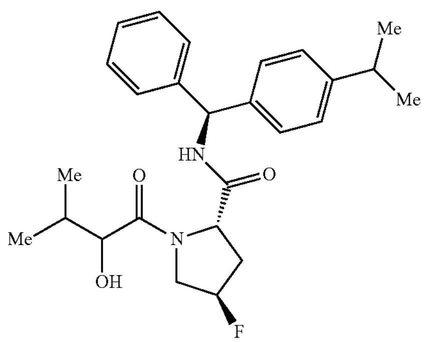 [SMILES: CC(C)c1ccc([C@@H](NC(=O)[C@@H]2C[C@@H](F)CN2C(=O)C(O)C(C)C)c2ccccc2)cc1] | (2S,4R)-4-fluoro-1-(2-hydroxy-3-methylbutanoyl)-N-[(S)-phenyl[4-(propan-2-yl)phenyl]methyl]pyrrolidine-2-carboxamide | 440.2 | 441.3 |
| 186 | 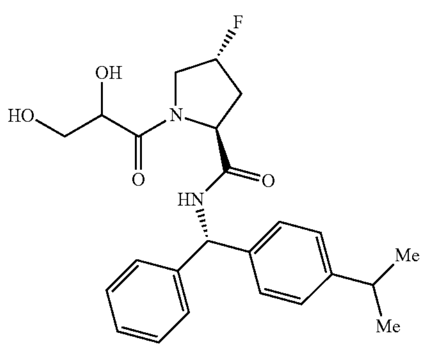 [SMILES: CC(C)c1ccc([C@@H](NC(=O)[C@@H]2C[C@@H](F)CN2C(=O)C(O)CO)c2ccccc2)cc1] | (2S,4R)-1-(2,3-dihydroxypropanoyl)-4-fluoro-N-[(S)-phenyl[4-(propan-2-yl)phenyl]methyl]pyrrolidine-2-carboxamide | 428.2 | 429.3 |
| 187 | 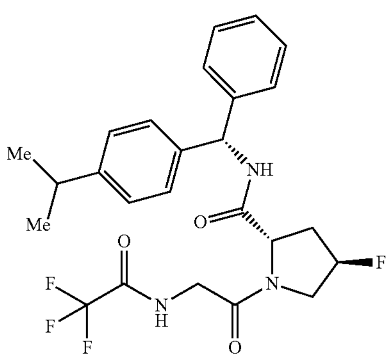 [SMILES: CC(C)c1ccc([C@@H](NC(=O)[C@@H]2C[C@@H](F)CN2C(=O)CNC(=O)C(F)(F)F)c2ccccc2)cc1] | (2S,4R)-4-fluoro-N-[(S)-phenyl[4-(propan-2-yl)phenyl]methyl]-1-[2-(2,2,2-trifluoroacetamido)acetyl]pyrrolidine-2-carboxamide | 493.2 | 494.1 |

TABLE T-1-continued

| Compound No. | Structure | IUPAC | Exact mass (g/mol) | LCMS, Found [M + H]+ |
| --- | --- | --- | --- | --- |
| 188 | 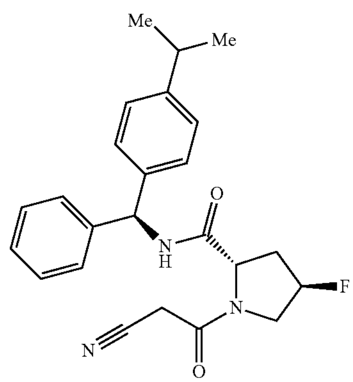 [SMILES: CC(C)c1ccc([C@@H](NC(=O)[C@@H]2C[C@@H](F)CN2C(=O)CC#N)c2ccccc2)cc1] | (2S,4R)-1-(2-cyanoacetyl)-4-fluoro-N-[(S)-phenyl[4-(propan-2-yl)phenyl]methyl]pyrrolidine-2-carboxamide | 407.2 | 408.1 |
| 189 | 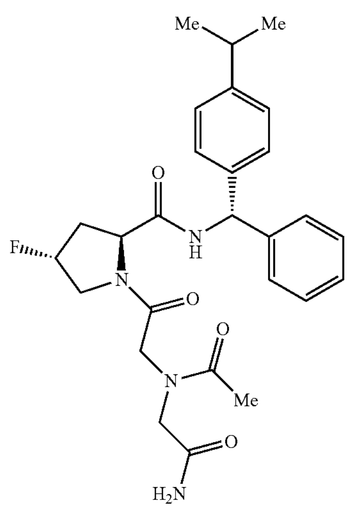 [SMILES: CC(=O)N(CC(N)=O)CC(=O)N1C[C@H](F)C[C@H]1C(=O)N[C@@H](c1ccccc1)c1ccc(C(C)C)cc1] | (2S,4R)-1-{2-[N-(carbamoylmethyl)acetamido]acetyl}-4-fluoro-N-[(S)-phenyl[4-(propan-2-yl)phenyl]methyl]pyrrolidine-2-carboxamide | 496.2 | 497.1 |
| 190 | 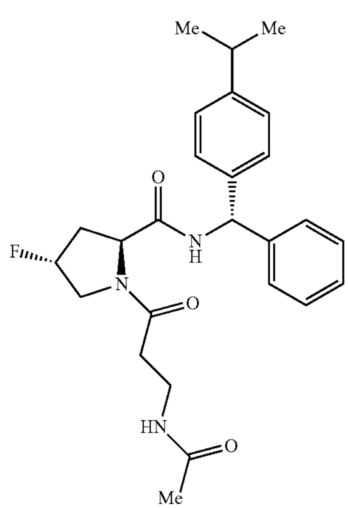 [SMILES: CC(=O)NCCC(=O)N1C[C@H](F)C[C@H]1C(=O)N[C@@H](c1ccccc1)c1ccc(C(C)C)cc1] | (2S,4R)-1-(3-acetamidopropanoyl)-4-fluoro-N-[(S)-phenyl[4-(propan-2-yl)phenyl]methyl]pyrrolidine-2-carboxamide | 453.2 | 454.1 |

TABLE T-1-continued

| Compound No. | Structure | IUPAC | Exact mass (g/mol) | LCMS, Found [M + H]+ |
| --- | --- | --- | --- | --- |
| 191 | 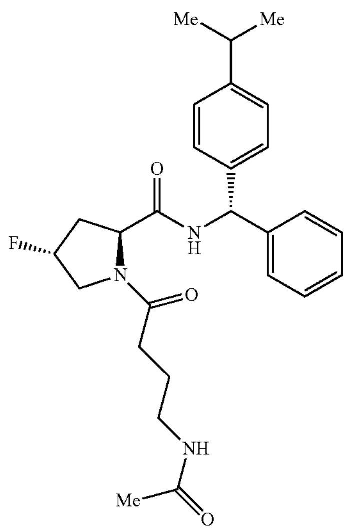 [SMILES: CC(=O)NCCCC(=O)N1C[C@H](F)C[C@H]1C(=O)N[C@@H](c1ccccc1)c1ccc(C(C)C)cc1] | (2S,4R)-1-(4-acetamidobutanoyl)-4-fluoro-N-[(S)-phenyl[4-(propan-2-yl)phenyl]methyl]pyrrolidine-2-carboxamide | 467.3 | 468.3 |
| 192 | 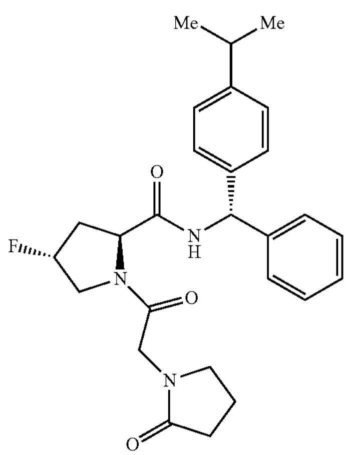 [SMILES: CC(C)c1ccc([C@@H](NC(=O)[C@@H]2C[C@@H](F)CN2C(=O)CN2CCCC2=O)c2ccccc2)cc1] | (2S,4R)-4-fluoro-1-[2-(2-oxopyrrolidin-1-yl)acetyl]-N-[(S)-phenyl[4-(propan-2-yl)phenyl]methyl]pyrrolidine-2-carboxamide | 465.2 | 466.2 |
| 193 | 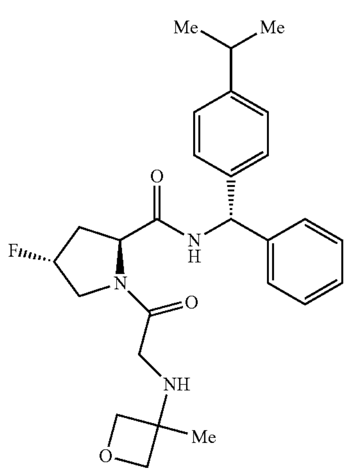 [SMILES: CC(C)c1ccc([C@@H](NC(=O)[C@@H]2C[C@@H](F)CN2C(=O)CNC2(C)COC2)c2ccccc2)cc1] | (2S,4R)-4-fluoro-1-{2-[(3-methyloxetan-3-yl)amino]acetyl}-N-[(S)-phenyl[4-(propan-2-yl)phenyl]methyl]pyrrolidine-2-carboxamide | 467.3 | 468.1 |

TABLE T-1-continued

| Compound No. | Structure | IUPAC | Exact mass (g/mol) | LCMS, Found [M + H]+ |
|---|---|---|---|---|
| 194 | 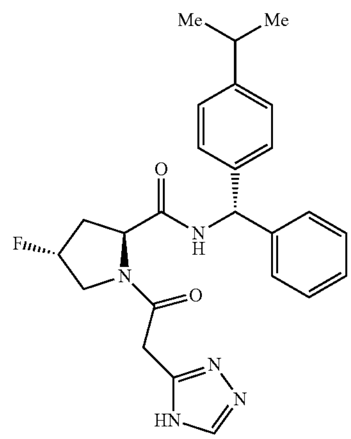 [SMILES: CC(C)c1ccc([C@@H](NC(=O)[C@@H]2C[C@@H](F)CN2C(=O)Cc2nnc[nH]2)c2ccccc2)cc1] | (2S,4R)-4-fluoro-N-[(S)-phenyl[4-(propan-2-yl)phenyl]methyl]-1-[2-(4H-1,2,4-triazol-3-yl)acetyl]pyrrolidine-2-carboxamide | 449.2 | 450.2 |
| 195 | 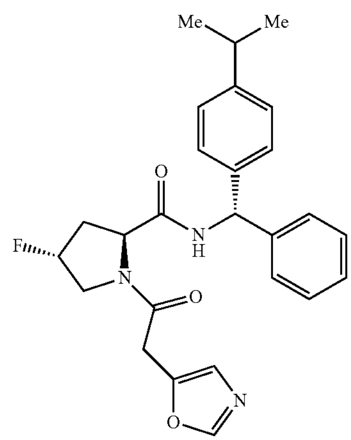 [SMILES: CC(C)c1ccc([C@@H](NC(=O)[C@@H]2C[C@@H](F)CN2C(=O)Cc2cnco2)c2ccccc2)cc1] | (2S,4R)-4-fluoro-1-[2-(1,3-oxazol-5-yl)acetyl]-N-[(S)-phenyl[4-(propan-2-yl)phenyl]methyl]pyrrolidine-2-carboxamide | 449.2 | 450.2 |
| 196 | 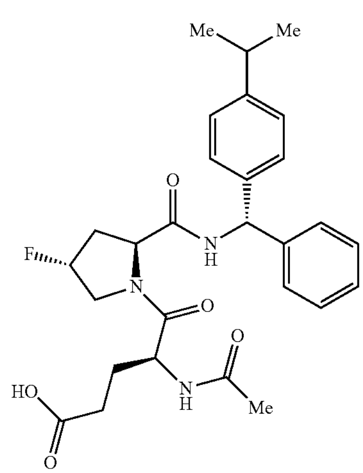 [SMILES: CC(=O)N[C@@H](CCC(=O)O)C(=O)N1C[C@H](F)C[C@H]1C(=O)N[C@@H](c1ccccc1)c1ccc(C(C)C)cc1] | (4S)-4-acetamido-5-[(2S,4R)-4-fluoro-2-{[(S)-phenyl[4-(propan-2-yl)phenyl]methyl]carbamoyl}pyrrolidin-1-yl]-5-oxopentanoic acid | 511.2 | 512.3 |

TABLE T-1-continued

| Compound No. | Structure | IUPAC | Exact mass (g/mol) | LCMS, Found [M + H]+ |
| --- | --- | --- | --- | --- |
| 197 | 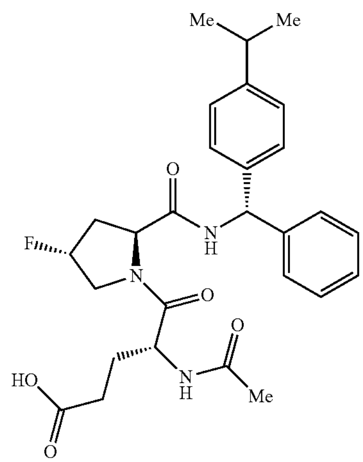 [SMILES: CC(=O)N[C@H](CCC(=O)O)C(=O)N1C[C@H](F)C[C@H]1C(=O)N[C@@H](c1ccccc1)c1ccc(C(C)C)cc1] | (4R)-4-acetamido-5-[(2S,4R)-4-fluoro-2-{[(S)-phenyl[4-(propan-2-yl)phenyl]methyl]carbamoyl}pyrrolidin-1-yl]-5-oxopentanoic acid | 511.2 | 512.3 |
| 198 | 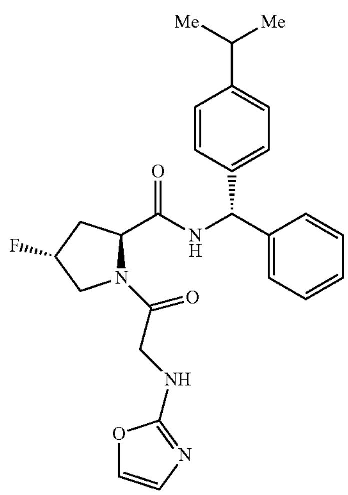 [SMILES: CC(C)c1ccc([C@@H](NC(=O)[C@@H]2C[C@@H](F)CN2C(=O)CNc2ncco2)c2ccccc2)cc1] | (2S,4R)-4-fluoro-1-{2-[(1,3-oxazol-2-yl)amino]acetyl}-N-[(S)-phenyl[4-(propan-2-yl)phenyl]methyl]pyrrolidine-2-carboxamide | 464.2 | 465.1 |
| 199 | 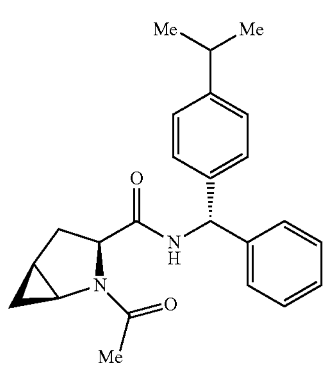 [SMILES: CC(=O)N1[C@H](C(=O)N[C@@H](c2ccccc2)c2ccc(C(C)C)cc2)C[C@@H]2C[C@@H]21] | (1S,3S,5S)-2-acetyl-N-[(S)-phenyl[4-(propan-2-yl)phenyl]methyl]-2-azabicyclo[3.1.0]hexane-3-carboxamide | 376.2 | 377.1 |

TABLE T-1-continued

| Compound No. | Structure | IUPAC | Exact mass (g/mol) | LCMS, Found [M + H]+ |
|---|---|---|---|---|
| 200 | 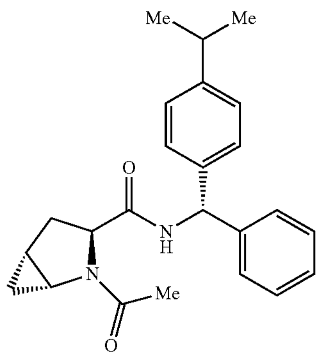 [SMILES: CC(=O)N1[C@@H]2C[C@@H]2C[C@H]1C(=O)N[C@@H](c1ccccc1)c1ccc(C(C)C)cc1] | (1R,3S,5R)-2-acetyl-N-[(S)-phenyl[4-(propan-2-yl)phenyl]methyl]-2-azabicyclo[3.1.0]hexane-3-carboxamide | 376.2 | 377.1 |
| 201 | 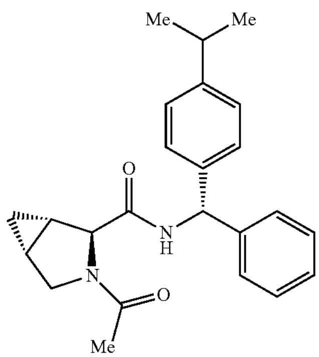 [SMILES: CC(=O)N1C[C@@H]2C[C@@H]2[C@H]1C(=O)N[C@@H](c1ccccc1)c1ccc(C(C)C)cc1] | (1S,2S,5R)-3-acetyl-N-[(S)-phenyl[4-(propan-2-yl)phenyl]methyl]-3-azabicyclo[3.1.0]hexane-2-carboxamide | 376.2 | 377.1 |
| 202 | 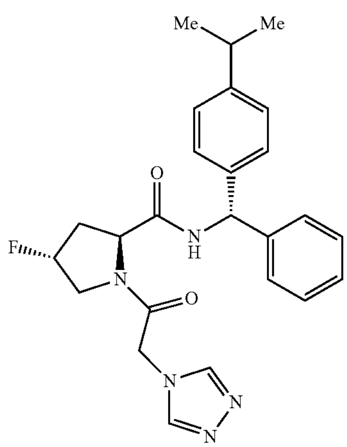 [SMILES: CC(C)c1ccc([C@@H](NC(=O)[C@@H]2C[C@@H](F)CN2C(=O)Cn2cnnc2)c2ccccc2)cc1] | (2RS,4R)-4-fluoro-N-[(S)-phenyl[4-(propan-2-yl)phenyl]methyl]-1-[2-(4H-1,2,4-triazol-4-yl)acetyl]pyrrolidine-2-carboxamide | 449.2 | 450.3 |
| 203 | 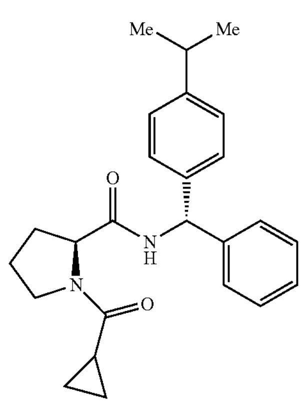 [SMILES: CC(C)c1ccc([C@@H](NC(=O)[C@@H]2CCCN2C(=O)C2CC2)c2ccccc2)cc1] | (2S)-1-cyclopropanecarbonyl-N-[(S)-phenyl[4-(propan-2-yl)phenyl]methyl]pyrrolidine-2-carboxamide | 390.2 | 391.3 |

TABLE T-1-continued

| Compound No. | Structure | IUPAC | Exact mass (g/mol) | LCMS, Found [M + H]+ |
|---|---|---|---|---|
| 204 | 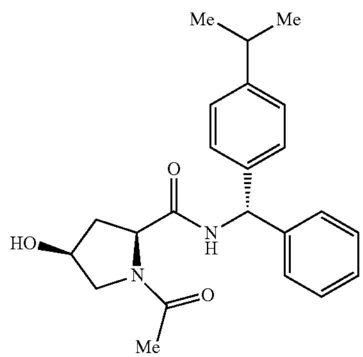 [SMILES: CC(=O)N1C[C@@H](O)C[C@H]1C(=O)N[C@@H](c1ccccc1)c1ccc(C(C)C)cc1] | (2S,4S)-1-acetyl-4-hydroxy-N-[(S)-phenyl[4-(propan-2-yl)phenyl]methyl]pyrrolidine-2-carboxamide | 380.2 | 381.2 |
| 205 | 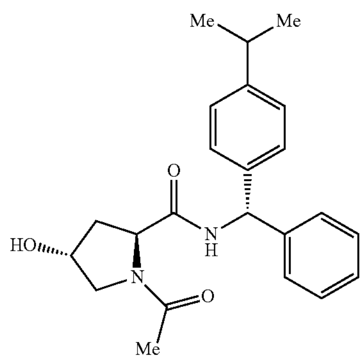 [SMILES: CC(=O)N1C[C@H](O)C[C@H]1C(=O)N[C@@H](c1ccccc1)c1ccc(C(C)C)cc1] | (2S,4R)-1-acetyl-4-hydroxy-N-[(S)-phenyl[4-(propan-2-yl)phenyl]methyl]pyrrolidine-2-carboxamide | 380.2 | 381.3 |
| 206 | 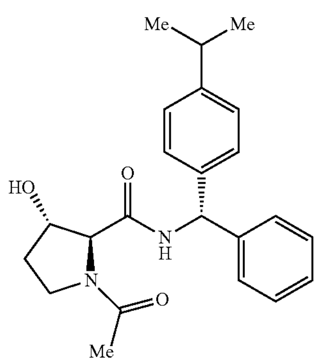 [SMILES: CC(=O)N1CC[C@H](O)[C@H]1C(=O)N[C@@H](c1ccccc1)c1ccc(C(C)C)cc1] | (2S,3S)-1-acetyl-3-hydroxy-N-[(S)-phenyl[4-(propan-2-yl)phenyl]methyl]pyrrolidine-2-carboxamide | 380.2 | 381.1 |
| 207 | 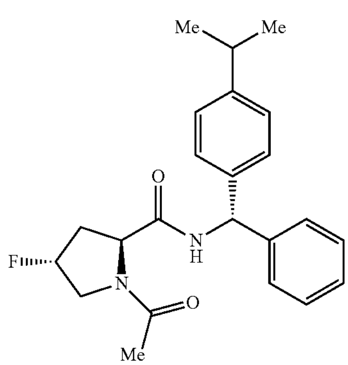 [SMILES: CC(=O)N1C[C@H](F)C[C@H]1C(=O)N[C@@H](c1ccccc1)c1ccc(C(C)C)cc1] | (2S,4R)-1-acetyl-4-fluoro-N-[(S)-phenyl[4-(propan-2-yl)phenyl]methyl]pyrrolidine-2-carboxamide | 382.2 | 422.2 |

TABLE T-1-continued

| Compound No. | Structure | IUPAC | Exact mass (g/mol) | LCMS, Found [M + H]+ |
|---|---|---|---|---|
| 208 | 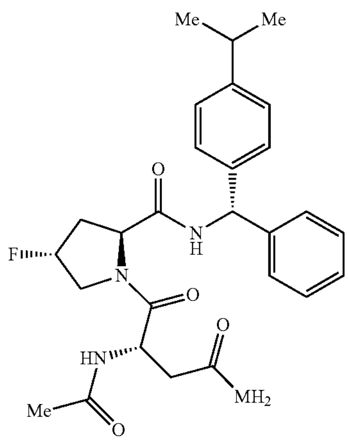 | (2S,4R)-1-[(2S)-3-carbamoyl-2-acetamidopropanoyl]-4-fluoro-N-[(S)-phenyl[4-(propan-2-yl)phenyl]methyl]pyrrolidine-2-carboxamide | 496.2 | 383.3 |
| 209 | 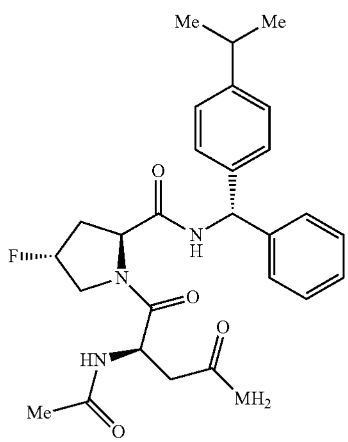 | (2S,4R)-1-[(2R)-3-carbamoyl-2-acetamidopropanoyl]-4-fluoro-N-[(S)-phenyl[4-(propan-2-yl)phenyl]methyl]pyrrolidine-2-carboxamide | 496.2 | 497.1 |
| 210 | 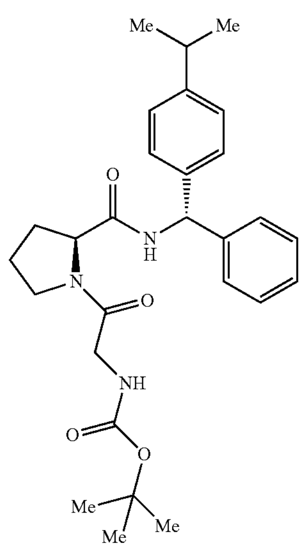 [SMILES: CC(C)c1ccc([C@@H](NC(=O)[C@@H]2CCCN2C(=O)CNC(=O)OC(C)(C)C)c2ccccc2)cc1] | tert-butyl N-{2-oxo-2-[(2S)-2-{[(S)-phenyl[4-(propan-2-yl)phenyl]methyl]carbamoyl}pyrrolidin-1-yl]ethyl}carbamate | 479.3 | 497.2 |

TABLE T-1-continued

| Compound No. | Structure | IUPAC | Exact mass (g/mol) | LCMS, Found [M + H]+ |
| --- | --- | --- | --- | --- |
| 211 | 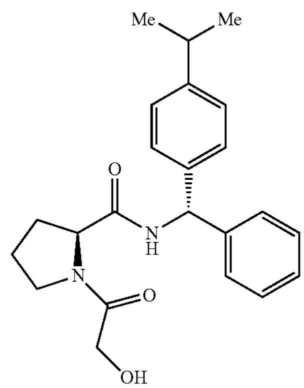 [SMILES: CC(C)c1ccc([C@@H](NC(=O)[C@@H]2CCCN2C(=O)CO)c2ccccc2)cc1] | (2S)-1-(2-hydroxyacetyl)-N-[(S)-phenyl[4-(propan-2-yl)phenyl]methyl]pyrrolidine-2-carboxamide | 380.2 | 381.2 |
| 212 | 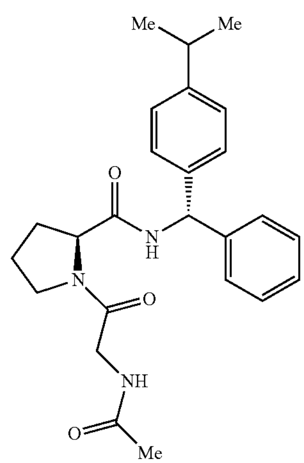 [SMILES: CC(=O)NCC(=O)N1CCC[C@H]1C(=O)N[C@@H](c1ccccc1)c1ccc(C(C)C)cc1] | (2S)-1-(2-acetamidoacetyl)-N-[(S)-phenyl[4-(propan-2-yl)phenyl]methyl]pyrrolidine-2-carboxamide | 421.2 | 422.2 |
| 213 | 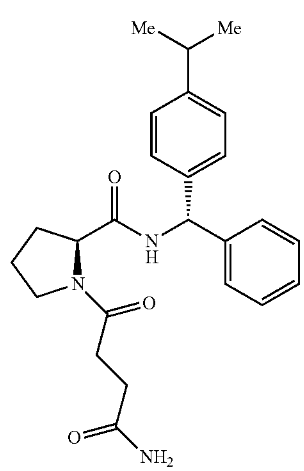 [SMILES: CC(C)c1ccc([C@@H](NC(=O)[C@@H]2CCCN2C(=O)CCC(N)=O)c2ccccc2)cc1] | (2S)-1-(3-carbamoylpropanoyl)-N-[(S)-phenyl[4-(propan-2-yl)phenyl]methyl]pyrrolidine-2-carboxamide | 421.2 | 422.3 |

TABLE T-1-continued

| Compound No. | Structure | IUPAC | Exact mass (g/mol) | LCMS, Found [M + H]+ |
|---|---|---|---|---|
| 214 | 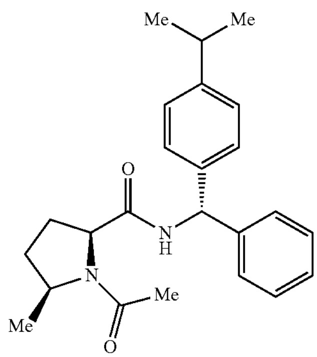 [SMILES: CC(=O)N1[C@@H](C)CC[C@H]1C(=O)N[C@@H](c1ccccc1)c1ccc(C(C)C)cc1] | (2S,5S)-1-acetyl-5-methyl-N-[(S)-phenyl[4-(propan-2-yl)phenyl]methyl]pyrrolidine-2-carboxamide | 378.2 | 379.2 |
| 215 | 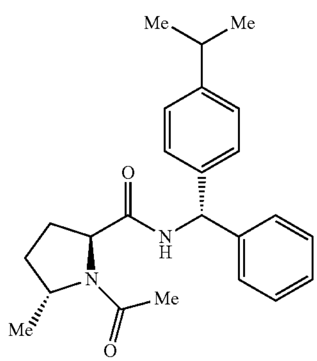 [SMILES: CC(=O)N1[C@H](C)CC[C@H]1C(=O)N[C@@H](c1ccccc1)c1ccc(C(C)C)cc1] | (2S,5R)-1-acetyl-5-methyl-N-[(S)-phenyl[4-(propan-2-yl)phenyl]methyl]pyrrolidine-2-carboxamide | 378.2 | 379.2 |
| 216 | 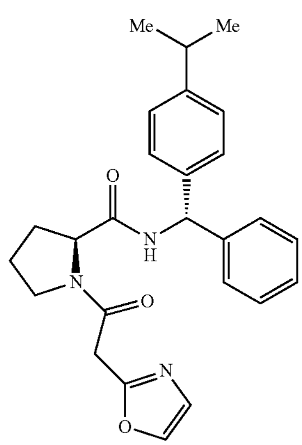 [SMILES: CC(C)c1ccc([C@@H](NC(=O)[C@@H]2CCCN2C(=O)Cc2ncco2)c2ccccc2)cc1] | (2S)-1-[2-(1,3-oxazol-2-yl)acetyl]-N-[(S)-phenyl[4-(propan-2-yl)phenyl]methyl]pyrrolidine-2-carboxamide | 431.2 | 432.3 |

TABLE T-1-continued

| Compound No. | Structure | IUPAC | Exact mass (g/mol) | LCMS, Found [M + H]+ |
| --- | --- | --- | --- | --- |
| 217 | 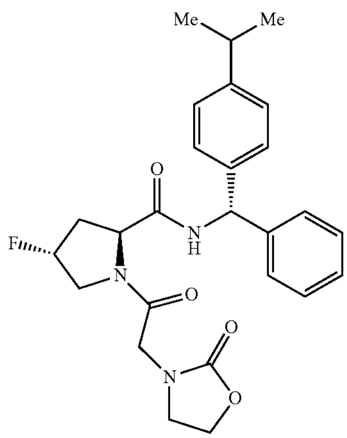 [SMILES: CC(C)c1ccc([C@@H](NC(=O)[C@@H]2C[C@@H](F)CN2C(=O)CN2CCOC2=O)c2ccccc2)cc1] | (2S,4R)-4-fluoro-1-[2-(2-oxo-1,3-oxazolidin-3-yl)acetyl]-N-[(S)-phenyl[4-(propan-2-yl)phenyl]methyl]pyrrolidine-2-carboxamide | 467.2 | 468.1 |
| 218 | 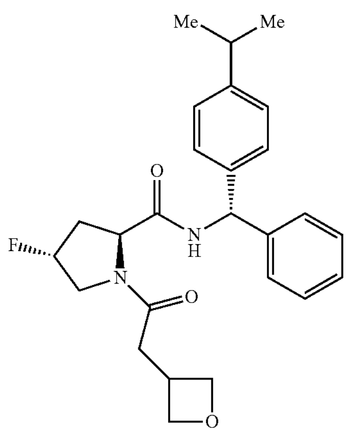 [SMILES: CC(C)c1ccc([C@@H](NC(=O)[C@@H]2C[C@@H](F)CN2C(=O)CC2COC2)c2ccccc2)cc1] | (2S,4R)-4-fluoro-1-[2-(oxetan-3-yl)acetyl]-N-[(S)-phenyl[4-(propan-2-yl)phenyl]methyl]pyrrolidine-2-carboxamide | 438.2 | 439.3 |
| 219 | 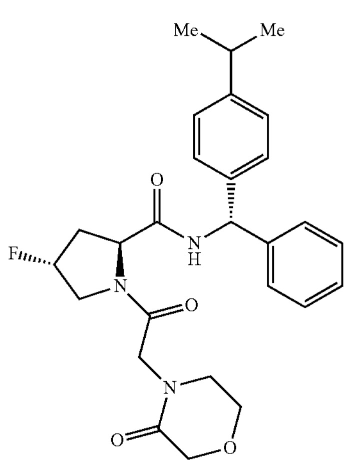 [SMILES: CC(C)c1ccc([C@@H](NC(=O)[C@@H]2C[C@@H](F)CN2C(=O)CN2CCOCC2=O)c2ccccc2)cc1] | (2S,4R)-4-fluoro-1-[2-(3-oxomorpholin-4-yl)acetyl]-N-[(S)-phenyl[4-(propan-2-yl)phenyl]methyl]pyrrolidine-2-carboxamide | 481.2 | 482.2 |

TABLE T-1-continued

| Compound No. | Structure | IUPAC | Exact mass (g/mol) | LCMS, Found [M + H]+ |
|---|---|---|---|---|
| 220 | 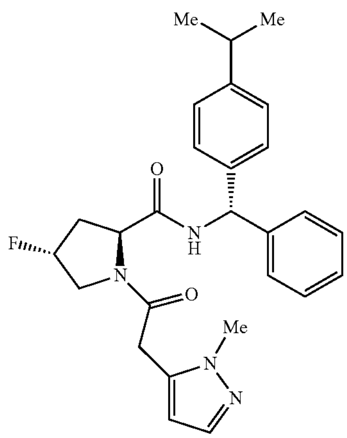 [SMILES: CC(C)c1ccc([C@@H](NC(=O)[C@@H]2C[C@@H](F)CN2C(=O)Cc2ccnn2C)c2ccccc2)cc1] | (2S,4RS)-4-fluoro-1-[2-(1-methyl-1H-pyrazol-5-yl)acetyl]-N-[(S)-phenyl[4-(propan-2-yl)phenyl]methyl]pyrrolidine-2-carboxamide | 462.2 | 463.2 |
| 221 | 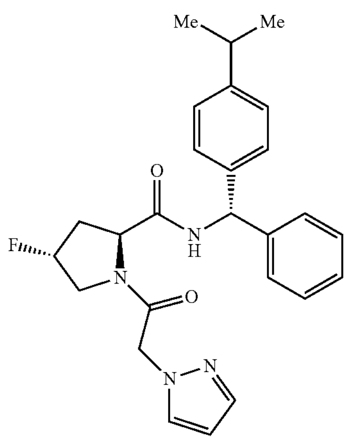 [SMILES: CC(C)c1ccc([C@@H](NC(=O)[C@@H]2C[C@@H](F)CN2C(=O)Cn2cccn2)c2ccccc2)cc1] | (2S,4RS)-4-fluoro-N-[(S)-phenyl[4-(propan-2-yl)phenyl]methyl]-1-[2-(1H-pyrazol-1-yl)acetyl]pyrrolidine-2-carboxamide | 448.2 | 449.9 |
| 222 | 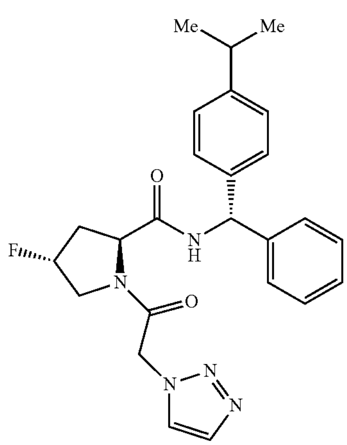 [SMILES: CC(C)c1ccc([C@@H](NC(=O)[C@@H]2C[C@@H](F)CN2C(=O)Cn2ccnn2)c2ccccc2)cc1] | (2RS,4R)-4-fluoro-N-[(S)-phenyl[4-(propan-2-yl)phenyl]methyl]-1-[2-(1H-1,2,3-triazol-1-yl)acetyl]pyrrolidine-2-carboxamide | 449.2 | 450.1 |

TABLE T-1-continued

| Compound No. | Structure | IUPAC | Exact mass (g/mol) | LCMS, Found [M + H]+ |
|---|---|---|---|---|
| 223 | 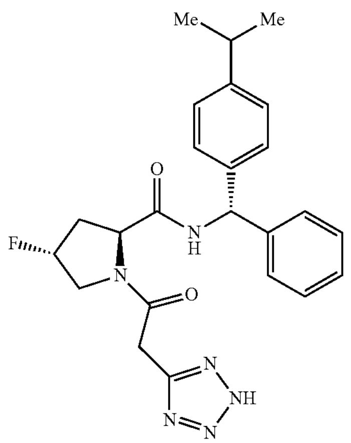 [SMILES: CC(C)c1ccc([C@@H](NC(=O)[C@@H]2C[C@@H](F)CN2C(=O)Cc2nn[nH]n2)c2ccccc2)cc1] | (2RS,4R)-4-fluoro-N-[(S)-phenyl[4-(propan-2-yl)phenyl]methyl]-1-[2-(2H-1,2,3,4-tetrazol-5-yl)acetyl]pyrrolidine-2-carboxamide | 450.2 | 451.2 |
| 224 | 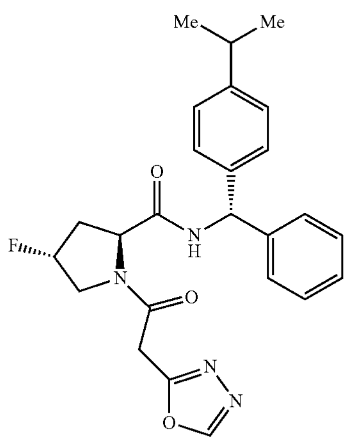 [SMILES: CC(C)c1ccc([C@@H](NC(=O)[C@@H]2C[C@@H](F)CN2C(=O)Cc2nnco2)c2ccccc2)cc1] | (2RS,4R)-4-fluoro-1-[2-(1,3,4-oxadiazol-2-yl)acetyl]-N-[(S)-phenyl[4-(propan-2-yl)phenyl]methyl]pyrrolidine-2-carboxamide | 450.2 | 451.1 |
| 225 | 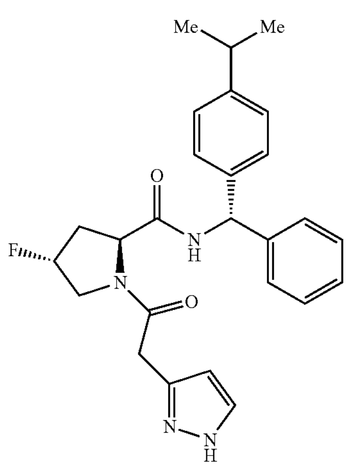 [SMILES: CC(C)c1ccc([C@@H](NC(=O)[C@@H]2C[C@@H](F)CN2C(=O)Cc2cc[nH]n2)c2ccccc2)cc1] | (2RS,4R)-4-fluoro-N-[(S)-phenyl[4-(propan-2-yl)phenyl]methyl]-1-[2-(1H-pyrazol-3-yl)acetyl]pyrrolidine-2-carboxamide | 448.2 | 449.2 |

TABLE T-1-continued

| Compound No. | Structure | IUPAC | Exact mass (g/mol) | LCMS, Found [M + H]+ |
|---|---|---|---|---|
| 226 | 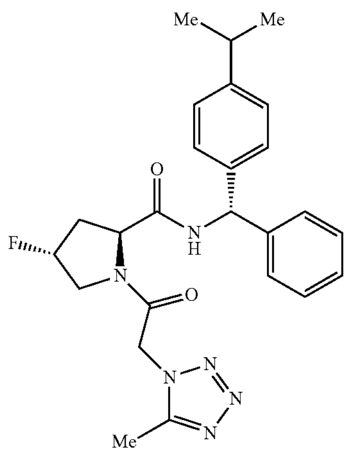 [SMILES: Cc1nnnn1CC(=O)N1C[C@H](F)C[C@H]1C(=O)N[C@@H](c1ccccc1)c1ccc(C(C)C)cc1] | (2RS,4R)-4-fluoro-1-[2-(5-methyl-1H-1,2,3,4-tetrazol-1-yl)acetyl]-N-[(S)-phenyl[4-(propan-2-yl)phenyl]methyl]pyrrolidine-2-carboxamide | 464.2 | 465.3 |
| 227 | 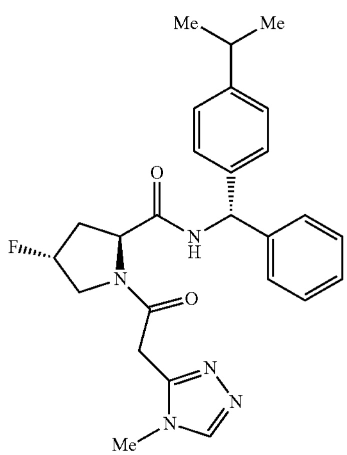 [SMILES: CC(C)c1ccc([C@@H](NC(=O)[C@@H]2C[C@@H](F)CN2C(=O)Cc2nncn2C)c2ccccc2)cc1] | (2RS,4R)-4-fluoro-1-[2-(4-methyl-4H-1,2,4-triazol-3-yl)acetyl]-N-[(S)-phenyl[4-(propan-2-yl)phenyl]methyl]pyrrolidine-2-carboxamide | 463.2 | 464.3 |
| 228 | 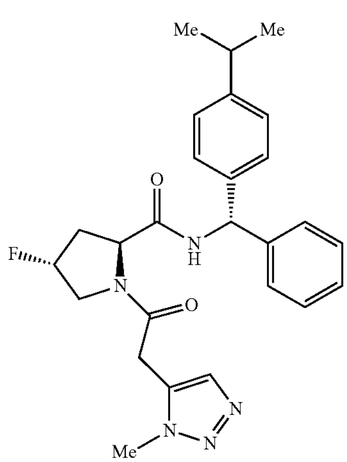 [SMILES: CC(C)c1ccc([C@@H](NC(=O)[C@@H]2C[C@@H](F)CN2C(=O)Cc2cnnn2C)c2ccccc2)cc1] | (2RS,4R)-4-fluoro-1-[2-(1-methyl-1H-1,2,3-triazol-5-yl)acetyl]-N-[(S)-phenyl[4-(propan-2-yl)phenyl]methyl]pyrrolidine-2-carboxamide | 463.2 | 464.3 |

TABLE T-1-continued
| Compound No. | Structure | IUPAC | Exact mass (g/mol) | LCMS, Found [M + H]+ |
|---|---|---|---|---|
| 229 | 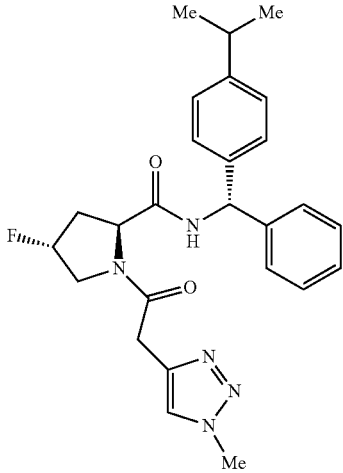 [SMILES: CC(C)c1ccc([C@@H](NC(=O)[C@@H]2C[C@@H](F)CN2C(=O)Cc2cn(C)nn2)c2ccccc2)cc1] | (2RS,4R)-4-fluoro-1-[2-(1-methyl-1H-1,2,3-triazol-4-yl)acetyl]-N-[(S)-phenyl[4-(propan-2-yl)phenyl]methyl]pyrrolidine-2-carboxamide | 463.2 | 464.2 |
| 230 | 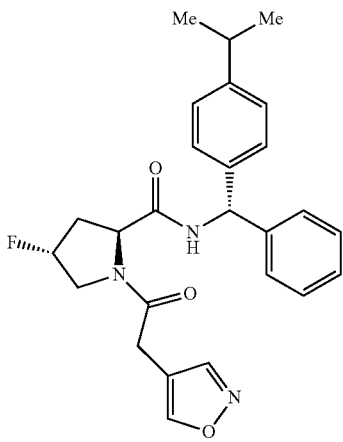 [SMILES: CC(C)c1ccc([C@@H](NC(=O)[C@@H]2C[C@@H](F)CN2C(=O)Cc2cnoc2)c2ccccc2)cc1] | (2S,4R)-4-fluoro-1-[2-(1,2-oxazol-4-yl)acetyl]-N-[(S)-phenyl[4-(propan-2-yl)phenyl]methyl]pyrrolidine-2-carboxamide | 449.2 | 450.3 |
| 231 | 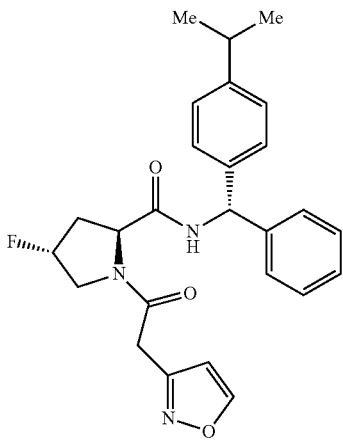 [SMILES: CC(C)c1ccc([C@@H](NC(=O)[C@@H]2C[C@@H](F)CN2C(=O)Cc2ccon2)c2ccccc2)cc1] | (2S,4R)-4-fluoro-1-[2-(1,2-oxazol-3-yl)acetyl]-N-[(S)-phenyl[4-(propan-2-yl)phenyl]methyl]pyrrolidine-2-carboxamide | 449.2 | 450.3 |

TABLE T-1-continued

| Compound No. | Structure | IUPAC | Exact mass (g/mol) | LCMS, Found [M + H]+ |
|---|---|---|---|---|
| 232 | 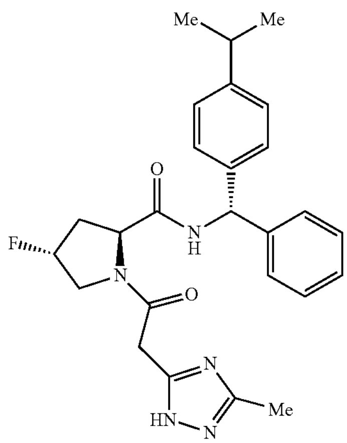 [SMILES: Cc1n[nH]c(CC(=O)N2C[C@H](F)C[C@H]2C(=O)N[C@@H](c2ccccc2)c2ccc(C(C)C)cc2)n1] | (2S,4R)-4-fluoro-1-[2-(3-methyl-1H-1,2,4-triazol-5-yl)acetyl]-N-[(S)-phenyl[4-(propan-2-yl)phenyl]methyl]pyrrolidine-2-carboxamide | 463.2 | 464.2 |
| 233 | 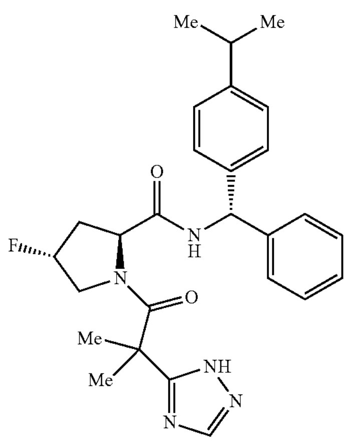 [SMILES: CC(C)c1ccc([C@@H](NC(=O)[C@@H]2C[C@@H](F)CN2C(=O)C(C)(C)c2ncn[nH]2)c2ccccc2)cc1] | (2S,4R)-4-fluoro-1-[2-methyl-2-(1H-1,2,4-triazol-5-yl)propanoyl]-N-[(S)-phenyl[4-(propan-2-yl)phenyl]methyl]pyrrolidine-2-carboxamide | 477.3 | 478.2 |
| 234 | 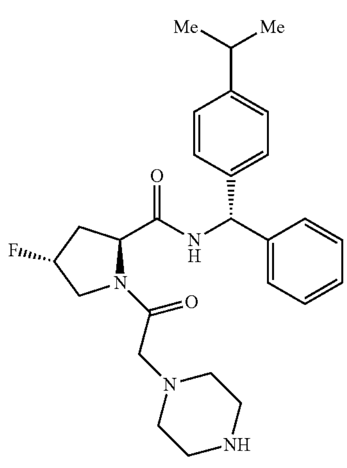 [SMILES: CC(C)c1ccc([C@@H](NC(=O)[C@@H]2C[C@@H](F)CN2C(=O)CN2CCNCC2)c2ccccc2)cc1] | (2S,4R)-4-fluoro-N-[(S)-phenyl[4-(propan-2-yl)phenyl]methyl]-1-[2-(piperazin-1-yl)acetyl]pyrrolidine-2-carboxamide | 466.3 | 467.2 |

TABLE T-1-continued

| Compound No. | Structure | IUPAC | Exact mass (g/mol) | LCMS, Found [M + H]+ |
|---|---|---|---|---|
| 235 | 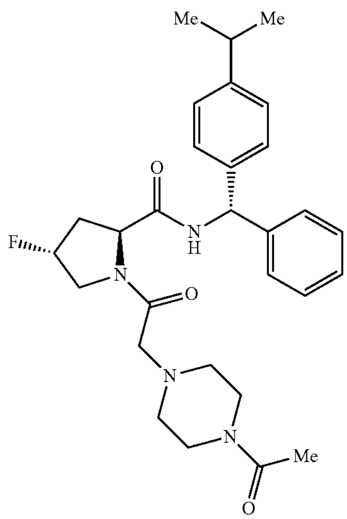 [SMILES: CC(=O)N1CCN(CC(=O)N2C[C@H](F)C[C@H]2C(=O)N[C@@H](c2ccccc2)c2ccc(C(C)C)cc2)CC1] | (2S,4R)-1-[2-(4-acetylpiperazin-1-yl)acetyl]-4-fluoro-N-[(S)-phenyl[4-(propan-2-yl)phenyl]methyl]pyrrolidine-2-carboxamide | 508.3 | 509.3 |
| 236 | 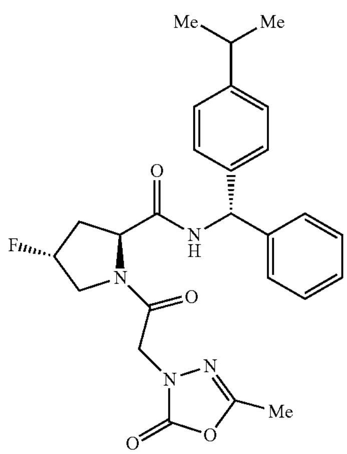 [SMILES: Cc1nn(CC(=O)N2C[C@H](F)C[C@H]2C(=O)N[C@@H](c2ccccc2)c2ccc(C(C)C)cc2)c(=O)o1] | (2S,4R)-4-fluoro-1-[2-(5-methyl-2-oxo-2,3-dihydro-1,3,4-oxadiazol-3-yl)acetyl]-N-[(S)-phenyl[4-(propan-2-yl)phenyl]methyl]pyrrolidine-2-carboxamide | 480.2 | 481.1 |
| 237 | 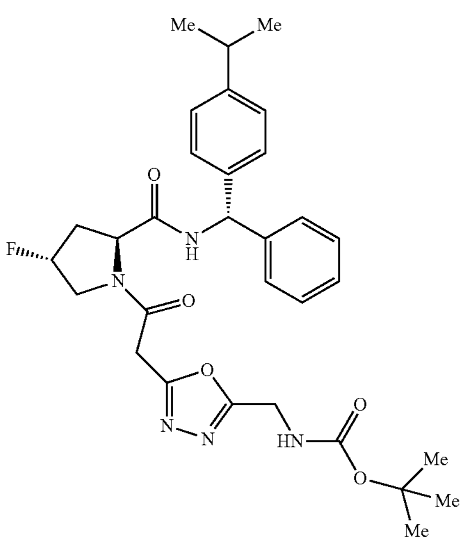 [SMILES: CC(C)c1ccc([C@@H](NC(=O)[C@@H]2C[C@@H](F)CN2C(=O)Cc2nnc(CNC(=O)OC(C)(C)C)o2)c2ccccc2)cc1] | tert-butyl N-[(5-{2-[(2S,4R)-4-fluoro-2-{[(S)-phenyl[4-(propan-2-yl)phenyl]methyl]carbamoyl}pyrrolidin-1-yl]-2-oxoethyl}-1,3,4-oxadiazol-2-yl)methyl]carbamate | 579.3 | 580.3 |

TABLE T-1-continued

| Compound No. | Structure | IUPAC | Exact mass (g/mol) | LCMS, Found [M + H]+ |
| --- | --- | --- | --- | --- |
| 238 | 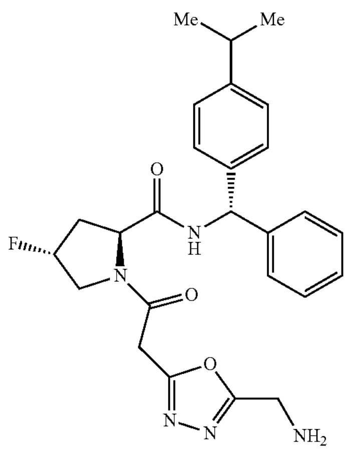 [SMILES: CC(C)c1ccc([C@@H](NC(=O)[C@@H]2C[C@@H](F)CN2C(=O)Cc2nnc(CN)o2)c2ccccc2)cc1] | (2S,4R)-1-{2-[5-(aminomethyl)-1,3,4-oxadiazol-2-yl]acetyl}-4-fluoro-N-[(S)-phenyl[4-(propan-2-yl)phenyl]methyl]pyrrolidine-2-carboxamide | 479.2 | 480.2 |
| 239 | 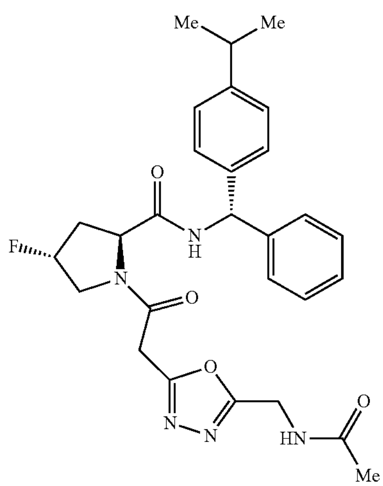 [SMILES: CC(=O)NCc1nnc(CC(=O)N2C[C@H](F)C[C@H]2C(=O)N[C@@H](c2ccccc2)c2ccc(C(C)C)cc2)o1] | (2S,4R)-1-{2-[5-(acetamidomethyl)-1,3,4-oxadiazol-2-yl]acetyl}-4-fluoro-N-[(S)-phenyl[4-(propan-2-yl)phenyl]methyl]pyrrolidine-2-carboxamide | 521.2 | 522.2 |
| 240 | 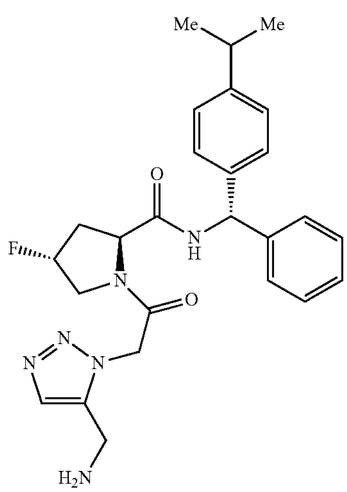 [SMILES: CC(C)c1ccc([C@@H](NC(=O)[C@@H]2C[C@@H](F)CN2C(=O)Cn2nncc2CN)c2ccccc2)cc1] | (2S,4R)-1-{2-[5-(aminomethyl)-1H-1,2,3-triazol-1-yl]acetyl}-4-fluoro-N-[(S)-phenyl[4-(propan-2-yl)phenyl]methyl]pyrrolidine-2-carboxamide | 478.2 | 479.2 |

TABLE T-1-continued

| Compound No. | Structure | IUPAC | Exact mass (g/mol) | LCMS, Found [M + H]+ |
|---|---|---|---|---|
| 241 | 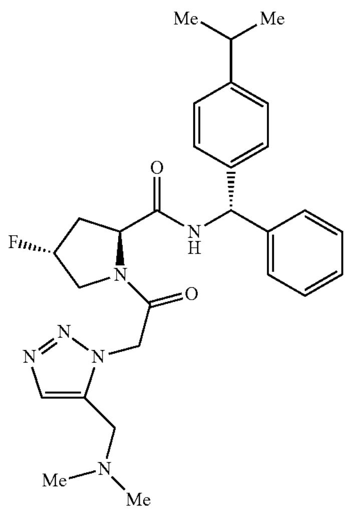 [SMILES: CC(C)c1ccc([C@@H](NC(=O)[C@@H]2C[C@@H](F)CN2C(=O)Cn2nncc2CN(C)C)c2ccccc2)cc1] | (2S,4R)-1-(2-{5-[(dimethylamino)methyl]-1H-1,2,3-triazol-1-yl}acetyl)-4-fluoro-N-[(S)-phenyl[4-(propan-2-yl)phenyl]methyl]pyrrolidine-2-carboxamide | 506.3 | 507.2 |
| 242 | 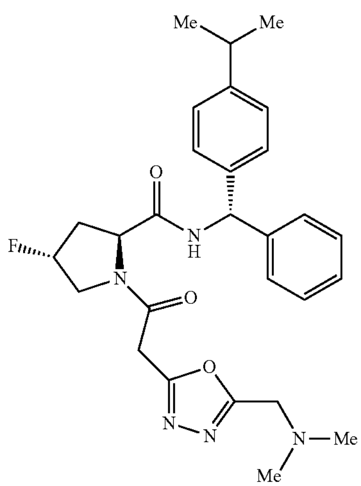 [SMILES: CC(C)c1ccc([C@@H](NC(=O)[C@@H]2C[C@@H](F)CN2C(=O)Cc2nnc(CN(C)C)o2)c2ccccc2)cc1] | (2S,4R)-1-(2-{5-[(dimethylamino)methyl]-1,3,4-oxadiazol-2-yl}acetyl)-4-fluoro-N-[(S)-phenyl[4-(propan-2-yl)phenyl]methyl]pyrrolidine-2-carboxamide | 507.3 | 508.2 |
| 243 | 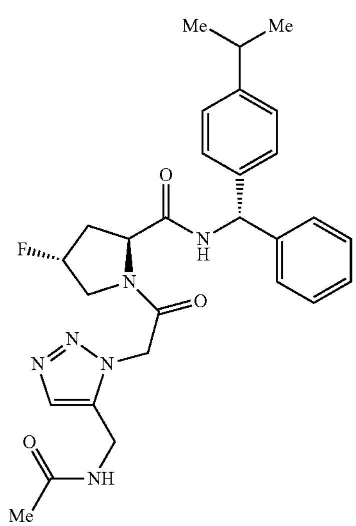 [SMILES: CC(=O)NCc1cnnn1CC(=O)N1C[C@H](F)C[C@H]1C(=O)N[C@@H](c1ccccc1)c1ccc(C(C)C)cc1] | (2S,4R)-1-{2-[5-(acetamidomethyl)-1H-1,2,3-triazol-1-yl]acetyl}-4-fluoro-N-[(S)-phenyl[4-(propan-2-yl)phenyl]methyl]pyrrolidine-2-carboxamide | 520.3 | 521.2 |

TABLE T-1-continued

| Compound No. | Structure | IUPAC | Exact mass (g/mol) | LCMS, Found [M + H]+ |
| --- | --- | --- | --- | --- |
| 701 | 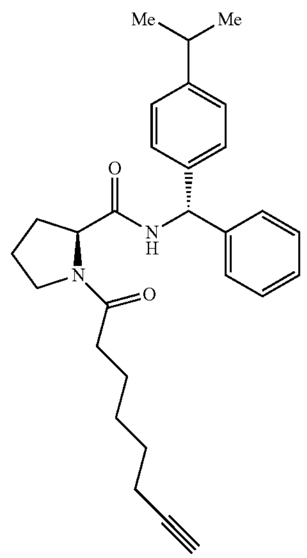 [SMILES: C#CCCCCCC(=O)N1CCC[C@H]1C(=O)N[C@@H](c1ccccc1)c1ccc(C(C)C)cc1] | (2S)-1-(oct-7-ynoyl)-N-[(S)-phenyl[4-(propan-2-yl)phenyl]methyl]pyrrolidine-2-carboxamide | 444.3 | 445.5 |
| 702 | 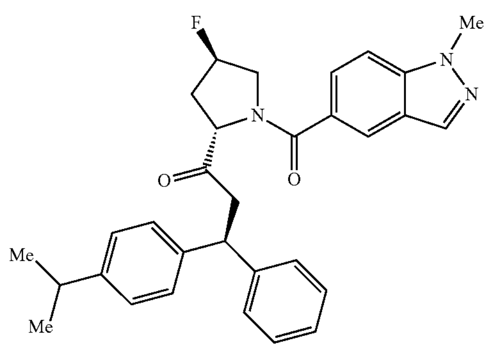 [SMILES: CC(C)c1ccc([C@@H](CC(=O)[C@@H]2C[C@@H](F)CN2C(=O)c2ccc3c(cnn3C)c2)c2ccccc2)cc1] | (2S,4R)-4-fluoro-1-(1-methyl-1H-indazole-5-carobnyl)-N-[(S)-phenyl[4-(propan-2-yl)phenyl]methyl]pyrrolidine-2-carboxamide | 498.2 | 499.3 |
| 703 | 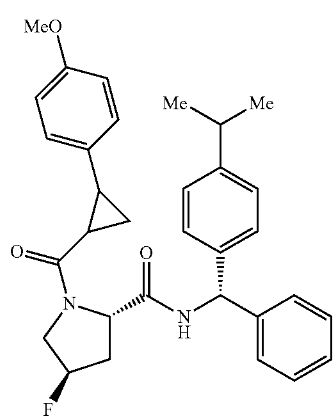 [SMILES: COc1ccc(C2CC2C(=O)N2C[C@H](F)C[C@H]2C(=O)N[C@@H](c2ccccc2)c2ccc(C(C)C)cc2)cc1] | (2S,4R)-4-fluoro-1-[2-(4-methoxyphenyl)cyclopropanecarbonyl]-N-[(S)-phenyl[4-(propan-2-yl)phenyl]methyl]pyrrolidine-2-carboxamide | 514.3 | 515.3 |

TABLE T-1-continued

| Compound No. | Structure | IUPAC | Exact mass (g/mol) | LCMS, Found [M + H]+ |
|---|---|---|---|---|
| 704 | 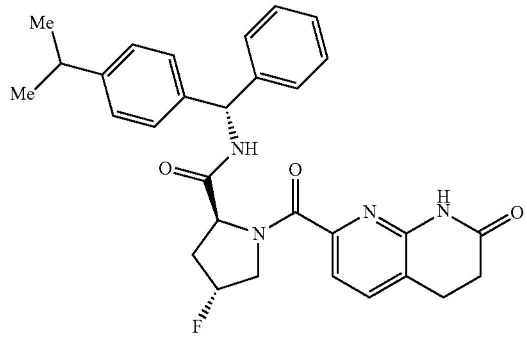 [SMILES: CC(C)c1ccc([C@@H](NC(=O)[C@@H]2C[C@@H](F)CN2C(=O)c2ccc3c(n2)NC(=O)CC3)c2ccccc2)cc1] | (2S,4R)-4-fluoro-1-(7-oxo-5,6,7,8-tetrahydro-1,8-naphthyridine-2-carbonyl)-N-[(S)-phenyl[4-(propan-2-yl)phenyl]methyl]pyrrolidine-2-carboxamide | 514.2 | 515.3 |
| 705 | 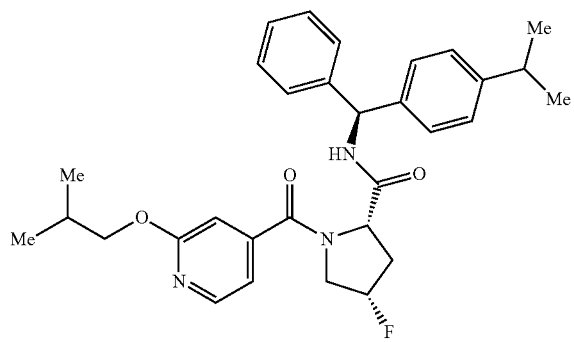 [SMILES: CC(C)COc1cc(C(=O)N2C[C@@H](F)C[C@H]2C(=O)N[C@@H](c2ccccc2)c2ccc(C(C)C)cc2)ccn1] | (2S,4R)-4-fluoro-1-[2-(2-methylpropoxy)pyridine-4-carbonyl]-N-[(S)-phenyl[4-(propan-2-yl)phenyl]methyl]pyrrolidine-2-carboxamide | 517.3 | 518.3 |
| 707 | 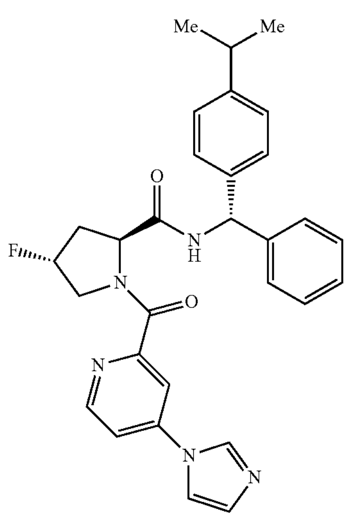 [SMILES: CC(C)c1ccc([C@@H](NC(=O)[C@@H]2C[C@@H](F)CN2C(=O)c2cc(-n3ccnc3)ccn2)c2ccccc2)cc1] | (2S,4R)-4-fluoro-1-[4-(1H-imidazol-1-yl)pyridine-2-carbonyl]-N-[(S)-phenyl[4-(propan-2-yl)phenyl]methyl]pyrrolidine-2-carboxamide | 511.2 | 512.3 |
| 708 | 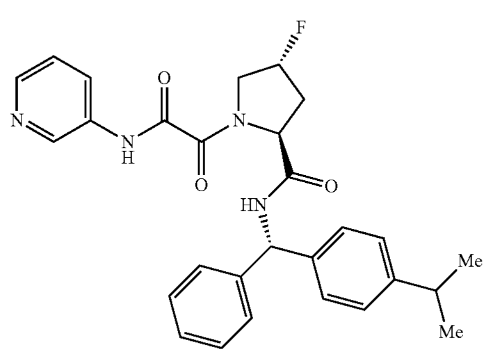 [SMILES: CC(C)c1ccc([C@@H](NC(=O)[C@@H]2C[C@@H](F)CN2C(=O)C(=O)Nc2cccnc2)c2ccccc2)cc1] | (2S,4R)-4-fluoro-N-[(S)-phenyl[4-(propan-2-yl)phenyl]methyl]-1-{[(pyridin-3-yl)carbamoyl]carbonyl}pyrrolidine-2-carboxamide | 488.2 | 489.2 |

TABLE T-1-continued
| Compound No. | Structure | IUPAC | Exact mass (g/mol) | LCMS, Found [M + H]+ |
|---|---|---|---|---|
| 709 | 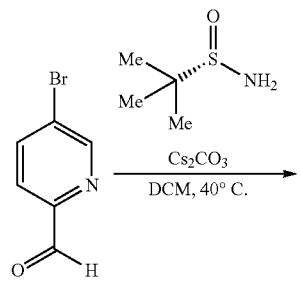 | (2S,4R)-4-fluoro-1-(5-methoxy-1-methyl-1H-pyrazole-3-carbonyl)-N-[(S)-phenyl[4-(propan-2-yl)phenyl]methyl]pyrrolidine-2-carboxamide | 478.2 | 479.3 |
Example S-2: Synthesis of (2S,4R)-1-(2-(1H-1,2,3-triazol-5-yl)acetyl)-4-fluoro-N—((S)-(5-isopropylpyridin-2-yl)(phenyl)methyl)pyrrolidine-2-carboxamide
Compound 244
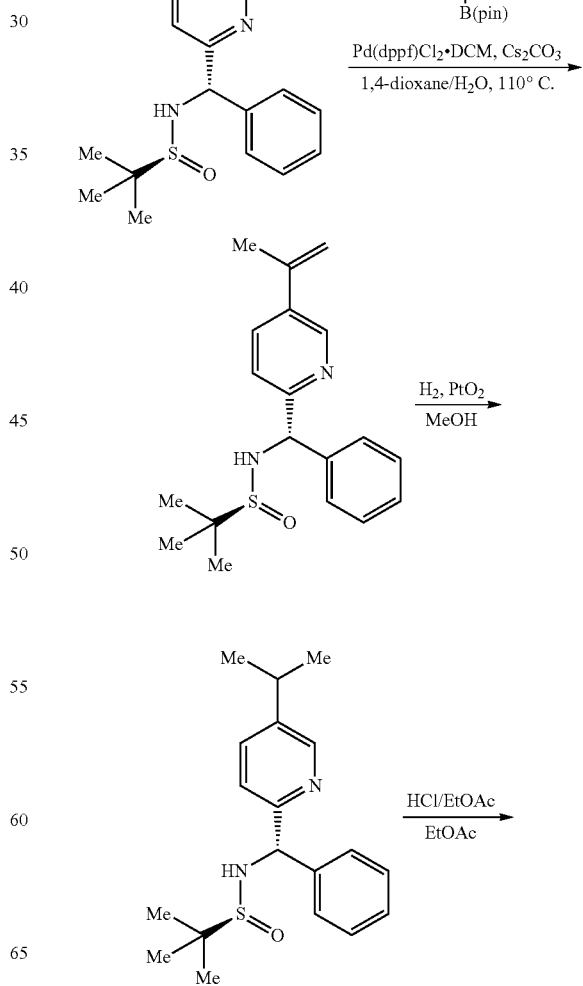

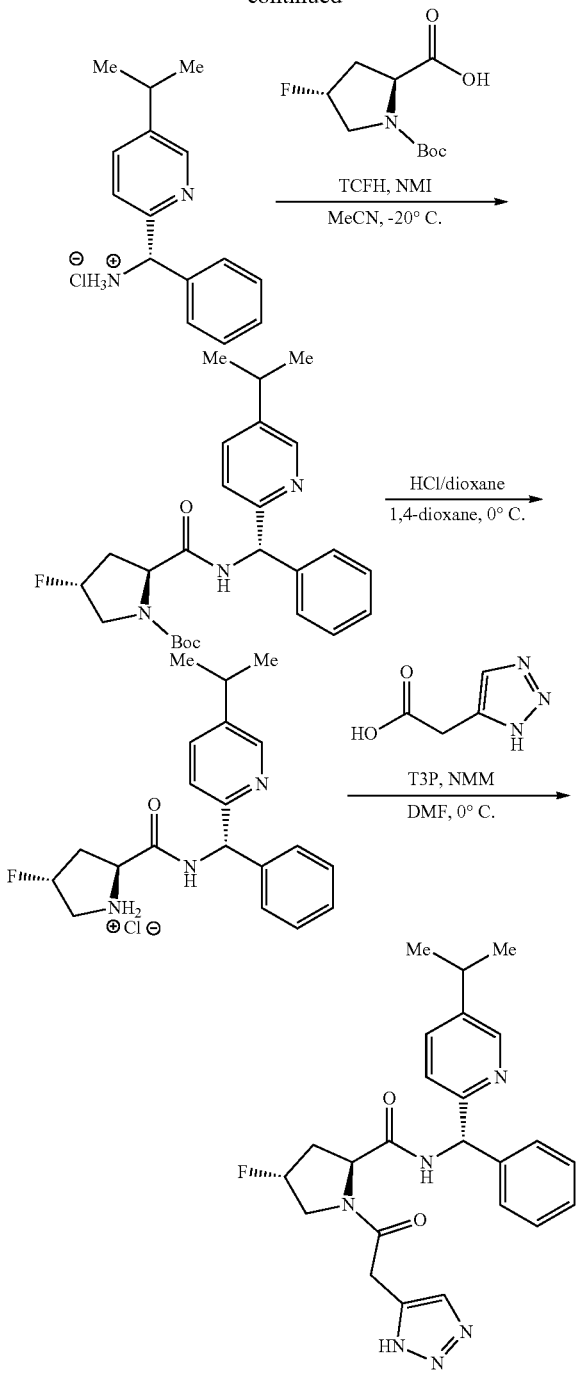

Step a: To a solution of 5-bromopicolinaldehyde (15 g, 80.6 mmol, 1 eq) in DCM (150 mL) at 25° C. was added (S)-2-methylpropane-2-sulfinamide (10.8 g, 88.7 mmol, 1.1 eq) and $Cs_2CO_3$ (28.9 g, 88.7 mmol, 1.1 eq). The resulting mixture was degassed and charged with nitrogen three times before it was warmed to 40° C. and stirred 2 h under $N_2$ atmosphere. After cooling to room temperature, the reaction mixture was filtered and concentrated under reduced pressure. The resulting crude residue was purified by column chromatography to give (S,E)-N-((5-bromopyridin-2-yl)methylene)-2-methylpropane-2-sulfinamide. LC-MS (ESI): m/z: $[M+H]^+$ calculated for $C_{10}H_{13}BrN_2OS$: 289.0; found 289.0.

Step b: A solution of (S,E)-N-((5-bromopyridin-2-yl)methylene)-2-methylpropane-2-sulfinamide (20 g, 69.2 mmol, 1 eq) in DCM (100 mL) was degassed with $N_2$ and cooled to −70° C. To the cooled solution was added PhMgBr (3 M in $Et_2O$, 27.7 mL, 1.2 eq) in a dropwise manner. The resulting reaction mixture was stirred at −70° C. for 2 h, warmed to room temperature, and stirred for another 1 h. The reaction mixture then was quenched with water (150 mL) and extracted with ethyl acetate (3×100 mL). The combined organic extracts were washed with brine (3×50 mL), dried over anhydrous $Na_2SO_4$, filtered, and concentrated under reduced pressure. The resulting crude residue was purified by column chromatography to give (S)—N—((S)-(5-bromopyridin-2-yl)(phenyl)methyl)-2-methylpropane-2-sulfinamide. LC-MS (ESI): m/z: $[M+H]^+$ calculated for $C_{16}H_{19}BrN_2OS$: 367.0; found 367.0.

Step c: To a solution of (S)—N—((S)-(5-bromopyridin-2-yl)(phenyl)methyl)-2-methylpropane-2-sulfinamide (23 g, 62.6 mmol, 1 eq) in 1,4-dioxane (150 mL) and water (40 mL) at 25° C. was added 2-isopropenyl-4,4,5,5-tetramethyl-1,3,2-dioxaborolane (15.8 g, 93.9 mmol, 1.5 eq), $Cs_2CO_3$ (40.8 g, 125 mmol, 2 eq) and $Pd(dppf)Cl_2 \cdot CH_2Cl_2$ (5.11 g, 6.26 mmol, 0.1 eq). The resulting mixture was degassed and charged with nitrogen three times, and the reaction mixture was warmed to 110° C. and stirred for 8 h. After cooling, the reaction mixture was concentrated under reduced pressure, and water (150 mL) was added. The resulting mixture was extracted with ethyl acetate (3×150 mL). The combined organic extracts were washed with brine (3×100 mL), dried over anhydrous $Na_2SO_4$, filtered, and concentrated under reduced pressure. The resulting crude residue was purified by column chromatography to give (S)-2-methyl-N—((S)-phenyl(5-(prop-1-en-2-yl)pyridin-2-yl)methyl)propane-2-sulfinamide. LC-MS (ESI): m/z: $[M+H]^+$ calculated for $C_{19}H_{24}N_2OS$: 329.2; found 329.2.

Step d: To a solution of (S)-2-methyl-N—((S)-phenyl(5-(prop-1-en-2-yl)pyridin-2-yl)methyl)propane-2-sulfinamide (11.5 g, 35 mmol, 1 eq) in MeOH (80 mL) at 25° C. was added $PtO_2$ (795 mg, 3.50 mmol, 0.1 eq). The system was degassed and charged with hydrogen three times, and the reaction mixture was stirred under $H_2$ atmosphere (15 psi) at 25° C. for 2 h. The mixture was then filtered through a pad of Celite, and the filter cake was washed with MeOH (2×30 mL). The filtrate was then concentrated under reduced pressure to give (S)—N—((S)-(5-isopropylpyridin-2-yl)(phenyl)methyl)-2-methylpropane-2-sulfinamide, which was used directly for the next step without further purification. LC-MS (ESI): m/z: $[M+H]^+$ calculated for $C_{19}H_{26}N_2OS$: 331.2; found 331.2.

Step e: To a solution of (S)—N—((S)-(5-isopropylpyridin-2-yl)(phenyl)methyl)-2-methylpropane-2-sulfinamide (12.0 g, 36.3 mmol, 1 eq) in EtOAc (20 mL) at 25° C. was added HCl/EtOAc (4 M, 109 mL, 436 mmol, 12.0 eq). The resulting mixture was stirred for 1 h before it was filtered. The filter cake was then washed with petroleum ether, and the collected solid dried under reduced pressure to give (S)-(5-isopropylpyridin-2-yl)(phenyl)methanamine hydrochloride. LC-MS (ESI): m/z: $[M+H]^+$ calculated for $C_{15}H_{18}N_2$: 227.2; found 227.2.

Step f: To a solution of (S)-(5-isopropylpyridin-2-yl)(phenyl)methanamine hydrochloride (5.00 g, 19.0 mmol, 1 eq, HCl salt) in MeCN (70 mL) at −20° C. under $N_2$ atmosphere was added 1-methyl-1H-imidazole (NMI, 4.69 g, 57.1 mmol, 3 eq) and (2S,4R)-1-(tert-butoxycarbonyl)-4-fluoropyrrolidine-2-carboxylic acid (4.9 g, 20.1 mmol, 1.1 eq), and the resulting mixture was stirred for 10 min. To this mixture was added chloro-N,N,N',N'-tetramethylformamidinium hexafluorophosphate (TCFH, 5.87 g, 20.9 mmol, 1.1 eq) in portions. The resulting reaction mixture was stirred at −20° C. for 3 h under $N_2$ atmosphere. The reaction mixture was then quenched with $H_2O$ (30 mL), and the resulting biphasic mixture was extracted with ethyl acetate (3×30 mL). The combined organic extracts were washed with brine (3×30 mL), dried over anhydrous $Na_2SO_4$, filtered, and concentrated under reduced pressure. The resulting crude residue was purified by column chromatography to give tert-butyl (2S,4R)-4-fluoro-2-(((S)-(5-isopropylpyridin-2-yl)(phenyl)methyl)carbamoyl)pyrrolidine-1-carboxylate. LC-MS (ESI): m/z: [M+H]$^+$ calculated for $C_{25}H_{32}FN_3O_3$: 442.2; found 442.3.

Step g: To a solution of tert-butyl (2S,4R)-4-fluoro-2-(((S)-(5-isopropylpyridin-2-yl)(phenyl)methyl)carbamoyl)pyrrolidine-1-carboxylate (3.9 g, 8.8 mmol) in 1,4-dioxane (5 mL) at 0° C. was added HCl/dioxane (4 M, 50 mL) and the resulting mixture was stirred at 0° C. for 2 h. The reaction mixture was then concentrated at low temperature under reduced pressure. The resulting solid was washed with MTBE (3×10 mL), collected via filtration, and dried under reduced pressure to give (2S,4R)-4-fluoro-2-(((S)-(5-isopropylpyridin-2-yl)(phenyl)methyl)carbamoyl)pyrrolidin-1-ium chloride. LC-MS (ESI): m/z: [M+H]$^+$ calculated for $C_{20}H_{24}FN_3O$: 342.2; found 342.2.

Step h: To a solution of (2S,4R)-4-fluoro-2-(((S)-(5-isopropylpyridin-2-yl)(phenyl)methyl)carbamoyl)pyrrolidin-1-ium chloride (2.50 g, 6.62 mmol, 1 eq, HCl), 4-methylmorpholine (NMM, 2.01 g, 19.9 mmol, 3 eq), and 2-(1H-1,2,3-triazol-5-yl)acetic acid (Intermediate A-1, 1.26 g, 9.92 mmol, 1.5 eq) in DMF (30 mL) at 0° C. was added T3P (50% in ethyl acetate, 8.42 g, 13.3 mmol, 2 eq). The resulting mixture was then stirred at 0° C. for 2 h under $N_2$ atmosphere. The reaction mixture was then quenched by addition of $H_2O$ (60 mL) at 0° C., and the biphasic mixture was extracted with DCM (3×15 mL). The combined organic extracts were dried over anhydrous $Na_2SO_4$, filtered, and concentrated under reduced pressure. The crude residue was then purified by prep-HPLC to give (2S,4R)-1-(2-(1H-1,2,3-triazol-5-yl)acetyl)-4-fluoro-N—((S)-(5-isopropylpyridin-2-yl)(phenyl)methyl)pyrrolidine-2-carboxamide. $^1$H NMR (2.4:1 rotamer ratio, asterisk denotes distinct minor rotamer peaks, obscured peaks not reported, 400 MHz, DMSO-d6) δ 15.17-14.54 (m, 1H), 9.32*(d, J=8.0 Hz, 1H), 8.90 (d, J=8.3 Hz, 1H), 8.43*(d, J=2.3 Hz, 1H), 8.39 (d, J=2.3 Hz, 1H), 7.71-7.59 (m, 1H), 7.40-7.15 (m, 6H), 6.14*(d, J=7.9 Hz, 1H), 6.05 (d, J=8.2 Hz, 1H), 5.50-5.21 (m, 1H), 4.99-4.88*(m, 1H), 4.64 (t, J=8.3 Hz, 1H), 4.14-3.63 (m, 3H), 3.55-3.36*(m, 1H), 2.99-2.83 (m, 1H), 2.76-2.59*(m, 1H), 2.47-2.35 (m, 1H), 2.27-1.90 (m, 1H), 1.20 (d, J=7.0, 1.3 Hz, 6H). LC-MS (ESI): m/z: [M+H]$^+$ calculated for $C_{24}H_{27}FN_6O_2$: 451.2; found 451.3.

The following compounds in Table T-2 were synthesized using procedures similar to Compound 244 using the appropriate starting materials.

TABLE T-2

| Compound No. | Structure | IUPAC | Exact mass (g/mol) | LCMS, Found [M + H]$^+$ |
|---|---|---|---|---|
| 245 | 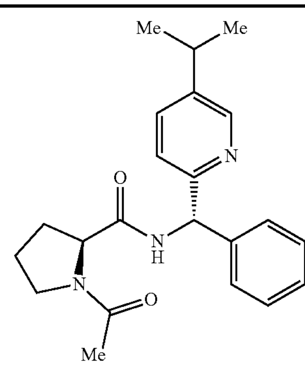 | (2S)-1-acetyl-N-[(S)-phenyl[5-(propan-2-yl)pyridin-2-yl]methyl]pyrrolidine-2-carboxamide | 365.2 | 366.3 |
| 246 | 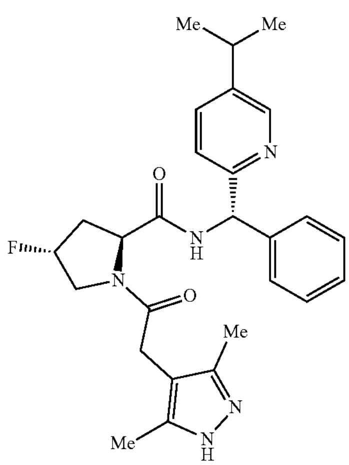 [SMILES: Cc1n[nH]c(C)c1CC(=O)N1C[C@H](F)C[C@H]1C(=O)N[C@@H](c1ccccc1)c1ccc(C(C)C)cn1] | (2S,4R)-1-[2-(3,5-dimethyl-1H-pyrazol-4-yl)acetyl]-4-fluoro-N-[(S)-phenyl[5-(propan-2-yl)pyridin-2-yl]methyl]pyrrolidine-2-carboxamide | 477.3 | 478.1 |

TABLE T-2-continued

| Compound No. | Structure | IUPAC | Exact mass (g/mol) | LCMS, Found [M + H]+ |
| --- | --- | --- | --- | --- |
| 247 | 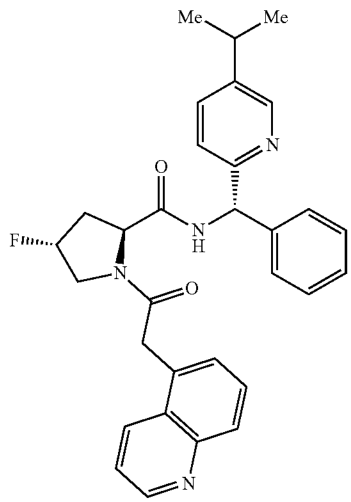 [SMILES: CC(C)c1ccc([C@@H](NC(=O)[C@@H]2C[C@@H](F)CN2C(=O)Cc2cccc3ncccc23)c2ccccc2)nc1] | (2S,4R)-4-fluoro-N-[(S)-phenyl[5-(propan-2-yl)pyridin-2-yl]methyl]-1-[2-(quinolin-5-yl)acetyl]pyrrolidine-2-carboxamide | 510.2 | 511.2 |
| 248 | 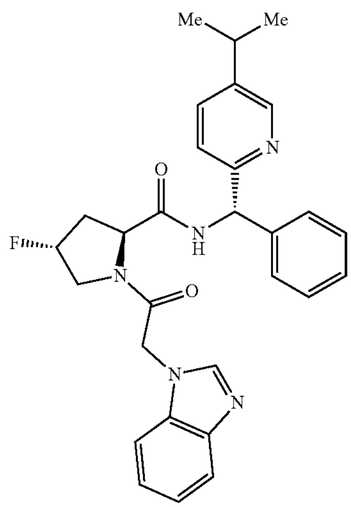 [SMILES: CC(C)c1ccc([C@@H](NC(=O)[C@@H]2C[C@@H](F)CN2C(=O)Cn2cnc3ccccc32)c2ccccc2)nc1] | (2S,4R)-1-[2-(1H-1,3-benzodiazol-1-yl)acetyl]-4-fluoro-N-[(S)-phenyl[5-(propan-2-yl)pyridin-2-yl]methyl]pyrrolidine-2-carboxamide | 499.2 | 500.1 |
| 249 | 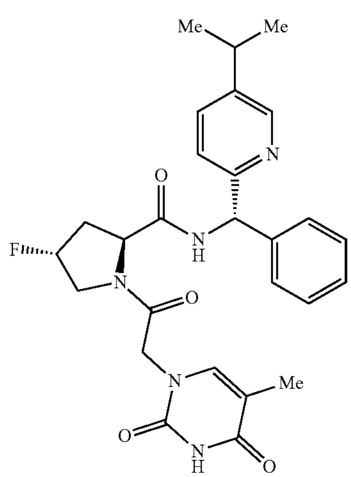 [SMILES: Cc1cn(CC(=O)N2C[C@H](F)C[C@H]2C(=O)N[C@@H](c2ccccc2)c2ccc(C(C)C)cn2)c(=O)[nH]c1=O] | (2S,4R)-4-fluoro-1-[2-(5-methyl-2,4-dioxo-1,2,3,4-tetrahydropyrimidin-1-yl)acetyl]-N-[(S)-phenyl[5-(propan-2-yl)pyridin-2-yl]methyl]pyrrolidine-2-carboxamide | 507.2 | 508.2 |

TABLE T-2-continued

| Compound No. | Structure | IUPAC | Exact mass (g/mol) | LCMS, Found [M + H]+ |
|---|---|---|---|---|
| 250 | 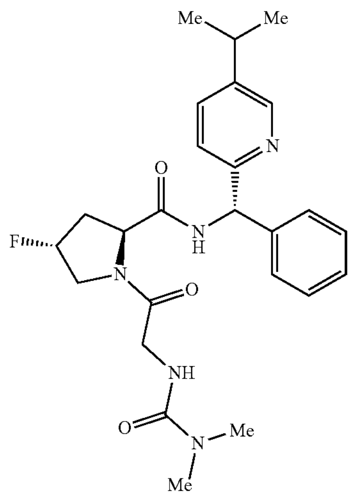 [SMILES: CC(C)c1ccc([C@@H](NC(=O)[C@@H]2C[C@@H](F)CN2C(=O)CNC(=O)N(C)C)c2ccccc2)nc1] | (2S,4R)-1-{2-[(dimethylcarbamoyl)amino]acetyl}-4-fluoro-N-[(S)-phenyl[5-(propan-2-yl)pyridin-2-yl]methyl]pyrrolidine-2-carboxamide | 469.2 | 470.3 |
| 251 | 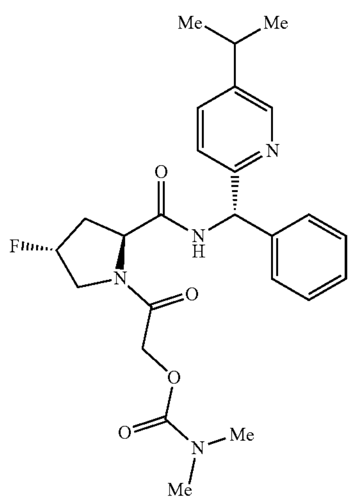 [SMILES: CC(C)c1ccc([C@@H](NC(=O)[C@@H]2C[C@@H](F)CN2C(=O)COC(=O)N(C)C)c2ccccc2)nc1] | 2-[(2S,4R)-4-fluoro-2-{[(S)-phenyl[5-(propan-2-yl)pyridin-2-yl]methyl]carbamoyl}pyrrolidin-1-yl]-2-oxoethyl N,N-dimethylcarbamate | 470.2 | 471.1 |
| 252 | 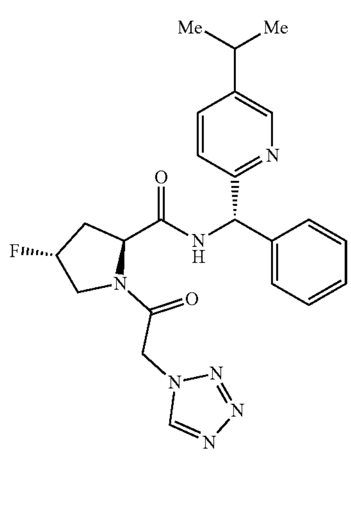 [SMILES: CC(C)c1ccc([C@@H](NC(=O)[C@@H]2C[C@@H](F)CN2C(=O)Cn2cnnn2)c2ccccc2)nc1] | (2S,4R)-4-fluoro-N-[(S)-phenyl[5-(propan-2-yl)pyridin-2-yl]methyl]-1-[2-(1H-1,2,3,4-tetrazol-1-yl)acetyl]pyrrolidine-2-carboxamide | 451.2 | 452.2 |

TABLE T-2-continued

| Compound No. | Structure | IUPAC | Exact mass (g/mol) | LCMS, Found [M + H]+ |
|---|---|---|---|---|
| 253 | 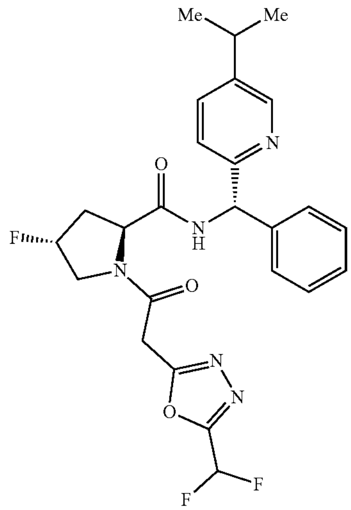 [SMILES: CC(C)c1ccc([C@@H](NC(=O)[C@@H]2C[C@@H](F)CN2C(=O)Cc2nnc(C(F)F)o2)c2ccccc2)nc1] | (2S,4R)-1-{2-[5-(difluoromethyl)-1,3,4-oxadiazol-2-yl]acetyl}-4-fluoro-N-[(S)-phenyl[5-(propan-2-yl)pyridin-2-yl]methyl]pyrrolidine-2-carboxamide | 501.2 | 502.1 |
| 254 | 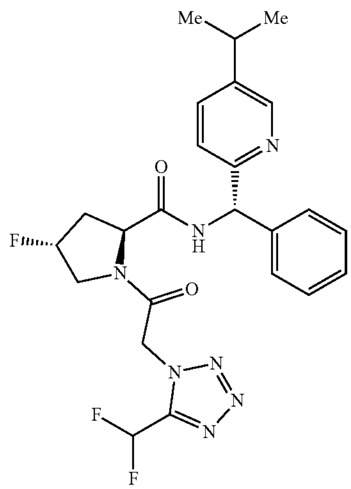 [SMILES: CC(C)c1ccc([C@@H](NC(=O)[C@@H]2C[C@@H](F)CN2C(=O)Cn2nnnc2C(F)F)c2ccccc2)nc1] | (2S,4R)-1-{2-[5-(difluoromethyl)-1H-1,2,3,4-tetrazol-1-yl]acetyl}-4-fluoro-N-[(S)-phenyl[5-(propan-2-yl)pyridin-2-yl]methyl]pyrrolidine-2-carboxamide | 501.2 | 502.3 |
| 255 | 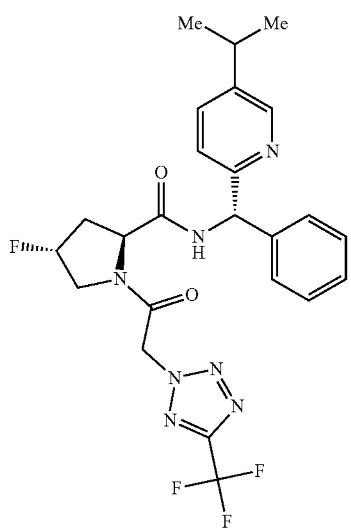 [SMILES: CC(C)c1ccc([C@@H](NC(=O)[C@@H]2C[C@@H](F)CN2C(=O)Cn2nnc(C(F)(F)F)n2)c2ccccc2)nc1] | (2S,4R)-4-fluoro-N-[(S)-phenyl[5-(propan-2-yl)pyridin-2-yl]methyl]-1-{2-[2-(trifluoromethyl)-2H-1,2,3,4-tetrazol-2-yl]acetyl}pyrrolidine-2-carboxamide | 519.2 | 520.2 |

TABLE T-2-continued

| Compound No. | Structure | IUPAC | Exact mass (g/mol) | LCMS, Found [M + H]+ |
|---|---|---|---|---|
| 256 | 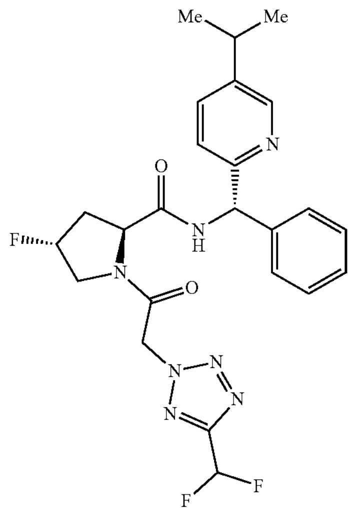 [SMILES: CC(C)c1ccc([C@@H](NC(=O)[C@@H]2C[C@@H](F)CN2C(=O)Cn2nnc(C(F)F)n2)c2ccccc2)nc1] | (2S,4R)-1-{2-[5-(difluoromethyl)-2H-1,2,3,4-tetrazol-2-yl]acetyl}-4-fluoro-N-[(S)-phenyl[5-(propan-2-yl)pyridin-2-yl]methyl]pyrrolidine-2-carboxamide | 501.2 | 502.2 |
| 257 | 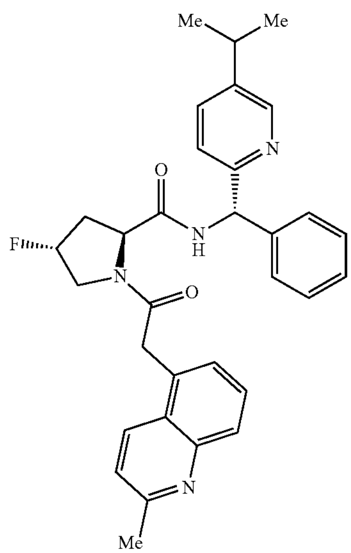 [SMILES: Cc1ccc2c(CC(=O)N3C[C@H](F)C[C@H]3C(=O)N[C@@H](c3ccccc3)c3ccc(C(C)C)cn3)cccc2n1] | (2S,4R)-4-fluoro-1-[2-(2-methylquinolin-5-yl)acetyl]-N-[(S)-phenyl[5-(propan-2-yl)pyridin-2-yl]methyl]pyrrolidine-2-carboxamide | 524.3 | 525.3 |
| 258 | 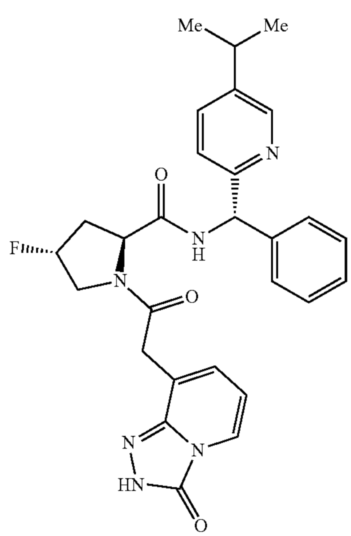 [SMILES: CC(C)c1ccc([C@@H](NC(=O)[C@@H]2C[C@@H](F)CN2C(=O)Cc2cccn3c(=O)[nH]nc23)c2ccccc2)nc1] | (2S,4R)-4-fluoro-1-(2-{3-oxo-2H,3H-[1,2,4]triazolo[4,3-a]pyridin-8-yl}acetyl)-N-[(S)-phenyl[5-(propan-2-yl)pyridin-2-yl]methyl]pyrrolidine-2-carboxamide | 516.2 | 517.3 |

TABLE T-2-continued

| Compound No. | Structure | IUPAC | Exact mass (g/mol) | LCMS, Found [M + H]+ |
|---|---|---|---|---|
| 259 | 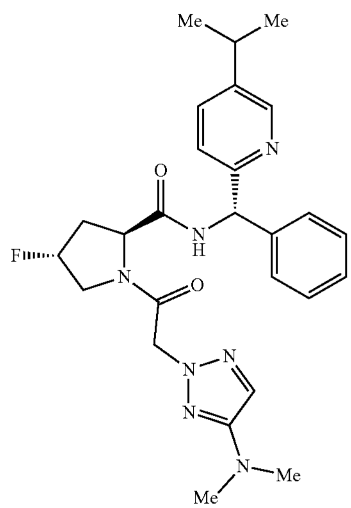 [SMILES: CC(C)c1ccc([C@@H](NC(=O)[C@@H]2C[C@@H](F)CN2C(=O)Cn2ncc(N(C)C)n2)c2ccccc2)nc1] | (2S,4R)-1-{2-[4-(dimethylamino)-2H-1,2,3-triazol-2-yl]acetyl}-4-fluoro-N-[(S)-phenyl[5-(propan-2-yl)pyridin-2-yl]methyl]pyrrolidine-2-carboxamide | 493.3 | 494.3 |
| 260 | 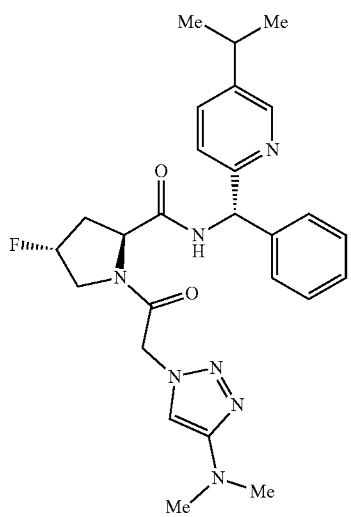 [SMILES: CC(C)c1ccc([C@@H](NC(=O)[C@@H]2C[C@@H](F)CN2C(=O)Cn2cc(N(C)C)nn2)c2ccccc2)nc1] | (2S,4R)-1-{2-{4-(dimethylamino)-1H-1,2,3-triazol-1-yl]acetyl}-4-fluoro-N-[(S)-phenyl[5-(propan-2-yl)pyridin-2-yl]methyl]pyrrolidine-2-carboxamide | 493.3 | 494.2 |
| 261 | 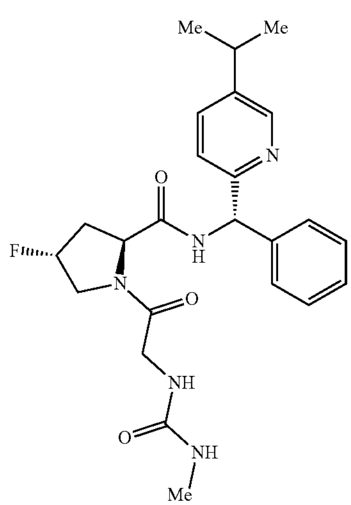 [SMILES: CNC(=O)NCC(=O)N1C[C@H](F)C[C@H]1C(=O)N[C@@H](c1ccccc1)c1ccc(C(C)C)cn1] | (2S,4R)-4-fluoro-1-{2-[(methylcarbamoyl)amino]acetyl}-N-[(S)-phenyl[5-(propan-2-yl)pyridin-2-yl]methyl]pyrrolidine-2-carboxamide | 455.2 | 456.2 |

TABLE T-2-continued

| Compound No. | Structure | IUPAC | Exact mass (g/mol) | LCMS, Found [M + H]+ |
|---|---|---|---|---|
| 262 | 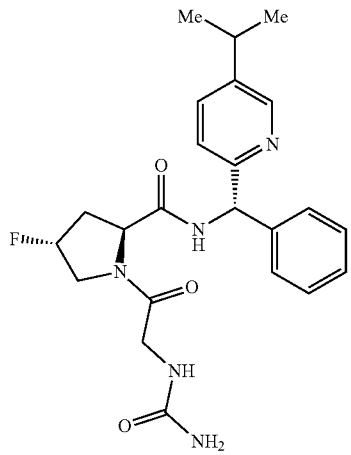 [SMILES: CC(C)c1ccc([C@@H](NC(=O)[C@@H]2C[C@@H](F)CN2C(=O)CNC(N)=O)c2ccccc2)nc1] | (2S,4R)-1-[2-(carbamoylamino)acetyl]-4-fluoro-N-[(S)-phenyl[5-(propan-2-yl)pyridin-2-yl]methyl]pyrrolidine-2-carboxamide | 441.2 | 442.1 |
| 263 | 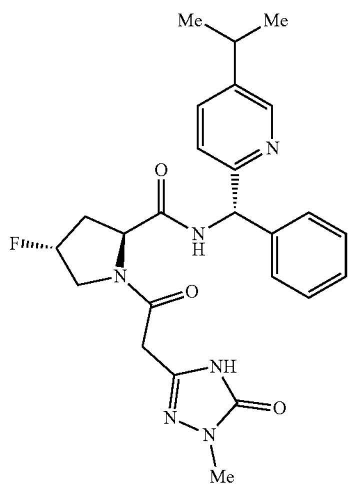 | (2S,4R)-4-fluoro-1-[2-(1-methyl-5-oxo-4,5-dihydro-1H-1,2,4-triazol-3-yl)acetyl]-N-[(S)-phenyl[5-(propan-2-yl)pyridin-2-yl]methyl]pyrrolidine-2-carboxamide | 480.2 | 481.3 |
| 264 | 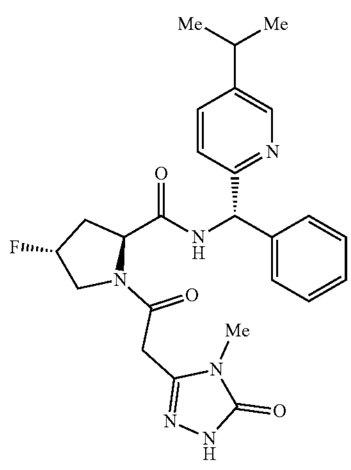 [SMILES: CC(C)c1ccc([C@@H](NC(=O)[C@@H]2C[C@@H](F)CN2C(=O)Cc2n[nH]c(=O)n2C)c2ccccc2)nc1] | (2S,4R)-4-fluoro-1-[2-(4-methyl-5-oxo-4,5-dihydro-1H-1,2,4-triazol-3-yl)acetyl]-N-[(S)-phenyl[5-(propan-2-yl)pyridin-2-yl]methyl]pyrrolidine-2-carboxamide | 480.2 | 481.2 |

TABLE T-2-continued

| Compound No. | Structure | IUPAC | Exact mass (g/mol) | LCMS, Found [M + H]+ |
|---|---|---|---|---|
| 265 | 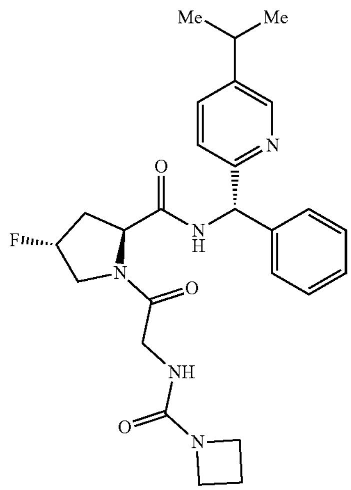 [SMILES: CC(C)c1ccc([C@@H](NC(=O)[C@@H]2C[C@@H](F)CN2C(=O)CNC(=O)N2CCC2)c2ccccc2)nc1] | (2S,4R)-1-{2-[(azetidine-1-carbonyl)amino]acetyl}-4-fluoro-N-[(S)-phenyl[5-(propan-2-yl)pyridin-2-yl]methyl]pyrrolidine-2-carboxamide | 481.2 | 482.2 |
| 266 | 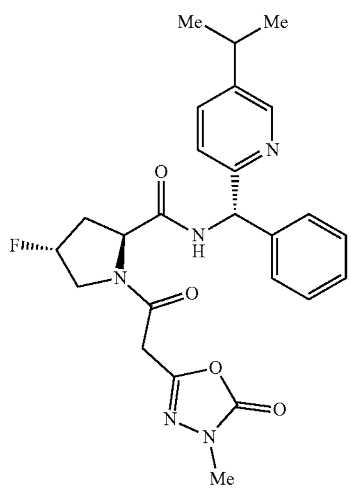 [SMILES: CC(C)c1ccc([C@@H](NC(=O)[C@@H]2C[C@@H](F)CN2C(=O)Cc2nn(C)c(=O)o2)c2ccccc2)nc1] | (2S,4R)-4-fluoro-1-[2-(4-methyl-5-oxo-4,5-dihydro-1,3,4-oxadiazol-2-yl)acetyl]-N-[(S)-phenyl[5-(propan-2-yl)pyridin-2-yl]methyl]pyrrolidine-2-carboxamide | 481.2 | 482.3 |
| 267 | 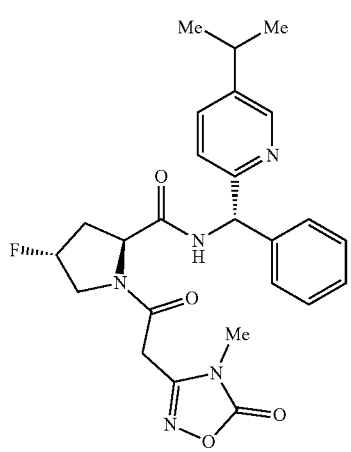 [SMILES: CC(C)c1ccc([C@@H](NC(=O)[C@@H]2C[C@@H](F)CN2C(=O)Cc2noc(=O)n2C)c2ccccc2)nc1] | (2S,4R)-4-fluoro-1-[2-(4-methyl-5-oxo-4,5-dihydro-1,2,4-oxadiazol-3-yl)acetyl]-N-[(S)-phenyl[5-(propan-2-yl)pyridin-2-yl]methyl]pyrrolidine-2-carboxamide | 481.2 | 482.3 |

TABLE T-2-continued

| Compound No. | Structure | IUPAC | Exact mass (g/mol) | LCMS, Found [M + H]+ |
|---|---|---|---|---|
| 268 | 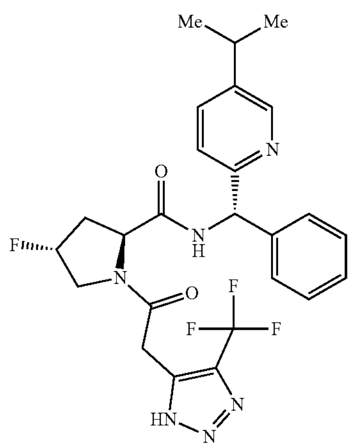 [SMILES: CC(C)c1ccc([C@@H](NC(=O)[C@@H]2C[C@@H](F)CN2C(=O)Cc2[nH]nnc2C(F)(F)F)c2ccccc2)nc1] | (2S,4R)-4-fluoro-N-[(S)-phenyl[5-(propan-2-yl)pyridin-2-yl]methyl]-1-{2-[4-(trifluoromethyl)-1H-1,2,3-triazol-5-yl]acetyl}pyrrolidine-2-carboxamide | 518.2 | 519.3 |
| 269 | 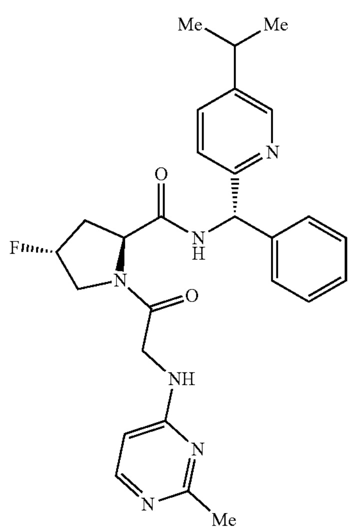 [SMILES: Cc1nccc(NCC(=O)N2C[C@H](F)C[C@H]2C(=O)N[C@@H](c2ccccc2)c2ccc(C(C)C)cn2)n1] | (2S,4R)-4-fluoro-1-{2-[(2-methylpyrimidin-4-yl)amino]acetyl}-N-[(S)-phenyl[5-(propan-2-yl)pyridin-2-yl]methyl]pyrrolidine-2-carboxamide | 490.2 | 491.2 |
| 270 | 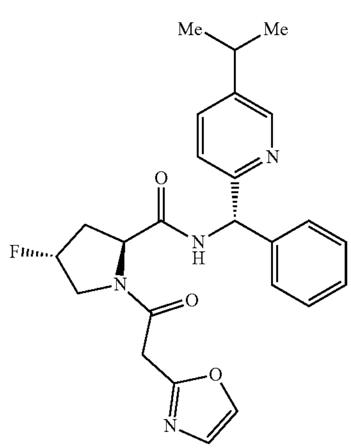 [SMILES: CC(C)c1ccc([C@@H](NC(=O)[C@@H]2C[C@@H](F)CN2C(=O)Cc2ncco2)c2ccccc2)nc1] | (2S,4R)-4-fluoro-1-[2-(1,3-oxazol-2-yl)acetyl]-N-[(S)-phenyl[5-(propan-2-yl)pyridin-2-yl]methyl]pyrrolidine-2-carboxamide | 450.2 | 451.3 |

TABLE T-2-continued

| Compound No. | Structure | IUPAC | Exact mass (g/mol) | LCMS, Found [M + H]+ |
|---|---|---|---|---|
| 271 | 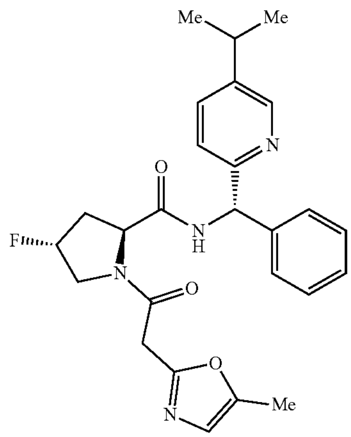 [SMILES: Cc1cnc(CC(=O)N2C[C@H](F)C[C@H]2C(=O)N[C@@H](c2ccccc2)c2ccc(C(C)C)cn2)o1] | (2S,4R)-4-fluoro-1-[2-(5-methyl-1,3-oxazol-2-yl)acetyl]-N-[(S)-phenyl[5-(propan-2-yl)pyridin-2-yl]methyl]pyrrolidine-2-carboxamide | 464.2 | 465.2 |
| 272 | 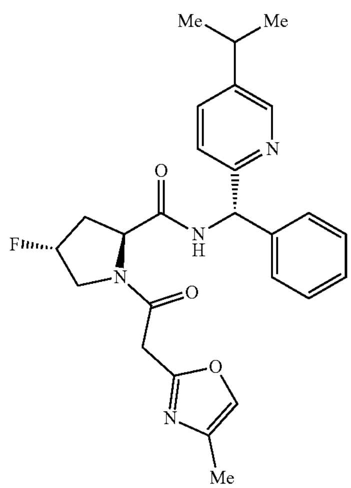 [SMILES: Cc1coc(CC(=O)N2C[C@H](F)C[C@H]2C(=O)N[C@@H](c2ccccc2)c2ccc(C(C)C)cn2)n1] | (2S,4R)-4-fluoro-1-[2-(4-methyl-1,3-oxazol-2-yl)acetyl]-N-[(S)-phenyl[5-(propan-2-yl)pyridin-2-yl]methyl]pyrrolidine-2-carboxamide | 464.2 | 465.2 |
| 273 | 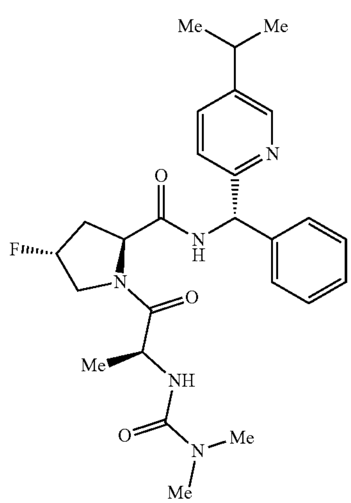 [SMILES: CC(C)c1ccc([C@@H](NC(=O)[C@@H]2C[C@@H](F)CN2C(=O)[C@H](C)NC(=O)N(C)C)c2ccccc2)nc1] | (2S,4R)-1-[(2S)-2-[(dimethylcarbamoyl)amino]propanoyl]-4-fluoro-N-[(S)-phenyl[5-(propan-2-yl)pyridin-2-yl]methyl]pyrrolidine-2-carboxamide | 483.3 | 484.3 |

TABLE T-2-continued

| Compound No. | Structure | IUPAC | Exact mass (g/mol) | LCMS, Found [M + H]+ |
|---|---|---|---|---|
| 274 | 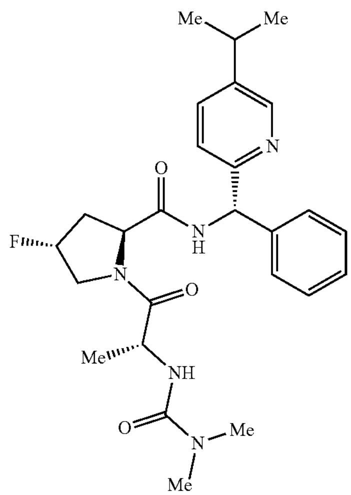 [SMILES: CC(C)c1ccc([C@@H](NC(=O)[C@@H]2C[C@@H](F)CN2C(=O)[C@@H](C)NC(=O)N(C)C)c2ccccc2)nc1] | (2S,4R)-1-[(2R)-2-[(dimethylcarbamoyl)amino]propanoyl]-4-fluoro-N-[(S)-phenyl[5-(propan-2-yl)pyridin-2-yl]methyl]pyrrolidine-2-carboxamide | 483.3 | 484.3 |
| 275 | 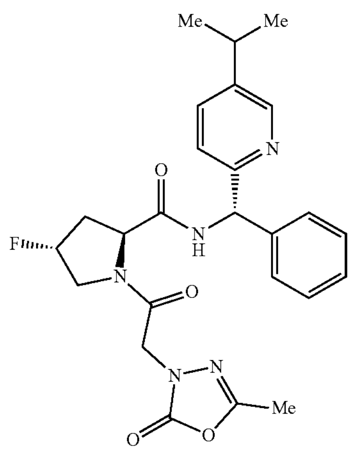 | (2S,4R)-4-fluoro-1-[2-(5-methyl-2-oxo-2,3-dihydro-1,3,4-oxadiazol-3-yl)acetyl]-N-[(S)-phenyl[5-(propan-2-yl)pyridin-2-yl]methyl]pyrrolidine-2-carboxamide | 481.2 | 482.3 |
| 276 | 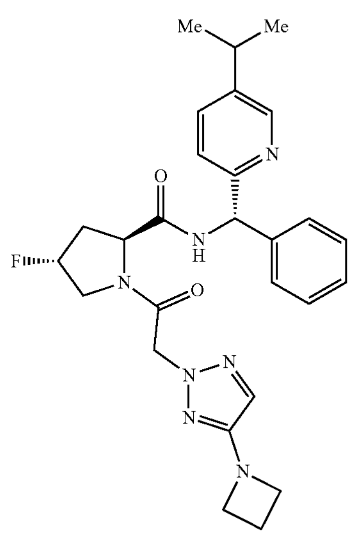 [SMILES: CC(C)c1ccc([C@@H](NC(=O)[C@@H]2C[C@@H](F)CN2C(=O)Cn2ncc(N3CCC3)n2)c2ccccc2)nc1] | (2S,4R)-1-{2-[4-(azetidin-1-yl)-2H-1,2,3-triazol-2-yl]acetyl}-4-fluoro-N-[(S)-phenyl[5-(propan-2-yl)pyridin-2-yl]methyl]pyrrolidine-2-carboxamide | 505.3 | 506.3 |

TABLE T-2-continued

| Compound No. | Structure | IUPAC | Exact mass (g/mol) | LCMS, Found [M + H]+ |
|---|---|---|---|---|
| 277 | 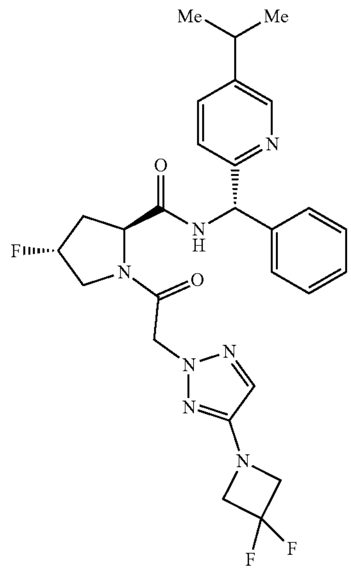 [SMILES: CC(C)c1ccc([C@@H](NC(=O)[C@@H]2C[C@@H](F)CN2C(=O)Cn2ncc(N3CC(F)(F)C3)n2)c2ccccc2)nc1] | (2S,4R)-1-{2-[4-(3,3-difluoroazetidin-1-yl)-2H-1,2,3-triazol-2-yl]acetyl}-4-fluoro-N-phenyl[5-(propan-2-yl)pyridin-2-yl]methyl]pyrrolidine-2-carboxamide | 541.2 | 542.3 |
| 278 | 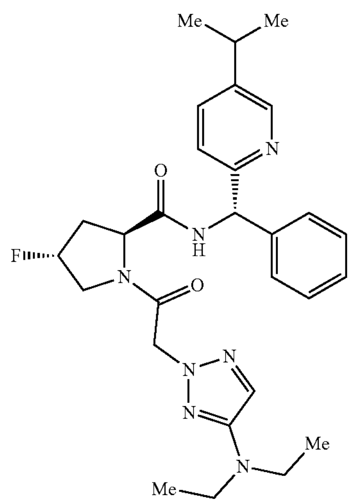 [SMILES: CCN(CC)c1cnn(CC(=O)N2C[C@H](F)C[C@H]2C(=O)N[C@@H](c2ccccc2)c2ccc(C(C)C)cn2)n1] | (2S,4R)-1-{2-[4-(diethylamino)-2H-1,2,3-triazol-2-yl]acetyl}-4-fluoro-N-[(S)-phenyl[5-(propan-2-yl)pyridin-2-yl]methyl]pyrrolidine-2-carboxamide | 521.3 | 522.5 |
| 279 | 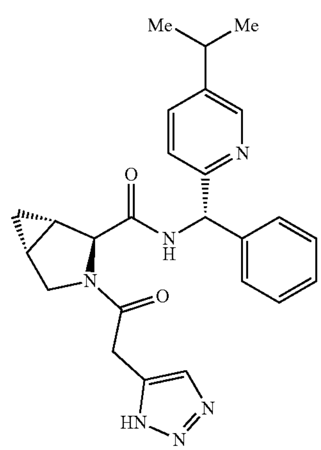 [SMILES: CC(C)c1ccc([C@@H](NC(=O)[C@@H]2[C@H]3C[C@H]3CN2C(=O)Cc2cnn[nH]2)c2ccccc2)nc1] | (1S,2S,5R)-N-[(S)-phenyl[5-(propan-2-yl)pyridin-2-yl]methyl]-3-[2-(1H-1,2,3-triazol-5-yl)acetyl]-3-azabicyclo[3.1.0]hexane-2-carboxamide | 444.2 | 445.4 |

TABLE T-2-continued

| Compound No. | Structure | IUPAC | Exact mass (g/mol) | LCMS, Found [M + H]+ |
|---|---|---|---|---|
| 280 | 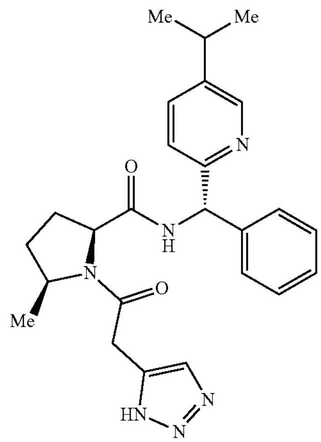 [SMILES: CC(C)c1ccc([C@@H](NC(=O)[C@@H]2CC[C@H](C)N2C(=O)Cc2cnn[nH]2)c2ccccc2)nc1] | (2S,5S)-5-methyl-N-[(S)-phenyl[5-(propan-2-yl)pyridin-2-yl]methyl]-1-[2-(1H-1,2,3-triazol-5-yl)acetyl]pyrrolidine-2-carboxamide | 446.2 | 447.3 |
| 281 | 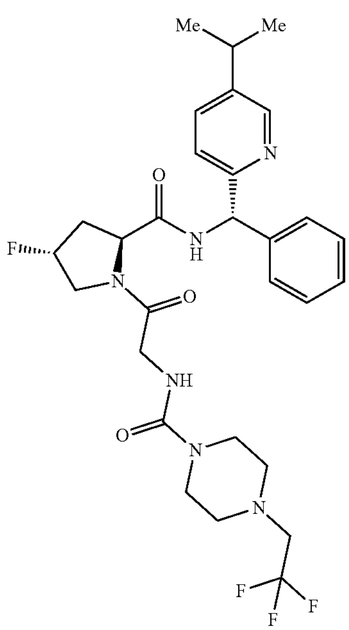 [SMILES: CC(C)c1ccc([C@@H](NC(=O)[C@@H]2C[C@@H](F)CN2C(=O)CNC(=O)N2CCN(CC(F)(F)F)CC2)c2ccccc2)nc1] | N-{2-[(2S,4R)-4-fluoro-2-{[(S)-phenyl[5-(propan-2-yl)pyridin-2-yl]methyl]carbamoyl}pyrrolidin-1-yl]-2-oxoethyl}-4-(2,2,2-trifluoroethyl)piperazine-1-carboxamide | 592.3 | 593.2 |

TABLE T-2-continued

| Compound No. | Structure | IUPAC | Exact mass (g/mol) | LCMS, Found [M + H]+ |
| --- | --- | --- | --- | --- |
| 282 | 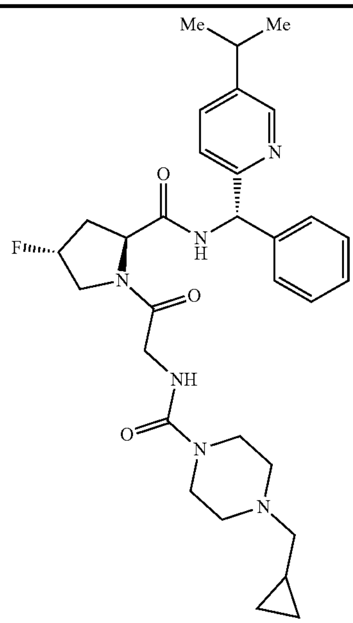 | 4-(cyclopropylmethyl)-N-{2-[(2S,4R)-4-fluoro-2-phenyl[5-(propan-2-yl)pyridin-2-yl]methyl carbamoyl}pyrrolidin-1-yl]-2-oxoethyl}piperazine-1-carboxamide | 564.3 | 565.5 |
| 283 | 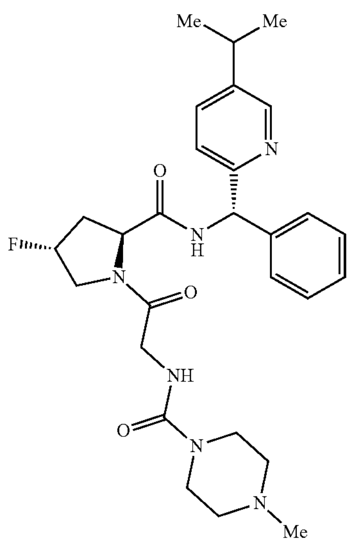 [SMILES: CC(C)c1ccc([C@@H](NC(=O)[C@@H]2C[C@@H](F)CN2C(=O)CNC(=O)N2CCN(C)CC2)c2ccccc2)nc1] | N-{2-[(2S,4R)-4-fluoro-2-{[(S)-phenyl[5-(propan-2-yl)pyridin-2-yl]}pyrrolidin-1-yl]-2-oxoethyl}-4-methylpiperazine-1-carboxamide | 524.3 | 525.3 |
| 284 | 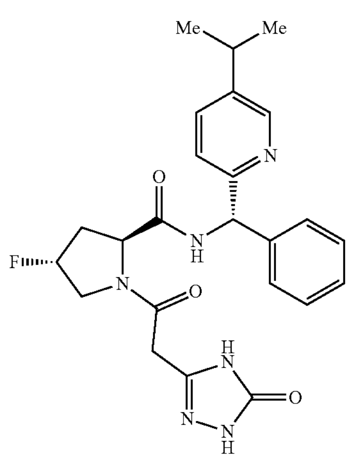 [SMILES: CC(C)c1ccc([C@@H](NC(=O)[C@@H]2C[C@@H](F)CN2C(=O)Cc2n[nH]c(=O)[nH]2)c2ccccc2)nc1] | (2S,4R)-4-fluoro-1-[2-(5-oxo-4,5-dihydro-1H-1,2,4-triazol-3-yl)acetyl]-N-[(S)-phenyl[5-(propan-2-yl)pyridin-2-yl]methyl]pyrrolidine-2-carboxamide | 466.2 | 467.0 |

TABLE T-2-continued

| Compound No. | Structure | IUPAC | Exact mass (g/mol) | LCMS, Found [M + H]+ |
|---|---|---|---|---|
| 285 | 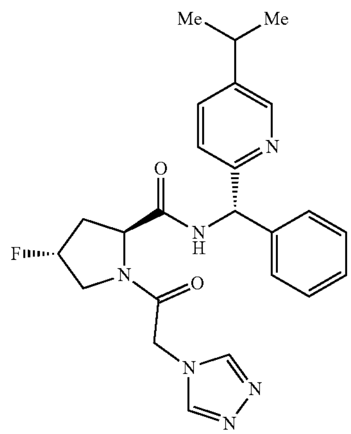 [SMILES: CC(C)c1ccc([C@@H](NC(=O)[C@@H]2C[C@@H](F)CN2C(=O)Cn2cnnc2)c2ccccc2)nc1] | (2S,4R)-4-fluoro-N-[(S)-phenyl[5-(propan-2-yl)pyridin-2-yl]methyl]-1-[2-(4H-1,2,4-triazol-4-yl)acetyl]pyrrolidine-2-carboxamide | 450.2 | 451.3 |
| 286 | 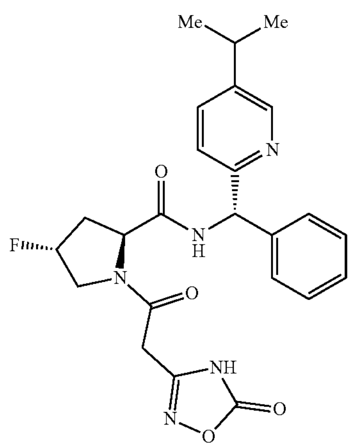 [SMILES: CC(C)c1ccc([C@@H](NC(=O)[C@@H]2C[C@@H](F)CN2C(=O)Cc2noc(=O)[nH]2)c2ccccc2)nc1] | (2S,4R)-4-fluoro-1-[2-(5-oxo-4,5-dihydro-1,2,4-oxadiazol-3-yl)acetyl]-N-[(S)-phenyl[5-(propan-2-yl)pyridin-2-yl]methyl]pyrrolidine-2-carboxamide | 467.2 | 468.2 |
| 287 | 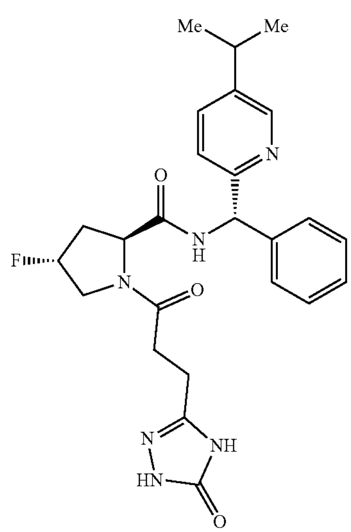 [SMILES: CC(C)c1ccc([C@@H](NC(=O)[C@@H]2C[C@@H](F)CN2C(=O)CCc2n[nH]c(=O)[nH]2)c2ccccc2)nc1] | (2S,4R)-4-fluoro-1-[3-(5-oxo-4,5-dihydro-1H-1,2,4-triazol-3-yl)propanoyl]-N-[(S)-phenyl[5-(propan-2-yl)pyridin-2-yl]methyl]pyrrolidine-2-carboxamide | 480.2 | 481.0 |

TABLE T-2-continued

| Compound No. | Structure | IUPAC | Exact mass (g/mol) | LCMS, Found [M + H]+ |
|---|---|---|---|---|
| 288 | 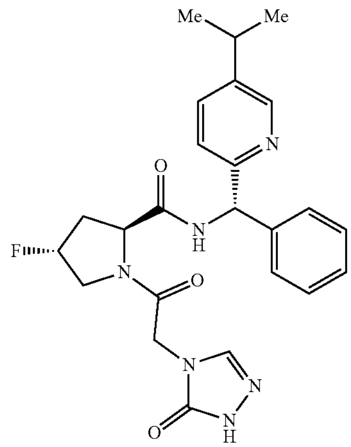 [SMILES: CC(C)c1ccc([C@@H](NC(=O)[C@@H]2C[C@@H](F)CN2C(=O)Cn2cn[nH]c2=O)c2ccccc2)nc1] | (2S,4R)-4-fluoro-1-[2-(5-oxo-4,5-dihydro-1H-1,2,4-triazol-4-yl)acetyl]-N-[(S)-phenyl[5-(propan-2-yl)pyridin-2-yl]methyl]pyrrolidine-2-carboxamide | 466.2 | 467.2 |
| 289 | 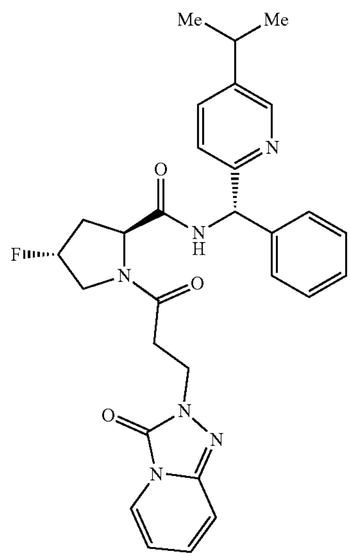 [SMILES: CC(C)c1ccc([C@@H](NC(=O)[C@@H]2C[C@@H](F)CN2C(=O)CCn2nc3ccccn3c2=O)c2ccccc2)nc1] | (2S,4R)-4-fluoro-1-(3-{3-oxo-2H,3H-[1,2,4]triazolo[4,3-a]pyridin-2-propanoyl)-N-[(S)-phenyl[5-(propan-2-yl)pyridin-2-yl]methyl]pyrrolidine-2-carboxamide | 530.2 | 531.2 |
| 290 | 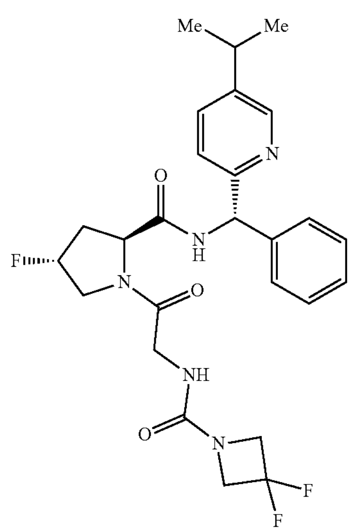 [SMILES: CC(C)c1ccc([C@@H](NC(=O)[C@@H]2C[C@@H](F)CN2C(=O)CNC(=O)N2CC(F)(F)C2)c2ccccc2)nc1] | (2S,4R)-1-{2-[(3,3-difluoroazetidine-1-carbonyl)amino]acetyl}-4-fluoro-N-[(S)-phenyl[5-(propan-2-yl)pyridin-2-yl]methyl]pyrrolidine-2-carboxamide | 517.2 | 517.2 |

TABLE T-2-continued

| Compound No. | Structure | IUPAC | Exact mass (g/mol) | LCMS, Found [M + H]+ |
|---|---|---|---|---|
| 291 | 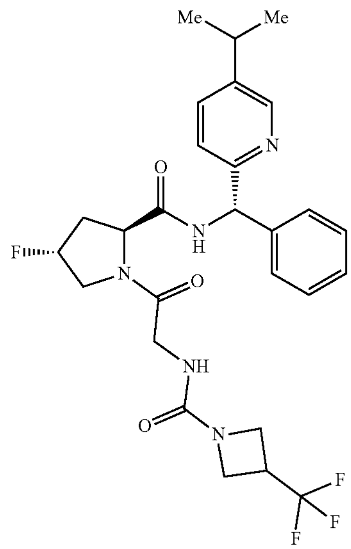 [SMILES: CC(C)c1ccc([C@@H](NC(=O)[C@@H]2C[C@@H](F)CN2C(=O)CNC(=O)N2CC(C(F)(F)F)C2)c2ccccc2)nc1] | (2S,4R)-4-fluoro-N-[(S)-phenyl[5-(propan-2-yl)pyridin-2-yl]methyl]-1-(2-{[3-(trifluoromethyl)azetidine-1-carbonyl]amino}acetyl)pyrrolidine-2-carboxamide | 549.2 | 549.2 |
| 292 | 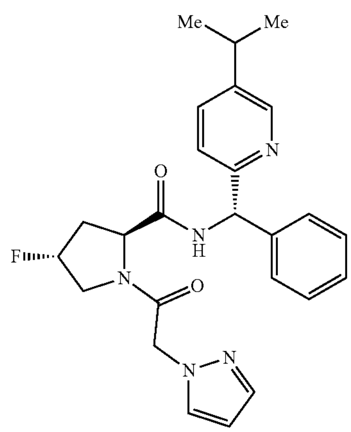 [SMILES: CC(C)c1ccc([C@@H](NC(=O)[C@@H]2C[C@@H](F)CN2C(=O)Cn2cccn2)c2ccccc2)nc1] | (2S,4R)-4-fluoro-N-[(S)-phenyl[5-(propan-2-yl)pyridin-2-yl]methyl]-1-[2-(1H-pyrazol-1-yl)acetyl]pyrrolidine-2-carboxamide | 449.2 | 449.2 |
| 710 | 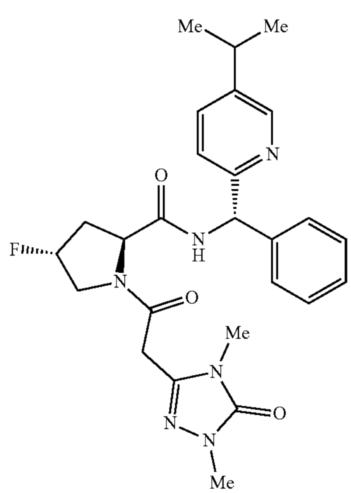 [SMILES: CC(C)c1ccc([C@@H](NC(=O)[C@@H]2C[C@@H](F)CN2C(=O)Cc2nn(C)c(=O)n2C)c2ccccc2)nc1] | (2S,4R)-1-[2-(1,4-dimethyl-5-oxo-4,5-dihydro-1H-1,2,4-triazol-3-yl)acetyl]-4-fluoro-N-[(S)-phenyl[5-(propan-2-yl)pyridin-2-yl]methyl]pyrrolidine-2-carboxamide | 494.2 | 495.3 |

TABLE T-2-continued

| Compound No. | Structure | IUPAC | Exact mass (g/mol) | LCMS, Found [M + H]+ |
| --- | --- | --- | --- | --- |
| 711 | 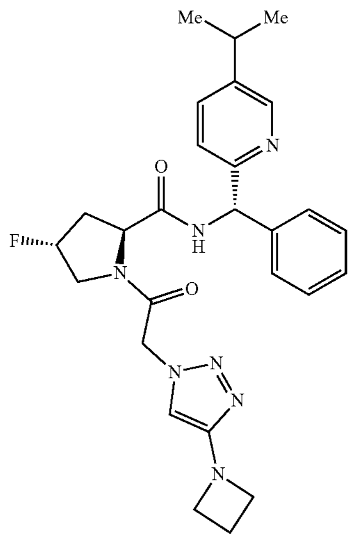 [SMILES: CC(C)c1ccc([C@@H](NC(=O)[C@@H]2C[C@@H](F)CN2C(=O)Cn2cc(N3CCC3)nn2)c2ccccc2)nc1] | (2S,4R)-1-{2-[4-(azetidin-1-yl)-1H-1,2,3-triazol-1-yl]acetyl}-4-fluoro-N-[(S)-phenyl[5-(propan-2-yl)pyridin-2-yl]methyl]pyrrolidine-2-carboxamide | 505.3 | 506.3 |
| 712 | 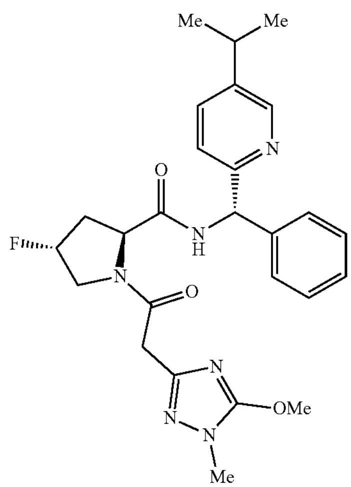 [SMILES: COc1nc(CC(=O)N2C[C@H](F)C[C@H]2C(=O)N[C@@H](c2ccccc2)c2ccc(C(C)C)cn2)nn1C] | (2S,4R)-4-fluoro-1-[2-(5-methoxy-1-methyl-1H-1,2,4-triazol-3-yl)acetyl]-N-[(S)-phenyl[5-(propan-2-yl)pyridin-2-yl]methyl]pyrrolidine-2-carboxamide | 494.2 | 495.3 |
| 713 | 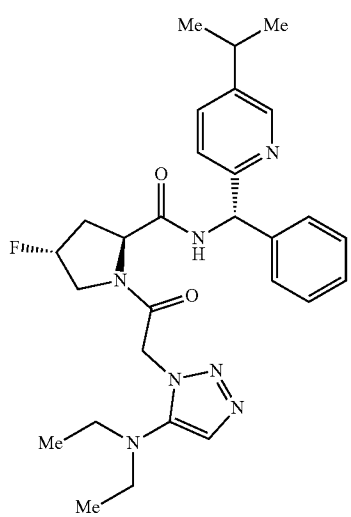 [SMILES: CCN(CC)c1cnnn1CC(=O)N1C[C@H](F)C[C@H]1C(=O)N[C@@H](c1ccccc1)c1ccc(C(C)C)cn1] | (2S,4R)-1-{2-[5-(diethylamino)-1H-1,2,3-triazol-1-yl]acetyl}-4-fluoro-N-[(S)-phenyl[5-(propan-2-yl)pyridin-2-yl]methyl]pyrrolidine-2-carboxamide | 521.3 | 522.3 |

TABLE T-2-continued

| Compound No. | Structure | IUPAC | Exact mass (g/mol) | LCMS, Found [M + H]+ |
|---|---|---|---|---|
| 714 | 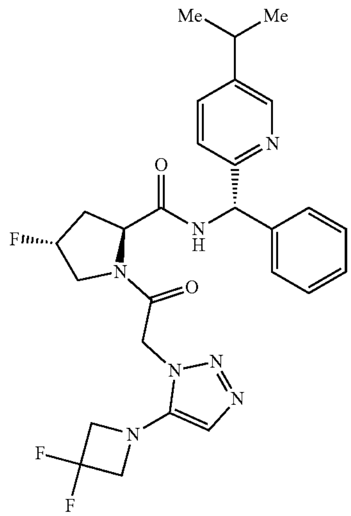 [SMILES: CC(C)c1ccc([C@@H](NC(=O)[C@@H]2C[C@@H](F)CN2C(=O)Cn2nncc2N2CC(F)(F)C2)c2ccccc2)nc1] | (2S,4R)-1-{2-[5-(3,3-difluoroazetidin-1-yl)-1H-1,2,3-triazol-1-yl]acetyl}-4-fluoro-N-[(S)-phenyl[5-(propan-2-yl)pyridin-2-yl]methyl]pyrrolidine-2-carboxamide | 541.2 | 542.3 |
| 715 | 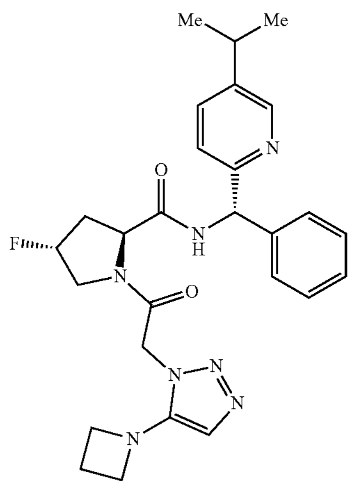 [SMILES: CC(C)c1ccc([C@@H](NC(=O)[C@@H]2C[C@@H](F)CN2C(=O)Cn2nncc2N2CCC2)c2ccccc2)nc1] | (2S,4R)-1-{2-[5-(azetidin-1-yl)-1H-1,2,3-triazol-1-yl]acetyl}-4-fluoro-N-[(S)-phenyl[5-(propan-2-yl)pyridin-2-yl]methyl]pyrrolidine-2-carboxamide | 505.2 | 506.3 |

Example S-3: Synthesis of (2S,4R)—N—((S)-(5-cyclopropyl-6-fluoropyridin-2-yl)(phenyl)methyl)-1-(2-(5-(difluoromethyl)-1H-tetrazol-1-yl)acetyl)-4-fluoropyrrolidine-2-carboxamide Compound 293

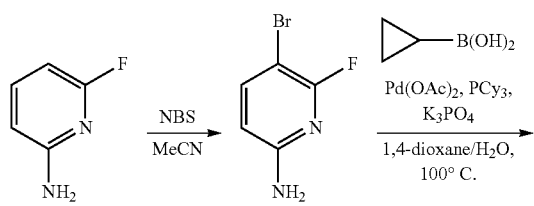

-continued

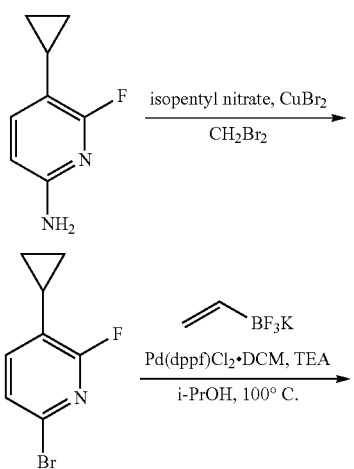

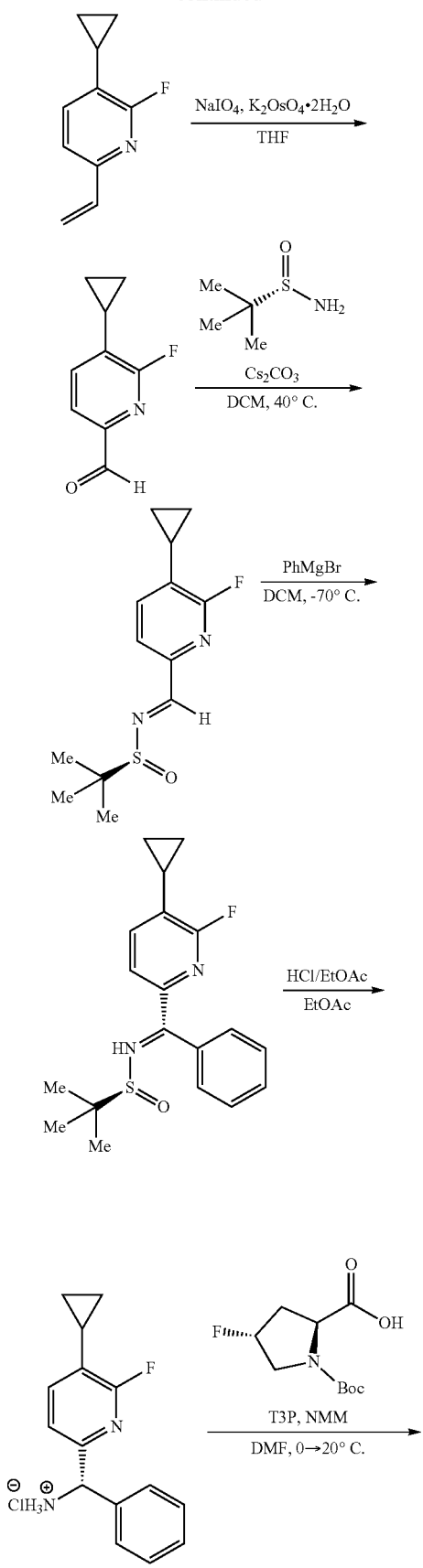
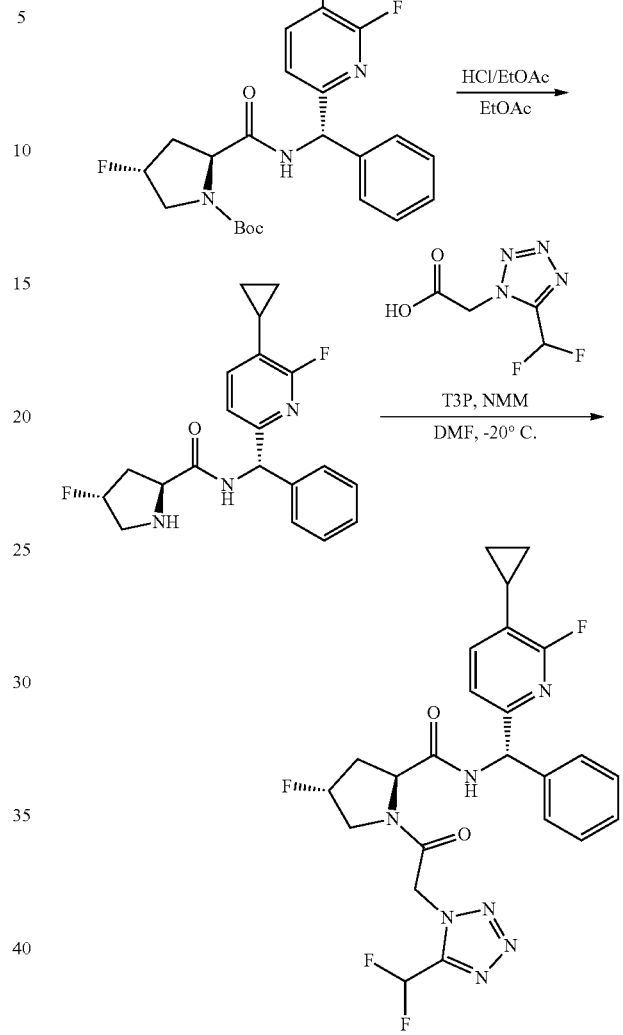

Step a: In four parallel reactions, 6-fluoropyridin-2-amine (125 g, 1.11 mol, 1 eq) in MeCN (1.2 L) at 0° C. under N₂ was treated with NBS (209 g, 1.17 mmol, 1.05 eq) in MeCN (1.2 L). The reaction mixtures were stirred at 20° C. for 2 h. The four parallel reactions were combined, and the resulting mixture was concentrated under reduced pressure. The resulting crude residue was purified by column chromatography to give 5-bromo-6-fluoropyridin-2-amine. LC-MS (ESI): m/z: [M+H]⁺ calculated for C₅H₄BrFN₂: 190.9; found 191.0.

Step b: To a mixture of 5-bromo-6-fluoropyridin-2-amine (200 g, 1.04 mol, 1 eq) and cyclopropylboronic acid (226 g, 2.63 mol, 2.5 eq) in 1,4-dioxane (2 L) and H₂O (200 mL) under N₂ were added K₃PO₄ (666 g, 3.14 mol, 3 eq), PCy₃ (58.6 g, 209 mmol, 0.2 eq), and Pd(OAc)₂ (11.7 g, 52.3 mmol, 0.05 eq). The system was then degassed and charged with nitrogen three times. The reaction mixture was warmed to 100° C. and stirred for 12 h. The reaction mixture was then cooled to room temperature and filtered through Celite. The resulting filtrate was diluted with H₂O (2 L) and then extracted with EtOAc (3×500 mL). The combined organic extracts were washed with brine (2×300 mL), dried over anhydrous Na$_2$SO$_4$, filtered, and concentrated under reduced pressure. The crude residue obtained was purified by column chromatography to give 5-cyclopropyl-6-fluoropyridin-2-amine. LC-MS (ESI): m/z: [M+H]$^+$ calculated for C$_8$H$_9$FN$_2$: 153.1; found 153.0.

Step c: To a mixture of 5-cyclopropyl-6-fluoropyridin-2-amine (120 g, 788 mmol, 1 eq) in dibromomethane (564 mL) under N$_2$ was added isopentyl nitrite (110 g, 946 mmol, 127 mL, 1.2 eq). To the resulting mixture was added CuBr$_2$ (211 g, 946 mmol, 44.3 mL, 1.2 eq) over 0.5 h. The final mixture was then degassed and charged with nitrogen three times before stirring at 20° C. for 16 h. The reaction mixture was then filtered, and the filtrate was diluted with H$_2$O (500 mL) and extracted with EtOAc (3×300 mL). The combined organic extracts were washed with brine (300 mL), dried over anhydrous Na$_2$SO$_4$, filtered, and concentrated under reduced pressure. The crude residue obtained was purified by column chromatography to give 6-bromo-3-cyclopropyl-2-fluoropyridine. LC-MS (ESI): m/z: [M+H]$^+$ calculated for C$_8$H$_7$BrFN: 216.0; found 216.1.

Step d: To a mixture of 6-bromo-3-cyclopropyl-2-fluoropyridine (90 g, 416 mmol, 1 eq) and trifluoro(vinyl)-λ4-borane, potassium salt (83.7 g, 624 mmol, 1.5 eq) in i-PrOH (900 mL) at 20° C. under N$_2$ was added TEA (126 g, 1.25 mol, 3 eq) and Pd(dppf)Cl$_2$·DCM (17 g, 20.8 mmol, 0.05 eq). The resulting mixture was degassed and charged with nitrogen three times. The reaction mixture was then warmed to 100° C. and stirred for 2 h. The reaction mixture was then cooled to room temperature and filtered. The filtrate was diluted with H$_2$O (500 mL) and extracted with EtOAc (3×300 mL). The combined organic extracts were washed with brine (300 mL), dried over anhydrous Na$_2$SO$_4$, filtered, and concentrated under reduced pressure. The crude residue obtained was then purified by column chromatography to give 3-cyclopropyl-2-fluoro-6-vinylpyridine. LC-MS (ESI): m/z: [M+H]$^+$ calculated for C$_{10}$H$_{10}$FN: 164.1; found 164.1.

Step e: To a mixture of 3-cyclopropyl-2-fluoro-6-vinylpyridine (47 g, 288 mmol, 1 eq) in THF (800 mL) and H$_2$O (160 mL) at 20° C. under N$_2$ was added NaIO$_4$ (246 g, 1.15 mol, 4 eq) and K$_2$OsO$_4$·2H$_2$O (2.12 g, 5.76 mmol, 0.02 eq). The resulting mixture was degassed and charged with nitrogen three times before stirring for 2 h. The reaction mixture was then filtered, and the filtrate was diluted with H$_2$O (500 mL), and extracted with EtOAc (3×300 mL). The combined organic extracts were washed with brine (300 mL), dried over anhydrous Na$_2$SO$_4$, filtered, and concentrated under reduced pressure. The resulting crude residue was purified by column chromatography to give 5-cyclopropyl-6-fluoropicolinaldehyde. LC-MS (ESI): m/z: [M+H]$^+$ calculated for C$_9$H$_8$FNO: 166.1; found 166.2.

Step f: To a mixture of 5-cyclopropyl-6-fluoropicolinaldehyde (38 g, 230 mmol, 1 eq) and (S)-2-methylpropane-2-sulfinamide (30.6 g, 253 mmol, 1.1 eq) in DCM (200 mL) at 20° C. under N$_2$ was added Cs$_2$CO$_3$ (82.4 g, 253 mmol, 1.1 eq). The system was then degassed and charged with nitrogen three times. The resulting mixture was then warmed to 40° C. and stirred for 12 h. The reaction solution was then diluted with H$_2$O (300 mL) and extracted with DCM (3×200 mL). The combined organic extracts were washed with brine (200 mL), dried over anhydrous Na$_2$SO$_4$, filtered, and concentrated under reduced pressure. The resulting crude residue was then purified by column chromatography to give (S,E)-N-((5-cyclopropyl-6-fluoropyridin-2-yl)methylene)-2-methylpropane-2-sulfinamide. LC-MS (ESI): m/z: [M+H]$^+$ calculated for C$_{13}$H$_{17}$FN$_2$OS: 269.1; found 269.2.

Step g: To a solution of (S,E)-N-((5-cyclopropyl-6-fluoropyridin-2-yl)methylene)-2-methylpropane-2-sulfinamide (58 g, 216 mmol, 1 eq) in dry DCM (600 mL) at −70° C. under nitrogen was added PhMgBr (3 M in Et$_2$O, 93.6 mL, 281 mmol, 1.3 eq) in a dropwise manner. The resulting reaction mixture was stirred at −70° C. for 1 h. The reaction mixture was then quenched with saturated aqueous NH$_4$Cl solution (500 mL), warmed to room temperature, and extracted with EtOAc (3×200 mL). The combined organic extracts were washed with brine (200 mL), dried over anhydrous Na$_2$SO$_4$, filtered, and concentrated under reduced pressure. The crude residue obtained was purified by column chromatography to give (S)—N—((S)-(5-cyclopropyl-6-fluoropyridin-2-yl)(phenyl)methyl)-2-methylpropane-2-sulfinamide. LC-MS (ESI): m/z: [M+H]$^+$ calculated for C$_{19}$H$_{23}$FN$_2$OS: 347.2; found 347.3.

Step h: To a solution of (S)—N—((S)-(5-cyclopropyl-6-fluoropyridin-2-yl)(phenyl)methyl)-2-methylpropane-2-sulfinamide (74 g, 213 mmol, 1 eq) in EtOAc (100 mL) at 0° C. under N$_2$ was added HCl/EtOAc (4 M, 740 mL, 2940 mmol, 13.8 eq). The resulting mixture was then warmed 20° C. and stirred for 1 h. The reaction mixture was then concentrated under reduced pressure, and the crude residue obtained was triturated with MTBE (500 mL). The resulting solid was collected by filtration and dried under reduced pressure to give (S)-(5-cyclopropyl-6-fluoropyridin-2-yl)(phenyl)methanamine chloride. LC-MS (ESI): m/z: [M+H]$^+$ calculated for C$_{15}$H$_{15}$FN$_2$: 243.1; found 243.2.

Step i: To a mixture of (S)-(5-cyclopropyl-6-fluoropyridin-2-yl)(phenyl)methanaminium chloride (56 g, 200 mmol, 1 eq) and (2S,4R)-1-(tert-butoxycarbonyl)-4-fluoropyrrolidine-2-carboxylic acid (60.9 g, 261 mmol, 1.3 eq) in DMF (500 mL) at 0° C. under N$_2$ was added N-methylmorpholine (NMM, 101 g, 1.00 mol, 110 mL, 5 eq) and T3P (50% in ethyl acetate, 166 g, 261 mmol, 155 mL, 1.3 eq). The resulting mixture was degassed and charged with nitrogen three times, warmed to 20° C. and stirred 1 h. The reaction mixture was then diluted with H$_2$O (200 mL) and extracted with EtOAc (3×300 mL). The combined organic extracts were washed with brine (500 mL), dried over anhydrous Na$_2$SO$_4$, filtered, and concentrated under reduced pressure. The crude residue obtained was purified by column chromatography to give tert-butyl (2S,4R)-2-(((S)-(5-cyclopropyl-6-fluoropyridin-2-yl)(phenyl)methyl)carbamoyl)-4-fluoropyrrolidine-1-carboxylate. LC-MS (ESI): m/z: [M+H]$^+$ calculated for C$_{25}$H$_{29}$F$_2$N$_3$O$_3$: 458.2; found 458.2.

Step j: To a solution of tert-butyl (2S,4R)-2-(((S)-(5-cyclopropyl-6-fluoropyridin-2-yl)(phenyl)methyl)carbamoyl)-4-fluoropyrrolidine-1-carboxylate (90 g, 196 mmol, 1 eq) in EtOAc (100 mL) at 0° C. under N$_2$ was added HCl/EtOAc (4 M, 900 mL, 18.3 eq). The resulting mixture was warmed to 20° C. and stirred for 1 h. The reaction mixture was then concentrated under reduced pressure, and the resulting crude residue was added to H$_2$O (100 mL). The resulting mixture was cooled to 0° C., adjusted to pH=7-8 with saturated aqueous NaHCO$_3$ and extracted with EtOAc (3×200 mL). The combined organic extracts were washed with brine (100 mL), dried with anhydrous Na$_2$SO$_4$, filtered, and concentrated under reduced pressure. The resulting crude material was then triturated with i-PrOH (500 mL), and the resulting solid was isolated via filtration. The solid obtained was dried under reduced pressure to give (2S, 4R)—N—((S)-(5-cyclopropyl-6-fluoropyridin-2-yl)(phenyl)methyl)-4-fluoropyrrolidine-2-carboxamide. LC-MS (ESI): m/z: [M+H]$^+$ calculated for C$_{20}$H$_{21}$F$_2$N$_3$O: 358.2; found 358.3.

Step k: To a mixture of 2-(5-(difluoromethyl)-1H-tetrazol-1-yl)acetic acid (Intermediate A-2, 4.53 g, 25.5 mmol, 1.30 eq) and (2S,4R)—N—((S)-(5-cyclopropyl-6-fluoropyridin-2-yl)(phenyl)methyl)-4-fluoropyrrolidine-2-carboxamide (7 g, 19.6 mmol, 1.00 eq) in DMF (70 mL) at −20° C. was added N-methylmorpholine (11.2 g, 117 mmol, 6 eq) and T3P (50% in ethyl acetate, 25.0 g, 39.1 mmol, 2.00 eq). The reaction mixture was then warmed to −10° C. and stirred for 2 h. The reaction mixture was then quenched with water (100 mL) and extracted with dichloromethane (2×100 mL). The combined organic extracts were washed with brine (200 mL), dried over anhydrous $Na_2SO_4$, filtered, and concentrated under reduced pressure. The crude residue was purified by prep-HPLC to give (2S,4R)—N—((S)-(5-cyclopropyl-6-fluoropyridin-2-yl)(phenyl)methyl)-1-(2-(5-(difluoromethyl)-1H-tetrazol-1-yl)acetyl)-4-fluoropyrrolidine-2-carboxamide. $^1$H NMR (4.2:1 rotamer ratio, asterisk denotes distinct minor rotamer peaks, obscured peaks not reported, 400 MHz, DMSO-d6) δ 9.29*(d, J=7.7 Hz, 1H), 8.92 (d, J=8.0 Hz, 1H), 7.65-7.17 (m, 8H), 6.11*(d, J=7.7 Hz, 1H), 6.03-5.66 (m, 3H), 5.60-5.23 (m, 1H), 5.10-4.92* (m, 2H), 4.65 (t, J=8.4 Hz, 1H), 4.17-3.76 (m, 2H), 3.61-3.40*(m, 1H), 2.92-2.75*(m, 1H), 2.15-1.89 (m, 2H), 1.03-0.91 (m, 2H), 0.82-0.69 (m, 2H). LC-MS (ESI): m/z: [M+H]$^+$ calculated for $C_{24}H_{23}F_4N_7O_2$: 518.2; found 518.1.

The following compounds in Table T-3 were synthesized using procedures similar to Compound 293 using the appropriate starting materials.

TABLE T-3

| Compound No. | Structure | IUPAC | Exact mass (g/mol) | LCMS, Found [M + H]$^+$ |
|---|---|---|---|---|
| 294 | 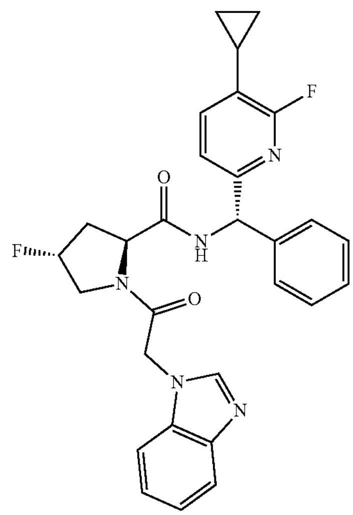 [SMILES: O=C(N[C@@H](c1ccccc1)c1ccc(C2CC2)c(F)n1)[C@@H]1C[C@@H](F)CN1C(=O)Cn1cnc2ccccc21] | (2S,4R)-1-[2-(1H-1,3-benzodiazol-1-yl)acetyl]-N-[(S)-(5-cyclopropyl-6-fluoropyridin-2-yl)(phenyl)methyl]-4-fluoropyrrolidine-2-carboxamide | 515.2 | 516.2 |
| 295 | 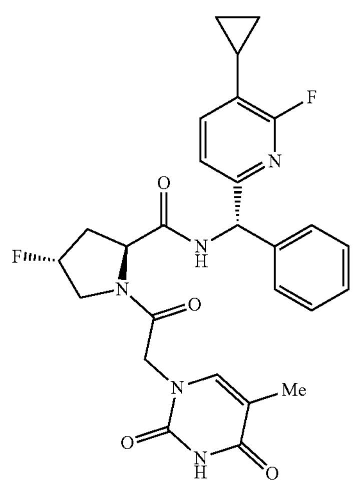 [SMILES: Cc1cn(CC(=O)N2C[C@H](F)C[C@H]2C(=O)N[C@@H](c2ccccc2)c2ccc(C3CC3)c(F)n2)c(=O)[nH]c1=O] | (2S,4R)-N-[(S)-(5-cyclopropyl-6-fluoropyridin-2-yl)(phenyl)methyl]-4-fluoro-1-[2-(5-methyl-2,4-dioxo-1,2,3,4-tetrahydropyrimidin-1-yl)acetyl]pyrrolidine-2-carboxamide | 523.2 | 524.3 |

TABLE T-3-continued

| Compound No. | Structure | IUPAC | Exact mass (g/mol) | LCMS, Found [M + H]+ |
|---|---|---|---|---|
| 296 | 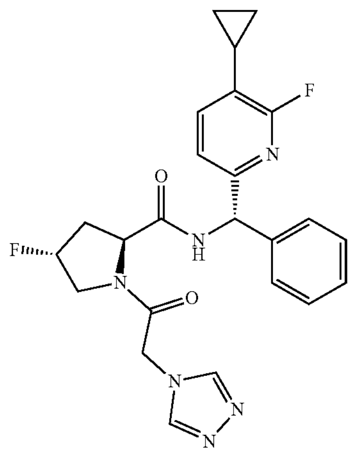 [SMILES: O=C(N[C@@H](c1ccccc1)c1ccc(C2CC2)c(F)n1)[C@@H]1C[C@@H](F)CN1C(=O)Cn1cnnc1] | (2S,4R)-N-[(S)-(5-cyclopropyl-6-fluoropyridin-2-yl)(phenyl)methyl]-4-fluoro-1-[2-(4H-1,2,4-triazol-4-yl)acetyl]pyrrolidine-2-carboxamide | 466.2 | 467.2 |
| 297 | 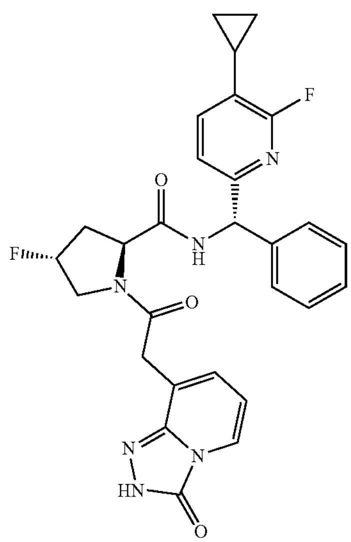 [SMILES: O=C(N[C@@H](c1ccccc1)c1ccc(C2CC2)c(F)n1)[C@@H]1C[C@@H](F)CN1C(=O)Cc1cccn2c(=O)[nH]nc12] | (2S,4R)-N-[(S)-(5-cyclopropyl-6-fluoropyridin-2-yl)(phenyl)methyl]-4-fluoro-1-(2-{3-oxo-2H,3H-[1,2,4]triazolo[4,3-a]pyridin-8-yl}acetyl)pyrrolidine-2-carboxamide | 532.2 | 533.3 |
| 298 | 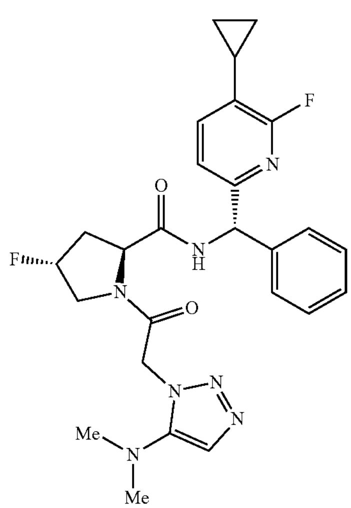 [SMILES: CN(C)c1cnnn1CC(=O)N1C[C@H](F)C[C@H]1C(=O)N[C@@H](c1ccccc1)c1ccc(C2CC2)c(F)n1] | (2S,4R)-N-[(S)-(5-cyclopropyl-6-fluoropyridin-2-yl)(phenyl)methyl]-1-{2-[5-(dimethylamino)-1H-1,2,3-triazol-1-yl]acetyl}-4-fluoropyrrolidine-2-carboxamide | 509.2 | 510.2 |

TABLE T-3-continued

| Compound No. | Structure | IUPAC | Exact mass (g/mol) | LCMS, Found [M + H]+ |
|---|---|---|---|---|
| 299 | 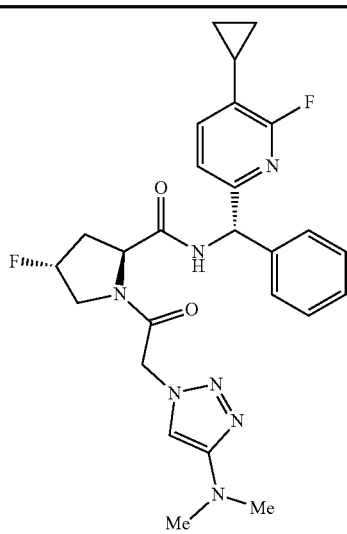 | (2S,4R)-N-[(S)-(5-cyclopropyl-6-fluoropyridin-2-yl)(phenyl)methyl]-1-{2-[4-(dimethylamino)-1H-1,2,3-triazol-1-yl]acetyl}-4-fluoropyrrolidine-2-carboxamide | 509.2 | 510.2 |
| 300 | 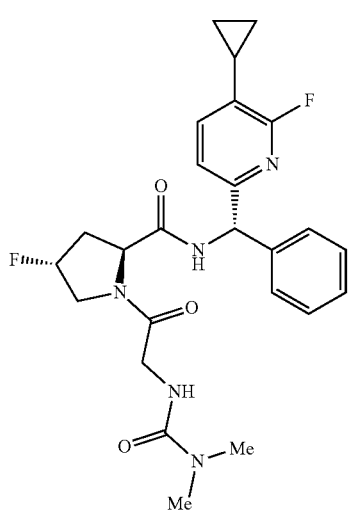 [SMILES: CN(C)C(=O)NCC(=O)N1C[C@H](F)C[C@H]1C(=O)N[C@@H](c1ccccc1)c1ccc(C2CC2)c(F)n1] | (2S,4R)-N-[(S)-(5-cyclopropyl-6-fluoropyridin-2-yl)(phenyl)methyl]-1-{2-[(dimethylcarbamoyl)amino]acetyl}-4-fluoropyrrolidine-2-carboxamide | 485.2 | 486.2 |
| 301 | 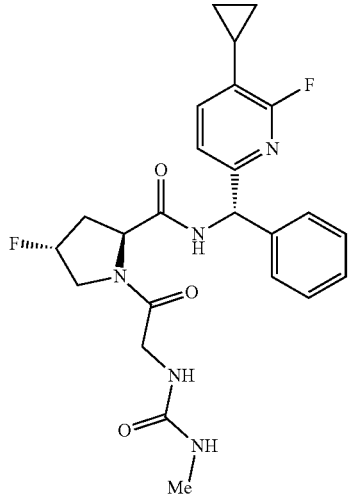 [SMILES: CNC(=O)NCC(=O)N1C[C@H](F)C[C@H]1C(=O)N[C@@H](c1ccccc1)c1ccc(C2CC2)c(F)n1] | (2S,4R)-N-[(S)-(5-cyclopropyl-6-fluoropyridin-2-yl)(phenyl)methyl]-4-fluoro-1-{2-[(methylcarbamoyl)amino]acetyl}pyrrolidine-2-carboxamide | 471.2 | 472.2 |

TABLE T-3-continued

| Compound No. | Structure | IUPAC | Exact mass (g/mol) | LCMS, Found [M + H]⁺ |
|---|---|---|---|---|
| 302 | 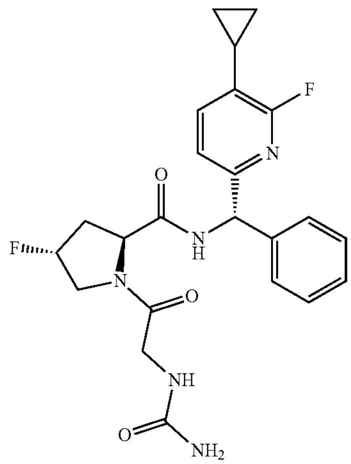 [SMILES: NC(=O)NCC(=O)N1C[C@H](F)C[C@H]1C(=O)N[C@@H](c1ccccc1)c1ccc(C2CC2)c(F)n1] | (2S,4R)-1-[2-(carbamoylamino)acetyl]-N-[(S)-(5-cyclopropyl-6-fluoropyridin-2-yl)(phenyl)methyl]-4-fluoropyrrolidine-2-carboxamide | 457.2 | 458.3 |
| 303 | 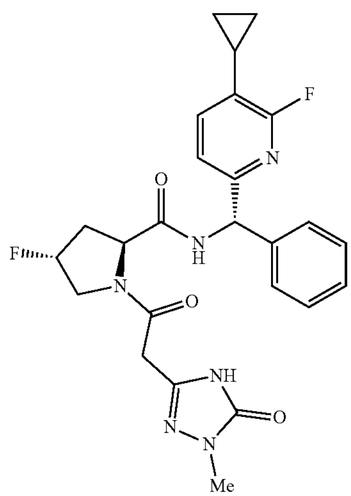 | (2S,4R)-N-[(S)-(5-cyclopropyl-6-fluoropyridin-2-yl)(phenyl)methyl]-4-fluoro-1-[2-(1-methyl-5-oxo-4,5-dihydro-1H-1,2,4-triazol-3-yl)acetyl]pyrrolidine-2-carboxamide | 496.2 | 497.3 |
| 304 | 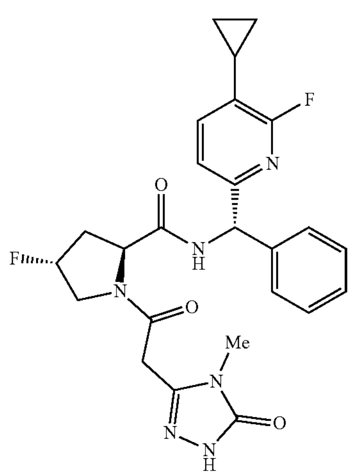 [SMILES: Cn1c(CC(=O)N2C[C@H](F)C[C@H]2C(=O)N[C@@H](c2ccccc2)c2ccc(C3CC3)c(F)n2)n[nH]c1=O] | (2S,4R)-N-[(S)-(5-cyclopropyl-6-fluoropyridin-2-yl)(phenyl)methyl]-4-fluoro-1-[2-(4-methyl-5-oxo-4,5-dihydro-1H-1,2,4-triazol-3-yl)acetyl]pyrrolidine-2-carboxamide | 496.2 | 497.1 |

TABLE T-3-continued

| Compound No. | Structure | IUPAC | Exact mass (g/mol) | LCMS, Found [M + H]+ |
|---|---|---|---|---|
| 305 | 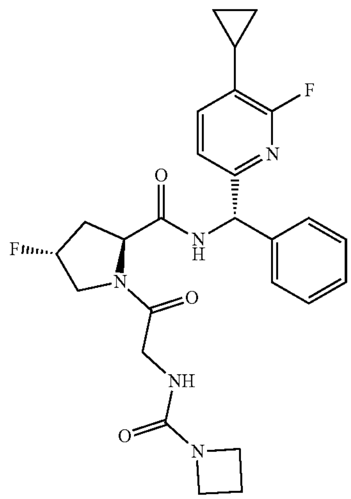 [SMILES: O=C(N[C@@H](c1ccccc1)c1ccc(C2CC2)c(F)n1)[C@@H]1C[C@@H](F)CN1C(=O)CNC(=O)N1CCC1] | (2S,4R)-1-{2-[(azetidine-1-carbonyl)amino]acetyl}-N-[(S)-(5-cyclopropyl-6-fluoropyridin-2-yl)(phenyl)methyl]-4-fluoropyrrolidine-2-carboxamide | 497.2 | 498.2 |
| 306 | 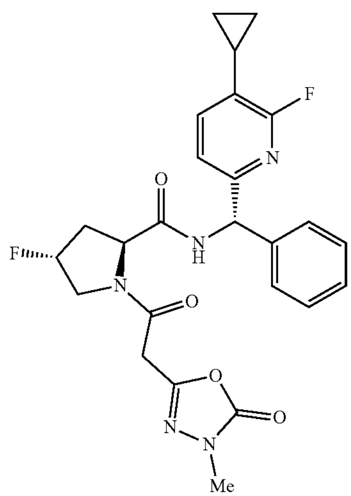 [SMILES: Cn1nc(CC(=O)N2C[C@H](F)C[C@H]2C(=O)N[C@@H](c2ccccc2)c2ccc(C3CC3)c(F)n2)oc1=O] | (2S,4R)-N-[(S)-(5-cyclopropyl-6-fluoropyridin-2-yl)(phenyl)methyl]-4-fluoro-1-[2-(4-methyl-5-oxo-4,5-dihydro-1,3,4-oxadiazol-2-yl)acetyl]pyrrolidine-2-carboxamide | 497.2 | 498.2 |
| 307 | 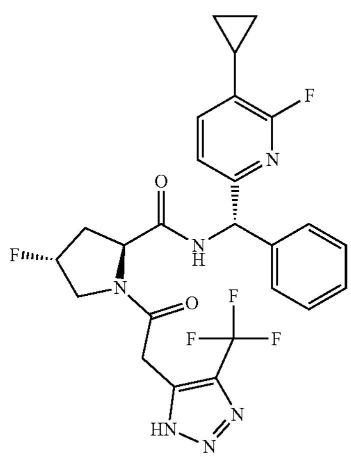 [SMILES: O=C(N[C@@H](c1ccccc1)c1ccc(C2CC2)c(F)n1)[C@@H]1C[C@@H](F)CN1C(=O)Cc1[nH]nnc1C(F)(F)F] | (2S,4R)-N-[(S)-(5-cyclopropyl-6-fluoropyridin-2-yl)(phenyl)methyl]-4-fluoro-1-{2-[4-(trifluoromethyl)-1H-1,2,3-triazol-5-yl]acetyl}pyrrolidine-2-carboxamide | 534.2 | 535.1 |

TABLE T-3-continued

| Compound No. | Structure | IUPAC | Exact mass (g/mol) | LCMS, Found [M + H]+ |
|---|---|---|---|---|
| 308 | 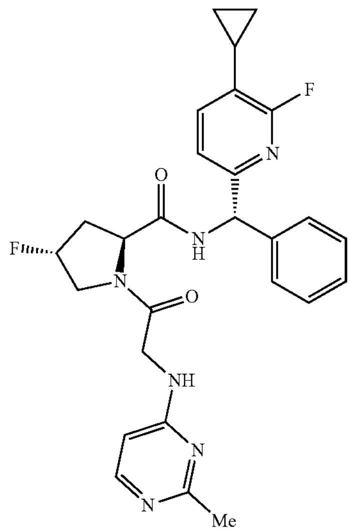 | (2S,4R)-N-[(S)-(5-cyclopropyl-6-fluoropyridin-2-yl)(phenyl)methyl]-4-fluoro-1-{2-[(2-methylpyrimidin-4-yl)amino]acetyl}pyrrolidine-2-carboxamide | 506.2 | 507.3 |
| 309 | 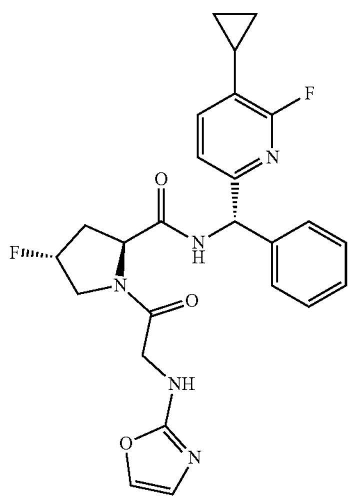 [SMILES: O=C(N[C@@H](c1ccccc1)c1ccc(C2CC2)c(F)n1)[C@@H]1C[C@@H](F)CN1C(=O)CNc1ncco1] | (2S,4R)-N-[(S)-(5-cyclopropyl-6-fluoropyridin-2-yl)(phenyl)methyl]-4-fluoro-1-{2-[(1,3-oxazol-2-yl)amino]acetyl}pyrrolidine-2-carboxamide | 481.2 | 482.4 |
| 310 | 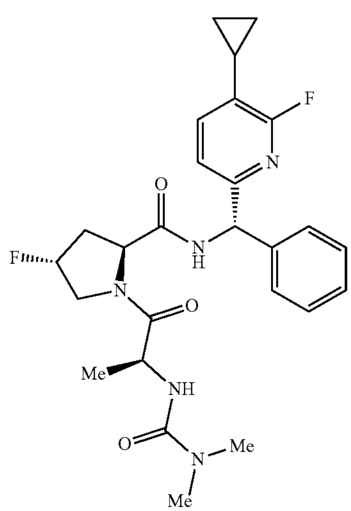 [SMILES: C[C@H](NC(=O)N(C)C)C(=O)N1C[C@H](F)C[C@H]1C(=O)N[C@@H](c1ccccc1)c1ccc(C2CC2)c(F)n1] | (2S,4R)-N-[(S)-(5-cyclopropyl-6-fluoropyridin-2-yl)(phenyl)methyl]-1-[(2S)-2-[(dimethylcarbamoyl)amino]propanoyl]-4-fluoropyrrolidine-2-carboxamide | 499.2 | 500.3 |

TABLE T-3-continued

| Compound No. | Structure | IUPAC | Exact mass (g/mol) | LCMS, Found [M + H]+ |
|---|---|---|---|---|
| 311 | 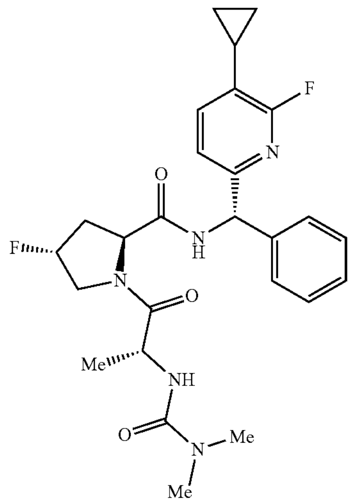 [SMILES: C[C@@H](NC(=O)N(C)C)C(=O)N1C[C@H](F)C[C@H]1C(=O)N[C@@H](c1ccccc1)c1ccc(C2CC2)c(F)n1] | (2S,4R)-N-[(S)-(5-cyclopropyl-6-fluoropyridin-2-yl)(phenyl)methyl]-1-[(2R)-2-[(dimethylcarbamoyl)amino]propanoyl]-4-fluoropyrrolidine-2-carboxamide | 499.2 | 500.3 |
| 312 | 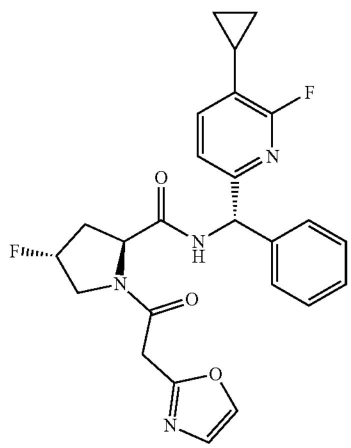 [SMILES: O=C(N[C@@H](c1ccccc1)c1ccc(C2CC2)c(F)n1)[C@@H]1C[C@@H](F)CN1C(=O)Cc1ncco1] | (2S,4R)-N-[(S)-(5-cyclopropyl-6-fluoropyridin-2-yl)(phenyl)methyl]-4-fluoro-1-[2-(1,3-oxazol-2-yl)acetyl]pyrrolidine-2-carboxamide | 466.2 | 467.2 |
| 313 | 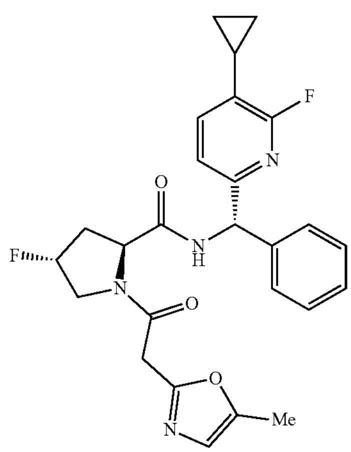 [SMILES: Cc1cnc(CC(=O)N2C[C@H](F)C[C@H]2C(=O)N[C@@H](c2ccccc2)c2ccc(C3CC3)c(F)n2)o1] | (2S,4R)-N-[(S)-(5-cyclopropyl-6-fluoropyridin-2-yl)(phenyl)methyl]-4-fluoro-1-[2-(5-methyl-1,3-oxazol-2-yl)acetyl]pyrrolidine-2-carboxamide | 480.2 | 481.3 |

TABLE T-3-continued

| Compound No. | Structure | IUPAC | Exact mass (g/mol) | LCMS, Found [M + H]+ |
|---|---|---|---|---|
| 314 | 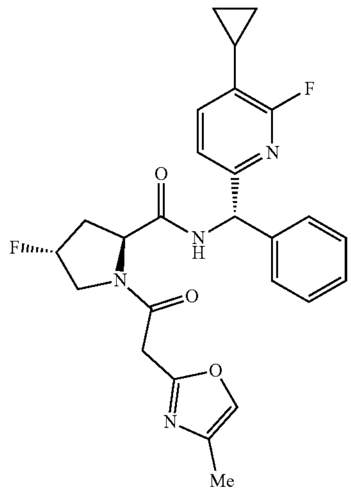 [SMILES: Cc1coc(CC(=O)N2C[C@H](F)C[C@H]2C(=O)N[C@@H](c2ccccc2)c2ccc(C3CC3)c(F)n2)n1] | (2S,4R)-N-[(S)-(5-cyclopropyl-6-fluoropyridin-2-yl)(phenyl)methyl]-4-fluoro-1-[2-(4-methyl-1,3-oxazol-2-yl)acetyl]pyrrolidine-2-carboxamide | 480.2 | 481.2 |
| 315 | 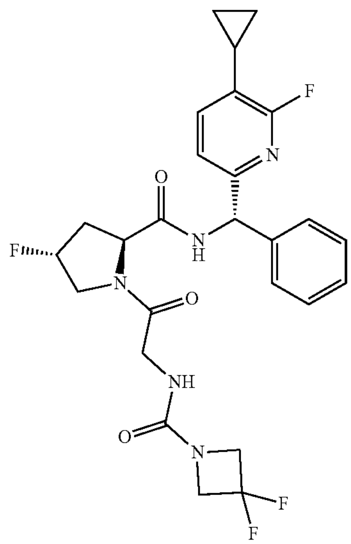 [SMILES: O=C(N[C@@H](c1ccccc1)c1ccc(C2CC2)c(F)n1)[C@@H]1C[C@@H](F)CN1C(=O)CNC(=O)N1CC(F)(F)C1] | (2S,4R)-N-[(S)-(5-cyclopropyl-6-fluoropyridin-2-yl)(phenyl)methyl]-1-{2-[(3,3-difluoroazetidine-1-carbonyl)amino]acetyl}-4-fluoropyrrolidine-2-carboxamide | 533.2 | 534.3 |
| 316 | 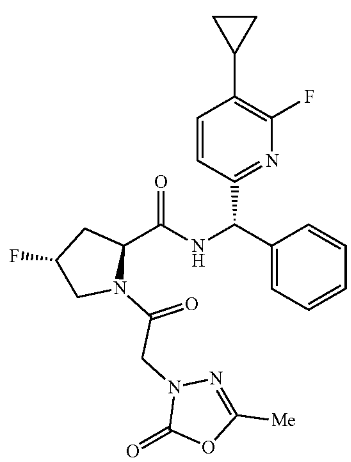 [SMILES: Cc1nn(CC(=O)N2C[C@H](F)C[C@H]2C(=O)N[C@@H](c2ccccc2)c2ccc(C3CC3)c(F)n2)c(=O)o1] | (2S,4R)-N-[(S)-(5-cyclopropyl-6-fluoropyridin-2-yl)(phenyl)methyl]-4-fluoro-1-[2-(5-methyl-2-oxo-2,3-dihydro-1,3,4-oxadiazol-3-yl)acetyl]pyrrolidine-2-carboxamide | 497.2 | 498.2 |

TABLE T-3-continued

| Compound No. | Structure | IUPAC | Exact mass (g/mol) | LCMS, Found [M + H]+ |
|---|---|---|---|---|
| 317 | 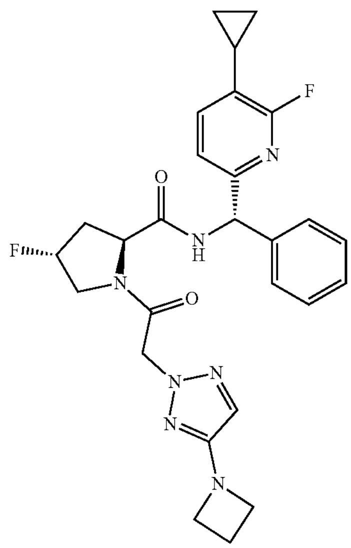 [SMILES: O=C(N[C@@H](c1ccccc1)c1ccc(C2CC2)c(F)n1)[C@@H]1C[C@@H](F)CN1C(=O)Cn1ncc(N2CCC2)n1] | (2S,4R)-1-{2-[4-(azetidin-1-yl)-2H-1,2,3-triazol-2-yl]acetyl}-N-[(S)-(5-cyclopropyl-6-fluoropyridin-2-yl)(phenyl)methyl]-4-fluoropyrrolidine-2-carboxamide | 521.2 | 522.3 |
| 318 | 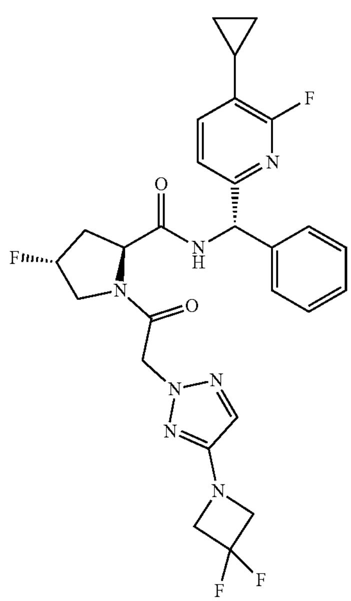 [SMILES: O=C(N[C@@H](c1ccccc1)c1ccc(C2CC2)c(F)n1)[C@@H]1C[C@@H](F)CN1C(=O)Cn1ncc(N2CC(F)(F)C2)n1] | (2S,4R)-N-[(S)-(5-cyclopropyl-6-fluoropyridin-2-yl)(phenyl)methyl]-1-{2-[4-(3,3-difluoroazetidin-1-yl)-2H-1,2,3-triazol-2-yl]acetyl}-4-fluoropyrrolidine-2-carboxamide | 557.2 | 558.2 |

TABLE T-3-continued

| Compound No. | Structure | IUPAC | Exact mass (g/mol) | LCMS, Found [M + H]+ |
|---|---|---|---|---|
| 319 | 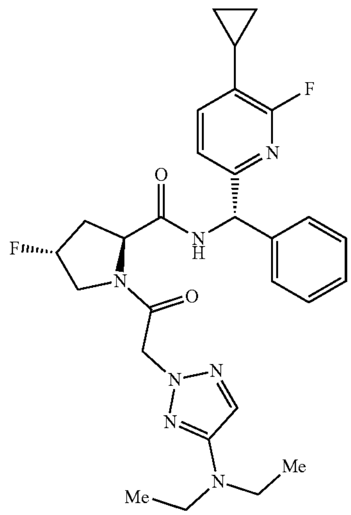 [SMILES: CCN(CC)c1cnn(CC(=O)N2C[C@H](F)C[C@H]2C(=O)N[C@@H](c2ccccc2)c2ccc(C3CC3)c(F)n2)n1] | (2S,4R)-N-[(S)-(5-cyclopropyl-6-fluoropyridin-2-yl)(phenyl)methyl]-1-{2-[4-(diethylamino)-2H-1,2,3-triazol-2-yl]acetyl}-4-fluoropyrrolidine-2-carboxamide | 537.3 | 538.4 |
| 320 | 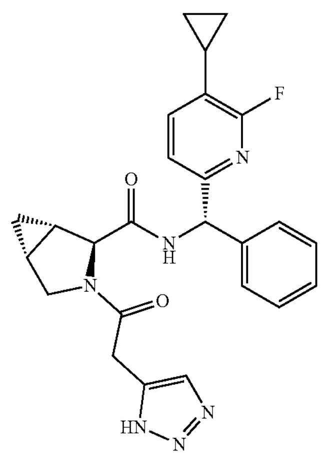 [SMILES: O=C(N[C@@H](c1ccccc1)c1ccc(C2CC2)c(F)n1)[C@@H]1[C@H]2C[C@H]2CN1C(=O)Cc1cnn[nH]1] | (1S,2S,5R)-N-[(S)-(5-cyclopropyl-6-fluoropyridin-2-yl)(phenyl)methyl]-3-[2-(1H-1,2,3-triazol-5-yl)acetyl]-3-azabicyclo[3.1.0]hexane-2-carboxamide | 460.2 | 461.3 |
| 321 | 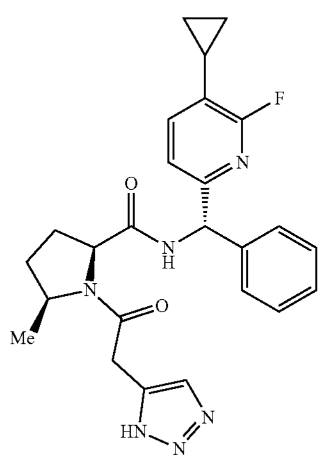 [SMILES: C[C@H]1CC[C@@H](C(=O)N[C@@H](c2ccccc2)c2ccc(C3CC3)c(F)n2)N1C(=O)Cc1cnn[nH]1] | (2S,5S)-N-[(S)-(5-cyclopropyl-6-fluoropyridin-2-yl)(phenyl)methyl]-5-methyl-1-[2-(1H-1,2,3-triazol-5-yl)acetyl]pyrrolidine-2-carboxamide | 462.2 | 463.1 |

TABLE T-3-continued
| Compound No. | Structure | IUPAC | Exact mass (g/mol) | LCMS, Found [M + H]+ |
|---|---|---|---|---|
| 716 | 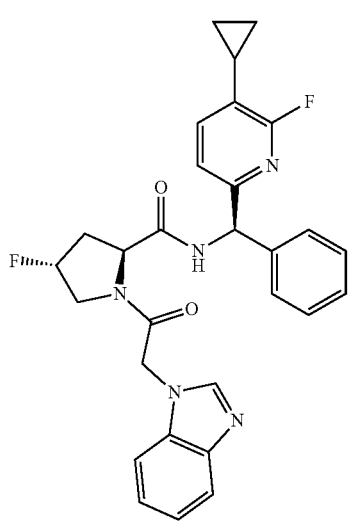 [SMILES: O=C(N[C@H](c1ccccc1)c1ccc(C2CC2)c(F)n1)[C@@H]1C[C@@H](F)CN1C(=O)Cn1cnc2ccccc21] | (2S,4R)-1-[2-(1H-1,3-benzodiazol-1-yl)acetyl]-N-[(R)-(5-cyclopropyl-6-fluoropyridin-2-yl)(phenyl)methyl]-4-fluoropyrrolidine-2-carboxamide | 515.2 | 516.3 |
| 717 | 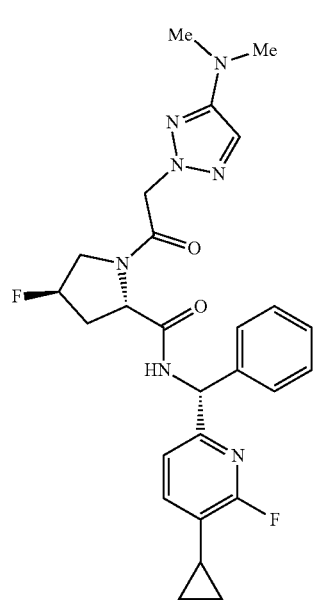 [SMILES: CN(C)c1cnn(CC(=O)N2C[C@H](F)C[C@H]2C(=O)N[C@H](c2ccccc2)c2ccc(C3CC3)c(F)n2)n1] | (2S,4R)-N-[(R)-(5-cyclopropyl-6-fluoropyridin-2-yl)(phenyl)methyl]-1-{2-[4-(dimethylamino)-2H-1,2,3-triazol-2-yl]acetyl}-4-fluoropyrrolidine-2-carboxamide | 509.2 | 510.2 |

TABLE T-3-continued

| Compound No. | Structure | IUPAC | Exact mass (g/mol) | LCMS, Found [M + H]+ |
|---|---|---|---|---|
| 718 | 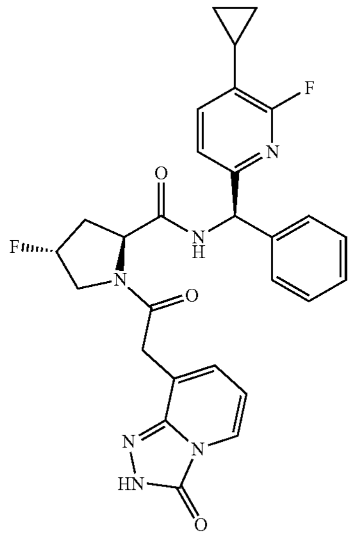 [SMILES: O=C(N[C@H](c1ccccc1)c1ccc(C2CC2)c(F)n1)[C@@H]1C[C@@H](F)CN1C(=O)Cc1cccn2c(=O)[nH]nc12] | (2S,4R)-N-[(R)-(5-cyclopropyl-6-fluoropyridin-2-yl)(phenyl)methyl]-4-fluoro-1-(2-{3-oxo-2H,3H-[1,2,4]triazolo[4,3-a]pyridin-8-yl}acetyl)pyrrolidine-2-carboxamide | 532.2 | 533.2 |
| 719 | 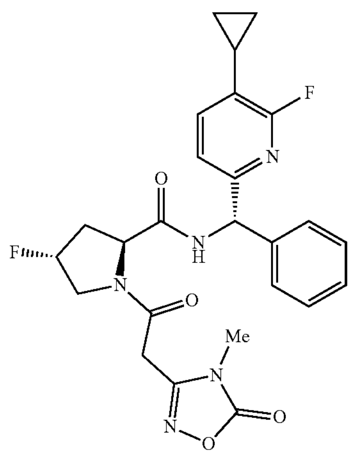 | (2S,4R)-N-[(S)-(5-cyclopropyl-6-fluoropyridin-2-yl)(phenyl)methyl]-4-fluoro-1-[2-(4-methyl-5-oxo-4,5-dihydro-1,2,4-oxadiazol-3-yl)acetyl]pyrrolidine-2-carboxamide | 497.2 | 498.2 |
| 720 | 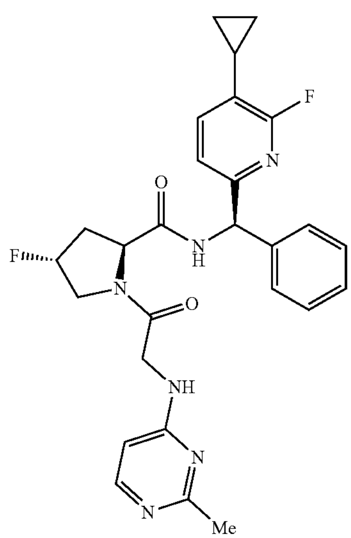 [SMILES: Cc1nccc(NCC(=O)N2C[C@H](F)C[C@H]2C(=O)N[C@H](c2ccccc2)c2ccc(C3CC3)c(F)n2)n1] | (2S,4R)-N-[(R)-(5-cyclopropyl-6-fluoropyridin-2-yl)(phenyl)methyl]-4-fluoro-1-{2-[(2-methylpyrimidin-4-yl)amino]acetyl}pyrrolidine-2-carboxamide | 506.2 | 507.3 |

TABLE T-3-continued

| Compound No. | Structure | IUPAC | Exact mass (g/mol) | LCMS, Found [M + H]+ |
|---|---|---|---|---|
| 721 | 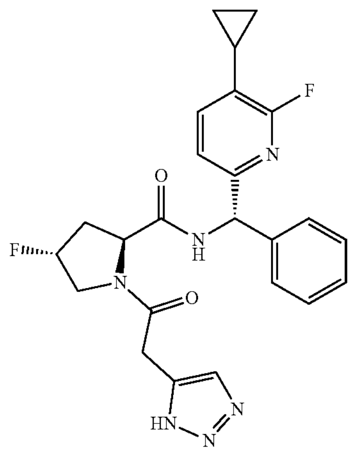 | (2S,4R)-N-[(S)-(5-cyclopropyl-6-fluoropyridin-2-yl)(phenyl)methyl]-4-fluoro-1-[2-(1H-1,2,3-triazol-5-yl)acetyl]pyrrolidine-2-carboxamide | 466.2 | 467.1 |
| 722 | 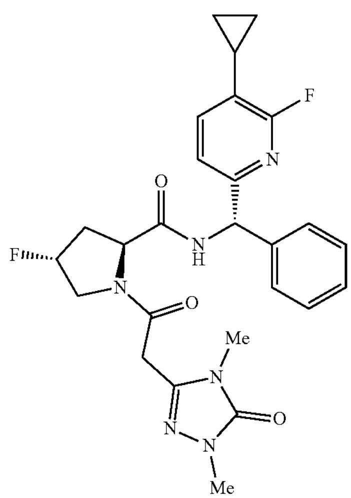 [SMILES: Cn1nc(CC(=O)N2C[C@H](F)C[C@H]2C(=O)N[C@@H](c2ccccc2)c2ccc(C3CC3)c(F)n2)n(C)c1=O] | (2S,4R)-N-[(S)-(5-cyclopropyl-6-fluoropyridin-2-yl)(phenyl)methyl]-1-[2-(1,4-dimethyl-5-oxo-4,5-dihydro-1H-1,2,4-triazol-3-yl)acetyl]-4-fluoropyrrolidine-2-carboxamide | 510.2 | 511.3 |
| 723 | 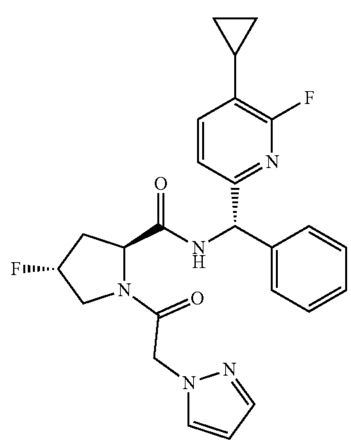 [SMILES: O=C(N[C@@H](c1ccccc1)c1ccc(C2CC2)c(F)n1)[C@@H]1C[C@@H](F)CN1C(=O)Cn1cccn1] | (2S,4R)-N-[(S)-(5-cyclopropyl-6-fluoropyridin-2-yl)(phenyl)methyl]-4-fluoro-1-[2-(1H-pyrazol-1-yl)acetyl]pyrrolidine-2-carboxamide | 465.2 | 466.1 |

TABLE T-3-continued

| Compound No. | Structure | IUPAC | Exact mass (g/mol) | LCMS, Found [M + H]+ |
|---|---|---|---|---|
| 724 | 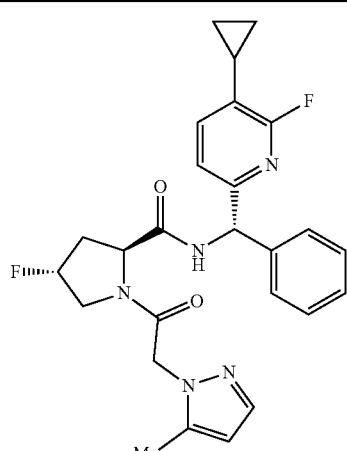 | (2S,4R)-N-[(S)-(5-cyclopropyl-6-fluoropyridin-2-yl)(phenyl)methyl]-4-fluoro-1-[2-(5-methyl-1H-pyrazol-1-yl)acetyl]pyrrolidine-2-carboxamide | 479.2 | 480.1 |
| 725 | 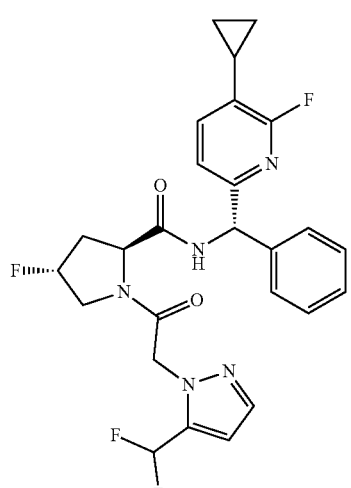 | (2S,4R)-N-[(S)-(5-cyclopropyl-6-fluoropyridin-2-yl)(phenyl)methyl]-1-{2-[5-(difluoromethyl)-1H-pyrazol-1-yl]acetyl}-4-fluoropyrrolidine-2-carboxamide | 515.2 | 516.3 |
| 726 | 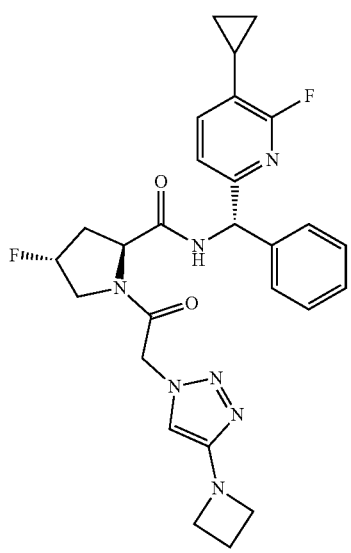 | (2S,4R)-1-{2-[4-(azetidin-1-yl)-1H-1,2,3-triazol-1-yl]acetyl}-N-[(S)-(5-cyclopropyl-6-fluoropyridin-2-yl)(phenyl)methyl]-4-fluoropyrrolidine-2-carboxamide | 521.2 | 522.3 |

TABLE T-3-continued

| Compound No. | Structure | IUPAC | Exact mass (g/mol) | LCMS, Found [M + H]+ |
|---|---|---|---|---|
| 727 | 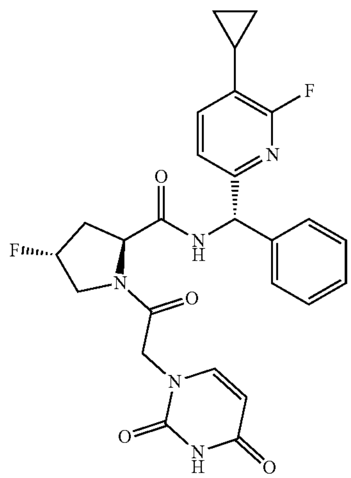 [SMILES: O=C(N[C@@H](c1ccccc1)c1ccc(C2CC2)c(F)n1)[C@@H]1C[C@@H](F)CN1C(=O)Cn1ccc(=O)[nH]c1=O] | (2S,4R)-N-[(S)-(5-cyclopropyl-6-fluoropyridin-2-yl)(phenyl)methyl]-1-[2-(2,4-dioxo-1,2,3,4-tetrahydropyrimidin-1-yl)acetyl]-4-fluoropyrrolidine-2-carboxamide | 509.2 | 510.1 |
| 728 | 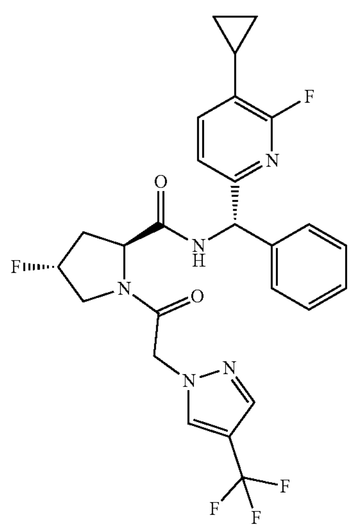 [SMILES: O=C(N[C@@H](c1ccccc1)c1ccc(C2CC2)c(F)n1)[C@@H]1C[C@@H](F)CN1C(=O)Cn1cc(C(F)(F)F)cn1] | (2S,4R)-N-[(S)-(5-cyclopropyl-6-fluoropyridin-2-yl)(phenyl)methyl]-4-fluoro-1-{2-[4-(trifluoromethyl)-1H-pyrazol-1-yl]acetyl}pyrrolidine-2-carboxamide | 533.2 | 534.1 |
| 729 | 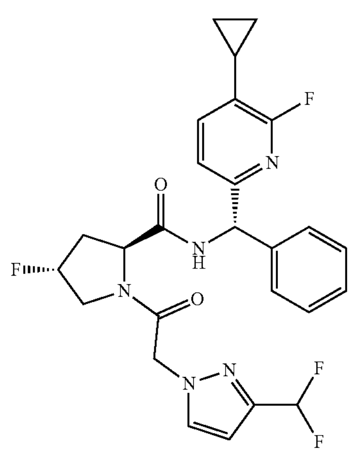 [SMILES: O=C(N[C@@H](c1ccccc1)c1ccc(C2CC2)c(F)n1)[C@@H]1C[C@@H](F)CN1C(=O)Cn1ccc(C(F)F)n1] | (2S,4R)-N-[(S)-(5-cyclopropyl-6-fluoropyridin-2-yl)(phenyl)methyl]-1-{2-[3-(difluoromethyl)-1H-pyrazol-1-yl]acetyl}-4-fluoropyrrolidine-2-carboxamide | 515.2 | 516.1 |

TABLE T-3-continued

| Compound No. | Structure | IUPAC | Exact mass (g/mol) | LCMS, Found [M + H]+ |
|---|---|---|---|---|
| 730 | 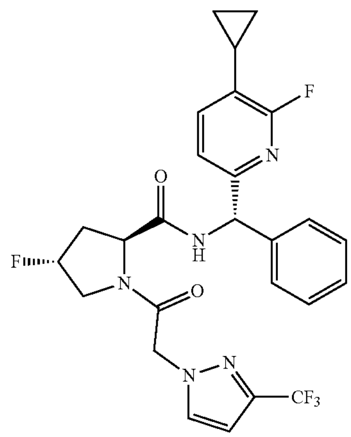 [SMILES: O=C(N[C@@H](c1ccccc1)c1ccc(C2CC2)c(F)n1)[C@@H]1C[C@@H](F)CN1C(=O)Cn1ccc(C(F)(F)F)n1] | (2S,4R)-N-[(S)-(5-cyclopropyl-6-fluoropyridin-2-yl)(phenyl)methyl]-4-fluoro-1-{2-[3-(trifluoromethyl)-1H-pyrazol-1-yl]acetyl}pyrrolidine-2-carboxamide | 533.2 | 534.3 |
| 731 | 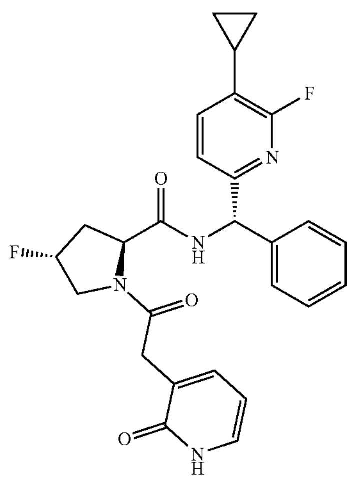 [SMILES: O=C(N[C@@H](c1ccccc1)c1ccc(C2CC2)c(F)n1)[C@@H]1C[C@@H](F)CN1C(=O)Cc1ccc[nH]c1=O] | (2S,4R)-N-[(S)-(5-cyclopropyl-6-fluoropyridin-2-yl)(phenyl)methyl]-4-fluoro-1-[2-(2-oxo-1,2-dihydropyridin-3-yl)acetyl]pyrrolidine-2-carboxamide | 492.2 | 515.3 |
| 732 | 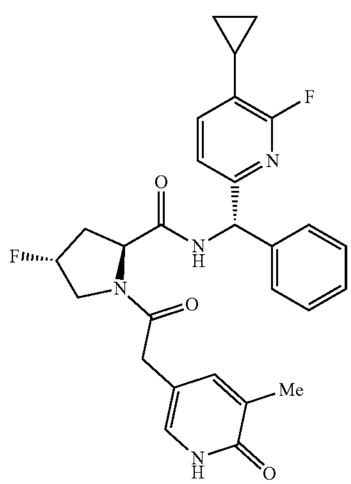 [SMILES: Cc1cc(CC(=O)N2C[C@H](F)C[C@H]2C(=O)N[C@@H](c2ccccc2)c2ccc(C3CC3)c(F)n2)c[nH]c1=O] | (2S,4R)-N-[(S)-(5-cyclopropyl-6-fluoropyridin-2-yl)(phenyl)methyl]-4-fluoro-1-[2-(5-methyl-6-oxo-1,6-dihydropyridin-3-yl)acetyl]pyrrolidine-2-carboxamide | 506.2 | 507.1 |

TABLE T-3-continued

| Compound No. | Structure | IUPAC | Exact mass (g/mol) | LCMS, Found [M + H]⁺ |
| --- | --- | --- | --- | --- |
| 733 | 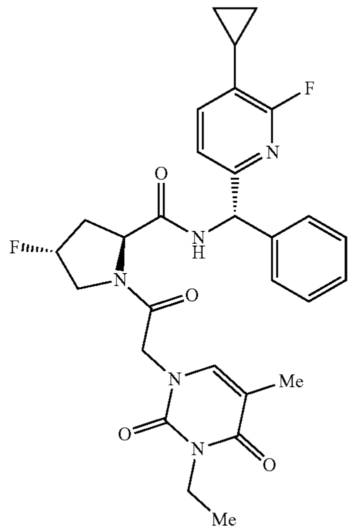 [SMILES: CCn1c(=O)c(C)cn(CC(=O)N2C[C@H](F)C[C@H]2C(=O)N[C@@H](c2ccccc2)c2ccc(C3CC3)c(F)n2)c1=O] | (2S,4R)-N-[(S)-(5-cyclopropyl-6-fluoropyridin-2-yl)(phenyl)methyl]-1-[2-(3-ethyl-5-methyl-2,4-dioxo-1,2,3,4-tetrahydropyrimidin-1-yl)acetyl]-4-fluoropyrrolidine-2-carboxamide | 551.2 | 552.1 |
| 734 | 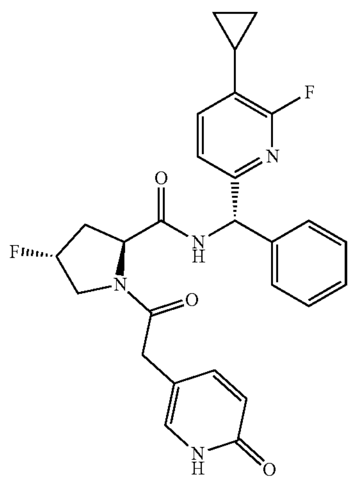 | (2S,4R)-N-[(S)-(5-cyclopropyl-6-fluoropyridin-2-yl)(phenyl)methyl]-4-fluoro-1-[2-(6-oxo-1,6-dihydropyridin-3-yl)acetyl]pyrrolidine-2-carboxamide | 492.2 | 493.2 |
| 735 | 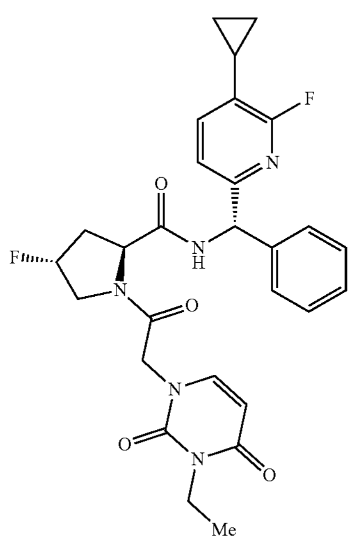 [SMILES: CCn1c(=O)ccn(CC(=O)N2C[C@H](F)C[C@H]2C(=O)N[C@@H](c2ccccc2)c2ccc(C3CC3)c(F)n2)c1=O] | (2S,4R)-N-[(S)-(5-cyclopropyl-6-fluoropyridin-2-yl)(phenyl)methyl]-1-[2-(3-ethyl-2,4-dioxo-1,2,3,4-tetrahydropyrimidin-1-yl)acetyl]-4-fluoropyrrolidine-2-carboxamide | 537.2 | 538.1 |

TABLE T-3-continued

| Compound No. | Structure | IUPAC | Exact mass (g/mol) | LCMS, Found [M + H]+ |
|---|---|---|---|---|
| 736 | 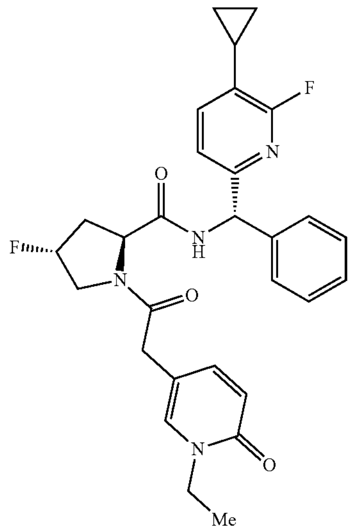 | (2S,4R)-N-[(S)-(5-cyclopropyl-6-fluoropyridin-2-yl)(phenyl)methyl]-1-[2-(1-ethyl-6-oxo-1,6-dihydropyridin-3-yl)acetyl]-4-fluoropyrrolidine-2-carboxamide | 520.2 | 521.4 |
| 737 | 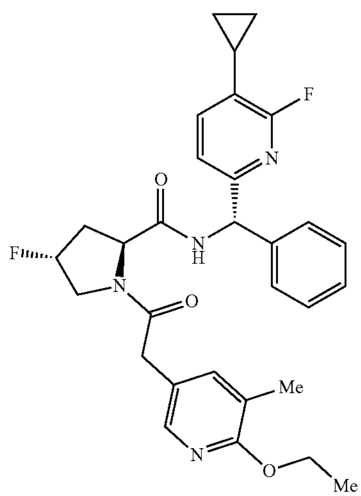 [SMILES: CCOc1ncc(CC(=O)N2C[C@H](F)C[C@H]2C(=O)N[C@@H](c2ccccc2)c2ccc(C3CC3)c(F)n2)cc1C] | (2S,4R)-N-[(S)-(5-cyclopropyl-6-fluoropyridin-2-yl)(phenyl)methyl]-1-[2-(6-ethoxy-5-methylpyridin-3-yl)acetyl]-4-fluoropyrrolidine-2-carboxamide | 534.2 | 535.2 |
| 738 | 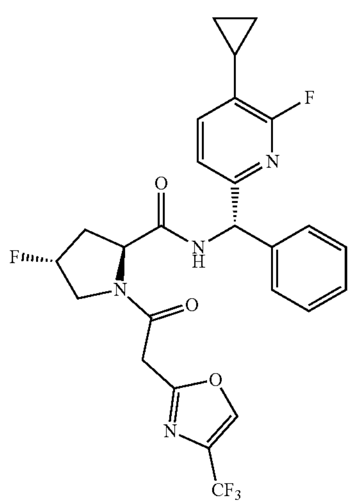 [SMILES: O=C(N[C@@H](c1ccccc1)c1ccc(C2CC2)c(F)n1)[C@@H]1C[C@@H](F)CN1C(=O)Cc1nc(C(F)(F)F)co1] | (2S,4R)-N-[(S)-(5-cyclopropyl-6-fluoropyridin-2-yl)(phenyl)methyl]-4-fluoro-1-{2-[4-(trifluoromethyl)-1,3-oxazol-2-yl]acetyl}pyrrolidine-2-carboxamide | 534.2 | 535.1 |

TABLE T-3-continued

| Compound No. | Structure | IUPAC | Exact mass (g/mol) | LCMS, Found [M + H]+ |
|---|---|---|---|---|
| 739 | 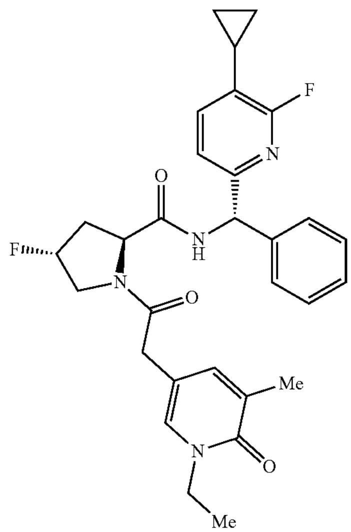 [SMILES: CCn1cc(CC(=O)N2C[C@H](F)C[C@H]2C(=O)N[C@@H](c2ccccc2)c2ccc(C3CC3)c(F)n2)cc(C)c1=O] | (2S,4R)-N-[(S)-(5-cyclopropyl-6-fluoropyridin-2-yl)(phenyl)methyl]-1-[2-(1-ethyl-5-methyl-6-oxo-1,6-dihydropyridin-3-yl)acetyl]-4-fluoropyrrolidine-2-carboxamide | 534.2 | 535.2 |
| 740 | 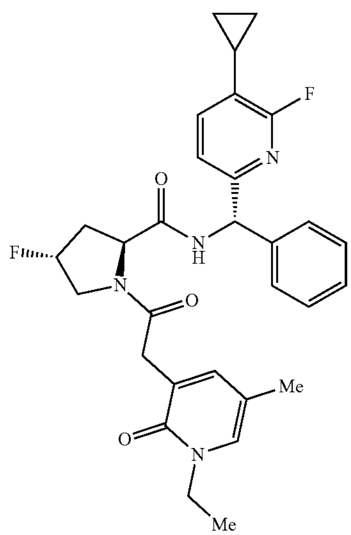 [SMILES: CCn1cc(C)cc(CC(=O)N2C[C@H](F)C[C@H]2C(=O)N[C@@H](c2ccccc2)c2ccc(C3CC3)c(F)n2)c1=O] | (2S,4R)-N-[(S)-(5-cyclopropyl-6-fluoropyridin-2-yl)(phenyl)methyl]-1-[2-(1-ethyl-5-methyl-2-oxo-1,2-dihydropyridin-3-yl)acetyl]-4-fluoropyrrolidine-2-carboxamide | 534.2 | 535.2 |
| 741 | 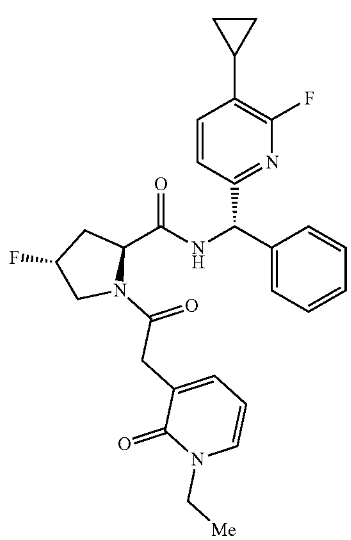 | (2S,4R)-N-[(S)-(5-cyclopropyl-6-fluoropyridin-2-yl)(phenyl)methyl]-1-[2-(1-ethyl-2-oxo-1,2-dihydropyridin-3-yl)acetyl]-4-fluoropyrrolidine-2-carboxamide | 520.2 | 521.2 |

TABLE T-3-continued

| Compound No. | Structure | IUPAC | Exact mass (g/mol) | LCMS, Found [M + H]+ |
|---|---|---|---|---|
| 742 | 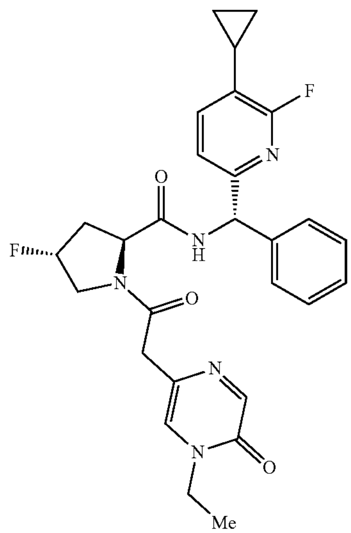 | (2S,4R)-N-[(S)-(5-cyclopropyl-6-fluoropyridin-2-yl)(phenyl)methyl]-1-[2-(4-ethyl-5-oxo-4,5-dihydropyrazin-2-yl)acetyl]-4-fluoropyrrolidine-2-carboxamide | 521.2 | 522.2 |
| 743 | 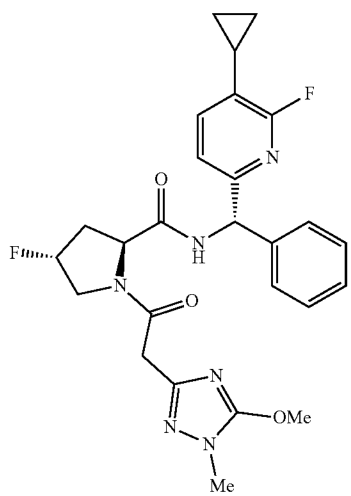 [SMILES: COc1nc(CC(=O)N2C[C@H](F)C[C@H]2C(=O)N[C@@H](c2ccccc2)c2ccc(C3CC3)c(F)n2)nn1C] | (2S,4R)-N-[(S)-(5-cyclopropyl-6-fluoropyridin-2-yl)(phenyl)methyl]-4-fluoro-1-[2-(5-methoxy-1-methyl-1H-1,2,4-triazol-3-yl)acetyl]pyrrolidine-2-carboxamide | 510.2 | 511.3 |
| 744 | 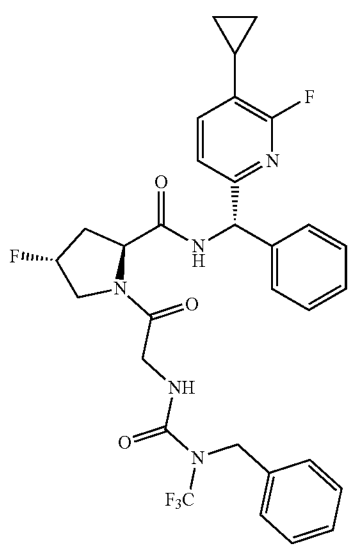 [SMILES: O=C(N[C@@H](c1ccccc1)c1ccc(C2CC2)c(F)n1)[C@@H]1C[C@@H](F)CN1C(=O)CNC(=O)N(Cc1ccccc1)C(F)(F)F] | (2S,4R)-1-(2-{[benzyl(trifluoromethyl)carbamoyl]amino}acetyl)-N-[(S)-(5-cyclopropyl-6-fluoropyridin-2-yl)(phenyl)methyl]-4-fluoropyrrolidine-2-carboxamide | 615.2 | 616.3 |

| Compound No. | Structure | IUPAC | Exact mass (g/mol) | LCMS, Found [M + H]+ |
|---|---|---|---|---|
| 745 | 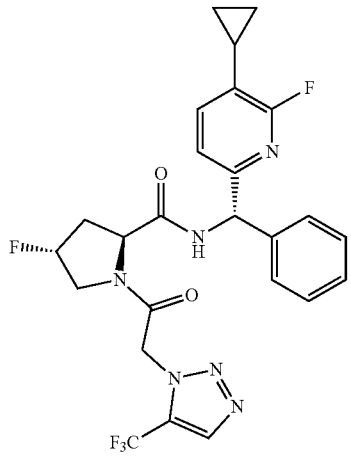 [SMILES: O=C(N[C@@H](c1ccccc1)c1ccc(C2CC2)c(F)n1)[C@@H]1C[C@@H](F)CN1C(=O)Cn1nncc1C(F)(F)F] | (2S,4R)-N-[(S)-(5-cyclopropyl-6-fluoropyridin-2-yl)(phenyl)methyl]-4-fluoro-1-{2-[5-(trifluoromethyl)-1H-1,2,3-triazol-1-yl]acetyl}pyrrolidine-2-carboxamide | 534.2 | 535.1 |
| 746 | 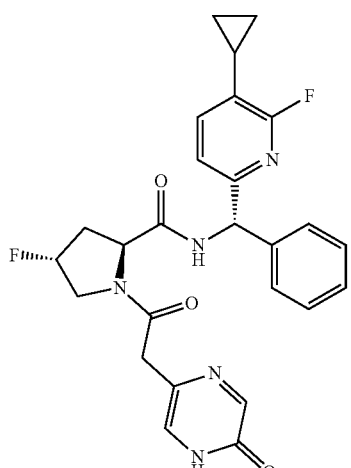 | (2S,4R)-N-[(S)-(5-cyclopropyl-6-fluoropyridin-2-yl)(phenyl)methyl]-4-fluoro-1-[2-(5-oxo-4,5-dihydropyrazin-2-yl)acetyl]pyrrolidine-2-carboxamide | 493.2 | 494.3 |
| 747 | 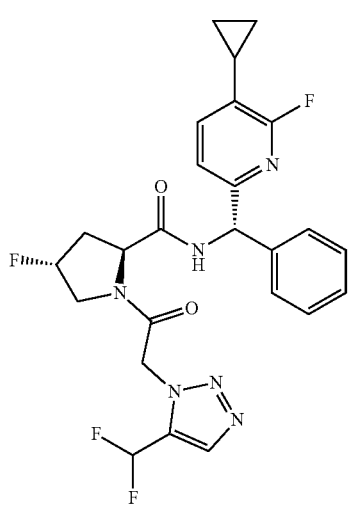 | (2S,4R)-N-[(S)-(5-cyclopropyl-6-fluoropyridin-2-yl)(phenyl)methyl]-1-{2-[5-(difluoromethyl)-1H-1,2,3-triazol-1-yl]acetyl}-4-fluoropyrrolidine-2-carboxamide | 516.2 | 517.3 |

TABLE T-3-continued

| Compound No. | Structure | IUPAC | Exact mass (g/mol) | LCMS, Found [M + H]+ |
|---|---|---|---|---|
| 748 | 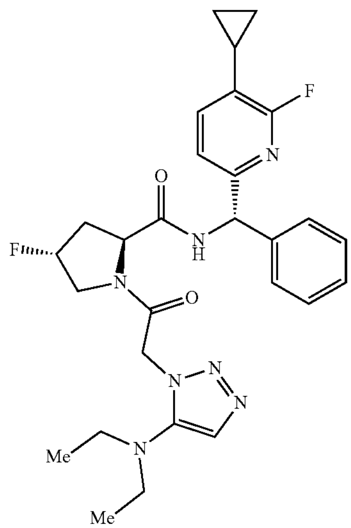 [SMILES: CCN(CC)c1cnnn1CC(=O)N1C[C@H](F)C[C@H]1C(=O)N[C@@H](c1ccccc1)c1ccc(C2CC2)c(F)n1] | (2S,4R)-N-[(S)-(5-cyclopropyl-6-fluoropyridin-2-yl)(phenyl)methyl]-1-{2-[5-(diethylamino)-1H-1,2,3-triazol-1-yl]acetyl}-4-fluoropyrrolidine-2-carboxamide | 537.3 | 538.3 |
| 749 | 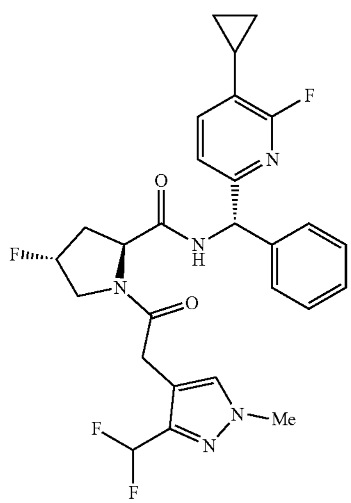 | (2S,4R)-N-[(S)-(5-cyclopropyl-6-fluoropyridin-2-yl)(phenyl)methyl]-1-{2-[3-(difluoromethyl)-1-methyl-1H-pyrazol-4-yl]acetyl}-4-fluoropyrrolidine-2-carboxamide | 529.2 | 530.3 |
| 750 | 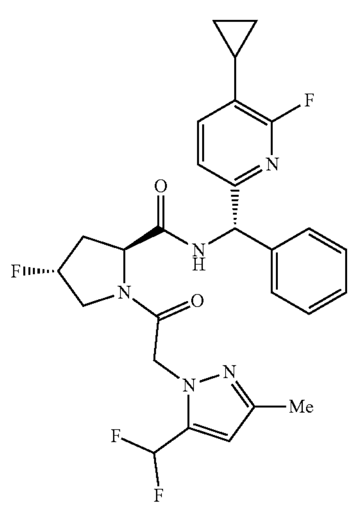 [SMILES: Cc1cc(C(F)F)n(CC(=O)N2C[C@H](F)C[C@H]2C(=O)N[C@@H](c2ccccc2)c2ccc(C3CC3)c(F)n2)n1] | (2S,4R)-N-[(S)-(5-cyclopropyl-6-fluoropyridin-2-yl)(phenyl)methyl]-1-{2-[5-(difluoromethyl)-3-methyl-1H-pyrazol-1-yl]acetyl}-4-fluoropyrrolidine-2-carboxamide | 529.2 | 530.2 |

TABLE T-3-continued

| Compound No. | Structure | IUPAC | Exact mass (g/mol) | LCMS, Found [M + H]+ |
|---|---|---|---|---|
| 751 | 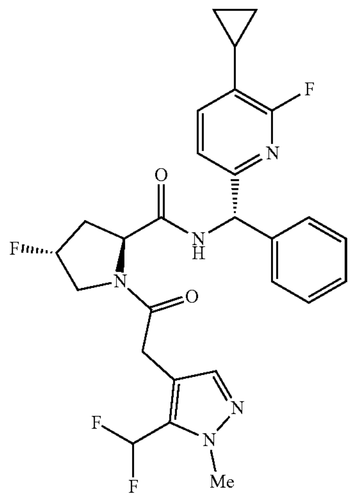 [SMILES: Cn1ncc(CC(=O)N2C[C@H](F)C[C@H]2C(=O)N[C@@H](c2ccccc2)c2ccc(C3CC3)c(F)n2)c1C(F)F] | (2S,4R)-N-[(S)-(5-cyclopropyl-6-fluoropyridin-2-yl)(phenyl)methyl]-1-{2-[5-(difluoromethyl)-1-methyl-1H-pyrazol-4-yl]acetyl}-4-fluoropyrrolidine-2-carboxamide | 529.2 | 530.3 |
| 752 | 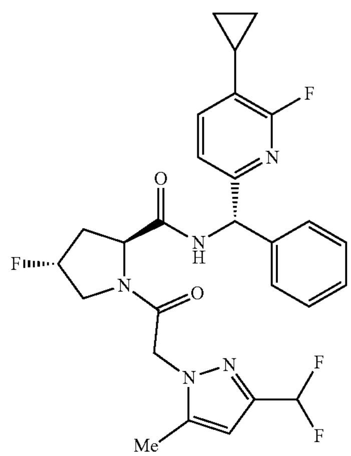 [SMILES: Cc1cc(C(F)F)nn1CC(=O)N1C[C@H](F)C[C@H]1C(=O)N[C@@H](c1ccccc1)c1ccc(C2CC2)c(F)n1] | (2S,4R)-N-[(S)-(5-cyclopropyl-6-fluoropyridin-2-yl)(phenyl)methyl]-1-{2-[3-(difluoromethyl)-5-methyl-1H-pyrazol-1-yl]acetyl}-4-fluoropyrrolidine-2-carboxamide | 529.2 | 530.3 |
| 753 | 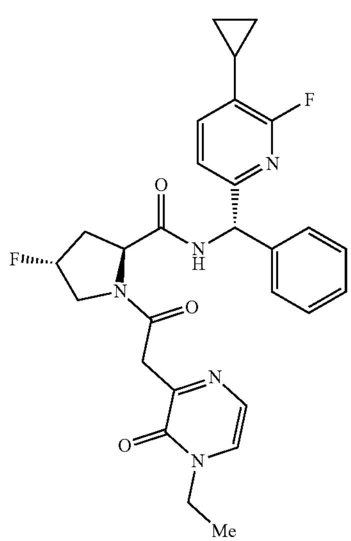 | (2S,4R)-N-[(S)-(5-cyclopropyl-6-fluoropyridin-2-yl)(phenyl)methyl]-1-[2-(4-ethyl-3-oxo-3,4-dihydropyrazin-2-yl)acetyl]-4-fluoropyrrolidine-2-carboxamide | 521.2 | 522.2 |

TABLE T-3-continued

| Compound No. | Structure | IUPAC | Exact mass (g/mol) | LCMS, Found [M + H]+ |
|---|---|---|---|---|
| 754 | 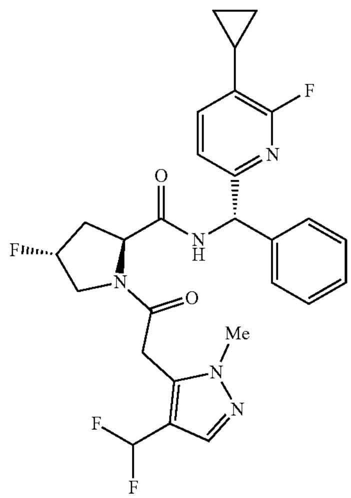 [SMILES: Cn1ncc(C(F)F)c1CC(=O)N1C[C@H](F)C[C@H]1C(=O)N[C@@H](c1ccccc1)c1ccc(C2CC2)c(F)n1] | (2S,4R)-N-[(S)-(5-cyclopropyl-6-fluoropyridin-2-yl)(phenyl)methyl]-1-{2-[4-(difluoromethyl)-1-methyl-1H-pyrazol-5-yl]acetyl}-4-fluoropyrrolidine-2-carboxamide | 529.2 | 530.2 |
| 755 | 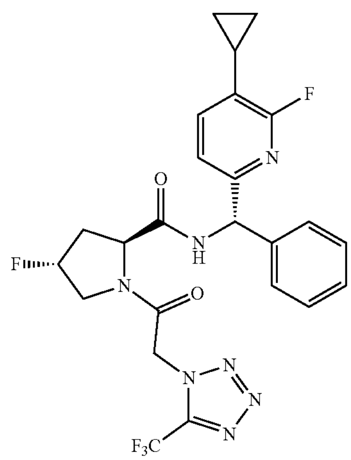 [SMILES: O=C(N[C@@H](c1ccccc1)c1ccc(C2CC2)c(F)n1)[C@@H]1C[C@@H](F)CN1C(=O)Cn1nnnc1C(F)(F)F] | (2S,4R)-N-[(S)-(5-cyclopropyl-6-fluoropyridin-2-yl)(phenyl)methyl]-4-fluoro-1-{2-[5-(trifluoromethyl)-1H-1,2,3,4-tetrazol-1-yl]acetyl}pyrrolidine-2-carboxamide | 535.2 | 536.1 |
| 756 | 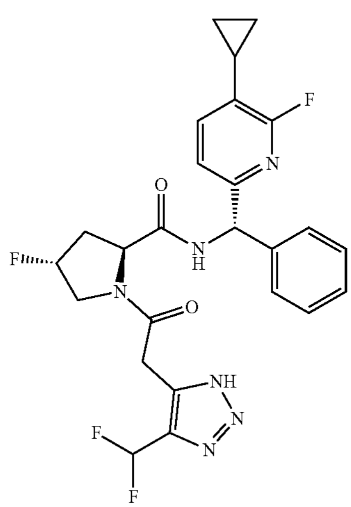 [SMILES: O=C(N[C@@H](c1ccccc1)c1ccc(C2CC2)c(F)n1)[C@@H]1C[C@@H](F)CN1C(=O)Cc1[nH]nnc1C(F)F] | (2S,4R)-N-[(S)-(5-cyclopropyl-6-fluoropyridin-2-yl)(phenyl)methyl]-1-{2-[4-(difluoromethyl)-1H-1,2,3-triazol-5-yl]acetyl}-4-fluoropyrrolidine-2-carboxamide | 516.2 | 517.2 |

TABLE T-3-continued

| Compound No. | Structure | IUPAC | Exact mass (g/mol) | LCMS, Found [M + H]+ |
|---|---|---|---|---|
| 757 | 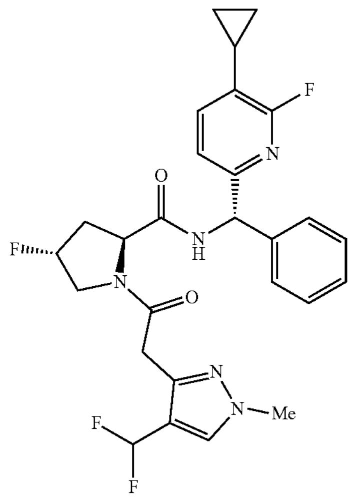 [SMILES: Cn1cc(C(F)F)c(CC(=O)N2C[C@H](F)C[C@H]2C(=O)N[C@@H](c2ccccc2)c2ccc(C3CC3)c(F)n2)n1] | (2S,4R)-N-[(S)-(5-cyclopropyl-6-fluoropyridin-2-yl)(phenyl)methyl]-1-{2-[4-(difluoromethyl)-1-methyl-1H-pyrazol-3-yl]acetyl}-4-fluoropyrrolidine-2-carboxamide | 529.2 | 530.2 |
| 758 | 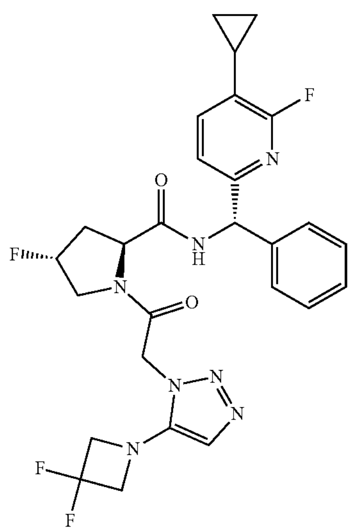 [SMILES: O=C(N[C@@H](c1ccccc1)c1ccc(C2CC2)c(F)n1)[C@@H]1C[C@@H](F)CN1C(=O)Cn1nncc1N1CC(F)(F)C1] | (2S,4R)-N-[(S)-(5-cyclopropyl-6-fluoropyridin-2-yl)(phenyl)methyl]-1-{2-[5-(3,3-difluoroazetidin-1-yl)-1H-1,2,3-triazol-1-yl]acetyl}-4-fluoropyrrolidine-2-carboxamide | 557.2 | 558.3 |
| 759 | 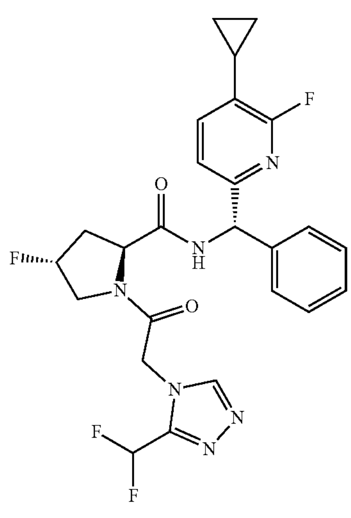 | (2S,4R)-N-[(S)-(5-cyclopropyl-6-fluoropyridin-2-yl)(phenyl)methyl]-1-{2-[3-(difluoromethyl)-4H-1,2,4-triazol-4-yl]acetyl}-4-fluoropyrrolidine-2-carboxamide | 516.2 | 517.2 |

TABLE T-3-continued

| Compound No. | Structure | IUPAC | Exact mass (g/mol) | LCMS, Found [M + H]+ |
|---|---|---|---|---|
| 760 | 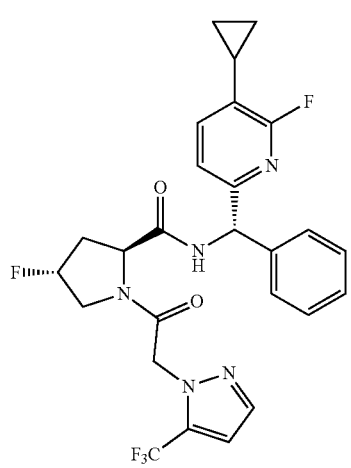 [SMILES: O=C(N[C@@H](c1ccccc1)c1ccc(C2CC2)c(F)n1)[C@@H]1C[C@@H](F)CN1C(=O)Cn1nccc1C(F)(F)F] | (2S,4R)-N-[(S)-(5-cyclopropyl-6-fluoropyridin-2-yl)(phenyl)methyl]-4-fluoro-1-{2-[5-(trifluoromethyl)-1H-pyrazol-1-yl]acetyl}pyrrolidine-2-carboxamide | 533.2 | 534.2 |
| 761 | 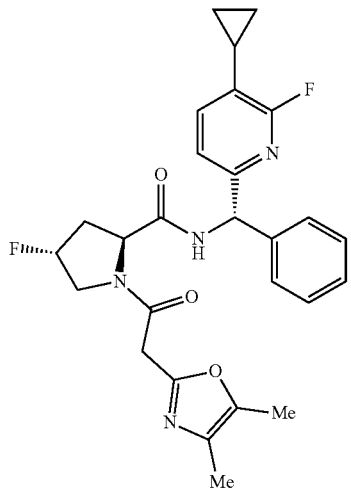 [SMILES: Cc1nc(CC(=O)N2C[C@H](F)C[C@H]2C(=O)N[C@@H](c2ccccc2)c2ccc(C3CC3)c(F)n2)oc1C] | (2S,4R)-N-[(S)-(5-cyclopropyl-6-fluoropyridin-2-yl)(phenyl)methyl]-1-[2-(4,5-dimethyl-1,3-oxazol-2-yl)acetyl]-4-fluoropyrrolidine-2-carboxamide | 494.2 | 495.1 |
| 762 | 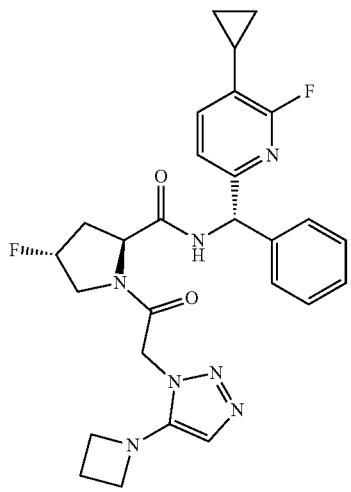 [SMILES: O=C(N[C@@H](c1ccccc1)c1ccc(C2CC2)c(F)n1)[C@@H]1C[C@@H](F)CN1C(=O)Cn1nncc1N1CCC1] | (2S,4R)-1-{2-[5-(azetidin-1-yl)-1H-1,2,3-triazol-1-yl]acetyl}-N-[(S)-(5-cyclopropyl-6-fluoropyridin-2-yl)(phenyl)methyl]-4-fluoropyrrolidine-2-carboxamide | 521.2 | 522.3 |

TABLE T-3-continued

| Compound No. | Structure | IUPAC | Exact mass (g/mol) | LCMS, Found [M + H]+ |
|---|---|---|---|---|
| 763 | 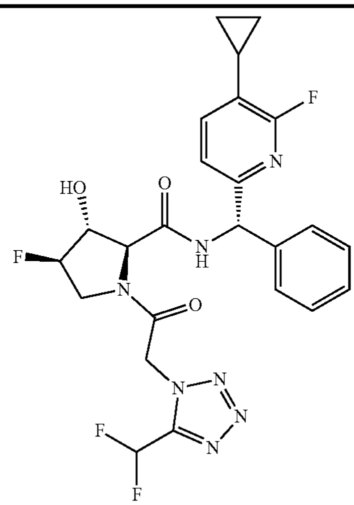 | (2S,3R,4R)-N-[(S)-(5-cyclopropyl-6-fluoropyridin-2-yl)(phenyl)methyl]-1-{2-[5-(difluoromethyl)-1H-1,2,3,4-tetrazol-1-yl]acetyl}-4-fluoro-3-hydroxypyrrolidine-2-carboxamide | 533.2 | 534.2 |
| 764 | 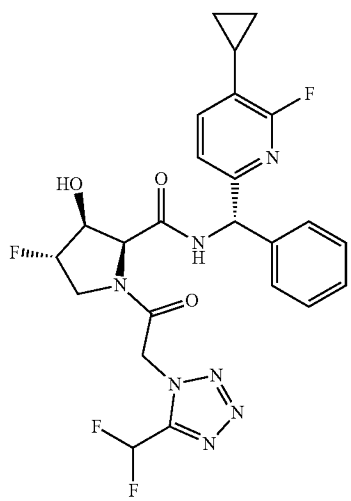 [SMILES: O=C(N[C@@H](c1ccccc1)c1ccc(C2CC2)c(F)n1)[C@@H]1[C@H](O)[C@@H](F)CN1C(=O)Cn1nnnc1C(F)F] | (2S,3S,4S)-N-[(S)-(5-cyclopropyl-6-fluoropyridin-2-yl)(phenyl)methyl]-1-{2-[5-(difluoromethyl)-1H-1,2,3,4-tetrazol-1-yl]acetyl}-4-fluoro-3-hydroxypyrrolidine-2-carboxamide | 533.2 | 534.1 |

Example S-4: Synthesis of (2S,4R)-4-fluoro-N—((S)-(3-fluoro-4-isopropylphenyl)(phenyl)methyl)-1-(2-(5-(trifluoromethyl)-1H-1,2,3-triazol-1-yl)acetyl)pyrrolidine-2-carboxamide Compound 322

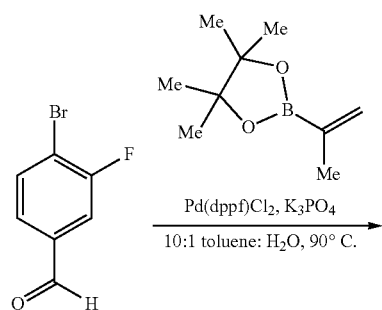

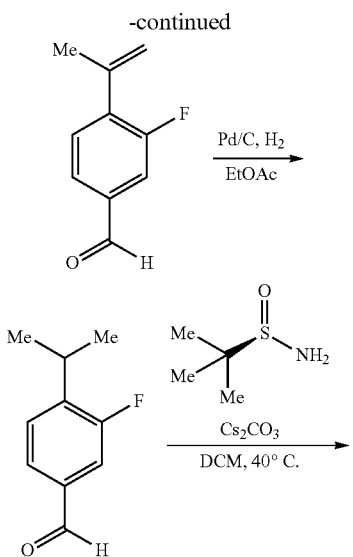

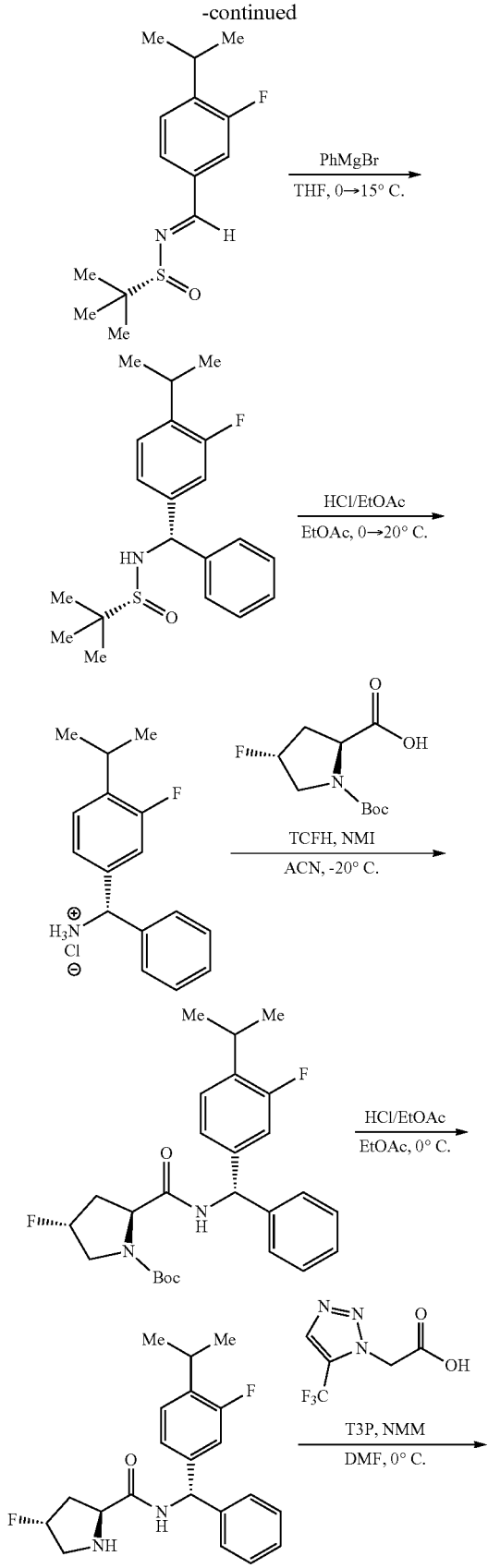

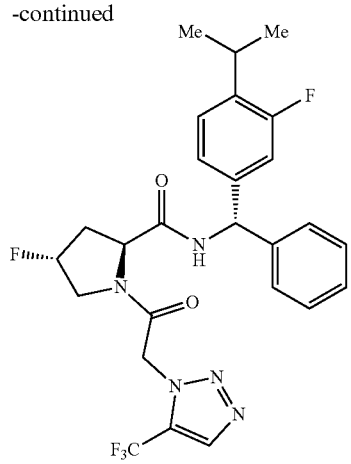

Step a: To a mixture of 4-bromo-3-fluoro-benzaldehyde (200 g, 985 mmol, 1.00 eq) and 2-isopropenyl-4,4,5,5-tetramethyl-1,3,2-dioxaborolane (215 g, 1.28 mol, 1.30 eq) in toluene (3.70 L) and $H_2O$ (410 mL) at 25° C. under $N_2$ was added Pd(dppf)$Cl_2$ (36.0 g, 49.3 mmol, 0.05 eq) and $K_3PO_4$ (418 g, 1.97 mol, 2.00 eq). The mixture was warmed to 90° C. and stirred for 12 h. The reaction mixture was then filtered, and the filtrate was concentrated under reduced pressure. The resulting crude residue was purified by column chromatography to give 3-fluoro-4-isopropenyl-benzaldehyde. The compound was carried forward to the next step without further characterization.

Step b: To a solution of 3-fluoro-4-isopropenyl-benzaldehyde (124 g, 755 mmol, 1.00 eq) in EtOAc (1.20 L) under $N_2$ was added Pd/C (85.0 g, 10 wt. %). The suspension was degassed and purged with $H_2$ several times. The mixture was stirred at 25° C. under $H_2$ (15 psi) for 1 h. The reaction mixture was then filtered, and the filtrate was concentrated under reduced pressure. The resulting crude residue was purified by column chromatography to give 3-fluoro-4-isopropyl-benzaldehyde. The compound was carried forward to the next step without further characterization.

Step c: To a mixture of 3-fluoro-4-isopropyl-benzaldehyde (80.0 g, 481 mmol, 1.00 eq) and (R)-2-methylpropane-2-sulfinamide (64.2 g, 523 mmol, 1.10 eq) in DCM (450 mL) at 25° C. was added $Cs_2CO_3$ (173 g, 530 mmol, 1.10 eq). The mixture was warmed to 40° C. and stirred for 16 h. The reaction mixture was filtered, and the filtrate was concentrated under reduced pressure. The residue was purified by column chromatography to obtain (R,E)-N-(3-fluoro-4-isopropylbenzylidene)-2-methylpropane-2-sulfinamide. LC-MS (ESI): m/z: [M+H]$^+$ calculated for $C_{14}H_{20}FNOS$: 270.1; found 270.0.

Step d: To a solution of (R,E)-N-(3-fluoro-4-isopropyl-benzylidene)-2-methylpropane-2-sulfinamide (30.0 g, 111 mmol, 1.00 eq) in DCM (400 mL) −65° C. under $N_2$ was added, dropwise, a solution of phenylmagnesium bromide (3 M in $Et_2O$, 55.7 mL, 1.50 eq) over a period of 30 min. The reaction mixture was stirred at −65° C. for 6 h, then warmed to 25° C. and stirred for an additional 6 h. The reaction mixture was quenched with saturated aqueous $NH_4Cl$ (50 mL) and extracted with EtOAc (3×30 mL). The combined organic extracts were washed with water (3×30 mL), dried over anhydrous $Na_2SO_4$, filtered, and concentrated under reduced pressure. The resulting crude residue was purified by column chromatography to obtain (R)—N—((S)-(3-fluoro-4-isopropylphenyl)(phenyl)methyl)-2-methylpropane-2-sulfinamide. The compound was carried forward to the next step without further characterization.

Step e: To a mixture of (R)—N—((S)-(3-fluoro-4-isopropylphenyl)(phenyl)methyl)-2-methylpropane-2-sulfinamide (35.0 g, 101 mmol, 1.00 eq) in DCM (300 mL) at 25° C. was added HCl/EtOAc (4 M, 50.4 mL, 2.00 eq), and the mixture was stirred for 2 h. The reaction mixture was filtered and the solid so obtained was set aside. The filtrate was concentrated under reduced pressure and the resulting residue was combined with the previously obtained solid. The mixture was dissolved in MTBE (200 mL) and filtered, and the filtrate was concentrated under reduced pressure to give (S)-(3-fluoro-4-isopropylphenyl)(phenyl)methanaminium chloride. The compound was carried forward to the next step without further characterization.

Step f: To a solution of (S)-(3-fluoro-4-isopropylphenyl)(phenyl)methanaminium chloride (600 mg, 2.14 mmol, 1 eq), and 1-methylimidazole (880 mg, 10.7 mmol, 5 eq) in $CH_3CN$ (10 mL) at −20° C. was added (2S,4R)-1-(tert-butoxycarbonyl)-4-fluoropyrrolidine-2-carboxylic acid (600 mg, 2.57 mmol, 1.2 eq). After 10 min, chloro-N,N,N,N-tetramethylformamidinium hexafluorophosphate (TCFH, 722 mg, 2.57 mmol, 1.2 eq) was added at −20° C., and the resulting mixture was stirred for 2 h. The reaction mixture was warmed to 25° C., quenched with $H_2O$ (30 mL), and extracted with EtOAc (3×30 mL). The combined organic extracts were washed with brine (30 mL), dried over $Na_2SO_4$, filtered, and concentrated under reduced pressure. The resulting crude residue was purified by column chromatography to afford tert-butyl (2S,4R)-4-fluoro-2-(((S)-(3-fluoro-4-isopropylphenyl)(phenyl)methyl)carbamoyl)pyrrolidine-1-carboxylate. LC-MS (ESI): m/z: [M+H]$^+$ calculated for $C_{26}H_{32}F_2N_2O_3$: 459.2; found 459.1.

Step g: To a mixture of tert-butyl (2S,4R)-4-fluoro-2-(((S)-(3-fluoro-4-isopropylphenyl)(phenyl)methyl)carbamoyl)pyrrolidine-1-carboxylate (0.8 g, 1.74 mmol, 1 eq) in EtOAc (3 mL) at 0° C. was added 4M HCl/EtOAc (10 mL). The resulting mixture was stirred at 0° C. for 2 h. The reaction was then concentrated directly at low temperature under reduced pressure. The solid so obtained was washed with MTBE (3×10 mL), filtered, and dried under reduced pressure to give (2S,4R)-4-fluoro-N—((S)-(3-fluoro-4-isopropylphenyl)(phenyl)methyl)pyrrolidine-2-carboxamide. LC-MS (ESI): m/z: [M+H]$^+$ calculated for $C_{21}H_{24}F_2N_2O$: 359.2; found 359.1.

Step h: To a mixture of (2S,4R)-4-fluoro-N—((S)-(3-fluoro-4-isopropylphenyl)(phenyl)methyl)pyrrolidine-2-carboxamide (50 mg, 139 μmol, 1 eq), 4-methylmorpholine (28.22 mg, 279 μmol, 2 eq) and 2-(5-(trifluoromethyl)-1H-1,2,3-triazol-1-yl)acetic acid (Intermediate A-3, 32.8 mg, 167 μmol, 1.2 eq) in DMF (3 mL) was added T3P (267 mg, 418 μmol, 50% in EtOAc, 3 eq) at −20° C. The mixture was stirred at −20° C. for 2 h under $N_2$ atmosphere. The reaction mixture was then quenched with $H_2O$ (20 mL) at 0° C. and extracted with ethyl acetate (3×10 mL). The combined organic layers were washed with brine (2×10 mL), dried over $Na_2SO_4$, filtered, and concentrated under reduced pressure to give a residue. The residue was purified by prep-HPLC to give (2S,4R)-4-fluoro-N—((S)-(3-fluoro-4-isopropylphenyl)(phenyl)methyl)-1-(2-(5-(trifluoromethyl)-1H-1,2,3-triazol-1-yl)acetyl)pyrrolidine-2-carboxamide. $^1$H NMR (3.9:1 rotamer ratios, asterisk denotes minor rotamer peaks, obscured peaks not reported, 400 MHz, DMSO-$d_6$) δ 9.25* (d, J=8.0 Hz, 1H), 8.89 (d, J=8.2 Hz, 1H), 8.51-8.44 (m, 1H), 7.38-7.18 (m, 6H), 7.15-6.93 (m, 2H), 6.14*(d, J=8.0 Hz, 1H), 6.01 (d, J=8.2 Hz, 1H), 5.88-5.79 (m, 1H), 5.79-5.70* (m, 1H), 5.64-5.55 (m, 1H), 5.56-5.24 (m, 1H), 4.97-4.81* (m, 1H), 4.57 (t, J=8.4 Hz, 1H), 4.22-4.09 (m, 1H), 4.00-3.76 (m, 1H), 3.58-3.40*(m, 1H), 3.18-3.05 (m, 1H), 2.92-2.77*(m, 1H), 2.30-1.91 (m, 1H), 1.22-1.15 (m, 6H). LC-MS (ESI): m/z: [M+H]$^+$ calculated for $C_{26}H_{26}F_5N_5O_2$: 536.2; found 536.2.

The following compounds in Table T-4 were synthesized using procedures similar to Compound 322 using the appropriate starting materials.

TABLE T-4

| Compound No. | Structure | IUPAC | Exact mass (g/mol) | LCMS, Found [M + H]$^+$ |
|---|---|---|---|---|
| 323 | 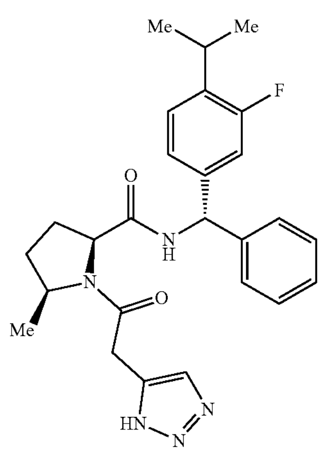 [SMILES: CC(C)c1ccc([C@@H](NC(=O)[C@@H]2CC[C@H](C)N2C(=O)Cc2cnn[nH]2)c2ccccc2)cc1F] | (2S,5S)-N-[(S)-[3-fluoro-4-(propan-2-yl)phenyl](phenyl)methyl]-5-methyl-1-[2-(1H-1,2,3-triazol-5-yl)acetyl]pyrrolidine-2-carboxamide | 463.2 | 464.2 |

TABLE T-4-continued

| Compound No. | Structure | IUPAC | Exact mass (g/mol) | LCMS, Found [M + H]+ |
|---|---|---|---|---|
| 324 | 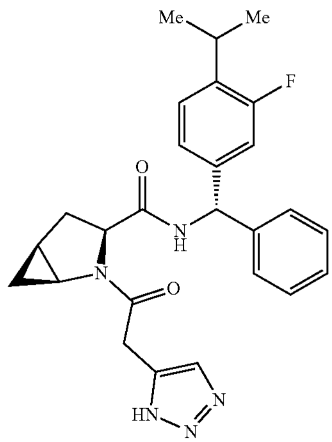 [SMILES: CC(C)c1ccc([C@@H](NC(=O)[C@@H]2C[C@@H]3C[C@@H]3N2C(=O)Cc2cnn[nH]2)c2ccccc2)cc1F] | (1S,3S,5S)-N-[(S)-[3-fluoro-4-(propan-2-yl)phenyl](phenyl)methyl]-2-[2-(1H-1,2,3-triazol-5-yl)acetyl]-2-azabicyclo[3.1.0]hexane-3-carboxamide | 461.2 | 462.1 |
| 325 | 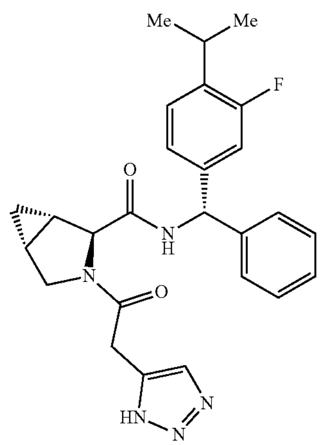 [SMILES: CC(C)c1ccc([C@@H](NC(=O)[C@@H]2[C@H]3C[C@H]3CN2C(=O)Cc2cnn[nH]2)c2ccccc2)cc1F] | (1S,2S,5R)-N-[(S)-[3-fluoro-4-(propan-2-yl)phenyl](phenyl)methyl]-3-[2-(1H-1,2,3-triazol-5-yl)acetyl]-3-azabicyclo[3.1.0]hexane-2-carboxamide | 461.2 | 462.1 |
| 326 | 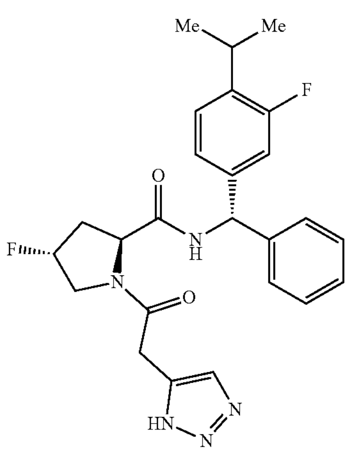 | (2S,4R)-4-fluoro-N-[(S)-[3-fluoro-4-(propan-2-yl)phenyl](phenyl)methyl]-1-[2-(1H-1,2,3-triazol-5-yl)acetyl]pyrrolidine-2-carboxamide | 467.2 | 468.1 |

TABLE T-4-continued

| Compound No. | Structure | IUPAC | Exact mass (g/mol) | LCMS, Found [M + H]+ |
|---|---|---|---|---|
| 327 | 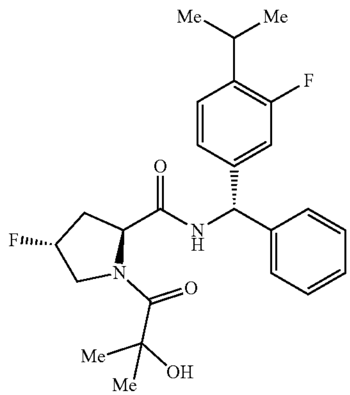 [SMILES: CC(C)c1ccc([C@@H](NC(=O)[C@@H]2C[C@@H](F)CN2C(=O)C(C)(C)O)c2ccccc2)cc1F] | (2S,4R)-4-fluoro-N-[(S)-[3-fluoro-4-(propan-2-yl)phenyl](phenyl)methyl]-1-(2-hydroxy-2-methylpropanoyl)pyrrolidine-2-carboxamide | 444.2 | 445.1 |
| 328 | 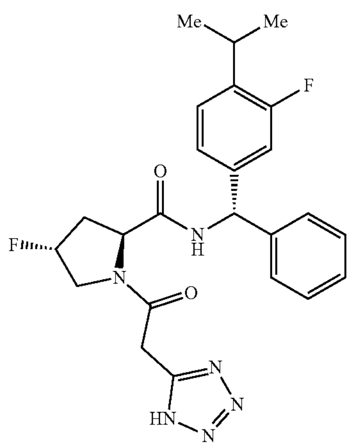 | (2S,4R)-4-fluoro-N-[(S)-[3-fluoro-4-(propan-2-yl)phenyl](phenyl)methyl]-1-[2-(1H-1,2,3,4-tetrazol-5-yl)acetyl]pyrrolidine-2-carboxamide | 468.2 | 469.1 |
| 329 | 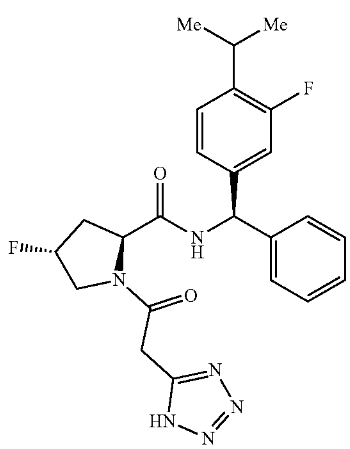 | (2S,4R)-4-fluoro-N-[(R)-[3-fluoro-4-(propan-2-yl)phenyl](phenyl)methyl]-1-[2-(1H-1,2,3,4-tetrazol-5-yl)acetyl]pyrrolidine-2-carboxamide | 468.2 | 469.1 |

TABLE T-4-continued

| Compound No. | Structure | IUPAC | Exact mass (g/mol) | LCMS, Found [M + H]+ |
|---|---|---|---|---|
| 330 | 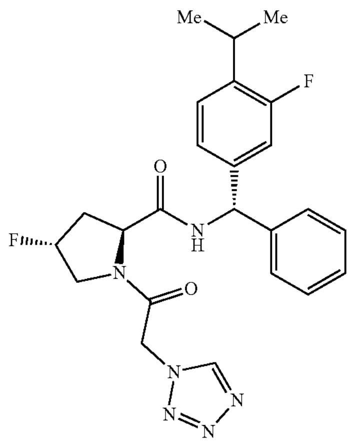 | (2S,4R)-4-fluoro-N-[(S)-[3-fluoro-4-(propan-2-yl)phenyl](phenyl)methyl]-1-[2-(1H-1,2,3,4-tetrazol-1-yl)acetyl]pyrrolidine-2-carboxamide | 468.2 | 469.1 |
| 331 | 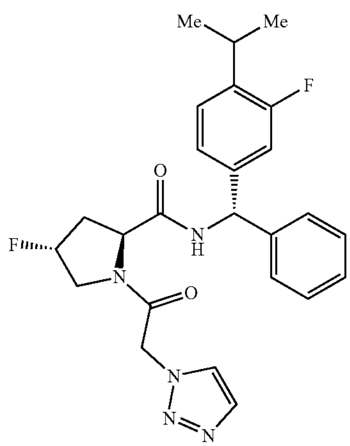 [SMILES: CC(C)c1ccc([C@@H](NC(=O)[C@@H]2C[C@@H](F)CN2C(=O)Cn2ccnn2)c2ccccc2)cc1F] | (2S,4R)-4-fluoro-N-[(S)-[3-fluoro-4-(propan-2-yl)phenyl](phenyl)methyl]-1-[2-(1H-1,2,3-triazol-1-yl)acetyl]pyrrolidine-2-carboxamide | 467.2 | 468.1 |
| 332 | 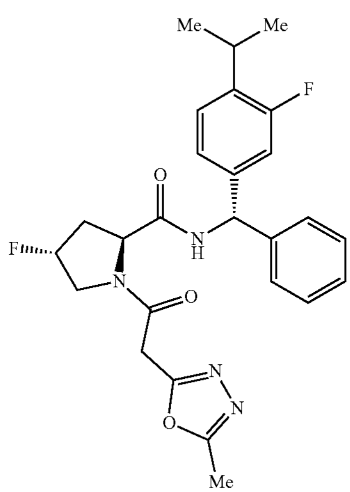 [SMILES: Cc1nnc(CC(=O)N2C[C@H](F)C[C@H]2C(=O)N[C@@H](c2ccccc2)c2ccc(C(C)C)c(F)c2)o1] | (2S,4R)-4-fluoro-N-[(S)-[3-fluoro-4-(propan-2-yl)phenyl](phenyl)methyl]-1-[2-(5-methyl-1,3,4-oxadiazol-2-yl)acetyl]pyrrolidine-2-carboxamide | 482.2 | 493.1 |

TABLE T-4-continued

| Compound No. | Structure | IUPAC | Exact mass (g/mol) | LCMS, Found [M + H]+ |
|---|---|---|---|---|
| 333 | 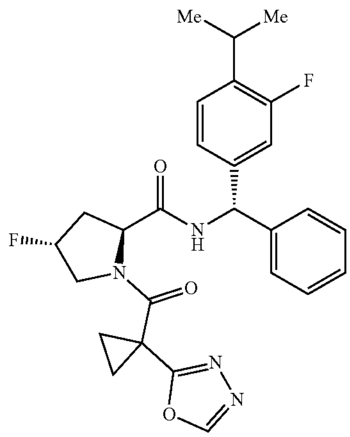 [SMILES: CC(C)c1ccc([C@@H](NC(=O)[C@@H]2C[C@@H](F)CN2C(=O)C2(c3nnco3)CC2)c2ccccc2)cc1F] | (2S,4R)-4-fluoro-N-[(S)-[3-fluoro-4-(propan-2-yl)phenyl](phenyl)methyl]-1-[1-(1,3,4-oxadiazol-2-yl)cyclopropanecarbonyl]pyrrolidine-2-carboxamide | 494.2 | 495.1 |
| 334 | 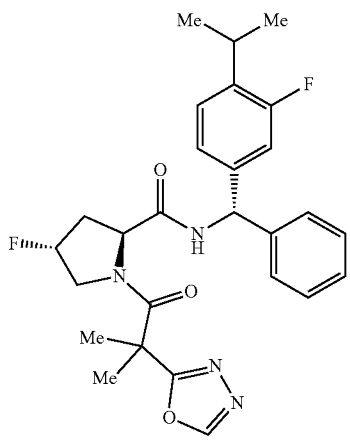 [SMILES: CC(C)c1ccc([C@@H](NC(=O)[C@@H]2C[C@@H](F)CN2C(=O)C(C)(C)c2nnco2)c2ccccc2)cc1F] | (2S,4R)-4-fluoro-N-[(S)-[3-fluoro-4-(propan-2-yl)phenyl[(phenyl)methyl]-1-[2-methyl-2-(1,3,4-oxadiazol-2-yl)propanoyl]pyrrolidine-2-carboxamide | 496.2 | 497.1 |
| 335 | 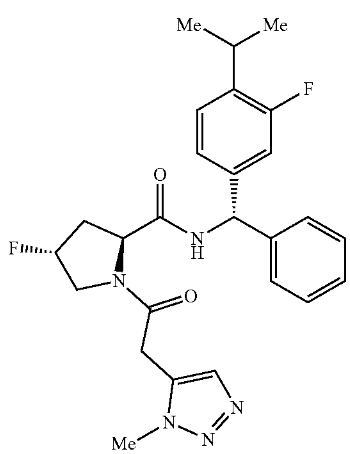 | (2S,4R)-4-fluoro-N-[(S)-[3-fluoro-4-(propan-2-yl)phenyl](phenyl)methyl]-1-[2-(1-methyl-1H-1,2,3-triazol-5-yl)acetyl]pyrrolidine-2-carboxamide | 481.2 | 480.1 |

TABLE T-4-continued

| Compound No. | Structure | IUPAC | Exact mass (g/mol) | LCMS, Found [M + H]+ |
| --- | --- | --- | --- | --- |
| 336 | 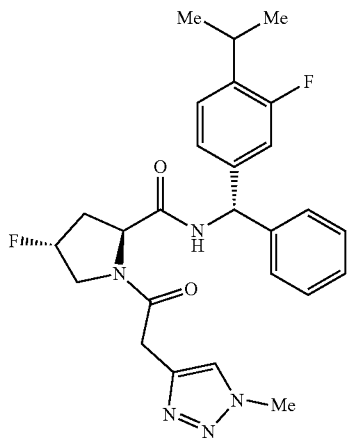 [SMILES: CC(C)c1ccc([C@@H](NC(=O)[C@@H]2C[C@@H](F)CN2C(=O)Cc2cn(C)nn2)c2ccccc2)cc1F] | (2S,4R)-4-fluoro-N-[(S)-[3-fluoro-4-(propan-2-yl)phenyl[(phenyl)methyl]-1-[2-(1-methyl-1H-1,2,3-triazol-4-yl)acetyl]pyrrolidine-2-carboxamide | 481.2 | 482.1 |
| 337 | 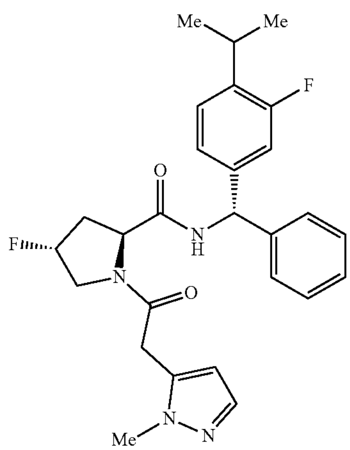 | (2S,4R)-4-fluoro-N-[(S)-[3-fluoro-4-(propan-2-yl)phenyl](phenyl)methyl]-1-[2-(1-methyl-1H-pyrazol-5-yl)acetyl]pyrrolidine-2-carboxamide | 480.2 | 481.3 |
| 338 | 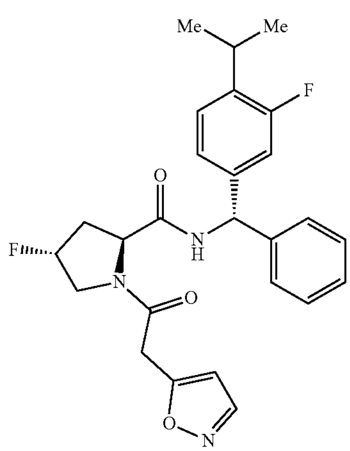 [SMILES: CC(C)c1ccc([C@@H](NC(=O)[C@@H]2C[C@@H](F)CN2C(=O)Cc2ccno2)c2ccccc2)cc1F] | (2S,4R)-4-fluoro-N-[(S)-[3-fluoro-4-(propan-2-yl)phenyl](phenyl)methyl]-1-[2-(1,2-oxazol-5-yl)acetyl]pyrrolidine-2-carboxamide | 467.2 | 468.1 |

TABLE T-4-continued

| Compound No. | Structure | IUPAC | Exact mass (g/mol) | LCMS, Found [M + H]+ |
|---|---|---|---|---|
| 339 | 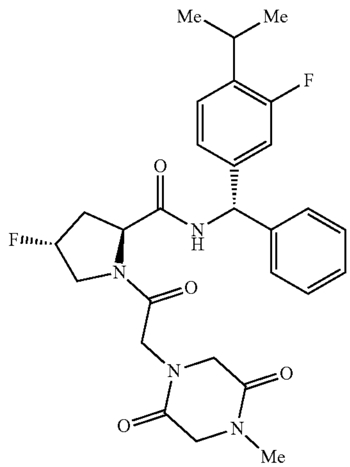 [SMILES: CC(C)c1ccc([C@@H](NC(=O)[C@@H]2C[C@@H](F)CN2C(=O)CN2CC(=O)N(C)CC2=O)c2ccccc2)cc1F] | (2S,4R)-4-fluoro-N-[(S)-[3-fluoro-4-(propan-2-yl)phenyl](phenyl)methyl]-1-[2-(4-methyl-2,5-dioxopiperazin-1-yl)acetyl]pyrrolidine-2-carboxamide | 526.2 | 527.1 |
| 340 | 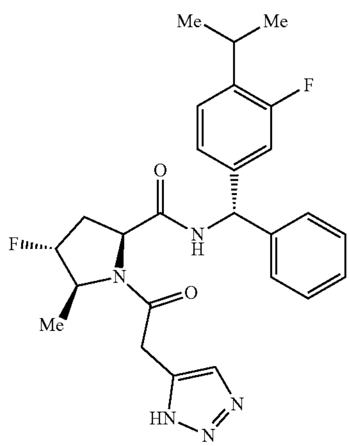 [SMILES: CC(C)c1ccc([C@@H](NC(=O)[C@@H]2C[C@@H](F)[C@H](C)N2C(=O)Cc2cnn[nH]2)c2ccccc2)cc1F] | (2S,4R,5S)-4-fluoro-N-[(S)-[3-fluoro-4-(propan-2-yl)phenyl](phenyl)methyl]-5-methyl-1-[2-(1H-1,2,3-triazol-5-yl)acetyl]pyrrolidine-2-carboxamide | 481.2 | 482.2 |
| 341 | 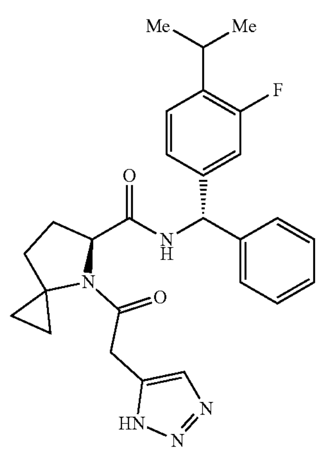 [SMILES: CC(C)c1ccc([C@@H](NC(=O)[C@@H]2CCC3(CC3)N2C(=O)Cc2cnn[nH]2)c2ccccc2)cc1F] | (5S)-N-[(S)-[3-fluoro-4-(propan-2-yl)phenyl](phenyl)methyl]-4-[2-(1H-1,2,3-triazol-5-yl)acetyl]-4-azaspiro[2.4]heptane-5-carboxamide | 475.2 | 476.1 |

TABLE T-4-continued

| Compound No. | Structure | IUPAC | Exact mass (g/mol) | LCMS, Found [M + H]+ |
| --- | --- | --- | --- | --- |
| 342 | 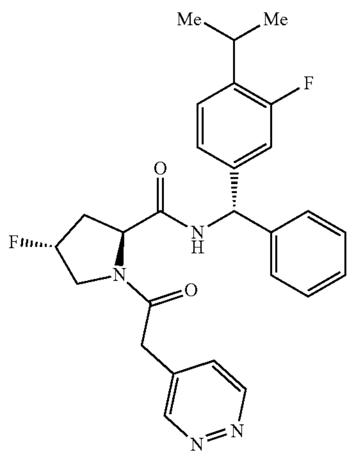 | (2S,4R)-4-fluoro-N-[(S)-[3-fluoro-4-(propan-2-yl)phenyl](phenyl)methyl]-1-[2-(pyridazin-4-yl)acetyl]pyrrolidine-2-carboxamide | 478.2 | 479.3 |
| 343 | 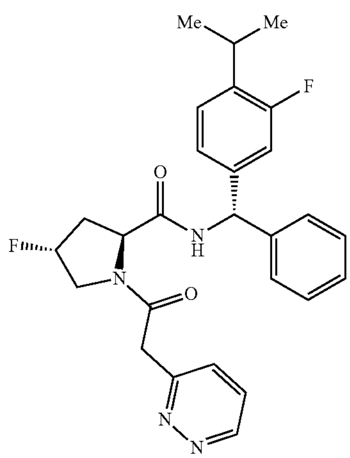 | (2S,4R)-4-fluoro-N-[(S)-[3-fluoro-4-(propan-2-yl)phenyl](phenyl)methyl]-1-[2-(pyridazin-3-yl)acetyl]pyrrolidine-2-carboxamide | 478.2 | 479.1 |
| 344 | 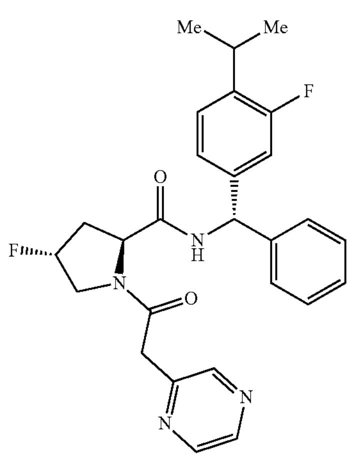 | (2S,4R)-4-fluoro-N-[(S)-[3-fluoro-4-(propan-2-yl)phenyl[(phenyl)methyl]-1-[2-(pyrazin-2-yl)acetyl]pyrrolidine-2-carboxamide | 478.2 | 479.2 |

TABLE T-4-continued

| Compound No. | Structure | IUPAC | Exact mass (g/mol) | LCMS, Found [M + H]+ |
|---|---|---|---|---|
| 345 | 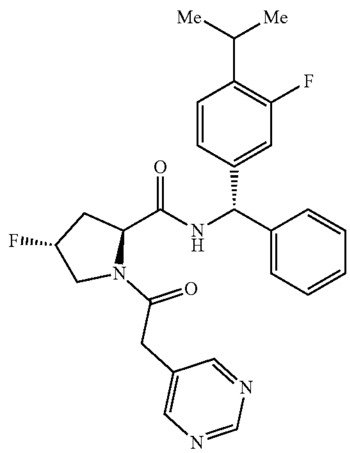 | (2S,4R)-4-fluoro-N-[(S)-[3-fluoro-4-(propan-2-yl)phenyl](phenyl)methyl]-1-[2-(pyrimidin-5-yl)acetyl]pyrrolidine-2-carboxamide | 478.2 | 479.1 |
| 346 | 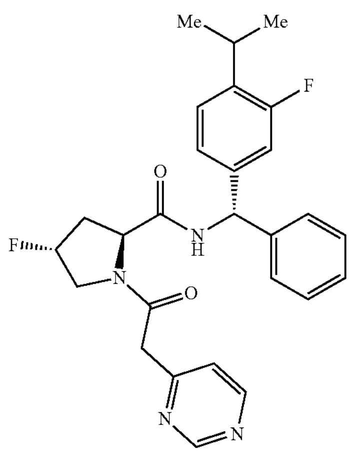 [SMILES: CC(C)c1ccc([C@@H](NC(=O)[C@@H]2C[C@@H](F)CN2C(=O)Cc2ccncn2)c2ccccc2)cc1F] | (2S,4R)-4-fluoro-N-[(S)-[3-fluoro-4-(propan-2-yl)phenyl](phenyl)methyl]-1-[2-(pyrimidin-4-yl)acetyl]pyrrolidine-2-carboxamide | 478.2 | 479.2 |
| 347 | 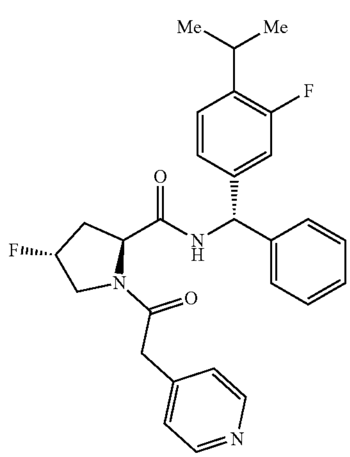 [SMILES: CC(C)c1ccc([C@@H](NC(=O)[C@@H]2C[C@@H](F)CN2C(=O)Cc2ccncc2)c2ccccc2)cc1F] | (2S,4R)-4-fluoro-N-[(S)-[3-fluoro-4-(propan-2-yl)phenyl](phenyl)methyl]-1-[2-(pyridin-4-yl)acetyl]pyrrolidine-2-carboxamide | 477.2 | 478.2 |

TABLE T-4-continued

| Compound No. | Structure | IUPAC | Exact mass (g/mol) | LCMS, Found [M + H]+ |
|---|---|---|---|---|
| 348 | 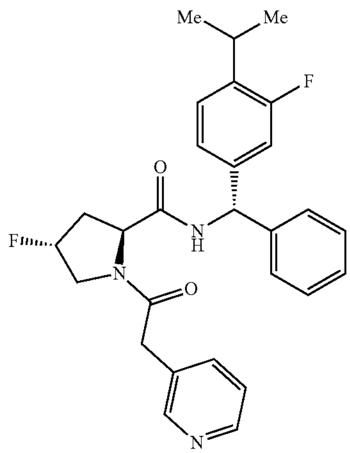 | (2S,4R)-4-fluoro-N-[(S)-[3-fluoro-4-(propan-2-yl)phenyl](phenyl)methyl]-1-[2-(pyridin-3-yl)acetyl]pyrrolidine-2-carboxamide | 477.2 | 478.2 |
| 349 | 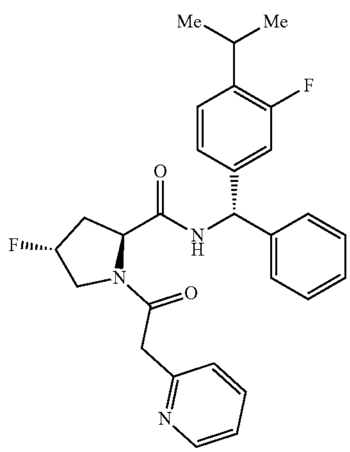 [SMILES: CC(C)c1ccc([C@@H](NC(=O)[C@@H]2C[C@@H](F)CN2C(=O)Cc2ccccn2)c2ccccc2)cc1F] | (2S,4R)-4-fluoro-N-[(S)-[3-fluoro-4-(propan-2-yl)phenyl](phenyl)methyl]-1-[2-(pyridin-2-yl)acetyl]pyrrolidine-2-carboxamide | 477.2 | 478.1 |
| 350 | 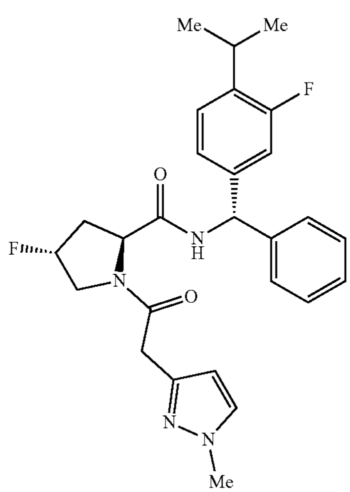 | (2S,4R)-4-fluoro-N-[(S)-[3-fluoro-4-(propan-2-yl)phenyl](phenyl)methyl]-[2-(1-methyl-1H-pyrazol-3-yl)acetyl]pyrrolidine-2-carboxamide | 480.2 | 481.3 |

TABLE T-4-continued

| Compound No. | Structure | IUPAC | Exact mass (g/mol) | LCMS, Found [M + H]+ |
|---|---|---|---|---|
| 351 | 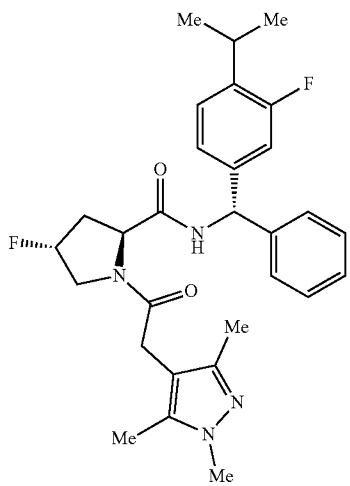 [SMILES: Cc1nn(C)c(C)c1CC(=O)N1C[C@H](F)C[C@H]1C(=O)N[C@@H](c1ccccc1)c1ccc(C(C)C)c(F)c1] | (2S,4R)-4-fluoro-N-[(S)-[3-fluoro-4-(propan-2-yl)phenyl](phenyl)methyl]-1-[2-(1,3,5-trimethyl-1H-pyrazol-4-yl)acetyl]pyrrolidine-2-carboxamide | 508.3 | 509.3 |
| 352 | 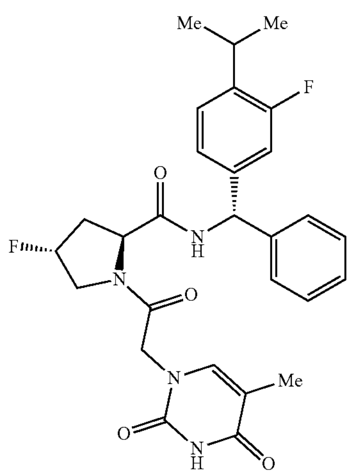 [SMILES: Cc1cn(CC(=O)N2C[C@H](F)C[C@H]2C(=O)N[C@@H](c2ccccc2)c2ccc(C(C)C)c(F)c2)c(=O)[nH]c1=O] | (2S,4R)-4-fluoro-N-[(S)-[3-fluoro-4-(propan-2-yl)phenyl](phenyl)methyl]-1-[2-(5-methyl-2,4-dioxo-1,2,3,4-tetrahydropyrimidin-1-yl)acetyl]pyrrolidine-2-carboxamide | 524.2 | 525.0 |
| 353 | 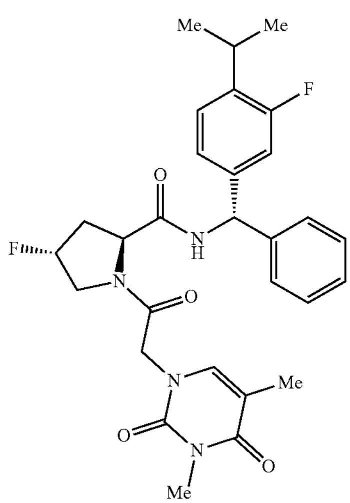 | (2S,4R)-1-[2-(3,5-dimethyl-2,4-dioxo-1,2,3,4-tetrahydropyrimidin-1-yl)acetyl]-4-fluoro-N-[(S)-[3-fluoro-4-(propan-2-yl)phenyl](phenyl)methyl]pyrrolidine-2-carboxamide | 538.2 | 539.1 |

TABLE T-4-continued

| Compound No. | Structure | IUPAC | Exact mass (g/mol) | LCMS, Found [M + H]+ |
|---|---|---|---|---|
| 354 | 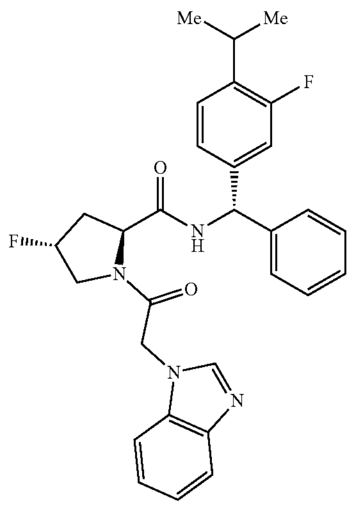 | (2S,4R)-1-[2-(1H-1,3-benzodiazol-1-yl)acetyl]-4-fluoro-N-[(S)-[3-fluoro-4-(propan-2-yl)phenyl](phenyl)methyl]pyrrolidine-2-carboxamide | 516.2 | 517.2 |
| 355 | 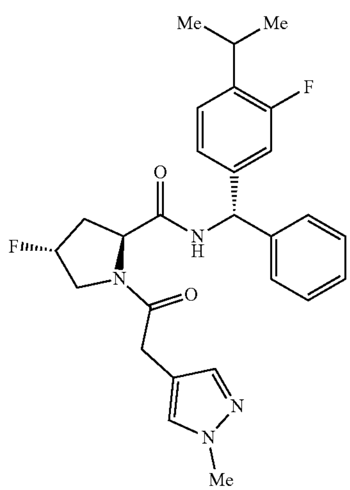 | (2S,4R)-4-fluoro-N-[(S)-[3-fluoro-4-(propan-2-yl)phenyl](phenyl)methyl]-1-[2-(1-methyl-1H-pyrazol-4-yl)acetyl]pyrrolidine-2-carboxamide | 480.2 | 481.1 |
| 356 | 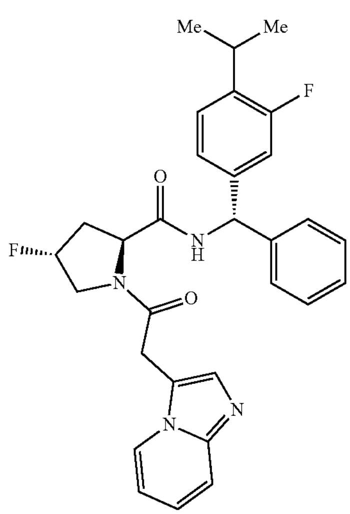 [SMILES: CC(C)c1ccc([C@@H](NC(=O)[C@@H]2C[C@@H](F)CN2C(=O)Cc2cnc3ccccn23)c2ccccc2)cc1F] | (2S,4R)-4-fluoro-N-[(S)-[3-fluoro-4-(propan-2-yl)phenyl](phenyl)methyl]-1-(2-{imidazo[1,2-a]pyridin-3-yl}acetyl)pyrrolidine-2-carboxamide | 516.2 | 517.1 |

TABLE T-4-continued

| Compound No. | Structure | IUPAC | Exact mass (g/mol) | LCMS, Found [M + H]+ |
|---|---|---|---|---|
| 357 | 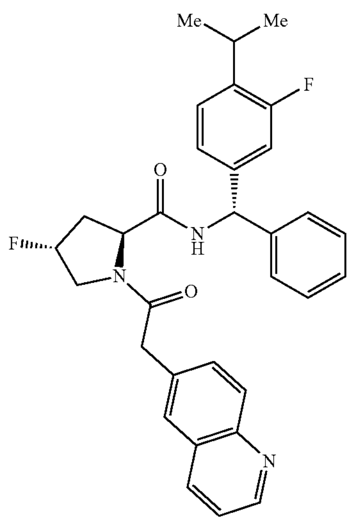 [SMILES: CC(C)c1ccc([C@@H](NC(=O)[C@@H]2C[C@@H](F)CN2C(=O)Cc2ccc3ncccc3c2)c2ccccc2)cc1F] | (2S,4R)-4-fluoro-N-[(S)-[3-fluoro-4-(propan-2-yl)phenyl](phenyl)methyl]-1-[2-(quinolin-6-yl)acetyl]pyrrolidine-2-carboxamide | 527.2 | 528.1 |
| 358 | 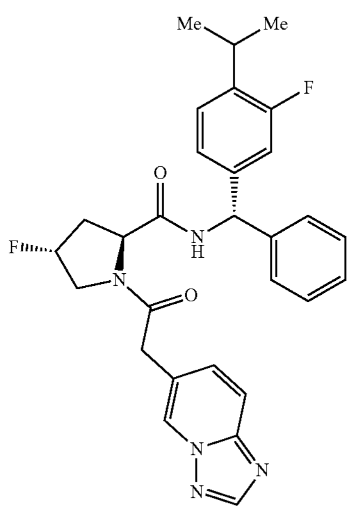 [SMILES: CC(C)c1ccc([C@@H](NC(=O)[C@@H]2C[C@@H](F)CN2C(=O)Cc2ccc3ncnn3c2)c2ccccc2)cc1F] | (2S,4R)-4-fluoro-N-[(S)-[3-fluoro-4-(propan-2-yl)phenyl](phenyl)methyl]-1-(2-{[1,2,4]triazolo[1,5-a]pyridin-6-yl}acetyl)pyrrolidine-2-carboxamide | 517.2 | 518.1 |
| 359 | 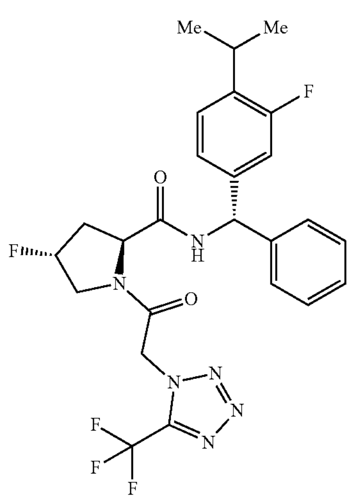 [SMILES: CC(C)c1ccc([C@@H](NC(=O)[C@@H]2C[C@@H](F)CN2C(=O)Cn2nnnc2C(F)(F)F)c2ccccc2)cc1F] | (2S,4R)-4-fluoro-N-[(S)-[3-fluoro-4-(propan-2-yl)phenyl[(phenyl)methyl]-1-{2-[5-(trifluoromethyl)-1H-1,2,3,4-tetrazol-1-yl]acetyl}pyrrolidine-2-carboxamide | 536.2 | 559.2 [M + Na]+ |

TABLE T-4-continued

| Compound No. | Structure | IUPAC | Exact mass (g/mol) | LCMS, Found [M + H]+ |
|---|---|---|---|---|
| 360 | 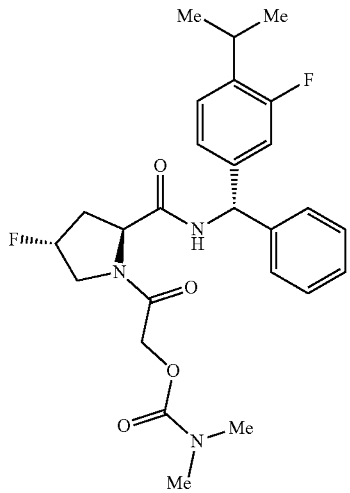 [SMILES: CC(C)c1ccc([C@@H](NC(=O)[C@@H]2C[C@@H](F)CN2C(=O)COC(=O)N(C)C)c2ccccc2)cc1F] | 2-[(2S,4R)-4-fluoro-2-{[(S)-[3-fluoro-4-(propan-2-yl)phenyl](phenyl)methyl]carbamoyl}pyrrolidin-1-yl]-2-oxoethyl N,N-dimethylcarbamate | 487.2 | 488.1 |
| 361 | 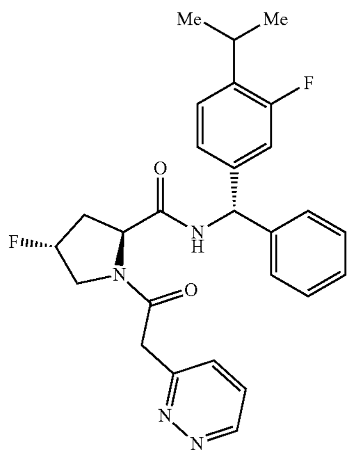 | (2S,4R)-1-{2-[(dimethylcarbamoyl)amino]acetyl}-4-fluoro-N-[(S)-[3-fluoro-4-(propan-2-yl)phenyl](phenyl)methyl]pyrrolidine-2-carboxamide | 486.2 | 487.1 |
| 362 | 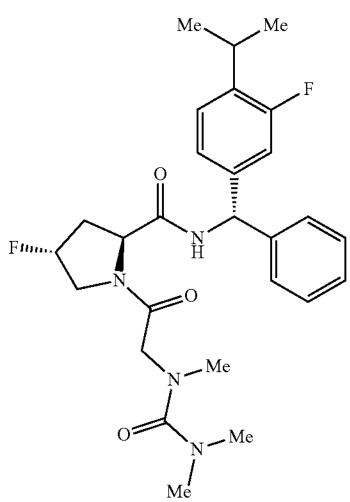 [SMILES: CC(C)c1ccc([C@@H](NC(=O)[C@@H]2C[C@@H](F)CN2C(=O)CN(C)C(=O)N(C)C)c2ccccc2)cc1F] | (2S,4R)-1-{2-[(dimethylcarbamoyl)(methyl)amino]acetyl}-4-fluoro-N-[(S)-[3-fluoro-4-(propan-2-yl)phenyl](phenyl)methyl]pyrrolidine-2-carboxamide | 500.3 | 501.2 |

TABLE T-4-continued
| Compound No. | Structure | IUPAC | Exact mass (g/mol) | LCMS, Found [M + H]+ |
|---|---|---|---|---|
| 363 | 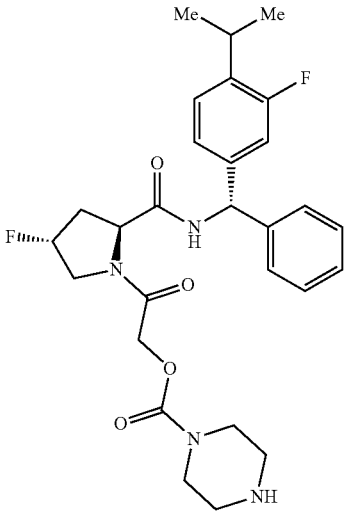 [SMILES: CC(C)c1ccc([C@@H](NC(=O)[C@@H]2C[C@@H](F)CN2C(=O)COC(=O)N2CCNCC2)c2ccccc2)cc1F] | 2-[(2S,4R)-4-fluoro-2-{[(S)-[3-fluoro-4-(propan-2-yl)phenyl](phenyl)methyl]carbamoyl}pyrrolidin-1-yl]-2-oxoethyl piperazine-1-carboxylate | 528.3 | 529.3 |
| 364 | 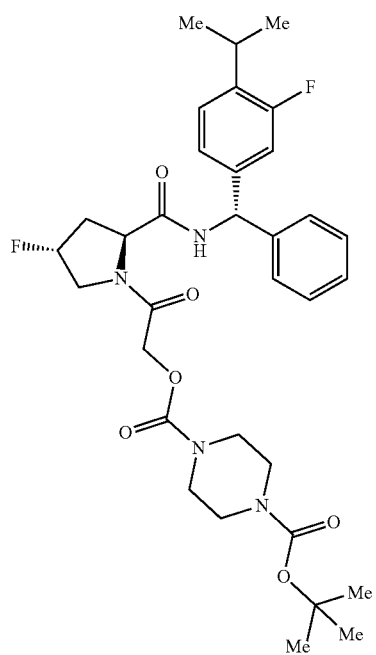 [SMILES: CC(C)c1ccc([C@@H](NC(=O)[C@@H]2C[C@@H](F)CN2C(=O)COC(=O)N2CCN(C(=O)OC(C)(C)C)CC2)c2ccccc2)cc1F] | 1-tert-butyl 4-{2-[(2S,4R)-4-fluoro-2-{[(S)-[3-fluoro-4-(propan-2-yl)phenyl](phenyl)methyl]carbamoyl}pyrrolidin-1-yl]-2-oxoethyl} piperazine-1,4-dicarboxylate | 628.3 | 529.3 [M − Boc + 1]+ |

TABLE T-4-continued

| Compound No. | Structure | IUPAC | Exact mass (g/mol) | LCMS, Found [M + H]⁺ |
|---|---|---|---|---|
| 365 | 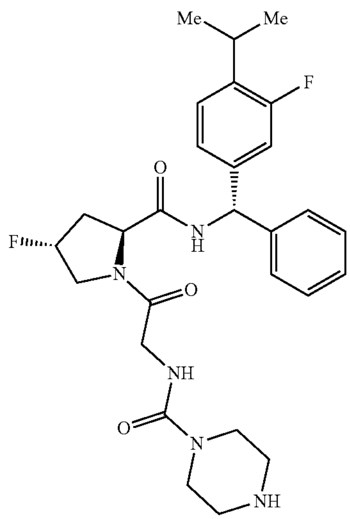 [SMILES: CC(C)c1ccc([C@@H](NC(=O)[C@@H]2C[C@@H](F)CN2C(=O)CNC(=O)N2CCNCC2)c2ccccc2)cc1F] | N-{2-[(2S,4R)-4-fluoro-2-{[(S)-[3-fluoro-4-(propan-2-yl)phenyl](phenyl)methyl]carbamoyl}pyrrolidin-1-yl]-2-oxoethyl}piperazine-1-carboxamide | 527.3 | 528.1 |
| 366 | 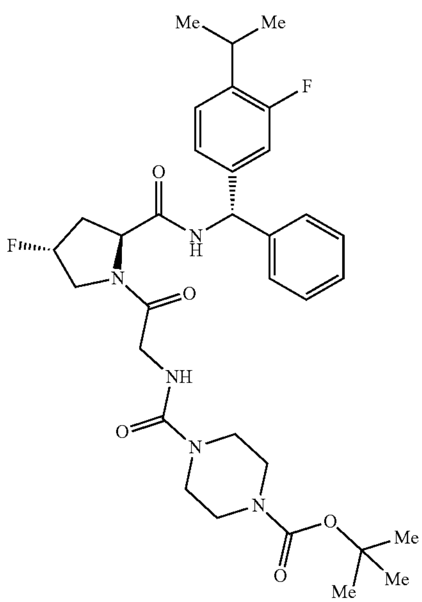 [SMILES: CC(C)c1ccc([C@@H](NC(=O)[C@@H]2C[C@@H](F)CN2C(=O)CNC(=O)N2CCN(C(=O)OC(C)(C)C)CC2)c2ccccc2)cc1F] | tert-butyl 4-({2-[(2S,4R)-4-fluoro-2-{[(S)-[3-fluoro-4-(propan-2-yl)phenyl](phenyl)methyl]carbamoyl}pyrrolidin-1-yl]-2-oxoethyl}carbamoyl)piperazine-1-carboxylate | 627.3 | 628.3 |
| 367 | 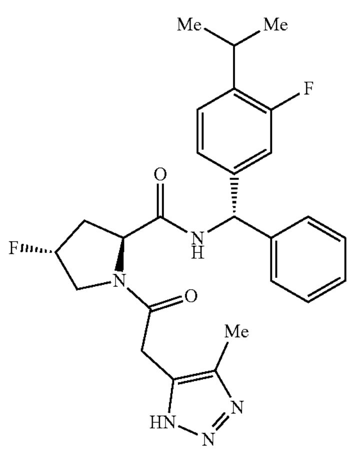 [SMILES: Cc1nn[nH]c1CC(=O)N1C[C@H](F)C[C@H]1C(=O)N[C@@H](c1ccccc1)c1ccc(C(C)C)c(F)c1] | (2S,4R)-4-fluoro-N-[(S)-[3-fluoro-4-(propan-2-yl)phenyl](phenyl)methyl]-1-[2-(4-methyl-1H-1,2,3-triazol-5-yl)acetyl]pyrrolidine-2-carboxamide | 481.2 | 482.2 |

TABLE T-4-continued

| Compound No. | Structure | IUPAC | Exact mass (g/mol) | LCMS, Found [M + H]+ |
|---|---|---|---|---|
| 368 | 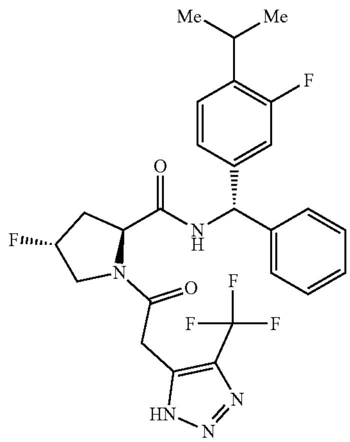 | (2S,4R)-4-fluoro-N-[(S)-[3-fluoro-4-(propan-2-yl)phenyl](phenyl)methyl]-1-{2-[4-(trifluoromethyl)-1H-1,2,3-triazol-5-yl]acetyl}pyrrolidine-2-carboxamide | 535.2 | 536.3 |
| 369 | 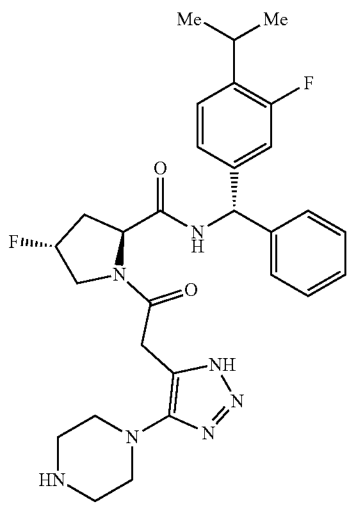 | (2S,4R)-4-fluoro-N-[(S)-[3-fluoro-4-(propan-2-yl)phenyl](phenyl)methyl]-1-{2-[4-(piperazin-1-yl)-1H-1,2,3-triazol-5-yl]acetyl}pyrrolidine-2-carboxamide | 551.3 | 552.3 |
| 370 | 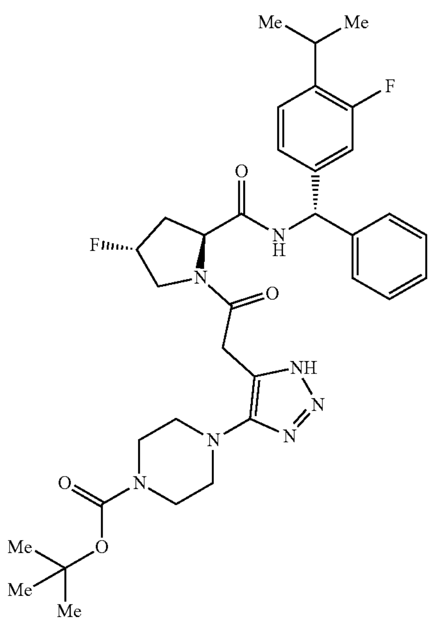 [SMILES: CC(C)c1ccc([C@@H](NC(=O)[C@@H]2C[C@@H](F)CN2C(=O)Cc2[nH]nnc2N2CCN(C(=O)OC(C)(C)C)CC2)c2ccccc2)cc1F] | tert-butyl 4-(5-{2-[(2S,4R)-4-fluoro-2-{[(S)-[3-fluoro-4-(propan-2-yl)phenyl](phenyl)methyl]carbamoyl}pyrrolidin-1-yl]-2-oxoethyl}-1H-1,2,3-triazol-4-yl)piperazine-1-carboxylate | 651.3 | 652.4 |

TABLE T-4-continued

| Compound No. | Structure | IUPAC | Exact mass (g/mol) | LCMS, Found [M + H]+ |
|---|---|---|---|---|
| 371 | 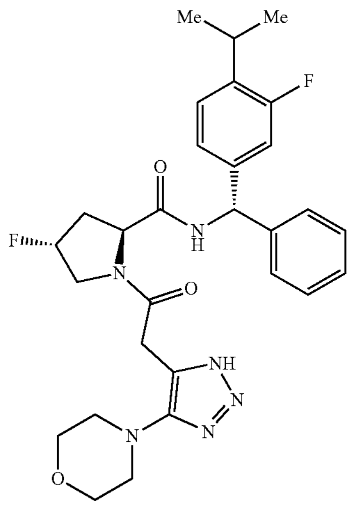 [SMILES: CC(C)c1ccc([C@@H](NC(=O)[C@@H]2C[C@@H](F)CN2C(=O)Cc2[nH]nnc2N2CCOCC2)c2ccccc2)cc1F] | (2S,4R)-4-fluoro-N-[(S)-[3-fluoro-4-(propan-2-yl)phenyl](phenyl)methyl]-1-{2-[4-(morpholin-4-yl)-1H-1,2,3-triazol-5-yl]acetyl}pyrrolidine-2-carboxamide | 552.3 | 553.3 |
| 372 | 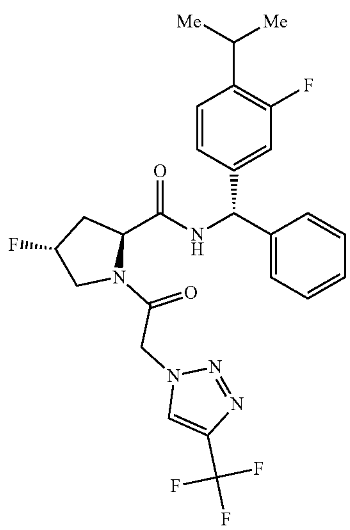 [SMILES: CC(C)c1ccc([C@@H](NC(=O)[C@@H]2C[C@@H](F)CN2C(=O)Cn2cc(C(F)(F)F)nn2)c2ccccc2)cc1F] | (2S,4R)-4-fluoro-N-[(S)-[3-fluoro-4-(propan-2-yl)phenyl](phenyl)methyl]-1-{2-[4-(trifluoromethyl)-1H-1,2,3-triazol-1-yl]acetyl}pyrrolidine-2-carboxamide | 535.2 | 558.0 [M + Na]+ |
| 373 | 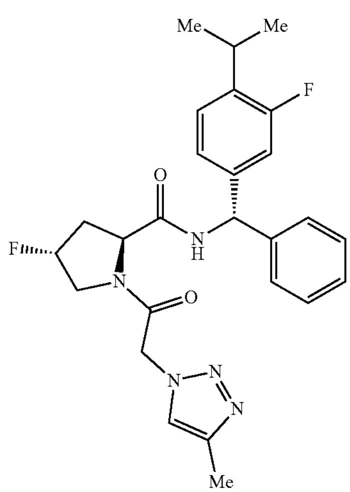 [SMILES: Cc1cn(CC(=O)N2C[C@H](F)C[C@H]2C(=O)N[C@@H](c2ccccc2)c2ccc(C(C)C)c(F)c2)nn1] | (2S,4R)-4-fluoro-N-[(S)-[3-fluoro-4-(propan-2-yl)phenyl](phenyl)methyl]-1-[2-(4-methyl-1H-1,2,3-triazol-1-yl)acetyl]pyrrolidine-2-carboxamide | 481.2 | 482.2 |

TABLE T-4-continued

| Compound No. | Structure | IUPAC | Exact mass (g/mol) | LCMS, Found [M + H]+ |
|---|---|---|---|---|
| 374 | 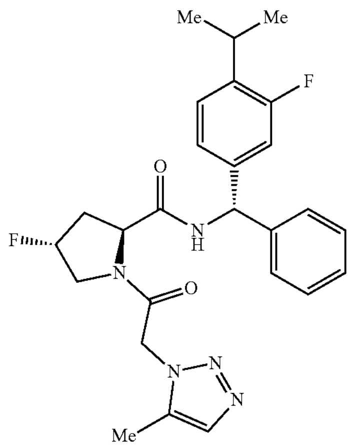 [SMILES: Cc1cnnn1CC(=O)N1C[C@H](F)C[C@H]1C(=O)N[C@@H](c1ccccc1)c1ccc(C(C)C)c(F)c1] | (2S,4R)-4-fluoro-N-[(S)-[3-fluoro-4-(propan-2-yl)phenyl](phenyl)methyl]-1-[2-(5-methyl-1H-1,2,3-triazol-1-yl)acetyl]pyrrolidine-2-carboxamide | 481.2 | 482.2 |
| 375 | 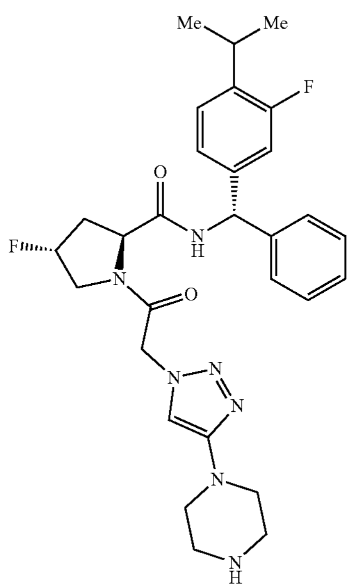 [SMILES: CC(C)c1ccc([C@@H](NC(=O)[C@@H]2C[C@@H](F)CN2C(=O)Cn2cc(N3CCNCC3)nn2)c2ccccc2)cc1F] | (2S,4R)-4-fluoro-N-[(S)-[3-fluoro-4-(propan-2-yl)phenyl](phenyl)methyl]-1-{2-[4-(piperazin-1-yl)-1H-1,2,3-triazol-1-yl]acetyl}pyrrolidine-2-carboxamide | 551.3 | 552.3 |

TABLE T-4-continued

| Compound No. | Structure | IUPAC | Exact mass (g/mol) | LCMS, Found [M + H]+ |
|---|---|---|---|---|
| 376 | 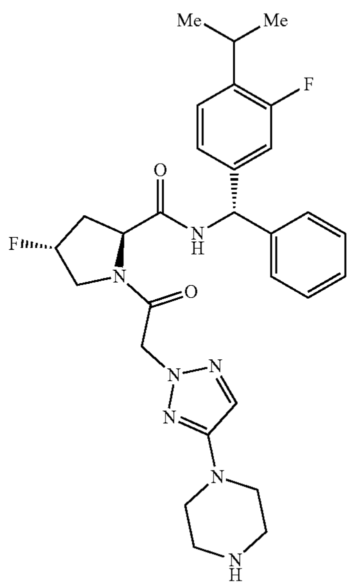 [SMILES: CC(C)c1ccc([C@@H](NC(=O)[C@@H]2C[C@@H](F)CN2C(=O)Cn2ncc(N3CCNCC3)n2)c2ccccc2)cc1F] | (2S,4R)-4-fluoro-N-[(S)-[3-fluoro-4-(propan-2-yl)phenyl](phenyl)methyl]-1-{2-[4-(piperazin-1-yl)-2H-1,2,3-triazol-2-yl]acetyl}pyrrolidine-2-carboxamide | 551.3 | 552.3 |
| 377 | 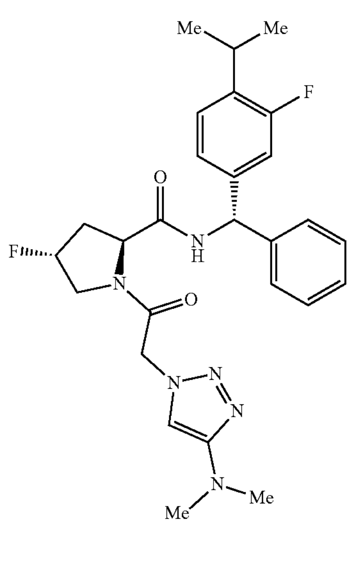 | (2S,4R)-1-{2-[4-(dimethylamino)-1H-1,2,3-triazol-1-yl]acetyl}-4-fluoro-N-[(S)-[3-fluoro-4-(propan-2-yl)phenyl](phenyl)methyl]pyrrolidine-2-carboxamide | 510.3 | 511.2 |

TABLE T-4-continued

| Compound No. | Structure | IUPAC | Exact mass (g/mol) | LCMS, Found [M + H]+ |
|---|---|---|---|---|
| 378 | 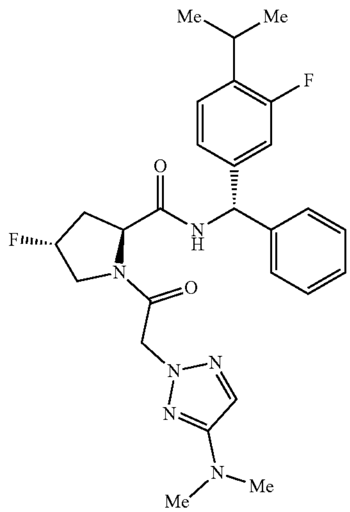 [SMILES: CC(C)c1ccc([C@@H](NC(=O)[C@@H]2C[C@@H](F)CN2C(=O)Cn2ncc(N(C)C)n2)c2ccccc2)cc1F] | (2S,4R)-1-{2-[4-(dimethylamino)-2H-1,2,3-triazol-2-yl]acetyl}-4-fluoro-N-[(S)-[3-fluoro-4-(propan-2-yl)phenyl](phenyl)methyl]pyrrolidine-2-carboxamide | 510.3 | 511.2 |
| 379 | 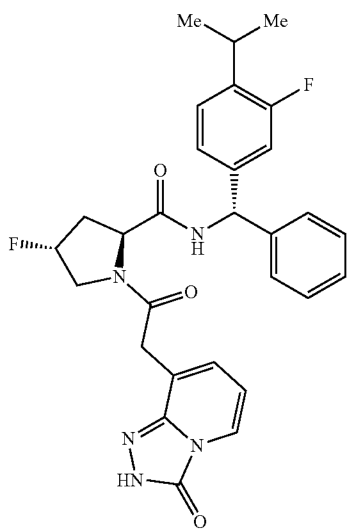 [SMILES: CC(C)c1ccc([C@@H](NC(=O)[C@@H]2C[C@@H](F)CN2C(=O)Cc2cccn3c(=O)[nH]nc23)c2ccccc2)cc1F] | (2S,4R)-4-fluoro-N-[(S)-[3-fluoro-4-(propan-2-yl)phenyl](phenyl)methyl]-1-(2-{3-oxo-2H,3H-[1,2,4]triazolo[4,3-a]pyridin-8-yl}acetyl)pyrrolidine-2-carboxamide | 533.2 | 534.2 |
| 380 | 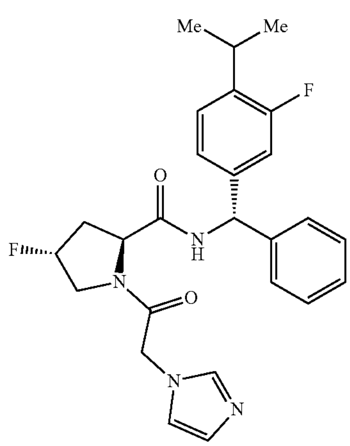 [SMILES: CC(C)c1ccc([C@@H](NC(=O)[C@@H]2C[C@@H](F)CN2C(=O)Cn2ccnc2)c2ccccc2)cc1F] | (2S,4R)-4-fluoro-N-[(S)-[3-fluoro-4-(propan-2-yl)phenyl](phenyl)methyl]-1-[2-(1H-imidazol-1-yl)acetyl]pyrrolidine-2-carboxamide | 466.2 | 467.2 |

TABLE T-4-continued

| Compound No. | Structure | IUPAC | Exact mass (g/mol) | LCMS, Found [M + H]+ |
|---|---|---|---|---|
| 381 | 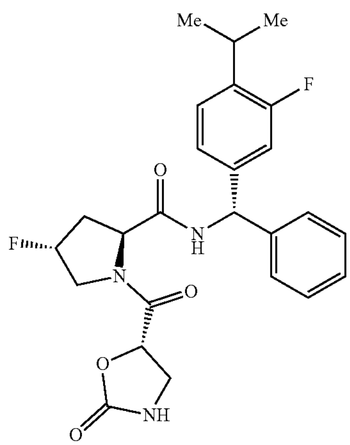 [SMILES: CC(C)c1ccc([C@@H](NC(=O)[C@@H]2C[C@@H](F)CN2C(=O)[C@@H]2CNC(=O)O2)c2ccccc2)cc1F] | (2S,4R)-4-fluoro-N-[(S)-[3-fluoro-4-(propan-2-yl)phenyl](phenyl)methyl]-1-[(5S)-2-oxo-1,3-oxazolidine-5-carbonyl]pyrrolidine-2-carboxamide | 471.2 | 489.2 [M + NH4]+ |
| 382 | 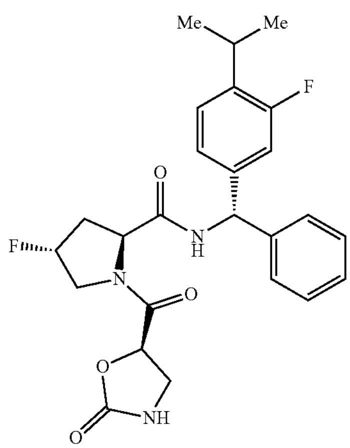 [SMILES: CC(C)c1ccc([C@@H](NC(=O)[C@@H]2C[C@@H](F)CN2C(=O)[C@H]2CNC(=O)O2)c2ccccc2)cc1F] | (2S,4R)-4-fluoro-N-[(S)-[3-fluoro-4-(propan-2-yl)phenyl](phenyl)methyl]-1-[(5R)-2-oxo-1,3-oxazolidine-5-carbonyl]pyrrolidine-2-carboxamide | 471.2 | 472.2 |
| 383 | 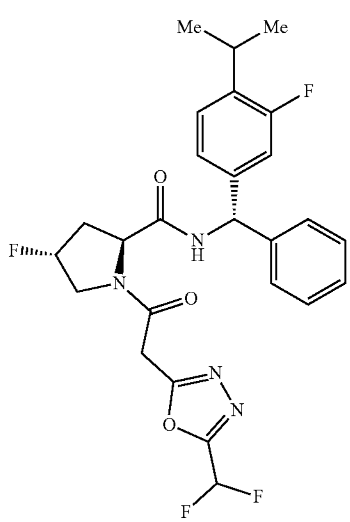 [SMILES: CC(C)c1ccc([C@@H](NC(=O)[C@@H]2C[C@@H](F)CN2C(=O)Cc2nnc(C(F)F)o2)c2ccccc2)cc1F] | (2S,4R)-1-{2-[5-(difluoromethyl)-1,3,4-oxadiazol-2-yl]acetyl}-4-fluoro-N-[(S)-[3-fluoro-4-(propan-2-yl)phenyl](phenyl)methyl] pyrrolidine-2-carboxamide | 518.2 | 519.1 |

TABLE T-4-continued

| Compound No. | Structure | IUPAC | Exact mass (g/mol) | LCMS, Found [M + H]+ |
|---|---|---|---|---|
| 384 | 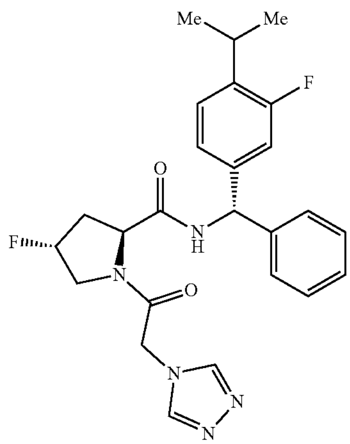 [SMILES: CC(C)c1ccc([C@@H](NC(=O)[C@@H]2C[C@@H](F)CN2C(=O)Cn2cnnc2)c2ccccc2)cc1F] | (2S,4R)-4-fluoro-N-[(S)-[3-fluoro-4-(propan-2-yl)phenyl](phenyl)methyl]-1-[2-(4H-1,2,4-triazol-4-yl)acetyl]pyrrolidine-2-carboxamide | 467.2 | 467.9 |
| 765 | 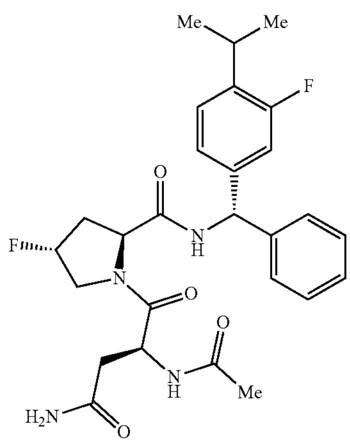 [SMILES: CC(=O)N[C@@H](CC(N)=O)C(=O)N1C[C@H](F)C[C@H]1C(=O)N[C@@H](c1ccccc1)c1ccc(C(C)C)c(F)c1] | (2S,4R)-1-[(2S)-3-carbamoyl-2-acetamidopropanoyl]-4-fluoro-N-[(S)-[3-fluoro-4-(propan-2-yl)phenyl](phenyl)methyl]pyrrolidine-2-carboxamide | 514.2 | 515.2 |
| 766 | 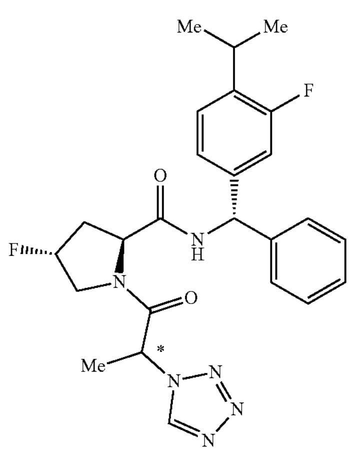 [SMILES: CC(C)c1ccc([C@@H](NC(=O)[C@@H]2C[C@@H](F)CN2C(=O)C(C)n2cnnn2)c2ccccc2)cc1F] | (2S,4R)-4-fluoro-N-[(S)-[3-fluoro-4-(propan-2-yl)phenyl](phenyl)methyl]-1-[(2R) or (2S)-2-(1H-1,2,3,4-tetrazol-1-yl)propanoyl]pyrrolidine-2-carboxamide (column: DAICEL CHIRALPAK AD-3, second-eluting isomer) | 482.2 | 483.2 |

TABLE T-4-continued

| Compound No. | Structure | IUPAC | Exact mass (g/mol) | LCMS, Found [M + H]+ |
|---|---|---|---|---|
| 767 | 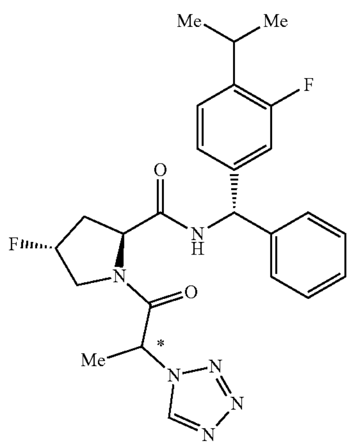 [SMILES: CC(C)c1ccc([C@@H](NC(=O)[C@@H]2C[C@@H](F)CN2C(=O)C(C)n2cnnn2)c2ccccc2)cc1F] | (2S,4R)-4-fluoro-N-[(S)-[3-fluoro-4-(propan-2-yl)phenyl](phenyl)methyl]-1-[(2S) or (2R)-2-(1H-1,2,3,4-tetrazol-1-yl)propanoyl]pyrrolidine-2-carboxamide (column: DAICEL CHIRALPAK AD-3, first-eluting isomer) | 482.2 | 483.2 |
| 768 | 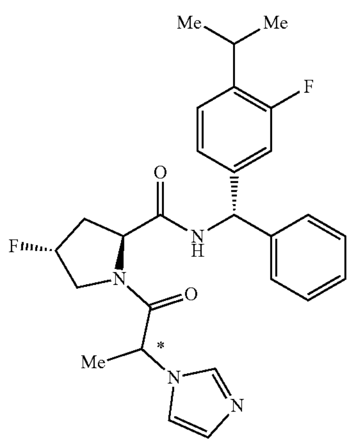 [SMILES: CC(C)c1ccc([C@@H](NC(=O)[C@@H]2C[C@@H](F)CN2C(=O)C(C)n2ccnc2)c2ccccc2)cc1F] | (2S,4R)-4-fluoro-N-[(S)-[3-fluoro-4-(propan-2-yl)phenyl](phenyl)methyl]-1-[(2R) or (2S)-2-(1H-imidazol-1-yl)propanoyl]pyrrolidine-2-carboxamide (column: DAICEL CHIRALPAK IG-3, first-eluting isomer) | 480.2 | 481.2 |
| 769 | 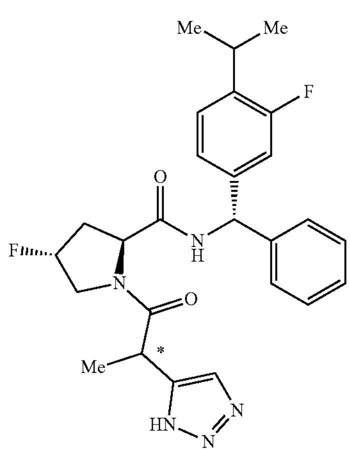 | (2S,4R)-4-fluoro-N-[(S)-[3-fluoro-4-(propan-2-yl)phenyl](phenyl)methyl]-1-[(2R) or (2S)-2-(1H-1,2,3-triazol-5-yl)propanoyl]pyrrolidine-2-carboxamide (column: Phenomenex Luna C18, first-eluting isomer) | 481.2 | 482.1 |

TABLE T-4-continued

| Compound No. | Structure | IUPAC | Exact mass (g/mol) | LCMS, Found [M + H]+ |
|---|---|---|---|---|
| 770 | 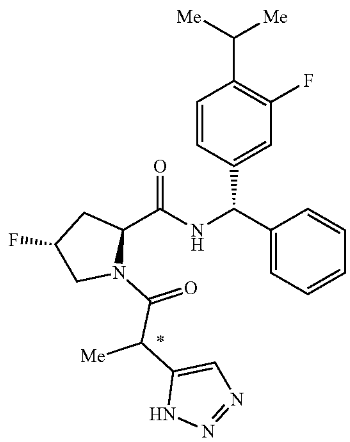 | (2S,4R)-4-fluoro-N-[(S)-[3-fluoro-4-(propan-2-yl)phenyl](phenyl)methyl]-1-[(2S) or (2R)-2-(1H-1,2,3-triazol-5-yl)propanoyl]pyrrolidine-2-carboxamide (column: Phenomenex Luna C18, second-eluting isomer) | 481.2 | 482.1 |
| 771 | 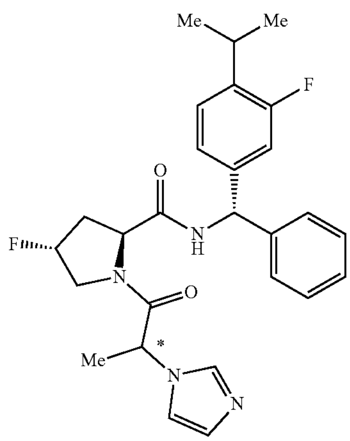 [SMILES: CC(C)c1ccc([C@@H](NC(=O)[C@@H]2C[C@@H](F)CN2C(=O)C(C)n2ccnc2)c2ccccc2)cc1F] | (2S,4R)-4-fluoro-N-[(S)-[3-fluoro-4-(propan-2-yl)phenyl](phenyl)methyl]-1-[(2S) or (2R)-2-(1H-imidazol-1-yl)propanoyl]pyrrolidine-2-carboxamide (column: DAICEL CHIRALPAK IG-3, second-eluting isomer) | 480.2 | 481.2 |
| 772 | 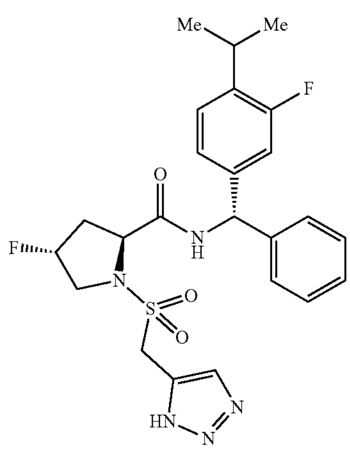 [SMILES: CC(C)c1ccc([C@@H](NC(=O)[C@@H]2C[C@@H](F)CN2S(=O)(=O)Cc2cnn[nH]2)c2ccccc2)cc1F] | (2S,4R)-4-fluoro-N-[(S)-[3-fluoro-4-(propan-2-yl)phenyl](phenyl)methyl]-1-[(1H-1,2,3-triazol-5-yl)methanesulfonyl]pyrrolidine-2-carboxamide | 503.2 | 504.1 |

TABLE T-4-continued

| Compound No. | Structure | IUPAC | Exact mass (g/mol) | LCMS, Found [M + H]+ |
|---|---|---|---|---|
| 773 | 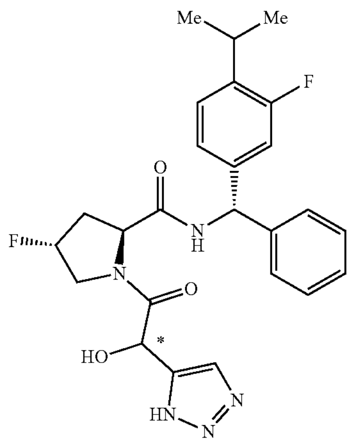 | (2S,4R)-4-fluoro-N-[(S)-[3-fluoro-4-(propan-2-yl)phenyl](phenyl)methyl]-1-[(2R) or (2S)-2-hydroxy-2-(1H-1,2,3-triazol-5-yl)acetyl]pyrrolidine-2-carboxamide (column: DAICEL CHIRALPAK AD-3, first-eluting isomer) | 483.2 | 484.2 |
| 774 | 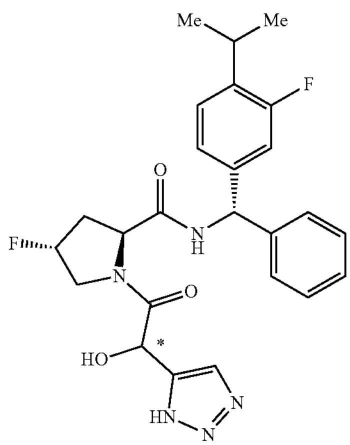 | (2S,4R)-4-fluoro-N-[(S)-[3-fluoro-4-(propan-2-yl)phenyl](phenyl)methyl]-1-[(2S) or (2R)-2-hydroxy-2-(1H-1,2,3-triazol-5-yl)acetyl]pyrrolidine-2-carboxamide (column: DAICEL CHIRALPAK AD-3, second-eluting isomer) | 483.2 | 484.2 |
| 775 | 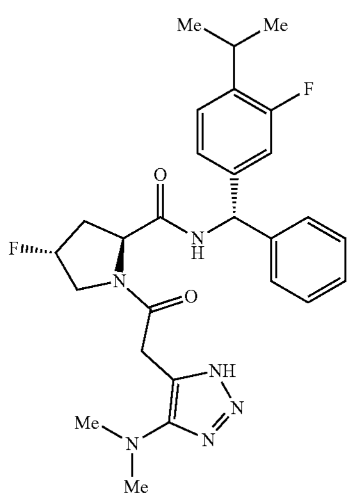 [SMILES: CC(C)c1ccc([C@@H](NC(=O)[C@@H]2C[C@@H](F)CN2C(=O)Cc2[nH]nnc2N(C)C)c2ccccc2)cc1F] | (2S,4R)-1-{2-[4-(dimethylamino)-1H-1,2,3-triazol-5-yl]acetyl}-4-fluoro-N-[(S)-[3-fluoro-4-(propan-2-yl)phenyl](phenyl)methyl]pyrrolidine-2-carboxamide | 510.3 | 511.3 |

Example S-5: Synthesis of (2S,4R)-1-(2-(1H-1,2,3-triazol-5-yl)acetyl)-4-fluoro-N—((S)-(6-fluoro-5-isopropylpyridin-2-yl)(phenyl)methyl)pyrrolidine-2-carboxamide Compound 385

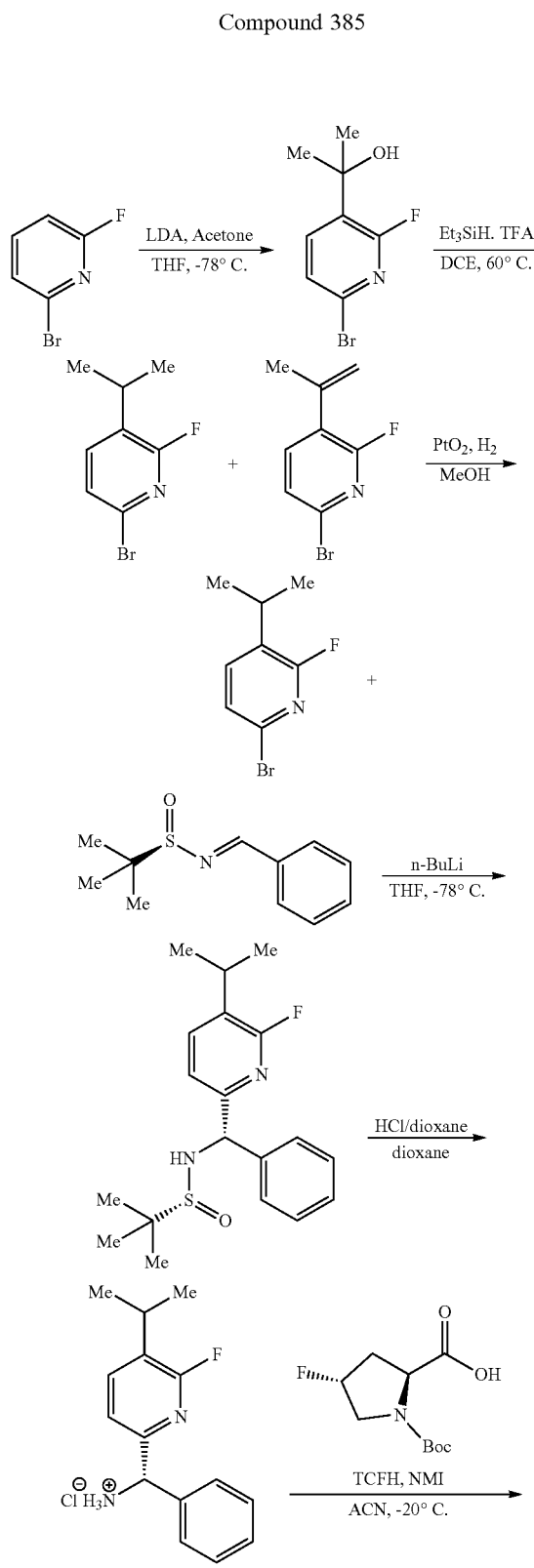

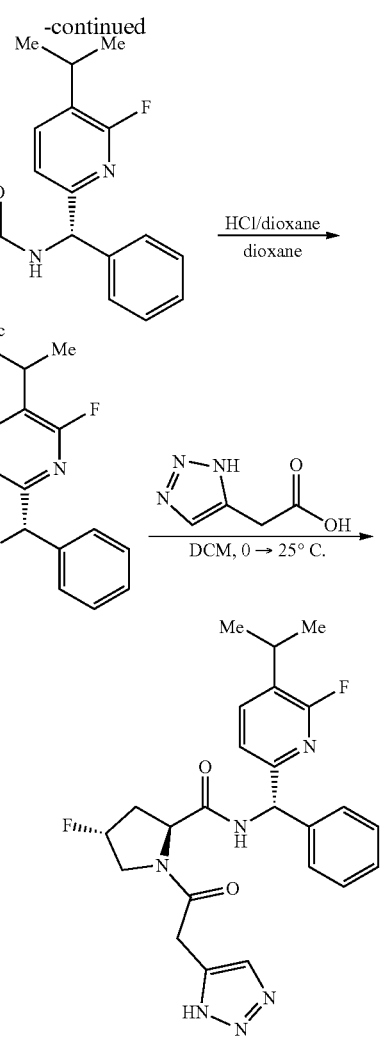

Step a: To a solution of 2-bromo-6-fluoropyridine (50 g, 284 mmol, 1 eq) in THF (500 mL) at −78° C. was added LDA (2 M in THF, 142 mL, 1 eq) in a dropwise manner. The resulting mixture was stirred at −78° C. for 30 min. To this mixture was added acetone (24.7 g, 426 mmol, 1.5 eq) in a dropwise manner, and the resulting reaction mixture was stirred at −78° C. for 1.5 h. The reaction mixture was then cooled to 0° C. and quenched by dropwise addition of water (500 mL), and the resulting mixture was extracted with EtOAc (2×500 mL). The combined organic extracts were washed with brine (2×200 mL), dried over anhydrous $Na_2SO_4$, filtered, and concentrated under reduced pressure. The resulting crude residue was purified by column chromatography to give 2-(6-bromo-2-fluoropyridin-3-yl)propan-2-ol. LC-MS (ESI): m/z: $[M+H]^+$ calculated for $C_8H_9BrFNO$: 234.0; found 234.0.

Step b: To a solution of 2-(6-bromo-2-fluoropyridin-3-yl)propan-2-ol (60 g, 256 mmol, 1 eq) in DCE (500 mL) at 25° C. was added $Et_3SiH$ (149 g, 1.28 mol, 5 eq) and TFA (292 g, 2.56 mol, 10 eq). The reaction mixture was then warmed to 60° C. and stirred for 15 h. After cooling, the mixture was concentrated under reduced pressure. The resulting residue was poured into ice-water (300 mL) and adjusted to pH=7 by addition of saturated aqueous $Na_2CO_3$ solution. The resulting biphasic mixture was extracted with EtOAc (3×500 mL). The combined organic extracts were washed with brine (3×300 mL), dried over anhydrous Na$_2$SO$_4$, and filtered. The filtrate was then concentrated under reduced pressure, and the resulting crude residue was purified by column chromatography to give a mixture of 6-bromo-2-fluoro-3-isopropylpyridine and 6-bromo-2-fluoro-3-(prop-1-en-2-yl)pyridine. LC-MS (ESI): m/z: [M+H]$^+$ calculated for C$_8$H$_9$BrFN: 218.0; found 218.1. [M+H]$^+$ calculated for C$_8$H$_7$BrFN: 216.0; found 215.9.

Step c: To a solution of 6-bromo-2-fluoro-3-isopropylpyridine and 6-bromo-2-fluoro-3-(prop-1-en-2-yl)pyridine (58 g, crude) in MeOH (500 mL) at 25° C. was added PtO$_2$ (4.17 g, 18.3 mmol). The resulting mixture was degassed and purged with H$_2$. The reaction mixture was then stirred at 25° C. under H$_2$ atmosphere (50 psi) for 12 h. The reaction mixture was then filtered through a pad of Celite, and the filter cake was washed with MeOH (2×200 mL). The combined filtrate was concentrated under reduced pressure, and the resulting crude residue was purified by column chromatography to give 6-bromo-2-fluoro-3-isopropylpyridine. LC-MS (ESI): m/z: [M+H]$^+$ calculated for C$_8$H$_9$BrFN: 218.0; found 218.1.

Step d: To a solution of 6-bromo-2-fluoro-3-isopropylpyridine (32.0 g, 146 mmol, 1 eq) in THF (250 mL) at −78° C. was added n-BuLi (2.5 M in hexane, 88.0 mL, 1.5 eq) in a dropwise manner. The resulting mixture was stirred at −78° C. for 30 min. To this mixture was added (R,E)-N-benzylidene-2-methylpropane-2-sulfinamide (30.7 g, 146 mmol, 1 eq) as a solution in THF (250 mL) in a dropwise manner. The resulting mixture was then stirred at −78° C. for 4 h. The reaction mixture was then poured into ice-water (500 mL) and extracted with EtOAc (3×500 mL). The combined organic extracts were washed with brine (300 mL), dried over anhydrous Na$_2$SO$_4$, filtered, and concentrated under reduced pressure. The resulting crude residue was purified by column chromatography followed by prep-HPLC to give (R)—N—((S)-(6-fluoro-5-isopropylpyridin-2-yl)(phenyl)methyl)-2-methylpropane-2-sulfinamide. LC-MS (ESI): m/z: [M+H]$^+$ calculated for C$_{19}$H$_{25}$FN$_2$OS: 349.2; found 349.2.

Step e: To a solution of (R)—N—((S)-(6-fluoro-5-isopropylpyridin-2-yl)(phenyl)methyl)-2-methylpropane-2-sulfinamide (12.0 g, 34.4 mmol, 1 eq) in dioxane (10 mL) at 0° C. was added HCl/dioxane (4 M, 500 mL). The reaction mixture was warmed to 25° C. and stirred for 2 h. The reaction mixture was concentrated under reduced pressure to give (S)-(6-fluoro-5-isopropylpyridin-2-yl)(phenyl)methanaminium chloride, which was used in the next step without further purification. LC-MS (ESI): m/z: [M+H]$^+$ calculated for C$_{15}$H$_{17}$FN$_2$: 245.1; found 245.2.

Step f: To a mixture of (S)-(6-fluoro-5-isopropylpyridin-2-yl)(phenyl)methanaminium chloride (11 g, crude, 1 eq) and (2S,4R)-1-(tert-butoxycarbonyl)-4-fluoropyrrolidine-2-carboxylic acid (10.0 g, 43.1 mmol, 1.1 eq) in CH$_3$CN (200 mL) at −20° C. was added 1-methylimidazole (NMI, 48.2 g, 587 mmol, 46.8 mL, 15 eq) and chloro-N,N,N,N-tetramethylformamidinium hexafluorophosphate (TCFH, 12.1 g, 43.1 mmol, 1.1 eq). The reaction mixture was then stirred at −20° C. for 2 h. The reaction mixture was then poured into H$_2$O (500 mL) and extracted with EtOAc (3×500 mL). The combined organic extracts were washed with brine (200 mL), dried over anhydrous Na$_2$SO$_4$, filtered, and concentrated under reduced pressure. The resulting crude residue was purified by column chromatography to give tert-butyl (2S,4R)-4-fluoro-2-(((S)-(6-fluoro-5-isopropylpyridin-2-yl)(phenyl)methyl)carbamoyl)pyrrolidine-1-carboxylate. LC-MS (ESI): m/z: [M+H]$^+$ calculated for C$_{25}$H$_{31}$F$_2$N$_3$O$_3$: 460.2; found 460.2.

Step g: To a solution of tert-butyl (2S,4R)-4-fluoro-2-(((S)-(6-fluoro-5-isopropylpyridin-2-yl)(phenyl)methyl)carbamoyl)pyrrolidine-1-carboxylate (14.0 g, 30.4 mmol, 1 eq) in dioxane (50 mL) at 25° C. was added HCl/dioxane (4 M, 300 mL, 45.9 eq), and the resulting mixture was stirred at 25° C. for 2 h. The reaction mixture was then concentrated under reduced pressure to give (2S,4R)-4-fluoro-N—((S)-(6-fluoro-5-isopropylpyridin-2-yl)(phenyl)methyl)pyrrolidine-2-carboxamide hydrochloride. LC-MS (ESI): m/z: [M+H]$^+$ calculated for C$_{20}$H$_{23}$F$_2$N$_3$O: 360.2; found 360.1.

Step h: To a mixture of (2S,4R)-4-fluoro-N—((S)-(6-fluoro-5-isopropylpyridin-2-yl)(phenyl)methyl)pyrrolidine-2-carboxamide hydrochloride (8 g, 22.2 mmol, 1 eq) and 2-(1H-1,2,3-triazol-5-yl)acetic acid (Intermediate A-1, 3.39 g, 26.7 mmol, 1.2 eq) in DCM (200 mL) at 0° C. was added 1-methylimidazole (NMI, 27.4 g, 333 mmol, 15 eq) and T3P (17.0 g, 26.7 mmol, 15.8 mL, 50% in EtOAc, 1.2 eq). The reaction mixture was then warmed to 25° C. and stirred for 12 h. The reaction mixture was then poured into H$_2$O (200 mL) and extracted with EtOAc (3×200 mL). The combined organic extracts were washed with brine (100 mL), dried over anhydrous Na$_2$SO$_4$, filtered, and concentrated under reduced pressure. The resulting crude residue was purified by column chromatography followed by prep-HPLC to give (2S,4R)-1-(2-(1H-1,2,3-triazol-5-yl)acetyl)-4-fluoro-N—((S)-(6-fluoro-5-isopropylpyridin-2-yl)(phenyl)methyl)pyrrolidine-2-carboxamide. $^1$H NMR (3:1 rotamer ratio, asterisk denotes distinct minor rotamer peaks, obscured peaks not reported, 400 MHz, DMSO-d$_6$) δ 14.71 (br s, 1H), 9.30*(d, J=7.8 Hz, 1H), 8.92 (d, J=8.1 Hz, 1H), 7.92-7.80 (m, 1H), 7.67 (s, 1H), 7.54*(s, 1H), 7.40-7.18 (m, 6H), 6.09*(d, J=7.8 Hz, 1H), 5.98 (d, J=8.1 Hz, 1H), 5.48-5.20 (m, 1H), 4.90*(t, J=8.0 Hz, 1H), 4.62 (t, J=8.3 Hz, 1H), 4.12-3.63 (m, 3H), 3.12-2.95 (m, 1H), 2.79-2.61*(m, 1H), 2.28-1.91 (m, 1H), 1.24-1.16 (m, 6H). LC-MS (ESI): m/z: [M+H]$^+$ calculated for C$_{24}$H$_{26}$F$_2$N$_6$O$_2$: 469.2; found 469.3.

The following compounds in Table T-5 were synthesized using procedures similar to Compound 385 using the appropriate starting materials.

TABLE T-5

| Compound No. | Structure | IUPAC | Exact mass (g/mol) | LCMS, Found [M + H]+ |
|---|---|---|---|---|
| 386 | 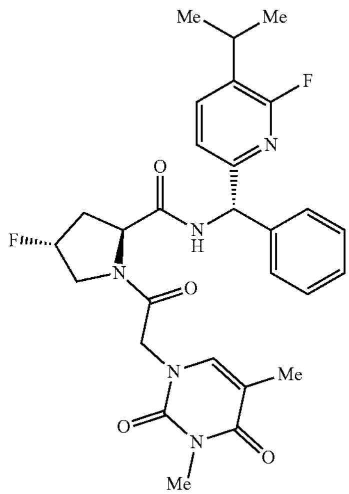 [SMILES: Cc1cn(CC(=O)N2C[C@H](F)C[C@H]2C(=O)N[C@@H](c2ccccc2)c2ccc(C(C)C)c(F)n2)c(=O)n(C)c1=O] | (2S,4R)-1-[2-(3,5-dimethyl-2,4-dioxo-1,2,3,4-tetrahydropyrimidin-1-yl)acetyl]-4-fluoro-N-[(S)-[6-fluoro-5-(propan-2-yl)pyridin-2-yl](phenyl)methyl]pyrrolidine-2-carboxamide | 539.2 | 540.1 |
| 387 | 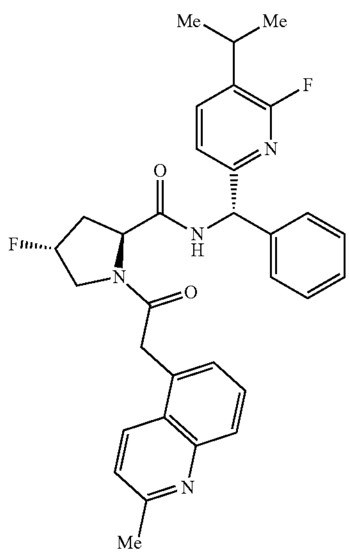 [SMILES: Cc1ccc2c(CC(=O)N3C[C@H](F)C[C@H]3C(=O)N[C@@H](c3ccccc3)c3ccc(C(C)C)c(F)n3)cccc2n1] | (2S,4R)-4-fluoro-N-[(S)-[6-fluoro-5-(propan-2-yl)pyridin-2-yl](phenyl)methyl]-1-[2-(2-methylquinolin-5-yl)acetyl]pyrrolidine-2-carboxamide | 542.2 | 543.2 |
| 388 | 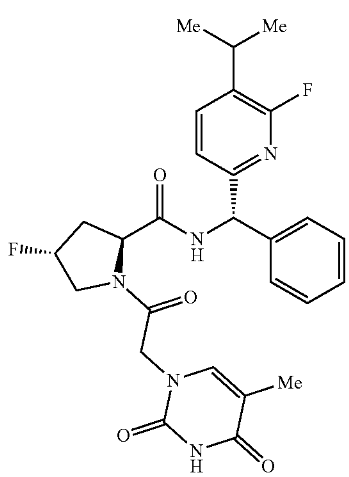 [SMILES: Cc1cn(CC(=O)N2C[C@H](F)C[C@H]2C(=O)N[C@@H](c2ccccc2)c2ccc(C(C)C)c(F)n2)c(=O)[nH]c1=O] | (2S,4R)-4-fluoro-N-[(S)-[6-fluoro-5-(propan-2-yl)pyridin-2-yl](phenyl)methyl]-1-[2-(5-methyl-2,4-dioxo-1,2,3,4-tetrahydropyrimidin-1-yl)acetyl]pyrrolidine-2-carboxamide | 525.2 | 526.3 |

TABLE T-5-continued

| Compound No. | Structure | IUPAC | Exact mass (g/mol) | LCMS, Found [M + H]+ |
| --- | --- | --- | --- | --- |
| 389 | 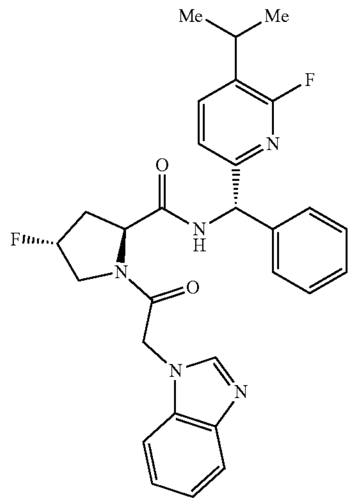 [SMILES: CC(C)c1ccc([C@@H](NC(=O)[C@@H]2C[C@@H](F)CN2C(=O)Cn2cnc3ccccc32)c2ccccc2)nc1F] | (2S,4R)-1-[2-(1H-1,3-benzodiazol-1-yl)acetyl]-4-fluoro-N-[(S)-[6-fluoro-5-(propan-2-yl)pyridin-2-yl](phenyl)methyl]pyrrolidine-2-carboxamide | 517.2 | 518.3 |
| 390 | 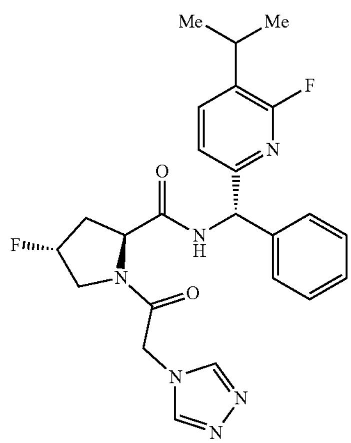 [SMILES: CC(C)c1ccc([C@@H](NC(=O)[C@@H]2C[C@@H](F)CN2C(=O)Cn2cnnc2)c2ccccc2)nc1F] | (2S,4R)-4-fluoro-N-[(S)-[6-fluoro-5-(propan-2-yl)pyridin-2-yl](phenyl)methyl]-1-[2-(4H-1,2,4-triazol-4-yl)acetyl]pyrrolidine-2-carboxamide | 468.2 | 469.2 |
| 391 | 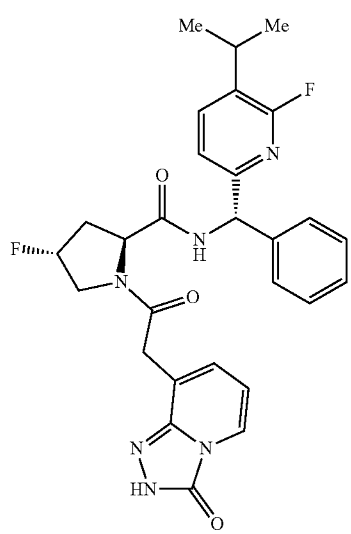 [SMILES: CC(C)c1ccc([C@@H](NC(=O)[C@@H]2C[C@@H](F)CN2C(=O)Cc2cccn3c(=O)[nH]nc23)c2ccccc2)nc1F] | (2S,4R)-4-fluoro-N-[(S)-[6-fluoro-5-(propan-2-yl)pyridin-2-yl](phenyl)methyl]-1-(2-{3-oxo-2H,3H-[1,2,4]triazolo[4,3-a]pyridin-8-yl}acetyl)pyrrolidine-2-carboxamide | 534.2 | 535.2 |

TABLE T-5-continued

| Compound No. | Structure | IUPAC | Exact mass (g/mol) | LCMS, Found [M + H]+ |
|---|---|---|---|---|
| 392 | 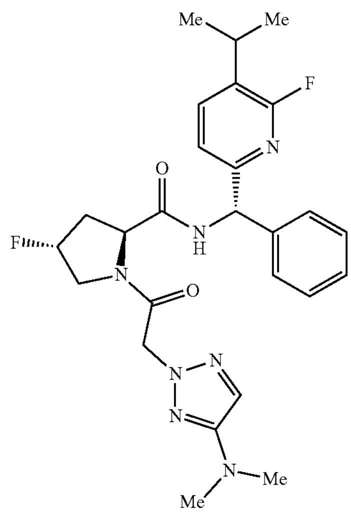 [SMILES: CC(C)c1ccc([C@@H](NC(=O)[C@@H]2C[C@@H](F)CN2C(=O)Cn2ncc(N(C)C)n2)c2ccccc2)nc1F] | (2S,4R)-1-{2-[4-(dimethylamino)-2H-1,2,3-triazol-2-yl]acetyl}-4-fluoro-N-[(S)-[6-fluoro-5-(propan-2-yl)pyridin-2-yl](phenyl)methyl]pyrrolidine-2-carboxamide | 511.3 | 512.3 |
| 393 | 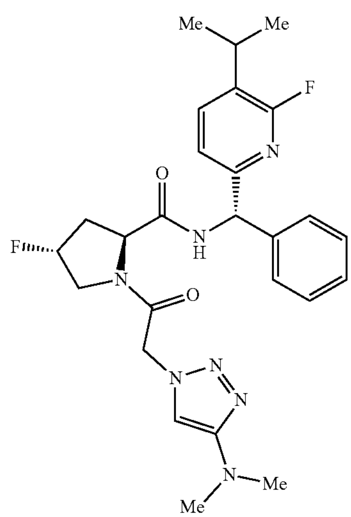 [SMILES: CC(C)c1ccc([C@@H](NC(=O)[C@@H]2C[C@@H](F)CN2C(=O)Cn2cc(N(C)C)nn2)c2ccccc2)nc1F] | (2S,4R)-1-{2-[4-(dimethylamino)-1H-1,2,3-triazol-1-yl]acetyl}-4-fluoro-N-[(S)-[6-fluoro-5-(propan-2-yl)pyridin-2-yl](phenyl)methyl]pyrrolidine-2-carboxamide | 511.3 | 512.2 |
| 394 | 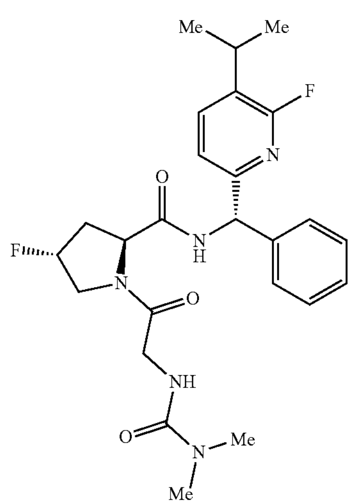 [SMILES: CC(C)c1ccc([C@@H](NC(=O)[C@@H]2C[C@@H](F)CN2C(=O)CNC(=O)N(C)C)c2ccccc2)nc1F] | (2S,4R)-1-{2-[(dimethylcarbamoyl)amino]acetyl}-4-fluoro-N-[(S)-[6-fluoro-5-(propan-2-yl)pyridin-2-yl](phenyl)methyl]pyrrolidine-2-carboxamide | 487.2 | 488.3 |

TABLE T-5-continued

| Compound No. | Structure | IUPAC | Exact mass (g/mol) | LCMS, Found [M + H]+ |
|---|---|---|---|---|
| 395 | 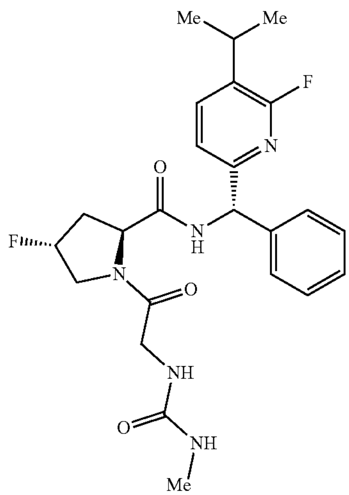 [SMILES: CNC(=O)NCC(=O)N1C[C@H](F)C[C@H]1C(=O)N[C@@H](c1ccccc1)c1ccc(C(C)C)c(F)n1] | (2S,4R)-4-fluoro-N-[(S)-[6-fluoro-5-(propan-2-yl)pyridin-2-yl](phenyl)methyl]-1-{2-[(methylcarbamoyl)amino]acetyl}pyrrolidine-2-carboxamide | 473.2 | 474.2 |
| 396 | 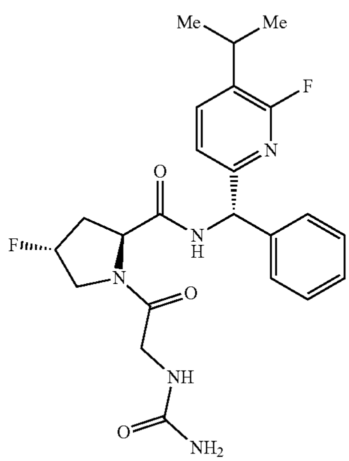 [SMILES: CC(C)c1ccc([C@@H](NC(=O)[C@@H]2C[C@@H](F)CN2C(=O)CNC(N)=O)c2ccccc2)nc1F] | (2S,4R)-1-[2-(carbamoylamino)acetyl]-4-fluoro-N-[(S)-[6-fluoro-5-(propan-2-yl)pyridin-2-yl](phenyl)methyl]pyrrolidine-2-carboxamide | 459.2 | 460.1 |
| 397 | 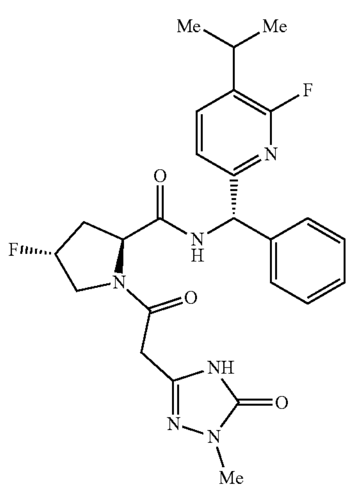 [SMILES: CC(C)c1ccc([C@@H](NC(=O)[C@@H]2C[C@@H](F)CN2C(=O)Cc2nn(C)c(=O)[nH]2)c2ccccc2)nc1F] | (2S,4R)-4-fluoro-N-[(S)-[6-fluoro-5-(propan-2-yl)pyridin-2-yl](phenyl)methyl]-1-[2-(1-methyl-5-oxo-4,5-dihydro-1H-1,2,4-triazol-3-yl)acetyl]pyrrolidine-2-carboxamide | 498.2 | 499.4 |

TABLE T-5-continued

| Compound No. | Structure | IUPAC | Exact mass (g/mol) | LCMS, Found [M + H]⁺ |
|---|---|---|---|---|
| 398 | 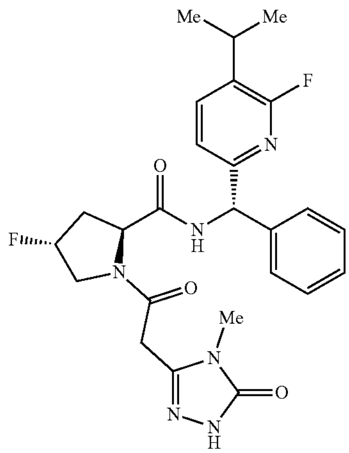 [SMILES: CC(C)c1ccc([C@@H](NC(=O)[C@@H]2C[C@@H](F)CN2C(=O)Cc2n[nH]c(=O)n2C)c2ccccc2)nc1F] | (2S,4R)-4-fluoro-N-[(S)-[6-fluoro-5-(propan-2-yl)pyridin-2-yl](phenyl)methyl]-1-[2-(4-methyl-5-oxo-4,5-dihydro-1H-1,2,4-triazol-3-yl)acetyl]pyrrolidine-2-carboxamide | 498.2 | 499.2 |
| 399 | 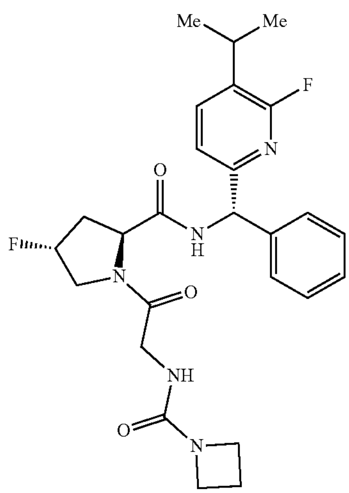 [SMILES: CC(C)c1ccc([C@@H](NC(=O)[C@@H]2C[C@@H](F)CN2C(=O)CNC(=O)N2CCC2)c2ccccc2)nc1F] | (2S,4R)-1-{2-[(azetidine-1-carbonyl)amino]acetyl}-4-fluoro-N-[(S)-[6-fluoro-5-(propan-2-yl)pyridin-2-yl](phenyl)methyl]pyrrolidine-2-carboxamide | 499.2 | 500.3 |
| 400 | 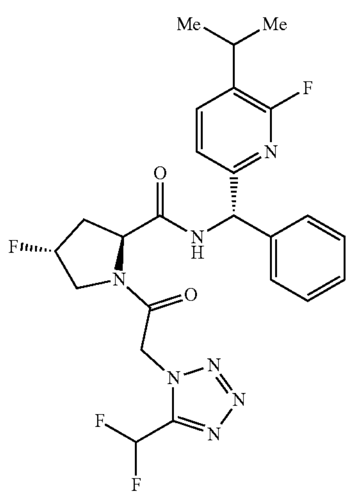 [SMILES: CC(C)c1ccc([C@@H](NC(=O)[C@@H]2C[C@@H](F)CN2C(=O)Cn2nnnc2C(F)F)c2ccccc2)nc1F] | (2S,4R)-1-{2-[5-(difluoromethyl)-1H-1,2,3,4-tetrazol-1-yl]acetyl}-4-fluoro-N-[(S)-[6-fluoro-5-(propan-2-yl)pyridin-2-yl](phenyl)methyl]pyrrolidine-2-carboxamide | 519.2 | 520.1 |

TABLE T-5-continued

| Compound No. | Structure | IUPAC | Exact mass (g/mol) | LCMS, Found [M + H]+ |
| --- | --- | --- | --- | --- |
| 401 | 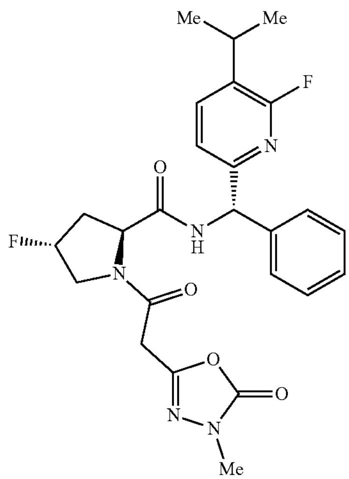 [SMILES: CC(C)c1ccc([C@@H](NC(=O)[C@@H]2C[C@@H](F)CN2C(=O)Cc2nn(C)c(=O)o2)c2ccccc2)nc1F] | (2S,4R)-4-fluoro-N-[(S)-[6-fluoro-5-(propan-2-yl)pyridin-2-yl](phenyl)methyl]-1-[2-(4-methyl-5-oxo-4,5-dihydro-1,3,4-oxadiazol-2-yl)acetyl]pyrrolidine-2-carboxamide | 499.2 | 500.3 |
| 402 | 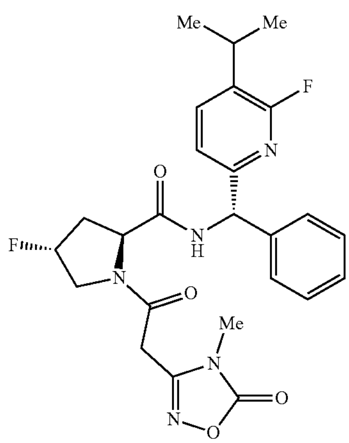 [SMILES: CC(C)c1ccc([C@@H](NC(=O)[C@@H]2C[C@@H](F)CN2C(=O)Cc2noc(=O)n2C)c2ccccc2)nc1F] | (2S,4R)-4-fluoro-N-[(S)-[6-fluoro-5-(propan-2-yl)pyridin-2-yl](phenyl)methyl]-1-[2-(4-methyl-5-oxo-4,5-dihydro-1,2,4-oxadiazol-3-yl)acetyl]pyrrolidine-2-carboxamide | 499.2 | 500.2 |
| 403 | 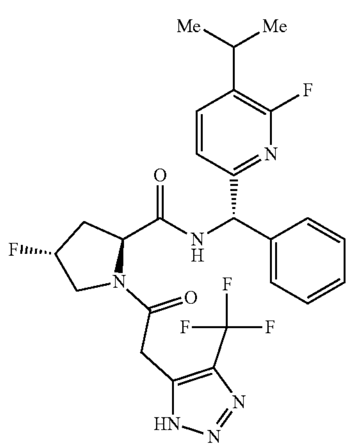 [SMILES: CC(C)c1ccc([C@@H](NC(=O)[C@@H]2C[C@@H](F)CN2C(=O)Cc2[nH]nnc2C(F)(F)F)c2ccccc2)nc1F] | (2S,4R)-4-fluoro-N-[(S)-[6-fluoro-5-(propan-2-yl)pyridin-2-yl](phenyl)methyl]-1-{2-[4-(trifluoromethyl)-1H-1,2,3-triazol-5-yl]acetyl}pyrrolidine-2-carboxamide | 536.2 | 537.1 |

TABLE T-5-continued

| Compound No. | Structure | IUPAC | Exact mass (g/mol) | LCMS, Found [M + H]+ |
|---|---|---|---|---|
| 404 | 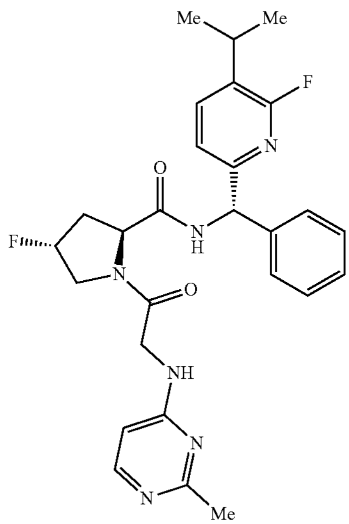 [SMILES: Cc1nccc(NCC(=O)N2C[C@H](F)C[C@H]2C(=O)N[C@@H](c2ccccc2)c2ccc(C(C)C)c(F)n2)n1] | (2S,4R)-4-fluoro-N-[(S)-[6-fluoro-5-(propan-2-yl)pyridin-2-yl](phenyl)methyl]-1-{2-[(2-methylpyrimidin-4-yl)amino]acetyl}pyrrolidine-2-carboxamide | 508.2 | 509.3 |
| 405 | 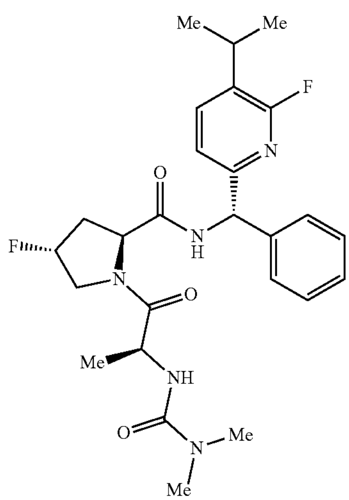 [SMILES: CC(C)c1ccc([C@@H](NC(=O)[C@@H]2C[C@@H](F)CN2C(=O)[C@H](C)NC(=O)N(C)C)c2ccccc2)nc1F] | (2S,4R)-1-[(2S)-2-[(dimethylcarbamoyl)amino]propanoyl]-4-fluoro-N-[(S)-[6-fluoro-5-(propan-2-yl)pyridin-2-yl](phenyl)methyl]pyrrolidine-2-carboxamide | 501.3 | 502.4 |
| 406 | 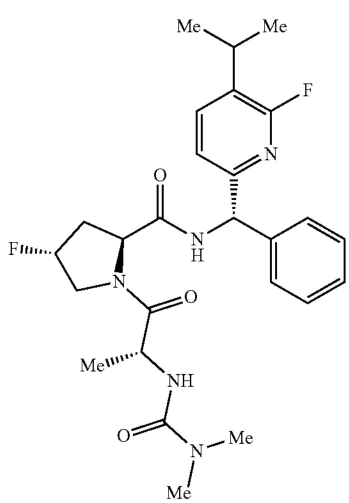 [SMILES: CC(C)c1ccc([C@@H](NC(=O)[C@@H]2C[C@@H](F)CN2C(=O)[C@@H](C)NC(=O)N(C)C)c2ccccc2)nc1F] | (2S,4R)-1-[(2R)-2-[(dimethylcarbamoyl)amino]propanoyl]-4-fluoro-N-[(S)-[6-fluoro-5-(propan-2-yl)pyridin-2-yl](phenyl)methyl]pyrrolidine-2-carboxamide | 501.3 | 502.4 |

TABLE T-5-continued

| Compound No. | Structure | IUPAC | Exact mass (g/mol) | LCMS, Found [M + H]+ |
| --- | --- | --- | --- | --- |
| 407 | 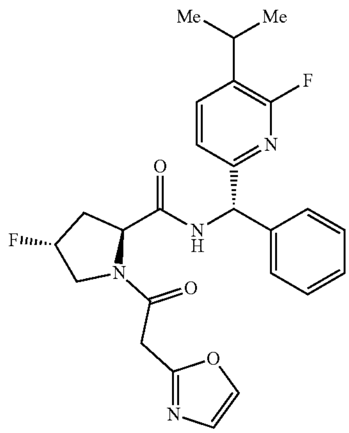 [SMILES: CC(C)c1ccc([C@@H](NC(=O)[C@@H]2C[C@@H](F)CN2C(=O)Cc2ncco2)c2ccccc2)nc1F] | (2S,4R)-4-fluoro-N-[(S)-[6-fluoro-5-(propan-2-yl)pyridin-2-yl](phenyl)methyl]-1-[2-(1,3-oxazol-2-yl)acetyl]pyrrolidine-2-carboxamide | 468.2 | 469.2 |
| 408 | 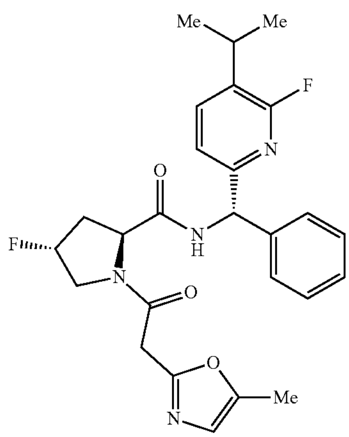 [SMILES: Cc1cnc(CC(=O)N2C[C@H](F)C[C@H]2C(=O)N[C@@H](c2ccccc2)c2ccc(C(C)C)c(F)n2)o1] | (2S,4R)-4-fluoro-N-[(S)-[6-fluoro-5-(propan-2-yl)pyridin-2-yl](phenyl)methyl]-1-[2-(5-methyl-1,3-oxazol-2-yl)acetyl]pyrrolidine-2-carboxamide | 482.2 | 483.1 |
| 409 | 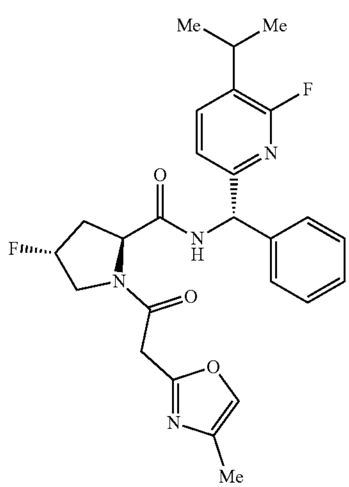 [SMILES: Cc1coc(CC(=O)N2C[C@H](F)C[C@H]2C(=O)N[C@@H](c2ccccc2)c2ccc(C(C)C)c(F)n2)n1] | (2S,4R)-4-fluoro-N-[(S)-[6-fluoro-5-(propan-2-yl)pyridin-2-yl](phenyl)methyl]-1-[2-(4-methyl-1,3-oxazol-2-yl)acetyl]pyrrolidine-2-carboxamide | 482.2 | 483.3 |

TABLE T-5-continued

| Compound No. | Structure | IUPAC | Exact mass (g/mol) | LCMS, Found [M + H]+ |
|---|---|---|---|---|
| 410 | 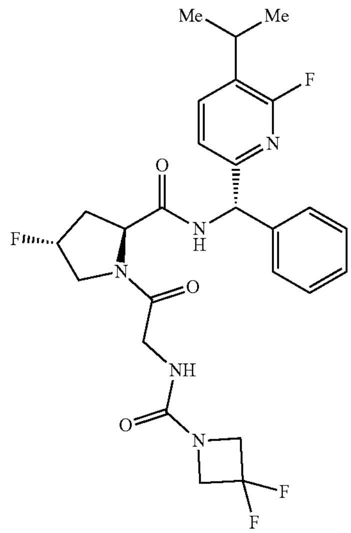 [SMILES: CC(C)c1ccc([C@@H](NC(=O)[C@@H]2C[C@@H](F)CN2C(=O)CNC(=O)N2CC(F)(F)C2)c2ccccc2)nc1F] | (2S,4R)-1-{2-[(3,3-difluoroazetidine-1-carbonyl)amino]acetyl}-4-fluoro-N-[(S)-[6-fluoro-5-(propan-2-yl)pyridin-2-yl](phenyl)methyl]pyrrolidine-2-carboxamide | 535.2 | 536.2 |
| 411 | 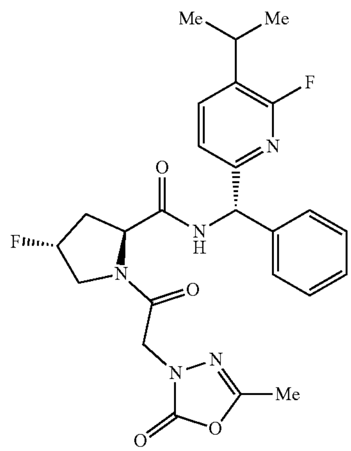 [SMILES: Cc1nn(CC(=O)N2C[C@H](F)C[C@H]2C(=O)N[C@@H](c2ccccc2)c2ccc(C(C)C)c(F)n2)c(=O)o1] | (2S,4R)-4-fluoro-N-[(S)-[6-fluoro-5-(propan-2-yl)pyridin-2-yl](phenyl)methyl]-1-[2-(5-methyl-2-oxo-2,3-dihydro-1,3,4-oxadiazol-3-yl)acetyl]pyrrolidine-2-carboxamide | 499.2 | 500.2 |
| 412 | 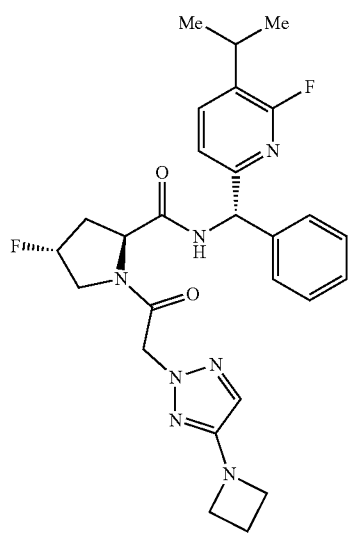 | (2S,4R)-1-{2-[4-(azetidin-1-yl)-2H-1,2,3-triazol-2-yl]acetyl}-4-fluoro-N-[(S)-[6-fluoro-5-(propan-2-yl)pyridin-2-yl](phenyl)methyl]pyrrolidine-2-carboxamide | 523.3 | 524.3 |

TABLE T-5-continued

| Compound No. | Structure | IUPAC | Exact mass (g/mol) | LCMS, Found [M + H]+ |
| --- | --- | --- | --- | --- |
| 413 | 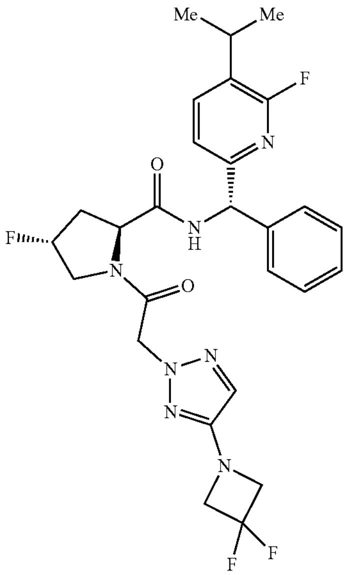 [SMILES: CC(C)c1ccc([C@@H](NC(=O)[C@@H]2C[C@@H](F)CN2C(=O)Cn2ncc(N3CC(F)(F)C3)n2)c2ccccc2)nc1F] | (2S,4R)-1-{2-[4-(3,3-difluoroazetidin-1-yl)-2H-1,2,3-triazol-2-yl]acetyl}-4-fluoro-N-[(S)-[6-fluoro-5-(propan-2-yl)pyridin-2-yl](phenyl)methyl]pyrrolidine-2-carboxamide | 559.2 | 560.3 |
| 414 | 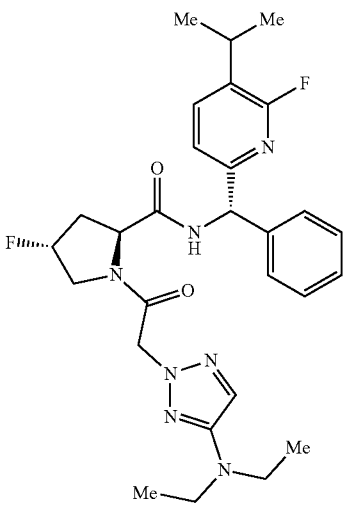 [SMILES: CCN(CC)c1cnn(CC(=O)N2C[C@H](F)C[C@H]2C(=O)N[C@@H](c2ccccc2)c2ccc(C(C)C)c(F)n2)n1] | (2S,4R)-1-{2-[4-(diethylamino)-2H-1,2,3-triazol-2-yl]acetyl(-4-fluoro-N-[(S)-[6-fluoro-5-(propan-2-yl)pyridin-2-yl](phenyl)methyl]pyrrolidine-2-carboxamide | 539.3 | 540.4 |
| 415 | 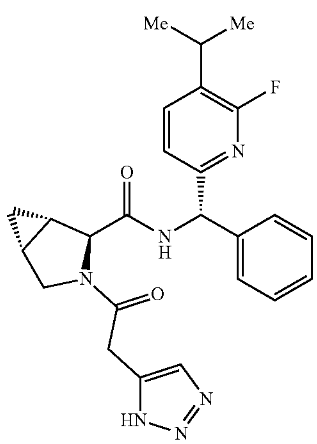 [SMILES: CC(C)c1ccc([C@@H](NC(=O)[C@@H]2[C@H]3C[C@H]3CN2C(=O)Cc2cnn[nH]2)c2ccccc2)nc1F] | (1S,2S,5R)-N-[(S)-[6-fluoro-5-(propan-2-yl)pyridin-2-yl](phenyl)methyl]-3-[2-(1H-1,2,3-triazol-5-yl)acetyl]-3-azabicyclo[3.1.0]hexane-2-carboxamide | 462.2 | 463.4 |

TABLE T-5-continued

| Compound No. | Structure | IUPAC | Exact mass (g/mol) | LCMS, Found [M + H]+ |
|---|---|---|---|---|
| 416 | 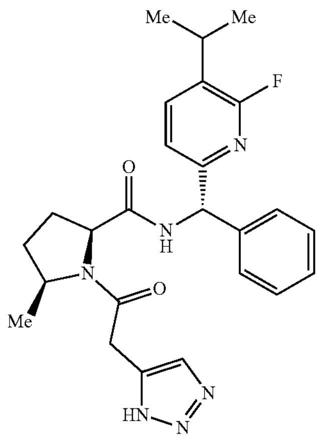 [SMILES: CC(C)c1ccc([C@@H](NC(=O)[C@@H]2CC[C@H](C)N2C(=O)Cc2cnn[nH]2)c2ccccc2)nc1F] | (2S,5S)-N-[(S)-[6-fluoro-5-(propan-2-yl)pyridin-2-yl](phenyl)methyl]-5-methyl-1-[2-(1H-1,2,3-triazol-5-yl)acetyl]pyrrolidine-2-carboxamide | 464.2 | 465.4 |
| 776 | 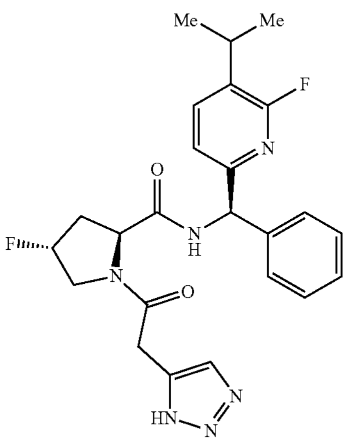 [SMILES: CC(C)c1ccc([C@H](NC(=O)[C@@H]2C[C@@H](F)CN2C(=O)Cc2cnn[nH]2)c2ccccc2)nc1F] | (2S,4R)-4-fluoro-N-[(R*)-[6-fluoro-5-(propan-2-yl)pyridin-2-yl](phenyl)methyl]-1-[2-(1H-1,2,3-triazol-5-yl)acetyl]pyrrolidine-2-carboxamide | 468.2 | 469.2 |
| 777 | 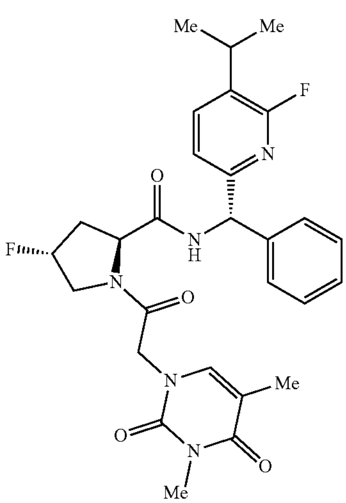 [SMILES: Cc1cn(CC(=O)N2C[C@H](F)C[C@H]2C(=O)N[C@@H](c2ccccc2)c2ccc(C(C)C)c(F)n2)c(=O)n(C)c1=O] | (2S,4R)-1-[2-(3,5-dimethyl-2,4-dioxo-1,2,3,4-tetrahydropyrimidin-1-yl)acetyl]-4-fluoro-N-[(R*)-[6-fluoro-5-(propan-2-yl)pyridin-2-yl](phenyl)methyl]pyrrolidine-2-carboxamide | 539.2 | 540.1 |

TABLE T-5-continued

| Compound No. | Structure | IUPAC | Exact mass (g/mol) | LCMS, Found [M + H]+ |
|---|---|---|---|---|
| 778 | 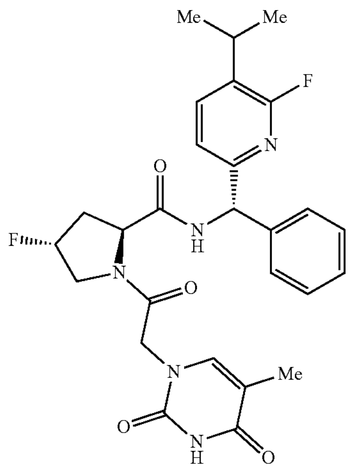 [SMILES: Cc1cn(CC(=O)N2C[C@H](F)C[C@H]2C(=O)N[C@@H](c2ccccc2)c2ccc(C(C)C)c(F)n2)c(=O)[nH]c1=O] | (2S,4R)-4-fluoro-N-[(R*)-[6-fluoro-5-(propan-2-yl)pyridin-2-yl](phenyl)methyl]-1-[2-(5-methyl-2,4-dioxo-1,2,3,4-tetrahydropyrimidin-1-yl)acetyl]pyrrolidine-2-carboxamide | 525.2 | 526.3 |
| 779 | 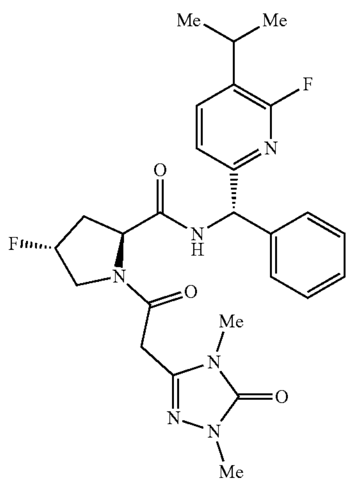 [SMILES: CC(C)c1ccc([C@@H](NC(=O)[C@@H]2C[C@@H](F)CN2C(=O)Cc2nn(C)c(=O)n2C)c2ccccc2)nc1F] | (2S,4R)-1-[2-(1,4-dimethyl-5-oxo-4,5-dihydro-1H-1,2,4-triazol-3-yl)acetyl]-4-fluoro-N-[(S)-[6-fluoro-5-(propan-2-yl)pyridin-2-yl](phenyl)methyl]pyrrolidine-2-carboxamide | 512.2 | 513.3 |
| 780 | 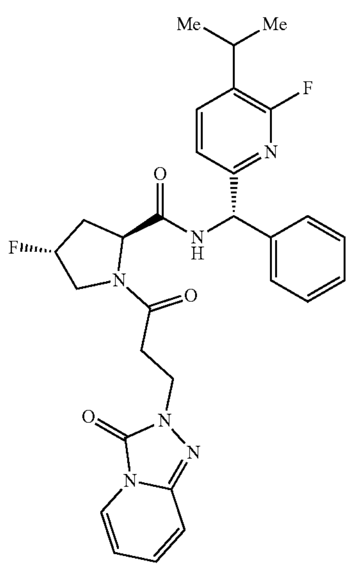 [SMILES: CC(C)c1ccc([C@@H](NC(=O)[C@@H]2C[C@@H](F)CN2C(=O)CCn2nc3ccccn3c2=O)c2ccccc2)nc1F] | (2S,4R)-4-fluoro-N-[(S)-[6-fluoro-5-(propan-2-yl)pyridin-2-yl](phenyl)methyl]-1-{3-{3-oxo-2H,3H-[1,2,4]triazolo[4,3-a]pyridin-2-yl}propanoyl)pyrrolidine-2-carboxamide | 548.2 | 549.2 |

TABLE T-5-continued

| Compound No. | Structure | IUPAC | Exact mass (g/mol) | LCMS, Found [M + H]+ |
|---|---|---|---|---|
| 781 | 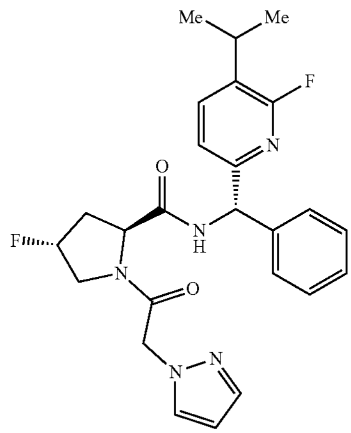 [SMILES: CC(C)c1ccc([C@@H](NC(=O)[C@@H]2C[C@@H](F)CN2C(=O)Cn2cccn2)c2ccccc2)nc1F] | (2S,4R)-4-fluoro-N-[(S)-[6-fluoro-5-(propan-2-yl)pyridin-2-yl](phenyl)methyl]-1-[2-(1H-pyrazol-1-yl)acetyl]pyrrolidine-2-carboxamide | 467.2 | 468.1 |
| 782 | 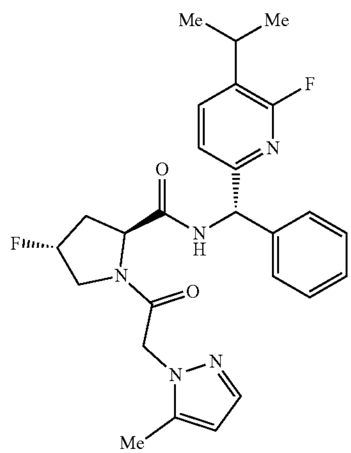 [SMILES: Cc1ccnn1CC(=O)N1C[C@H](F)C[C@H]1C(=O)N[C@@H](c1ccccc1)c1ccc(C(C)C)c(F)n1] | (2S,4R)-4-fluoro-N-[(S)-[6-fluoro-5-(propan-2-yl)pyridin-2-yl](phenyl)methyl]-1-[2-(5-methyl-1H-pyrazol-1-yl)acetyl]pyrrolidine-2-carboxamide | 481.2 | 482.2 |
| 783 | 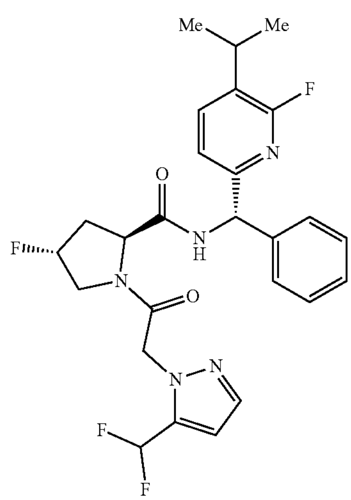 [SMILES: CC(C)c1ccc([C@@H](NC(=O)[C@@H]2C[C@@H](F)CN2C(=O)Cn2nccc2C(F)F)c2ccccc2)nc1F] | (2S,4R)-1-{2-[5-(difluoromethyl)-1H-pyrazol-1-yl]acetyl}-4-fluoro-N-[(S)-[6-fluoro-5-(propan-2-yl)pyridin-2-yl](phenyl)methyl]pyrrolidine-2-carboxamide | 517.2 | 518.2 |

TABLE T-5-continued

| Compound No. | Structure | IUPAC | Exact mass (g/mol) | LCMS, Found [M + H]+ |
|---|---|---|---|---|
| 784 | 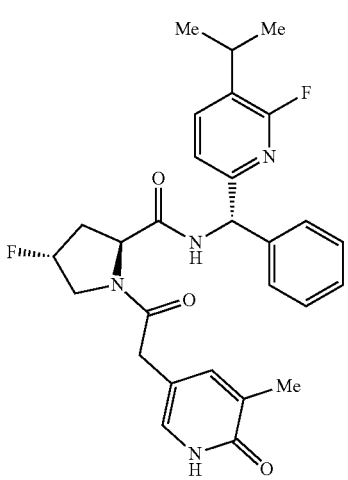 [SMILES: Cc1cc(CC(=O)N2C[C@H](F)C[C@H]2C(=O)N[C@@H](c2ccccc2)c2ccc(C(C)C)c(F)n2)c[nH]c1=O] | (2S,4R)-4-fluoro-N-[(S)-[6-fluoro-5-(propan-2-yl)pyridin-2-yl](phenyl)methyl]-1-[2-(5-methyl-6-oxo-1,6-dihydropyridin-3-yl)acetyl]pyrrolidine-2-carboxamide | 508.2 | 509.1 |
| 785 | 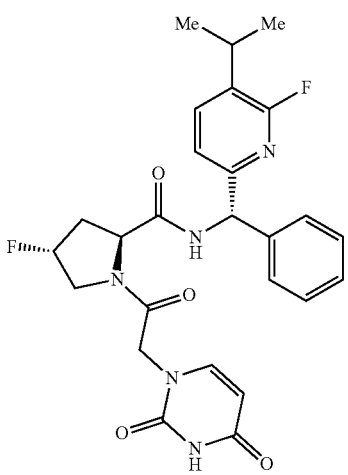 [SMILES: CC(C)c1ccc([C@@H](NC(=O)[C@@H]2C[C@@H](F)CN2C(=O)Cn2ccc(=O)[nH]c2=O)c2ccccc2)nc1F] | (2S,4R)-1-[2-(2,4-dioxo-1,2,3,4-tetrahydropyrimidin-1-yl)acetyl]-4-fluoro-N-[(S)-[6-fluoro-5-(propan-2-yl)pyridin-2-yl](phenyl)methyl]pyrrolidine-2-carboxamide | 511.2 | 512.1 |
| 786 | 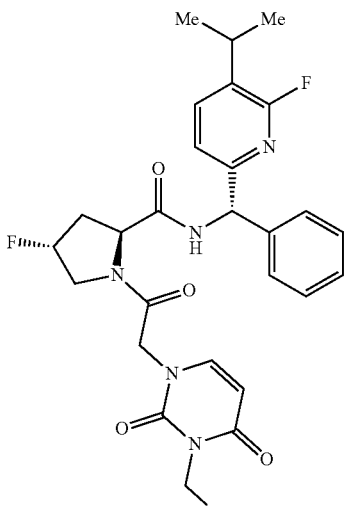 | (2S,4R)-1-[2-(3-ethyl-2,4-dioxo-1,2,3,4-tetrahydropyrimidin-1-yl)acetyl]-4-fluoro-N-[(S)-[6-fluoro-5-(propan-2-yl)pyridin-2-yl](phenyl)methyl]pyrrolidine-2-carboxamide | 539.2 | 540.2 |

TABLE T-5-continued

| Compound No. | Structure | IUPAC | Exact mass (g/mol) | LCMS, Found [M + H]+ |
|---|---|---|---|---|
| 787 | 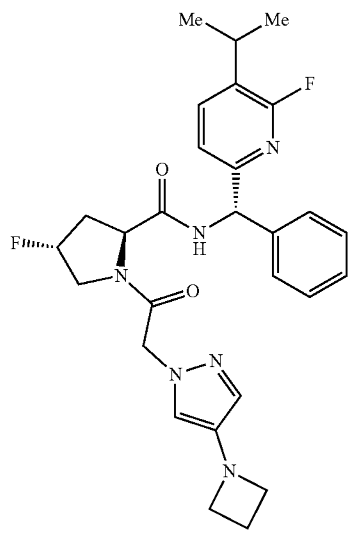 [SMILES: CC(C)c1ccc([C@@H](NC(=O)[C@@H]2C[C@@H](F)CN2C(=O)Cn2cc(N3CCC3)cn2)c2ccccc2)nc1F] | (2S,4R)-1-{2-[4-(azetidin-1-yl)-1H-1,2,3-triazol-1-yl]acetyl}-4-fluoro-N-[(S)-[6-fluoro-5-(propan-2-yl)pyridin-2-yl](phenyl)methyl] pyrrolidine-2-carboxamide | 523.3 | 524.3 |
| 788 | 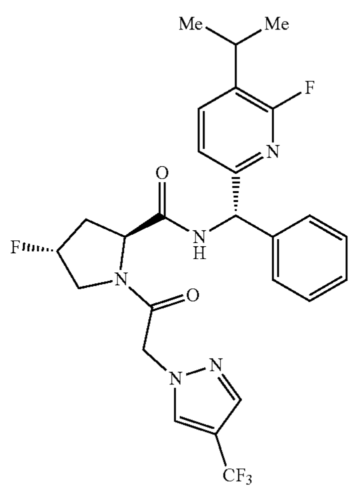 [SMILES: CC(C)c1ccc([C@@H](NC(=O)[C@@H]2C[C@@H](F)CN2C(=O)Cn2cc(C(F)(F)F)cn2)c2ccccc2)nc1F] | (2S,4R)-4-fluoro-N-[(S)-[6-fluoro-5-(propan-2-yl)pyridin-2-yl](pheny])methyl]-1-{2-[4-(trifluoromethyl)-1H-pyrazol-1-yl]acetyl} pyrrolidine-2-carboxamide | 535.2 | 536.2 |
| 789 | 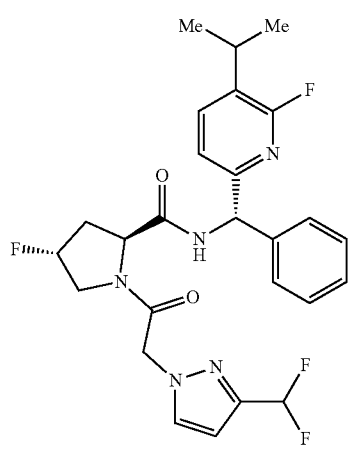 [SMILES: CC(C)c1ccc([C@@H](NC(=O)[C@@H]2C[C@@H](F)CN2C(=O)Cn2ccc(C(F)F)n2)c2ccccc2)nc1F] | (2S,4R)-1-{2-[3-(difluoromethyl)-1H-pyrazol-1-yl]acetyl}-4-fluoro-N-[(S)-[6-fluoro-5-(propan-2-yl)pyridin-2-yl](phenyl)methyl] pyrrolidine-2-carboxamide | 517.2 | 518.2 |

TABLE T-5-continued

| Compound No. | Structure | IUPAC | Exact mass (g/mol) | LCMS, Found [M + H]+ |
| --- | --- | --- | --- | --- |
| 790 | 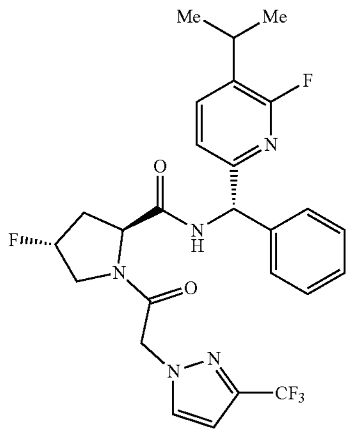 [SMILES: CC(C)c1ccc([C@@H](NC(=O)[C@@H]2C[C@@H](F)CN2C(=O)Cn2ccc(C(F)(F)F)n2)c2ccccc2)nc1F] | (2S,4R)-4-fluoro-N-[(S)-[6-fluoro-5-(propan-2-yl)pyridin-2-yl](phenyl)methyl]-1-{2-[3-(trifluoromethyl)-1H-pyrazol-1-yl]acetyl} pyrrolidine-2-carboxamide | 535.2 | 559.1 [M + Na] |
| 791 | 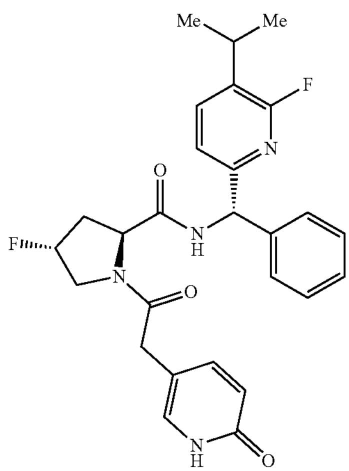 [SMILES: CC(C)c1ccc([C@@H](NC(=O)[C@@H]2C[C@@H](F)CN2C(=O)Cc2ccc(=O)[nH]c2)c2ccccc2)nc1F] | (2S,4R)-4-fluoro-N-[(S)-[6-fluoro-5-(propan-2-yl)pyridin-2-yl](phenyl)methyl]-1-[2-(6-oxo-1,6-dihydropyridin-3-yl)acetyl]pyrrolidine-2-carboxamide | 494.2 | 495.2 |
| 792 | 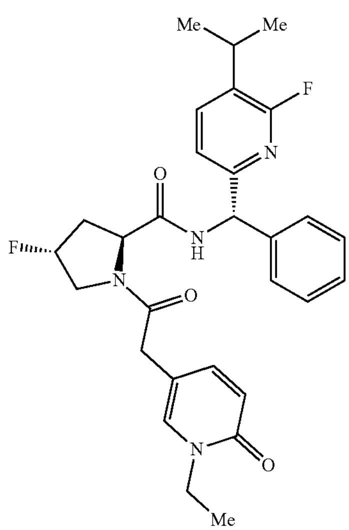 [SMILES: CCn1cc(CC(=O)N2C[C@H](F)C[C@H]2C(=O)N[C@@H](c2ccccc2)c2ccc(C(C)C)c(F)n2)ccc1=O] | (2S,4R)-1-[2-(1-ethyl-6-oxo-1,6-dihydropyridin-3-yl)acetyl]-4-fluoro-N-[(S)-[6-fluoro-5-(propan-2-yl)pyridin-2-yl](phenyl)methyl] pyrrolidine-2-carboxamide | 522.2 | 523.4 |

TABLE T-5-continued

| Compound No. | Structure | IUPAC | Exact mass (g/mol) | LCMS, Found [M + H]+ |
|---|---|---|---|---|
| 793 | 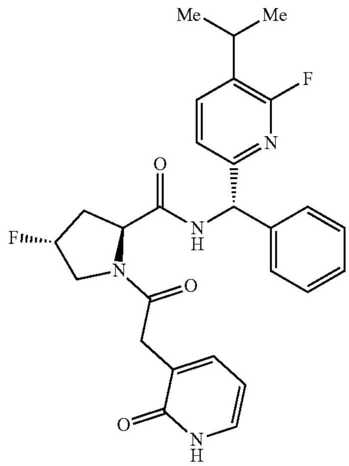 [SMILES: CC(C)c1ccc([C@@H](NC(=O)[C@@H]2C[C@@H](F)CN2C(=O)Cc2ccc[nH]c2=O)c2ccccc2)nc1F] | (2S,4R)-4-fluoro-N-[(S)-[6-fluoro-5-(propan-2-yl)pyridin-2-yl](phenyl)methyl]-1-[2-(2-oxo-1,2-dihydropyridin-3-yl)acetyl]pyrrolidine-2-carboxamide | 494.2 | 495.3 |
| 794 | 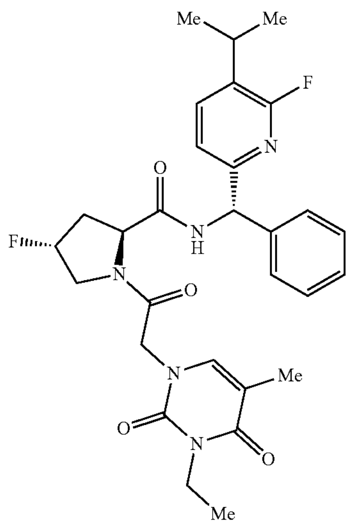 [SMILES: CCn1c(=O)c(C)cn(CC(=O)N2C[C@H](F)C[C@H]2C(=O)N[C@@H](c2ccccc2)c2ccc(C(C)C)c(F)n2)c1=O] | (2S,4R)-1-[2-(3-ethyl-5-methyl-2,4-dioxo-1,2,3,4-tetrahydropyrimidin-1-yl)acetyl]-4-fluoro-N-[(S)-[6-fluoro-5-(propan-2-yl)pyridin-2-yl](phenyl)methyl]pyrrolidine-2-carboxamide | 553.3 | 554.2 |
| 795 | 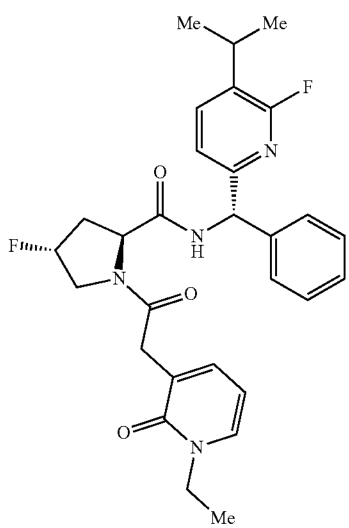 [SMILES: CCn1cccc(CC(=O)N2C[C@H](F)C[C@H]2C(=O)N[C@@H](c2ccccc2)c2ccc(C(C)C)c(F)n2)c1=O] | (2S,4R)-1-[2-(1-ethyl-2-oxo-1,2-dihydropyridin-3-yl)acetyl]-4-fluoro-N-[(S)-[6-fluoro-5-(propan-2-yl)pyridin-2-yl](phenyl)methyl]pyrrolidine-2-carboxamide | 522.2 | 523.3 |

TABLE T-5-continued

| Compound No. | Structure | IUPAC | Exact mass (g/mol) | LCMS, Found [M + H]+ |
|---|---|---|---|---|
| 796 | 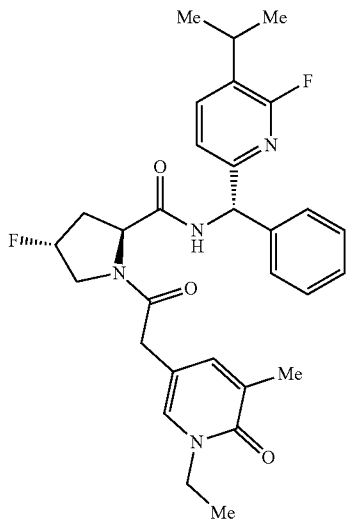 [SMILES: CCn1cc(CC(=O)N2C[C@H](F)C[C@H]2C(=O)N[C@@H](c2ccccc2)c2ccc(C(C)C)c(F)n2)cc(C)c1=O] | (2S,4R)-1-[2-(1-ethyl-5-methyl-6-oxo-1,6-dihydropyridin-3-yl)acetyl]-4-fluoro-N-[(S)-[6-fluoro-5-(propan-2-yl)pyridin-2-yl](phenyl)methyl]pyrrolidine-2-carboxamide | 536.3 | 537.2 |
| 797 | 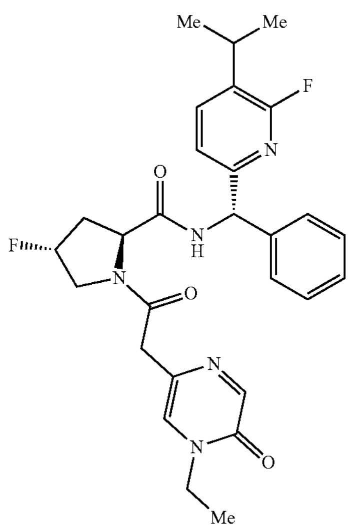 [SMILES: CCn1cc(CC(=O)N2C[C@H](F)C[C@H]2C(=O)N[C@@H](c2ccccc2)c2ccc(C(C)C)c(F)n2)ncc1=O] | (2S,4R)-1-[2-(4-ethyl-5-oxo-4,5-dihydropyrazin-2-yl)acetyl]-4-fluoro-N-[(S)-[6-fluoro-5-(propan-2-yl)pyridin-2-yl](phenyl)methyl]pyrrolidine-2-carboxamide | 523.2 | 524.3 |
| 798 | 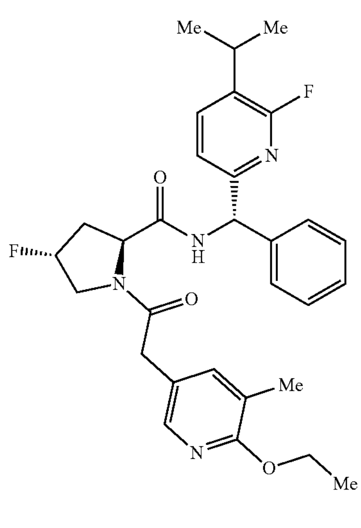 [SMILES: CCOc1ncc(CC(=O)N2C[C@H](F)C[C@H]2C(=O)N[C@@H](c2ccccc2)c2ccc(C(C)C)c(F)n2)cc1C] | (2S,4R)-1-[2-(6-ethoxy-5-methylpyridin-3-yl)acetyl]-4-fluoro-N-[(S)-[6-fluoro-5-(propan-2-yl)pyridin-2-yl](phenyl)methyl]pyrrolidine-2-carboxamide | 536.3 | 537.2 |

TABLE T-5-continued

| Compound No. | Structure | IUPAC | Exact mass (g/mol) | LCMS, Found [M + H]+ |
| --- | --- | --- | --- | --- |
| 799 | 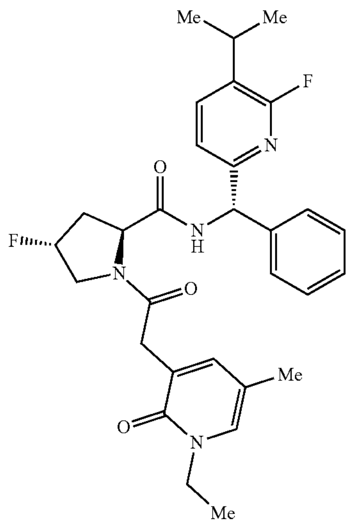 [SMILES: CCn1cc(C)cc(CC(=O)N2C[C@H](F)C[C@H]2C(=O)N[C@@H](c2ccccc2)c2ccc(C(C)C)c(F)n2)c1=O] | (2S,4R)-1-[2-(1-ethyl-5-methyl-2-oxo-1,2-dihydropyridin-3-yl)acetyl]-4-fluoro-N-[(S)-[6-fluoro-5-(propan-2-yl)pyridin-2-yl](phenyl)methyl] pyrrolidine-2-carboxamide | 536.3 | 537.2 |
| 800 | 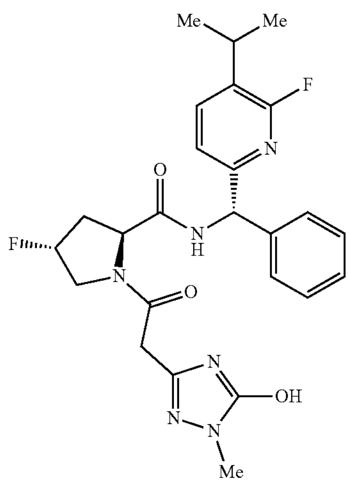 [SMILES: CC(C)c1ccc([C@@H](NC(=O)[C@@H]2C[C@@H](F)CN2C(=O)Cc2nc(O)n(C)n2)c2ccccc2)nc1F] | (2S,4R)-4-fluoro-N-[(S)-[6-fluoro-5-(propan-2-yl)pyridin-2-yl](phenyl)methyl]-1-[2-(5-methoxy-1-methyl-1H-1,2,4-triazol-3-yl)acetyl] pyrrolidine-2-carboxamide | 512.2 | 513.4 |
| 801 | 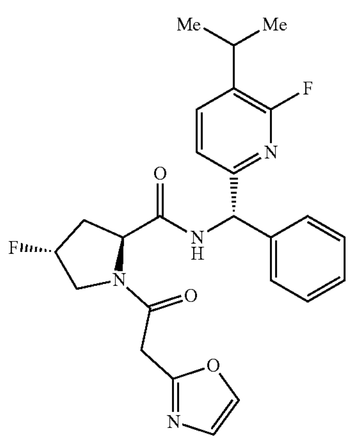 [SMILES: CC(C)c1ccc([C@@H](NC(=O)[C@@H]2C[C@@H](F)CN2C(=O)Cc2ncco2)c2ccccc2)nc1F] | (2S,4R)-4-fluoro-N-[(S)-[6-fluoro-5-(propan-2-yl)pyridin-2-yl](phenyl)methyl]-1-{2-[4-(trifluoromethyl)-1,3-oxazol-2-yl]acetyl} pyrrolidine-2-carboxamide | 536.2 | 537.3 |

TABLE T-5-continued

| Compound No. | Structure | IUPAC | Exact mass (g/mol) | LCMS, Found [M + H]+ |
|---|---|---|---|---|
| 802 | 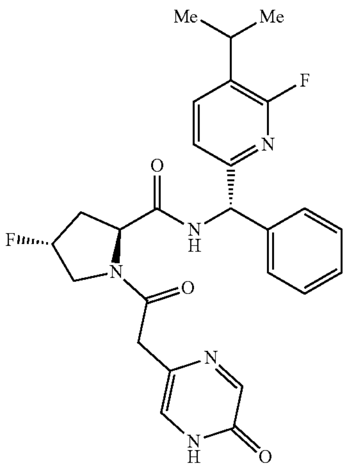 | (2S,4R)-4-fluoro-N-[(S)-[6-fluoro-5-(propan-2-yl)pyridin-2-yl](phenyl)methyl]-1-[2-(5-oxo-4,5-dihydropyrazin-2-yl)acetyl]pyrrolidine-2-carboxamide | 495.2 | 496.3 |
| 803 | 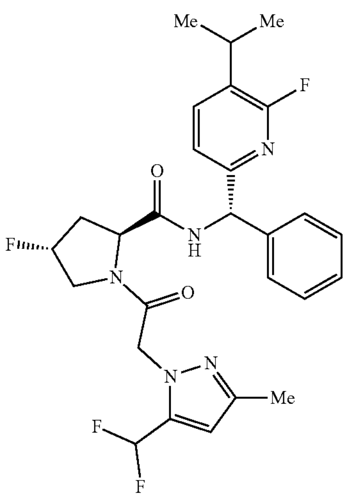 [SMILES: Cc1cc(C(F)F)n(CC(=O)N2C[C@H](F)C[C@H]2C(=O)N[C@@H](c2ccccc2)c2ccc(C(C)C)c(F)n2)n1] | (2S,4R)-1-{2-[5-(difluoromethyl)-3-methyl-1H-pyrazol-1-yl]acetyl}-4-fluoro-N-[(S)-[6-fluoro-5-(propan-2-yl)pyridin-2-yl](phenyl)methyl]pyrrolidine-2-carboxamide | 531.2 | 532.3 |
| 804 | 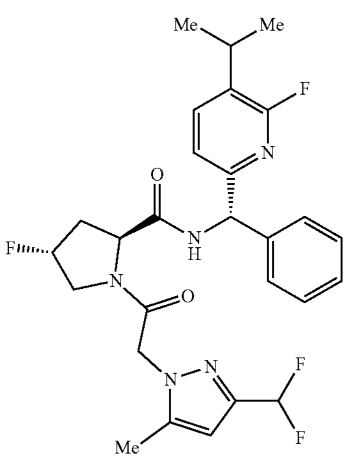 [SMILES: Cc1cc(C(F)F)nn1CC(=O)N1C[C@H](F)C[C@H]1C(=O)N[C@@H](c1ccccc1)c1ccc(C(C)C)c(F)n1] | (2S,4R)-1-{2-[3-(difluoromethyl)-5-methyl-1H-pyrazol-1-yl]acetyl}-4-fluoro-N-[(S)-[6-fluoro-5-(propan-2-yl)pyridin-2-yl](phenyl)methyl]pyrrolidine-2-carboxamide | 531.2 | 532.3 |

TABLE T-5-continued

| Compound No. | Structure | IUPAC | Exact mass (g/mol) | LCMS, Found [M + H]+ |
|---|---|---|---|---|
| 805 | 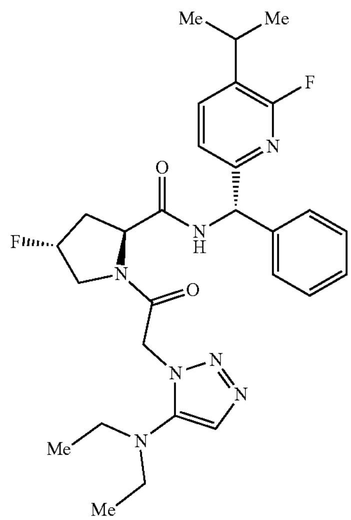 [SMILES: CCN(CC)c1cnnn1CC(=O)N1C[C@H](F)C[C@H]1C(=O)N[C@@H](c1ccccc1)c1ccc(C(C)C)c(F)n1] | (2S,4R)-1-{2-[5-(diethylamino)-1H-1,2,3-triazol-1-yl]acetyl}-4-fluoro-N-[(S)-[6-fluoro-5-(propan-2-yl)pyridin-2-yl](phenyl)methyl]pyrrolidine-2-carboxamide | 539.3 | 540.2 |
| 806 | 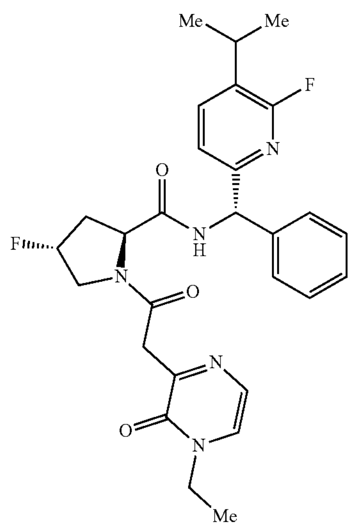 [SMILES: CCn1ccnc(CC(=O)N2C[C@H](F)C[C@H]2C(=O)N[C@@H](c2ccccc2)c2ccc(C(C)C)c(F)n2)c1=O] | (2S,4R)-1-[2-(4-ethyl-3-oxo-3,4-dihydropyrazin-2-yl)acetyl]-4-fluoro-N-[(S)-[6-fluoro-5-(propan-2-yl)pyridin-2-yl](phenyl)methyl]pyrrolidine-2-carboxamide | 523.2 | 524.3 |
| 807 | 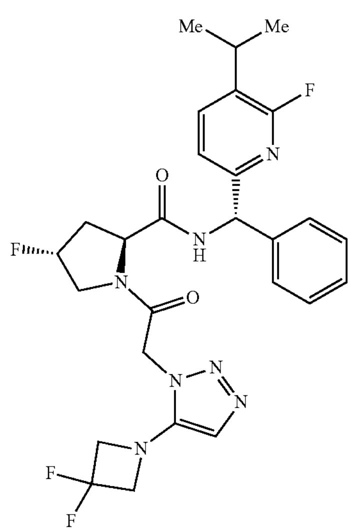 [SMILES: CC(C)c1ccc([C@@H](NC(=O)[C@@H]2C[C@@H](F)CN2C(=O)Cn2nncc2N2CC(F)(F)C2)c2ccccc2)nc1F] | (2S,4R)-1-{2-[5-(3,3-difluoroazetidin-1-yl)-1H-1,2,3-triazol-1-yl]acetyl}-4-fluoro-N-[(S)-[6-fluoro-5-(propan-2-yl)pyridin-2-yl](phenyl)methyl]pyrrolidine-2-carboxamide | 559.2 | 560.3 |

TABLE T-5-continued
| Compound No. | Structure | IUPAC | Exact mass (g/mol) | LCMS, Found [M + H]+ |
|---|---|---|---|---|
| 808 | 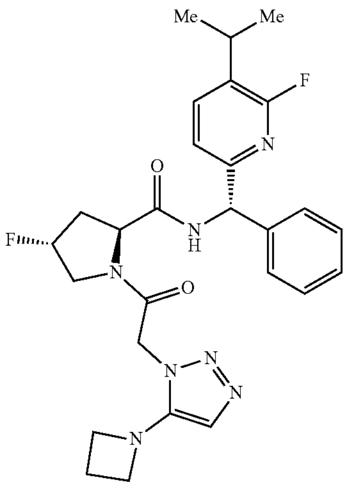 [SMILES: CC(C)c1ccc([C@@H](NC(=O)[C@@H]2C[C@@H](F)CN2C(=O)Cn2nncc2N2CCC2)c2ccccc2)nc1F] | (2S,4R)-1-{2-[5-(azetidin-1-yl)-1H-1,2,3-triazol-1-yl]acetyl}-4-fluoro-N-[(S)-[6-fluoro-5-(propan-2-yl)pyridin-2-yl](phenyl)methyl]pyrrolidine-2-carboxamide | 523.2 | 524.1 |
Example S-6: Synthesis of (2S,4R)-1-(2-(1H-benzo[d]imidazol-1-yl)acetyl)-N—((S)-(4-cyclopropyl-3-fluorophenyl)(phenyl)methyl)-4-fluoropyrrolidine-2-carboxamide
Compound 417
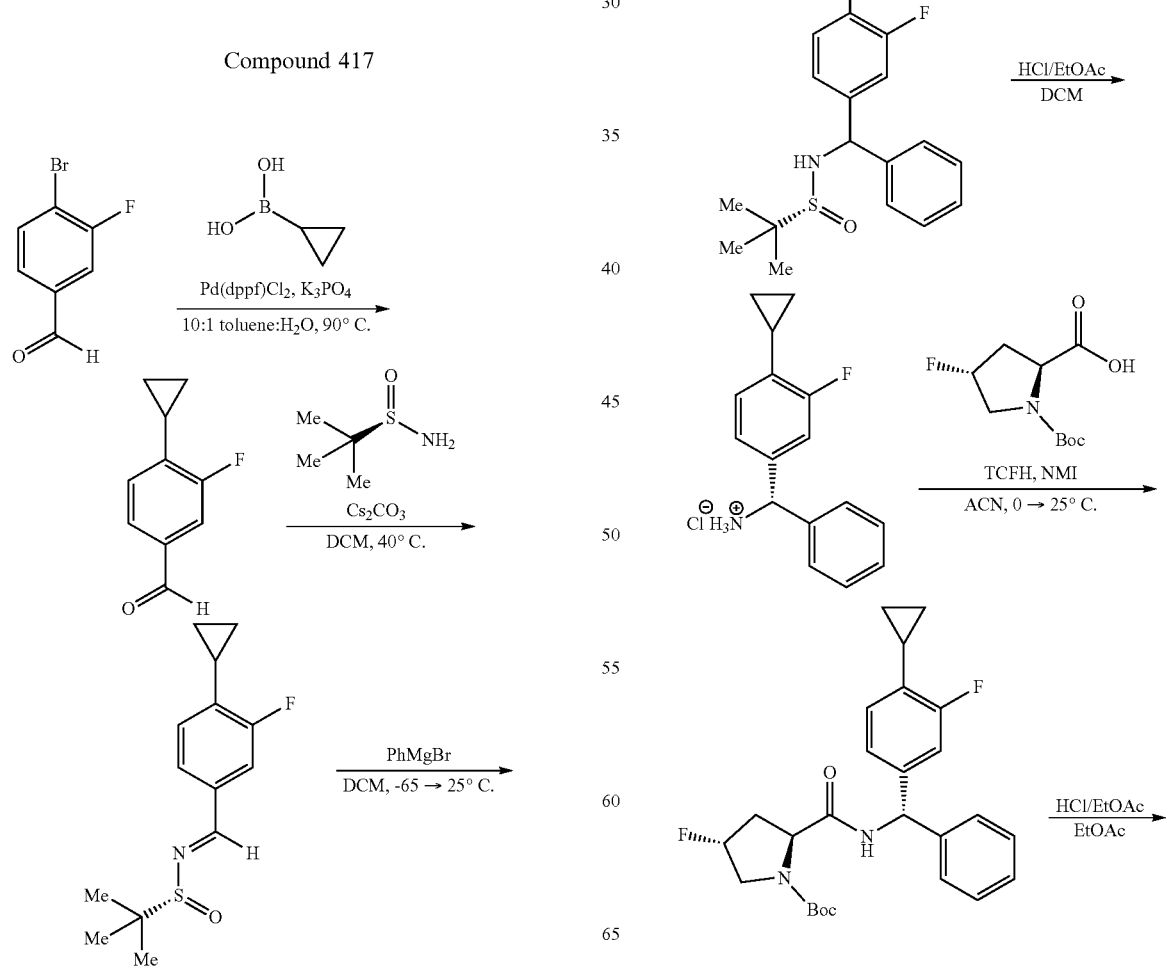

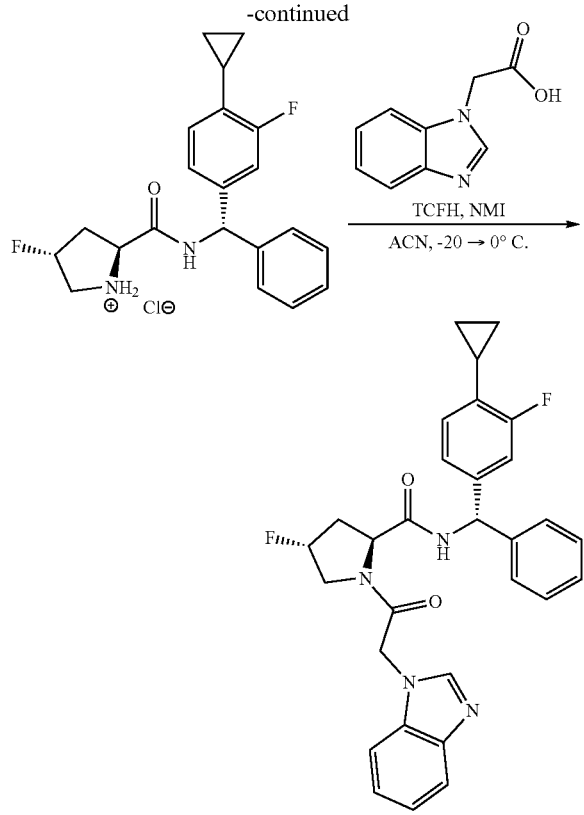

Step a: To a solution of 4-bromo-3-fluorobenzaldehyde (150 g, 738 mmol, 1.00 eq) in toluene (2.00 L) and H$_2$O (240 mL) under nitrogen atmosphere was added cyclopropylboronic acid (82.5 g, 960 mmol, 1.30 eq), K$_3$PO$_4$ (360 g, 1.70 mol, 2.30 eq) and Pd(dppf)Cl$_2$ (27.0 g, 36.9 mmol, 0.05 eq). The resulting mixture was degassed and purged with N$_2$, warmed to 90° C., and stirred for 16 h. The reaction mixture was then filtered through Celite, and the solvent was removed under reduced pressure. The resulting crude material was purified by column chromatography to give 4-cyclopropyl-3-fluorobenzaldehyde, which was carried forward to the next step without further characterization.

Step b: To a solution of 4-cyclopropyl-3-fluorobenzaldehyde (146 g, 889 mmol, 1.00 eq) in DCM (1320 mL) under nitrogen atmosphere was added (R)-2-methylpropane-2-sulfinamide (118 g, 978 mmol, 1.10 eq), and Cs$_2$CO$_3$ (318 g, 978 mmol, 1.10 eq). The resulting mixture was warmed to 40° C. and stirred for 16 h. The reaction mixture was then filtered, and the filtrate was concentrated under reduced pressure. The resulting crude material was purified by column chromatography to give (R,E)-N-(4-cyclopropyl-3-fluorobenzylidene)-2-methylpropane-2-sulfinamide, which was carried forward to the next step without further characterization.

Step c: To a solution of (R,E)-N-(4-cyclopropyl-3-fluorobenzylidene)-2-methylpropane-2-sulfinamide (47.7 g, 178 mmol, 1.00 eq) in DCM (477 mL) at −65° C. under N$_2$ was added phenylmagnesium bromide (3 M in Et$_2$O, 77.3 mL, 1.30 eq) in a dropwise manner. The resulting mixture was stirred while warming to 25° C. over 4 h. The reaction mixture was then quenched with saturated aqueous NH$_4$Cl (500 mL). The resulting biphasic mixture was extracted with EtOAc (3×500 mL). The organic extracts were dried over anhydrous Na$_2$SO$_4$, filtered, and concentrated under reduced pressure. The resulting crude material was purified by column chromatography to give (R)—N—((S)-(4-cyclopropyl-3-fluorophenyl)(phenyl)methyl)-2-methylpropane-2-sulfinamide, which was carried forward to the next step without further characterization.

Step d: To a solution of (R)—N—((S)-(4-cyclopropyl-3-fluorophenyl)(phenyl)methyl)-2-methylpropane-2-sulfinamide (81.6 g, 236 mmol, 1.00 eq) in DCM (1632 mL) at 25° C. was added HCl/EtOAc (4 M, 147 mL, 2.50 eq) in one portion. The resulting mixture was stirred for 2 h. The mixture was then filtered, and the solid obtained was set aside. The filtrate was then concentrated under reduced pressure, and the resulting material was suspended in MTBE (800 mL) and filtered. The solids obtained from both filtrations were combined and dissolved in aqueous Na$_2$CO$_3$ (0.5 N, 1.00 L) and DCM (1.00 L). The isolated organic layer was washed with water (500 mL), dried over anhydrous Na$_2$SO$_4$, filtered, and concentrated under reduced pressure to give (S)-(4-cyclopropyl-3-fluorophenyl)(phenyl)methanaminium chloride, which was carried forward to the next step without further characterization.

Step e: To a mixture of (S)-(4-cyclopropyl-3-fluorophenyl)(phenyl)methanaminium chloride (12.5 g, 51.8 mmol, 1 eq) and (2S,4R)-1-(tert-butoxycarbonyl)-4-fluoropyrrolidine-2-carboxylic acid (13.2 g, 56.9 mmol, 1.1 eq) in MeCN (125 mL) at 0° C. was added 1-methylimidazole (NMI, 12.7 g, 155 mmol, 12.3 mL, 3 eq) and chloro-N,N,N',N'-tetramethylformamidinium hexafluorophosphate (TCFH, 17.4 g, 62.1 mmol, 1.2 eq). The resulting mixture was warmed to 25° C. and stirred for 2 h under N$_2$ atmosphere. The reaction mixture was then quenched with H$_2$O (50 mL) and extracted with EtOAc (200 mL). The combined organic extracts were washed with brine (200 mL), dried over Na$_2$SO$_4$, filtered, and concentrated under reduced pressure. The resulting crude residue was purified by column chromatography to give tert-butyl (2S,4R)-2-(((S)-(4-cyclopropyl-3-fluorophenyl)(phenyl)methyl)carbamoyl)-4-fluoropyrrolidine-1-carboxylate. LC-MS (ESI): m/z: [M+H]$^+$ calculated for C$_{26}$H$_{30}$F$_2$N$_2$O$_3$: 457.2; found 457.1.

Step f: To a solution of tert-butyl (2S,4R)-2-(((S)-(4-cyclopropyl-3-fluorophenyl)(phenyl)methyl)carbamoyl)-4-fluoropyrrolidine-1-carboxylate (15.0 g, 32.8 mmol, 1 eq) in EtOAc (50 mL) was added HCl/EtOAc (4 M, 50 mL, 6.09 eq), and the resulting mixture was stirred at 25° C. for 2 h under N$_2$ atmosphere. MTBE (50 mL) was then added to the reaction mixture, which was then stirred for 10 min. The reaction mixture was then filtered and the filter cake was dried under reduced pressure to give (2S,4R)—N—((S)-(4-cyclopropyl-3-fluorophenyl)(phenyl)methyl)-4-fluoropyrrolidine-2-carboxamide hydrochloride. LC-MS (ESI): m/z: [M+H]$^+$ calculated for C$_{21}$H$_{22}$F$_2$N$_2$O: 357.2; found 357.2.

Step g: To a mixture of (2S,4R)—N—((S)-(4-cyclopropyl-3-fluorophenyl)(phenyl)methyl)-4-fluoropyrrolidine-2-carboxamide hydrochloride (3.50 g, 8.91 mmol, 1 eq) and 2-(1H-benzo[d]imidazol-1-yl)acetic acid (Intermediate A-4, 2.46 g, 11.6 mmol, 1.3 eq) in MeCN (35 mL) at −20° C. was added 1-methylimidazole (NMI, 5.85 g, 71.3 mmol, 8 eq), and chloro-N,N,N',N'-tetramethylformamidinium hexafluorophosphate (TCFH, 3.25 g, 11.6 mmol, 1.3 eq). The resulting mixture was then warmed to 0° C. and stirred for 2 h. The reaction mixture was then quenched by addition of H$_2$O (100 mL), and the resulting biphasic mixture was extracted with EtOAc (3×100 mL). The combined organic extracts were washed with brine (200 mL), dried over anhydrous Na$_2$SO$_4$, filtered, and concentrated under reduced pressure. The crude residue obtained was purified by column chromatography followed by prep-HPLC to give (2S,4R)-1-(2-

(1H-benzo[d]imidazol-1-yl)acetyl)-N—((S)-(4-cyclopropyl-3-fluorophenyl)(phenyl)methyl)-4-fluoropyrrolidine-2-carboxamide (5.16 g). $^1$H NMR (6.4:1 rotamer ratio, asterisk denotes distinct minor rotamer peaks, obscured peaks not reported, 400 MHz, methanol-$d_4$) δ 8.09 (s, 1H), 7.91*(s, 1H), 7.73-7.61 (m, 1H), 7.51-7.42 (m, 1H), 7.37-7.05 (m, 7H), 7.03-6.83 (m, 3H), 6.27*(s, 1H), 6.06 (s, 1H), 5.52-5.03 (m, 3H), 4.74-4.65 (m, 1H), 4.62-4.48*(m, 1H), 4.23-3.82 (m, 2H), 3.61*(ddd, J=37.1, 13.8, 3.2 Hz, OH), 2.97-2.81* (m, 1H), 2.67-2.49 (m, 1H), 2.46-2.26*(m, 1H), 2.25-1.96 (m, 2H), 0.99-0.92 (m, 2H), 0.72-0.65 (m, 2H). LC-MS (ESI): m/z: [M+H]$^+$ calculated for $C_{30}H_{28}F_2N_4O_2$: 515.2; found 515.4.

The following compounds in Table T-6 were synthesized using procedures similar to Compound 417 using the appropriate starting materials.

TABLE T-6

| Compound No. | Structure | IUPAC | Exact mass (g/mol) | LCMS, Found [M + H]$^+$ |
|---|---|---|---|---|
| 418 | 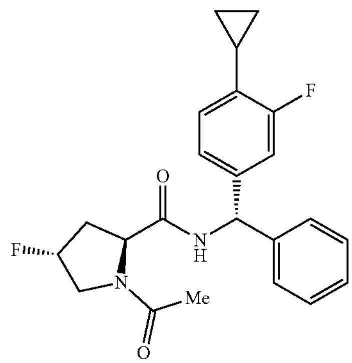 [SMILES: CC(=O)N1C[C@H](F)C[C@H]1C(=O)N[C@@H](c1ccccc1)c1ccc(C2CC2)c(F)c1] | (2S,4R)-1-acetyl-N-[(S)-(4-cyclopropyl-3-fluorophenyl)(phenyl)methyl]-4-fluoropyrrolidine-2-carboxamide | 398.2 | 399.2 |
| 419 | 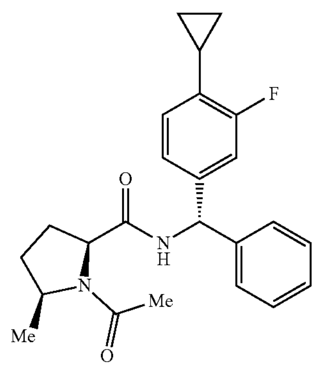 [SMILES: CC(=O)N1[C@@H](C)CC[C@H]1C(=O)N[C@@H](c1ccccc1)c1ccc(C2CC2)c(F)c1] | (2S,5S)-1-acetyl-N-[(S)-(4-cyclopropyl-3-fluorophenyl)(phenyl)methyl]-5-methylpyrrolidine-2-carboxamide | 394.2 | 395.2 |
| 420 | 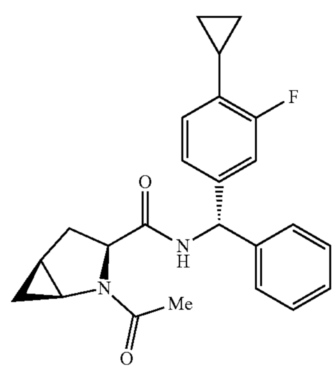 [SMILES: CC(=O)N1[C@H](C(=O)N[C@@H](c2ccccc2)c2ccc(C3CC3)c(F)c2)C[C@@H]2C[C@@H]21] | (1S,3S,5S)-2-acetyl-N-[(S)-(4-cyclopropyl-3-fluorophenyl)(phenyl)methyl]-2-azabicyclo[3.1.0]hexane-3-carboxamide | 392.2 | 393.1 |

TABLE T-6-continued

| Compound No. | Structure | IUPAC | Exact mass (g/mol) | LCMS, Found [M + H]+ |
| --- | --- | --- | --- | --- |
| 421 | 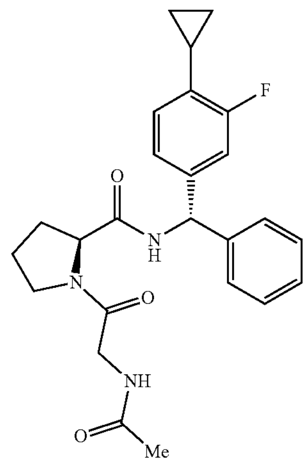 [SMILES: CC(=O)NCC(=O)N1CCC[C@H]1C(=O)N[C@@H](c1ccccc1)c1ccc(C2CC2)c(F)c1] | (2S)-N-[(S)-(4-cyclopropyl-3-fluorophenyl)(phenyl)methyl]-1-(2-acetamidoacetyl)pyrrolidine-2-carboxamide | 437.2 | 438.1 |
| 422 | 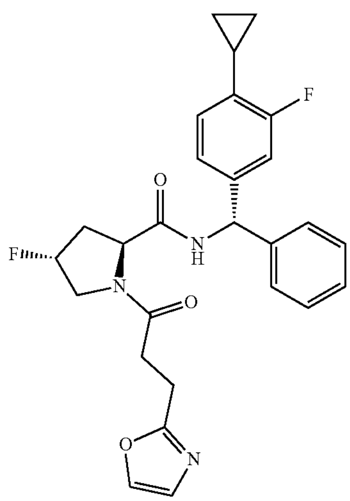 [SMILES: O=C(N[C@@H](c1ccccc1)c1ccc(C2CC2)c(F)c1)[C@@H]1C[C@@H](F)CN1C(=O)CCc1ncco1] | (2S,4R)-N-[(S)-(4-cyclopropyl-3-fluorophenyl)(phenyl)methyl]-4-fluoro-1-[3-(1,3-oxazol-2-yl)propanoyl]pyrrolidine-2-carboxamide | 479.2 | 480.1 |
| 423 | 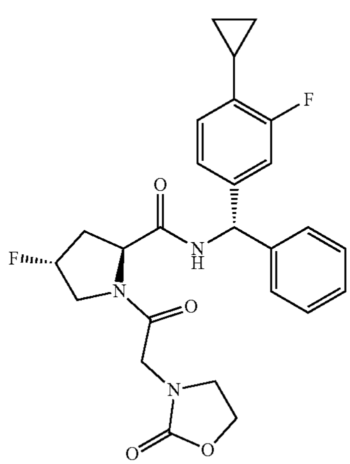 [SMILES: O=C(N[C@@H](c1ccccc1)c1ccc(C2CC2)c(F)c1)[C@@H]1C[C@@H](F)CN1C(=O)CN1CCOC1=O] | (2S,4R)-N-[(S)-(4-cyclopropyl-3-fluorophenyl)(phenyl)methyl]-4-fluoro-1-[2-(3-oxomorpholin-4-yl)acetyl]pyrrolidine-2-carboxamide | 497.2 | 498.1 |

TABLE T-6-continued

| Compound No. | Structure | IUPAC | Exact mass (g/mol) | LCMS, Found [M + H]+ |
|---|---|---|---|---|
| 424 | 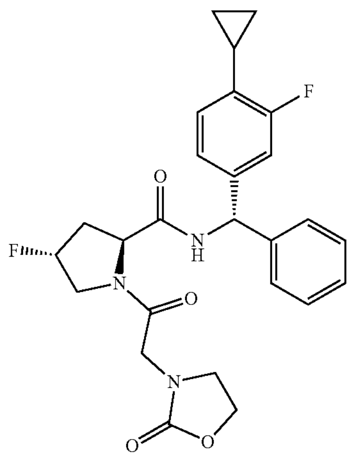 [SMILES: O=C(N[C@@H](c1ccccc1)c1ccc(C2CC2)c(F)c1)[C@@H]1C[C@@H](F)CN1C(=O)CN1CCOC1=O] | (2S,4R)-N-[(S)-(4-cyclopropyl-3-fluorophenyl)(phenyl)methyl]-4-fluoro-1-[2-(2-oxo-1,3-oxazolidin-3-yl)acetyl]pyrrolidine-2-carboxamide | 483.2 | 484.1 |
| 425 | 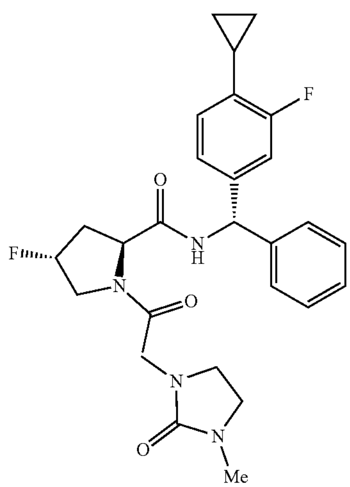 | (2S,4R)-N-[(S)-(4-cyclopropyl-3-fluorophenyl)(phenyl)methyl]-4-fluoro-1-[2-(3-methyl-2-oxoimidazolidin-1-yl)acetyl]pyrrolidine-2-carboxamide | 496.2 | 497.1 |
| 426 | 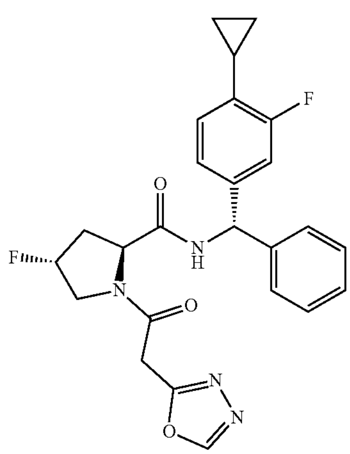 [SMILES: O=C(N[C@@H](c1ccccc1)c1ccc(C2CC2)c(F)c1)[C@@H]1C[C@@H](F)CN1C(=O)Cc1nnco1] | (2S,4R)-N-[(S)-(4-cyclopropyl-3-fluorophenyl)(phenyl)methyl]-4-fluoro-1-[2-(1,3,4-oxadiazol-2-yl)acetyl]pyrrolidine-2-carboxamide | 466.2 | 467.1 |

TABLE T-6-continued

| Compound No. | Structure | IUPAC | Exact mass (g/mol) | LCMS, Found [M + H]+ |
| --- | --- | --- | --- | --- |
| 427 | 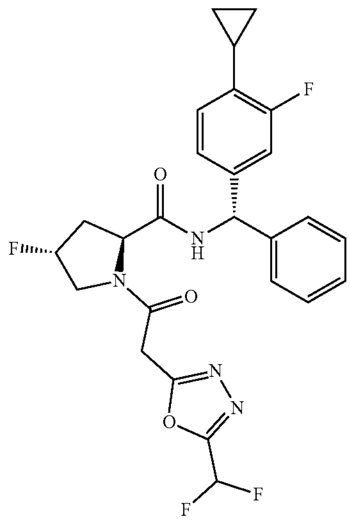 [SMILES: O=C(N[C@@H](c1ccccc1)c1ccc(C2CC2)c(F)c1)[C@@H]1C[C@@H](F)CN1C(=O)Cc1nnc(C(F)F)o1] | (2S,4R)-N-[(S)-(4-cyclopropyl-3-fluorophenyl)(phenyl)methyl]-1-{2-[5-(difluoromethyl)-1,3,4-oxadiazol-2-yl]acetyl}-4-fluoropyrrolidine-2-carboxamide | 516.2 | 517.1 |
| 428 | 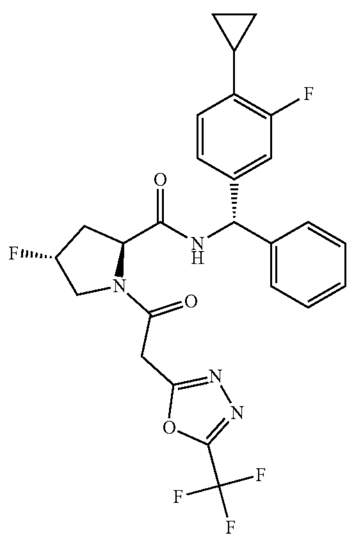 [SMILES: O=C(N[C@@H](c1ccccc1)c1ccc(C2CC2)c(F)c1)[C@@H]1C[C@@H](F)CN1C(=O)Cc1nnc(C(F)(F)F)o1] | (2S,4R)-N-[(S)-(4-cyclopropyl-3-fluorophenyl)(phenyl)methyl]-4-fluoro-1-{2-[5-(trifluoromethyl)-1,3,4-oxadiazol-2-yl]acetyl}pyrrolidine-2-carboxamide | 534.2 | 535.2 |
| 429 | 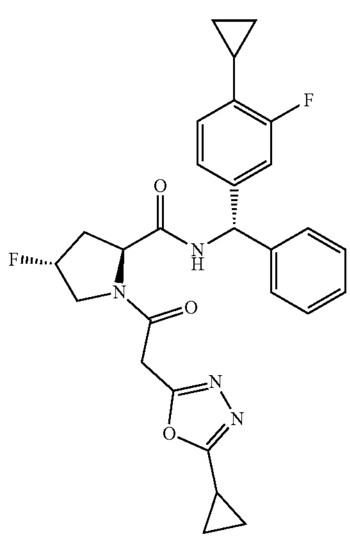 [SMILES: O=C(N[C@@H](c1ccccc1)c1ccc(C2CC2)c(F)c1)[C@@H]1C[C@@H](F)CN1C(=O)Cc1nnc(C2CC2)o1] | (2S,4R)-1-[2-(5-cyclopropyl-1,3,4-oxadiazol-2-yl)acetyl]-N-[(S)-(4-cyclopropyl-3-fluorophenyl)(phenyl)methyl]-4-fluoropyrrolidine-2-carboxamide | 506.2 | 507.1 |

TABLE T-6-continued

| Compound No. | Structure | IUPAC | Exact mass (g/mol) | LCMS, Found [M + H]+ |
|---|---|---|---|---|
| 430 | 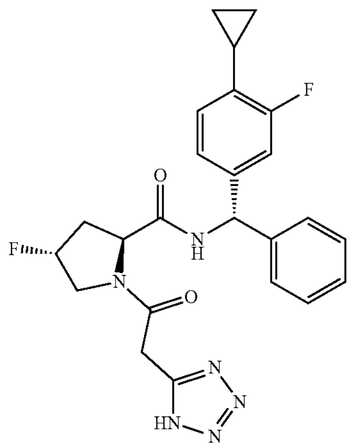 [SMILES: O=C(N[C@@H](c1ccccc1)c1ccc(C2CC2)c(F)c1)[C@@H]1C[C@@H](F)CN1C(=O)Cc1nnn[nH]1] | (2S,4R)-N-[(S)-(4-cyclopropyl-3-fluorophenyl)(phenyl)methyl]-4-fluoro-1-[2-(1H-1,2,3,4-tetrazol-5-yl)acetyl]pyrrolidine-2-carboxamide | 466.2 | 467.1 |
| 431 | 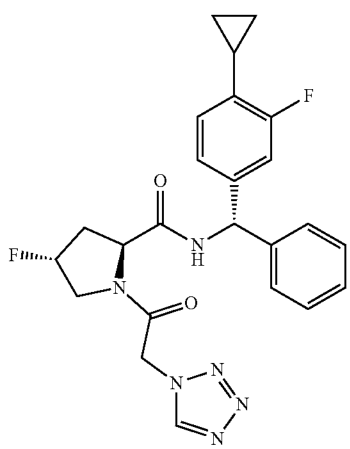 [SMILES: O=C(N[C@@H](c1ccccc1)c1ccc(C2CC2)c(F)c1)[C@@H]1C[C@@H](F)CN1C(=O)Cn1cnnn1] | (2S,4R)-N-[(S)-(4-cyclopropyl-3-fluorophenyl)(phenyl)methyl]-4-fluoro-1-[2-(1H-1,2,3,4-tetrazol-1-yl)acetyl]pyrrolidine-2-carboxamide | 466.2 | 467.2 |
| 432 | 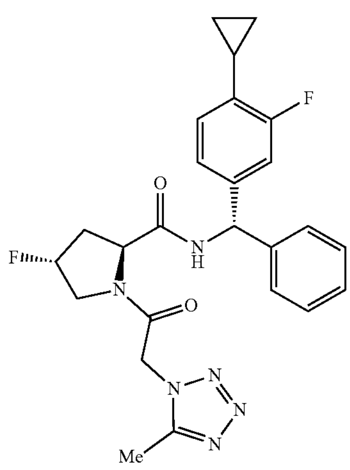 [SMILES: Cc1nnnn1CC(=O)N1C[C@H](F)C[C@H]1C(=O)N[C@@H](c1ccccc1)c1ccc(C2CC2)c(F)c1] | (2S,4R)-N-[(S)-(4-cyclopropyl-3-fluorophenyl)(phenyl)methyl]-4-fluoro-1-[2-(5-methyl-1H-1,2,3,4-tetrazol-1-yl)acetyl]pyrrolidine-2-carboxamide | 480.2 | 481.2 |

TABLE T-6-continued

| Compound No. | Structure | IUPAC | Exact mass (g/mol) | LCMS, Found [M + H]⁺ |
|---|---|---|---|---|
| 433 | 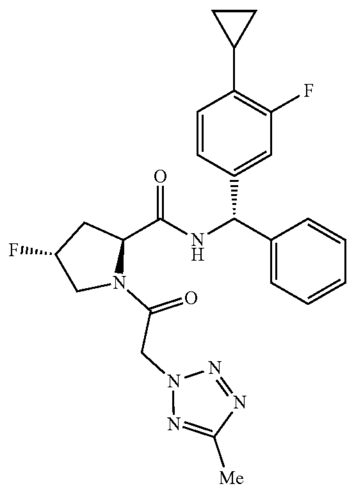 [SMILES: Cc1nnn(CC(=O)N2C[C@H](F)C[C@H]2C(=O)N[C@@H](c2ccccc2)c2ccc(C3CC3)c(F)c2)n1] | (2S,4R)-N-[(S)-(4-cyclopropyl-3-fluorophenyl)(phenyl)methyl]-4-fluoro-1-[2-(5-methyl-2H-1,2,3,4-tetrazol-2-yl)acetyl]pyrrolidine-2-carboxamide | 480.2 | 481.1 |
| 434 | 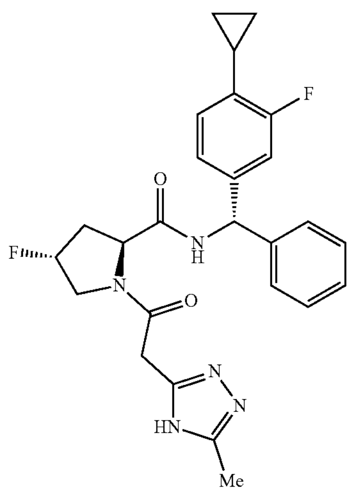 [SMILES: Cc1nnc(CC(=O)N2C[C@H](F)C[C@H]2C(=O)N[C@@H](c2ccccc2)c2ccc(C3CC3)c(F)c2)[nH]1] | (2S,4R)-N-[(S)-(4-cyclopropyl-3-fluorophenyl)(phenyl)methyl]-4-fluoro-1-[2-(5-methyl-4H-1,2,4-triazol-3-yl)acetyl]pyrrolidine-2-carboxamide | 479.2 | 480.1 |
| 435 | 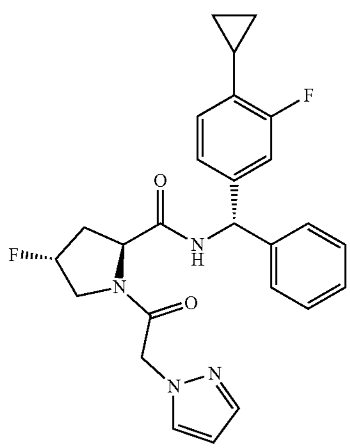 [SMILES: O=C(N[C@@H](c1ccccc1)c1ccc(C2CC2)c(F)c1)[C@@H]1C[C@@H](F)CN1C(=O)Cn1cccn1] | (2S,4R)-N-[(S)-(4-cyclopropyl-3-fluorophenyl)(phenyl)methyl]-4-fluoro-1-[2-(1H-pyrazol-1-yl)acetyl]pyrrolidine-2-carboxamide | 464.2 | 465.1 |

TABLE T-6-continued

| Compound No. | Structure | IUPAC | Exact mass (g/mol) | LCMS, Found [M + H]+ |
|---|---|---|---|---|
| 436 | 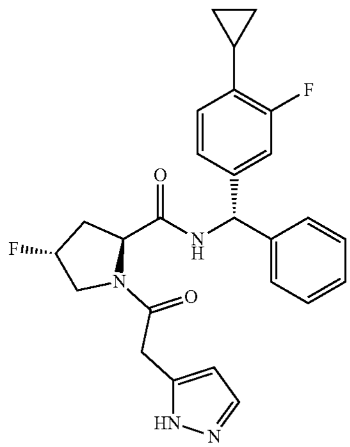 [SMILES: O=C(N[C@@H](c1ccccc1)c1ccc(C2CC2)c(F)c1)[C@@H]1C[C@@H](F)CN1C(=O)Cc1ccn[nH]1] | (2S,4R)-N-[(S)-(4-cyclopropyl-3-fluorophenyl)(phenyl)methyl]-4-fluoro-1-[2-(1H-pyrazol-5-yl)acetyl]pyrrolidine-2-carboxamide | 464.2 | 465.3 |
| 437 | 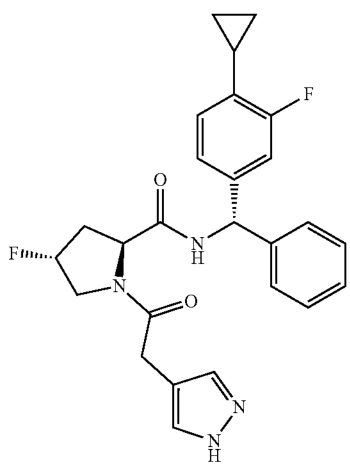 [SMILES: O=C(N[C@@H](c1ccccc1)c1ccc(C2CC2)c(F)c1)[C@@H]1C[C@@H](F)CN1C(=O)Cc1cn[nH]c1] | (2S,4R)-N-[(S)-(4-cyclopropyl-3-fluorophenyl)(phenyl)methyl]-4-fluoro-1-[2-(1H-pyrazol-4-yl)acetyl]pyrrolidine-2-carboxamide | 464.2 | 465.1 |
| 438 | 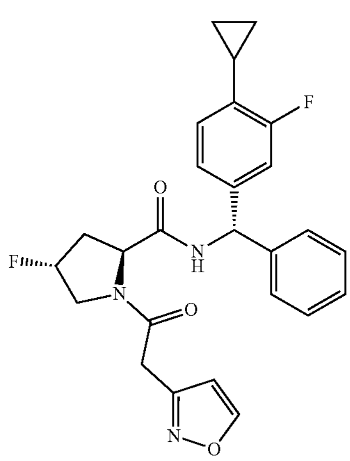 [SMILES: O=C(N[C@@H](c1ccccc1)c1ccc(C2CC2)c(F)c1)[C@@H]1C[C@@H](F)CN1C(=O)Cc1ccon1] | (2S,4R)-N-[(S)-(4-cyclopropyl-3-fluorophenyl)(phenyl)methyl]-4-fluoro-1-[2-(1,2-oxazol-3-yl)acetyl]pyrrolidine-2-carboxamide | 465.2 | 466.1 |

TABLE T-6-continued

| Compound No. | Structure | IUPAC | Exact mass (g/mol) | LCMS, Found [M + H]⁺ |
|---|---|---|---|---|
| 439 | 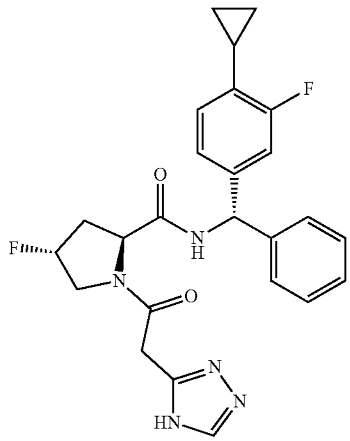 [SMILES: O=C(N[C@@H](c1ccccc1)c1ccc(C2CC2)c(F)c1)[C@@H]1C[C@@H](F)CN1C(=O)Cc1nnc[nH]1] | (2S,4R)-N-[(S)-(4-cyclopropyl-3-fluorophenyl)(phenyl)methyl]-4-fluoro-1-[2-(1H-1,2,3-triazol-5-yl)acetyl]pyrrolidine-2-carboxamide | 465.2 | 466.1 |
| 440 | 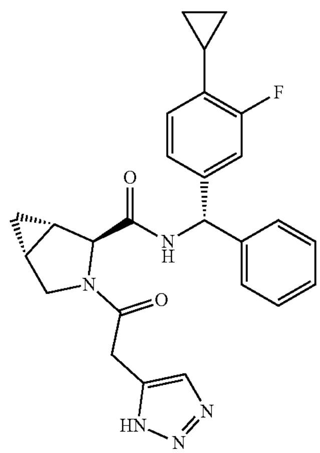 [SMILES: O=C(N[C@@H](c1ccccc1)c1ccc(C2CC2)c(F)c1)[C@@H]1[C@H]2C[C@H]2CN1C(=O)Cc1cnn[nH]1] | (1S,2S,5R)-N-[(S)-(4-cyclopropyl-3-fluorophenyl)(phenyl)methyl]-3-[2-(1H-1,2,3-triazol-5-yl)acetyl]-3-azabicyclo[3.1.0]hexane-2-carboxamide | 459.2 | 460.1 |
| 441 | 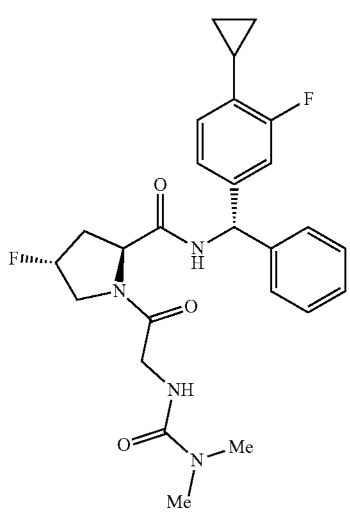 [SMILES: CN(C)C(=O)NCC(=O)N1C[C@H](F)C[C@H]1C(=O)N[C@@H](c1ccccc1)c1ccc(C2CC2)c(F)c1] | (2S,4R)-N-[(S)-(4-cyclopropyl-3-fluorophenyl)(phenyl)methyl]-1-{2-[(dimethylcarbamoyl)amino]acetyl}-4-fluoropyrrolidine-2-carboxamide | 484.2 | 485.1 |

TABLE T-6-continued

| Compound No. | Structure | IUPAC | Exact mass (g/mol) | LCMS, Found [M + H]+ |
|---|---|---|---|---|
| 442 | 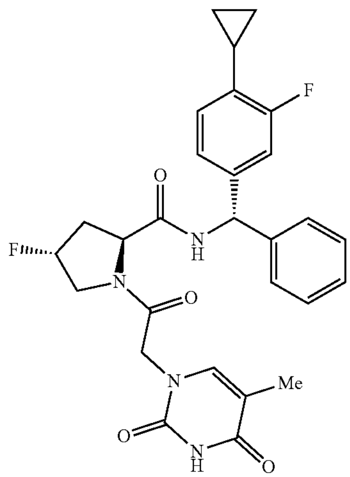 [SMILES: Cc1cn(CC(=O)N2C[C@H](F)C[C@H]2C(=O)N[C@@H](c2ccccc2)c2ccc(C3CC3)c(F)c2)c(=O)[nH]c1=O] | (2S,4R)-N-[(S)-(4-cyclopropyl-3-fluorophenyl)(phenyl)methyl]-4-fluoro-1-[2-(5-methyl-2,4-dioxo-1,2,3,4-tetrahydropyrimidin-1-yl)acetyl]pyrrolidine-2-carboxamide | 522.2 | 523.2 |
| 443 | 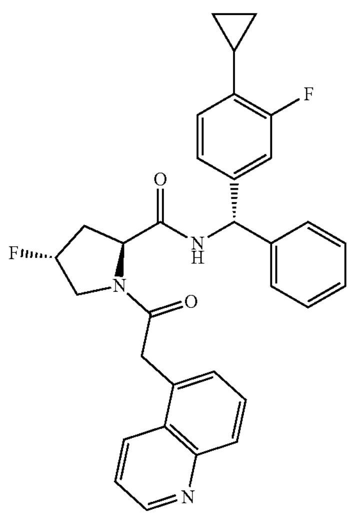 [SMILES: O=C(N[C@@H](c1ccccc1)c1ccc(C2CC2)c(F)c1)[C@@H]1C[C@@H](F)CN1C(=O)Cc1cccc2ncccc12] | (2S,4R)-N-[(S)-(4-cyclopropyl-3-fluorophenyl)(phenyl)methyl]-4-fluoro-1-[2-(quinolin-5-yl)acetyl]pyrrolidine-2-carboxamide | 525.2 | 526.2 |
| 444 | 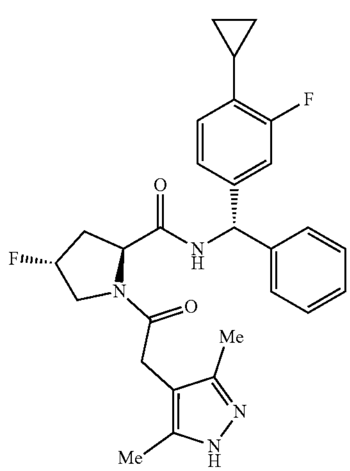 [SMILES: Cc1n[nH]c(C)c1CC(=O)N1C[C@H](F)C[C@H]1C(=O)N[C@@H](c1ccccc1)c1ccc(C2CC2)c(F)c1] | (2S,4R)-N-[(S)-(4-cyclopropyl-3-fluorophenyl)(phenyl)methyl]-1-[2-(3,5-dimethyl-1H-pyrazol-4-yl)acetyl]-4-fluoropyrrolidine-2-carboxamide | 492.2 | 493.2 |

TABLE T-6-continued
| Compound No. | Structure | IUPAC | Exact mass (g/mol) | LCMS, Found [M + H]+ |
|---|---|---|---|---|
| 445 | 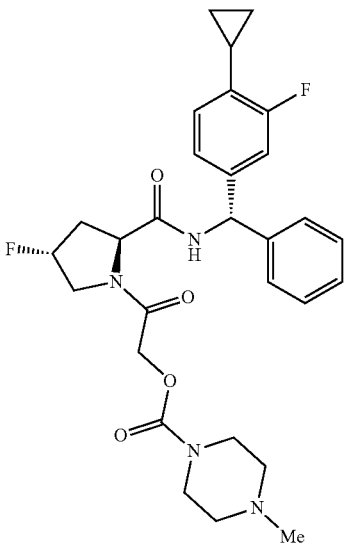 [SMILES: CN1CCN(C(=O)OCC(=O)N2C[C@H](F)C[C@H]2C(=O)N[C@@H](c2ccccc2)c2ccc(C3CC3)c(F)c2)CC1] | 2-[(2S,4R)-2-{[(S)-(4-cyclopropyl-3-fluorophenyl)(phenyl)methyl]carbamoyl}-4-fluoropyrrolidin-1-yl]-2-oxoethyl 4-methylpiperazine-1-carboxylate | 540.3 | 541.3 |
| 446 | 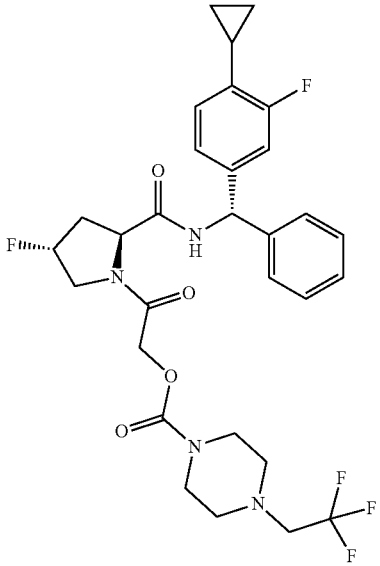 [SMILES: O=C(N[C@@H](c1ccccc1)c1ccc(C2CC2)c(F)c1)[C@@H]1C[C@@H](F)CN1C(=O)COC(=O)N1CCN(CC(F)(F)F)CC1] | 2-[(2S,4R)-2-{[(S)-(4-cyclopropyl-3-fluorophenyl)(phenyl)methyl]carbamoyl}-4-fluoropyrrolidin-1-yl]-2-oxoethyl 4-(2,2,2-trifluoroethyl)piperazine-1-carboxylate | 608.2 | 609.2 |

TABLE T-6-continued
| Compound No. | Structure | IUPAC | Exact mass (g/mol) | LCMS, Found [M + H]+ |
|---|---|---|---|---|
| 447 | 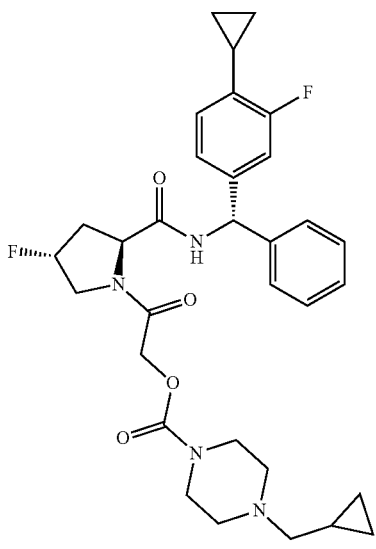 [SMILES: O=C(N[C@@H](c1ccccc1)c1ccc(C2CC2)c(F)c1)[C@@H]1C[C@@H](F)CN1C(=O)COC(=O)N1CCN(CC2CC2)CC1] | 2-[(2S,4R)-2-{[(S)-(4-cyclopropyl-3-fluorophenyl)(phenyl)methyl]carbamoyl}-4-fluoropyrrolidin-1-yl]-2-oxoethyl 4-(cyclopropylmethyl)piperazine-1-carboxylate | 580.3 | 591.3 |
| 448 | 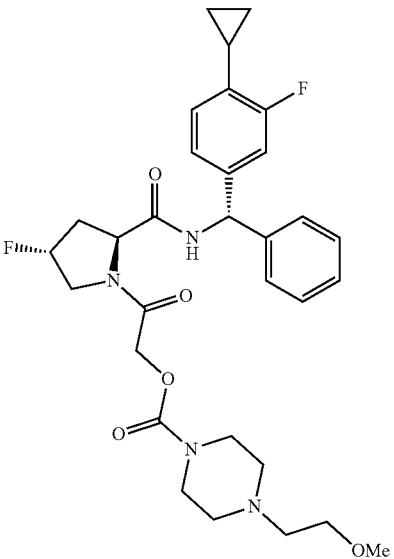 [SMILES: COCCN1CCN(C(=O)OCC(=O)N2C[C@H](F)C[C@H]2C(=O)N[C@@H](c2ccccc2)c2ccc(C3CC3)c(F)c2)CC1] | 2-[(2S,4R)-2-{[(S)-(4-cyclopropyl-3-fluorophenyl)(phenyl)methyl]carbamoyl}-4-fluoropyrrolidin-1-yl]-2-oxoethyl 4-(2-methoxyethyl)piperazine-1-carboxylate | 584.3 | 585.3 |

TABLE T-6-continued

| Compound No. | Structure | IUPAC | Exact mass (g/mol) | LCMS, Found [M + H]+ |
|---|---|---|---|---|
| 449 | 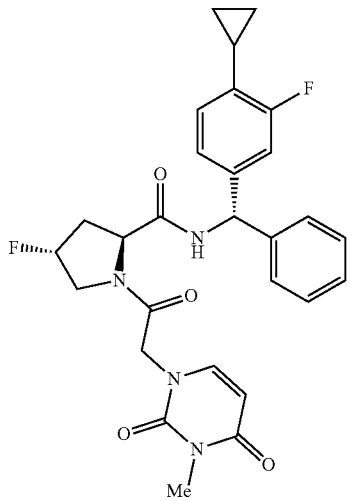 [SMILES: Cn1c(=O)ccn(CC(=O)N2C[C@H](F)C[C@H]2C(=O)N[C@@H](c2ccccc2)c2ccc(C3CC3)c(F)c2)c1=O] | (2S,4R)-N-[(S)-(4-cyclopropyl-3-fluorophenyl)(phenyl)methyl]-4-fluoro-1-[2-(3-methyl-2,4-dioxo-1,2,3,4-tetrahydropyrimidin-1-yl)acetyl]pyrrolidine-2-carboxamide | 522.2 | 523.2 |
| 450 | 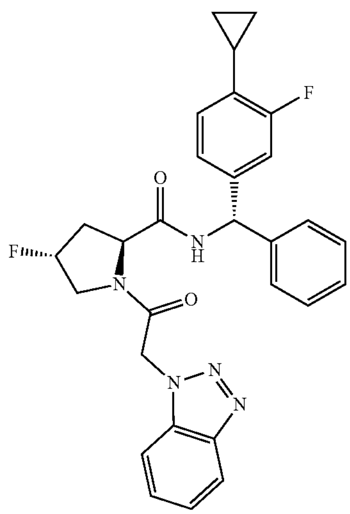 [SMILES: O=C(N[C@@H](c1ccccc1)c1ccc(C2CC2)c(F)c1)[C@@H]1C[C@@H](F)CN1C(=O)Cn1nnc2ccccc21] | (2S,4R)-1-[2-(1H-1,2,3-benzotriazol-1-yl)acetyl]-N-[(S)-(4-cyclopropyl-3-fluorophenyl)(phenyl)methyl]-4-fluoropyrrolidine-2-carboxamide | 515.2 | 516.3 |
| 451 | 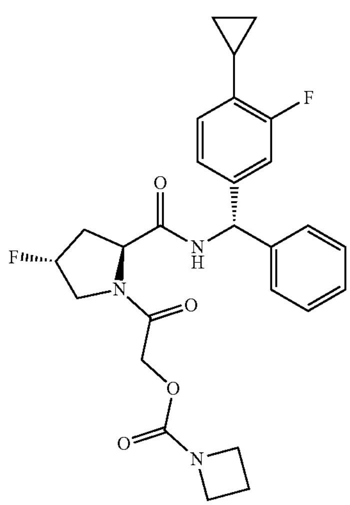 [SMILES: O=C(N[C@@H](c1ccccc1)c1ccc(C2CC2)c(F)c1)[C@@H]1C[C@@H](F)CN1C(=O)COC(=O)N1CCC1] | 2-[(2S,4R)-2-{[(S)-(4-cyclopropyl-3-fluorophenyl)(phenyl)methyl]carbamoyl}-4-fluoropyrrolidin-1-yl]-2-oxoethyl azetidine-1-carboxylate | 497.2 | 498.3 |

TABLE T-6-continued

| Compound No. | Structure | IUPAC | Exact mass (g/mol) | LCMS, Found [M + H]+ |
|---|---|---|---|---|
| 452 | 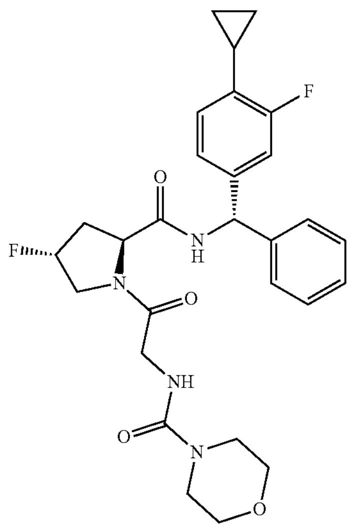 [SMILES: O=C(N[C@@H](c1ccccc1)c1ccc(C2CC2)c(F)c1)[C@@H]1C[C@@H](F)CN1C(=O)CNC(=O)N1CCOCC1] | N-{2-[(2S,4R)-2-{[(S)-(4-cyclopropyl-3-fluorophenyl)(phenyl)methyl]carbamoyl}-4-fluoropyrrolidin-1-yl]-2-oxoethyl}morpholine-4-carboxamide | 526.2 | 527.3 |
| 453 | 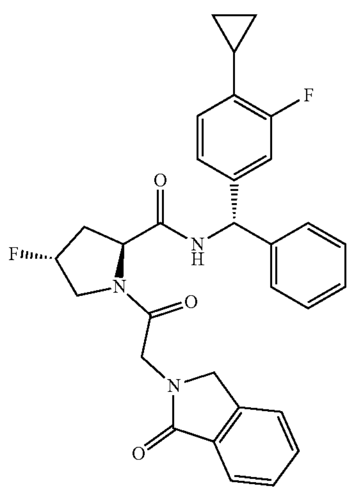 [SMILES: O=C(N[C@@H](c1ccccc1)c1ccc(C2CC2)c(F)c1)[C@@H]1C[C@@H](F)CN1C(=O)CN1Cc2ccccc2C1=O] | (2S,4R)-N-[(S)-(4-cyclopropyl-3-fluorophenyl)(phenyl)methyl]-4-fluoro-1-[2-(1-oxo-2,3-dihydro-1H-isoindol-2-yl)acetyl]pyrrolidine-2-carboxamide | 529.2 | 530.2 |
| 454 | 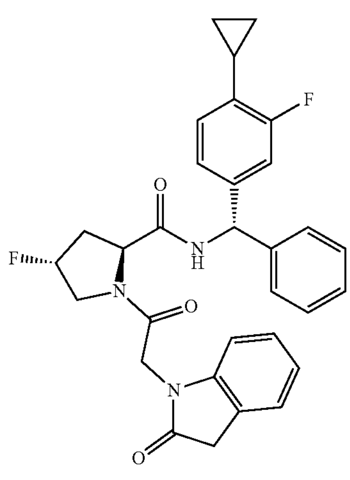 [SMILES: O=C(N[C@@H](c1ccccc1)c1ccc(C2CC2)c(F)c1)[C@@H]1C[C@@H](F)CN1C(=O)CN1C(=O)Cc2ccccc21] | (2S,4R)-N-[(S)-(4-cyclopropyl-3-fluorophenyl)(phenyl)methyl]-4-fluoro-1-[2-(2-oxo-2,3-dihydro-1H-indol-1-yl)acetyl]pyrrolidine-2-carboxamide | 529.2 | 530.1 |

TABLE T-6-continued

| Compound No. | Structure | IUPAC | Exact mass (g/mol) | LCMS, Found [M + H]⁺ |
|---|---|---|---|---|
| 455 | 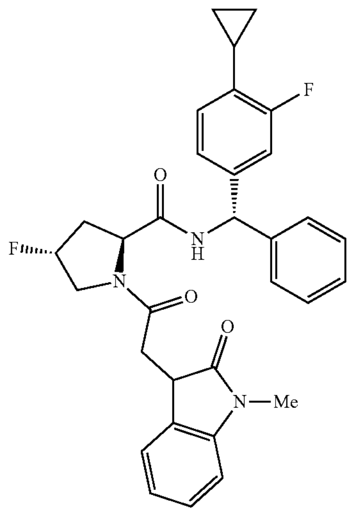 | (2S,4R)-N-[(S)-(4-cyclopropyl-3-fluorophenyl)(phenyl)methyl]-4-fluoro-1-[2-(1-methyl-2-oxo-2,3-dihydro-1H-indol-3-yl)acetyl]pyrrolidine-2-carboxamide | 543.2 | 544.3 |
| 456 | 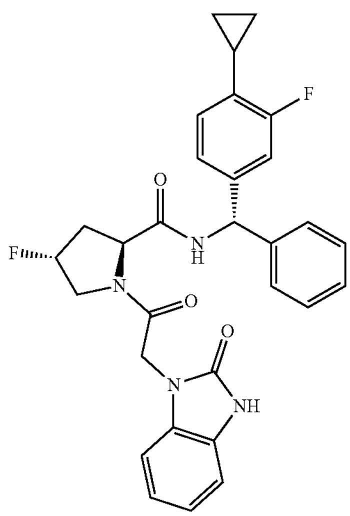 | (2S,4R)-N-[(S)-(4-cyclopropyl-3-fluorophenyl)(phenyl)methyl]-4-fluoro-1-[2-(2-oxo-2,3-dihydro-1H-1,3-benzodiazol-1-yl)acetyl]pyrrolidine-2-carboxamide | 530.2 | 531.2 |
| 457 | 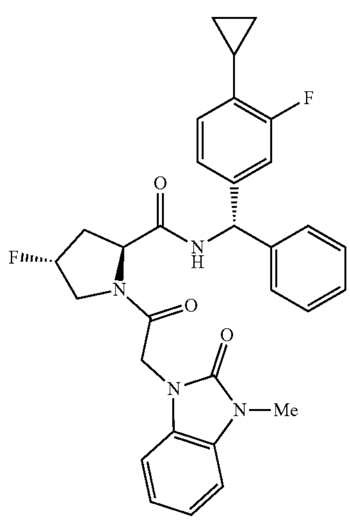 | (2S,4R)-N-[(S)-(4-cyclopropyl-3-fluorophenyl)(phenyl)methyl]-4-fluoro-1-[2-(3-methyl-2-oxo-2,3-dihydro-1H-1,3-benzodiazol-1-yl)acetyl]pyrrolidine-2-carboxamide | 544.2 | 545.2 |

TABLE T-6-continued

| Compound No. | Structure | IUPAC | Exact mass (g/mol) | LCMS, Found [M + H]+ |
|---|---|---|---|---|
| 458 | 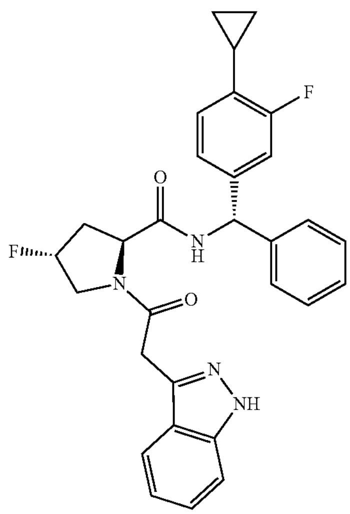 [SMILES: O=C(N[C@@H](c1ccccc1)c1ccc(C2CC2)c(F)c1)[C@@H]1C[C@@H](F)CN1C(=O)Cc1n[nH]c2ccccc12] | (2S,4R)-N-[(S)-(4-cyclopropyl-3-fluorophenyl)(phenyl)methyl]-4-fluoro-1-[2-(1H-indazol-3-yl)acetyl]pyrrolidine-2-carboxamide | 514.2 | 515.1 |
| 459 | 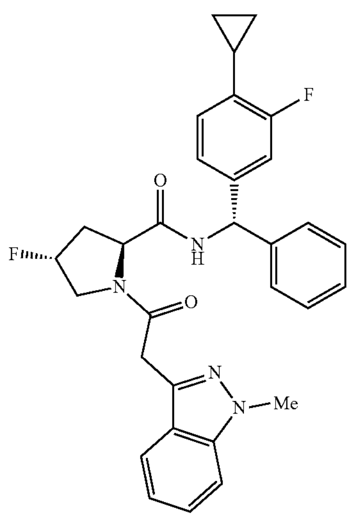 [SMILES: Cn1nc(CC(=O)N2C[C@H](F)C[C@H]2C(=O)N[C@@H](c2ccccc2)c2ccc(C3CC3)c(F)c2)c2ccccc21] | (2S,4R)-N-[(S)-(4-cyclopropyl-3-fluorophenyl)(phenyl)methyl]-4-fluoro-1-[2-(1-methyl-1H-indazol-3-yl)acetyl]pyrrolidine-2-carboxamide | 528.2 | 529.2 |
| 460 | 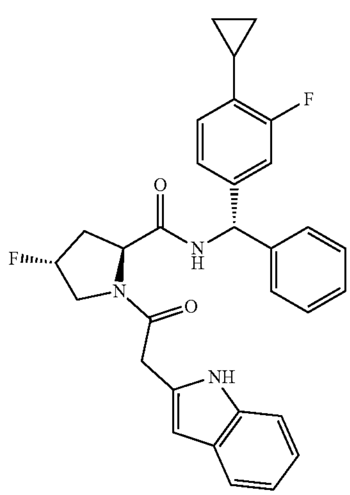 [SMILES: O=C(N[C@@H](c1ccccc1)c1ccc(C2CC2)c(F)c1)[C@@H]1C[C@@H](F)CN1C(=O)Cc1cc2ccccc2[nH]1] | (2S,4R)-N-[(S)-(4-cyclopropyl-3-fluorophenyl)(phenyl)methyl]-4-fluoro-1-[2-(1H-indol-2-yl)acetyl]pyrrolidine-2-carboxamide | 513.2 | 514.3 |

TABLE T-6-continued

| Compound No. | Structure | IUPAC | Exact mass (g/mol) | LCMS, Found [M + H]+ |
|---|---|---|---|---|
| 461 | 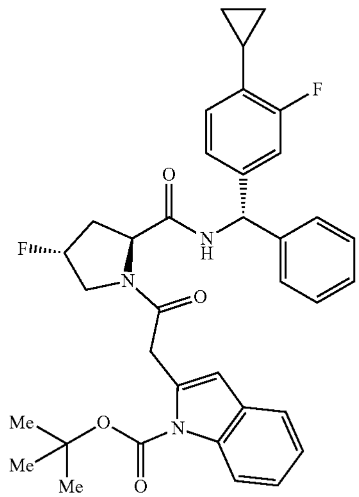 [SMILES: CC(C)(C)OC(=O)n1c(CC(=O)N2C[C@H](F)C[C@H]2C(=O)N[C@@H](c2ccccc2)c2ccc(C3CC3)c(F)c2)cc2ccccc21] | tert-butyl 2-{2-[(2S,4R)-2-{[(S)-(4-cyclopropyl-3-fluorophenyl)(phenyl)methyl]carbamoyl}-4-fluoropyrrolidin-1-yl]-2-oxoethyl}-1H-indole-1-carboxylate | 613.3 | 514.3 [M − Boc + H]+ |
| 462 | 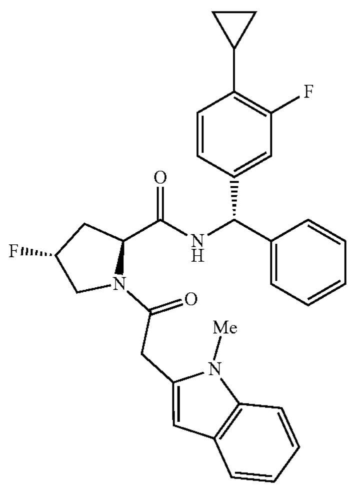 [SMILES: Cn1c(CC(=O)N2C[C@H](F)C[C@H]2C(=O)N[C@@H](c2ccccc2)c2ccc(C3CC3)c(F)c2)cc2ccccc21] | (2S,4R)-N-[(S)-(4-cyclopropyl-3-fluorophenyl)(phenyl)methyl]-4-fluoro-1-[2-(1-methyl-1H-indol-2-yl)acetyl]pyrrolidine-2-carboxamide | 527.2 | 528.3 |
| 463 | 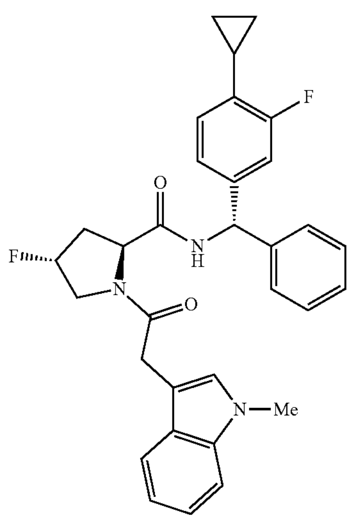 [SMILES: Cn1cc(CC(=O)N2C[C@H](F)C[C@H]2C(=O)N[C@@H](c2ccccc2)c2ccc(C3CC3)c(F)c2)c2ccccc21] | (2S,4R)-N-[(S)-(4-cyclopropyl-3-fluorophenyl)(phenyl)methyl]-4-fluoro-1-[2-(1-methyl-1H-indol-3-yl)acetyl]pyrrolidine-2-carboxamide | 527.2 | 528.2 |

TABLE T-6-continued

| Compound No. | Structure | IUPAC | Exact mass (g/mol) | LCMS, Found [M + H]+ |
|---|---|---|---|---|
| 464 | 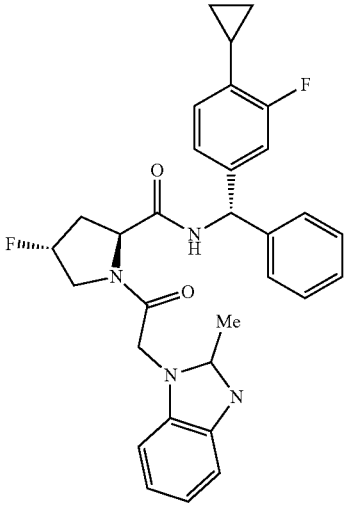 [SMILES: CC1Nc2ccccc2N1CC(=O)N1C[C@H](F)C[C@H]1C(=O)N[C@@H](c1ccccc1)c1ccc(C2CC2)c(F)c1] | (2S,4R)-N-[(S)-(4-cyclopropyl-3-fluorophenyl)(phenyl)methyl]-4-fluoro-1-[2-(2-methyl-1H-1,3-benzodiazol-1-yl)acetyl]pyrrolidine-2-carboxamide | 528.2 | 529.3 |
| 465 | 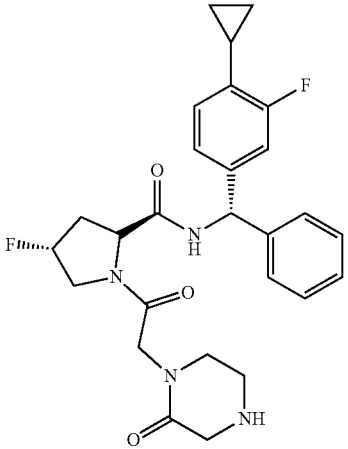 | (2S,4R)-N-[(S)-(4-cyclopropyl-3-fluorophenyl)(phenyl)methyl]-4-fluoro-1-[2-(2-oxopiperazin-1-yl)acetyl]pyrrolidine-2-carboxamide | 496.2 | 497.2 |
| 466 | 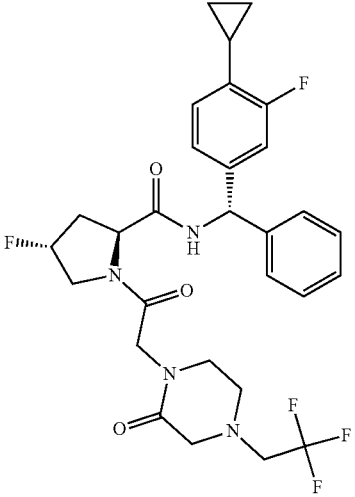 [SMILES: O=C(N[C@@H](c1ccccc1)c1ccc(C2CC2)c(F)c1)[C@@H]1C[C@@H](F)CN1C(=O)CN1CCN(CC(F)(F)F)CC1=O] | (2S,4R)-N-[(S)-(4-cyclopropyl-3-fluorophenyl)(phenyl)methyl]-4-fluoro-1-{2-[2-oxo-4-(2,2,2-trifluoroethyl)piperazin-1-yl]acetyl}pyrrolidine-2-carboxamide | 578.2 | 579.2 |

TABLE T-6-continued

| Compound No. | Structure | IUPAC | Exact mass (g/mol) | LCMS, Found [M + H]+ |
|---|---|---|---|---|
| 467 | 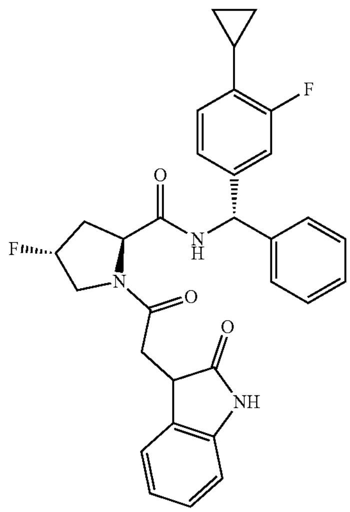 | (2S,4R)-N-[(S)-(4-cyclopropyl-3-fluorophenyl)(phenyl)methyl]-4-fluoro-1-[2-(2-oxo-2,3-dihydro-1H-indol-3-yl)acetyl]pyrrolidine-2-carboxamide | 529.2 | 530.2 |
| 468 | 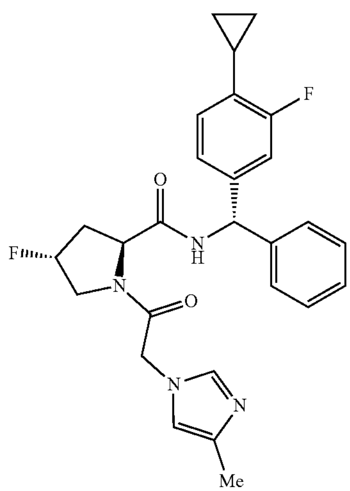 [SMILES: Cc1cn(CC(=O)N2C[C@H](F)C[C@H]2C(=O)N[C@@H](c2ccccc2)c2ccc(C3CC3)c(F)c2)cn1] | (2S,4R)-N-[(S)-(4-cyclopropyl-3-fluorophenyl)(phenyl)methyl]-4-fluoro-1-[2-(4-methyl-1H-imidazol-1-yl)acetyl]pyrrolidine-2-carboxamide | 478.2 | 479.2 |
| 469 | 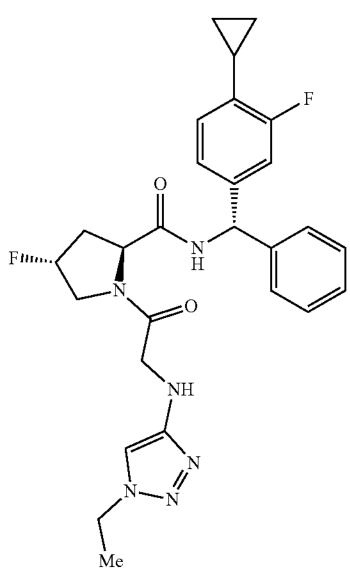 [SMILES: CCn1cc(NCC(=O)N2C[C@H](F)C[C@H]2C(=O)N[C@@H](c2ccccc2)c2ccc(C3CC3)c(F)c2)nn1] | (2S,4R)-N-[(S)-(4-cyclopropyl-3-fluorophenyl)(phenyl)methyl]-1-{2-[(1-ethyl-1H-1,2,3-triazol-4-yl)amino]acetyl}-4-fluoropyrrolidine-2-carboxamide | 508.2 | 509.3 |

TABLE T-6-continued
| Compound No. | Structure | IUPAC | Exact mass (g/mol) | LCMS, Found [M + H]+ |
|---|---|---|---|---|
| 470 | 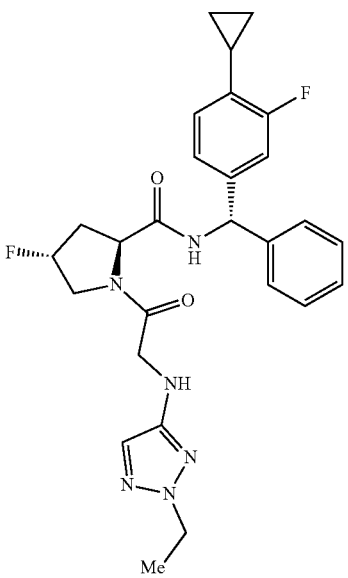 [SMILES: CCn1ncc(NCC(=O)N2C[C@H](F)C[C@H]2C(=O)N[C@@H](c2ccccc2)c2ccc(C3CC3)c(F)c2)n1] | (2S,4R)-N-[(S)-(4-cyclopropyl-3-fluorophenyl)(phenyl)methyl]-1-{2-[(2-ethyl-2H-1,2,3-triazol-4-yl)amino]acetyl}-4-fluoropyrrolidine-2-carboxamide | 508.2 | 509.3 |
| 471 | 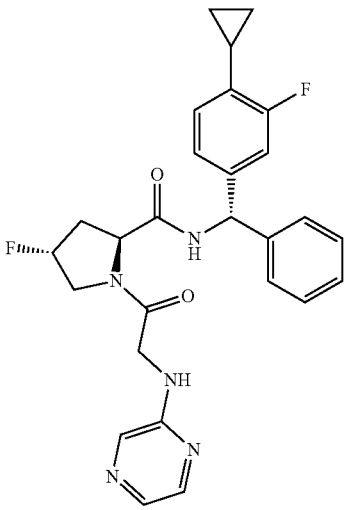 [SMILES: O=C(N[C@@H](c1ccccc1)c1ccc(C2CC2)c(F)c1)[C@@H]1C[C@@H](F)CN1C(=O)CNc1cnccn1] | (2S,4R)-N-[(S)-(4-cyclopropyl-3-fluorophenyl)(phenyl)methyl]-4-fluoro-1-{2-[(pyrazin-2-yl)amino]acetyl}pyrrolidine-2-carboxamide | 491.2 | 492.2 |

TABLE T-6-continued
| Compound No. | Structure | IUPAC | Exact mass (g/mol) | LCMS, Found [M + H]+ |
|---|---|---|---|---|
| 472 | 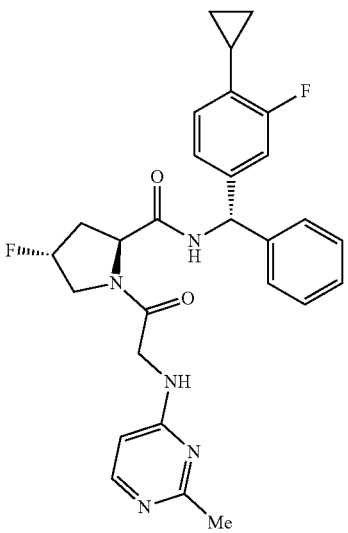 [SMILES: Cc1nccc(NCC(=O)N2C[C@H](F)C[C@H]2C(=O)N[C@@H](c2ccccc2)c2ccc(C3CC3)c(F)c2)n1] | (2S,4R)-N-[(S)-(4-cyclopropyl-3-fluorophenyl)(phenyl)methyl]-4-fluoro-1-{2-[(2-methylpyrimidin-4-yl)amino]acetyl}pyrrolidine-2-carboxamide | 505.2 | 506.3 |
| 473 | 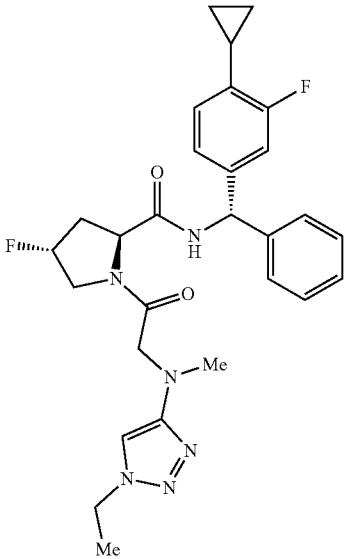 [SMILES: CCn1cc(N(C)CC(=O)N2C[C@H](F)C[C@H]2C(=O)N[C@@H](c2ccccc2)c2ccc(C3CC3)c(F)c2)nn1] | (2S,4R)-N-[(S)-(4-cyclopropyl-3-fluorophenyl)(phenyl)methyl]-1-{2-[(1-ethyl-1H-1,2,3-triazol-4-yl)(methyl)amino]acetyl}-4-fluoropyrrolidine-2-carboxamide | 522.3 | 523.2 |

TABLE T-6-continued

| Compound No. | Structure | IUPAC | Exact mass (g/mol) | LCMS, Found [M + H]+ |
|---|---|---|---|---|
| 474 | 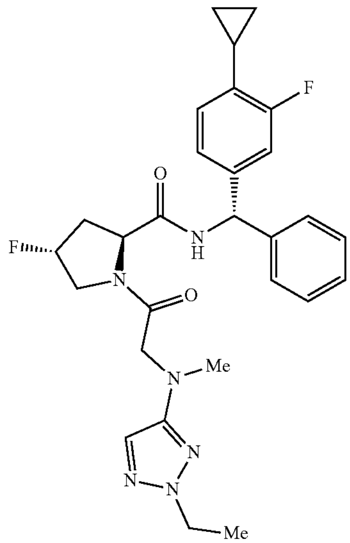 [SMILES: CCn1ncc(N(C)CC(=O)N2C[C@H](F)C[C@H]2C(=O)N[C@@H](c2ccccc2)c2ccc(C3CC3)c(F)c2)n1] | (2S,4R)-N-[(S)-(4-cyclopropyl-3-fluorophenyl)(phenyl)methyl]-1-{2-[(2-ethyl-2H-1,2,3-triazol-4-yl)(methyl)amino]acetyl}-4-fluoropyrrolidine-2-carboxamide | 522.3 | 523.2 |
| 475 | 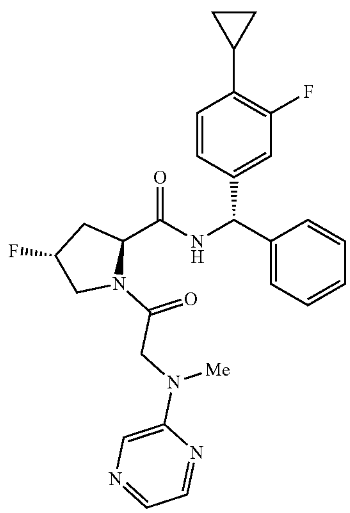 [SMILES: CN(CC(=O)N1C[C@H](F)C[C@H]1C(=O)N[C@@H](c1ccccc1)c1ccc(C2CC2)c(F)c1)c1cnccn1] | (2S,4R)-N-[(S)-(4-cyclopropyl-3-fluorophenyl)(phenyl)methyl]-4-fluoro-1-{2-[methyl(pyrazin-2-yl)amino]acetyl}pyrrolidine-2-carboxamide | 505.2 | 506.1 |
| 476 | 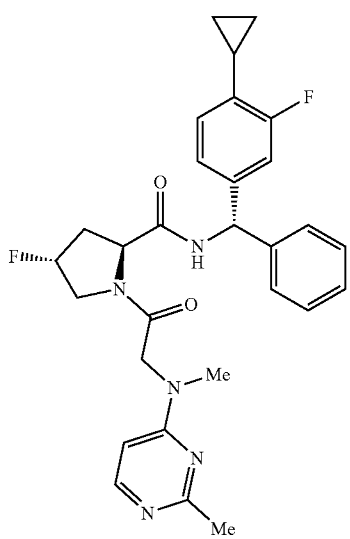 | (2S,4R)-N-[(S)-(4-cyclopropyl-3-fluorophenyl)(phenyl)methyl]-4-fluoro-1-{2-[methyl(2-methylpyrimidin-4-yl)amino]acetyl}pyrrolidine-2-carboxamide | 519.2 | 520.3 |

TABLE T-6-continued

| Compound No. | Structure | IUPAC | Exact mass (g/mol) | LCMS, Found [M + H]⁺ |
| --- | --- | --- | --- | --- |
| 477 | 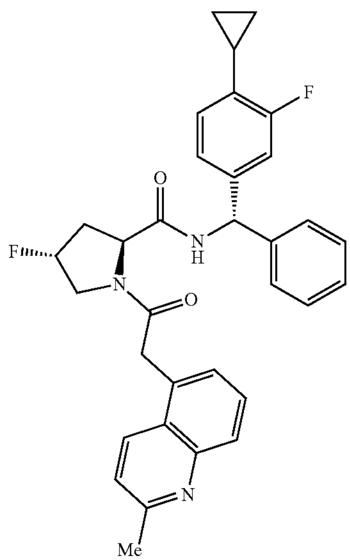 [SMILES: Cc1ccc2c(CC(=O)N3C[C@H](F)C[C@H]3C(=O)N[C@@H](c3ccccc3)c3ccc(C4CC4)c(F)c3)cccc2n1] | (2S,4R)-N-[(S)-(4-cyclopropyl-3-fluorophenyl)(phenyl)methyl]-4-fluoro-1-[2-(2-methylquinolin-5-yl)acetyl]pyrrolidine-2-carboxamide | 539.2 | 540.2 |
| 478 | 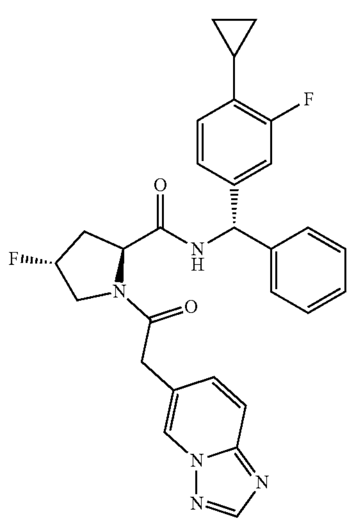 [SMILES: O=C(N[C@@H](c1ccccc1)c1ccc(C2CC2)c(F)c1)[C@@H]1C[C@@H](F)CN1C(=O)Cc1ccc2ncnn2c1] | (2S,4R)-N-[(S)-(4-cyclopropyl-3-fluorophenyl)(phenyl)methyl]-4-fluoro-1-(2-{[1,2,4]triazolo[1,5-a]pyridin-6-yl}acetyl)pyrrolidine-2-carboxamide | 515.2 | 516.3 |

TABLE T-6-continued

| Compound No. | Structure | IUPAC | Exact mass (g/mol) | LCMS, Found [M + H]+ |
|---|---|---|---|---|
| 479 | 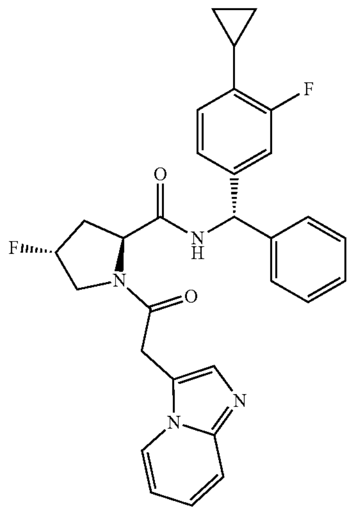 [SMILES: O=C(N[C@@H](c1ccccc1)c1ccc(C2CC2)c(F)c1)[C@@H]1C[C@@H](F)CN1C(=O)Cc1cnc2ccccn12] | (2S,4R)-N-[(S)-(4-cyclopropyl-3-fluorophenyl)(phenyl)methyl]-4-fluoro-1-(2-{imidazo[1,2-a]pyridin-3-yl}acetyl)pyrrolidine-2-carboxamide | 514.2 | 515.3 |
| 480 | 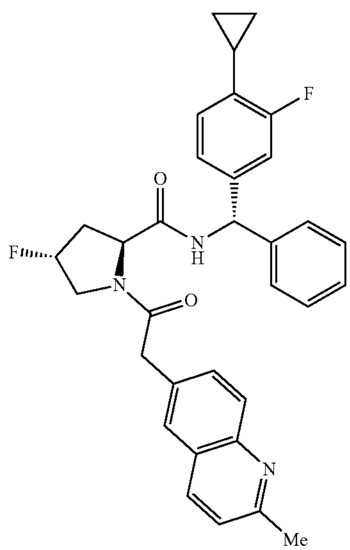 [SMILES: Cc1ccc2cc(CC(=O)N3C[C@H](F)C[C@H]3C(=O)N[C@@H](c3ccccc3)c3ccc(C4CC4)c(F)c3)ccc2n1] | (2S,4R)-N-[(S)-(4-cyclopropyl-3-fluorophenyl)(phenyl)methyl]-4-fluoro-1-[2-(2-methylquinolin-6-yl)acetyl]pyrrolidine-2-carboxamide | 539.2 | 540.2 |
| 481 | 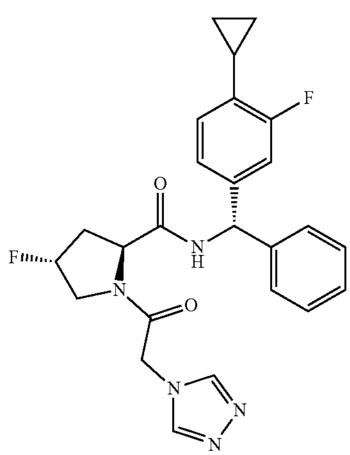 [SMILES: O=C(N[C@@H](c1ccccc1)c1ccc(C2CC2)c(F)c1)[C@@H]1C[C@@H](F)CN1C(=O)Cn1cnnc1] | (2S,4R)-N-[(S)-(4-cyclopropyl-3-fluorophenyl)(phenyl)methyl]-4-fluoro-1-[2-(4H-1,2,4-triazol-4-yl)acetyl]pyrrolidine-2-carboxamide | 465.2 | 466.3 |

TABLE T-6-continued

| Compound No. | Structure | IUPAC | Exact mass (g/mol) | LCMS, Found [M + H]+ |
|---|---|---|---|---|
| 482 | 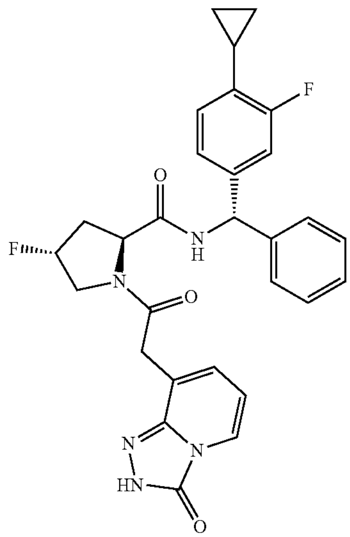 | (2S,4R)-N-[(S)-(4-cyclopropyl-3-fluorophenyl)(phenyl)methyl]-4-fluoro-1-(2-{3-oxo-2H,3H-[1,2,4]triazolo[4,3-a]pyridin-8-yl}acetyl)pyrrolidine-2-carboxamide | 531.2 | 532.2 |
| 483 | 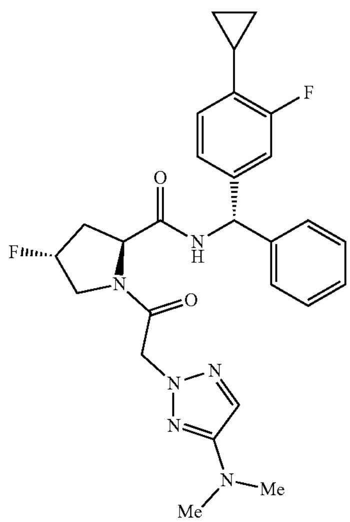 [SMILES: CN(C)c1cnn(CC(=O)N2C[C@H](F)C[C@H]2C(=O)N[C@@H](c2ccccc2)c2ccc(C3CC3)c(F)c2)n1] | (2S,4R)-N-[(S)-(4-cyclopropyl-3-fluorophenyl)(phenyl)methyl]-1-{2-[4-(dimethylamino)-2H-1,2,3-triazol-2-yl]acetyl}-4-fluoropyrrolidine-2-carboxamide | 508.2 | 509.2 |
| 484 | 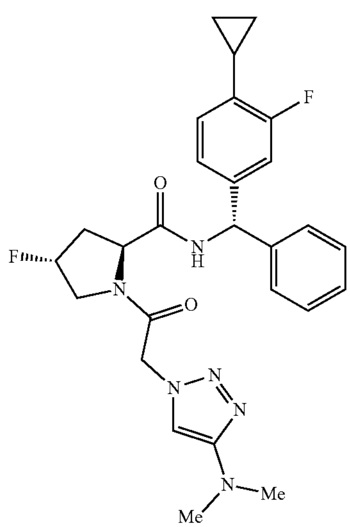 [SMILES: CN(C)c1cn(CC(=O)N2C[C@H](F)C[C@H]2C(=O)N[C@@H](c2ccccc2)c2ccc(C3CC3)c(F)c2)nn1] | (2S,4R)-N-[(S)-(4-cyclopropyl-3-fluorophenyl)(phenyl)methyl]-1-{2-[4-(dimethylamino)-1H-1,2,3-triazol-1-yl]acetyl}-4-fluoropyrrolidine-2-carboxamide | 508.2 | 509.2 |

TABLE T-6-continued
| Compound No. | Structure | IUPAC | Exact mass (g/mol) | LCMS, Found [M + H]+ |
|---|---|---|---|---|
| 485 | 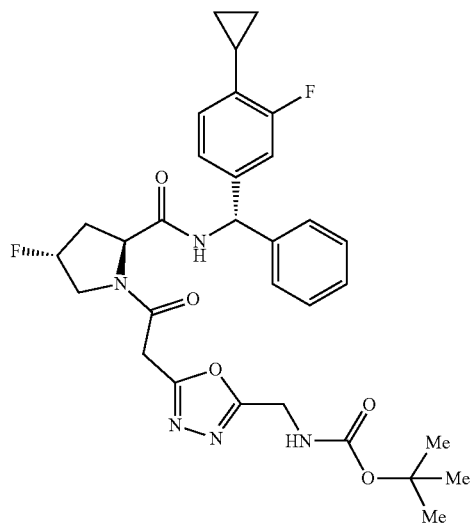 [SMILES: CC(C)(C)OC(=O)NCc1nnc(CC(=O)N2C[C@H](F)C[C@H]2C(=O)N[C@@H](c2ccccc2)c2ccc(C3CC3)c(F)c2)o1] | tert-butyl N-[(5-{2-[(2S,4R)-2-{[(S)-(4-cyclopropyl-3-fluorophenyl)(phenyl)methyl]carbamoyl}-4-fluoropyrrolidin-1-yl]-2-oxoethyl}-1,3,4-oxadiazol-2-yl)methyl]carbamate | 595.3 | 596.3 |
| 486 | 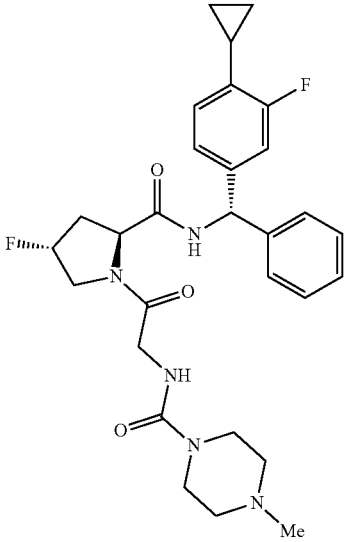 [SMILES: CN1CCN(C(=O)NCC(=O)N2C[C@H](F)C[C@H]2C(=O)N[C@@H](c2ccccc2)c2ccc(C3CC3)c(F)c2)CC1] | N-{2-[(2S,4R)-2-{[(S)-(4-cyclopropyl-3-fluorophenyl)(phenyl)methyl]carbamoyl}-4-fluoropyrrolidin-1-yl]-2-oxoethyl}-4-methylpiperazine-1-carboxamide | 539.3 | 540.2 |

TABLE T-6-continued
| Compound No. | Structure | IUPAC | Exact mass (g/mol) | LCMS, Found [M + H]+ |
|---|---|---|---|---|
| 487 | 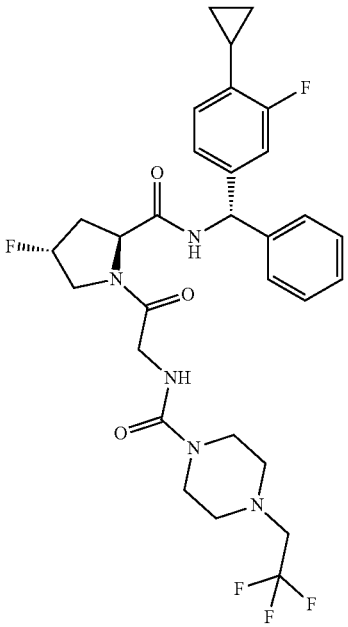 [SMILES: O=C(N[C@@H](c1ccccc1)c1ccc(C2CC2)c(F)c1)[C@@H]1C[C@@H](F)CN1C(=O)CNC(=O)N1CCN(CC(F)(F)F)CC1] | N-{2-[(2S,4R)-2-{[(S)-(4-cyclopropyl-3-fluorophenyl)(phenyl)methyl]carbamoyl}-4-fluoropyrrolidin-1-yl]-2-oxoethyl}-4-(2,2,2-trifluoroethyl)piperazine-1-carboxamide | 607.3 | 608.2 |
| 488 | 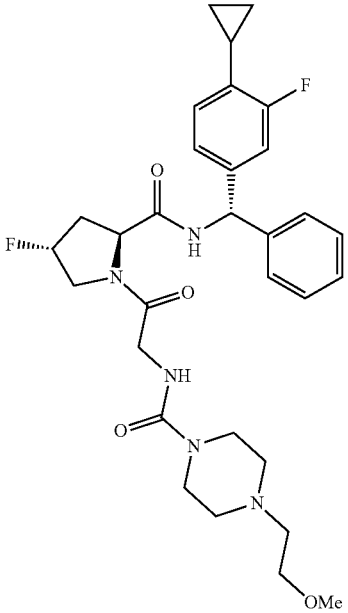 [SMILES: COCCN1CCN(C(=O)NCC(=O)N2C[C@H](F)C[C@H]2C(=O)N[C@@H](c2ccccc2)c2ccc(C3CC3)c(F)c2)CC1] | N-{2-[(2S,4R)-2-{[(S)-(4-cyclopropyl-3-fluorophenyl)(phenyl)methyl]carbamoyl}-4-fluoropyrrolidin-1-yl]-2-oxoethyl}-4-(2-methoxyethyl)piperazine-1-carboxamide | 583.3 | 584.2 |

TABLE T-6-continued

| Compound No. | Structure | IUPAC | Exact mass (g/mol) | LCMS, Found [M + H]+ |
|---|---|---|---|---|
| 489 | 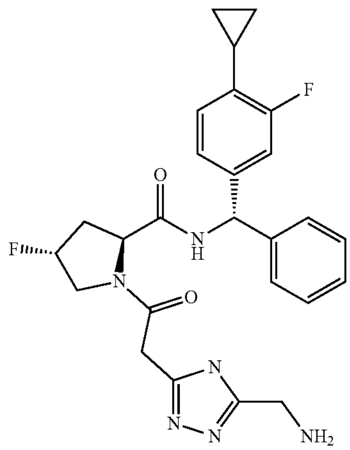 [SMILES: NCc1nnc(CC(=O)N2C[C@H](F)C[C@H]2C(=O)N[C@@H](c2ccccc2)c2ccc(C3CC3)c(F)c2)[nH]1] | (2S,4R)-1-{2-[5-(aminomethyl)-1,3,4-oxadiazol-2-yl]acetyl}-N-[(S)-(4-cyclopropyl-3-fluorophenyl)(phenyl)methyl]-4-fluoropyrrolidine-2-carboxamide | 495.2 | 496.1 |
| 490 | 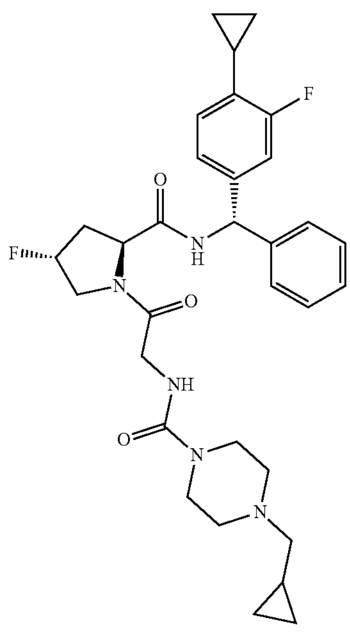 [SMILES: O=C(N[C@@H](c1ccccc1)c1ccc(C2CC2)c(F)c1)[C@@H]1C[C@@H](F)CN1C(=O)CNC(=O)N1CCN(CC2CC2)CC1] | N-{2-[(2S,4R)-2-{[(S)-(4-cyclopropyl-3-fluorophenyl)(phenyl)methyl]carbamoyl}-4-fluoropyrrolidin-1-yl]-2-oxoethyl}-4-(cyclopropylmethyl)piperazine-1-carboxamide | 579.3 | 580.2 |
| 491 | 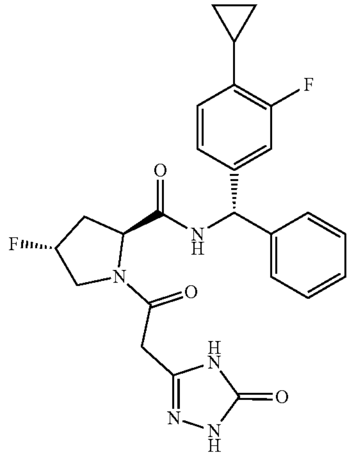 [SMILES: O=C(N[C@@H](c1ccccc1)c1ccc(C2CC2)c(F)c1)[C@@H]1C[C@@H](F)CN1C(=O)Cc1n[nH]c(=O)[nH]1] | (2S,4R)-N-[(S)-(4-cyclopropyl-3-fluorophenyl)(phenyl)methyl]-4-fluoro-1-[2-(5-oxo-4,5-dihydro-1H-1,2,4-triazol-3-yl)acetyl]pyrrolidine-2-carboxamide | 481.2 | 482.3 |

TABLE T-6-continued

| Compound No. | Structure | IUPAC | Exact mass (g/mol) | LCMS, Found [M + H]+ |
| --- | --- | --- | --- | --- |
| 492 | 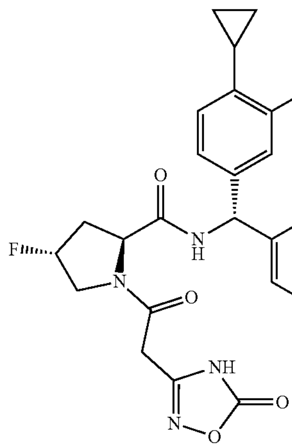 | (2S,4R)-N-[(S)-(4-cyclopropyl-3-fluorophenyl)(phenyl)methyl]-4-fluoro-1-[2-(5-oxo-4,5-dihydro-1,2,4-oxadiazol-3-yl)acetyl]pyrrolidine-2-carboxamide | 482.2 | 483.1 |
| 493 | 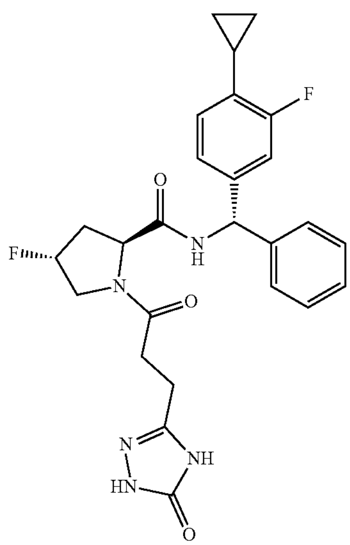 [SMILES: O=C(N[C@@H](c1ccccc1)c1ccc(C2CC2)c(F)c1)[C@@H]1C[C@@H](F)CN1C(=O)CCc1n[nH]c(=O)[nH]1] | (2S,4R)-N-[(S)-(4-cyclopropyl-3-fluorophenyl)(phenyl)methyl]-4-fluoro-1-[3-(5-oxo-4,5-dihydro-1H-1,2,4-triazol-3-yl)propanoyl]pyrrolidine-2-carboxamide | 495.2 | 496.2 |
| 494 | 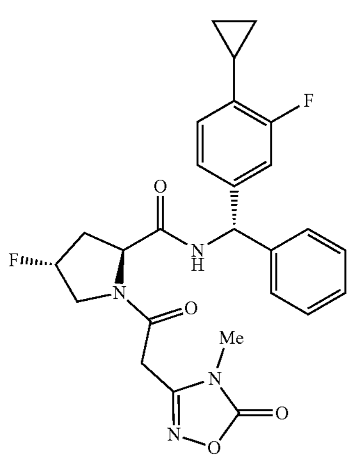 [SMILES: Cn1c(CC(=O)N2C[C@H](F)C[C@H]2C(=O)N[C@@H](c2ccccc2)c2ccc(C3CC3)c(F)c2)noc1=O] | (2S,4R)-N-[(S)-(4-cyclopropyl-3-fluorophenyl)(phenyl)methyl]-4-fluoro-1-[2-(4-methyl-5-oxo-4,5-dihydro-1,2,4-oxadiazol-3-yl)acetyl]pyrrolidine-2-carboxamide | 496.2 | 497.1 |

TABLE T-6-continued

| Compound No. | Structure | IUPAC | Exact mass (g/mol) | LCMS, Found [M + H]+ |
|---|---|---|---|---|
| 495 | 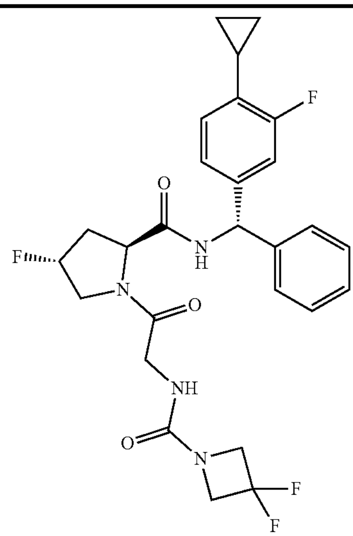 | (2S,4R)-N-[(S)-(4-cyclopropyl-3-fluorophenyl)(phenyl)methyl]-1-{2-[(3,3-difluoroazetidine-1-carbonyl)amino]acetyl}-4-fluoropyrrolidine-2-carboxamide | 532.2 | 533.1 |
| 496 | 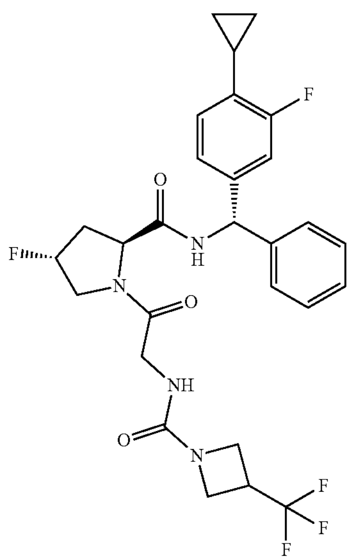 [SMILES: O=C(N[C@@H](c1ccccc1)c1ccc(C2CC2)c(F)c1)[C@@H]1C[C@@H](F)CN1C(=O)CNC(=O)N1CC(C(F)(F)F)C1] | (2S,4R)-N-[(S)-(4-cyclopropyl-3-fluorophenyl)(phenyl)methyl]-4-fluoro-1-(2-{[3-(trifluoromethyl)azetidine-1-carbonyl]amino}acetyl)pyrrolidine-2-carboxamide | 564.2 | 565.2 |
| 809 | 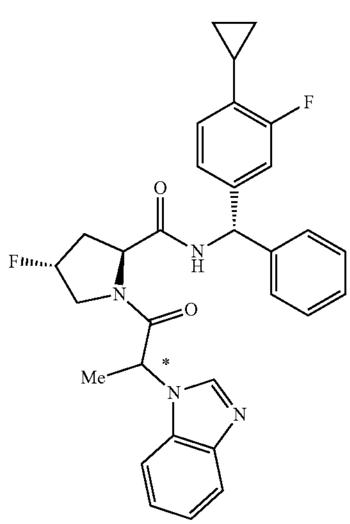 [SMILES: CC(C(=O)N1C[C@H](F)C[C@H]1C(=O)N[C@@H](c1ccccc1)c1ccc(C2CC2)c(F)c1)n1cnc2ccccc21] | (2S,4R)-1-[(2S) or (2R)-2-(1H-1,3-benzodiazol-1-yl)propanoyl]-N-[(S)-(4-cyclopropyl-3-fluorophenyl)(phenyl)methyl]-4-fluoropyrrolidine-2-carboxamide (column: DAICEL CHIRALPAK AD, second-eluting isomer) | 528.2 | 529.2 |

TABLE T-6-continued

| Compound No. | Structure | IUPAC | Exact mass (g/mol) | LCMS, Found [M + H]+ |
|---|---|---|---|---|
| 810 | 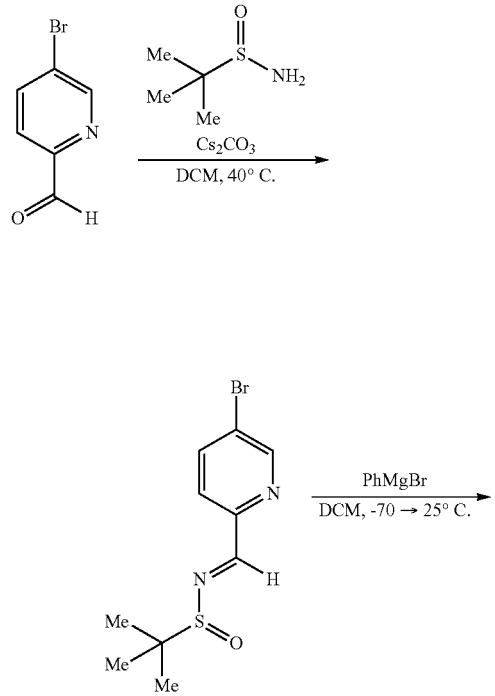 | (2S,4R)-1-[(2R) or (2S)-2-(1H-1,3-benzodiazol-1-yl)propanoyl]-N-[(S)-(4-cyclopropyl-3-fluorophenyl)(phenyl)methyl]-4-fluoropyrrolidine-2-carboxamide (column: DAICEL CHIRALPAK AD, first-eluting isomer) | 528.2 | 529.3 |

Example S-7: Synthesis of (2S,4R)-1-(2-(1H-1,2,3-triazol-5-yl)acetyl)-N—((S) or (R)-(5-cyclopropylpyridin-2-yl)(phenyl)methyl)-4-fluoropyrrolidine-2-carboxamide and (2S,4R)-1-(2-(1H-1,2,3-triazol-5-yl)acetyl)-N—((R) or (S)-(5-cyclopropylpyridin-2-yl)(phenyl)methyl)-4-fluoropyrrolidine-2-carboxamide Compound 497 & Compound 498

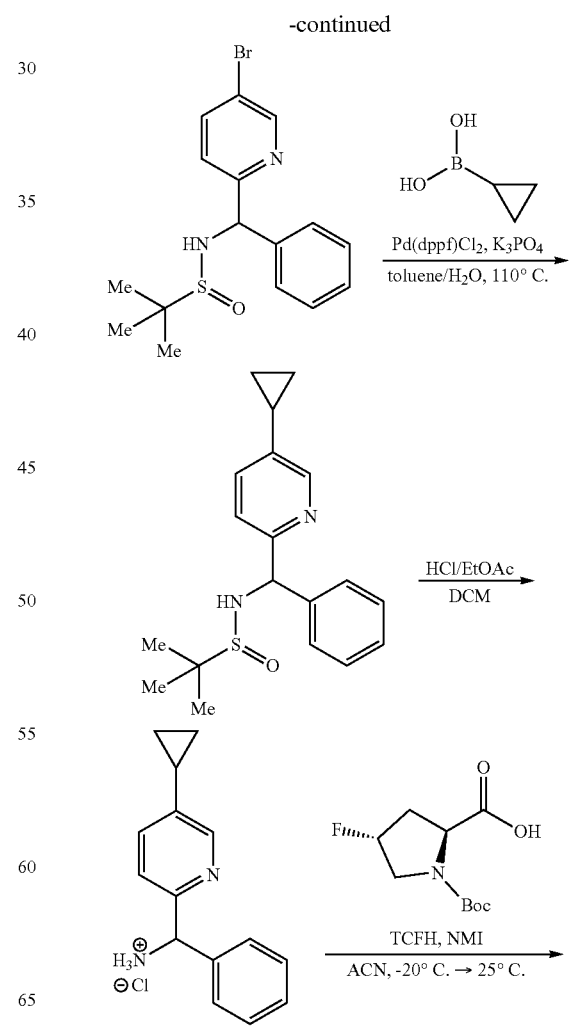

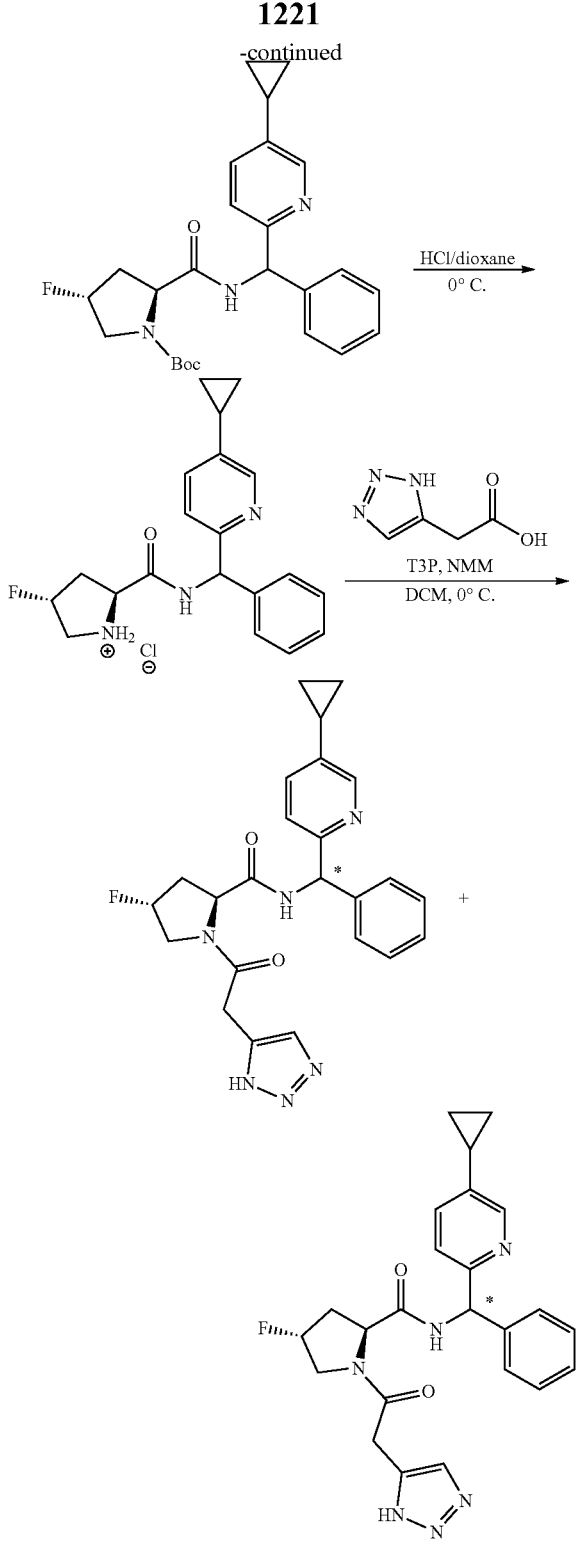

give (E)-N-((5-bromopyridin-2-yl)methylene)-2-methylpropane-2-sulfinamide. LC-MS (ESI): m/z: [M+H]+ calculated for $C_{10}H_{13}BrN_2OS$: 289.0; found 289.1.

Step b: A solution of (E)-N-((5-bromopyridin-2-yl)methylene)-2-methylpropane-2-sulfinamide (7.5 g, 25.9 mmol, 1 eq) in DCM (80 mL) was degassed and charged with nitrogen three times and cooled to −70° C. To the cooled solution was added PhMgBr (3 M in $Et_2O$, 10.4 mL, 1.2 eq) in a dropwise manner under $N_2$ atmosphere. The reaction mixture was then stirred at −70° C. for 2 h, warmed to room temperature, and stirred for another 1 h under $N_2$ atmosphere. The reaction mixture was then quenched with water (100 mL) and extracted with ethyl acetate (3×100 mL). The combined organic extracts were washed with brine (3×50 mL), dried over anhydrous $Na_2SO_4$, filtered, and concentrated under reduced pressure. The resulting crude residue was purified by column chromatography to give N-((5-bromopyridin-2-yl)(phenyl)methyl)-2-methylpropane-2-sulfinamide. LC-MS (ESI): m/z: [M+H]+ calculated for $C_{16}H_{19}BrN_2OS$: 367.0; found 367.1.

Step c: To a solution of N-((5-bromopyridin-2-yl)(phenyl)methyl)-2-methylpropane-2-sulfinamide (9.00 g, 24.5 mmol, 1 eq) in toluene (200 mL) and $H_2O$ (20 mL) at 25° C. was added cyclopropylboronic acid (16.8 g, 196 mmol, 8 eq), $K_3PO_4$ (15.6 g, 73.5 mmol, 3 eq) and Pd(dppf)$Cl_2$·$CH_2Cl_2$ (2.00 g, 2.45 mmol, 0.1 eq). The reaction mixture was degassed and purged with nitrogen three times, warmed to 110° C., and stirred for 16 h under $N_2$ atmosphere. After cooling, the reaction mixture was concentrated under reduced pressure. To the resulting residue was added water (150 mL), and the biphasic mixture was extracted with ethyl acetate (3×150 mL). The combined organic extracts were washed with brine (3×100 mL), dried over anhydrous $Na_2SO_4$, filtered, and concentrated under reduced pressure. The resulting residue was purified by column chromatography to give N-((5-cyclopropylpyridin-2-yl)(phenyl)methyl)-2-methylpropane-2-sulfinamide. LC-MS (ESI): m/z: [M+H]+ calculated for $C_{19}H_{24}N_2OS$: 329.2; found 329.2.

Step d: To a solution of N-((5-cyclopropylpyridin-2-yl)(phenyl)methyl)-2-methylpropane-2-sulfinamide (5 g, 15.2 mmol, 1 eq) in ethyl acetate (10 mL) at 0° C. under $N_2$ atmosphere was added HCl in ethyl acetate (4 M, 20 mL). The reaction mixture was stirred at 0° C. for 1 h. The reaction mixture was then filtered, and the solid obtained was dried under reduced pressure to give (5-cyclopropylpyridin-2-yl)(phenyl)methanamine hydrochloride, which was used without further purification. LC-MS (ESI): m/z: [M+H]+ calculated for $C_{15}H_{16}N_2$: 225.1; found 225.2.

Step e: To a solution of (5-cyclopropylpyridin-2-yl)(phenyl)methanamine hydrochloride (3.50 g, 13.4 mmol, 1 eq) in $CH_3CN$ (30 mL) at −20° C. under $N_2$ atmosphere was added 1-methyl-1H-imidazole (NMI, 4.69 g, 57.1 mmol, 3 eq) and (2S,4R)-1-(tert-butoxycarbonyl)-4-fluoropyrrolidine-2-carboxylic acid (3.76 g, 16.1 mmol, 1.2 eq). After stirring for 10 min, N,N,N′,N′-tetramethylchloroformamidinium hexafluorophosphate (4.52 g, 16.1 mmol, 1.2 eq) was added in portions. The reaction mixture was then stirred at −20° C. for 2 h under $N_2$ atmosphere. The reaction mixture was then quenched with $H_2O$ (30 mL) and extracted with ethyl acetate (3×30 mL). The combined organic extracts were washed with brine (3×30 mL), dried over $Na_2SO_4$, filtered, and concentrated under reduced pressure. The resulting crude residue was purified by column chromatography to give tert-butyl (2S,4R)-2-(((5-cyclopropylpyridin-2-yl)(phenyl)methyl)carbamoyl)-4-fluoropyrrolidine-1-carboxylate LC-MS (ESI): m/z: [M+H]+ calculated for $C_{25}H_{30}FN_3O_3$: 440.2; found 440.3.

Step a: To a solution of 5-bromopicolinaldehyde (5.00 g 26.9 mmol, 1 eq) in DCM (50 mL) at 25° C. was added 2-methylpropane-2-sulfinamide (3.58 g 29.6 mmol, 1.1 eq) and $Cs_2CO_3$ (9.63 g 29.6 mmol, 1.1 eq). The system was degassed and charged with nitrogen, and the reaction mixture was warmed to 40° C. and stirred for 2 h under $N_2$ atmosphere. After cooling, the reaction solution was filtered and concentrated under reduced pressure. The resulting crude residue was purified by column chromatography to Step f: To a solution of tert-butyl (2S,4R)-2-(((5-cyclopropylpyridin-2-yl)(phenyl)methyl)carbamoyl)-4-fluoropyrrolidine-1-carboxylate (7 g, crude) in 1,4-dioxane (5 mL) at 0° C. was added HCl/dioxane (4 M, 50 mL). The resulting mixture was stirred at 0° C. for 4 h. The reaction was then concentrated under reduced pressure. The resulting solid was washed with MTBE (3×10 mL) and dried under reduced pressure to give (2S,4R)—N-((5-cyclopropylpyridin-2-yl)(phenyl)methyl)-4-fluoropyrrolidine-2-carboxamide hydrochloride (6.5 g). LC-MS (ESI): m/z: [M+H]$^+$ calculated for $C_{20}H_{22}FN_3O$: 340.2; found 340.2.

Step g: To a solution of (2S,4R)—N-((5-cyclopropylpyridin-2-yl)(phenyl)methyl)-4-fluoropyrrolidine-2-carboxamide hydrochloride (6.50 g, 17.3 mmol, 1 eq) in DMF (50 mL) at 0° C. was added 4-methylmorpholine (NMM, 7.00 g, 69.2 mmol, 4 eq), 2-(1H-1,2,3-triazol-5-yl)acetic acid (2.63 g, 20.8 mmol, 1.2 eq), and T3P (27.5 g, 43.2 mmol, 50% in ethyl acetate, 2.5 eq). The reaction mixture was then stirred at 0° C. for 2 h under $N_2$ atmosphere. The reaction mixture was then quenched with $H_2O$ (60 mL) at 0° C. and extracted with ethyl acetate (3×100 mL). The combined organic extracts were washed with brine (70 mL), dried over $Na_2SO_4$, filtered, and concentrated under reduced pressure. The resulting residue was purified by column chromatography and chiral SFC (column: REGIS (s,s) WHELK-01 (250 mm×50 mm, 10 μm); mobile phase: [Phase A: $CO_2$, Phase B: 0.1% $NH_{3(aq)}$ in EtOH]; isocratic at 40% B, 3.4 min) to give (2S,4R)-1-(2-(1H-1,2,3-triazol-5-yl)acetyl)-N—((S) or (R)-(5-cyclopropylpyridin-2-yl)(phenyl)methyl)-4-fluoropyrrolidine-2-carboxamide (Compound 497; first-eluting isomer) and (2S,4R)-1-(2-(1H-1,2,3-triazol-5-yl)acetyl)-N—((R) or (S)-(5-cyclopropylpyridin-2-yl)(phenyl)methyl)-4-fluoropyrrolidine-2-carboxamide (Compound 498; second-eluting isomer).

First-eluting isomer (Compound 497): $^1$H NMR (4.4:1 rotamer ratio, asterisk denotes distinct minor rotamer peaks, obscured peaks not reported, 400 MHz, methanol-$d_4$) δ 8.30-8.21 (m, 1H), 7.55-7.39 (m, 2H), 7.38-7.14 (m, 5H), 6.18*(s, 1H), 6.09 (s, 1H), 5.44-5.18 (m, 1H), 4.70 (t, 1H), 4.15-4.02 (m, 1H), 3.97-3.75 (m, 3H), 3.70-3.50*(m, 2H), 2.85-2.70*(m, 1H), 2.65-2.50 (m, 1H), 2.37-2.06 (m, 1H), 2.00-1.84 (m, 1H), 1.08-0.95 (m, 2H), 0.75-0.62 (m, 2H). LC-MS (ESI): m/z: [M+H]$^+$ calculated for $C_{26}H_{25}FN_6O_2$: 449.2; found 449.2.

Second-eluting isomer (Compound 498): $^1$H NMR (4.4:1 rotamer ratio, asterisk denotes distinct minor rotamer peaks, obscured peaks not reported, 400 MHz, methanol-$d_4$) δ 8.30-8.21 (m, 1H), 7.53-7.39 (m, 2H), 7.38-7.17 (m, 6H), 6.18*(s, 1H), 6.09 (s, 1H), 5.44-5.18 (m, 1H), 4.70 (t, J=9.3, 7.7 Hz, 1H), 4.15-4.02 (m, 1H), 3.98-3.75 (m, 3H), 3.68-3.51*(m, 2H), 2.85-2.69*(m, 1H), 2.65-2.50 (m, 1H), 2.38-2.05 (m, 1H), 2.00-1.83 (m, 1H), 1.08-0.95 (m, 2H), 0.79-0.60 (m, 2H). LC-MS (ESI): m/z: [M+H]$^+$ calculated for $C_{26}H_{25}FN_6O_2$: 449.2; found 449.1.

The following compounds in Table T-7 were synthesized using procedures similar to Compound 497 and Compound 498 using the appropriate starting materials.

TABLE T-7

| Compound No. | Structure | IUPAC | Exact mass (g/mol) | LCMS, Found [M + H]$^+$ |
| --- | --- | --- | --- | --- |
| 499 | 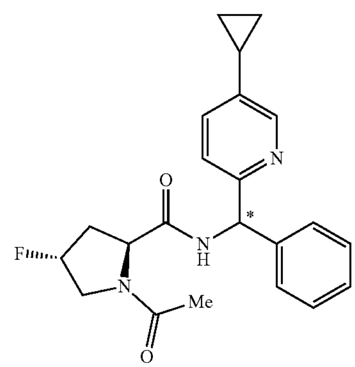 [SMILES: CC(=O)N1C[C@H](F)C[C@H]1C(=O)NC(c1ccccc1)c1ccc(C2CC2)cn1] | (2S,4R)-1-acetyl-N-[(S) or (R)-(5-cyclopropylpyridin-2-yl)(phenyl)methyl]-4-fluoropyrrolidine-2-carboxamide (column: REGIS (s, s) WHELK-O1, first-eluting isomer) | 381.2 | 382.2 |
| 500 | 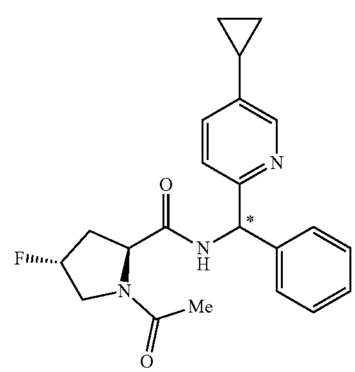 [SMILES: CC(=O)N1C[C@H](F)C[C@H]1C(=O)NC(c1ccccc1)c1ccc(C2CC2)cn1] | (2S,4R)-1-acetyl-N-[(R) or (S)-(5-cyclopropylpyridin-2-yl)(phenyl)methyl]-4-fluoropyrrolidine-2-carboxamide (column: REGIS (s,s) WHELK-O1, second-eluting isomer) | 381.2 | 382.4 |

Example S-8: Synthesis of (2S,4R)—N—((S)-(5-(3,3-difluorocyclobutyl)-6-fluoropyridin-2-yl)(phenyl)methyl)-1-(2-(3-ethyl-5-methyl-2,4-dioxo-3,4-dihydropyrimidin-1(2H)-yl)acetyl)-4-fluoropyrrolidine-2-carboxamide Compound 501

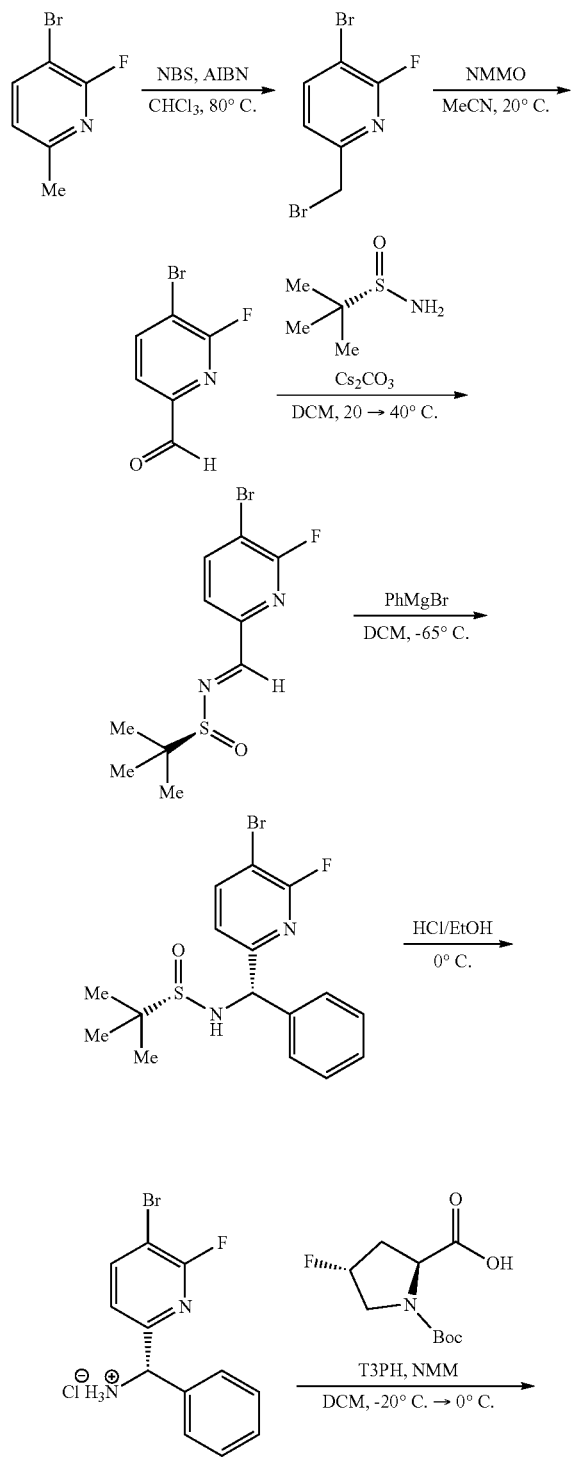

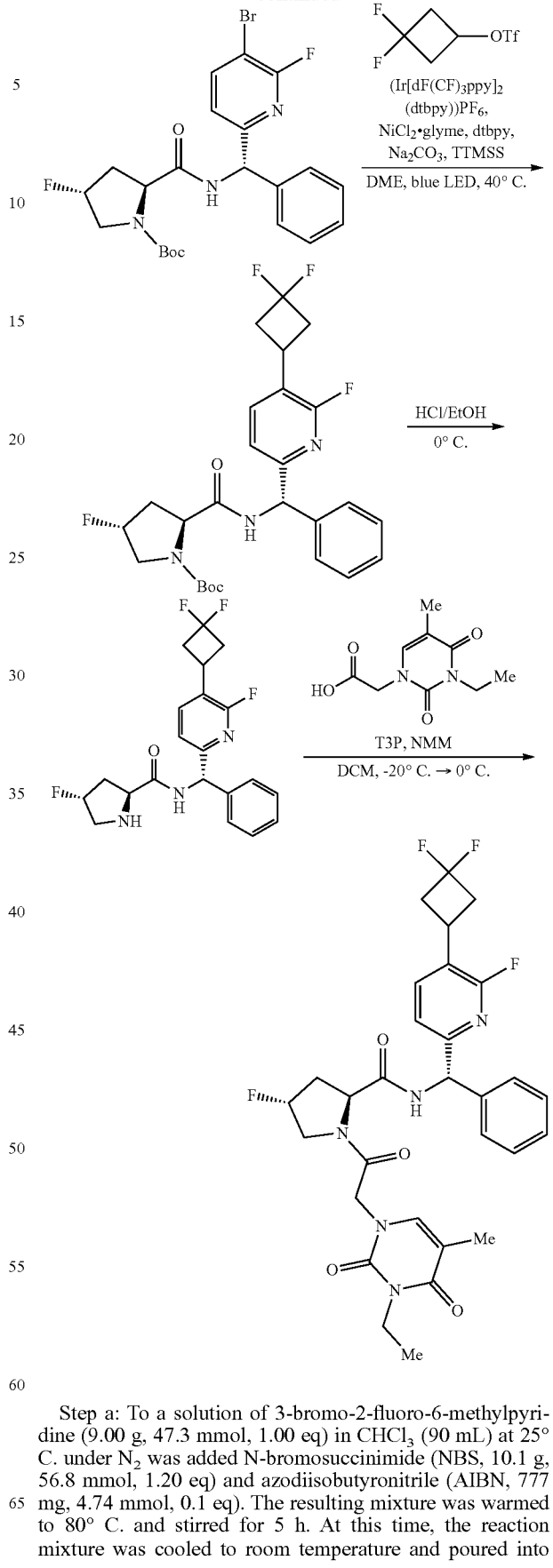

Step a: To a solution of 3-bromo-2-fluoro-6-methylpyridine (9.00 g, 47.3 mmol, 1.00 eq) in CHCl₃ (90 mL) at 25° C. under N₂ was added N-bromosuccinimide (NBS, 10.1 g, 56.8 mmol, 1.20 eq) and azodiisobutyronitrile (AIBN, 777 mg, 4.74 mmol, 0.1 eq). The resulting mixture was warmed to 80° C. and stirred for 5 h. At this time, the reaction mixture was cooled to room temperature and poured into water (200 mL). The resulting biphasic mixture was extracted with dichloromethane (2×100 mL). The combined organic extracts were washed with brine (200 mL), dried over anhydrous $Na_2SO_4$, filtered, and concentrated under reduced pressure. The crude residue obtained was purified by column chromatography to obtain 3-bromo-6-(bromomethyl)-2-fluoropyridine. LC-MS (ESI): m/z: $[M+H]^+$ calculated for $C_6H_4Br_2FN$: 267.9; found 267.9.

Step b: To a solution of 3-bromo-6-(bromomethyl)-2-fluoropyridine (13.0 g, 38.6 mmol, 80% purity, 1.00 eq) in MeCN (130 mL) at 20° C. under $N_2$ was added N-methylmorpholine N-oxide (NMMO, 9.06 g, 77.3 mmol, 8.16 mL, 2.00 eq). The resulting mixture was stirred at 20° C. for 2 h. The reaction mixture was then poured into water (200 mL) and extracted with dichloromethane (2×100 mL). The combined organic phases were washed with brine (200 mL), dried over anhydrous $Na_2SO_4$, filtered, and concentrated under reduced pressure. The crude residue obtained was purified by column chromatography to obtain 5-bromo-6-fluoropicolinaldehyde.

Step c: To a mixture of 5-bromo-6-fluoropicolinaldehyde (5.00 g, 24.5 mmol, 1.00 eq) and (S)-2-methylpropane-2-sulfinamide (3.27 g, 26.9 mmol, 1.10 eq) in DCM (50 mL) at 20° C. under $N_2$ was added $Cs_2CO_3$ (8.78 g, 26.9 mmol, 1.10 eq). The resulting mixture was stirred for 10 min before it was warmed 40° C. and stirred for 2 h. The reaction mixture was then cooled to room temperature and poured into water (50 mL). The resulting biphasic mixture was extracted with dichloromethane (2×50 mL). The combined organic extracts were washed with brine (200 mL), dried over anhydrous $Na_2SO_4$, filtered, and concentrated under reduced pressure. The crude residue obtained was purified by column chromatography to obtain (S,E)-N-((5-bromo-6-fluoropyridin-2-yl)methylene)-2-methylpropane-2-sulfinamide.

Step d: To a solution of (S,E)-N-((5-bromo-6-fluoropyridin-2-yl)methylene)-2-methylpropane-2-sulfinamide (7.04 g, 22.9 mmol, 1.00 eq) in DCM (70 mL) −65° C. under $N_2$ was added in a dropwise manner phenylmagnesium bromide (5.41 g, 29.8 mmol, 1.30 eq). The resulting mixture was stirred at −65° C. for 1 h. The reaction mixture was then poured into water (100 mL) at room temperature. The resulting biphasic mixture was extracted with dichloromethane (2×100). The combined organic extracts were washed with brine (100 mL), dried over anhydrous $Na_2SO_4$, filtered, and concentrated under reduced pressure. The crude residue obtained was purified by column chromatography to obtain (S)—N—((S)-(5-bromo-6-fluoropyridin-2-yl)(phenyl)methyl)-2-methylpropane-2-sulfinamide, which was carried forward to the next step without further characterization.

Step e: To a solution of (S)—N—((S)-(5-bromo-6-fluoropyridin-2-yl)(phenyl)methyl)-2-methylpropane-2-sulfinamide (7.50 g, 19.4 mmol, 1.00 eq) in EtOAc (30 mL) at 0° C. was added HCl/EtOAc (30 mL). The resulting mixture was stirred at 0° C. for 1 h. The reaction mixture was then concentrated under reduce pressure to obtain (S)-(5-bromo-6-fluoropyridin-2-yl)(phenyl)methanamine hydrochloride (6.18 g). LC-MS (ESI): m/z: $[M+H]^+$ calculated for $C_{12}H_{10}BrFN_2$: 281.0; found: 281.0.

Step f: To a mixture of (S)-(5-bromo-6-fluoropyridin-2-yl)(phenyl)methanamine hydrochloride (0.5 g, 1.78 mmol, 1.00 eq) and (2S,4R)-1-(tert-butoxycarbonyl)-4-fluoropyrrolidine-2-carboxylic acid (456 mg, 1.96 mmol, 1.10 eq) in DMF (5 mL) at −20° C. was added N-methylmorpholine (NMM, 5.34 mmol, 3.00 eq) and 2,4,6-tripropyl-1,3,5,2,4,6-trioxatriphosphorinane-2,4,6-trioxide (T3P, 3.56 mmol, 2.12 mL, 50% purity, 2.00 eq). The resulting mixture was allowed to warm to 0° C. and stirred for 1 h. The reaction mixture was then poured into water (20 mL) at room temperature. The resulting biphasic mixture was extracted with dichloromethane (2×50 mL). The combined organic phases were washed with brine (20 mL), dried over anhydrous $Na_2SO_4$, filtered, and concentrated under reduced pressure. The crude residue obtained was purified by column chromatography to give tert-butyl (2S,4R)-2-(((S)-(5-bromo-6-fluoropyridin-2-yl)(phenyl)methyl)carbamoyl)-4-fluoropyrrolidine-1-carboxylate (0.7 g). LC-MS (ESI): m/z: $[M-t-Bu+H+H]^+$ calculated for $C_{22}H_{24}BrF_2N_3O_3$: 440.0; found: 440.1.

Step g: To a solution of tert-butyl (2S,4R)-2-(((S)-(5-bromo-6-fluoropyridin-2-yl)(phenyl)methyl)carbamoyl)-4-fluoropyrrolidine-1-carboxylate (700 mg, 1.41 mmol, 1.00 eq) and 3-bromo-1,1-difluorocyclobutane (482 mg, 2.82 mmol, 2.00 eq) in 1,2-Dimethoxyethane (DME, 12 mL) at 25° C. under $N_2$ was added nickel(II) chloride ethylene glycol dimethyl ether complex ($NiCl_2$·glyme, 3.1 mg, 14.1 µmol, 0.01 eq), 4,4-di-tert-butyl-2,2-bipyridyl (dtbpy, 3.79 mg, 14.1 µmol, 0.01 eq), $Na_2CO_3$ (298 mg, 2.82 mmol, 2.00 eq), tris(trimethylsilyl)silane (TTMSS, 350 mg, 1.41 mmol, 1 eq) and $(Ir[dF(CF_3)ppy]_2(dtbpy))PF_6$ (CAS: 870987-63-6, 15.8 mg, 14.1 µmol, 0.01 eq) in one portion. The resulting mixture was stirred for 16 h under $N_2$ at 25° C. under a 34 W blue LED. The reaction mixture was then filtered and concentrated under reduced pressure to give a crude residue that was purified by column chromatography to give tert-butyl (2S,4R)-2-(((S)-(5-(3,3-difluorocyclobutyl)-6-fluoropyridin-2-yl)(phenyl)methyl)carbamoyl)-4-fluoropyrrolidine-1-carboxylate. LC-MS (ESI): m/z: $[M-t-Bu+H+H]^+$ calculated for $C_{26}H_{29}F_4N_3O_3$: 452.1; found: 452.1.

Step h: To a solution of tert-butyl (2S,4R)-2-(((S)-(5-(3,3-difluorocyclobutyl)-6-fluoropyridin-2-yl)(phenyl)methyl)carbamoyl)-4-fluoropyrrolidine-1-carboxylate (173 mg, 341 µmol, 1.00 eq) in EtOAc (1 mL) at 0° C. was added HCl/EtOAc (4 M, 2 mL). The resulting mixture was stirred at 0° C. for 2 h. The reaction mixture was then concentrated under reduced pressure to give a crude residue. This residue was diluted in DCM (20 mL) and adjusted to pH=7 with saturated aqueous $NaHCO_3$ solution. The reaction mixture was then extracted with DCM (3×45 mL). The combined organic extracts were dried over $Na_2SO_4$, filtered, and concentrated under reduced pressure to give (2S,4R)—N—((S)-(5-(3,3-difluorocyclobutyl)-6-fluoropyridin-2-yl)(phenyl)methyl)-4-fluoropyrrolidine-2-carboxamide. LC-MS (ESI): m/z: $[M+H]^+$ calculated for $C_{21}H_{21}F_4N_3O$: 408.2; found: 408.2.

Step i: To a mixture of (2S,4R)—N—((S)-(5-(3,3-difluorocyclobutyl)-6-fluoropyridin-2-yl)(phenyl)methyl)-4-fluoropyrrolidine-2-carboxamide (80.0 mg, 196 µmol, 1 eq) and 2-(3-ethyl-5-methyl-2,4-dioxo-3,4-dihydropyrimidin-1(2H)-yl)acetic acid (62.5 mg, 295 µmol, 1.5 eq) in DMF (3 mL) at 0° C. under $N_2$ was added 2,4,6-tripropyl-1,3,5,2,4,6-trioxatriphosphorinane-2,4,6-trioxide (T3P, 250 mg, 393 µmol, 50% purity, 2 eq) and N-methylmorpholine (NMM, 79.5 mg, 785 µmol, 4 eq) in one portion. The resulting mixture was stirred at 0° C. for 1 h. The reaction was then allowed to warm to 20° C. and stirred 1 h. The reaction mixture was then diluted with $H_2O$ (20 mL) at 20° C. and extracted with EtOAc (3×10 mL). The combined organic extracts were washed with brine (20 mL), dried over $Na_2SO_4$, filtered, and concentrated under reduced pressure. The crude residue obtained was purified by prep-HPLC to obtain (2S,4R)—N—((S)-(5-(3,3-difluorocyclobutyl)-6-fluoropyridin-2-yl)(phenyl)methyl)-1-(2-(3-ethyl-5-methyl-2,4-dioxo-3,4-dihydropyrimidin-1(2H)-yl)acetyl)-4-fluoropyrrolidine-2-carboxamide. ¹H NMR (4.3:1 rotamer ratio, asterisk denotes distinct minor rotamer peaks, obscured peaks not reported, 400 MHz, methanol-d₄) δ 7.88-7.78 (m, 1H), 7.44-7.37*(m, 2H), 7.37-7.18 (m, 7H), 7.06*(d, J=1.3 Hz, 1H), 6.19*(s, 1H), 6.08 (s, 1H), 5.50-5.18 (m, 1H), 4.92-4.77 (m, 1H), 4.76-4.68 (m, 1H), 4.58*(d, J=16.3 Hz, 1H), 4.48 (d, J=16.7 Hz, 1H), 4.15-3.77 (m, 4H), 3.53-3.43 (m, 1H), 3.06-2.91 (m, 2H), 2.86-2.55 (m, 3H), 2.27-2.07 (m, 1H), 1.92-1.84 (m, 3H), 1.16 (t, J=7.0 Hz, 3H). LC-MS (ESI): m/z: [M+H]⁺ calculated for $C_{30}H_{31}F_4N_5O_4$: 602.2; found: 602.3.

The following compounds in Table T-8 were synthesized using procedures similar to Compound 501 using the appropriate starting materials.

TABLE T-8

| Compound No. | Structure | IUPAC | Exact mass (g/mol) | LCMS, Found [M + H]⁺ |
|---|---|---|---|---|
| 502 | 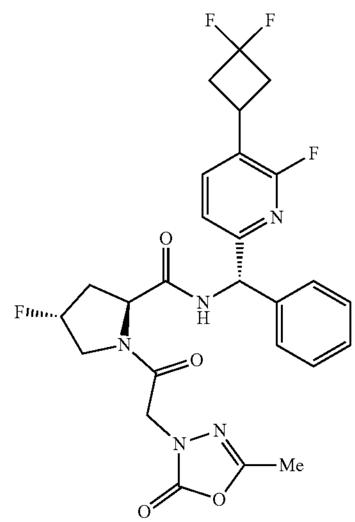 [SMILES: Cc1nn(CC(=O)N2C[C@H](F)C[C@H]2C(=O)N[C@@H](c2ccccc2)c2ccc(C3CC(F)(F)C3)c(F)n2)c(=O)o1] | (2S,4R)-N-[(S)-[5-(3,3-difluorocyclobutyl)-6-fluoropyridin-2-yl](phenyl)methyl]-4-fluoro-1-[2-(5-methyl-2-oxo-2,3-dihydro-1,3,4-oxadiazol-3-yl)acetyl]pyrrolidine-2-carboxamide | 547.2 | 548.30 |
| 503 | 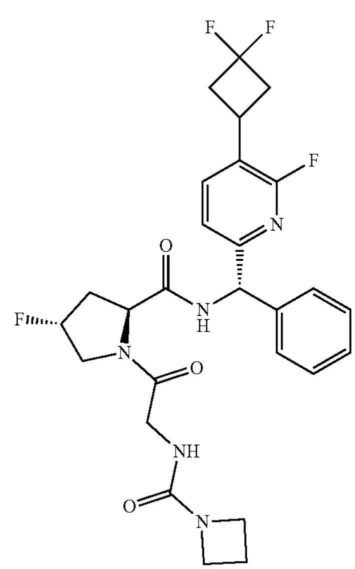 [SMILES: O=C(N[C@@H](c1ccccc1)c1ccc(C2CC(F)(F)C2)c(F)n1)[C@@H]1C[C@@H](F)CN1C(=O)CNC(=O)N1CCC1] | (2S,4R)-1-{2-[(azetidine-1-carbonyl)amino]acetyl}-N-[(S)-[5-(3,3-difluorocyclobutyl)-6-fluoropyridin-2-yl](phenyl)methyl]-4-fluoropyrrolidine-2-carboxamide | 547.2 | 548.30 |

TABLE T-8-continued

| Compound No. | Structure | IUPAC | Exact mass (g/mol) | LCMS, Found [M + H]+ |
|---|---|---|---|---|
| 504 | 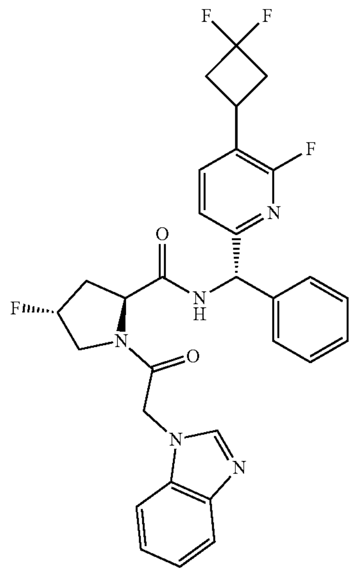 | (2S,4R)-1-[2-(1H-1,3-benzodiazol-1-yl)acetyl]-N-[(S)-[5-(3,3-difluorocyclobutyl)-6-fluoropyridin-2-yl](phenyl)methyl]-4-fluoropyrrolidine-2-carboxamide | 565.2 | 566.20 |
| 505 | 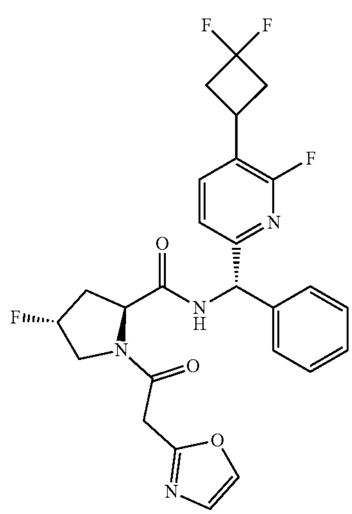 [SMILES: O=C(N[C@@H](c1ccccc1)c1ccc(C2CC(F)(F)C2)c(F)n1)[C@@H]1C[C@@H](F)CN1C(=O)Cc1ncco1] | (2S,4R)-N-[(S)-[5-(3,3-difluorocyclobutyl)-6-fluoropyridin-2-yl](phenyl)methyl]-4-fluoro-1-[2-(1,3-oxazol-2-yl)acetyl]pyrrolidine-2-carboxamide | 516.2 | 517.10 |

TABLE T-8-continued

| Compound No. | Structure | IUPAC | Exact mass (g/mol) | LCMS, Found [M + H]+ |
|---|---|---|---|---|
| 506 | 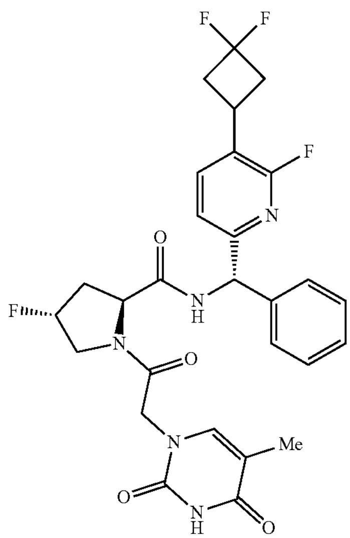 [SMILES: Cc1cn(CC(=O)N2C[C@H](F)C[C@H]2C(=O)N[C@@H](c2ccccc2)c2ccc(C3CC(F)(F)C3)c(F)n2)c(=O)[nH]c1=O] | (2S,4R)-N-[(S)-[5-(3,3-difluorocyclobutyl)-6-fluoropyridin-2-yl](phenyl)methyl]-4-fluoro-1-[2-(5-methyl-2,4-dioxo-1,2,3,4-tetrahydropyrimidin-1-yl)acetyl]pyrrolidine-2-carboxamide | 573.2 | 574.1 |
| 507 | 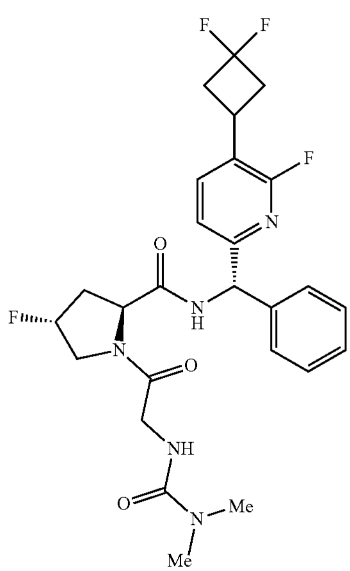 | (2S,4R)-N-[(S)-[5-(3,3-difluorocyclobutyl)-6-fluoropyridin-2-yl](phenyl)methyl]-1-{2-[(dimethylcarbamoyl)amino]acetyl}-4-fluoropyrrolidine-2-carboxamide | 535.2 | 536.3 |

TABLE T-8-continued

| Compound No. | Structure | IUPAC | Exact mass (g/mol) | LCMS, Found [M + H]+ |
|---|---|---|---|---|
| 508 | 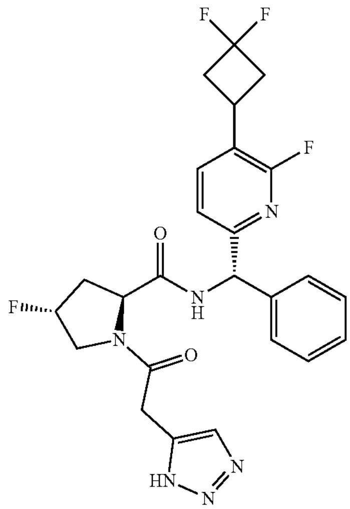 [SMILES: O=C(N[C@@H](c1ccccc1)c1ccc(C2CC(F)(F)C2)c(F)n1)[C@@H]1C[C@@H](F)CN1C(=O)Cc1cnn[nH]1] | (2S,4R)-N-[(S)-[5-(3,3-difluorocyclobutyl)-6-fluoropyridin-2-yl](phenyl)methyl]-4-fluoro-1-[2-(1H-1,2,3-triazol-5-yl)acetyl]pyrrolidine-2-carboxamide | 516.2 | 517.2 |
| 509 | 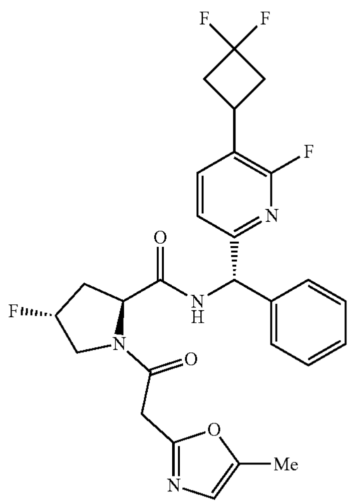 [SMILES: Cc1cnc(CC(=O)N2C[C@H](F)C[C@H]2C(=O)N[C@@H](c2ccccc2)c2ccc(C3CC(F)(F)C3)c(F)n2)o1] | (2S,4R)-N-[(S)-[5-(3,3-difluorocyclobutyl)-6-fluoropyridin-2-yl](phenyl)methyl]-4-fluoro-1-[2-(5-methyl-1,3-oxazol-2-yl)acetyl]pyrrolidine-2-carboxamide | 530.2 | 531.2 |
| 510 | 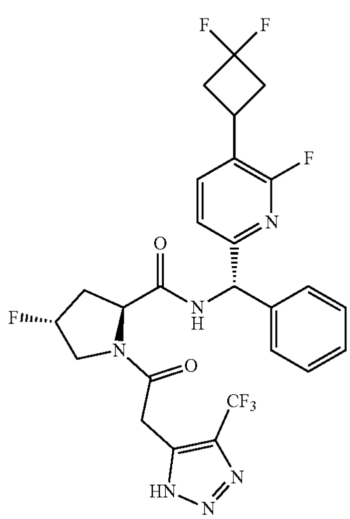 | (2S,4R)-N-[(S)-[5-(3,3-difluorocyclobutyl)-6-fluoropyridin-2-yl](phenyl)methyl]-4-fluoro-1-{2-[4-(trifluoromethyl)-1H-1,2,3-triazol-5-yl]acetyl}pyrrolidine-2-carboxamide | 584.2 | 585.2 |

TABLE T-8-continued

| Compound No. | Structure | IUPAC | Exact mass (g/mol) | LCMS, Found [M + H]+ |
|---|---|---|---|---|
| 511 | 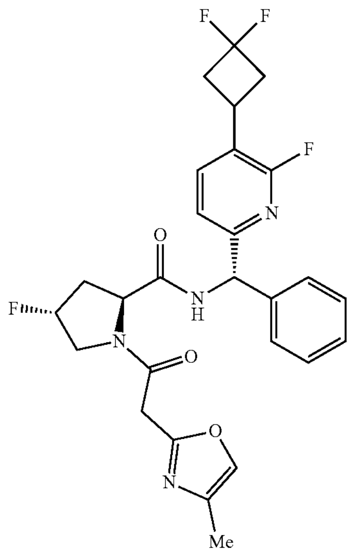 | (2S,4R)-N-[(S)-[5-(3,3-difluorocyclobutyl)-6-fluoropyridin-2-yl](phenyl)methyl]-4-fluoro-1-[2-(4-methyl-1,3-oxazol-2-yl)acetyl]pyrrolidine-2-carboxamide | 530.2 | 531.2 |
| 512 | 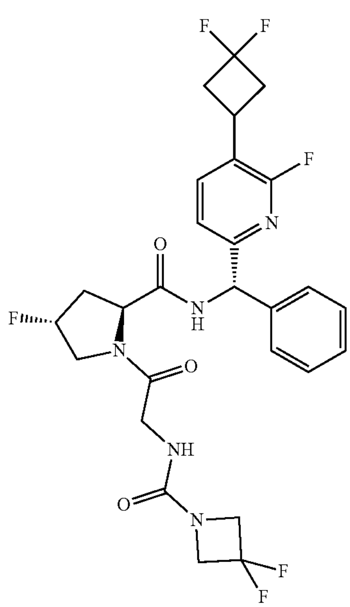 [SMILES: O=C(N[C@@H](c1ccccc1)c1ccc(C2CC(F)(F)C2)c(F)n1)[C@@H]1C[C@@H](F)CN1C(=O)CNC(=O)N1CC(F)(F)C1] | (2S,4R)-1-{2-[(3,3-difluoroazetidine-1-carbonyl)amino]acetyl}-N-[(S)-[5-(3,3-difluorocyclobutyl)-6-fluoropyridin-2-yl](phenyl)methyl]-4-fluoropyrrolidine-2-carboxamide | 583.2 | 584.3 |

TABLE T-8-continued
| Compound No. | Structure | IUPAC | Exact mass (g/mol) | LCMS, Found [M + H]+ |
|---|---|---|---|---|
| 513 | 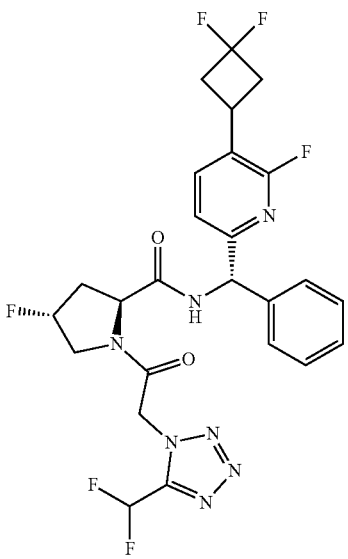 [SMILES: O=C(N[C@@H](c1ccccc1)c1ccc(C2CC(F)(F)C2)c(F)n1)[C@@H]1C[C@@H](F)CN1C(=O)Cn1nnnc1C(F)F] | (2S,4R)-N-[(S)-[5-(3,3-difluorocyclobutyl)-6-fluoropyridin-2-yl](phenyl)methyl]-1-{2-[5-(difluoromethyl)-1H-1,2,3,4-tetrazol-1-yl]acetyl}-4-fluoropyrrolidine-2-carboxamide | 567.2 | 568.1 |
| 514 | 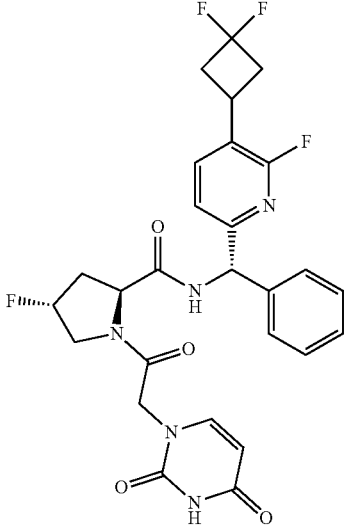 [SMILES: O=C(N[C@@H](c1ccccc1)c1ccc(C2CC(F)(F)C2)c(F)n1)[C@@H]1C[C@@H](F)CN1C(=O)Cn1ccc(=O)[nH]c1=O] | (2S,4R)-N-[(S)-[5-(3,3-difluorocyclobutyl)-6-fluoropyridin-2-yl](phenyl)methyl]-1-[2-(2,4-dioxo-1,2,3,4-tetrahydropyrimidin-1-yl)acetyl]-4-fluoropyrrolidine-2-carboxamide | 559.2 | 560.1 |

TABLE T-8-continued

| Compound No. | Structure | IUPAC | Exact mass (g/mol) | LCMS, Found [M + H]+ |
|---|---|---|---|---|
| 515 | 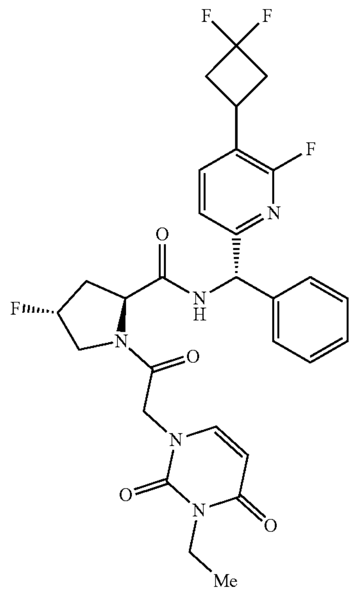 [SMILES: CCn1c(=O)ccn(CC(=O)N2C[C@H](F)C[C@H]2C(=O)N[C@@H](c2ccccc2)c2ccc(C3CC(F)(F)C3)c(F)n2)c1=O] | (2S,4R)-N-[(S)-[5-(3,3-difluorocyclobutyl)-6-fluoropyridin-2-yl](phenyl)methyl]-1-[2-(3-ethyl-2,4-dioxo-1,2,3,4-tetrahydropyrimidin-1-yl)acetyl]-4-fluoropyrrolidine-2-carboxamide | 587.2 | 588.2 |
| 516 | 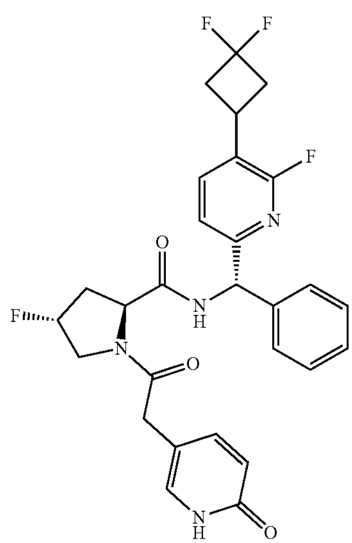 | (2S,4R)-N-[(S)-[5-(3,3-difluorocyclobutyl)-6-fluoropyridin-2-yl](phenyl)methyl]-4-fluoro-1-[2-(6-oxo-1,6-dihydropyridin-3-yl)acetyl]pyrrolidine-2-carboxamide | 542.2 | 543.3 |

TABLE T-8-continued

| Compound No. | Structure | IUPAC | Exact mass (g/mol) | LCMS, Found [M + H]+ |
|---|---|---|---|---|
| 517 | 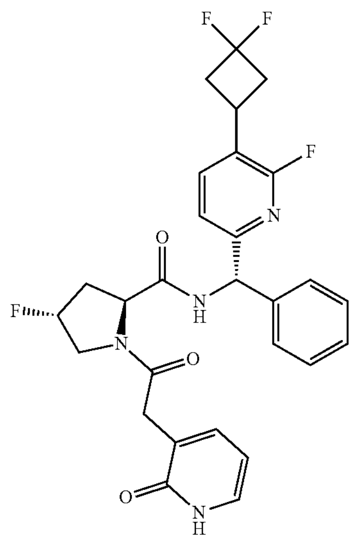 [SMILES: O=C(N[C@@H](c1ccccc1)c1ccc(C2CC(F)(F)C2)c(F)n1)[C@@H]1C[C@@H](F)CN1C(=O)Cc1ccc[nH]c1=O] | (2S,4R)-N-[(S)-[5-(3,3-difluorocyclobutyl)-6-fluoropyridin-2-yl](phenyl)methyl]-4-fluoro-1-[2-(2-oxo-1,2-dihydropyridin-3-yl)acetyl]pyrrolidine-2-carboxamide | 542.2 | 543.3 |
| 518 | 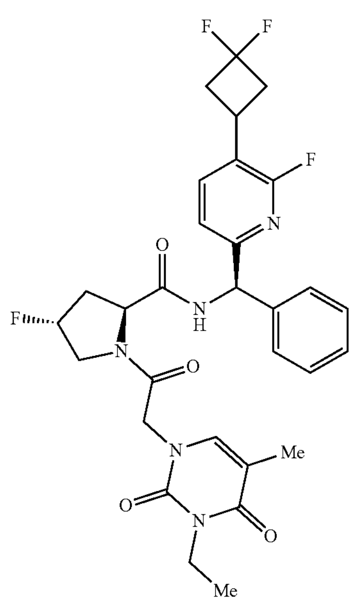 [SMILES: CCn1c(=O)c(C)cn(CC(=O)N2C[C@H](F)C[C@H]2C(=O)N[C@H](c2ccccc2)c2ccc(C3CC(F)(F)C3)c(F)n2)c1=O] | (2S,4R)-N-[(R)-[5-(3,3-difluorocyclobutyl)-6-fluoropyridin-2-yl](phenyl)methyl]-1-[2-(3-ethyl-5-methyl-2,4-dioxo-1,2,3,4-tetrahydropyrimidin-1-yl)acetyl]-4-fluoropyrrolidine-2-carboxamide | 601.2 | 602.3 |

TABLE T-8-continued

| Compound No. | Structure | IUPAC | Exact mass (g/mol) | LCMS, Found [M + H]+ |
| --- | --- | --- | --- | --- |
| 519 | 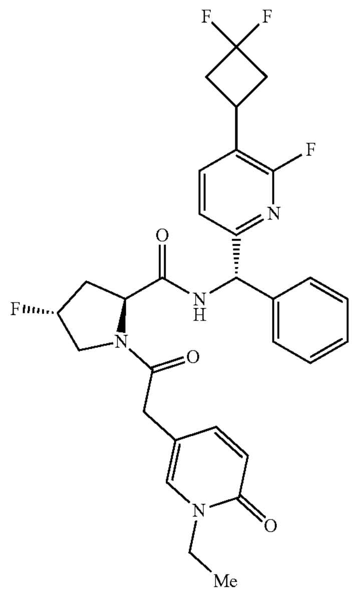 | (2S,4R)-N-[(S)-[5-(3,3-difluorocyclobutyl)-6-fluoropyridin-2-yl](phenyl)methyl]-1-[2-(1-ethyl-6-oxo-1,6-dihydropyridin-3-yl)acetyl]-4-fluoropyrrolidine-2-carboxamide | 570.2 | 571.3 |
| 520 | 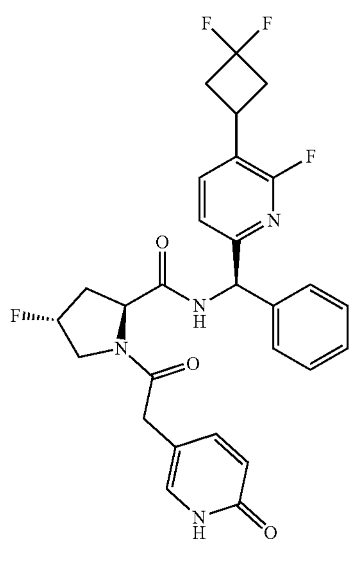 [SMILES: O=C(N[C@H](c1ccccc1)c1ccc(C2CC(F)(F)C2)c(F)n1)[C@@H]1C[C@@H](F)CN1C(=O)Cc1ccc(=O)[nH]c1] | (2S,4R)-N-[(R)-[5-(3,3-difluorocyclobutyl)-6-fluoropyridin-2-yl](phenyl)methyl]-4-fluoro-1-[2-(6-oxo-1,6-dihydropyridin-3-yl)acetyl]pyrrolidine-2-carboxamide | 542.2 | 543.3 |

TABLE T-8-continued

| Compound No. | Structure | IUPAC | Exact mass (g/mol) | LCMS, Found [M + H]+ |
|---|---|---|---|---|
| 521 | 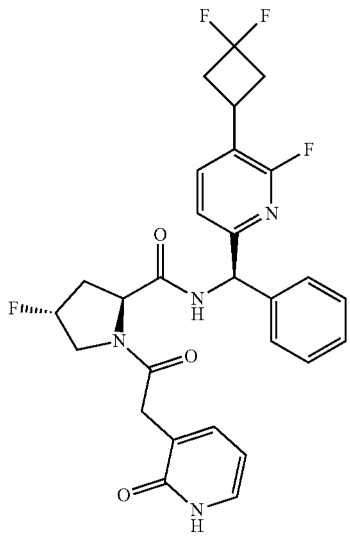 [SMILES: O=C(N[C@H](c1ccccc1)c1ccc(C2CC(F)(F)C2)c(F)n1)[C@@H]1C[C@@H](F)CN1C(=O)Cc1ccc[nH]c1=O] | (2S,4R)-N-[(R)-[5-(3,3-difluorocyclobutyl)-6-fluoropyridin-2-yl](phenyl)methyl]-4-fluoro-1-[2-(2-oxo-1,2-dihydropyridin-3-yl)acetyl]pyrrolidine-2-carboxamide | 542.2 | 543.3 |
| 522 | 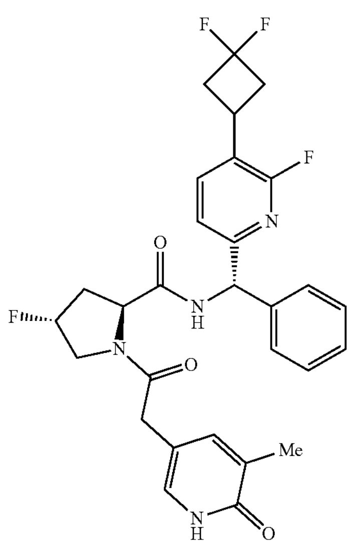 [SMILES: Cc1cc(CC(=O)N2C[C@H](F)C[C@H]2C(=O)N[C@@H](c2ccccc2)c2ccc(C3CC(F)(F)C3)c(F)n2)c[nH]c1=O] | (2S,4R)-N-[(S)-[5-(3,3-difluorocyclobutyl)-6-fluoropyridin-2-yl](phenyl)methyl]-4-fluoro-1-[2-(5-methyl-6-oxo-1,6-dihydropyridin-3-yl)acetyl]pyrrolidine-2-carboxamide | 556.2 | 557.2 |

TABLE T-8-continued

| Compound No. | Structure | IUPAC | Exact mass (g/mol) | LCMS, Found [M + H]+ |
|---|---|---|---|---|
| 523 | 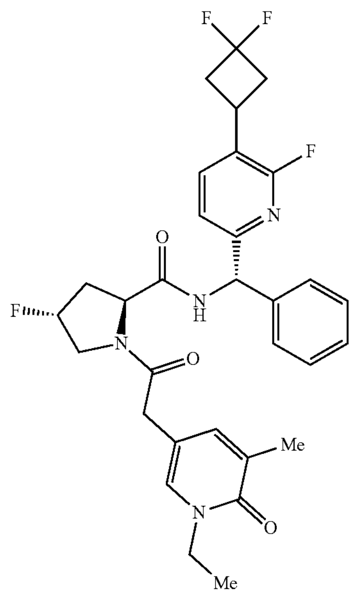 [SMILES: CCn1cc(CC(=O)N2C[C@H](F)C[C@H]2C(=O)N[C@@H](c2ccccc2)c2ccc(C3CC(F)(F)C3)c(F)n2)cc(C)c1=O] | (2S,4R)-N-[(S)-[5-(3,3-difluorocyclobutyl)-6-fluoropyridin-2-yl](phenyl)methyl]-1-[2-(1-ethyl-5-methyl-6-oxo-1,6-dihydropyridin-3-yl)acetyl]-4-fluoropyrrolidine-2-carboxamide | 584.2 | 585.2 |
| 524 | 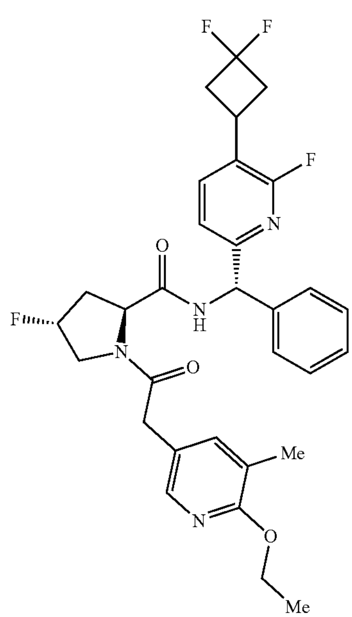 [SMILES: CCOc1ncc(CC(=O)N2C[C@H](F)C[C@H]2C(=O)N[C@@H](c2ccccc2)c2ccc(C3CC(F)(F)C3)c(F)n2)cc1C] | (2S,4R)-N-[(S)-[5-(3,3-difluorocyclobutyl)-6-fluoropyridin-2-yl](phenyl)methyl]-1-[2-(6-ethoxy-5-methylpyridin-3-yl)acetyl]-4-fluoropyrrolidine-2-carboxamide | 584.2 | 585.2 |

TABLE T-8-continued
| Compound No. | Structure | IUPAC | Exact mass (g/mol) | LCMS, Found [M + H]+ |
|---|---|---|---|---|
| 525 | 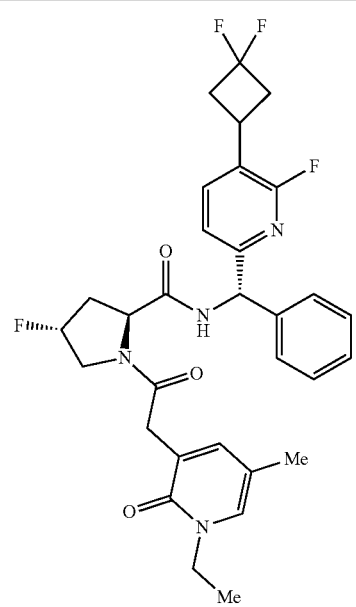 [SMILES: CCn1cc(C)cc(CC(=O)N2C[C@H](F)C[C@H]2C(=O)N[C@@H](c2ccccc2)c2ccc(C3CC(F)(F)C3)c(F)n2)c1=O] | (2S,4R)-N-[(S)-[5-(3,3-difluorocyclobutyl)-6-fluoropyridin-2-yl](phenyl)methyl]-1-[2-(1-ethyl-5-methyl-2-oxo-1,2-dihydropyrdin-3-yl)acetyl]-4-fluoropyrrolidine-2-carboxamide | 584.2 | 585.2 |
| 526 | 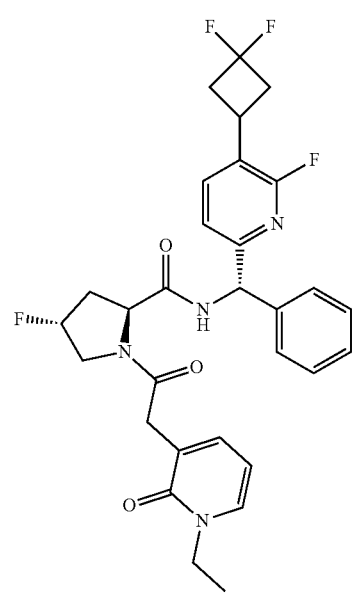 [SMILES: CCn1cccc(CC(=O)N2C[C@H](F)C[C@H]2C(=O)N[C@@H](c2ccccc2)c2ccc(C3CC(F)(F)C3)c(F)n2)c1=O] | (2S,4R)-N-[(S)-[5-(3,3-difluorocyclobutyl)-6-fluoropyridin-2-yl](phenyl)methyl]-1-[2-(1-ethyl-2-oxo-1,2-dihydropyridin-3-yl)acetyl]-4-fluoropyrrolidine-2-carboxamide | 570.2 | 571.2 |

TABLE T-8-continued

| Compound No. | Structure | IUPAC | Exact mass (g/mol) | LCMS, Found [M + H]+ |
|---|---|---|---|---|
| 527 | 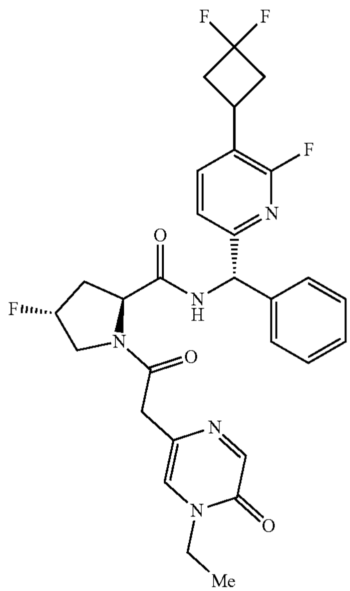 | (2S,4R)-N-[(S)-[5-(3,3-difluorocyclobutyl)-6-fluoropyridin-2-yl](phenyl)methyl]-1-[2-(4-ethyl-5-oxo-4,5-dihydropyrazin-2-yl)acetyl]-4-fluoropyrrolidine-2-carboxamide | 571.2 | 572.3 |
| 528 | 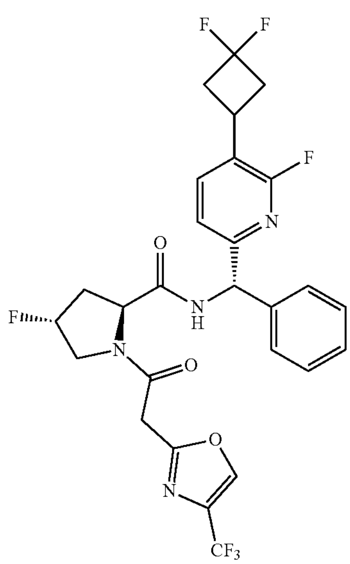 | (2S,4R)-N-[(S)-[5-(3,3-difluorocyclobutyl)-6-fluoropyridin-2-yl](phenyl)methyl]-4-fluoro-1-{2-[4-(trifluoromethyl)-1,3-oxazol-2-yl]acetyl}pyrrolidine-2-carboxamide | 584.2 | 585.1 |

TABLE T-8-continued

| Compound No. | Structure | IUPAC | Exact mass (g/mol) | LCMS, Found [M + H]+ |
| --- | --- | --- | --- | --- |
| 529 | 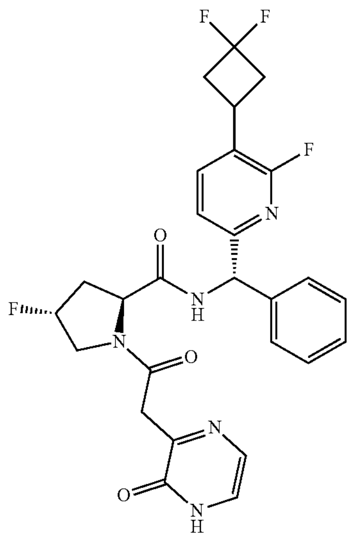 [SMILES: O=C(N[C@@H](c1ccccc1)c1ccc(C2CC(F)(F)C2)c(F)n1)[C@@H]1C[C@@H](F)CN1C(=O)Cc1ncc[nH]c1=O] | (2S,4R)-N-[(S)-[5-(3,3-difluorocyclobutyl)-6-fluoropyridin-2-yl](phenyl)methyl]-4-fluoro-1-[2-(3-oxo-3,4-dihydropyrazin-2-yl)acetyl]pyrrolidine-2-carboxamide | 543.2 | 544.3 |
| 530 | 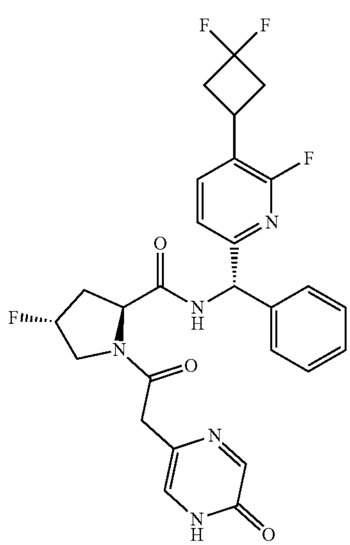 | (2S,4R)-N-[(S)-[5-(3,3-difluorocyclobutyl)-6-fluoropyridin-2-yl](phenyl)methyl]-4-fluoro-1-[2-(5-oxo-4,5-dihydropyrazin-2-yl)acetyl]pyrrolidine-2-carboxamide | 543.3 | 544.3 |

TABLE T-8-continued
| Compound No. | Structure | IUPAC | Exact mass (g/mol) | LCMS, Found [M + H]+ |
|---|---|---|---|---|
| 531 | 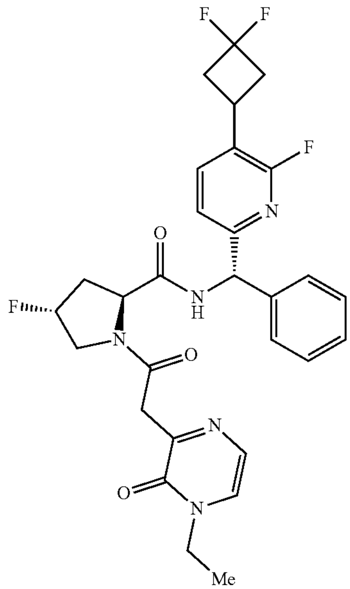 [SMILES: CCn1ccnc(CC(=O)N2C[C@H](F)C[C@H]2C(=O)N[C@@H](c2ccccc2)c2ccc(C3CC(F)(F)C3)c(F)n2)c1=O] | (2S,4R)-N-[(S)-[5-(3,3-difluorocyclobutyl)-6-fluoropyridin-2-yl](phenyl)methyl]-1-[2-(4-ethyl-3-oxo-3,4-dihydropyrazin-2-yl)acetyl]-4-fluoropyrrolidine-2-carboxamide | 571.2 | 572.3 |
Example S-9: Synthesis of (2S,4R)—N—((S)-(5-(3,3-difluorocyclobutyl)pyridin-2-yl)(phenyl)methyl)-1-(((dimethylcarbamoyl)glycyl)-4-fluoropyrrolidine-2-carboxamide
Compound 532
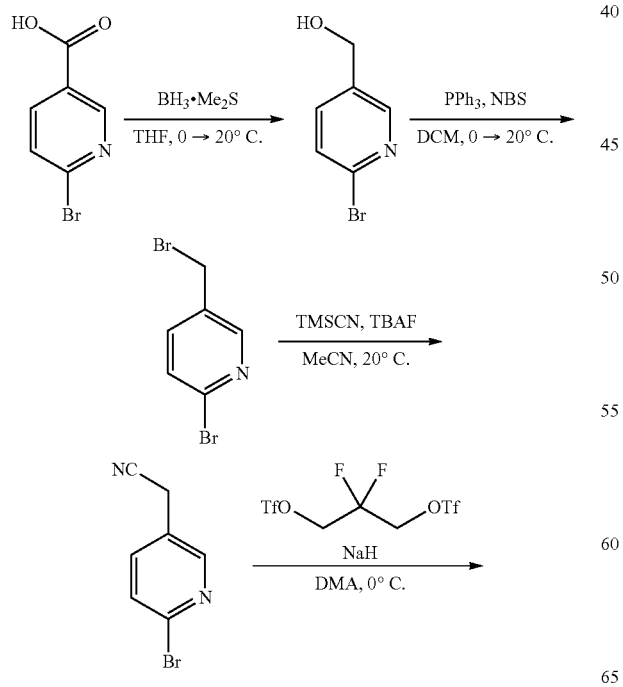
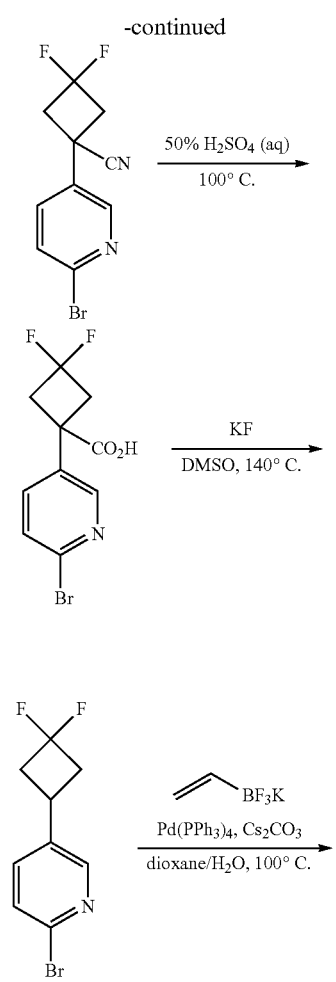

1259
-continued

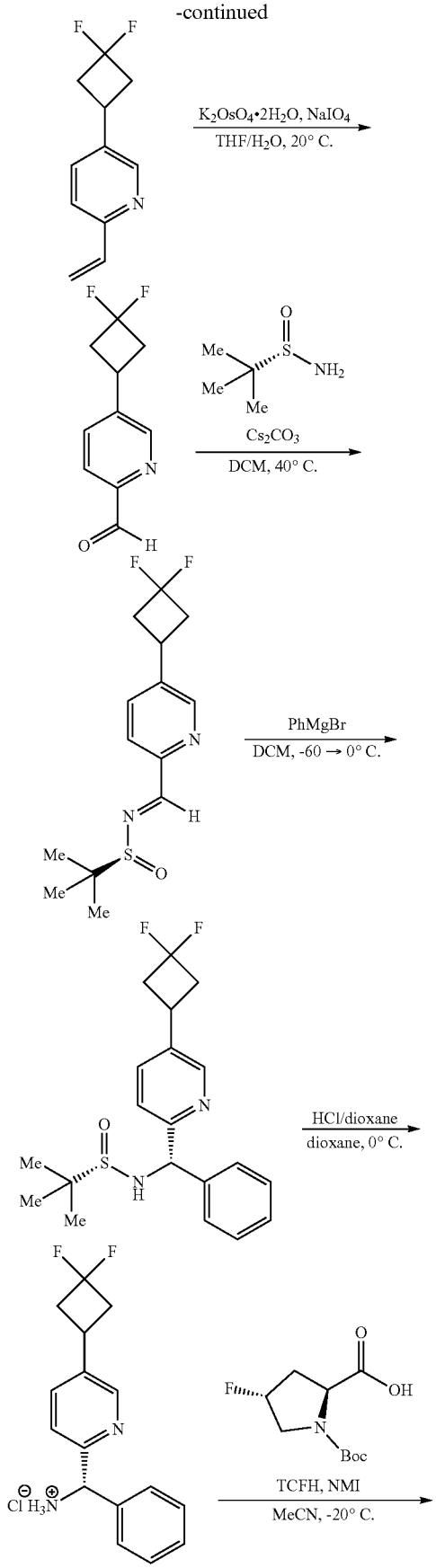

1260
-continued

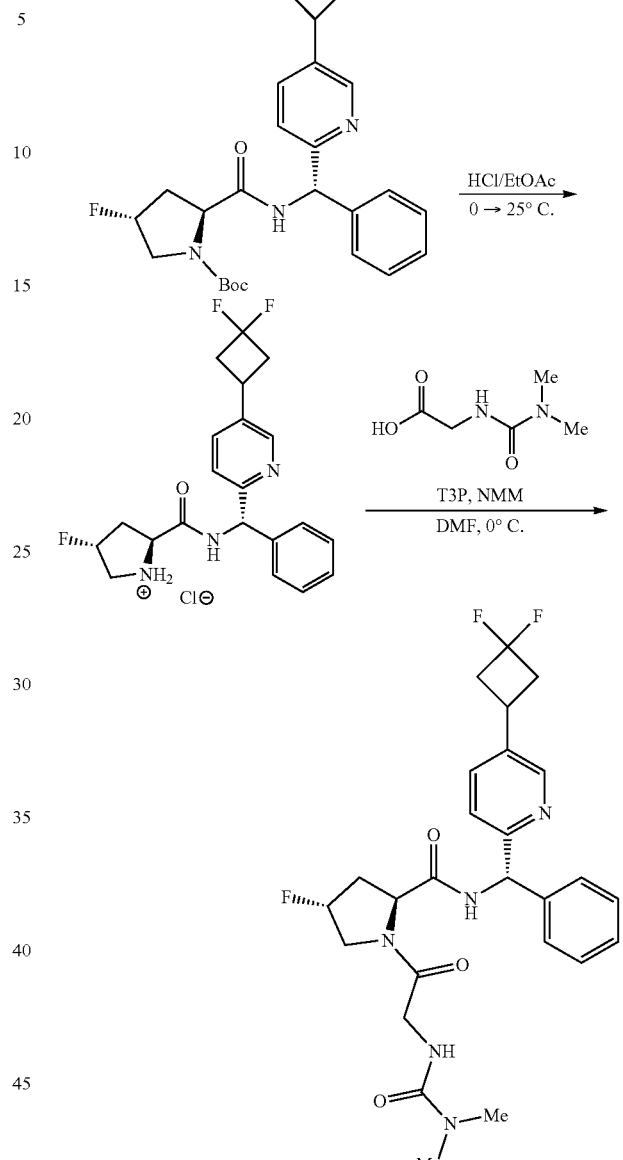

Step a: To a solution of 6-bromonicotinic acid (40 g, 198 mmol, 1 eq) in THF (400 mL) at 0° C. under N₂ was added BH₃·Me₂S (10 M, 59.40 mL, 3 eq). The mixture was then warmed to 20° C. and stirred for 3 h. The reaction mixture was then cooled to 0° C., quenched with MeOH (200 mL), H₂O (100 mL), and saturated aqueous K₂CO₃ (100 mL), sequentially. The resulting biphasic mixture was then extracted with EtOAc (3×200 mL), and the combined organic extracts were washed with water, dried over anhydrous Na₂SO₄, and concentrated under reduced pressure. The crude residue obtained was purified by column chromatography to give (6-bromopyridin-3-yl)methanol. LC-MS (ESI): m/z: [M+H]⁺ calculated for C₆H₆BrNO: 188.0; found: 188.0.

Step b: To a solution of (6-bromopyridin-3-yl)methanol (16.2 g, 86.3 mmol, 1 eq) and PPh₃ (26.0 g, 99.7 mmol, 1.15 eq) in DCM (150 mL) at 0° C. was added N-bromosuccinimide (NBS, 17.7 g, 99.7 mmol, 1.15 eq). The resulting mixture was then allowed to warm to 20° C. and stirred for 3 h. The reaction mixture was then quenched by addition H$_2$O (200 mL) at 20° C., and the resulting biphasic mixture was extracted with EtOAc (3×200 mL). The combined organic layers were washed with brine (400 mL), dried over anhydrous Na$_2$SO$_4$, filtered, and concentrated under reduced pressure. The crude residue obtained was purified by column chromatography to give 2-bromo-5-(bromomethyl)pyridine. LC-MS (ESI): m/z: [M+H]$^+$ calculated for C$_6$H$_5$Br$_2$N: 249.9; found: 249.9.

Step c: To a solution of trimethylsilyl cyanide (TMSCN, 12.5 g, 126 mmol, 15.7 mL, 1 eq) in CH$_3$CN (30 mL) at 0° C. was added tetrabutylammonium fluoride (TBAF, 1 M, 126 mL, 1.5 eq), and the resulting mixture was stirred for 0.5 h at 0° C. 2-bromo-5-(bromomethyl)pyridine (21.1 g, 84.9 mmol, 1 eq) in CH$_3$CN (100 mL) was then added to the reaction mixture, and the resulting mixture was warmed to 20° C. and stirred for 0.5 h. The reaction mixture was then cooled to 0° C. and quenched by addition H$_2$O (150 mL). The resulting biphasic mixture was then extracted with EtOAc (3×100 mL). The combined organic extracts were washed with brine (200 mL), dried over anhydrous Na$_2$SO$_4$, filtered, and concentrated under reduced pressure. The crude residue obtained was purified by column chromatography to give 2-(6-bromopyridin-3-yl)acetonitrile. LC-MS (ESI): m/z: [M+H]$^+$ calculated for C$_7$H$_5$BrN$_2$: 197.0; found: 197.0.

Step d: To a solution of 2-(6-bromopyridin-3-yl)acetonitrile (13.5 g, 68.5 mmol, 1 eq) in dimethylacetamide (DMA, 130 mL) at 0° C. under N$_2$ was added NaH (5.48 g, 137 mmol, 60% purity, 2 eq). The resulting mixture was stirred at 0° C. for 30 min, and then [2,2-difluoro-3-(trifluoromethylsulfonyloxy)propyl] trifluoromethanesulfonate (30.9 g, 82.2 mmol, 1.2 eq) was added to the reaction mixture. The resulting mixture was then stirred at 0° C. for 1 h. The reaction mixture was then quenched by addition ice-water (100 mL) at 0° C. The resulting biphasic mixture was extracted with EtOAc (3×100 mL). The combined organic extracts were washed with brine (200 mL), dried over anhydrous Na$_2$SO$_4$, filtered, and concentrated under reduced pressure. The crude residue obtained was purified by column chromatography to give 1-(6-bromopyridin-3-yl)-3,3-difluorocyclobutane-1-carbonitrile. LC-MS (ESI): m/z: [M+H]$^+$ calculated for C$_{10}$H$_7$BrF$_2$N$_2$: 273.0; found: 273.0.

Step e: A mixture of 1-(6-bromopyridin-3-yl)-3,3-difluorocyclobutane-1-carbonitrile (2.34 g, 8.57 mmol, 1 eq) in aqueous H$_2$SO$_4$ (40 mL, 50%) was warmed to 100° C. and stirred 16 h. The reaction mixture was then cooled to 0° C. and adjusted to pH=6 with saturated aqueous K$_2$CO$_3$ at 0° C. The resulting mixture was then extracted with EtOAc (2×50 mL). The combined organic extracts were washed with brine (50 mL), dried over anhydrous Na$_2$SO$_4$, filtered, and concentrated under reduced pressure to give 1-(6-bromopyridin-3-yl)-3,3-difluorocyclobutane-1-carboxylic acid. The crude residue obtained was used for next step without further purification. LC-MS (ESI): m/z: [M+H]$^+$ calculated for C$_{10}$H$_8$BrF$_2$NO$_2$: 292.0; found: 292.0.

Step f: A mixture of 1-(6-bromopyridin-3-yl)-3,3-difluorocyclobutane-1-carboxylic acid (2.30 g, 7.87 mmol, 1 eq) and KF (2.29 g, 39.4 mmol, 5 eq) in DMSO (10 mL) was warmed to 140° C. and stirred for 3 h. The mixture was then cooled to room temperature and poured into ice-water (50 mL). The resulting biphasic mixture was extracted with EtOAc (2×50 mL). The combined organic extracts were washed with brine (50 mL), dried over anhydrous Na$_2$SO$_4$, and concentrated under reduced pressure. The crude residue obtained was purified by column chromatography to give 2-bromo-5-(3,3-difluorocyclobutyl)pyridine. LC-MS (ESI): m/z: [M+H]$^+$ calculated for C$_9$H$_8$BrF$_2$N: 248.0; found: 248.1.

Step g: A mixture of 2-bromo-5-(3,3-difluorocyclobutyl) pyridine (6 g, 24.1 mmol, 1 eq), potassium vinyltrifluoroborate (4.86 g, 36.2 mmol, 1.5 eq), Cs$_2$CO$_3$ (15.7 g, 48.3 mmol, 2 eq), and Pd(PPh$_3$)$_4$ (2 g, 1.73 mmol, 0.07 eq) in dioxane (100 mL) and H$_2$O (10 mL) was de-gassed, placed under N$_2$, warmed to 100° C., and stirred for 16 h. The reaction mixture was concentrated in vacuum to obtain 5-(3,3-difluorocyclobutyl)-2-vinylpyridine, which was used directly in the next step without further purification or characterization.

Step h: To a solution of 5-(3,3-difluorocyclobutyl)-2-vinylpyridine (4 g, 20.4 mmol, 1 eq) in THF (100 mL) and H$_2$O (30 mL) at 0° C. was added NaIO$_4$ (17.5 g, 81.9 mmol, 4 eq) and K$_2$OsO$_4$·2H$_2$O (377 mg, 1.02 mmol, 0.05 eq). The mixture was allowed to warm to 20° C. and stirred at 20° C. for 16 h. The reaction mixture was then filtered, and the biphasic mixture was extracted with ethyl acetate (3×50 mL). The combined organic phase was washed with brine (30 mL), dried with anhydrous Na$_2$SO$_4$, filtered, and concentrated under reduced pressure. The crude residue obtained was purified by column chromatography to give 5-(3,3-difluorocyclobutyl)picolinaldehyde. LC-MS (ESI): m/z: [M+H]$^+$ calculated for C$_{10}$H$_9$F$_2$NO: 198.0; found: 198.0.

Step i: A mixture of 5-(3,3-difluorocyclobutyl)picolinaldehyde (2.5 g, 12.6 mmol, 1 eq), (S)-2-methylpropane-2-sulfinamide (1.69 g, 13.9 mmol, 1.1 eq), and Cs$_2$CO$_3$ (6.20 g, 19.0 mmol, 1.5 eq) in DCM (50 mL) was warmed to 40° C. and stirred for 1 h. The reaction mixture was then filtered, and the filtrate was concentrated under reduced pressure. The crude residue obtained was purified by column chromatography to obtain (S,E)-N-((5-(3,3-difluorocyclobutyl)pyridin-2-yl)methylene)-2-methylpropane-2-sulfinamide. LC-MS (ESI): m/z: [M+H]$^+$ calculated for C$_{14}$H$_{18}$F$_2$N$_2$OS: 301.1; found: 301.1.

Step j: To a stirring solution of (S,E)-N-((5-(3,3-difluorocyclobutyl)pyridin-2-yl)methylene)-2-methylpropane-2-sulfinamide (3.50 g, 11.6 mmol, 1 eq) in DCM (50 mL) at −60° C. was added phenylmagnesium bromide (3 M, 5.83 mL, 1.5 eq) in a dropwise manner. The mixture was then allowed to warm to 0° C. and stirred for 2 h. The reaction mixture was then quenched with saturated aqueous NH$_4$Cl (30 mL) at 0° C. The resulting biphasic mixture was then extracted with DCM (2×30 mL). The combined organic extracts were washed with brine (80 mL), dried over anhydrous Na$_2$SO$_4$, filtered, and concentrated under reduced pressure. The crude residue obtained was purified by column chromatography to obtain (S)—N—[(S)-[5-(3,3-difluorocyclobutyl)-2-pyridyl]-phenyl-methyl]-2-methyl-propane-2-sulfinamide. LC-MS (ESI): m/z: [M+H]$^+$ calculated for C$_{20}$H$_{24}$F$_2$N$_2$OS: 379.2; found: 379.2.

Step k: To a mixture of (S)—N—[(S)-[5-(3,3-difluorocyclobutyl)-2-pyridyl]-phenyl-methyl]-2-methyl-propane-2-sulfinamide (4.0 g, 10.5 mmol, 1 eq) in dioxane (20 mL) at 0° C. was added HCl/dioxane (4 M, 30 mL, 11.3 eq). The resulting mixture was stirred at 0° C. for 1 h The reaction mixture was then concentrated under reduced pressure to give (S)-(5-(3,3-difluorocyclobutyl)pyridin-2-yl)(phenyl) methanaminium chloride, which was used in the next step without further purification. LC-MS (ESI): m/z: [M+H]$^+$ calculated for C$_{16}$H$_{16}$F$_2$N$_2$: 275.1; found: 275.2.

Step l: To a mixture of (S)-(5-(3,3-difluorocyclobutyl) pyridin-2-yl)(phenyl)methanaminium chloride (3.09 g, 10.3 mmol, 1 eq) and (2S,4R)-1-tert-butoxycarbonyl-4-fluoropyrrolidine-2-carboxylic acid (2.88 g, 12.3 mmol, 1.2 eq) in MeCN (50 mL) at −20° C. under $N_2$ was added 1-methylimidazole (NMI, 2.54 g, 30.8 mmol, 3 eq) and chloro-N,N,N′,N-tetramethylformamidinium hexafluorophosphate (TCFH, 3.47 g, 12.3 mmol, 1.2 eq). The resulting mixture was stirred at −20° C. for 1 h. The reaction was then quenched with $H_2O$ (100 mL), and the resulting biphasic mixture was extracted with EtOAc (2×100 mL). The combined organic extracts were washed with brine (100 mL), dried over anhydrous $Na_2SO_4$, filtered, and concentrated under reduced pressure. The crude residue obtained was purified by column chromatography to give tert-butyl (2S,4R)-2-(((S)-(5-(3,3-difluorocyclobutyl)pyridin-2-yl)(phenyl)methyl)carbamoyl)-4-fluoropyrrolidine-1-carboxylate. LC-MS (ESI): m/z: $[M+H]^+$ calculated for $C_{26}H_{30}F_3N_3O_3$: 490.2; found: 490.3.

Step m: To a solution of tert-butyl (2S,4R)-2-(((S)-(5-(3,3-difluorocyclobutyl)pyridin-2-yl)(phenyl)methyl)carbamoyl)-4-fluoropyrrolidine-1-carboxylate (5.00 g, 10.2 mmol, 1 eq) in EtOAc (30 mL) at 0° C. was added HCl/EtOAc (4 M, 30 mL) in a dropwise manner. The reaction was then allowed to warm to 25° C. and stirred for 1 h. The reaction mixture was then concentrated under reduced pressure. The crude residue obtained was triturated with i-PrOH/EtOH (ratio=4:1, 150 mL) to give (2S,4R)-2-(((S)-(5-(3,3-difluorocyclobutyl)pyridin-2-yl)(phenyl)methyl)carbamoyl)-4-fluoropyrrolidin-1-ium chloride. LC-MS (ESI): m/z: $[M+H]^+$ calculated for $C_{21}H_{22}F_3N_3O$: 390.2; found: 390.3.

Step n: To a solution of (2S,4R)-2-(((S)-(5-(3,3-difluorocyclobutyl)pyridin-2-yl)(phenyl)methyl)carbamoyl)-4-fluoropyrrolidin-1-ium chloride (80 mg, 205 μmol, 1 eq) and (dimethylcarbamoyl)glycine (36.0 mg, 246 μmol, 1.2 eq) in DCM (3 mL) at 0° C. was added N-methylmorpholine (NMM, 104 mg, 1.03 mmol, 5 eq) and 2,4,6-tripropyl-1,3,5,2,4,6-trioxatriphosphorinane-2,4,6-trioxide (T3P, 196 mg, 308 μmol, 50% purity, 1.5 eq). The resulting mixture was stirred at 0° C. for 2 h. The reaction mixture was then poured into water (10 mL) at 0° C. and stirred for 10 min. The biphasic mixture was then extracted with ethyl acetate (3×10 mL). The combined organic extracts were washed with brine (10 mL), dried with anhydrous $Na_2SO_4$, filtered, and concentrated under reduced pressure. The crude residue obtained was purified by prep-HPLC to give (2S,4R)—N—((S)-(5-(3,3-difluorocyclobutyl)pyridin-2-yl)(phenyl)methyl)-1-((dimethylcarbamoyl)glycyl)-4-fluoropyrrolidine-2-carboxamide. $^1$H NMR (2.3:1 rotamer ratio, asterisk denotes minor rotamer peaks, obscured peaks not reported, 400 MHz, DMSO-$d_6$) δ 9.27*(d, J=7.9 Hz, 1H), 8.88 (d, J=8.4 Hz, 1H), 8.50-8.41 (m, 1H), 7.80-7.71 (m, 1H), 7.48-7.40 (m, 1H), 7.37-7.18 (m, 4H), 6.46 (t, J=5.5 Hz, 1H), 6.35*(t, J=5.6 Hz, 1H), 6.16-6.05 (m, 1H), 5.46-5.18 (m, 1H), 4.85*(t, J=8.0 Hz, 1H), 4.60 (t, J=8.3 Hz, 1H), 4.03-3.83 (m, 2H), 3.75-3.57 (m, 2H), 3.51-3.22 (m, 4H), 3.06-2.91 (m, 2H), 2.84-2.68 (m, 4H), 2.23-1.85 (m, 2H). LC-MS (ESI): m/z: $[M+H]^+$ calculated for $C_{26}H_{30}F_3N_5O_3$: 518.2; found: 518.4.

The following compounds in Table T-9 were synthesized using procedures similar to Compound 532 using the appropriate starting materials.

TABLE T-9

| Compound No. | Structure | IUPAC | Exact mass (g/mol) | LCMS, Found $[M + H]^+$ |
|---|---|---|---|---|
| 533 | 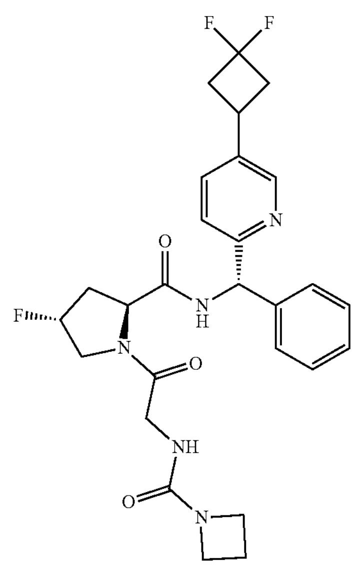 [SMILES: O=C(N[C@@H](c1ccccc1)c1ccc(C2CC(F)(F)C2)cn1)[C@@H]1C[C@@H](F)CN1C(=O)CNC(=O)N1CCC1] | (2S,4R)-1-{2-[(azetidine-1-carbonyl)amino]acetyl}-N-[(S)-[5-(3,3-difluorocyclobutyl)pyridin-2-yl](phenyl)methyl]-4-fluoropyrrolidine-2-carboxamide | 529.2 | 530.2 |

TABLE T-9-continued

| Compound No. | Structure | IUPAC | Exact mass (g/mol) | LCMS, Found [M + H]+ |
| --- | --- | --- | --- | --- |
| 534 | 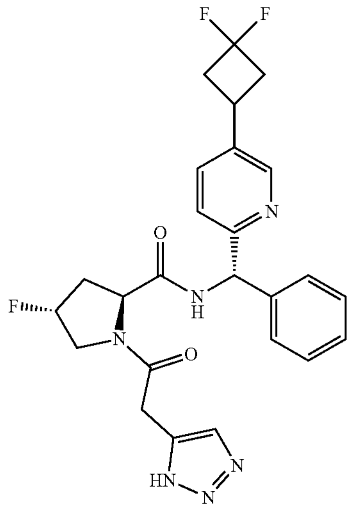 [SMILES: O=C(N[C@@H](c1ccccc1)c1ccc(C2CC(F)(F)C2)cn1)[C@@H]1C[C@@H](F)CN1C(=O)Cc1cnn[nH]1] | (2S,4R)-N-[(S)-[5-(3,3-difluorocyclobutyl)pyridin-2-yl](phenyl)methyl]-4-fluoro-1-[2-(1H-1,2,3-triazol-5-yl)acetyl]pyrrolidine-2-carboxamide | 498.2 | 499.3 |
| 535 | 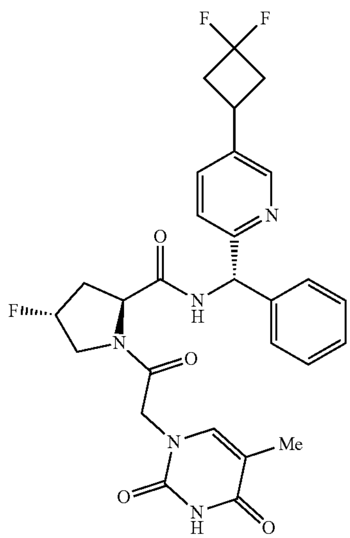 [SMILES: Cc1cn(CC(=O)N2C[C@H](F)C[C@H]2C(=O)N[C@@H](c2ccccc2)c2ccc(C3CC(F)(F)C3)cn2)c(=O)[nH]c1=O] | (2S,4R)-N-[(S)-[5-(3,3-difluorocyclobutyl)pyridin-2-yl](phenyl)methyl]-4-fluoro-1-[2-(5-methyl-2,4-dioxo-1,2,3,4-tetrahydropyrimidin-1-yl)acetyl]pyrrolidine-2-carboxamide | 555.2 | 556.4 |
| 536 | 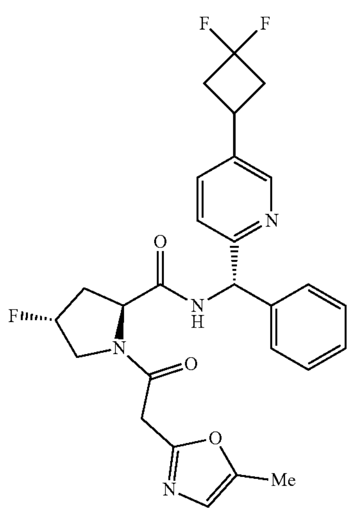 [SMILES: Cc1cnc(CC(=O)N2C[C@H](F)C[C@H]2C(=O)N[C@@H](c2ccccc2)c2ccc(C3CC(F)(F)C3)cn2)o1] | (2S,4R)-N-[(S)-[5-(3,3-difluorocyclobutyl)pyridin-2-yl](phenyl)methyl]-4-fluoro-1-[2-(5-methyl-1,3-oxazol-2-yl)acetyl]pyrrolidine-2-carboxamide | 512.2 | 513.1 |

TABLE T-9-continued

| Compound No. | Structure | IUPAC | Exact mass (g/mol) | LCMS, Found [M + H]+ |
|---|---|---|---|---|
| 537 | 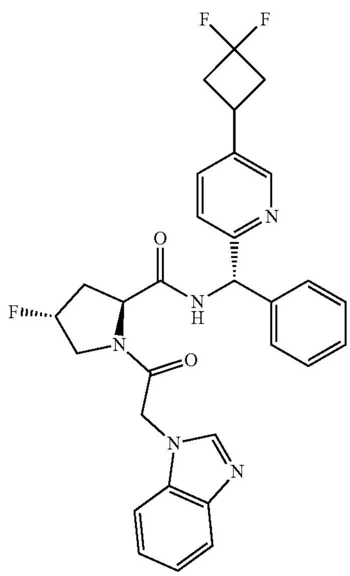 [SMILES: O=C(N[C@@H](c1ccccc1)c1ccc(C2CC(F)(F)C2)cn1)[C@@H]1C[C@@H](F)CN1C(=O)Cn1cnc2ccccc21] | (2S,4R)-1-[2-(1H-1,3-benzodiazol-1-yl)acetyl]-N-[(S)-[5-(3,3-difluorocyclobutyl)pyridin-2-yl](phenyl)methyl]-4-fluoropyrrolidine-2-carboxamide | 547.2 | 548.1 |
| 538 | 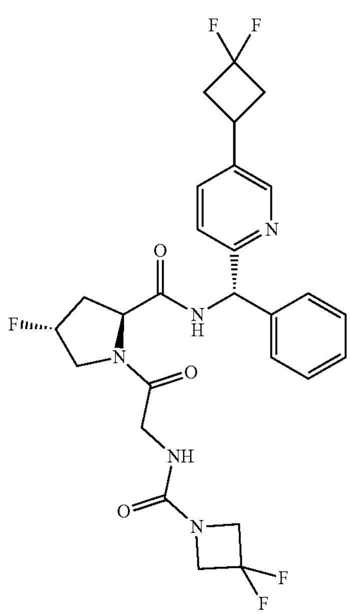 [SMILES: O=C(N[C@@H](c1ccccc1)c1ccc(C2CC(F)(F)C2)cn1)[C@@H]1C[C@@H](F)CN1C(=O)CNC(=O)N1CC(F)(F)C1] | (2S,4R)-1-{2-[(3,3-difluoroazetidine-1-carbonyl)amino]acetyl}-N-[(S)-[5-(3,3-difluorocyclobutyl)pyridin-2-yl](phenyl)methyl]-4-fluoropyrrolidine-2-carboxamide | 565.2 | 566.2 |

TABLE T-9-continued

| Compound No. | Structure | IUPAC | Exact mass (g/mol) | LCMS, Found [M + H]+ |
|---|---|---|---|---|
| 539 | 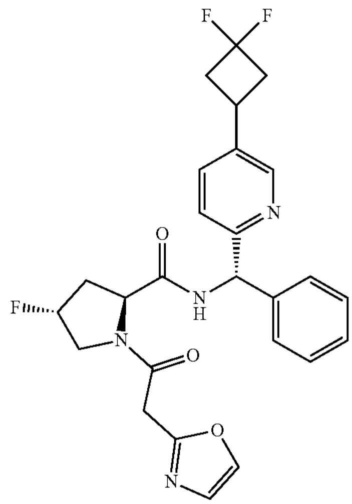 [SMILES: O=C(N[C@@H](c1ccccc1)c1ccc(C2CC(F)(F)C2)cn1)[C@@H]1C[C@@H](F)CN1C(=O)Cc1ncco1] | (2S,4R)-N-[(S)-[5-(3,3-difluorocyclobutyl)pyridin-2-yl](phenyl)methyl]-4-fluoro-1-[2-(1,3-oxazol-2-yl)acetyl]pyrrolidine-2-carboxamide | 498.2 | 499.4 |
| 540 | 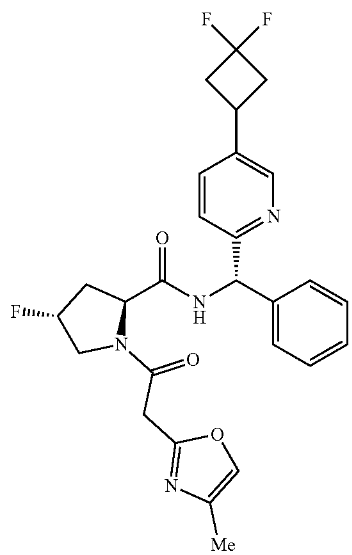 [SMILES: Cc1coc(CC(=O)N2C[C@H](F)C[C@H]2C(=O)N[C@@H](c2ccccc2)c2ccc(C3CC(F)(F)C3)cn2)n1] | (2S,4R)-N-[(S)-[5-(3,3-difluorocyclobutyl)pyridin-2-yl](phenyl)methyl]-4-fluoro-1-[2-(4-methyl-1,3-oxazol-2-yl)acetyl]pyrrolidine-2-carboxamide | 512.2 | 513.4 |
| 541 | 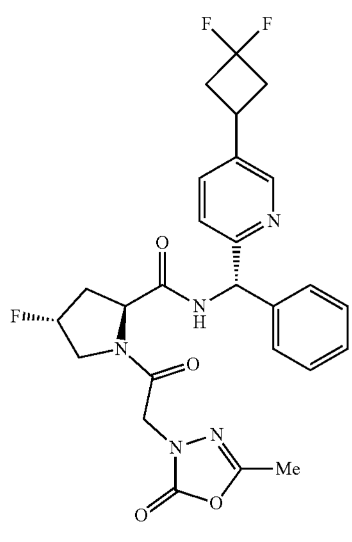 [SMILES: Cc1nn(CC(=O)N2C[C@H](F)C[C@H]2C(=O)N[C@@H](c2ccccc2)c2ccc(C3CC(F)(F)C3)cn2)c(=O)o1] | (2S,4R)-N-[(S)-[5-(3,3-difluorocyclobutyl)pyridin-2-yl](phenyl)methyl]-4-fluoro-1-[2-(5-methyl-2-oxo-2,3-dihydro-1,3,4-oxadiazol-3-yl)acetyl]pyrrolidine-2-carboxamide | 529.2 | 530.2 |

TABLE T-9-continued
| Compound No. | Structure | IUPAC | Exact mass (g/mol) | LCMS, Found [M + H]+ |
|---|---|---|---|---|
| 542 | 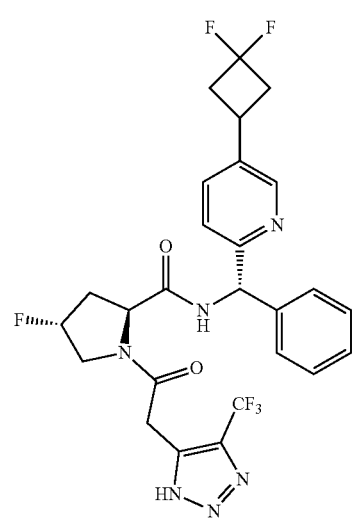 [SMILES: O=C(N[C@@H](c1ccccc1)c1ccc(C2CC(F)(F)C2)cn1)[C@@H]1C[C@@H](F)CN1C(=O)Cc1[nH]nnc1C(F)(F)F] | (2S,4R)-N-[(S)-[5-(3,3-difluorocyclobutyl)pyridin-2-yl](phenyl)methyl]-4-fluoro-1-{2-[4-(trifluoromethyl)-1H-1,2,3-triazol-5-yl]acetyl}pyrrolidine-2-carboxamide | 566.2 | 567.1 |
| 543 | 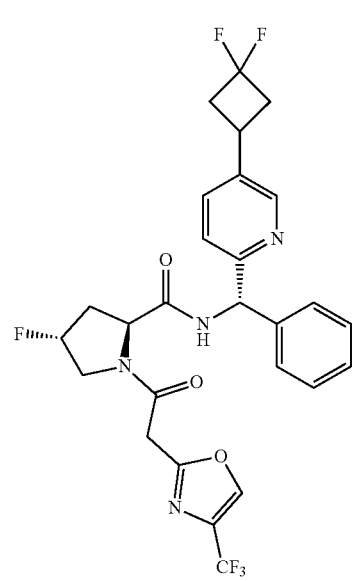 [SMILES: O=C(N[C@@H](c1ccccc1)c1ccc(C2CC(F)(F)C2)cn1)[C@@H]1C[C@@H](F)CN1C(=O)Cc1nc(C(F)(F)F)co1] | (2S,4R)-N-[(S)-[5-(3,3-difluorocyclobutyl)pyridin-2-yl](phenyl)methyl]-4-fluoro-1-{2-[4-(trifluoromethyl)-1,3-oxazol-2-yl]acetyl}pyrrolidine-2-carboxamide | 566.2 | 567.1 |

Example S-10: Synthesis of (2S,4R)-1-((azetidine-1-carbonyl)glycyl)-N—((S)-(4-(3,3-difluorocyclobutyl)-3-fluorophenyl)(phenyl)methyl)-4-fluoropyrrolidine-2-carboxamide and (2S,4R)-1-((azetidine-1-carbonyl)glycyl)-N—((R)-(4-(3,3-difluorocyclobutyl)-3-fluorophenyl)(phenyl)methyl)-4-fluoropyrrolidine-2-carboxamide
Compounds 544 and 545
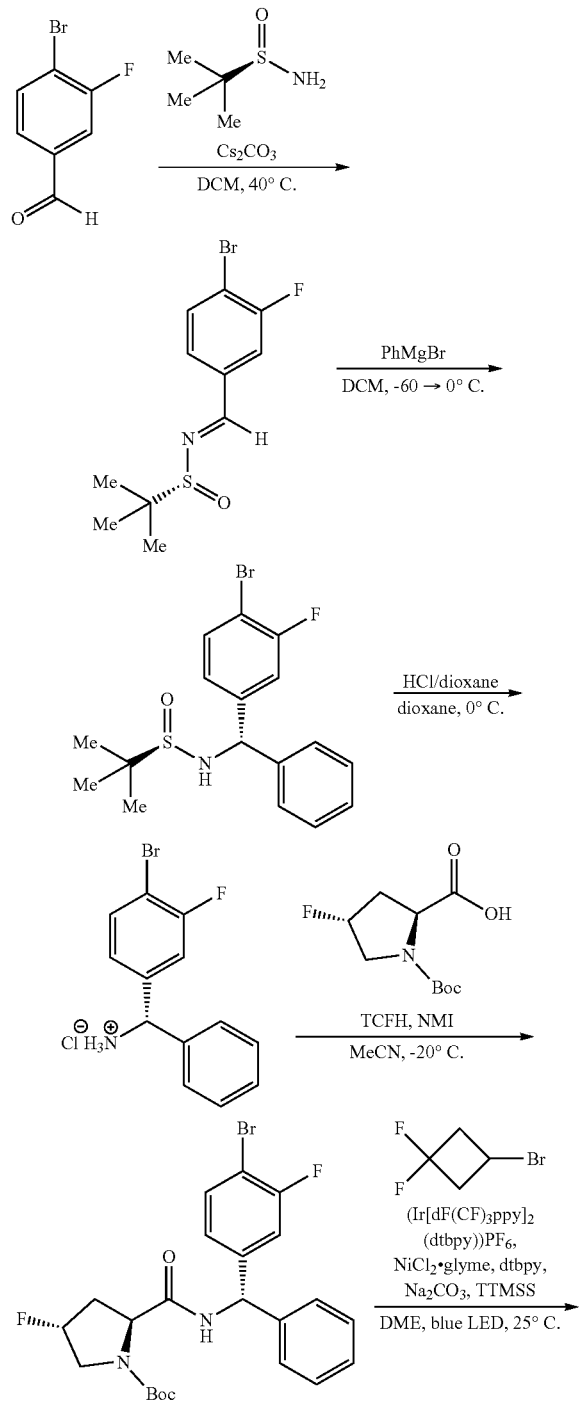
-continued
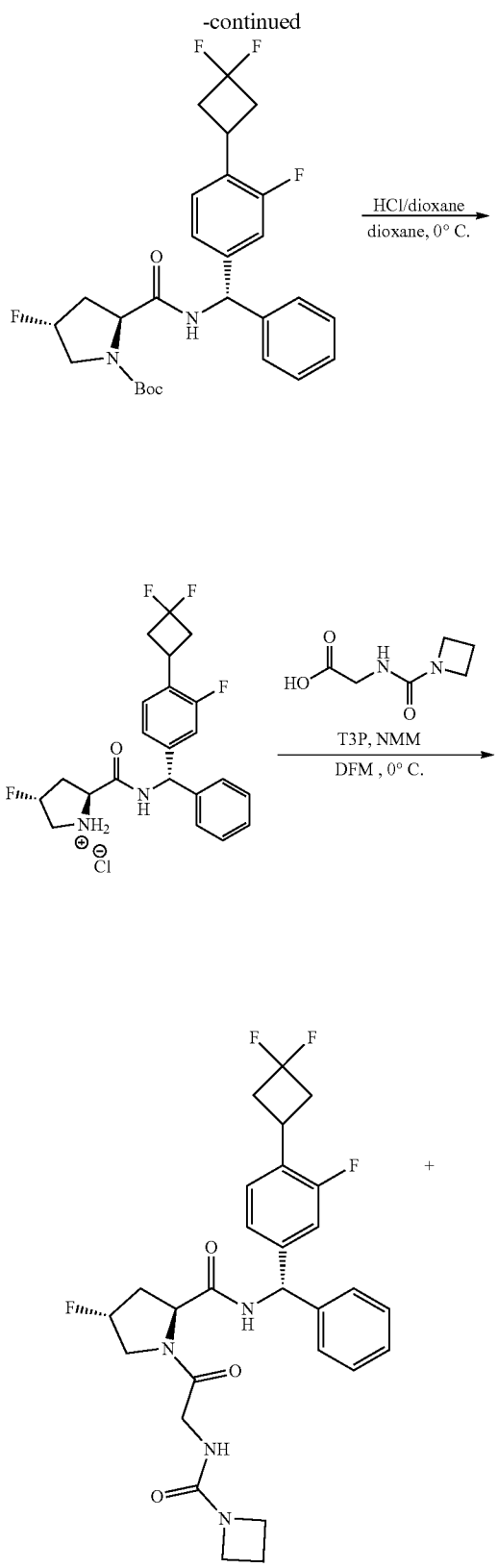

-continued

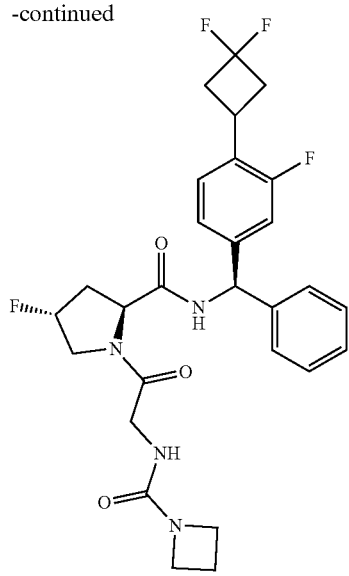

Step a: A mixture of 4-bromo-3-fluorobenzaldehyde (25 g, 123 mmol, 1 eq), (R)-2-methylpropane-2-sulfinamide (16.4 g, 135 mmol, 1.1 eq) and Cs$_2$CO$_3$ (60.1 g, 184 mmol, 1.5 eq) in DCM (150 mL) at 40° C. was stirred for 1 h. The reaction mixture was then filtered, and the filtrate was concentrated under reduced pressure. The crude residue obtained was purified by column chromatography to give (R,E)-N-(4-bromo-3-fluorobenzylidene)-2-methylpropane-2-sulfinamide (37 g). LC-MS (ESI): m/z: [M+H]$^+$ calculated for C$_{11}$H$_{13}$BrFNOS: 306.0; found: 305.9.

Step b: To a solution of (R,E)-N-(4-bromo-3-fluorobenzylidene)-2-methylpropane-2-sulfinamide (37 g, 120 mmol, 1 eq) in DCM (150 mL) at −60° C. was added phenylmagnesium bromide (3 M, 48.3 mL, 1.2 eq) in a dropwise manner. The resulting mixture was and stirred at −60° C. for 1 h before it was warmed to 0° C. and stirred for 1 h. The reaction mixture was then quenched by addition of saturated aqueous NH$_4$Cl (300 mL) at 0° C. The resulting biphasic mixture was extracted with EtOAc (3×150 mL). The combined organic extracts were washed with brine (100 mL), dried over anhydrous Na$_2$SO$_4$, filtered, and concentrated under reduced pressure. The crude residue obtained was purified by column chromatography to obtain (R)—N—((S)-(4-bromo-3-fluorophenyl)(phenyl)methyl)-2-methylpropane-2-sulfinamide. LC-MS (ESI): m/z: [M+H]$^+$ calculated for C$_{17}$H$_{19}$BrFNOS: 384.0; found: 383.9.

Step c: To a mixture of (R)—N—((S)-(4-bromo-3-fluorophenyl)(phenyl)methyl)-2-methylpropane-2-sulfinamide (45 g, 117 mmol, 1 eq) in dioxane (200 mL) at 0° C. was added HCl/dioxane (4 M, 500 mL). The resulting mixture was stirred at 0° C. for 2 h. The reaction mixture was then filtered, and the white solid was washed with petroleum ether (3×50 mL). The washed solid was then dried under reduced pressure. The residue obtained was triturated with 2-methoxy-2-methylpropane to obtain (S)-(4-bromo-3-fluorophenyl)(phenyl)methanaminium chloride. LC-MS (ESI): m/z: [M−NH$_2$]$^+$ calculated for C$_{13}$H$_{11}$BrFN: 263.0; found: 263.0.

Step d: To a solution of (S)-(4-bromo-3-fluorophenyl)(phenyl)methanaminium chloride (20 g, 63.1 mmol, 1 eq), (2S,4R)-1-(tert-butoxycarbonyl)-4-fluoropyrrolidine-2-carboxylic acid (17.6 g, 75.8 mmol, 1.2 eq) in CH$_3$CN (300 mL) at −20° C. was added N-methylimidazole (NMI, 25.9 g, 315 mmol, 5 eq) and chloro-N,N,N,N-tetramethylformamidinium hexafluorophosphate (TCFH, 19.5 g, 69.4 mmol, 1.1 eq). The resulting mixture was then stirred at −20° C. for 1 h. The reaction mixture was then quenched by addition H$_2$O (500 mL) at 20° C. and extracted with EtOAc (3×200 mL). The combined organic extracts were washed with brine (100 mL), dried over anhydrous Na$_2$SO$_4$, filtered, and concentrated under reduced pressure. The crude residue obtained was purified by column chromatography to obtain tert-butyl (2S,4R)-2-(((S)-(4-bromo-3-fluorophenyl)(phenyl)methyl)carbamoyl)-4-fluoropyrrolidine-1-carboxylate. LC-MS (ESI): m/z: [M+H]$^+$ calculated for C$_{23}$H$_{25}$BrF$_2$N$_2$O$_3$: 495.1; found: 495.0.

Step e: To a solution of tert-butyl (2S,4R)-2-(((S)-(4-bromo-3-fluorophenyl)(phenyl)methyl)carbamoyl)-4-fluoropyrrolidine-1-carboxylate (5 g, 10.0 mmol, 1 eq) in dimethylacetamide (DME, 10 mL) at 25° C. under N$_2$ was added 3-bromo-1,1-difluorocyclobutane (2.59 g, 15.1 mmol, 1.5 eq), nickel(II) chloride ethylene glycol dimethyl ether complex (NiCl$_2$·glyme, 11.0 mg, 50.4 µmol, 0.005 eq), 4,4-di-tert-butyl-2,2-bipyridyl (dtbpy, 13.5 mg, 50.4 µmol, 0.005 eq), Na$_2$CO$_3$ (2.14 g, 20.1 mmol, 2 eq), tris(trimethylsilyl)silane (TTMSS, 2.51 g, 10.0 mmol, 3.11 mL, 1 eq) and (Ir[dF(CF$_3$)ppy]$_2$(dtbpy))PF$_6$ (113 mg, 100 µmol, 0.01 eq). The resulting mixture was stirred under N$_2$ at 25° C. under 34 W blue LED for 16 h. The reaction mixture was then filtered, and the filtrate was concentrated under reduced pressure. The crude residue obtained was purified by column chromatography to give tert-butyl (2S,4R)-2-(((S)-(4-(3,3-difluorocyclobutyl)-3-fluorophenyl)(phenyl)methyl)carbamoyl)-4-fluoropyrrolidine-1-carboxylate. LC-MS (ESI): m/z: [M+H]$^+$ calculated for C$_{27}$H$_{30}$F$_4$N$_2$O$_3$: 507.2; found: 507.2.

Step f: To a mixture of tert-butyl (2S,4R)-2-(((S)-(4-(3,3-difluorocyclobutyl)-3-fluorophenyl)(phenyl)methyl)carbamoyl)-4-fluoropyrrolidine-1-carboxylate (2.5 g, 4.94 mmol, 1 eq) in dioxane (20 mL) at 0° C. was added HCl/dioxane (4 M, 20 mL), and the resulting mixture was stirred at 0° C. for 1 h. The reaction mixture was then concentrated under reduced pressure, and the crude residue obtained was recrystallized from isopropanol (20 mL) to give (2S,4R)-2-(((S)-(4-(3,3-difluorocyclobutyl)-3-fluorophenyl)(phenyl)methyl)carbamoyl)-4-fluoropyrrolidin-1-ium chloride. LC-MS (ESI): m/z: [M+H]$^+$ calculated for C$_{22}$H$_{22}$F$_4$N$_2$O: 407.2; found: 407.1.

Step g: To a solution of (2S,4R)-2-(((S)-(4-(3,3-difluorocyclobutyl)-3-fluorophenyl)(phenyl)methyl)carbamoyl)-4-fluoropyrrolidin-1-ium chloride (130 mg, 294 µmol, 1 eq) in DMF (1 mL) at 0° C. was added 2-(azetidine-1-carboxamido)acetic acid (68.6 mg, 352 µmol, 1.2 eq, HCl salt), N-methylmorpholine (NMM, 178 mg, 1.76 mmol, 6 eq) and 2,4,6-tripropyl-1,3,5,2,4,6-trioxatriphosphorinane-2,4,6-trioxide (T3P, 374 mg, 587 µmol, 50% purity, 2 eq). The resulting mixture was stirred at 0° C. for 2 h. The reaction mixture was then quenched by addition of H$_2$O (10 mL). The resulting biphasic mixture was then extracted with EtOAc (3×10 mL). The combined organic layers were washed with saturated aqueous NaCl (3×10 mL), dried over anhydrous Na$_2$SO$_4$, filtered, and concentrated under reduced pressure. The crude residue obtained was purified by prep-HPLC to give a mixture of (2S,4R)-1-((azetidine-1-carbonyl)glycyl)-N—((S)-(4-(3,3-difluorocyclobutyl)-3-fluorophenyl)(phenyl)methyl)-4-fluoropyrrolidine-2-carboxamide and (2S,4R)-1-((azetidine-1-carbonyl)glycyl)-N—((R)-(4-(3,3-difluorocyclobutyl)-3-fluorophenyl)(phenyl)methyl)-4-fluoropyrrolidine-2-carboxamide. This purified mixture was then separated using chiral SFC to give (2S,4R)-1-((azetidine-1-carbonyl)glycyl)-N—((S)-(4-(3,3-difluorocyclobutyl)-3-fluorophenyl)(phenyl)methyl)-4-fluoropyrrolidine-2-carboxamide (major isomer, Compound 544) and (2S,4R)-1-((azetidine-1-carbonyl)glycyl)-N—((R)-(4-(3,3-difluorocyclobutyl)-3-fluorophenyl)(phenyl)methyl)-4-fluoropyrrolidine-2-carboxamide (minor isomer, Compound 545).

Major isomer (Compound 544): $^1$H NMR (3:1 rotamer ratio, asterisk denotes minor rotamer peaks, obscured peaks not reported, 400 MHz, DMSO-d$_6$) δ 9.22 (d, J=8.1 Hz, OH), 8.85 (d, J=8.5 Hz, 1H), 7.42-7.21 (m, 7H), 7.18-7.04 (m, 3H), 6.40 (t, J=5.7 Hz, 1H), 6.28 (t, J=5.8 Hz, OH), 6.14-6.03 (m, 1H), 5.47-5.19 (m, 2H), 4.72 (t, J=8.1 Hz, OH), 4.52 (t, J=8.4 Hz, 1H), 4.02-3.58 (m, 11H), 3.55-3.43 (m, 1H), 3.05-2.90 (m, 2H), 2.83-2.64 (m, 2H), 2.48-2.36 (m, 1H), 2.18-2.05 (m, 3H), 2.04-1.83 (m, 1H). LC-MS (ESI): m/z: [M+H]$^+$ calculated for C$_{28}$H$_{30}$F$_4$N$_4$O$_3$: 547.2; found 547.3.

Minor isomer (Compound 545): $^1$H NMR (2.6:1 rotamer ratio, asterisk denotes minor rotamer peaks, obscured peaks not reported, 400 MHz, DMSO-d$_6$) δ 9.22*(d, J=8.2 Hz, 1H), 8.89 (d, J=8.6 Hz, 1H), 7.41-7.08 (m, 7H), 6.38 (t, J=5.7 Hz, 1H), 6.28*(t, J=5.8 Hz, 1H), 6.14-6.03 (m, 1H), 5.48-5.20 (m, 1H), 4.72*(t, J=8.1 Hz, 1H), 4.53 (t, J=8.4 Hz, 1H), 4.01-3.70 (m, 5H), 3.69-3.59 (m, 1H), 3.55-3.43 (m, 1H), 3.05-2.90 (m, 2H), 2.83-2.67 (m, 2H), 2.46-2.35 (m, 1H), 2.18-2.06 (m, 2H), 2.07-1.85 (in, 1H). LC-MS (ESI): m/z: [M+H]$^+$ calculated for C$_{28}$H$_{30}$F$_4$N$_4$O$_3$: 547.2; found 547.3.

The following compounds in Table T-10 were synthesized using procedures similar to Compounds 544 and 545 using the appropriate starting materials.

TABLE T-10

| Compound No. | Structure | IUPAC | Exact mass (g/mol) | LCMS, Found [M + H]$^+$ |
|---|---|---|---|---|
| 546 | 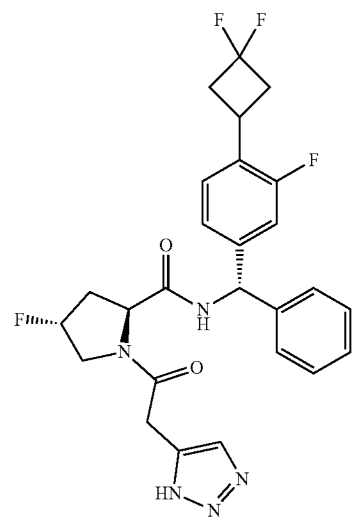 [SMILES: O=C(N[C@@H](c1ccccc1)c1ccc(C2CC(F)(F)C2)c(F)c1)[C@@H]1C[C@@H](F)CN1C(=O)Cc1cnn[nH]1] | (2S,4R)-N-[(S)-[4-(3,3-difluorocyclobutyl)-3-fluorophenyl](phenyl)methyl]-4-fluoro-1-[2-(1H-1,2,3-triazol-5-yl)acetyl]pyrrolidine-2-carboxamide | 515.2 | 516.3 |
| 547 | 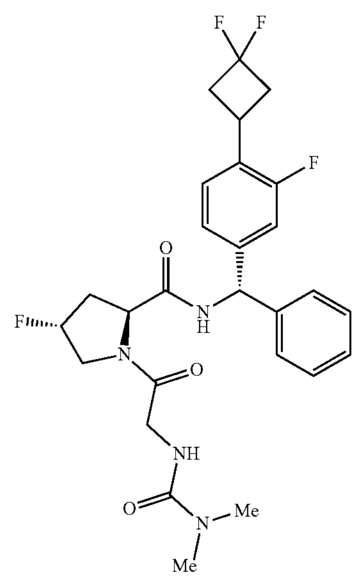 [SMILES: CN(C)C(=O)NCC(=O)N1C[C@H](F)C[C@H]1C(=O)N[C@@H](c1ccccc1)c1ccc(C2CC(F)(F)C2)c(F)c1] | (2S,4R)-N-[(S)-[4-(3,3-difluorocyclobutyl)-3-fluorophenyl](phenyl)methyl]-1-{2-[(dimethylcarbamoyl)amino]acetyl}-4-fluoropyrrolidine-2-carboxamide | 534.2 | 535.2 |

TABLE T-10-continued
| Compound No. | Structure | IUPAC | Exact mass (g/mol) | LCMS, Found [M + H]+ |
|---|---|---|---|---|
| 548 | 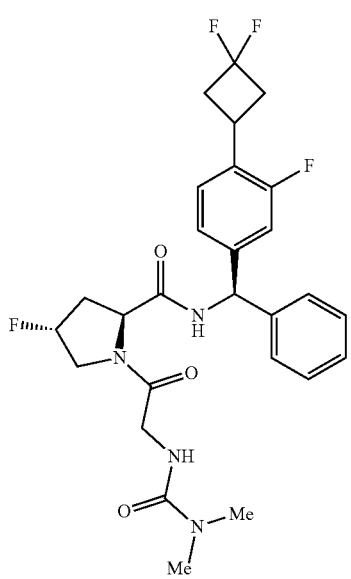 [SMILES: CN(C)C(=O)NCC(=O)N1C[C@H](F)C[C@H]1C(=O)N[C@H](c1ccccc1)c1ccc(C2CC(F)(F)C2)c(F)c1] | (2S,4R)-N-[(R)-[4-(3,3-difluorocyclobutyl)-3-fluorophenyl](phenyl)methyl]-1-{2-[(dimethylcarbamoyl)amino]acetyl}-4-fluoropyrrolidine-2-carboxamide | 534.2 | 535.2 |
| 549 | 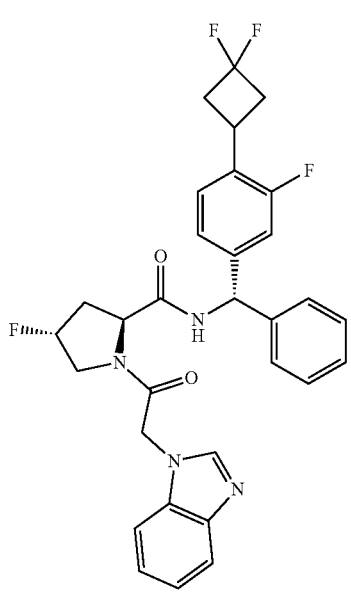 [SMILES: O=C(N[C@@H](c1ccccc1)c1ccc(C2CC(F)(F)C2)c(F)c1)[C@@H]1C[C@@H](F)CN1C(=O)Cn1cnc2ccccc21] | (2S,4R)-1-[2-(1H-1,3-benzodiazol-1-yl)acetyl]-N-[(S)-[4-(3,3-difluorocyclobutyl)-3-fluorophenyl](phenyl)methyl]-4-fluoropyrrolidine-2-carboxamide | 564.2 | 565.1 |

TABLE T-10-continued

| Compound No. | Structure | IUPAC | Exact mass (g/mol) | LCMS, Found [M + H]+ |
|---|---|---|---|---|
| 550 | 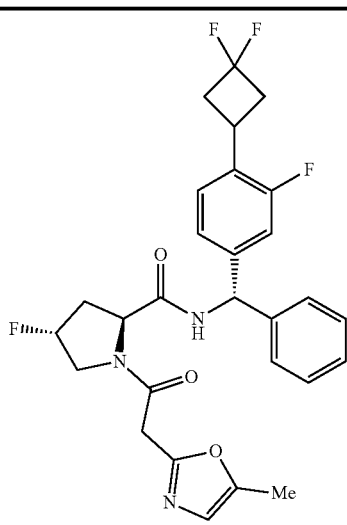 | (2S,4R)-N-[(S)-[4-(3,3-difluorocyclobutyl)-3-fluorophenyl](phenyl)methyl]-4-fluoro-1-[2-(5-methyl-1,3-oxazol-2-yl)acetyl]pyrrolidine-2-carboxamide | 529.2 | 530.1 |
| 551 | 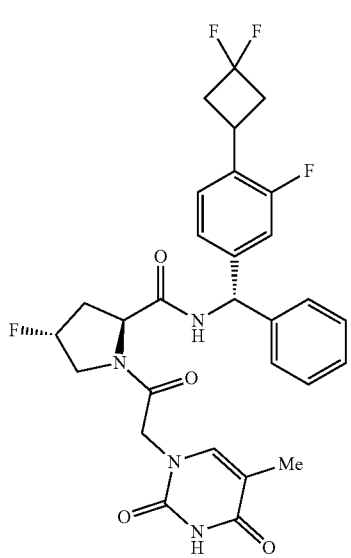 [SMILES: Cc1cn(CC(=O)N2C[C@H](F)C[C@H]2C(=O)N[C@@H](c2ccccc2)c2ccc(C3CC(F)(F)C3)c(F)c2)c(=O)[nH]c1=O] | (2S,4R)-N-[(S)-[4-(3,3-difluorocyclobutyl)-3-fluorophenyl](phenyl)methyl]-4-fluoro-1-[2-(5-methyl-2,4-dioxo-1,2,3,4-tetrahydropyrimidin-1-yl)acetyl]pyrrolidine-2-carboxamide | 572.2 | 488.3 |
| 552 | 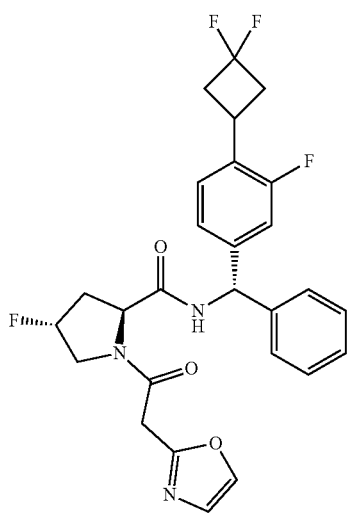 [SMILES: O=C(N[C@@H](c1ccccc1)c1ccc(C2CC(F)(F)C2)c(F)c1)[C@@H]1C[C@@H](F)CN1C(=O)Cc1ncco1] | (2S,4R)-N-[(S)-[4-(3,3-difluorocyclobutyl)-3-fluorophenyl](phenyl)methyl]-4-fluoro-1-[2-(1,3-oxazol-2-yl)acetyl]pyrrolidine-2-carboxamide | 515.2 | 516.4 |

TABLE T-10-continued

| Compound No. | Structure | IUPAC | Exact mass (g/mol) | LCMS, Found [M + H]+ |
|---|---|---|---|---|
| 553 | 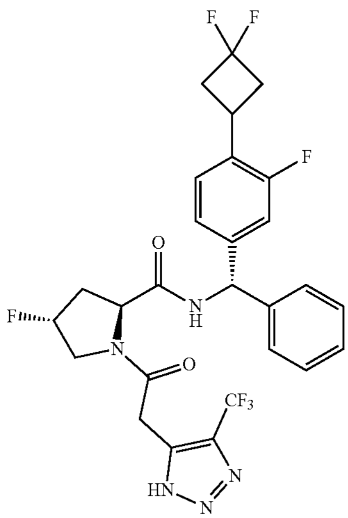 [SMILES: O=C(N[C@@H](c1ccccc1)c1ccc(C2CC(F)(F)C2)c(F)c1)[C@@H]1C[C@@H](F)CN1C(=O)Cc1[nH]nnc1C(F)(F)F] | (2S,4R)-N-[(S)-[4-(3,3-difluorocyclobutyl)-3-fluorophenyl](phenyl)methyl]-4-fluoro-1-{2-[4-(trifluoromethyl)-1H-1,2,3-triazol-5-yl]acetyl}pyrrolidine-2-carboxamide | 583.2 | 584.2 |
| 554 | 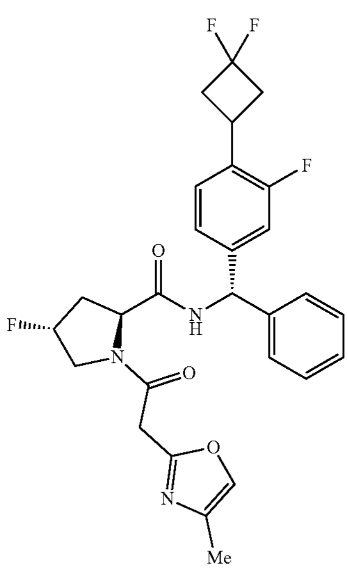 [SMILES: Cc1coc(CC(=O)N2C[C@H](F)C[C@H]2C(=O)N[C@@H](c2ccccc2)c2ccc(C3CC(F)(F)C3)c(F)c2)n1] | (2S,4R)-N-[(S)-[4-(3,3-difluorocyclobutyl)-3-fluorophenyl](phenyl)methyl]-4-fluoro-1-[2-(4-methyl-1,3-oxazol-2-yl)acetyl]pyrrolidine-2-carboxamide | 529.2 | 530.2 |

TABLE T-10-continued

| Compound No. | Structure | IUPAC | Exact mass (g/mol) | LCMS, Found [M + H]+ |
|---|---|---|---|---|
| 555 | 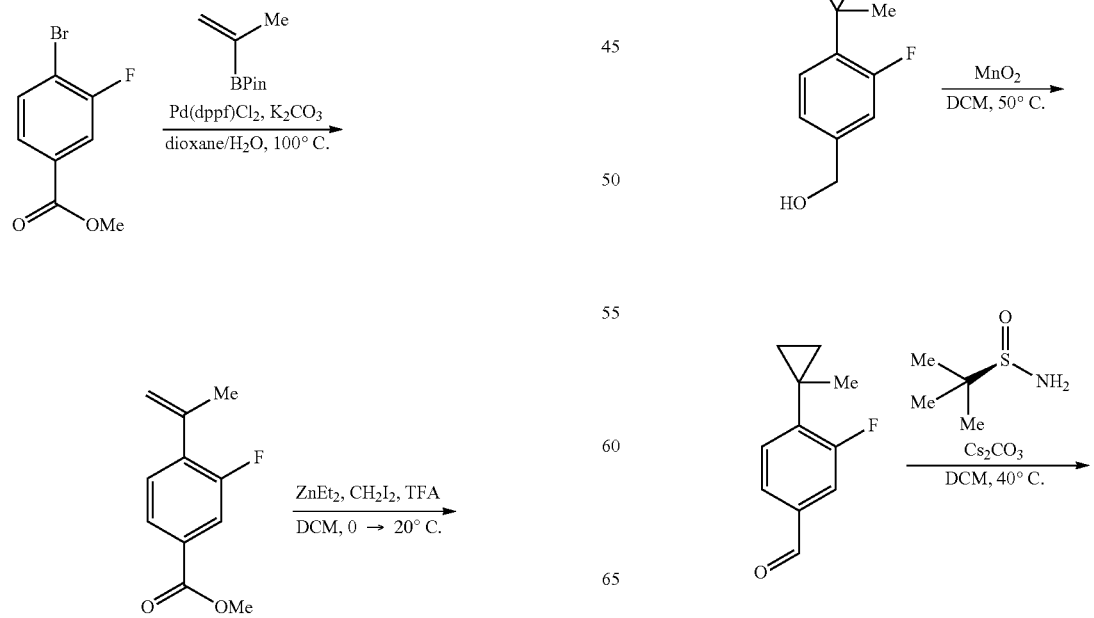 | (2S,4R)-N-[(S)-[4-(3,3-difluorocyclobutyl)-3-fluorophenyl](phenyl)methyl]-4-fluoro-1-{2-[4-(trifluoromethyl)-1,3-oxazol-2-yl]acetyl}pyrrolidine-2-carboxamide | 583.2 | 584.1 |

Example S-11: Synthesis of (2S,4R)-4-fluoro-N—((S)-(3-fluoro-4-(1-methylcyclopropyl)phenyl)(phenyl)methyl)-1-(2-(5-methyl-2,4-dioxo-3,4-dihydropyrimidin-1(2H)-yl)acetyl)pyrrolidine-2-carboxamide and (2S,4R)-4-fluoro-N—((R)-(3-fluoro-4-(1-methylcyclopropyl)phenyl)(phenyl)methyl)-1-(2-(5-methyl-2,4-dioxo-3,4-dihydropyrimidin-1(2H)-yl)acetyl)pyrrolidine-2-carboxamide Compounds 556 and 557

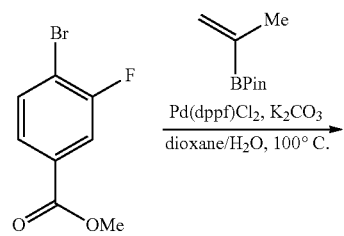

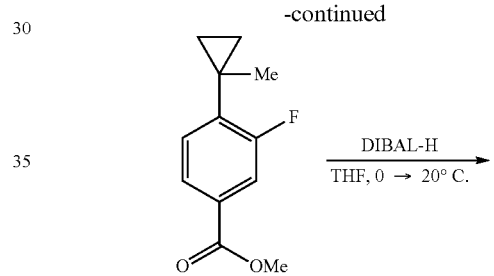

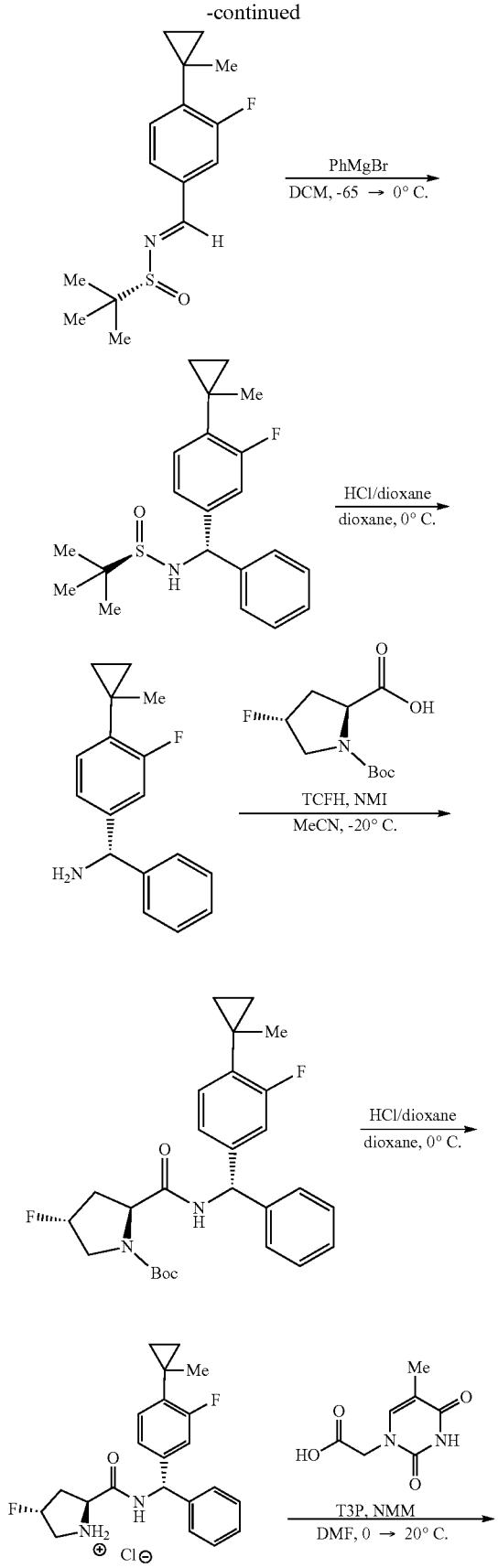

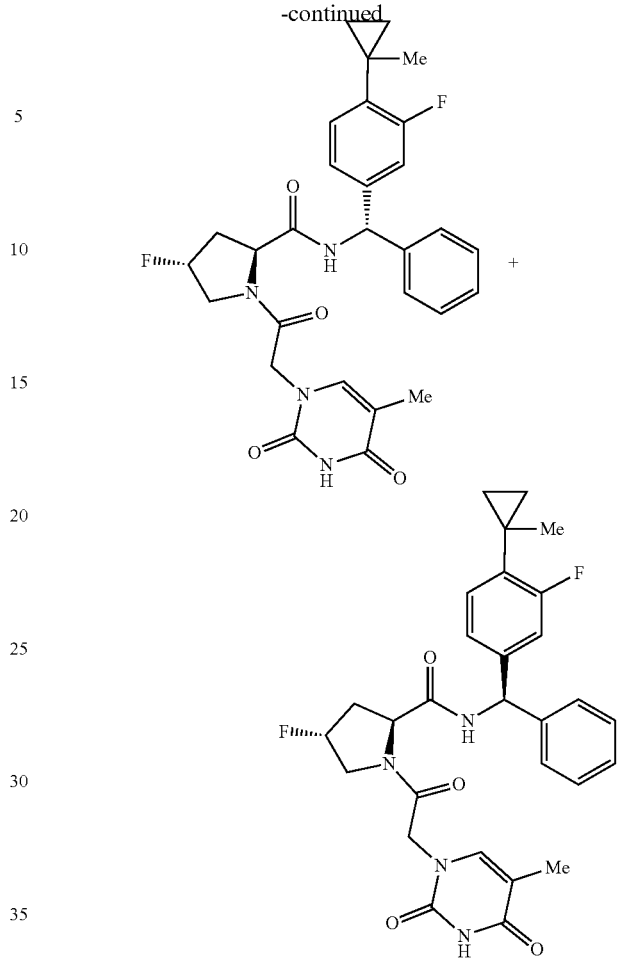

Step a: To a solution of methyl 4-bromo-3-fluoro-benzoate (25.0 g, 107 mmol, 1 eq) and 2-isopropenyl-4,4,5,5-tetramethyl-1,3,2-dioxaborolane (36.0 g, 214 mmol, 2 eq) in dioxane (200 mL) and H$_2$O (10 mL) under N$_2$ was added K$_2$CO$_3$ (44.4 g, 321 mmol, 3 eq) and Pd(dppf)Cl$_2$ (3.15 g, 4.30 mmol, 0.04 eq). The reaction was then warmed to 100° C. and stirred for 16 h under N$_2$. The reaction mixture was then cooled to 0° C. and quenched by addition H$_2$O (100 mL). The resulting biphasic mixture was then extracted with EtOAc (3×100 mL). The combined organic extracts were washed with H$_2$O (2×50 mL) and brine (2×50 mL), dried over anhydrous Na$_2$SO$_4$, filtered, and concentrated under reduced pressure. The crude residue obtained was purified by column chromatography to give methyl 3-fluoro-4-(prop-1-en-2-yl)benzoate. LC-MS (ESI): m/z: [M+H]$^+$ calculated for C$_{11}$H$_{11}$FO$_2$: 195.1; found: 195.1.

Step b: To a solution of ZnEt$_2$ (1 M in hexane, 154 mL, 2.50 eq) in DCM (100 mL) at 0° C. was dropwise added TFA (18.3 g, 160 mmol, 2.61 eq) in DCM (30 ml) over 15 min. Diiodomethane (41.3 g, 154 mmol, 12.4 mL, 2.50 eq) in DCM (30 mL) was then dropwise added at 0° C. After 15 min, methyl 3-fluoro-4-(prop-1-en-2-yl)benzoate (12 g, 61.7 mmol, 1 eq) in DCM (30 mL) was added dropwise at 0° C. The reaction mixture was then allowed to warm to 20° C. and stirred for 16 h. The reaction was then poured into saturated aqueous NH$_4$Cl (200 mL) at 0° C. and stirred for 10 min. The biphasic mixture was then extracted with ethyl acetate (3×100 mL). The combined organic extracts were washed with brine (100 mL), dried over anhydrous Na$_2$SO$_4$, filtered, and concentrated under reduced pressure. The crude residue obtained was purified by column chromatography to give methyl 3-fluoro-4-(1-methylcyclopropyl)benzoate. LC-MS (ESI): m/z: [M+H]$^+$ calculated for $C_{12}H_{13}FO_2$: 209.1; found: 209.1.

Step c: To a solution of methyl 3-fluoro-4-(1-methylcyclopropyl)benzoate (12 g, 46.1 mmol, 18.1 mL, 80% purity, 1 eq) in THF (100 mL) at 0° C. was added diisobutylaluminum hydride (DIBAL-H, 1 M in THF, 138 mL, 3 eq). The reaction was then allowed to warm to 20° C. and stirred for 2 h. The reaction mixture was then poured into saturated aqueous NH$_4$Cl (100 mL) at 0° C. and stirred for 10 min. The biphasic mixture was then extracted with ethyl acetate (3×100 mL). The combined organic extracts were washed with brine (50 mL), dried over anhydrous Na$_2$SO$_4$, filtered, and concentrated under reduced pressure to give (3-fluoro-4-(1-methylcyclopropyl)phenyl)methanol, which was carried into the next step without further purification. LC-MS (ESI): m/z: [M–H$_2$O]$^+$ calculated for $C_{11}H_{13}FO$: 163.1; found: 163.1.

Step d: To a solution of (3-fluoro-4-(1-methylcyclopropyl)phenyl)methanol (8 g, 44.3 mmol, 1 eq) in DCM (150 mL) at 25° C. was added MnO$_2$ (57.8 g, 665 mmol, 15 eq). The resulting mixture was warmed to 50° C. and stirred for 16 h. The reaction mixture was then poured into H$_2$O (100 mL) at 0° C., and the resulting biphasic mixture was extracted with DCM (3×50 mL). The combined organic extracts were washed with brine (50 mL), dried over anhydrous Na$_2$SO$_4$, filtered, and concentrated under reduced pressure to give 3-fluoro-4-(1-methylcyclopropyl)benzaldehyde, which was carried into the next step without further purification. LC-MS (ESI): m/z: [M+H]$^+$ calculated for $C_{11}H_{11}FO$: 179.1; found: 179.1.

Step e: To a mixture of 3-fluoro-4-(1-methylcyclopropyl)benzaldehyde (10 g, 56.1 mmol, 1 eq) and (R)-2-methylpropane-2-sulfinamide (7.48 g, 61.7 mmol, 1.1 eq) in DCM (150 mL) at 25° C. was added Cs$_2$CO$_3$ (27.4 g, 84.1 mmol, 1.5 eq). The resulting mixture was warmed to 40° C. and stirred for 1 h. The reaction mixture was then poured into H$_2$O (50 mL) at 0° C., and the resulting biphasic mixture was extracted with DCM (3×50 mL). The combined organic extracts were washed with brine (50 mL), dried over anhydrous Na$_2$SO$_4$, filtered, and concentrated under reduced pressure. The crude residue obtained was purified by column chromatography to give (R,E)-N-(3-fluoro-4-(1-methylcyclopropyl)benzylidene)-2-methylpropane-2-sulfinamide. LC-MS (ESI): m/z: [M+H]$^+$ calculated for $C_{15}H_{20}FNOS$: 282.1; found: 282.0.

Step f: To a solution of (R,E)-N-(3-fluoro-4-(1-methylcyclopropyl)benzylidene)-2-methylpropane-2-sulfinamide (13 g, 46.2 mmol, 1 eq) in DCM (150 mL) at −60° C. was added phenylmagnesium bromide (3 M, 18.4 mL, 1.2 eq) in a dropwise manner. The resulting mixture was stirred at −60° C. for 1 h. The reaction mixture was then allowed to warm to 0° C. and stirred for 1 h. The reaction mixture was then quenched by addition of saturated aqueous NH$_4$Cl (100 mL) at 0° C., and the resulting biphasic mixture was extracted with EtOAc (3×50 mL). The combined organic extracts were washed with brine (30 mL), dried over anhydrous Na$_2$SO$_4$, filtered, and concentrated under reduced pressure. The crude residue obtained was purified by column chromatography to give (R)—N—((S)-(3-fluoro-4-(1-methylcyclopropyl)phenyl)(phenyl)methyl)-2-methylpropane-2-sulfinamide. LC-MS (ESI): m/z: [M+H]$^+$ calculated for $C_{21}H_{26}FNOS$: 360.2; found: 360.1.

Step g: To a mixture of (R)—N—((S)-(3-fluoro-4-(1-methylcyclopropyl)phenyl)(phenyl)methyl)-2-methylpropane-2-sulfinamide (15 g, 41.7 mmol, 1 eq) in dioxane (100 mL) at 0° C. was added HCl/dioxane (4 M, 150 mL), and the resulting mixture was stirred at 0° C. for 1 h. The reaction mixture was filtered and the filter cake was washed with petroleum ether (3×50 mL). The filter cake was then added to saturated aqueous NaHCO$_3$ (200 mL) and stirred for 20 min. The resulting biphasic mixture was then extracted with ethyl acetate (3×100 mL). The combined organic extracts were washed with brine (50 mL), dried over anhydrous Na$_2$SO$_4$, filtered, and concentrated under reduced pressure obtain (S)-(3-fluoro-4-(1-methylcyclopropyl)phenyl)(phenyl)methanamine. LC-MS (ESI): m/z: [M–NH$_2$]$^+$ calculated for $C_{17}H_{18}FN$: 240.1; found: 240.0.

Step h: To a solution of (S)-(3-fluoro-4-(1-methylcyclopropyl)phenyl)(phenyl)methanamine (1.2 g, 4.70 mmol, 1 eq) and (2S,4R)-1-(tert-butoxycarbonyl)-4-fluoropyrrolidine-2-carboxylic acid (1.32 g, 5.64 mmol, 1.2 eq) in CH$_3$CN (20 mL) at −20° C. was added N-methylimidazole (NMI, 1.93 g, 23.5 mmol, 1.87 mL, 5 eq) and chloro-N,N,N',N'-tetramethylformamidinium hexafluorophosphate (TCFH, 1.58 g, 5.64 mmol, 1.2 eq). The resulting mixture was stirred at −20° C. for 1 h. The reaction mixture was then warmed to 0° C. and quenched with H$_2$O (50 mL). The resulting biphasic mixture was extracted with EtOAc (3×30 mL). The combined organic extracts were washed with brine (20 mL), dried over anhydrous Na$_2$SO$_4$, filtered, and concentrated under reduced pressure. The crude residue obtained was purified by column chromatography to give tert-butyl (2S,4R)-4-fluoro-2-(((S)-(3-fluoro-4-(1-methylcyclopropyl)phenyl)(phenyl)methyl)carbamoyl)pyrrolidine-1-carboxylate. LC-MS (ESI): m/z: [M+H]$^+$ calculated for $C_{27}H_{32}F_2N_2O_3$: 471.2; found: 471.1.

Step i: To a solution of tert-butyl (2S,4R)-4-fluoro-2-(((S)-(3-fluoro-4-(1-methylcyclopropyl)phenyl)(phenyl)methyl)carbamoyl)pyrrolidine-1-carboxylate (2 g, 4.25 mmol, 1 eq) in dioxane (10 mL) at 0° C. was added HCl/dioxane (4M, 20 mL). The resulting mixture was stirred at 0° C. for 1 h. The reaction mixture was then concentrated under reduced pressure to give (2S,4R)-4-fluoro-2-(((S)-(3-fluoro-4-(1-methylcyclopropyl)phenyl)(phenyl)methyl)carbamoyl)pyrrolidin-1-ium chloride. LC-MS (ESI): m/z: [M+H]$^+$ calculated for $C_{22}H_{24}F_2N_2O$: 371.2; found: 371.1.

Step j: To a solution of (2S,4R)-4-fluoro-2-(((S)-(3-fluoro-4-(1-methylcyclopropyl)phenyl)(phenyl)methyl)carbamoyl)pyrrolidin-1-ium chloride (100 mg, 270 µmol, 1 eq) in DMF (1.00 mL) at 0° C. was added 2-(5-methyl-2,4-dioxo-pyrimidin-1-yl)acetic acid (64.6 mg, 351 µmol, 1.3 eq), N-methylmorpholine (NMM, 149 mg, 1.47 mmol, 6 eq) and 2,4,6-tripropyl-1,3,5,2,4,6-trioxatriphosphorinane-2,4,6-trioxide (T3P, 344 mg, 540 µmol, 50% purity, 2 eq), and the resulting mixture was stirred at 0° C. for 1 h. The reaction was then allowed to warm to 20° C. and for 15 h. The reaction mixture was then quenched by addition of H$_2$O (10 mL), and the resulting biphasic mixture was extracted with EtOAc (3×10 mL). The combined organic extracts were washed with saturated aqueous NaCl (2×10 mL), dried over anhydrous Na$_2$SO$_4$, filtered, and concentrated under reduced pressure. The crude residue obtained residue was purified by prep-HPLC to give (2S,4R)-4-fluoro-N—((S)-(3-fluoro-4-(1-methylcyclopropyl)phenyl)(phenyl)methyl)-1-(2-(5-methyl-2,4-dioxo-3,4-dihydropyrimidin-1(2H)-yl)acetyl)pyrrolidine-2-carboxamide (major isomer, Compound 556) and (2S,4R)-4-fluoro-N—((R)-3-fluoro-4-(1-methylcyclopropyl)phenyl)(phenyl)methyl)-1-(2-(5-methyl-2,4-dioxo-3,4-dihydropyrimidin-1(2H)-yl)acetyl) pyrrolidine-2-carboxamide (minor isomer, compound 557).

Major isomer (Compound 556): $^1$H NMR (3.1:1 rotamer ratio, asterisk denotes minor rotamer peaks, obscured peaks not reported, 400 MHz, DMSO-d$_6$) δ 11.30 (br s, 1H), 9.26*(d, J=8.0 Hz, 1H), 8.86 (d, J=8.2 Hz, 1H), 7.38-7.20 (m, 7H), 7.11-7.02*(m, 2H), 7.02-6.93 (m, 2H), 6.10*(d, J=7.9 Hz, 1H), 6.01 (d, J=8.2 Hz, 1H), 5.52-5.22 (m, 1H), 4.77*(t, J=8.2 Hz, 1H), 4.66 (d, J=16.8 Hz, 1H), 4.58-4.41 (m, 2H), 4.06-3.89 (m, 1H), 3.82-3.65 (m, 1H), 3.53-3.36* (m, 1H), 2.82-2.68*(m, 1H), 2.27-2.09*(m, 1H), 2.09-1.88 (m, 1H), 1.78-1.70 (m, 3H), 1.31-1.25 (m, 3H), 0.77-0.63 (m, 4H). LC-MS (ESI): m/z: [M+H]$^+$ calculated for C$_{29}$H$_{30}$F$_2$N$_4$O$_4$: 537.2; found 537.3.

Minor isomer (compound 557): $^1$H NMR (3.3:1 rotamer ratio, asterisk denotes minor rotamer peaks, obscured peaks not reported, 400 MHz, DMSO-d$_6$) δ 11.30 (br s, 1H), 9.27*(d, J=8.1 Hz, 1H), 8.89 (d, J=8.3 Hz, 1H), 7.41-7.20 (m, 6H), 7.17-6.94 (m, 2H), 6.11*(d, J=8.0 Hz, 1H), 6.01 (d, J=8.2 Hz, 1H), 5.54-5.21 (m, 1H), 4.77*(t, J=8.2 Hz, 1H), 4.68 (d, J=16.8 Hz, 1H), 4.54 (t, J=8.1 Hz, 1H), 4.45 (d, J=16.9 Hz, 1H), 4.05-3.86 (m, 1H), 3.83-3.65 (m, 1H), 3.53-3.36*(in, 1H), 2.25-1.87 (m, 1H), 1.78-1.70 (m, 3H), 1.30-1.21 (m, 3H), 0.75-0.62 (in, 4H). LC-MS (ESI): m/z: [M+H]$^+$ calculated for C$_{29}$H$_{30}$F$_2$N$_4$O$_4$: 537.2; found 537.3.

The following compounds in Table T-11 were synthesized using procedures similar to Compounds 556 and 557 using the appropriate starting materials.

TABLE T-11

| Compound No. | Structure | IUPAC | Exact mass (g/mol) | LCMS, Found [M + H]$^+$ |
|---|---|---|---|---|
| 558 | 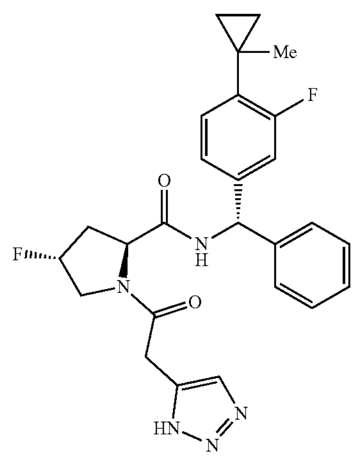 [SMILES: CC1(c2ccc([C@@H](NC(=O)[C@@H]3C[C@@H](F)CN3C(=O)Cc3cnn[nH]3)c3ccccc3)cc2F)CC1] | (2S,4R)-4-fluoro-N-[(S)-[3-fluoro-4-(1-methylcyclopropyl)phenyl](phenyl)methyl]-1-[2-(1H-1,2,3-triazol-5-yl)acetyl]pyrrolidine-2-carboxamide | 479.2 | 480.2 |
| 559 | 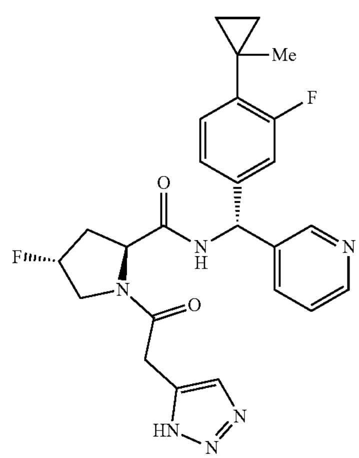 [SMILES: CC1(c2ccc([C@@H](NC(=O)[C@@H]3C[C@@H](F)CN3C(=O)Cc3cnn[nH]3)c3cccnc3)cc2F)CC1] | (2S,4R)-4-fluoro-N-[(R)-[3-fluoro-4-(1-methylcyclopropyl)phenyl](pyridin-3-yl)methyl]-1-[2-(1H-1,2,3-triazol-5-yl)acetyl]pyrrolidine-2-carboxamide | 480.2 | 481.3 |

TABLE T-11-continued

| Compound No. | Structure | IUPAC | Exact mass (g/mol) | LCMS, Found [M + H]+ |
|---|---|---|---|---|
| 560 | 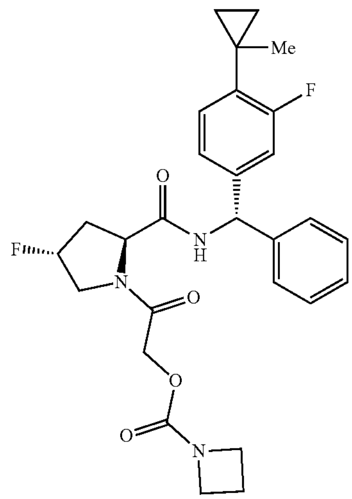 [SMILES: CC1(c2ccc([C@@H](NC(=O)[C@@H]3C[C@@H](F)CN3C(=O)COC(=O)N3CCC3)c3ccccc3)cc2F)CC1] | 2-[(2S,4R)-4-fluoro-2-{[(S)-[3-fluoro-4-(1-methylcyclopropyl)phenyl](phenyl)methyl]carbamoyl}pyrrolidin-1-yl]-2-oxoethyl azetidine-1-carboxylate | 511.2 | 512.3 |
| 561 | 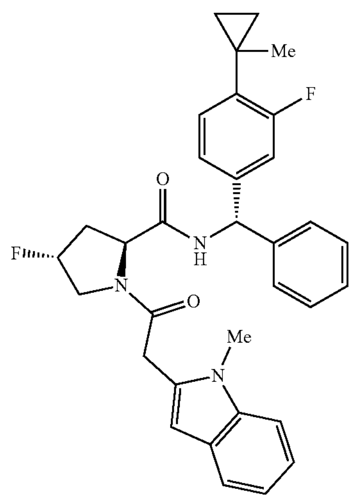 [SMILES: Cn1c(CC(=O)N2C[C@H](F)C[C@H]2C(=O)N[C@@H](c2ccccc2)c2ccc(C3(C)CC3)c(F)c2)cc2ccccc21] | (2S,4R)-4-fluoro-N-[(S)-[3-fluoro-4-(1-methylcyclopropyl)phenyl](phenyl)methyl]-1-[2-(1-methyl-1H-indol-2-yl)acetyl]pyrrolidine-2-carboxamide | 541.3 | 542.3 |
| 562 | 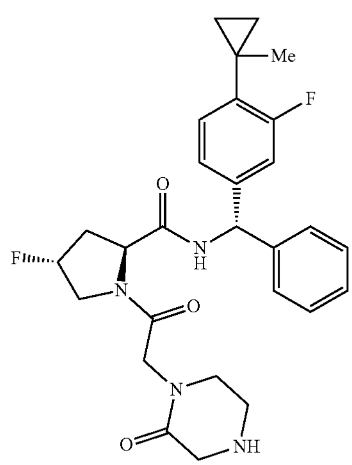 [SMILES: CC1(c2ccc([C@@H](NC(=O)[C@@H]3C[C@@H](F)CN3C(=O)CN3CCNCC3=O)c3ccccc3)cc2F)CC1] | (2S,4R)-4-fluoro-N-[(S)-[3-fluoro-4-(1-methylcyclopropyl)phenyl](phenyl)methyl]-1-[2-(2-oxopiperazin-1-yl)acetyl]pyrrolidine-2-carboxamide | 510.2 | 511.3 |

TABLE T-11-continued

| Compound No. | Structure | IUPAC | Exact mass (g/mol) | LCMS, Found [M + H]+ |
|---|---|---|---|---|
| 563 | 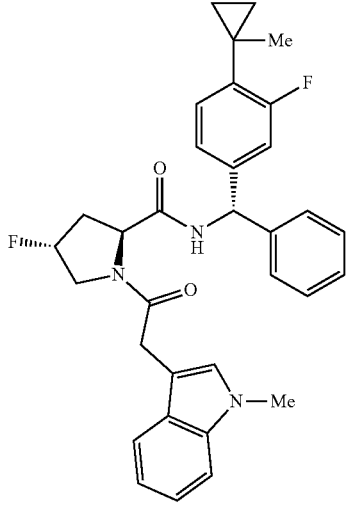 [SMILES: Cn1cc(CC(=O)N2C[C@H](F)C[C@H]2C(=O)N[C@@H](c2ccccc2)c2ccc(C3(C)CC3)c(F)c2)c2ccccc21] | (2S,4R)-4-fluoro-N-[(S)-[3-fluoro-4-(1-methylcyclopropyl)phenyl](phenyl)methyl]-1-[2-(1-methyl-1H-indol-3-yl)acetyl]pyrrolidine-2-carboxamide | 541.3 | 542.3 |
| 564 | 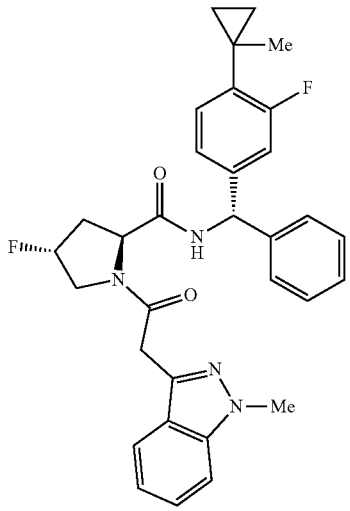 [SMILES: Cn1nc(CC(=O)N2C[C@H](F)C[C@H]2C(=O)N[C@@H](c2ccccc2)c2ccc(C3(C)CC3)c(F)c2)c2ccccc21] | (2S,4R)-4-fluoro-N-[(S)-[3-fluoro-4-(1-methylcyclopropyl)phenyl](phenyl)methyl]-1-[2-(1-methyl-1H-indazol-3-yl)acetyl]pyrrolidine-2-carboxamide | 542.2 | 543.1 |
| 565 | 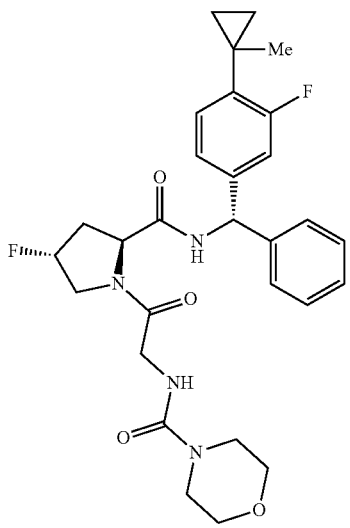 [SMILES: CC1(c2ccc([C@@H](NC(=O)[C@@H]3C[C@@H](F)CN3C(=O)CNC(=O)N3CCOCC3)c3ccccc3)cc2F)CC1] | N-{2-[(2S,4R)-4-fluoro-2-{[(S)-[3-fluoro-4-(1-methylcyclopropyl)phenyl](phenyl)methyl]carbamoyl}pyrrolidin-1-yl]-2-oxoethyl}morpholine-4-carboxamide | 540.3 | 541.3 |

TABLE T-11-continued

| Compound No. | Structure | IUPAC | Exact mass (g/mol) | LCMS, Found [M + H]+ |
|---|---|---|---|---|
| 566 | 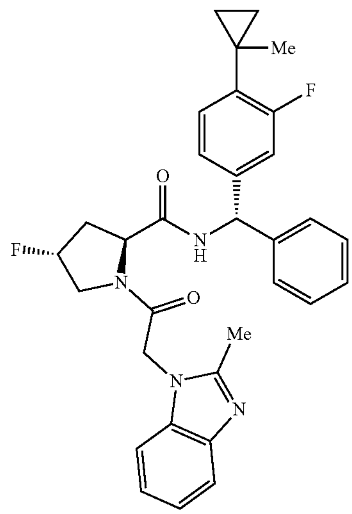 [SMILES: Cc1nc2ccccc2n1CC(=O)N1C[C@H](F)C[C@H]1C(=O)N[C@@H](c1ccccc1)c1ccc(C2(C)CC2)c(F)c1] | (2S,4R)-4-fluoro-N-[(S)-[3-fluoro-4-(1-methylcyclopropyl)phenyl](phenyl)methyl]-1-[2-(2-methyl-1H-1,3-benzodiazol-1-yl)acetyl]pyrrolidine-2-carboxamide | 542.2 | 543.3 |
| 567 | 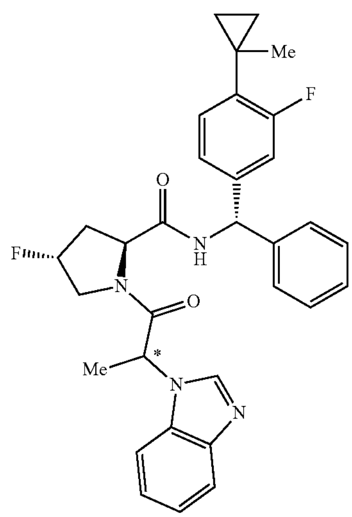 [SMILES: CC(C(=O)N1C[C@H](F)C[C@H]1C(=O)N[C@@H](c1ccccc1)c1ccc(C2(C)CC2)c(F)c1)n1cnc2ccccc21] | (2S,4R)-1-[(2R) or (2S)-2-(1H-1,3-benzodiazol-1-yl)propanoyl]-4-fluoro-N-[(S)-[3-fluoro-4-(1-methylcyclopropyl)phenyl](phenyl)methyl]pyrrolidine-2-carboxamide (column: DAICEL CHIRALPAK IG-3, first-eluting isomer) | 542.2 | 543.3 |
| 568 | 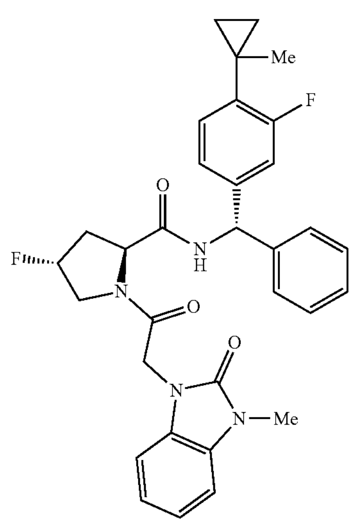 [SMILES: Cn1c(=O)n(CC(=O)N2C[C@H](F)C[C@H]2C(=O)N[C@@H](c2ccccc2)c2ccc(C3(C)CC3)c(F)c2)c2ccccc21] | (2S,4R)-4-fluoro-N-[(S)-[3-fluoro-4-(1-methyl cyclopropyl)phenyl](phenyl)methyl]-1-[2-(3-methyl-2-oxo-2,3-dihydro-1H-1,3-benzodiazol-1-yl)acetyl]pyrrolidine-2-carboxamide | 558.2 | 559.3 |

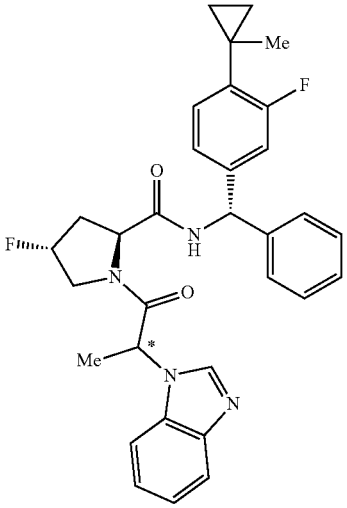

TABLE T-11-continued

| Compound No. | Structure | IUPAC | Exact mass (g/mol) | LCMS, Found [M + H]+ |
| --- | --- | --- | --- | --- |
| 569 | 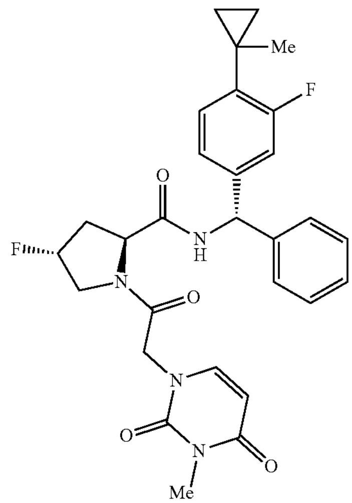 [SMILES: Cn1c(=O)ccn(CC(=O)N2C[C@H](F)C[C@H]2C(=O)N[C@@H](c2ccccc2)c2ccc(C3(C)CC3)c(F)c2)c1=O] | (2S,4R)-4-fluoro-N-[(S)-[3-fluoro-4-(1-methylcyclopropyl)phenyl](phenyl)methyl]-1-[2-(3-methyl-2,4-dioxo-1,2,3,4-tetrahydropyrimidin-1-yl)acetyl]pyrrolidine-2-carboxamide | 536.2 | 537.2 |
| 570 | 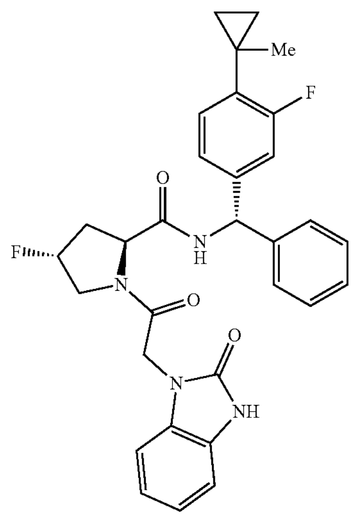 [SMILES: CC1(c2ccc([C@@H](NC(=O)[C@@H]3C[C@@H](F)CN3C(=O)Cn3c(=O)[nH]c4ccccc43)c3ccccc3)cc2F)CC1] | (2S,4R)-4-fluoro-N-[(S)-[3-fluoro-4-(1-methylcyclopropyl)phenyl](phenyl)methyl]-1-[2-(2-oxo-2,3-dihydro-1H-1,3-benzodiazol-1-yl)acetyl]pyrrolidine-2-carboxamide | 544.2 | 545.3 |
| 571 | 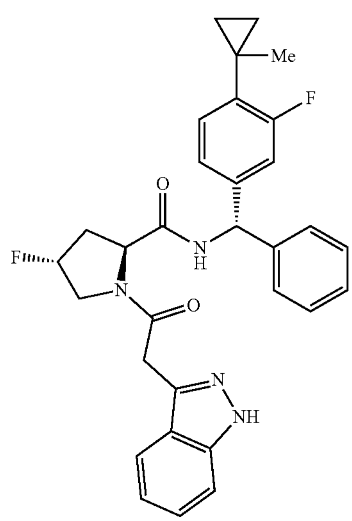 [SMILES: CC1(c2ccc([C@@H](NC(=O)[C@@H]3C[C@@H](F)CN3C(=O)Cc3n[nH]c4ccccc34)c3ccccc3)cc2F)CC1] | (2S,4R)-4-fluoro-N-[(S)-[3-fluoro-4-(1-methylcyclopropyl)phenyl](phenyl)methyl]-1-[2-(1H-indazol-3-yl)acetyl]pyrrolidine-2-carboxamide | 528.2 | 529.1 |

TABLE T-11-continued

| Compound No. | Structure | IUPAC | Exact mass (g/mol) | LCMS, Found [M + H]+ |
|---|---|---|---|---|
| 572 | 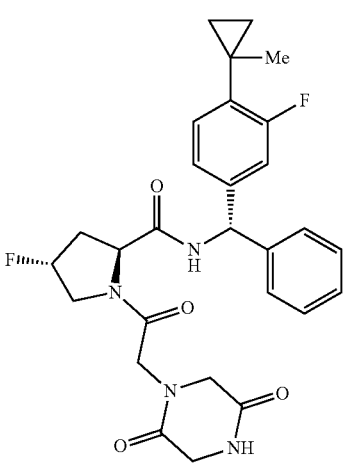 [SMILES: CC1(c2ccc([C@@H](NC(=O)[C@@H]3C[C@@H](F)CN3C(=O)CN3CC(=O)NCC3=O)c3ccccc3)cc2F)CC1] | (2S,4R)-1-[2-(2,5-dioxopiperazin-1-yl)acetyl]-4-fluoro-N-[(S)-[3-fluoro-4-(1-methylcyclopropyl)phenyl](phenyl)methyl]pyrrolidine-2-carboxamide | 524.2 | 525.2 |
| 573 | 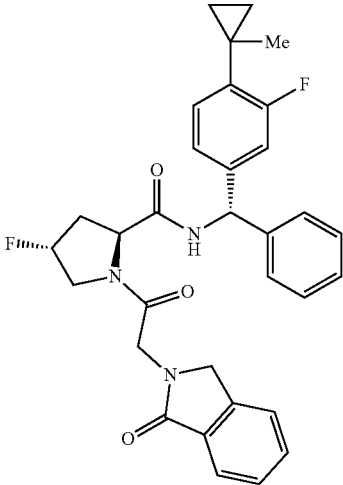 [SMILES: CC1(c2ccc([C@@H](NC(=O)[C@@H]3C[C@@H](F)CN3C(=O)CN3Cc4ccccc4C3=O)c3ccccc3)cc2F)CC1] | (2S,4R)-4-fluoro-N-[(S)-[3-fluoro-4-(1-methylcyclopropyl)phenyl](phenyl)methyl]-1-[2-(1-oxo-2,3-dihydro-1H-isoindol-2-yl)acetyl]pyrrolidine-2-carboxamide | 543.2 | 544.1 |
| 574 | 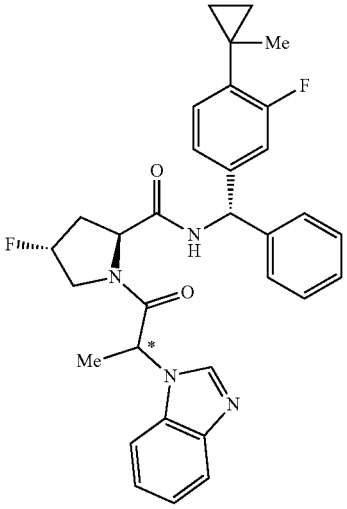 [SMILES: CC(C(=O)N1C[C@H](F)C[C@H]1C(=O)N[C@@H](c1ccccc1)c1ccc(C2(C)CC2)c(F)c1)n1cnc2ccccc21] | (2S,4R)-1-[(2S) or 2R)-2-(1H-1,3-benzodiazol-1-yl)propanoyl]-4-fluoro-N-[(S)-[3-fluoro-4-(1-methylcyclopropyl)phenyl](phenyl)methyl]pyrrolidine-2-carboxamide (column: DAICEL CHIRALPAK IG-3, second-eluting isomer) | 542.2 | 543.3 |

TABLE T-11-continued

| Compound No. | Structure | IUPAC | Exact mass (g/mol) | LCMS, Found [M + H]+ |
|---|---|---|---|---|
| 575 | 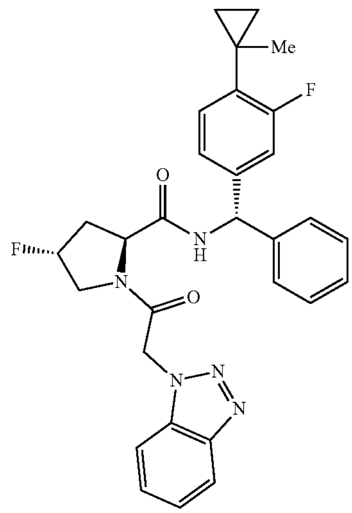 [SMILES: CC1(c2ccc([C@@H](NC(=O)[C@@H]3C[C@@H](F)CN3C(=O)Cn3nnc4ccccc43)c3ccccc3)cc2F)CC1] | (2S,4R)-1-[2-(1H-1,2,3-benzotriazol-1-yl)acetyl]-4-fluoro-N-[(S)-[3-fluoro-4-(1-methylcyclopropyl)phenyl](phenyl)methyl]pyrrolidine-2-carboxamide | 529.2 | 530.1 |
| 576 | 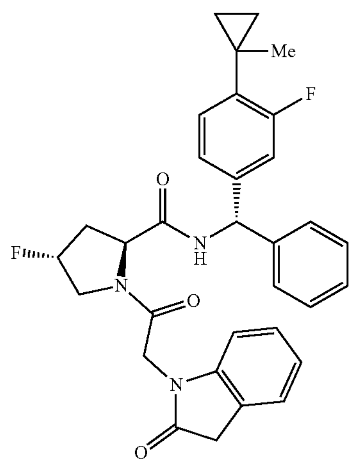 [SMILES: CC1(c2ccc([C@@H](NC(=O)[C@@H]3C[C@@H](F)CN3C(=O)CN3C(=O)Cc4ccccc43)c3ccccc3)cc2F)CC1] | (2S,4R)-4-fluoro-N-[(S)-[3-fluoro-4-(1-methylcyclopropyl)phenyl](phenyl)methyl]-1-[2-(2-oxo-2,3-dihydro-1H-indol-1-yl)acetyl]pyrrolidine-2-carboxamide | 543.2 | 544.2 |
| 577 | 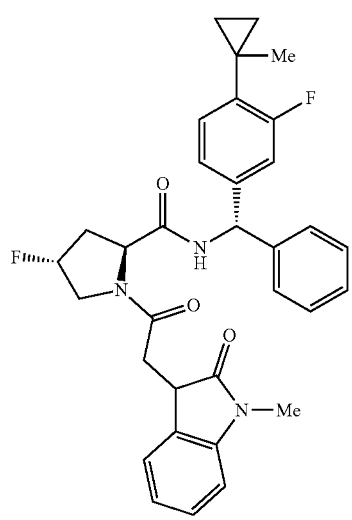 | (2S,4R)-4-fluoro-N-[(S)-[3-fluoro-4-(1-methylcyclopropyl)phenyl](phenyl)methyl]-1-[2-(1-methyl-2-oxo-2,3-dihydro-1H-indol-3-yl)acetyl]pyrrolidine-2-carboxamide | 557.2 | 558.3 |

TABLE T-11-continued

| Compound No. | Structure | IUPAC | Exact mass (g/mol) | LCMS, Found [M + H]+ |
| --- | --- | --- | --- | --- |
| 578 | 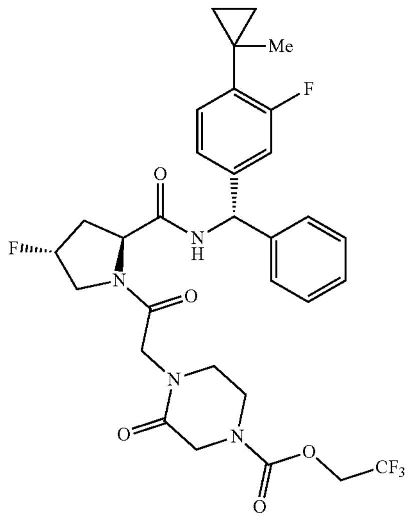 [SMILES: CC1(c2ccc([C@@H](NC(=O)[C@@H]3C[C@@H](F)CN3C(=O)CN3CCN(C(=O)OCC(F)(F)F)CC3=O)c3ccccc3)cc2F)CC1] | 2,2,2-trifluoroethyl 4-{2-[(2S,4R)-4-fluoro-2-{[(S)-[3-fluoro-4-(1-methylcyclopropyl)phenyl](phenyl)methyl]carbamoyl}pyrrolidin-1-yl]-2-oxoethyl}-3-oxopiperazine-1-carboxylate | 636.2 | 637.2 |
| 579 | 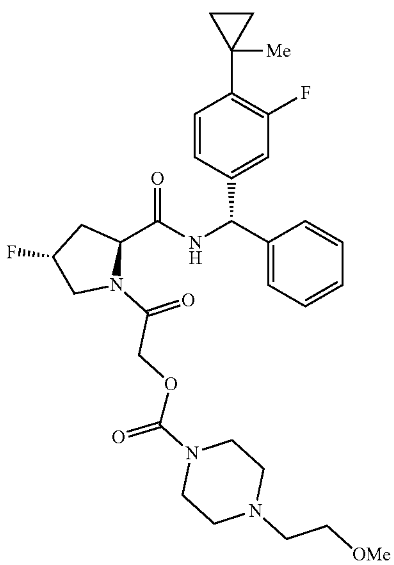 [SMILES: COCCN1CCN(C(=O)OCC(=O)N2C[C@H](F)C[C@H]2C(=O)N[C@@H](c2ccccc2)c2ccc(C3(C)CC3)c(F)c2)CC1] | 2-[(2S,4R)-4-fluoro-2-{[(S)-[3-fluoro-4-(1-methylcyclopropyl)phenyl](phenyl)methyl]carbamoyl}pyrrolidin-1-yl]-2-oxoethyl 4-(2-methoxyethyl)piperazine-1-carboxylate | 598.3 | 599.2 |
| 580 | 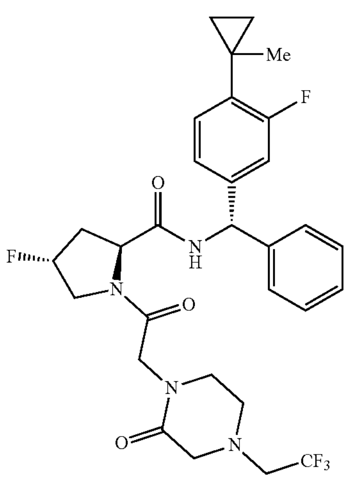 [SMILES: CC1(c2ccc([C@@H](NC(=O)[C@@H]3C[C@@H](F)CN3C(=O)CN3CCN(CC(F)(F)F)CC3=O)c3ccccc3)cc2F)CC1] | (2S,4R)-4-fluoro-N-[(S)-[3-fluoro-4-(1-methylcyclopropyl)phenyl](phenyl)methyl]-1-{2-[2-oxo-4-(2,2,2-trifluoroethyl)piperazin-1-yl]acetyl}pyrrolidine-2-carboxamide | 592.2 | 593.2 |

TABLE T-11-continued

| Compound No. | Structure | IUPAC | Exact mass (g/mol) | LCMS, Found [M + H]+ |
|---|---|---|---|---|
| 581 | 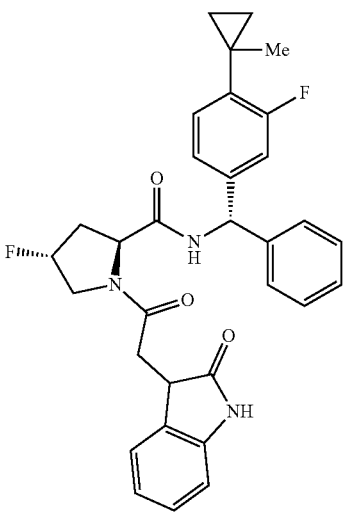 [SMILES: CC1(c2ccc([C@@H](NC(=O)[C@@H]3C[C@@H](F)CN3C(=O)CC3C(=O)Nc4ccccc43)c3ccccc3)cc2F)CC1] | (2S,4R)-4-fluoro-N-[(S)-[3-fluoro-4-(1-methylcyclopropyl)phenyl](phenyl)methyl]-1-[2-(2-oxo-2,3-dihydro-1H-indol-3-yl)acetyl]pyrrolidine-2-carboxamide | 543.2 | 544.2 |
| 582 | 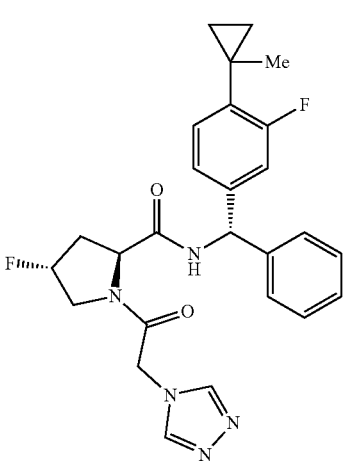 [SMILES: CC1(c2ccc([C@@H](NC(=O)[C@@H]3C[C@@H](F)CN3C(=O)Cn3cnnc3)c3ccccc3)cc2F)CC1] | (2S,4R)-4-fluoro-N-[(S)-[3-fluoro-4-(1-methylcyclopropyl)phenyl](phenyl)methyl]-1-[2-(4H-1,2,4-triazol-4-yl)acetyl]pyrrolidine-2-carboxamide | 479.2 | 480.3 |
| 583 | 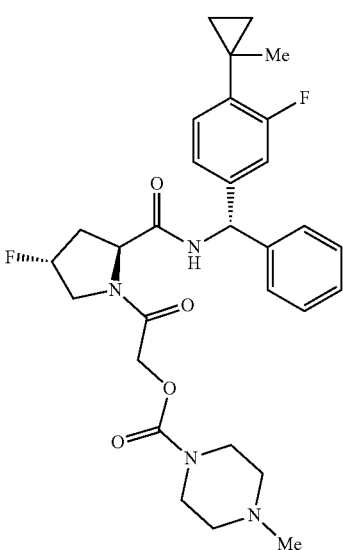 [SMILES: CN1CCN(C(=O)OCC(=O)N2C[C@H](F)C[C@H]2C(=O)N[C@@H](c2ccccc2)c2ccc(C3(C)CC3)c(F)c2)CC1] | 2-[(2S,4R)-4-fluoro-2-{[(S)-[3-fluoro-4-(1-methylcyclopropyl)phenyl](phenyl)methyl]carbamoyl}pyrrolidin-1-yl]-2-oxoethyl 4-methylpiperazine-1-carboxylate | 554.3 | 555.3 |

TABLE T-11-continued

| Compound No. | Structure | IUPAC | Exact mass (g/mol) | LCMS, Found [M + H]+ |
|---|---|---|---|---|
| 584 | 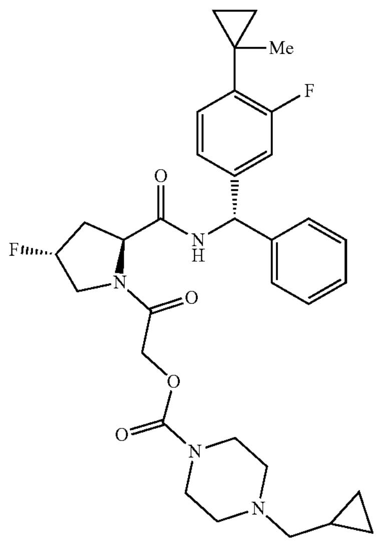 [SMILES: CC1(c2ccc([C@@H](NC(=O)[C@@H]3C[C@@H](F)CN3C(=O)COC(=O)N3CCN(CC4CC4)CC3)c3ccccc3)cc2F)CC1] | 2-[(2S,4R)-4-fluoro-2-{[(S)-[3-fluoro-4-(1-methylcyclopropyl)phenyl](phenyl)methyl]carbamoyl}pyrrolidin-1-yl]-2-oxoethyl 4-(cyclopropylmethyl)piperazine-1-carboxylate | 594.3 | 595.3 |
| 585 | 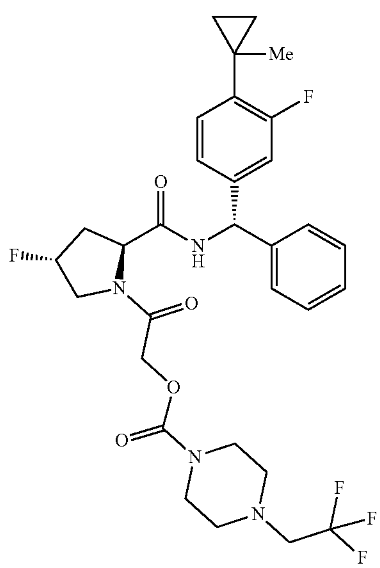 [SMILES: CC1(c2ccc([C@@H](NC(=O)[C@@H]3C[C@@H](F)CN3C(=O)COC(=O)N3CCN(CC(F)(F)F)CC3)c3ccccc3)cc2F)CC1] | 2-[(2S,4R)-4-fluoro-2-{[(S)-[3-fluoro-4-(1-methylcyclopropyl)phenyl](phenyl)methyl]carbamoyl}pyrrolidin-1-yl]-2-oxoethyl 4-(2,2,2-trifluoroethyl)piperazine-1-carboxylate | 622.3 | 623.3 |

1311
Example S-12: Synthesis of (2S,4R)-1-((S) or (R)-2-(1H-benzo[d]imidazol-1-yl)propanoyl)-4-fluoro-N—((S)-(6-fluoro-5-(1-methylcyclopropyl)pyridin-2-yl)(phenyl)methyl)pyrrolidine-2-carboxamide and (2S,4R)-1-((R) or (S)-2-(1H-benzo[d]imidazol-1-yl)propanoyl)-4-fluoro-N—((S)-(6-fluoro-5-(1-methylcyclopropyl)pyridin-2-yl)(phenyl)methyl)pyrrolidine-2-carboxamide
Compounds 586 and 587
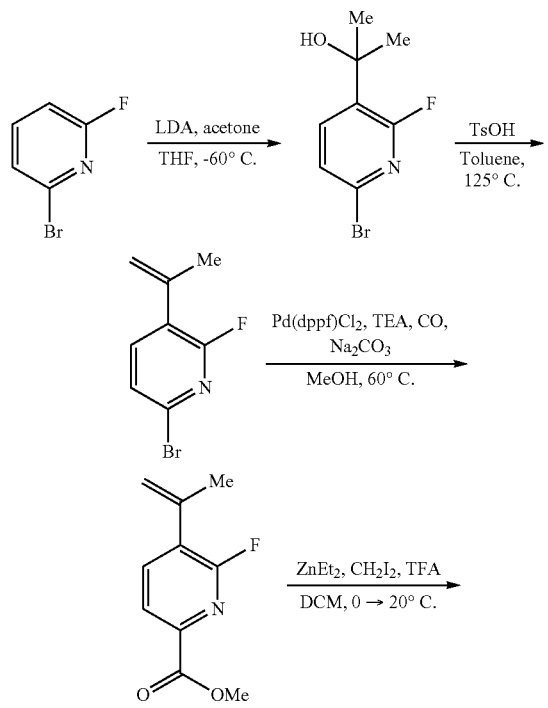
1312
-continued
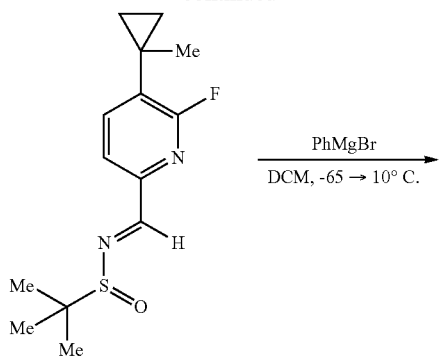
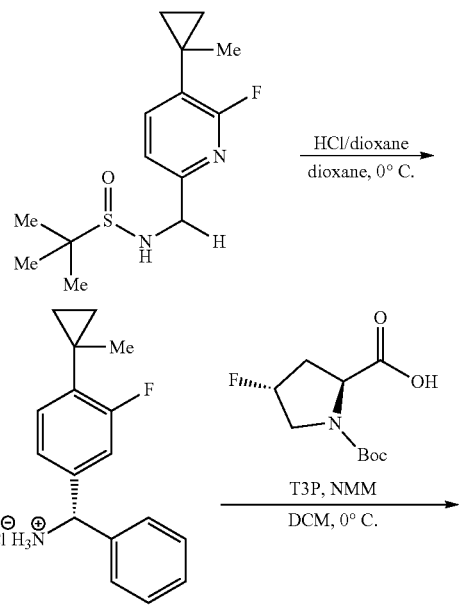
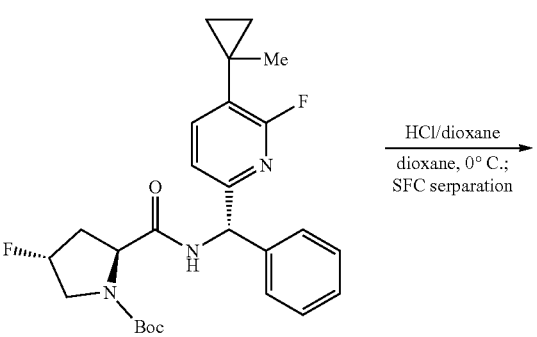
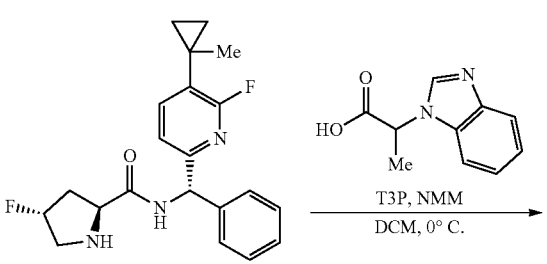

-continued

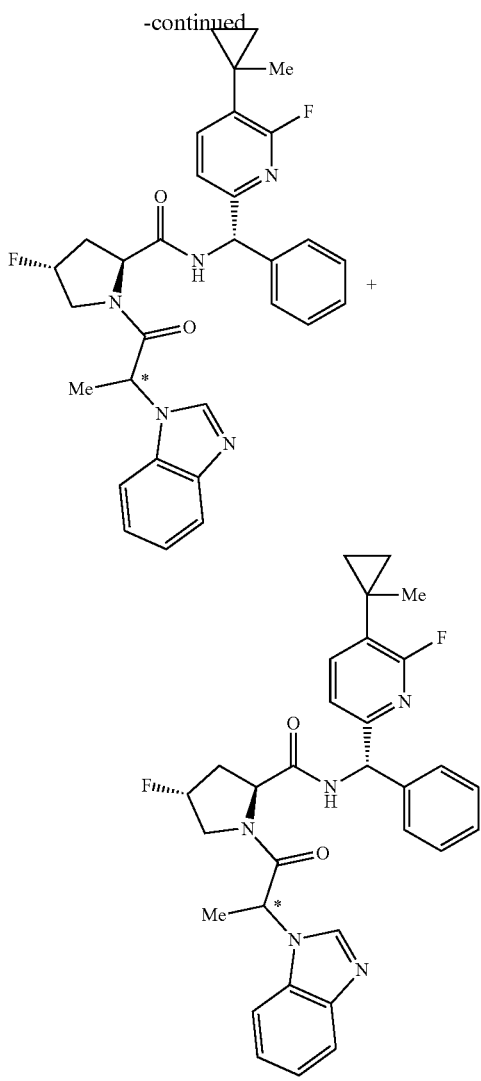

Step a: To a solution of 2-bromo-6-fluoropyridine (12.5 g, 71.0 mmol, 1.00 eq) in THF (125 mL) at −60° C. under $N_2$ was added lithium diisopropylamide (LDA, 2 M in THF, 35.5 mL, 1.00 eq) in a dropwise manner. The resulting mixture was stirred at −60° C. for 0.5 h. Acetone (6.19 g, 106 mmol, 1.50 eq) was then added in a dropwise manner at −60° C. The resulting mixture was then stirred at −60° C. for 0.5 h. The reaction was then allowed to warm to 0° C., quenched by addition of $H_2O$ (60 mL), and stirred for 10 min. The resulting biphasic mixture was extracted with ethyl acetate (3×100 mL). The combined organic extracts were washed with brine (20 mL), dried over anhydrous $Na_2SO_4$, filtered, and concentrated under reduced pressure. The crude residue obtained was purified by column chromatography to give 2-(6-bromo-2-fluoropyridin-3-yl)propan-2-ol. LC-MS (ESI): m/z: [M+H]$^+$ calculated for $C_8H_9BrFNO$: 234.0; found: 234.0.

Step b: To a solution of 2-(6-bromo-2-fluoropyridin-3-yl)propan-2-ol (13.5 g, 57.7 mmol, 1.00 eq) in toluene (135 mL) at 25° C. was added TsOH (1.99 g, 11.5 mmol, 0.20 eq) in a dropwise manner. The reaction mixture was the warmed to 125° C. and stirred for 16 h. The reaction mixture was then cooled to 0° C. and quenched by addition of $H_2O$ (50 mL). The resulting biphasic mixture was extracted with ethyl acetate (3×50 mL). The combined organic extracts were washed with brine (20 mL), dried over anhydrous $Na_2SO_4$, filtered, and concentrated under reduced pressure. The crude residue obtained was purified by column chromatography to give 6-bromo-2-fluoro-3-(prop-1-en-2-yl)pyridine. LC-MS (ESI): m/z: [M+H]$^+$ calculated for $C_8H_7BrFN$: 216.0; found: 216.0.

Step c: To a solution of 6-bromo-2-fluoro-3-(prop-1-en-2-yl)pyridine (6.5 g, 30.1 mmol, 1.00 eq) in MeOH (65 mL) was added TEA (6.09 g, 60.17 mmol, 2.00 eq) and Pd(dppf)Cl$_2$ (2.46 g, 3.01 mmol, 0.10 eq). The reaction mixture was then placed under an atmosphere of CO (50 psi), warmed to 60° C., and stirred for 2 h. The reaction mixture was then concentrated under reduced pressure. The crude residue obtained was purified by column chromatography to give methyl 6-fluoro-5-(prop-1-en-2-yl)picolinate. LC-MS (ESI): m/z: [M+H]$^+$ calculated for $C_{10}H_{10}FNO_2$: 196.1; found: 196.1.

Step d: To a solution of ZnEt$_2$ (1 M in hexane, 102 mL, 5.00 eq) at 0° C. was added TFA (102 mmol, 7.6 mL, 5.00 eq) in DCM (24 mL) in a dropwise manner. The resulting mixture was stirred at 0° C. for 0.5 h. CH$_2$I$_2$ (27.4 g, 102 mmol, 5.00 eq) in DCM (22 mL) was then added in a dropwise manner at 0° C., and the resulting mixture was stirred at 0° C. for 0.5 h. Methyl 6-fluoro-5-(prop-1-en-2-yl)picolinate (4 g, 20 mmol, 1.00 eq) in DCM (12 mL) was then added in a dropwise manner at 0° C. The resulting mixture was then allowed to warm to 20° C. and stirred for 15 h. The reaction mixture was then quenched by addition of saturated aqueous NH$_4$Cl (100 ml) at 0° C., and the resulting biphasic mixture was extracted with ethyl acetate (3×100 mL). The combined organic extracts were washed with brine (20 mL), dried over anhydrous Na$_2$SO$_4$, filtered, and concentrated under reduced pressure. The crude residue was obtained was purified by column chromatography and prep-HPLC to give methyl 6-fluoro-5-(1-methylcyclopropyl)picolinate (2.56 g). LC-MS (ESI): m/z: [M+H]$^+$ calculated for $C_{11}H_{12}FNO_2$: 210.1; found: 210.1.

Step e: A solution of 6-fluoro-5-(1-methylcyclopropyl) picolinate (1.25 g, 5.97 mmol, 1 eq) in THF (12.5 mL) was degassed and purged with N$_2$ and cooled to −65° C. To this solution was added diisobutylaluminium hydride (DIBAL-H, 1 M in THF, 11.9 mL, 2 eq) in a dropwise manner. The resulting mixture was stirred at −65° C. for 2 h. The reaction mixture was then warmed to 0° C. and quenched by addition water (50 mL). The resulting biphasic mixture was then filtered and extracted with ethyl acetate (2×50 mL). The combined organic extracts were washed with brine (2×50 mL), dried over anhydrous Na$_2$SO$_4$, filtered, and concentrated under reduced pressure. The crude residue obtained was purified by column chromatography to give 6-fluoro-5-(1-methylcyclopropyl)picolinaldehyde. LC-MS (ESI): m/z: [M+H]$^+$ calculated for $C_{10}H_{10}FNO$: 180.1; found: 180.1.

Step f: To a mixture of 6-fluoro-5-(1-methylcyclopropyl) picolinaldehyde (0.8 g, 4.46 mmol, 1 eq) and 2-methylpropane-2-sulfinamide (1.08 g, 8.93 mmol, 2 eq) in THF (8 mL) at 25° C. under N$_2$ was added Ti(Oi-Pr)$_4$ (2.54 g, 8.93 mmol, 2.64 mL, 2 eq). The resulting mixture was warmed to 80° C. and stirred for 2 h. The reaction mixture was then poured into ice-water (15 mL) and stirred for 10 min. The resulting biphasic mixture was extracted with ethyl acetate (2×50 mL). The combined organic extracts were washed with brine (2×30 mL), dried over anhydrous Na$_2$SO$_4$, filtered, and concentrated under reduced pressure. The crude residue obtained was purified by column chromatography to give (E)-N-((6-fluoro-5-(1-methylcyclopropyl)pyridin-2-yl)

methylene)-2-methylpropane-2-sulfinamide. LC-MS (ESI): m/z: [M+H]$^+$ calculated for $C_{14}H_{19}FN_2OS$: 283.1; found: 283.1.

Step g: To a solution of (E)-N-((6-fluoro-5-(1-methylcyclopropyl)pyridin-2-yl)methylene)-2-methylpropane-2-sulfinamide (1.15 g, 4.07 mmol, 1 eq) in DCM (11.5 mL) at −60° C. was added phenylmagnesium bromide (3 M in diethyl ether, 2.04 mL, 1.5 eq) in a dropwise manner. The resulting mixture was stirred at −60° C. for 1 h before it was warmed to 10° C. and stirred for 1 h. The reaction mixture was then poured into saturated aqueous NH$_4$Cl (30 mL) and stirred for 10 min. The resulting biphasic mixture was then extracted with DCM (2×50 mL). The combined organic extracts were washed with brine (2×30 mL), dried over anhydrous Na$_2$SO$_4$, filtered, and concentrated under reduced pressure. The crude residue obtained was purified by column chromatography to give N-((6-fluoro-5-(1-methylcyclopropyl)pyridin-2-yl)(phenyl)methyl)-2-methylpropane-2-sulfinamide. LC-MS (ESI): m/z: [M+H]$^+$ calculated for $C_{20}H_{25}FN_2OS$: 361.2; found: 361.2.

Step h: To a solution of N-((6-fluoro-5-(1-methylcyclopropyl)pyridin-2-yl)(phenyl)methyl)-2-methylpropane-2-sulfinamide (1.45 g, 4.02 mmol, 1 eq) in dioxane (3 mL) at 0° C. was added HCl/dioxane (4 M, 6.44 mL, 6.41 eq), and the resulting mixture was stirred at 0° C. for 1 h. The reaction mixture was then concentrated under reduced pressure. The crude residue was then triturated with methyl tert-butyl ether (10 mL) at 25° C. for 10 min and filtered. The filter cake was dried under reduced pressure to give (6-fluoro-5-(1-methylcyclopropyl)pyridin-2-yl)(phenyl)methanaminium chloride. LC-MS (ESI): m/z: [M+H]$^+$ calculated for $C_{16}H_{17}FN_2$: 257.1; found: 257.2.

Step i: To a mixture of (6-fluoro-5-(1-methylcyclopropyl)pyridin-2-yl)(phenyl)methanaminium chloride (1.20 g, 4.1 mmol, 1 eq) and (2S,4R)-1-(tert-butoxycarbonyl)-4-fluoropyrrolidine-2-carboxylic acid (1.15 g, 4.92 mmol, 1.2 eq) in DCM (20 mL) at 25° C. under N$_2$ was added N-methylmorpholine (NMM, 1.24 g, 12.3 mmol, 1.35 mL, 3 eq). The resulting mixture was cooled to −20° C. before 2,4,6-tripropyl-1,3,5,2,4,6-trioxatriphosphorinane-2,4,6-trioxide (T3P, 5.22 g, 8.20 mmol, 4.88 mL, 50% purity, 2 eq) was added in a dropwise manner. The resulting mixture was stirred at −20° C. for 1 h before the reaction mixture was poured into ice-water (15 mL) and stirred for 10 min. The aqueous phase was extracted with ethyl acetate (3×15 mL). The combined organic extracts were washed with brine (3×15 mL), dried over anhydrous Na$_2$SO$_4$, filtered, and concentrated under reduced pressure. The crude residue obtained was purified by column chromatography to give tert-butyl (2S,4R)-4-fluoro-2-(((6-fluoro-5-(1-methylcyclopropyl)pyridin-2-yl)(phenyl)methyl)carbamoyl)pyrrolidine-1-carboxylate. LC-MS (ESI): m/z: [M+H]$^+$ calculated for $C_{26}H_{31}F_2N_3O_3$: 472.2; found: 472.2.

Step j: To a solution of tert-butyl (2S,4R)-4-fluoro-2-(((6-fluoro-5-(1-methylcyclopropyl)pyridin-2-yl)(phenyl)methyl)carbamoyl)pyrrolidine-1-carboxylate (3.8 g, 8.06 mmol, 1 eq) in dioxane (20 mL) at 0° C. was added HCl/dioxane (4 M, 20 mL). The resulting mixture was then stirred at 0° C. for 1 h. The reaction mixture was then concentrated under reduced pressure. The crude product was added diluted with saturated aqueous NaHCO$_3$, and the aqueous phase was extracted with ethyl acetate (2×50 mL). The combined organic extracts were washed with brine (2×30 mL), dried over anhydrous Na$_2$SO$_4$, filtered, and concentrated under reduced pressure. The crude residue obtained was purified by SFC (column: REGIS(S,S) WHELK-O1) to give (2S,4R)-4-fluoro-N—((S)-(6-fluoro-5-(1-methylcyclopropyl)pyridin-2-yl)(phenyl)methyl)pyrrolidine-2-carboxamide and (2S,4R)-4-fluoro-N—((R)-(6-fluoro-5-(1-methylcyclopropyl)pyridin-2-yl)(phenyl)methyl)pyrrolidine-2-carboxamide as separate diastereomers. LC-MS (ESI): m/z: [M+H]$^+$ calculated for $C_{21}H_{23}F_2N_3O$: 372.2; found: 372.2.

Step k: To a mixture of 2-(1H-benzo[d]imidazol-1-yl)propanoic acid (80.0 mg, 421 µmol, 1.00 eq) and (2S,4R)-4-fluoro-N—((S)-(6-fluoro-5-(1-methylcyclopropyl)pyridin-2-yl)(phenyl)methyl)pyrrolidine-2-carboxamide (156 mg, 421 µmol, 1.00 eq) in DCM (2 mL) at −20° C. under N$_2$ was added N-methylmorpholine (NMM, 421 µmol, 46.2 µL, 1.00 eq) and 2,4,6-tripropyl-1,3,5,2,4,6-trioxatriphosphorinane-2,4,6-trioxide (T3P, 841 µmol, 500 µL, 50% purity, 2.00 eq). The resulting mixture was warmed to 0° C. and stirred for 1 h. The reaction was then quenched by addition H$_2$O (10 mL) at 0° C. The resulting biphasic mixture was then extracted with EtOAc (3×20 mL). The combined organic extracts were washed with brine (20 mL), dried over anhydrous Na$_2$SO$_4$, filtered, and concentrated under reduced pressure. The crude residue obtained was purified by prep-HPLC followed by SCF (column: REGIS (R,R)WHELK-O1) to give (2S,4R)-1-((R) or (S)-2-(1H-benzo[d]imidazol-1-yl)propanoyl)-4-fluoro-N—((S)-(6-fluoro-5-(1-methylcyclopropyl)pyridin-2-yl)(phenyl)methyl)pyrrolidine-2-carboxamide (Compound 587; first-eluting isomer) and (2S,4R)-1-((S) or (R)-2-(1H-benzo[d]imidazol-1-yl)propanoyl)-4-fluoro-N—((S)-(6-fluoro-5-(1-methylcyclopropyl)pyridin-2-yl)(phenyl)methyl)pyrrolidine-2-carboxamide (Compound 586; second-eluting isomer).

First-eluting isomer (Compound 587): $^1$H NMR (4:1 rotamer ratio, asterisk denotes minor rotamer peaks, obscured peaks not reported, 400 MHz, DMSO-d$_6$) δ 9.61* (d, J=8.3 Hz, 1H), 8.94 (d, J=7.8 Hz, 1H), 8.25 (s, 1H), 7.90-7.81*(m, 1H), 7.81-7.70 (m, 1H), 7.70-7.55 (m, 2H), 7.52-7.42 (m, 1H), 7.39-7.11 (m, 7H), 6.19*(d, J=8.0 Hz, 1H), 5.95 (d, J=7.7 Hz, 1H), 5.72-5.66 (m, 1H), 5.43-5.17 (m, 1H), 5.12-5.02*(m, 1H), 4.71 (t, J=8.4 Hz, 1H), 4.09-3.97 (m, 1H), 2.03-1.79 (m, 2H), 1.59-1.53 (m, 3H), 1.32-1.22 (m, 3H), 0.83-0.62 (m, 4H). LC-MS (ESI): m/z: [M+H]$^+$ calculated for $C_{31}H_{31}F_2N_5O_2$: 544.2; found 544.2.

Second-eluting isomer (Compound 586): $^1$H NMR (4.4:1 rotamer ratio, asterisk denotes minor rotamer peaks, obscured peaks not reported, 400 MHz, DMSO-d$_6$) δ 9.55* (d, J=8.0 Hz, 1H), 8.90 (d, J=8.0 Hz, 1H), 8.34 (s, 1H), 8.23*(s, 1H), 7.84 (dd, J=10.1, 7.5 Hz, 1H), 7.69-7.62 (m, 1H), 7.57*(d, J=8.0 Hz, 1H), 7.52-7.43 (m, 1H), 7.39-7.15 (m, 7H), 7.14-7.07*(m, 1H), 6.95*(d, J=4.1 Hz, 1H), 6.17* (d, J=8.0 Hz, 1H), 6.00 (d, J=7.9 Hz, 1H), 5.70 (q, J=7.0 Hz, 1H), 5.54-5.24 (m, 1H), 5.08*(t, J=7.9 Hz, 1H), 4.88*(q, J=7.1 Hz, 1H), 4.62 (t, J=8.4 Hz, 1H), 4.27 (dd, J=20.4, 12.6 Hz, 1H), 3.97-3.74 (m, 1H), 3.57-3.39*(m, 1H), 2.87-2.71* (m, 1H), 2.14-1.92 (m, 1H), 1.79-1.68 (m, 3H), 1.30-1.26 (m, 3H), 0.81-0.67 (m, 4H). LC-MS (ESI): m/z: [M+H]$^+$ calculated for $C_{31}H_{31}F_2N_5O_2$: 544.2; found 544.2.

The following compounds in Table T-12 were synthesized using procedures similar to Compound 586 and Compound 587 using the appropriate starting materials.

TABLE T-12

| Compound No. | Structure | IUPAC | Exact mass (g/mol) | LCMS, Found [M + H]+ |
| --- | --- | --- | --- | --- |
| 588 | 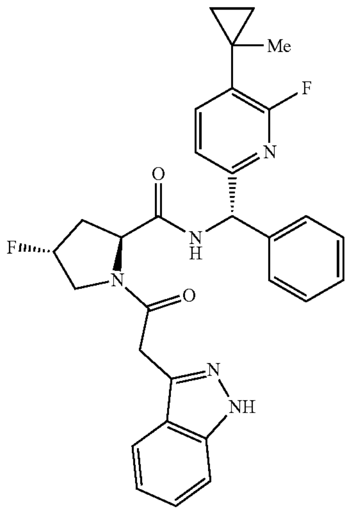 [SMILES: CC1(c2ccc([C@@H](NC(=O)[C@@H]3C[C@@H](F)CN3C(=O)Cc3n[nH]c4ccccc34)c3ccccc3)nc2F)CC1] | (2S,4R)-4-fluoro-N-[(S)-[6-fluoro-5-(1-methylcyclopropyl)pyridin-2-yl](phenyl)methyl]-1-[2-(1H-indazol-3-yl)acetyl]pyrrolidine-2-carboxamide | 529.2 | 530.3 |
| 589 | 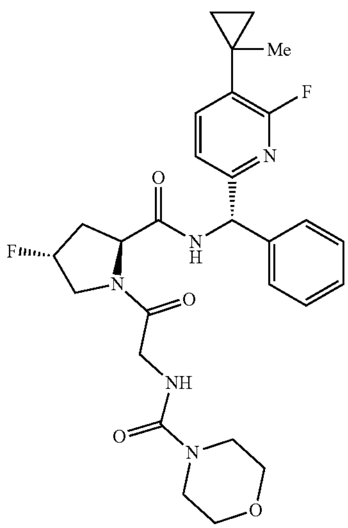 [SMILES: CC1(c2ccc([C@@H](NC(=O)[C@@H]3C[C@@H](F)CN3C(=O)CNC(=O)N3CCOCC3)c3ccccc3)nc2F)CC1] | N-{2-[(2S,4R)-4-fluoro-2-{[(S)-[6-fluoro-5-(1-methylcyclopropyl)pyridin-2-yl](phenyl)methyl]carbamoyl}pyrrolidin-1-yl]-2-oxoethyl}morpholine-4-carboxamide | 541.3 | 542.3 |
| 590 | 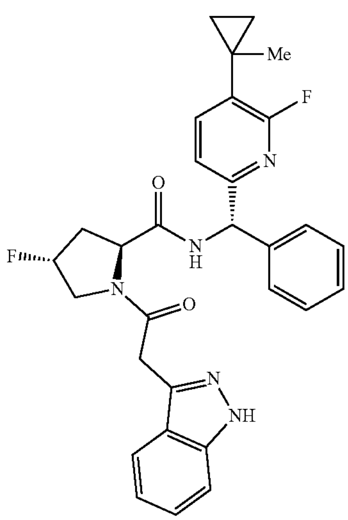 [SMILES: CC1(c2ccc([C@@H](NC(=O)[C@@H]3C[C@@H](F)CN3C(=O)Cc3n[nH]c4ccccc34)c3ccccc3)nc2F)CC1] | (2S,4R)-4-fluoro-N-[(R)-[6-fluoro-5-(1-methylcyclopropyl)pyridin-2-yl](phenyl)methyl]-1-[2-(1H-indazol-3-yl)acetyl]pyrrolidine-2-carboxamide | 529.2 | 530.3 |

TABLE T-12-continued

| Compound No. | Structure | IUPAC | Exact mass (g/mol) | LCMS, Found [M + H]+ |
|---|---|---|---|---|
| 591 | 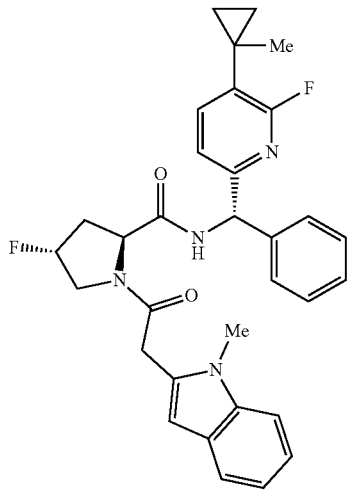 | (2S,4R)-4-fluoro-N-[(S)-[6-fluoro-5-(1-methylcyclopropyl)pyridin-2-yl](phenyl)methyl]-1-[2-(1-methyl-1H-indol-2-yl)acetyl]pyrrolidine-2-carboxamide | 542.2 | 543.2 |
| 592 | 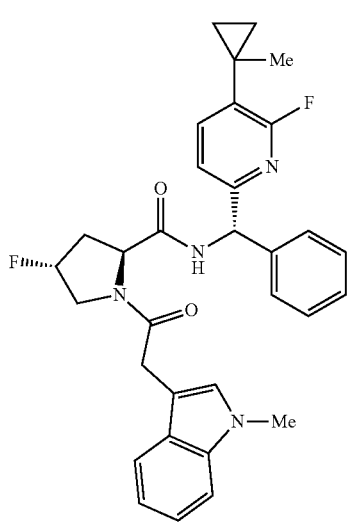 [SMILES: Cn1cc(CC(=O)N2C[C@H](F)C[C@H]2C(=O)N[C@@H](c2ccccc2)c2ccc(C3(C)CC3)c(F)n2)c2ccccc21] | (2S,4R)-4-fluoro-N-[(S)-[6-fluoro-5-(1-methylcyclopropyl)pyridin-2-yl](phenyl)methyl]-1-[2-(1-methyl-1H-indol-3-yl)acetyl]pyrrolidine-2-carboxamide | 542.2 | 543.2 |
| 593 | 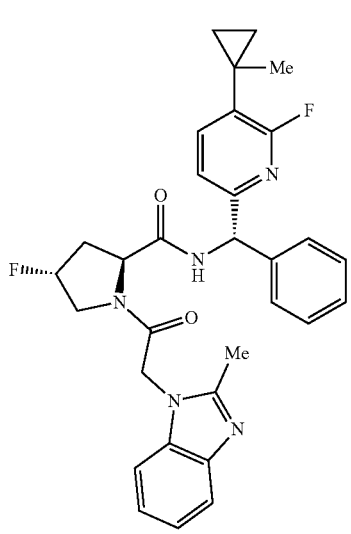 | (2S,4R)-4-fluoro-N-[(S)-[6-fluoro-5-(1-methylcyclopropyl)pyridin-2-yl](phenyl)methyl]-1-[2-(2-methyl-1H-1,3-benzodiazol-1-yl)acetyl]pyrrolidine-2-carboxamide | 543.2 | 544.3 |

TABLE T-12-continued

| Compound No. | Structure | IUPAC | Exact mass (g/mol) | LCMS, Found [M + H]+ |
|---|---|---|---|---|
| 594 | 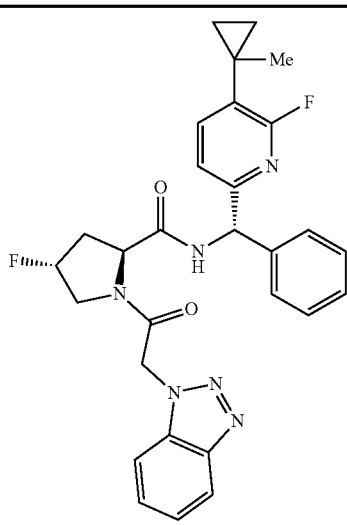 | (2S,4R)-1-[2-(1H-1,2,3-benzotriazol-1-yl)acetyl]-4-fluoro-N-[(S)-[6-fluoro-5-(1-methylcyclopropyl)pyridin-2-yl](phenyl)methyl]pyrrolidine-2-carboxamide | 530.2 | 531.3 |
| 595 | 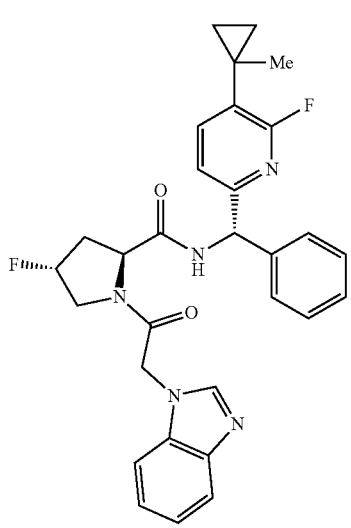 | (2S,4R)-1-[2-(1H-1,3-benzodiazol-1-yl)acetyl]-4-fluoro-N-[(S)-[6-fluoro-5-(1-methylcyclopropyl)pyridin-2-yl](phenyl)methyl]pyrrolidine-2-carboxamide | 529.2 | 530.2 |
| 596 | 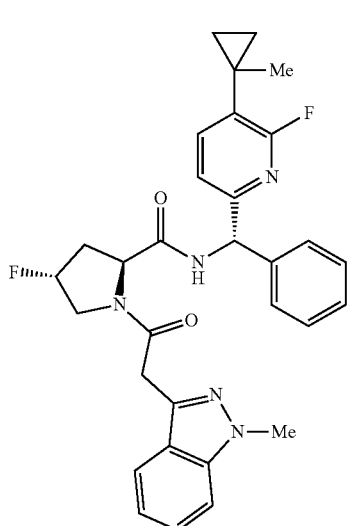 | (2S,4R)-4-fluoro-N-[(S)-[6-fluoro-5-(1-methylcyclopropyl)pyridin-2-yl](phenyl)methyl]-1-[2-(1-methyl-1H-indazol-3-yl)acetyl]pyrrolidine-2-carboxamide | 543.2 | 544.2 |

TABLE T-12-continued

| Compound No. | Structure | IUPAC | Exact mass (g/mol) | LCMS, Found [M + H]+ |
|---|---|---|---|---|
| 597 | 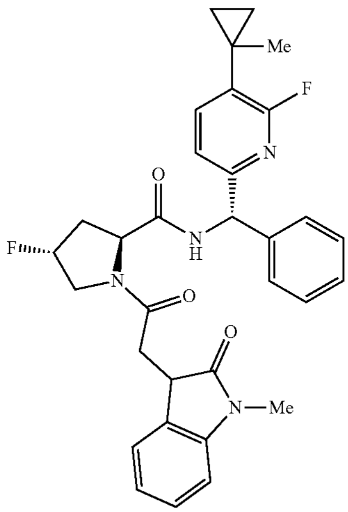 [SMILES: CN1C(=O)C(CC(=O)N2C[C@H](F)C[C@H]2C(=O)N[C@@H](c2ccccc2)c2ccc(C3(C)CC3)c(F)n2)c2ccccc21] | (2S,4R)-4-fluoro-N-[(S)-[6-fluoro-5-(1-methylcyclopropyl)pyridin-2-yl](phenyl)methyl]-1-[2-(1-methyl-2-oxo-2,3-dihydro-1H-indol-3-yl)acetyl]pyrrolidine-2-carboxamide | 558.2 | 559.2 |
| 598 | 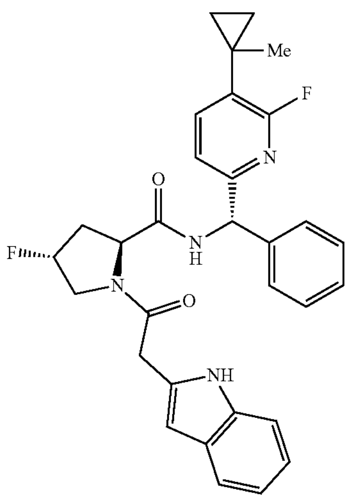 [SMILES: CC1(c2ccc([C@@H](NC(=O)[C@@H]3C[C@@H](F)CN3C(=O)Cc3cc4ccccc4[nH]3)c3ccccc3)nc2F)CC1] | (2S,4R)-4-fluoro-N-[(S)-[6-fluoro-5-(1-methylcyclopropyl)pyridin-2-yl](phenyl)methyl]-1-[2-(1H-indol-2-yl)acetyl]pyrrolidine-2-carboxamide | 528.2 | 529.2 |
| 599 | 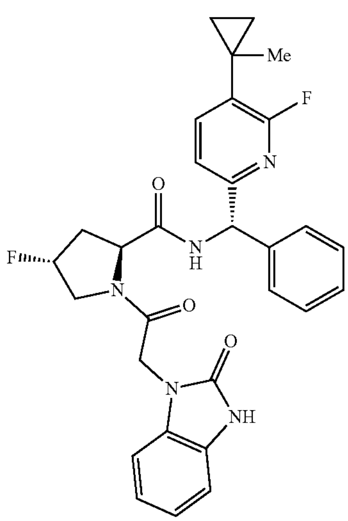 [SMILES: CC1(c2ccc([C@@H](NC(=O)[C@@H]3C[C@@H](F)CN3C(=O)Cn3c(=O)[nH]c4ccccc43)c3ccccc3)nc2F)CC1] | (2S,4R)-4-fluoro-N-[(S)-[6-fluoro-5-(1-methylcyclopropyl)pyridin-2-yl](phenyl)methyl]-1-[2-(2-oxo-2,3-dihydro-1H-1,3-benzodiazol-1-yl)acetyl]pyrrolidine-2-carboxamide | 545.2 | 546.2 |

TABLE T-12-continued
| Compound No. | Structure | IUPAC | Exact mass (g/mol) | LCMS, Found [M + H]+ |
|---|---|---|---|---|
| 600 | 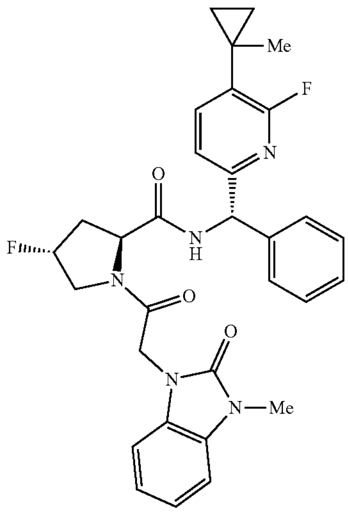 [SMILES: Cn1c(=O)n(CC(=O)N2C[C@H](F)C[C@H]2C(=O)N[C@@H](c2ccccc2)c2ccc(C3(C)CC3)c(F)n2)c2ccccc21] | (2S,4R)-4-fluoro-N-[(S)-[6-fluoro-5-(1-methylcyclopropyl)pyridin-2-yl](phenyl)methyl]-1-[2-(3-methyl-2-oxo-2,3-dihydro-1H-1,3-benzodiazol-1-yl)acetyl]pyrrolidine-2-carboxamide | 559.2 | 560.2 |
| 601 | 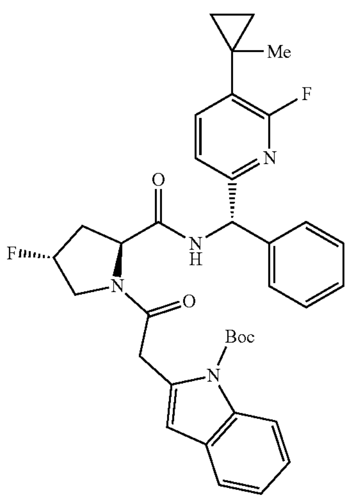 | tert-butyl 2-{2-[(2S,4R)-4-fluoro-2-{[(S)-[6-fluoro-5-(1-methylcyclopropyl)pyridin-2-yl](phenyl)methyl]carbamoyl}pyrrolidin-1-yl]-2-oxoethyl}-1H-indole-1-carboxylate | 628.3 | 629.3 |
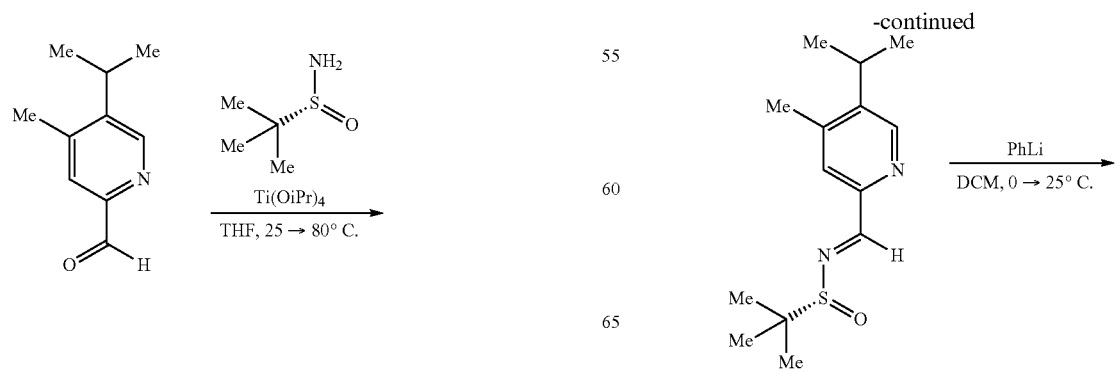

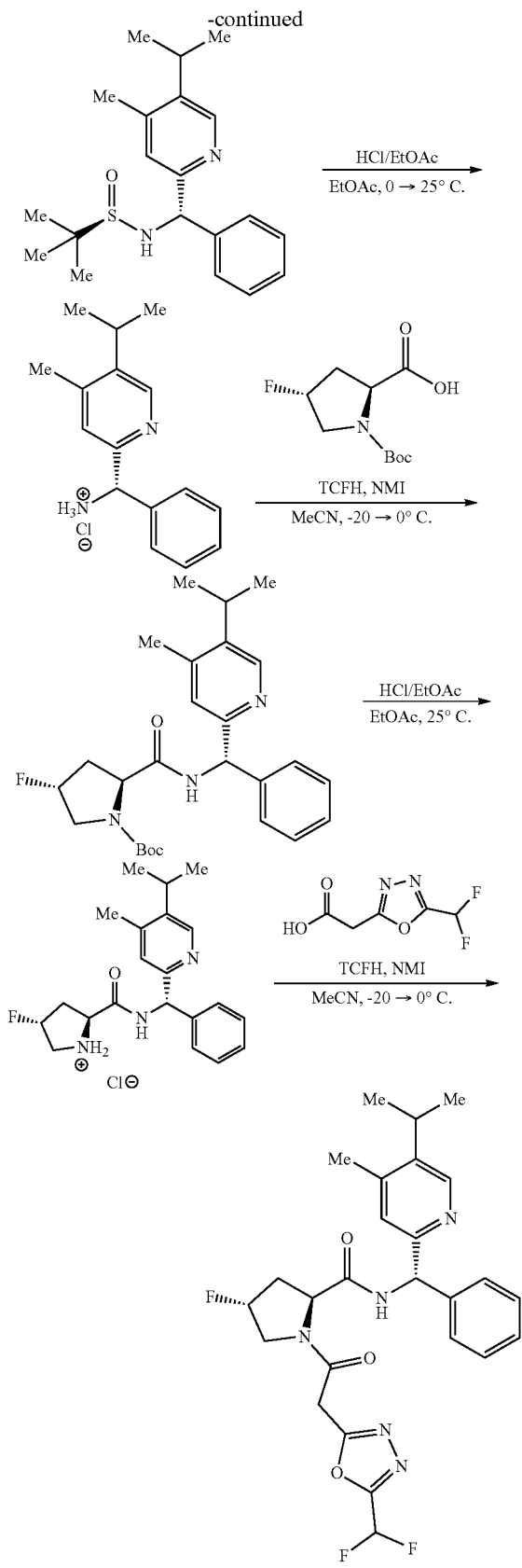

Step a: To a mixture of 5-isopropyl-4-methylpicolinaldehyde (3 g, 18.4 mmol, 1 eq) and (R)-2-methylpropane-2-sulfinamide (2.90 g, 23.9 mmol, 1.3 eq) in THF (5 mL) at 25° C. under N$_2$ was added Ti(Oi-Pr)$_4$ (10.4 g, 36.7 mmol, 2 eq). The resulting mixture was warmed to 80° C. and stirred for 1 h. The reaction mixture was then quenched with H$_2$O (30 mL) and extracted with EtOAc (3×30 mL). The combined organic extracts were washed with brine (30 mL), dried over anhydrous Na$_2$SO$_4$, filtered, and concentrated under reduced pressure. The crude residue obtained was purified by column chromatography to give (R,E)-N-((5-isopropyl-4-methylpyridin-2-yl)methylene)-2-methylpropane-2-sulfinamide. LC-MS (ESI): m/z: [M+H]$^+$ calculated for C$_{14}$H$_{22}$N$_2$OS: 267.1; found: 267.1.

Step b: To a mixture of (R,E)-N-((5-isopropyl-4-methylpyridin-2-yl)methylene)-2-methylpropane-2-sulfinamide (850 mg, 3.19 mmol, 1 eq) in DCM (5 mL) at 0° C. under N$_2$ was added PhLi (1 M in Et$_2$O, 8.0 mL, 2.5 eq). The resulting mixture was warmed to 25° C. and stirred for 16 h. The reaction mixture was then quenched with aq. NH$_4$Cl solution (10 mL), and the resulting biphasic mixture was extracted with EtOAc (3×30 mL). The combined organic extracts were washed with brine (30 mL), dried over anhydrous Na$_2$SO$_4$, filtered, and concentrated under reduced pressure. The crude residue obtained was purified by prep-HPLC to give (R)—N—((S)-(5-isopropyl-4-methylpyridin-2-yl)(phenyl)methyl)-2-methylpropane-2-sulfinamide. LC-MS (ESI): m/z: [M+H]$^+$ calculated for C$_{20}$H$_{28}$N$_2$OS: 345.2; found: 345.1.

Step c: To a solution of (R)—N—((S)-(5-isopropyl-4-methylpyridin-2-yl)(phenyl)methyl)-2-methylpropane-2-sulfinamide (75 mg, 217 μmol, 1 eq) in EtOAc (2 mL) at 0° C. was added HCl/EtOAc (4 M, 5 mL), and the resulting mixture was warmed to 25° C. and stirred for 1 h. The reaction mixture was then concentrated under reduced pressure to give (S)-(5-isopropyl-4-methylpyridin-2-yl)(phenyl)methanaminium chloride. LC-MS (ESI): m/z: [M+H]$^+$ calculated for C$_{16}$H$_{20}$N$_2$: 241.2; found: 241.1.

Step d: To a mixture of (S)-(5-isopropyl-4-methylpyridin-2-yl)(phenyl)methanaminium chloride (65 mg, 234 μmol, 1 eq) and (2S,4R)-1-(tert-butoxycarbonyl)-4-fluoropyrrolidine-2-carboxylic acid (71.2 mg, 305 μmol, 1.3 eq) in MeCN (3 mL) at −20° C. under N$_2$ was added N-methylimidazole (57.8 mg, 704 μmol, 56.1 μL, 3 eq) and chloro-N,N,N,N-tetramethylformamidinium hexafluorophosphate (TCFH, 85.7 mg, 305 μmol, 1.3 eq), and the resulting mixture was warmed to 0° C. and stirred for 1 h. The reaction mixture was then quenched with H$_2$O (10 mL), and the resulting biphasic mixture was extracted with EtOAc (3×10 mL). The combined organic extracts were washed with brine (10 mL), dried over anhydrous Na$_2$SO$_4$, filtered, and concentrated under reduced pressure. The crude residue obtained was purified by prep-TLC to give tert-butyl (2S,4R)-4-fluoro-2-(((S)-(5-isopropyl-4-methylpyridin-2-yl)(phenyl)methyl)carbamoyl)pyrrolidine-1-carboxylate. LC-MS (ESI): m/z: [M+H]$^+$ calculated for C$_{26}$H$_{34}$FN$_3$O$_3$: 456.3; found: 456.1.

Step e: To a solution of tert-butyl (2S,4R)-4-fluoro-2-(((S)-(5-isopropyl-4-methylpyridin-2-yl)(phenyl)methyl)carbamoyl)pyrrolidine-1-carboxylate (35 mg, 76.8 μmol, 1 eq) in EtOAc (2 mL) at 25° C. under N$_2$ was added HCl/EtOAc (4 M, 2 mL). The resulting mixture was stirred at 25° C. for 1 h. The reaction mixture was then concentrated under reduced pressure to give (2S,4R)-4-fluoro-2-(((S)-(5-isopropyl-4-methylpyridin-2-yl)(phenyl)methyl)carbamoyl)pyrrolidin-1-ium chloride. LC-MS (ESI): m/z: [M+H]$^+$ calculated for C$_{21}$H$_{26}$FN$_3$O: 356.2; found: 356.1.

Step f: To a mixture of (2S,4R)-4-fluoro-2-(((S)-(5-isopropyl-4-methylpyridin-2-yl)(phenyl)methyl)carbamoyl)

pyrrolidin-1-ium chloride (45.3 mg, 127 μmol, 1 eq) and 2-(5-(difluoromethyl)-1,3,4-oxadiazol-2-yl)acetic acid (34.1 mg, 191 μmol, 1.5 eq) in MeCN (3 mL) at −20° C. under N$_2$ was added chloro-N,N,N',N'-tetramethylformamidinium hexafluorophosphate (TCFH, 53.7 mg, 191 μmol, 1.5 eq) and N-methylimidazole (31.4 mg, 382 μmol, 3 eq). The resulting mixture was warmed to 0° C. and stirred for 1 h. The reaction mixture was then diluted with H$_2$O (10 mL), and the resulting biphasic mixture was extracted with EtOAc (3×10 mL). The combined organic extracts were washed with brine (10 mL), dried over anhydrous Na$_2$SO$_4$, filtered, and concentrated under reduced pressure. The crude residue obtained was purified by prep-HPLC to give (2S,4R)-1-(2-(5-(difluoromethyl)-1,3,4-oxadiazol-2-yl)acetyl)-4-fluoro-N—((S)-(5-isopropyl-4-methylpyridin-2-yl)(phenyl)methyl)pyrrolidine-2-carboxamide. $^1$H NMR (4.7:1 rotamer ratio, asterisk denotes distinct minor rotamer peaks, obscured peaks not reported, 400 MHz, methanol-d$_4$) δ 8.39*(s, 1H), 8.32 (s, 1H), 7.38-7.19 (m, 5H), 7.16-7.12 (m, 1H), 7.09*(s, 1H), 7.01*(s, 1H), 6.15*(s, 1H), 6.11 (s, 1H), 5.48-5.20 (m, 1H), 4.74-4.67 (m, 1H), 4.23*(s, 1H), 4.16-4.03 (m, 1H), 3.99-3.81 (m, 1H), 3.24-3.13 (m, 1H), 2.70-2.56 (m, 1H), 2.37-2.32 (m, 3H), 2.28-2.07 (m, 1H), 1.32-1.25 (m, 6H). LC-MS (ESI): m/z: [M+H]$^+$ calculated for C$_{26}$H$_{28}$F$_3$N$_5$O$_3$: 516.2; found 516.2.

The following compounds in Table T-13 were synthesized using procedures similar to Compound 602 using the appropriate starting materials.

TABLE T-13

| Compound No. | Structure | IUPAC | Exact mass (g/mol) | LCMS, Found [M + H]$^+$ |
|---|---|---|---|---|
| 603 | 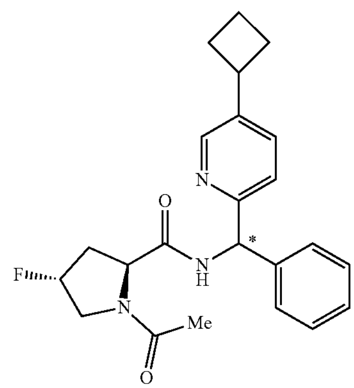 [SMILES: CC(=O)N1C[C@H](F)C[C@H]1C(=O)NC(c1ccccc1)c1ccc(C2CCC2)cn1] | (2S,4R)-1-acetyl-N-[(S) or (R)-(5-cyclobutylpyridin-2-yl)(phenyl)methyl]-4-fluoropyrrolidine-2-carboxamide (column: REGIS (s,s) WHELK-O1, first-eluting isomer) | 395.2 | 396.2 |
| 604 | 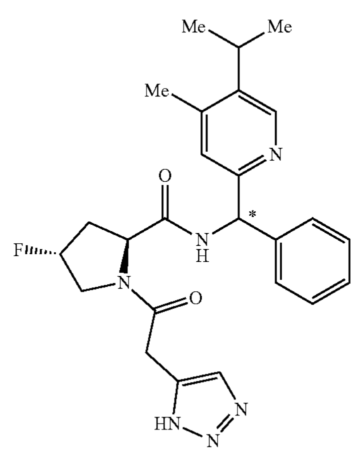 [SMILES: Cc1cc(C(NC(=O)[C@@H]2C[C@@H](F)CN2C(=O)Cc2cnn[nH]2)c2ccccc2)ncc1C(C)C] | (2S,4R)-4-fluoro-N-[(S) or (R)-[4-methyl-5-(propan-2-yl)pyridin-2-yl](phenyl)methyl]-1-[2-(1H-1,2,3-triazol-5-yl)acetyl]pyrrolidine-2-carboxamide (column: REGIS (s,s) WHELK-O1, first-eluting isomer) | 464.2 | 465.2 |

TABLE T-13-continued

| Compound No. | Structure | IUPAC | Exact mass (g/mol) | LCMS, Found [M + H]+ |
|---|---|---|---|---|
| 605 | 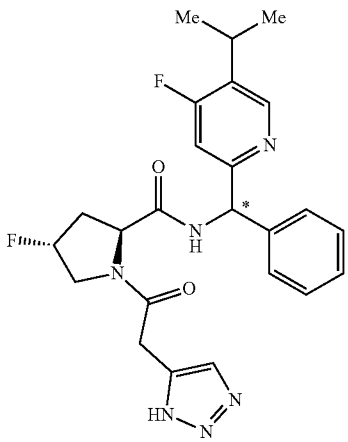 [SMILES: CC(C)c1cnc(C(NC(=O)[C@@H]2C[C@@H](F)CN2C(=O)Cc2cnn[nH]2)c2ccccc2)cc1F] | (2S,4R)-4-fluoro-N-[(S) or (R)-[4-fluoro-5-(propan-2-yl)pyridin-2-yl](phenyl)methyl]-1-[2-(1H-1,2,3-triazol-5-yl)acetyl]pyrrolidine-2-carboxamide (column: REGIS (s,s) WHELK-O1, first-eluting isomer) | 468.2 | 469.1 |
| 606 | 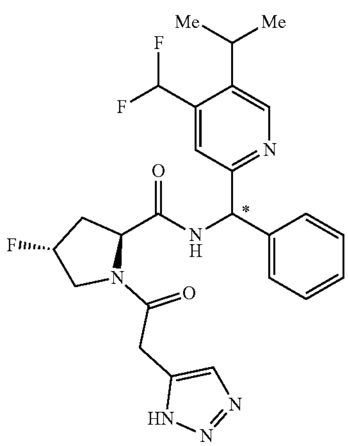 [SMILES: CC(C)c1cnc(C(NC(=O)[C@@H]2C[C@@H](F)CN2C(=O)Cc2cnn[nH]2)c2ccccc2)cc1C(F)F] | (2S,4R)-N-[(S) or (R)-[4-(difluoromethyl)-5-(propan-2-yl)pyridin-2-yl](phenyl)methyl]-4-fluoro-1-[2-(1H-1,2,3-triazol-5-yl)acetyl]pyrrolidine-2-carboxamide (column: REGIS (s,s) WHELK-O1, first-eluting isomer) | 500.2 | 501.2 |
| 607 | 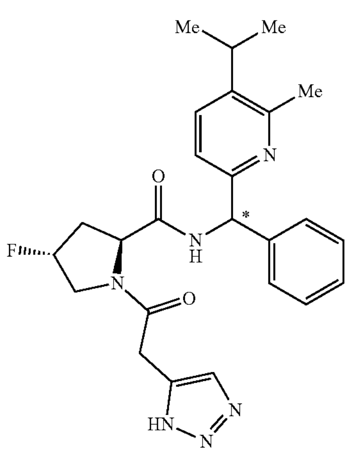 [SMILES: Cc1nc(C(NC(=O)[C@@H]2C[C@@H](F)CN2C(=O)Cc2cnn[nH]2)c2ccccc2)ccc1C(C)C] | (2S,4R)-4-fluoro-N-[(S) or (R)-[6-methyl-5-(propan-2-yl)pyridin-2-yl](phenyl)methyl]-1-[2-(1H-1,2,3-triazol-5-yl)acetyl]pyrrolidine-2-carboxamide (column: REGIS (s,s) WHELK-O1, first-eluting isomer) | 464.2 | 465.2 |

TABLE T-13-continued

| Compound No. | Structure | IUPAC | Exact mass (g/mol) | LCMS, Found [M + H]+ |
| --- | --- | --- | --- | --- |
| 608 | 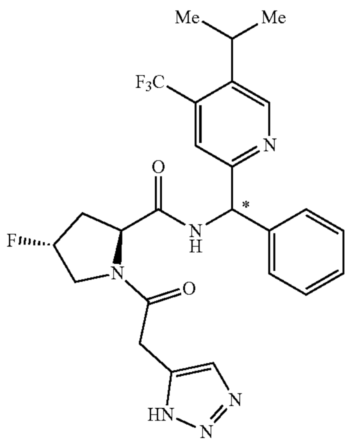 [SMILES: CC(C)c1cnc(C(NC(=O)[C@@H]2C[C@@H](F)CN2C(=O)Cc2cnn[nH]2)c2ccccc2)cc1C(F)(F)F] | (2S,4R)-4-fluoro-N-[(S) or (R)-phenyl[5-(propan-2-yl)-4-(trifluoromethyl)pyridin-2-yl]methyl]-1-[2-(1H-1,2,3-triazol-5-yl)acetyl]pyrrolidine-2-carboxamide (column: REGIS (s,s) WHELK-O1, first-eluting isomer) | 518.2 | 519.2 |
| 609 | 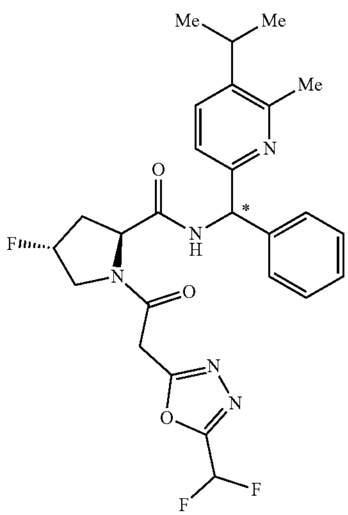 [SMILES: Cc1nc(C(NC(=O)[C@@H]2C[C@@H](F)CN2C(=O)Cc2nnc(C(F)F)o2)c2ccccc2)ccc1C(C)C] | (2S,4R)-1-{2-[5-(difluoromethyl)-1,3,4-oxadiazol-2-yl]acetyl}-4-fluoro-N-[(S) or (R)-[6-methyl-5-(propan-2-yl)pyridin-2-yl](phenyl)methyl]pyrrolidine-2-carboxamide (column: REGIS (s,s) WHELK-O1, first-eluting isomer) | 515.2 | 516.2 |
| 610 | 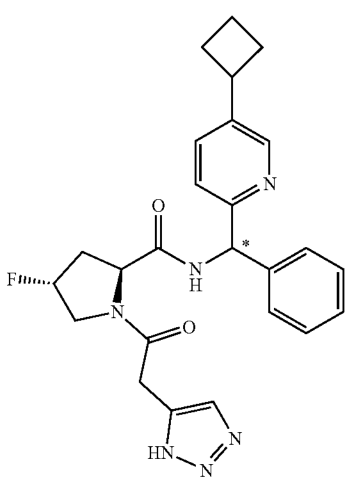 [SMILES: O=C(NC(c1ccccc1)c1ccc(C2CCC2)cn1)[C@@H]1C[C@@H](F)CN1C(=O)Cc1cnn[nH]1] | (2S,4R)-N-[(S) or (R)-(5-cyclobutylpyridin-2-yl)(phenyl)methyl]-4-fluoro-1-[2-(1H-1,2,3-triazol-5-yl)acetyl]pyrrolidine-2-carboxamide (column: REGIS (s,s) WHELK-O1, first-eluting isomer) | 462.2 | 463.2 |

TABLE T-13-continued

| Compound No. | Structure | IUPAC | Exact mass (g/mol) | LCMS, Found [M + H]+ |
|---|---|---|---|---|
| 611 | 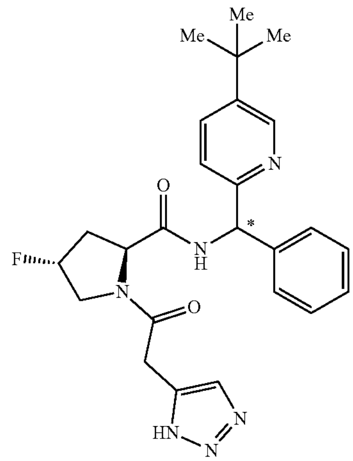 [SMILES: CC(C)(C)c1ccc(C(NC(=O)[C@@H]2C[C@@H](F)CN2C(=O)Cc2cnn[nH]2)c2ccccc2)nc1] | (2S,4R)-N-[(S) or (R)-(5-tert-butylpyridin-2-yl)(phenyl)methyl]-4-fluoro-1-[2-(1H-1,2,3-triazol-5-yl)acetyl]pyrrolidine-2-carboxamide (column: REGIS (s,s) WHELK-O1, first-eluting isomer) | 464.2 | 465.1 |
| 612 | 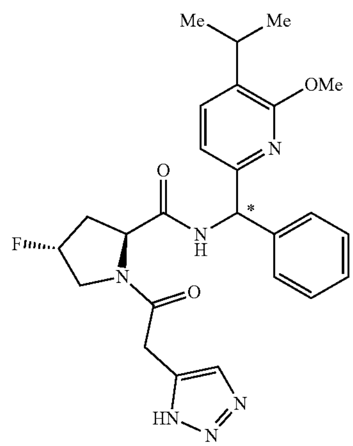 [SMILES: COc1nc(C(NC(=O)[C@@H]2C[C@@H](F)CN2C(=O)Cc2cnn[nH]2)c2ccccc2)ccc1C(C)C] | (2S,4R)-4-fluoro-N-[(S) or (R)-[6-methoxy-5-(propan-2-yl)pyridin-2-yl](phenyl)methyl]-1-[2-(1H-1,2,3-triazol-5-yl)acetyl]pyrrolidine-2-carboxamide (column: REGIS (s,s) WHELK-O1, first-eluting isomer) | 480.2 | 481.1 |

Example S-14: Synthesis of (2S,4R)-1-(2-(1H-1,2,3-triazol-5-yl)acetyl)-N—((R)-(2-aminopyridin-3-yl)(3-fluoro-4-isopropylphenyl)methyl)-4-fluoropyrrolidine-2-carboxamide Compound 613

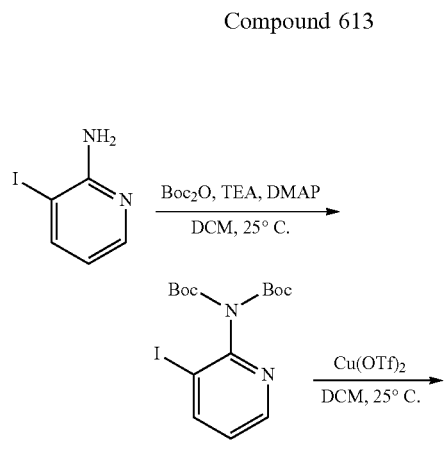

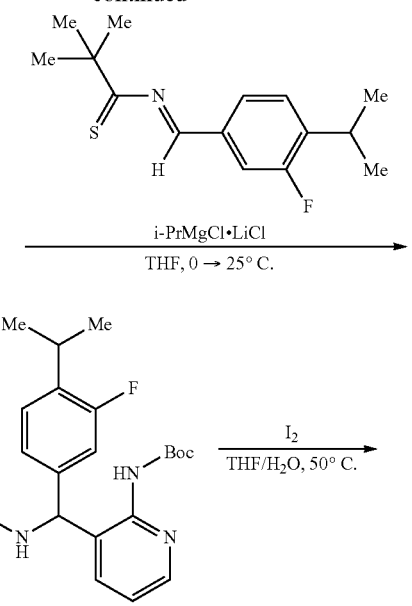

-continued

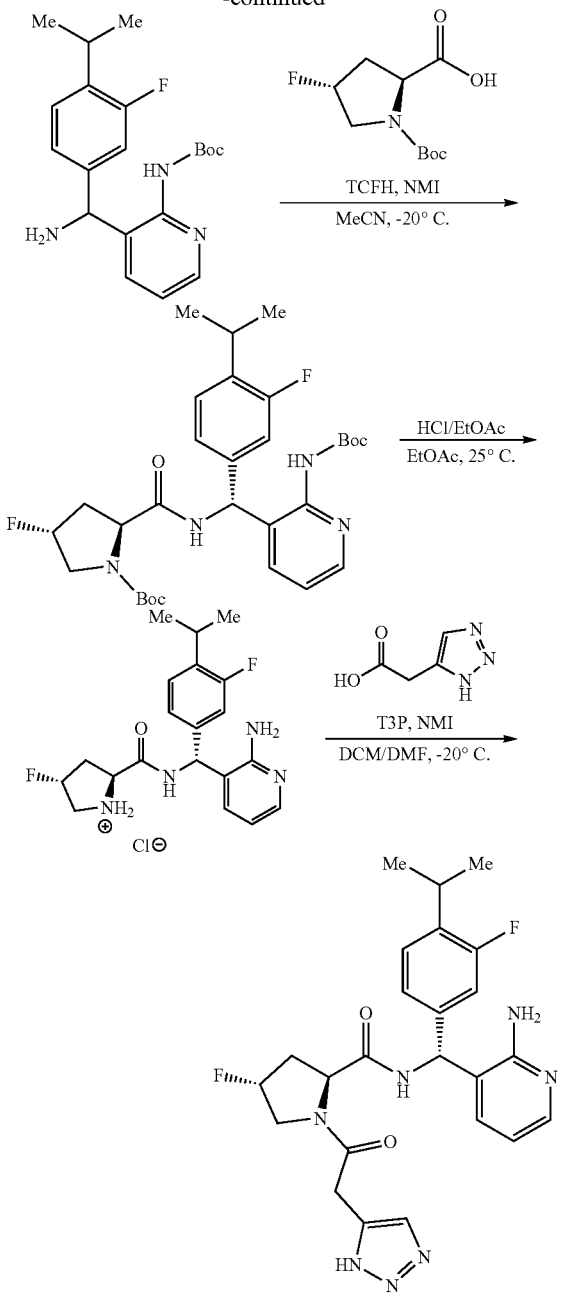

Step a: To a solution of 3-iodopyridin-2-amine (9.00 g, 40.9 mmol, 1 eq) in DCM (200 mL) was added TEA (102 mmol, 14.2 mL, 2.5 eq) and Boc₂O (49.1 mmol, 11.3 mL, 1.2 eq), DMAP (500 mg, 4.09 mmol, 0.1 eq). The resulting mixture was stirred at 25° C. for 15 h. The reaction mixture was then cooled to 0° C. and quenched by addition of water (100 mL), and the resulting biphasic mixture was adjusted to pH=6 using aq. HCl solution (4 N). The resulting mixture was extracted with EtOAc (3×100 mL). The combined organic extracts were washed with brine (2×100 mL), dried over anhydrous Na₂SO₄, filtered, and concentrated under reduced pressure. The crude residue obtained was triturated with petroleum ether to give tert-butyl (tert-butoxycarbonyl)(3-iodopyridin-2-yl)carbamate. LC-MS (ESI): m/z: [M+H]⁺ calculated for $C_{15}H_{21}IN_2O_4$: 421.0; found 421.1.

Step b: To a solution of tert-butyl (tert-butoxycarbonyl)(3-iodopyridin-2-yl)carbamate (15.0 g, 35.7 mmol, 1 eq) in DCM (100 mL) was added bis(trifluoromethylsulfonyloxy)copper (12.9 g, 35.7 mmol, 1 eq). The resulting mixture was stirred at 25° C. for 20 min. The reaction mixture was then cooled to 0° C. and quenched by addition of water (100 mL). The resulting biphasic mixture was then extracted with EtOAc (2×100 mL). The combined organic extracts were washed with brine (2×100 mL), dried over anhydrous Na₂SO₄, filtered, and concentrated under reduced pressure to give tert-butyl (3-iodopyridin-2-yl)carbamate, which was carried forward to the next step without further purification or characterization.

Step c: To a solution of tert-butyl (3-iodopyridin-2-yl)carbamate (7.13 g, 22.3 mmol, 3 eq) in THF (45 mL) at 0° C. was added i-PrMgCl·LiCl (1.3 M in THF, 28.6 mL, 5 eq), and the resulting mixture was stirred at 0° C. for 2 h. Then, (E)-N-(3-fluoro-4-isopropylbenzylidene)-2-methylpropane-2-sulfinamide (2 g, 7.42 mmol, 1 eq) in THF (0.5 mL) was added dropwise. The resulting mixture was allowed to warm to 25° C. and stirred for 2 h. The reaction mixture was then cooled to 0° C. and quenched by addition of saturated aq. NH₄Cl solution (50 mL). The resulting biphasic mixture was then extracted with EtOAc (2×30 mL). The combined organic extracts were washed with brine (2×50 mL), dried over anhydrous Na₂SO₄, filtered, and concentrated under reduced pressure. The crude residue obtained was purified by column chromatography to give tert-butyl (3-(((tert-butylsulfinyl)amino)(3-fluoro-4-isopropylphenyl)methyl)pyridin-2-yl)carbamate. LC-MS (ESI): m/z: [M+H]⁺ calculated for $C_{24}H_{34}FN_3O_3S$: 464.2; found 464.1.

Step d: To a solution of tert-butyl (3-(((tert-butylsulfinyl)amino)(3-fluoro-4-isopropylphenyl)methyl)pyridin-2-yl)carbamate (3.3 g, 7.12 mmol, 1 eq) in THF (25 mL) and H₂O (5 mL) was added I₂ (4.52 g, 17.8 mmol, 2.5 eq). The resulting mixture was warmed to 50° C. and stirred for 1 h. The reaction mixture was then cooled to 0° C. and quenched by addition of saturated aq. Na₂S2O3 solution (30 mL), and the resulting biphasic mixture was extracted with EtOAc (2×30 mL). The combined organic extracts were washed with brine (2×50 mL), dried over anhydrous Na₂SO₄, filtered, and concentrated under reduced pressure to give tert-butyl (3-(amino(3-fluoro-4-isopropylphenyl)methyl)pyridin-2-yl)carbamate, which was carried forward to the next step without further purification. LC-MS (ESI): m/z: [M+H]⁺ calculated for $C_{20}H_{26}FN_3O_2$: 360.2; found 360.1.

Step e: To a solution of tert-butyl (3-(amino(3-fluoro-4-isopropylphenyl)methyl)pyridin-2-yl)carbamate (2.4 g, 6.68 mmol, 1 eq) and (2S,4R)-1-(tert-butoxycarbonyl)-4-fluoropyrrolidine-2-carboxylic acid (1.87 g, 8.01 mmol, 1.2 eq) in MeCN (25 mL) at −20° C. was added N-methylimidazole (NMI, 2.74 g, 33.4 mmol, 2.6 mL, 5 eq) and chloro-N,N,N',N'-tetramethylformamidinium hexafluorophosphate (TCFH, 2.06 g, 7.34 mmol, 1.1 eq). The resulting mixture was stirred at −20° C. for 0.5 h. The reaction mixture was then warmed to 0° C. and quenched by addition of water (20 mL), and the resulting biphasic mixture was extracted with EtOAc (3×20 mL). The combined organic extracts were washed with brine (2×50 mL), dried over anhydrous Na₂SO₄, filtered, and concentrated under reduced pressure. The crude residue obtained was purified by column chromatography to give tert-butyl (2S,4R)-2-(((R)-(2-((tert-butoxycarbonyl)amino)pyridin-3-yl)(3-fluoro-4-isopropylphenyl)methyl)carbamoyl)-4-fluoropyrrolidine-1-carboxylate (first-eluting isomer) and tert-butyl (2S,4R)-2-(((S)-(2-((tert-butoxycarbonyl)amino)pyridin-3-yl)(3-fluoro-4-isopropylphenyl)methyl)carbamoyl)-4-fluoropyrrolidine-1- carboxylate (second-eluting isomer) as separate diastereomers that were carried forward individually. LC-MS (ESI): m/z: [M+H]$^+$ calculated for $C_{30}H_{40}F_2N_4O_5$: 575.3; found 575.2.

Step f: To a solution of tert-butyl (2S,4R)-2-(((R)-(2-((tert-butoxycarbonyl)amino)pyridin-3-yl)(3-fluoro-4-isopropylphenyl)methyl)carbamoyl)-4-fluoropyrrolidine-1-carboxylate (700 mg, 1.22 mmol, 1 eq) in EtOAc (10 mL) was added HCl/EtOAc (4 M, 20 mL). The resulting mixture was stirred at 25° C. for 15 h. The reaction mixture was then concentrated under reduced pressure to give (2S,4R)-2-(((R)-(2-aminopyridin-3-yl)(3-fluoro-4-isopropylphenyl)methyl)carbamoyl)-4-fluoropyrrolidin-1-ium chloride, which was carried forward to the next step without additional purification. LC-MS (ESI): m/z: [M+H]$^+$ calculated for $C_{20}H_{24}F_2N_4O$: 375.2; found 375.1.

Step g: To a solution of (2S,4R)-2-(((R)-(2-aminopyridin-3-yl)(3-fluoro-4-isopropylphenyl)methyl)carbamoyl)-4-fluoropyrrolidin-1-ium chloride (200 mg, 487 µmol, 1 eq) and 2-(1H-1,2,3-triazol-5-yl)acetic acid (61.9 mg, 487 µmol, 1 eq) in DCM (5 mL) and DMF (0.5 mL) at −20° C. was added N-methylimidazole (NMI, 400 mg, 4.87 mmol, 10 eq) and T3P (633 µmol, 370 µL, 50% purity, 1.3 eq). The resulting mixture was stirred at −20° C. for 1 h. The reaction mixture was then warmed to 0° C. and quenched by addition of water (10 mL), and the resulting biphasic mixture was extracted with EtOAc (2×15 mL). The combined organic extracts were washed with brine (20 mL), dried over anhydrous $Na_2SO_4$, filtered, and concentrated under reduced pressure. The crude residue obtained was purified by prep-HPLC to give (2S,4R)-1-(2-(1H-1,2,3-triazol-5-yl)acetyl)-N—((R)-(2-aminopyridin-3-yl)(3-fluoro-4-isopropylphenyl)methyl)-4-fluoropyrrolidine-2-carboxamide. $^1$H NMR (4.3:1 rotamer ratio, asterisk denotes distinct minor rotamer peaks, obscured peaks not reported, 400 MHz, DMSO-d$_6$) δ 14.69 (br s, 1H), 9.16*(d, J=8.1 Hz, 1H), 8.87 (d, J=8.1 Hz, 1H), 7.90-7.83 (m, 1H), 7.65 (br s, 1H), 7.37-7.24 (m, 1H), 7.18-6.93 (m, 3H), 6.55-6.44 (m, 1H), 6.12*(d, J=8.1 Hz, 1H), 5.94 (d, J=7.9 Hz, 1H), 5.77*(s, 2H), 5.62 (s, 2H), 5.49-5.19 (m, 1H), 4.83-4.73*(m, 1H), 4.48 (t, J=8.5 Hz, 1H), 4.09-3.96 (m, 1H), 3.88-3.67 (m, 2H), 3.19-3.09 (m, 1H), 2.09-1.86 (m, 1H), 1.20 (d, J=6.9 Hz, 6H). LC-MS (ESI): m/z: [M+H]$^+$ calculated for $C_{24}H_{27}F_2N_7O_2$: 484.2; found 484.1.

The following compounds in Table T-14 were synthesized using procedures similar to Compound 613 using the appropriate starting materials.

TABLE T-14

| Compound No. | Structure | IUPAC | Exact mass (g/mol) | LCMS, Found [M + H]$^+$ |
|---|---|---|---|---|
| 614 | (structure) | (2S,4R)-1-acetyl-4-fluoro-N-[(S)-[4-(propan-2-yl)phenyl](1H-pyrazol-5-yl)methyl]pyrrolidine-2-carboxamide | 372.2 | 373.2 |
| 615 | (structure) | (2S)-N-[(R) or (S)-(4-cyclopropyl-3-fluorophenyl)(1H-pyrazol-5-yl)methyl]-1-(2-acetamidoacetyl)pyrrolidine-2-carboxamide (column: REGIS (s,s) WHELK-O1, second-eluting isomer) | 427.2 | 428.1 |

TABLE T-14-continued

| Compound No. | Structure | IUPAC | Exact mass (g/mol) | LCMS, Found [M + H]+ |
|---|---|---|---|---|
| 616 | 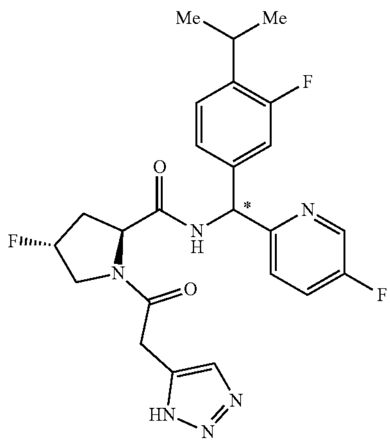 [SMILES: CC(C)c1ccc(C(NC(=O)[C@@H]2C[C@@H](F)CN2C(=O)Cc2cnn[nH]2)c2ccc(F)cn2)cc1F] | (2S,4R)-4-fluoro-N-[(R) or (S)-[3-fluoro-4-(propan-2-yl)phenyl](5-fluoropyridin-2-yl)methyl]-1-[2-(1H-1,2,3-triazol-5-yl)acetyl]pyrrolidine-2-carboxamide (column: REGIS (s,s) WHELK-O1, first-eluting isomer) | 486.2 | 487.1 |
| 617 | 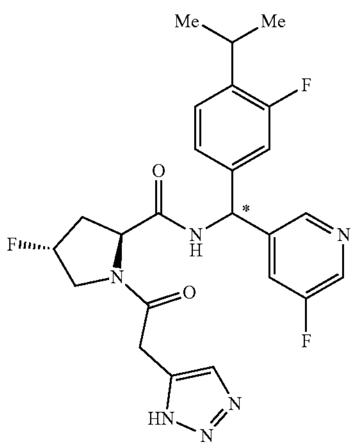 [SMILES: CC(C)c1ccc(C(NC(=O)[C@@H]2C[C@@H](F)CN2C(=O)Cc2cnn[nH]2)c2cncc(F)c2)cc1F] | (2S,4R)-4-fluoro-N-[(R) or (S)-[3-fluoro-4-(propan-2-yl)phenyl](5-fluoropyridin-3-yl)methyl]-1-[2-(1H-1,2,3-triazol-5-yl)acetyl]pyrrolidine-2-carboxamide (column: REGIS (s,s) WHELK-O1, first-eluting isomer) | 486.2 | 487.1 |
| 618 | 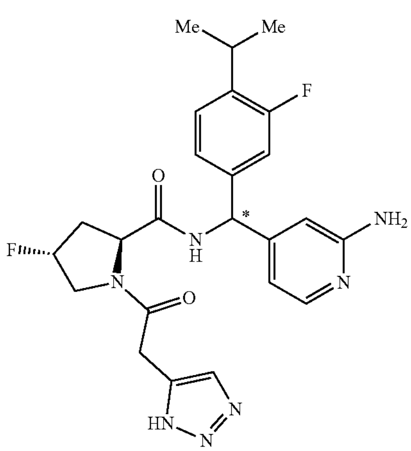 [SMILES: CC(C)c1ccc(C(NC(=O)[C@@H]2C[C@@H](F)CN2C(=O)Cc2cnn[nH]2)c2ccnc(N)c2)cc1F] | (2S,4R)-N-[(S) or (R)-(2-aminopyridin-4-yl)[3-fluoro-4-(propan-2-yl)phenyl]methyl]-4-fluoro-1-[2-(1H-1,2,3-triazol-5-yl)acetyl]pyrrolidine-2-carboxamide (column: REGIS (s,s) WHELK-O1, first-eluting isomer) | 483.2 | 484.1 |

TABLE T-14-continued

| Compound No. | Structure | IUPAC | Exact mass (g/mol) | LCMS, Found [M + H]+ |
|---|---|---|---|---|
| 619 | 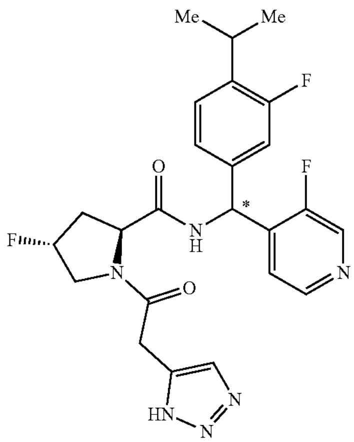 [SMILES: CC(C)c1ccc(C(NC(=O)[C@@H]2C[C@@H](F)CN2C(=O)Cc2cnn[nH]2)c2ccncc2F)cc1F] | (2S,4R)-4-fluoro-N-[(R) or (S)-[3-fluoro-4-(propan-2-yl)phenyl](3-fluoropyridin-4-yl)methyl]-1-[2-(1H-1,2,3-triazol-5-yl)acetyl]pyrrolidine-2-carboxamide (column: REGIS (s,s) WHELK-O1, first-eluting isomer) | 486.2 | 487.1 |
| 620 | 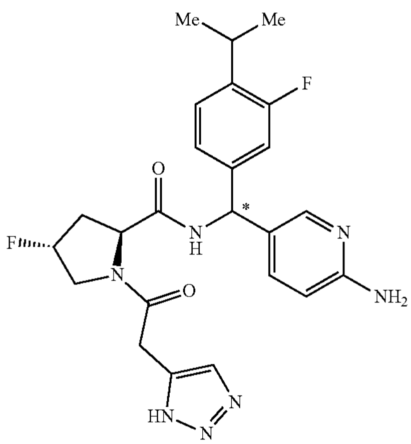 [SMILES: CC(C)c1ccc(C(NC(=O)[C@@H]2C[C@@H](F)CN2C(=O)Cc2cnn[nH]2)c2ccc(N)nc2)cc1F] | (2S,4R)-N-[(R) or (S)-(6-aminopyridin-3-yl)[3-fluoro-4-(propan-2-yl)phenyl]methyl]-4-fluoro-1-[2-(1H-1,2,3-triazol-5-yl)acetyl]pyrrolidine-2-carboxamide (column: DAICEL CHIRALPAK IG-3, first-eluting isomer) | 483.2 | 484.1 |
| 621 | 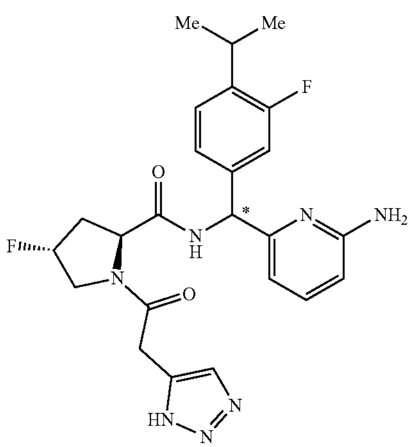 [SMILES: CC(C)c1ccc(C(NC(=O)[C@@H]2C[C@@H](F)CN2C(=O)Cc2cnn[nH]2)c2cccc(N)n2)cc1F] | (2S,4R)-N-[(R) or (S)-(6-aminopyridin-2-yl)[3-fluoro-4-(propan-2-yl)phenyl]methyl]-4-fluoro-1-[2-(1H-1,2,3-triazol-5-yl)acetyl]pyrrolidine-2-carboxamide (column: REGIS (s,s) WHELK-O1, second-eluting isomer) | 483.2 | 484.1 |

TABLE T-14-continued

| Compound No. | Structure | IUPAC | Exact mass (g/mol) | LCMS, Found [M + H]+ |
|---|---|---|---|---|
| 622 | 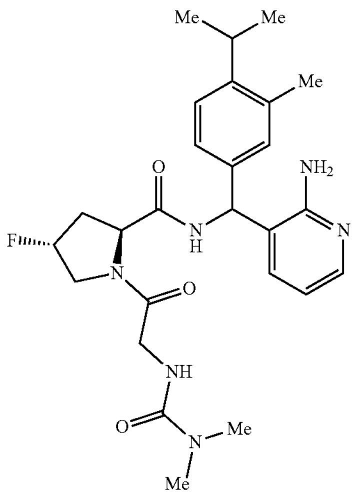 [SMILES: Cc1cc(C(NC(=O)[C@@H]2C[C@@H](F)CN2C(=O)CNC(=O)N(C)C)c2cccnc2N)ccc1C(C)C] | (2S,4R)-N-[(R) or (S)-(2-aminopyridin-3-yl)[3-methyl-4-(propan-2-yl)phenyl]methyl]-1-{2-[(dimethylcarbamoyl)amino]acetyl}-4-fluoropyrrolidine-2-carboxamide (column: Waters Xbridge BEH C18, second-eluting isomer) | 498.3 | 499.2 |
| 623 | 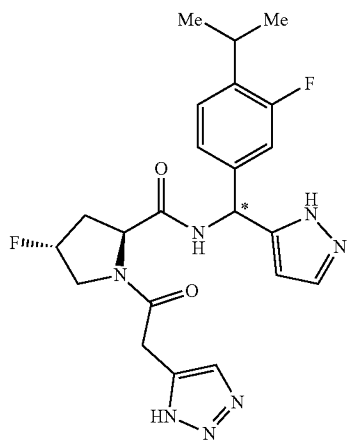 [SMILES: CC(C)c1ccc(C(NC(=O)[C@@H]2C[C@@H](F)CN2C(=O)Cc2cnn[nH]2)c2ccn[nH]2)cc1F] | (2S,4R)-4-fluoro-N-[(R) or (S)-[3-fluoro-4-(propan-2-yl)phenyl](1H-pyrazol-5-yl)methyl]-1-[2-(1H-1,2,3-triazol-5-yl)acetyl]pyrrolidine-2-carboxamide (column: REGIS (s,s) WHELK-O1, second-eluting isomer) | 457.2 | 458.1 |
| 624 | 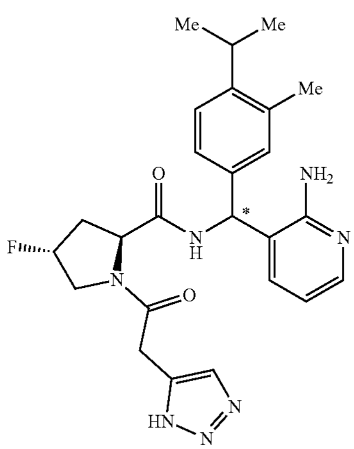 [SMILES: Cc1cc(C(NC(=O)[C@@H]2C[C@@H](F)CN2C(=O)Cc2cnn[nH]2)c2cccnc2N)ccc1C(C)C] | (2S,4R)-N-[(R) or (S)-(2-aminopyridin-3-yl)[3-methyl-4-(propan-2-yl)phenyl]methyl]-4-fluoro-1-[2-(1H-1,2,3-triazol-5-yl)acetyl]pyrrolidine-2-carboxamide (column: Lux Cellulose-2, second-eluting isomer) | 479.2 | 480.1 |

TABLE T-14-continued

| Compound No. | Structure | IUPAC | Exact mass (g/mol) | LCMS, Found [M + H]+ |
|---|---|---|---|---|
| 625 | 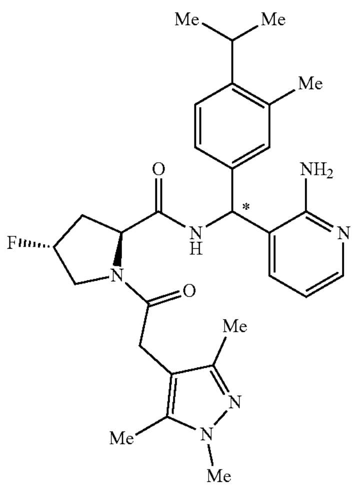 [SMILES: Cc1cc(C(NC(=O)[C@@H]2C[C@@H](F)CN2C(=O)Cc2c(C)nn(C)c2C)c2cccnc2N)ccc1C(C)C] | (2S,4R)-N-[(R) or (S)-(2-aminopyridin-3-yl)[3-methyl-4-(propan-2-yl)phenyl]methyl]-4-fluoro-1-[2-(1,3,5-trimethyl-1H-pyrazol-4-yl)acetyl]pyrrolidine-2-carboxamide (column: DAICEL CHIRALPAK AD-3, first-eluting isomer) | 520.3 | 521.2 |
| 626 | 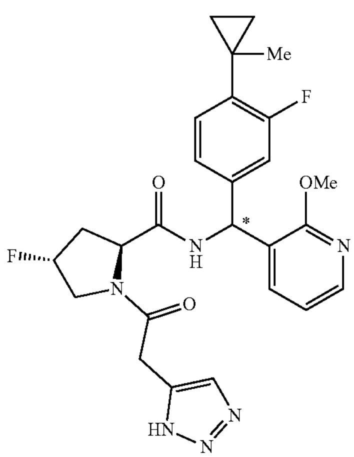 [SMILES: COc1ncccc1C(NC(=O)[C@@H]1C[C@@H](F)CN1C(=O)Cc1cnn[nH]1)c1ccc(C2(C)CC2)c(F)c1] | (2S,4R)-4-fluoro-N-[(R) or (S)-[3-fluoro-4-(1-methylcyclopropyl)phenyl](2-methoxypyridin-3-yl)methyl]-1-[2-(1H-1,2,3-triazol-5-yl)acetyl]pyrrolidine-2-carboxamide (column: DAICEL CHIRALPAK AD-3, second-eluting isomer) | 510.2 | 511.3 |
| 627 | 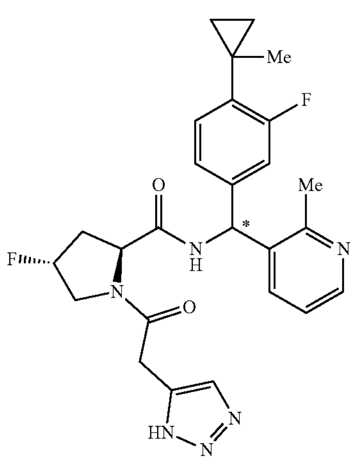 [SMILES: Cc1ncccc1C(NC(=O)[C@@H]1C[C@@H](F)CN1C(=O)Cc1cnn[nH]1)c1ccc(C2(C)CC2)c(F)c1] | (2S,4R)-4-fluoro-N-[(R) or (S)-[3-fluoro-4-(1-methylcyclopropyl)phenyl](2-methylpyridin-3-yl)methyl]-1-[2-(1H-1,2,3-triazol-5-yl)acetyl]pyrrolidine-2-carboxamide (column: REGIS (s,s) WHELK-O1, first-eluting isomer) | 494.2 | 495.2 |

TABLE T-14-continued

| Compound No. | Structure | IUPAC | Exact mass (g/mol) | LCMS, Found [M + H]+ |
|---|---|---|---|---|
| 628 | 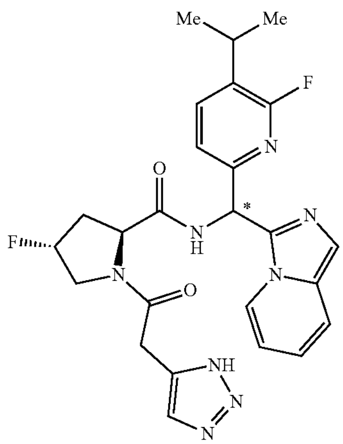 [SMILES: CC(C)c1ccc(C(NC(=O)[C@@H]2C[C@@H](F)CN2C(=O)Cc2cnn[nH]2)c2ncc3ccccn23)nc1F] | (2S,4R)-4-fluoro-N-[(R) or (S)-[6-fluoro-5-(propan-2-yl)pyridin-2-yl]({imidazo[1,5-a]pyridin-3-yl})methyl]-1-[2-(1H-1,2,3-triazol-5-yl)acetyl]pyrrolidine-2-carboxamide (column: DAICEL CHIRALPAK AD-3, first-eluting isomer) | 508.2 | 509.2 |
| 629 | 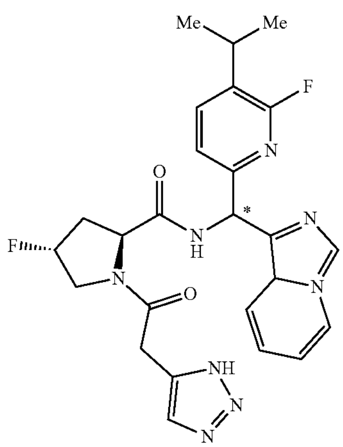 | (2S,4R)-4-fluoro-N-[(S) or (R)-[6-fluoro-5-(propan-2-yl)pyridin-2-yl]({imidazo[1,5-a]pyridin-1-yl})methyl]-1-[2-(1H-1,2,3-triazol-5-yl)acetyl]pyrrolidine-2-carboxamide (column: DAICEL CHIRALPAK AD-3, first-eluting isomer) | 508.2 | 509.1 |
| 630 | 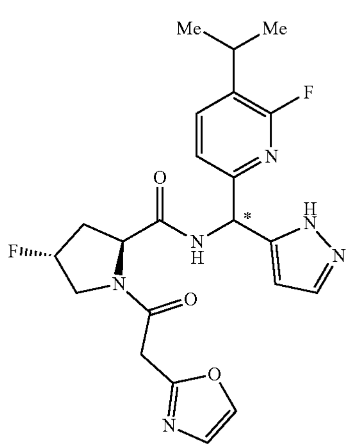 [SMILES: CC(C)c1ccc(C(NC(=O)[C@@H]2C[C@@H](F)CN2C(=O)Cc2ncco2)c2ccn[nH]2)nc1F] | (2S,4R)-4-fluoro-N-[(S) or (R)-[6-fluoro-5-(propan-2-yl)pyridin-2-yl](1H-pyrazol-5-yl)methyl]-1-[2-(1,3-oxazol-2-yl)acetyl]pyrrolidine-2-carboxamide (column: DAICEL CHIRALPAK AD-3, second-eluting isomer) | 458.2 | 459.1 |

TABLE T-14-continued

| Compound No. | Structure | IUPAC | Exact mass (g/mol) | LCMS, Found [M + H]+ |
| --- | --- | --- | --- | --- |
| 631 | 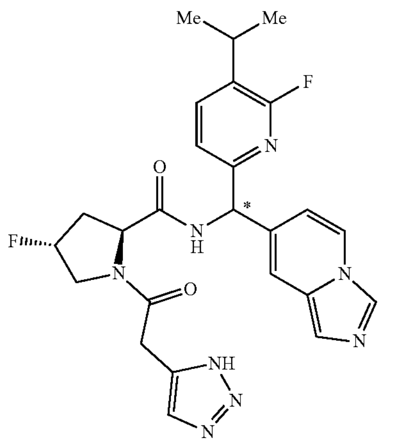 [SMILES: CC(C)c1ccc(C(NC(=O)[C@@H]2C[C@@H](F)CN2C(=O)Cc2cnn[nH]2)c2ccn3cncc3c2)nc1F] | (2S,4R)-4-fluoro-N-[(S) or (R)-[6-fluoro-5-(propan-2-yl)pyridin-2-yl]({imidazo[1,5-a]pyridin-7-yl})methyl]-1-[2-(1H-1,2,3-triazol-5-yl)acetyl]pyrrolidine-2-carboxamide (column: REGIS (s,s) WHELK-O1, first-eluting isomer) | 508.2 | 509.2 |
| 632 | 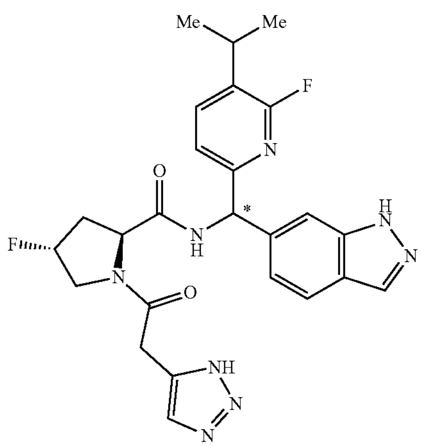 [SMILES: CC(C)c1ccc(C(NC(=O)[C@@H]2C[C@@H](F)CN2C(=O)Cc2cnn[nH]2)c2ccc3cn[nH]c3c2)nc1F] | (2S,4R)-4-fluoro-N-[(S) or (R)-[6-fluoro-5-(propan-2-yl)pyridin-2-yl](1H-indazol-6-yl)methyl]-1-[2-(1H-1,2,3-triazol-5-yl)acetyl]pyrrolidine-2-carboxamide (column: REGIS (s,s) WHELK-O1, first-eluting isomer) | 508.2 | 509.1 |
| 633 | 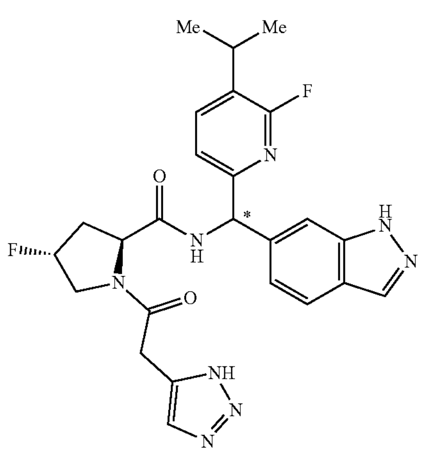 [SMILES: CC(C)c1ccc(C(NC(=O)[C@@H]2C[C@@H](F)CN2C(=O)Cc2cnn[nH]2)c2ccc3cn[nH]c3c2)nc1F] | (2S,4R)-4-fluoro-N-[(R) or (S)-[6-fluoro-5-(propan-2-yl)pyridin-2-yl](1H-indazol-6-yl)methyl]-1-[2-(1H-1,2,3-triazol-5-yl)acetyl]pyrrolidine-2-carboxamide (column: REGIS (s,s) WHELK-O1, second-eluting isomer) | 508.2 | 509.3 |

TABLE T-14-continued

| Compound No. | Structure | IUPAC | Exact mass (g/mol) | LCMS, Found [M + H]+ |
|---|---|---|---|---|
| 634 | 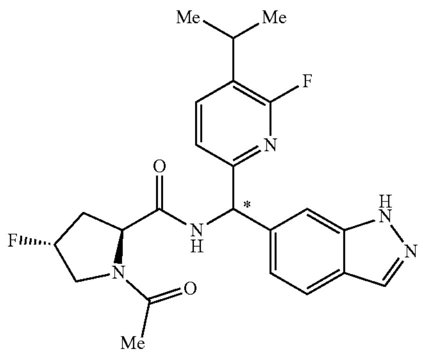 [SMILES: CC(=O)N1C[C@H](F)C[C@H]1C(=O)NC(c1ccc2cn[nH]c2c1)c1ccc(C(C)C)c(F)n1] | (2S,4R)-1-acetyl-4-fluoro-N-[(S) or (R)-[6-fluoro-5-(propan-2-yl)pyridin-2-yl](1H-indazol-6-yl)methyl]pyrrolidine-2-carboxamide (column: REGIS (s,s) WHELK-O1, first-eluting isomer) | 441.2 | 442.1 |
| 635 | 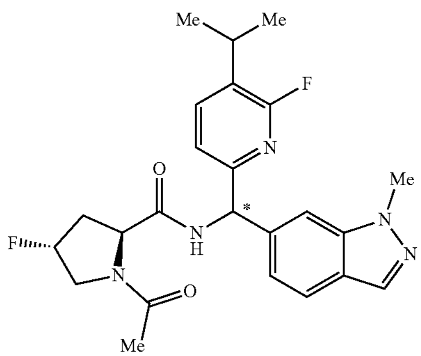 [SMILES: CC(=O)N1C[C@H](F)C[C@H]1C(=O)NC(c1ccc2cnn(C)c2c1)c1ccc(C(C)C)c(F)n1] | (2S,4R)-1-acetyl-4-fluoro-N-[(S) or (R)-[6-fluoro-5-(propan-2-yl)pyridin-2-yl](1-methyl-1H-indazol-6-yl)methyl]pyrrolidine-2-carboxamide (column: REGIS (s,s) WHELK-O1, first-eluting isomer) | 455.2 | 456.2 |
| 636 | 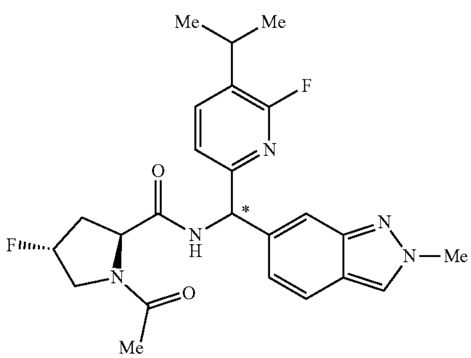 [SMILES: CC(=O)N1C[C@H](F)C[C@H]1C(=O)NC(c1ccc2cn(C)nc2c1)c1ccc(C(C)C)c(F)n1] | (2S,4R)-1-acetyl-4-fluoro-N-[(S) or (R)-[6-fluoro-5-(propan-2-yl)pyridin-2-yl](2-methyl-2H-indazol-6-yl)methyl]pyrrolidine-2-carboxamide (column: REGIS (s,s) WHELK-O1, first-eluting isomer) | 455.2 | 456.1 |
| 637 | 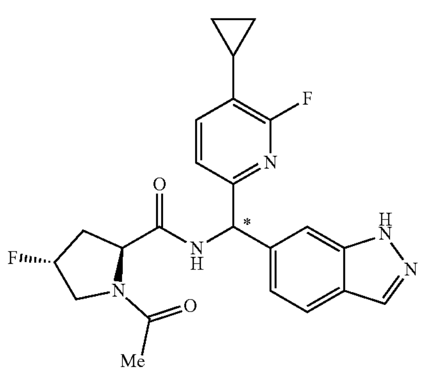 [SMILES: CC(=O)N1C[C@H](F)C[C@H]1C(=O)NC(c1ccc2cn[nH]c2c1)c1ccc(C2CC2)c(F)n1] | (2S,4R)-1-acetyl-N-[(S) or (R)-(5-cyclopropyl-6-fluoropyridin-2-yl)(1H-indazol-6-yl)methyl]-4-fluoropyrrolidine-2-carboxamide (column: REGIS (s,s) WHELK-O1, second-eluting isomer) | 439.1 | 440.1 |

Example S-15: Synthesis of methyl (3-((S)-((2S,4R)-1-(2-(1H-1,2,3-triazol-5-yl)acetyl)-4-fluoropyrrolidine-2-carboxamido)(6-fluoro-5-isopropylpyridin-2-yl)methyl)benzyl)carbamate

Compound 638

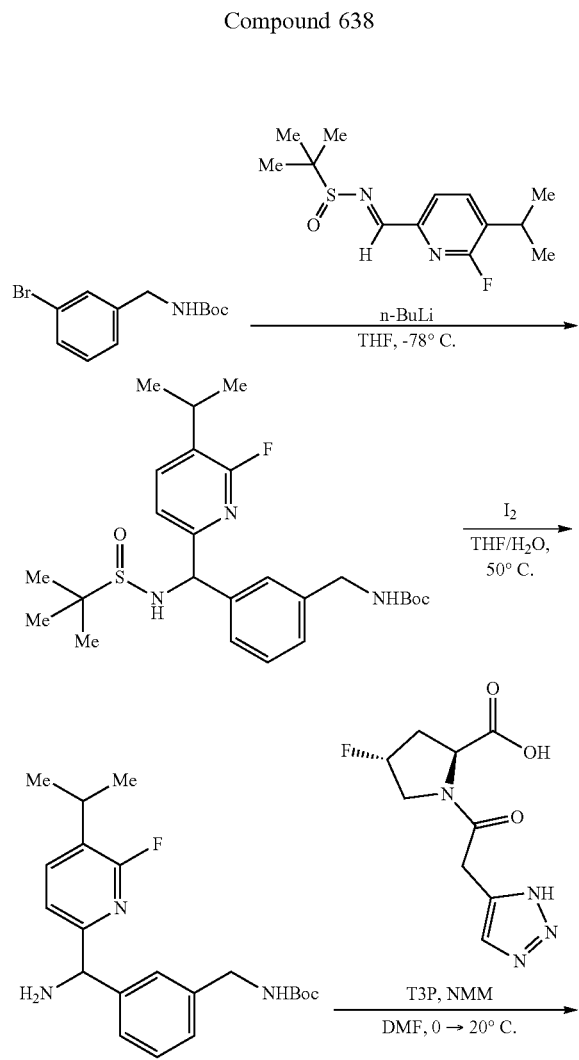

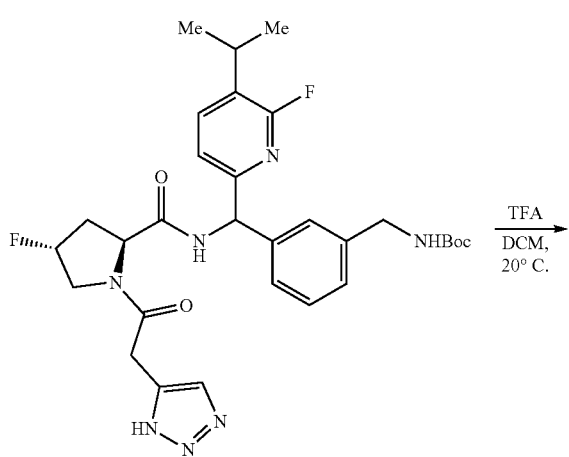

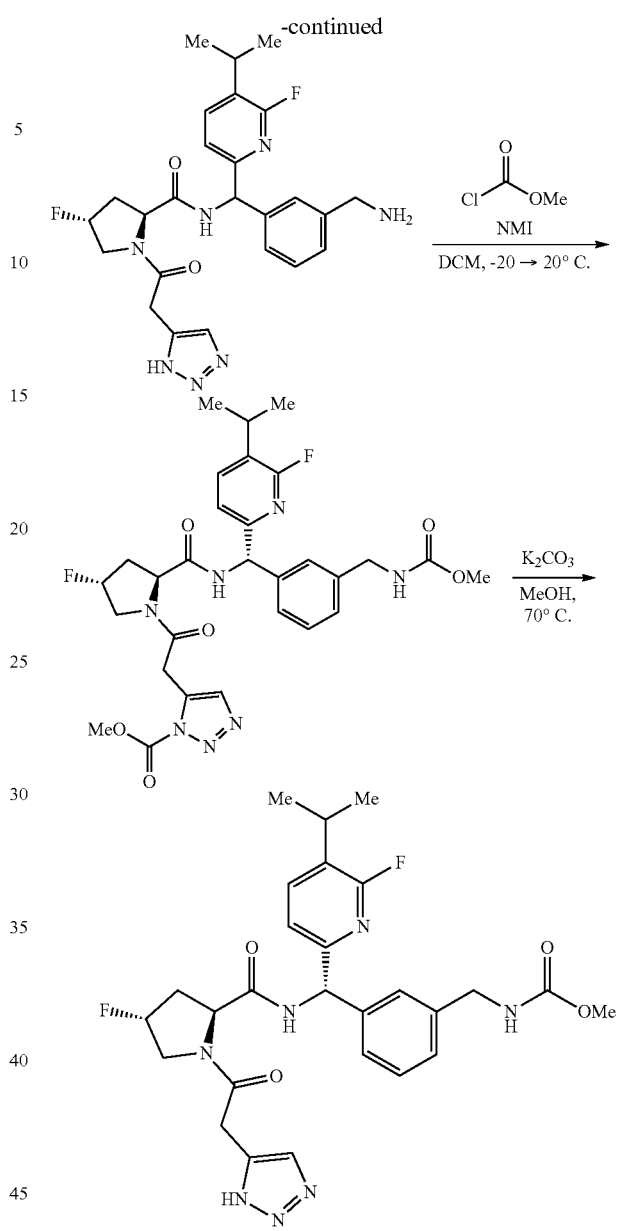

Step a: To a solution of tert-butyl (3-bromobenzyl)carbamate (7.94 g, 27.7 mmol, 1.5 eq) in THF (30 mL) at −78° C. under $N_2$ was added n-BuLi (2.5 M in hexane, 18.5 mL, 2.5 eq), and the resulting mixture was stirred at −78° C. for 0.5 h. (E)-N-(((6-fluoro-5-isopropylpyridin-2-yl)methylene)-2-methylpropane-2-sulfinamide (5 g, 18.5 mmol, 1 eq) in THF (20 mL) was then added at −78° C. The resulting mixture was stirred at −78° C. for 1.5 h. The reaction was then quenched by addition of saturated aq. $NH_4Cl$ solution (20 mL), and the resulting biphasic mixture was extracted with ethyl acetate (3×30 mL), dried over anhydrous $Na_2SO_4$, filtered, and concentrated under reduced pressure. The crude residue obtained was purified by column chromatography to give tert-butyl (3-(((tert-butylsulfinyl)amino)(6-fluoro-5-isopropylpyridin-2-yl)methyl)benzyl)carbamate. LC-MS (ESI): m/z: [M+H]$^+$ calculated for $C_{25}H_{36}FN_3O_3S$: 478.3; found 478.3.

Step b: To a solution of tert-butyl (3-(((tert-butylsulfinyl)amino)(6-fluoro-5-isopropylpyridin-2-yl)methyl)benzyl)

carbamate (6 g, 12.5 mmol, 1 eq) in THF: H$_2$O (5:1, 60 mL) was added I$_2$ (2.55 g, 10.1 mmol, 0.8 eq). The resulting mixture was warmed to 50° C. and stirred for 1 h. The reaction was then quenched with saturated aq. Na$_2$S$_2$O$_3$ solution (100 mL), and the resulting biphasic mixture was extracted with ethyl acetate (3×50 mL), dried over anhydrous Na$_2$SO$_4$, filtered, and concentrated under reduced pressure to give tert-butyl (3-(amino(6-fluoro-5-isopropylpyridin-2-yl)methyl)benzyl)carbamate, which was carried forward to the next step without additional purification. LC-MS (ESI): m/z: [M+H]$^+$ calculated for C$_{21}$H$_{28}$FN$_3$O$_2$: 374.2; found 374.2.

Step c: To a solution of tert-butyl (3-(amino(6-fluoro-5-isopropylpyridin-2-yl)methyl)benzyl)carbamate (2 g, 5.36 mmol, 1 eq) in DMF (20 mL) at 0° C. was added (2S,4R)-1-(2-(1H-1,2,3-triazol-5-yl)acetyl)-4-fluoropyrrolidine-2-carboxylic acid (2.94 g, 8.04 mmol, 80% purity, 1.3 eq), N-methylmorpholine (NMM, 16.1 mmol, 1.7 mL, 3 eq), and T3P (10.7 mmol, 6.3 mL, 50% purity, 2 eq), sequentially. The resulting mixture was warmed to 20° C. and stirred for 16 h. The reaction mixture was then quenched with H$_2$O (50 mL), and the resulting biphasic mixture was extracted with ethyl acetate (3×30 mL). The combined organic extracts were dried over Na$_2$SO$_4$, filtered, and concentrated under reduced pressure. The crude residue obtained was purified by column chromatography to give tert-butyl (3-(((2S,4R)-1-(2-(1H-1,2,3-triazol-5-yl)acetyl)-4-fluoropyrrolidine-2-carboxamido)(6-fluoro-5-isopropylpyridin-2-yl)methyl)benzyl)carbamate. LC-MS (ESI): m/z: [M+H]$^+$ calculated for C$_{30}$H$_{37}$F$_2$N$_7$O$_4$: 598.3; found 598.4.

Step d: To a solution of tert-butyl (3-(((2S,4R)-1-(2-(1H-1,2,3-triazol-5-yl)acetyl)-4-fluoropyrrolidine-2-carboxamido)(6-fluoro-5-isopropylpyridin-2-yl)methyl)benzyl)carbamate (1.2 g, 2.00 mmol, 1 eq) in DCM (12 mL) was added TFA (6.75 mmol, 3 mL, 40 eq). The resulting mixture was stirred at 20° C. for 1 h. The reaction mixture was then adjusted to pH to 5-6 using saturated aq. NaHCO$_3$ solution, and the resulting biphasic mixture was extracted with ethyl acetate (3×50 mL), dried over anhydrous Na$_2$SO$_4$, filtered, and concentrated under reduced pressure. The crude residue obtained was purified by prep-HPLC (column: Phenomenex Luna C$_{18}$) to give (2S,4R)-1-(2-(1H-1,2,3-triazol-5-yl)acetyl)-N—((R)-(3-(aminomethyl)phenyl)(6-fluoro-5-isopropylpyridin-2-yl)methyl)-4-fluoropyrrolidine-2-carboxamide (first-eluting isomer) and (2S,4R)-1-(2-(1H-1,2,3-triazol-5-yl)acetyl)-N—((S)-(3-(aminomethyl)phenyl)(6-fluoro-5-isopropylpyridin-2-yl)methyl)-4-fluoropyrrolidine-2-carboxamide (second-eluting isomer) as separated diastereomers that were carried forward individually. LC-MS (ESI): m/z: [M+H]$^+$ calculated for C$_{25}$H$_{29}$F$_2$N$_7$O$_2$: 498.2; found 498.2.

Step e: To a solution of (2S,4R)-1-(2-(1H-1,2,3-triazol-5-yl)acetyl)-N—((S)-(3-(aminomethyl)phenyl)(6-fluoro-5-isopropylpyridin-2-yl)methyl)-4-fluoropyrrolidine-2-carboxamide (35 mg, 65.5 µmol, 1 eq) in DCM (1 mL) at −20° C. was added N-methylimidazole (NMI, 262 µmol, 20.9 µL, 4 eq), methyl chloroformate (190 mg, 2.01 mmol, 30.7 eq). The resulting mixture was warmed to 25° C. and stirred for 3 h. The reaction was then quenched with H$_2$O (10 mL), and the resulting biphasic mixture was extracted with ethyl acetate (3×15 mL), dried over anhydrous Na$_2$SO$_4$, filtered, and concentrated under reduced pressure to give methyl 5-(2-((2S,4R)-4-fluoro-2-(((S)-(6-fluoro-5-isopropylpyridin-2-yl)(3-(((methoxycarbonyl)amino)methyl)phenyl)methyl)carbamoyl)pyrrolidin-1-yl)-2-oxoethyl)-1H-1,2,3-triazole-1-carboxylate, which was carried forward to the next step without further purification. LC-MS (ESI): m/z: [M+H]$^+$ calculated for C$_{29}$H$_{33}$F$_2$N$_7$O$_6$: 614.3 found 614.3.

Step f: To a solution of methyl 5-(2-((2S,4R)-4-fluoro-2-(((S)-(6-fluoro-5-isopropylpyridin-2-yl)(3-(((methoxycarbonyl)amino)methyl)phenyl)methyl)carbamoyl)pyrrolidin-1-yl)-2-oxoethyl)-1H-1,2,3-triazole-1-carboxylate (36 mg, 58.7 µmol, 1 eq) in MeOH (0.5 mL) was added K$_2$CO$_3$ (16.2 mg, 117 µmol, 2 eq). The resulting mixture was warmed to 70° C. and stirred at for 1 h. The reaction mixture was then filtered, and the filtrate was concentrated under reduced pressure. The crude residue obtained was purified by prep-HPLC to give methyl (3-((S)-((2S,4R)-1-(2-(1H-1,2,3-triazol-5-yl)acetyl)-4-fluoropyrrolidine-2-carboxamido)(6-fluoro-5-isopropylpyridin-2-yl)methyl)benzyl)carbamate.

$^1$H NMR (2.9:1 rotamer ratio, asterisk denotes distinct minor rotamer peaks, obscured peaks not reported, 400 MHz, DMSO-d$_6$) δ 14.75 (br s, 1H), 9.28*(d, J=7.9 Hz, 1H), 8.90 (d, J=8.1 Hz, 1H), 7.92-7.80 (m, 1H), 7.62 (s, 1H), 7.41-7.05 (m, 5H), 6.07*(d, J=7.6 Hz, 1H), 5.95 (d, J=7.8 Hz, 1H), 5.49-5.19 (m, 1H), 4.90*(t, J=8.0 Hz, 1H), 4.62 (t, J=8.3 Hz, 1H), 4.22-3.62 (m, 5H), 3.54-3.49 (m, 3H), 3.09-2.99 (m, 1H), 2.16-1.91 (m, 1H), 1.24-1.12 (m, 6H). LC-MS (ESI): m/z: [M+H]$^+$ calculated for C$_{27}$H$_{31}$F$_2$N$_7$O$_4$: 556.2; found 556.3.

The following compounds in Table T-15 were synthesized using procedures similar to Compound 638 using the appropriate starting materials.

TABLE T-15

| Compound No. | Structure | IUPAC | Exact mass (g/mol) | LCMS, Found [M + H]$^+$ |
|---|---|---|---|---|
| 639 | 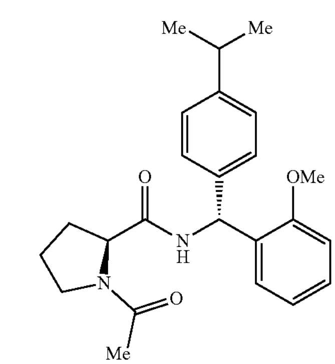 [SMILES: COc1ccccc1[C@H](NC(=O)[C@@H]1CCCN1C(C)=O)c1ccc(C(C)C)cc1] | (2S)-1-acetyl-N-[(R)-(2-methoxyphenyl)[4-(propan-2-yl)phenyl]methyl]pyrrolidine-2-carboxamide | 394.2 | 395.3 |

TABLE T-15-continued

| Compound No. | Structure | IUPAC | Exact mass (g/mol) | LCMS, Found [M + H]+ |
|---|---|---|---|---|
| 640 | 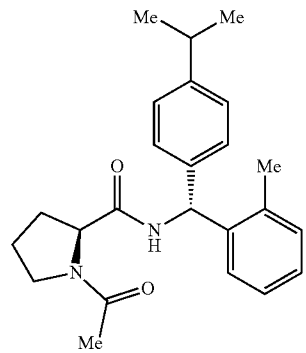 [SMILES: CC(=O)N1CCC[C@H]1C(=O)N[C@H](c1ccc(C(C)C)cc1)c1ccccc1C] | (2S)-1-acetyl-N-[(R)-(2-methylphenyl)[4-(propan-2-yl)phenyl]methyl]pyrrolidine-2-carboxamide | 378.2 | 379.3 |
| 641 | 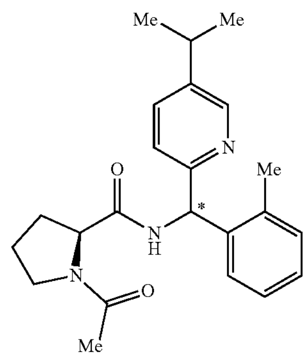 [SMILES: CC(=O)N1CCC[C@H]1C(=O)NC(c1ccc(C(C)C)cn1)c1ccccc1C] | (2S)-1-acetyl-N-[(S) or (R)-(2-methylphenyl)[5-(propan-2-yl)pyridin-2-yl]methyl]pyrrolidine-2-carboxamide (column: REGIS (s,s) WHELK-O1, first-eluting isomer) | 379.2 | 380.2 |
| 642 | 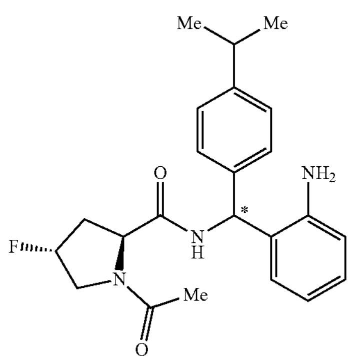 [SMILES: CC(=O)N1C[C@H](F)C[C@H]1C(=O)NC(c1ccc(C(C)C)cc1)c1ccccc1N] | (2S,4R)-1-acetyl-N-[(R) or (S)-(2-aminophenyl)[4-(propan-2-yl)phenyl]methyl]-4-fluoropyrrolidine-2-carboxamide (column: DAICEL CHIRALPAK AD-3, first-eluting isomer) | 397.2 | 398.1 |
| 643 | 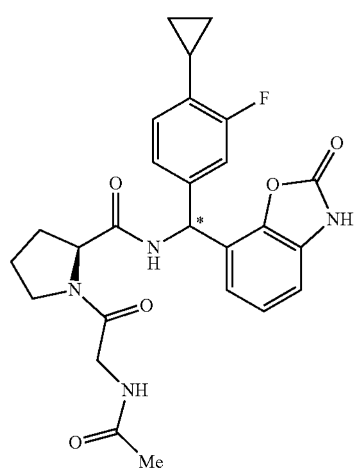 [SMILES: CC(=O)NCC(=O)N1CCC[C@H]1C(=O)NC(c1ccc(C2CC2)c(F)c1)c1cccc2[nH]c(=O)oc12] | (2S)-N-[(R) or (S)-(4-cyclopropyl-3-fluorophenyl)(2-oxo-2,3-dihydro-1,3-benzoxazol-7-yl)methyl]-1-(2-acetamidoacetyl)pyrrolidine-2-carboxamide (column: REGIS (s,s) WHELK-O1, second-eluting isomer) | 494.2 | 495.2 |

TABLE T-15-continued

| Compound No. | Structure | IUPAC | Exact mass (g/mol) | LCMS, Found [M + H]+ |
| --- | --- | --- | --- | --- |
| 644 | 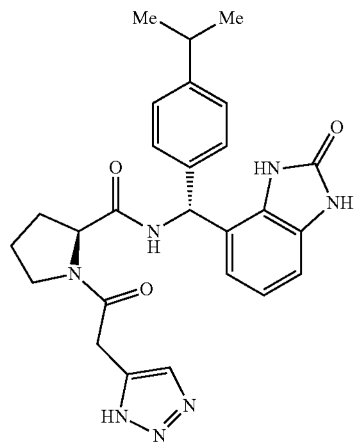 [SMILES: CC(C)c1ccc([C@@H](NC(=O)[C@@H]2CCCN2C(=O)Cc2cnn[nH]2)c2cccc3[nH]c(=O)[nH]c23)cc1] | (2S)-N-[(R)-(2-oxo-2,3-dihydro-1H-1,3-benzodiazol-4-yl)[4-(propan-2-yl)phenyl]methyl]-1-[2-(1H-1,2,3-triazol-5-yl)acetyl]pyrrolidine-2-carboxamide | 487.2 | 488.1 |
| 645 | 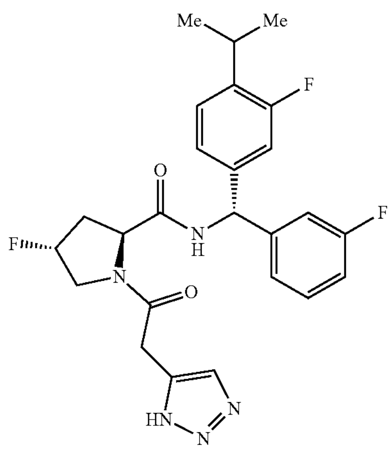 [SMILES: CC(C)c1ccc([C@@H](NC(=O)[C@@H]2C[C@@H](F)CN2C(=O)Cc2cnn[nH]2)c2cccc(F)c2)cc1F] | (2S,4R)-4-fluoro-N-[(S)-[3-fluoro-4-(propan-2-yl)phenyl](3-fluoropheny)methyl]-1-[2-(1H-1,2,3-triazol-5-yl)acetyl]pyrrolidine-2-carboxamide | 485.2 | 486.1 |
| 646 | 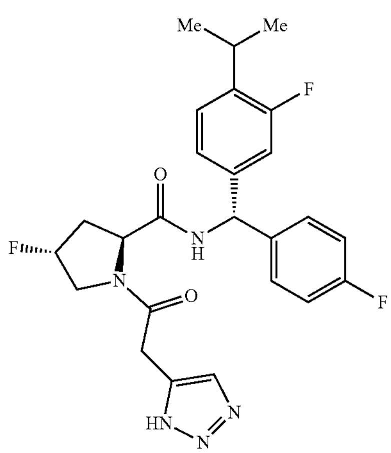 [SMILES: CC(C)c1ccc([C@@H](NC(=O)[C@@H]2C[C@@H](F)CN2C(=O)Cc2cnn[nH]2)c2ccc(F)cc2)cc1F] | (2S,4R)-4-fluoro-N-[(S)-[3-fluoro-4-(propan-2-yl)phenyl](4-fluorophenyl)methyl]-1-[2-(1H-1,2,3-triazol-5-yl)acetyl]pyrrolidine-2-carboxamide | 485.2 | 486.1 |

TABLE T-15-continued

| Compound No. | Structure | IUPAC | Exact mass (g/mol) | LCMS, Found [M + H]+ |
|---|---|---|---|---|
| 647 | 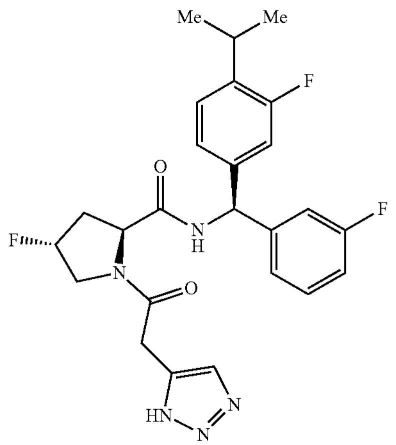 [SMILES: CC(C)c1ccc([C@H](NC(=O)[C@@H]2C[C@@H](F)CN2C(=O)Cc2cnn[nH]2)c2cccc(F)c2)cc1F] | (2S,4R)-4-fluoro-N-[(R)-[3-fluoro-4-(propan-2-yl)phenyl](3-fluorophenyl)methyl]-1-[2-(1H-1,2,3-triazol-5-yl)acetyl]pyrrolidine-2-carboxamide | 485.2 | 486.1 |
| 648 | 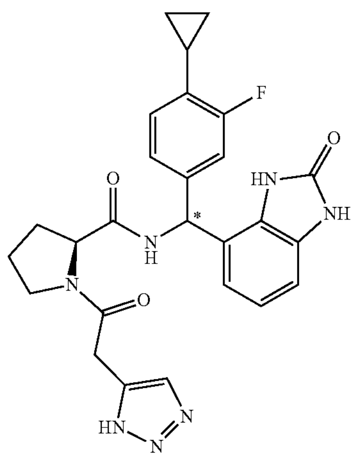 [SMILES: O=C(NC(c1ccc(C2CC2)c(F)c1)c1cccc2[nH]c(=O)[nH]c12)[C@@H]1CCCN1C(=O)Cc1cnn[nH]1] | (2S)-N-[(S)-(4-cyclopropyl-3-fluorophenyl)(2-oxo-2,3-dihydro-1H-1,3-benzodiazol-4-yl)methyl]-1-[2-(1H-1,2,3-triazol-5-yl)acetyl]pyrrolidine-2-carboxamide (column: REGIS (s,s) WHELK-O1, second-eluting isomer) | 503.2 | 504.1 |
| 649 | 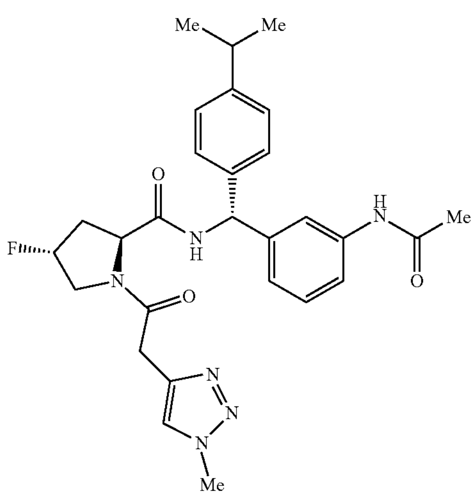 [SMILES: CC(=O)Nc1cccc([C@H](NC(=O)[C@@H]2C[C@@H](F)CN2C(=O)Cc2cn(C)nn2)c2ccc(C(C)C)cc2)c1] | (2S,4R)-N-[(R)-(3-acetamidophenyl)[4-(propan-2-yl)phenyl]methyl]-4-fluoro-1-[2-(1-methyl-1H-1,2,3-triazol-4-yl)acetyl]pyrrolidine-2-carboxamide | 520.3 | 521.2 |

| Compound No. | Structure | IUPAC | Exact mass (g/mol) | LCMS, Found [M + H]+ |
|---|---|---|---|---|
| 650 | 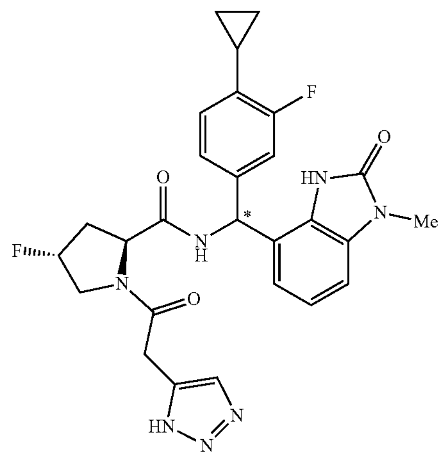 [SMILES: Cn1c(=O)[nH]c2c(C(NC(=O)[C@@H]3C[C@@H](F)CN3C(=O)Cc3cnn[nH]3)c3ccc(C4CC4)c(F)c3)cccc21] | (2S,4R)-N-[(R) or (S)-(4-cyclopropyl-3-fluorophenyl)(1-methyl-2-oxo-2,3-dihydro-1H-1,3-benzodiazol-4-yl)methyl]-4-fluoro-1-[2-(1H-1,2,3-triazol-5-yl)acetyl]pyrrolidine-2-carboxamide (column: REGIS (s,s) WHELK-O1, second-eluting isomer) | 535.2 | 536.1 |
| 651 | 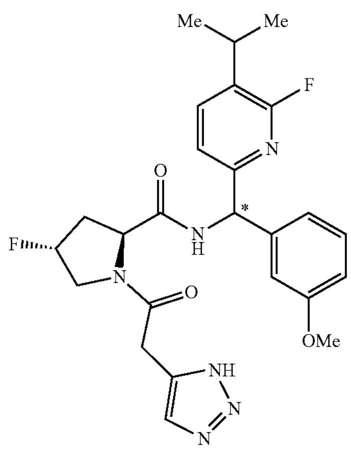 [SMILES: COc1cccc(C(NC(=O)[C@@H]2C[C@@H](F)CN2C(=O)Cc2cnn[nH]2)c2ccc(C(C)C)c(F)n2)c1] | (2S,4R)-4-fluoro-N-[(S) or (R)-[6-fluoro-5-(propan-2-yl)pyridin-2-yl](3-methoxyphenyl)methyl]-1-[2-(1H-1,2,3-triazol-5-yl)acetyl]pyrrolidine-2-carboxamide (column: REGIS (s,s) WHELK-O1, first-eluting isomer) | 498.2 | 499.1 |
| 652 | 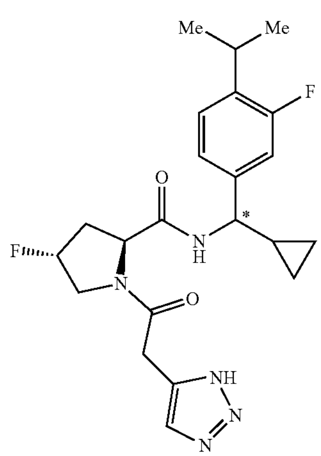 [SMILES: CC(C)c1ccc(C(NC(=O)[C@@H]2C[C@@H](F)CN2C(=O)Cc2cnn[nH]2)C2CC2)cc1F] | (2S,4R)-N-[(S) or (R)-cyclopropyl[3-fluoro-4-(propan-2-yl)phenyl]methyl]-4-fluoro-1-[2-(1H-1,2,3-triazol-5-yl)acetyl]pyrrolidine-2-carboxamide (column: DAICEL CHIRALPAK IC-3, second-eluting isomer) | 431.2 | 432.3 |

TABLE T-15-continued

| Compound No. | Structure | IUPAC | Exact mass (g/mol) | LCMS, Found [M + H]+ |
|---|---|---|---|---|
| 653 | 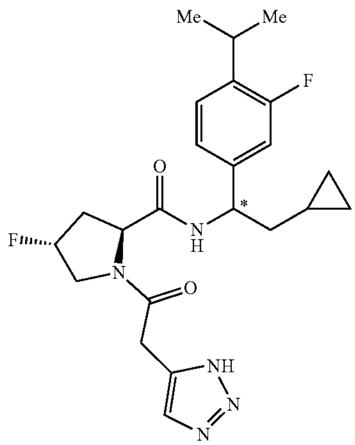 [SMILES: CC(C)c1ccc(C(CC2CC2)NC(=O)[C@@H]2C[C@@H](F)CN2C(=O)Cc2cnn[nH]2)cc1F] | (2S,4R)-N-[(1S) or (1R)-2-cyclopropyl-1-[3-fluoro-4-(propan-2-yl)phenyl]ethyl]-4-fluoro-1-[2-(1H-1,2,3-triazol-5-yl)acetyl]pyrrolidine-2-carboxamide (column: REGIS (s,s) WHELK-O1, second-eluting isomer) | 445.2 | 446.1 |
| 654 | 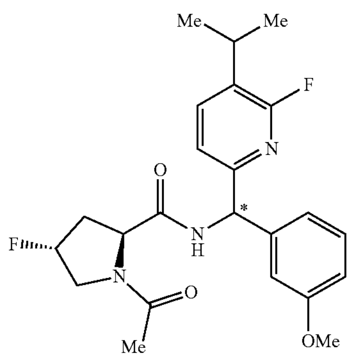 [SMILES: COc1cccc(C(NC(=O)[C@@H]2C[C@@H](F)CN2C(C)=O)c2ccc(C(C)C)c(F)n2)c1] | (2S,4R)-1-acetyl-4-fluoro-N-[(S) or (R)-[6-fluoro-5-(propan-2-yl)pyridin-2-yl](3-methoxyphenyl)methyl]pyrrolidine-2-carboxamide (column: DAICEL CHIRALPAK IC-3, first-eluting isomer) | 431.2 | 432.1 |
| 655 | 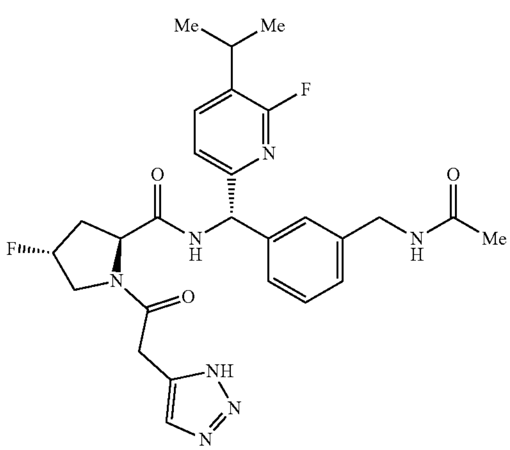 [SMILES: CC(=O)NCc1cccc([C@H](NC(=O)[C@@H]2C[C@@H](F)CN2C(=O)Cc2cnn[nH]2)c2ccc(C(C)C)c(F)n2)c1] | (2S,4R)-N-[(S)-[3-(acetamidomethyl)phenyl][6-fluoro-5-(propan-2-yl)pyridin-2-yl]methyl]-4-fluoro-1-[2-(1H-1,2,3-triazol-5-yl)acetyl]pyrrolidine-2-carboxamide | 539.2 | 540.3 |

TABLE T-15-continued

| Compound No. | Structure | IUPAC | Exact mass (g/mol) | LCMS, Found [M + H]+ |
|---|---|---|---|---|
| 656 | 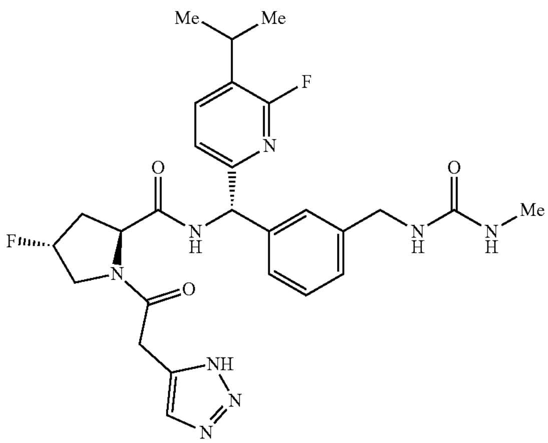 [SMILES: CNC(=O)NCc1cccc([C@H](NC(=O)[C@@H]2C[C@@H](F)CN2C(=O)Cc2cnn[nH]2)c2ccc(C(C)C)c(F)n2)c1] | (2S,4R)-4-fluoro-N-[(S)-[6-fluoro-5-(propan-2-yl)pyridin-2-yl](3-{[(methylcarbamoyl)amino]methyl}phenyl)methyl]-1-[2-(1H-1,2,3-triazol-5-yl)acetyl]pyrrolidine-2-carboxamide | 554.3 | 555.2 |
| 657 | 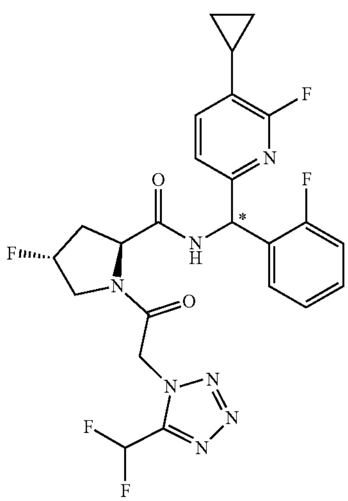 [SMILES: O=C(NC(c1ccc(C2CC2)c(F)n1)c1ccccc1F)[C@@H]1C[C@@H](F)CN1C(=O)Cn1nnnc1C(F)F] | (2S,4R)-N-[(S) or (R)-(5-cyclopropyl-6-fluoropyridin-2-yl)(2-fluorophenyl)methyl]-1-{2-[5-(difluoromethyl)-1H-1,2,3,4-tetrazol-1-yl]acetyl}-4-fluoropyrrolidine-2-carboxamide (column: REGIS (s,s) WHELK-O1, first-eluting isomer) | 535.2 | 536.3 |
| 658 | 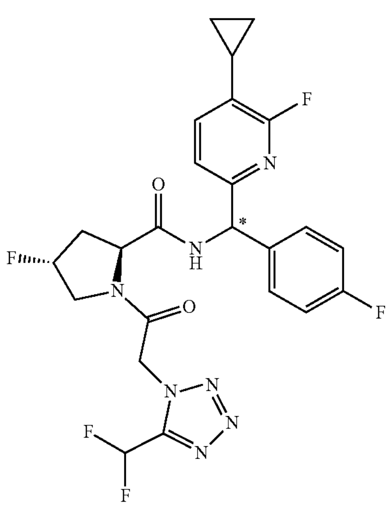 [SMILES: O=C(NC(c1ccc(F)cc1)c1ccc(C2CC2)c(F)n1)[C@@H]1C[C@@H](F)CN1C(=O)Cn1nnnc1C(F)F] | (2S,4R)-N-[(S) or (R)-(5-cyclopropyl-6-fluoropyridin-2-yl)(4-fluorophenyl)methyl]-1-{2-[5-(difluoromethyl)-1H-1,2,3,4-tetrazol-1-yl]acetyl}-4-fluoropyrrolidine-2-carboxamide (column: DAICEL CHIRALPAK AD-3, second-eluting isomer) | 535.2 | 536.2 |

Example S-16: Synthesis of (2S,4R)-1-(((1H-1,2,3-triazol-5-yl)methyl)sulfonyl)-N—((S)-(3,5-difluoro-4-isopropylphenyl)(phenyl)methyl)-4-fluoropyrrolidine-2-carboxamide Compound 659

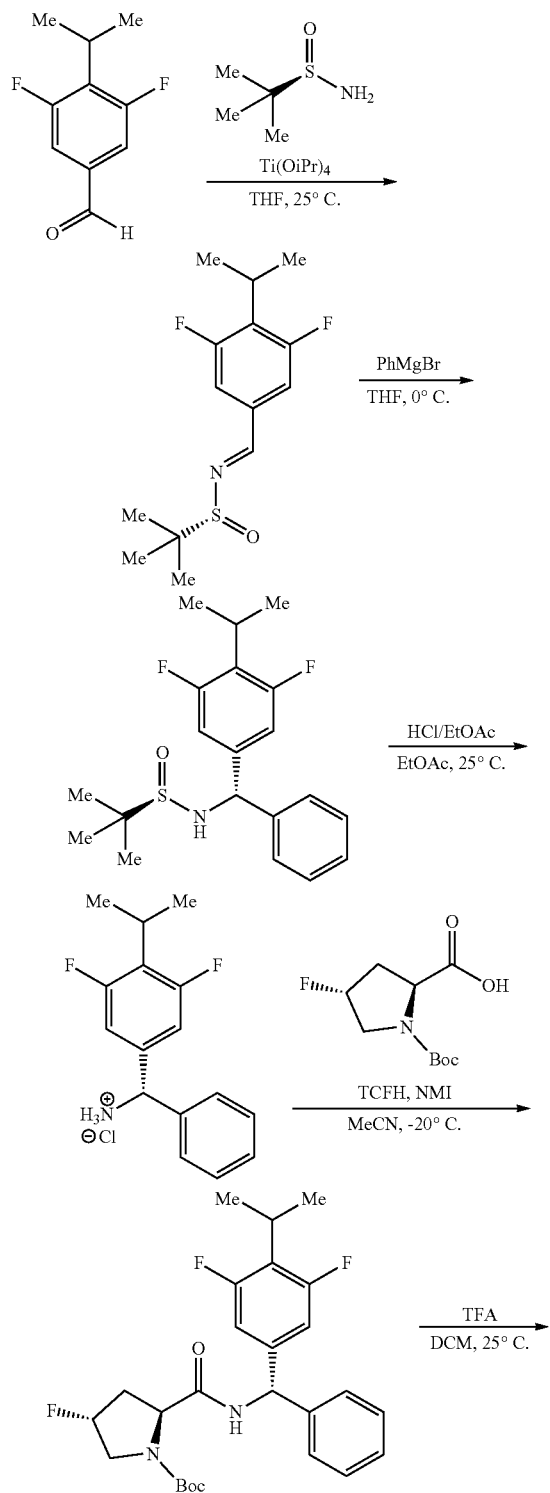

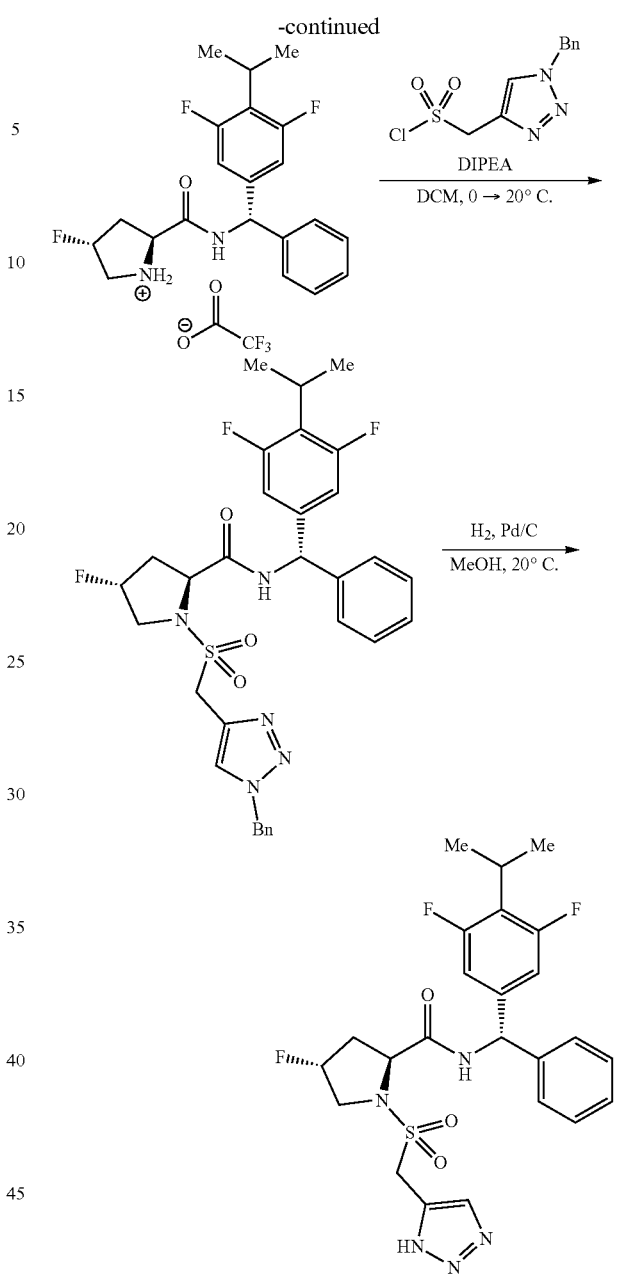

Step a: To a solution of 3,5-difluoro-4-isopropylbenzaldehyde (1.05 g, 5.70 mmol, 1 eq) and (R)-2-methylpropane-2-sulfinamide (1.04 g, 8.55 mmol, 1.5 eq) in THF (20 mL) was added Ti(Oi-Pr)$_4$ (3.24 g, 11.4 mmol, 3.37 mL, 2 eq). The resulting mixture was stirred at 25° C. for 15 h. The reaction mixture was then quenched with water (20 mL). The resulting biphasic mixture was filtered, and the filtrate was extracted with EtOAc (2×50 mL). The combined organic extracts were washed with brine (2×30 mL), dried over anhydrous Na$_2$SO$_4$, filtered, and concentrated under reduced pressure. The crude residue obtained was purified by column chromatography to give (R,E)-N-(3,5-difluoro-4-isopropylbenzylidene)-2-methylpropane-2-sulfinamide, which was carried forward to the next step without further purification or characterization.

Step b: To a solution of (R,E)-N-(3,5-difluoro-4-isopropylbenzylidene)-2-methylpropane-2-sulfinamide (1.4 g, 4.87 mmol, 1 eq) in THF (15 mL) at 0° C. was added phenylmagnesium bromide (3 M in diethyl ether, 2.44 mL, 1.5 eq). The resulting mixture was stirred at 0° C. for 1 h. The reaction mixture was then quenched by addition of saturated aq. NH$_4$C$_1$ solution (15 mL), and the resulting biphasic mixture was extracted with EtOAc (2×30 mL). The combined organic extracts were washed with brine (2×20 mL), dried over anhydrous Na$_2$SO$_4$, filtered, and concentrated under reduced pressure. The crude residue obtained was purified by column chromatography to give (R)—N—((S)-(3,5-difluoro-4-isopropylphenyl)(phenyl)methyl)-2-methylpropane-2-sulfinamide. LC-MS (ESI): m/z: [M+H]$^+$ calculated for C$_{20}$H$_{25}$F$_2$NOS: 366.2; found 366.1.

Step c: To a solution of (R)—N—((S)-(3,5-difluoro-4-isopropylphenyl)(phenyl)methyl)-2-methylpropane-2-sulfinamide (540 mg, 1.48 mmol, 1 eq) in EtOAc (10 mL) was added HCl/EtOAc (4 M, 10 mL). The resulting mixture was stirred at 25° C. for 0.5 h. The reaction mixture was then filtered, and the solid was washed with petroleum ether to give (S)-(3,5-difluoro-4-isopropylphenyl)(phenyl)methanaminium chloride, which was carried forward to the next step without further purification or characterization.

Step d: To a solution of (S)-(3,5-difluoro-4-isopropylphenyl)(phenyl)methanaminium chloride (0.22 g, 739 µmol, 1 eq) and (2S,4R)-1-(tert-butoxycarbonyl)-4-fluoropyrrolidine-2-carboxylic acid (190 mg, 813 µmol, 1.1 eq) in MeCN (10 mL) at −20° C. was added N-methylimidazole (NMI, 303 mg, 3.69 mmol, 294 µL, 5 eq) and chloro-N,N,N',N'-tetramethylformamidinium hexafluorophosphate (TCFH, 228 mg, 813 µmol, 1.1 eq). The resulting mixture was stirred at −20° C. for 1 h. The reaction mixture was then quenched by addition of ice-water (5 mL) at −20° C., and the resulting biphasic mixture was adjusted to pH=5 with aqueous HCl (4 N). The resulting biphasic mixture was then extracted with EtOAc (2×20 mL). The combined organic extracts were washed with brine (2×10 mL), dried over anhydrous Na$_2$SO$_4$, filtered, and concentrated under reduced pressure. The crude residue obtained was purified by column chromatography to give tert-butyl (2S,4R)-2-(((S)-(3,5-difluoro-4-isopropylphenyl)(phenyl)methyl)carbamoyl)-4-fluoropyrrolidine-1-carboxylate. LC-MS (ESI): m/z: [M+H]$^+$ calculated for C$_{26}$H$_{31}$F$_3$N$_2$O$_3$: 477.2; found 477.3.

Step e: To a solution of tert-butyl (2S,4R)-2-(((S)-(3,5-difluoro-4-isopropylphenyl)(phenyl)methyl)carbamoyl)-4-fluoropyrrolidine-1-carboxylate (0.35 g, 734 µmol, 1 eq) in DCM (10 mL) was added TFA (3.08 g, 27.0 mmol, 2 mL, 36.8 eq). The mixture was stirred at 25° C. for 1 h. The mixture was then concentrated under reduced pressure to give (2S,4R)-2-(((S)-(3,5-difluoro-4-isopropylphenyl)(phenyl)methyl)carbamoyl)-4-fluoropyrrolidin-1-ium 2,2,2-trifluoroacetate. LC-MS (ESI): m/z: [M+H]$^+$ calculated for C$_{21}$H$_{23}$F$_3$N$_2$O: 377.2; found 377.1.

Step f: To a mixture of (2S,4R)-2-(((S)-(3,5-difluoro-4-isopropylphenyl)(phenyl)methyl)carbamoyl)-4-fluoropyrrolidin-1-ium 2,2,2-trifluoroacetate (100 mg, 265 µmol, 1 eq) and DIPEA (343 mg, 2.66 mmol, 10 eq) in DCM (5 mL) at 0° C. was added (1-benzyl-1H-1,2,3-triazol-4-yl)methanesulfonyl chloride (216 mg, 797 µmol, 3 eq) in portions. The resulting mixture was warmed to 20° C. and stirred for 3 h. The reaction mixture was then poured into ice-water (30 mL) and stirred for 10 min. The resulting biphasic mixture was extracted with ethyl acetate (3×30 mL). The combined organic extracts were washed with brine (20 mL), dried over anhydrous Na$_2$SO$_4$, filtered, and concentrated under reduced pressure. The crude residue obtained was purified by prep-HPLC to give (2S,4R)-1-(((1-benzyl-1H-1,2,3-triazol-4-yl)methyl)sulfonyl)-N—((S)-(3,5-difluoro-4-isopropylphenyl)(phenyl)methyl)-4-fluoropyrrolidine-2-carboxamide. LC-MS (ESI): m/z: [M+H]$^+$ calculated for C$_{31}$H$_{32}$F$_3$N$_5$O$_3$S: 612.2; found 612.3.

Step g: To a solution of (2S,4R)-1-(((1-benzyl-1H-1,2,3-triazol-4-yl)methyl)sulfonyl)-N—((S)-(3,5-difluoro-4-isopropylphenyl)(phenyl)methyl)-4-fluoropyrrolidine-2-carboxamide (20 mg, 32.7 µmol, 1 eq) in MeOH (50 mL) was added Pd/C (100 mg, 10% purity). The resulting suspension was degassed under vacuum and purged with H$_2$. The resulting mixture was stirred under H$_2$ (50 psi) at 20° C. for 16 h. The reaction mixture was then filtered, and the filtrate was concentrated under reduced pressure. The crude residue obtained was purified by prep-HPLC to give (2S,4R)-1-(((1H-1,2,3-triazol-5-yl)methyl)sulfonyl)-N—((S)-(3,5-difluoro-4-isopropylphenyl)(phenyl)methyl)-4-fluoropyrrolidine-2-carboxamide. $^1$H NMR (400 MHz, DMSO-d$_6$) δ 15.04 (br s, 1H), 9.05 (d, J=8.1 Hz, 1H), 7.79 (br s, 1H), 7.40-7.23 (m, 5H), 6.96 (d, J=9.4 Hz, 2H), 6.11 (d, J=8.0 Hz, 1H), 5.32 (d, J=52.6 Hz, 1H), 4.68-4.48 (m, 3H), 3.79-3.66 (m, 1H), 3.51 (dd, J=39.0, 12.6 Hz, 1H), 3.29-3.19 (m, 1H), 2.75-2.54 (m, 1H), 2.18-1.97 (m, 1H), 1.25 (d, J=7.1 Hz, 6H). LC-MS (ESI): m/z: [M+H]$^+$ calculated for C$_{24}$H$_{26}$F$_3$N$_5$O$_3$S: 522.2; found 522.1.

The following compounds in Table T-16 were synthesized using procedures similar to Compound 659 using the appropriate starting materials.

TABLE T-16

| Compound No. | Structure | IUPAC | Exact mass (g/mol) | LCMS, Found [M + H]$^+$ |
|---|---|---|---|---|
| 660 | 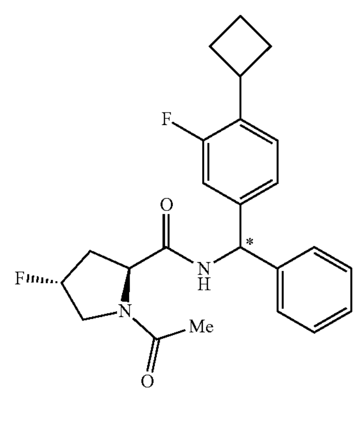 [SMILES: CC(=O)N1C[C@H](F)C[C@H]1C(=O)NC(c1ccccc1)c1ccc(C2CCC2)c(F)c1] | (2S,4R)-1-acetyl-N-[(S) or (R)-(4-cyclobutyl-3-fluorophenyl)(phenyl)methyl]-4-fluoropyrrolidine-2-carboxamide (column: DAICEL CHIRALPAK AS-3, first-eluting isomer) | 412.2 | 413.2 |

TABLE T-16-continued

| Compound No. | Structure | IUPAC | Exact mass (g/mol) | LCMS, Found [M + H]+ |
|---|---|---|---|---|
| 661 | 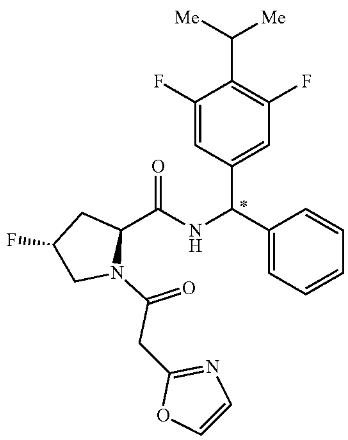 [SMILES: CC(C)c1c(F)cc(C(NC(=O)[C@@H]2C[C@@H](F)CN2C(=O)Cc2ncco2)c2ccccc2)cc1F] | (2S,4R)-N-[(S) or (R)-[3,5-difluoro-4-(propan-2-yl)phenyl](phenyl)methyl]-4-fluoro-1-[2-(1,3-oxazol-2-yl)acetyl]pyrrolidine-2-carboxamide (column: CHIRALCEL OD-3, first-eluting isomer) | 485.2 | 486.1 |
| 662 | 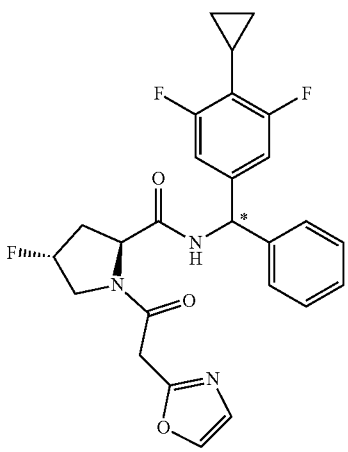 [SMILES: O=C(NC(c1ccccc1)c1cc(F)c(C2CC2)c(F)c1)[C@@H]1C[C@@H](F)CN1C(=O)Cc1ncco1] | (2S,4R)-N-[(S)-(4-cyclopropyl-3,5-difluorophenyl)(phenyl)methyl]-4-fluoro-1-[2-(1,3-oxazol-2-yl)acetyl]pyrrolidine-2-carboxamide (column: CHIRALCEL OD-3, first-eluting isomer) | 483.2 | 484.1 |
| 663 | 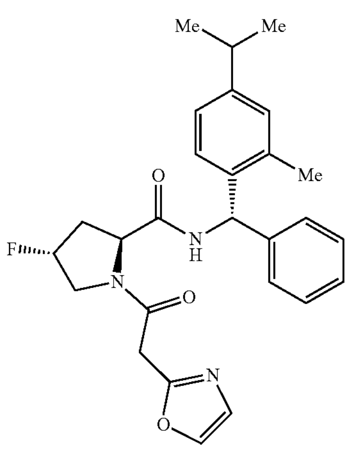 [SMILES: Cc1cc(C(C)C)ccc1[C@@H](NC(=O)[C@@H]1C[C@@H](F)CN1C(=O)Cc1ncco1)c1ccccc1] | (2S,4R)-4-fluoro-N-[(S)-[2-methyl-4-(propan-2-yl)phenyl](phenyl)methyl]-1-[2-(1,3-oxazol-2-yl)acetyl]pyrrolidine-2-carboxamide | 463.2 | 486.1 (M + Na) |

TABLE T-16-continued

| Compound No. | Structure | IUPAC | Exact mass (g/mol) | LCMS, Found [M + H]+ |
| --- | --- | --- | --- | --- |
| 664 | 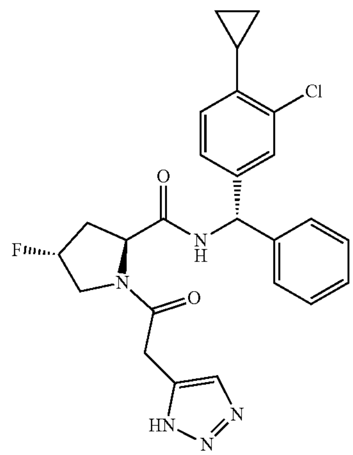 [SMILES: O=C(N[C@@H](c1ccccc1)c1ccc(C2CC2)c(Cl)c1)[C@@H]1C[C@@H](F)CN1C(=O)Cc1cnn[nH]1] | (2S,4R)-N-[(S)-(3-chloro-4-cyclopropylphenyl)(phenyl)methyl]-4-fluoro-1-[2-(1H-1,2,3-triazol-5-yl)acetyl]pyrrolidine-2-carboxamide | 481.2 | 482.2 |
| 665 | 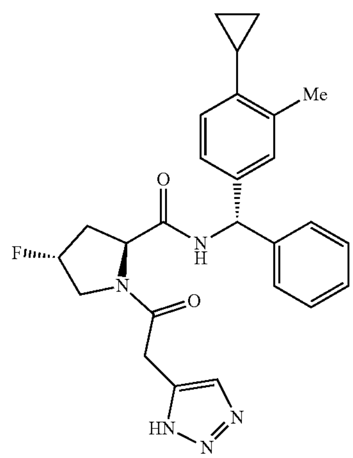 [SMILES: Cc1cc([C@@H](NC(=O)[C@@H]2C[C@@H](F)CN2C(=O)Cc2cnn[nH]2)c2ccccc2)ccc1C1CC1] | (2S,4R)-N-[(S)-(4-cyclopropyl-3-methylphenyl)(phenyl)methyl]-4-fluoro-1-[2-(1H-1,2,3-triazol-5-yl)acetyl]pyrrolidine-2-carboxamide | 461.2 | 462.3 |
| 666 | 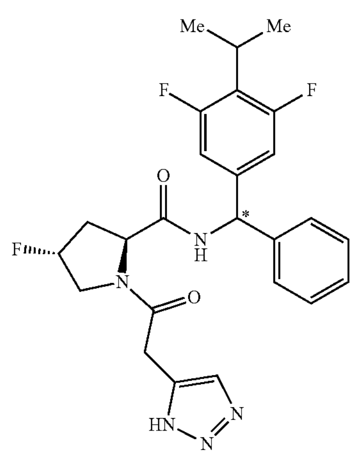 [SMILES: CC(C)c1c(F)cc(C(NC(=O)[C@@H]2C[C@@H](F)CN2C(=O)Cc2cnn[nH]2)c2ccccc2)cc1F] | (2S,4R)-N-[(R) or (S)-[3,5-difluoro-4-(propan-2-yl)phenyl](phenyl)methyl]-4-fluoro-1-[2-(1H-1,2,3-triazol-5-yl)acetyl]pyrrolidine-2-carboxamide | 485.2 | 486.1 |

TABLE T-16-continued

| Compound No. | Structure | IUPAC | Exact mass (g/mol) | LCMS, Found [M + H]+ |
|---|---|---|---|---|
| 667 | 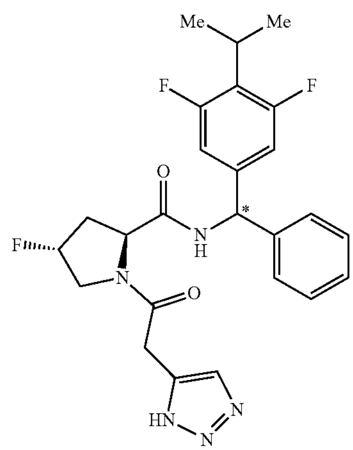 [SMILES: CC(C)c1c(F)cc(C(NC(=O)[C@@H]2C[C@@H](F)CN2C(=O)Cc2cnn[nH]2)c2ccccc2)cc1F] | (2S,4R)-N-[(S) or (R)-[3,5-difluoro-4-(propan-2-yl)phenyl](phenyl)methyl]-4-fluoro-1-[2-(1H-1,2,3-triazol-5-yl)acetyl]pyrrolidine-2-carboxamide | 485.2 | 486.1 |
| 668 | 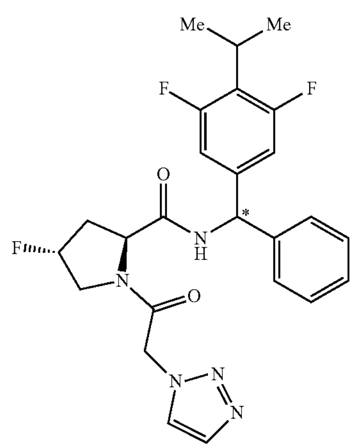 [SMILES: CC(C)c1c(F)cc(C(NC(=O)[C@@H]2C[C@@H](F)CN2C(=O)Cn2ccnn2)c2ccccc2)cc1F] | (2S,4R)-N-[(S) or (R)-[3,5-difluoro-4-(propan-2-yl)phenyl](phenyl)methyl]-4-fluoro-1-[2-(1H-1,2,3-triazol-1-yl)acetyl]pyrrolidine-2-carboxamide (column: CHIRALCEL OD-3, first-eluting isomer) | 485.2 | 486.1 |
| 669 | 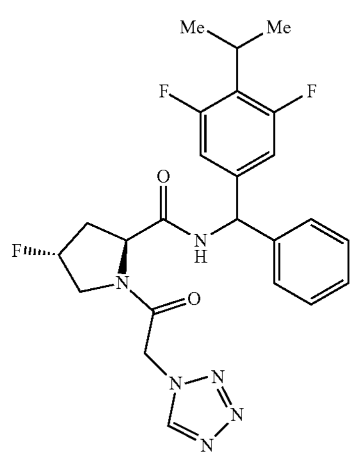 [SMILES: CC(C)c1c(F)cc(C(NC(=O)[C@@H]2C[C@@H](F)CN2C(=O)Cn2cnnn2)c2ccccc2)cc1F] | (2S,4R)-N-[(S)-[3,5-difluoro-4-(propan-2-yl)phenyl](phenyl)methyl]-4-fluoro-1-[2-(1H-1,2,3,4-tetrazol-1-yl)acetyl]pyrrolidine-2-carboxamide | 486.2 | 487.1 |

TABLE T-16-continued

| Compound No. | Structure | IUPAC | Exact mass (g/mol) | LCMS, Found [M + H]+ |
|---|---|---|---|---|
| 670 | 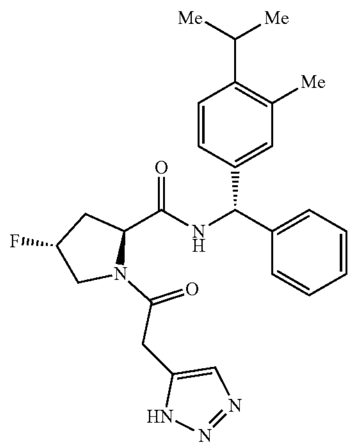 [SMILES: Cc1cc([C@@H](NC(=O)[C@@H]2C[C@@H](F)CN2C(=O)Cc2cnn[nH]2)c2ccccc2)ccc1C(C)C] | (2S,4R)-4-fluoro-N-[(S)-[3-methyl-4-(propan-2-yl)phenyl](phenyl)methyl]-1-[2-(1H-1,2,3-triazol-5-yl)acetyl]pyrrolidine-2-carboxamide | 463.2 | 464.1 |
| 671 | 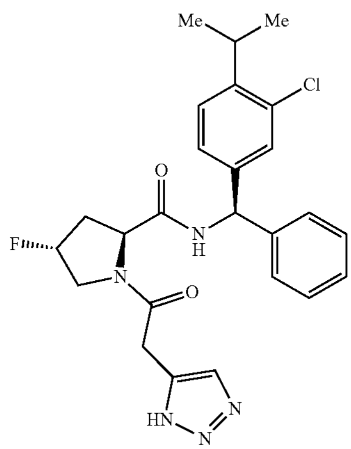 [SMILES: CC(C)c1ccc([C@H](NC(=O)[C@@H]2C[C@@H](F)CN2C(=O)Cc2cnn[nH]2)c2ccccc2)cc1Cl] | (2S,4R)-N-[(R)-[3-chloro-4-(propan-2-yl)phenyl](phenyl)methyl]-4-fluoro-1-[2-(1H-1,2,3-triazol-5-yl)acetyl]pyrrolidine-2-carboxamide | 483.2 | 484.2 |
| 672 | 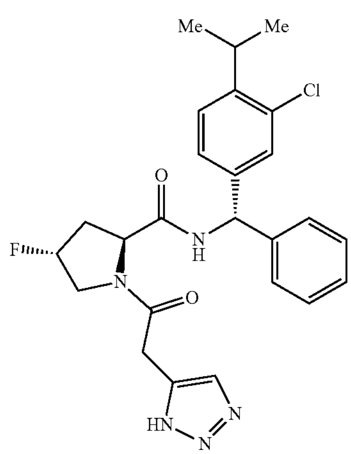 [SMILES: CC(C)c1ccc([C@@H](NC(=O)[C@@H]2C[C@@H](F)CN2C(=O)Cc2cnn[nH]2)c2ccccc2)cc1Cl] | (2S,4R)-N-[(S)-[3-chloro-4-(propan-2-yl)phenyl](phenyl)methyl]-4-fluoro-1-[2-(1H-1,2,3-triazol-5-yl)acetyl]pyrrolidine-2-carboxamide | 483.2 | 484.2 |

TABLE T-16-continued

| Compound No. | Structure | IUPAC | Exact mass (g/mol) | LCMS, Found [M + H]+ |
|---|---|---|---|---|
| 673 | 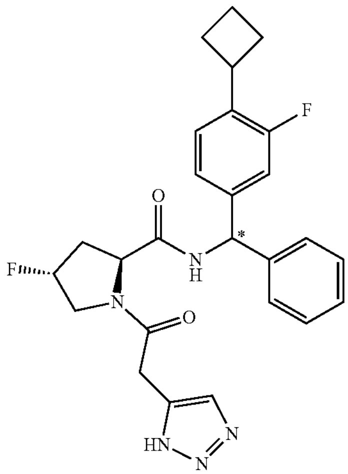 [SMILES: O=C(NC(c1ccccc1)c1ccc(C2CCC2)c(F)c1)[C@@H]1C[C@@H](F)CN1C(=O)Cc1cnn[nH]1] | (2S,4R)-N-[(R) or (S)-(4-cyclobutyl-3-fluorophenyl)(phenyl)methyl]-4-fluoro-1-[2-(1H-1,2,3-triazol-5-yl)acetyl]pyrrolidine-2-carboxamide (column: CHIRALCEL OD-3, second-eluting isomer) | 479.2 | 480.2 |
| 674 | 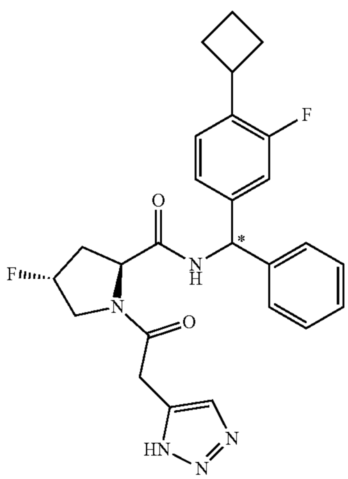 [SMILES: O=C(NC(c1ccccc1)c1ccc(C2CCC2)c(F)c1)[C@@H]1C[C@@H](F)CN1C(=O)Cc1cnn[nH]1] | (2S,4R)-N-[(S) or (R)-(4-cyclobutyl-3-fluorophenyl)(phenyl)methyl]-4-fluoro-1-[2-(1H-1,2,3-triazol-5-yl)acetyl]pyrrolidine-2-carboxamide (column: CHIRALCEL OD-3, first-eluting isomer) | 479.2 | 480.2 |
| 675 | 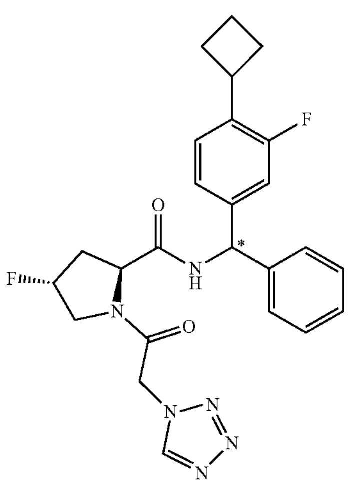 [SMILES: O=C(NC(c1ccccc1)c1ccc(C2CCC2)c(F)c1)[C@@H]1C[C@@H](F)CN1C(=O)Cn1cnnn1] | (2S,4R)-N-[(S) or (R)-(4-cyclobutyl-3-fluorophenyl)(phenyl)methyl]-4-fluoro-1-[2-(1H-1,2,3,4-tetrazol-1-yl)acetyl]pyrrolidine-2-carboxamide (column: CHIRALCEL AD-3, first-eluting isomer) | 480.2 | 481.2 |

TABLE T-16-continued

| Compound No. | Structure | IUPAC | Exact mass (g/mol) | LCMS, Found [M + H]+ |
| --- | --- | --- | --- | --- |
| 676 | 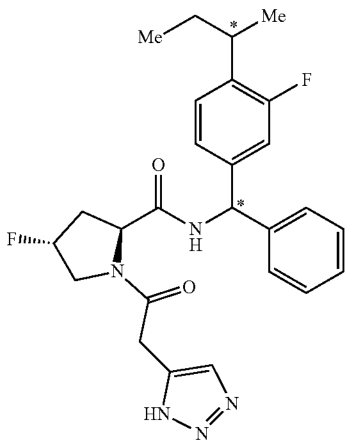 [SMILES: CCC(C)c1ccc(C(NC(=O)[C@@H]2C[C@@H](F)CN2C(=O)Cc2cnn[nH]2)c2ccccc2)cc1F] | (2S,4R)-N-[(R) or (S)-{4-[(2R) or (2S)-butan-2-yl]-3-fluorophenyl}(phenyl)methyl]-4-fluoro-1-[2-(1H-1,2,3-triazol-5-yl)acetyl]pyrrolidine-2-carboxamide (column: REGIS (s,s) WHELK-O1, second-eluting isomer) | 481.2 | 482.1 |
| 677 | 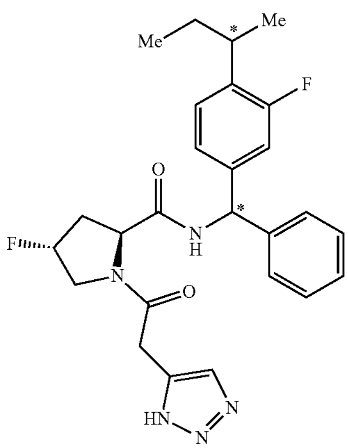 [SMILES: CCC(C)c1ccc(C(NC(=O)[C@@H]2C[C@@H](F)CN2C(=O)Cc2cnn[nH]2)c2ccccc2)cc1F] | (2S,4R)-N-[(S) or (R)-{4-[(2R) or (2S)-butan-2-yl]-3-fluorophenyl}(phenyl)methyl]-4-fluoro-1-[2-(1H-1,2,3-triazol-5-yl)acetyl]pyrrolidine-2-carboxamide (column: REGIS (s,s) WHELK-O1, first-eluting isomer) | 481.2 | 482.1 |
| 678 | 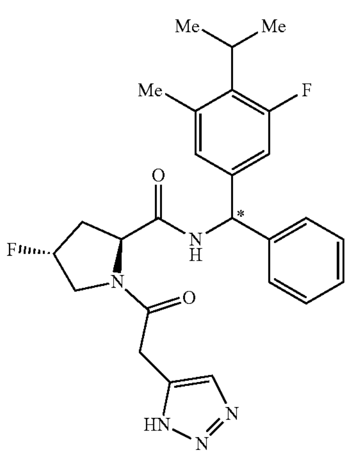 [SMILES: Cc1cc(C(NC(=O)[C@@H]2C[C@@H](F)CN2C(=O)Cc2cnn[nH]2)c2ccccc2)cc(F)c1C(C)C] | (2S,4R)-4-fluoro-N-[(R) or (S)-[3-fluoro-5-methyl-4-(propan-2-yl)phenyl](phenyl)methyl]-1-[2-(1H-1,2,3-triazol-5-yl)acetyl]pyrrolidine-2-carboxamide (column: CHIRALCEL IC-3, second-eluting isomer) | 481.2 | 482.3 |

TABLE T-16-continued

| Compound No. | Structure | IUPAC | Exact mass (g/mol) | LCMS, Found [M + H]+ |
| --- | --- | --- | --- | --- |
| 679 | 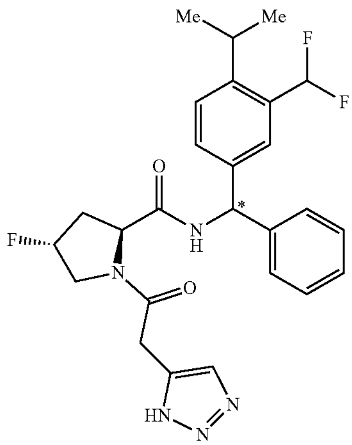 [SMILES: CC(C)c1ccc(C(NC(=O)[C@@H]2C[C@@H](F)CN2C(=O)Cc2cnn[nH]2)c2ccccc2)cc1C(F)F] | (2S,4R)-N-[(S)-[3-(difluoromethyl)-4-(propan-2-yl)phenyl](phenyl)methyl]-4-fluoro-1-[2-(1H-1,2,3-triazol-5-yl)acetyl]pyrrolidine-2-carboxamide | 499.2 | 500.2 |
| 680 | 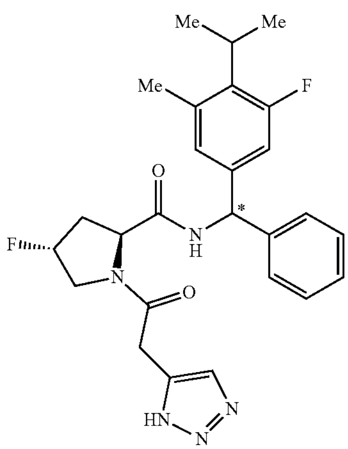 [SMILES: Cc1cc(C(NC(=O)[C@@H]2C[C@@H](F)CN2C(=O)Cc2cnn[nH]2)c2ccccc2)cc(F)c1C(C)C] | (2S,4R)-4-fluoro-N-[(S) or (R)-[3-fluoro-5-methyl-4-(propan-2-yl)phenyl](phenyl)methyl]-1-[2-(1H-1,2,3-triazol-5-yl)acetyl]pyrrolidine-2-carboxamide (column: CHIRALCEL IC-3, first-eluting isomer) | 481.2 | 482.3 |
| 681 | 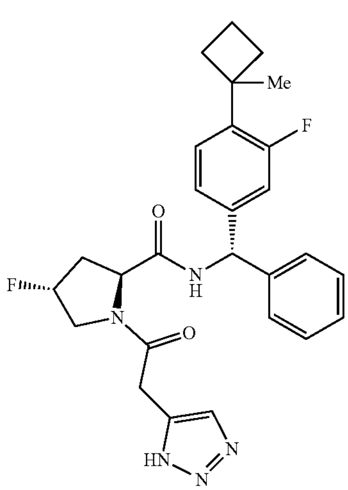 [SMILES: CC1(c2ccc([C@@H](NC(=O)[C@@H]3C[C@@H](F)CN3C(=O)Cc3cnn[nH]3)c3ccccc3)cc2F)CCC1] | (2S,4R)-4-fluoro-N-[(S)-[3-fluoro-4-(1-methylcyclobutyl)phenyl](phenyl)methyl]-1-[2-(1H-1,2,3-triazol-5-yl)acetyl]pyrrolidine-2-carboxamide | 493.2 | 494.3 |

TABLE T-16-continued

| Compound No. | Structure | IUPAC | Exact mass (g/mol) | LCMS, Found [M + H]+ |
|---|---|---|---|---|
| 682 | 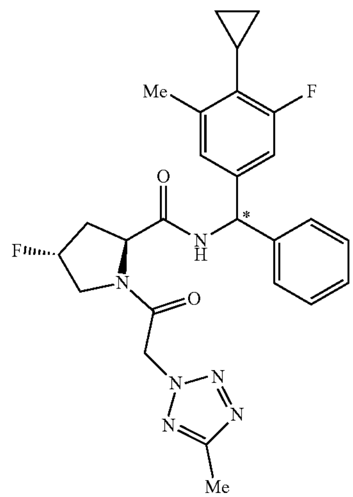 [SMILES: Cc1nnn(CC(=O)N2C[C@H](F)C[C@H]2C(=O)NC(c2ccccc2)c2cc(C)c(C3CC3)c(F)c2)n1] | (2S,4R)-N-[(S) or (R)-(4-cyclopropyl-3-fluoro-5-methylphenyl)(phenyl)methyl]-4-fluoro-1-[2-(5-methyl-2H-1,2,3,4-tetrazol-2-yl)acetyl]pyrrolidine-2-carboxamide (column: REGIS (s,s) WHELK-O1, second-eluting isomer) | 494.2 | 512.2 |
| 683 | 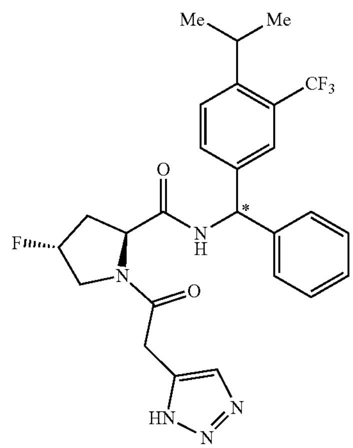 | (2S,4R)-4-fluoro-N-[(S) or (R)-phenyl[4-(propan-2-yl)-3-(trifluoromethyl)phenyl]methyl]-1-[2-(1H-1,2,3-triazol-5-yl)acetyl]pyrrolidine-2-carboxamide (column: CHIRALCEL IC-3, first-eluting isomer) | 517.2 | 518.1 |
| 684 | 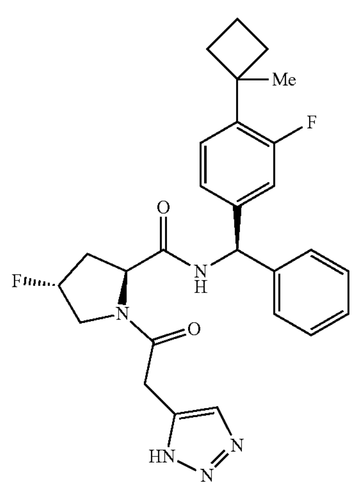 [SMILES: CC1(c2ccc([C@H](NC(=O)[C@@H]3C[C@@H](F)CN3C(=O)Cc3cnn[nH]3)c3ccccc3)cc2F)CCC1] | (2S,4R)-4-fluoro-N-[(R)-[3-fluoro-4-(1-methylcyclobutyl)phenyl](phenyl)methyl]-1-[2-(1H-1,2,3-triazol-5-yl)acetyl]pyrrolidine-2-carboxamide | 493.2 | 494.3 |

TABLE T-16-continued

| Compound No. | Structure | IUPAC | Exact mass (g/mol) | LCMS, Found [M + H]+ |
|---|---|---|---|---|
| 685 | 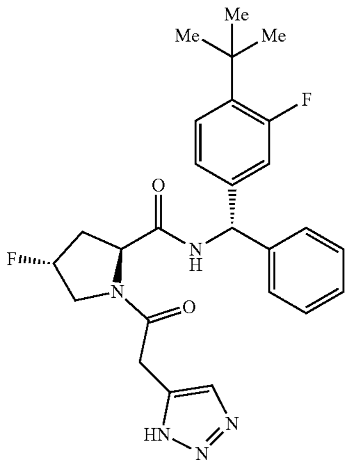 [SMILES: CC(C)(C)c1ccc([C@@H](NC(=O)[C@@H]2C[C@@H](F)CN2C(=O)Cc2cnn[nH]2)c2ccccc2)cc1F] | (2S,4R)-N-[(S)-(4-tert-butyl-3-fluorophenyl)(phenyl)methyl]-4-fluoro-1-[2-(1H-1,2,3-triazol-5-yl)acetyl]pyrrolidine-2-carboxamide | 481.2 | 482.3 |

Example S-17: Synthesis of (2S,4R)-1-(2-(1H-1,2,3-triazol-5-yl)acetyl)-N—((S) or (R)-(3-(1H-pyrazol-5-yl)phenyl)(6-fluoro-5-isopropylpyridin-2-yl)methyl)-4-fluoropyrrolidine-2-carboxamide and (2S,4R)-1-(2-(1H-1,2,3-triazol-5-yl)acetyl)-N—((R) or (S)-(3-(1H-pyrazol-5-yl)phenyl)(6-fluoro-5-isopropylpyridin-2-yl)methyl)-4-fluoropyrrolidine-2-carboxamide Compounds 686 and 687

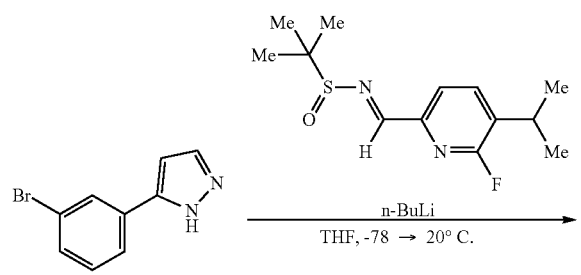

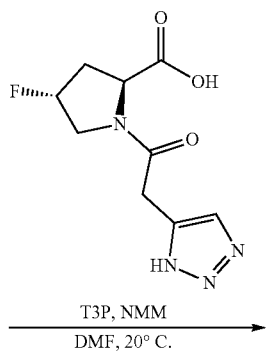

-continued

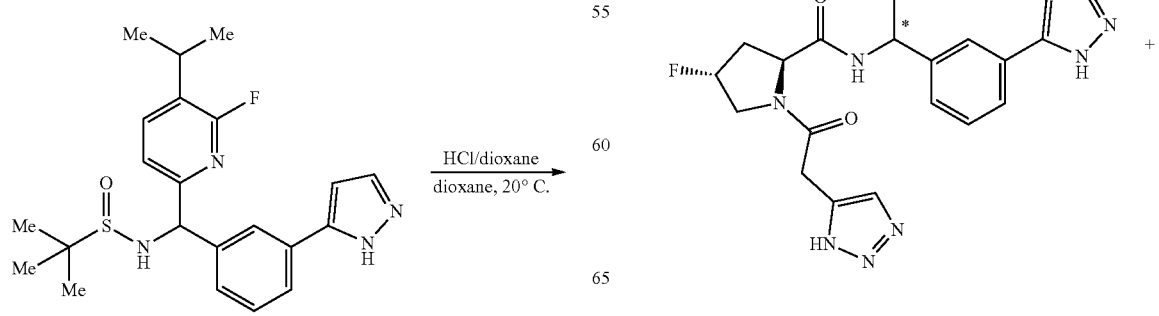

-continued

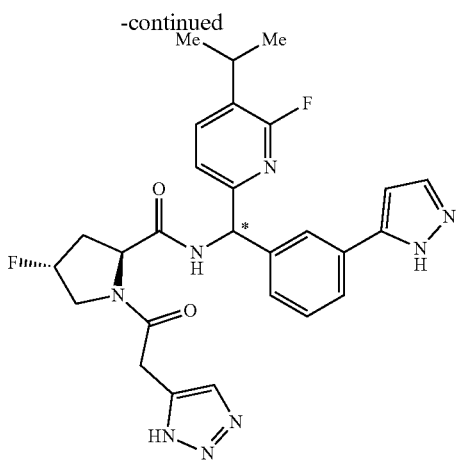

Step a: To a solution of 5-(3-bromophenyl)-1H-pyrazole (619 mg, 2.77 mmol, 1.5 eq) in THF (5 mL) at −78° C. under $N_2$ was added n-BuLi (2.5 M in hexane, 1.85 mL, 2.5 eq), and the resulting mixture was stirred at −78° C. for 0.5 h. (E)-N-((6-fluoro-5-isopropylpyridin-2-yl)methylene)-2-methylpropane-2-sulfinamide (0.5 g, 1.85 mmol, 1 eq) in THF (1 mL) was then added dropwise at −78° C. The resulting mixture was allowed to warm to 20° C. and stirred for 2 h. The reaction was then quenched with saturated aq. $NH_4Cl$ (10 mL), and the resulting biphasic mixture was extracted with ethyl acetate (2×20 mL). The combined organic extracts were dried over anhydrous $Na_2SO_4$, filtered, and concentrated under reduced pressure. The crude residue obtained was purified by column chromatography to give N-((3-(1H-pyrazol-5-yl)phenyl)(6-fluoro-5-isopropylpyridin-2-yl)methyl)-2-methylpropane-2-sulfinamide. LC-MS (ESI): m/z: [M+H]$^+$ calculated for $C_{22}H_{27}FN_4OS$: 415.2; found 415.2.

Step b: To a solution of N-((3-(1H-pyrazol-5-yl)phenyl)(6-fluoro-5-isopropylpyridin-2-yl)methyl)-2-methylpropane-2-sulfinamide (0.5 g, 1.21 mmol, 1 eq) in dioxane (5 mL) was added HCl/dioxane (4 M, 5 mL). The resulting mixture was stirred at 20° C. for 2 h. The mixture was then concentrated under reduced pressure. The crude residue obtained was triturated with MTBE (5 mL) to give (3-(1H-pyrazol-5-yl)phenyl)(6-fluoro-5-isopropylpyridin-2-yl)methanaminium chloride. LC-MS (ESI): m/z: [M+H]$^+$ calculated for $C_{18}H_{19}FN_4$: 311.2; found 311.2.

Step c: To a solution of (3-(1H-pyrazol-5-yl)phenyl)(6-fluoro-5-isopropylpyridin-2-yl)methanaminium chloride (0.15 g, 432 μmol, 1 eq) and (2S,4R)-1-(2-(1H-1,2,3-triazol-5-yl)acetyl)-4-fluoropyrrolidine-2-carboxylic acid (136 mg, 562 μmol, 1.3 eq) in DMF (2 mL) at 0° C. was added N-methylmorpholine (NMM, 175 mg, 1.73 mmol, 190 μL, 4 eq) and T3P (550 mg, 865 μmol, 50% purity, 2 eq). The resulting mixture was warmed to 20° C. and stirred for 16 h. The reaction mixture was then diluted with water and extracted with ethyl acetate (3×20 mL). The combined organic extracts were dried over $Na_2SO_4$, filtered, and concentrated under reduced pressure. The crude residue obtained was purified by prep-HPLC (column: Phenomenex $C_{18}$) to give (2S,4R)-1-(2-(1H-1,2,3-triazol-5-yl)acetyl)-N—((R)-(3-(1H-pyrazol-5-yl)phenyl)(6-fluoro-5-isopropylpyridin-2-yl)methyl)-4-fluoropyrrolidine-2-carboxamide (Compound 687; first-eluting isomer) and (2S,4R)-1-(2-(1H-1,2,3-triazol-5-yl)acetyl)-N—((S)-(3-(1H-pyrazol-5-yl)phenyl)(6-fluoro-5-isopropylpyridin-2-yl)methyl)-4-fluoropyrrolidine-2-carboxamide (Compound 686; second-eluting isomer).

First-eluting isomer (Compound 687): $^1$H NMR (2.9:1 rotamer ratio, asterisk denotes minor rotamer peaks, obscured peaks not reported, 400 MHz, DMSO-d$_6$) δ 12.89 (s, 1H), 9.41*(d, J=7.8 Hz, 1H), 9.06 (d, J=8.3 Hz, 1H), 7.86 (t, J=8.9 Hz, 1H), 7.82-7.59 (m, 3H), 7.54 (d, J=7.6 Hz, 1H), 7.44-7.26 (m, 2H), 7.26-7.14 (m, 1H), 6.67 (s, 1H), 6.15*(d, J=7.9 Hz, 1H), 6.03 (d, J=8.1 Hz, 1H), 5.48-5.19 (m, 1H), 4.96-4.85*(m, 1H), 4.65 (t, J=8.3 Hz, 1H), 4.14-3.62 (m, 3H), 3.11-2.92 (m, 1H), 2.10-1.89 (m, 1H), 1.23-1.17 (m, 6H), 1.17-1.12*(m, 6H). LC-MS (ESI): m/z: [M+H]$^+$ calculated for $C_{27}H_{28}F_2N_8O_2$: 535.2; found 535.2.

Second-eluting isomer (Compound 686): $^1$H NMR (3.3:1 rotamer ratio, asterisk denotes minor rotamer peaks, obscured peaks not reported, 400 MHz, DMSO-d$_6$) δ 14.77 (br s, 1H), 13.24*(br s, 1H), 12.85 (br s, 1H), 9.35*(d, J=7.8 Hz, 1H), 9.01 (d, J=8.1 Hz, 1H), 7.93-7.77 (m, 2H), 7.77-7.56 (m, 3H), 7.41-7.25 (m, 2H), 7.16 (d, J=7.7 Hz, 1H), 6.75-6.70 (m, 1H), 6.61*(s, 1H), 6.13*(d, J=7.8 Hz, 1H), 6.03 (d, J=8.0 Hz, 1H), 5.50-5.21 (m, 1H), 4.92*(t, J=8.0 Hz, 1H), 4.66 (t, J=8.3 Hz, 1H), 4.13-3.65 (m, 4H), 3.05 (hept, J=6.9 Hz, 1H), 2.14-1.93 (m, 1H), 1.24-1.17 (m, 6H). LC-MS (ESI): m/z: [M+H]$^+$ calculated for $C_{27}H_{28}F_2N_8O_2$: 535.2; found 535.2.

Example S-18: Synthesis of (2S,4R)—N—((S) or (R)-(3-(4H-1,2,4-triazol-3-yl)phenyl)(6-fluoro-5-isopropylpyridin-2-yl)methyl)-1-acetyl-4-fluoropyrrolidine-2-carboxamide and (2S,4R)—N—((R) or (S)-(3-(4H-1,2,4-triazol-3-yl)phenyl)(6-fluoro-5-isopropylpyridin-2-yl)methyl)-1-acetyl-4-fluoropyrrolidine-2-carboxamide Compounds 688 and 689

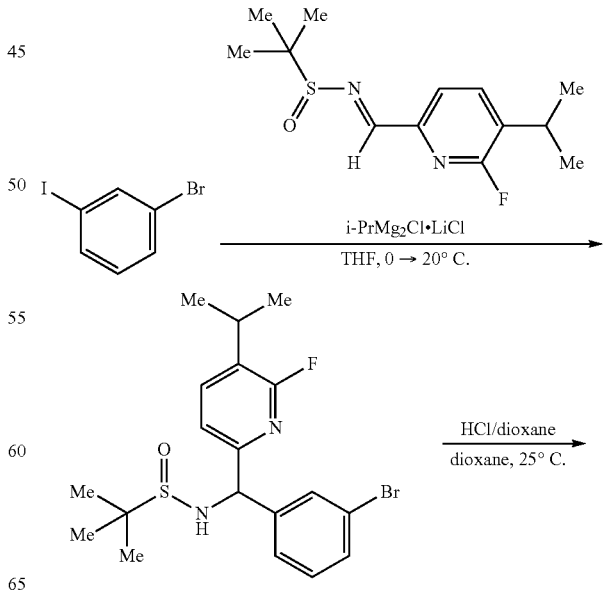

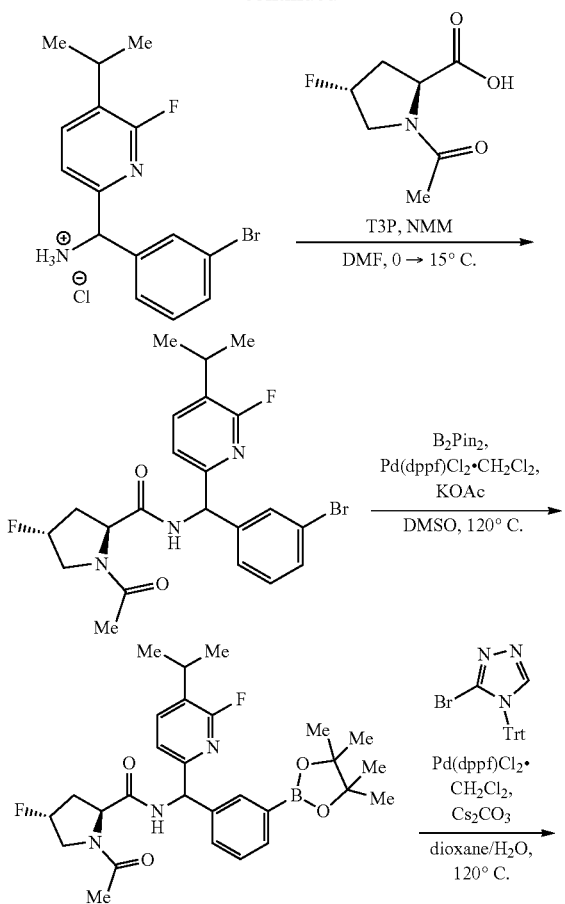

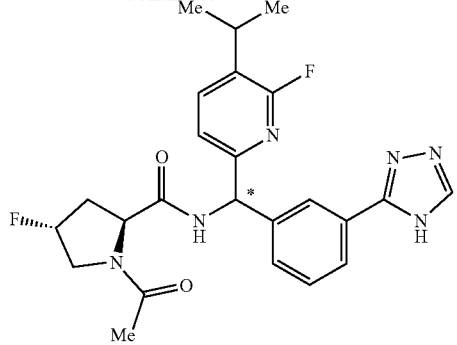

Step a: To a solution of 1-bromo-3-iodobenzene (8.06 g, 28.4 mmol, 1.1 eq) in THF (40 mL) at 0° C. under N₂ was added i-PrMgCl·LiCl (1.3 M in THF, 21.9 mL, 1.1 eq) in a dropwise manner. The resulting mixture was stirred at 0° C. for 2 h before (E)-N-((6-fluoro-5-isopropylpyridin-2-yl) methylene)-2-methylpropane-2-sulfinamide (7 g, 25.8 mmol, 1 eq) in THF (20 mL) was added in a dropwise manner at 0° C. The resulting mixture was allowed to warm to 20° C. and stirred for 1 h. The reaction was then quenched with saturated aq. NH₄Cl solution (20 mL), and the resulting biphasic mixture was extracted with ethyl acetate (3×40 mL). The combined organic extracts were washed with brine (30 mL), dried over anhydrous Na₂SO₄, filtered, and concentrated under reduced pressure. The crude residue obtained was purified by column chromatography to give N-((3-bromophenyl)(6-fluoro-5-isopropylpyridin-2-yl) methyl)-2-methylpropane-2-sulfinamide. LC-MS (ESI): m/z: [M+H]⁺ calculated for $C_{19}H_{24}BrFN_2OS$: 427.1; found 427.1.

Step b: To a solution of N-((3-bromophenyl)(6-fluoro-5-isopropylpyridin-2-yl)methyl)-2-methylpropane-2-sulfinamide (6 g, 14.0 mmol, 1 eq) in dioxane (20 mL) at 25° C. was added HCl/dioxane (50 mL). The resulting mixture was stirred at 25° C. for 1 h. The reaction mixture was then filtered to give (3-bromophenyl)(6-fluoro-5-isopropylpyridin-2-yl)methanaminium chloride. LC-MS (ESI): m/z: [M+H]⁺ calculated for $C_{15}H_{16}BrFN_2$: 323.0; found 323.0.

Step c: To a solution of (3-bromophenyl)(6-fluoro-5-isopropylpyridin-2-yl)methanaminium chloride (5.8 g, 16.1 mmol, 1 eq) in DMF (30 mL) at 0° C. was added NMM (64.5 mmol, 7 mL, 4 eq), (2S,4R)-1-acetyl-4-fluoropyrrolidine-2-carboxylic acid (4.24 g, 24.2 mmol, 1.5 eq), and T3P (32.3 mmol, 19 mL, 50% purity, 2 eq), sequentially. The resulting mixture was warmed to 15° C. and stirred for 1 h. The reaction mixture was then poured into ice-water (50 mL) and stirred for 5 min. The resulting biphasic mixture was extracted with ethyl acetate (3×30 mL). The combined organic extracts were washed with brine (30 mL), dried over anhydrous Na₂SO₄, filtered, and concentrated under reduced pressure. The crude residue obtained was purified by column chromatography to give (2S,4R)-1-acetyl-N-((3-bromophenyl)(6-fluoro-5-isopropylpyridin-2-yl)methyl)-4-fluoropyrrolidine-2-carboxamide. LC-MS (ESI): m/z: [M+H]⁺ calculated for $C_{22}H_{24}BrF_2N_3O_2$: 480.1; found 480.0.

Step d: To a mixture of (2S,4R)-1-acetyl-N-((3-bromophenyl)(6-fluoro-5-isopropylpyridin-2-yl)methyl)-4-fluoropyrrolidine-2-carboxamide (2 g, 4.16 mmol, 1 eq) and bis(pinacolato)diboron (1.16 g, 4.58 mmol, 1.1 eq) in DMSO (20 mL) was added potassium acetate (1.02 g, 10.4 mmol, 2.5 eq). The resulting mixture was then degassed and purged with N₂. To this mixture added Pd(dppf)Cl₂·CH₂Cl₂

(340 mg, 416 μmol, 0.1 eq), and the resulting mixture was degassed and purged with $N_2$. The reaction mixture was then warmed to 120° C. and stirred for 2 h under $N_2$ atmosphere. The reaction mixture was then filtered, and the filtrate was concentrated under reduced pressure. The crude residue obtained was purified by column chromatography to give (2S,4R)-1-acetyl-4-fluoro-N-((6-fluoro-5-isopropylpyridin-2-yl)(3-(4,4,5,5-tetramethyl-1,3,2-dioxaborolan-2-yl)phenyl)methyl)pyrrolidine-2-carboxamide. LC-MS (ESI): m/z: [M+H]$^+$ calculated for $C_{28}H_{36}BF_2N_3O_4$: 528.3; found 528.4.

Step e: To a mixture of (2S,4R)-1-acetyl-4-fluoro-N-((6-fluoro-5-isopropylpyridin-2-yl)(3-(4,4,5,5-tetramethyl-1,3,2-dioxaborolan-2-yl)phenyl)methyl)pyrrolidine-2-carboxamide (1 g, 1.90 mmol, 1 eq) and 3-bromo-4-trityl-4H-1,2,4-triazole (888 mg, 2.28 mmol, 1.2 eq) in dioxane (7 mL) and $H_2O$ (0.5 mL) was added $Cs_2CO_3$ (1.24 g, 3.79 mmol, 2 eq). The resulting mixture was degassed and purged with $N_2$, and then Pd(dppf)Cl$_2$·CH$_2$Cl$_2$ (310 mg, 379 μmol, 0.2 eq) was added in one portion. The resulting mixture was degassed and purged with $N_2$. The reaction mixture was then warmed to 120° C. and stirred for 1 h under $N_2$ atmosphere. The reaction solution was then filtered, and the filtrate was concentrated under reduced pressure. The crude residue obtained was purified by column chromatography to give (2S,4R)-1-acetyl-4-fluoro-N-((6-fluoro-5-isopropylpyridin-2-yl)(3-(4-trityl-4H-1,2,4-triazol-3-yl)phenyl)methyl)pyrrolidine-2-carboxamide. LC-MS (ESI): m/z: [M+H]$^+$ calculated for $C_{43}H_{40}F_2N_6O_2$: 711.3; found 711.3.

Step f: To a solution of (2S,4R)-1-acetyl-4-fluoro-N-((6-fluoro-5-isopropylpyridin-2-yl)(3-(4-trityl-4H-1,2,4-triazol-3-yl)phenyl)methyl)pyrrolidine-2-carboxamide (0.7 g, 984 μmol, 1 eq) in MeOH (5 mL) at 0° C. was added HCl/dioxane (4M, 10 mL). The resulting mixture was allowed to warm to 20° C. and stirred for 2 h. The reaction mixture was then concentrated under reduced pressure. The crude residue obtained was purified by prep-TLC to give (2S,4R)—N—((S)-(3-(4H-1,2,4-triazol-3-yl)phenyl)(6-fluoro-5-isopropylpyridin-2-yl)methyl)-1-acetyl-4-fluoropyrrolidine-2-carboxamide. This mixture of diastereomers was then purified by prep-HPLC (column: Phenomenex Luna $C_{18}$) to give (2S,4R)—N—(R) or (S)-(3-(4H-1,2,4-triazol-3-yl)phenyl)(6-fluoro-5-isopropylpyridin-2-yl)methyl)-1-acetyl-4-fluoropyrrolidine-2-carboxamide (Compound 689, first-eluting isomer) and (2S,4R)—N—((S) or (R)-(3-(4H-1,2,4-triazol-3-yl)phenyl)(6-fluoro-5-isopropylpyridin-2-yl)methyl)-1-acetyl-4-fluoropyrrolidine-2-carboxamide (Compound 688, second-eluting isomer).

First-eluting isomer (Compound 689): $^1$H NMR (2:1 rotamer ratio, asterisk denotes minor rotamer peaks, obscured peaks not reported, 400 MHz, DMSO-d$_6$) δ 9.34* (d, J=7.9 Hz, 1H), 9.09 (d, J=8.1 Hz, 1H), 8.52-8.39 (m, 1H), 8.04-7.99*(m, 1H), 7.97-7.85 (m, 3H), 7.64-7.58 (m, 1H), 7.50-7.31 (m, 2H), 6.15*(d, J=7.8 Hz, 1H), 6.03 (d, J=8.0 Hz, 1H), 5.46-5.17 (m, 1H), 4.73*(t, J=8.0 Hz, 1H), 4.60 (t, J=8.3 Hz, 1H), 3.96-3.60 (m, 2H), 3.12-2.98 (m, 1H), 2.47-2.37 (m, 1H), 2.12-1.89 (m, 4H), 1.81*(s, 3H), 1.25-1.16 (m, 6H). LC-MS (ESI): m/z: [M+H]$^+$ calculated for $C_{24}H_{26}F_2N_6O_2$: 469.2; found 469.2.

Second-eluting isomer (Compound 688): $^1$H NMR (2:1 rotamer ratio, asterisk denotes minor rotamer peaks, obscured peaks not reported, 400 MHz, DMSO-d$_6$) δ 14.20 (br s, 1H), 9.32*(d, J=8.0 Hz, 1H), 9.02 (d, J=8.1 Hz, 1H), 8.47 (br s, 1H), 8.07-7.82 (m, 3H), 7.49-7.35 (m, 3H), 6.15*(d, J=8.0 Hz, 1H), 6.06 (d, J=8.0 Hz, 1H), 5.48-5.17 (m, 1H), 4.75*(t, J=8.1 Hz, 1H), 4.62 (t, J=8.4 Hz, 1H), 3.96-3.62 (m, 2H), 3.12-3.00 (m, 1H), 2.24-1.92 (m, 4H), 1.77*(s, 3H), 1.24-1.17 (m, 6H). LC-MS (ESI): m/z: [M+H]$^+$ calculated for $C_{24}H_{26}F_2N_6O_2$: 469.2; found 469.2.

The following compounds in Table T-17 were synthesized using procedures similar to Compound 686, 687, 688 and 689 using the appropriate starting materials.

TABLE T-17

| Compound No. | Structure | IUPAC | Exact mass (g/mol) | LCMS, Found [M + H]$^+$ |
|---|---|---|---|---|
| 690 | 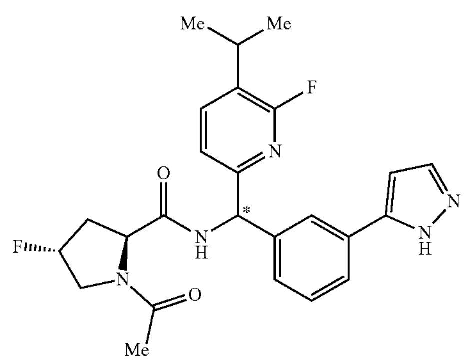 [SMILES: CC(=O)N1C[C@H](F)C[C@H]1C(=O)NC(c1cccc(-c2ccn[nH]2)c1)c1ccc(C(C)C)c(F)n1] | (2S,4R)-1-acetyl-4-fluoro-N-[(S) or (R)-[6-fluoro-5-(propan-2-yl)pyridin-2-yl][3-(1H-pyrazol-5-yl)phenyl]methyl]pyrrolidine-2-carboxamide (column: REGIS (s,s) WHELK-O1, first-eluting isomer) | 467.2 | 468.2 |

TABLE T-17-continued

| Compound No. | Structure | IUPAC | Exact mass (g/mol) | LCMS, Found [M + H]+ |
|---|---|---|---|---|
| 691 | 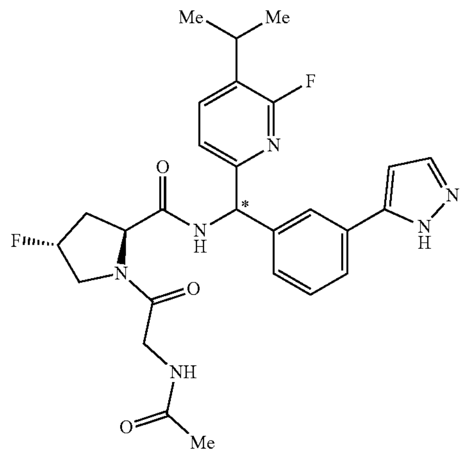 [SMILES: CC(=O)NCC(=O)N1C[C@H](F)C[C@H]1C(=O)NC(c1cccc(-c2ccn[nH]2)c1)c1ccc(C(C)C)c(F)n1] | (2S,4R)-1-(2-acetamidoacetyl)-4-fluoro-N-[(S) or (R)-[6-fluoro-5-(propan-2-yl)pyridin-2-yl][3-(1H-pyrazol-5-yl)phenyl]methyl]pyrrolidine-2-carboxamide (column: REGIS (s,s) WHELK-O1, first-eluting isomer) | 524.2 | 525.1 |
| 692 | 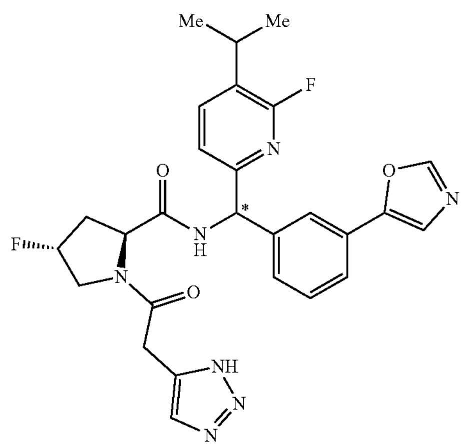 [SMILES: CC(C)c1ccc(C(NC(=O)[C@@H]2C[C@@H](F)CN2C(=O)Cc2cnn[nH]2)c2cccc(-c3cnco3)c2)nc1F] | (2S,4R)-4-fluoro-N-[(R) or (S)-[6-fluoro-5-(propan-2-yl)pyridin-2-yl][3-(1,3-oxazol-5-yl)phenyl]methyl]-1-[2-(1H-1,2,3-triazol-5-yl)acetyl]pyrrolidine-2-carboxamide (column: REGIS (s,s) WHELK-O1, second-eluting isomer) | 535.2 | 536.1 |
| 693 | 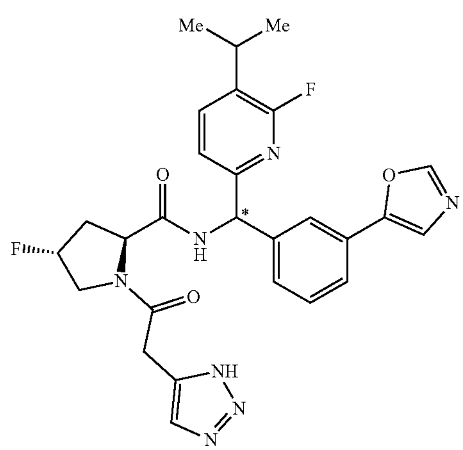 [SMILES: CC(C)c1ccc(C(NC(=O)[C@@H]2C[C@@H](F)CN2C(=O)Cc2cnn[nH]2)c2cccc(-c3cnco3)c2)nc1F] | (2S,4R)-4-fluoro-N-[(S) or (R)-[6-fluoro-5-(propan-2-yl)pyridin-2-yl][3-(1,3-oxazol-5-yl)phenyl]methyl]-1-[2-(1H-1,2,3-triazol-5-yl)acetyl]pyrrolidine-2-carboxamide (column: REGIS (s,s) WHELK-O1, first-eluting isomer) | 535.2 | 536.1 |

TABLE T-17-continued

| Compound No. | Structure | IUPAC | Exact mass (g/mol) | LCMS, Found [M + H]+ |
|---|---|---|---|---|
| 694 | 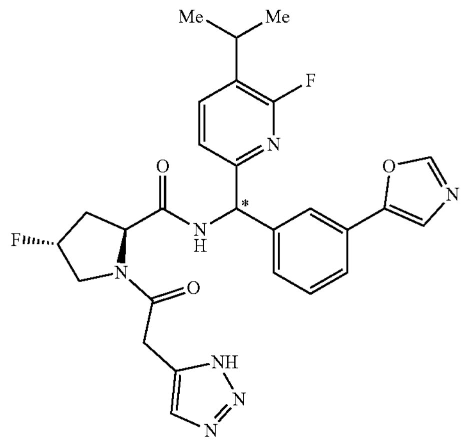 [SMILES: CC(C)c1ccc(C(NC(=O)[C@@H]2C[C@@H](F)CN2C(=O)Cc2cnn[nH]2)c2cccc(-c3cnco3)c2)nc1F] | (2S,4R)-4-fluoro-N-[(S) or (R)-[6-fluoro-5-(propan-2-yl)pyridin-2-yl][3-(1,2-oxazol-5-yl)phenyl]methyl]-1-[2-(1H-1,2,3-triazol-5-yl)acetyl]pyrrolidine-2-carboxamide (column: REGIS (s,s) WHELK-O1, first-eluting isomer) | 535.2 | 536.2 |
| 695 | 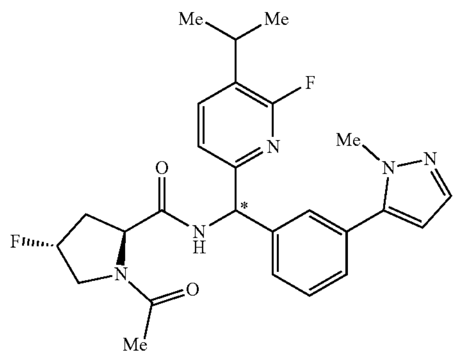 [SMILES: CC(=O)N1C[C@H](F)C[C@H]1C(=O)NC(c1cccc(-c2ccnn2C)c1)c1ccc(C(C)C)c(F)n1] | (2S,4R)-1-acetyl-4-fluoro-N-[(S) or (R)-[6-fluoro-5-(propan-2-yl)pyridin-2-yl][3-(1-methyl-1H-pyrazol-5-yl)phenyl]methyl]pyrrolidine-2-carboxamide (column: REGIS (s,s) WHELK-O1, first-eluting isomer) | 481.2 | 482.1 |
| 696 | 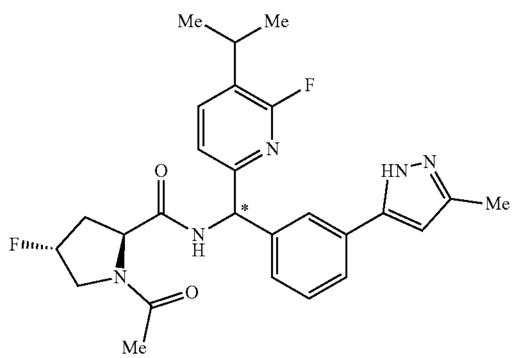 [SMILES: CC(=O)N1C[C@H](F)C[C@H]1C(=O)NC(c1cccc(-c2cc(C)n[nH]2)c1)c1ccc(C(C)C)c(F)n1] | (2S,4R)-1-acetyl-4-fluoro-N-[(S) or (R)-[6-fluoro-5-(propan-2-yl)pyridin-2-yl][3-(3-methyl-1H-pyrazol-5-yl)phenyl]methyl]pyrrolidine-2-carboxamide (column: REGIS (s,s) WHELK-O1, first-eluting isomer) | 481.2 | 482.2 |
| 697 | 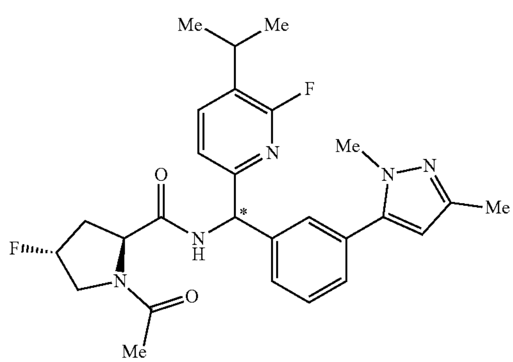 [SMILES: CC(=O)N1C[C@H](F)C[C@H]1C(=O)NC(c1cccc(-c2cc(C)nn2C)c1)c1ccc(C(C)C)c(F)n1] | (2S,4R)-1-acetyl-N-[(S) or (R)-[3-(1,3-dimethyl-1H-pyrazol-5-yl)phenyl][6-fluoro-5-(propan-2-yl)pyridin-2-yl]methyl]-4-fluoropyrrolidine-2-carboxamide (column: REGIS (s,s) WHELK-O1, first-eluting isomer) | 495.2 | 496.2 |

TABLE T-17-continued

| Compound No. | Structure | IUPAC | Exact mass (g/mol) | LCMS, Found [M + H]+ |
|---|---|---|---|---|
| 698 | 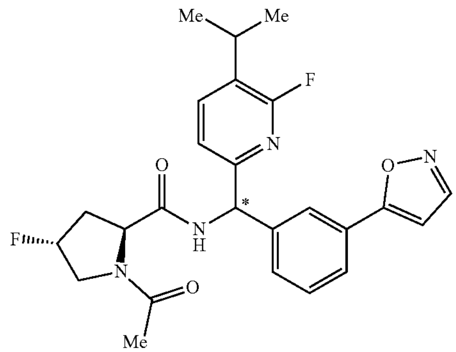 [SMILES: CC(=O)N1C[C@H](F)C[C@H]1C(=O)NC(c1cccc(-c2ccno2)c1)c1ccc(C(C)C)c(F)n1] | (2S,4R)-1-acetyl-4-fluoro-N-[(S) or (R)-[6-fluoro-5-(propan-2-yl)pyridin-2-yl][3-(1,2-oxazol-5-yl)phenyl]methyl]pyrrolidine-2-carboxamide (column: REGIS (s,s) WHELK-O1, first-eluting isomer) | 468.2 | 469.1 |
| 699 | 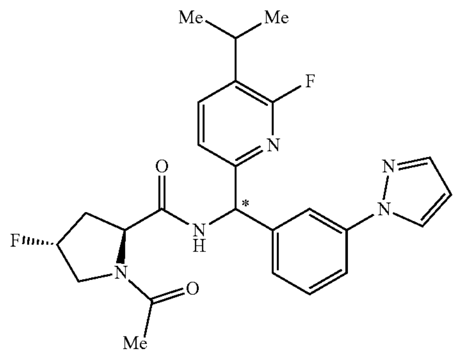 [SMILES: CC(=O)N1C[C@H](F)C[C@H]1C(=O)NC(c1cccc(-n2cccn2)c1)c1ccc(C(C)C)c(F)n1] | (2S,4R)-1-acetyl-4-fluoro-N-[(S) or (R)-[6-fluoro-5-(propan-2-yl)pyridin-2-yl][3-(1H-pyrazol-1-yl)phenyl]methyl]pyrrolidine-2-carboxamide (column: REGIS (s,s) WHELK-O1, first-eluting isomer) | 467.2 | 468.1 |
| 700 | 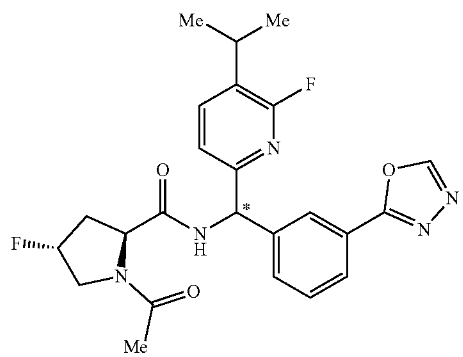 [SMILES: CC(=O)N1C[C@H](F)C[C@H]1C(=O)NC(c1cccc(-c2nnco2)c1)c1ccc(C(C)C)c(F)n1] | (2S,4R)-1-acetyl-4-fluoro-N-[(S) or (R)-[6-fluoro-5-(propan-2-yl)pyridin-2-yl][3-(1,3,4-oxadiazol-2-yl)phenyl]methyl]pyrrolidine-2-carboxamide (column: REGIS (s,s) WHELK-O1, first-eluting isomer) | 469.1 | 470.2 |

BIOLOGICAL EXAMPLES

Example B-1

The GYS1 coupled enzyme assay is a kinetic biochemical assay that indirectly quantifies the rate of glycogen synthesis by coupling the conversion of GYS1 substrate UDP-glucose into UDP with downstream enzymatic reactions. UDP is released from UDP-glucose as glucose monomers are linked into the growing glycogen strand by GYS1. The coupled assay then proceeds with pyruvate kinase utilizing UDP and phospho(enol)pyruvate (PEP) to form pyruvate. Lactate dehydrogenase then converts pyruvate and NADH into lactate and NAD+. Oxidation of NADH to NAD+ can be measured continuously with a plate reader by quantifying the decrease in NADH absorbance at 340 nm over time.

Compounds that inhibit the hGYS1 enzyme and, subsequently, the downstream conversion of NADH to NAD+, were tested using assay ready plates (black, clear bottom 384 well plates) in a final DMSO reaction volume of 2.5% DMSO. The Assay Buffer contained 50 mM Tris pH 7.5, 2 mM $MgCl_2$, and 100 mM KCl. Fresh stocks of BSA at a final concentration of 0.02% and TCEP at 1 mM were added before splitting buffer into hGYS1 buffer and substrate buffer. To the hGYS1 buffer, rabbit liver glycogen was added at a final concentration of 0.2% glycogen. Glucose-6-Phosphate was added at 1 mM, recombinant hGYS1/GN1 protein was added at 50 nM to the substrate buffer, phosphoenolpyruvate (PEP) was added at 2 mM, UDP-Glucose was added at 0.8 mM, NADH) was added at 0.6 mM, and Pyruvate Kinase/Lactate Dehydrogenase was added at 20 units/mL. The reaction was initiated by mixing hGYS1 buffer and substrate buffer at a 1:1 ratio. Both buffers were plated using a liquid dispensing device with hGYS1 buffer plated first followed by the substrate buffer. Plates were spun briefly to eliminate air bubbles and are immediately read in continuous mode at an absorbance of 340 nm, for 10 time points in one-minute increments, for a total of 10 minutes.

The slope from these 10 time points was normalized to the positive and negative control wells. The duplicate % inhibition values are then averaged and fit to a Hill equation for dose response according to the Levenberg-Marquardt algorithm with the Hill equation maximum set to 100 and the minimum set to 0.

The results are shown in Table 2 below, which reports the $IC_{50}$ of each compound. Unless otherwise specified, $IC_{50}$ values are reported as the geometric mean of at least 2 assay runs on separate days. Each run represents the average of a technical replicate, where each compound was assayed twice in the same plate. As shown in the table below, the compounds of the present invention are potent inhibitors of human GYS1. A superscript "#" symbol in Table 2 indicates results from a single assay run.

Note that, in Table 2, the compounds are referred to by the corresponding Compound No. in Table 1, which is also referred to in the synthetic examples. When one or more of the numbered compounds are identified by stereochemistry (for example, (R)- or (S)—), the specific stereoisomer for which data is provided in Table 2 may be identified by the elution order of such compound as described in the synthetic examples. To illustrate, Compound 497 is the first-eluting isomer in step g of Example S-7 and Compound 498 is the second-eluting isomer in step g of Example S-7.

TABLE 2

| Compound No. | PK/LDH $IC_{50}$ (μM) |
| --- | --- |
| 1 | 0.033 |
| 2 | 0.059 |
| 3 | 0.168 |
| 4 | 0.998 |
| 5 | 0.353 |
| 6 | 0.211 |
| 7 | 0.113 |
| 8 | 0.042 |
| 9 | 0.059 |
| 10 | 0.050 |
| 11 | 0.091 |
| 12 | 0.415 |
| 13 | 0.147 |
| 14 | 0.129 |
| 15 | 0.048 |
| 16 | 0.033 |
| 17 | 0.034 |
| 18 | 0.045 |
| 19 | 0.047 |
| 20 | 0.046 |
| 21 | 0.027 |
| 22 | 0.043 |
| 23 | 0.070 |
| 24 | 0.050 |
| 25 | 0.235 |
| 26 | 0.036 |
| 27 | 0.023 |
| 28 | 0.060 |
| 29 | 0.070 |
| 30 | 0.947 |
| 31 | 0.048 |
| 32 | 0.023 |
| 33 | 0.106 |
| 34 | 0.075 |
| 35 | 0.185 |
| 36 | 0.073 |
| 37 | 0.045 |
| 38 | 0.051 |
| 39 | 0.050 |
| 40 | 0.026 |
| 41 | 0.031 |
| 42 | 0.495 |
| 43 | 0.091 |
| 44 | 0.106 |

TABLE 2-continued

| Compound No. | PK/LDH $IC_{50}$ (μM) |
| --- | --- |
| 45 | 0.058 |
| 46 | 0.136 |
| 47 | 0.138 |
| 48 | 0.044 |
| 49 | 0.039 |
| 50 | 0.017 |
| 51 | 0.019 |
| 52 | 0.037 |
| 53 | 0.789 |
| 54 | 0.047 |
| 55 | 0.043 |
| 56 | 0.041 |
| 57 | 0.231 |
| 58 | 0.145 |
| 59 | 0.085 |
| 60 | 0.188 |
| 61 | 0.243 |
| 62 | 0.064 |
| 63 | 0.015 |
| 64 | 0.081 |
| 65 | 0.076 |
| 66 | 0.082 |
| 67 | 0.010 |
| 68 | 0.034 |
| 69 | 0.036 |
| 70 | 0.050 |
| 71 | 0.375 |
| 72 | 0.472 |
| 73 | 0.105 |
| 74 | 0.705 |
| 75 | 0.224 |
| 76 | 0.106 |
| 77 | 0.008 |
| 78 | 0.953 |
| 79 | 0.313 |
| 80 | 0.318 |
| 81 | 0.025 |
| 82 | 0.504 |
| 83 | 0.015 |
| 84 | 0.010 |
| 85 | 0.154 |
| 86 | 0.012 |
| 87 | 0.028 |
| 88 | 0.049 |
| 89 | 0.060 |
| 90 | 0.032 |
| 91 | 0.047 |
| 92 | 0.439 |
| 93 | 0.108 |
| 94 | 0.188 |
| 95 | 0.130 |
| 96 | 0.021 |
| 97 | 0.712 |
| 98 | 0.244 |
| 99 | 0.065 |
| 100 | 0.073 |
| 101 | 0.054 |
| 102 | 0.058 |
| 103 | 0.162 |
| 104 | 0.061 |
| 105 | 0.249 |
| 106 | 0.186 |
| 107 | 0.019 |
| 108 | 0.077 |
| 109 | 0.041 |
| 110 | 0.033 |
| 111 | 1.085 |
| 112 | 0.854 |
| 113 | 1.042 |
| 114 | 0.208 |
| 115 | 0.493 |
| 116 | 0.121 |
| 117 | 0.049 |
| 118 | 0.020 |
| 119 | 0.109 |
| 120 | 0.343 |
| 121 | 0.015 |

TABLE 2-continued

| Compound No. | PK/LDH IC$_{50}$ (μM) |
|---|---|
| 122 | 0.989 |
| 123 | 1.001 |
| 124 | 0.078 |
| 125 | 0.023 |
| 126 | 0.011 |
| 127 | 0.318 |
| 128 | 0.056 |
| 129 | 0.217 |
| 130 | 0.007 |
| 131 | 0.563 |
| 132 | 0.099 |
| 133 | 0.010 |
| 134 | 0.041 |
| 135 | 0.044 |
| 136 | 0.009 |
| 137 | 0.017 |
| 138 | 0.012 |
| 139 | 0.357 |
| 140 | 0.067 |
| 141 | 0.181 |
| 142 | 0.077 |
| 143 | 0.323 |
| 144 | 0.168 |
| 145 | 0.915 |
| 146 | 0.206 |
| 147 | 0.127 |
| 148 | 0.344 |
| 149 | 0.332 |
| 150 | 0.554 |
| 151 | 0.241 |
| 152 | 0.132 |
| 153 | 0.412 |
| 154 | 0.285 |
| 155 | 0.206 |
| 156 | 0.304 |
| 157 | 0.392 |
| 158 | 0.070 |
| 159 | 0.740 |
| 160 | 0.069 |
| 161 | 0.374 |
| 162 | 0.136 |
| 163 | 0.135 |
| 164 | 0.467 |
| 165 | 0.361 |
| 166 | 0.056 |
| 167 | 0.116 |
| 168 | 0.439 |
| 169 | 0.091 |
| 170 | 0.306 |
| 171 | 0.097 |
| 172 | 0.255 |
| 173 | 0.844 |
| 174 | 0.179 |
| 175 | 0.582 |
| 176 | 0.410 |
| 177 | 0.349 |
| 178 | 0.038 |
| 179 | 0.031 |
| 180 | 0.235 |
| 181 | 0.449 |
| 182 | 0.748 |
| 183 | 0.041 |
| 184 | 0.075 |
| 185 | 0.026 |
| 186 | 0.097 |
| 187 | 0.073 |
| 188 | 0.237 |
| 189 | 0.095 |
| 190 | 0.220 |
| 191 | 0.131 |
| 192 | 0.076 |
| 193 | 0.303 |
| 194 | 0.027 |
| 195 | 0.044 |
| 196 | 0.143 |
| 197 | 0.128 |
| 198 | 0.031 |
| 199 | 1.190 |
| 200 | 4.419 |
| 201 | 0.461 |
| 202 | 0.071 |
| 203 | 0.862 |
| 204 | 3.527 |
| 205 | 3.737 |
| 206 | 2.484 |
| 207 | 0.387 |
| 208 | 0.113 |
| 209 | 0.091 |
| 210 | 0.107 |
| 211 | 0.469 |
| 212 | 0.095 |
| 213 | 0.282 |
| 214 | 0.853 |
| 215 | 3.772 |
| 216 | 0.247 |
| 217 | 0.096 |
| 218 | 0.293 |
| 219 | 0.101 |
| 220 | 0.038 |
| 221 | 0.043 |
| 222 | 0.040 |
| 223 | 0.062 |
| 224 | 0.070 |
| 225 | 0.044 |
| 226 | 0.083 |
| 227 | 0.076 |
| 228 | 0.077 |
| 229 | 0.025 |
| 230 | 0.117 |
| 231 | 0.105 |
| 232 | 0.025 |
| 233 | 0.252 |
| 234 | 0.695 |
| 235 | 0.342 |
| 236 | 0.058 |
| 237 | 0.054 |
| 238 | 0.046 |
| 239 | 0.067 |
| 240 | 0.060 |
| 241 | 0.082 |
| 242 | 0.079 |
| 243 | 0.086 |
| 244 | 0.077 |
| 245 | 1.312 |
| 246 | 0.033 |
| 247 | 0.010 |
| 248 | 0.012 |
| 249 | 0.021 |
| 250 | 0.043 |
| 251 | 0.053 |
| 252 | 0.186 |
| 253 | 0.067 |
| 254 | 0.075 |
| 255 | 0.088 |
| 256 | 0.039 |
| 257 | 0.007 |
| 258 | 0.026 |
| 259 | 0.015 |
| 260 | 0.035 |
| 261 | 0.059 |
| 262 | 0.062 |
| 263 | 0.080 |
| 264 | 0.130 |
| 265 | 0.041 |
| 266 | 0.089 |
| 267 | 0.464 |
| 268 | 0.018 |
| 269 | 0.014 |
| 270 | 0.096 |
| 271 | 0.036 |
| 272 | 0.054 |
| 273 | 0.149 |
| 274 | 0.264 |
| 275 | 0.076 |

TABLE 2-continued

| Compound No. | PK/LDH IC$_{50}$ (μM) |
|---|---|
| 276 | 0.020 |
| 277 | 0.031 |
| 278 | 0.011 |
| 279 | 0.234 |
| 280 | 0.149 |
| 281 | 0.059 |
| 282 | 0.049 |
| 283 | 0.058 |
| 284 | 0.090 |
| 285 | 0.149 |
| 286 | 0.147 |
| 287 | 0.124 |
| 288 | 0.109 |
| 289 | 0.056 |
| 290 | 0.056 |
| 291 | 0.053 |
| 292 | 0.1109 |
| 293 | 0.038 |
| 294 | 0.006 |
| 295 | 0.013 |
| 296 | 0.087 |
| 297 | 0.015 |
| 298 | 0.012 |
| 299 | 0.022 |
| 300 | 0.028 |
| 301 | 0.046 |
| 302 | 0.067 |
| 303 | 0.036 |
| 304 | 0.073 |
| 305 | 0.024 |
| 306 | 0.078 |
| 307 | 0.010 |
| 308 | 0.011 |
| 309 | 0.055 |
| 310 | 0.075 |
| 311 | 0.127 |
| 312 | 0.097 |
| 313 | 0.039 |
| 314 | 0.063 |
| 315 | 0.023 |
| 316 | 0.037 |
| 317 | 0.017 |
| 318 | 0.020 |
| 319 | 0.007 |
| 320 | 0.197 |
| 321 | 0.124 |
| 322 | 0.013 |
| 323 | 0.074 |
| 324 | 0.142 |
| 325 | 0.075 |
| 326 | 0.020 |
| 327 | 0.121 |
| 328 | 0.016 |
| 329 | 0.336 |
| 330 | 0.021 |
| 331 | 0.023 |
| 332 | 0.025 |
| 333 | 0.165 |
| 334 | 0.145 |
| 335 | 0.037 |
| 336 | 0.015 |
| 337 | 0.027 |
| 338 | 0.034 |
| 339 | 0.018 |
| 340 | 0.018 |
| 341 | 0.780 |
| 342 | 0.034 |
| 343 | 0.027 |
| 344 | 0.013 |
| 345 | 0.032 |
| 346 | 0.024 |
| 347 | 0.030 |
| 348 | 0.024 |
| 349 | 0.025 |
| 350 | 0.020 |
| 351 | 0.008 |
| 352 | 0.005 |
| 353 | 0.007 |
| 354 | 0.005 |
| 355 | 0.018 |
| 356 | 0.013 |
| 357 | 0.021 |
| 358 | 0.011 |
| 359 | 0.063 |
| 360 | 0.019 |
| 361 | 0.010 |
| 362 | 0.090 |
| 363 | 0.019 |
| 364 | 0.080 |
| 365 | 0.007 |
| 366 | 0.020 |
| 367 | 0.016 |
| 368 | 0.005 |
| 369 | 0.537 |
| 370 | 0.569 |
| 371 | 0.343 |
| 372 | 0.036 |
| 373 | 0.014 |
| 374 | 0.022 |
| 375 | 0.006 |
| 376 | 0.008 |
| 377 | 0.012 |
| 378 | 0.006 |
| 379 | 0.008 |
| 380 | 0.047 |
| 381 | 0.058 |
| 382 | 0.034 |
| 383 | 0.027 |
| 384 | 0.033 |
| 385 | 0.017 |
| 386 | 0.005 |
| 387 | 0.005 |
| 388 | 0.005 |
| 389 | 0.004 |
| 390 | 0.027 |
| 391 | 0.006 |
| 392 | 0.005 |
| 393 | 0.008 |
| 394 | 0.007 |
| 395 | 0.008 |
| 396 | 0.013 |
| 397 | 0.009 |
| 398 | 0.009 |
| 399 | 0.008 |
| 400 | 0.012 |
| 401 | 0.010 |
| 402 | 0.059 |
| 403 | 0.004 |
| 404 | 0.006 |
| 405 | 0.020 |
| 406 | 0.041 |
| 407 | 0.015 |
| 408 | 0.008 |
| 409 | 0.010 |
| 410 | 0.008 |
| 411 | 0.010 |
| 412 | 0.007 |
| 413 | 0.006 |
| 414 | 0.003 |
| 415 | 0.048 |
| 416 | 0.025 |
| 417 | 0.023 |
| 418 | 0.697 |
| 419 | 2.190 |
| 420 | 3.563 |
| 421 | 0.294 |
| 422 | 0.166 |
| 423 | 0.350 |
| 424 | 0.287 |
| 425 | 0.224 |
| 426 | 0.363 |
| 427 | 0.165 |
| 428 | 0.374 |
| 429 | 0.114 |

TABLE 2-continued

| Compound No. | PK/LDH IC$_{50}$ (μM) |
|---|---|
| 430 | 0.191 |
| 431 | 0.221 |
| 432 | 0.185 |
| 433 | 0.091 |
| 434 | 0.109 |
| 435 | 0.149 |
| 436 | 0.173 |
| 437 | 0.157 |
| 438 | 0.303 |
| 439 | 0.185 |
| 440 | 0.447 |
| 441 | 0.051 |
| 442 | 0.023 |
| 443 | 0.028 |
| 444 | 0.044 |
| 445 | 0.075 |
| 446 | 0.098 |
| 447 | 0.096 |
| 448 | 0.071 |
| 449 | 0.039 |
| 450 | 0.094 |
| 451 | 0.095 |
| 452 | 0.040 |
| 453 | 0.077 |
| 454 | 0.072 |
| 455 | 0.291 |
| 456 | 0.055 |
| 457 | 0.032 |
| 458 | 0.071 |
| 459 | 0.028 |
| 460 | 0.187 |
| 461 | 0.026 |
| 462 | 0.024 |
| 463 | 0.025 |
| 464 | 0.023 |
| 465 | 0.547 |
| 466 | 0.238 |
| 467 | 0.324 |
| 468 | 0.091 |
| 469 | 0.061 |
| 470 | 0.082 |
| 471 | 0.029 |
| 472 | 0.022 |
| 473 | 0.100 |
| 474 | 0.043 |
| 475 | 0.077 |
| 476 | 0.039 |
| 477 | 0.020 |
| 478 | 0.069 |
| 479 | 0.055 |
| 480 | 0.079 |
| 481 | 0.247 |
| 482 | 0.068 |
| 483 | 0.049 |
| 484 | 0.066 |
| 485 | 0.210 |
| 486 | 0.041 |
| 487 | 0.068 |
| 488 | 0.031 |
| 489 | 0.353 |
| 490 | 0.052 |
| 491 | 0.093 |
| 492 | 0.138 |
| 493 | 0.103 |
| 494 | 0.661 |
| 495 | 0.066 |
| 496 | 0.086 |
| 497 | 0.369 |
| 498 | >10 |
| 499 | 2.258 |
| 500 | >100 |
| 501 | 0.003 |
| 502 | 0.01 |
| 503 | 0.008 |
| 504 | 0.003 |
| 505 | 0.02 |
| 506 | 0.004 |
| 507 | 0.022 |
| 508 | 0.021 |
| 509 | 0.008 |
| 510 | 0.009 |
| 511 | 0.012 |
| 512 | 0.015 |
| 513 | 0.014 |
| 514 | 0.007 |
| 515 | 0.004 |
| 516 | 0.008 |
| 517 | 0.008 |
| 518 | 1.498 |
| 519 | 0.008 |
| 520 | 0.557 |
| 521 | 2.606 |
| 522 | 0.005 |
| 523 | 0.005 |
| 524 | 0.006 |
| 525 | 0.004 |
| 526 | 0.011 |
| 527 | 0.007 |
| 528 | 0.015 |
| 529 | 0.016 |
| 530 | 0.012 |
| 531 | 0.008 |
| 532 | 0.065 |
| 533 | 0.043 |
| 534 | 0.057 |
| 535 | 0.012 |
| 536 | 0.024 |
| 537 | 0.011 |
| 538 | 0.048 |
| 539 | 0.068 |
| 540 | 0.047 |
| 541 | 0.055 |
| 542 | 0.011 |
| 543 | 0.049 |
| 544 | 0.011 |
| 545 | 1.68 |
| 546 | 0.027 |
| 547 | 0.016 |
| 548 | 0.328 |
| 549 | 0.006 |
| 550 | 0.042 |
| 551 | 0.007 |
| 552 | 0.082 |
| 553 | 0.008 |
| 554 | 0.034 |
| 555 | 0.097 |
| 556 | 0.027 |
| 557 | 0.424 |
| 558 | 0.136 |
| 559 | 1.58 |
| 560 | 0.144 |
| 561 | 0.036 |
| 562 | 0.685 |
| 563 | 0.063 |
| 564 | 0.056 |
| 565 | 0.048 |
| 566 | 0.046 |
| 567 | 0.642 |
| 568 | 0.089 |
| 569 | 0.066 |
| 570 | 0.082 |
| 571 | 0.075 |
| 572 | 0.205 |
| 573 | 0.178 |
| 574 | 0.022 |
| 575 | 0.119 |
| 576 | 0.085 |
| 577 | 0.478 |
| 578 | 0.613 |
| 579 | 0.059 |
| 580 | 0.249 |
| 581 | 0.269 |
| 582 | 0.319 |
| 583 | 0.105 |

TABLE 2-continued

| Compound No. | PK/LDH IC$_{50}$ (μM) |
|---|---|
| 584 | 0.104 |
| 585 | 0.202 |
| 586 | 0.010 |
| 587 | 0.109 |
| 588 | 0.036 |
| 589 | 0.101 |
| 590 | 2.553 |
| 591 | 0.032 |
| 592 | 0.01 |
| 593 | 0.019 |
| 594 | 0.05 |
| 595 | 0.025 |
| 596 | 0.02 |
| 597 | 0.064 |
| 598 | 0.153 |
| 599 | 0.04 |
| 600 | 0.036 |
| 601 | 0.034 |
| 602 | 0.092 |
| 603 | 0.602 |
| 604 | 0.176 |
| 605 | 0.168 |
| 606 | 1.125 |
| 607 | 0.333 |
| 608 | 2.856 |
| 609 | 0.225 |
| 610 | 0.107 |
| 611 | 0.547 |
| 612 | 2.182 |
| 613 | 0.130 |
| 614 | 1.149 |
| 615 | 1.578 |
| 616 | 1.324 |
| 617 | 1.644 |
| 618 | 1.515 |
| 619 | 1.157 |
| 620 | 0.142 |
| 621 | 0.555 |
| 622 | 0.443 |
| 623 | 0.111 |
| 624 | 0.408 |
| 625 | 0.139 |
| 626 | 0.805 |
| 627 | 1.618 |
| 628 | 2.778 |
| 629 | 1.483 |
| 630 | 0.092 |
| 631 | 0.176 |
| 632 | 0.013 |
| 633 | 1.598 |
| 634 | 0.043 |
| 635 | 0.082 |
| 636 | 0.071 |
| 637 | 0.453 |
| 638 | 0.399 |
| 639 | 0.921 |
| 640 | 1.445 |
| 641 | 2.95 |
| 642 | 1.333 |
| 643 | 2.185 |
| 644 | 0.273 |
| 645 | 0.1 |
| 646 | 0.048 |
| 647 | 1.643 |
| 648 | 0.616 |
| 649 | 0.483 |
| 650 | 1.436 |
| 651 | 0.077 |
| 652 | 1.203 |
| 653 | 0.262 |
| 654 | 0.252 |
| 655 | 1.008 |
| 656 | 1.301 |
| 657 | 0.127 |
| 658 | 0.099 |
| 659 | 0.331 |
| 660 | 0.309 |

TABLE 2-continued

| Compound No. | PK/LDH IC$_{50}$ (μM) |
|---|---|
| 661 | 0.043 |
| 662 | 0.227 |
| 663 | 2.022 |
| 664 | 0.115 |
| 665 | 0.099 |
| 666 | 2.273 |
| 667 | 0.023 |
| 668 | 0.025 |
| 669 | 0.04 |
| 670 | 0.071 |
| 671 | 0.849 |
| 672 | 0.082 |
| 673 | 1.74 |
| 674 | 0.096 |
| 675 | 0.101 |
| 676 | 0.554 |
| 677 | 0.051 |
| 678 | 1.065 |
| 679 | 0.577 |
| 680 | 0.015 |
| 681 | 0.03 |
| 682 | 0.116 |
| 683 | 2.362 |
| 684 | 1.332 |
| 685 | 0.204 |
| 686 | 0.013 |
| 687 | 3.82 |
| 688 | 0.106 |
| 689 | >10.0 |
| 690 | 0.047 |
| 691 | 0.015 |
| 692 | 2.48 |
| 693 | 0.056 |
| 694 | 0.034 |
| 695 | 0.929 |
| 696 | 0.103 |
| 697 | 1.777 |
| 698 | 0.151 |
| 699 | 0.051 |
| 700 | 0.321 |
| 701 | 0.446 |
| 702 | 1.256 |
| 703 | 2.159 |
| 704 | 2.218 |
| 705 | 1.722 |
| 707 | 1.992 |
| 708 | 2.508 |
| 709 | 1.144 |
| 710 | 0.146 |
| 711 | 0.03 |
| 712 | 0.015 |
| 713 | 0.074 |
| 714 | 0.045 |
| 715 | 0.105 |
| 716 | 2.161 |
| 717 | 1.481 |
| 718 | 2.618 |
| 719 | 0.254 |
| 720 | 2.45 |
| 721 | 0.079 |
| 722 | 0.085 |
| 723 | 0.046 |
| 724 | 0.034 |
| 725 | 0.015 |
| 726 | 0.03 |
| 727 | 0.017 |
| 728 | 0.036 |
| 729 | 0.039 |
| 730 | 0.037 |
| 731 | 0.066 |
| 732 | 0.027 |
| 733 | 0.005 |
| 734 | 0.026 |
| 735 | 0.005 |
| 736 | 0.02 |
| 737 | 0.037 |
| 738 | 0.105 |

TABLE 2-continued

| Compound No. | PK/LDH IC$_{50}$ (µM) |
|---|---|
| 739 | 0.017 |
| 740 | 0.009 |
| 741 | 0.016 |
| 742 | 0.024 |
| 743 | 0.028 |
| 744 | 0.046 |
| 745 | 0.024 |
| 746 | 0.07 |
| 747 | 0.016 |
| 748 | 0.015 |
| 749 | 0.006 |
| 750 | 0.011 |
| 751 | 0.013 |
| 752 | 0.021 |
| 753 | 0.021 |
| 754 | 0.027 |
| 755 | 0.102 |
| 756 | 0.023 |
| 757 | 0.029 |
| 758 | 0.032 |
| 759 | 0.018 |
| 760 | 0.017 |
| 761 | 0.055 |
| 762 | 0.027 |
| 763 | 0.466 |
| 764 | 0.155 |
| 765 | 0.047 |
| 766 | 0.038 |
| 767 | 0.106 |
| 768 | 0.121 |
| 769 | 0.022 |
| 770 | 0.062 |
| 771 | 0.033 |
| 772 | 0.356 |
| 773 | 0.124 |
| 774 | 0.022 |
| 775 | 1.08 |
| 776 | 1.151 |
| 777 | 0.042 |
| 778 | 0.381 |
| 779 | 0.016 |
| 780 | 0.009 |
| 781 | 0.011 |
| 782 | 0.011 |
| 783 | 0.005 |
| 784 | 0.005 |
| 785 | 0.006 |
| 786 | 0.003 |
| 787 | 0.007 |
| 788 | 0.02 |
| 789 | 0.01 |
| 790 | 0.008 |
| 791 | 0.007 |
| 792 | 0.006 |
| 793 | 0.012 |
| 794 | 0.002 |
| 795 | 0.011 |
| 796 | 0.005 |
| 797 | 0.016 |
| 798 | 0.012 |
| 799 | 0.004 |
| 800 | 0.009 |
| 801 | 0.024 |
| 802 | 0.009 |
| 803 | 0.004 |
| 804 | 0.017 |
| 805 | 0.012 |
| 806 | 0.006 |
| 807 | 0.019 |
| 808 | 0.012 |
| 809 | 0.007 |
| 810 | 0.357 |

Example B-2

The GYS1 cell based assay is a bioluminescent assay that quantifies the glucose resulting from glycogen digestion; the quantified glucose is an indirect measure of GYS1 glycogen synthesis. Newly synthesized glycogen is digested using Glucoamylase; the resulting glucose is quantified by using the Glucose-glo assay kit from Promega. Glucose-glo works by coupling glucose oxidation and NADH production with a bioluminescent system that is activated with NADH. Glucose is oxidized by Glucose dehydrogenase and the reaction reduces NAD+ to NADH; NADH activates Reductase which reduces a pro-luciferin Reductase Substrate to luciferin. Luciferin is detected in a luciferase reaction using Ultra-Glo rLuciferase and ATP, and the luminesce produced is proportional to the glucose in the sample. The luminescence is measured as a single point read in a plate reader.

Compounds that inhibit the hGYS1 enzyme and, subsequently, the glycogen synthesis in cells, were tested using assay ready plates (white, clear bottom 384 well plates) in a final DMSO reaction volume of 1% DMSO. Compounds in the assay ready plates were mixed with media with no additives, except for 20 mM glucose prior to cell addition. HeLa cells were starved in media with no additives, except for 1× Glutamax for 24 h. Starved HeLa cells were plated, in a 1:1 ratio to the media in the assay ready plate and incubated for 24 h at 37° C. and 5% $C_{O2}$. Cells were washed in 1×PBS buffer and lysed in lysis buffer containing 50% 1×PBS and 25% 0.3 N HCl of the final volume in the well or reaction volume; cells were incubated with lysis buffer for 10 minutes and quenched with the remaining 25% of the reaction volume that consisted of 450 mM Tris pH 8.0. Lysates were mixed in a 1:1 ratio with Glucoamylase in 100 mM Sodium Acetate buffer, pH 5.3; the mixture was incubated for 1 h at 37° C. The digested lysate was mixed in a 1:1 ratio with Glucose-glo detection mixture as per vendor recommendations (Luciferase detection buffer, Reductase, Reductase substrate, Glucose dehydrogenase, and NAD) in read-out plates (solid white 384-well plates) and incubated for 1 h at RT. The plates were read using a plate reader with luminescence capabilities. Each compound concentration Relative Luminescence Unit (RLU) was averaged and normalized to the average RLU of the positive and negative controls to obtain a percentage inhibition. The normalized data vs. concentration was plotted; to determine the half-maximal concentration (IC$_{50}$), the Levenberg-Marquardt algorithm was used to fit a Hill equation to the dose response data.

The results are shown in Table 3 below, which reports the IC$_{50}$ of each compound. Unless otherwise specified, IC$_{50}$ values are reported as the geometric mean of at least 2 assay runs on separate days. As shown in the table below, the compounds of the present invention are potent inhibitors of human GYS1. Unless otherwise specified, IC$_{50}$ values are reported as the geometric mean of at least two assay runs on separate days. Each run represents the average of a technical replicate, where each compound was assayed twice in the same plate. A superscript "#" symbol in Table 3 indicates results from a single assay run.

TABLE 3

| Compound No. | Avg IC$_{50}$ (µM) |
|---|---|
| 1 | 0.42 |
| 2 | 1.09 |
| 17 | 0.33 |

TABLE 3-continued

| Compound No. | Avg IC$_{50}$ (μM) |
|---|---|
| 21 | 0.47 |
| 49 | 0.36 |
| 77 | 0.12 |
| 126 | 0.17 |
| 136 | 0.17 |
| 138 | 0.27 |
| 145 | >10.00 |
| 149 | >10.00 |
| 166 | 0.78 |
| 177 | 2.09 |
| 178 | 0.41 |
| 179 | 0.4 |
| 183 | 0.93 |
| 184 | 3.03 |
| 198 | 0.39 |
| 201 | 3.7 |
| 202 | 1.86 |
| 219 | 1.41 |
| 227 | 1.31 |
| 236 | 0.81 |
| 239 | 1.56 |
| 240 | 2.09 |
| 241 | 1.14 |
| 242 | 1.14 |
| 243 | 2.25 |
| 244 | 1.8 |
| 246 | 0.62 |
| 247 | 0.18 |
| 248 | 0.2 |
| 249 | 1.15 |
| 250 | 1.27 |
| 252 | 2.48 |
| 253 | 1.09 |
| 254 | 1.23 |
| 255 | 1.01 |
| 256 | 0.99 |
| 257 | 0.24 |
| 258 | 0.74 |
| 259 | 0.28 |
| 260 | 0.53 |
| 261 | 1.8 |
| 262 | 3.63 |
| 263 | 1.95 |
| 264 | 4.29 |
| 265 | 0.83 |
| 266 | 1.22 |
| 267 | 4.3 |
| 268 | 0.83 |
| 269 | 0.24 |
| 270 | 1.4 |
| 271 | 0.87 |
| 272 | 0.71 |
| 273 | 1.79 |
| 274 | 3.23 |
| 275 | 1.05 |
| 276 | 0.4 |
| 277 | 0.65 |
| 278 | 0.23 |
| 279 | 2.31 |
| 280 | 1.53 |
| 281 | 1.56 |
| 282 | 4.18 |
| 283 | 2.4 |
| 284 | 5.19 |
| 285 | >18.64 |
| 286 | >30.00 |
| 287 | 11.81 |
| 293 | 0.66 |
| 294 | 0.16 |
| 295 | 0.59 |
| 296 | 4.44 |
| 297 | 0.7 |
| 298 | 0.26 |
| 299 | 0.42 |
| 300 | 0.57 |
| 301 | 0.9 |
| 302 | 1.23 |
| 303 | 1.52 |
| 304 | 2.33 |
| 305 | 0.63 |
| 306 | 0.81 |
| 307 | 0.5 |
| 308 | 0.33 |
| 309 | 0.97 |
| 310 | 1.29 |
| 311 | 2.1 |
| 312 | 0.83 |
| 313 | 0.86 |
| 314 | 1.01 |
| 315 | 0.73 |
| 316 | 0.93 |
| 317 | 0.39 |
| 318 | 0.58 |
| 319 | 0.24 |
| 320 | 1.59 |
| 321 | 1.24 |
| 322 | 0.29 |
| 323 | 0.9 |
| 326 | 0.34 |
| 330 | 0.56 |
| 332 | 0.27 |
| 335 | 0.45 |
| 336 | 0.28 |
| 338 | 0.39 |
| 339 | 0.31 |
| 340 | 0.25 |
| 342 | 0.37 |
| 343 | 0.46 |
| 347 | 0.4 |
| 348 | 0.27 |
| 349 | 0.4 |
| 351 | 0.13 |
| 352 | 0.11 |
| 353 | 0.09 |
| 354 | 0.06 |
| 355 | 0.16 |
| 356 | 0.19 |
| 357 | 0.22 |
| 358 | 0.19 |
| 359 | 0.96 |
| 360 | 0.31 |
| 361 | 0.21 |
| 362 | 1.15 |
| 363 | 0.32 |
| 364 | 0.48 |
| 365 | 1.19 |
| 367 | 0.47 |
| 368 | 0.15 |
| 369 | >30.00 |
| 371 | 3.88 |
| 372 | 1.1 |
| 373 | 0.21 |
| 374 | 0.36 |
| 375 | 0.57 |
| 377 | 0.14 |
| 378 | 0.17 |
| 379 | 0.19 |
| 380 | 0.45 |
| 381 | 0.44 |
| 382 | 0.52 |
| 383 | 0.41 |
| 384 | 0.7 |
| 385 | 0.39 |
| 386 | 0.08 |
| 387 | 0.03 |
| 388 | 0.12 |
| 389 | 0.05 |
| 390 | 1.03 |
| 391 | 0.15 |
| 392 | 0.1 |
| 393 | 0.12 |
| 394 | 0.15 |
| 395 | 0.24 |
| 396 | 0.33 |

TABLE 3-continued

| Compound No. | Avg IC$_{50}$ (μM) |
|---|---|
| 397 | 0.4 |
| 398 | 0.28 |
| 399 | 0.15 |
| 400 | 0.17 |
| 401 | 0.29 |
| 402 | 0.85 |
| 403 | 0.14 |
| 404 | 0.07 |
| 405 | 0.49 |
| 406 | 0.76 |
| 407 | 0.42 |
| 408 | 0.35 |
| 409 | 0.29 |
| 410 | 0.13 |
| 411 | 0.22 |
| 412 | 0.12 |
| 413 | 0.16 |
| 414 | 0.06 |
| 415 | 0.71 |
| 416 | 0.47 |
| 417 | 0.45 |
| 423 | >9.26 |
| 425 | 3.59 |
| 427 | 1.96 |
| 431 | 3.35 |
| 433 | 1.48 |
| 442 | 0.86 |
| 445 | 1.66 |
| 446 | 2.19 |
| 447 | 5.32 |
| 448 | 1.35 |
| 449 | 0.7 |
| 450 | 1.73 |
| 451 | 1.57 |
| 452 | 0.98 |
| 453 | 1.84 |
| 454 | 1.6 |
| 455 | 3.62 |
| 456 | 1.08 |
| 457 | 0.72 |
| 458 | 1.33 |
| 459 | 0.75 |
| 460 | 2.42 |
| 461 | 0.57 |
| 462 | 0.64 |
| 463 | 0.67 |
| 464 | 0.65 |
| 465 | 6.04 |
| 466 | 2.32 |
| 467 | 4.81 |
| 468 | 1.43 |
| 469 | 1.18 |
| 470 | 0.96 |
| 471 | 0.7 |
| 472 | 0.54 |
| 473 | 1.77 |
| 474 | 0.88 |
| 475 | 1.29 |
| 476 | 0.9 |
| 477 | 0.63 |
| 478 | 1.19 |
| 479 | 1.43 |
| 480 | 1.12 |
| 481 | 7.77 |
| 482 | 1.41 |
| 483 | 0.72 |
| 484 | 0.82 |
| 485 | 3.72 |
| 486 | 1.02 |
| 487 | 2.09 |
| 488 | 0.88 |
| 490 | 2.87 |
| 491 | 5.55 |
| 492 | >30.00 |
| 493 | 15.77 |
| 494 | 12.41 |
| 495 | 1.5 |
| 496 | 1.82 |
| 497 | >5.67 |
| 498 | >10.00 |
| 501 | 0.05 |
| 502 | 0.17 |
| 503 | 0.24 |
| 504 | 0.06 |
| 505 | 0.35 |
| 506 | 0.37 |
| 507 | 0.26 |
| 508 | 0.31 |
| 509 | 0.18 |
| 510 | 0.23 |
| 511 | 0.26 |
| 512 | 0.29 |
| 513 | 0.22 |
| 514 | 0.77 |
| 515 | 0.1 |
| 516 | 0.71 |
| 517 | 0.54 |
| 518 | 10.68 |
| 519 | 0.22 |
| 520 | >30.00 |
| 521 | >30.00 |
| 522 | 0.45 |
| 523 | 0.08 |
| 524 | 0.19 |
| 525 | 0.05 |
| 526 | 0.13 |
| 527 | 0.25 |
| 528 | 0.33 |
| 529 | 1.04 |
| 530 | 0.91 |
| 531 | 0.06 |
| 532 | 1.18 |
| 533 | 1.21 |
| 534 | 1.28 |
| 535 | 1.22 |
| 536 | 0.35 |
| 537 | 0.16 |
| 538 | 1.22 |
| 539 | 0.96 |
| 540 | 0.59 |
| 541 | 0.65 |
| 542 | 1.48 |
| 543 | 0.61 |
| 544 | 0.26 |
| 545 | >30.00 |
| 546 | 0.51 |
| 547 | 0.36 |
| 548 | 5.76 |
| 549 | 0.12 |
| 550 | 0.65 |
| 551 | 0.21 |
| 552 | 1.12 |
| 553 | 0.4 |
| 554 | 0.38 |
| 555 | 0.66 |
| 556 | 0.76 |
| 557 | 5.78 |
| 558 | 2.46 |
| 559 | >22.13 |
| 560 | 1.8 |
| 561 | 0.87 |
| 562 | 7.07 |
| 563 | 0.78 |
| 564 | 0.79 |
| 565 | 1.21 |
| 566 | 0.77 |
| 567 | 11.54 |
| 568 | 0.96 |
| 569 | 0.96 |
| 570 | 1.22 |
| 571 | 0.93 |
| 572 | 3.6 |
| 573 | 1.66 |
| 574 | 0.2 |

TABLE 3-continued

| Compound No. | Avg IC$_{50}$ (μM) |
|---|---|
| 575 | 2.09 |
| 576 | 1.8 |
| 577 | 3.98 |
| 578 | 6.66 |
| 579 | 1.83 |
| 580 | 4.27 |
| 581 | 3.92 |
| 582 | 8.08 |
| 583 | 1.64 |
| 584 | 4.07 |
| 585 | 3.21 |
| 586 | 0.15 |
| 587 | 2.39 |
| 588 | 0.48 |
| 589 | 1.42 |
| 590 | 23.43 |
| 591 | 0.31 |
| 592 | 0.33 |
| 593 | 0.28 |
| 594 | 0.72 |
| 595 | 0.46 |
| 596 | 0.28 |
| 597 | 1.32 |
| 598 | 2.18 |
| 599 | 0.72 |
| 600 | 0.62 |
| 601 | 0.71 |
| 602 | 0.76 |
| 604 | 1.59 |
| 605 | 2.13 |
| 607 | 3.29 |
| 608 | >10.00 |
| 609 | 1.65 |
| 610 | 1.01 |
| 611 | 5.32 |
| 612 | >28.95 |
| 622 | >10.00 |
| 623 | 4.07 |
| 624 | 5.79 |
| 625 | 1.14 |
| 626 | >30.00 |
| 627 | 29.51 |
| 628 | >30.00 |
| 629 | >23.95 |
| 630 | 2.13 |
| 631 | 13.62 |
| 632 | 0.66 |
| 633 | >30.00 |
| 638 | >23.41 |
| 650 | >10.00 |
| 651 | 1.57 |
| 652 | 21.64 |
| 653 | 3.75 |
| 654 | 3.29 |
| 655 | >30.00 |
| 656 | 10.85 |
| 657 | 1.5 |
| 658 | 1.66 |
| 659 | 4.35 |
| 667 | 0.29 |
| 668 | 0.32 |
| 669 | 0.47 |
| 670 | 0.66 |
| 672 | 1.22 |
| 674 | 0.71 |
| 675 | 1.13 |
| 676 | 13.99 |
| 677 | 0.99 |
| 678 | >10.00 |
| 679 | 8.49 |
| 680 | 0.27 |
| 681 | 0.43 |
| 682 | 2.09 |
| 683 | >30.00 |
| 684 | 13.81 |
| 685 | 2.71 |
| 686 | 0.64 |
| 687 | >30 |
| 690 | 0.9 |
| 691 | 0.39 |
| 692 | >30.00 |
| 693 | 1.15 |
| 694 | 1.21 |
| 695 | >26.28 |
| 696 | 2.71 |
| 697 | 9.2 |
| 710 | 2.34 |
| 711 | 0.63 |
| 712 | 0.33 |
| 713 | 0.86 |
| 714 | 1.39 |
| 716 | 22.26 |
| 717 | >25.76 |
| 718 | >30.00 |
| 719 | 2.22 |
| 720 | >30.00 |
| 721 | 1.09 |
| 722 | 1.45 |
| 723 | 0.72 |
| 724 | 0.63 |
| 725 | 0.31 |
| 726 | 0.54 |
| 727 | 0.91 |
| 728 | 0.79 |
| 729 | 0.71 |
| 730 | 0.76 |
| 731 | 1.62 |
| 732 | 1.37 |
| 733 | 0.15 |
| 734 | 1.73 |
| 735 | 0.27 |
| 736 | 0.78 |
| 737 | 0.55 |
| 738 | 1.21 |
| 739 | 0.34 |
| 740 | 0.32 |
| 741 | 0.71 |
| 742 | 0.63 |
| 743 | 0.48 |
| 744 | 1.52 |
| 745 | 0.51 |
| 746 | 1.62 |
| 747 | 0.42 |
| 748 | 0.53 |
| 749 | 0.25 |
| 750 | 0.26 |
| 751 | 0.47 |
| 752 | 0.64 |
| 753 | 0.32 |
| 754 | 0.42 |
| 755 | 1.06 |
| 756 | 1.7 |
| 757 | 0.4 |
| 758 | 1.16 |
| 759 | 0.59 |
| 760 | 0.37 |
| 766 | 0.35 |
| 768 | 1.23 |
| 769 | 0.29 |
| 771 | 0.54 |
| 772 | 4.53 |
| 773 | 1.2 |
| 774 | 0.19 |
| 775 | >17.54 |
| 776 | >9.01 |
| 777 | 0.93 |
| 778 | 7.01 |
| 779 | 0.33 |
| 780 | 0.28 |
| 781 | 0.27 |
| 782 | 0.22 |
| 783 | 0.08 |
| 784 | 0.31 |
| 785 | 0.13 |

TABLE 3-continued

| Compound No. | Avg IC$_{50}$ (μM) |
|---|---|
| 786 | 0.05 |
| 787 | 0.13 |
| 788 | 0.34 |
| 789 | 0.28 |
| 790 | 0.25 |
| 791 | 0.39 |
| 792 | 0.21 |
| 793 | 0.58 |
| 794 | 0.04 |
| 795 | 0.24 |
| 796 | 0.11 |
| 797 | 0.29 |
| 798 | 0.22 |
| 799 | 0.1 |
| 800 | 0.18 |
| 801 | 0.38 |
| 802 | 0.37 |
| 803 | 0.08 |
| 804 | 0.14 |
| 805 | 0.28 |
| 806 | 0.09 |
| 807 | 0.45 |
| 809 | 0.19 |
| 810 | 5.28 |

Example B-3

The GYS2 coupled enzyme assay is a kinetic biochemical assay that indirectly quantifies the rate of glycogen synthesis by coupling the conversion of GYS2 substrate UDP-glucose into UDP with downstream enzymatic reactions. UDP is released from UDP-glucose as glucose monomers are linked into the growing glycogen strand by GYS2. The coupled assay then proceeds with pyruvate kinase utilizing UDP and phospho(enol)pyruvate (PEP) to form pyruvate. Lactate dehydrogenase then converts pyruvate and NADH into lactate and NAD+. Oxidation of NADH to NAD+ can be measured continuously with a plate reader by quantifying the decrease in NADH absorbance at 340 nm over time.

Compounds that inhibit the hGYS2 enzyme and, subsequently, the downstream conversion of NADH to NAD+, were tested using assay ready plates (black, clear bottom 384 well plates) in a final DMSO reaction volume of 2.5% DMSO. The Assay Buffer contained 50 mM Tris pH 7.5, 2 mM MgCl$_2$, and 100 mM KCl. Fresh stocks of BSA at a final concentration of 0.02% and TCEP 1 mM were added before splitting buffer into hGYS2 buffer and substrate buffer. To the hGYS2 buffer, rabbit liver glycogen was added at a final concentration of 0.2% glycogen. Glucose-6-Phosphate was added at 2 mM, recombinant hGYS2/GN1 protein was added at 200 nM to the substrate buffer, phosphoenolpyruvate (PEP) was added at 2 mM, UDP-Glucose was added at 2 mM, NADH was added at 0.6 mM, and Pyruvate Kinase/Lactate Dehydrogenase was added at 20 units/mL. The reaction was initiated by mixing hGYS2 buffer and substrate buffer at a 1:1 ratio. Both buffers were plated using a liquid dispensing device with hGYS2 buffer plated first followed by the substrate buffer. Plates were spun briefly to eliminate air bubbles and are immediately read in continuous mode at an absorbance of 340 nm, for 10 time points in one-minute increments, for a total of 10 minutes. The slope from these 10 time points was normalized to the positive and negative control wells. The duplicate % inhibition values are then averaged and fit to a Hill equation for dose response according to the Levenberg-Marquardt algorithm with the Hill equation maximum set to 100 and the minimum set to 0.

The results are shown in Table 4 below, which reports the IC$_{50}$ of each compound. Unless otherwise specified, IC$_{50}$ values are reported as the geometric mean of at least 2 assay runs on separate days. As shown in the table below, the compounds of the present invention are not potent inhibitors of human GYS2. Unless otherwise specified, IC$_{50}$ values are reported as the geometric mean of at least two assay runs on separate days. Each run represents the average of a technical replicate, where each compound was assayed twice in the same plate. A superscript "#" symbol in Table 4 indicates results from a single assay run.

TABLE 4

| Compound No. | Avg_IC50 (μM) |
|---|---|
| 1 | >100.0 |
| 2 | >100.0 |
| 3 | >100.0 |
| 6 | >100.0 |
| 7 | >100.0 |
| 8 | >100.0 |
| 9 | >100.0 |
| 10 | >100.0 |
| 11 | >100.0 |
| 13 | >100.0 |
| 14 | >100.0 |
| 15 | >100.0 |
| 16 | >100.0 |
| 17 | >100.0 |
| 18 | >100.0 |
| 21 | >100.0 |
| 22 | >100.0 |
| 23 | >100.0 |
| 24 | >100.0 |
| 25 | >100.0 |
| 26 | >100.0 |
| 27 | >100.0 |
| 28 | >100.0 |
| 29 | >100.0 |
| 31 | >100.0 |
| 32 | >100.0 |
| 33 | >100.0 |
| 34 | >100.0 |
| 35 | >100.0 |
| 36 | >100.0 |
| 37 | >100.0 |
| 38 | >100.0 |
| 40 | >100.0 |
| 41 | >100.0 |
| 44 | >100.0 |
| 46 | >100.0 |
| 48 | >100.0 |
| 49 | >100.0 |
| 50 | >100.0 |
| 51 | >100.0 |
| 52 | >100.0 |
| 55 | >100.0 |
| 56 | >100.0 |
| 57 | >100.0 |
| 58 | >100.0 |
| 59 | >100.0 |
| 60 | >100.0 |
| 61 | >100.0 |
| 62 | >100.0 |
| 63 | >100.0 |
| 64 | >100.0 |
| 65 | >100.0 |
| 67 | >100.0 |
| 68 | >100.0 |
| 69 | >100.0 |
| 70 | >100.0 |
| 73 | >100.0 |
| 75 | >100.0 |
| 76 | >100.0 |
| 77 | >100.0 |
| 81 | >100.0 |
| 83 | >100.0 |

TABLE 4-continued

| Compound No. | Avg_IC50 (μM) |
|---|---|
| 84 | >100.0 |
| 85 | >100.0 |
| 86 | >100.0 |
| 87 | >100.0 |
| 88 | >100.0 |
| 89 | >100.0 |
| 90 | >100.0 |
| 91 | >100.0 |
| 93 | >100.0 |
| 94 | >100.0 |
| 95 | >100.0 |
| 96 | >100.0 |
| 98 | >100.0 |
| 99 | >100.0 |
| 100 | >100.0 |
| 101 | >100.0 |
| 102 | >100.0 |
| 103 | >100.0 |
| 104 | >100.0 |
| 105 | >100.0 |
| 106 | >100.0 |
| 107 | >100.0 |
| 108 | >100.0 |
| 109 | >100.0 |
| 110 | >100.0 |
| 114 | >100.0 |
| 117 | >100.0 |
| 118 | >100.0 |
| 119 | >100.0 |
| 121 | >100.0 |
| 125 | >100.0 |
| 126 | >100.0 |
| 128 | >100.0 |
| 129 | >100.0 |
| 130 | >100.0 |
| 133 | >100.0 |
| 134 | >100.0 |
| 135 | >100.0 |
| 136 | >100.0 |
| 137 | >100.0 |
| 138 | >100.0 |
| 140 | >100.0 |
| 141 | >100.0 |
| 142 | >100.0 |
| 144 | >100.0 |
| 146 | >100.0 |
| 147 | >100.0 |
| 151 | >100.0 |
| 154 | >100.0 |
| 155 | >100.0 |
| 158 | >100.0 |
| 160 | >100.0 |
| 162 | >100.0 |
| 163 | >100.0 |
| 166 | >100.0 |
| 167 | >100.0 |
| 169 | >100.0 |
| 171 | >100.0 |
| 172 | >100.0 |
| 174 | >100.0 |
| 178 | >100.0 |
| 179 | >100.0 |
| 180 | >100.0 |
| 183 | >100.0 |
| 184 | >100.0 |
| 185 | >100.0 |
| 187 | >100.0 |
| 188 | >100.0 |
| 189 | >100.0 |
| 190 | >100.0 |
| 191 | >100.0 |
| 192 | >100.0 |
| 193 | >100.0 |
| 194 | >100.0 |
| 195 | >100.0 |
| 196 | >100.0 |
| 197 | >100.0 |
| 198 | >100.0 |
| 202 | >100.0 |
| 203 | >100.0 |
| 204 | >100.0 |
| 205 | >100.0 |
| 206 | >100.0 |
| 207 | >100.0 |
| 208 | >100.0 |
| 209 | >100.0 |
| 210 | >100.0 |
| 213 | >100.0 |
| 214 | >100.0 |
| 216 | >100.0 |
| 217 | >100.0 |
| 218 | >100.0 |
| 219 | >100.0 |
| 220 | >100.0 |
| 221 | >100.0 |
| 222 | >100.0 |
| 223 | >100.0 |
| 224 | >100.0 |
| 226 | >100.0 |
| 227 | >100.0 |
| 228 | >100.0 |
| 229 | >100.0 |
| 231 | >100.0 |
| 232 | >100.0 |
| 233 | >100.0 |
| 236 | >100.0 |
| 237 | >100.0 |
| 238 | >100.0 |
| 239 | >100.0 |
| 240 | >100.0 |
| 241 | >100.0 |
| 242 | >100.0 |
| 243 | >100.0 |
| 244 | >100.0 |
| 245 | >100.0 |
| 246 | >100.0 |
| 247 | >100.0 |
| 248 | >100.0 |
| 249 | >100.0 |
| 250 | >100.0 |
| 251 | >100.0 |
| 252 | >100.0 |
| 253 | >100.0 |
| 254 | >100.0 |
| 255 | >100.0 |
| 256 | >100.0 |
| 257 | >100.0 |
| 258 | >100.0 |
| 259 | >100.0 |
| 260 | >100.0 |
| 261 | >100.0 |
| 262 | >100.0 |
| 263 | >100.0 |
| 264 | >100.0 |
| 265 | >100.0 |
| 266 | >100.0 |
| 268 | >100.0 |
| 269 | >100.0 |
| 270 | >100.0 |
| 271 | >100.0 |
| 272 | >100.0 |
| 273 | >100.0 |
| 274 | >100.0 |
| 275 | >100.0 |
| 276 | >100.0 |
| 277 | >100.0 |
| 278 | >100.0 |
| 279 | >100.0 |
| 280 | >100.0 |
| 281 | >100.0 |
| 282 | >100.0 |
| 283 | >100.0 |
| 284 | >100.0 |
| 287 | >100.0 |

TABLE 4-continued

| Compound No. | Avg_IC50 (μM) |
|---|---|
| 288 | >100.0 |
| 289 | >100.0 |
| 290 | >100.0 |
| 291 | >100.0 |
| 292 | >100.0 |
| 293 | >100.0 |
| 294 | >100.0 |
| 295 | >100.0 |
| 296 | >100.0 |
| 298 | >100.0 |
| 299 | >100.0 |
| 300 | >100.0 |
| 301 | >100.0 |
| 302 | >100.0 |
| 303 | >100.0 |
| 304 | >100.0 |
| 306 | >100.0 |
| 307 | >100.0 |
| 308 | >100.0 |
| 309 | >100.0 |
| 310 | >100.0 |
| 311 | >100.0 |
| 312 | >100.0 |
| 313 | >100.0 |
| 314 | >100.0 |
| 315 | >100.0 |
| 316 | >100.0 |
| 317 | >100.0 |
| 318 | >100.0 |
| 319 | >100.0 |
| 320 | >100.0 |
| 321 | >100.0 |
| 322 | >100.0 |
| 323 | >100.0 |
| 324 | >100.0 |
| 325 | >100.0 |
| 326 | >100.0 |
| 328 | >100.0 |
| 330 | >100.0 |
| 331 | >100.0 |
| 332 | >100.0 |
| 333 | >100.0 |
| 334 | >100.0 |
| 335 | >100.0 |
| 336 | >100.0 |
| 337 | >100.0 |
| 338 | >100.0 |
| 339 | >100.0 |
| 340 | >100.0 |
| 342 | >100.0 |
| 343 | >100.0 |
| 344 | >100.0 |
| 345 | >100.0 |
| 346 | >100.0 |
| 347 | >100.0 |
| 348 | >100.0 |
| 349 | >100.0 |
| 350 | >100.0 |
| 351 | >100.0 |
| 352 | >100.0 |
| 353 | >100.0 |
| 354 | >100.0 |
| 355 | >100.0 |
| 356 | >100.0 |
| 357 | >100.0 |
| 358 | >100.0 |
| 359 | >100.0 |
| 360 | >100.0 |
| 361 | >100.0 |
| 362 | >100.0 |
| 363 | >100.0 |
| 364 | >100.0 |
| 365 | >100.0 |
| 366 | >100.0 |
| 367 | >100.0 |
| 368 | >82.29 |
| 369 | >100.0 |

TABLE 4-continued

| Compound No. | Avg_IC50 (μM) |
|---|---|
| 371 | >100.0 |
| 372 | >100.0 |
| 373 | >100.0 |
| 374 | >100.0 |
| 375 | >77.43 |
| 376 | >100.0 |
| 377 | >100.0 |
| 378 | >100.0 |
| 379 | >100.0 |
| 380 | >100.0 |
| 381 | >100.0 |
| 382 | >100.0 |
| 383 | >100.0 |
| 384 | >100.0 |
| 385 | >100.0 |
| 386 | >100.0 |
| 387 | 36.22 |
| 388 | >100.0 |
| 389 | >90.29 |
| 390 | >100.0 |
| 391 | 89.32 |
| 392 | >100.0 |
| 393 | >100.0 |
| 394 | >100.0 |
| 395 | >100.0 |
| 396 | >100.0 |
| 398 | >100.0 |
| 399 | >100.0 |
| 400 | >100.0 |
| 401 | >100.0 |
| 402 | >100.0 |
| 403 | >100.0 |
| 404 | >100.0 |
| 405 | >100.0 |
| 406 | >100.0 |
| 407 | >100.0 |
| 408 | >100.0 |
| 409 | >100.0 |
| 410 | >100.0 |
| 411 | >100.0 |
| 412 | >100.0 |
| 413 | >100.0 |
| 414 | 78.66 |
| 415 | >100.0 |
| 416 | >100.0 |
| 417 | >100.0 |
| 418 | >100.0 |
| 421 | >100.0 |
| 422 | >100.0 |
| 424 | >100.0 |
| 425 | >100.0 |
| 426 | >100.0 |
| 427 | >100.0 |
| 428 | >100.0 |
| 430 | >100.0 |
| 431 | >100.0 |
| 432 | >100.0 |
| 433 | >100.0 |
| 434 | >100.0 |
| 435 | >100.0 |
| 436 | >100.0 |
| 437 | >100.0 |
| 439 | >100.0 |
| 441 | >100.0 |
| 442 | >100.0 |
| 443 | >100.0 |
| 444 | >100.0 |
| 445 | >100.0 |
| 446 | >100.0 |
| 447 | >100.0 |
| 448 | >100.0 |
| 449 | >100.0 |
| 450 | >100.0 |
| 451 | >100.0 |
| 452 | >100.0 |
| 453 | >100.0 |
| 454 | >100.0 |

TABLE 4-continued

| Compound No. | Avg_IC50 (μM) |
|---|---|
| 455 | >100.0 |
| 456 | >100.0 |
| 457 | >100.0 |
| 458 | >100.0 |
| 459 | >100.0 |
| 462 | >100.0 |
| 463 | >100.0 |
| 464 | >100.0 |
| 465 | >100.0 |
| 466 | >100.0 |
| 467 | >100.0 |
| 468 | >100.0 |
| 469 | >100.0 |
| 470 | >100.0 |
| 471 | >100.0 |
| 472 | >100.0 |
| 474 | >100.0 |
| 475 | >100.0 |
| 476 | >100.0 |
| 477 | >100.0 |
| 478 | 68.22 |
| 479 | >100.0 |
| 480 | >100.0 |
| 481 | >100.0 |
| 482 | >100.0 |
| 483 | >100.0 |
| 484 | >100.0 |
| 485 | >100.0 |
| 486 | >100.0 |
| 487 | >100.0 |
| 488 | >100.0 |
| 490 | >100.0 |
| 491 | >100.0 |
| 492 | >100.0 |
| 495 | >100.0 |
| 496 | >100.0 |
| 497 | >100.0 |
| 501 | >100.0 |
| 502 | >100.0 |
| 503 | >100.0 |
| 504 | >100.0 |
| 505 | >100.0 |
| 506 | >100.0 |
| 507 | >100.0 |
| 508 | >100.0 |
| 509 | >100.0 |
| 510 | >100.0 |
| 511 | >100.0 |
| 512 | >100.0 |
| 513 | >100.0 |
| 514 | >100.0 |
| 515 | >100.0 |
| 516 | >100.0 |
| 517 | >100.0 |
| 518 | >100.0 |
| 519 | >100.0 |
| 520 | >100.0 |
| 522 | >100.0 |
| 532 | >100.0 |
| 533 | >100.0 |
| 534 | >100.0 |
| 535 | >100.0 |
| 536 | >100.0 |
| 537 | >100.0 |
| 538 | >100.0 |
| 539 | >100.0 |
| 540 | >100.0 |
| 541 | >100.0 |
| 542 | >100.0 |
| 544 | >100.0 |
| 546 | >100.0 |
| 547 | >100.0 |
| 548 | >100.0 |
| 549 | >100.0 |
| 550 | >100.0 |
| 551 | >100.0 |
| 552 | >100.0 |

TABLE 4-continued

| Compound No. | Avg_IC50 (μM) |
|---|---|
| 553 | >100.0 |
| 554 | >100.0 |
| 556 | >100.0 |
| 558 | >100.0 |
| 560 | >100.0 |
| 561 | >100.0 |
| 562 | >100.0 |
| 563 | >100.0 |
| 564 | >100.0 |
| 565 | >100.0 |
| 566 | >100.0 |
| 567 | >100.0 |
| 568 | 94.24 |
| 569 | >100.0 |
| 570 | >100.0 |
| 571 | >100.0 |
| 572 | >100.0 |
| 573 | >100.0 |
| 574 | >100.0 |
| 575 | >100.0 |
| 576 | >100.0 |
| 577 | 41.18 |
| 578 | 79.27 |
| 579 | >100.0 |
| 580 | >100.0 |
| 581 | >100.0 |
| 582 | >100.0 |
| 583 | >100.0 |
| 584 | >91.76 |
| 585 | >100.0 |
| 586 | >100.0 |
| 587 | >100.0 |
| 588 | >100.0 |
| 589 | >100.0 |
| 590 | >100.0 |
| 591 | >100.0 |
| 592 | >100.0 |
| 593 | >100.0 |
| 594 | >100.0 |
| 595 | >100.0 |
| 596 | >96.68 |
| 597 | >100.0 |
| 599 | >100.0 |
| 600 | >100.0 |
| 602 | >100.0 |
| 603 | >100.0 |
| 604 | >100.0 |
| 605 | >100.0 |
| 607 | >100.0 |
| 609 | >100.0 |
| 611 | >100.0 |
| 613 | >100.0 |
| 620 | >100.0 |
| 623 | >100.0 |
| 625 | >100.0 |
| 630 | >100.0 |
| 631 | >100.0 |
| 632 | >100.0 |
| 639 | >100.0 |
| 640 | >100.0 |
| 642 | >100.0 |
| 644 | >100.0 |
| 645 | >100.0 |
| 646 | >100.0 |
| 651 | >100.0 |
| 653 | >100.0 |
| 659 | 17.53 |
| 660 | >100.0 |
| 661 | >100.0 |
| 662 | >100.0 |
| 664 | >100.0 |
| 665 | >100.0 |
| 667 | >100.0 |
| 668 | >100.0 |
| 669 | >100.0 |
| 670 | >100.0 |
| 671 | >100.0 |

TABLE 4-continued

| Compound No. | Avg_IC50 (µM) |
|---|---|
| 672 | >100.0 |
| 674 | >100.0 |
| 675 | >100.0 |
| 676 | >100.0 |
| 677 | >100.0 |
| 679 | >100 |
| 680 | 93.0 |
| 681 | >100.0 |
| 682 | >100.0 |
| 685 | >100.0 |
| 686 | >100.0 |
| 690 | >100.0 |
| 710 | >100.0 |
| 711 | >100.0 |
| 719 | >100.0 |
| 722 | >100.0 |
| 723 | >100.0 |
| 724 | >100.0 |
| 725 | >100.0 |
| 726 | >100.0 |
| 727 | >100.0 |
| 728 | >100.0 |
| 729 | >100.0 |
| 731 | >100.0 |
| 732 | >100.0 |
| 733 | >100.0 |
| 734 | >100.0 |
| 735 | >100.0 |
| 736 | >100.0 |
| 765 | >100.0 |
| 766 | >100.0 |
| 767 | >100.0 |
| 768 | >100.0 |
| 769 | >100.0 |
| 770 | >100.0 |
| 771 | >100.0 |
| 772 | >100.0 |
| 773 | >100.0 |
| 774 | >100.0 |
| 777 | >100.0 |
| 779 | >100.0 |
| 780 | >100.0 |
| 781 | >100.0 |
| 782 | >100.0 |
| 783 | >100.0 |
| 784 | >100.0 |
| 785 | >100.0 |
| 786 | >100.0 |
| 787 | >100.0 |
| 788 | >100.0 |
| 789 | >100.0 |
| 790 | >100.0 |
| 791 | >100.0 |
| 792 | >100.0 |
| 793 | >100.0 |
| 794 | >100.0 |
| 795 | >100.0 |
| 809 | >100.0 |
| 810 | >100.0 |

Example B-4

Pompe disease is a glycogen storage disease caused by mutations in the enzyme acid alpha-glucosidase resulting in pathological accumulation of glycogen. Glycogen can accumulate in virtually all tissues, but the primary pathology affects skeletal and cardiac muscle. Inhibiting the synthesis of muscle glycogen could reduce the pathologic build-up of glycogen by acting as a substrate reduction therapy. Savage et. al. identified a predicted protein truncating variant (PTV) in the PPP1R3A gene (a regulator of glycogen metabolism) in ~0.5% of Europeans, which results in ~65% reduction in muscle glycogen (Savage et. al., A Prevalent Variant in PPP1R3A Impairs Glycogen Synthesis and Reduces Muscle Glycogen Content in Humans and Mice. *PLoS Medicine.* 2008; herein incorporated by reference in its entirety). PPP1R3A functions as a key activator of muscle glycogen synthase 1 (GYS1) by dephosphorylating the enzyme and maximizing activity. FIG. 1 demonstrates the pathway in which PPP1R3A (loss of function) LoF leads to reduction in muscle glycogen.

Large biobanks enable investigation of the consequences of genetic variation on many health-related phenotypes. To assess the consequences of a predicted 65% loss of muscle glycogen, association study was performed in the UK Biobank comparing phenotypes between PPP1R3A PTV carriers and non-carriers. Genetic association studies were performed using REGENIE (Mbatchou, J., Barnard, L., Backman, J. et al. Computationally efficient whole-genome regression for quantitative and binary traits. Nat Genet 53, 1097-1103, 2021), adjusted for age, sex, and the first 10 principal components of ancestry. Quantitative traits were normalized using an inverse rank normal transformation.

With regards to FIGS. 2A-2H, the association between PPP1R3A PTV and the quantitative phenotypes of left ventricular ejection (LVEF) (%) (FIG. 2A), left ventricle wall thickness (mm) (FIG. 2B), exercise output (watts) (FIG. 2C), max heart rate (HR) exercise (bpm) (FIG. 2D), PQ interval (ms) (FIG. 2E), QRS duration (ms) (FIG. 2F), QT interval (ms) (FIG. 2G), and serum glucose (mmol/L) (FIG. 2H), are depicted. Phenotype values are plotted by PPP1R3A dosage for UK Biobank participants. No association between PPP1R3A PTV and the quantitative phenotypes in the UK Biobank was identified.

Table 5 below lists the P-value and number of participants (N) for the results depicted in FIGS. 2A-H. No associations between PPP1R3A PTV and cardiac parameters, including left ventricular ejection fraction (p=0.871) and wall thickness (p=0.168) were identified. There was no evidence of changes in EKG cardiac conduction intervals nor in any muscle performance measurements (n=49,616), including maximum heart rate (p=0.444) and maximum workload during an exercise test (p=0.100). Further, no changes in serum glucose (p=0.71) or any other members of a panel of ~170 serum metabolites were observed.

TABLE 5

| Phenotype | P-value | N |
|---|---|---|
| LVEF | 0.871 | 27,716 |
| LV Wall Thickness | 0.168 | 27,579 |
| Exercise Output | 0.100 | 49,616 |
| Max HR Exercise | 0.444 | 49,603 |
| QRS Duration | 0.527 | 29,507 |
| PQ Interval | 0.366 | 16,694 |
| QT Interval | 0.222 | 17,574 |
| Serum Glucose | 0.477 | 294,042 |

As shown in Table 6 below, no association between PPP1R3A PTV and key health outcomes was also observed. In addition to the phenotypes in Table 6, no phenome-wide significant associations between PPP1R3A PTV and rates of any ICD10 code with over 100 occurrences in UK Biobank was observed.

TABLE 6

| Disease | Effect (SE) | P-value | N Cases |
|---|---|---|---|
| Type 2 Diabetes | −0.094 (0.073) | 0.200 | 18,868 |

TABLE 6-continued

| Disease | Effect (SE) | P-value | N Cases |
|---|---|---|---|
| Liver Cirrhosis | −0.041 (0.273) | 0.880 | 1,325 |
| Heart Failure | −0.061 (0.127) | 0.630 | 6,117 |

After performing an extensive Phenome-wide association study in UK Biobank, no significant associations between any key outcomes or phenotypes and loss of function of PPP1R3A were found. The results provided herein demonstrate that loss of function variants in the PPP1R3A gene are not associated with adverse health outcomes in a large biobank population. This suggests that partial reduction in muscle glycogen (~65%) from birth is well tolerated and supports the potential safety of pharmacologic reduction of muscle glycogen.

All publications, patent applications, patents, and other references mentioned herein are expressly incorporated by reference in their entireties, to the same extent as if each were incorporated by reference individually.

It is to be understood that, while the disclosure has been described in conjunction with the above embodiments, the foregoing description and examples are intended to illustrate and not limit the scope of the disclosure. Other aspects, advantages and modifications within the scope of the disclosure will be apparent to those skilled in the art to which the disclosure pertains.

What is claimed is:

1. A compound of formula (I-A):

(I-A)

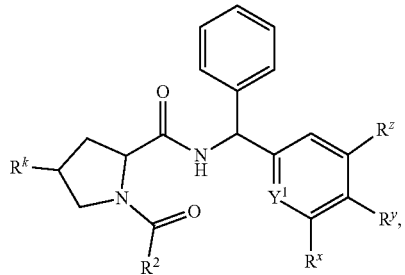

or a stereoisomer or tautomer thereof, or a pharmaceutically acceptable salt of any of the foregoing, wherein:
$Y^1$ is CH or N;
$R^x$ and $R^z$ are independently H, halo, $C_{1-6}$alkyl, or —$NH_2$, wherein, when $Y^1$ is CH, the $C_{1-6}$alkyl of $R^x$ or $R^z$ may be optionally substituted with one or more halo;
$R^y$ is (i) $C_{1-6}$alkyl, or (ii) $C_{3-10}$cycloalkyl, wherein the $C_{3-10}$cycloalkyl is optionally substituted with one or more halo or $C_{1-6}$alkyl;
$R^k$ is H, halo, —OH, —$NH_2$, or —NH—C(O)$C_{1-6}$alkyl:
$R^2$ is $C_{1-6}$alkyl, wherein the $C_{1-6}$alkyl of $R^2$ is substituted with one or more $R^a$, wherein $R^a$ is —OH or 5-20 membered heteroaryl, wherein the 5-20 membered heteroaryl of $R^a$ is optionally substituted with one or more $R^b$; and
$R^b$ is halo, $C_{1-6}$alkyl, $C_{1-6}$alkoxy, —$NH_2$, —NH($C_{1-6}$alkyl), —N($C_{1-6}$alkyl)$_2$, $C_{3-10}$cycloalkyl, 3-15 membered heterocyclyl, or —C(O)—$C_{1-6}$alkoxy, wherein the $C_{1-6}$alkyl of $R^b$ is optionally substituted with one or more halo, —$NH_2$, —NH($C_{1-6}$alkyl), —N($C_{1-6}$alkyl)$_2$, —NH—C(O)$C_{1-6}$alkyl, or —NH—C(O)—$C_{1-6}$alkoxy, and the 3-15-membered heterocyclyl of $R^b$ is optionally substituted with one or more halo or —C(O)—$C_{1-6}$alkoxy.

2. The compound of claim 1, or a stereoisomer or tautomer thereof, or a pharmaceutically acceptable salt of any of the foregoing, wherein the moiety represented by

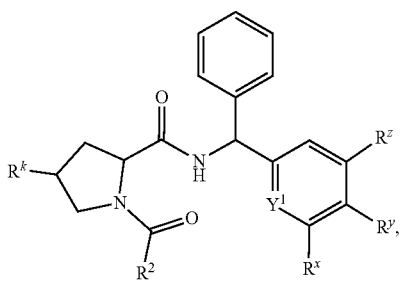

has a stereochemical configuration of the formula:

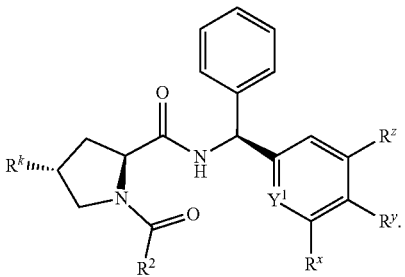

3. The compound of claim 1, or a stereoisomer or tautomer thereof, or a pharmaceutically acceptable salt of any of the foregoing, wherein the moiety represented by

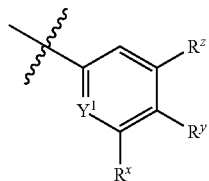

is selected from the group consisting

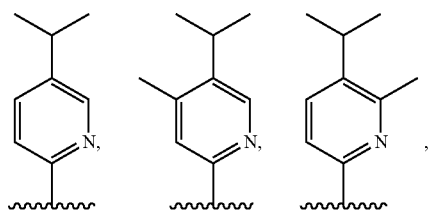

1435

-continued

1436

5. The compound of claim 1, or a stereoisomer or tautomer thereof, or a pharmaceutically acceptable salt of any of the foregoing, wherein $R^x$ is H, fluoro, or methyl, and $R^y$ is (i) isopropyl, or (ii) $C_{3-4}$cycloalkyl, wherein the $C_{3-4}$cycloalkyl is optionally substituted with one or more fluoro or methyl.

6. The compound of claim 1, or a stereoisomer or tautomer thereof, or a pharmaceutically acceptable salt of any of the foregoing, wherein $R^k$ is H or halo.

7. The compound of claim 1, or a stereoisomer or tautomer thereof, or a pharmaceutically acceptable salt of any of the foregoing, wherein $R^2$ is selected from the group consisting of 4. The compound of claim 3, or a stereoisomer or tautomer thereof, or a pharmaceutically acceptable salt of any of the foregoing, wherein the moiety represented by

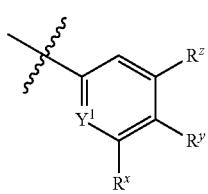

is selected from the group consisting

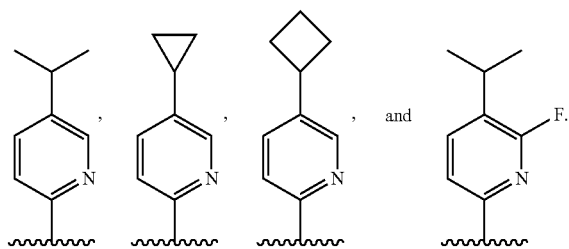

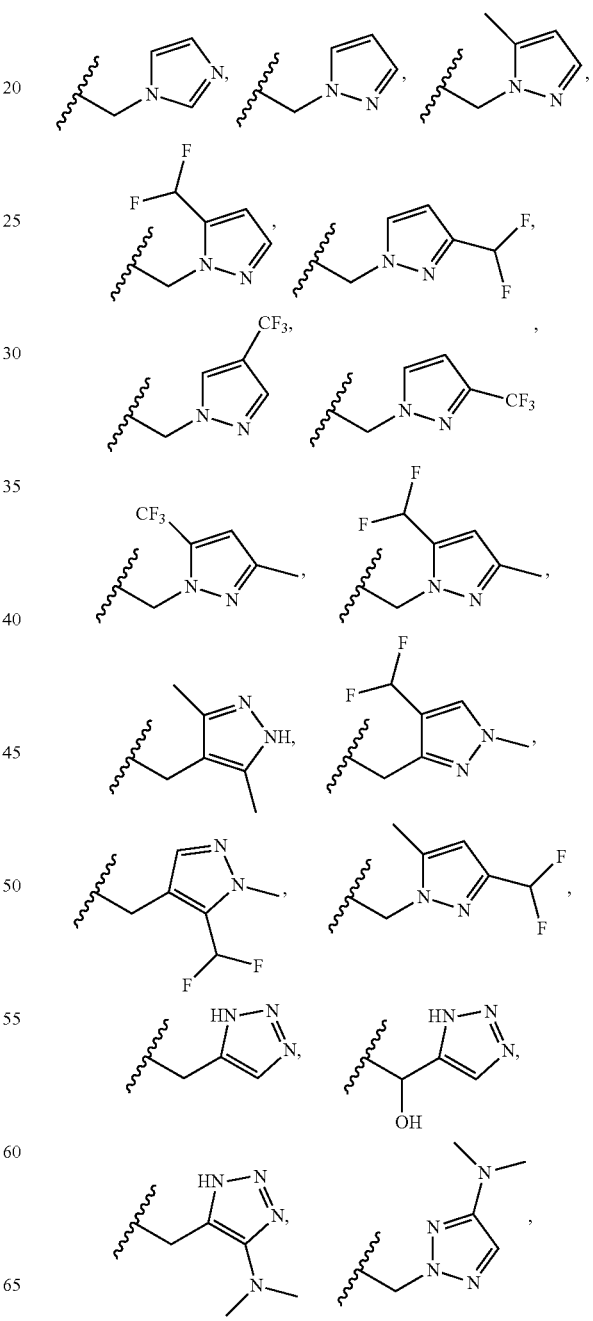

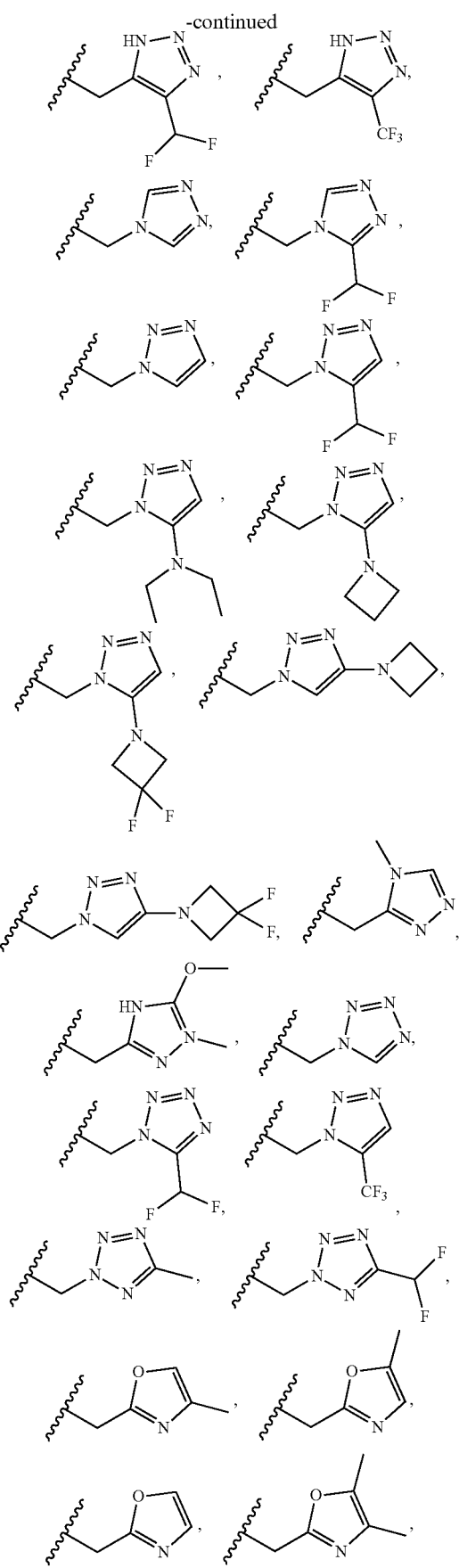
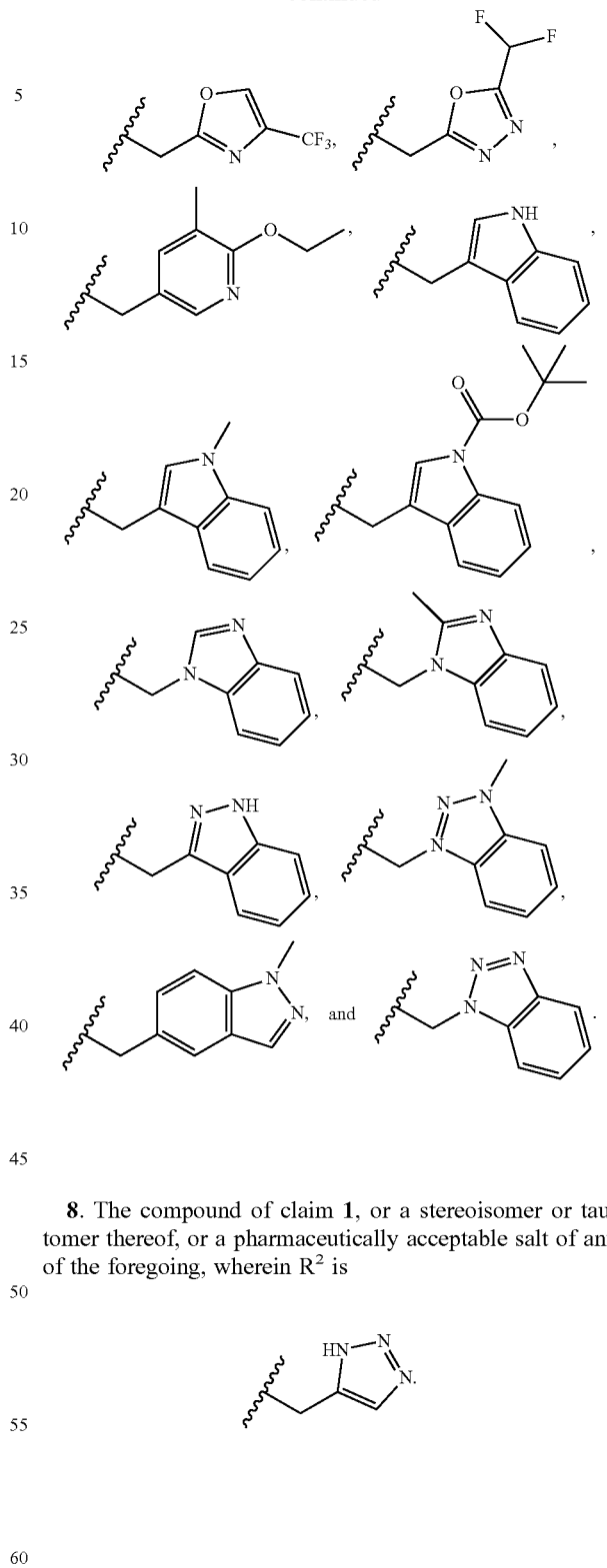
8. The compound of claim 1, or a stereoisomer or tautomer thereof, or a pharmaceutically acceptable salt of any of the foregoing, wherein R² is
9. The compound of claim 1, or a stereoisomer or tautomer thereof, or a pharmaceutically acceptable salt of any of the foregoing, is selected from the group consisting of

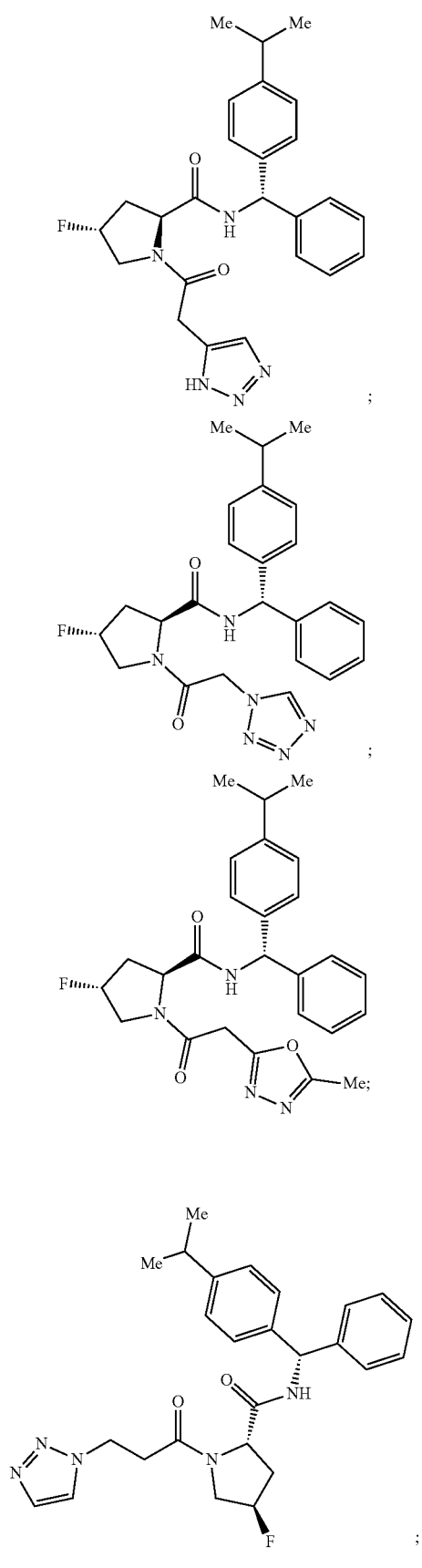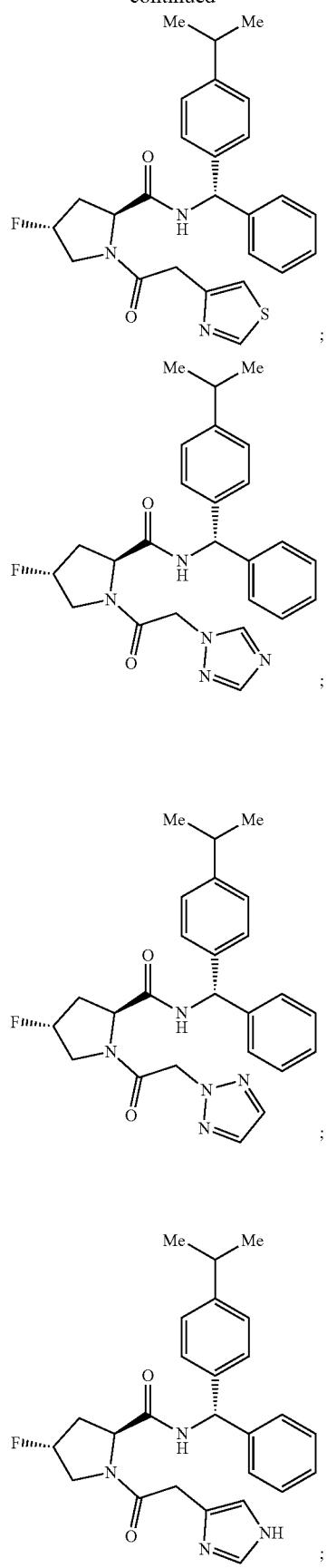

1441
-continued
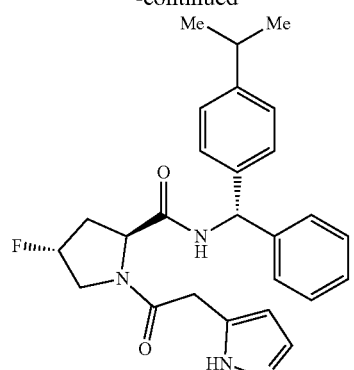
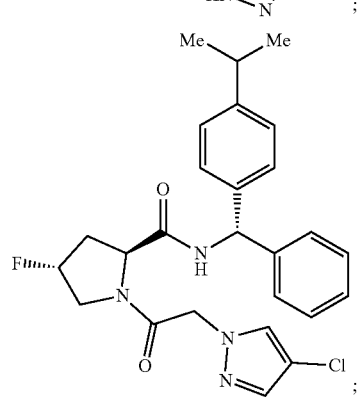
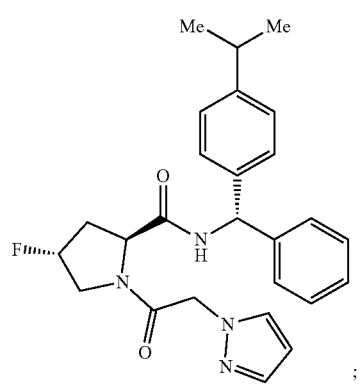
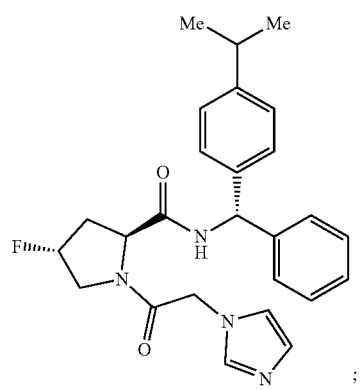
1442
-continued
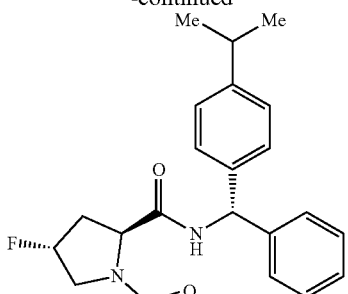
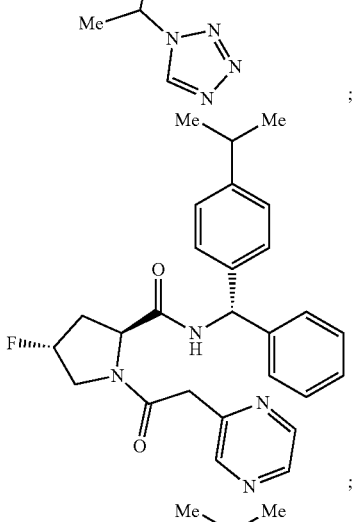
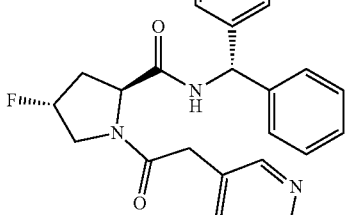
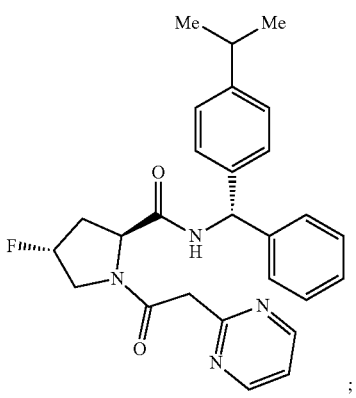

1443
-continued
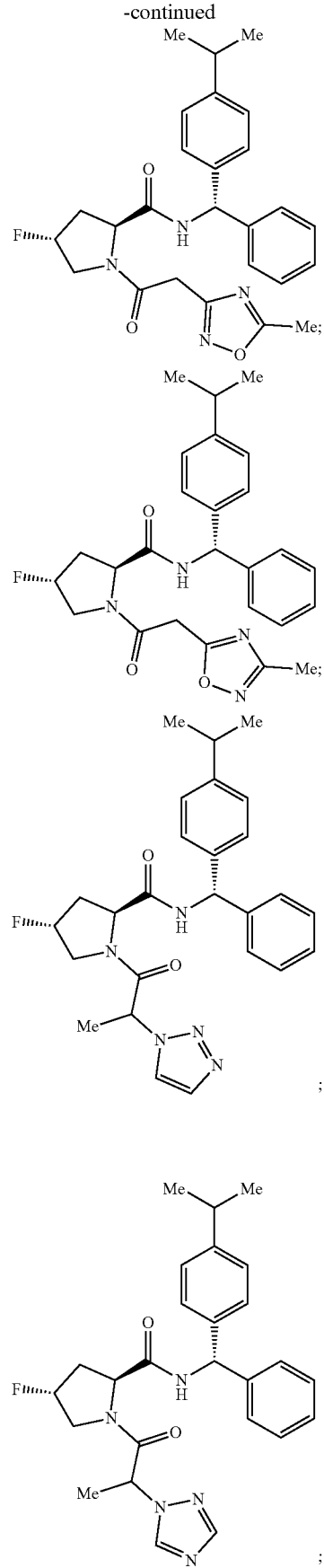
1444
-continued
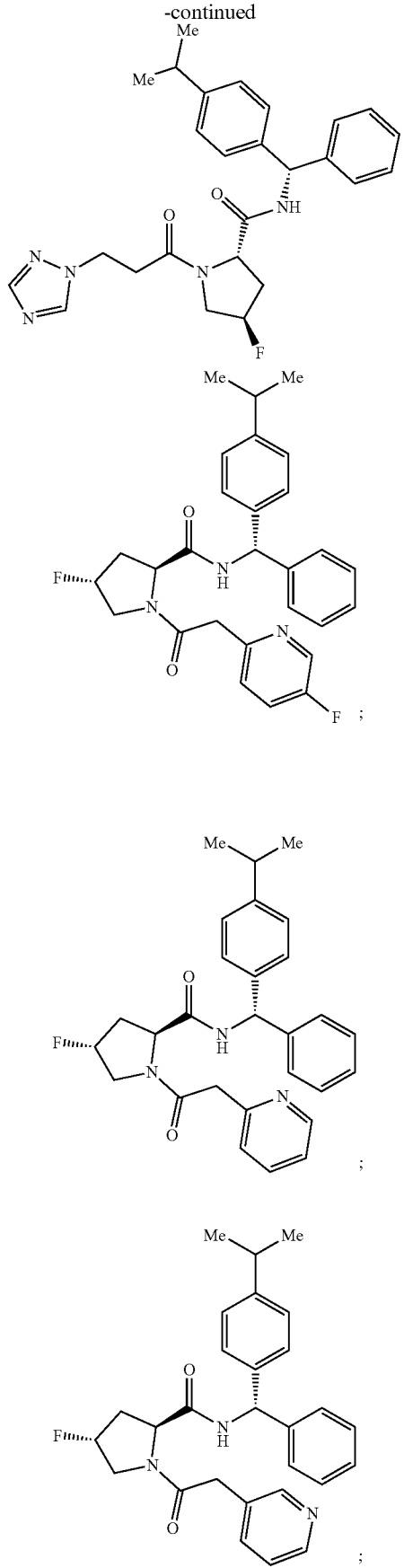

1445
-continued
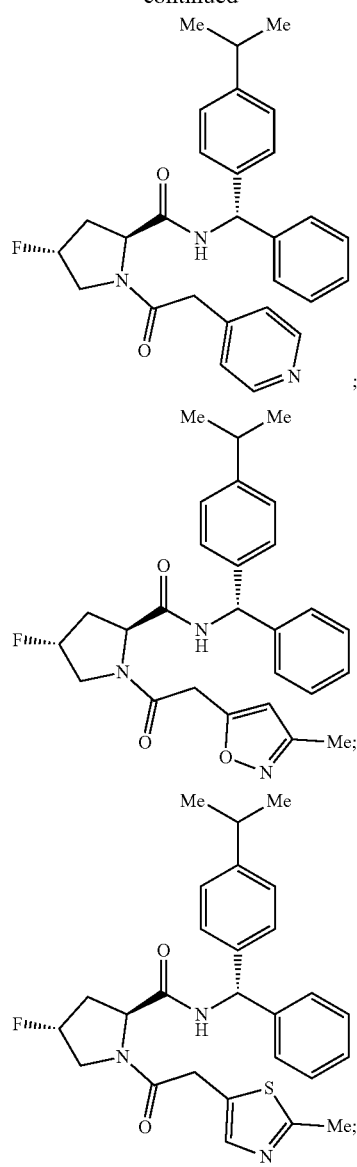
1446
-continued
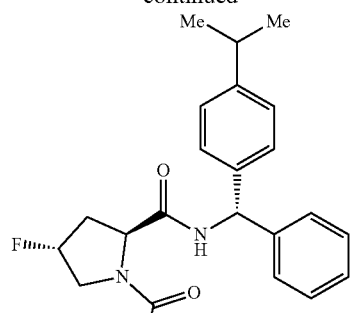
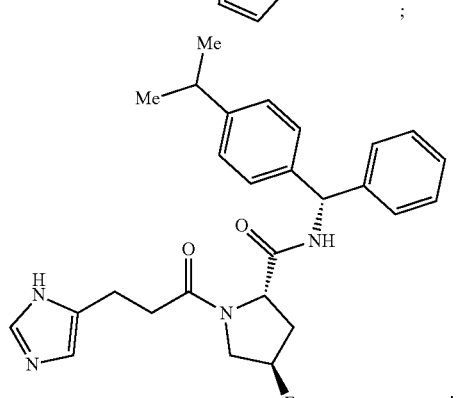
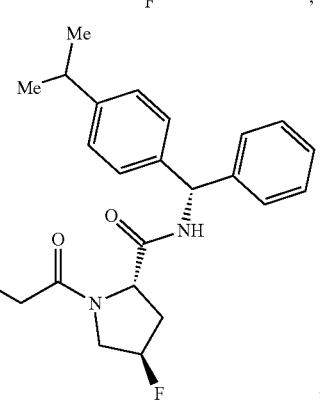
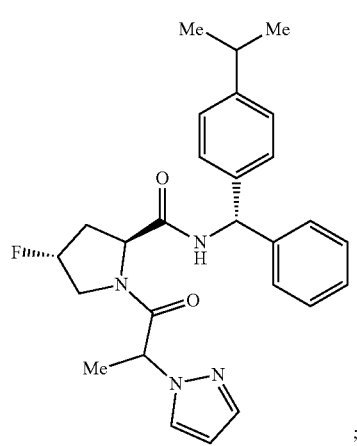
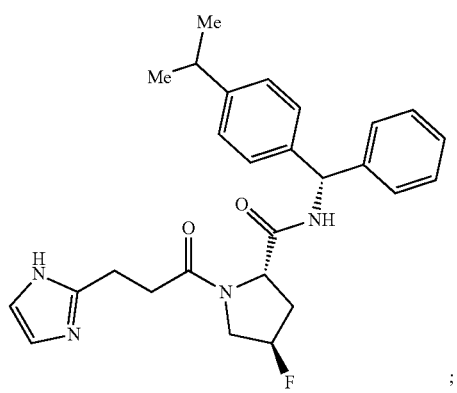

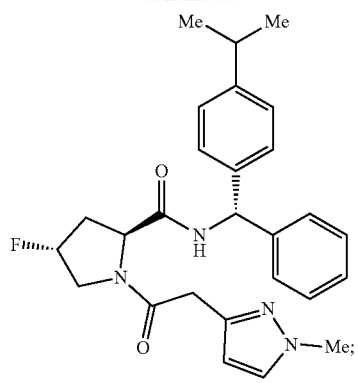
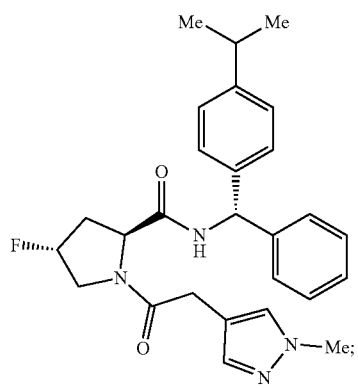
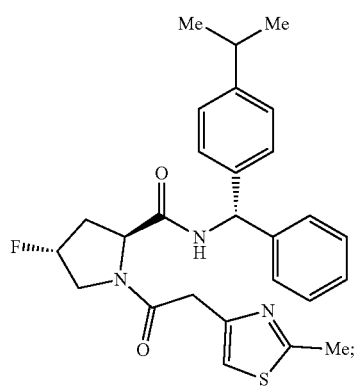
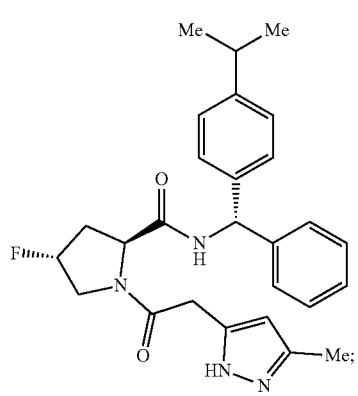
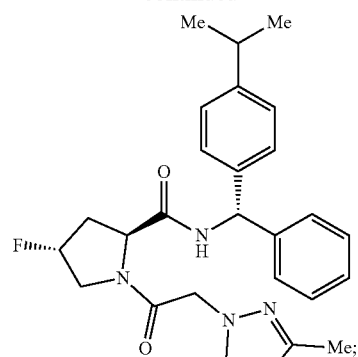
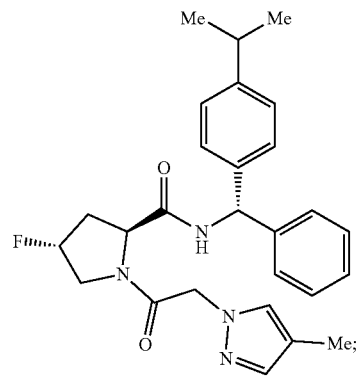
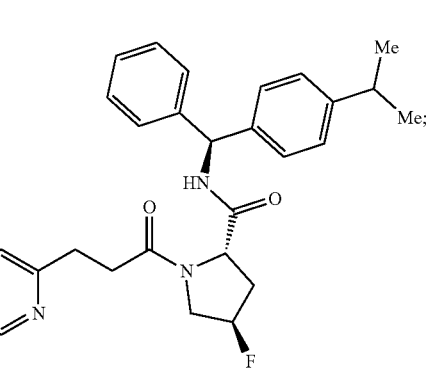
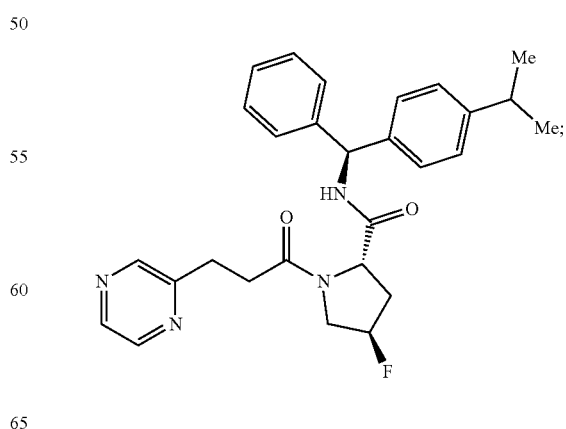

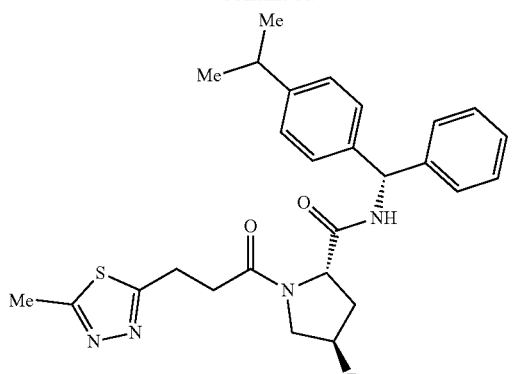
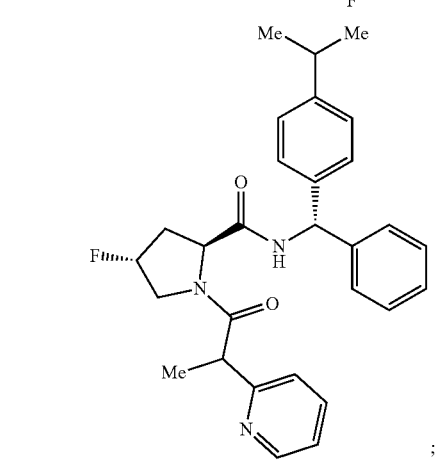
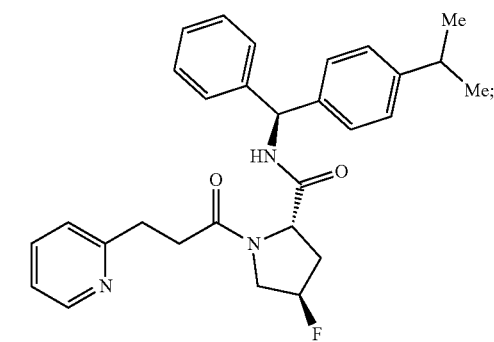
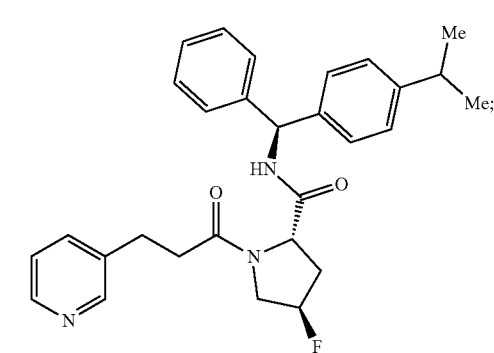
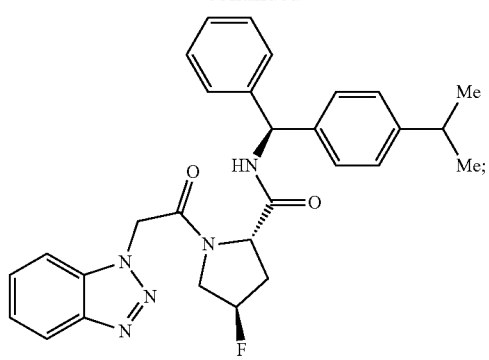
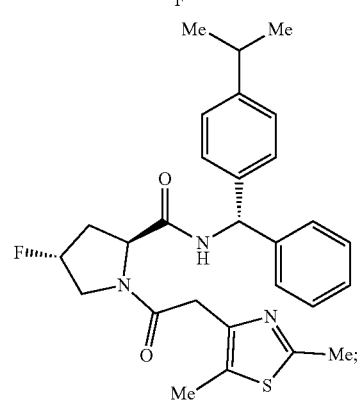
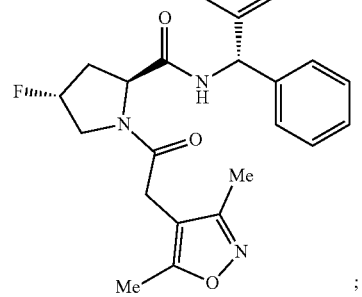
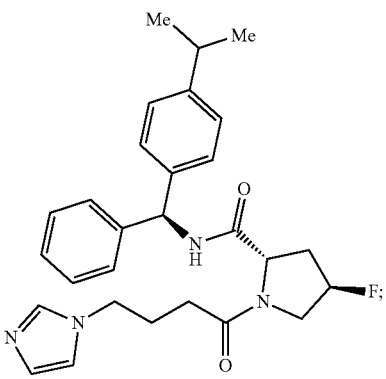

1451
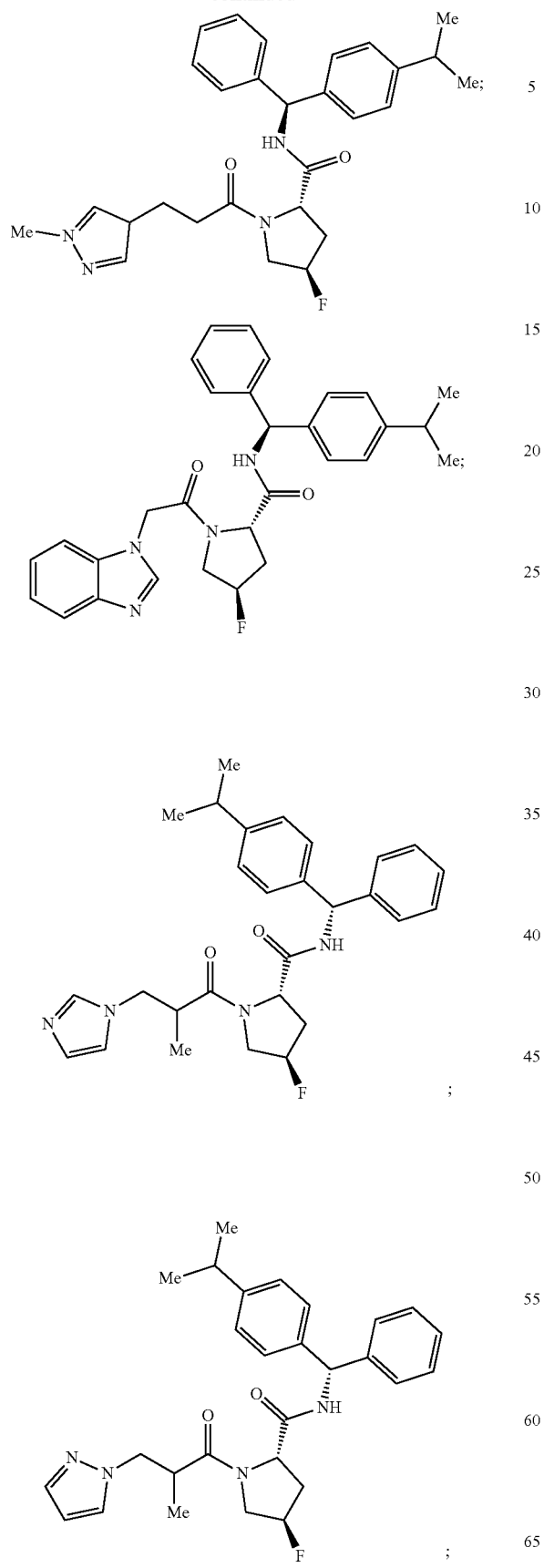
1452
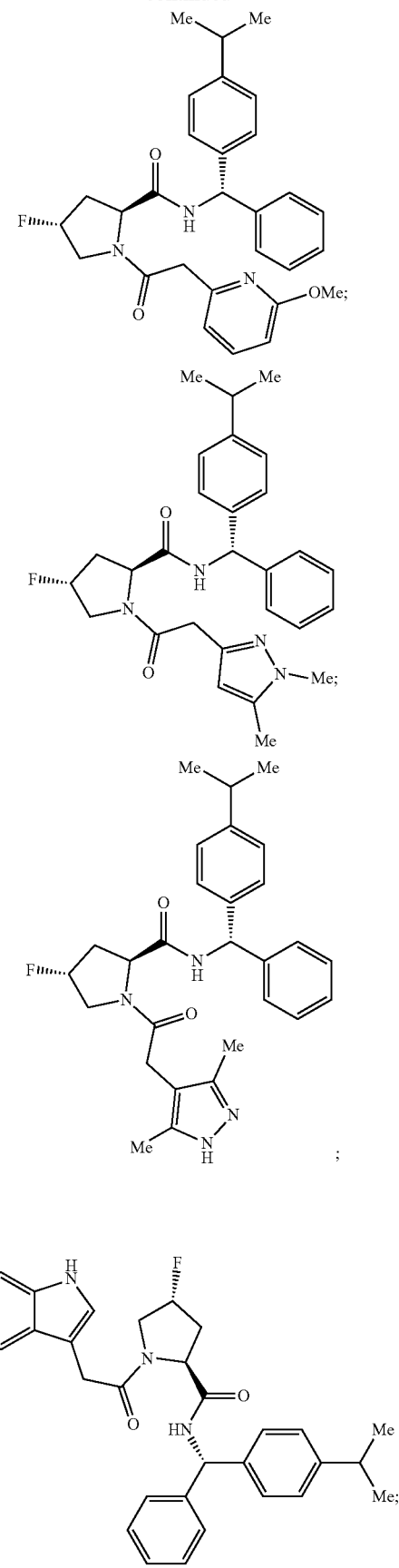

1453
-continued
1454
-continued
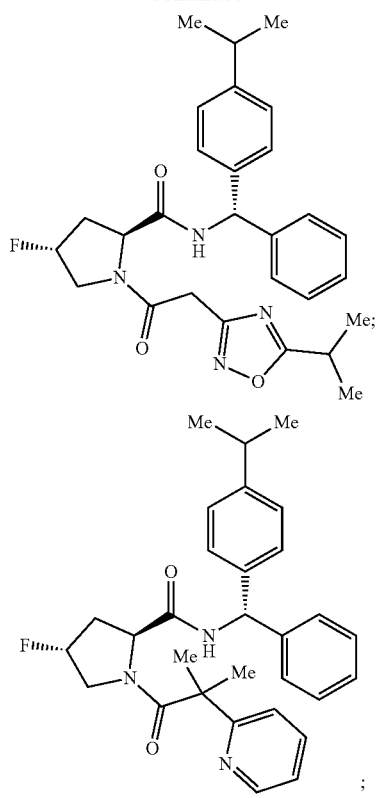
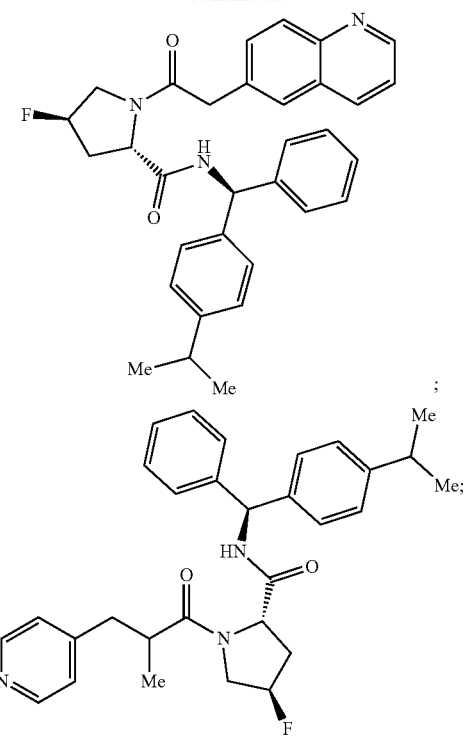
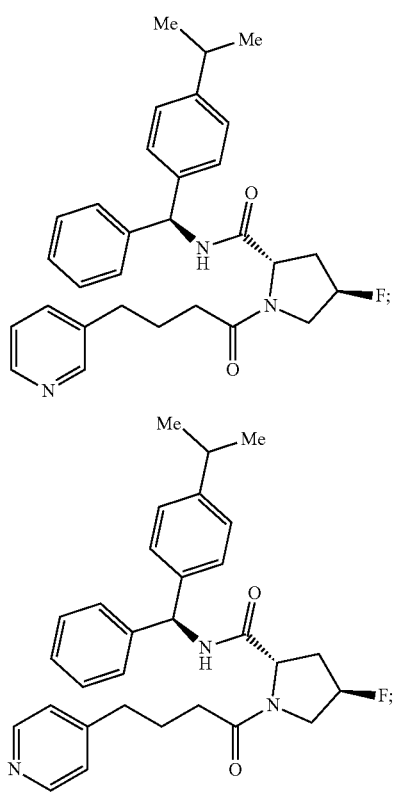
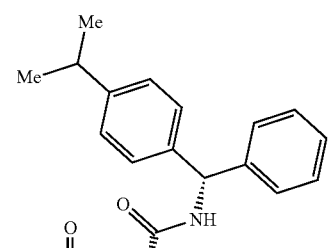

1455
-continued
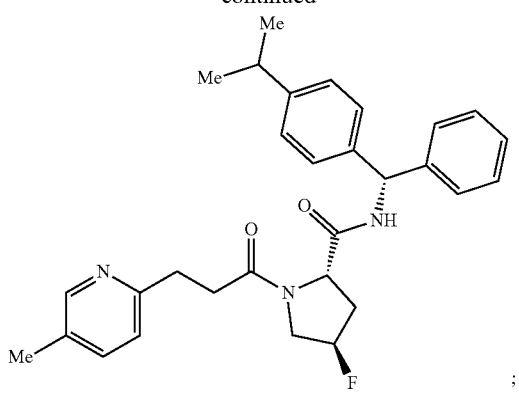
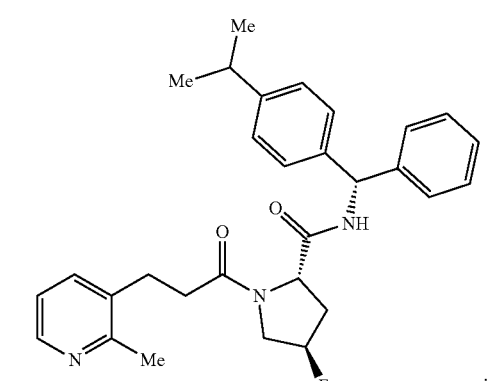
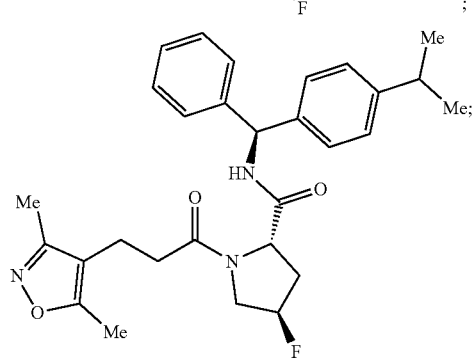
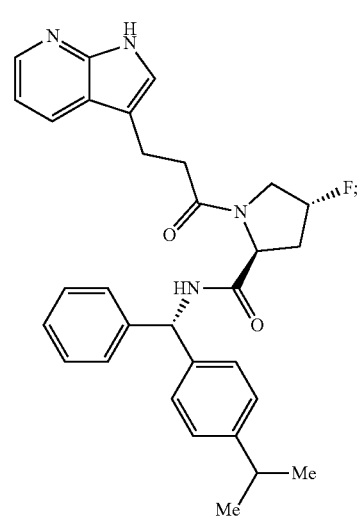
1456
-continued
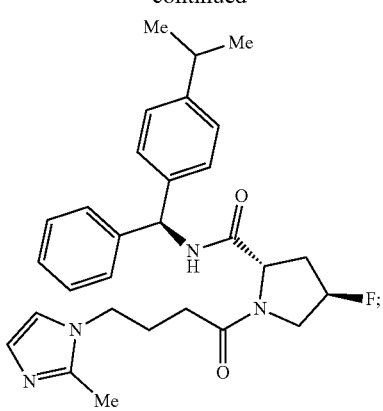
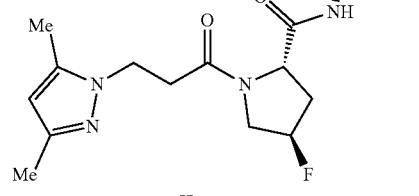
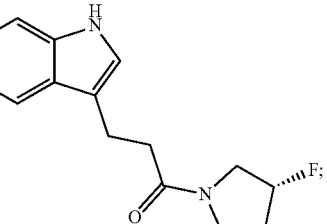
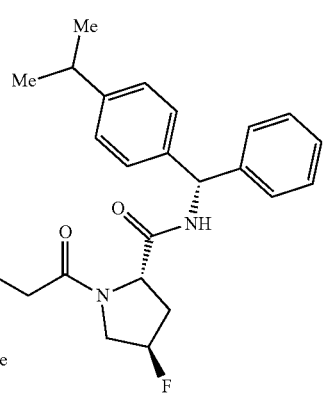

1457
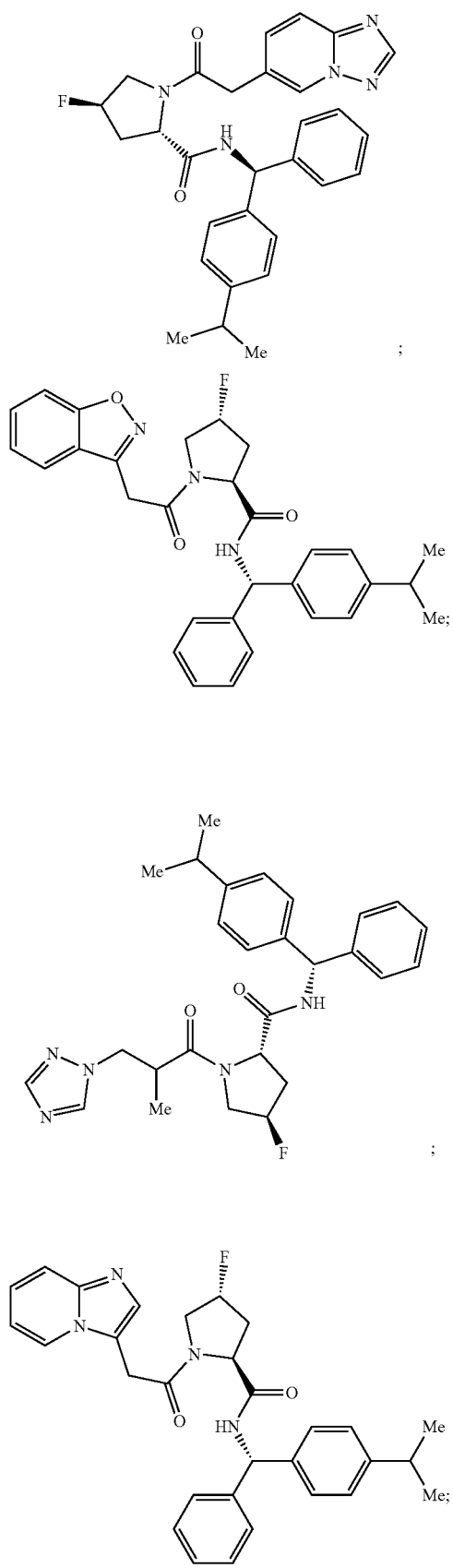
1458
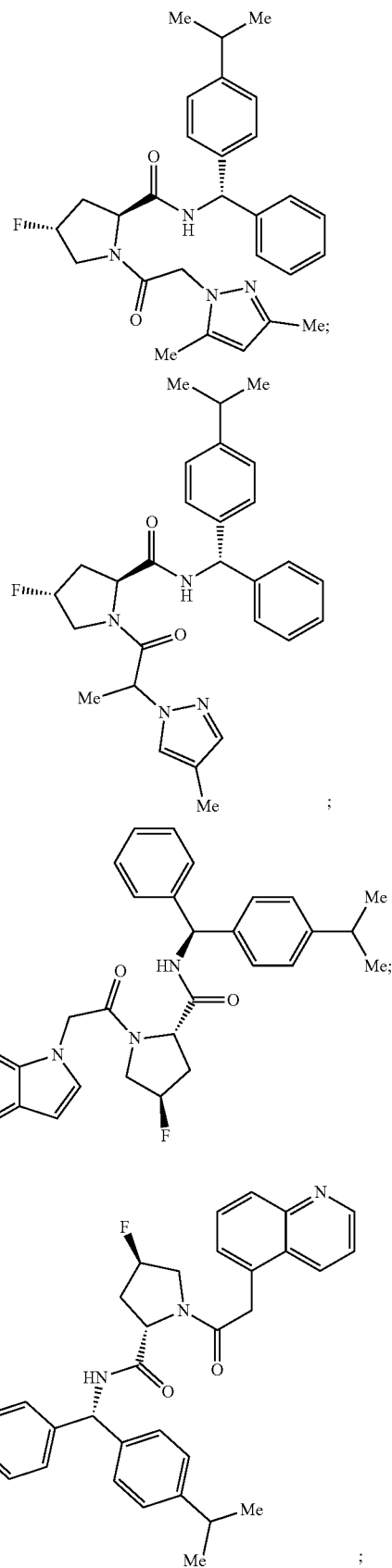

1459 -continued
1460 -continued
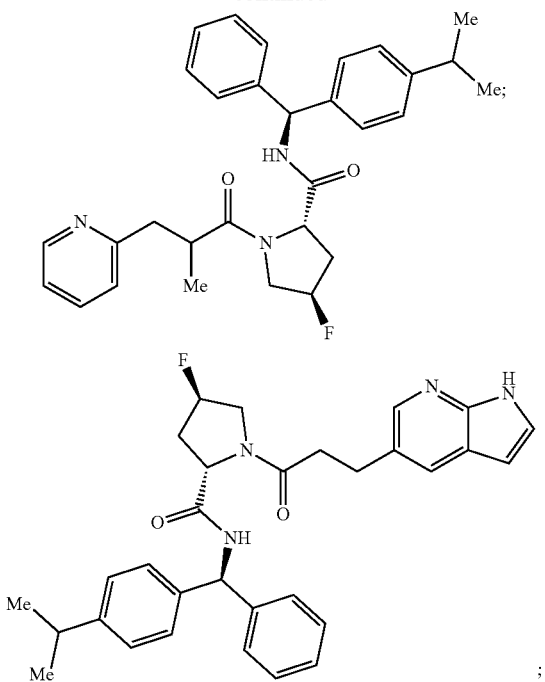
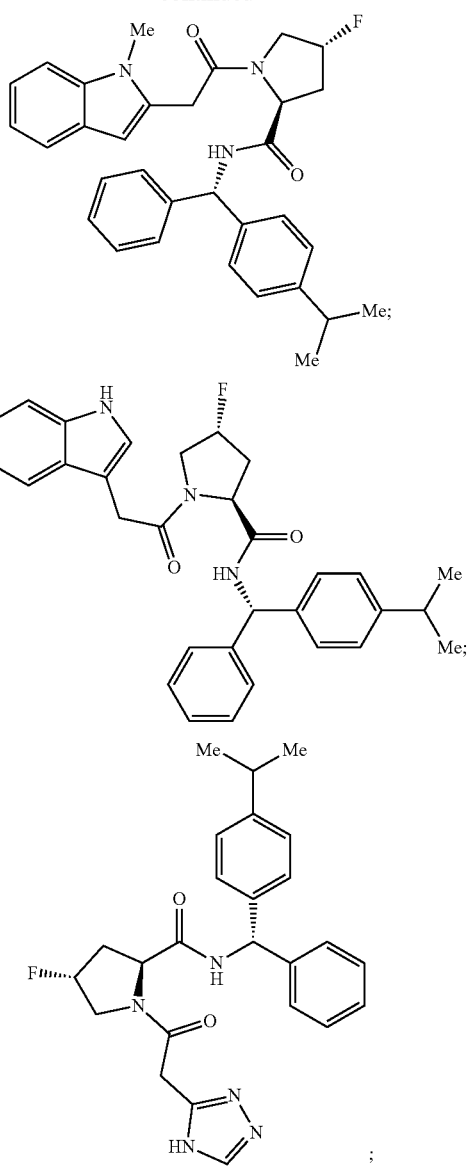
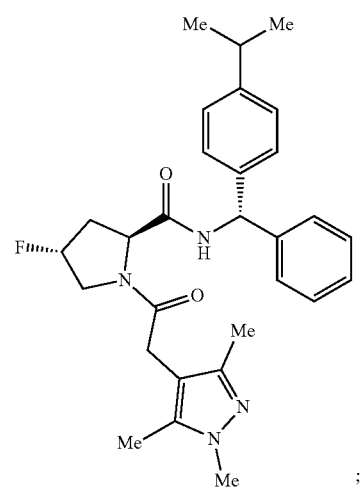
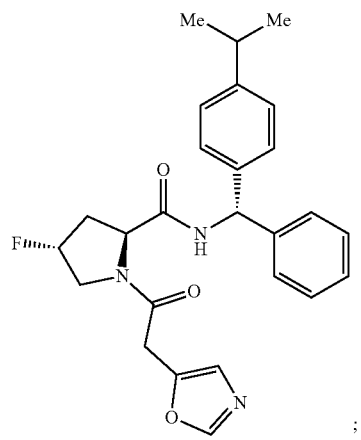

1461 -continued
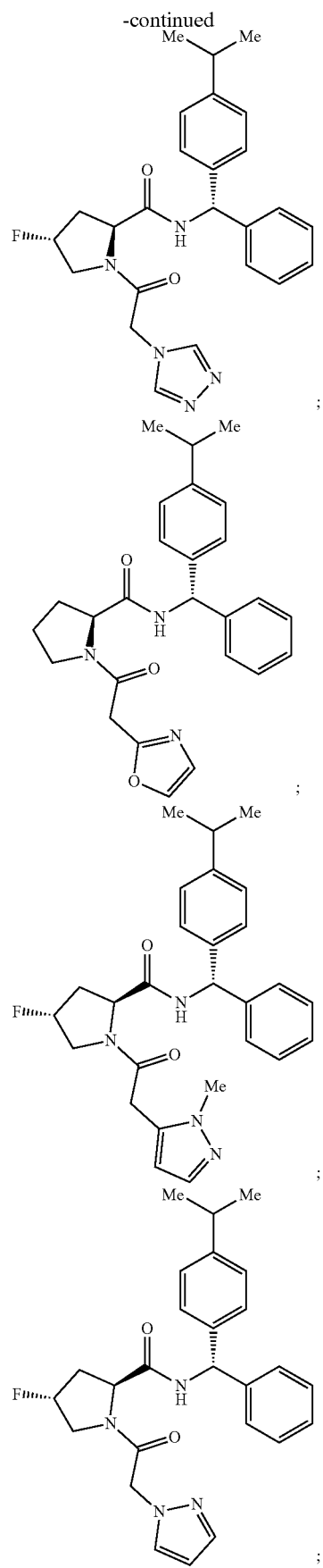
1462 -continued
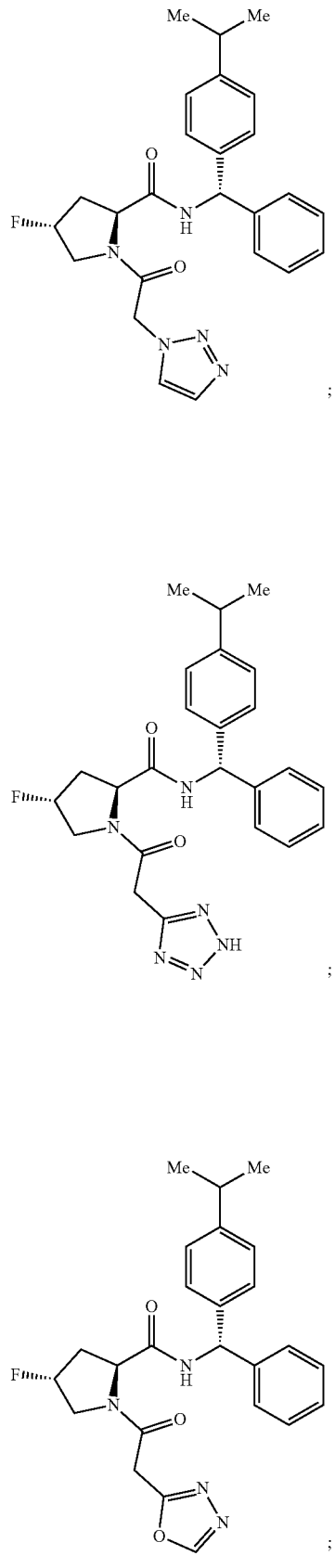

1463
-continued
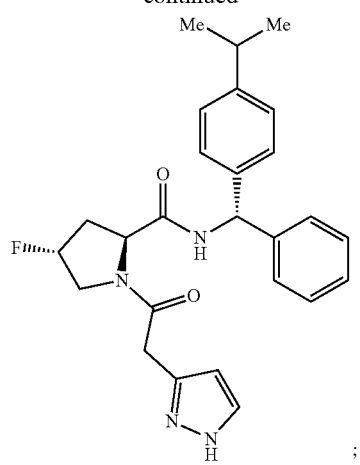
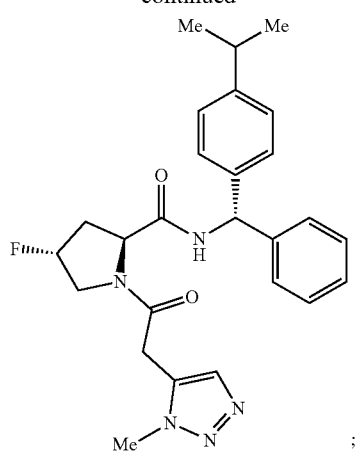
;
1464
-continued
;
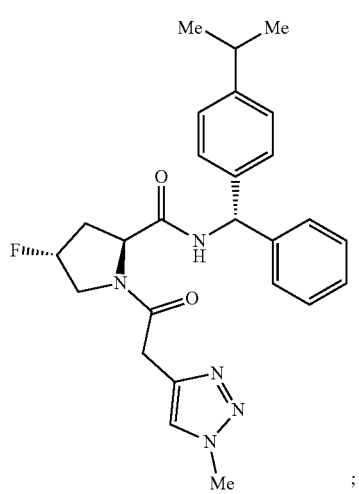
;
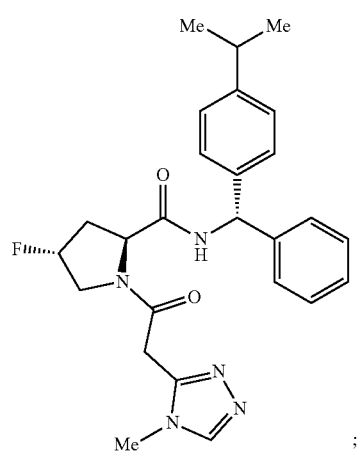
;
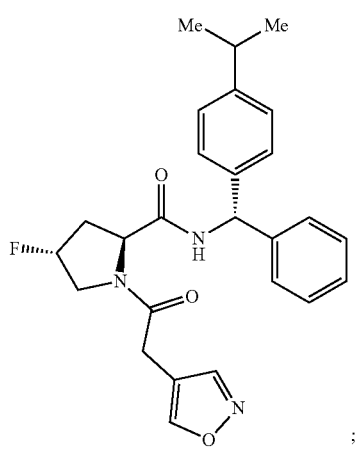
;

1465
-continued
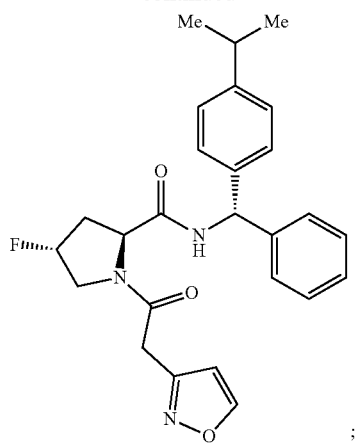
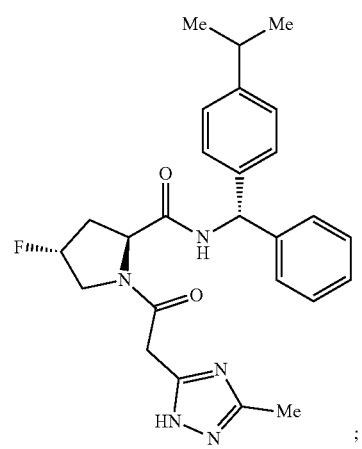
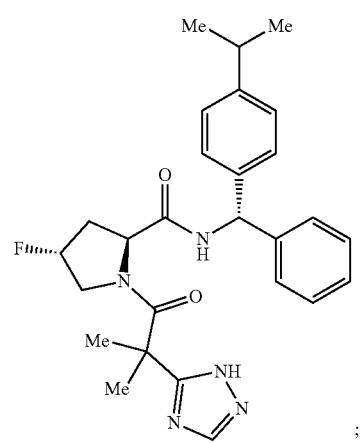
1466
-continued
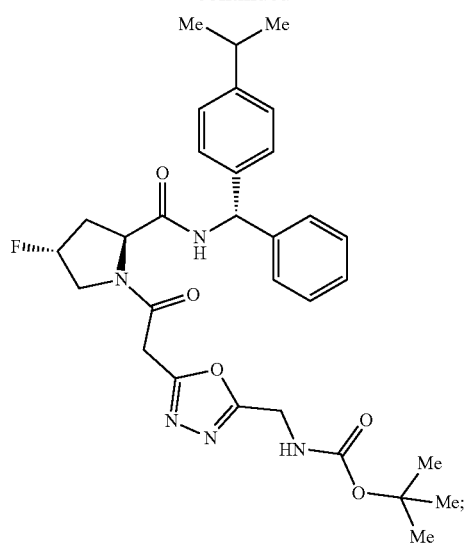
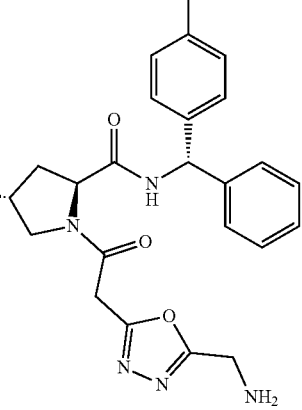
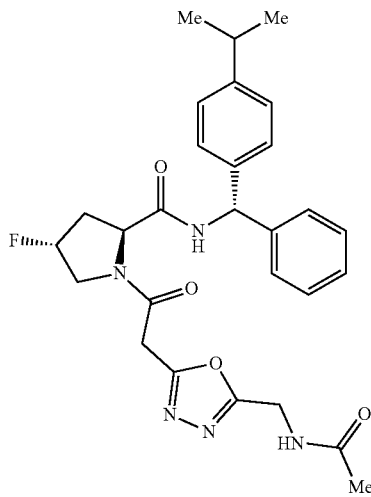

1467
-continued
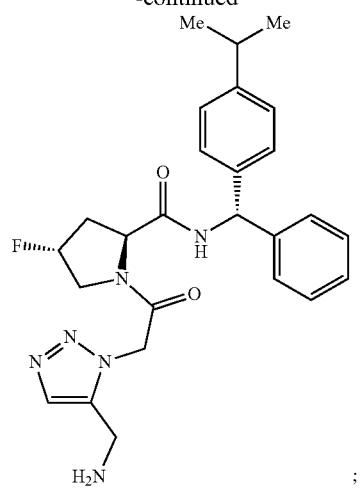
;
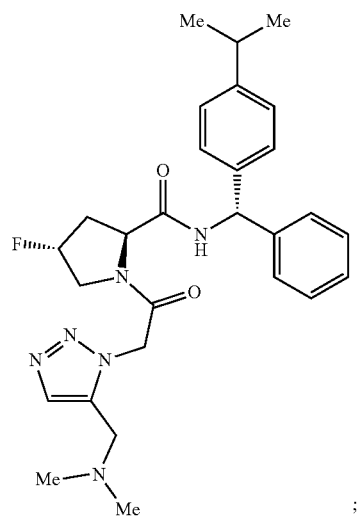
;
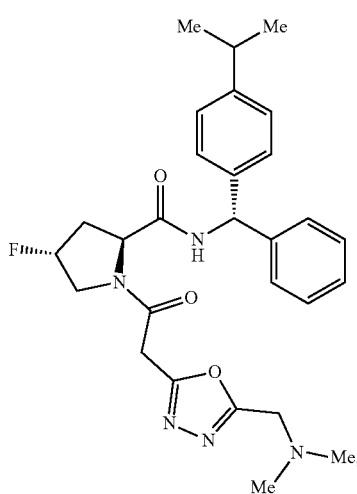
;
1468
-continued
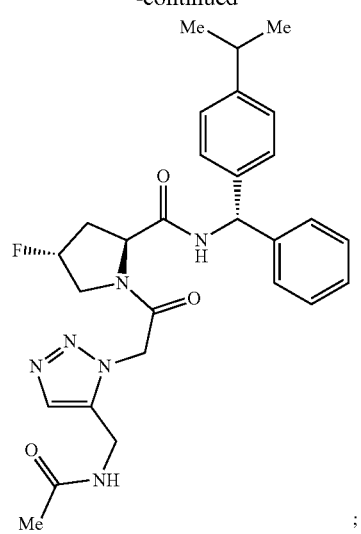
;
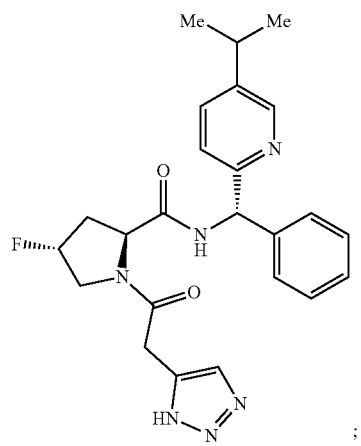
;
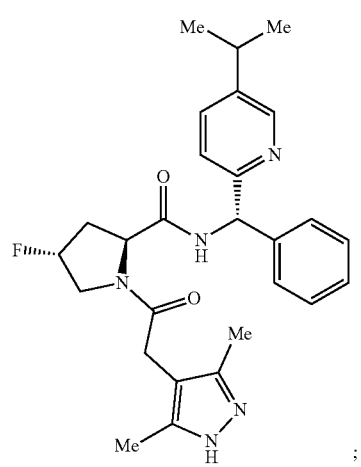
;

1469
-continued
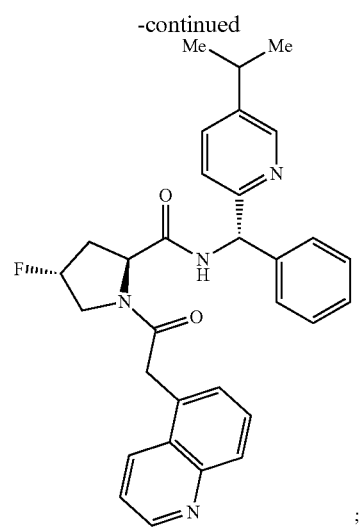
;
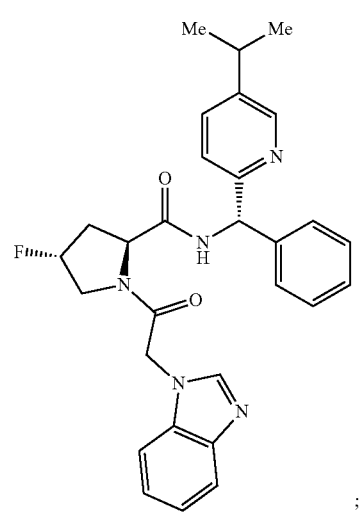
;
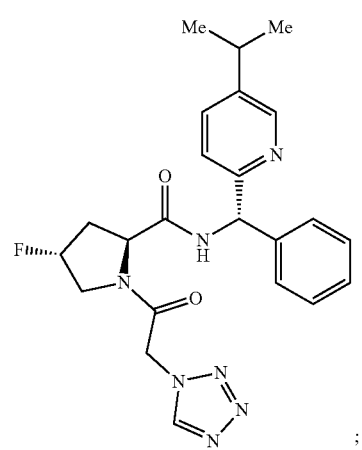
;
1470
-continued
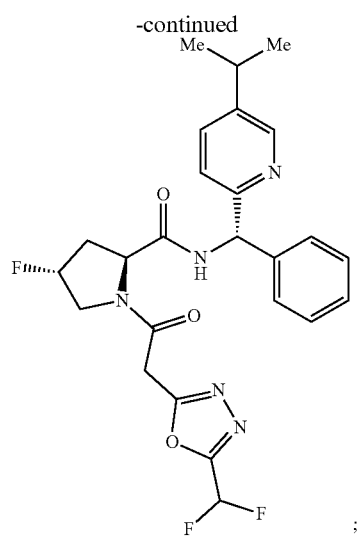
;
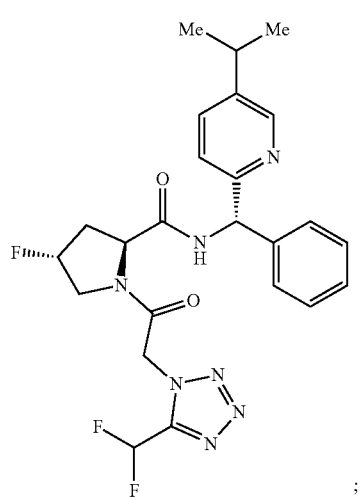
;
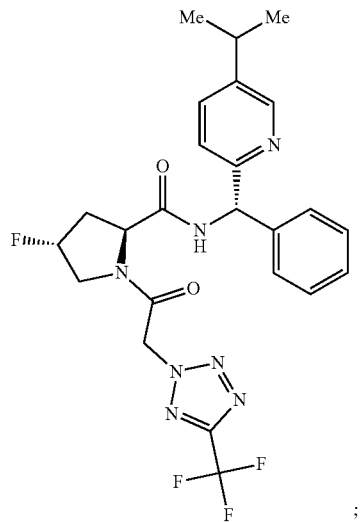
;

1471
-continued
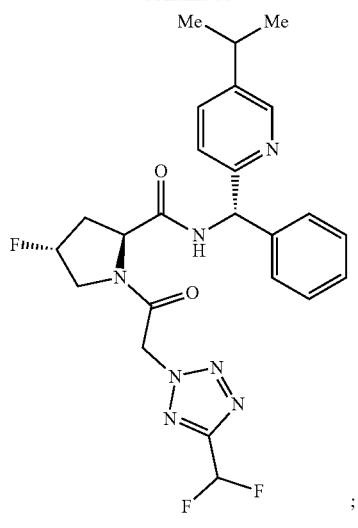
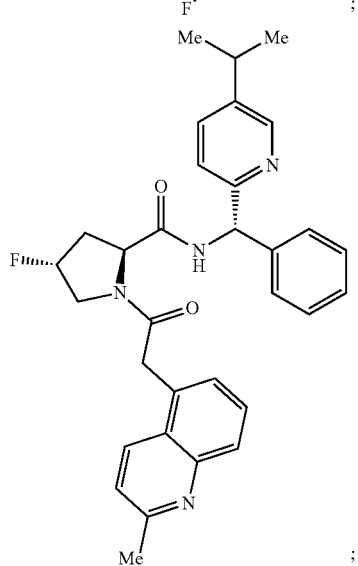
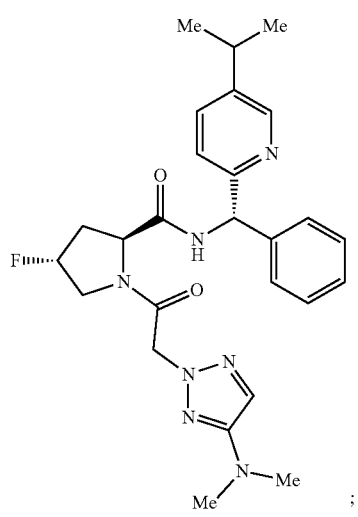
1472
-continued
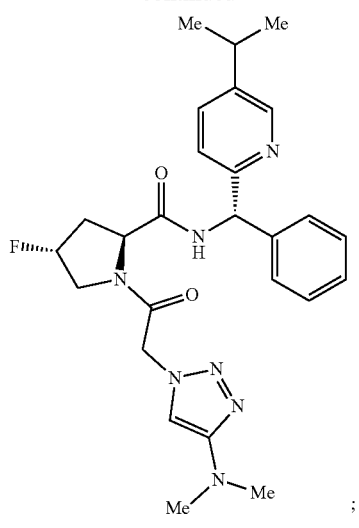
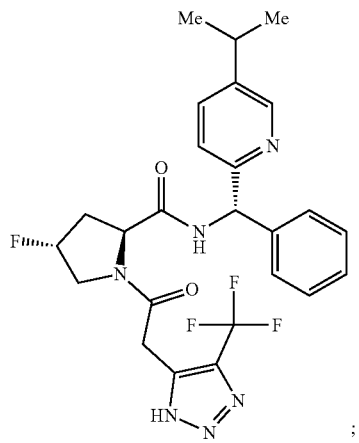
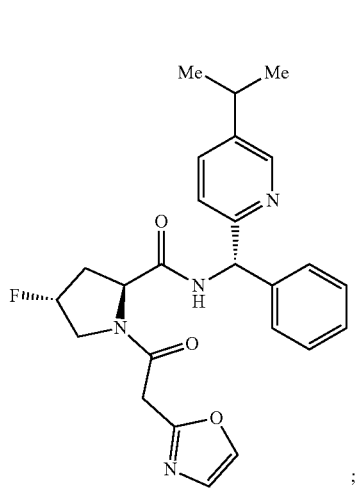

1473
-continued
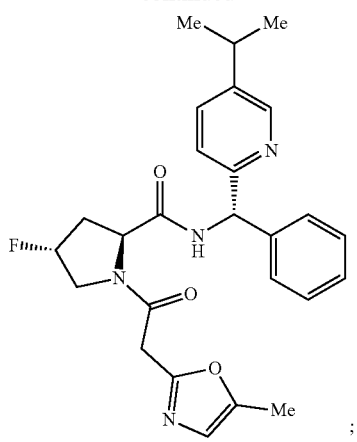
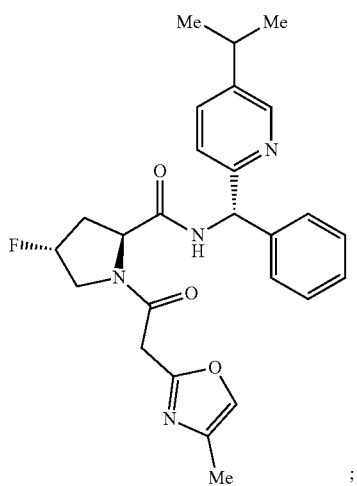
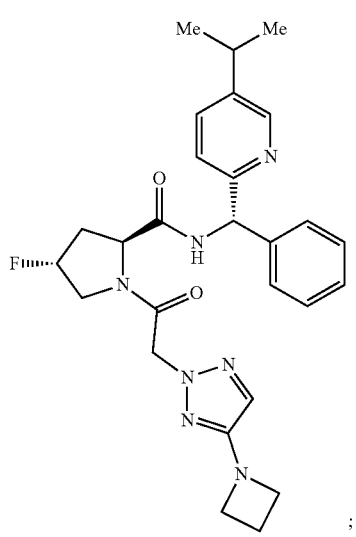
1474
-continued
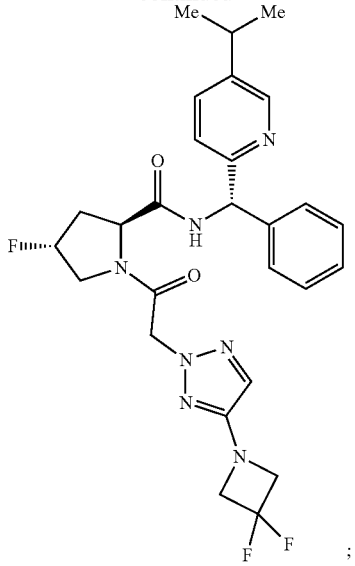
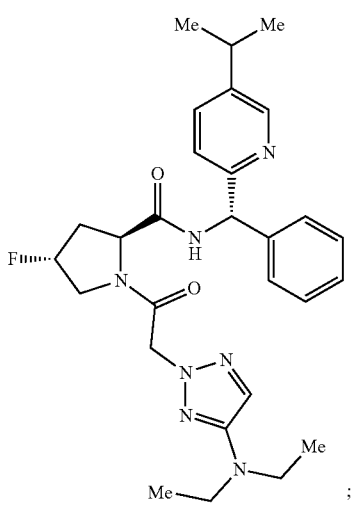
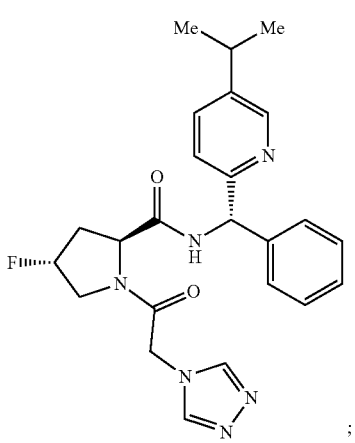

1475
-continued
1476
-continued
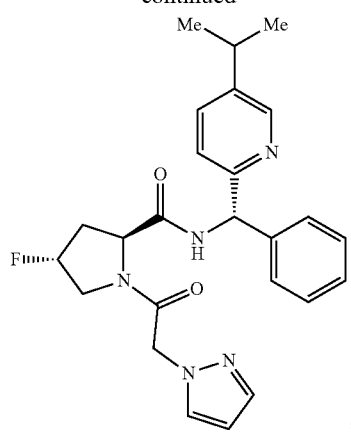
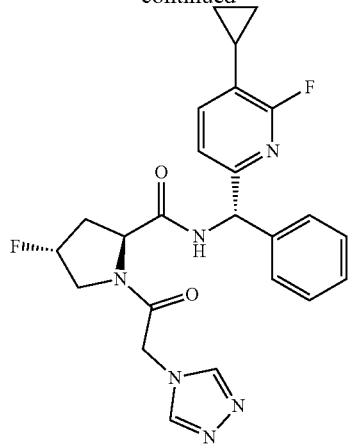
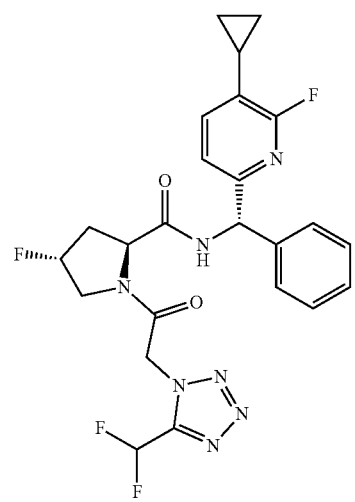
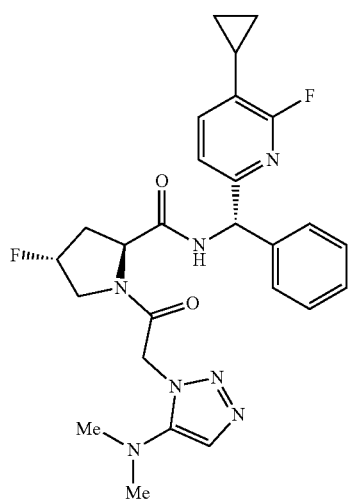
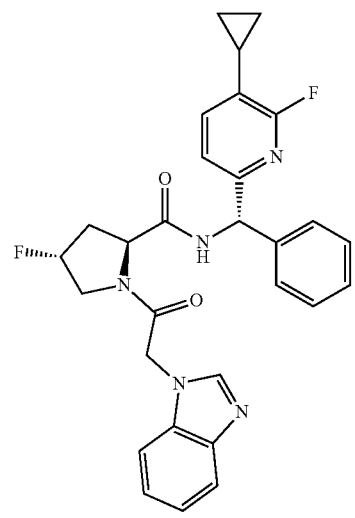
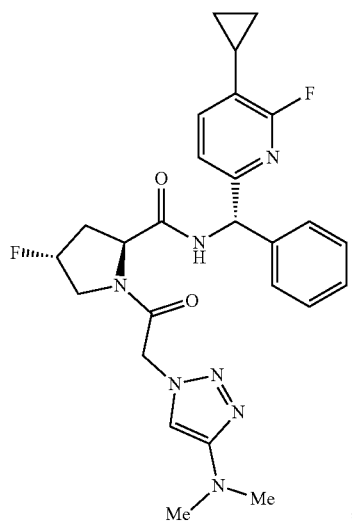

1477
-continued
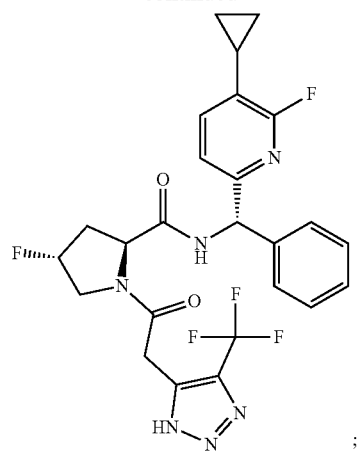
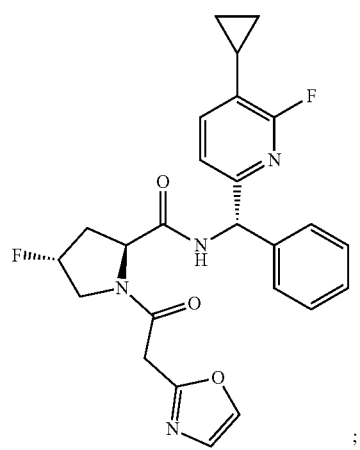
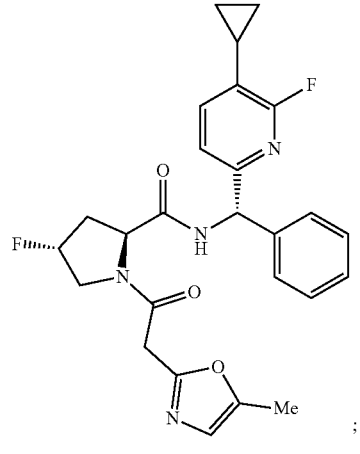
1478
-continued
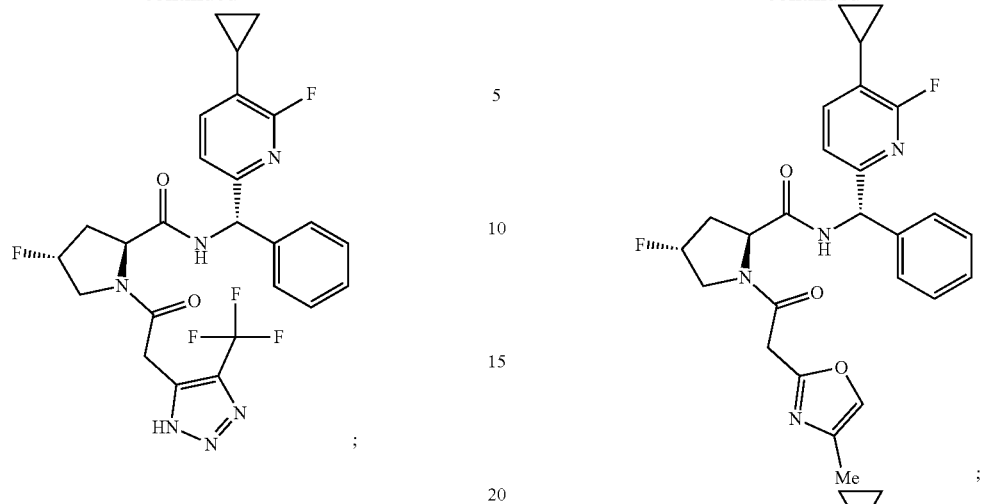
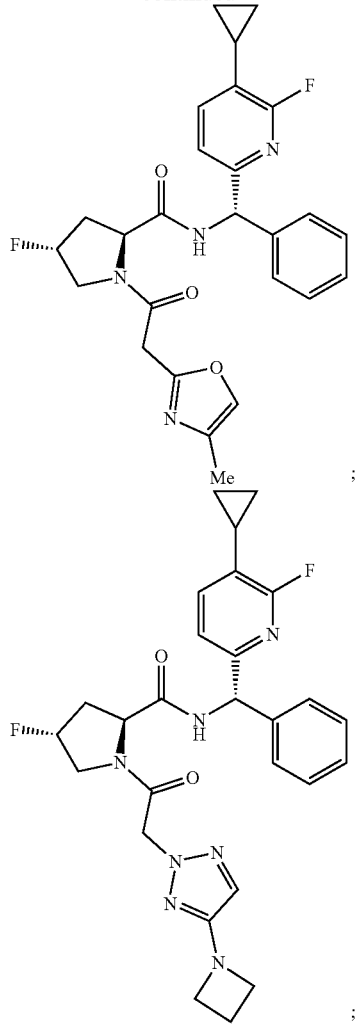
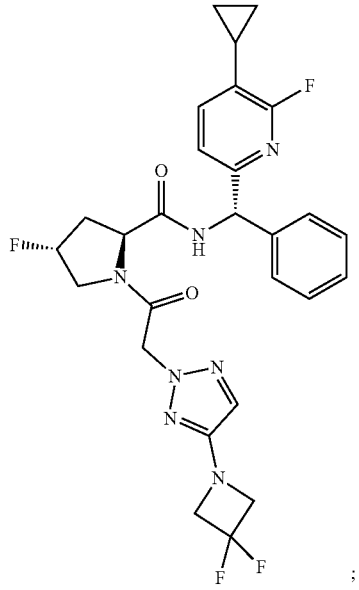

1479
-continued
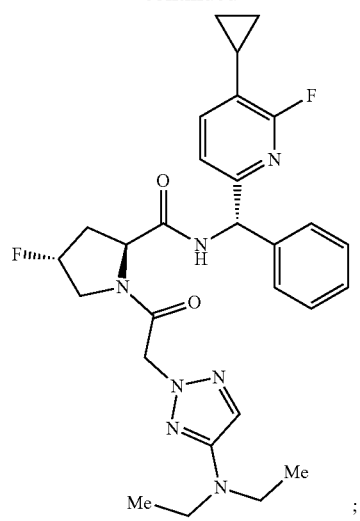
;
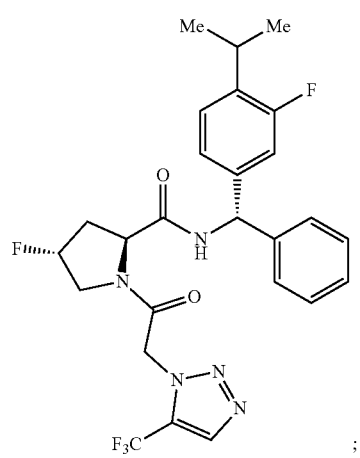
;
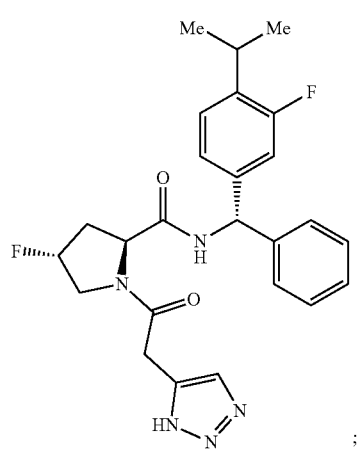
;
1480
-continued
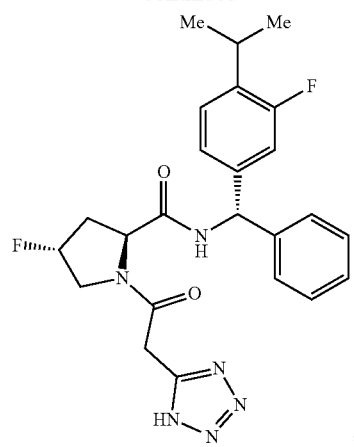
;
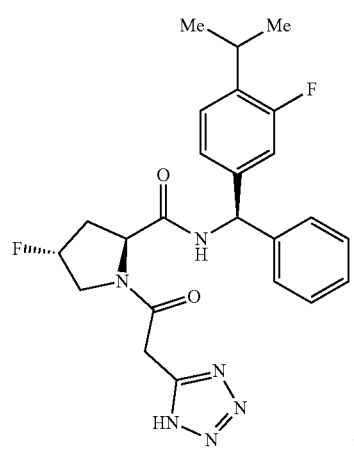
;
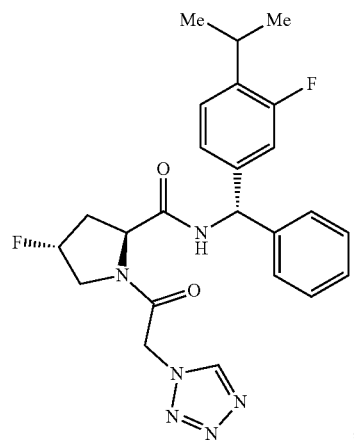
;

1481
-continued
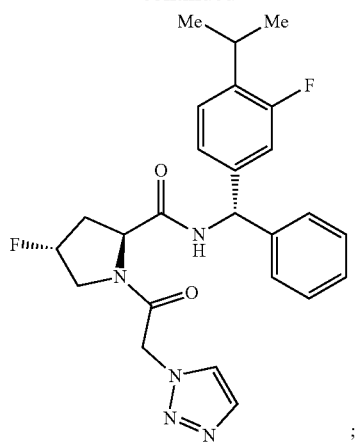
;
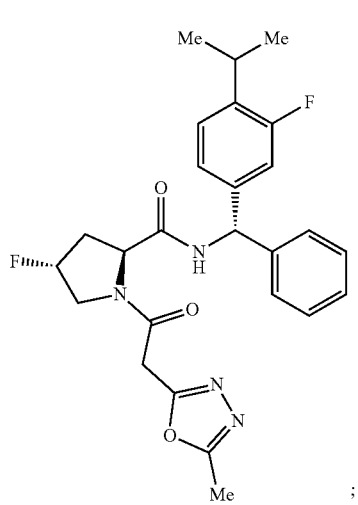
;
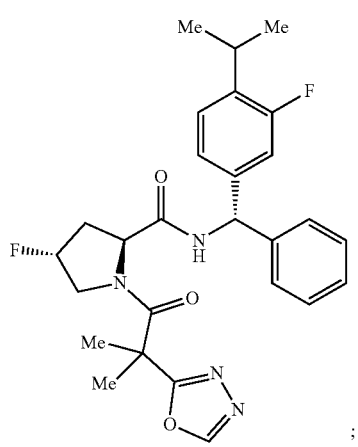
;
1482
-continued
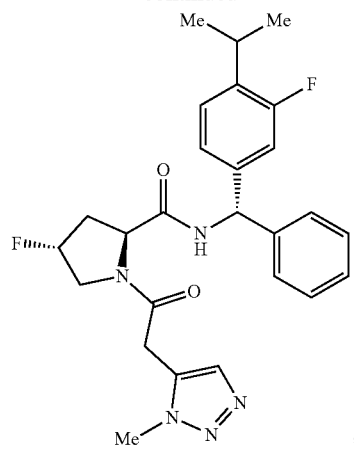
;
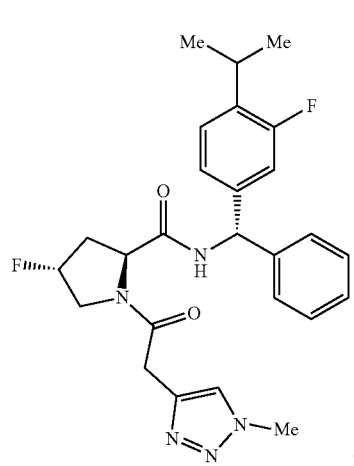
;
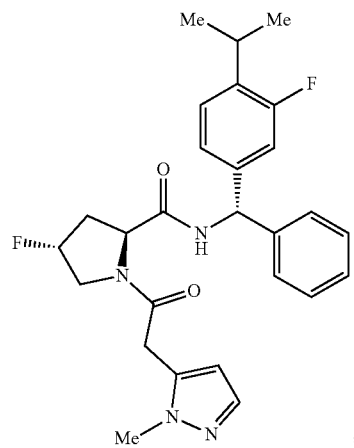
;

1483
-continued
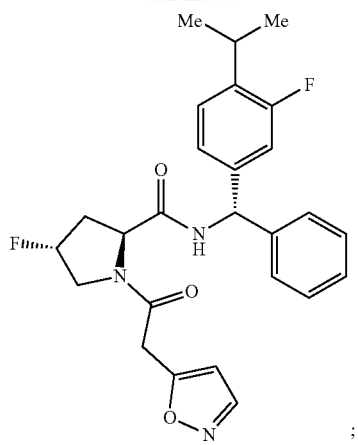
;
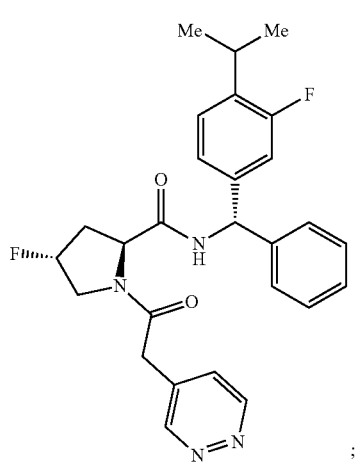
;
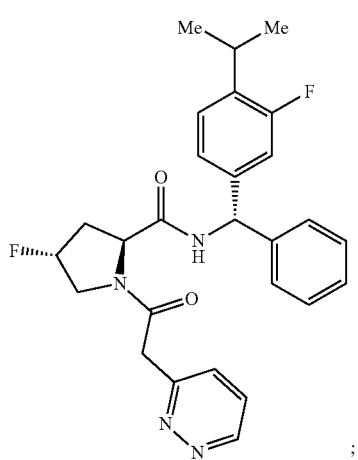
;
1484
-continued
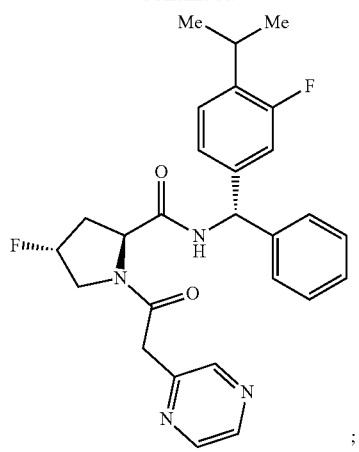
;
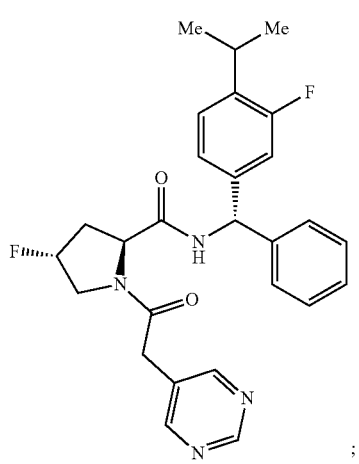
;
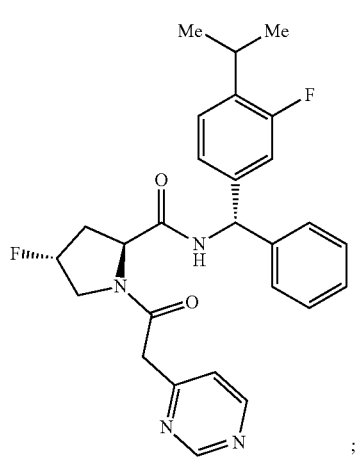
;

1485
-continued
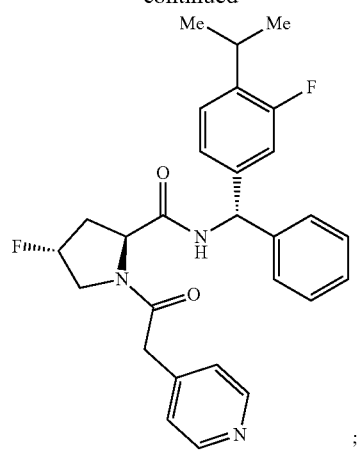
;
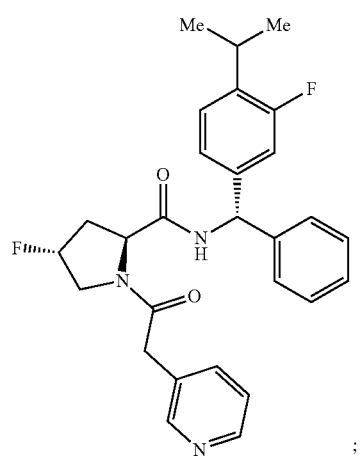
;
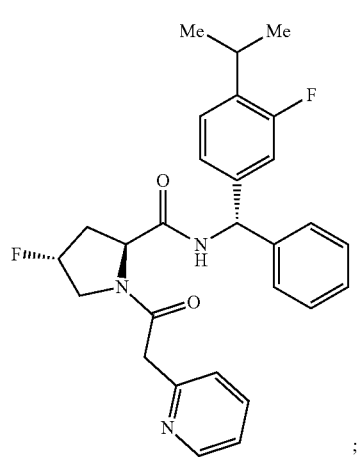
;
1486
-continued
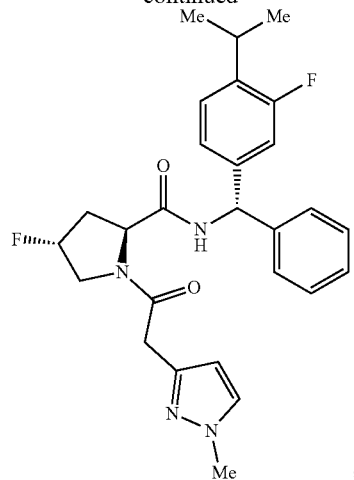
;
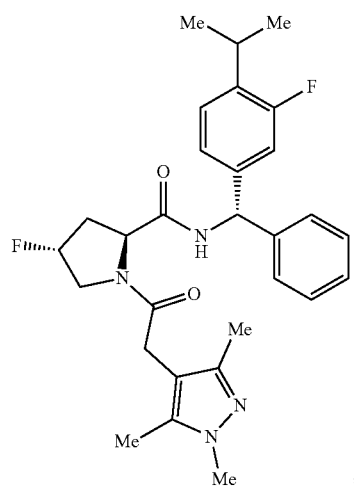
;
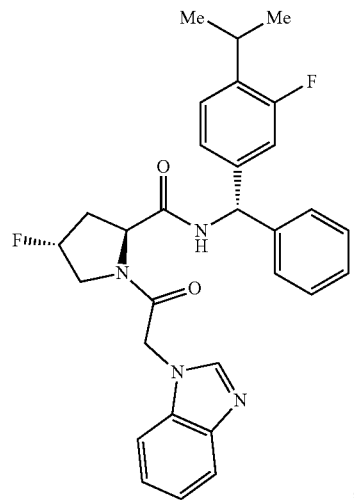
;

1487
-continued
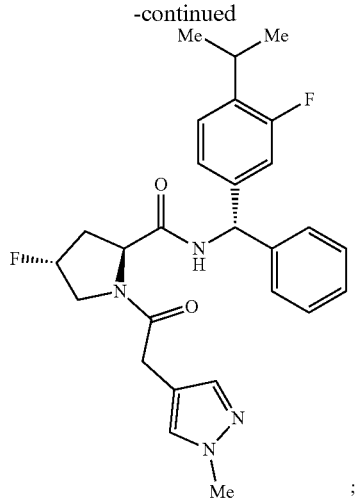
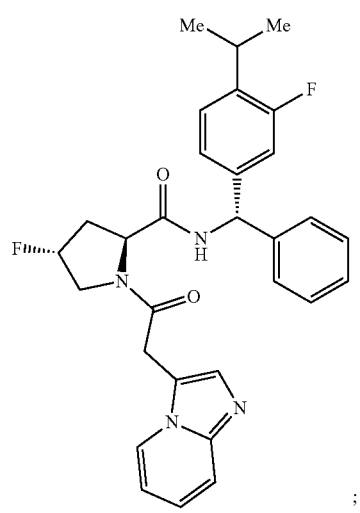
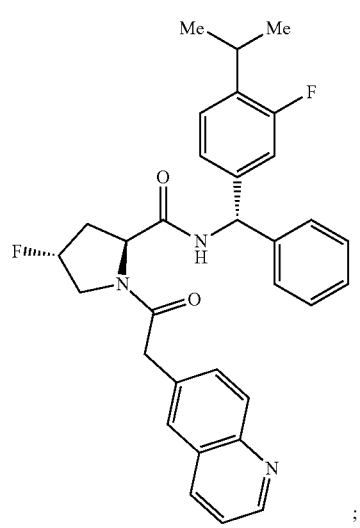
1488
-continued
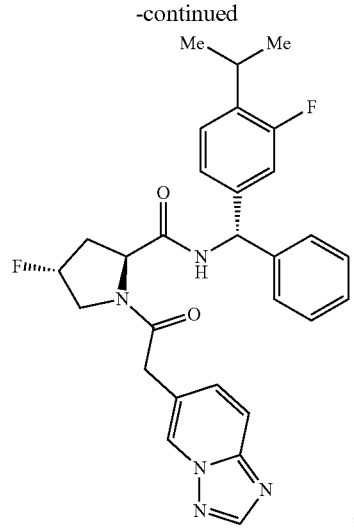
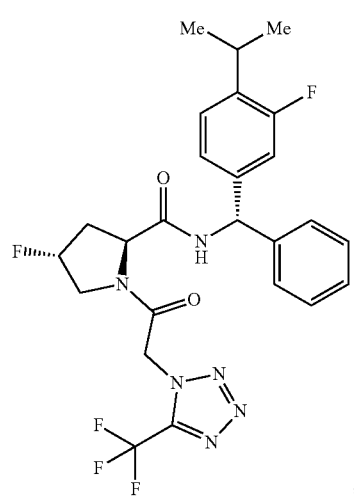
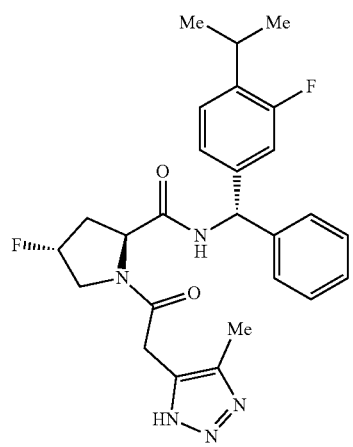

1489
-continued
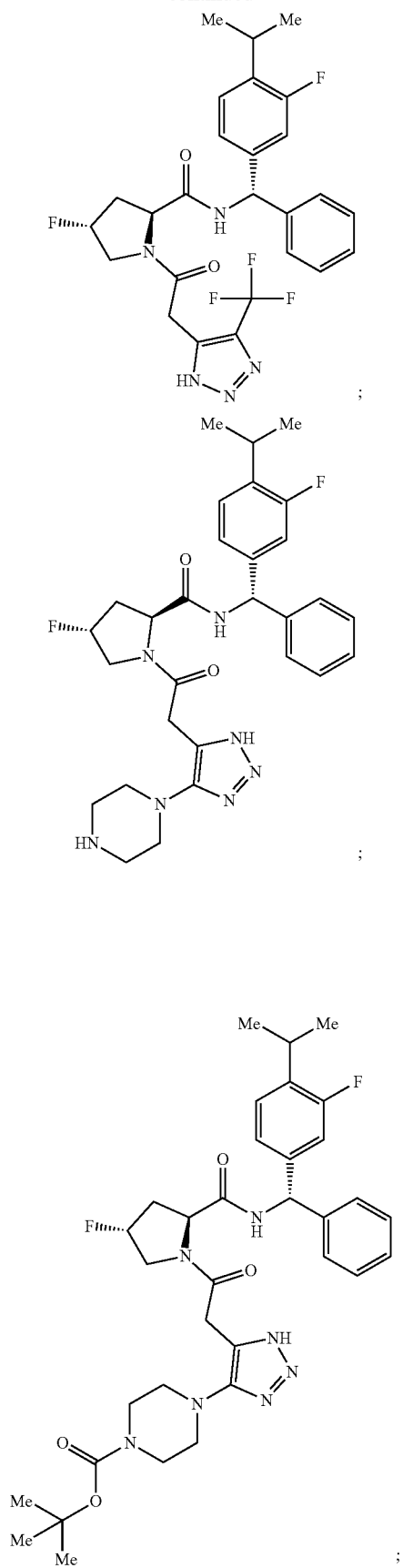
1490
-continued
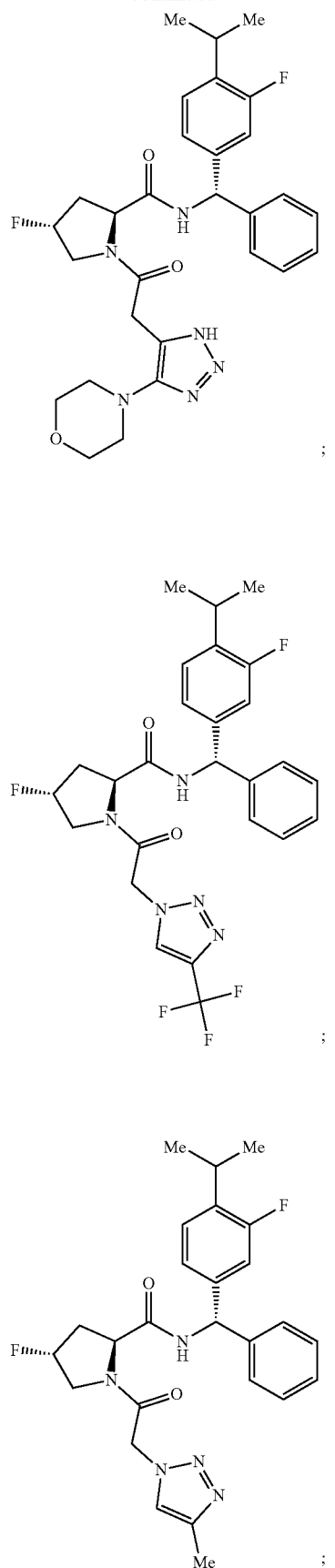

1491
-continued
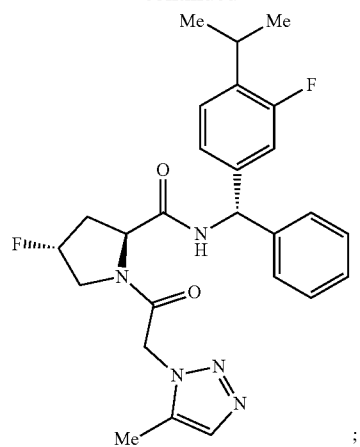
;
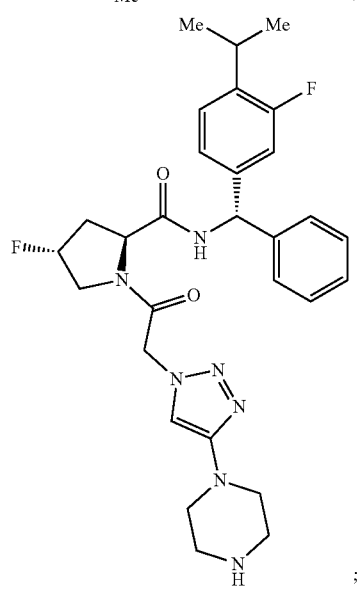
;
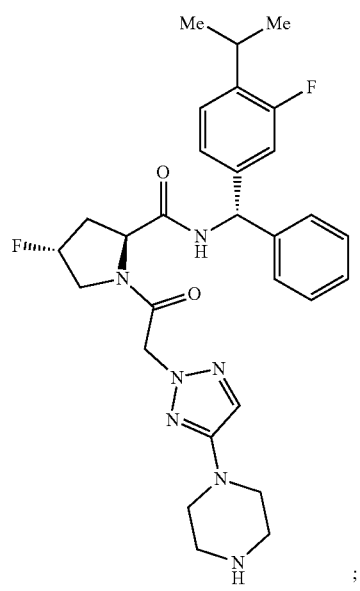
;
1492
-continued
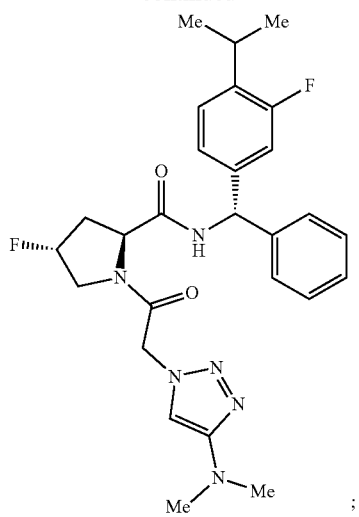
;
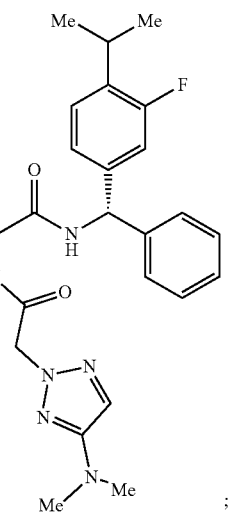
;
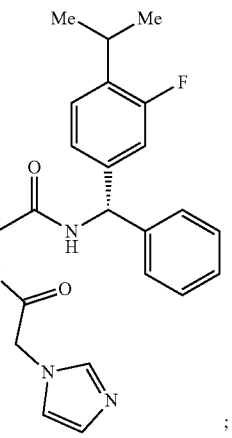
;

1493
-continued
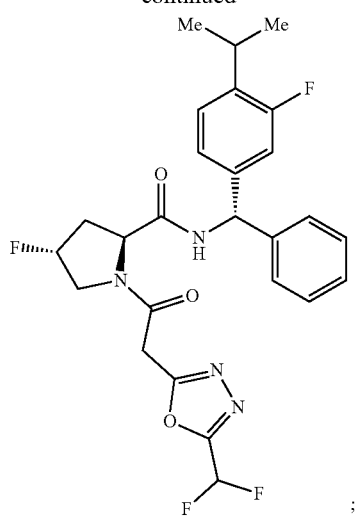
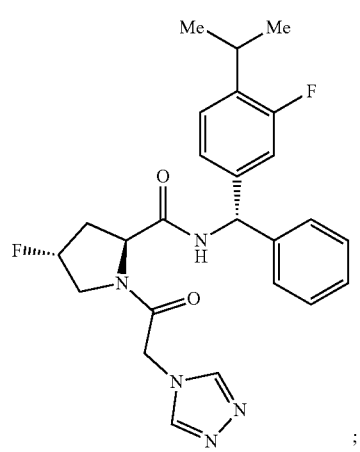
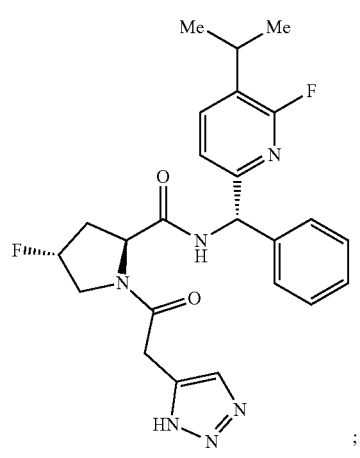
1494
-continued
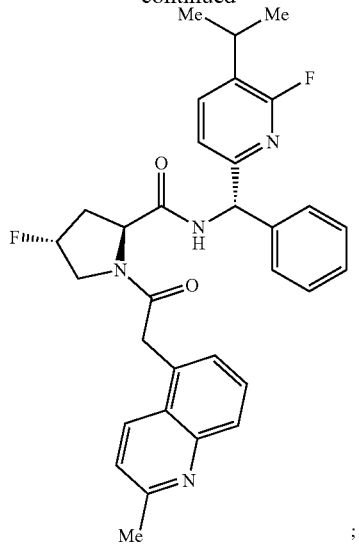
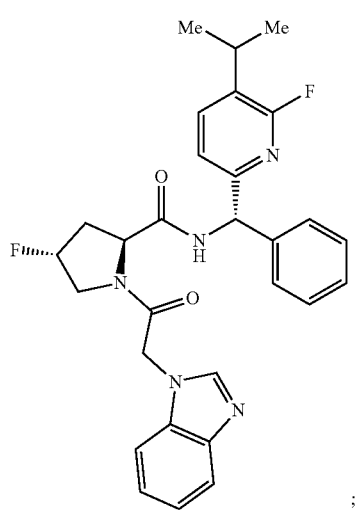
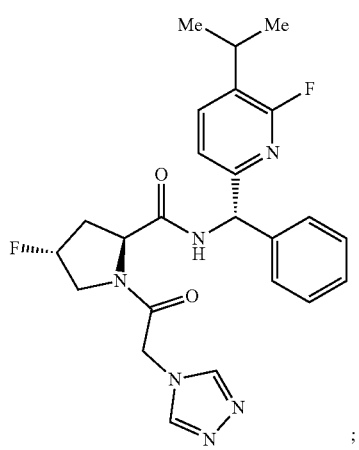

1495
-continued
1496
-continued
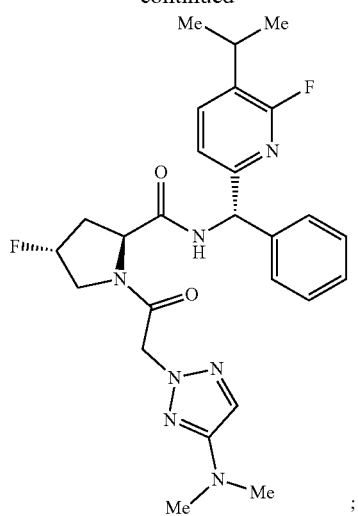
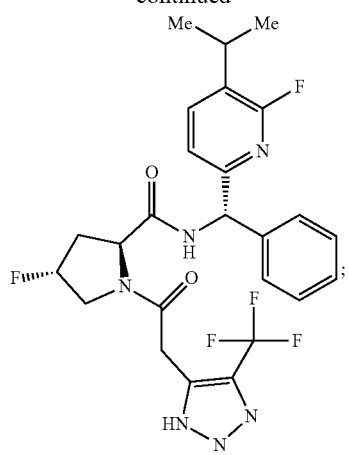

1497
-continued
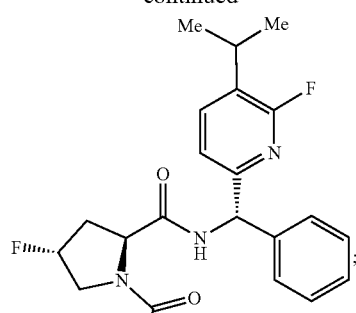
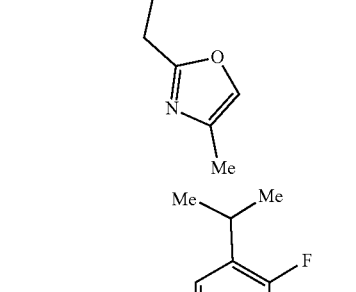
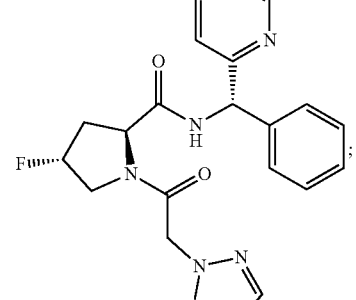
1498
-continued
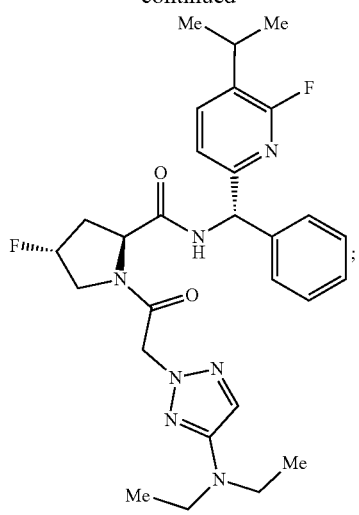
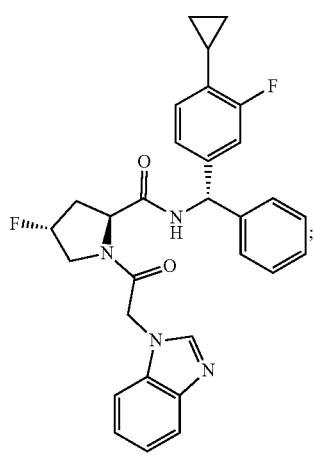
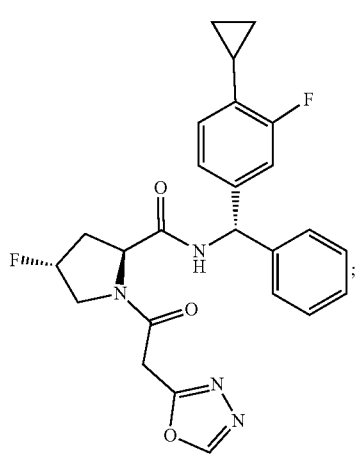

1499
-continued
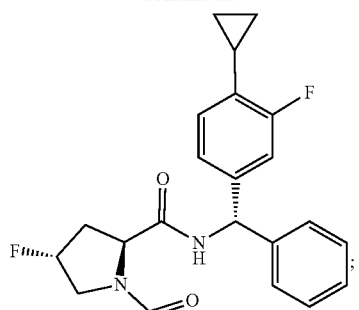
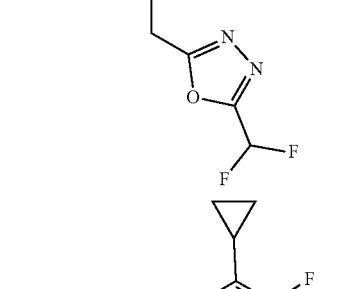
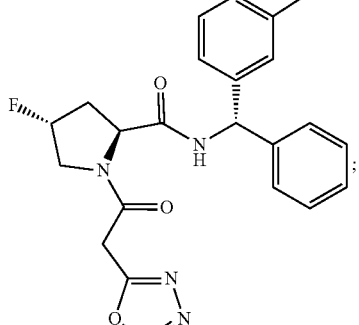
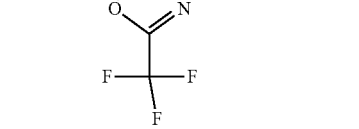
1500
-continued
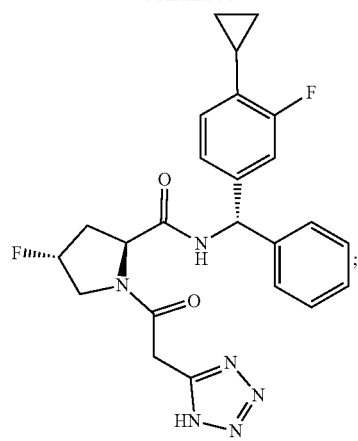
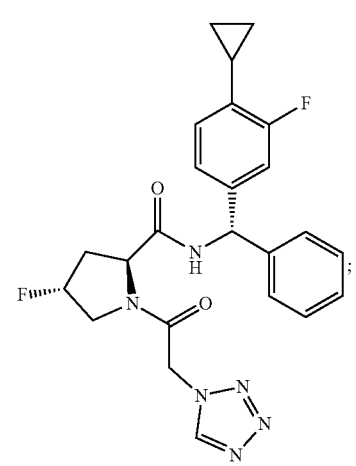
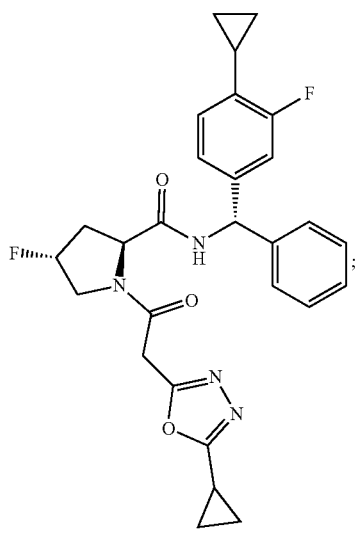
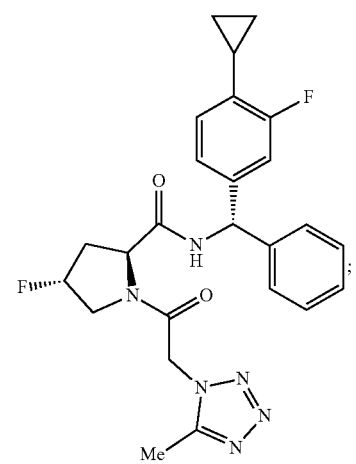

1501
-continued
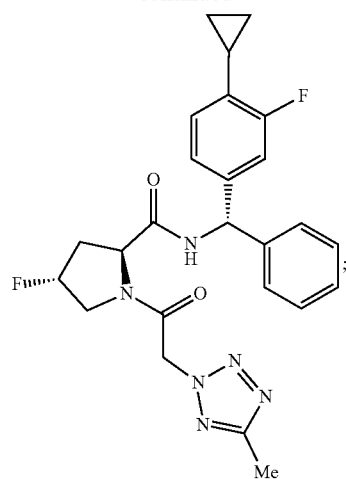
;
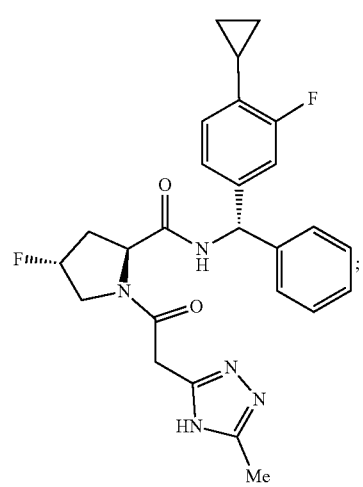
;
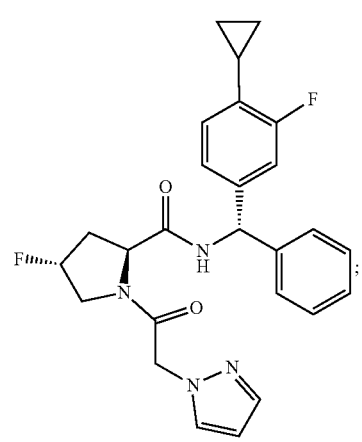
;
1502
-continued
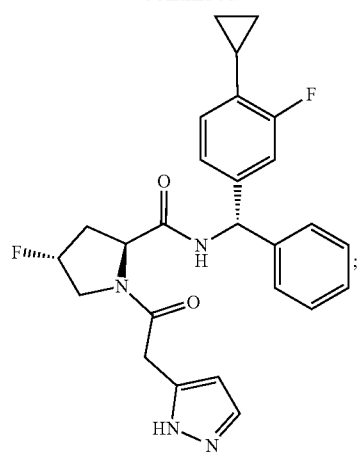
;
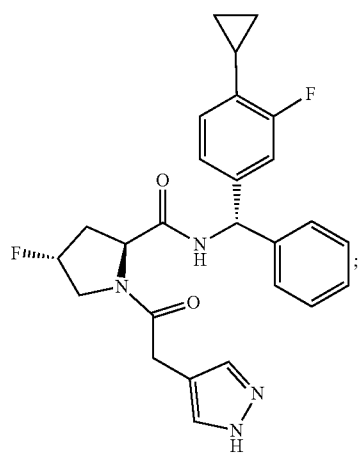
;
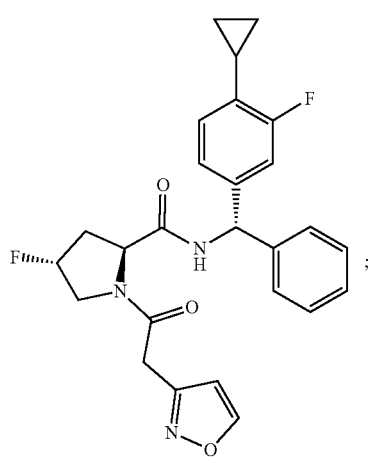
;

1503
-continued
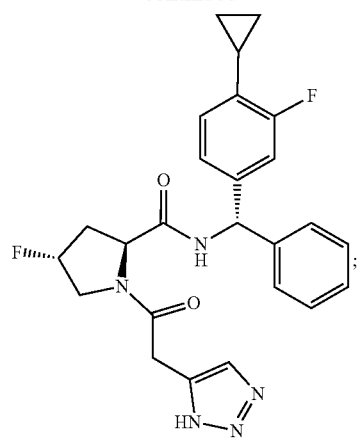
;
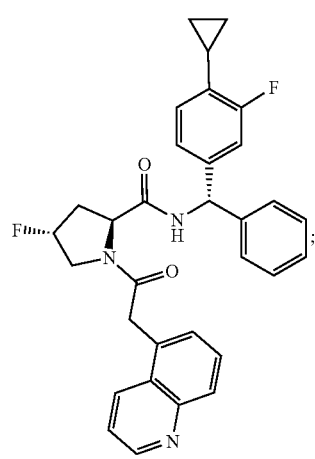
;
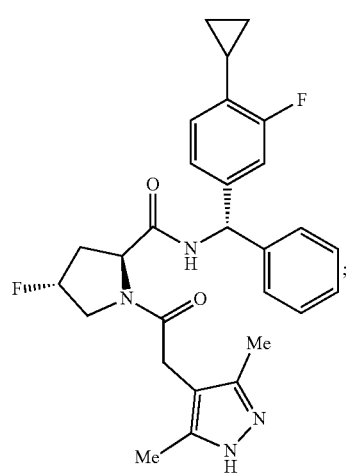
;
1504
-continued
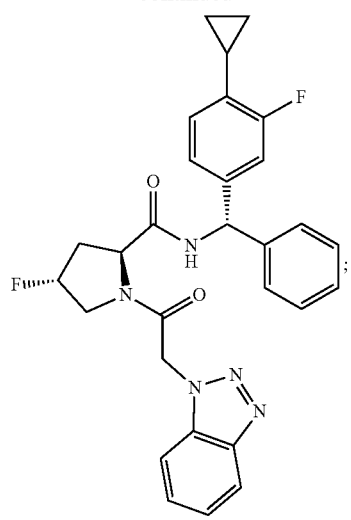
;
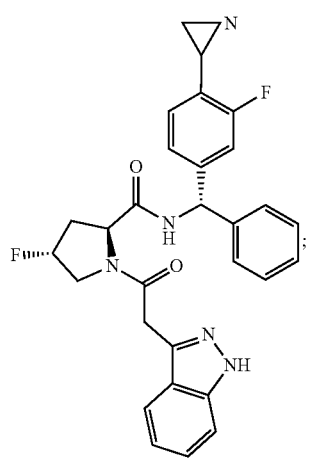
;
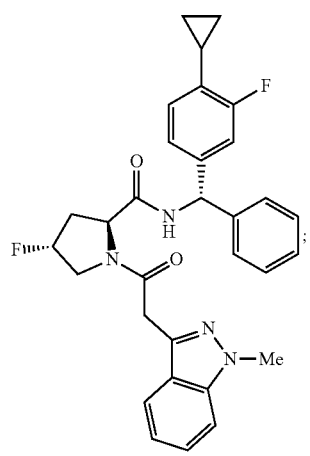
;

1505
-continued
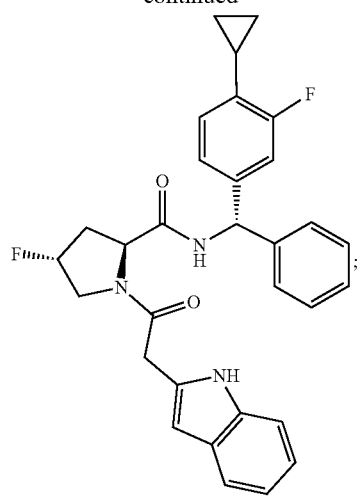
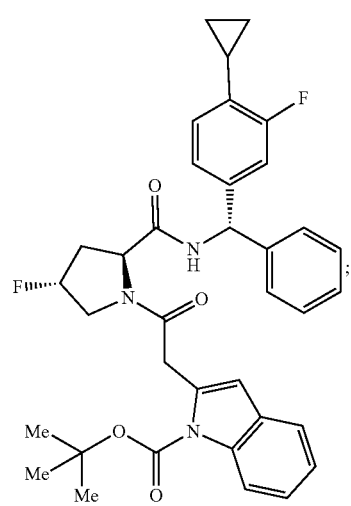
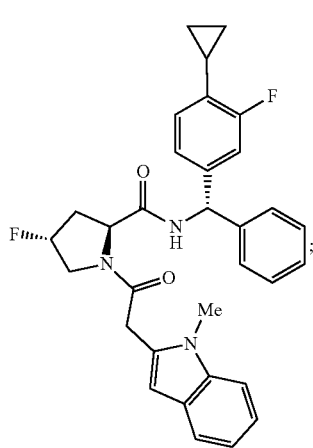
1506
-continued
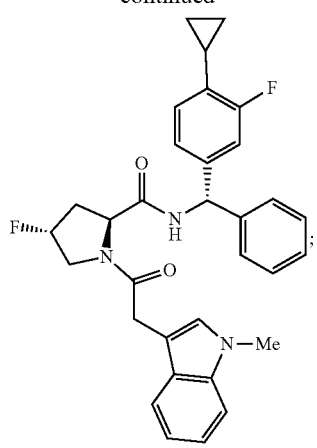
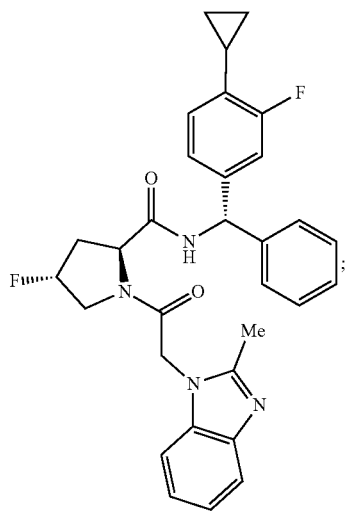
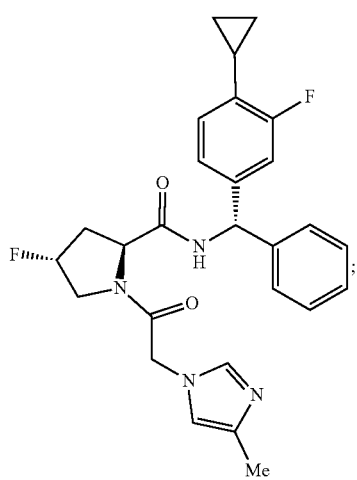

1507
-continued
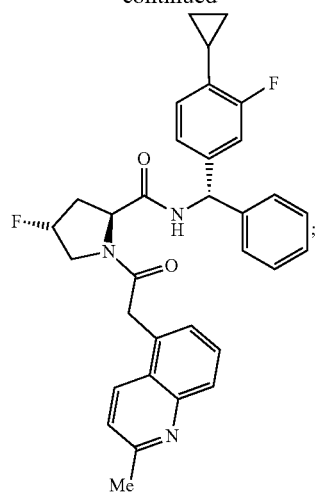
1508
-continued
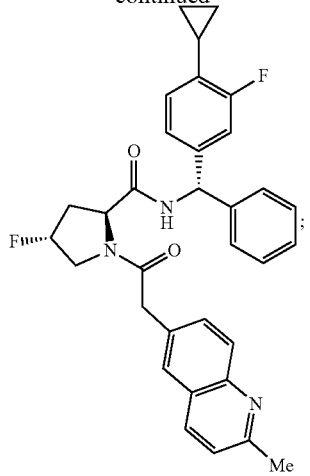
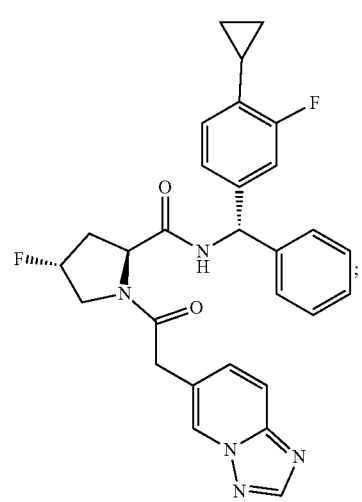
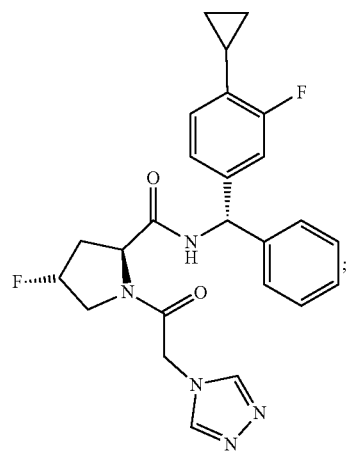
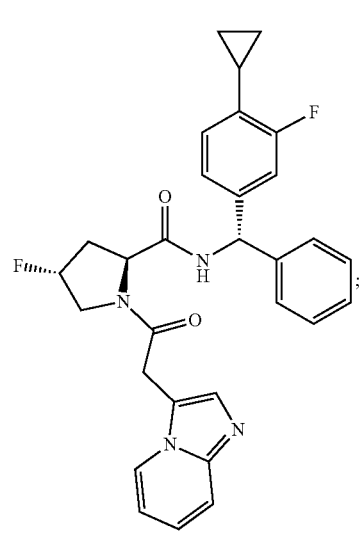
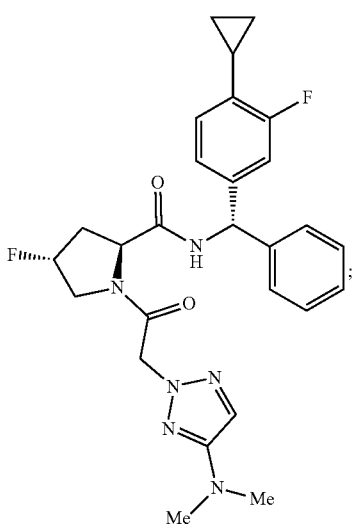

1509
-continued
1510
-continued
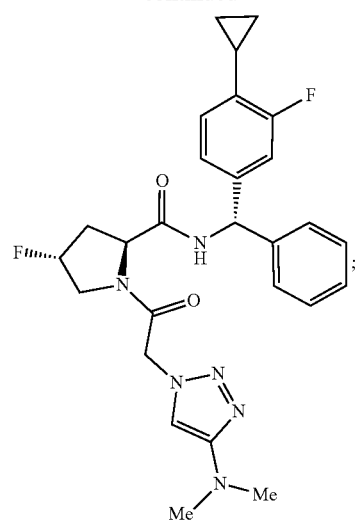
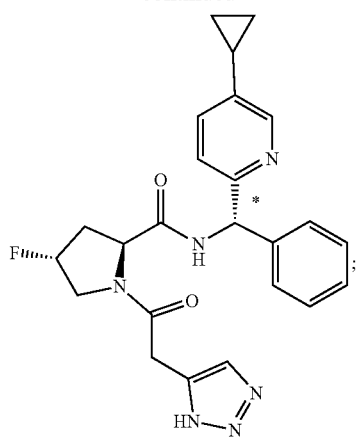

1511
-continued
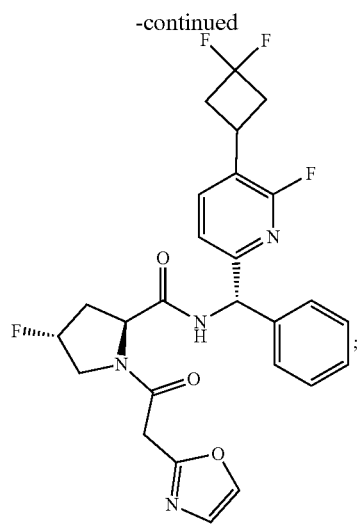
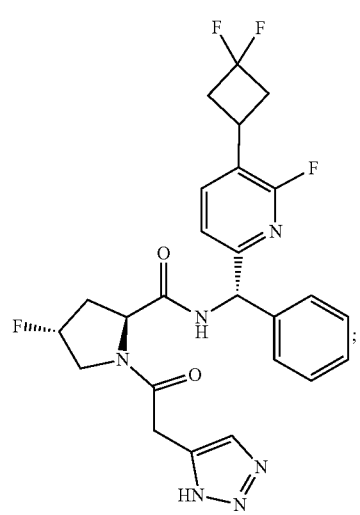
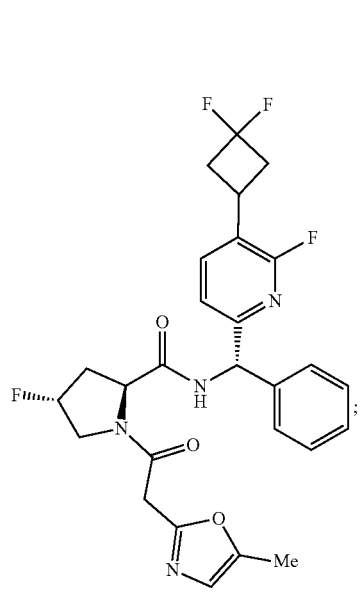
1512
-continued
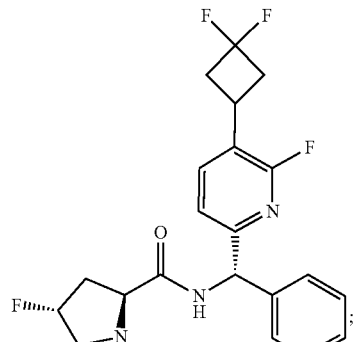
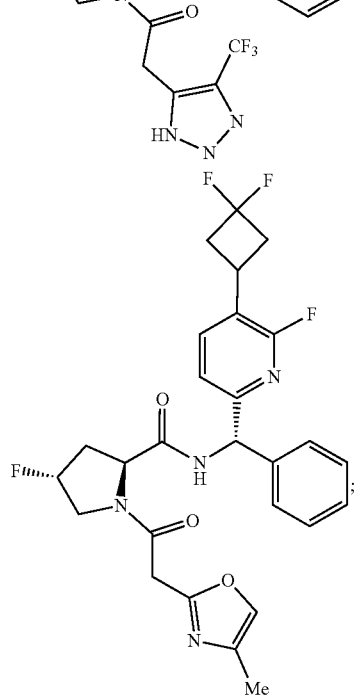
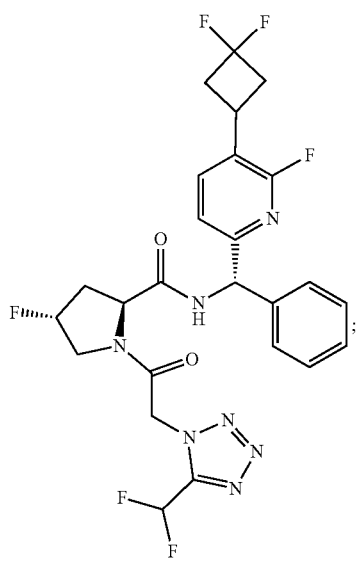

1513
-continued
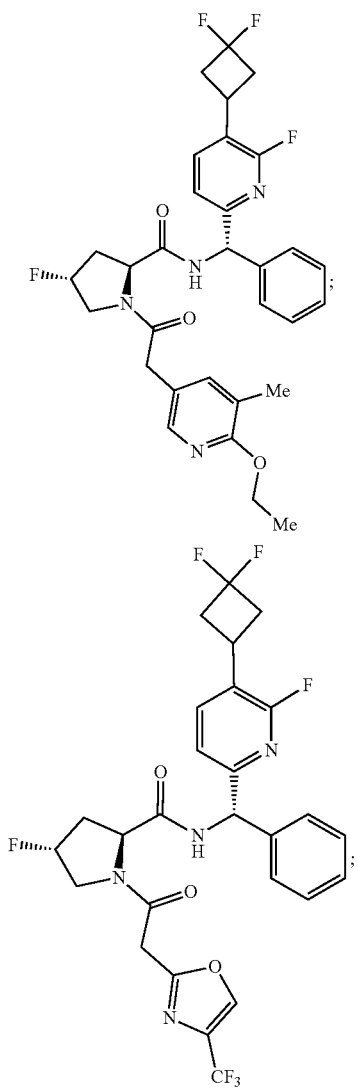
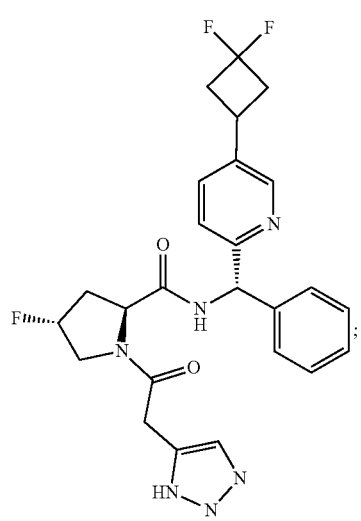
1514
-continued
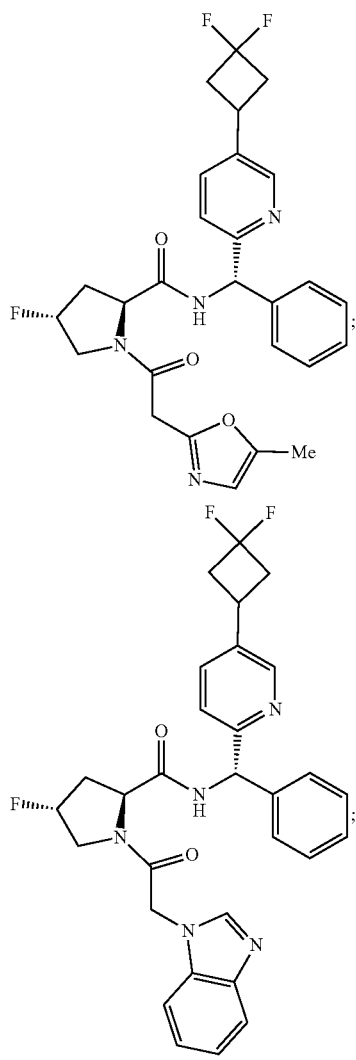
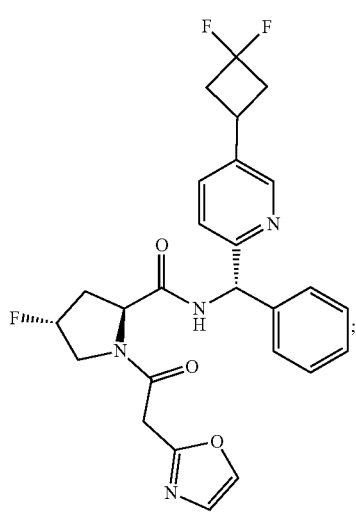

1515
-continued
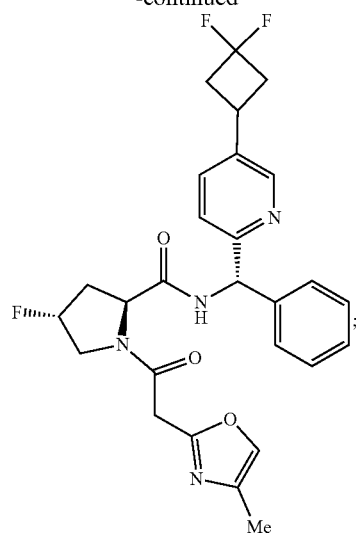
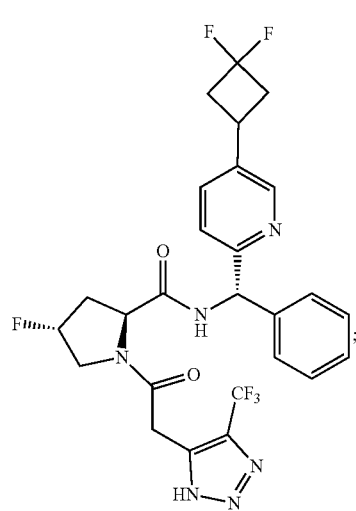
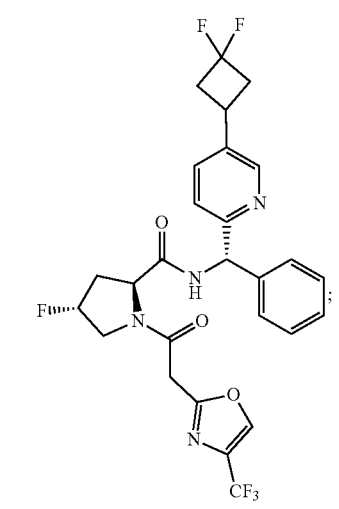
1516
-continued
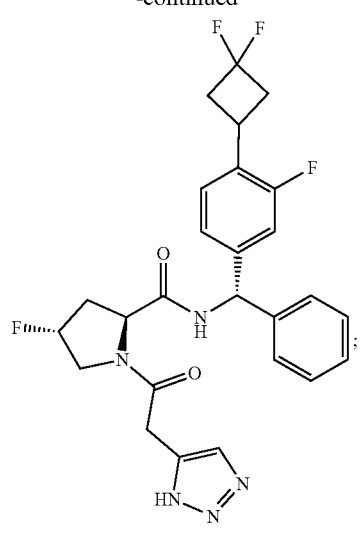
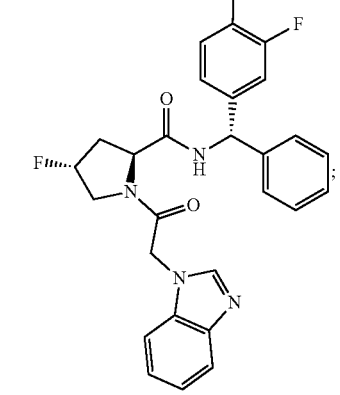
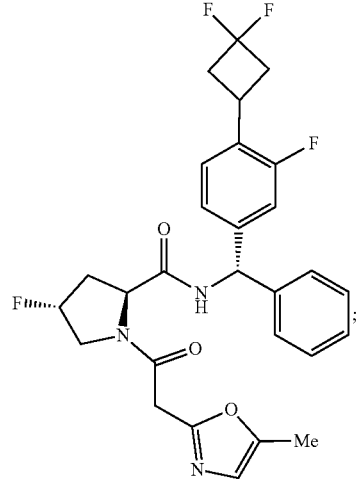

1517
-continued
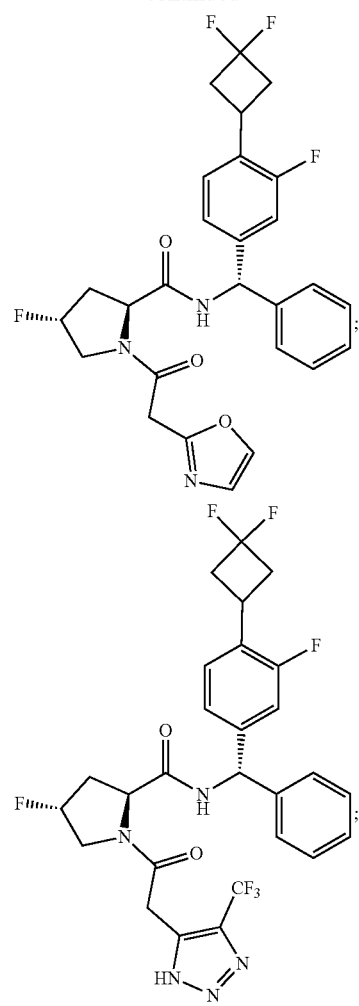
1518
-continued
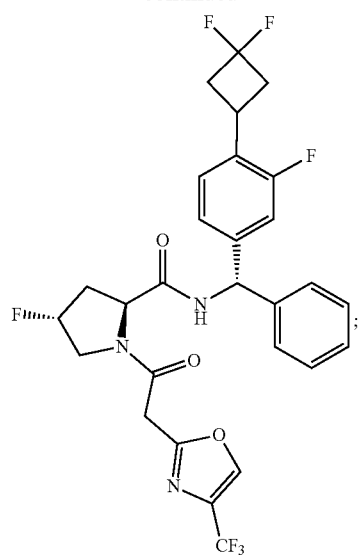
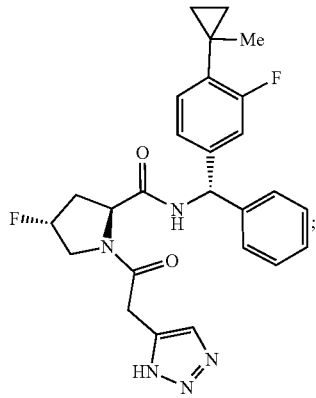
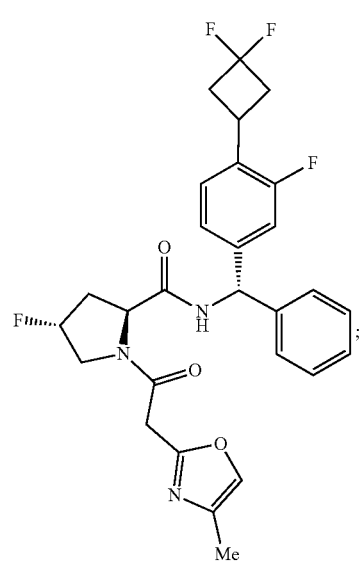
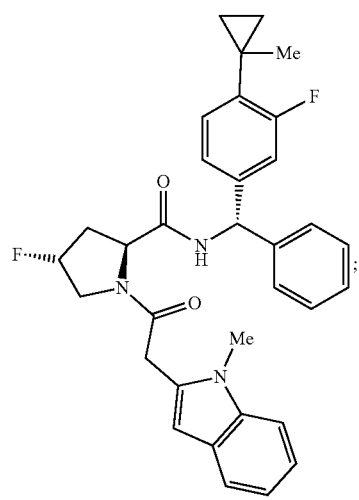

1519
-continued
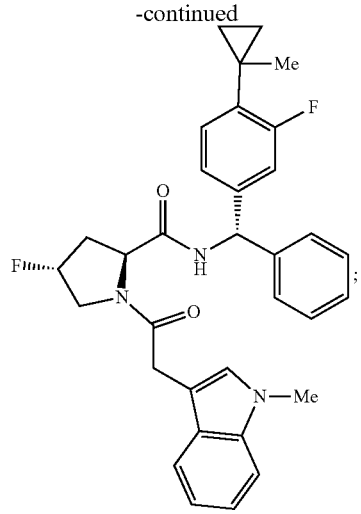
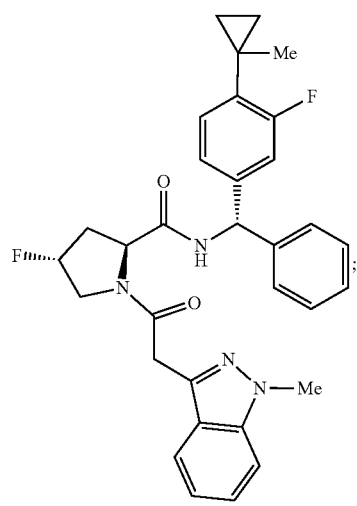
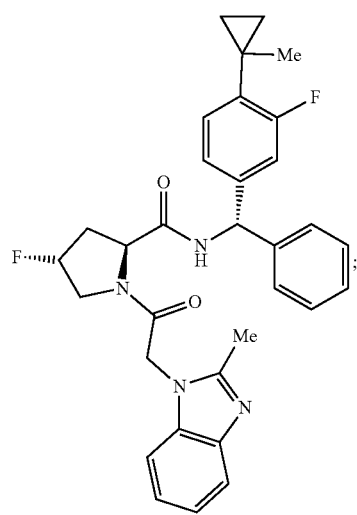
1520
-continued
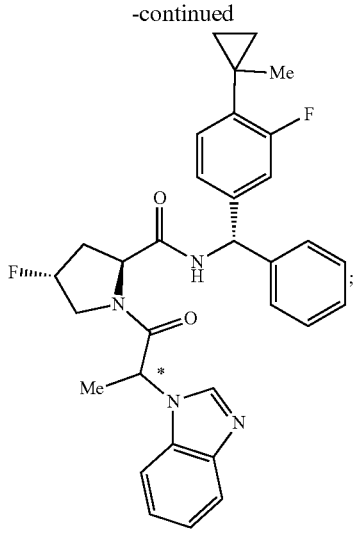
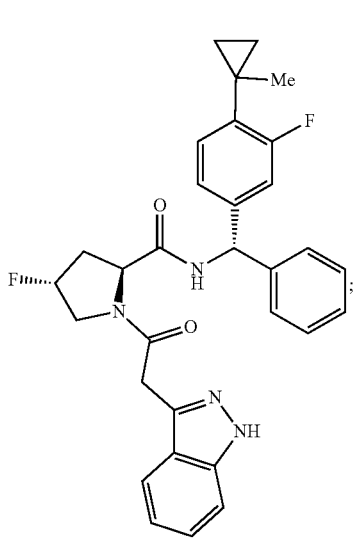
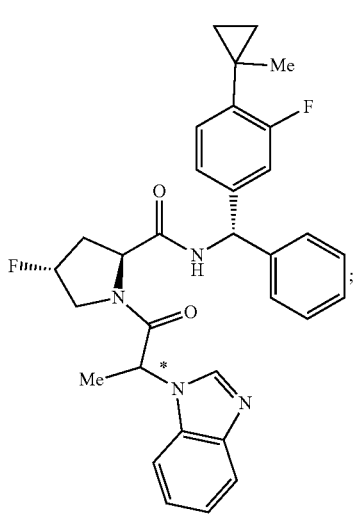

1521
-continued
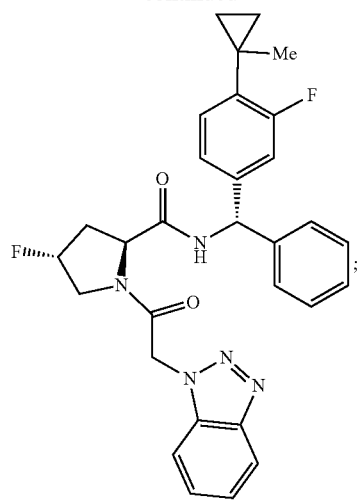
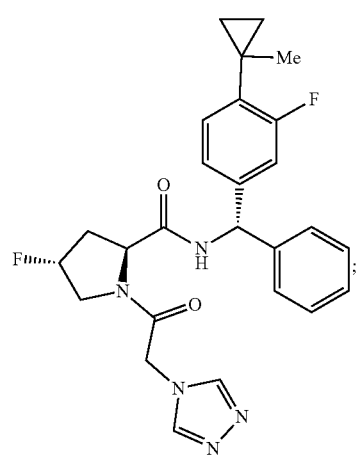
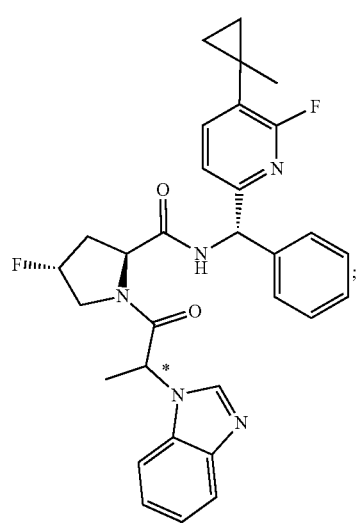
1522
-continued
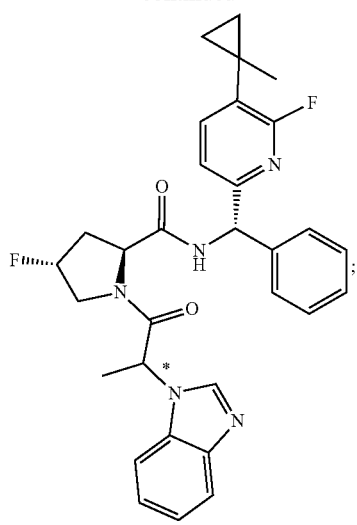
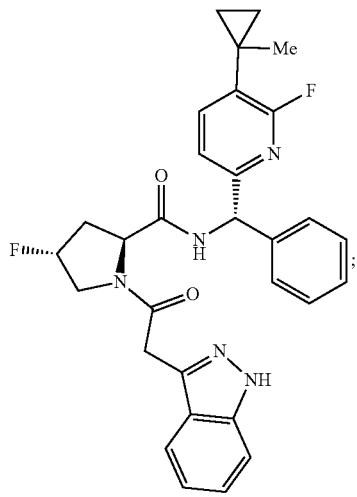
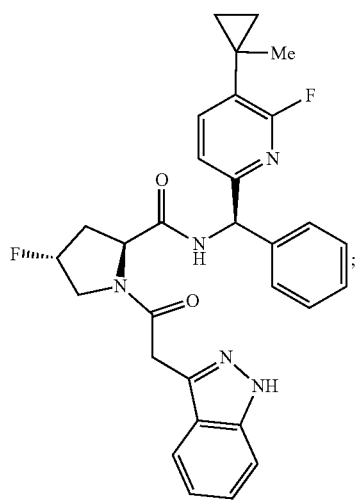

1523
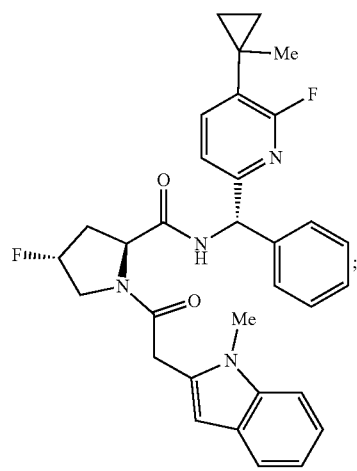
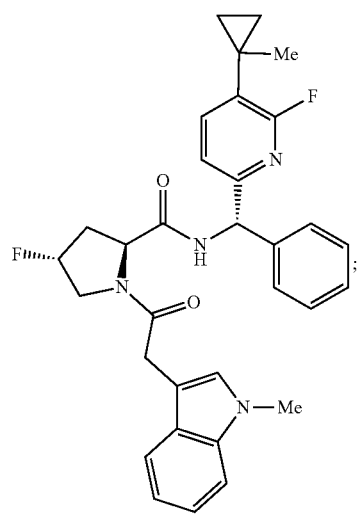
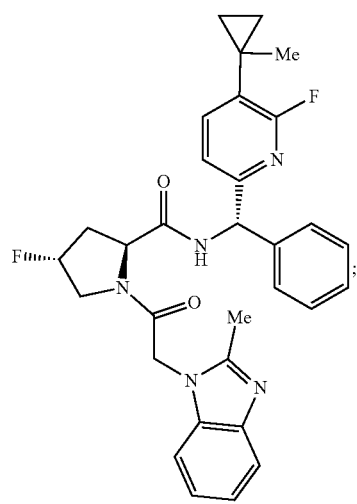
1524
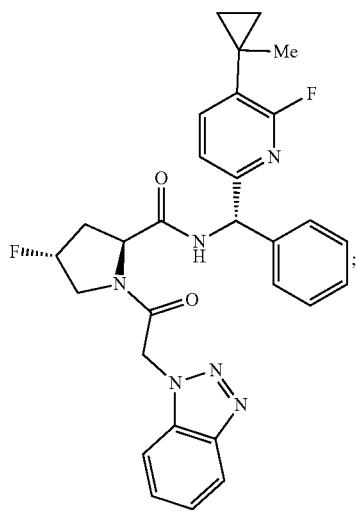
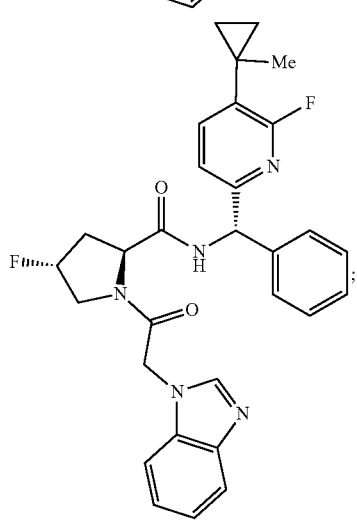
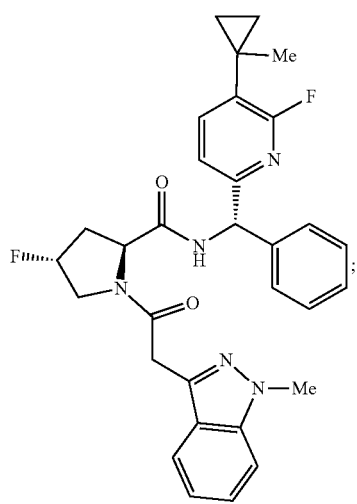

1525
-continued
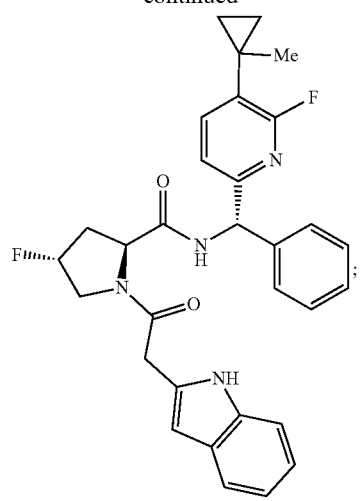
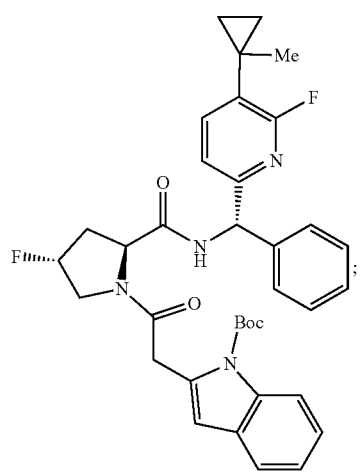
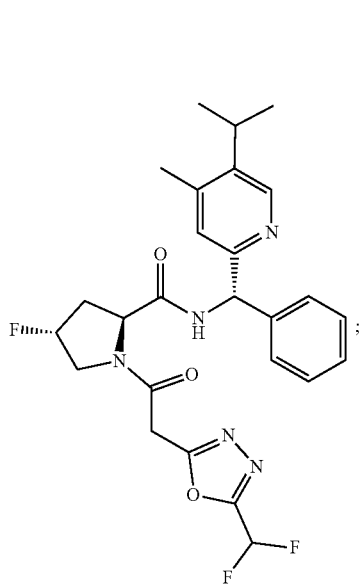
1526
-continued
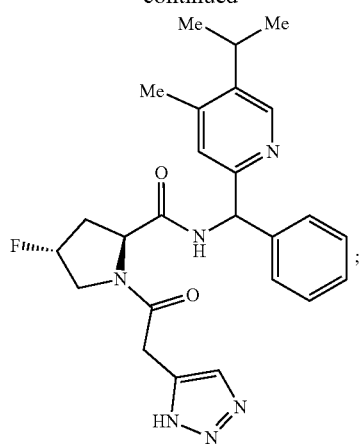
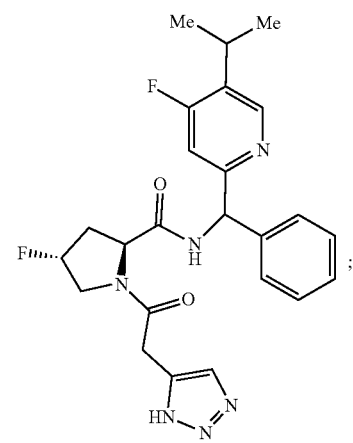
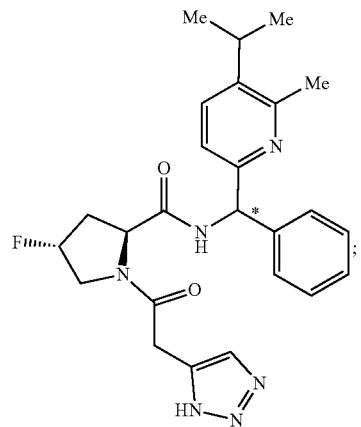

1527
-continued
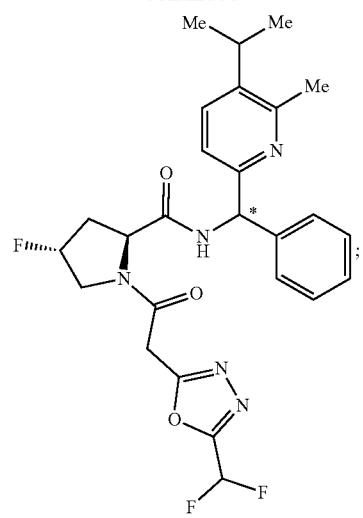
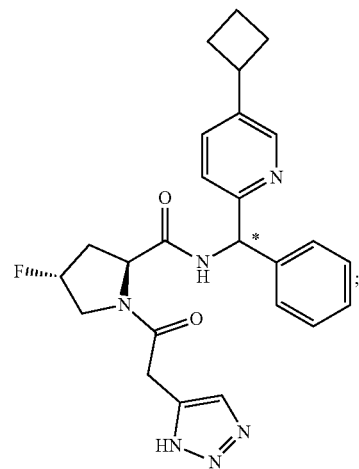
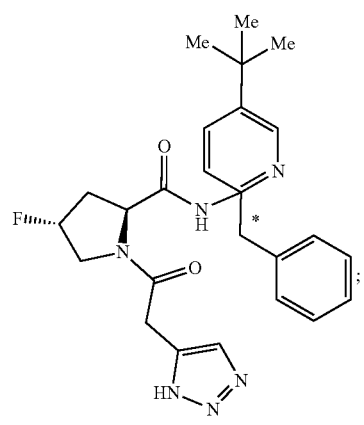
1528
-continued
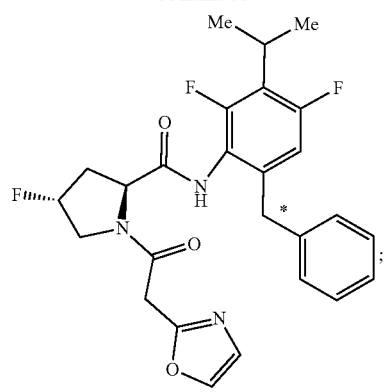
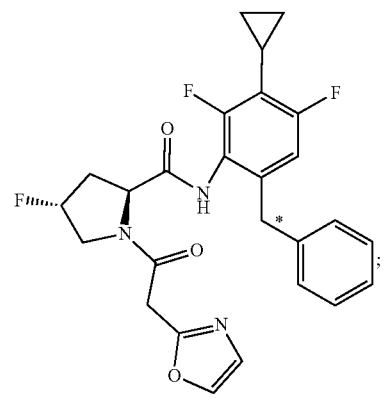
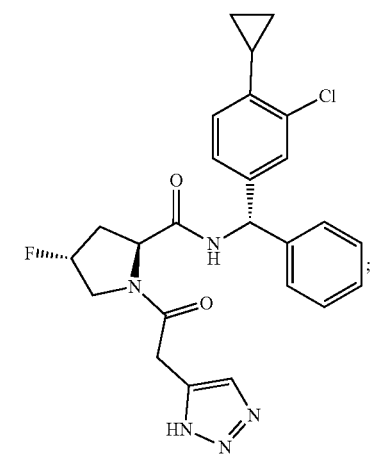
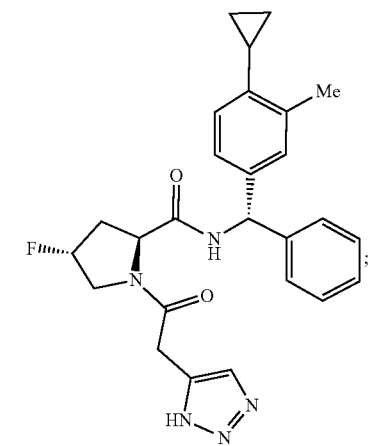

1529
-continued
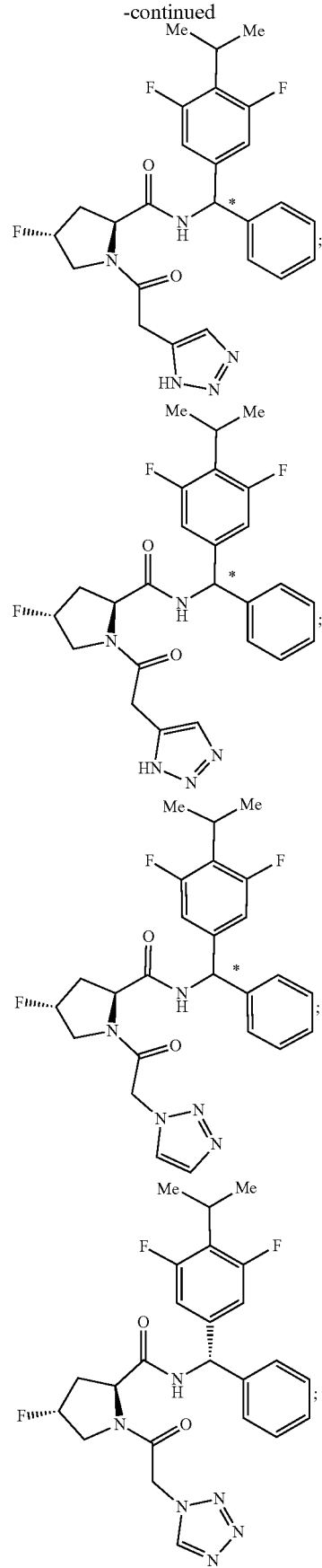
1530
-continued
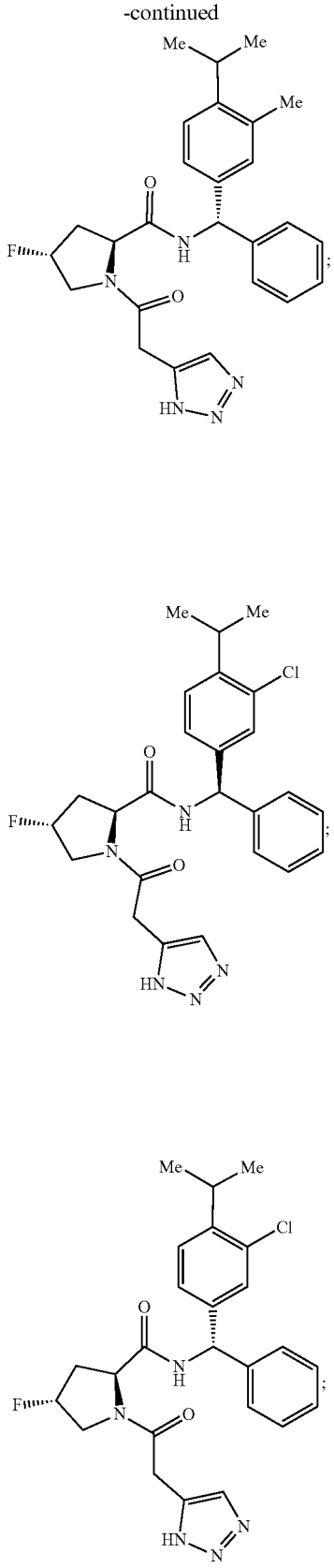

1531
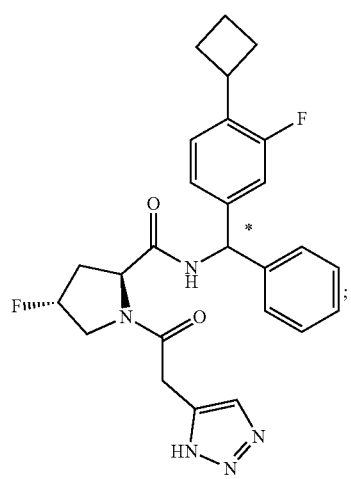
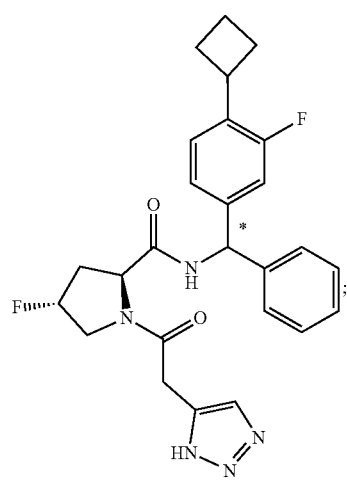
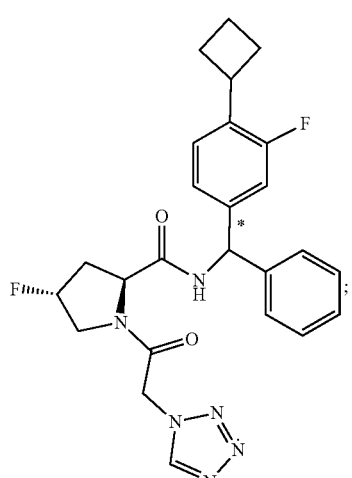
1532
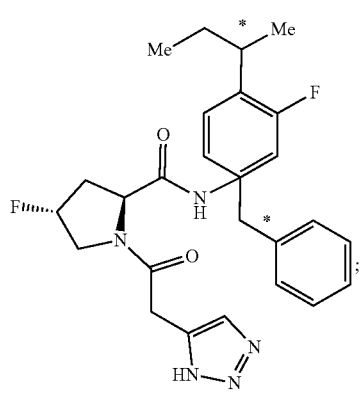
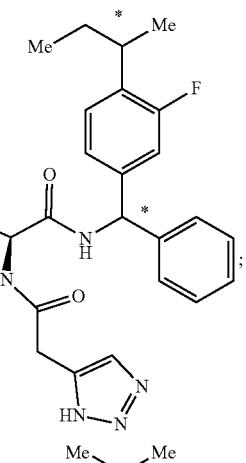
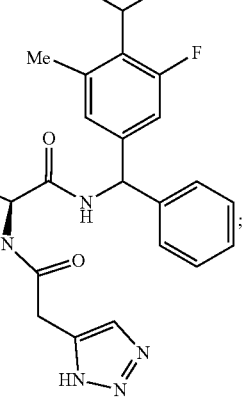
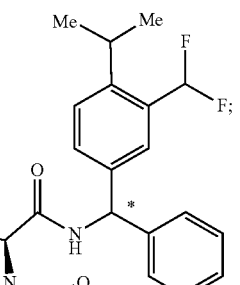
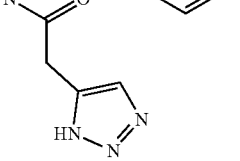

1533
-continued
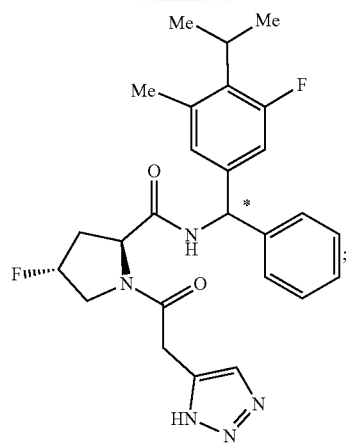
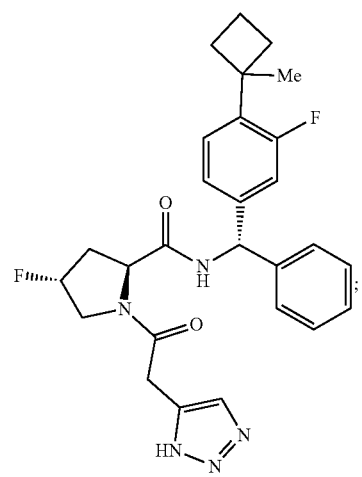
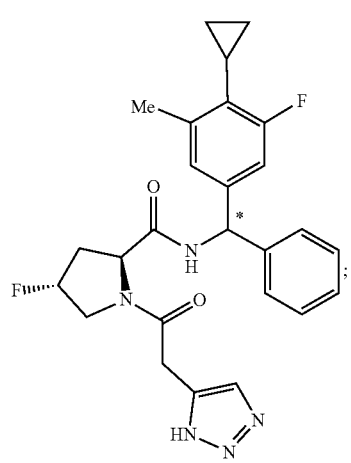
1534
-continued
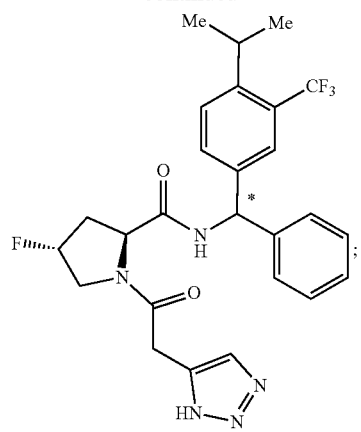
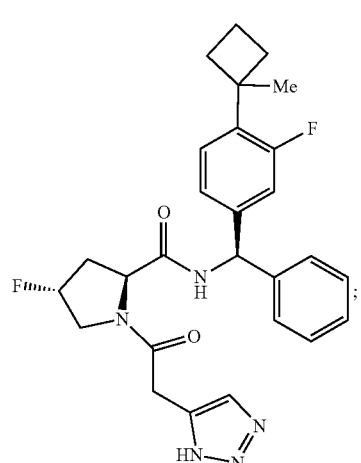
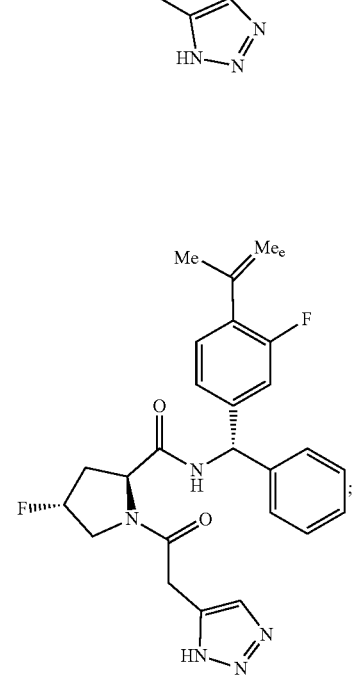

1535
-continued
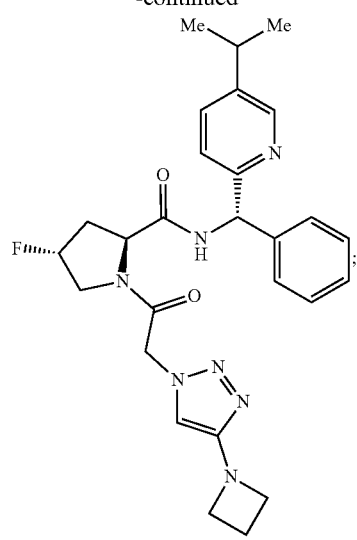
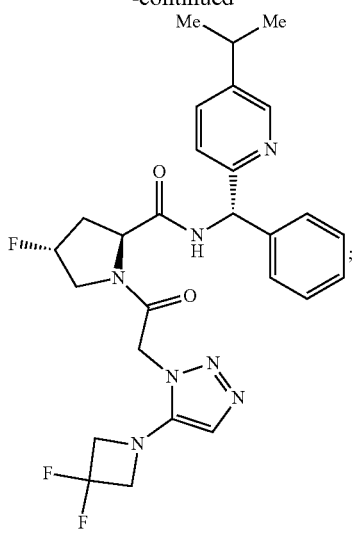
1536
-continued
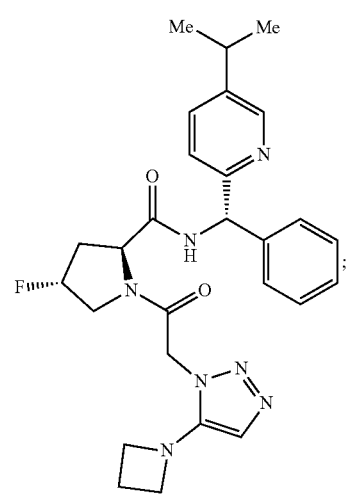
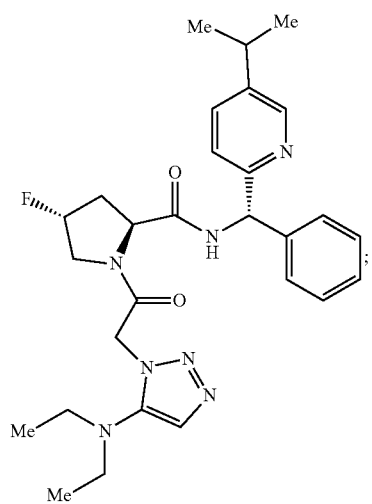
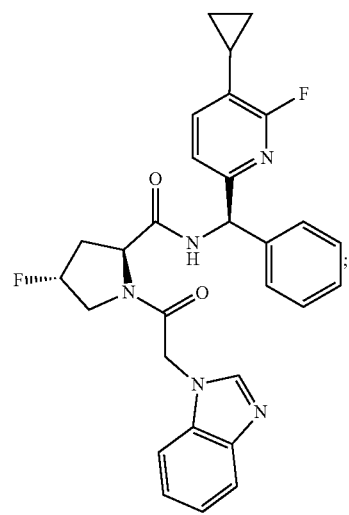

1537
-continued
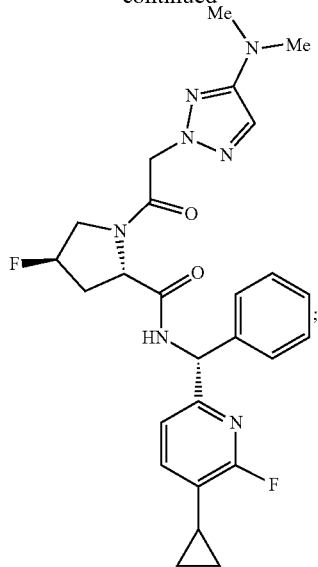
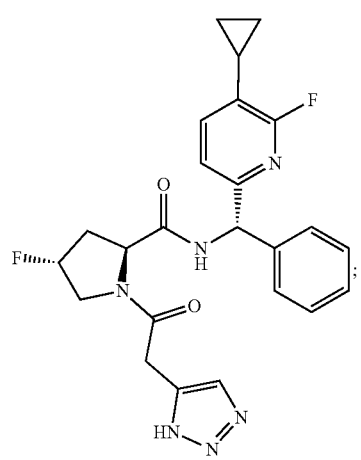
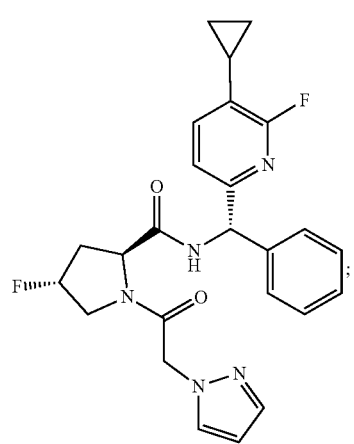
1538
-continued
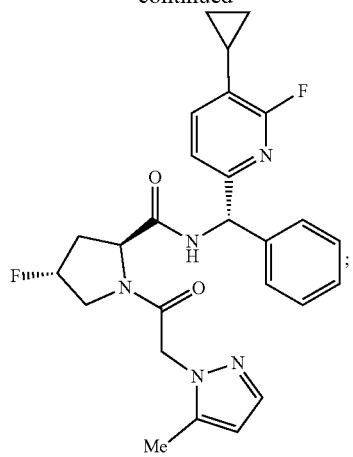
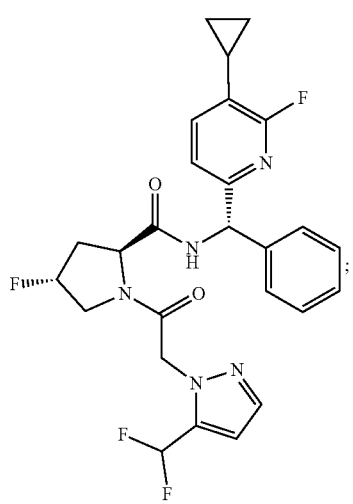
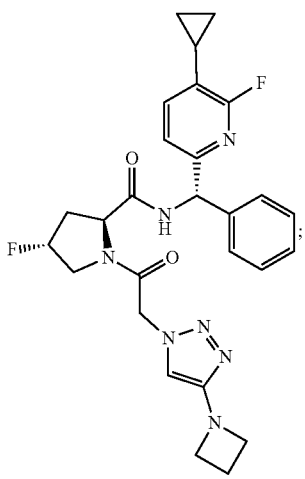

1539
-continued
1540
-continued
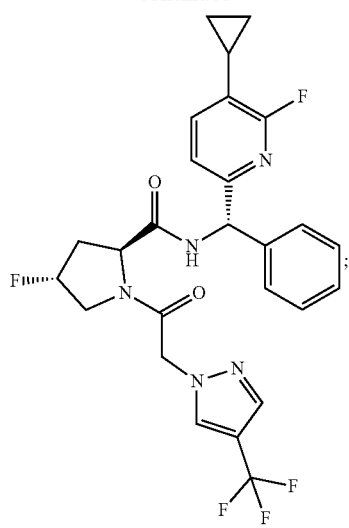
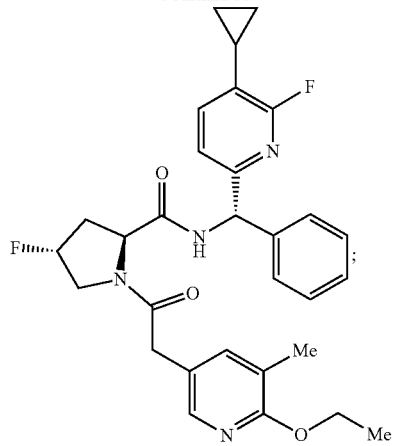
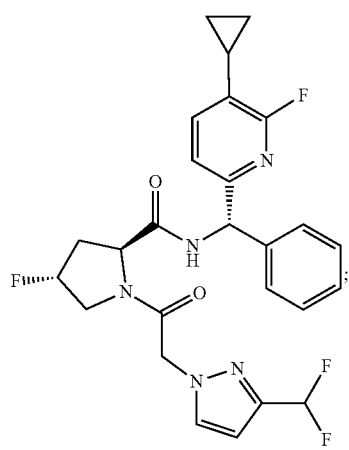
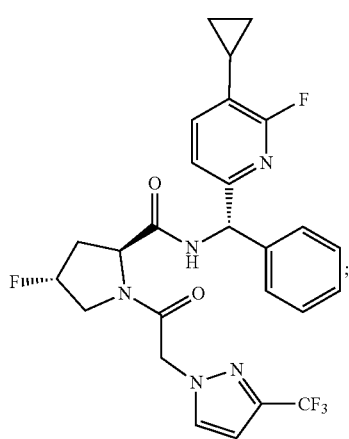
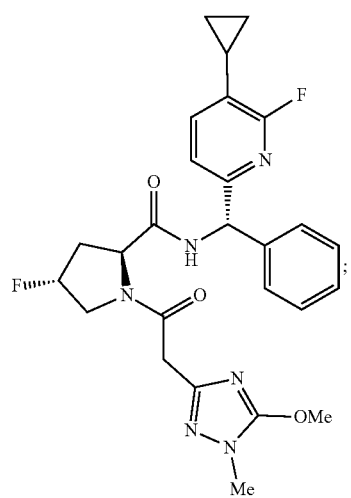

1541
-continued
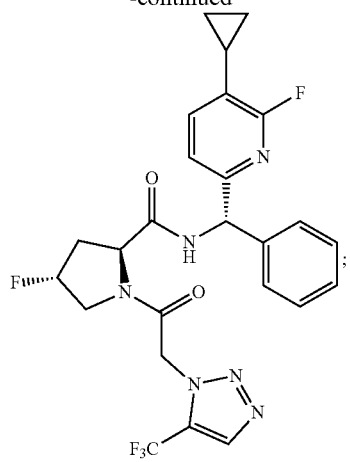;
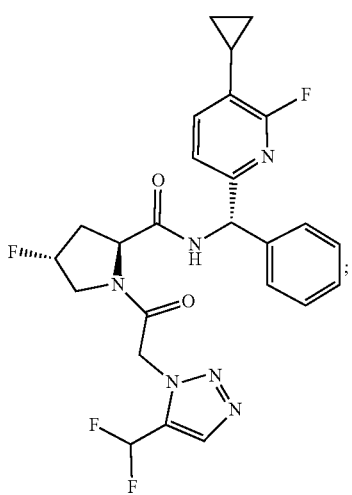;
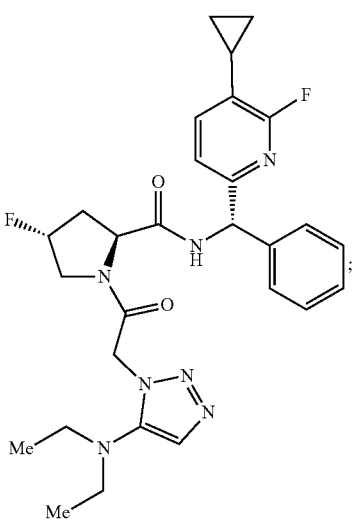;
1542
-continued
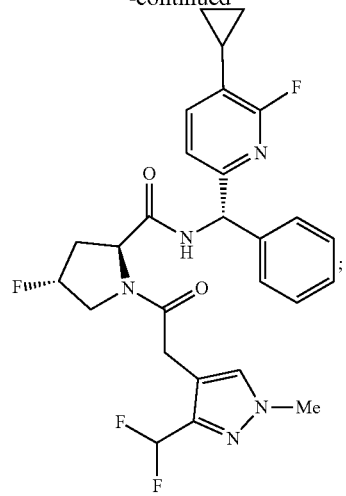;
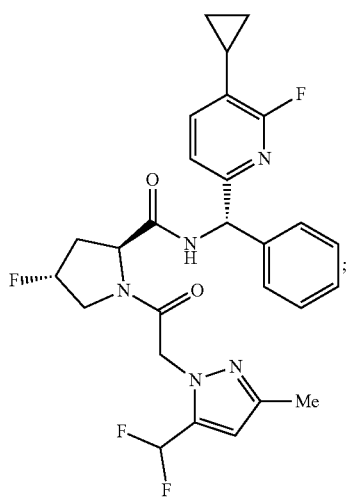;
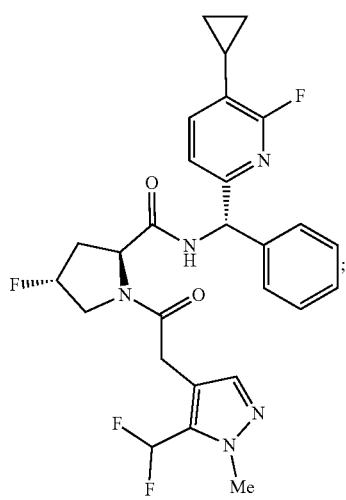;

1543
-continued
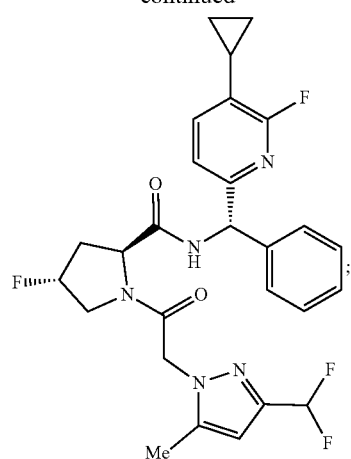
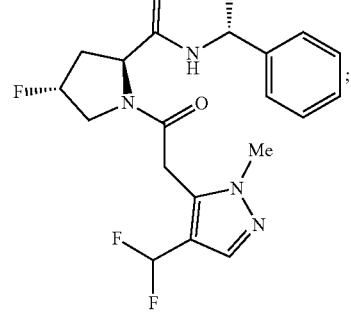
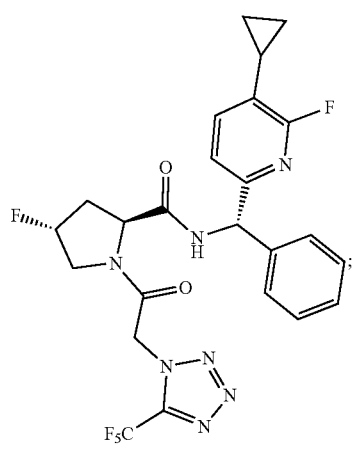
1544
-continued
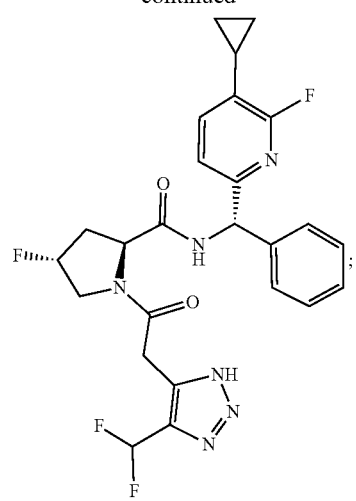
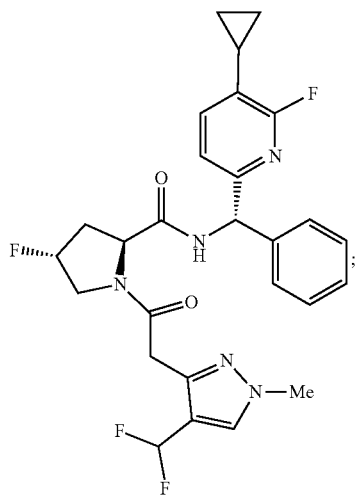

1545
-continued
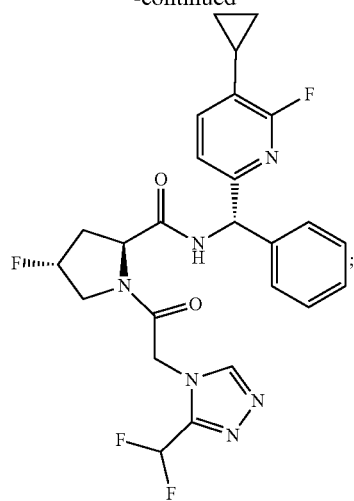
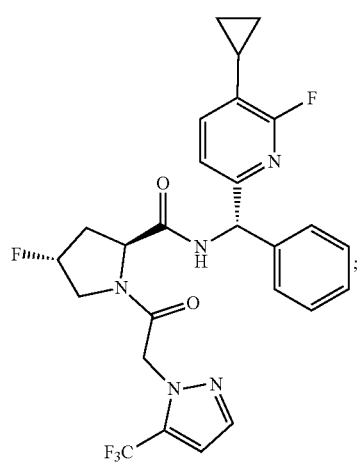
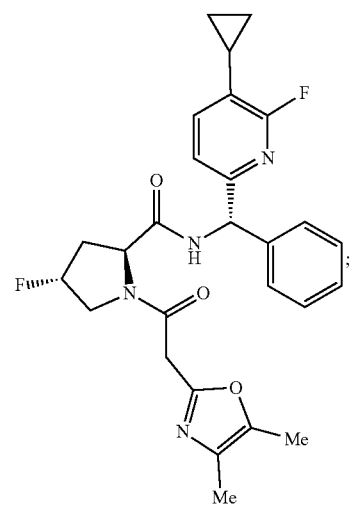
1546
-continued
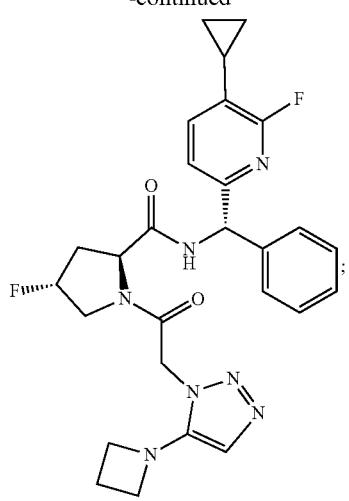
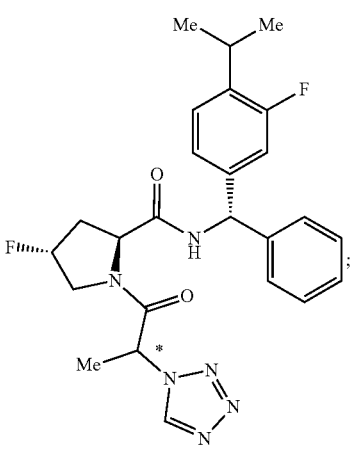
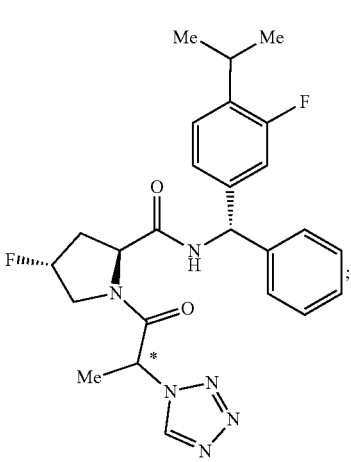

1547
-continued
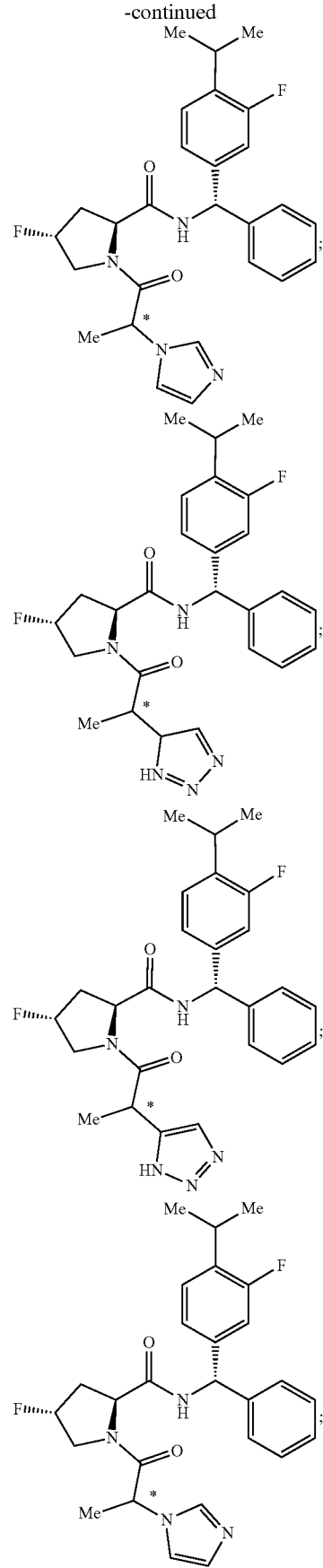
1548
-continued
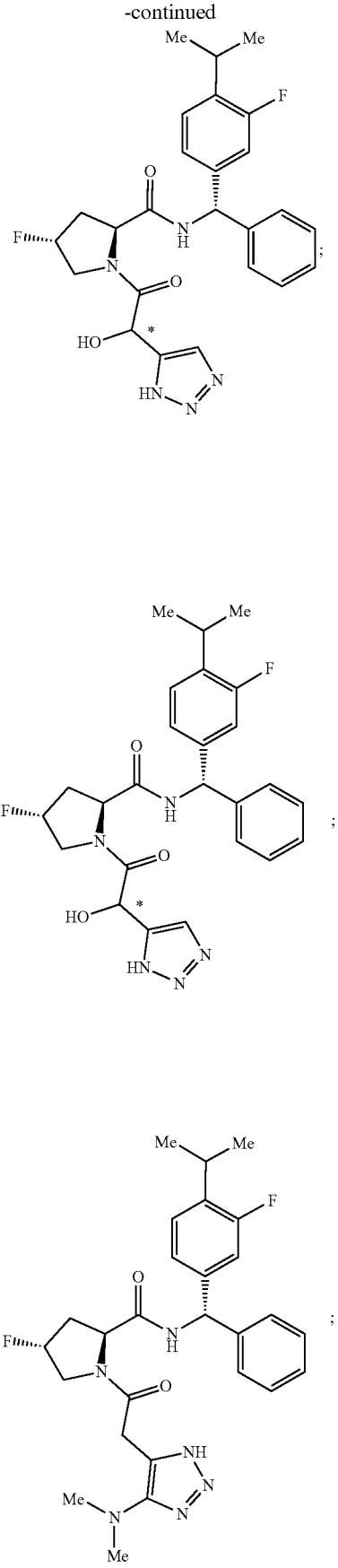

1549
-continued
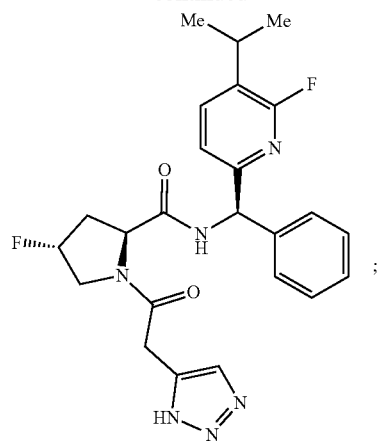
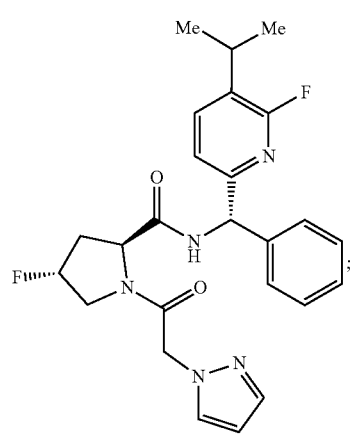
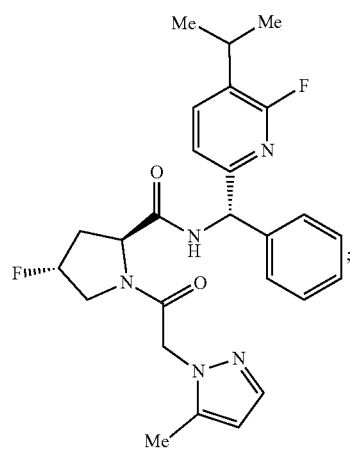
1550
-continued
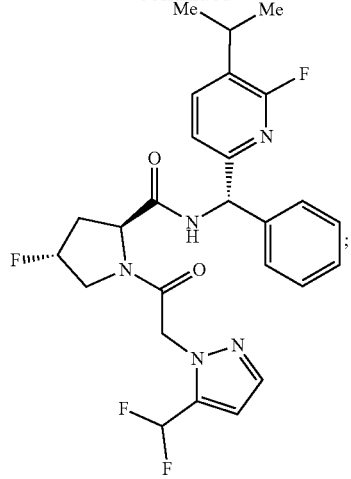
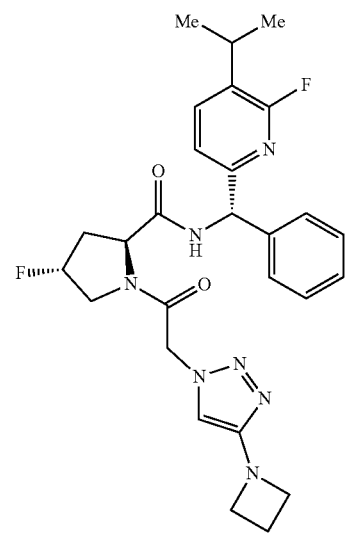
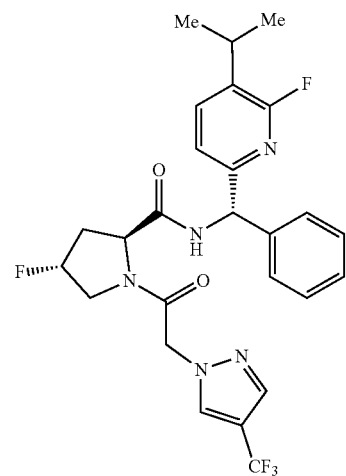

1551          1552
-continued    -continued
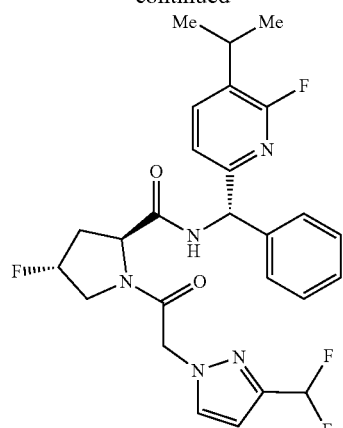
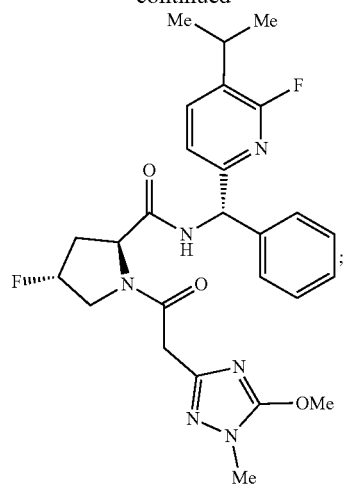
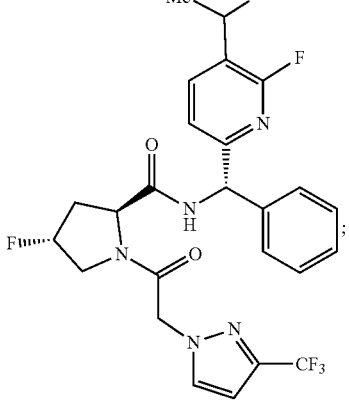
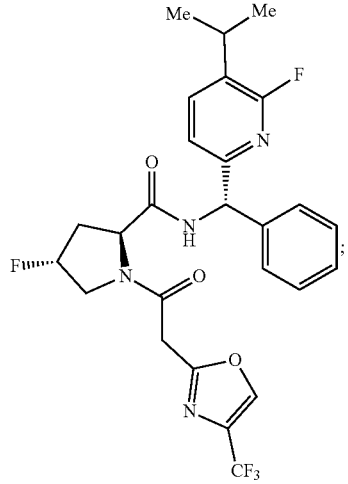
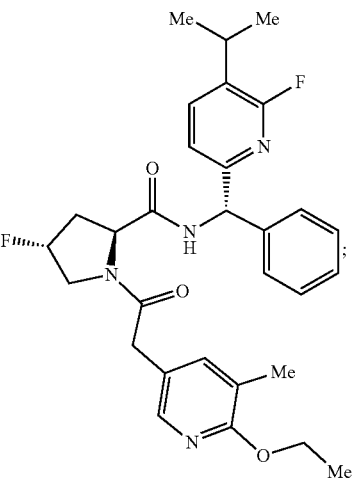
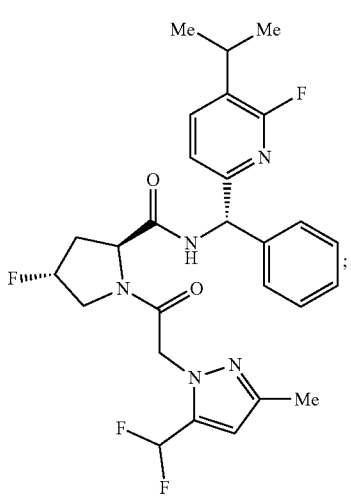

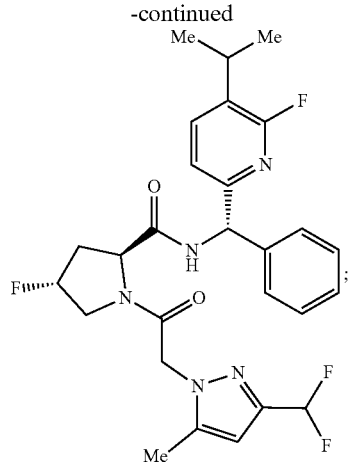
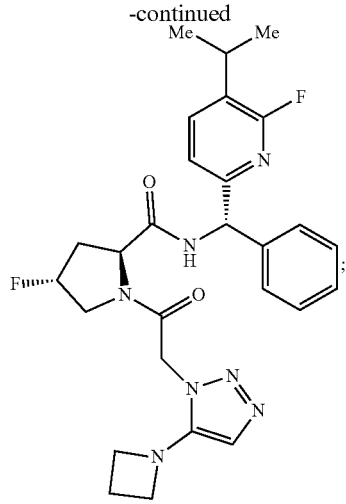
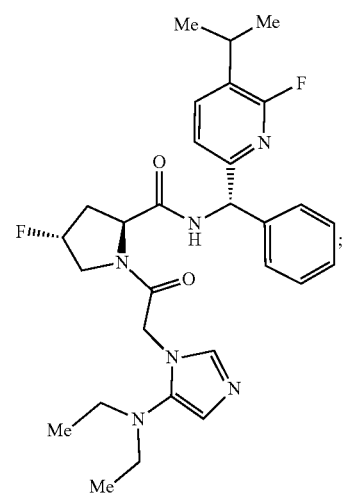
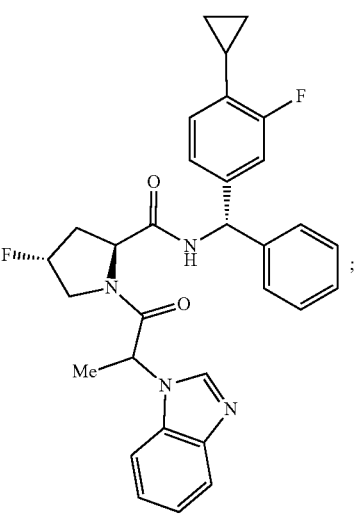
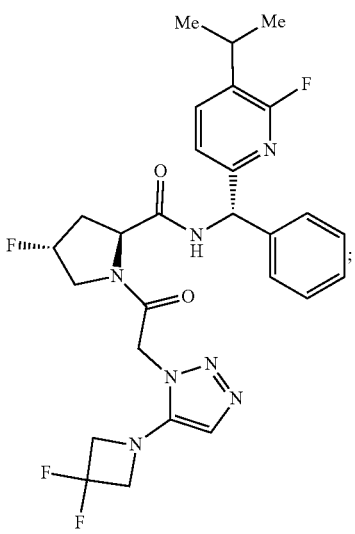
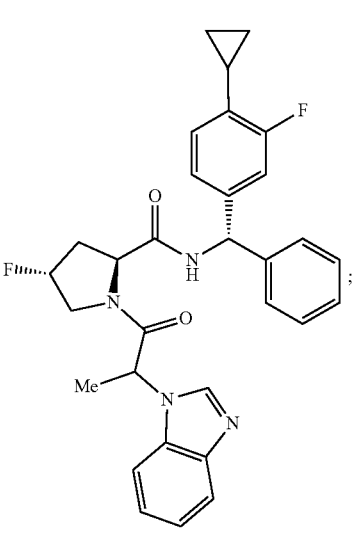

-continued

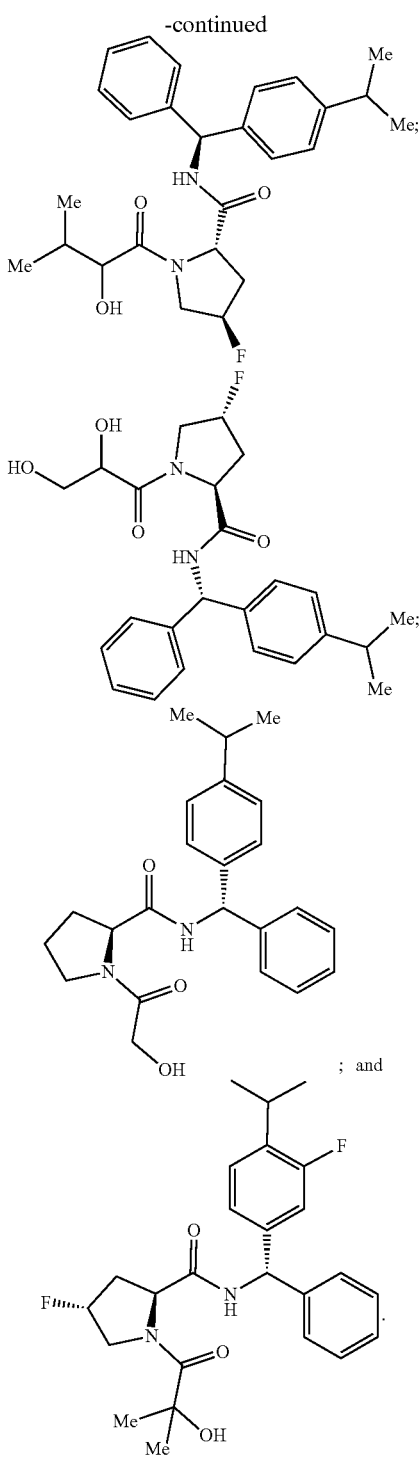
; and

10. A pharmaceutical composition comprising (i) a compound of claim 1, or a stereoisomer or tautomer thereof, or a pharmaceutically acceptable salt of any of the foregoing, and (ii) one or more pharmaceutically acceptable excipients.

11. A method of treating a GYS1-mediated disease, disorder, or condition in an individual in need thereof, comprising administering to the individual an effective amount of a compound of claim 1, or a stereoisomer or tautomer thereof, or a pharmaceutically acceptable salt of any of the foregoing.

12. A kit, comprising (i) a compound of claim 1, or a stereoisomer or tautomer thereof, or a pharmaceutically acceptable salt of any of the foregoing, or the pharmaceutical composition of claim 10, and (ii) instructions for use in treating an GYS1-mediated disease, disorder, or condition in an individual in need thereof.

13. A method of modulating GYS1 in a cell, comprising exposing the cell to a composition comprising an effective amount of a compound of claim 1, or a stereoisomer or tautomer thereof, or a pharmaceutically acceptable salt of any of the foregoing, or a pharmaceutical composition comprising a compound of claim 1, or a stereoisomer or tautomer thereof, or a pharmaceutically acceptable salt of any of the foregoing.

14. A method of inhibiting GYS1 in a cell, comprising exposing the cell to a composition comprising an effective amount of a compound of claim 1, or a stereoisomer or tautomer thereof, or a pharmaceutically acceptable salt of any of the foregoing, or a pharmaceutical composition comprising a compound of claim 1, or a stereoisomer or tautomer thereof, or a pharmaceutically acceptable salt of any of the foregoing.

15. A method of reducing tissue glycogen stores in an individual in need thereof, comprising administering to the individual an effective amount of a compound of claim 1, or a stereoisomer or tautomer thereof, or a pharmaceutically acceptable salt of any of the foregoing, or a pharmaceutical composition comprising a compound of claim 1, or a stereoisomer or tautomer thereof, or a pharmaceutically acceptable salt of any of the foregoing.

16. A method of treating a GYS1-mediated disease, disorder, or condition in an individual in need thereof, comprising administering to the individual an effective amount of a pharmaceutical composition of claim 10.

17. The compound of claim 1, wherein the compound is a compound of formula (I-A3):

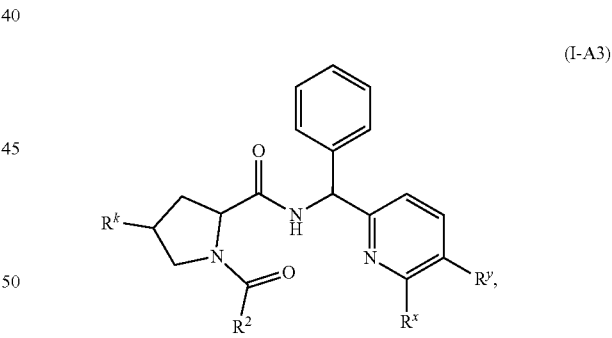

(I-A3)

or a stereoisomer or tautomer thereof, or a pharmaceutically acceptable salt of any of the foregoing, wherein $R^x$ is H, halo, $C_{1-6}$alkyl, or —$NH_2$, wherein the $C_{1-6}$alkyl is optionally substituted with one or more halo.

18. The compound of claim 1, wherein the compound is (2S,4R)-1-(2-(1H-1,2,3-triazol-5-yl)acetyl)-4-fluoro-N—((S)-(4-isopropylphenyl)(phenyl)methyl)pyrrolidine-2-carboxamide having the structure

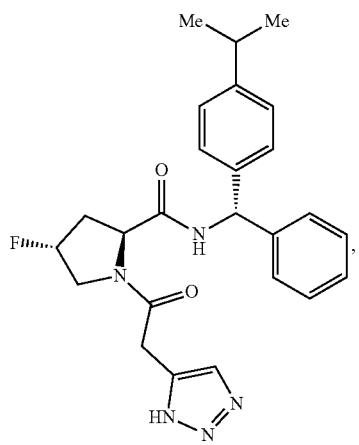

or a pharmaceutically acceptable salt thereof.

19. The compound of claim 18, wherein the compound is (2S,4R)-1-(2-(1H-1,2,3-triazol-5-yl)acetyl)-4-fluoro-N—((S)-(4-isopropylphenyl)(phenyl)methyl)pyrrolidine-2-carboxamide having the structure

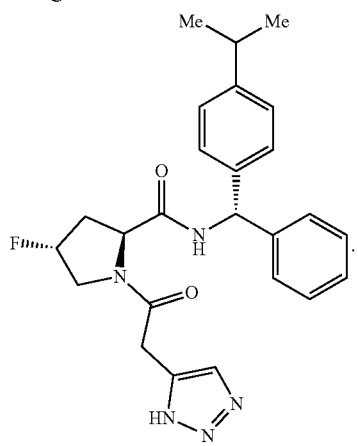

20. The compound of claim 1, wherein the compound is (2S,4R)-1-(2-(1H-1,2,3-triazol-5-yl)acetyl)-4-fluoro-N—((S)-(5-isopropylpyridin-2-yl)(phenyl)methyl)pyrrolidine-2-carboxamide having the structure

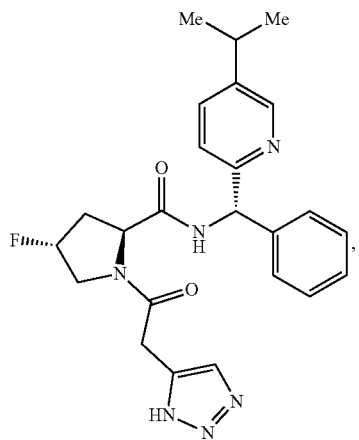

or a pharmaceutically acceptable salt thereof.

21. The compound of claim 20, wherein the compound is (2S,4R)-1-(2-(1H-1,2,3-triazol-5-yl)acetyl)-4-fluoro-N—((S)-(5-isopropylpyridin-2-yl)(phenyl)methyl)pyrrolidine-2-carboxamide having the structure

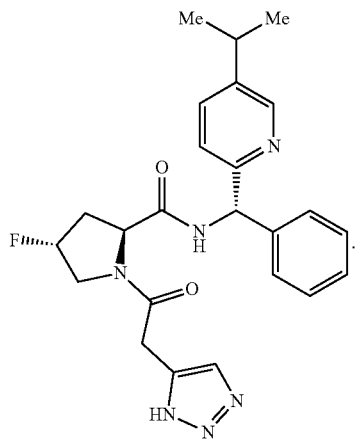 [SMILES: CC(C)c1ccc([C@@H](NC(=O)[C@@H]2C[C@@H](F)CN2C(=O)Cc2cnn[nH]2)c2ccccc2)nc1]

22. The compound of claim 1, wherein the compound is (2S,4R)—N—((S)-(5-cyclopropyl-6-fluoropyridin-2-yl)(phenyl)methyl)-1-(2-(5-(difluoromethyl)-1H-tetrazol-1-yl)acetyl)-4-fluoropyrrolidine-2-carboxamide having the structure

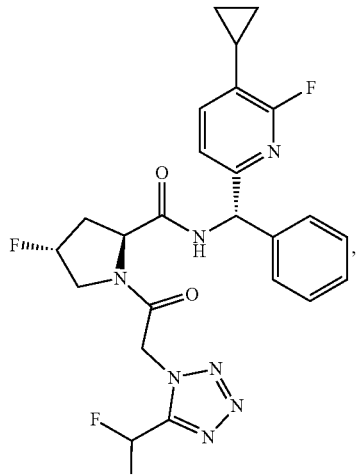

or a pharmaceutically acceptable salt thereof.

23. The compound of claim 22, wherein the compound is (2S,4R)—N—((S)-(5-cyclopropyl-6-fluoropyridin-2-yl)(phenyl)methyl)-1-(2-(5-(difluoromethyl)-1H-tetrazol-1-yl)acetyl)-4-fluoropyrrolidine-2-carboxamide having the structure

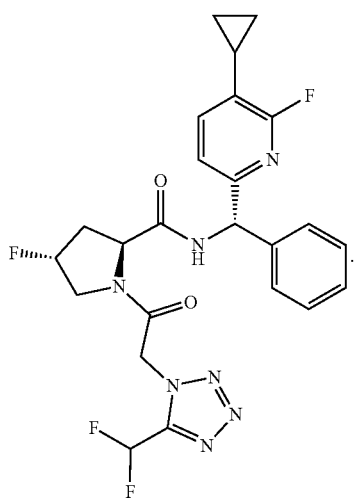 [SMILES: O=C(N[C@@H](c1ccccc1)c1ccc(C2CC2)c(F)n1)[C@@H]1C[C@@H](F)CN1C(=O)Cn1nnnc1C(F)F]

24. The compound of claim 1, wherein the compound is (2S,4R)-4-fluoro-N—((S)-(3-fluoro-4-isopropylphenyl)(phenyl)methyl)-1-(2-(5-(trifluoromethyl)-1H-1,2,3-triazol-1-yl)acetyl)pyrrolidine-2-carboxamide having the structure

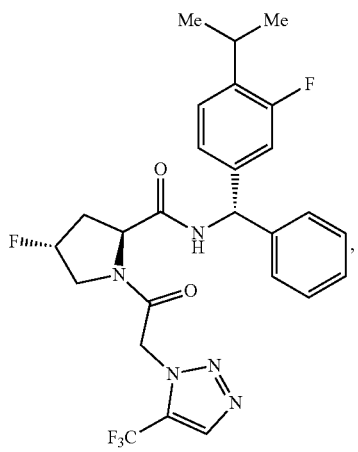 [SMILES: CC(C)c1ccc([C@@H](NC(=O)[C@@H]2C[C@@H](F)CN2C(=O)Cn2nncc2C(F)(F)F)c2ccccc2)cc1F]

or a pharmaceutically acceptable salt thereof.

25. The compound of claim 24, wherein the compound is (2S,4R)-4-fluoro-N—((S)-(3-fluoro-4-isopropylphenyl)(phenyl)methyl)-1-(2-(5-(trifluoromethyl)-1H-1,2,3-triazol-1-yl)acetyl)pyrrolidine-2-carboxamide having the structure

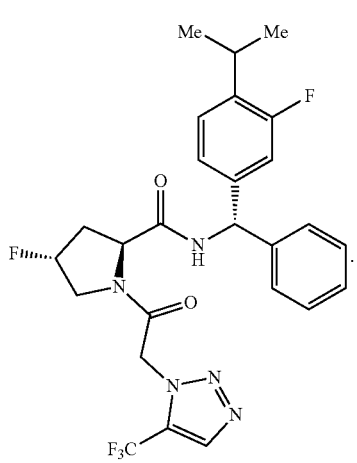 [SMILES: CC(C)c1ccc([C@@H](NC(=O)[C@@H]2C[C@@H](F)CN2C(=O)Cn2nncc2C(F)(F)F)c2ccccc2)cc1F]

26. The compound of claim 1, wherein the compound is (2S,4R)-1-(2-(1H-1,2,3-triazol-5-yl)acetyl)-4-fluoro-N—((S)-(6-fluoro-5-isopropylpyridin-2-yl)(phenyl)methyl)pyrrolidine-2-carboxamide having the structure

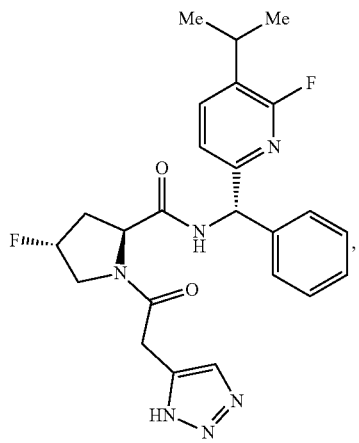 [SMILES: CC(C)c1ccc([C@@H](NC(=O)[C@@H]2C[C@@H](F)CN2C(=O)Cc2cnn[nH]2)c2ccccc2)nc1F]

or a pharmaceutically acceptable salt thereof.

27. The compound of claim 26, wherein the compound is (2S,4R)-1-(2-(1H-1,2,3-triazol-5-yl)acetyl)-4-fluoro-N—((S)-(6-fluoro-5-isopropylpyridin-2-yl)(phenyl)methyl)pyrrolidine-2-carboxamide having the structure

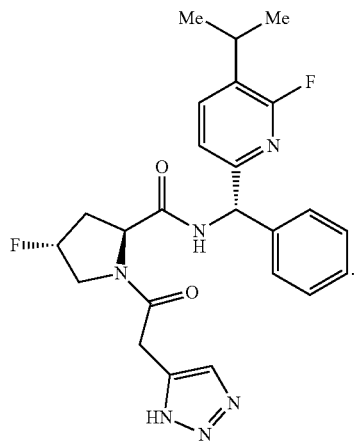 [SMILES: CC(C)c1ccc([C@@H](NC(=O)[C@@H]2C[C@@H](F)CN2C(=O)Cc2cnn[nH]2)c2ccccc2)nc1F]

28. The compound of claim 1, wherein the compound is (2S,4R)-1-(2-(1H-benzo[d]imidazol-1-yl)acetyl)-N—((S)-(4-cyclopropyl-3-fluorophenyl)(phenyl)methyl)-4-fluoropyrrolidine-2-carboxamide having the structure

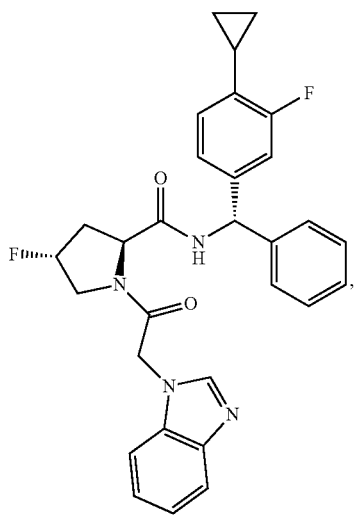 [SMILES: O=C(N[C@@H](c1ccccc1)c1ccc(C2CC2)c(F)c1)[C@@H]1C[C@@H](F)CN1C(=O)Cn1cnc2ccccc21]

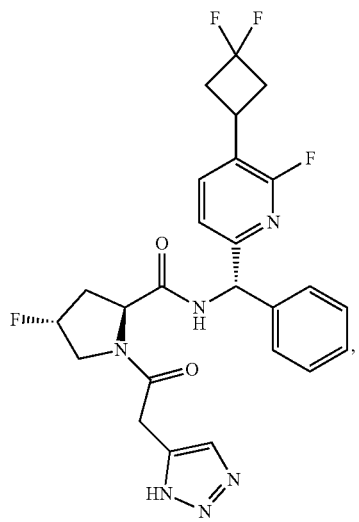

or a pharmaceutically acceptable salt thereof.

29. The compound of claim 28, wherein the compound is (2S,4R)-1-(2-(1H-benzo[d]imidazol-1-yl)acetyl)-N—((S)-(4-cyclopropyl-3-fluorophenyl)(phenyl)methyl)-4-fluoro-pyrrolidine-2-carboxamide having the structure

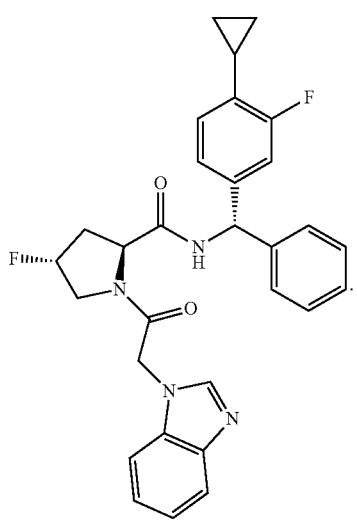 [SMILES: O=C(N[C@@H](c1ccccc1)c1ccc(C2CC2)c(F)c1)[C@@H]1C[C@@H](F)CN1C(=O)Cn1cnc2ccccc21]

30. The compound of claim 1, wherein the compound is (2S,4R)—N—[(S)-[5-(3,3-difluorocyclobutyl)-6-fluoro-pyridin-2-yl](phenyl)methyl]-4-fluoro-1-[2-(1H-1,2,3-tri-azol-5-yl)acetyl]pyrrolidine-2-carboxamide having the structure or a pharmaceutically acceptable salt thereof.

31. The compound of claim 30, wherein the compound is (2S,4R)—N—[(S)-[5-(3,3-difluorocyclobutyl)-6-fluoro-pyridin-2-yl](phenyl)methyl]-4-fluoro-1-[2-(1H-1,2,3-tri-azol-5-yl)acetyl]pyrrolidine-2-carboxamide having the structure

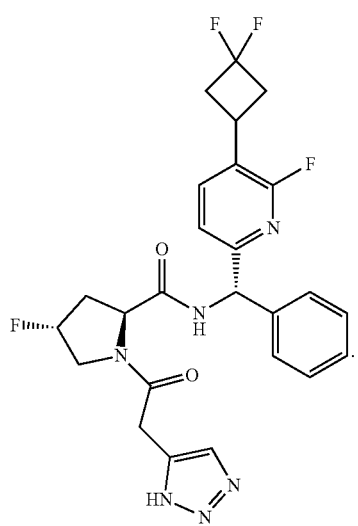 [SMILES: O=C(N[C@@H](c1ccccc1)c1ccc(C2CC(F)(F)C2)c(F)n1)[C@@H]1C[C@@H](F)CN1C(=O)Cc1cnn[nH]1]

32. The compound of claim 1, wherein the compound is (2S,4R)—N—[(S)-[5-(3,3-difluorocyclobutyl)pyridin-2-yl](phenyl)methyl]-4-fluoro-1-[2-(1H-1,2,3-triazol-5-yl)acetyl]pyrrolidine-2-carboxamide having the structure

1563

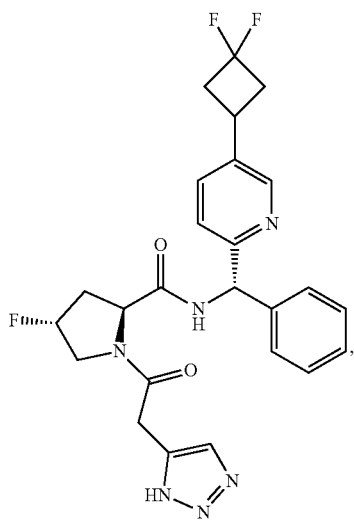 [SMILES: O=C(N[C@@H](c1ccccc1)c1ccc(C2CC(F)(F)C2)cn1)[C@@H]1C[C@@H](F)CN1C(=O)Cc1cnn[nH]1]

or a pharmaceutically acceptable salt thereof.

33. The compound of claim 32, wherein the compound is (2S,4R)—N—[(S)-[5-(3,3-difluorocyclobutyl)pyridin-2-yl](phenyl)methyl]-4-fluoro-1-[2-(1H-1,2,3-triazol-5-yl)acetyl]pyrrolidine-2-carboxamide having the structure

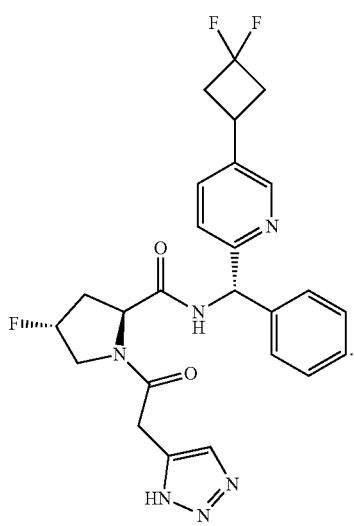

34. The compound of claim 1, wherein the compound is (2S,4R)—N—[(S)-[4-(3,3-difluorocyclobutyl)-3-fluorophenyl](phenyl)methyl]-4-fluoro-1-[2-(1H-1,2,3-triazol-5-yl)acetyl]pyrrolidine-2-carboxamide having the structure

1564

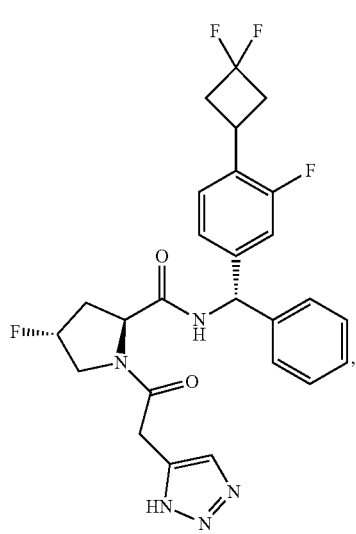 [SMILES: O=C(N[C@@H](c1ccccc1)c1ccc(C2CC(F)(F)C2)c(F)c1)[C@@H]1C[C@@H](F)CN1C(=O)Cc1cnn[nH]1]

or a pharmaceutically acceptable salt thereof.

35. The compound of claim 34, wherein the compound is (2S,4R)—N—[(S)-[4-(3,3-difluorocyclobutyl)-3-fluorophenyl](phenyl)methyl]-4-fluoro-1-[2-(1H-1,2,3-triazol-5-yl)acetyl]pyrrolidine-2-carboxamide having the structure

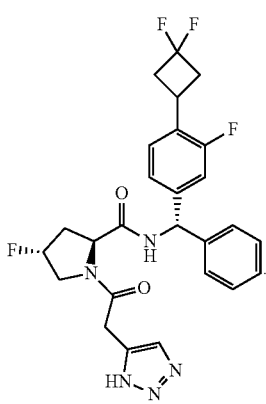 [SMILES: O=C(N[C@@H](c1ccccc1)c1ccc(C2CC(F)(F)C2)c(F)c1)[C@@H]1C[C@@H](F)CN1C(=O)Cc1cnn[nH]1]

36. The compound of claim 1, wherein the compound is (2S,4R)-4-fluoro-N—[(S)-[3-fluoro-4-(1-methylcyclopropyl)phenyl](phenyl)methyl]-1-[2-(1H-1,2,3-triazol-5-yl)acetyl]pyrrolidine-2-carboxamide having the structure

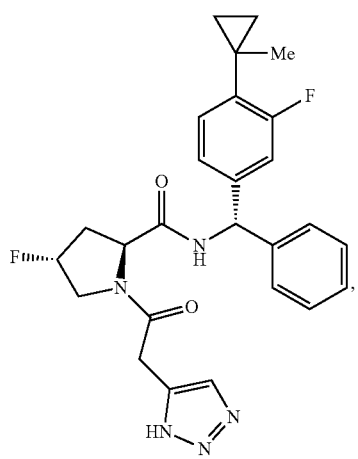 [SMILES: CC1(c2ccc([C@@H](NC(=O)[C@@H]3C[C@@H](F)CN3C(=O)Cc3cnn[nH]3)c3ccccc3)cc2F)CC1]

or a pharmaceutically acceptable salt thereof.

37. The compound of claim 36, wherein the compound is (2S,4R)-4-fluoro-N—[(S)-[3-fluoro-4-(1-methylcyclopropyl)phenyl](phenyl)methyl]-1-[2-(1H-1,2,3-triazol-5-yl)acetyl]pyrrolidine-2-carboxamide having the structure

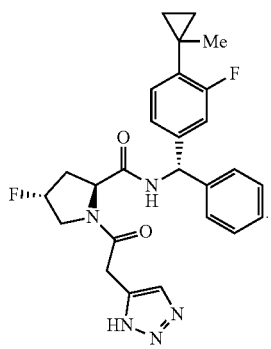 [SMILES: CC1(c2ccc([C@@H](NC(=O)[C@@H]3C[C@@H](F)CN3C(=O)Cc3cnn[nH]3)c3ccccc3)cc2F)CC1]

38. The compound of claim 1, wherein the compound is (2S,4R)-1-[2-(1H-1,3-benzodiazol-1-yl)acetyl]-4-fluoro-N—[(S)-[6-fluoro-5-(1-methylcyclopropyl)pyridin-2-yl](phenyl)methyl]pyrrolidine-2-carboxamide having the structure

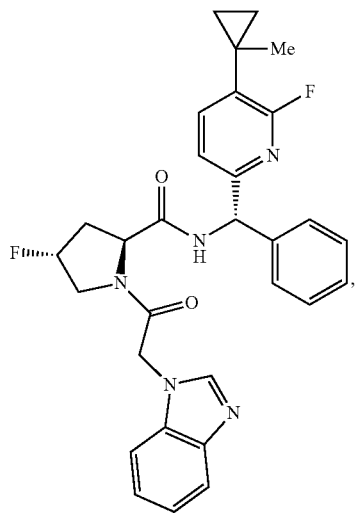 [SMILES: CC1(c2ccc([C@@H](NC(=O)[C@@H]3C[C@@H](F)CN3C(=O)Cn3cnc4ccccc43)c3ccccc3)nc2F)CC1]

or a pharmaceutically acceptable salt thereof.

39. The compound of claim 38, wherein the compound is (2S,4R)-1-[2-(1H-1,3-benzodiazol-1-yl)acetyl]-4-fluoro-N—[(S)-[6-fluoro-5-(1-methylcyclopropyl)pyridin-2-yl](phenyl)methyl]pyrrolidine-2-carboxamide having the structure

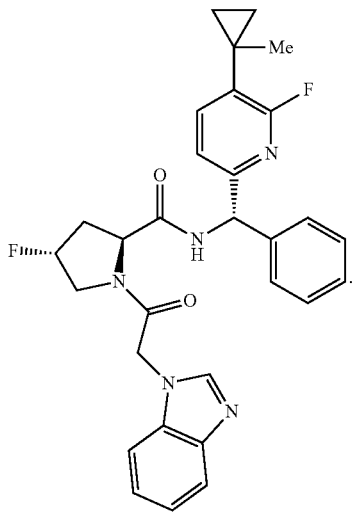 [SMILES: CC1(c2ccc([C@@H](NC(=O)[C@@H]3C[C@@H](F)CN3C(=O)Cn3cnc4ccccc43)c3ccccc3)nc2F)CC1]

40. The compound of claim 1, wherein the compound is (2S,4R)-1-(2-(5-(difluoromethyl)-1,3,4-oxadiazol-2-yl)acetyl)-4-fluoro-N—((S)-(5-isopropyl-4-methylpyridin-2-yl)(phenyl)methyl)pyrrolidine-2-carboxamide having the structure

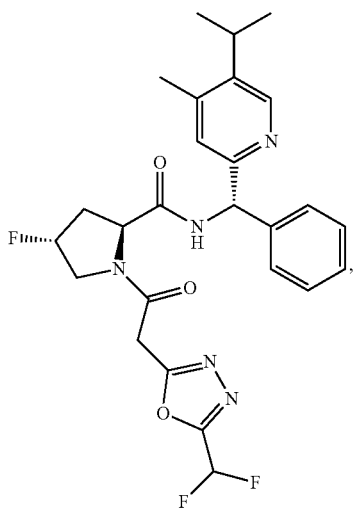

or a pharmaceutically acceptable salt thereof.

41. The compound of claim 40, wherein the compound is (2S,4R)-1-(2-(5-(difluoromethyl)-1,3,4-oxadiazol-2-yl)acetyl)-4-fluoro-N—((S)-(5-isopropyl-4-methylpyridin-2-yl)(phenyl)methyl)pyrrolidine-2-carboxamide having the structure

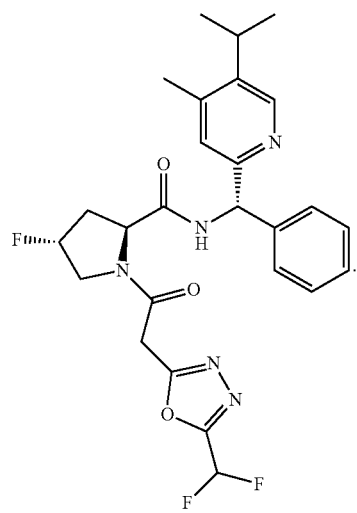 [SMILES: Cc1cc([C@@H](NC(=O)[C@@H]2C[C@@H](F)CN2C(=O)Cc2nnc(C(F)F)o2)c2ccccc2)ncc1C(C)C]
* * * * *